US007960544B2

(12) United States Patent (10) Patent No.: US 7,960,544 B2
Bartolini et al. (45) Date of Patent: Jun. 14, 2011

(54) USEFUL INDOLE COMPOUNDS

(75) Inventors: Wilmin Bartolini, Amesbury, MA (US);
Brian M. Cali, Arlington, MA (US);
Barbara Chen, Northbrook, IL (US);
Yueh-Tyng Chien, Newton, MA (US);
Mark G. Currie, Sterling, MA (US); G. Todd Milne, Brookline, MA (US);
James Philip Pearson, Cambridge, MA (US); John Jeffrey Talley, Somerville, MA (US); Jane Yang, Boxborough, MA (US); Craig Zimmerman, Topsfield, MA (US); Charles Kim, Cambridge, MA (US); Kevin Sprott, Boston, MA (US); Timothy Barden, Salem, MA (US); Regina Lundigran, Duxbury, MA (US); Ara Mermerian, Somerville, MA (US)

(73) Assignee: Ironwood Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 12/097,616

(22) PCT Filed: Dec. 18, 2006

(86) PCT No.: PCT/US2006/062265
§ 371 (c)(1),
(2), (4) Date: Mar. 3, 2009

(87) PCT Pub. No.: WO2007/070892
PCT Pub. Date: Jun. 21, 2007

(65) Prior Publication Data
US 2009/0264653 A1 Oct. 22, 2009

Related U.S. Application Data

(60) Provisional application No. 60/751,443, filed on Dec. 16, 2005.

(51) Int. Cl.
*C07D 403/06* (2006.01)
*C07D 239/26* (2006.01)
*C07D 471/04* (2006.01)
*C07D 401/06* (2006.01)
*C07D 271/06* (2006.01)
*C07D 271/10* (2006.01)
*C07D 417/06* (2006.01)
*C07D 413/06* (2006.01)
*C07D 263/32* (2006.01)
*C07D 261/08* (2006.01)

(52) U.S. Cl. ........ 544/238; 544/335; 546/113; 546/115; 546/278.1; 548/131; 548/143; 548/159; 548/204; 548/217; 548/236; 548/248

(58) Field of Classification Search .................. None
See application file for complete search history.

(56) References Cited

U.S. PATENT DOCUMENTS

| 3,856,967 | A | 12/1974 | Allais et al. |
| 3,946,029 | A | 3/1976 | Descamps et al. |
| 4,105,777 | A | 8/1978 | Allais et al. |
| 4,233,312 | A | 11/1980 | Allais et al. |
| 6,069,156 | A | 5/2000 | Oku et al. |
| 2002/0022218 | A1 | 2/2002 | Li et al. |
| 2003/0162825 | A1 | 8/2003 | Heefner et al. |
| 2007/0203209 | A1 | 8/2007 | Bartolini et al. |
| 2009/0118503 | A1 | 5/2009 | Sprott et al. |

FOREIGN PATENT DOCUMENTS

| WO | WO 03/022274 | * | 3/2003 |
| WO | WO03066047 | | 8/2003 |
| WO | WO2006036994 | | 4/2006 |
| WO | WO2007/022501 | | 2/2007 |

OTHER PUBLICATIONS

Drew et al. J. Chem. Crystallogr. (2008) 38: 507-512.*
STN Registry file record for RN 501659-75-2. Entered STN Apr. 4, 2003. Accessed database entry on Jun. 21, 2010.*
Ajuebor et al., "Cyclooxygenase-2-derived prostaglandin D2 is an early anti-inflammatory signal in experimental colitis," Am. J. Physiol. Gastrointest. Live Physiol., 279:G238-G244, 2000.
Arora and Yamazaki, "Eosinophilic Esophagitis: Asthma of the Esophagus?" Clinical Gastroenterology and Heptology, 2:523-530, 2004.
Black et al., "From Iodomethacin to a Selective Cox-2 Inhibitors," Bioorganic & Medicinal Chemistry Letters, 6(6): 725-730, 1996.
Chen et al., "Flavoenzymes Inhibited by Indomethacin," Drug Metabolism and Drug Interactions, 11(2): 153-160, 1994.
Cravatt and Lichtman, "Fatty acid amide hydrolase: an emerging therapeutic target in the endocannabinoid system," Current Opinion in Chemical Biology, 7:469-475, 2003.
Deutsch et al., "The fatty acid amide hydrolase (FAAH)," Prostaglandins, Leukotrienes and Essential Fatty Acids, 66 (2&3): 201-210, 2002.
Duggan et al., "Metabolism of Indomethacin in Man," The Journal of Pharmacology, 181: 563-575, 1972.
Fride and Mechoulam, "Pharmacological activity of the cannabinoid receptor agonist, anandamide, a brain constituent," European Journal of Pharmacology, 231: 313-314, 1993.
Harman et al., "The Metabolites of Indomethacin, A New Anti-Inflammatory Drug," The Journal of Pharmacology, 143: 215-220, 1964.
Hecht et al., "Heterologous desensitization of T cell functions by CCR5 and CXCR4 ligands: inhibition of cellular signaling, adhesion and chemotaxis," International Immunology, 15(1): 29-38, 2003.
Helleberg, Lars, "Clinical Pharmacokinetics of Indomethacin," Clinical Pharmacokinetics, 6: 245-258, 1981.
Huang et al., "Sequence variants of the gene encoding chemoattractant receptor expressed on Th2 cells (CRTH2) are associated with asthma and differentially influence mRNA stability," Human Molecular Genetics, 13(21): 2691-2697, 2004.
Kiehl et al., "Tissue eosinophilia in acute and chronic atopic dermatitis: a morphometric approach using quantitative image analysis of immunostaining," British Journal of Dermatology, 145: 720-729, 2001.

(Continued)

Primary Examiner — Rebecca L Anderson
Assistant Examiner — Alicia L Otton
(74) Attorney, Agent, or Firm — Honigman Miller Schwartz Cohn LLC; Kelly T. Murphy; Jonathan P. O'Brien

(57) ABSTRACT

Indoles that have activity as inhibitors of FAAH are described as are indoles and indole derivatives that have activity as inhibitors of DAO.

34 Claims, 84 Drawing Sheets

OTHER PUBLICATIONS

Lau et al., "From Indomethacin to a Selective Cox-2 Inhibitor: Development of Indolalkanoic Acids as Potent and Selective Cyclooxygenase-2 Inhibitors," in: Honn et al., Eicosanoids and Other Bioactive Lipids in Cancer, Inflammation, and Radiation Injury 3, (New York, Plenum Press), 73-78, 1997.

Monneret et al., "15R-Methyl-Prostaglandin D2 is a potent and selective CRTH2/DP2 Receptor Agonist in Human Eosinophils," The Journal of Pharmacology and Experimental Therapeutics, 304(1): 349-355, 2003.

Nagata et al., "CRTH2, an orphan receptor of T-helper-2-cells, is expressed on basophils and eosinophils and responds to mast cell-derived factor(s)," FEBS Letters, 459: 195-199, 1999.

Shen and Winter, "Chemical and Biological Studies on Indomethacin, Sulindac and their Analogs," in: Harper and Simmonds, Advances in Drug Research, vol. 12 (London Academic Press), 89-245, 1977.

Shen et al., "Non-Steroid Anti-Inflammatory Agents," Communications to the Editor, 85: 488-489, 1963.

Shichijo et al., "Chemoattractant Receptor-Homologous Molecule Expressed on Th2 Cells Activation in Vivo Increases Book Leukocyte Counts and Its Blockge Abrogats 13,14-Dihydro-15-keto-prostagladin D2-Induced Eosinophilia in Rats," The Journal of Pharmacology and Experimental Therapeutics, 307(2): 518-525, 2003.

Strachan et al., "Synthesis of Indomethacin Metabolites," Notes, 799-800, 1964.

Stubbs et al., "Indomethacin Causes Prostaglandin D2-like and Eotaxin-like Selective Responses in Eosinophils and Basophils," The Journal of Biological Chemistry, 277(29): 26012-26020, 2002.

Touhey et al., "Structure-activity relationship of indomethacin analogues for MRP-1, COX-1 and COX-2 inhibition: identification of novel chemotherapeutic drug resistance modulators," European Journal of Cancer, 38: 1661-1670, 2002.

Walker et al., "Pain modulation by release of the endogenous cannabinoid annadamide," PNAS, 96(21): 12198-12203, 1999.

Weber et al., "Formation of prostamides from anadamide in FAAH knockout mice analyzed by HPLC with tandem mass spectrometry," Journal of Lipid Research, 45: 757-763, 2004.

Yoshimura-Uchiyama et al., "Differential modulation of human basophil functions through prostaglandin D2-receptors DP and chemoattractant receptor-homologous molecule expressed on Th2 cells/DP2," Clin. Exp. Allergy, 34: 1283-1290, 2004.

* cited by examiner

FIG. 1A

| Row | IUPAC Name | COX-1 purified enzyme assay IC50 (uM) | COX-2 purified enzyme assay IC50 (uM) |
|---|---|---|---|
| 1 | [1-(4-chlorobenzoyl)-5-methoxy-2-methyl-1H-indol-3-yl]acetic acid | <1 | <1 |
| 2 | {5-methoxy-2-methyl-1-[(2E)-3-phenylprop-2-enoyl]-1H-indol-3-yl}acetic acid | <1 | 1-10 |
| 3 | {5-hydroxy-2-methyl-1-[(2E)-3-phenylprop-2-enoyl]-1H-indol-3-yl}acetic acid | <1 | >8 |
| 4 | [1-(4-ethylbenzoyl)-5-methoxy-2-methyl-1H-indol-3-yl]acetic acid | <1 | >10 |
| 5 | {6-fluoro-5-methoxy-2-methyl-1-[4-(methylthio)benzoyl]-1H-indol-3-yl}acetic acid | <1 | <1 |
| 6 | {(1-benzoyl-5-methoxy-2-methyl-1H-indol-3-yl]acetic acid | <1 | <1 |
| 7 | {6-fluoro-5-hydroxy-2-methyl-1-[4-(methylthio)benzoyl]-1H-indol-3-yl}acetic acid | <1 | <1 |
| 8 | {5-hydroxy-2-methyl-1-(4-methylthiobenzoyl)-1H-indol-3-yl}acetic acid | <1 | <1 |
| 9 | [1-(4-fluorobenzoyl)-5-methoxy-2-methyl-1H-indol-3-yl]acetic acid | <1 | <1 |
| 10 | [6-fluoro-5-methoxy-2-methyl-1-(4-methylbenzoyl)-1H-indol-3-yl]acetic acid | 1-10 | <1 |
| 11 | [1-(4-bromobenzoyl)-6-fluoro-5-methoxy-2-methyl-1H-indol-3-yl]acetic acid | 1-10 | <1 |
| 12 | [1-(4-chlorobenzoyl)-6-fluoro-5-methoxy-2-methyl-1H-indol-3-yl]acetic acid | 1-10 | 1-10 |
| 13 | [1-benzoyl-5-hydroxy-2-methyl-1H-indol-3-yl]acetic acid | 1-10 | <1 |
| 14 | {6-fluoro-5-methoxy-2-methyl-1-[(5-methyl-2-thienyl)carbonyl]-1H-indol-3-yl}acetic acid | 1-10 | <1 |
| 15 | [6-fluoro-5-methoxy-2-methyl-1-(4-methylbenzoyl)-1H-indol-3-yl]acetic acid | 1-10 | <1 |
| 16 | {6-chloro-5-methoxy-2-methyl-1-[3-(trifluoromethyl)benzoyl]-1H-indol-3-yl}acetic acid | 10-50 | >100 |
| 17 | [6-chloro-1-(3-chlorobenzoyl)-2,5-dimethyl-1H-indol-3-yl]acetic acid | 10-50 | >100 |
| 18 | [5-hydroxy-2-methyl-1-(3-phenylprop-2-ynoyl)-1H-indol-3-yl]acetic acid | 1-10 | >10 |
| 19 | {1-[4-(difluoromethoxy)benzoyl]-5-methoxy-2-methyl-1H-indol-3-yl}acetic acid | 1-10 | <1 |
| 20 | {1-[(5-chloro-2-thienyl)carbonyl]-5-methoxy-2-methyl-1H-indol-3-yl}acetic acid | 1-10 | <1 |
| 21 | propyl [1-(4-chlorobenzoyl)-5-hydroxy-2-methyl-1H-indol-3-yl]acetate | 1-10 | 1-10 |
| 22 | {1-[(5-chloro-2-thienyl)carbonyl]-5-hydroxy-2-methyl-1H-indol-3-yl}acetic acid | 1-10 | <1 |
| 23 | [6-fluoro-5-methoxy-2-methyl-1-(2-thienylcarbonyl)-1H-indol-3-yl]acetic acid | 1-10 | <1 |
| 24 | [1-(4-chlorobenzoyl)-5-fluoro-2-methyl-1H-indol-3-yl]acetic acid | 1-10 | <1 |
| 25 | [6-fluoro-1-(4-fluorobenzoyl)-5-methoxy-2-methyl-1H-indol-3-yl]acetic acid | 1-10 | <1 |
| 26 | ethyl N-{[1-(4-chlorobenzoyl)-5-methoxy-2-methyl-1H-indol-3-yl]acetyl}glycinate | 1-10 | >10 |

FIG. 1B

| Row | IUPAC Name | COX-1 purified enzyme assay IC50 (uM) | COX-2 purified enzyme assay IC50 (uM) |
|---|---|---|---|
| 27 | [6-chloro-1-(3-chlorobenzyl)-5-methoxy-2-methyl-1H-indol-3-yl]acetic acid | 10-50 | >100 |
| 28 | [4-chloro-1-(4-chlorobenzyl)-2,5-dimethyl-1H-indol-3-yl]acetic acid | 10-50 | >100 |
| 29 | [6-chloro-1-(3,5-dimethylbenzyl)-5-methoxy-2-methyl-1H-indol-3-yl]acetic acid | >10 | >100 |
| 30 | [1-(4-bromobenzyl)-6-chloro-5-methoxy-2-methyl-1H-indol-3-yl]acetic acid | 10-50 | >10 |
| 31 | (1-benzyl-6-fluoro-5-hydroxy-2-methyl-1H-indol-3-yl)acetic acid | 10-50 | <1 |
| 32 | isopropyl [1-(4-chlorobenzyl)-6-fluoro-5-hydroxy-2-methyl-1H-indol-3-yl]acetate | 10-50 | <1 |
| 33 | 4-[5-(4-methylphenyl)-3-(trifluoromethyl)-1H-pyrazol-1-yl]benzenesulfonamide | 10-50 | 10-50 |
| 34 | ethyl [(4-chlorobenzoyl)-3-hydroxy-2-methyl-1H-indol-3-yl]acetate | 10-50 | <1 |
| 35 | [1-(4-fluorobenzyl)-5-hydroxy-2-methyl-1H-indol-3-yl]acetic acid | 10-50 | <1 |
| 36 | methyl [1-(4-chlorobenzyl)-5-hydroxy-2-methoxy-2-methyl-1H-indol-3-yl]acetate | 10-50 | >100 |
| 37 | [6-chloro-1-(4-chlorobenzyl)-5-methoxy-2-methyl-1H-indol-3-yl]acetic acid | >100 | >100 |
| 38 | [6-chloro-5-hydroxy-2-methyl-1-[(5-methyl-2-thienyl)carbonyl]-1H-indol-3-yl]acetic acid | 10-50 | <1 |
| 39 | [5-methoxy-2-methyl-1-[4-(trifluoromethoxy)benzoyl]-1H-indol-3-yl]acetic acid | 10-50 | <1 |
| 40 | [1-(4-difluoromethoxybenzoyl)-6-fluoro-5-methoxy-2-methyl-1H-indol-3-yl]acetic acid | 10-50 | <1 |
| 41 | [6-chloro-1-(4-chlorobenzyl)-5-methoxy-2-methyl-1H-indol-3-yl]acetic acid | 10-50 | 1-10 |
| 42 | [1-(4-bromobenzyl)-6-fluoro-5-methoxy-2-methyl-1H-indol-3-yl]acetic acid | 10-50 | <1 |
| 43 | [1-(4-bromobenzyl)-6-fluoro-5-hydroxy-2-methyl-1H-indol-3-yl]acetate | 10-50 | <1 |
| 44 | butyl [1-(4-chlorobenzyl)-6-fluoro-5-methoxy-2-methyl-1H-indol-3-yl]acetate | 10-50 | 1-10 |
| 45 | [5,6-dichloro-2-methyl-1-[3-(trifluoromethoxy)benzyl]-1H-indol-3-yl]acetic acid | 50-100 | >100 |
| 46 | [1-(4-bromobenzyl)-4,6-difluoro-5-methoxy-2-methyl-1H-indol-3-yl]acetic acid | 10-50 | >10 |
| 47 | [6-chloro-5-methoxy-2-methyl-1-[4-(trifluoromethyl)benzoyl]-1H-indol-3-yl]acetic acid | 10-50 | >100 |
| 48 | [1-(4-chloromethoxybenzoyl)-6-fluoro-5-hydroxy-2-methyl-1H-indol-3-yl]acetic acid | 10-50 | <1 |
| 49 | [5-hydroxy-2-methyl-1-[4-(trifluoromethyl)benzoyl]-1H-indol-3-yl]acetic acid | 10-50 | >100 |
| 50 | [6-fluoro-5-methoxy-2-methyl-1-(2-thienylcarbonyl)-1H-indol-3-yl]acetic acid | 10-50 | <1 |
| 51 | propyl [1-(4-chlorobenzoyl)-5-hydroxy-2-methyl-1H-indol-3-yl]acetate | 10-50 | 1-10 |
| 52 | [1-(2,4-difluorobenzoyl)-5-hydroxy-2-methyl-1H-indol-3-yl]acetic acid | 10-50 | >10 |

FIG. 1C

| Row | IUPAC Name | COX-1 purified enzyme assay IC50 (uM) | COX-2 purified enzyme assay IC50 (uM) |
|---|---|---|---|
| 53 | methyl [1-(4-chlorobenzoyl)-6-fluoro-5-hydroxy-2-methyl-1H-indol-3-yl]acetate | 10-50 | 10-50 |
| 54 | 5-methoxy-1-(4-methoxybenzoyl)-2-methyl-1H-indol-3-yl]acetic acid | 10-50 | >100 |
| 55 | ethyl [1-(4-chlorobenzoyl)-6-fluoro-5-hydroxy-2-methyl-1H-indol-3-yl]acetate | 10-50 | 1-10 |
| 56 | {1-[(5-chloro-2-thienyl)carbonyl]-6-fluoro-3-methoxy-2-methyl-1H-indol-3-yl}acetic acid | 10-50 | <1 |
| 57 | ethyl [1-(4-chlorobenzoyl)-5-methoxy-2-methyl-1H-indol-3-yl]acetate | >100 | >50 |
| 58 | {1-[4-(difluoromethoxy)benzoyl]-5-hydroxy-2-methyl-1H-indol-3-yl}acetic acid | 10-50 | <1 |
| 59 | [1-(4-chlorobenzoyl)-4-fluoro-5-methoxy-2-methyl-1H-indol-3-yl]acetic acid | 50-100 | 1-10 |
| 60 | [1-(4-chlorobenzoyl)-5-methoxy-2-methyl-1H-indol-3-yl]acetic acid | 50-100 | >10 |
| 61 | {6-chloro-2-thienyl)carbonyl]-5-methoxy-2-methyl-1H-indol-3-yl}acetic acid | >100 | >100 |
| 62 | [1-(4-cyanobenzoyl)-5-hydroxy-2-methyl-1H-indol-3-yl]acetic acid | 50-100 | 1-10 |
| 63 | {6-fluoro-5-methoxy-2-methyl-1-[4-(trifluoromethyl)benzoyl]-1H-indol-3-yl}acetic acid | 50-100 | <1 |
| 64 | {1-[(5-chloro-2-thienyl)carbonyl]-6-fluoro-5-hydroxy-2-methyl-1H-indol-3-yl}acetic acid | 50-100 | <1 |
| 65 | [6-chloro-1-(4-chlorobenzoyl)-5-fluoro-2-methyl-1H-indol-3-yl]acetic acid | >100 | >100 |
| 66 | (6-fluoro-5-methoxy-2-methyl-1-{4-[(trifluoromethyl)thio]benzoyl}-1H-indol-3-yl)acetic acid | 50-100 | >100 |
| 67 | {6-fluoro-2,5-dimethyl-1-[3-(trifluoromethoxy)benzoyl]-1H-indol-3-yl}acetic acid | 50-100 | >100 |
| 68 | {1-[3,5-bis(trifluoromethyl)benzoyl]-6-chloro-5-methoxy-2-methyl-1H-indol-3-yl}acetic acid | 50-100 | >100 |
| 69 | {5-chloro-2-methyl-1-[3-(trifluoromethyl)benzoyl]-1H-indol-3-yl}acetic acid | 50-100 | >100 |
| 70 | [6-chloro-1-(3,5-difluorobenzoyl)-5-methoxy-2-methyl-1H-indol-3-yl]acetic acid | 50-100 | >100 |
| 71 | [6-chloro-1-(2-chlorobenzoyl)-5-methoxy-2-methyl-1H-indol-3-yl]acetic acid | 50-100 | >100 |
| 72 | {6-chloro-5-fluoro-3-methyl-1-[3-(trifluoromethoxy)benzoyl]-1H-indol-3-yl}acetic acid | 50-100 | >100 |
| 73 | {6-chloro-5-fluoro-2-methyl-1-[3-(trifluoromethoxy)benzoyl]-1H-indol-3-yl}acetic acid | 50-100 | >100 |
| 74 | 4-{[3-(carboxymethyl)-6-chloro-5-methoxy-2-methyl-1H-indol-1-yl]methyl}benzoic acid | <10 | >100 |
| 75 | [1-(4-bromobenzoyl)-6-fluoro-5-methoxy-2-methyl-1H-indol-3-yl]acetic acid | <10 | >10 |
| 76 | (6-fluoro-5-hydroxy-2-methyl-1-{4-[(trifluoromethyl)thio]benzoyl}-1H-indol-3-yl)acetic acid | >100 | >100 |
| 77 | {6-chloro-2-thienyl)carbonyl]-5-chloro-2-methyl-1H-indol-3-yl}acetic acid | >10 | >10 |
| 78 | (6-fluoro-5-methoxy-2-methyl-1-{4-[(trifluoromethyl)thio]benzoyl}-1H-indol-3-yl)acetic acid | >10 | >10 |

FIG. 1D

| Row | IUPAC Name | COX-1 purified enzyme assay IC50 (uM) | COX-2 purified enzyme assay IC50 (uM) |
|---|---|---|---|
| 79 | {1-(1,3-benzothiazol-2-ylmethyl)-6-chloro-5-methoxy-2-methyl-1H-indol-3-yl]acetic acid | >100 | >100 |
| 80 | [6-chloro-1-[(5-chloro-2-thienyl)carbonyl]-5-fluoro-2-methyl-1H-indol-3-yl]acetic acid | >10 | >10 |
| 81 | [1-(1,3-benzothiazol-2-ylmethyl)-6-fluoro-5-methoxy-2-methyl-1H-indol-3-yl]acetic acid | >100 | >100 |
| 82 | {1-[(4-chlorophenyl)sulfonyl]-6-fluoro-5-methoxy-2-methyl-1H-indol-3-yl]acetic acid | >100 | >100 |
| 83 | [6-chloro-5-methoxy-2-methyl-1-(quinolin-2-ylmethyl)-1H-indol-3-yl]acetic acid | >100 | >100 |
| 84 | [6-chloro-1-[(6-chloropyridin-3-yl)methyl]-5-methoxy-2-methyl-1H-indol-3-yl]acetic acid | >10 | >10 |
| 85 | {6-chloro-5-methoxy-2-methyl-1-[3-(trifluoromethyl)benzyl]-1H-indol-3-yl}acetic acid | >10 | >10 |
| 86 | [6-chloro-1-(2-chloro-4-fluorobenzyl)-5-methoxy-2-methyl-1H-indol-3-yl]acetic acid | >100 | >100 |
| 87 | [6-fluoro-1-(4-fluorobenzyl)-5-methoxy-2-methyl-1H-indol-3-yl]acetic acid | >10 | >10 |
| 88 | [6-chloro-1-(4-chlorobenzyl)-2,5-dimethyl-1H-indol-3-yl]acetic acid | >100 | >100 |
| 89 | [6-chloro-1-(3-fluorobenzyl)-5-methoxy-2-methyl-1H-indol-3-yl]acetic acid | >10 | >100 |
| 90 | [6-chloro-5-methoxy-2-methyl-1-(3-methylbenzyl)-1H-indol-3-yl]acetic acid | >10 | >100 |
| 91 | [6-bromo-5-methoxy-2-methyl-1-(3-methylbenzyl)-1H-indol-3-yl]acetic acid | >10 | >100 |
| 92 | [6-chloro-5-methoxy-2-methyl-1-(3-nitrobenzyl)-1H-indol-3-yl]acetic acid | >100 | >100 |
| 93 | {1-benzyl-5-hydroxy-2-methyl-1H-indol-3-yl]acetic acid | >100 | >10 |
| 94 | 4-(5-methyl-3-phenylisoxazol-4-yl)benzenesulfonamide | >100 | <1 |
| 95 | [1-(4-chlorobenzoyl)-4-fluoro-5-hydroxy-2-methyl-1H-indol-3-yl]acetic acid | >100 | 1-10 |
| 96 | {1-(3,4-dichlorobenzoyl)-5-hydroxy-2-methyl-1H-indol-3-yl]acetic acid | >100 | >100 |
| 97 | [1-(3,4-dichlorobenzoyl)-5-hydroxy-1H-indol-3-yl]acetic acid | >100 | >100 |
| 98 | [5-hydroxy-2-methyl-1-[4-(trifluoromethoxy)benzoyl]-1H-indol-3-yl]acetic acid | >100 | 10-50 |
| 99 | {1-(cyclohexylcarbonyl)-5-methoxy-2-methyl-1H-indol-3-yl]acetic acid | >100 | <1 |
| 100 | [1-(2,3-dichlorobenzoyl)-5-methoxy-2-methyl-1H-indol-3-yl]acetic acid | >100 | >10 |
| 101 | {1-(3,4-dichlorobenzoyl)-5-hydroxy-2-methyl-1H-indol-3-yl]acetic acid | >100 | >10 |
| 102 | {1-[(6-chloropyridin-3-yl)carbonyl]-5-methoxy-2-methyl-1H-indol-3-yl]acetic acid | >100 | >10 |
| 103 | {1-(4-chloropyridin-3-yl)-1H-indol-3-yl}acetic acid | >100 | 1-10 |
| 104 | {5-methoxy-2-methyl-1-[4-(trifluoromethoxy)benzoyl]-1H-indol-3-yl]acetic acid | >100 | <1 |

FIG. 1E

| Row | IUPAC Name | COX-1 purified enzyme assay IC50 (uM) | COX-2 purified enzyme assay IC50 (uM) |
|---|---|---|---|
| 105 | [1-(3-chlorobenzoyl)-5-methoxy-2-methyl-1H-indol-3-yl]acetic acid | >100 | >10 |
| 106 | [1-(3-chlorobenzoyl)-5-hydroxy-2-methyl-1H-indol-3-yl]acetic acid | >100 | >10 |
| 107 | [1-(3,4-difluorobenzoyl)-5-methoxy-2-methyl-1H-indol-3-yl]acetic acid | >100 | >10 |
| 108 | [1-(3,4-difluorobenzoyl)-5-hydroxy-2-methyl-1H-indol-3-yl]acetic acid | >100 | >10 |
| 109 | [1-(4-bromobenzyl)-5-hydroxy-2-methyl-1H-indol-3-yl]acetic acid | >100 | >10 |
| 110 | [1-(4-bromobenzoyl)-4,6-difluoro-5-hydroxy-2-methyl-1H-indol-3-yl]acetic acid | >100 | >10 |
| 111 | [1-(4-fluorobenzoyl)-5-hydroxy-2-methyl-1H-indol-3-yl]acetic acid | >100 | >10 |
| 112 | [5-hydroxy-2-methyl-1-(3-methylbenzoyl)-1H-indol-3-yl]acetic acid | >100 | >10 |
| 113 | [1-(4-chlorophenylsulfonyl)-5-hydroxy-2-methyl-1H-indol-3-yl]acetic acid | >100 | >10 |
| 114 | [1-(4-chlorophenyl)sulfonyl-5-hydroxy-2-methyl-1H-indol-3-yl]acetic acid | >100 | >10 |
| 115 | [1-(cyclohexylcarbonyl)-5-hydroxy-2-methyl-1H-indol-3-yl]acetic acid | >100 | 1-10 |
| 116 | [1-(cyclohexylcarbonyl)-6-fluoro-5-methoxy-2-methyl-1H-indol-3-yl]acetic acid | >100 | <1 |
| 117 | [1-(4-chlorobenzoyl)-4,6-difluoro-5-hydroxy-2-methyl-1H-indol-3-yl]acetic acid | >100 | >10 |
| 118 | [6-fluoro-5-hydroxy-2-methyl-1-[4-(trifluoromethyl)benzoyl]-1H-indol-3-yl]acetic acid | >100 | >8 |
| 119 | [6-fluoro-5-methoxy-2-methyl-1-[4-(trifluoromethoxy)benzoyl]-1H-indol-3-yl]acetic acid | >100 | <1 |
| 120 | [5-methoxy-2-methyl-1-(piperidin-1-ylcarbonyl)-1H-indol-3-yl]acetic acid | >100 | 10-50 |
| 121 | [5-hydroxy-2-methyl-1-(piperidin-1-ylcarbonyl)-1H-indol-3-yl]acetic acid | >100 | 1-10 |
| 122 | [6-fluoro-5-hydroxy-2-methyl-1-[4-(trifluoromethoxy)benzoyl]-1H-indol-3-yl]acetic acid | >100 | >8 |
| 123 | 4-[4-(methylsulfonyl)phenyl]-3-phenylfuran-2(3H)-one | >100 | 1-10 |
| 124 | [6-fluoro-1-(4-fluorobenzoyl)-5-hydroxy-2-methyl-1H-indol-3-yl]acetic acid | >100 | <1 |
| 125 | [6-fluoro-5-hydroxy-2-methyl-1-[4-(1,1,2,2,2-tetrafluoroethoxy)benzoyl]-1H-indol-3-yl]acetic acid | >100 | >10 |
| 126 | [6-fluoro-5-methoxy-2-methyl-1-[4-(1,1,2,2,2-tetrafluoroethoxy)benzoyl]-1H-indol-3-yl]acetic acid | >100 | >10 |
| 127 | [1-(4-difluoromethoxy)benzoyl)-6-fluoro-5-hydroxy-2-methyl-1H-indol-3-yl]acetic acid | >100 | <1 |
| 128 | [1-(cyclohex-1-en-1-ylcarbonyl)-6-fluoro-5-methoxy-2-methyl-1H-indol-3-yl]acetic acid | >100 | 1-10 |
| 129 | 2-(trimethylsilyl)ethyl [6-fluoro-5-methoxy-2-methyl-1H-indol-3-yl]acetate | >100 | >10 |
| 130 | propyl (5-hydroxy-2-methyl-1H-indol-3-yl)acetate | >100 | >50 |

FIG. 1F

| Row | IUPAC Name | COX-1 purified enzyme assay IC50 (uM) | COX-2 purified enzyme assay IC50 (uM) |
|---|---|---|---|
| 131 | 2-[1-(4-chlorobenzoyl)-5-methoxy-2-methyl-1H-indol-3-yl]ethanol | >100 | 1-10 |
| 132 | ethyl N-{[1-(4-chlorobenzoyl)-6-fluoro-5-methoxy-2-methyl-1H-indol-3-yl]acetyl}glycinate | >100 | >10 |
| 133 | (4-chloro-1-(4-chlorobenzoyl)-5-methoxy-2-methyl-1H-indol-3-yl)acetic acid | >100 | >50 |
| 134 | [6-chloro-1-(4-chlorobenzoyl)-5-hydroxy-2-methyl-1H-indol-3-yl]acetic acid | >100 | 1-10 |
| 135 | ethyl 4-{[[1-(4-chlorobenzoyl)-6-fluoro-5-hydroxy-2-methyl-1H-indol-3-yl]acetyl]amino}butanoate | >100 | >50 |
| 136 | methyl N-{[1-(4-chlorobenzoyl)-6-fluoro-5-hydroxy-2-methyl-1H-indol-3-yl]acetyl}-b-alaninate | >100 | >10 |
| 137 | [6-chloro-1-{4-(difluoromethoxy)benzoyl]-5-methoxy-2-methyl-1H-indol-3-yl]acetic acid | >100 | <1 |
| 138 | sec-butyl [1-(4-chlorobenzoyl)-6-fluoro-5-hydroxy-2-methyl-1H-indol-3-yl]acetate | >100 | >50 |
| 139 | 2-[1-(4-chlorobenzoyl)-6-fluoro-5-methoxy-2-methyl-1H-indol-3-yl]acetamide | >100 | >10 |
| 140 | methyl [1-(4-chlorobenzoyl)-6-fluoro-5-methoxy-2-methyl-1H-indol-3-yl]acetate | >100 | >10 |
| 141 | 2-[1-(4-chlorobenzoyl)-5-methoxy-2-methyl-1H-indol-3-yl]-N-(2-hydroxyethyl)acetamide | >100 | >10 |
| 142 | ethyl [6-chloro-1-(4-chlorobenzoyl)-5-methoxy-2-methyl-1H-indol-3-yl]acetate | >100 | >10 |
| 143 | methyl [6-chloro-1-(4-chlorobenzoyl)-5-methoxy-2-methyl-1H-indol-3-yl]acetate | >100 | >100 |
| 144 | 2-[1-(4-chlorobenzoyl)-5-methoxy-2-methyl-1H-indol-3-yl]ethyl acetate | >100 | >10 |
| 145 | 2-[1-(4-chlorobenzoyl)-5-methoxy-2-methyl-1H-indol-3-yl]ethyl 4-chlorobenzoate | >100 | >10 |
| 146 | propyl [6-chloro-1-(4-chlorobenzoyl)-5-methoxy-2-methyl-1H-indol-3-yl]acetate | >100 | >10 |
| 147 | ethyl [6-chloro-1-[4-(difluoromethoxy)benzoyl]-5-methoxy-2-methyl-1H-indol-3-yl]acetate | >100 | >10 |
| 148 | sec-butyl [6-chloro-1-(4-chlorobenzoyl)-5-methoxy-2-methyl-1H-indol-3-yl]acetate | >100 | >10 |
| 149 | sec-butyl {6-chloro-1-[4-(difluoromethoxy)benzoyl]-5-methoxy-2-methyl-1H-indol-3-yl}acetate | >100 | >10 |
| 150 | [6-chloro-5-methoxy-2-methyl-1-(4-chlorobenzoyl)-3-methyl-1H-indol-3-yl]acetic acid | >100 | >100 |
| 151 | N-{[6-chloro-1-(4-chlorobenzoyl)-5-methoxy-2-methyl-1H-indol-3-yl]acetyl}glycine | >100 | >100 |
| 152 | 2-[(3R)-3-{[(4-fluorophenyl)sulfonyl]amino}-1,2,3,4-tetrahydro-9H-carbazol-9-yl]propanoic acid | >100 | >100 |
| 153 | [5-methoxy-2-methyl-1-{4-(trifluoromethoxy)benzyl]-1H-indol-3-yl]acetic acid | >100 | >100 |
| 154 | {1-[(5-chloro-2-thienyl)methyl]-5-methoxy-2-methyl-1H-indol-3-yl}acetic acid | >100 | >100 |
| 155 | [5-hydroxy-2-methyl-1-[4-(trifluoromethoxy)benzyl]-1H-indol-3-yl]acetic acid | >100 | >100 |
| 156 | {1-[(5-chloro-2-thienyl)methyl]-5-hydroxy-2-methyl-1H-indol-3-yl}acetic acid | >100 | >100 |

FIG. 1G

| Row | IUPAC Name | COX-1 purified enzyme assay IC50 (uM) | COX-2 purified enzyme assay IC50 (uM) |
|---|---|---|---|
| 157 | {5-fluoro-2-methyl-1H-indol-3-yl}acetic acid | >100 | >100 |
| 158 | {6-chloro-5-hydroxy-2-methyl-1-[4-(trifluoromethoxy)benzoyl]-1H-indol-3-yl}acetic acid | >100 | >100 |
| 159 | {1-(4-chlorobenzyl)-5-fluoro-2-methyl-1H-indol-3-yl}acetic acid | >100 | >100 |
| 160 | {6-chloro-5-hydroxy-2-methyl-1-[4-(trifluoromethoxy)benzyl]-1H-indol-3-yl}acetic acid | >100 | >100 |
| 161 | {6-chloro-1-[(5-chloro-2-thienyl)methyl]-5-fluoro-2-methyl-1H-indol-3-yl}acetic acid | >100 | >10 |
| 162 | {1-[(5-chloro-2-thienyl)methyl]-5-fluoro-2-methyl-1H-indol-3-yl}acetic acid | >100 | >10 |
| 163 | {5-fluoro-2-methyl-1-[4-(trifluoromethoxy)benzyl]-1H-indol-3-yl}acetic acid | >100 | >10 |
| 164 | {1-benzoyl-6-chloro-2-methoxy-2-methyl-1H-indol-3-yl}acetic acid | >100 | <1 |
| 165 | {1-benzoyl-5-chloro-2-methyl-1H-indol-3-yl}acetic acid | >100 | <1 |
| 166 | {1-benzyl-5-fluoro-2-methoxy-1H-indol-3-yl}acetic acid | >100 | >100 |
| 167 | {5-fluoro-1-(4-fluorophenyl)-2-methyl-1H-indol-3-yl}acetic acid | >100 | >100 |
| 168 | {6-chloro-5-methoxy-2-methyl-1-{[4-(trifluoromethyl)thio]benzyl}-1H-indol-3-yl}acetic acid | >100 | >100 |
| 169 | {6-chloro-1-(3-chlorobenzyl)-5-methoxy-2-fluorobenzyl)-5-methoxy-2-methyl-1H-indol-3-yl}acetic acid | >100 | >100 |
| 170 | {6-chloro-5-methoxy-2-methyl-1-{[4-(trifluoromethylthio)benzyl}-1H-indol-3-yl}acetic acid | >100 | >100 |
| 171 | {6-chloro-5-methoxy-2-methyl-1-[4-(methylsulfonyl)benzyl]-1H-indol-3-yl}acetic acid | >100 | >100 |
| 172 | {6-chloro-5-methoxy-2-methyl-1-[4-(methoxycarbonyl)benzyl]-2-methyl-1H-indol-3-yl}acetic acid | >100 | >100 |
| 173 | 5-fluoro-1H-indole-2-carboxylic acid | >100 | >100 |
| 174 | {1-benzyl-6-chloro-5-methoxy-2-methyl-1H-indol-3-yl}acetic acid | >100 | >100 |
| 175 | {6-chloro-1-(cyclohexylmethyl)-5-methoxy-2-methyl-1H-indol-3-yl}acetic acid | >100 | >100 |
| 176 | {6-chloro-1-(4-chloro-2-fluorobenzyl)-5-methoxy-2-methyl-1H-indol-3-yl}acetic acid | >100 | >100 |
| 177 | {1-(2-chlorobenzyl)-6-fluoro-5-methoxy-2-methyl-1H-indol-3-yl}acetic acid | >100 | >10 |
| 178 | {6-chloro-1-(4-chlorophenyl)-5-methoxy-2-methyl-1H-indol-3-yl}acetic acid | >100 | >100 |
| 179 | {6-chloro-5-methoxy-2-methyl-1-(2-methyl-1,3-thiazol-4-yl)-1H-indol-3-yl}acetic acid | >100 | >100 |
| 180 | 3-{[6-chlorobenzyl]-5-methoxy-2-methyl-1H-indol-3-yl}propanoic acid | >100 | >100 |
| 181 | {1-(1,3-benzothiazol-2-ylmethyl)-5-fluoro-2-methyl-1H-indol-3-yl}acetic acid | >100 | >100 |
| 182 | {6-chloro-5-methoxy-2-methyl-1-[3-(trifluoromethoxy)benzyl]-1H-indol-3-yl}acetic acid | >100 | >100 |

FIG. 1H

| Row | IUPAC Name | COX-1 purified enzyme assay IC50 (uM) | COX-2 purified enzyme assay IC50 (uM) |
|---|---|---|---|
| 183 | [6-chloro-1-(3-cyanobenzyl)-5-methoxy-2-methyl-1H-indol-3-yl]acetic acid | >100 | >100 |
| 184 | [1-(1,3-benzothiazol-2-ylmethyl)-6-chloro-2,5-dimethyl-1H-indol-3-yl]acetic acid | >100 | >100 |
| 185 | 3-[6-chloro-1-(3-chlorobenzyl)-5-fluoro-2-methyl-1H-indol-3-yl]propanoic acid | >100 | >100 |
| 186 | 3-[1-(1,3-benzothiazol-2-ylmethyl)-6-chloro-5-fluoro-2-methyl-1H-indol-3-yl]propanoic acid | >100 | >100 |
| 187 | 3-[4,6-dichloro-1-(3-chlorobenzyl)-2-methyl-1H-indol-3-yl]propanoic acid | >100 | >100 |
| 188 | 3-[1-(1,3-benzothiazol-2-ylmethyl)-4,6-dichloro-2-methyl-1H-indol-3-yl]propanoic acid | >100 | >100 |
| 189 | 3-[1-(1,3-benzothiazol-2-ylmethyl)-6-chloro-2,5-dimethyl-1H-indol-3-yl]propanoic acid | >100 | >100 |
| 190 | {6-chloro-2,5-dimethyl-1-[3-(trifluoromethoxy)benzyl]-1H-indol-3-yl}acetic acid | >100 | >100 |
| 191 | {6-chloro-2,5-dimethyl-1-[4-(trifluoromethoxy)benzyl]-1H-indol-3-yl}acetic acid | >100 | >100 |
| 192 | [1-(1,3-benzothiazol-2-ylmethyl)-6-chloro-5-fluoro-2-methyl-1H-indole-3-carboxylic acid | >100 | >100 |
| 193 | [1-(1,3-benzothiazol-2-ylmethyl)-5-fluoro-2-methyl-1H-indol-3-yl]acetic acid | >100 | >100 |
| 194 | [1-(1,3-benzothiazol-2-ylmethyl)-5-methoxy-2-methyl-1H-indol-3-yl]acetic acid | >100 | >100 |
| 195 | {3-[(trifluoromethyl)sulfonyl]benzyl}amino]-1,2,3,4-tetrahydro-9H-carbazol-9-yl}acetic acid | >100 | >100 |
| 196 | {3-[[(4-fluorophenyl)sulfonyl](methyl)amino]-1,2,3,4-tetrahydro-9H-carbazol-9-yl}acetic acid | >100 | >100 |
| 197 | [6-chloro-1-(3,5-dichlorobenzyl)-5-methoxy-2-methyl-1H-indol-3-yl]acetic acid | >100 | >100 |
| 198 | [6-chloro-1-(2,3-dichlorobenzyl)-5-methoxy-2-methyl-1H-indol-3-yl]acetic acid | >100 | >100 |
| 199 | {5-fluoro-1-[3-(trifluoromethoxy)benzyl]-1H-indol-2-yl}(oxo)acetic acid | >100 | >100 |
| 200 | {4,6-dichloro-2-methyl-1-[3-(trifluoromethoxy)benzyl]-1H-indol-3-yl}acetic acid | >100 | >100 |
| 201 | {2-methyl-1-[3-(trifluoromethoxy)benzyl]-1H-indol-3-yl}acetic acid | >100 | >100 |
| 202 | {5-methoxy-2-methyl-1-[3-(trifluoromethoxy)benzyl]-1H-indol-3-yl}acetic acid | >100 | >100 |
| 203 | {5-methoxy-2-methyl-1-[4-(trifluoromethoxy)benzyl]-1H-indol-3-yl}acetic acid | >100 | >100 |
| 204 | {2-oxo-1-[3-(trifluoromethoxy)benzyl]-2,3-dihydro-1H-indol-3-yl}acetic acid | >100 | >100 |
| 205 | {6-chloro-5-methoxy-2-methyl-1-[3-(trifluoromethoxy)benzyl]-1H-indol-3-yl}acetic acid | >100 | >100 |
| 206 | {2-chloro-1-[3-(trifluoromethoxy)benzyl]-1H-indol-3-yl}acetic acid | >100 | >100 |
| 207 | {5-chloro-2-methyl-1-[3-(trifluoromethoxy)benzyl]-1H-indol-3-yl}acetic acid | >100 | >100 |
| 208 | {5-fluoro-2-methyl-1-[3-(trifluoromethoxy)benzyl]-1H-indol-3-yl}acetic acid | >100 | >100 |

FIG. 1I

| Row | IUPAC Name | COX-1 purified enzyme assay IC50 (uM) | COX-2 purified enzyme assay IC50 (uM) |
|---|---|---|---|
| 209 | (2E)-3-{5-methoxy-2-methyl-1-[3-(trifluoromethoxy)benzyl]-1H-indol-3-yl}acrylic acid | >100 | >100 |
| 210 | (2E)-3-{5-chloro-2-methyl-1-[3-(trifluoromethoxy)benzyl]-1H-indol-3-yl}acrylic acid | >100 | >100 |
| 211 | 6-chloro-2,3-dimethyl-1-[3-(trifluoromethoxy)benzyl]-1H-indole acetate | | >100 |
| 212 | {1-(4-chlorobenzyl)-5-methoxy-2-methyl-1H-indol-3-yl}acetic acid | >100 | 1-10 |
| 213 | {6-chloro-1-(3,5-dichlorobenzyl)-2,3-dimethyl-1H-indol-3-yl}acetic acid | | >100 |
| 214 | 5-fluoro-2-methyl-1-[3-(trifluoromethoxy)benzyl]-1H-indole-3-carbaldehyde | | >100 |
| 215 | (2E)-3-{5-fluoro-2-methyl-1-[3-(trifluoromethoxy)benzyl]-1H-indol-3-yl}acrylic acid | | >100 |
| 216 | {5-methoxy-2-methyl-1-[3-(trifluoromethoxy)benzyl]-1H-indol-3-yl}acetic acid | | >100 |

FIG. 2A

| Row | IUPAC Name | COX-1 human whole blood assay IC50 (uM) | COX-2 human whole blood assay IC50 (uM) |
|---|---|---|---|
| 1 | [1-(4-chlorobenzoyl)-5-methoxy-2-methyl-1H-indol-3-yl]acetic acid | <1 | <1 |
| 2 | [1-(4-chlorophenyl)-5-hydroxy-2-methyl-1H-indol-3-yl]acetic acid | 10-50 | <1 |
| 3 | [6-fluoro-1-(4-fluorobenzoyl)-5-methoxy-2-methyl-1H-indol-3-yl]acetic acid | 1-10 | <1 |
| 4 | [4-chloro-1-(4-chlorobenzoyl)-2,5-dimethyl-1H-indol-3-yl]acetic acid | | >100 |
| 5 | 4-[5-(4-methylphenyl)-3-(trifluoromethyl)-1H-pyrazol-1-yl]benzenesulfonamide | | <1 |
| 6 | [1-(4-(difluoromethoxy)benzoyl)-6-fluoro-5-methoxy-1H-indol-3-yl]acetic acid | 10-50 | <1 |
| 7 | [6-chloro-1-(4-chlorobenzoyl)-5-methoxy-2-methyl-1H-indol-3-yl]acetic acid | 10-50 | <1 |
| 8 | [1-(4-bromobenzoyl)-6-fluoro-5-hydroxy-2-methyl-1H-indol-3-yl]acetic acid | 50-100 | >100 |
| 9 | [6-chloro-5-methoxy-2-methyl-1-(4-(trifluoromethoxy)benzoyl)-1H-indol-3-yl]acetic acid | | |
| 10 | [1-(4-chlorobenzoyl)-6-fluoro-5-hydroxy-2-methyl-1-(2-thienylcarbonyl)-1H-indol-3-yl]acetic acid | 10-50 | <1 |
| 11 | [6-fluoro-5-hydroxy-2-methyl-1-(2-thienylcarbonyl)-1H-indol-3-yl]acetic acid | 10-50 | <1 |
| 12 | [1-(5-chloro-2-thienylcarbonyl)-6-fluoro-5-methoxy-2-methyl-1H-indol-3-yl]acetic acid | 1-10 | <1 |
| 13 | [1-(4-(difluoromethoxy)benzoyl)-5-hydroxy-1-(4-(trifluoromethyl)benzoyl)-1H-indol-3-yl]acetic acid | 50-100 | <1 |
| 14 | [6-fluoro-5-methoxy-2-methyl-1-(4-(trifluoromethyl)benzoyl)-1H-indol-3-yl]acetic acid | 10-50 | <1 |
| 15 | [1-(5-chloro-2-thienylcarbonyl)-6-fluoro-5-methoxy-2-methyl-1H-indol-3-yl]acetic acid | 10-50 | <1 |
| 16 | [6-chloro-1-(4-chlorobenzoyl)-5-fluoro-2-methyl-1H-indol-3-yl]acetic acid | >100 | >100 |
| 17 | [1-(4-bromobenzoyl)-6-fluoro-5-methoxy-2-methyl-1H-indol-3-yl]acetic acid | | <10 |
| 18 | [6-fluoro-1-(4-fluorobenzoyl)-5-methoxy-2-methyl-1H-indol-3-yl]acetic acid | | >100 |
| 19 | [6-chloro-1-(4-chlorobenzoyl)-2,5-dimethyl-1H-indol-3-yl]acetic acid | | >100 |
| 20 | 4-(5-methyl-3-phenylisoxazol-4-yl)benzenesulfonamide | 50-100 | <1 |
| 21 | [1-(4-chlorobenzoyl)-4-fluoro-5-hydroxy-1-(4-(trifluoromethyl)benzoyl)-1H-indol-3-yl]acetic acid | 10-50 | 1-10 |
| 22 | [5-methoxy-2-methyl-1-(4-(trifluoromethoxy)benzoyl)-1H-indol-3-yl]acetic acid | 10-50 | <1 |
| 23 | [6-fluoro-5-methoxy-2-methyl-1-(4-(trifluoromethoxy)benzoyl)-1H-indol-3-yl]acetic acid | 10-50 | <1 |
| 24 | 4-[4-(methylsulfonyl)phenyl]-3-phenylfuran-2(5H)-one | | <1 |
| 25 | [6-fluoro-1-(4-fluorobenzoyl)-5-hydroxy-2-methyl-1H-indol-3-yl]acetic acid | 10-50 | <1 |
| 26 | [1-(4-(difluoromethoxy)benzoyl)-6-fluoro-5-hydroxy-2-methyl-1H-indol-3-yl]acetic acid | 50-100 | <1 |

FIG. 2B

| Row | IUPAC Name | COX-1 human whole blood assay IC50 (uM) | COX-2 human whole blood assay IC50 (uM) |
|---|---|---|---|
| 27 | 2-[1-(4-chlorobenzyl)-5-methoxy-2-methyl-1H-indol-3-yl]ethanol | 50-100 | 1-10 |
| 28 | [6-chloro-1-[4-(difluoromethoxy)benzoyl]-5-methoxy-2-methyl-1H-indol-3-yl]acetic acid | 50-100 | <1 |
| 29 | ethyl [6-chloro-1-(4-chlorobenzoyl)-5-methoxy-2-methyl-1H-indol-3-yl]acetate | >100 | >100 |
| 30 | [6-chloro-5-methoxy-2-methyl-1-[4-(trifluoromethoxy)benzoyl]-1H-indol-3-yl]acetic acid | >100 | >100 |
| 31 | [1-(2-chlorobenzoyl)-5-methoxy-6-fluoro-2-methyl-1H-indol-3-yl]acetic acid | | >100 |
| 32 | [6-chloro-1-(4-chlorophenyl)-5-methoxy-2-methyl-1H-indol-3-yl]acetic acid | | >100 |
| 33 | [6-chloro-5-methoxy-2-methyl-1-[(2-methyl-1,3-thiazol-4-yl)methyl]-1H-indol-3-yl]acetic acid | | >100 |
| 34 | 3-[6-chloro-1-(4-chlorobenzoyl)-5-methoxy-2-methyl-1H-indol-3-yl]propanoic acid | >100 | >100 |
| 35 | tert-butyl [6-chloro-1-(4-chlorobenzoyl)-5-methoxy-2-methyl-1H-indol-3-yl]acetate | >100 | >100 |
| 36 | 2-[1-(4-chlorobenzoyl)-5-methoxy-2-methyl-1H-indol-3-yl]-N-(2-phenylethyl)acetamide | >100 | >100 |
| 37 | N-{[1-(4-chlorobenzoyl)-5-methoxy-2-methyl-1H-indol-3-yl]acetyl}glycine | 50-100 | >100 |
| 38 | ethyl N-{[6-chloro-1-(4-chlorobenzoyl)-5-methoxy-2-methyl-1H-indol-3-yl]acetyl}glycinate | >100 | >100 |

FIG. 3A

| Row | IUPAC Name | Human Brain FAAH Percent Inhibition @ 10um | Human Brain FAAH IC50 (uM) |
|---|---|---|---|
| 1 | (1-benzoyl-5-hydroxy-2-methyl-1H-indol-3-yl)acetic acid | 1-10 | |
| 2 | (1-benzoyl-5-methoxy-2-methyl-1H-indol-3-yl)acetic acid | 10-50 | |
| 3 | (1-benzyl-6-chloro-5-methoxy-2-methyl-1H-indol-3-yl)acetic acid | 10-50 | >100 |
| 4 | (1-benzoyl-6-fluoro-5-hydroxy-2-methyl-1H-indol-3-yl)acetic acid | 10-50 | |
| 5 | (1-benzoyl-5-fluoro-2-methyl-1H-indol-3-yl)acetic acid | 1-10 | |
| 6 | (1-benzyl-5-hydroxy-2-methyl-1H-indol-3-yl)acetic acid | <1 | |
| 7 | (1-benzyl-6-chloro-5-methoxy-2-methyl-1H-indol-3-yl)acetic acid | 1-10 | |
| 8 | (6-chloro-1-{[(4-chlorophenyl)amino]carbonyl}-5-methoxy-2-methyl-1H-indol-3-yl)acetic acid | 10-50 | |
| 9 | (6-chloro-5-methoxy-2-methyl-1-{4-[(trifluoromethyl)thio]benzoyl}-1H-indol-3-yl)acetic acid | 1-10 | |
| 10 | (6-chloro-5-methoxy-2-methyl-1-{4-[(trifluoromethyl)thio]benzoyl}-1H-indol-3-yl)acetic acid | 10-50 | |
| 11 | (6-fluoro-5-hydroxy-2-methyl-1-{4-[(trifluoromethyl)thio]benzoyl}-1H-indol-3-yl)acetic acid | <1 | |
| 12 | (6-fluoro-5-methoxy-2-methyl-1-{4-[(trifluoromethyl)thio]benzoyl}-1H-indol-3-yl)acetic acid | 10-50 | |
| 13 | (6-fluoro-5-methoxy-2-methyl-1-{4-[(trifluoromethyl)thio]benzoyl}-1H-indol-3-yl)acetic acid | 10-50 | |
| 14 | [1-(1,3-benzothiazol-2-ylmethyl)-4-chloro-5-methoxy-2-methyl-1H-indol-3-yl]acetic acid | 10-50 | |
| 15 | [1-(1,3-benzothiazol-2-ylmethyl)-6-chloro-2,5-dimethyl-1H-indol-3-yl]acetic acid | 1-10 | |
| 16 | [1-(1,3-benzothiazol-2-ylmethyl)-6-chloro-5-fluoro-2-methyl-1H-indol-3-yl]acetic acid | 10-50 | |
| 17 | [1-(1,3-benzothiazol-2-ylmethyl)-6-chloro-5-methoxy-2-methyl-1H-indol-3-yl]acetic acid | 10-50 | |
| 18 | [1-(1,3-benzothiazol-2-ylmethyl)-6-fluoro-5-methoxy-2-methyl-1H-indol-3-yl]acetic acid | 1-10 | |
| 19 | [1-(1,3-benzoxazol-2-ylmethyl)-6-chloro-5-methoxy-2-methyl-1H-indol-3-yl]acetic acid | 1-10 | |
| 20 | [1-(2,3-dichlorobenzoyl)-5-hydroxy-2-methyl-1H-indol-3-yl]acetic acid | 10-50 | |
| 21 | [1-(2,3-dichlorobenzoyl)-5-methoxy-2-methyl-1H-indol-3-yl]acetic acid | 10-50 | |
| 22 | [1-(2,4-dichlorobenzoyl)-5-hydroxy-2-methyl-1H-indol-3-yl]acetic acid | 1-10 | |
| 23 | [1-(2-chlorobenzoyl)-6-fluoro-5-methoxy-2-methyl-1H-indol-3-yl]acetic acid | 1-10 | |
| 24 | [1-(3,4-dichlorobenzoyl)-5-hydroxy-2-methyl-1H-indol-3-yl]acetic acid | 10-50 | |
| 25 | [1-(3,4-dichlorobenzoyl)-5-methoxy-2-methyl-1H-indol-3-yl]acetic acid | 10-50 | |
| 26 | [1-(3,4-difluorobenzoyl)-5-hydroxy-2-methyl-1H-indol-3-yl]acetic acid | 1-10 | |
| 27 | [1-(3,4-difluorobenzoyl)-5-methoxy-2-methyl-1H-indol-3-yl]acetic acid | 10-50 | |
| 28 | [1-(3-chlorobenzoyl)-5-hydroxy-2-methyl-1H-indol-3-yl]acetic acid | 1-10 | |

FIG. 3B

| Row | IUPAC Name | Human Brain FAAH Percent Inhibition @ 10um | Human Brain FAAH IC50 (nM) |
|---|---|---|---|
| 29 | [1-(3-chlorobenzoyl)-5-methoxy-2-methyl-1H-indol-3-yl]acetic acid | 1-10 | |
| 30 | [1-(4-bromobenzoyl)-6-fluoro-5-hydroxy-2-methyl-1H-indol-3-yl]acetic acid | 10-50 | |
| 31 | [1-(4-bromobenzoyl)-6-fluoro-5-methoxy-2-methyl-1H-indol-3-yl]acetic acid | 10-50 | |
| 32 | [1-(4-bromobenzyl)-4,6-difluoro-5-hydroxy-2-methyl-1H-indol-3-yl]acetic acid | 10-50 | |
| 33 | [1-(4-bromobenzyl)-4,6-difluoro-5-methoxy-2-methyl-1H-indol-3-yl]acetic acid | 1-10 | |
| 34 | [1-(4-bromobenzyl)-5-hydroxy-2-methyl-1H-indol-3-yl]acetic acid | 10-50 | |
| 35 | [1-(4-bromobenzyl)-5-methoxy-2-methyl-1H-indol-3-yl]acetic acid | 10-50 | |
| 36 | [1-(4-bromobenzyl)-6-chloro-5-methoxy-2-methyl-1H-indol-3-yl]acetic acid | 10-50 | |
| 37 | [1-(4-bromobenzyl)-6-fluoro-5-hydroxy-2-methyl-1H-indol-3-yl]acetic acid | 10-50 | |
| 38 | [1-(4-bromobenzyl)-4,6-difluoro-5-hydroxy-2-methyl-1H-indol-3-yl]acetic acid | 10-50 | |
| 39 | [1-(4-chlorobenzoyl)-4-fluoro-5-hydroxy-2-methyl-1H-indol-3-yl]acetic acid | 10-50 | |
| 40 | [1-(4-chlorobenzoyl)-4-fluoro-5-methoxy-2-methyl-1H-indol-3-yl]acetic acid | 10-50 | |
| 41 | [1-(4-chlorobenzoyl)-5-hydroxy-2-methyl-1H-indol-3-yl]acetic acid | | >100 |
| 42 | [1-(4-chlorobenzoyl)-5-methoxy-2-methyl-1H-indol-3-yl]acetic acid | | 50-100 |
| 43 | [1-(4-chlorobenzoyl)-6-fluoro-5-hydroxy-2-methyl-1H-indol-3-yl]acetic acid | | 50-100 |
| 44 | [1-(4-chlorobenzoyl)-6-fluoro-5-methoxy-2-methyl-1H-indol-3-yl]acetic acid | | 50-100 |
| 45 | [1-(4-chlorobenzoyl)-5-fluoro-2-methyl-1H-indol-3-yl]acetic acid | 1-10 | |
| 46 | [1-(4-chlorobenzyl)-5-hydroxy-2-methyl-1H-indol-3-yl]acetic acid | 10-50 | |
| 47 | [1-(4-chlorobenzyl)-5-methoxy-2-methyl-1H-indol-3-yl]acetic acid | 10-50 | |
| 48 | [1-(4-cyanobenzoyl)-5-methoxy-2-methyl-1H-indol-3-yl]acetic acid | 1-10 | |
| 49 | [1-(4-ethylbenzoyl)-5-methoxy-2-methyl-1H-indol-3-yl]acetic acid | 10-50 | 10-50 |
| 50 | [1-(4-fluorobenzyl)-5-hydroxy-2-methyl-1H-indol-3-yl]acetic acid | 1-10 | |
| 51 | [1-(4-fluorobenzyl)-5-methoxy-2-methyl-1H-indol-3-yl]acetic acid | 10-50 | |
| 52 | [1-(4-fluorobenzoyl)-5-methoxy-2-methyl-1H-indol-3-yl]acetic acid | 10-50 | |
| 53 | [1-(4-tert-butylbenzoyl)-6-chloro-5-methoxy-2-methyl-1H-indol-3-yl]acetic acid | 10-50 | |
| 54 | [1-(biphenyl-3-ylmethyl)-4-chloro-5-methoxy-2-methyl-1H-indol-3-yl]acetic acid | 10-50 | |
| 55 | [1-(biphenyl-4-ylmethyl)-5-methoxy-2-methyl-1H-indol-3-yl]acetic acid | 1-10 | |
| 56 | [1-(cyclohex-1-en-1-ylcarbonyl)-6-fluoro-5-methoxy-2-methyl-1H-indol-3-yl]acetic acid | <1 | |

FIG. 3C

| Row | IUPAC Name | Human Brain FAAH Percent Inhibition @ 10um | Human Brain FAAH IC50 (uM) |
|---|---|---|---|
| 57 | [1-(cyclohexylcarbonyl)-3-hydroxy-2-methyl-1H-indol-3-yl]acetic acid | 10-50 | |
| 58 | [1-(cyclohexylcarbonyl)-5-methoxy-2-methyl-1H-indol-3-yl]acetic acid | 10-50 | |
| 59 | [1-(cyclohexylcarbonyl)-6-fluoro-5-methoxy-1H-indol-3-yl]acetic acid | 10-50 | |
| 60 | [4-chloro-1-(4-chlorobenzoyl)-5-methoxy-2-methyl-1H-indol-3-yl]acetic acid | 10-50 | |
| 61 | [4-chloro-1-(4-chlorobenzoyl)-2,5-dimethyl-1H-indol-3-yl]acetic acid | 1-10 | |
| 62 | [5-fluoro-1-(4-fluorobenzoyl)-2-methyl-1H-indol-3-yl]acetic acid | <1 | |
| 63 | [5-hydroxy-2-methyl-1-(3-methylbenzoyl)-1H-indol-3-yl]acetic acid | 10-50 | |
| 64 | [5-hydroxy-2-methyl-1-(3-phenylprop-2-ynoyl)-1H-indol-3-yl]acetic acid | 1-10 | |
| 65 | [5-hydroxy-2-methyl-1-(4-methylbenzoyl)-1H-indol-3-yl]acetic acid | 10-50 | |
| 66 | [5-hydroxy-2-methyl-1-(piperidin-1-ylcarbonyl)-1H-indol-3-yl]acetic acid | 1-10 | |
| 67 | [5-methoxy-1-(4-methoxybenzoyl)-2-methyl-1H-indol-3-yl]acetic acid | 10-50 | 50-100 |
| 68 | [5-methoxy-2-methyl-1-(piperidin-1-ylcarbonyl)-1H-indol-3-yl]acetic acid | 10-30 | |
| 69 | [6-chloro-1-(2,4-dichlorobenzoyl)-5-methoxy-1H-indol-3-yl]acetic acid | 10-50 | |
| 70 | [6-chloro-1-(2,5-dichlorobenzoyl)-5-methoxy-1H-indol-3-yl]acetic acid | 10-50 | |
| 71 | [6-chloro-1-(2,6-dichlorobenzoyl)-5-methoxy-1H-indol-3-yl]acetic acid | 1-10 | |
| 72 | [6-chloro-1-(2-chloro-4-fluorobenzoyl)-5-methoxy-1H-indol-3-yl]acetic acid | 10-50 | |
| 73 | [6-chloro-1-(2-chloro-6-fluorobenzoyl)-5-methoxy-1H-indol-3-yl]acetic acid | <1 | |
| 74 | [6-chloro-1-(3,4-dichlorobenzoyl)-5-methoxy-1H-indol-3-yl]acetic acid | 10-50 | |
| 75 | [6-chloro-1-(3,4-dichlorobenzoyl)-5-methoxy-2-methyl-1H-indol-3-yl]acetic acid | 10-20 | 10-50 |
| 76 | [6-chloro-1-(3,4-difluorobenzoyl)-5-methoxy-2-methyl-1H-indol-3-yl]acetic acid | 10-50 | |
| 77 | [6-chloro-1-(3-chlorobenzoyl)-2,5-dimethyl-1H-indol-3-yl]acetic acid | <1 | |
| 78 | [6-chloro-1-(3-chlorobenzoyl)-5-fluoro-2-methyl-1H-indol-3-yl]acetic acid | 10-50 | |
| 79 | [6-chloro-1-(3-chlorobenzoyl)-5-methoxy-2-methyl-1H-indol-3-yl]acetic acid | 10-50 | |
| 80 | [6-chloro-1-(3-chlorobenzoyl)-5-methoxy-1H-indol-3-yl]acetic acid | 10-50 | |
| 81 | [6-chloro-1-(3-cyanobenzoyl)-5-methoxy-2-methyl-1H-indol-3-yl]acetic acid | 1-10 | |
| 82 | [6-chloro-1-(3-fluorobenzoyl)-5-methoxy-2-methyl-1H-indol-3-yl]acetic acid | 10-50 | |
| 83 | [6-chloro-1-(3-fluorobenzoyl)-5-methoxy-1H-indol-3-yl]acetic acid | 10-50 | |
| 84 | [6-chloro-1-(4-chlorobenzoyl)-5-fluoro-2-methyl-1H-indol-3-yl]acetic acid | | 10-50 |

FIG. 3D

| Row | IUPAC Name | Human Brain FAAH Percent Inhibition @ 10um | Human Brain FAAH IC50 (nM) |
|---|---|---|---|
| 85 | [6-chloro-1-(4-chlorobenzoyl)-5-hydroxy-2-methyl-1H-indol-3-yl]acetic acid | | 50-100 |
| 86 | [6-chloro-1-(4-chlorobenzoyl)-5-methoxy-2-methyl-1H-indol-3-yl]acetic acid | | 10-50 |
| 87 | [6-chloro-1-(4-chlorobenzyl)-2,5-dimethyl-1H-indol-3-yl]acetic acid | 1-10 | |
| 88 | [6-chloro-1-(4-chlorobenzyl)-5-hydroxy-2-methyl-1H-indol-3-yl]acetic acid | 1-10 | |
| 89 | [6-chloro-1-(4-chlorobenzyl)-5-methoxy-2-methyl-1H-indol-3-yl]acetic acid | 10-50 | 50-100 |
| 90 | [6-chloro-1-(4-fluorobenzoyl)-5-methoxy-2-methyl-1H-indol-3-yl]acetic acid | 1-10 | |
| 91 | [6-chloro-1-(4-fluorobenzyl)-5-methoxy-2-methyl-1H-indol-3-yl]acetic acid | 10-50 | |
| 92 | [6-chloro-1-(cyclohexylmethyl)-5-methoxy-2-methyl-1H-indol-3-yl]acetic acid | 10-50 | |
| 93 | [6-chloro-5-methoxy-1-(3-methoxybenzyl)-2-methyl-1H-indol-3-yl]acetic acid | 10-50 | |
| 94 | [6-chloro-5-methoxy-2-methyl-1-(2-naphthylmethyl)-1H-indol-3-yl]acetic acid | 1-10 | |
| 95 | [6-chloro-5-methoxy-2-methyl-1-(3-methylbenzyl)-1H-indol-3-yl]acetic acid | 10-50 | |
| 96 | [6-chloro-5-methoxy-2-methyl-1-(pyridin-2-ylmethyl)-1H-indol-3-yl]acetic acid | <1 | |
| 97 | [6-chloro-5-methoxy-2-methyl-1-(quinolin-2-ylmethyl)-1H-indol-3-yl]acetic acid | 10-50 | |
| 98 | [6-fluoro-1-(4-fluorobenzoyl)-5-methoxy-2-methyl-1H-indol-3-yl]acetic acid | <1 | |
| 99 | [6-fluoro-1-(4-fluorobenzyl)-5-methoxy-2-methyl-1H-indol-3-yl]acetic acid | 1-10 | |
| 100 | [6-fluoro-1-(4-fluorobenzyl)-5-methoxy-2-methyl-1H-indol-3-yl]acetic acid | 10-50 | |
| 101 | [6-fluoro-5-hydroxy-2-methyl-1-(2-thienylcarbonyl)-1H-indol-3-yl]acetic acid | <1 | |
| 102 | [6-fluoro-5-methoxy-2-methyl-1-(2-thienylcarbonyl)-1H-indol-3-yl]acetic acid | 10-50 | |
| 103 | {1-[(4-chlorophenyl)sulfonyl]-5-hydroxy-2-methyl-1H-indol-3-yl}acetic acid | 1-10 | |
| 104 | {1-[(4-chlorophenyl)sulfonyl]-5-methoxy-2-methyl-1H-indol-3-yl}acetic acid | <1 | |
| 105 | {1-[(4-chlorophenyl)sulfonyl]-6-fluoro-5-methoxy-2-methyl-1H-indol-3-yl}acetic acid | <1 | |
| 106 | {1-[(5-chloro-2-thienyl)carbonyl]-5-hydroxy-2-methyl-1H-indol-3-yl}acetic acid | 1-10 | |
| 107 | {1-[(5-chloro-2-thienyl)carbonyl]-5-methoxy-2-methyl-1H-indol-3-yl}acetic acid | <1 | |
| 108 | {1-[(5-chloro-2-thienyl)carbonyl]-6-fluoro-5-hydroxy-2-methyl-1H-indol-3-yl}acetic acid | 10-50 | |
| 109 | {1-[(5-chloro-2-thienyl)carbonyl]-6-fluoro-5-methoxy-2-methyl-1H-indol-3-yl}acetic acid | 10-50 | |
| 110 | {1-[(5-chloro-2-thienyl)methyl]-5-fluoro-2-methyl-1H-indol-3-yl}acetic acid | <1 | |
| 111 | {1-[(5-chloro-2-thienyl)methyl]-5-hydroxy-2-methoxy-2-methyl-1H-indol-3-yl}acetic acid | 10-50 | >100 |
| 112 | {1-[(5-chloro-2-thienyl)methyl]-5-methoxy-2-methyl-1H-indol-3-yl}acetic acid | 10-50 | 50-100 |

FIG. 3E

| Row | IUPAC Name | Human Brain FAAH Percent Inhibition @ 10um | Human Brain FAAH IC50 (uM) |
|---|---|---|---|
| 113 | {1-[(6-chloropyridin-3-yl)carbonyl]-5-hydroxy-2-methyl-1H-indol-3-yl}acetic acid | 1-10 | |
| 114 | {1-[(6-chloropyridin-3-yl)carbonyl]-5-methoxy-2-methyl-1H-indol-3-yl}acetic acid | 10-50 | |
| 115 | {1-[4-(difluoromethoxy)benzoyl]-5-hydroxy-2-methyl-1H-indol-3-yl}acetic acid | <1 | |
| 116 | {1-[4-(difluoromethoxy)benzoyl]-5-methoxy-2-methyl-1H-indol-3-yl}acetic acid | 1-10 | |
| 117 | {1-[4-(difluoromethoxy)benzoyl]-6-fluoro-5-hydroxy-2-methyl-1H-indol-3-yl}acetic acid | | 50-100 |
| 118 | {1-[4-(difluoromethoxy)benzoyl]-6-fluoro-5-methoxy-2-methyl-1H-indol-3-yl}acetic acid | | >100 |
| 119 | {5-fluoro-2-methyl-1-[4-(trifluoromethoxy)benzoyl]-1H-indol-3-yl}acetic acid | 1-10 | |
| 120 | {5-hydroxy-2-methyl-1-[(2E)-3-phenylprop-2-enoyl]-1H-indol-3-yl}acetic acid | 1-10 | |
| 121 | {5-hydroxy-2-methyl-1-[4-(trifluoromethoxy)benzoyl]-1H-indol-3-yl}acetic acid | 10-50 | |
| 122 | {5-hydroxy-2-methyl-1-[4-(trifluoromethyl)benzoyl]-1H-indol-3-yl}acetic acid | 1-10 | |
| 123 | {5-hydroxy-2-methyl-1-[4-(trifluoromethyl)benzoyl]-1H-indol-3-yl}acetic acid | 10-50 | |
| 124 | {5-methoxy-2-methyl-1-[(2E)-3-phenylprop-2-enoyl]-1H-indol-3-yl}acetic acid | 10-50 | |
| 125 | {5-methoxy-2-methyl-1-[4-(trifluoromethoxy)benzoyl]-1H-indol-3-yl}acetic acid | 50-100 | >100 |
| 126 | {5-methoxy-2-methyl-1-[4-(trifluoromethyl)benzoyl]-1H-indol-3-yl}acetic acid | 10-50 | 10-50 |
| 127 | {5-methoxy-2-methyl-1-[4-(trifluoromethyl)benzoyl]-1H-indol-3-yl}acetic acid | 10-50 | |
| 128 | {6-chloro-1-[(4-chlorophenoxy)carbonyl]-3-methoxy-1H-indol-3-yl}acetic acid | 1-10 | |
| 129 | {6-chloro-1-[(5-chloro-3-thienyl)carbonyl]-5-hydroxy-2-methyl-1H-indol-3-yl}acetic acid | 10-50 | 10-50 |
| 130 | {6-chloro-1-[(5-chloro-2-thienyl)carbonyl]-5-methoxy-2-methyl-1H-indol-3-yl}acetic acid | 10-50 | |
| 131 | {6-chloro-1-[(5-chloro-2-thienyl)methyl]-5-methoxy-2-methyl-1H-indol-3-yl}acetic acid | 1-10 | |
| 132 | {6-chloro-1-[(6-chloropyridin-3-yl)methyl]-5-methoxy-2-methyl-1H-indol-3-yl}acetic acid | 10-50 | |
| 133 | {6-chloro-1-[4-(trifluoromethoxy)benzoyl]-5-methoxy-2-methyl-1H-indol-3-yl}acetic acid | 10-50 | |
| 134 | {6-chloro-1-[4-(difluoromethoxy)benzyl]-5-methoxy-2-methyl-1H-indol-3-yl}acetic acid | 10-50 | >100 |
| 135 | {6-chloro-2,5-dimethyl-1-[4-(trifluoromethyl)benzoyl]-1H-indol-3-yl}acetic acid | 10-50 | |
| 136 | {6-chloro-2,5-dimethyl-1-[3-(trifluoromethyl)benzoyl]-1H-indol-3-yl}acetic acid | 10-50 | |
| 137 | {6-chloro-5-fluoro-2-methyl-1-[3-(trifluoromethoxy)benzyl]-1H-indol-3-yl}acetic acid | <1 | |
| 138 | {6-chloro-5-hydroxy-2-methyl-1-[4-(trifluoromethoxy)benzyl]-1H-indol-3-yl}acetic acid | <1 | |
| 139 | {6-chloro-5-hydroxy-2-methyl-1-[4-(trifluoromethyl)benzyl]-1H-indol-3-yl}acetic acid | 1-10 | |
| 140 | {6-chloro-5-methoxy-1-[4-(methoxycarbonyl)benzyl]-2-methyl-1H-indol-3-yl}acetic acid | <1 | |

FIG. 3F

| Row | IUPAC Name | Human Brain FAAH Percent Inhibition @ 10um | Human Brain FAAH IC50 (uM) |
|---|---|---|---|
| 141 | {6-chloro-5-methoxy-2-methyl-1-[3-(trifluoromethoxy)benzyl]-1H-indol-3-yl}acetic acid | 10-50 | |
| 142 | {6-chloro-5-methoxy-2-methyl-1-[3-(trifluoromethyl)benzyl]-1H-indol-3-yl}acetic acid | 10-50 | |
| 143 | {6-chloro-5-methoxy-2-methyl-1-[4-(methylsulfonyl)benzyl]-1H-indol-3-yl}acetic acid | <1 | |
| 144 | {6-chloro-5-methoxy-2-methyl-1-[4-(trifluoromethoxy)benzyl]-1H-indol-3-yl}acetic acid | 10-50 | |
| 145 | {6-chloro-5-methoxy-2-methyl-1-[4-(trifluoromethyl)benzyl]-1H-indol-3-yl}acetic acid | 10-50 | |
| 146 | {6-fluoro-5-hydroxy-2-methyl-1-[(3-methyl-2-thienyl)carbonyl]-1H-indol-3-yl}acetic acid | <1 | |
| 147 | {6-fluoro-5-hydroxy-2-methyl-1-[4-(1,1,2,2-tetrafluoroethoxy)benzoyl]-1H-indol-3-yl}acetic acid | 10-50 | |
| 148 | {6-fluoro-5-hydroxy-2-methyl-1-[4-(methylthio)benzoyl]-1H-indol-3-yl}acetic acid | <1 | |
| 149 | {6-fluoro-5-hydroxy-2-methyl-1-[4-(trifluoromethoxy)benzoyl]-1H-indol-3-yl}acetic acid | 10-50 | |
| 150 | {6-fluoro-5-hydroxy-2-methyl-1-[4-(trifluoromethyl)benzoyl]-1H-indol-3-yl}acetic acid | 10-50 | |
| 151 | {6-fluoro-5-methoxy-2-methyl-1-[(5-methyl-2-thienyl)carbonyl]-1H-indol-3-yl}acetic acid | 10-50 | |
| 152 | {6-fluoro-5-methoxy-2-methyl-1-[4-(1,1,2,2-tetrafluoroethoxy)benzoyl]-1H-indol-3-yl}acetic acid | 10-50 | |
| 153 | {6-fluoro-5-methoxy-2-methyl-1-[4-(methylthio)benzoyl]-1H-indol-3-yl}acetic acid | 1-10 | |
| 154 | {6-fluoro-5-methoxy-2-methyl-1-[4-(trifluoromethoxy)benzoyl]-1H-indol-3-yl}acetic acid | 10-50 | 50-100 |
| 155 | {6-fluoro-5-methoxy-2-methyl-1-[4-(trifluoromethyl)benzoyl]-1H-indol-3-yl}acetic acid | | >100 |
| 156 | 1-(1,3-benzothiazol-2-ylmethyl)-5-methoxy-2-methyl-1H-indole-3-carboxylic acid | 10-50 | |
| 157 | 2-{1-(4-chlorobenzoyl)-5-methoxy-2-methyl-1H-indol-3-yl}-N-(2-phenylethyl)acetamide | | >100 |
| 158 | 2-[1-(4-chlorobenzoyl)-5-methoxy-2-methyl-1H-indol-3-yl]-N-piperidin-1-ylacetamide | 10-50 | |
| 159 | 2-[1-(4-chlorobenzoyl)-5-methoxy-2-methyl-1H-indol-3-yl]ethanol | | 1-10 |
| 160 | 2-[1-(4-chlorobenzoyl)-5-methoxy-2-methyl-1H-indol-3-yl]ethyl 4-chlorobenzoate | | >100 |
| 161 | 2-[1-(4-chlorobenzyl)-5-methoxy-2-methyl-1H-indol-3-yl]ethyl acetate | 10-50 | |
| 162 | 3-((3R)-3-{[(4-fluorophenyl)sulfonyl]amino}-1,2,3,4-tetrahydro-9H-carbazol-9-yl)propanoic acid | 1-10 | <1 |
| 163 | 3'-(aminocarbonyl)biphenyl-3-yl cyclohexylcarbamate | | <1 |
| 164 | 3-[1-(1,3-benzothiazol-2-ylmethyl)-4,6-dichloro-2-methyl-1H-indol-3-yl]propanoic acid | 1-10 | |
| 165 | 3-[1-(1,3-benzothiazol-2-ylmethyl)-6-chloro-2,5-dimethyl-1H-indol-3-yl]propanoic acid | <1 | |
| 166 | 3-[1-(1,3-benzothiazol-2-ylmethyl)-6-chloro-5-fluoro-2-methyl-1H-indol-3-yl]propanoic acid | 10-50 | |
| 167 | 3-[4,6-dichloro-1-(3-chlorobenzyl)-2-methyl-1H-indol-3-yl]propanoic acid | 10-50 | |
| 168 | 3-[6-chloro-1-(3-chlorobenzyl)-5-fluoro-2-methyl-1H-indol-3-yl]propanoic acid | 10-50 | |

FIG. 3G

| Row | IUPAC Name | Human Brain FAAH Percent Inhibition @ 10um | Human Brain FAAH IC50 (uM) |
|---|---|---|---|
| 169 | 4-(5-methyl-3-phenylisoxazol-4-yl)benzenesulfonamide | | 10-50 |
| 170 | 4-[4-(methylsulfonyl)phenyl]-3-phenylfuran-2(5H)-one | | >100 |
| 171 | 4-[5-(4-methylphenyl)-3-(trifluoromethyl)-1H-pyrazol-1-yl]benzenesulfonamide | | 10-50 |
| 172 | 4-{[3-(carboxymethyl)-6-chloro-5-methoxy-2-methyl-1H-indol-1-yl]methyl}benzoic acid | <1 | |
| 173 | 5-benzoyl-2,3-dihydro-1H-pyrrolizine-1-carboxylic acid | | 50-100 |
| 174 | ethyl [6-chloro-1-(4-chlorobenzoyl)-5-methoxy-2-methyl-1H-indol-3-yl]acetate | | 10-30 |
| 175 | ethyl [6-chloro-1-(4-(difluoromethoxy)benzoyl)-5-methoxy-2-methyl-1H-indol-3-yl]acetate | | 50-100 |
| 176 | ethyl 4-{[1-(4-chlorobenzoyl)-6-fluoro-5-hydroxy-2-methyl-1H-indol-3-yl]acetyl]amino}butanoate | | 1-10 |
| 177 | ethyl N-{[1-(4-chlorobenzoyl)-5-methoxy-2-methyl-1H-indol-3-yl]acetyl}glycinate | | >100 |
| 178 | ethyl N-{[1-(4-chlorobenzoyl)-6-fluoro-5-methoxy-2-methyl-1H-indol-3-yl]acetyl}glycinate | | 10-50 |
| 179 | ethyl N-{[6-chloro-1-(4-chlorobenzoyl)-5-methoxy-2-methyl-1H-indol-3-yl]acetyl}glycinate | <1 | |
| 180 | methyl [1-benzoyl-5-hydroxy-2-methyl-1H-indol-3-yl]acetate | | 1-10 |
| 181 | methyl [1-benzoyl-5-methoxy-2-methyl-1H-indol-3-yl]acetate | | 1-10 |
| 182 | methyl [1-(4-chlorobenzoyl)-5-methoxy-2-methyl-1H-indol-3-yl]acetate | | 1-10 |
| 183 | methyl [1-(4-chlorobenzoyl)-5-methoxy-2-methyl-1H-indol-3-yl]acetate | | <1 |
| 184 | methyl [1-(4-chlorobenzoyl)-6-fluoro-5-hydroxy-2-methyl-1H-indol-3-yl]acetate | | 1-10 |
| 185 | methyl [1-(4-chlorobenzoyl)-6-fluoro-5-methoxy-2-methyl-1H-indol-3-yl]acetate | | <1 |
| 186 | methyl [6-chloro-1-(4-chlorobenzoyl)-5-methoxy-2-methyl-1H-indol-3-yl]acetate | | 1-10 |
| 187 | N-{[1-(4-chlorobenzoyl)-5-methoxy-2-methyl-1H-indol-3-yl]acetyl}glycine | | >100 |
| 188 | N-{[6-chloro-1-(4-chlorobenzoyl)-5-methoxy-2-methyl-1H-indol-3-yl]acetyl}glycine | <1 | |
| 189 | propyl [6-chloro-1-(4-chlorobenzoyl)-5-methoxy-2-methyl-1H-indol-3-yl]acetate | | 10-30 |
| 190 | sec-butyl [6-chloro-1-(4-chlorobenzoyl)-5-methoxy-2-methyl-1H-indol-3-yl]acetate | | 50-100 |

FIG. 4A

| Row | IUPAC Name | Rat Brain FAAH IC50 (uM) | Rat Brain FAAH Percent Inhibition @ 0.1uM | Rat Brain FAAH Percent Inhibition @ 1uM |
|---|---|---|---|---|
| 1 | [1-(4-chlorobenzoyl)-5-methoxy-2-methyl-1H-indol-3-yl]acetic acid | 10-50 | | |
| 2 | [1-(4-chlorobenzoyl)-5-methoxy-2-methyl-1H-indol-3-yl]acetic acid | 10-50 | | |
| 3 | [1-(4-chlorobenzoyl)-5-hydroxy-2-methyl-1H-indol-3-yl]acetic acid | | 1-10 | 1-10 |
| 4 | methyl [1-(4-chlorobenzoyl)-5-hydroxy-3-methyl-1H-indol-3-yl]acetate | <1 | 10-50 | 50-100 |
| 5 | 4-[5-(4-methylphenyl)-3-(trifluoromethyl)-1H-pyrazol-1-yl]benzenesulfonamide | 50-100 | | |
| 6 | 4-(5-methyl-3-phenylisoxazol-4-yl)benzenesulfonamide | >100 | | |
| 7 | [1-(4-chlorobenzoyl)-6-fluoro-5-hydroxy-2-methyl-1H-indol-3-yl]acetic acid | 50-100 | 1-10 | 1-10 |
| 8 | [1-(4-chlorobenzoyl)-6-fluoro-5-methoxy-2-methyl-1H-indol-3-yl]acetic acid | 10-50 | 1-10 | 1-10 |
| 9 | 3-methoxy-2-methyl-1-[4-(trifluoromethoxy)benzoyl]-1H-indol-3-yl]acetic acid | 50-100 | | |
| 10 | [6-fluoro-5-methoxy-2-methyl-1-[4-(trifluoromethyl)benzoyl]-1H-indol-3-yl]acetic acid | 10-50 | | |
| 11 | [6-fluoro-5-methyl-1-[4-(trifluoromethoxy)benzoyl]-1H-indol-3-yl]acetic acid | 10-50 | | |
| 12 | 4-[4-(methylsulfonyl)phenyl]-3-phenylfuran-2(5H)-one | >100 | | |
| 13 | [1-(4-difluoromethoxybenzoyl)-6-fluoro-5-methoxy-2-methyl-1H-indol-3-yl]acetic acid | 50-100 | 10-50 | 50-100 |
| 14 | [1-(4-difluoromethoxybenzoyl)-6-fluoro-5-hydroxy-2-methyl-1H-indol-3-yl]acetic acid | 10-50 | 1-10 | 1-10 |
| 15 | 5-benzoyl-2,3-dihydro-1H-pyrrolizine-1-carboxylic acid | 50-100 | | |
| 16 | methyl [1-(4-chlorobenzoyl)-6-fluoro-5-methoxy-2-methyl-1H-indol-3-yl]acetate | <1 | | 50-100 |
| 17 | [6-chloro-1-(4-chlorobenzoyl)-5-methoxy-2-methyl-1H-indol-3-yl]acetic acid | 10-50 | 1-10 | 1-10 |
| 18 | 3-(aminocarbonyl)biphenyl-3-yl cyclohexylcarbamate | <1 | 50-100 | 50-100 |
| 19 | ethyl [1-(4-chlorobenzoyl)-6-fluoro-5-hydroxy-2-methyl-1H-indol-3-yl]acetate | <1 | | |
| 20 | propyl [1-(4-chlorobenzoyl)-6-fluoro-5-hydroxy-2-methyl-1H-indol-3-yl]acetate | <1 | | |
| 21 | 2-[1-(4-chlorobenzoyl)-5-methoxy-2-methyl-1H-indol-3-yl]ethanol | 1-10 | | |
| 22 | isopropyl [1-(4-chlorobenzoyl)-6-fluoro-5-hydroxy-2-methyl-1H-indol-3-yl]glycinate | 10-50 | | |
| 23 | ethyl N-{[1-(4-chlorobenzoyl)-6-fluoro-5-hydroxy-2-methyl-1H-indol-3-yl]acetyl}glycinate | 1-10 | | |

FIG. 4B

| Run | IUPAC Name | Rat Brain FAAH IC50 (uM) | Rat Brain FAAH Percent Inhibition @ 0.1uM | Rat Brain FAAH Percent Inhibition @ 1uM |
|---|---|---|---|---|
| 24 | ethyl 4-{[(1-(4-chlorobenzoyl)-6-fluoro-5-hydroxy-2-methyl-1H-indol-3-yl]acetyl}aminobutanoate | 1-10 | | |
| 25 | methyl N-{[1-(4-chlorobenzoyl)-6-fluoro-5-hydroxy-2-methyl-1H-indol-3-yl]acetyl}-b-alaninate | 1-10 | | |
| 26 | ethyl [1-(4-chlorobenzoyl)-5-methoxy-2-methyl-1H-indol-3-yl]acetate | <1 | | |
| 27 | [6-chloro-1-(4-difluoromethoxybenzoyl)-5-methoxy-2-methyl-1H-indol-3-yl]acetic acid | 50-100 | | |
| 28 | sec-butyl [1-(4-chlorobenzoyl)-6-fluoro-5-hydroxy-2-methyl-1H-indol-3-yl]acetate | 10-50 | | |
| 29 | 2-[1-(4-chlorobenzoyl)-6-fluoro-5-hydroxy-2-methyl-1H-indol-3-yl]acetamide | >100 | | |
| 30 | methyl (6-fluoro-5-hydroxy-2-methyl-1H-indol-3-yl)acetate | >100 | | |
| 31 | methyl [1-(4-chlorobenzoyl)-6-fluoro-5-methoxy-2-methyl-1H-indol-3-yl]acetate | <1 | 10-50 | 50-100 |
| 32 | 2-[1-(4-chlorobenzoyl)-5-methoxy-2-methyl-1H-indol-3-yl]-N-(2-hydroxyethyl)acetamide | 1-10 | | |
| 33 | ethyl [6-chloro-1-(4-chlorobenzoyl)-5-methoxy-2-methyl-1H-indol-3-yl]acetate | 1-10 | | |
| 34 | methyl [6-chloro-1-(4-chlorobenzoyl)-5-methoxy-2-methyl-1H-indol-3-yl]acetate | 1-10 | | |
| 35 | 2-[1-(4-chlorobenzoyl)-5-methoxy-2-methyl-1H-indol-3-yl]ethyl acetate | 1-10 | | |
| 36 | methyl [1-benzoyl-5-hydroxy-2-methyl-1H-indol-3-yl]acetate | <1 | 1-10 | 50-100 |
| 37 | methyl [1-(4-chlorobenzoyl)-5-methoxy-2-methyl-1H-indol-3-yl]acetate | <1 | 10-50 | 50-100 |
| 38 | methyl [1-benzoyl-5-methoxy-2-hydroxy-2-methyl-1H-indol-3-yl]acetate | <1 | 10-50 | 50-100 |
| 39 | methyl [1-benzoyl-5-hydroxy-2-methyl-1H-indol-3-yl]acetate | <1 | 10-50 | 50-100 |
| 40 | methyl [1-benzoyl-6-fluoro-5-hydroxy-2-methyl-1H-indol-3-yl]acetate | <1 | 10-50 | 50-100 |
| 41 | methyl [1-(4-chlorobenzoyl)-4-fluoro-5-methoxy-2-methyl-1H-indol-3-yl]acetate | | 10-50 | 10-50 |
| 42 | methyl [1-(4-chlorobenzoyl)-4-fluoro-5-hydroxy-2-methyl-1H-indol-3-yl]acetate | | 1-10 | 10-50 |
| 43 | methyl [1-(3,4-dichlorobenzoyl)-5-methoxy-2-methyl-1H-indol-3-yl]acetate | | 10-50 | 50-100 |
| 44 | methyl [1-(4-fluorobenzoyl)-5-methoxy-2-methyl-1H-indol-3-yl]acetate | <1 | 10-50 | 50-100 |
| 45 | methyl [5-methoxy-2-methyl-1H-indol-3-yl]acetate | | 10-50 | 50-100 |
| 46 | methyl [5-methoxy-2-methyl-1-{4-(trifluoromethyl)benzoyl}-1H-indol-3-yl]acetate | | 10-50 | 50-100 |

FIG. 4C

| Row | IUPAC Name | Rat Brain FAAH IC50 (uM) | Rat Brain FAAH Percent Inhibition @ 0.1uM | Rat Brain FAAH Percent Inhibition @ 1uM |
|---|---|---|---|---|
| 47 | methyl [1-(3-chlorobenzoyl)-5-methoxy-2-methyl-1H-indol-3-yl]acetate | <1 | 50-100 | 50-100 |
| 48 | methyl [1-(4-bromobenzyl)-5-methoxy-2-methyl-1H-indol-3-yl]acetate | <1 | 10-50 | 50-100 |
| 49 | methyl [1-(4-bromobenzyl)-5-hydroxy-2-methyl-1H-indol-3-yl]acetate | | 10-50 | 50-100 |
| 50 | methyl [1-(4-bromobenzyl)-4,6-difluoro-2-methyl-1H-indol-3-yl]acetate | | 1-10 | 10-50 |
| 51 | methyl [1-{(5-chloro-2-thienyl)carbonyl}-5-methoxy-2-methyl-1H-indol-3-yl]acetate | <1 | 10-50 | 50-100 |
| 52 | methyl [1-{(cyclohexylcarbonyl)-6-fluoro-5-methoxy-2-methyl-1H-indol-3-yl}]acetate | | 1-10 | 10-50 |
| 53 | methyl [1-{(5-chloro-2-thienyl)carbonyl}-6-fluoro-5-methoxy-1H-indol-3-yl]acetate | <1 | 10-50 | 50-100 |
| 54 | methyl [6-fluoro-5-methoxy-2-methyl-1-(4-methylbenzoyl)-1H-indol-3-yl]acetate | <1 | 10-50 | 50-100 |
| 55 | methyl [6-fluoro-5-hydroxy-2-methyl-1-(4-methylbenzoyl)-5-methoxy-2-methyl-1H-indol-3-yl]acetate | | 50-100 | 50-100 |
| 56 | methyl [6-fluoro-1-(4-fluorobenzoyl)-5-methoxy-2-methyl-1H-indol-3-yl]acetate | | 10-50 | 50-100 |
| 57 | methyl [6-fluoro-5-hydroxy-1-{(5-methyl-2-thienyl)carbonyl}-1H-indol-2-yl]acetate | <1 | 10-50 | 50-100 |
| 58 | methyl [6-chloro-5-methoxy-2-methyl-1-[4-(trifluoromethoxy)benzoyl]-1H-indol-3-yl]acetate | | <1 | 10-50 |
| 59 | methyl [6-chloro-1-{(5-chloro-2-thienyl)methyl}-5-methoxy-2-methyl-1H-indol-3-yl]acetate | <1 | 10-50 | 10-50 |
| 60 | methyl [6-chloro-1-{(5-chloro-2-thienyl)carbonyl}-5-hydroxy-2-methyl-1H-indol-3-yl]acetate | | 10-50 | 50-100 |
| 61 | methyl [1-(4-chlorobenzoyl)-5-methoxy-2-methyl-1H-indol-3-yl]acetate | <1 | 10-50 | 50-100 |
| 62 | methyl [6-fluoro-2,5-dimethyl-1-[3-(trifluoromethoxy)benzoyl]-1H-indol-3-yl]acetate | | <1 | 10-50 |
| 63 | (2E)-3-[5-chloro-2-methyl-1-[3-(trifluoromethoxy)benzoyl]-1H-indol-3-yl]acrylic acid | 1-10 | | |
| 64 | methyl [5-hydroxy-2-methyl-1-(4-methylbenzoyl)-1H-indol-3-yl]acetate | | <1 | 10-50 |
| 65 | methyl [5-hydroxy-2-methyl-1-[4-(trifluoromethyl)benzoyl]-1H-indol-3-yl]acetate | | 10-50 | 50-100 |
| 66 | methyl [5-hydroxy-2-methyl-1-[4-(trifluoromethyl)benzoyl]-1H-indol-3-yl]acetate | | 1-10 | 10-50 |
| 67 | methyl [1-(3,4-difluorobenzoyl)-5-hydroxy-2-methyl-1H-indol-3-yl]acetate | | 10-50 | 50-100 |
| 68 | methyl [1-(2-thienylcarbonyl)-5-methoxy-2-methyl-1H-indol-3-yl]acetate | | <1 | 10-50 |
| 69 | methyl [6-chloro-1-(4-fluorobenzoyl)-5-methoxy-2-methyl-1H-indol-3-yl]acetate | | 1-10 | 10-50 |

FIG. 4D

| Row | IUPAC Name | Rat Brain FAAH IC50 (uM) | Rat Brain FAAH Percent Inhibition @ 0.1uM | Rat Brain FAAH Percent Inhibition @ 1uM |
|---|---|---|---|---|
| 70 | methyl {6-chloro-1-[(5-chloro-2-thienyl)carbonyl]-5-methoxy-2-methyl-1H-indol-3-yl}acetate | | <1 | 10-50 |
| 71 | methyl [6-chloro-1-(4-chlorobenzyl)-2,5-dimethyl-1H-indol-3-yl]acetate | | <1 | 10-50 |
| 72 | methyl [6-chloro-1-(3-chlorobenzyl)-5-fluoro-2-methyl-1H-indol-3-yl]acetate | | <1 | 1-10 |
| 73 | methyl [6-chloro-1-(3-chlorobenzyl)-2,5-dimethyl-1H-indol-3-yl]acetate | | <1 | 10-50 |
| 74 | methyl [6-chloro-2,5-dimethyl-1-{[3-(trifluoromethoxy)benzyl]-1H-indol-3-yl}acetate | | <1 | 10-50 |
| 75 | methyl 1-(1,3-benzothiazol-2-ylmethyl)-5-fluoro-2-methyl-1H-indole-3-carboxylate | | <1 | <1 |
| 76 | methyl {5-fluoro-2-methyl-1-[3-(trifluoromethoxy)benzyl]-1H-indol-3-yl}(oxo)acetate | | <1 | <1 |

FIG. 5A

| Row | IUPAC Name | FAAH Rat brain AAMCA % Inhibition (0.1 uM) | FAAH Rat brain AAMCA % Inhibition (1 uM) | FAAH Rat Brain AAMCA EC50 (uM) |
|---|---|---|---|---|
| 1 | [6-chloro-1-(4-chlorobenzoyl)-5-hydroxy-2-methyl-1H-indol-3-yl]acetic acid | | | 10-50 |
| 2 | [1-(4-chlorobenzoyl)-5-methoxy-2-methyl-1H-indol-3-yl]acetic acid | | | 10-50 |
| 3 | [1-(4-chlorobenzoyl)-5-hydroxy-2-methyl-1H-indol-3-yl]acetic acid | 1-10 | | <1 |
| 4 | methyl [1-(4-chlorobenzoyl)-5-hydroxy-2-methyl-1H-indol-3-yl]acetate | 50-100 | 50-100 | |
| 5 | 4-[3-(4-methylphenyl)-3-(trifluoromethyl)-1H-pyrazol-1-yl]benzenesulfonamide | | | >100 |
| 6 | 1-(4-chlorobenzoyl)-6-fluoro-5-hydroxy-2-methyl-1H-indol-3-yl]acetic acid | 1-10 | 1-10 | |
| 7 | [1-(4-chlorobenzoyl)-6-fluoro-5-methoxy-2-methyl-1H-indol-3-yl]acetic acid | 1-10 | 1-10 | |
| 8 | 4-[4-(methylsulfonyl)phenyl]-3-phenylfuran-2(5H)-one | | | >100 |
| 9 | methyl [1-(4-chlorobenzoyl)-6-fluoro-5-hydroxy-2-methyl-1H-indol-3-yl]acetate | 50-100 | 50-100 | <1 |
| 10 | [6-chloro-1-(4-chlorobenzoyl)-5-methoxy-2-methyl-1H-indol-3-yl]acetic acid | 1-10 | 10-50 | |
| 11 | 3'-(aminocarbonyl)biphenyl-3-yl cyclohexylcarbamate | | | <1 |
| 12 | methyl (6-fluoro-3-hydroxy-2-methyl-1H-indol-3-yl)acetate | | | >10 |
| 13 | methyl [1-(4-chlorobenzoyl)-6-fluoro-5-methoxy-2-methyl-1H-indol-3-yl]acetate | 10-50 | 50-100 | |
| 14 | methyl [6-chloro-1-(4-chlorobenzoyl)-5-methoxy-2-methyl-1H-indol-3-yl]acetate | | 50-100 | <1 |
| 15 | methyl [1-benzoyl-5-hydroxy-2-methyl-1H-indol-3-yl]acetate | 10-50 | 50-100 | |
| 16 | methyl [1-(4-chlorobenzoyl)-5-hydroxy-2-methyl-1H-indol-3-yl]acetate | 10-50 | 50-100 | |
| 17 | methyl (1-benzoyl-5-methoxy-2-methyl-1H-indol-3-yl)acetate | 10-50 | 50-100 | |
| 18 | methyl (1-benzoyl-5-hydroxy-2-methyl-1H-indol-3-yl)acetate | 10-50 | 50-100 | |
| 19 | methyl (1-benzoyl-6-fluoro-5-methoxy-2-methyl-1H-indol-3-yl)acetate | 10-50 | 50-100 | |
| 20 | methyl [1-(4-chlorobenzoyl)-4-fluoro-5-hydroxy-2-methyl-1H-indol-3-yl]acetate | 10-50 | 10-50 | |
| 21 | methyl [3-(4-chlorobenzoyl)-5-methoxy-2-methyl-1H-indol-3-yl]acetate | 10-50 | 50-100 | |
| 22 | methyl [1-(3,4-dichlorobenzoyl)-5-methoxy-2-methyl-1H-indol-3-yl]acetate | 50-100 | 50-100 | |
| 23 | methyl [1-(4-fluorobenzoyl)-5-methoxy-2-methyl-1H-indol-3-yl]acetate | 10-50 | 50-100 | |
| 24 | methyl [1-(4-fluorobenzoyl)-5-hydroxy-2-methyl-1H-indol-3-yl]acetate | | 50-100 | <1 |
| 25 | methyl {5-methoxy-2-methyl-1-[4-(trifluoromethyl)benzoyl]-1H-indol-3-yl}acetate | 10-50 | 50-100 | |

FIG. 5B

| Row | IUPAC Name | FAAH Rat brain AAMCA % Inhibition (0.1uM) | FAAH Rat brain AAMCA % Inhibition (1uM) | FAAH Rat Brain AAMCA IC50 (nM) |
|---|---|---|---|---|
| 26 | methyl [1-(3-chlorobenzoyl)-5-methoxy-2-methyl-1H-indol-3-yl]acetate | 50-100 | 50-100 | <1 |
| 27 | methyl [1-(4-bromobenzoyl)-5-methoxy-2-methyl-1H-indol-3-yl]acetate | 50-100 | 50-100 | <1 |
| 28 | methyl [1-(4-bromobenzoyl)-5-hydroxy-2-methyl-1H-indol-3-yl]acetate | 10-50 | 50-100 | |
| 29 | methyl [1-(4-bromobenzoyl)-4,6-difluoro-5-methoxy-1H-indol-3-yl]acetate | 10-50 | 50-100 | |
| 30 | methyl {1-[(5-chloro-2-thienyl)carbonyl]-5-methoxy-2-methyl-1H-indol-3-yl}acetate | 50-100 | 50-100 | <1 |
| 31 | methyl [1-(cyclohexycarbonyl)-6-fluoro-5-methoxy-2-methyl-1H-indol-3-yl]acetate | 10-50 | 50-100 | |
| 32 | methyl {1-[(5-chloro-2-thienyl)carbonyl]-6-fluoro-5-methoxy-1H-indol-3-yl]acetate | 10-50 | 50-100 | |
| 33 | methyl [6-fluoro-5-methoxy-2-methyl-1-(4-methylbenzoyl)-1H-indol-3-yl]acetate | 50-100 | 50-100 | <1 |
| 34 | methyl [6-fluoro-5-hydroxy-2-methyl-1-(4-methylbenzoyl)-1H-indol-3-yl]acetate | 50-100 | 50-100 | <1 |
| 35 | methyl {6-fluoro-5-methoxy-2-methyl-1-[(4-fluorobenzoyl)]-1H-indol-3-yl}acetate | 10-50 | 50-100 | |
| 36 | methyl {6-chloro-5-hydroxy-2-methyl-1-[(5-methyl-2-thienyl)carbonyl]-1H-indol-3-yl}acetate | 10-50 | 50-100 | |
| 37 | methyl {6-chloro-5-methoxy-2-methyl-1-[4-(trifluoromethoxy)benzoyl]-1H-indol-3-yl}acetate | 10-50 | 50-100 | 1-10 |
| 38 | methyl {6-chloro-1-[(5-chloro-2-thienyl)methyl]-5-methoxy-1H-indol-3-yl}acetate | 10-50 | 50-100 | |
| 39 | methyl {6-chloro-1-[(5-chloro-2-thienyl)carbonyl]-5-hydroxy-2-methyl-1H-indol-3-yl}acetate | 10-50 | 50-100 | |
| 40 | methyl [1-(4-chlorobenzoyl)-5-methoxy-2-methyl-1H-indol-3-yl]acetate | 50-100 | 50-100 | <1 |
| 41 | (2E)-3-{5-chloro-2-methyl-1-[3-(trifluoromethoxy)benzyl]-1H-indol-3-yl}acrylic acid | 50-100 | 50-100 | 1-10 |

FIG. 6A

| Row | IUPAC Name | Rat Brain Extract FAAH IC50 (uM) | Human brain FAAH Extract IC50 (uM) |
|---|---|---|---|
| 1 | (5-chloro-1-(4-chlorobenzyl)-2-methyl-1H-indol-3-yl)(5-pyridin-2-yl-1,3,4-oxadiazol-2-yl)methanone | 1-10 | 50-100 |
| 2 | (5-chloro-1-(4-fluorobenzyl)-2-methyl-1H-indol-3-yl)(5-pyridin-2-yl-1,3,4-oxadiazol-2-yl)methanone | 1-10 | 50-100 |
| 3 | (5-chloro-1-(4-methoxybenzyl)-2-methyl-1H-indol-3-yl)(5-pyridin-2-yl-1,3,4-oxadiazol-2-yl)methanone | 1-10 | >100 |
| 4 | (1-(4-chlorobenzyl)-5-methoxy-2-methyl-1H-indol-3-yl)(5-pyridin-2-yl-1,3,4-oxadiazol-2-yl)methanone | 1-10 | >100 |
| 5 | (1-(4-bromobenzyl)-5-methoxy-2-methyl-1H-indol-3-yl)(5-pyridin-2-yl-1,3,4-oxadiazol-2-yl)methanone | 1-10 | 1-10 |
| 6 | (1-(4-chlorobenzyl)-5-methoxy-2-methyl-1H-indol-3-yl)(5-pyridin-2-yl-1,3,4-oxadiazol-2-yl)methanone | <1 | <1 |
| 7 | (1-(3-chlorobenzyl)-5-methoxy-2-methyl-1H-indol-3-yl)(5-pyridin-2-yl-1,3,4-oxadiazol-2-yl)methanone | 50-100 | 10-50 |
| 8 | (1-(2-chlorobenzyl)-5-methoxy-2-methyl-1H-indol-3-yl)(5-pyridin-2-yl-1,3,4-oxadiazol-2-yl)methanone | 10-50 | 50-100 |
| 9 | (5-methoxy-2-methyl-1-(4-(trifluoromethoxy)benzyl)-1H-indol-3-yl)(5-pyridin-2-yl-1,3,4-oxadiazol-2-yl)methanone | 10-50 | 50-100 |
| 10 | (5-methoxy-2-methyl-1-(4-(trifluoromethyl)benzyl)-1H-indol-3-yl)(5-pyridin-2-yl-1,3,4-oxadiazol-2-yl)methanone | 1-10 | 10-50 |
| 11 | (1-(3,5-dichlorobenzyl)-5-methoxy-2-methyl-1H-indol-3-yl)(5-pyridin-2-yl-1,3,4-oxadiazol-2-yl)methanone | 10-50 | 10-50 |
| 12 | (1-(3,4-fluorobenzyl)-5-methoxy-2-methyl-1H-indol-3-yl)(5-pyridin-2-yl-1,3,4-oxadiazol-2-yl)methanone | <1 | <1 |
| 13 | (1-(4-fluorobenzyl)-5-methoxy-2-methyl-1H-indol-3-yl)(5-pyridin-3-yl-1,3,4-oxadiazol-2-yl)methanone | 1-10 | 1-10 |
| 14 | (1-benzyl-5-methoxy-2-methyl-1H-indol-3-yl)(5-pyridin-2-yl-1,3,4-oxadiazol-2-yl)methanone | 10-50 | 10-50 |
| 15 | (5-methoxy-2-methyl-1-(4-methylbenzyl)-1H-indol-3-yl)(5-pyridin-2-yl-1,3,4-oxadiazol-2-yl)methanone | 1-10 | 1-10 |
| 16 | (5-methoxy-2-methyl-1-(4-methylbenzyl)-1H-indol-3-yl)(5-pyridin-2-yl-1,3,4-oxadiazol-3-yl)methanone | 10-50 | >100 |
| 17 | (5-methoxy-2-methyl-1-(3-methylbenzyl)-1H-indol-3-yl)(5-pyridin-2-yl-1,3,4-oxadiazol-2-yl)methanone | <1 | 1-10 |
| 18 | (5-methoxy-1-(3-methoxybenzyl)-2-methyl-1H-indol-3-yl)(5-pyridin-2-yl-1,3,4-oxadiazol-2-yl)methanone | 1-10 | 1-10 |
| 19 | (5-methoxy-1-(2-methoxybenzyl)-2-methyl-1H-indol-3-yl)(5-pyridin-2-yl-1,3,4-oxadiazol-2-yl)methanone | 10-50 | >100 |
| 20 | (1-(3,4-dichlorobenzyl)-5-hydroxy-2-methyl-1H-indol-3-yl)(5-pyridin-2-yl-1,3,4-oxadiazol-2-yl)methanone | >100 | 10-50 |
| 21 | (5-hydroxy-2-methyl-1-(4-methylbenzyl)-1H-indol-3-yl)(5-pyridin-2-yl-1,3,4-oxadiazol-2-yl)methanone | 1-10 | 10-50 |
| 22 | (1-(4-bromobenzyl)-5-methoxy-2-methyl-1H-indol-3-yl)(5-pyridin-2-yl-1,2,4-oxadiazol-3-yl)methanone | 1-10 | 1-10 |
| 23 | (1-(4-chlorobenzyl)-5-methoxy-2-methyl-1H-indol-3-yl)(5-pyridin-3-yl-1,2,4-oxadiazol-3-yl)methanone | not determined | <1 |
| 24 | (1-(4-chlorobenzyl)-5-methoxy-2-methyl-1H-indol-3-yl)(3-pyridin-4-yl-1,2,4-oxadiazol-5-yl)methanone | not determined | <1 |
| 25 | (1-(4-chlorobenzyl)-5-methoxy-2-methyl-1H-indol-3-yl)(3-pyridin-3-yl-1,2,4-oxadiazol-5-yl)methanone | <1 | <1 |
| 26 | (1-(2,4-chlorobenzyl)-5-methoxy-2-methyl-1H-indol-3-yl)(3-pyridin-3-yl-1,2,4-oxadiazol-5-yl)methanone | <1 | <1 |
| 27 | (1-(4-chlorobenzyl)-5-methoxy-2-methyl-1H-indol-3-yl)(3-phenyl-1,2,4-oxadiazol-5-yl)methanone | not determined | <1 |
| 28 | (1-(4-chlorobenzyl)-5-methoxy-2-methyl-1H-indol-3-yl)(3-pyridin-2-yl-1,2,4-oxadiazol-5-yl)methanone | <1 | <1 |

FIG. 6B

| Row | IUPAC Name | Rat Brain Extract FAAH IC50 (uM) | Human brain FAAH Extract IC50 (uM) |
|---|---|---|---|
| 29 | (1-(4-chlorobenzyl)-5-methoxy-2-methyl-1H-indol-3-yl)(5-pyridin-3-yl-1,3,4-oxadiazol-2-yl)methanone | <1 | 1-10 |
| 30 | (1-(4-chlorobenzyl)-5-methoxy-1H-indol-3-yl)(5-phenyl-1,3,4-oxadiazol-2-yl)methanone | 1-10 | 1-10 |
| 31 | (1-(4-chlorobenzyl)-5-methoxy-1H-indol-3-yl)(5-pyridin-4-yl-1,3,4-oxadiazol-2-yl)methanone | 1-10 | 1-10 |
| 32 | (1-(4-chlorobenzyl)-5-methoxy-1H-indol-3-yl)(5-(2-furyl)-1,3,4-oxadiazol-2-yl)methanone | 1-10 | <1 |
| 33 | (1-(4-chlorobenzyl)-5-methoxy-1H-indol-3-yl)(5-pyridin-2-yl-2-thienyl)methanone | 1-10 | 50-100 |
| 34 | (1-(2,4-dichlorobenzyl)-5-methoxy-1H-indol-3-yl)(3-pyridin-2-yl-1,2,4-oxadiazol-5-yl)methanone | <1 | <1 |
| 35 | (5-methoxy-1-(4-methoxybenzyl)-1H-indol-3-yl)(3-pyridin-2-yl-1,2,4-oxadiazol-5-yl)methanone | <1 | <1 |
| 36 | (2-chloro-1-(4-chlorobenzyl)-5-methoxy-1H-indol-3-yl)(3-pyridin-2-yl-1,2,4-oxadiazol-5-yl)methanone | <1 | <1 |
| 37 | (1-(4-chlorobenzyl)-5-methoxy-1H-indol-3-yl)(3-pyridin-2-yl-1,2,4-oxadiazol-5-yl)methanone | not determined | 50-100 |
| 38 | (1-(4-chlorobenzyl)-5-methoxy-1H-indol-3-yl)(5-pyridin-2-yl-1,3,4-oxadiazol-2-yl)methanone | not determined | >1000 |
| 39 | (1-(4-chlorobenzyl)-7-methoxy-1H-indol-3-yl)(3-pyridin-2-yl-1,2,4-oxadiazol-5-yl)methanone | not determined | >10 |
| 40 | (1-(4-chlorobenzyl)-5-ethoxy-1H-indol-3-yl)(3-pyridin-2-yl-1,2,4-oxadiazol-5-yl)methanone | not determined | >10 |
| 41 | (1-(4-chlorobenzyl)-5-ethoxy-1H-indol-3-yl)(5-pyridin-2-yl-1,3,4-oxadiazol-2-yl)methanone | not determined | 1-10 |
| 42 | (1-(4-chlorobenzyl)-1H-indol-3-yl)(3-pyridin-2-yl-1,2,4-oxadiazol-5-yl)methanone | not determined | <1 |
| 43 | (1-(4-chlorobenzyl)-5-methoxy-1H-indol-3-yl)([1,3]oxazolo[4,5-b]pyridin-2-yl)methanone | <1 | <1 |
| 44 | | | |

FIG. 7A

| Row | IUPAC Name | CD11b Agonist activity at 1 uM | CD11b Agonist activity at 10 uM | CD11b Agonist activity EC50 (nM) |
|---|---|---|---|---|
| 1 | (1-benzoyl-6-chloro-5-methoxy-2-methyl-1H-indol-3-yl)acetic acid | 10-50 | 10-50 | |
| 2 | (1-benzoyl-5-fluoro-2-methyl-1H-indol-3-yl)acetic acid | 1-10 | <1 | |
| 3 | (1-benzoyl-5-hydroxy-2-methyl-1H-indol-3-yl)acetic acid | | <1 | >100,000 |
| 4 | (1-benzoyl-6-chloro-5-methoxy-2-methyl-1H-indol-3-yl)acetic acid | | <1 | |
| 5 | (2E)-3-[5-chloro-2-methyl-1-[3-(trifluoromethoxy)benzoyl]-1H-indol-3-yl]acrylic acid | | <1 | |
| 6 | (2E)-3-[5-fluoro-2-methyl-1-[3-(trifluoromethoxy)benzoyl]-1H-indol-3-yl]acrylic acid | 1-10 | 1-10 | |
| 7 | (6-chloro-2-methyl-1-{[(4-chlorophenyl)amino]carbonyl}-5-methoxy-1H-indol-3-yl)acetic acid | | <1 | |
| 8 | (6-chloro-5-methoxy-2-methyl-1-{4-[(trifluoromethyl)thio]benzoyl}-1H-indol-3-yl)acetic acid | | >100 | |
| 9 | (6-chloro-5-methoxy-2-methyl-1-{4-[(trifluoromethyl)thio]benzoyl}-1H-indol-3-yl)acetic acid | | 1-10 | |
| 10 | (6-fluoro-5-hydroxy-2-methyl-1-{4-[(trifluoromethyl)thio]benzoyl}-1H-indol-3-yl)acetic acid | | <1 | |
| 11 | (6-fluoro-5-methoxy-2-methyl-1-{4-[(trifluoromethyl)thio]benzoyl}-1H-indol-3-yl)acetic acid | | 10-50 | |
| 12 | (6-fluoro-5-methoxy-2-methyl-1-{4-[(trifluoromethyl)thio]benzyl}-1H-indol-3-yl)acetic acid | | <1 | |
| 13 | [1-(1,3-benzothiazol-2-ylmethyl)-4-chloro-5-methoxy-2-methyl-1H-indol-3-yl]acetic acid | | <1 | |
| 14 | [1-(1,3-benzothiazol-2-ylmethyl)-5-fluoro-2-methyl-1H-indol-3-yl](oxo)acetic acid | | <1 | |
| 15 | [1-(1,3-benzothiazol-2-ylmethyl)-5-fluoro-2-methyl-1H-indol-3-yl]acetic acid | | <1 | |
| 16 | [1-(1,3-benzothiazol-2-ylmethyl)-6-chloro-2,5-dimethyl-1H-indol-3-yl]acetic acid | 1-10 | 1-10 | |

FIG. 7B

| Row | IUPAC Name | CD11b Agonist activity at 1 uM | CD11b Agonist activity at 10 uM | CD11b Agonist activity EC50 (uM) |
|---|---|---|---|---|
| 17 | [1-(1,3-benzothiazol-2-ylmethyl)-6-chloro-5-fluoro-2-methyl-1H-indol-3-yl]acetic acid | | <1 | |
| 18 | [1-(1,3-benzothiazol-2-ylmethyl)-6-chloro-5-methoxy-2-methyl-1H-indol-3-yl]acetic acid | | <1 | |
| 19 | [1-(1,3-benzothiazol-2-ylmethyl)-5-fluoro-5-methoxy-2-methyl-1H-indol-3-yl]acetic acid | | <1 | |
| 20 | [1-(1,3-benzoxazol-2-ylmethyl)-6-chloro-5-methoxy-2-methyl-1H-indol-3-yl]acetic acid | | <1 | |
| 21 | [1-(2,4-dichlorobenzoyl)-5-hydroxy-1H-indol-1H-indol-3-yl]acetic acid | 1-10 | 1-10 | |
| 22 | [1-(2-chlorobenzyl)-6-fluoro-5-methoxy-2-methyl-1H-indol-3-yl]acetic acid | | 1-10 | |
| 23 | [1-(3,4-dichlorobenzoyl)-5-hydroxy-1H-indol-1H-indol-3-yl]acetic acid | <1 | 1-10 | |
| 24 | [1-(3,4-dichlorobenzoyl)-5-methoxy-2-methyl-1H-indol-3-yl]acetic acid | 1-10 | 1-10 | |
| 25 | [1-(3,4-dichlorobenzoyl)-5-hydroxy-2-methyl-1H-indol-3-yl]acetic acid | | <1 | |
| 26 | [1-(3,4-difluorobenzoyl)-5-methoxy-2-methyl-1H-indol-3-yl]acetic acid | | 10-50 | |
| 27 | [1-(3-bromobenzyl)-6-chloro-5-methoxy-1H-indol-3-yl]acetic acid | | <1 | |
| 28 | [1-(3-chlorobenzoyl)-5-hydroxy-2-methyl-1H-indol-3-yl]acetic acid | | | >100,000 |
| 29 | [1-(3-chlorobenzoyl)-5-methoxy-2-methyl-1H-indol-3-yl]acetic acid | | | 1-100 |
| 30 | [1-(4-bromobenzoyl)-6-fluoro-5-hydroxy-1H-indol-3-yl]acetic acid | | <1 | |
| 31 | [1-(4-bromobenzoyl)-4,6-difluoro-5-hydroxy-1H-indol-3-yl]acetic acid | | | |
| 32 | [1-(4-bromobenzoyl)-5-hydroxy-2-methyl-1H-indol-3-yl]acetic acid | | <1 | |
| 33 | [1-(4-bromobenzoyl)-6-chloro-5-methoxy-2-methyl-1H-indol-3-yl]acetic acid | | <1 | |

FIG. 7C

| Row | IUPAC Name | CD11b Agonist activity at 1 uM | CD11b Agonist activity at 10 uM | CD11b Agonist activity EC 50 (nM) |
|---|---|---|---|---|
| 33 | [1-(4-bromobenzyl)-6-fluoro-5-methoxy-2-methyl-1H-indol-3-yl]acetic acid | | <1 | |
| 34 | [1-(4-chlorobenzyl)-4-fluoro-5-methoxy-2-methyl-1H-indol-3-yl]acetic acid | 50-100 | >100 | |
| 35 | [1-(4-chlorobenzyl)-6-fluoro-5-methoxy-2-methyl-1H-indol-3-yl]acetic acid | >100 | 50-100 | |
| 36 | [1-(4-chlorobenzyl)-5-fluoro-2-methyl-1H-indol-3-yl]acetic acid | 1-10 | 1-10 | |
| 37 | [1-(4-chlorobenzyl)-5-hydroxy-2-methyl-1H-indol-3-yl]acetic acid | | | partial agonist at 100 uM |
| 38 | [1-(4-tert-butylbenzyl)-6-chloro-5-methoxy-2-methyl-1H-indol-3-yl]acetic acid | | 10-50 | |
| 39 | [1-(biphenyl-2-ylmethyl)-6-chloro-5-methoxy-2-methyl-1H-indol-3-yl]acetic acid | | 10-50 | |
| 40 | [1-(biphenyl-4-ylmethyl)-6-chloro-5-methoxy-2-methyl-1H-indol-3-yl]acetic acid | | <1 | |
| 41 | [1-(cyclohexylcarbonyl)-5-methoxy-2-methyl-1H-indol-3-yl]acetic acid | 1-10 | <1 | |
| 42 | [3-(1,3-benzothiazol-2-ylmethyl)-1H-indol-1-yl]acetic acid | | <1 | |
| 43 | [4-chloro-1-(4-chlorobenzyl)-5-methoxy-3-methyl-1H-indol-3-yl]acetic acid | 10-50 | 50-100 | partial agonist at 10 uM |
| 44 | [4-chloro-1-(4-chlorobenzyl)-5-methoxy-2,5-dimethyl-1H-indol-3-yl]acetic acid | | <1 | |
| 45 | [5-fluoro-1-(4-fluorobenzyl)-2-methyl-1H-indol-3-yl]acetic acid | <1 | <1 | |
| 46 | [5-hydroxy-2-methyl-1-(piperidin-1-ylcarbonyl)-1H-indol-3-yl]acetic acid | | <1 | |
| 47 | [5-methoxy-1-(4-methoxybenzyl)-2-methyl-1H-indol-3-yl]acetic acid | 1-10 | 1-10 | partial agonist at 100 uM |
| 48 | [5-methoxy-2-methyl-1-(piperidin-1-ylcarbonyl)-1H-indol-3-yl]acetic acid | <1 | <1 | |

FIG. 7D

| Row | IUPAC Name | CD11b Agonist activity at 1 uM | CD11b Agonist activity at 10 uM | CD11b Agonist activity EC50 (nM) |
|---|---|---|---|---|
| 49 | [6-chloro-1-(2,3-dichlorobenzyl)-5-methoxy-2-methyl-1H-indol-3-yl]acetic acid | | <1 | |
| 50 | [6-chloro-1-(2,4-dichlorobenzyl)-5-methoxy-2-methyl-1H-indol-3-yl]acetic acid | | 1-10 | |
| 51 | [6-chloro-1-(2,5-dichlorobenzyl)-5-methoxy-2-methyl-1H-indol-3-yl]acetic acid | | 1-10 | |
| 52 | [6-chloro-1-(2,6-dichlorobenzyl)-5-methoxy-2-methyl-1H-indol-3-yl]acetic acid | | <1 | |
| 53 | [6-chloro-1-(2-chloro-4-fluorobenzyl)-5-methoxy-2-methyl-1H-indol-3-yl]acetic acid | | 1-10 | |
| 54 | [6-chloro-1-(2-chloro-6-fluorobenzyl)-5-methoxy-2-methyl-1H-indol-3-yl]acetic acid | | <1 | |
| 55 | [6-chloro-1-(2-chlorobenzyl)-5-methoxy-2-methyl-1H-indol-3-yl]acetic acid | | <1 | |
| 56 | [6-chloro-1-(3,4-dichlorobenzyl)-5-methoxy-2-methyl-1H-indol-3-yl]acetic acid | | 1-10 | |
| 57 | [6-chloro-1-(3,4-difluorobenzyl)-5-methoxy-2-methyl-1H-indol-3-yl]acetic acid | | 1-10 | |
| 58 | [6-chloro-1-(3,5-dichlorobenzyl)-2,5-dimethyl-1H-indol-3-yl]acetic acid | | <1 | |
| 59 | [6-chloro-1-(3,5-dichlorobenzyl)-5-methoxy-2-methyl-1H-indol-3-yl]acetic acid | | <1 | |
| 60 | [6-chloro-1-(3,5-difluorobenzyl)-5-methoxy-2-methyl-1H-indol-3-yl]acetic acid | | <1 | |
| 61 | [6-chloro-1-(3,5-dimethylbenzyl)-5-methoxy-2-methyl-1H-indol-3-yl]acetic acid | | <1 | |
| 62 | [6-chloro-1-(3-chlorobenzyl)-5-methoxy-2-methyl-1H-indol-3-yl]acetic acid | | 1-10 | |
| 63 | [6-chloro-1-(3-chlorobenzyl)-2,5-dimethyl-1H-indol-3-yl]acetic acid | | 10-30 | |
| 64 | [6-chloro-1-(3-chlorobenzyl)-5-fluoro-2-methyl-1H-indol-3-yl]acetic acid | | 1-10 | |

FIG. 7E

| Row | IUPAC Name | CD11b Agonist activity at 1 uM | CD11b Agonist activity at 10 uM | CD11b Agonist activity EC50 (uM) |
|---|---|---|---|---|
| 65 | {6-chloro-1-(3-chlorobenzyl)-5-methoxy-2-methyl-1H-indol-3-yl]acetic acid | | 1-10 | |
| 66 | {6-chloro-1-(3-cyanobenzyl)-5-methoxy-2-methyl-1H-indol-3-yl]acetic acid | | 1-10 | |
| 67 | {6-chloro-1-(3-fluorobenzyl)-5-methoxy-2-methyl-1H-indol-3-yl]acetic acid | | 10-50 | |
| 68 | {6-chloro-1-(4-chloro-3-fluorobenzyl)-5-methoxy-2-methyl-1H-indol-3-yl]acetic acid | | 10-50 | |
| 69 | {6-chloro-1-(4-chlorobenzyl)-5-fluoro-2-methyl-1H-indol-3-yl]acetic acid | | | 1-100 |
| 70 | {6-chloro-1-(4-chlorobenzyl)-5-methoxy-2-methyl-1H-indol-3-yl]acetic acid | | | 1-100 |
| 71 | {6-chloro-1-(4-chlorobenzyl)-2,5-dimethyl-1H-indol-3-yl]acetic acid | | <1 | |
| 72 | {6-chloro-1-(4-chlorobenzyl)-5-hydroxy-2-methyl-1H-indol-3-yl]acetic acid | | <1 | |
| 73 | {6-chloro-1-(4-chlorobenzyl)-5-methoxy-1H-indol-3-yl]acetic acid | 1-10 | <1 | |
| 74 | {6-chloro-1-(4-chlorobenzyl)-5-methoxy-2-methyl-1H-indol-3-yl]acetic acid | 10-50 | 50-100 | |
| 75 | {6-chloro-1-(4-chlorophenyl)-5-methoxy-2-methyl-1H-indol-3-yl]acetic acid | | 10-50 | |
| 76 | {6-chloro-1-(4-fluorobenzyl)-5-methoxy-2-methyl-1H-indol-3-yl]acetic acid | | <1 | |
| 77 | {6-chloro-1-(cyclohexylmethyl)-5-methoxy-2-methyl-1H-indol-3-yl]acetic acid | | <1 | |
| 78 | {6-chloro-5-methoxy-1-(3-methoxybenzyl)-2-methyl-1H-indol-3-yl]acetic acid | | <1 | |
| 79 | {6-chloro-5-methoxy-2-methyl-1-(2-naphthylmethyl)-1H-indol-3-yl]acetic acid | | 10-50 | |
| 80 | {6-chloro-5-methoxy-2-methyl-1-(3-methylbenzyl)-1H-indol-3-yl]acetic acid | | 1-10 | |

FIG. 7F

| Row | IUPAC Name | CD11b Agonist activity at 1 uM | CD11b Agonist activity at 10 uM | CD11b Agonist activity EC50 (nM) |
|---|---|---|---|---|
| 81 | [6-chloro-5-methoxy-2-methyl-1-(pyridin-3-ylmethyl)-1H-indol-3-yl]acetic acid | | >100 | |
| 82 | [6-chloro-5-methoxy-2-methyl-1-(quinolin-2-ylmethyl)-1H-indol-3-yl]acetic acid | | <1 | |
| 83 | [6-fluoro-1-(4-fluorobenzoyl)-5-hydroxy-2-methyl-1H-indol-3-yl]acetic acid | | | partial agonist at 10 uM |
| 84 | [6-fluoro-1-(4-fluorobenzoyl)-5-methoxy-2-methyl-1H-indol-3-yl]acetic acid | 1-10 | 1-10 | |
| 85 | [6-fluoro-5-hydroxy-2-methyl-1-(2-thienylcarbonyl)-1H-indol-3-yl]acetic acid | <1 | 1-10 | >100,000 |
| 86 | [6-fluoro-5-methoxy-2-methyl-1-(2-thienylcarbonyl)-1H-indol-3-yl]acetic acid | | <1 | |
| 87 | [1-[(4-chlorophenyl)sulfonyl]-5-hydroxy-2-methyl-1H-indol-3-yl]acetic acid | | <1 | |
| 88 | [1-[(4-chlorophenyl)sulfonyl]-6-fluoro-5-methoxy-2-methyl-1H-indol-3-yl]acetic acid | | <1 | |
| 89 | [1-[(4-chlorophenyl)carbonyl]-5-hydroxy-2-methyl-1H-indol-3-yl]acetic acid | <1 | <1 | |
| 90 | [1-[(5-chloro-2-thienyl)carbonyl]-5-methoxy-2-methyl-1H-indol-2-yl]acetic acid | 1-10 | <1 | |
| 91 | [1-[(5-chloro-2-thienyl)carbonyl]-5-hydroxy-2-methyl-1H-indol-3-yl]acetic acid | | <1 | |
| 92 | [1-[(5-chloro-2-thienyl)carbonyl]-6-fluoro-5-methoxy-2-methyl-1H-indol-3-yl]acetic acid | | <1 | >100,000 |
| 93 | [1-[(5-chloro-2-thienyl)methyl]-6-fluoro-5-methoxy-1H-indol-3-yl]acetic acid | 10-50 | 10-50 | |
| 94 | [1-[(5-chloro-2-thienyl)methyl]-5-fluoro-2-methyl-1H-indol-3-yl]acetic acid | 1-10 | 1-10 | |
| 95 | [1-[(5-chloro-2-thienyl)methyl]-5-hydroxy-1H-indol-3-yl]acetic acid | <1 | 1-10 | partial agonist at 100 uM |
| 96 | [1-[(5-chloro-2-thienyl)methyl]-5-methoxy-2-methyl-1H-indol-3-yl]acetic acid | 1-10 | 10-50 | >100,000 |

FIG. 7G

| Row | IUPAC Name | CD11b Agonist activity at 1 uM | CD11b Agonist activity at 10 uM | CD11b Agonist activity EC50 (uM) |
|---|---|---|---|---|
| 97 | ({1-[3,5-bis(trifluoromethyl)benzyl]-6-chloro-5-methoxy-2-methyl-1H-indol-3-yl}acetic acid | | <1 | |
| 98 | ({1-[4-(difluoromethoxy)benzoyl]-5-hydroxy-2-methyl-1H-indol-3-yl}acetic acid | | | partial agonist at 10 uM |
| 99 | ({1-[4-(difluoromethoxy)benzoyl]-6-fluoro-5-hydroxy-2-methyl-1H-indol-3-yl}acetic acid | | | 500-1000 |
| 100 | ({1-[4-(difluoromethoxy)benzoyl]-6-fluoro-5-methoxy-2-methyl-1H-indol-3-yl}acetic acid | | | 100-500 |
| 101 | {2-chloro-1-[3-(trifluoromethoxy)benzyl]-1H-indol-3-yl}acetic acid | | 1:10 | |
| 102 | {2-oxo-1-[3-(trifluoromethoxy)benzyl]-2,3-dihydro-1H-indol-3-yl}acetic acid | | <1 | |
| 103 | {3-[[(4-fluorophenyl)sulfonyl](methyl)amino]-1,2,3,4-tetrahydro-9H-carbazol-9-yl}acetic acid | | <1 | |
| 104 | {4,6-dichloro-2-methyl-1-[3-(trifluoromethoxy)benzyl]-1H-indol-3-yl}acetic acid | | <1 | |
| 105 | {5,6-dichloro-2-methyl-1-[3-(trifluoromethoxy)benzyl]-1H-indol-3-yl}acetic acid | | <1 | |
| 106 | {5-fluoro-1-[3-(trifluoromethoxy)benzyl]-1H-indol-2-yl}(oxo)acetic acid | | <1 | |
| 107 | {5-fluoro-1-[4-(trifluoromethoxy)benzyl]-2-methyl-1H-indol-3-yl}acetic acid | | <1 | |
| 108 | {5-fluoro-2-methyl-1-[4-(trifluoromethoxy)benzyl]-1H-indol-3-yl}acetic acid | 1:10 | | |
| 109 | {5-hydroxy-2-methyl-1-[4-(trifluoromethoxy)benzyl]-1H-indol-3-yl}acetic acid | 10-50 | 10-50 | |
| 110 | {5-hydroxy-2-methyl-1-[4-(trifluoromethoxy)benzyl]-1H-indol-3-yl}acetic acid | 10-50 | 10-50 | |
| 111 | {5-methoxy-2-methyl-1-[(2E)-3-phenylprop-2-enoyl]-1H-indol-3-yl}acetic acid | | <1 | |
| 112 | {5-methoxy-2-methyl-1-[3-(trifluoromethoxy)benzyl]-1H-indol-3-yl}acetic acid | | <1 | |

FIG. 7H

| Row | IUPAC Name | CD11b Agonist activity at 1 uM | CD11b Agonist activity at 10 uM | CD11b Agonist activity EC50 (nM) |
|---|---|---|---|---|
| 113 | {5-methoxy-2-methyl-1-[4-(trifluoromethoxy)benzoyl]-1H-indol-3-yl}acetic acid | | | >1000 |
| 114 | {5-methoxy-2-methyl-1-[4-(trifluoromethoxy)benzoyl]-1H-indol-3-yl}acetic acid | 1-10 | 1-10 | partial agonist at 100 uM |
| 115 | {5-methoxy-2-methyl-1-[4-(trifluoromethoxy)benzoyl]-1H-indol-3-yl}acetic acid | 10-50 | 10-50 | |
| 116 | {6-chloro-1-[(4-chlorophenoxy)carbonyl]-5-methoxy-2-methyl-1H-indol-2-yl}acetic acid | | 10-50 | |
| 117 | {6-chloro-1-[(5-chloro-2-thienyl)carbonyl]-5-fluoro-2-methyl-1H-indol-3-yl}acetic acid | | 1-10 | |
| 118 | {6-chloro-1-[(5-chloro-2-thienyl)carbonyl]-5-hydroxy-2-methyl-1H-indol-3-yl}acetic acid | | 10-50 | |
| 119 | {6-chloro-1-[(5-chloro-2-thienyl)carbonyl]-5-methoxy-1H-indol-3-yl}acetic acid | 10-50 | 10-50 | |
| 120 | {6-chloro-1-[(5-chloro-2-thienyl)methyl]-1H-indol-3-methoxy-1H-indol-3-yl}acetic acid | 1-10 | 1-10 | |
| 121 | {6-chloro-1-[(6-chloropyridin-3-yl)methyl]-5-methoxy-2-methyl-1H-indol-3-yl}acetic acid | | <1 | |
| 122 | {6-chloro-1-[(3-(difluoromethoxy)benzyl]-5-methoxy-2-methyl-1H-indol-3-yl}acetic acid | | 10-50 | |
| 123 | {6-chloro-1-[(4-(difluoromethoxy)benzyl]-5-methoxy-2-methyl-1H-indol-3-yl}acetic acid | | | 500-1000 |
| 124 | {6-chloro-2,5-dimethyl-1-[2-(trifluoromethoxy)benzyl]-1H-indol-3-yl}acetic acid | | <1 | |
| 125 | {6-chloro-2,5-dimethyl-1-[3-(trifluoromethyl)benzyl]-1H-indol-3-yl}acetic acid | | <1 | |
| 126 | {6-chloro-5-fluoro-2-methyl-1-[3-(trifluoromethoxy)benzyl]-1H-indol-3-yl}acetic acid | | <1 | |
| 127 | {6-chloro-5-fluoro-2-methyl-1-[3-(trifluoromethyl)benzyl]-1H-indol-3-yl}acetic acid | | <1 | |
| 128 | {6-chloro-5-hydroxy-2-methyl-1-[4-(trifluoromethoxy)benzyl]-1H-indol-3-yl}acetic acid | <1 | <1 | |

FIG. 7I

| Row | IUPAC Name | CD11b Agonist activity at 1 uM | CD11b Agonist activity at 10 uM | CD11b Agonist EC50 activity (nM) |
|---|---|---|---|---|
| 129 | {6-chloro-5-methoxy-1-[4-(methoxycarbamoyl)benzyl]-2-methyl-1H-indol-3-yl}acetic acid | | <1 | |
| 130 | {6-chloro-5-methoxy-2-methyl-1-[(2-methyl-1,3-thiazol-4-yl)methyl]-1H-indol-3-yl}acetic acid | | 10-50 | |
| 131 | {6-chloro-5-methoxy-2-methyl-1-[3-(trifluoromethoxy)benzyl]-1H-indol-3-yl}acetic acid | | <1 | |
| 132 | {6-chloro-5-methoxy-2-methyl-1-[3-(trifluoromethyl)benzyl]-1H-indol-3-yl}acetic acid | | 1-10 | |
| 133 | {6-chloro-5-methoxy-2-methyl-1-[4-(methylsulfanyl)benzyl]-1H-indol-3-yl}acetic acid | | <1 | |
| 134 | {6-chloro-5-methoxy-2-methyl-1-[4-(trifluoromethoxy)benzyl]-1H-indol-3-yl}acetic acid | 50-100 | 10-50 | |
| 135 | {6-chloro-5-methoxy-2-methyl-1-[3-(trifluoromethoxy)benzyl]-1H-indol-3-yl}acetic acid | <1 | 1-10 | |
| 136 | {6-chloro-5-methoxy-2-methyl-1-[4-(trifluoromethoxy)benzyl]-1H-indol-3-yl}acetic acid | | <1 | |
| 137 | {6-chloro-2,5-dimethyl-1-[3-(trifluoromethoxy)benzyl]-1H-indol-3-yl}acetic acid | | <1 | |
| 138 | {6-fluoro-5-hydroxy-2-methyl-1-[(5-methyl-2-thienyl)carbonyl]-1H-indol-3-yl}acetic acid | 1-10 | <1 | |
| 139 | {6-fluoro-5-hydroxy-2-methyl-1-[4-(1,1,2,2-tetrafluoroethoxy)benzoyl]-1H-indol-3-yl}acetic acid | 10-50 | 10-50 | |
| 140 | {6-fluoro-5-hydroxy-2-methyl-1-[4-(methylthio)benzoyl]-1H-indol-3-yl}acetic acid | | 50-100 | |
| 141 | {6-fluoro-5-methoxy-2-methyl-1-[(5-methyl-2-thienyl)carbonyl]-1H-indol-3-yl}acetic acid | 1-10 | 1-10 | |
| 142 | {6-fluoro-5-methoxy-2-methyl-1-[3-(trifluoromethoxy)benzyl]-1H-indol-3-yl}acetic acid | 1-10 | <1 | |
| 143 | {6-fluoro-5-methoxy-2-methyl-1-[4-(1,1,2,2-tetrafluoroethoxy)benzoyl]-1H-indol-3-yl}acetic acid | 10-50 | 10-50 | |
| 144 | {6-fluoro-5-methoxy-2-methyl-1-[4-(methylthio)benzoyl]-1H-indol-3-yl}acetic acid | | 50-100 | |

FIG. 7J

| Row | IUPAC Name | CD11b Agonist activity at 1 uM | CD11b Agonist activity at 10 uM | CD11b Agonist activity EC50 (uM) |
|---|---|---|---|---|
| 145 | [6-fluoro-5-methoxy-2-methyl-1-[4-(trifluoromethoxy)benzoyl]-1H-indol-3-yl] acetic acid | | | 1-100 |
| 146 | {6-fluoro-5-methoxy-2-methyl-1-[4-(trifluoromethyl)benzoyl]-1H-indol-3-yl}acetic acid | | | 100-500 |
| 147 | 1-(1,3-benzothiazol-2-ylmethyl)-5-fluoro-2-methyl-1H-indole-3-carboxylic acid | | <1 | |
| 148 | 2-[1-(4-chlorobenzoyl)-5-methoxy-2-methyl-1H-indol-3-yl]-N-piperidin-1-ylacetamide | | <1 | |
| 149 | 3-((3R)-2-{[(4-fluorophenyl)sulfonyl]amino}-1,2,3,4-tetrahydro-9H-carbazol-9-yl)propanoic acid | | <1 | |
| 150 | 3-[1-(1,3-benzothiazol-2-ylmethyl)-4,6-dichloro-2-methyl-1H-indol-3-yl]propanoic acid | | <1 | |
| 151 | 3-[1-(1,3-benzothiazol-2-ylmethyl)-6-chloro-2,5-dimethyl-1H-indol-3-yl]propanoic acid | | | |
| 152 | 3-[1-(1,3-benzothiazol-2-ylmethyl)-6-chloro-5-fluoro-2-methyl-1H-indol-3-yl]propanoic acid | | <1 | |
| 153 | 3-[4,6-dichloro-1-(3-chlorobenzyl)-2-methyl-1H-indol-3-yl]propanoic acid | | 10-50 | |
| 154 | 3-[6-chloro-1-(3-chlorobenzyl)-5-fluoro-2-methyl-1H-indol-3-yl]propanoic acid | | 10-50 | |
| 155 | 3-[6-chloro-1-(4-chlorobenzyl)-5-methoxy-2-methyl-1H-indol-3-yl]propanoic acid | | <1 | |
| 156 | 4-(5-methyl-3-phenylisoxazol-4-yl)benzenesulfonamide | | | >100,000 |
| 157 | 4-[4-(methylsulfonyl)phenyl]-3-phenylfuran-2(5H)-one | | | >100,000 |
| 158 | 4-{[3-(carboxymethyl)-6-chloro-5-methoxy-2-methyl-1H-indol-1-yl]methyl}benzoic acid | | 1-10 | |
| 159 | 5-fluoro-2-methyl-1-{[3-(trifluoromethoxy)benzyl]}-1H-indole-3-carbaldehyde | | 1-10 | |
| 160 | 6-chloro-2,3-dimethyl-1-{[3-(trifluoromethoxy)benzyl]}-1H-indole acetate | | <1 | |

FIG. 7K

| Row | IUPAC Name | CD11b Agonist activity at 1 uM | CD11b Agonist activity at 10 uM | CD11b Agonist activity EC50 (uM) |
|---|---|---|---|---|
| 161 | ethyl [1-({4-chlorobenzoyl})-6-fluoro-5-hydroxy-2-methyl-1H-indol-3-yl]acetate | | | >100 |
| 162 | methyl [1-({4-chlorobenzoyl})-5-hydroxy-2-methyl-1H-indol-3-yl]acetate | | | >100 |
| 163 | methyl [1-({4-chlorobenzoyl})-6-fluoro-5-hydroxy-2-methyl-1H-indol-3-yl]acetate | | | >100 |
| 164 | propyl [1-({4-chlorobenzoyl})-6-fluoro-5-hydroxy-2-methyl-1H-indol-3-yl]acetate | | | >100 |

FIG. 8A

| Row | IUPAC Name | CD11b Antagonist Activity @ 10uM | CD11b Antagonist IC50 (nM) |
|---|---|---|---|
| 1 | {(1-benzoyl-6-chloro-5-methoxy-2-methyl-1H-indol-3-yl)acetic acid | 10-50 | |
| 2 | {(1-benzoyl-6-fluoro-5-hydroxy-2-methyl-1H-indol-3-yl)acetic acid | 50-100 | |
| 3 | {(1-benzoyl-5-fluoro-2-methyl-1H-indol-3-yl)acetic acid | 50-100 | 100-500 |
| 4 | {(1-benzoyl-5-hydroxy-2-methyl-1H-indol-3-yl)acetic acid | 50-100 | >1000 |
| 5 | {(1-benzyl-6-chloro-5-methoxy-2-methyl-1H-indol-3-yl)acetic acid | | 10-50 |
| 6 | (2E)-3-[5-chloro-2-methyl-1-[3-(trifluoromethoxy)benzyl]-1H-indol-3-yl]acrylic acid | | 10-50 |
| 7 | (2E)-3-[5-fluoro-2-methyl-1-[3-(trifluoromethoxy)benzyl]-1H-indol-3-yl]acrylic acid | | 10-50 |
| 8 | (2E)-3-[5-methoxy-2-methyl-1-[3-(trifluoromethoxy)benzyl]-1H-indol-3-yl]acrylic acid | | 10-50 |
| 9 | (6-chloro-1-{[(4-chlorophenyl)amino]carbonyl}-5-methoxy-1H-indol-3-yl)acetic acid | | 100-500 |
| 10 | {6-chloro-5-methoxy-2-methyl-1-{4-[(trifluoromethyl)thio]benzyl}-1H-indol-3-yl]acetic acid | | >1000 |
| 11 | {6-chloro-5-methoxy-2-methyl-1-{4-[(trifluoromethyl)thio]benzyl}-1H-indol-3-yl]acetic acid | 50-100 | |
| 12 | {6-chloro-5-methoxy-2-methyl-1-{4-[(trifluoromethyl)thio]benzyl}-1H-indol-3-yl]acetic acid | 50-100 | 10-50 |
| 13 | {6-fluoro-5-hydroxy-2-methyl-1-{4-[(trifluoromethyl)thio]benzyl}-1H-indol-3-yl]acetic acid | | 50-100 |
| 14 | {6-fluoro-5-methoxy-2-methyl-1-{4-[(trifluoromethyl)thio]benzyl}-1H-indol-3-yl]acetic acid | | 100-500 |
| 15 | {[1-(1,3-benzothiazol-2-ylmethyl)-4-chloro-5-methoxy-2-methyl-1H-indol-3-yl]acetic acid | | 500-1000 |
| 16 | {[1-(1,3-benzothiazol-2-ylmethyl)-5-fluoro-2-methyl-1H-indol-3-yl](oxo)acetic acid | | >1uM |
| 17 | {[1-(1,3-benzothiazol-2-ylmethyl)-5-fluoro-2-methyl-1H-indol-3-yl]acetic acid | | 10-50 |
| 18 | {[1-(1,3-benzothiazol-2-ylmethyl)-6-chloro-2,5-dimethyl-1H-indol-3-yl]acetic acid | | 1-10 |
| 19 | {[1-(1,3-benzothiazol-2-ylmethyl)-6-chloro-5-fluoro-2-methyl-1H-indol-3-yl]acetic acid | | 1-10 |

FIG. 8B

| Row | IUPAC Name | CD11b Antagonist Activity @ 10uM | CD11b Antagonist IC50 (nM) |
|---|---|---|---|
| 20 | [1-(1,3-benzothiazol-2-ylmethyl)-6-chloro-5-methoxy-2-methyl-1H-indol-3-yl]acetic acid | | 10-50 |
| 21 | [1-(1,3-benzothiazol-2-ylmethyl)-6-fluoro-5-methoxy-2-methyl-1H-indol-3-yl]acetic acid | | 50-100 |
| 22 | [1-(1,3-benzoxazol-2-ylmethyl)-6-chloro-5-methoxy-2-methyl-1H-indol-3-yl]acetic acid | | 100-500 |
| 23 | [1-(2,3-dichlorobenzoyl)-5-hydroxy-2-methyl-1H-indol-3-yl]acetic acid | 50-100 | |
| 24 | [1-(2,3-dichlorobenzoyl)-5-methoxy-2-methyl-1H-indol-3-yl]acetic acid | 50-100 | |
| 25 | [1-(2,4-dichlorobenzoyl)-5-hydroxy-2-methyl-1H-indol-3-yl]acetic acid | 50-100 | 100-500 |
| 26 | [1-(2,4-dichlorobenzoyl)-6-fluoro-5-methoxy-2-methyl-1H-indol-3-yl]acetic acid | | 100-500 |
| 27 | [1-(3,4-dichlorobenzoyl)-5-hydroxy-2-methyl-1H-indol-3-yl]acetic acid | >100 | 100-500 |
| 28 | [1-(3,4-dichlorobenzoyl)-5-methoxy-2-methyl-1H-indol-3-yl]acetic acid | 50-100 | 100-500 |
| 29 | [1-(3,4-difluorobenzoyl)-5-hydroxy-2-methyl-1H-indol-3-yl]acetic acid | 50-100 | 100-500 |
| 30 | [1-(3,4-difluorobenzoyl)-5-methoxy-2-methyl-1H-indol-3-yl]acetic acid | 50-100 | |
| 31 | [1-(3-bromobenzoyl)-6-chloro-5-methoxy-2-methyl-1H-indol-3-yl]acetic acid | | 1-10 |
| 32 | [1-(3-chlorobenzoyl)-5-hydroxy-2-methyl-1H-indol-3-yl]acetic acid | 50-100 | 500-1000 |
| 33 | [1-(3-chlorobenzoyl)-5-methoxy-2-methyl-1H-indol-3-yl]acetic acid | 50-100 | 100-500 |
| 34 | [1-(4-bromobenzoyl)-4,6-difluoro-5-hydroxy-2-methyl-1H-indol-3-yl]acetic acid | 50-100 | 50-100 |
| 35 | [1-(4-bromobenzoyl)-5-hydroxy-2-methyl-1H-indol-3-yl]acetic acid | >100 | |
| 36 | [1-(4-bromobenzoyl)-5-methoxy-2-methyl-1H-indol-3-yl]acetic acid | 50-100 | 100-500 |
| 37 | [1-(4-bromobenzoyl)-6-chloro-5-methoxy-2-methyl-1H-indol-3-yl]acetic acid | | 100-500 |
| 38 | [1-(4-bromobenzoyl)-6-fluoro-5-methoxy-2-methyl-1H-indol-3-yl]acetic acid | | 50-100 |

FIG. 8C

| Row | IUPAC Name | CD11b Antagonist Activity @ 10uM | CD11b Antagonist IC50 (uM) |
|---|---|---|---|
| 39 | [1-(4-chlorobenzyl)-5-fluoro-2-methyl-1H-indol-3-yl]acetic acid | 50-100 | 100-500 |
| 40 | [1-(4-chlorobenzyl)-5-methoxy-2-methyl-1H-indol-3-yl]acetic acid | 50-100 | 100-500 |
| 41 | [1-(4-cyanobenzyl)-5-methoxy-2-methyl-1H-indol-3-yl]acetic acid | 10-50 | |
| 42 | [1-(4-fluorobenzyl)-5-methoxy-2-methyl-1H-indol-3-yl]acetic acid | 50-100 | 100-500 |
| 43 | [1-(4-tert-butylbenzyl)-6-chloro-5-methoxy-2-methyl-1H-indol-3-yl]acetic acid | | 100-500 |
| 44 | [1-(biphenyl-4-ylmethyl)-6-chloro-5-methoxy-2-methyl-1H-indol-3-yl]acetic acid | | |
| 45 | [1-(cyclohexylmethyl)-5-methoxy-2-methyl-1H-indol-3-yl]acetic acid | 50-100 | 100-500 |
| 46 | [1-(cyclohexyl)-5-methoxy-2-methyl-1H-indol-3-yl]acetic acid | 50-100 | 100-500 |
| 47 | [4-chloro-1-(4-chlorobenzyl)-2,5-dimethyl-1H-indol-3-yl]acetic acid | | 50-100 |
| 48 | [5-fluoro-1-(4-fluorobenzyl)-2-methyl-1H-indol-3-yl]acetic acid | 50-100 | >100, 10-50 |
| 49 | [5-hydroxy-2-methyl-1-(3-phenylprop-2-ynoyl)-1H-indol-3-yl]acetic acid | >100 | 500-1000 |
| 50 | [5-hydroxy-2-methyl-1-(piperidin-1-ylcarbonyl)-1H-indol-3-yl]acetic acid | 10-50 | |
| 51 | [5-methoxy-1-(4-methoxybenzyl)-2-methyl-1H-indol-3-yl]acetic acid | 10-50 | |
| 52 | [5-methoxy-2-methyl-1-(piperidin-1-ylcarbonyl)-1H-indol-3-yl]acetic acid | 1-10 | 10-50 |
| 53 | [6-chloro-1-(2,3-dichlorobenzyl)-5-methoxy-2-methyl-1H-indol-3-yl]acetic acid | | 50-100 |
| 54 | [6-chloro-1-(2,4-dichlorobenzyl)-5-methoxy-2-methyl-1H-indol-3-yl]acetic acid | | 10-50 |
| 55 | [6-chloro-1-(2,5-dichlorobenzyl)-5-methoxy-2-methyl-1H-indol-3-yl]acetic acid | | |
| 56 | [6-chloro-1-(2,6-dichlorobenzyl)-5-methoxy-2-methyl-1H-indol-3-yl]acetic acid | | 500-1000 |
| 57 | [6-chloro-1-(2-chloro-4-fluorobenzyl)-5-methoxy-2-methyl-1H-indol-3-yl]acetic acid | | 100-500 |

FIG. 8D

| Row | IUPAC Name | CD11b Antagonist Activity @ 10uM | CD11b Antagonist IC50 (uM) |
|---|---|---|---|
| 58 | [6-chloro-1-(2-chloro-6-fluorobenzyl)-5-methoxy-2-methyl-1H-indol-3-yl]acetic acid | | 100-500 |
| 59 | [6-chloro-1-(2-chlorobenzyl)-5-methoxy-2-methyl-1H-indol-3-yl]acetic acid | | 10-50 |
| 60 | [6-chloro-1-(3,4-dichlorobenzyl)-5-methoxy-2-methyl-1H-indol-3-yl]acetic acid | | 50-100 |
| 61 | [6-chloro-1-(3,4-difluorobenzyl)-5-methoxy-2-methyl-1H-indol-3-yl]acetic acid | | 100-500 |
| 62 | [6-chloro-1-(3,5-dichlorobenzyl)-2,5-dimethyl-1H-indol-3-yl]acetic acid | | 10-50 |
| 63 | [6-chloro-1-(3,5-dichlorobenzyl)-5-methoxy-2-methyl-1H-indol-3-yl]acetic acid | | 1-10 |
| 64 | [6-chloro-1-(3,5-difluorobenzyl)-5-methoxy-2-methyl-1H-indol-3-yl]acetic acid | | 10-50 |
| 65 | [6-chloro-1-(3,5-dimethylbenzyl)-5-methoxy-2-methyl-1H-indol-3-yl]acetic acid | | 1-10 |
| 66 | [6-chloro-1-(3-chlorobenzyl)-5-methoxy-2-methyl-1H-indol-3-yl]acetic acid | | 500-1000 |
| 67 | [6-chloro-1-(3-chlorobenzyl)-2,5-dimethyl-1H-indol-3-yl]acetic acid | | 10-50 |
| 68 | [6-chloro-1-(3-chlorobenzyl)-5-fluoro-2-methyl-1H-indol-3-yl]acetic acid | | 10-50 |
| 69 | [6-chloro-1-(3-chlorobenzyl)-5-methoxy-2-methyl-1H-indol-3-yl]acetic acid | | 10-50 |
| 70 | [6-chloro-1-(3-cyanobenzyl)-5-methoxy-2-methyl-1H-indol-3-yl]acetic acid | | 10-50 |
| 71 | [6-chloro-1-(3-fluorobenzyl)-5-methoxy-2-methyl-1H-indol-3-yl]acetic acid | | 50-100 |
| 72 | [6-chloro-1-(4-chloro-2-fluorobenzyl)-5-methoxy-2-methyl-1H-indol-3-yl]acetic acid | | 50-100 |
| 73 | [6-chloro-1-(4-chlorobenzyl)-2,5-dimethyl-1H-indol-3-yl]acetic acid | | 10-50 |
| 74 | [6-chloro-1-(4-chlorobenzyl)-5-hydroxy-2-methyl-1H-indol-3-yl]acetic acid | | 50-100 |
| 75 | [6-chloro-1-(4-chlorobenzyl)-5-methoxy-2-methyl-1H-indol-3-yl]acetic acid | 50-100 | 50-100 |
| 76 | [6-chloro-1-(4-chlorophenyl)-5-methoxy-2-methyl-1H-indol-3-yl]acetic acid | | partial agonist @10uM, 10-5 |

FIG. 8E

| Row | IUPAC Name | CD11b Antagonist Activity @ 10uM | CD11b Antagonist IC50 (nM) |
|---|---|---|---|
| 77 | [(6-chloro-1-(4-fluorobenzyl)-5-methoxy-2-methyl-1H-indol-3-yl]acetic acid | | 50-100 |
| 78 | [(6-chloro-1-(cyclohexylmethyl)-5-methoxy-2-methyl-1H-indol-3-yl]acetic acid | | 100-500 |
| 79 | [(6-chloro-5-methoxy-1-(3-methoxybenzyl)-2-methyl-1H-indol-3-yl]acetic acid | | 50-100 |
| 80 | [(6-chloro-5-methoxy-2-methyl-1-(3-methylbenzyl)-1H-indol-3-yl]acetic acid | | 10-50 |
| 81 | [(6-chloro-5-methoxy-2-methyl-1-(3-nitrobenzyl)-1H-indol-3-yl]acetic acid | | 10-50 |
| 82 | [(6-chloro-5-methoxy-2-methyl-1-(pyridin-2-ylmethyl)-1H-indol-3-yl]acetic acid | | 500-1000 |
| 83 | [(6-chloro-5-methoxy-2-methyl-1-(quinolin-2-ylmethyl)-1H-indol-3-yl]acetic acid | | 100-500 |
| 84 | [(6-fluoro-1-(4-fluorobenzyl)-5-methoxy-2-methyl-1H-indol-3-yl]acetic acid | | 100-500 |
| 85 | [(6-fluoro-5-hydroxy-2-methyl-1-(2-thienylcarbonyl)-1H-indol-3-yl]acetic acid | 50-100 | |
| 86 | [(6-fluoro-5-methoxy-2-methyl-1-(2-thienylcarbonyl)-1H-indol-3-yl]acetic acid | 50-100 | |
| 87 | [1-(4-(4-chlorophenyl)sulfonyl]-5-hydroxy-2-methyl-1H-indol-3-yl]acetic acid | >100 | 100-500 |
| 88 | [1-(4-(4-chlorophenyl)sulfonyl]-5-methoxy-2-methyl-1H-indol-3-yl]acetic acid | >100 | >1000 |
| 89 | [1-[(4-chlorophenyl)carbonyl]-6-fluoro-5-methoxy-2-methyl-1H-indol-3-yl]acetic acid | | 100-500 |
| 90 | [1-[(5-chloro-2-thienyl)carbonyl]-5-hydroxy-2-methyl-1H-indol-3-yl]acetic acid | 50-100 | 100-500 |
| 91 | [1-[(5-chloro-2-thienyl)carbonyl]-5-methoxy-2-methyl-1H-indol-3-yl]acetic acid | 50-100 | 10-50 |
| 92 | [1-[(5-chloro-2-thienyl)carbonyl]-6-fluoro-5-hydroxy-2-methyl-1H-indol-3-yl]acetic acid | | 50-100 |
| 93 | [1-[(5-chloro-2-thienyl)carbonyl]-6-fluoro-5-methoxy-2-methyl-1H-indol-3-yl]acetic acid | 50-100 | |
| 94 | [1-[(5-chloro-2-thienyl)methyl]-5-fluoro-2-methyl-1H-indol-3-yl]acetic acid | 50-100 | 50-100 |
| 95 | [1-[(5-chloro-2-thienyl)methyl]-5-hydroxy-2-methyl-1H-indol-3-yl]acetic acid | 50-100 | 100-500 |

FIG. 8F

| Rpv | IUPAC Name | CD11b Antagonist Activity @ 10uM | CD11b Antagonist IC50 (nM) |
|---|---|---|---|
| 96 | {1-[(5-chloro-2-thienyl)methyl]-5-methoxy-2-methyl-1H-indol-3-yl}acetic acid | 50-100 | |
| 97 | {1-[(3,5-bis(trifluoromethyl)phenyl]benzyl]-6-chloro-5-methoxy-2-methyl-1H-indol-3-yl}acetic acid | | 10-50 |
| 98 | {2-chloro-1-[3-(trifluoromethoxy)benzyl]-1H-indol-3-yl}acetic acid | | 10-50 |
| 99 | {2-chloro-3-[3-(trifluoromethoxy)benzyl]-1H-indol-1-yl}acetic acid | | 10-50 |
| 100 | {2-methyl-1-[3-(trifluoromethoxy)benzyl]-1H-indol-3-yl}acetic acid | | 10-50 |
| 101 | {2-oxo-1-[3-(trifluoromethoxy)benzyl]-2,3-dihydro-1H-indol-3-yl}acetic acid | | >1000 |
| 102 | (3-{[(4-fluorophenyl)sulfonyl](methyl)amino}-1,2,3,4-tetrahydro-9H-carbazol-9-yl)acetic acid | | <1 |
| 103 | {4,6-dichloro-2-methyl-1-[3-(trifluoromethoxy)benzyl]-1H-indol-3-yl}acetic acid | | 1-10 |
| 104 | {5,6-dichloro-2-methyl-1-[3-(trifluoromethoxy)benzyl]-1H-indol-3-yl}acetic acid | | 1-10 |
| 105 | {5-chloro-2-methyl-1-[3-(trifluoromethoxy)benzyl]-1H-indol-3-yl}acetic acid | | 10-50 |
| 106 | {5-chloro-2-methyl-1-[3-(trifluoromethyl)benzyl]-1H-indol-3-yl}acetic acid | | 10-50 |
| 107 | {5-chloro-1-[3-(trifluoromethoxy)benzyl]-1H-indol-2-yl(oxo)acetic acid | | 500-1000 |
| 108 | {5-fluoro-1-[3-(trifluoromethoxy)benzyl]-1H-indol-3-yl](oxo)acetic acid | | 100-500 |
| 109 | {5-fluoro-2-methyl-1-[3-(trifluoromethoxy)benzyl]-1H-indol-3-yl}acetic acid | | 10-50 |
| 110 | {5-fluoro-2-methyl-1-[4-(trifluoromethoxy)benzyl]-1H-indol-3-yl}acetic acid | 50-100 | 50-100 |
| 111 | {5-hydroxy-2-methyl-1-[(2E)-3-phenylprop-2-enoyl]-1H-indol-3-yl}acetic acid | | 100-500 |
| 112 | {5-methoxy-1-[3-(trifluoromethoxy)benzyl]-1H-indol-3-yl}acetic acid | 50-100 | 50-100 |
| 113 | {5-methoxy-2-methyl-1-[(2E)-3-phenylprop-2-enoyl]-1H-indol-3-yl}acetic acid | 50-100 | 10-50 |
| 114 | {5-methoxy-2-methyl-1-[3-(trifluoromethoxy)benzyl]-1H-indol-3-yl}acetic acid | | 10-50 |

FIG. 8G

| Row | IUPAC Name | CD11b Antagonist Activity @ 10uM | CD11b Antagonist IC50 (nM) |
|---|---|---|---|
| 115 | {5-methoxy-2-methyl-1-[4-(trifluoromethoxy)benzyl]-1H-indol-3-yl}acetic acid | 50-100 | |
| 116 | {6-chloro-1-[(4-chlorophenoxy)carbonyl]-5-methoxy-2-methyl-1H-indol-3-yl}acetic acid | | >1000 |
| 117 | {6-chloro-1-[(5-chloro-2-thienyl)carbonyl]-5-methoxy-2-methyl-1H-indol-3-yl}acetic acid | | 50-100 |
| 118 | {6-chloro-1-[(5-chloro-2-thienyl)carbonyl]-5-hydroxy-2-methyl-1H-indol-3-yl}acetic acid | | >1000 |
| 119 | {6-chloro-1-[(5-chloro-2-thienyl)carbonyl]-5-methoxy-1H-indol-3-yl}acetic acid | 10-50 | |
| 120 | {6-chloro-1-[(5-chloro-2-thienyl)methyl]-5-methoxy-2-methyl-1H-indol-3-yl}acetic acid | 50-100 | 100-500 |
| 121 | {6-chloro-1-[(6-chloropyridin-3-yl)methyl]-5-methoxy-2-methyl-1H-indol-3-yl}acetic acid | | 100-500 |
| 122 | {6-chloro-1-[3-(difluoromethoxy)benzyl]-5-methoxy-2-methyl-1H-indol-3-yl}acetic acid | | 1-10 |
| 123 | {6-chloro-2,5-dimethyl-1-[3-(trifluoromethoxy)benzyl]-1H-indol-3-yl}acetic acid | | 1-10 |
| 124 | {6-chloro-2,5-dimethyl-1-[3-(trifluoromethyl)benzyl]-1H-indol-3-yl}acetic acid | | 1-10 |
| 125 | {6-chloro-5-fluoro-2-methyl-1-[3-(trifluoromethoxy)benzyl]-1H-indol-3-yl}acetic acid | | 1-10 |
| 126 | {6-chloro-5-fluoro-2-methyl-1-[3-(trifluoromethyl)benzyl]-1H-indol-3-yl}acetic acid | | 1-10 |
| 127 | {6-chloro-5-hydroxy-2-methyl-1-[3-(trifluoromethoxy)benzyl]-1H-indol-3-yl}acetic acid | | 1-10 |
| 128 | {6-chloro-5-hydroxy-2-methyl-1-[3-(trifluoromethyl)benzyl]-1H-indol-3-yl}acetic acid | 50-100 | 100-500 |
| 129 | {6-chloro-5-methoxy-1-[4-(methoxycarbonyl)benzyl]-2-methyl-1H-indol-3-yl}acetic acid | | 100-500 |
| 130 | {6-chloro-5-methoxy-2-methyl-1-[(2-methyl-1,3-thiazol-4-yl)methyl]-1H-indol-3-yl}acetic acid | | 100-500 |
| 131 | {6-chloro-5-methoxy-2-methyl-1-[3-(trifluoromethoxy)benzyl]-1H-indol-3-yl}acetic acid | | 1-10 |
| 132 | {6-chloro-5-methoxy-2-methyl-1-[3-(trifluoromethyl)benzyl]-1H-indol-3-yl}acetic acid | | 1-10 |
| 133 | {6-chloro-5-methoxy-2-methyl-1-[4-(trifluoromethylsulfonyl)benzyl]-1H-indol-3-yl}acetic acid | | 500-1000 |

FIG. 8H

| Row | IUPAC Name | CD11b Antagonist Activity @ 10uM | CD11b Antagonist IC50 (uM) |
|---|---|---|---|
| 134 | {6-chloro-5-methoxy-2-methyl-1-[4-(trifluoromethoxy)benzyl]-1H-indol-3-yl}acetic acid | 50-100 | 100-500 |
| 135 | {6-chloro-5-methoxy-2-methyl-1-[4-(trifluoromethyl)benzyl]-1H-indol-3-yl}acetic acid | | 100-500 |
| 136 | {6-fluoro-2,5-dimethyl-1-[3-(trifluoromethoxy)benzyl]-1H-indol-3-yl}acetic acid | | 1-10 |
| 137 | {6-fluoro-5-hydroxy-2-methyl-1-[(5-methyl-2-thienyl)carbonyl]-1H-indol-3-yl}acetic acid | 50-100 | 100-500 |
| 138 | {6-fluoro-5-hydroxy-2-methyl-1-[4-(1,1,2,2-tetrafluoroethoxy)benzyl]-1H-indol-3-yl}acetic acid | 10-50 | |
| 139 | {6-fluoro-5-methoxy-2-methyl-1-[(5-methyl-2-thienyl)carbonyl]-1H-indol-3-yl}acetic acid | 50-100 | 100-500 |
| 140 | {6-fluoro-5-methoxy-2-methyl-1-[3-(trifluoromethyl)benzyl]-1H-indol-3-yl}acetic acid | | 10-50 |
| 141 | 1-[(1,3-benzothiazol-2-yl)methyl]-5-fluoro-2-methyl-1H-indole-3-carboxylic acid | | >1uM |
| 142 | 2-{1-(4-fluorophenyl)sulfonyl]azetine]-1,2,3,4-tetrahydro-9H-carbazol-9-yl}acetamide | | >10000 |
| 143 | 3-(3R)-3-{[(4-fluorophenyl)sulfonyl]amino}-1,2,3,4-tetrahydro-9H-carbazol-9-yl-N-piperidin-1-ylacetamide | 50-100 | 10-50 |
| 144 | 3-{1-(1,3-benzothiazol-2-yl)methyl]-4,6-dichloro-2-methyl-1H-indol-3-yl}propanoic acid | | 10-50 |
| 145 | 3-{1-(1,3-benzothiazol-2-yl)methyl]-6-chloro-2,5-dimethoxy-1H-indol-3-yl}propanoic acid | | 100-500 |
| 146 | 3-{1-(1,3-benzothiazol-2-yl)methyl]-6-chloro-5-fluoro-2-methyl-1H-indol-3-yl}propanoic acid | | 100-500 |
| 147 | 3-{4,6-dichloro-1-(3-chlorobenzyl)-2-methyl-1H-indol-3-yl}propanoic acid | | 50-100 |
| 148 | 3-{6-chloro-1-(3-chlorobenzyl)-5-fluoro-2-methyl-1H-indol-3-yl}propanoic acid | | 10-50 |
| 149 | 3-{6-chloro-1-(4-chlorobenzyl)-5-methoxy-2-methyl-1H-indol-3-yl}propanoic acid | | 100-500 |
| 150 | 4-{[3-(carboxymethyl)-6-chloro-5-methoxy-2-methyl-1H-indol-1-yl]methyl}benzoic acid | | >10000 |
| 151 | 5-fluoro-2-methyl-1-[3-(trifluoromethoxy)benzyl]-1H-indole-3-carbaldehyde | | >1000 |
| 152 | 6-chloro-2,3-dimethyl-1-[3-(trifluoromethoxy)benzyl]-1H-indole acetate | | 1-10 |

FIG. 9A

| Row | IUPAC Name | CD11b Antagonist IC50 (nM) in 10 % Human Plasma |
|---|---|---|
| 1 | [1-(4-bromobenzyl)-4,6-difluoro-5-hydroxy-2-methyl-1H-indol-3-yl]acetic acid | >10uM |
| 2 | [1-(5-chloro-2-thienyl)carbonyl]-5-methoxy-2-methyl-1H-indol-3-yl]acetic acid | >10uM |
| 3 | [5-methoxy-2-methyl-1-[(2E)-3-phenylprop-2-enoyl]-1H-indol-3-yl]acetic acid | >10uM |
| 4 | (6-fluoro-5-hydroxy-2-methyl-1-{4-[(trifluoromethyl)thio]benzoyl}-1H-indol-3-yl)acetic acid | 500-1000 |
| 5 | [6-chloro-1-(4-chlorobenzyl)-5-methoxy-2-methyl-1H-indol-3-yl]acetic acid | >1000 |
| 6 | 3-(3R)-3-{[(4-fluorophenyl)sulfonyl]amino}-1,2,3,4-tetrahydro-9H-carbazol-9-yl]propanoic acid | 500-1000 |
| 7 | [5-fluoro-2-methyl-1-[4-(trifluoromethoxy)benzyl]-1H-indol-3-yl]acetic acid | >10uM |
| 8 | [5-fluoro-1-(4-fluorobenzyl)-2-methyl-1H-indol-3-yl]acetic acid | >10uM |
| 9 | [1-(1,3-benzothiazol-2-ylmethyl)-6-chloro-5-methoxy-2-methyl-1H-indol-3-yl]acetic acid | 1000-5000 |
| 10 | [6-chloro-1-(4-chlorobenzyl)-5-hydroxy-2-methyl-1H-indol-3-yl]acetic acid | >10uM |
| 11 | [6-chloro-1-(2-chlorobenzyl)-5-methoxy-2-methyl-1H-indol-3-yl]acetic acid | >10uM |
| 12 | (1-benzyl-6-chloro-5-methoxy-2-methyl-1H-indol-3-yl)acetic acid | 5000-10000 |
| 13 | [6-chloro-1-(3-chlorobenzyl)-5-methoxy-2-methyl-1H-indol-3-yl]acetic acid | 1000-5000 |
| 14 | [6-chloro-1-(4-chlorobenzyl)-2,5-dimethyl-1H-indol-3-yl]acetic acid | >10uM |
| 15 | [6-chloro-1-(4-chlorophenyl)-5-methoxy-2-methyl-1H-indol-3-yl]acetic acid | >10uM |
| 16 | 3-[6-chloro-1-(4-chlorobenzyl)-5-methoxy-2-methyl-1H-indol-3-yl]propanoic acid | >10uM |
| 17 | [1-(1,3-benzothiazol-2-ylmethyl)-5-fluoro-2-methyl-1H-indol-3-yl]acetic acid | 100-500 |
| 18 | [6-chloro-1-(3-fluorobenzyl)-5-methoxy-2-methyl-1H-indol-3-yl]acetic acid | 5000-10000 |
| 19 | [6-chloro-1-(3-chlorobenzyl)-5-fluoro-2-methyl-1H-indol-3-yl]acetic acid | 1000-5000 |
| 20 | [6-chloro-5-methoxy-2-methyl-1-[3-(trifluoromethoxy)benzyl]-1H-indol-3-yl]acetic acid | 100-500 |
| 21 | [6-chloro-1-(3-cyanobenzyl)-5-methoxy-2-methyl-1H-indol-3-yl]acetic acid | 1000-5000 |
| 22 | [6-chloro-5-methoxy-2-methyl-1-(3-methylbenzyl)-1H-indol-3-yl]acetic acid | 1000-5000 |
| 23 | [6-chloro-5-methoxy-2-methyl-1-[3-(trifluoromethyl)benzyl]-1H-indol-3-yl]acetic acid | 1000-5000 |

FIG. 9B

| Row | IUPAC Name | CD11b Antagonist IC50 (nM) in 10 % Human Plasma |
|---|---|---|
| 24 | [6-chloro-1-(3-chlorobenzyl)-2,5-dimethyl-1H-indol-3-yl]acetic acid | 1000-5000 |
| 25 | [1-(1,3-benzothiazol-2-ylmethyl)-6-chloro-2,5-dimethyl-1H-indol-3-yl]acetic acid | 1000-5000 |
| 26 | 3-[6-chloro-1-(3-chlorobenzyl)-5-fluoro-2-methyl-1H-indol-3-yl]propanoic acid | >10uM |
| 27 | 3-[1-(1,3-benzothiazol-2-ylmethyl)-4,6-dichloro-2-methyl-1H-indol-3-yl]propanoic acid | >10uM |
| 28 | [6-chloro-2,5-dimethyl-1-[3-(trifluoromethyl)benzyl]-1H-indol-3-yl]acetic acid | 500-1000 |
| 29 | [6-chloro-2,5-dimethyl-1-[3-(trifluoromethyl)benzyl]-1H-indol-3-yl]acetic acid | 500-1000 |
| 30 | [1-(1,3-benzothiazol-2-ylmethyl)-6-chloro-5-fluoro-2-methyl-1H-indol-3-yl]acetic acid | 500-1000 |
| 31 | [6-chloro-5-fluoro-2-methyl-1-[3-(trifluoromethyl)benzyl]-1H-indol-3-yl]acetic acid | 500-1000 |
| 32 | [6-fluoro-5-methoxy-2-methyl-1-[3-(trifluoromethyl)benzyl]-1H-indol-3-yl]acetic acid | <1 |
| 33 | [3-[[(4-fluorophenyl)sulfonyl][methyl]amino]-1,2,3,4-tetrahydro-9H-carbazol-9-yl]acetic acid | 1000-5000 |
| 34 | [6-chloro-1-(3,5-dichlorobenzyl)-5-methoxy-2-methyl-1H-indol-3-yl]acetic acid | >10uM |
| 35 | [6-chloro-1-(2,3-dichlorobenzyl)-5-methoxy-2-methyl-1H-indol-3-yl]acetic acid | 1000-5000 |
| 36 | [6-chloro-5-fluoro-2-methyl-1-[3-(trifluoromethyl)benzyl]-1H-indol-3-yl]acetic acid | 1000-5000 |
| 37 | [6-fluoro-2,5-dimethyl-1-[3-(trifluoromethyl)benzyl]-1H-indol-3-yl]acetic acid | 500-1000 |
| 38 | [6-chloro-1-(3,5-dichlorobenzyl)-2,5-dimethyl-1H-indol-3-yl]acetic acid | 5000-10000 |
| 39 | [1-(3-bromobenzyl)-6-chloro-5-methoxy-2-methyl-1H-indol-3-yl]acetic acid | >1000 |
| 40 | (2E)-3-[5-fluoro-2-methyl-1-[3-(trifluoromethoxy)benzyl]-1H-indol-3-yl]acrylic acid | 1000-5000 |
| 41 | [5-methoxy-2-methyl-1-[3-(trifluoromethoxy)benzyl]-1H-indol-3-yl]acetic acid | 1000-5000 |
| 42 | [4,6-dichloro-2-methyl-1-[3-(trifluoromethyl)benzyl]-1H-indol-3-yl]acetic acid | 500-1000 |
| 43 | [6-chloro-1-(3,5-dimethylbenzyl)-5-methoxy-2-methyl-1H-indol-3-yl]acetic acid | 1000-5000 |
| 44 | [6-chloro-5-methoxy-2-methyl-1H-indol-3-yl]acetic acid | 5000-10000 |
| 45 | [1-[3,5-bis(trifluoromethyl)benzyl]-2,3-dihydro-1H-indol-3-yl]acetic acid | >10uM |
| 46 | [6-chloro-1-[3-(difluoromethoxy)benzyl]-5-methoxy-2-methyl-1H-indol-3-yl]acetic acid | 500-1000 |

FIG. 9C

| Row | IUPAC Name | CD11b Antagonist IC50 (uM) in 10 % Human Plasma |
|---|---|---|
| 47 | [5,6-dichloro-2-methyl-1-[3-(trifluoromethoxy)benzyl]-1H-indol-3-yl]acetic acid | 1000-5000 |
| 48 | (2-chloro-1-[3-(trifluoromethoxy)benzyl]-1H-indol-3-yl)acetic acid | 1000-5000 |
| 49 | [5-chloro-2-methoxy-1-[3-(trifluoromethoxy)benzyl]-1H-indol-3-yl]acetic acid | 500-1000 |
| 50 | (2E)-3-{5-methoxy-2-methyl-1-[3-(trifluoromethoxy)benzyl]-1H-indol-3-yl}acrylic acid | >1000 |
| 51 | (2E)-3-{5-chloro-2-methyl-1-[3-(trifluoromethoxy)benzyl]-1H-indol-3-yl}acrylic acid | >1000 |
| 52 | 6-chloro-2,3-dimethyl-1-[3-(trifluoromethoxy)benzyl]-1H-indole acetate | 100-500 |
| 53 | [6-chloro-5-hydroxy-2-methyl-1-{3-(trifluoromethoxy)benzyl]-1H-indol-3-yl}acetic acid | 100-500 |

FIG. 10A

| Row | IUPAC Name | DP-1 Agonist Assay % of maximal response | DP-1 Antagonist Assay % of maximal response |
|---|---|---|---|
| 1 | [6-chloro-1-(4-chlorobenzyl)-5-fluoro-2-methyl-1H-indol-3-yl]acetic acid | <1 | <1 |
| 2 | [6-chloro-1-(2,5-dichlorobenzyl)-5-methoxy-2-methyl-1H-indol-3-yl]acetic acid | <1 | 50-100 |
| 3 | [6-chloro-5-methoxy-2-methyl-1-[3-(trifluoromethoxy)benzyl]-1H-indol-3-yl]acetic acid | <1 | 10-50 |
| 4 | [6-chloro-1-(3,5-dichlorobenzyl)-2,5-dimethyl-1H-indol-3-yl]acetic acid | <1 | 10-50 |
| 5 | [1-(3-bromobenzyl)-6-chloro-5-methoxy-2-methyl-1H-indol-3-yl]acetic acid | <1 | 10-50 |
| 6 | [4,6-dichloro-2-methyl-1-[3-(trifluoromethoxy)benzyl]-1H-indol-3-yl]acetic acid | <1 | <1 |
| 7 | {2-methyl-1-[3-(trifluoromethoxy)benzyl]-1H-indol-3-yl}acetic acid | <1 | 10-50 |
| 8 | {2-chloro-3-[3-(trifluoromethoxy)benzyl]-1H-indol-1-yl}acetic acid | <1 | <1 |
| 9 | [6-chloro-1-(3,5-dimethylbenzyl)-5-methoxy-2-methyl-1H-indol-3-yl]acetic acid | <1 | 10-50 |
| 10 | {1-[3,5-bis(trifluoromethyl)benzyl]-6-chloro-5-methoxy-2-methyl-1H-indol-3-yl}acetic acid | <1 | 10-50 |
| 11 | {5-methoxy-1-[3-(trifluoromethoxy)benzyl]-1H-indol-3-yl}acetic acid | <1 | 10-50 |
| 12 | {2-oxo-1-[3-(trifluoromethoxy)benzyl]-2,3-dihydro-1H-indol-3-yl}acetic acid | <1 | 10-50 |

FIG. 10B

| Row | IUPAC Name | DP-1 Agonist Assay % of maximal response | DP-1 Antagonist Assay % of maximal response |
|---|---|---|---|
| 13 | {6-chloro-1-[3-(difluoromethoxy)benzyl]-5-methoxy-2-methyl-1H-indol-3-yl}acetic acid | <1 | 10-50 |
| 14 | {5,6-dichloro-2-methyl-1-[3-(trifluoromethoxy)benzyl]-1H-indol-3-yl}acetic acid | <1 | 10-50 |
| 15 | {2-chloro-1-[3-(trifluoromethoxy)benzyl]-1H-indol-3-yl}acetic acid | <1 | 1-10 |
| 16 | {5-chloro-2-methyl-1-[3-(trifluoromethoxy)benzyl]-1H-indol-3-yl}acetic acid | <1 | 10-50 |
| 17 | {5-chloro-2-methyl-1-[3-(trifluoromethyl)benzyl]-1H-indol-3-yl}acetic acid | <1 | 10-50 |
| 18 | {5-fluoro-2-methyl-1-[3-(trifluoromethoxy)benzyl]-1H-indol-3-yl}acetic acid | <1 | 10-50 |
| 19 | (2E)-3-{5-methoxy-2-methyl-1-[3-(trifluoromethoxy)benzyl]-1H-indol-3-yl}acrylic acid | <1 | <1 |
| 20 | [6-chloro-5-methoxy-2-methyl-1-(3-nitrobenzyl)-1H-indol-3-yl]acetic acid | <1 | 10-50 |
| 21 | [6-chloro-1-(3,5-difluorobenzyl)-5-methoxy-2-methyl-1H-indol-3-yl]acetic acid | <1 | <1 |
| 22 | (2E)-3-{5-chloro-2-methyl-1-[3-(trifluoromethoxy)benzyl]-1H-indol-3-yl}acrylic acid | <1 | 10-50 |
| 23 | 6-chloro-2,3-dimethyl-1-[3-(trifluoromethoxy)benzyl]-1H-indole acetate | <1 | <1 |
| 24 | {6-chloro-5-hydroxy-2-methyl-1-[3-(trifluoromethoxy)benzyl]-1H-indol-3-yl}acetic acid | <1 | <1 |

FIG. 10C

| Row | IUPAC Name | DP-1 Agonist Assay % of maximal response | DP-1 Antagonist Assay % of maximal response |
|---|---|---|---|
| 25 | (1-benzyl-5-hydroxy-2-methyl-1H-indol-3-yl)acetic acid | <1 | 10-50 |
| 26 | (1-benzoyl-6-fluoro-5-hydroxy-2-methyl-1H-indol-3-yl)acetic acid | <1 | <1 |
| 27 | [1-(3,4-dichlorobenzoyl)-5-methoxy-2-methyl-1H-indol-3-yl]acetic acid | <1 | 1-10 |
| 28 | [1-(3,4-dichlorobenzoyl)-5-hydroxy-2-methyl-1H-indol-3-yl]acetic acid | <1 | <1 |
| 29 | [1-(2,4-dichlorobenzoyl)-5-hydroxy-2-methyl-1H-indol-3-yl]acetic acid | <1 | 10-50 |
| 30 | [1-(cyclohexylcarbonyl)-5-methoxy-2-methyl-1H-indol-3-yl]acetic acid | <1 | <1 |
| 31 | [1-(2,3-dichlorobenzoyl)-5-methoxy-2-methyl-1H-indol-3-yl]acetic acid | <1 | 10-50 |
| 32 | [1-(2,3-dichlorobenzoyl)-5-hydroxy-2-methyl-1H-indol-3-yl]acetic acid | <1 | 10-50 |
| 33 | [1-(3-chlorobenzoyl)-5-methoxy-2-methyl-1H-indol-3-yl]acetic acid | <1 | 10-50 |
| 34 | [1-(3-chlorobenzoyl)-5-hydroxy-2-methyl-1H-indol-3-yl]acetic acid | <1 | 1-10 |
| 35 | [1-(3,4-difluorobenzoyl)-5-methoxy-2-methyl-1H-indol-3-yl]acetic acid | <1 | 10-50 |
| 36 | [1-(3,4-difluorobenzoyl)-5-hydroxy-2-methyl-1H-indol-3-yl]acetic acid | <1 | <1 |

FIG. 10D

| Row | IUPAC Name | DP-1 Agonist Assay % of maximal response | DP-1 Antagonist Assay % of maximal response |
|---|---|---|---|
| 37 | [1-(4-bromobenzyl)-5-methoxy-2-methyl-1H-indol-3-yl]acetic acid | <1 | 10-50 |
| 38 | [1-(4-bromobenzyl)-5-hydroxy-2-methyl-1H-indol-3-yl]acetic acid | <1 | <1 |
| 39 | [1-(4-bromobenzyl)-4,6-difluoro-5-hydroxy-2-methyl-1H-indol-3-yl]acetic acid | <1 | 10-50 |
| 40 | {1-[(5-chloro-2-thienyl)carbonyl]-5-hydroxy-2-methyl-1H-indol-3-yl}acetic acid | <1 | <1 |
| 41 | [1-(4-chlorobenzyl)-5-methoxy-2-methyl-1H-indol-3-yl]acetic acid | <1 | <1 |
| 42 | [1-(4-fluorobenzyl)-5-methoxy-2-methyl-1H-indol-3-yl]acetic acid | <1 | 10-50 |
| 43 | {1-[(4-chlorophenyl)sulfonyl]-5-methoxy-2-methyl-1H-indol-3-yl}acetic acid | <1 | 10-50 |
| 44 | {1-[(4-chlorophenyl)sulfonyl]-5-hydroxy-2-methyl-1H-indol-3-yl}acetic acid | <1 | <1 |
| 45 | [1-(4-cyanobenzoyl)-5-methoxy-2-methyl-1H-indol-3-yl]acetic acid | <1 | <1 |
| 46 | [1-(cyclohexylcarbonyl)-6-fluoro-5-methoxy-2-methyl-1H-indol-3-yl]acetic acid | <1 | <1 |
| 47 | {5-hydroxy-2-methyl-1-[(2E)-3-phenylprop-2-enoyl]-1H-indol-3-yl}acetic acid | <1 | 10-50 |
| 48 | [5-methoxy-2-methyl-1-(piperidin-1-ylcarbonyl)-1H-indol-3-yl]acetic acid | <1 | <1 |

FIG. 10E

| Row | IUPAC Name | DP-1 Agonist Assay % of maximal response | DP-1 Antagonist Assay % of maximal response |
|---|---|---|---|
| 49 | [5-hydroxy-2-methyl-1-(piperidin-1-ylcarbonyl)-1H-indol-3-yl]acetic acid | <1 | 10-50 |
| 50 | {1-[(5-chloro-2-thienyl)carbonyl]-6-fluoro-5-hydroxy-2-methyl-1H-indol-3-yl}acetic acid | <1 | <1 |
| 51 | {6-fluoro-5-hydroxy-2-methyl-1-[4-(trifluoromethylthio)benzoyl]-1H-indol-3-yl}acetic acid | 1-10 | 10-50 |
| 52 | [5-hydroxy-2-methyl-1-(3-phenylprop-2-ynoyl)-1H-indol-3-yl]acetic acid | <1 | 10-50 |
| 53 | {6-fluoro-5-hydroxy-2-methyl-1-[4-(methylthio)benzoyl]-1H-indol-3-yl}acetic acid | <1 | <1 |
| 54 | {6-fluoro-5-methoxy-2-methyl-1-[4-(methylthio)benzoyl]-1H-indol-3-yl}acetic acid | <1 | 1-10 |
| 55 | {6-fluoro-5-methoxy-2-methyl-1-(2-thienylcarbonyl)-1H-indol-3-yl}acetic acid | <1 | <1 |
| 56 | {6-fluoro-5-methoxy-2-methyl-1-[(5-methyl-2-thienyl)carbonyl]-1H-indol-3-yl}acetic acid | <1 | <1 |
| 57 | {6-fluoro-5-hydroxy-2-methyl-1-[(5-methyl-2-thienyl)carbonyl]-1H-indol-3-yl}acetic acid | <1 | <1 |
| 58 | [6-fluoro-5-hydroxy-2-methyl-1-(2-thienylcarbonyl)-1H-indol-3-yl}acetic acid | <1 | <1 |
| 59 | "{6-fluoro-5-hydroxy-2-methyl-1-[4-(1,1,2,2-tetrafluoroethoxy)benzoyl]-1H-indol-3-yl}acetic acid" | <1 | <1 |
| 60 | [6-chloro-1-(4-chlorobenzoyl)-5-methoxy-2-methyl-1H-indol-3-yl]acetic acid | <1 | <1 |

FIG. 10F

| Row | IUPAC Name | DP-1 Agonist Assay % of maximal response | DP-1 Antagonist Assay % of maximal response |
|---|---|---|---|
| 61 | 3-((3R)-3-{[[(4-fluorophenyl)sulfonyl]amino}-1,2,3,4-tetrahydro-9H-carbazol-9-yl]propanoic acid | <1 | 10-50 |
| 62 | [5-methoxy-1-(4-methoxybenzyl)-2-methyl-1H-indol-3-yl]acetic acid | <1 | <1 |
| 63 | [5-methoxy-2-methyl-1-[4-(trifluoromethoxy)benzyl]-1H-indol-3-yl]acetic acid | <1 | 10-50 |
| 64 | {1-[(5-chloro-2-thienyl)methyl]-5-methoxy-2-methyl-1H-indol-3-yl}acetic acid | <1 | 10-50 |
| 65 | {1-[(5-chloro-2-thienyl)methyl]-5-hydroxy-2-methyl-1H-indol-3-yl}acetic acid | <1 | <1 |
| 66 | {6-chloro-5-methoxy-2-methyl-1-[4-(trifluoromethoxy)benzyl]-1H-indol-3-yl}acetic acid | <1 | 10-50 |
| 67 | [1-(4-chlorobenzyl)-5-fluoro-2-methyl-1H-indol-3-yl]acetic acid | <1 | 1-10 |
| 68 | {6-chloro-5-hydroxy-2-methyl-1-[4-(trifluoromethoxy)benzyl]-1H-indol-3-yl}acetic acid | <1 | <1 |
| 69 | {5-fluoro-2-methyl-1-[4-(trifluoromethoxy)benzyl]-1H-indol-3-yl}acetic acid | 1-10 | <1 |
| 70 | [1-benzoyl-6-chloro-5-methoxy-2-methyl-1H-indol-3-yl]acetic acid | <1 | 10-50 |
| 71 | [1-benzyl-5-fluoro-2-methyl-1H-indol-3-yl]acetic acid | <1 | 1-10 |
| 72 | [5-fluoro-1-(4-fluorobenzyl)-2-methyl-1H-indol-3-yl]acetic acid | <1 | <1 |

FIG. 10G

| Row | IUPAC Name | DP-1 Agonist Assay % of maximal response | DP-1 Antagonist Assay % of maximal response |
|---|---|---|---|
| 73 | [6-chloro-1-[(5-chloro-2-thienyl)carbonyl]-5-methoxy-2-methyl-1H-indol-3-yl]acetic acid | <1 | <1 |
| 74 | (6-chloro-1-[(5-chloro-2-thienyl)carbonyl]-5-hydroxy-2-methyl-1H-indol-3-yl)acetic acid | <1 | <1 |
| 75 | (6-fluoro-5-methoxy-2-methyl-1-{4-[(trifluoromethyl)thio]benzyl}-1H-indol-3-yl)acetic acid | <1 | 10-50 |
| 76 | [6-chloro-1-(3,4-dichlorobenzoyl)-5-methoxy-2-methyl-1H-indol-3-yl]acetic acid | <1 | <1 |
| 77 | [6-chloro-1-(3,4-difluorobenzyl)-5-methoxy-2-fluoro-1H-indol-3-yl]acetic acid | <1 | 10-50 |
| 78 | [6-chloro-1-[(5-chloro-2-thienyl)carbonyl]-5-fluoro-2-methyl-1H-indol-3-yl]acetic acid | <1 | 10-50 |
| 79 | (6-chloro-5-methoxy-2-methyl-1-{4-[(trifluoromethyl)thio]benzyl}-1H-indol-3-yl)acetic acid | <1 | 10-50 |
| 80 | (6-fluoro-5-methoxy-2-methyl-1-{4-[(trifluoromethyl)thio]benzyl}-1H-indol-3-yl)acetic acid | <1 | 10-50 |
| 81 | 2-[1-(4-chlorobenzoyl)-5-methoxy-2-methyl-1H-indol-3-yl]-N-piperidin-1-ylacetamide | <1 | 10-50 |
| 82 | [1-(1,3-benzothiazol-2-ylmethyl)-6-fluoro-5-methoxy-2-methyl-1H-indol-3-yl]acetic acid | <1 | 10-50 |
| 83 | [6-chloro-1-(3-chlorobenzoyl)-5-methoxy-2-methyl-1H-indol-3-yl]acetic acid | <1 | 10-50 |
| 84 | (1-[(4-chlorophenyl)sulfonyl]-6-fluoro-5-methoxy-2-methyl-1H-indol-3-yl)acetic acid | <1 | 10-50 |

FIG. 10H

| Row | IUPAC Name | DP-1 Agonist Assay % of maximal response | DP-1 Antagonist Assay % of maximal response |
|---|---|---|---|
| 85 | [6-chloro-5-methoxy-2-methyl-1-(quinolin-2-ylmethyl)-1H-indol-3-yl]acetic acid | <1 | 10-50 |
| 86 | {6-chloro-1-[(6-chloropyridin-3-yl)methyl]-5-methoxy-2-methyl-1H-indol-3-yl}acetic acid | <1 | 10-50 |
| 87 | [6-chloro-1-(2,6-dichlorobenzyl)-5-methoxy-2-methyl-1H-indol-3-yl]acetic acid | <1 | 10-50 |
| 88 | [1-(biphenyl-4-ylmethyl)-6-chloro-5-methoxy-2-methyl-1H-indol-3-yl]acetic acid | <1 | 10-50 |
| 89 | [6-chloro-5-methoxy-2-methyl-1-(pyridin-2-ylmethyl)-1H-indol-3-yl]acetic acid | <1 | 10-50 |
| 90 | [1-(1,3-benzothiazol-2-ylmethyl)-4-chloro-5-methoxy-2-methyl-1H-indol-3-yl]acetic acid | <1 | 10-50 |
| 91 | [6-chloro-1-(4-chlorobenzyl)-5-hydroxy-2-methyl-1H-indol-3-yl]acetic acid | <1 | 10-50 |
| 92 | [6-chloro-5-methoxy-2-methyl-1-(2-napthylmethyl)-1H-indol-3-yl]acetic acid | <1 | 10-50 |
| 93 | {6-chloro-1-[(4-chlorophenoxy)carbonyl]-5-methoxy-2-methyl-1H-indol-3-yl}acetic acid | <1 | 10-50 |
| 94 | {6-chloro-1-{[(4-chlorophenyl)amino]carbonyl}-5-methoxy-2-methyl-1H-indol-3-yl}acetic acid | <1 | 10-50 |
| 95 | [1-(4-bromobenzyl)-6-chloro-5-methoxy-2-methyl-1H-indol-3-yl]acetic acid | <1 | 10-50 |
| 96 | {6-chloro-5-methoxy-2-methyl-1-[4-(methylsulfinyl)benzyl]-1H-indol-3-yl}acetic acid | <1 | <1 |

FIG. 10I

| Row | IUPAC Name | DP-1 Agonist Assay % of maximal response | DP-1 Antagonist Assay % of maximal response |
|---|---|---|---|
| 97 | [6-chloro-5-methoxy-1-[4-(methoxycarbonyl)benzyl]-2-methyl-1H-indol-3-yl]acetic acid | <1 | 10-50 |
| 98 | [6-chloro-1-(2,4-dichlorobenzyl)-5-methoxy-2-methyl-1H-indol-3-yl]acetic acid | <1 | |
| 99 | [1-(biphenyl-2-ylmethyl)-6-chloro-5-methoxy-2-methyl-1H-indol-3-yl]acetic acid | <1 | 10-50 |
| 100 | [6-chloro-1-(2-chloro-6-fluorobenzyl)-5-methoxy-2-methyl-1H-indol-3-yl]acetic acid | 1-10 | 10-50 |
| 101 | [6-chloro-1-(2-chlorobenzyl)-5-methoxy-2-methyl-1H-indol-3-yl]acetic acid | <1 | 10-50 |
| 102 | (1-benzyl-6-chloro-5-methoxy-2-methyl-1H-indol-3-yl)acetic acid | <1 | 10-50 |
| 103 | [6-chloro-1-(3-chlorobenzyl)-5-methoxy-2-methyl-1H-indol-3-yl]acetic acid | <1 | 10-50 |
| 104 | 3-[6-chloro-1-(4-chlorobenzyl)-5-methoxy-2-methyl-1H-indol-3-yl]propanoic acid | <1 | <1 |
| 105 | [6-chloro-1-(3-chlorobenzyl)-5-fluoro-2-methyl-1H-indol-3-yl]acetic acid | <1 | |
| 106 | [6-chloro-1-(3-cyanobenzyl)-5-methoxy-2-methyl-1H-indol-3-yl]acetic acid | <1 | <1 |
| 107 | [6-chloro-5-methoxy-2-methyl-1-(3-methylbenzyl)-1H-indol-3-yl]acetic acid | <1 | <1 |
| 108 | {6-chloro-5-methoxy-2-methyl-1-[3-(trifluoromethyl)benzyl]-1H-indol-3-yl}acetic acid | <1 | 10-50 |

FIG. 10J

| Row | IUPAC Name | DP-1 Agonist Assay % of maximal response | DP-1 Antagonist Assay % of maximal response |
|---|---|---|---|
| 109 | [6-chloro-1-(3-chlorobenzyl)-2,5-dimethyl-1H-indol-3-yl]acetic acid | <1 | 10-50 |
| 110 | [1-(1,3-benzothiazol-2-ylmethyl)-6-chloro-2,5-dimethyl-1H-indol-3-yl]acetic acid | <1 | 10-50 |
| 111 | 3-[1-(1,3-benzothiazol-2-ylmethyl)-6-chloro-5-fluoro-2-methyl-1H-indol-3-yl]propanoic acid | <1 | <1 |
| 112 | 3-[1-(1,3-benzothiazol-2-ylmethyl)-4,6-dichloro-2-methyl-1H-indol-3-yl]propanoic acid | <1 | 1-10 |
| 113 | {6-chloro-2,5-dimethyl-1-[3-(trifluoromethyl)benzyl]-1H-indol-3-yl}acetic acid | <1 | <1 |
| 114 | {6-chloro-2,5-dimethyl-1-[3-(trifluoromethoxy)benzyl]-1H-indol-3-yl}acetic acid | <1 | <1 |
| 115 | [1-(1,3-benzothiazol-2-ylmethyl)-6-chloro-5-fluoro-2-methyl-1H-indol-3-yl]acetic acid | <1 | <1 |
| 116 | {6-chloro-5-fluoro-2-methyl-1-[3-(trifluoromethoxy)benzyl]-1H-indol-3-yl}acetic acid | <1 | <1 |
| 117 | [5-fluoro-2-methyl-1-[3-(trifluoromethoxy)benzyl]-1H-indol-3-yl](oxo)acetic acid | <1 | <1 |
| 118 | [1-(1,3-benzothiazol-2-ylmethyl)-5-fluoro-2-methyl-1H-indol-3-yl]oxo)acetic acid | <1 | <1 |
| 119 | {6-fluoro-5-methoxy-2-methyl-1-[3-(trifluoromethyl)benzyl]-1H-indol-3-yl}acetic acid | <1 | |
| 120 | {3-[[(4-fluorophenyl)sulfonyl](methyl)amino]-1,2,3,4-tetrahydro-9H-carbazol-9-yl}acetic acid | <1 | |

FIG. 10K

| Row | IUPAC Name | DP-1 Agonist Assay % of maximal response | DP-1 Antagonist Assay % of maximal response |
|---|---|---|---|
| 121 | [6-chloro-1-{(3,5-dichlorobenzyl)-5-methoxy-2-methyl-1H-indol-3-yl]acetic acid | <1 | <1 |
| 122 | [6-chloro-1-{(2,3-dichlorobenzyl)-5-methoxy-2-methyl-1H-indol-3-yl]acetic acid | <1 | <1 |
| 123 | {5-fluoro-1-[3-(trifluoromethoxy)benzyl]-1H-indol-2-yl}(oxo)acetic acid | | |
| 124 | {6-chloro-5-fluoro-2-methyl-1-[3-(trifluoromethoxy)benzyl]-1H-indol-3-yl}acetic acid | <1 | <1 |
| 125 | {6-fluoro-2,5-dimethyl-1-[3-(trifluoromethoxy)benzyl]-1H-indol-3-yl}acetic acid | <1 | <1 |
| 126 | {5-methoxy-2-methyl-1-[(2E)-3-phenylprop-2-enoyl]-1H-indol-3-yl}acetic acid | <1 | <1 |
| 127 | [1-(1,3-benzothiazol-2-ylmethyl)-6-chloro-5-methoxy-2-methyl-1H-indol-3-yl]acetic acid | 1-10 | <1 |
| 128 | [6-chloro-1-(4-chlorobenzyl)-2,5-dimethyl-1H-indol-3-yl]acetic acid | 1-10 | 10-50 |
| 129 | {6-chloro-1-[(5-chloro-2-thienyl)methyl]-1H-indol-3-yl}acetic acid | 10-50 | |
| 130 | {1-[(5-chloro-2-thienyl)methyl]-5-methoxy-2-methyl-1H-indol-3-yl}acetic acid | | 1-10 |
| 131 | {1-[(5-chloro-2-thienyl)carbonyl]-6-fluoro-5-methoxy-2-methyl-1H-indol-3-yl}acetic acid | | <1 |
| 132 | {5-hydroxy-2-methyl-1-[4-(trifluoromethoxy)benzyl]-1H-indol-3-yl}acetic acid | | 1-10 |

FIG. 10L

| Row | IUPAC Name | DP-1 Agonist Assay % of maximal response | DP-1 Antagonist Assay % of maximal response |
|---|---|---|---|
| 133 | (5-fluoro-2-methyl-1H-indol-3-yl)acetic acid | | 1-10 |
| 134 | {1-[(5-chloro-2-thienyl)methyl]-5-fluoro-2-methyl-1H-indol-3-yl}acetic acid | | 10-50 |
| 135 | (6-chloro-5-methoxy-2-methyl-1-{4-[(trifluoromethyl)thio]benzyl}-1H-indol-3-yl)acetic acid | | 10-50 |
| 136 | 5-fluoro-1H-indole-2-carboxylic acid | | 10-50 |
| 137 | [6-fluoro-1-(4-fluorobenzyl)-5-methoxy-2-methyl-1H-indol-3-yl]acetic acid | | <1 |
| 138 | [1-(1,3-benzothiazol-2-ylmethyl)-5-fluoro-2-methyl-1H-indol-3-yl]acetic acid | | <1 |
| 139 | 5-fluoro-2-methyl-1-[3-(trifluoromethoxy)benzyl]-1H-indole-3-carbaldehyde | | 10-50 |
| 140 | (2E)-3-{5-fluoro-2-methyl-1-[3-(trifluoromethoxy)benzyl]-1H-indol-3-yl}acrylic acid | | 10-50 |
| 141 | {5-methoxy-2-methyl-1-[3-(trifluoromethoxy)benzyl]-1H-indol-3-yl}acetic acid | | 10-50 |

FIG. 11

| Row | IUPAC Name | Displacement @ 10 uM | Displacement @ 1 uM |
|---|---|---|---|
| 1 | [6-chloro-1-(4-chlorobenzyl)-5-methoxy-2-methyl-1H-indol-3-yl]acetic acid[A] | 39% | 14% |
| 2 | {6-fluoro-5-hydroxy-2-methyl-1-[4-(trifluoromethyl)thio]benzoyl]-1H-indol-3-yl}acetic acid[A] | 13% | 12% |
| 3 | [1-(1,3-benzothiazol-2-ylmethyl)-6-chloro-5-methoxy-2-methyl-1H-indol-3-yl]acetic acid[A] | 35% | 10% |
| 4 | {6-chloro-5-methoxy-2-methyl-1-[4-(trifluoromethyl)thio]benzoyl]-1H-indol-3-yl}acetic acid[A] | 43% | 19% |
| 5 | {6-chloro-1-[(5-chloro-2-thienyl)carbonyl]-5-fluoro-2-methyl-1H-indol-3-yl}acetic acid[A] | 35% | 10% |
| 6 | {6-chloro-2,3-dimethyl-1-[3-(trifluoromethoxy)benzyl]-1H-indol-3-yl}acetic acid[B] | 72% | 13% |
| 7 | {6-fluoro-5-methoxy-2-methyl-1-[3-(trifluoromethoxy)benzyl]-1H-indol-3-yl}acetic acid[B] | 78% | 18% |
| 8 | {6-chloro-5-fluoro-2-methyl-1-[3-(trifluoromethoxy)benzyl]-1H-indol-3-yl}acetic acid[B] | 72% | 16% |

A - Ramatroban control exhibited 91% displacement at 10 mm and 88% displacement at 1 mm
B - Ramatroban control exhibited 97% displacement at 10 mm and 96% displacement at 1 mm

FIG. 12A

| Row | IUPAC Name | DAO Activity Assay % Inhibition at 10uM | DAO IC50 (uM) |
|---|---|---|---|
| 1 | [6-fluoro-5-hydroxy-2-methyl-1-[4-(1,1,2,2-tetrafluoroethoxy)benzoyl]-1H-indol-3-yl]acetic acid | 10-50 | |
| 2 | [6-fluoro-5-methoxy-2-methyl-1-[4-(1,1,2,2-tetrafluoroethoxy)benzoyl]-1H-indol-3-yl]acetic acid | <1 | |
| 3 | (1-benzoyl-5-hydroxy-2-methyl-1H-indol-3-yl)acetic acid | 10-50 | |
| 4 | (1-benzoyl-5-methoxy-2-methyl-1H-indol-3-yl)acetic acid | <1 | |
| 5 | (1-benzoyl-6-chloro-5-methoxy-2-methyl-1H-indol-3-yl)acetic acid | <1 | |
| 6 | (1-benzoyl-6-fluoro-5-hydroxy-2-methyl-1H-indol-3-yl)acetic acid | 10-50 | 1-10 |
| 7 | (1-benzyl-5-fluoro-2-methyl-1H-indol-3-yl)acetic acid | <1 | |
| 8 | (1-benzyl-5-hydroxy-2-methyl-1H-indol-3-yl)acetic acid | 10-50 | 1-10 |
| 9 | (1-benzyl-6-chloro-5-methoxy-2-methyl-1H-indol-3-yl)acetic acid | 1-10 | |
| 10 | (1-methyl-1H-indol-3-yl)(oxo)acetic acid | <1 | |
| 11 | (2E)-2-[4-(dimethylamino)benzylidene]-1-benzothiophen-3(2H)-one | <1 | |
| 12 | (2E)-3-(1H-indol-3-yl)acrylic acid | 1-10 | |
| 13 | (2E)-3-{5-chloro-2-methyl-1-[3-(trifluoromethoxy)benzyl]-1H-indol-3-yl}acrylic acid | <1 | |
| 14 | (2E)-3-{5-methoxy-2-methyl-1-[3-(trifluoromethoxy)benzyl]-1H-indol-3-yl}acrylic acid | <1 | |
| 15 | (2S)-indoline-2-carboxylic acid | 10-50 | |
| 16 | (2Z)-2-(2-hydroxy-5-methylbenzylidene)-1-benzothiophen-3(2H)-one | <1 | |
| 17 | (2Z)-2-(2-thienylmethylene)-2,3-dihydro-1-benzofuran-3-ol | <1 | |
| 18 | (3S)-2,3,4,9-tetrahydro-1H-b-carboline-3-carboxylic acid | <1 | |
| 19 | (3Z)-5-ethoxy-1H-indole-2,3-dione 3-oxime | <1 | |
| 20 | (4Z)-4-(hydroxyimino)-4,5,6,7-tetrahydro-1-benzofuran-2-carboxylic acid | <1 | |
| 21 | (5-bromo-1H-indol-3-yl)acetic acid | 1-10 | |
| 22 | (6-chloro-2-methyl-1H-indol-3-yl)acetic acid | <1 | |
| 23 | (5-fluoro-2-methyl-1H-indol-3-yl)acetic acid | <1 | |

FIG. 12B

| Row | IUPAC Name | DAO Activity Assay % Inhibition at 10uM | DAO IC50 (uM) |
|---|---|---|---|
| 24 | (5-hydroxy-1H-indol-3-yl)acetic acid | 50-100 | 1-10 |
| 25 | (5-methoxy-1H-indol-3-yl)acetic acid | <1 | |
| 26 | (5-methyl-1-benzothien-3-yl)acetic acid | <1 | |
| 27 | (6-chloro-1-{[(4-chlorophenyl)amino]carbonyl}-5-methoxy-2-methyl-1H-indol-3-yl)acetic acid | <1 | |
| 28 | (6-chloro-5-methoxy-2-methyl-1-{4-[(trifluoromethyl)thio]benzoyl}-1H-indol-3-yl)acetic acid | <1 | |
| 29 | (6-chloro-5-methoxy-2-methyl-1-{4-[(trifluoromethyl)thio]benzyl}-1H-indol-3-yl)acetic acid | <1 | |
| 30 | (6-chloro-5-methoxy-2-methyl-1H-indol-3-yl)acetic acid | <1 | |
| 31 | (6-fluoro-5-hydroxy-2-methyl-1-{4-[(trifluoromethyl)thio]benzoyl}-1H-indol-3-yl)acetic acid | 10-50 | |
| 32 | (6-fluoro-5-methoxy-2-methyl-1-{4-[(trifluoromethyl)thio]benzoyl}-1H-indol-3-yl)acetic acid | <1 | |
| 33 | (6-fluoro-5-methoxy-2-methyl-1-{4-[(trifluoromethyl)thio]benzyl}-1H-indol-3-yl)acetic acid | <1 | |
| 34 | [1-(1,3-benzothiazol-2-ylmethyl)-4-chloro-5-methoxy-2-methyl-1H-indol-3-yl]acetic acid | 1-10 | |
| 35 | [1-(1,3-benzothiazol-2-ylmethyl)-5-fluoro-2-methyl-1H-indol-3-yl]acetic acid | <1 | |
| 36 | [1-(1,3-benzothiazol-2-ylmethyl)-6-chloro-2,5-dimethyl-1H-indol-3-yl]acetic acid | <1 | |
| 37 | [1-(1,3-benzothiazol-2-ylmethyl)-6-chloro-5-methoxy-2-methyl-1H-indol-3-yl]acetic acid | <1 | |
| 38 | [1-(1,3-benzothiazol-2-ylmethyl)-6-fluoro-5-methoxy-2-methyl-1H-indol-3-yl]acetic acid | <1 | |
| 39 | [1-(1,3-benzoxazol-2-ylmethyl)-6-chloro-5-methoxy-2-methyl-1H-indol-3-yl]acetic acid | <1 | |
| 40 | [1-(2,3-dichlorobenzoyl)-5-hydroxy-2-methyl-1H-indol-3-yl]acetic acid | <1 | |
| 41 | [1-(2,3-dichlorobenzoyl)-5-methoxy-2-methyl-1H-indol-3-yl]acetic acid | <1 | |
| 42 | [1-(2,4-dichlorobenzoyl)-5-hydroxy-2-methyl-1H-indol-3-yl]acetic acid | <1 | |
| 43 | [1-(2-chlorobenzyl)-6-fluoro-5-methoxy-2-methyl-1H-indol-3-yl]acetic acid | 10-50 | |
| 44 | [1-(3,4-dichlorobenzoyl)-5-hydroxy-2-methyl-1H-indol-3-yl]acetic acid | 10-50 | |
| 45 | [1-(3,4-dichlorobenzoyl)-5-methoxy-2-methyl-1H-indol-3-yl]acetic acid | <1 | |
| 46 | [1-(3,4-difluorobenzoyl)-5-hydroxy-2-methyl-1H-indol-3-yl]acetic acid | 10-50 | |

FIG. 12C

| Row | IUPAC Name | DAO Activity Assay % Inhibition at 10uM | DAO IC50 (uM) |
|---|---|---|---|
| 47 | [1-(3,4-difluorobenzoyl)-5-methoxy-2-methyl-1H-indol-3-yl]acetic acid | <1 | |
| 48 | [1-(3-chlorobenzoyl)-5-hydroxy-2-methyl-1H-indol-3-yl]acetic acid | 10-50 | |
| 49 | [1-(3-chlorobenzoyl)-5-methoxy-2-methyl-1H-indol-3-yl]acetic acid | <1 | |
| 50 | [1-(4-bromobenzoyl)-6-fluoro-5-hydroxy-2-methyl-1H-indol-3-yl]acetic acid | <1 | |
| 51 | [1-(4-bromobenzoyl)-6-fluoro-5-methoxy-2-methyl-1H-indol-3-yl]acetic acid | 1-10 | |
| 52 | [1-(4-bromobenzyl)-4,6-difluoro-5-hydroxy-2-methyl-1H-indol-3-yl]acetic acid | 10-50 | 1-10 |
| 53 | [1-(4-bromobenzoyl)-4,6-difluoro-5-methoxy-2-methyl-1H-indol-3-yl]acetic acid | <1 | |
| 54 | [1-(4-bromobenzyl)-5-hydroxy-2-methyl-1H-indol-3-yl]acetic acid | 10-50 | 1-10 |
| 55 | [1-(4-bromobenzyl)-5-methoxy-2-methyl-1H-indol-3-yl]acetic acid | <1 | |
| 56 | [1-(4-bromobenzyl)-6-fluoro-5-methoxy-2-methyl-1H-indol-3-yl]acetic acid | <1 | |
| 57 | [1-(4-chlorobenzoyl)-4,6-difluoro-5-hydroxy-2-methyl-1H-indol-3-yl]acetic acid | <1 | |
| 58 | [1-(4-chlorobenzoyl)-4-fluoro-5-hydroxy-2-methyl-1H-indol-3-yl]acetic acid | 10-50 | 1-10 |
| 59 | [1-(4-chlorobenzoyl)-4-fluoro-5-methoxy-2-methyl-1H-indol-3-yl]acetic acid | <1 | |
| 60 | [1-(4-chlorobenzoyl)-5-hydroxy-2-methyl-1H-indol-3-yl]acetic acid | 10-50 | |
| 61 | [1-(4-chlorobenzoyl)-5-methoxy-2-methyl-1H-indol-3-yl]acetic acid | <1 | |
| 62 | [1-(4-chlorobenzoyl)-6-fluoro-5-hydroxy-2-methyl-1H-indol-3-yl]acetic acid | 10-50 | |
| 63 | [1-(4-chlorobenzoyl)-6-fluoro-5-methoxy-2-methyl-1H-indol-3-yl]acetic acid | <1 | |
| 64 | [1-(4-chlorobenzyl)-5-hydroxy-2-methyl-1H-indol-3-yl]acetic acid | 10-50 | 1-10 |
| 65 | [1-(4-chlorobenzyl)-5-methoxy-2-methyl-1H-indol-3-yl]acetic acid | <1 | |
| 66 | [1-(4-cyanobenzoyl)-5-methoxy-2-methyl-1H-indol-3-yl]acetic acid | <1 | |
| 67 | [1-(4-ethylbenzoyl)-5-methoxy-2-methyl-1H-indol-3-yl]acetic acid | <1 | |
| 68 | [1-(4-fluorobenzoyl)-5-hydroxy-2-methyl-1H-indol-3-yl]acetic acid | 10-50 | |
| 69 | [1-(4-fluorobenzoyl)-5-methoxy-2-methyl-1H-indol-3-yl]acetic acid | <1 | |

FIG. 12D

| Row | IUPAC Name | DAO Activity Assay % Inhibition at 10uM | DAO IC50 (uM) |
|---|---|---|---|
| 70 | [1-(4-fluorobenzyl)-5-methoxy-2-methyl-1H-indol-3-yl]acetic acid | <1 | |
| 71 | [1-(4-tert-butylbenzyl)-6-chloro-5-methoxy-2-methyl-1H-indol-3-yl]acetic acid | <1 | |
| 72 | [1-(biphenyl-4-ylmethyl)-6-chloro-5-methoxy-2-methyl-1H-indol-3-yl]acetic acid | <1 | |
| 73 | [1-(cyclohex-1-en-1-ylcarbonyl)-6-fluoro-5-methoxy-2-methyl-1H-indol-3-yl]acetic acid | <1 | |
| 74 | [1-(cyclohexylcarbonyl)-5-hydroxy-2-methyl-1H-indol-3-yl]acetic acid | <1 | |
| 75 | [1-(cyclohexylcarbonyl)-5-methoxy-2-methyl-1H-indol-3-yl]acetic acid | <1 | |
| 76 | [1-(cyclohexylcarbonyl)-6-fluoro-5-methoxy-2-methyl-1H-indol-3-yl]acetic acid | <1 | |
| 77 | [1-(tert-butoxycarbonyl)-1H-indol-2-yl]boronic acid | <1 | |
| 78 | [3-(1,3-benzothiazol-2-ylmethyl)-1H-indol-1-yl]acetic acid | 1-10 | |
| 79 | [4-chloro-1-(4-chlorobenzoyl)-5-methoxy-2-methyl-1H-indol-3-yl]acetic acid | <1 | |
| 80 | [4-chloro-1-(4-chlorobenzoyl)-2,5-dimethyl-1H-indol-3-yl]acetic acid | <1 | |
| 81 | [5-fluoro-1-(4-fluorobenzyl)-2-methyl-1H-indol-3-yl]acetic acid | <1 | |
| 82 | [5-hydroxy-2-methyl-1-(3-methylbenzoyl)-1H-indol-3-yl]acetic acid | <1 | |
| 83 | [5-hydroxy-2-methyl-1-(3-phenylprop-2-ynoyl)-1H-indol-3-yl]acetic acid | 1-10 | |
| 84 | [5-hydroxy-2-methyl-1-(4-methylbenzoyl)-1H-indol-3-yl]acetic acid | 10-50 | |
| 85 | [5-hydroxy-2-methyl-1-(piperidin-1-ylcarbonyl)-1H-indol-3-yl]acetic acid | 10-50 | |
| 86 | [5-methoxy-1-(4-methoxybenzyl)-2-methyl-1H-indol-3-yl]acetic acid | <1 | |
| 87 | [5-methoxy-2-methyl-1-(piperidin-1-ylcarbonyl)-1H-indol-3-yl]acetic acid | <1 | |
| 88 | [6-chloro-1-(2,4-dichlorobenzyl)-5-methoxy-2-methyl-1H-indol-3-yl]acetic acid | <1 | |
| 89 | [6-chloro-1-(2,5-dichlorobenzyl)-5-methoxy-2-methyl-1H-indol-3-yl]acetic acid | <1 | |
| 90 | [6-chloro-1-(2,6-dichlorobenzyl)-5-methoxy-2-methyl-1H-indol-3-yl]acetic acid | <1 | |
| 91 | [6-chloro-1-(3,5-difluorobenzyl)-5-methoxy-2-methyl-1H-indol-3-yl]acetic acid | <1 | |
| 92 | [6-chloro-1-(3-chlorobenzoyl)-5-methoxy-2-methyl-1H-indol-3-yl]acetic acid | <1 | |

FIG. 12E

| Row | IUPAC Name | DAO Activity Assay % Inhibition at 10uM | DAO IC50 (uM) |
|---|---|---|---|
| 93 | [6-chloro-1-(3-chlorobenzyl)-2,5-dimethyl-1H-indol-3-yl]acetic acid | 1-10 | |
| 94 | [6-chloro-1-(3-chlorobenzyl)-5-fluoro-2-methyl-1H-indol-3-yl]acetic acid | 1-10 | |
| 95 | [6-chloro-1-(3-chlorobenzyl)-5-methoxy-2-methyl-1H-indol-3-yl]acetic acid | <1 | |
| 96 | [6-chloro-1-(3-cyanobenzyl)-5-methoxy-2-methyl-1H-indol-3-yl]acetic acid | <1 | |
| 97 | [6-chloro-1-(3-fluorobenzyl)-5-methoxy-2-methyl-1H-indol-3-yl]acetic acid | <1 | |
| 98 | [6-chloro-1-(4-chloro-2-fluorobenzyl)-5-methoxy-2-methyl-1H-indol-3-yl]acetic acid | <1 | |
| 99 | [6-chloro-1-(4-chlorobenzoyl)-5-fluoro-methyl-1H-indol-3-yl]acetic acid | <1 | |
| 100 | [6-chloro-1-(4-chlorobenzoyl)-5-hydroxy-2-methyl-1H-indol-3-yl]acetic acid | <1 | |
| 101 | [6-chloro-1-(4-chlorobenzoyl)-5-methoxy-2-methyl-1H-indol-3-yl]acetic acid | <1 | |
| 102 | [6-chloro-1-(4-chlorobenzyl)-2,5-dimethyl-1H-indol-3-yl]acetic acid | <1 | |
| 103 | [6-chloro-1-(4-chlorobenzyl)-5-hydroxy-2-methyl-1H-indol-3-yl]acetic acid | 50-100 | 1-10 |
| 104 | [6-chloro-1-(4-chlorobenzyl)-5-methoxy-2-methyl-1H-indol-3-yl]acetic acid | <1 | |
| 105 | [6-chloro-1-(4-chlorophenyl)-5-methoxy-2-methyl-1H-indol-3-yl]acetic acid | 10-50 | |
| 106 | [6-chloro-1-(4-fluorobenzoyl)-5-methoxy-2-methyl-1H-indol-3-yl]acetic acid | <1 | |
| 107 | [6-chloro-1-(4-fluorobenzyl)-5-methoxy-2-methyl-1H-indol-3-yl]acetic acid | 10-50 | |
| 108 | [6-chloro-5-methoxy-1-(3-methoxybenzyl)-2-methyl-1H-indol-3-yl]acetic acid | <1 | |
| 109 | [6-chloro-5-methoxy-2-methyl-1-(2-naphthylmethyl)-1H-indol-3-yl]acetic acid | <1 | |
| 110 | [6-chloro-5-methoxy-2-methyl-1-(3-methylbenzyl)-1H-indol-3-yl]acetic acid | <1 | |
| 111 | [6-chloro-5-methoxy-2-methyl-1-(3-nitrobenzyl)-1H-indol-3-yl]acetic acid | <1 | |
| 112 | [6-chloro-5-methoxy-2-methyl-1-(pyridin-2-ylmethyl)-1H-indol-3-yl]acetic acid | <1 | |
| 113 | [6-chloro-5-methoxy-2-methyl-1-(quinolin-2-ylmethyl)-1H-indol-3-yl]acetic acid | <1 | |
| 114 | [6-fluoro-1-(4-fluorobenzoyl)-5-hydroxy-2-methyl-1H-indol-3-yl]acetic acid | 1-10 | |
| 115 | [6-fluoro-1-(4-fluorobenzoyl)-5-methoxy-2-methyl-1H-indol-3-yl]acetic acid | 10-50 | |

FIG. 12F

| Row | IUPAC Name | DAO Activity Assay % Inhibition at 10uM | DAO IC50 (uM) |
|---|---|---|---|
| 116 | [6-fluoro-1-(4-fluorobenzyl)-5-methoxy-2-methyl-1H-indol-3-yl]acetic acid | 10-50 | |
| 117 | [6-fluoro-5-hydroxy-2-methyl-1-(2-thienylcarbonyl)-1H-indol-3-yl]acetic acid | 10-50 | 10-50 |
| 118 | [6-fluoro-5-hydroxy-2-methyl-1-(4-methylbenzoyl)-1H-indol-3-yl]acetic acid | 10-50 | |
| 119 | [6-fluoro-5-methoxy-2-methyl-1-(2-thienylcarbonyl)-1H-indol-3-yl]acetic acid | <1 | |
| 120 | [6-fluoro-5-methoxy-2-methyl-1-(4-methylbenzoyl)-1H-indol-3-yl]acetic acid | <1 | |
| 121 | [1-[(4-chlorophenyl)sulfonyl]-5-hydroxy-2-methyl-1H-indol-3-yl]acetic acid | <1 | |
| 122 | [1-[(4-chlorophenyl)sulfonyl]-5-methoxy-2-methyl-1H-indol-3-yl]acetic acid | <1 | |
| 123 | [1-[(4-chlorophenyl)sulfonyl]-6-fluoro-5-methoxy-2-methyl-1H-indol-3-yl]acetic acid | <1 | |
| 124 | [1-[(5-chloro-2-thienyl)carbonyl]-5-hydroxy-2-methyl-1H-indol-3-yl]acetic acid | 10-50 | 10-50 |
| 125 | [1-[(5-chloro-2-thienyl)carbonyl]-5-methoxy-2-methyl-1H-indol-3-yl]acetic acid | <1 | |
| 126 | [1-[(5-chloro-2-thienyl)carbonyl]-6-fluoro-5-hydroxy-2-methyl-1H-indol-3-yl]acetic acid | 10-50 | |
| 127 | [1-[(5-chloro-2-thienyl)carbonyl]-6-fluoro-5-methoxy-2-methyl-1H-indol-3-yl]acetic acid | <1 | |
| 128 | [1-[(5-chloro-2-thienyl)methyl]-5-fluoro-2-methyl-1H-indol-3-yl]acetic acid | 1-10 | |
| 129 | [1-[(5-chloro-2-thienyl)methyl]-5-hydroxy-2-methyl-1H-indol-3-yl]acetic acid | 50-100 | 1-10 |
| 130 | [1-[(5-chloro-2-thienyl)methyl]-5-methoxy-2-methyl-1H-indol-3-yl]acetic acid | 1-10 | |
| 131 | [1-[(6-chloropyridin-3-yl)carbonyl]-5-hydroxy-2-methyl-1H-indol-3-yl]acetic acid | <1 | |
| 132 | [1-[(6-chloropyridin-3-yl)carbonyl]-5-methoxy-2-methyl-1H-indol-3-yl]acetic acid | <1 | |
| 133 | [1-[4-(difluoromethoxy)benzoyl]-5-hydroxy-2-methyl-1H-indol-3-yl]acetic acid | <1 | |
| 134 | [1-[4-(difluoromethoxy)benzoyl]-5-methoxy-2-methyl-1H-indol-3-yl]acetic acid | <1 | |
| 135 | [1-[4-(difluoromethoxy)benzoyl]-6-fluoro-5-hydroxy-2-methyl-1H-indol-3-yl]acetic acid | <1 | |
| 136 | [1-[4-(difluoromethoxy)benzoyl]-6-fluoro-5-methoxy-2-methyl-1H-indol-3-yl]acetic acid | <1 | |
| 137 | [2-chloro-1-[3-(trifluoromethoxy)benzyl]-1H-indol-3-yl]acetic acid | <1 | |
| 138 | [2-oxo-1-[3-(trifluoromethoxy)benzyl]-2,3-dihydro-1H-indol-3-yl]acetic acid | <1 | |

FIG. 12G

| Row | IUPAC Name | DAO Activity Assay % Inhibition at 10uM | DAO IC50 (uM) |
|---|---|---|---|
| 139 | {5,6-dichloro-2-methyl-1-[3-(trifluoromethoxy)benzyl]-1H-indol-3-yl}acetic acid | <1 | |
| 140 | {5-chloro-2-methyl-1-[3-(trifluoromethoxy)benzyl]-1H-indol-3-yl}acetic acid | <1 | |
| 141 | {5-chloro-2-methyl-1-[3-(trifluoromethyl)benzyl]-1H-indol-3-yl}acetic acid | <1 | |
| 142 | {5-fluoro-2-methyl-1-[3-(trifluoromethoxy)benzyl]-1H-indol-3-yl}acetic acid | <1 | |
| 143 | {5-fluoro-2-methyl-1-[4-(trifluoromethoxy)benzyl]-1H-indol-3-yl}acetic acid | <1 | |
| 144 | {5-hydroxy-2-methyl-1-[(2E)-3-phenylprop-2-enoyl]-1H-indol-3-yl}acetic acid | <1 | |
| 145 | {5-hydroxy-2-methyl-1-[4-(trifluoromethoxy)benzoyl]-1H-indol-3-yl}acetic acid | 10-50 | |
| 146 | {5-hydroxy-2-methyl-1-[4-(trifluoromethoxy)benzyl]-1H-indol-3-yl}acetic acid | 10-50 | 1-10 |
| 147 | {5-hydroxy-2-methyl-1-[4-(trifluoromethyl)benzoyl]-1H-indol-3-yl}acetic acid | <1 | |
| 148 | {5-methoxy-2-methyl-1-[(2E)-3-phenylprop-2-enoyl]-1H-indol-3-yl}acetic acid | <1 | |
| 149 | {5-methoxy-2-methyl-1-[4-(trifluoromethoxy)benzoyl]-1H-indol-3-yl}acetic acid | <1 | |
| 150 | {5-methoxy-2-methyl-1-[4-(trifluoromethoxy)benzyl]-1H-indol-3-yl}acetic acid | <1 | |
| 151 | {5-methoxy-2-methyl-1-[4-(trifluoromethyl)benzoyl]-1H-indol-3-yl}acetic acid | 10-50 | |
| 152 | {6-chloro-1-[(4-chlorophenoxy)carbonyl]-5-methoxy-2-methyl-1H-indol-3-yl}acetic acid | <1 | |
| 153 | {6-chloro-1-[(5-chloro-2-thienyl)carbonyl]-5-fluoro-2-methyl-1H-indol-3-yl}acetic acid | <1 | |
| 154 | {6-chloro-1-[(5-chloro-2-thienyl)carbonyl]-5-hydroxy-2-methyl-1H-indol-3-yl}acetic acid | 10-50 | |
| 155 | {6-chloro-1-[(5-chloro-2-thienyl)carbonyl]-5-methoxy-2-methyl-1H-indol-3-yl}acetic acid | <1 | |
| 156 | {6-chloro-1-[(5-chloro-2-thienyl)methyl]-5-methoxy-2-methyl-1H-indol-3-yl}acetic acid | <1 | |
| 157 | {6-chloro-1-[(6-chloropyridin-3-yl)methyl]-5-methoxy-2-methyl-1H-indol-3-yl}acetic acid | <1 | |
| 158 | {6-chloro-1-[4-(difluoromethoxy)benzoyl]-5-methoxy-2-methyl-1H-indol-3-yl}acetic acid | <1 | |
| 159 | {6-chloro-2,5-dimethyl-1-[3-(trifluoromethoxy)benzyl]-1H-indol-3-yl}acetic acid | 1-10 | |
| 160 | {6-chloro-2,5-dimethyl-1-[3-(trifluoromethyl)benzyl]-1H-indol-3-yl}acetic acid | 1-10 | |
| 161 | {6-chloro-5-hydroxy-2-methyl-1-[4-(trifluoromethoxy)benzoyl]-1H-indol-3-yl}acetic acid | 10-50 | |

FIG. 12H

| Row | IUPAC Name | DAO Activity Assay % Inhibition at 10uM | DAO IC50 (uM) |
|---|---|---|---|
| 162 | {6-chloro-5-hydroxy-2-methyl-1-[4-(trifluoromethoxy)benzyl]-1H-indol-3-yl}acetic acid | 10-50 | 10-50 |
| 163 | {6-chloro-5-methoxy-2-methyl-1-[(2-methyl-1,3-thiazol-4-yl)methyl]-1H-indol-3-yl}acetic acid | <1 | |
| 164 | {6-chloro-5-methoxy-2-methyl-1-[3-(trifluoromethoxy)benzyl]-1H-indol-3-yl}acetic acid | <1 | |
| 165 | {6-chloro-5-methoxy-2-methyl-1-[3-(trifluoromethyl)benzyl]-1H-indol-3-yl}acetic acid | 1-10 | |
| 166 | {6-chloro-5-methoxy-2-methyl-1-[4-(methylsulfonyl)benzyl]-1H-indol-3-yl}acetic acid | <1 | |
| 167 | {6-chloro-5-methoxy-2-methyl-1-[4-(trifluoromethoxy)benzoyl]-1H-indol-3-yl}acetic acid | <1 | |
| 168 | {6-chloro-5-methoxy-2-methyl-1-[4-(trifluoromethoxy)benzyl]-1H-indol-3-yl}acetic acid | <1 | |
| 169 | {6-fluoro-5-hydroxy-2-methyl-1-[(5-methyl-2-thienyl)carbonyl]-1H-indol-3-yl}acetic acid | 10-50 | |
| 170 | {6-fluoro-5-hydroxy-2-methyl-1-[4-(methylthio)benzoyl]-1H-indol-3-yl}acetic acid | 10-50 | 50-100 |
| 171 | {6-fluoro-5-hydroxy-2-methyl-1-[4-(trifluoromethoxy)benzoyl]-1H-indol-3-yl}acetic acid | 10-50 | |
| 172 | {6-fluoro-5-hydroxy-2-methyl-1-[4-(trifluoromethyl)benzoyl]-1H-indol-3-yl}acetic acid | <1 | |
| 173 | {6-fluoro-5-methoxy-2-methyl-1-[(5-methyl-2-thienyl)carbonyl]-1H-indol-3-yl}acetic acid | <1 | |
| 174 | {6-fluoro-5-methoxy-2-methyl-1-[4-(methylthio)benzoyl]-1H-indol-3-yl}acetic acid | <1 | |
| 175 | {6-fluoro-5-methoxy-2-methyl-1-[4-(trifluoromethoxy)benzoyl]-1H-indol-3-yl}acetic acid | <1 | |
| 176 | {6-fluoro-5-methoxy-2-methyl-1-[4-(trifluoromethyl)benzoyl]-1H-indol-3-yl}acetic acid | <1 | |
| 177 | 1-(2,3-dihydro-1-benzofuran-2-yl)-N,N-dimethylmethanamine hydrochloride | <1 | |
| 178 | 1-(4,5,6,7-tetrahydro-1-benzothien-2-ylcarbonyl)indoline | <1 | |
| 179 | 1-(phenylsulfonyl)-1H-indole-3-carbaldehyde | <1 | |
| 180 | 1,2,3,4-tetrahydroisoquinoline-3-carboxylic acid hydrochloride | <1 | |
| 181 | 1,2,3,4-tetrahydroquinolin-8-ol | 50-100 | 1-10 |
| 182 | 1-[2-(dimethylamino)ethyl]-1H-indole-2-carboxylic acid hydrochloride | <1 | |
| 183 | 1-benzofuran-2,3-dicarboxylic acid | 10-50 | |
| 184 | 1-benzofuran-2-carboxylic acid | 50-100 | 1-10 |

FIG. 12I

| Row | IUPAC Name | DAO Activity Assay % Inhibition at 10uM | DAO IC50 (uM) |
|---|---|---|---|
| 185 | 1-benzofuran-2-ylboronic acid | <1 | |
| 186 | 1-benzothien-2-ylboronic acid | <1 | |
| 187 | 1-benzothiophene-2-carboxylic acid | 10-50 | |
| 188 | 1-benzyl-5-methoxy-2-methyl-1H-indole-3-carboxylic acid | <1 | |
| 189 | 1H-benzimidazole-2-sulfonic acid | <1 | |
| 190 | 1H-imidazole-2-carboxylic acid | 10-50 | >100 |
| 191 | 1H-indol-2-yl(pyridin-4-yl)methanol | 10-50 | |
| 192 | 1H-indol-2-ylmethanol | <1 | >100 |
| 193 | 1H-indol-3-ylacetic acid | <1 | |
| 194 | 1H-indole-2-carboxylic acid | 50-100 | <1 |
| 195 | 1H-indole-3-carboxylic acid | <1 | |
| 196 | 1H-indole-5-carboxylic acid | <1 | |
| 197 | 1H-indole-6-carboxylic acid | <1 | |
| 198 | 1H-pyrrole-2-carboxylic acid | 50-100 | 1-10 |
| 199 | 1-methyl-1H-indole-2-carboxylic acid | <1 | |
| 200 | 1-methyl-1H-pyrrole-2-carboxylic acid | <1 | |
| 201 | 2-(3-hydroxybenzyl)butanoic acid | <1 | |
| 202 | 2-(trimethylsilyl)ethyl (6-fluoro-5-methoxy-2-methyl-1H-indol-3-yl)acetate | <1 | |
| 203 | 2-(trimethylsilyl)ethyl [1-(4-bromobenzoyl)-6-fluoro-5-methoxy-2-methyl-1H-indol-3-yl]acetate | <1 | |
| 204 | 2-(trimethylsilyl)ethyl {1-[(5-chloro-2-thienyl)carbonyl]-6-fluoro-5-methoxy-2-methyl-1H-indol-3-yl}acetate | <1 | |
| 205 | 2,3,4,9-tetrahydro-1H-carbazole-6-carboxylic acid | <1 | |
| 206 | 2-[1-(4-chlorobenzoyl)-5-methoxy-2-methyl-1H-indol-3-yl]-N-(2-hydroxyethyl)acetamide | <1 | |
| 207 | 2-[1-(4-chlorobenzoyl)-5-methoxy-2-methyl-1H-indol-3-yl]-N-(2-phenylethyl)acetamide | <1 | |

FIG. 12J

| Row | IUPAC Name | DAO Activity Assay % Inhibition at 10uM | DAO IC50 (uM) |
|---|---|---|---|
| 208 | 2-[1-(4-chlorobenzoyl)-5-methoxy-2-methyl-1H-indol-3-yl]-N-piperidin-1-ylacetamide | <1 | |
| 209 | 2-[1-(4-chlorobenzoyl)-6-fluoro-5-hydroxy-2-methyl-1H-indol-3-yl]acetamide | <1 | |
| 210 | 2-[1-(4-chlorobenzyl)-5-methoxy-2-methyl-1H-indol-3-yl]ethanol | <1 | |
| 211 | 2-[1-(4-chlorobenzyl)-5-methoxy-2-methyl-1H-indol-3-yl]ethyl 4-chlorobenzoate | <1 | |
| 212 | 2-[1-(4-chlorobenzyl)-5-methoxy-2-methyl-1H-indol-3-yl]ethyl acetate | <1 | |
| 213 | 2-{[acetyl(isopropyl)amino]methyl}-6-bromo-4-hydroxy-5-methoxy-1-methyl-1H-indole-3-carboxylic acid | 10-50 | 1-10 |
| 214 | 2-furoic acid | <1 | |
| 215 | 2-hydroxy-3-(1H-indol-3-yl)propanoic acid | <1 | |
| 216 | 2'-hydroxy-3-methylisovaline | <1 | |
| 217 | 2-methyl-5-{[(4-methylphenyl)sulfonyl]amino}-1-benzofuran-3-carboxylic acid | 10-50 | >100 |
| 218 | 2-methylimidazo[1,2-a]pyridine-3-carboxylic acid | <1 | |
| 219 | 3-[(3R)-3-{[(4-fluorophenyl)sulfonyl]amino}-1,2,3,4-tetrahydro-9H-carbazol-9-yl]propanoic acid | <1 | |
| 220 | 3-{[(1E)-{4-(phenylethynyl)phenyl]methylene}amino}-1H-1,2,4-triazole-5-carboxylic acid | <1 | |
| 221 | 3-(1,3-dioxo-1,3-dihydro-2H-isoindol-2-yl)-1H-1,2,4-triazole-5-carboxylic acid | <1 | |
| 222 | 3-(1H-benzimidazol-2-yl)propanoic acid | <1 | |
| 223 | 3-(2-aminoethyl)-5-(aminosulfonyl)-1H-indole-2-carboxylic acid | <1 | |
| 224 | 3-(2-aminoethyl)-5-ethoxy-1H-indole-2-carboxylic acid | <1 | |
| 225 | 3-(2-thienyl)-1H-pyrazole-5-carboxylic acid | 10-50 | |
| 226 | 3-(4-methylphenyl)-1H-pyrazole-5-carboxylic acid | <1 | |
| 227 | 3-(acetylamino)-5-methoxy-1H-indole-2-carboxylic acid | <1 | |
| 228 | 3-(carboxymethyl)-1H-indole-2,5-dicarboxylic acid | <1 | |
| 229 | 3-(carboxymethyl)-1H-indole-2-carboxylic acid | <1 | |
| 230 | 3,5-bis(ethoxycarbonyl)-4-methyl-1H-pyrrole-2-carboxylic acid | <1 | |

FIG. 12K

| Row | IUPAC Name | DAO Activity Assay % Inhibition at 10uM | DAO IC50 (uM) |
|---|---|---|---|
| 231 | 3-[1-(1,3-benzothiazol-2-ylmethyl)-4,6-dichloro-2-methyl-1H-indol-3-yl]propanoic acid | <1 | |
| 232 | 3-[1-(1,3-benzothiazol-2-ylmethyl)-6-chloro-2,5-dimethyl-1H-indol-3-yl]propanoic acid | <1 | |
| 233 | 3-[1-(1,3-benzothiazol-2-ylmethyl)-6-chloro-5-fluoro-2-methyl-1H-indol-3-yl]propanoic acid | 1-10 | |
| 234 | 3-[2-(acetylamino)ethyl]-5-ethoxy-1H-indole-2-carboxylic acid | 1-10 | |
| 235 | 3-[4,6-dichloro-1-(3-chlorobenzyl)-2-methyl-1H-indol-3-yl]propanoic acid | 1-10 | |
| 236 | 3-[6-chloro-1-(3-chlorobenzyl)-5-fluoro-2-methyl-1H-indol-3-yl]propanoic acid | 10-50 | |
| 237 | 3-[6-chloro-1-(4-chlorobenzyl)-5-methoxy-2-methyl-1H-indol-3-yl]propanoic acid | <1 | |
| 238 | 3-anilino-1-benzothiophene-2-carboxylic acid | <1 | |
| 239 | 3-chloro-1-benzothiophene-2-carboxylic acid | <1 | |
| 240 | 3H-benzo[e]indole-2-carboxylic acid | <1 | |
| 241 | 3-methyl-4-oxo-6-(2-thienyl)-4,5,6,7-tetrahydro-1H-indole-2-carboxylic acid | <1 | |
| 242 | 4-(5-methyl-3-phenylisoxazol-4-yl)benzenesulfonamide | <1 | |
| 243 | 4-(benzyloxy)-1H-indole-2-carboxylic acid | 50-100 | 1-10 |
| 244 | 4,5,6,7-tetrahydro-1,2-benzisoxazole-3-carboxylic acid | <1 | |
| 245 | 4-[(dimethylamino)methyl]-3-[hydroxy(phenyl)methyl]-1-benzofuran-5-ol | <1 | |
| 246 | 4-[3-(4-chlorophenyl)propyl]-1H-pyrrole-2-carboxylic acid | 10-50 | 1-10 |
| 247 | 4-[4-(methylsulfonyl)phenyl]-3-phenylfuran-2(5H)-one | <1 | |
| 248 | 4-[5-(4-methylphenyl)-3-(trifluoromethyl)-1H-pyrazol-1-yl]benzenesulfonamide | <1 | |
| 249 | 4-chloro-1H-pyrazole-5-carboxylic acid | 10-50 | 1-10 |
| 250 | 4-oxo-4,5,6,7-tetrahydro-1-benzofuran-2-carboxylic acid | <1 | |
| 251 | 4-oxo-4,5,6,7-tetrahydro-1-benzofuran-3-carboxylic acid | <1 | |
| 252 | 5-(trifluoromethoxy)-1H-indole-2-carboxylic acid | <1 | |
| 253 | 5,6,7-trimethoxy-1H-indole-2-carboxylic acid | 1-10 | |

FIG. 12L

| Row | IUPAC Name | DAO Activity Assay % Inhibition at 10uM | DAO IC50 (uM) |
|---|---|---|---|
| 254 | 5,7-dichloro-8-hydroxyquinolin-2(1H)-one | <1 | |
| 255 | 5-{[(4-fluorophenyl)sulfonyl]amino}-2-methyl-1-benzofuran-3-carboxylic acid | <1 | |
| 256 | 5-butyl-1H-indole-2-carboxylic acid | <1 | |
| 257 | 5-chloro-1H-indole-2-carboxylic acid | 50-100 | 1-10 |
| 258 | 5-chloro-3-phenyl-1-benzofuran-2(3H)-one | 10-50 | 10-50 |
| 259 | 5-ethyl-1H-indole-2-carboxylic acid | 1-10 | 1-10 |
| 260 | 5-ethyl-3-phenyl-1-benzofuran-2(3H)-one | 10-50 | |
| 261 | 5-fluoro-1-benzothiophene-2-carboxylic acid | <1 | |
| 262 | 5-fluoro-1H-indole-2-carboxylic acid | 50-100 | <1 |
| 263 | 5-fluoro-2-methyl-1H-indole-3-carbaldehyde | <1 | |
| 264 | 5-hydroxy-1-(4-methoxyphenyl)-2-methyl-1H-indole-3-carboxylic acid | 10-50 | 1-10 |
| 265 | 5-hydroxy-1H-indole-2-carboxylic acid | 50-100 | 1-10 |
| 266 | 5-hydroxy-1H-indole-3-carboxylic acid | 50-100 | 1-10 |
| 267 | 5-hydroxy-2-methylnaphtho[1,2-b]furan-3-carboxylic acid | 50-100 | 1-10 |
| 268 | 5-isopropyl-1H-indole-2-carboxylic acid | <1 | |
| 269 | 5-methoxy-1H-indole-2-carboxylic acid | <1 | |
| 270 | 5-methoxy-2-methyl-1-benzofuran-3-carboxylic acid | <1 | |
| 271 | 5-methyl-1-phenyl-1H-pyrazole-3-carboxylic acid | <1 | |
| 272 | 5-methylthiophene-2-carboxylic acid | 50-100 | 1-10 |
| 273 | 5-oxo-L-proline | <1 | |
| 274 | 5-phenyl-2-furoic acid | <1 | |
| 275 | 5-sec-butyl-1H-indole-2-carboxylic acid | <1 | |
| 276 | 5-tert-butyl-1H-indole-2-carboxylic acid | <1 | |

FIG. 12M

| Row | IUPAC Name | DAO Activity Assay % Inhibition at 10uM | DAO IC50 (uM) |
|---|---|---|---|
| 277 | 6-benzyl-7-hydroxy-5-methyl[1,2,4]triazolo[1,5-a]pyrimidine-2-carboxylic acid | <1 | |
| 278 | 6-chloro-2,3-dimethyl-1-[3-(trifluoromethoxy)benzyl]-1H-indole acetate | <1 | |
| 279 | 6-ethyl-1H-indole-2-carboxylic acid | <1 | |
| 280 | 6-hydroxy-3-methyl-1-benzofuran-2-carboxylic acid | 10-50 | 1-10 |
| 281 | 6-isopropyl-1H-indole-2-carboxylic acid | <1 | |
| 282 | 7-hydroxy-1-benzothiophene-2-carboxylic acid | 10-50 | |
| 283 | 7-methoxy-1-benzothiophene-2-carboxylic acid | <1 | |
| 284 | 9-bromo-6-hydroxy-3a,4,5,9b-tetrahydro-3H-cyclopenta[c]quinoline-4-carboxylic acid | 10-50 | 1-10 |
| 285 | 9-nitro-4-propyl-3a,4,5,9b-tetrahydro-3H-cyclopenta[c]quinoline-6-carboxylic acid | 1-10 | |
| 286 | a-(hydroxymethyl)-D-tyrosine | <1 | |
| 287 | a-(hydroxymethyl)phenylalanine | <1 | |
| 288 | butyl [1-(4-chlorobenzoyl)-5-hydroxy-2-methyl-1H-indol-3-yl]acetate | <1 | |
| 289 | ethyl [1-(4-chlorobenzoyl)-5-hydroxy-2-methyl-1H-indol-3-yl]acetate | <1 | |
| 290 | ethyl [1-(4-chlorobenzoyl)-5-methoxy-2-methyl-1H-indol-3-yl]acetate | <1 | |
| 291 | ethyl [1-(4-chlorobenzoyl)-6-fluoro-5-hydroxy-2-methyl-1H-indol-3-yl]acetate | <1 | |
| 292 | ethyl [6-chloro-1-(4-chlorobenzoyl)-5-methoxy-2-methyl-1H-indol-3-yl]acetate | <1 | |
| 293 | ethyl 1-butyl-5-hydroxy-2-methyl-4-[(4-methylpiperazin-1-yl)methyl]-1H-indole-3-carboxylate | 10-50 | 1-10 |
| 294 | ethyl 2-(acetylamino)-7-methoxy-1-benzothiophene-3-carboxylate | <1 | |
| 295 | ethyl 2-methyl-1H-indole-3-carboxylate | <1 | |
| 296 | ethyl 4-({[1-(4-chlorobenzoyl)-6-fluoro-5-hydroxy-2-methyl-1H-indol-3-yl]acetyl}amino)butanoate | <1 | |
| 297 | ethyl 4-[(dimethylamino)methyl]-5-hydroxy-1-(4-methoxyphenyl)-2-methyl-1H-indole-3-carboxylate hydrochloride | | 1-10 |
| 298 | ethyl 4-[(dimethylamino)methyl]-5-hydroxy-1,2-dimethyl-1H-indole-3-carboxylate hydrochloride | 10-50 | 10-50 |
| 299 | ethyl 4-amino-3-(aminocarbonyl)isothiazole-5-carboxylate | 1-10 | |

FIG. 12N

| Row | IUPAC Name | DAO Activity Assay % Inhibition at 10uM | DAO IC50 (uM) |
|---|---|---|---|
| 300 | ethyl 5-hydroxy-2-methyl-1H-indole-3-carboxylate | 10-50 | 1-10 |
| 301 | ethyl 7-methoxy-1H-indole-2-carboxylate | <1 | |
| 302 | ethyl N-{[1-(4-chlorobenzoyl)-5-methoxy-2-methyl-1H-indol-3-yl]acetyl}glycinate | <1 | |
| 303 | ethyl N-{[1-(4-chlorobenzoyl)-6-fluoro-5-hydroxy-2-methyl-1H-indol-3-yl]acetyl}glycinate | 1-10 | |
| 304 | ethyl N-{[6-chloro-1-(4-chlorobenzoyl)-5-methoxy-2-methyl-1H-indol-3-yl]acetyl}glycinate | <1 | |
| 305 | indoline-2-carboxylic acid | 10-50 | 1-10 |
| 306 | isopropyl [1-(4-chlorobenzoyl)-6-fluoro-5-hydroxy-2-methyl-1H-indol-3-yl]acetate | 10-50 | |
| 307 | methyl [(3-nitro-1H-indol-2-yl)thio]acetate | <1 | |
| 308 | methyl [(5-fluoro-3-nitro-1H-indol-2-yl)thio]acetate | <1 | |
| 309 | methyl [1-(4-chlorobenzoyl)-6-fluoro-5-hydroxy-2-methyl-1H-indol-3-yl]acetate | <1 | |
| 310 | methyl [1-(4-chlorobenzoyl)-6-fluoro-5-methoxy-2-methyl-1H-indol-3-yl]acetate | <1 | |
| 311 | methyl [6-chloro-1-(4-chlorobenzoyl)-5-methoxy-2-methyl-1H-indol-3-yl]acetate | <1 | |
| 312 | methyl 1H-indole-3-carboxylate | <1 | |
| 313 | methyl 3-amino-6-methylthieno[2,3-b]pyridine-2-carboxylate | <1 | |
| 314 | methyl 4,6-dimethoxy-1H-indole-2-carboxylate | <1 | |
| 315 | methyl 4-methoxy-1H-indole-2-carboxylate | <1 | |
| 316 | methyl 6-methoxy-1H-indole-2-carboxylate | <1 | |
| 317 | methyl N-{[1-(4-chlorobenzoyl)-6-fluoro-5-hydroxy-2-methyl-1H-indol-3-yl]acetyl}-b-alaninate | <1 | |
| 318 | N-(1H-indol-3-ylacetyl)-L-alanine | <1 | |
| 319 | N-[3-hydroxy-2-oxo-3-(trifluoromethyl)-2,3-dihydro-1-benzofuran-6-yl]acetamide | <1 | |
| 320 | N-{[1-(4-chlorobenzoyl)-5-methoxy-2-methyl-1H-indol-3-yl]acetyl}glycine | <1 | |
| 321 | N-{[6-chloro-1-(4-chlorobenzoyl)-5-methoxy-2-methyl-1H-indol-3-yl]acetyl}glycine | <1 | |
| 322 | piperidine-2-carboxylic acid | <1 | |

FIG. 12O

| Row | IUPAC Name | DAO Activity Assay % Inhibition at 10uM | DAO IC50 (uM) |
|---|---|---|---|
| 323 | proline | <1 | |
| 324 | propyl (5-hydroxy-2-methyl-1H-indol-3-yl)acetate | 50-100 | 1-10 |
| 325 | propyl [1-(4-chlorobenzoyl)-5-hydroxy-2-methyl-1H-indol-3-yl]acetate | <1 | |
| 326 | propyl [1-(4-chlorobenzoyl)-6-fluoro-5-hydroxy-2-methyl-1H-indol-3-yl]acetate | <1 | |
| 327 | pyridine-2-carboxylic acid | <1 | |
| 328 | quinoline-2,8-diol | 10-50 | 50-100 |
| 329 | sec-butyl [1-(4-chlorobenzoyl)-6-fluoro-5-hydroxy-2-methyl-1H-indol-3-yl]acetate | <1 | |
| 330 | sec-butyl [6-chloro-1-(4-chlorobenzoyl)-5-methoxy-2-methyl-1H-indol-3-yl]acetate | <1 | |
| 331 | sec-butyl [6-chloro-1-[4-(difluoromethoxy)benzoyl]-5-methoxy-2-methyl-1H-indol-3-yl]acetate | <1 | |
| 332 | sodium (5E)-5-[(aminocarbonyl)hydrazono]-1-methyl-6-oxo-2,3,5,6-tetrahydro-1H-indole-2-sulfenate trihydrate | <1 | |
| 333 | sodium 6-methoxy-1,3-benzothiazole-2-carboxylate | <1 | |

FIG. 13A

| Row | IUPAC Name | Pig DAO % Inhibition (10 µM) | Pig DAO IC50 (µM) | Human DAO % Inhibition (10 µM) | Human DAO IC50 (µM) |
|---|---|---|---|---|---|
| 1 | 1-benzyl-5-fluoro-2-methyl-1H-indol-3-yl)acetic acid | 0 | not determined | not determined | not determined |
| 2 | 1-benzyl-5-methoxy-2-methyl-1H-indol-3-yl)acetic acid | 10-50 | not determined | 10-50 | not determined |
| 3 | (2-benzyl-6-chloro-5-methoxy-1H-indol-3-yl)acetic acid | 10-50 | not determined | not determined | not determined |
| 4 | (1E)-1-(1H-indol-2-yl)ethanone oxime | 10-50 | not determined | 1-10 | not determined |
| 5 | 1-methyl-1H-indol-2-yl)acetic acid | 0 | not determined | 0 | not determined |
| 6 | 1(2)-1-(1H-indol-3-yl)acetone oxime | 50-100 | not determined | 0 | not determined |
| 7 | (2E)-3-(1H-indol-3-yl)acrylic acid | 1-10 | not determined | not determined | not determined |
| 8 | (2E)-3-(5-chloro-2-methyl-1H-indol-3-yl)acrylic acid | 0 | not determined | not determined | not determined |
| 9 | (2E)-3-[5-methoxy-2-methyl-1-[3-(trifluoromethoxy)benzyl]-1H-indol-3-yl]acrylic acid | 0 | not determined | not determined | not determined |
| 10 | (2E)-3-(5-dihydroxyphenyl)-1H-indol-3-one oxime | not determined | not determined | 10-50 | not determined |
| 11 | 4-hydroxy-1H-indol-3-yl)acetic acid | not determined | not determined | 0 | not determined |
| 12 | 5-bromo-1H-indol-3-yl)acetic acid | 1-10 | not determined | not determined | not determined |
| 13 | (5-chloro-1H-indol-3-yl)acetic acid | 0 | >100 | not determined | not determined |
| 14 | (5-fluoro-2-methyl-1H-indol-3-yl)acetic acid | not determined | 1-10 | 10-50 | not determined |
| 15 | (5-fluoro-1H-indol-3-yl)acetic acid | 50-100 | not determined | not determined | not determined |
| 16 | (5-hydroxy-1H-indol-3-yl)acetic acid | 0 | not determined | not determined | not determined |
| 17 | (5-methoxy-1H-indol-3-yl)acetic acid | not determined | not determined | not determined | not determined |
| 18 | (5-chloro-5-methoxy-2-methyl-1H-indol-3-yl)acetic acid | 0 | not determined | not determined | not determined |
| 19 | 6-chloro-5-methoxy-2-methyl-1H-indol-3-yl)acetic acid | 1-10 | not determined | not determined | not determined |
| 20 | 8-fluoro-5-methoxy-2-methyl-1-[4-(trifluoromethyl)benzyl]-1H-indol-3-yl)acetic acid | 0 | not determined | not determined | not determined |
| 21 | (1-(1,3-benzothiazol-2-yl)methyl)-4-chloro-5-methoxy-2-methyl-1H-indol-3-yl)acetic acid | 1-10 | not determined | not determined | not determined |
| 22 | (1-(1,3-benzothiazol-2-yl)methyl)-5-fluoro-2-methyl-1H-indol-3-yl)acetic acid | 0 | not determined | not determined | not determined |
| 23 | (1-(1,3-benzothiazol-2-yl)methyl)-6-chloro-2,5-dimethyl-1H-indol-3-yl)acetic acid | 1-10 | not determined | not determined | not determined |
| 24 | (1-(1,3-benzothiazol-2-yl)methyl)-6-chloro-5-methoxy-2-methyl-1H-indol-3-yl)acetic acid | 10-50 | not determined | not determined | not determined |
| 25 | (1-(1,3-benzoxazol-2-yl)methyl-5-fluoro-2-methyl-1H-indol-3-yl)acetic acid | 10-50 | 1-10 | 50-100 | 10-50 |
| 26 | (1-(1,3-benzoxazol-2-yl)methyl)-6-chloro-5-methoxy-2-methyl-1H-indol-3-yl)acetic acid | 0 | not determined | not determined | not determined |
| 27 | (1-(1,3-benzoxazol-2-ylmethyl)-2-methyl-1H-indol-3-yl)acetic acid | 10-50 | 1-10 | 50-100 | not determined |
| 28 | (1-(1,3-chlorobenzyl)-6-fluoro-2,4-difluoro-5-methoxy-2-methyl-1H-indol-3-yl)acetic acid | 10-50 | not determined | not determined | not determined |
| 29 | (1-(4-bromobenzyl)-5-methoxy-2-methyl-1H-indol-3-yl)acetic acid | 0 | not determined | not determined | not determined |
| 30 | 1-(4-bromobenzyl)-2-methyl-1H-indol-3-yl)acetic acid | 10-50 | 1-10 | 50-100 | not determined |
| 31 | (1-(4-bromobenzyl)-5-methoxy-2-methyl-1H-indol-3-yl)acetic acid | 0 | not determined | not determined | not determined |
| 32 | (1-(4-bromobenzyl)-5-fluoro-5-methoxy-2-methyl-1H-indol-3-yl)acetic acid | 0 | not determined | not determined | not determined |
| 33 | (1-(4-chlorobenzyl)-5-hydroxy-2-methyl-1H-indol-3-yl)acetic acid | 10-50 | 1-10 | 10-50 | not determined |
| 34 | (1-(4-chlorobenzyl)-3,5-methoxy-2-methyl-1H-indol-3-yl)acetic acid | 0 | not determined | not determined | not determined |
| 35 | (1-(4-fluorophenyl)-5-methoxy-2-chloro-5-methoxy-2-methyl-1H-indol-3-yl)acetic acid | 0 | not determined | not determined | not determined |
| 36 | (1-(4-tert-butylbenzyl)-5-methoxy-2-methyl-1H-indol-3-yl)acetic acid | 0 | not determined | not determined | not determined |

FIG. 13B

| Row | IUPAC Name | Pig DAO % Inhibition (10 uM) | Pig DAO IC50 (uM) | Human DAO % Inhibition (10 uM) | Human DAO IC50 (uM) |
|---|---|---|---|---|---|
| 32 | 1-(biphenyl-4-ylmethyl)-6-chloro-5-methoxy-2-methyl-1H-indol-3-yl)acetic acid | 0 | not determined | not determined | not determined |
| 38 | [1-(1,3-benzodioxol-5-ylmethyl)-5-methoxy-1H-indol-3-yl]acetic acid | 1-10 | not determined | not determined | not determined |
| 39 | 2-(benzylsulfonyl)-1H-indol-3-yl)acetic acid | not determined | not determined | 0 | not determined |
| 40 | [5-bromo-1-(4-fluorobenzyl)-2,3-dimethyl-1H-indol-4-yl]acetic acid | 0 | not determined | not determined | not determined |
| 41 | [5-bromo-1-(4-fluorobenzyl)-2-methyl-1H-indol-3-yl]acetic acid | 0 | not determined | not determined | not determined |
| 42 | [5-methoxy-1-(4-methoxybenzyl)-2-methyl-1H-indol-3-yl]acetic acid | 0 | not determined | not determined | not determined |
| 43 | [6-chloro-1-(2,4-dichlorobenzyl)-5-methoxy-2-methyl-1H-indol-3-yl]acetic acid | 0 | not determined | not determined | not determined |
| 44 | [6-chloro-1-(4,5-difluorobenzyl)-5-methoxy-2-methyl-1H-indol-3-yl]acetic acid | 0 | not determined | not determined | not determined |
| 45 | [6-chloro-1-(2,4-difluorobenzyl)-5-methoxy-2-methyl-1H-indol-3-yl]acetic acid | 1-10 | not determined | not determined | not determined |
| 46 | [6-chloro-1-(3,5-difluorobenzyl)-5-methoxy-2-methyl-1H-indol-3-yl]acetic acid | 1-10 | not determined | not determined | not determined |
| 47 | [6-chloro-2-(3-chlorobenzyl)-5-methoxy-2-methyl-1H-indol-3-yl]acetic acid | 0 | not determined | not determined | not determined |
| 48 | [6-chloro-1-(3-cyanobenzyl)-5-methoxy-2-methyl-1H-indol-3-yl]acetic acid | 0 | not determined | not determined | not determined |
| 49 | [6-chloro-1-(3-fluorobenzyl)-5-methoxy-2-methyl-1H-indol-3-yl]acetic acid | 0 | not determined | not determined | not determined |
| 50 | [6-chloro-1-(4-fluorobenzyl)-5-methoxy-2-methyl-1H-indol-3-yl]acetic acid | <7 | not determined | not determined | not determined |
| 51 | [6-chloro-1-(4-chlorobenzyl)-2,3-dimethyl-1H-indol-4-yl]acetic acid | 50-100 | 1-10 | 10-50 | not determined |
| 52 | [6-chloro-1-(4-chlorobenzyl)-5-hydroxy-2-methyl-1H-indol-3-yl]acetic acid | 0 | not determined | not determined | not determined |
| 53 | [6-chloro-1-(4-chlorobenzyl)-5-methoxy-2-methyl-1H-indol-3-yl]acetic acid | 10-50 | not determined | not determined | not determined |
| 54 | [6-chloro-1-(4-chlorobenzyl)-5-methoxy-2-methyl-1H-indol-4-yl]acetic acid | 10-50 | not determined | not determined | not determined |
| 55 | [6-chloro-1-(4-fluorobenzyl)-5-methoxy-2-methyl-1H-indol-3-yl]acetic acid | 1-10 | 1-10 | not determined | not determined |
| 56 | [6-chloro-1-(4-methoxybenzyl)-2,3-dimethyl-1H-indol-4-yl]acetic acid | 1-10 | not determined | not determined | not determined |
| 57 | [6-chloro-1-(4-methoxybenzyl)-2-methyl-1H-indol-3-yl]acetic acid | 0 | not determined | not determined | not determined |
| 58 | [6-chloro-5-methoxy-2-methyl-1-(1-naphthylmethyl)-1H-indol-3-yl]acetic acid | 0 | not determined | not determined | not determined |
| 59 | [6-chloro-5-methoxy-2-methyl-1-(3-methylbenzyl)-1H-indol-3-yl]acetic acid | 0 | not determined | not determined | not determined |
| 60 | [6-chloro-5-methoxy-2-methyl-1-(pyridin-2-ylmethyl)-1H-indol-3-yl]acetic acid | 0 | not determined | not determined | not determined |
| 61 | [6-chloro-5-methoxy-2-methyl-1-(3-nitrobenzyl)-1H-indol-3-yl]acetic acid | 0 | not determined | not determined | not determined |
| 62 | [6-chloro-1-(4-fluorobenzyl)-2-methyl-1H-indol-3-yl]acetic acid | 10-50 | not determined | not determined | not determined |
| 63 | [6-chloro-1-(4-fluorobenzyl)-5-methoxy-2-methyl-1H-indol-4-yl]acetic acid | 1-10 | 1-10 | not determined | not determined |
| 66 | [6-chloro-2-thienylmethyl-5-methoxy-2-methyl-1H-indol-3-yl]acetic acid | 50-100 | 1-10 | not determined | not determined |
| 67 | [1-(5-chloro-2-thienylmethyl-5-methoxy-2-methyl-1H-indol-3-yl]acetic acid | 1-10 | not determined | not determined | not determined |
| 68 | [1-(3-chloro-2-methyl-1H-indol-3-yl)acetic acid | 0 | not determined | not determined | not determined |
| 69 | [6-chloro-1-(3-(trifluoromethoxy)benzyl)-1H-indol-3-yl]acetic acid | 0 | not determined | not determined | not determined |
| 70 | [6-chloro-2-methyl-1-(3-(trifluoromethoxy)benzyl)-1H-indol-3-yl]acetic acid | 0 | not determined | not determined | not determined |
| 71 | [6-fluoro-2-methyl-1-(2-(trifluoromethoxy)benzyl)-1H-indol-3-yl]acetic acid | 0 | not determined | not determined | not determined |
| 72 | [6-chloro-2-methyl-1-(3-(trifluoromethyl)benzyl)-1H-indol-3-yl]acetic acid | 0 | not determined | not determined | not determined |

FIG. 13C

| Row | IUPAC Name | Pig DAO % Inhibition (10 uM) | Pig DAO IC50 (uM) | Human DAO % Inhibition (10 uM) | Human DAO IC50 (uM) |
|---|---|---|---|---|---|
| 73 | (5-fluoro-2-methyl-1,4-trifluoromethoxybenzyl)-1H-indol-3-yl)acetic acid | 0 | not determined | not determined | not determined |
| 74 | (5-hydroxy-2-methyl-1-(4-trifluoromethoxybenzyl)-1H-indol-3-yl)acetic acid | 10-50 | 1-10 | not determined | not determined |
| 75 | (6-methoxy-2-methyl-1-(4-trifluoromethoxybenzyl)-1H-indol-3-yl)acetic acid | 0 | not determined | not determined | not determined |
| 76 | (6-chloro-1-(6-chloro-2-thienylcarbonyl)-5-hydroxy-2-methyl-1H-indol-3-yl)acetic acid | 10-50 | not determined | not determined | not determined |
| 77 | (6-chloro-1-(6-chloro-2-thienylcarbonyl)-5-methoxy-2-methyl-1H-indol-3-yl)acetic acid | 0 | not determined | not determined | not determined |
| 78 | (6-chloro-1-(5-chloro-2-thienylmethyl)-5-methoxy-2-methyl-1H-indol-3-yl)acetic acid | 0 | not determined | not determined | not determined |
| 79 | (6-chloro-4-trifluoroacetamido-2-methyl-5-methoxy-2-methyl-1H-indol-3-yl)acetic acid | 1-10 | not determined | not determined | not determined |
| 80 | (5-chloro-2,3-dimethyl-1,33-trifluoromethoxybenzyl)-1H-indol-5-yl)acetic acid | 1-10 | not determined | not determined | not determined |
| 81 | (5-chloro-2,3-dimethyl-1,33-trifluoromethoxybenzyl)-1H-indol-5-yl)acetic acid | 10-50 | not determined | 10-50 | not determined |
| 82 | (5-chloro-5-hydroxy-2-methyl-1-(4-fluorobenzyloxy)benzyl-1H-indol-3-yl)acetic acid | 0 | 1 | not determined | not determined |
| 83 | (5-chloro-5-methoxy-2-methyl-1,13-trifluoromethyl-1H-indol-4-yl)methyl-1H-indol-3-yl)acetic acid | 0 | not determined | not determined | not determined |
| 84 | (6-chloro-5-methoxy-2-methyl-1,13-trifluoromethoxybenzyl)-1H-indol-3-yl)acetic acid | 0 | not determined | not determined | not determined |
| 85 | (6-chloro-5-methoxy-2-methyl-1,14-trifluoromethoxybenzyl)-1H-indol-3-yl)acetic acid | 1-10 | not determined | not determined | 1-10 |
| 86 | (6-chloro-5-methoxy-2-methyl-1,14-trifluoromethoxybenzyl)-1H-indol-3-yl)acetic acid | 0 | not determined | not determined | not determined |
| 87 | 3-(1H-indol-2-yl)bethanone | 1-10 | not determined | 1-10 | not determined |
| 88 | 1,12-dimethylaminoethyl-1H-indole-2-carboxylic acid hydrochloride | 0 | not determined | 10-50 | 1-10 |
| 89 | 1-benzyl-5-methoxy-2-methyl-1H-indole-3-carboxylic acid | 0 | not determined | 0 | 1-10 |
| 90 | 1H-indol-2-ylpyridin-4-yl)methane | 10-50 | not determined | 0 | not determined |
| 91 | 1H-indol-3-yl)acetic acid | not determined | not determined | not determined | not determined |
| 92 | 1H-indol-2-yl)methane | 0 | not determined | 10-50 | not determined |
| 93 | 1H-indol-3-yl)acetic acid | 0 | not determined | 0 | 1-10 |
| 94 | 1H-indol-4-ol | not determined | not determined | not determined | not determined |
| 95 | 1H-indol-5-ol | 1-10 | <1 | 50-100 | 1-10 |
| 96 | 1H-indol-2-carboxylic acid | 50-100 | not determined | 50-100 | 1-10 |
| 97 | 1H-indole-3-carboxylic acid | 0 | not determined | 50-100 | 1-10 |
| 98 | 1H-indole-5-carboxylic acid | 0 | not determined | <1 | <1 |
| 99 | 1H-indole-2-carbonitrile | 50-100 | <1 | 50-100 | not determined |
| 100 | 1H-indole-2-carboxylic acid | 0 | not determined | 0 | not determined |
| 101 | 1H-indole-3-carboxylic acid | 0 | not determined | 10-50 | not determined |
| 102 | 1H-indole-5-carboxylic acid | 0 | not determined | 10-50 | not determined |
| 103 | 1H-indole-3-acetic acid | 0 | not determined | 0 | not determined |
| 104 | 1H-indole-7-carboxylic acid | 0 | not determined | 10-50 | 1-10 |
| 105 | 1-methyl-1H-indole-2-carboxylic acid | 0 | not determined | 10-50 | 1-10 |
| 106 | 2-(1H-indol-5-yl)-1H-indole | not determined | not determined | 10-50 | 1-10 |
| 107 | 2-(1H-tetrazol-5-yl)-methyl)-1H-indole | not determined | not determined | 10-50 | 1-10 |
| 108 | 2-(2H-tetrazol-5-ylmethyl)-1H-indole | not determined | not determined | 0 | >50 |

FIG. 13D

| Row | IUPAC Name | Pig DAO % Inhibition (10 uM) | Pig DAO IC50 (uM) | Human DAO % Inhibition (10 uM) | Human DAO IC50 (uM) |
|---|---|---|---|---|---|
| 109 | 2-(3-amino-1H-indol-2-yl)phenol | not determined | not determined | 1-10 | not determined |
| 110 | 5,-2-dimethoxyphenyl 4-hydroxy-1H-indole-2-carboxylate | not determined | not determined | 50-100 | not determined |
| 111 | 2-(1H-indol-3-ylmethyl)malonaldehyde | not determined | not determined | 50-100 | <1 |
| 112 | 2-[1-(2-chlorobenzyl)-5-methoxy-2-methyl-1H-indol-3-yl]ethyl-4-chlorobenzoate | 0 | not determined | not determined | not determined |
| 113 | 2-[1-(2-chloroacetyl)-5-methoxy-2-methyl-1H-indol-3-yl]ethyl 4-chlorobenzoate | 0 | not determined | not determined | not determined |
| 114 | 2-[1-(4-chloroacetyl)-5-methoxy-2-methyl-1H-indol-3-yl]ethyl acetate | 0 | not determined | not determined | not determined |
| 115 | 2-[acetyl(isopropyl)amino]methyl]-5-bromo-4-hydroxy-1-methyl-1H-indole-3-carboxylic acid | 10-50 | 1-10 | 10-50 | not determined |
| 116 | 2-hydroxy-1-(1H-indol-3-yl)ethanone | 0 | not determined | 10-50 | not determined |
| 117 | 2-hydroxy-3-(1H-indol-3-yl)propanoic acid | not determined | not determined | not determined | not determined |
| 118 | 3-(1H-indol-2-yl)phenol | not determined | not determined | 1-10 | <1 |
| 119 | 3-(2-aminoethyl)-1H-indole-4-carboxylic acid | 10-50 | not determined | 10-50 | not determined |
| 120 | 3-(2-aminoethyl)-5-ethoxy-1H-indole-2-carboxylic acid | 0 | not determined | 0 | not determined |
| 121 | 3-(acetylamino)-5-methoxy-1H-indole-2,5-dicarboxylic acid | 1-10 | not determined | 1-10 | not determined |
| 122 | 3-(carboxymethyl)-1H-indole-2-carboxylic acid | 1-10 | not determined | 0 | not determined |
| 123 | 3-(fluoromethyl)-1H-indole-2-carboxylic acid | 0 | not determined | 50-100 | not determined |
| 124 | 3-(iodomethyl)-1H-indole-2-carboxylic acid | not determined | not determined | 50-100 | not determined |
| 125 | 3-chloro-1H-indole-2-carboxylic acid | >50 | not determined | not determined | not determined |
| 126 | 3-[1-(3-benzoxazol-2-yl)methyl]-4,6-dichloro-2-methyl-1H-indol-3-yl]propenoic acid | 0 | not determined | not determined | not determined |
| 127 | 3-[1-(1,3-benzoxazol-2-yl)methyl-5-chloro-2,5-dimethyl-1H-indol-3-yl]propanoic acid | 0 | not determined | not determined | not determined |
| 128 | 3-[1-(3-bromophenyl)-2-[methyl 6-fluoro-2-methyl-1H-indol-3-yl]propanoic acid | 1-10 | not determined | 1-10 | not determined |
| 129 | 3-[2-(acetylamino)ethyl]-5-ethoxy-1H-indole-2-carboxylic acid | 1-10 | not determined | 1-10 | not determined |
| 130 | 3-[4,6-dichloro-1-(3-chlorobenzyl)-2-methyl-1H-indol-2-methyl-1H-indol-3-yl]propanoic acid | 10-50 | not determined | 50-100 | not determined |
| 131 | 5-[6-chloro-1-(4-chlorobenzyl)-3-fluoro-2-methyl-1H-indol-3-yl]propanoic acid | 0 | not determined | 0 | not determined |
| 132 | 5-amino-1H-indole-2-methyl-1H-indol-3-yl]propanoic acid | not determined | not determined | 50-100 | not determined |
| 133 | 3-amino-1H-indole-2-carboxylic acid | not determined | not determined | 50-100 | not determined |
| 134 | 3-bromo-1H-indole-4-carboxylic acid | not determined | not determined | 1-10 | <1 |
| 135 | 3-chloro-1H-indole-2-carbonitrile | 10-50 | not determined | not determined | not determined |
| 136 | 3-chloro-1H-indole-2-carboxamide | 10-50 | not determined | 50-100 | not determined |
| 137 | 3-chloro-1H-indole-5-carboxylic acid | not determined | not determined | 1-10 | <1 |
| 138 | 5-chloro-2-(1H-tetrazol-5-yl)-1H-indole | 10-50 | not determined | 50-100 | not determined |
| 139 | 3-fluoro-1H-indole-2-carboxylic acid | not determined | not determined | 50-100 | not determined |
| 140 | 3-fluoro-1H-indole-5-carboxylic acid | not determined | not determined | 10-50 | 1-10 |
| 141 | 3-iodo-1H-indole-2-carboxylic acid | >50 | not determined | 10-50 | not determined |
| 142 | 3-methyl-1H-indole-2-carboxylic acid | 10-50 | not determined | 50-100 | not determined |
| 143 | 3-phenyl-1H-indole-2-carboxylic acid | 10-50 | not determined | 0 | 1-10 |
| 144 | 4-[2-(phenylethynyl)-1H-indole-2-carboxylic acid | 10-50 | 1-10 | not determined | 1-10 |

FIG. 13E

| Row | IUPAC Name | Pig DAO % Inhibition (10 uM) | Pig DAO IC50 (uM) | Human DAO % Inhibition (10 uM) | Human DAO IC50 (uM) |
|---|---|---|---|---|---|
| 145 | 4-(3-phenylpropoxy)-1H-indole-2-carboxylic acid | 10-50 | 10-50 | not determined | not determined |
| 146 | 4,6-phenylethoxy)-1H-indole-2-carboxylic acid | 10-50 | not determined | not determined | not determined |
| 147 | 4-(benzyloxy)-1H-indole-2-carboxylic acid | 50-100 | 1-10 | 50-100 | >10 |
| 148 | bromo-1H-indole-2-carboxylic acid | not determined | not determined | 50-100 | 1-10 |
| 149 | 5-bromo-1H-indole-2-carboxylic acid | 50-100 | 1-10 | 50-100 | <1 |
| 150 | 5-hydroxy-1H-indole-2-carboxylic acid | 50-100 | >10 | 10-50 | 1-10 |
| 151 | 4-hydroxy-1H-indole-2-carboxylic acid | 10-50 | 1-10 | 50-100 | 50-100 |
| 152 | 5-chloro-1H-indole-2-carboxylic acid | 10-50 | not determined | 10-50 | <1 |
| 153 | 4-benzyl-1H-indole-2-carboxylic acid | 10-50 | not determined | 10-50 | not determined |
| 154 | 5,6,7-trimethoxy-1H-indole-2-carboxylic acid | 0 | not determined | 0 | not determined |
| 155 | 5-t-butyl-1H-indole-2-carboxylic acid | 1-10 | not determined | 0 | not determined |
| 156 | 5-chloro-1H-indole-2-carboxylic acid | 0 | 1-10 | 10-50 | 1-10 |
| 157 | 5-hydroxy-1H-indole-3-carboxylic acid | 50-100 | 1-10 | 50-100 | 1-10 |
| 158 | 5-ethyl-1H-indole-2-carboxylic acid | 1-10 | 1-10 | not determined | >100 |
| 159 | 5-fluoro-1H-indole-2-carboxylic acid | 50-100 | 1-10 | not determined | <1 |
| 160 | 5-fluoro-2-methyl-1H-indole-3-carboxaldehyde | 0 | not determined | not determined | not determined |
| 161 | 5-hydroxy-1-(3-hydroxybenzyl)-1H-indole-2-carboxylic acid | not determined | not determined | 50-100 | <1 |
| 162 | 5-hydroxy-1-(4-methoxybenzyl)-2-methyl-1H-indole-2-carboxylic acid | 10-50 | 1-10 | not determined | not determined |
| 163 | 5-hydroxy-1H-indole-2-carboxylic acid | 50-100 | 1-10 | 50-100 | 1-10 |
| 164 | 5-hydroxy-1H-indole-3-carboxylic acid | 50-100 | 1-10 | 50-100 | 1-10 |
| 165 | 6-chloro-2,3-dimethyl-1H-indole-1-(3-trifluoromethoxybenzyl)-1H-indole acetate | 0 | not determined | 0 | not determined |
| 166 | 6-methyl-1H-indole-2-carboxylic acid | 0 | not determined | 0 | not determined |
| 167 | 6-isopropyl-1H-indole-2-carboxylic acid | 0 | not determined | 0 | not determined |
| 168 | 5-methoxy-1H-indole-2-carboxylic acid | 1-10 | not determined | 1-10 | not determined |
| 169 | 6-methyl-1H-indole-3-carboxylic acid | 0 | not determined | 0 | not determined |
| 170 | 5-methyl-1H-indole-2-carboxylic acid | 0 | not determined | 0 | not determined |
| 171 | 6-isopropyl-1H-indole-2-carboxylic acid | 0 | not determined | 0 | not determined |
| 172 | benzyl 3-amino-1H-indole-2-carboxylate | not determined | not determined | 50-100 | 1-10 |
| 173 | benzyl 4-hydroxy-1H-indole-2-carboxylate | not determined | not determined | 50-100 | 1-10 |
| 174 | benzyl 5-hydroxy-1H-indole-2-carboxylate | not determined | not determined | 50-100 | 1-10 |
| 175 | ethyl 5-tert-butyl-1H-indole-2-carboxylate | 10-50 | 10-50 | 50-100 | 1-10 |
| 176 | ethyl 1-butyl-5-hydroxy-2-methyl-1H-indole-3-carboxylate | 0 | not determined | not determined | not determined |
| 177 | ethyl 2-methyl-1H-indole-3-carboxylate | 0 | not determined | not determined | not determined |
| 178 | ethyl 5-amino-1H-indole-2-carboxylate | not determined | not determined | 50-100 | 1-10 |
| 179 | ethyl 3-(dimethylaminomethyl)-5-hydroxy-1,6-dimethyl-1H-indole-2-carboxylate hydrochloride | not determined | not determined | not determined | not determined |
| 180 | ethyl 4-(dimethylaminomethyl)-5-hydroxy-1,2-dimethyl-1H-indole-3-carboxylate hydrochloride | 10-50 | 10-50 | not determined | not determined |

FIG. 13F

| Row | IUPAC Name | Pig DAO % Inhibition (10 uM) | Pig DAO IC50 (uM) | Human DAO % Inhibition (10 uM) | Human DAO IC50 (uM) |
|---|---|---|---|---|---|
| 181 | ethyl 4-amino-1H-indole-2-carboxylate | not determined | not determined | 50-100 | 1-10 |
| 182 | ethyl 4-hydroxy-1H-indole-2-carboxylate | not determined | not determined | 50-100 | 1-10 |
| 183 | ethyl 5-hydroxy-1H-indole-3-carboxylate | not determined | not determined | 50-100 | 1-10 |
| 184 | ethyl 5-hydroxy-2-methyl-1H-indole-3-carboxylate | 10-50 | 1-10 | not determined | not determined |
| 185 | ethyl 5-methoxy-1-(3-methoxybenzyl)-1H-indole-2-carboxylate | 0 | not determined | 0 | not determined |
| 186 | ethyl 7-methoxy-1H-indole-2-carboxylate | 0 | not determined | 0 | not determined |
| 187 | isopropyl 3-amino-1H-indole-2-carboxylate | not determined | not determined | 50-100 | 1-10 |
| 188 | isopropyl 4-hydroxy-1H-indole-2-carboxylate | not determined | not determined | 50-100 | <1 |
| 189 | methyl [(3-nitro-1H-indol-2-yl)thio]acetate | 0 | not determined | 0 | not determined |
| 190 | methyl [(5-fluoro-3-nitro-1H-indol-2-yl)thio]acetate | 0 | not determined | 0 | not determined |
| 191 | methyl 1H-indole-2-carboxylate | not determined | not determined | not determined | not determined |
| 192 | methyl 1H-indole-3-carboxylate | 0 | not determined | 10-50 | not determined |
| 193 | methyl 3-bromo-1H-indole-2-carboxylate | not determined | not determined | 50-100 | <1 |
| 194 | methyl 3-cyanomethyl-1H-indole-2-carboxylate | not determined | not determined | 0 | not determined |
| 195 | methyl 3-cyano-1H-indole-2-carboxylate | not determined | not determined | 50-100 | 10-50 |
| 196 | methyl 3-bromo-1H-indole-2-carboxylate | not determined | not determined | 0 | not determined |
| 197 | methyl 4-amino-1H-indole-2-carboxylate | <1 | not determined | 50-100 | not determined |
| 198 | methyl 3-hydroxy-1H-indole-2-carboxylate | 0 | not determined | 10-50 | not determined |
| 199 | methyl 4-phenyl-1H-indole-2-carboxylate | not determined | not determined | 1-10 | not determined |
| 200 | methyl 4-(benzyloxy)-1H-indole-2-carboxylate | 0 | not determined | 0 | not determined |
| 201 | methyl 4,6-dimethoxy-1H-indole-2-carboxylate | not determined | not determined | 10-50 | 1-10 |
| 202 | methyl 4-amino-1H-indole-2-carboxylate | not determined | not determined | 0 | not determined |
| 203 | methyl 4-hydroxy-1H-indole-2-carboxylate | 50-100 | not determined | 10-50 | 1-10 |
| 204 | methyl 4-bromo-1H-indole-2-carboxylate | 0 | not determined | 0 | not determined |
| 205 | methyl 4-hydroxy-1H-indole-2-carboxylate | 50-100 | 1-10 | 10-50 | 1-10 |
| 206 | methyl 4-methoxy-1H-indole-2-carboxylate | 0 | not determined | 50-100 | not determined |
| 207 | methyl 5-hydroxy-1H-indole-2-carboxylate | 0 | not determined | 0 | not determined |
| 208 | methyl 6-methoxy-1H-indole-2-carboxylate | 0 | not determined | 0 | not determined |
| 209 | N-(1H-indol-3-yl)acetyl-L-alanine | not determined | not determined | 10-50 | 1-10 |
| 210 | N-(2-hydroxyphenyl)-1H-indole-2-carboxamide | 50-100 | not determined | 50-100 | 1-10 |
| 211 | N-(benzyloxy)-1H-indole-2-carboxamide | 0 | not determined | 0 | not determined |
| 212 | N-hydroxy-1H-indole-2-carboxamide | 50-100 | not determined | 50-100 | 1-10 |
| 213 | N-hydroxy-(1H-indol-3-yl)acetamide | 0 | not determined | 0 | not determined |
| 214 | N-hydroxy-2-(1H-indol-3-yl)acetamide | not determined | not determined | 50-100 | <1 |
| 215 | N-hydroxy-3-phenyl-1H-indole-2-carboxamide | not determined | not determined | 10-50 | 1-10 |
| 216 | N-hydroxy-N-methyl-1H-indole-2-carboxamide | not determined | not determined | 10-50 | not determined |

FIG. 13G

| Row | IUPAC Name | Pig DAO % Inhibition (10 uM) | Pig DAO IC50 (uM) | Human DAO % Inhibition (10 uM) | Human DAO IC50 (uM) |
|---|---|---|---|---|---|
| 217 | N-methoxy-1H-indole-2-carboxamide | not determined | not determined | 10-50 | not determined |
| 218 | N-methoxy-N-methyl-1H-indole-2-carboxamide | not determined | not determined | 10-50 | not determined |
| 219 | N-methyl-1H-indole-2-carboxamide | not determined | not determined | 10-50 | not determined |
| 220 | phenyl 4-hydroxy-1H-indole-2-carboxylate | not determined | not determined | 50-100 | 1.10 |
| 221 | propyl (5-hydroxy-1-methyl-1H-indol-3-yl)acetate | 50-100 | 1.10 | not determined | 1.10 |

FIG. 14

| Row | IUPAC Name | Mouse oral Cmax (observed) (ng/mL) | Mouse oral Tmax (observed) (hr) | Rat oral Cmax (observed) (ng/mL) | Rat oral Tmax (observed) (hr) |
|---|---|---|---|---|---|
| 1 | [6-fluoro-5-hydroxy-2-methyl-1-[4-(trifluoromethylthio)benzyl]-1H-indol-3-yl]acetic acid | 100 | . | 1010 | 0.25 |
| 2 | [6-chloro-5-methoxy-2-methyl-1-[4-(trifluoromethylthio)benzyl]-1H-indol-3-yl]acetic acid | 2600 | 0.5 | 17800 | 7 |
| 3 | [6-chloro-1-(4-chlorobenzyl)-5-methoxy-2-methyl-1H-indol-3-yl]acetic acid | 4800 | 0.5 | 18400 | 7 |
| 4 | [1-(1,3-benzothiazol-2-ylmethyl)-6-chloro-5-methoxy-2-methyl-1H-indol-3-yl]acetic acid | 4800 | 0.25 | 48800 | 7 |
| 5 | [6-chloro-1-{[5-chloro-2-thienyl]carbonyl}-5-fluoro-2-methyl-1H-indol-3-yl]acetic acid | 17000 | 0.25 | 20400 | 0.25 |
| 6 | [6-chloro-2,5-dimethyl-1-{[3-(trifluoromethyl)benzyl]}-1H-indol-3-yl]acetic acid | 26020 | 1.5 | . | . |
| 7 | [6-chloro-2,5-dimethyl-1-{[3-(trifluoromethoxy)benzyl]}-1H-indol-3-yl]acetic acid | 15100 | 0.5 | . | . |
| 8 | [1-(1,3-benzothiazol-2-ylmethyl)-6-chloro-5-fluoro-2-methyl-1H-indol-3-yl]acetic acid | 46700 | 0.25 | . | . |
| 9 | [6-chloro-5-methoxy-2-methyl-1-{[3-(trifluoromethoxy)benzyl]}-1H-indol-3-yl]acetic acid | 18300 | 0.25 | . | . |
| 10 | [6-chloro-1-(2-chlorobenzyl)-5-methoxy-2-methyl-1H-indol-3-yl]acetic acid | 14200 | 20 | . | . |
| 11 | [6-chloro-5-methoxy-2-methyl-1-{[3-(trifluoromethoxy)benzyl]}-1H-indol-3-yl]acetic acid | 16000 | 24 | . | . |
| 12 | [6-chloro-5-methoxy-2-methyl-1-{[3-(trifluoromethyl)benzyl]}-1H-indol-3-yl]acetic acid | 32600 | 7 | . | . |
| 13 | [6-chloro-1-(2-chlorobenzyl)-5-methyl-1H-indol-3-yl]acetic acid | 40700 | 24 | . | . |
| 14 | [1-(1,3-benzothiazol-2-ylmethyl)-6-chloro-2,5-dimethyl-1H-indol-3-yl]acetic acid | 28000 | 1.5 | . | . |

USEFUL INDOLE COMPOUNDS

CROSS-REFERENCE TO RELATED APPLICATION

This application is a national stage filing under 35 U.S.C. §371 of international application PCT/US2006/062265, filed Dec. 18, 2006, which claims the benefit under 35 U.S.C. §119(e) of U.S. Provisional Application No. 60/751,443, filed Dec. 16, 2005.

BACKGROUND

Cox Inhibitors

Cyclooxygenases play an essential role in prostaglandin synthesis. Cyclooxygenase-1 (COX-1) is constitutive and relatively long-lived, whereas cyclooxygenase-2 (COX-2) is inducible and relatively short-lived. COX-1 is thought to be responsible for maintaining basal level prostaglandin production, which is important for normal gastrointestinal and renal function. COX-2 is induced by certain inflammatory agents, hormones, growth factors, cytokines, and other agents. COX-2 plays a significant role in prostaglandin synthesis within inflammatory cells such as macrophages and monocytes, and prostaglandin production associated with COX-2 induction can have a deleterious effect on the body. Thus, to reduce unwanted inflammation and to treat certain other conditions, it can be desirable to inhibit COX-2 activity without significantly inhibiting COX-1 activity.

Many non-steroidal anti-inflammatory drugs (NSAIDs) inhibit both COX-1 and COX-2. These non-selective inhibitors include indomethacin (Shen et al. 1963 *J Am Chem Soc* 85:4881; 4-chlorobenzoyl-5-methoxy-2-methyl-1H-indole-3-acetic acid). It is desirable to identify NSAIDs that inhibit COX-2 activity, but do not significantly inhibit COX-1 activity at physiological levels where COX-2 activity is significantly inhibited. Such selective inhibitors are expected to have the desirable anti-inflammatory, anti-pyretic, and analgesic properties associated with NSAIDs, while having reduced or no gastrointestinal or renal toxicity.

Subsequent to indomethacin administration, the unchanged parent compound, the desmethyl metabolite (O-desmethylindomethacin; (1-(4-chlorobenzoyl)-5-hydroxy-2-methyl-1H-indol-3-yl]acetic acid), the desbenzoyl metabolite (N-deschlorobenzoylindomethacin; (5-methoxy-2-methyl-1H-indol-3-yl)acetic acid) and the desmethyl-desbenzoyl metabolite (O-desmethy-N-deschlorobenzoylindomethacin; (5-hydroxy-2-methyl-1H-indol-3-yl)acetic acid) can be found in plasma in significant amounts (Strachman et al. 1964 *J Am Chem Soc* 8:799; Helleberg 1981 *Clin Pharmacokinet* 6:245), all in an unconjugated form (Harman et al. 1964 *J Pharmacol Exp Therap* 143:215). It has been reported that all three metabolites are devoid of anti-inflammatory activity (Helleberg 1981 *Clin Pharmacokine.* 6:245 and Duggan et al. 1972 *Pharmacol and Exp Ther* 181:562), although it has also been reported that the desmethyl metabolite has some ability to inhibit prostaglandin synthesis (Shen et al. 1977 *Adv Drug Res* 12:90).

Indomethacin derivatives in which the benzoyl group has been replaced by a 4-bromobenzyl group of the acetic acid side chain has been extended exhibit greater selectivity for inhibition of COX-2 relative to COX-1 (Black et al. 1996 *Bioorganic & Medicinal Chem Lett* 6:725 and Black et al. 1997 *Advances in Experimental Medicine and Biology* 407: 73). In addition, synthesis methodology has been demonstrated for the preparation of indomethacin analogues, some of which do not inhibit cyclooxygenases (Touhey et al. 2002 *Eur J Cancer* 38:1661).

FAAH Inhibitors

Many fatty acid amides are known to have analgesic activity. A number of fatty acid amides (e.g., arachidonyl amino acids and anandamide) induce analgesia in animal models of pain (see, for example, Walker et al. 1999 *Proc Natl Acad Sci* 96:12198, Fride and Mechoulam 1993 *Eur J Pharmacol* 231: 313). Anandamide and certain other fatty acid amides (e.g., N-palmitoyl ethanolamine, n-oleoyl ethanolamide, oleamide, 2-arachidonoylglycerol) are cleaved and inactivated by fatty acid amide hydrolase (FAAH) (Deutsch et al. 2003 *Prostaglandins Leukol Essent Fatty Acids* 66:201; and Cravatt and Lichtman 2003 *Current Opinion in Chemical Biology* 7:469).

Inhibition of FAAH is expected to lead to an increase in the level of anandamide and other fatty acid amides. This increase in fatty acid amides may lead to an increase in the nociceptive threshold. Thus, inhibitors of FAAH are useful in the treatment of pain. Such inhibitors might also be useful in the treatment of other disorders that can be treated using fatty acid amides or modulators of cannabinoid receptors (e.g., anxiety, eating disorders, and cardiovascular disorders). NPAA (N-palmitoylethanolamine acid anhydrolase) is a hydrolase that breaks down N-palmitoyl ethanolamine (PEA), a fatty acid amide. PEA is a naturally occurring substrate for the cannabinoid receptor 2 (CB2 receptor). Inhibition of NPAA may lead to increased PEA levels. Accordingly, NPAA inhibitors may be useful in the treatment of inflammation and nociceptive pain control. Monoacylglycerol lipase (MAGL, MGL) is a hydrolase which degrades the endocannabinoid ligand, 2-arachidonoylglycerol (2-AG). Although FAAH can also degrade 2-AG, MAGL is believed to be the main enzyme responsible for 2-AG metabolism in the brain. Thus 2-AG inhibitors may be useful in the treatment of cannabinoid receptor related therapies including anxiety, eating disorders, and cardiovascular disorders. Inhibitors of MAGL and FAAH are thought to have various therapeutic uses. Bahr et al. Expert Opin Investig Drugs—2006 Volume: 15 p. 351-65.

In addition, there is evidence (see, e.g., Weber et al. 2004 *J. Lipid Res.* 45:757) that when FAAH activity is reduced or absent, one of its substrates, anandamide, acts as a substrate for COX-2 that can be converted to a prostamide. Thus, certain prostamides may be elevated in the presence of an FAAH inhibitor. Given that certain prostamides are associated with reduced intraocular pressure and ocular hypotensivity, FAAH inhibitors may be useful agents for treating glaucoma.

CRTH2 Modulators

CRTH2 is a $G_{ai}$ protein-coupled receptor that is thought to be involved in both mediating $PGD_2$-induced chemoattraction and in activation of specific cell types involved in allergic inflammation. It has been reported that CRTH2 is expressed by Th2 cells, eosinophils and basophils, but not by Th1 cells, B cells or NK cells. (Nagata et al. 1999 *FEBS Letters* 459: 195-199).

$PGD_2$ is produced by allergen-activated mast cells and has been implicated in various allergic diseases as a pro-inflammatory mediator, although it may have anti-inflammatory activity in certain situations (Ajuebor et al. 2000 *Am J Physiol Gastrointest Liver Physiol* 279:G238-44). CRTH2 receptor is a high affinity receptor for $PGD_2$ as is DP-1, a $G_{aS}$ protein-coupled receptor.

CRTH2 agonists activate eosinophils, basophils and Th2 cells in vitro, resulting in induction of actin polymerization, calcium influx, CD11b expression and chemotaxis (Monneret et al 2003 *J Pharmacol Exp Ther* 304:349-55). An in vivo study has demonstrated that injection of a CRTH2 agonist can elicit transient recruitment of eosinophils from bone marrow into the blood (Shichijo 2003 *J Pharmacol Exp Ther* 307:518-525). A genetic study of African American and Chinese cohorts found that polymorphisms in CRTH2 were tightly associated with asthma susceptibility (Huang et al. 2004 *Hum Mol. Genet* 2791). It has been suggested that modulators of CRTH2 may be useful in the prevention and/or treatment of allergic asthma and other allergic disorders (US 2002/0022218 A1 and WO 03/066047). Recruitment and/or activation of eosinophils, basophils and Th2 cells is a prominent feature of the changes that occur in the asthmatic lung. Similar activation of these cell types, or subsets thereof, are believed to play an important role in the etiology of other diseases, including eosinophilic esophagitis and atopic dermatitis (Arora and Yamakazi 2004 *Clin Gastroenterol Hepatol* 2:523-30; Kiehl et al. 2001 *Br J Dermatol* 145:720-729). This fact, combined with the fact that CRTH2 mediates $PGD_2$-induced chemotaxis, suggests that compounds that alter chemotaxis by modulating CRTH2 activity could be useful in controlling chronic airway inflammation, atopic dermatitis, chronic obstructive pulmonary disease (COPD), and/or eosinophilic esophagitis. Compounds that alter chemotaxis by modulating CRTH2 activity could also be useful in controlling allergic rhinitis. Allergic rhinitis is classified as either seasonal (SAR) or perennial (PAR) depending upon the type of trigger and duration of symptoms. SAR symptoms occur in the spring, summer and/or early fall and can be triggered by outdoor allergens such as airborne tree, grass and weed pollens while PAR is usually persistent and chronic with symptoms occurring year-round and is commonly associated with indoor allergens such as dust mites, animal dander and/or mold spores. Symptoms of allergic rhinitis may include runny nose, nasal itching, sneezing, watery eyes and nasal congestion. CRTH2 modulators may be useful for treating SAR and/or PAR.

CRTH2 antagonists that reduce the ability of Th2 cells and eosinophils to respond to mast-cell derived $PGD_2$ could be useful for preventing and/or treating allergic disorders such as allergic rhinitis and asthma.

It is often found that agonists induce desensitization of the cell system by promoting internalization and down regulation of the cell surface receptor (*Int Immunol* 15:29-38, 2003). Therefore, certain CRTH2 agonists may be therapeutically useful because they can cause the desensitization of $PGD_2$-responsive cells. It has been shown that certain CRTH2 agonists can induce desensitization of $PGD_2$-responsive cells to subsequent activation by a CRTH2 agonist (see, e.g., Yoshimura-Uchiyama et al. 2004 *Clin Exp Allergy* 34:1283-1290). Importantly, CRTH2 agonists may also cause cross-desentization. Cross-desensitization, which can occur in many cell-signaling systems, refers to a phenomena whereby an agonist for one receptor can reduce or eliminate sensitivity of a cell type to an unrelated agonist/receptor signaling system. For example, it is known that treatment with the CRTH2 agonist indomethacin reduces expression of CCR3, the receptor for the chemoattractant, eotaxin (Stubbs et al. 2002, *J Biol Chem* 277:26012-26020).

DAO Inhibitors

It has been suggested that certain inhibitors of D-amino acid oxidase (DAO), including certain heterocylic-2-carboxylic acids, might be useful for improving memory, learning and cognition in patients suffering from neurodegenerative disorders US20030162825). Indomethacin has also been shown to be an inhibitor of DAO (Chen et. al 1994 Drug Metabol Drug Interact. 11:153-60). DAO degrades D-serine and other D-amino acids. D-glutamate and D-serine are thought to be agonists of N-methyl-D-aspartate (NMDA)-glutamate receptors that mediate a wide variety of brain activities, including the synaptic plasticity that is associated with certain types of memory and learning (US20030162825). Thus, it is thought that inhibition of DAO will lead to increased D-serine levels and improved cognitive function.

SUMMARY

Described herein are compounds having Formula I, Formula II, or Formula III pharmaceutically acceptable salts thereof, pharmaceutical compositions comprising such compounds and methods for treating a patient by administering such pharmaceutical compositions alone or in combination with one or more other therapeutic agents.

Useful compounds, e.g., useful FAAH inhibitors, include a compound having Formula I:

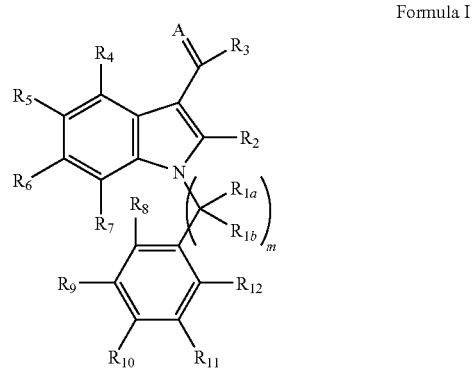

Formula I

Wherein:

A is O;

each $R_{1a}$ and $R_{1b}$ is independently; H, halogen, hydroxyl, —CN, an optionally substituted C1-C5 alkyl, an optionally substituted C2-C5 alkenyl, an optionally substituted C2-C5 alkynyl, an optionally substituted C1-C5 alkoxy, —$NO_2$; or an $R_{1a}$ and $R_{1b}$ attached to the same carbon, taken together with that carbon, form an optionally substituted C3-C6 cycloalkyl or carbocycle or an optionally substituted heterocycle; or an $R_{1a}$ attached to a carbon directly bonded to the ring bearing $R_8$, taken with $R_8$ and the carbon to which $R_{1a}$ is attached, form an optionally substituted C3-C6 cycloalkyl or carbocycle or an optionally substituted heterocycle; or an $R_{1a}$ attached to a carbon directly bonded to the ring bearing $R_{12}$, taken with $R_{12}$ and the carbon to which $R_{1a}$ is attached form an optionally substituted C3-C6 cycloalkyl or carbocycle or an optionally substituted heterocycle;

m=1, 2, or 3;

$R_2$ is H, hydroxyl, —$NO_2$, an optionally substituted C1-C5 alkoxy, —CN, an optionally substituted C1-C5 alkyl, an optionally substituted C2-C5 alkenyl, an optionally substituted C2-C5 alkynyl or halogen;

$R_3$ is an optionally substituted heteroaryl;

each of $R_4$, $R_5$, $R_6$ and $R_7$ are independently: H, a halogen, an optionally substituted C1-C5 alkyl, an optionally substituted C2-C5 alkenyl, an optionally substituted C2-C5 alkynyl, hydroxyl, $NO_2$, an optionally substituted C1-C5 alkoxy, —CN, —C(O)OH, an optionally substituted —$SO_2CH_3$, an optionally substituted —$SO_2NH_2$, an optionally substituted —$SO_2OH$, —C(O)H, an optionally substituted —C(O)CH$_3$, an optionally substituted —C(O)N(CH$_3$)$_2$, an optionally substituted —C(O)NH$_2$, an optionally substituted —SCH$_3$, an optionally substituted heterocycle or heteroaromatic, or —N(R$_{2a}$)(R$_{2b}$);

wherein each R$_{2a}$ and R$_{2b}$ is independently: H, hydroxy, an optionally substituted C1-C5 alkyl, an optionally substituted C2-C5 alkenyl; an optionally substituted C2-C5alkynyl; an optionally substituted C1-C5 alkoxy or an R$_{2a}$ and R$_{2b}$ attached to the same nitrogen, taken together with that nitrogen form an optionally substituted heterocycle or heteroaromatic; and each of R$_8$, R$_9$, R$_{10}$, R$_{11}$ and R$_{12}$ is independently H, —CN, hydroxyl, a halogen, an optionally substituted C1-C5 alkyl, an optionally substituted C2-C5 alkenyl, an optionally substituted C2-C5 alkynyl, hydroxyl, NO$_2$, an optionally substituted C1-C5 alkoxy, —N(R$_{2a}$)(R$_{2b}$), —C(O)OH, an optionally substituted —SO$_2$CH$_3$, an optionally substituted —SO$_2$NH$_2$, an optionally substituted —SO$_2$OH, —C(O)H, an optionally substituted —C(O)CH$_3$, an optionally substituted —C(O)N(CH$_3$)$_2$, an optionally substituted —C(O)NH$_2$, an optionally substituted —SCH$_3$, an optionally substituted heterocycle or heteroaromatic, or R$_8$ taken with an R$_{1a}$ attached to a carbon directly bonded to the ring bearing R$_8$ and the carbon to which the R$_{1a}$ is attached form an optionally substituted C3-C6 cycloalkyl or carbocycle or an optionally substituted heterocycle, or R$_{12}$ taken with an R$_{1a}$ attached to a carbon directly bonded to the ring bearing R$_{12}$ and the carbon to which the R$_{1a}$ is attached, form an optionally substituted C3-C6 cycloalkyl or carbocycle or an optionally substituted heterocycle and pharmaceutically acceptable salts thereof.

In some cases: R$_3$ is selected from R$_{3x}$, R$_{3y}$ and R$_{3z}$ wherein:

R$_{3x}$ is

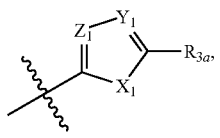

wherein X$_1$, Y$_1$, and Z$_1$ are: (a) O, N and N, respectively; (b) O, N and C(R$_{3c}$), respectively; (c) O, C(R$_{3c}$) and C(R$_{3c}$), respectively; (d) O, C(R$_{3c}$) and N respectively; (e) S, N and N, respectively; (f) S, N and C(R$_{3c}$), respectively; (g) S, C(R$_{3c}$) and C(R$_{3c}$), respectively; (h) S, C(R$_{3c}$) and N respectively; (i) N(R$_{3b}$), N and N, respectively; (j) N(R$_{3b}$), N and C(R$_{3c}$), respectively; (k) N(R$_{3b}$), C(R$_{3c}$) and C(R$_{3c}$), respectively; or (l) N(R$_{3b}$), C(R$_{3c}$) and N respectively;

R$_{3y}$ is

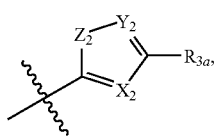

wherein X$_2$, Y$_2$, and Z$_2$ are: (a) N, N and O, respectively; (b) C(R$_{3c}$), N and O, respectively; (c) N, C(R$_{3c}$) and O, respectively; (d) C(R$_{3c}$), C(R$_{3c}$) and O, respectively; (e) N, N and S, respectively; (f) C(R$_{3c}$), N and S, respectively; (g) N, C(R$_{3c}$) and S, respectively; (h) C(R$_{3c}$), C(R$_{3c}$) and S, respectively; (i) N, N and N(R$_{3b}$), respectively; (j) C(R$_{3c}$), N and N(R$_{3b}$), respectively; (k) N, C(R$_{3c}$) and N(R$_{3b}$), respectively; or (l) C(R$_{3c}$), C(R$_{3c}$) and N(R$_{3b}$), respectively;

R$_{3z}$ is

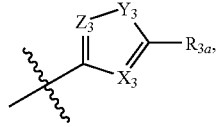

wherein X$_3$, Y$_3$, and Z$_3$ are: (a) N, O and N, respectively; (b) C(R$_{3c}$), O and N, respectively; (c) N, O and C(R$_{3c}$), respectively; (d) C(R$_{3c}$), O and C, respectively; (e) N, S and N, respectively; (f) C(R$_{3c}$), S and N, respectively; (g) N, S and C, respectively; (h) C(R$_{3c}$), S and C(R$_{3c}$), respectively; (i) N, N(R$_{3b}$) and N, respectively; (j) C(R$_{3c}$), N(R$_{3b}$) and N, respectively; (k) N, N(R$_{3b}$) and C(R$_{3c}$), respectively or (l) C(R$_{3c}$), N(R$_{3b}$) and C(R$_{3c}$), respectively;

R$_{3a}$ is selected from:

H, halogen, an optionally substituted aryl, an optionally substituted heteroaryl, an optionally substituted C1-C5 alkyl, an optionally substituted C2-C5 alkenyl, an optionally substituted C2-C5 alkynyl, an optionally substituted C1-C5 alkoxy, —NO$_2$, —CN, —C(O)OH, an optionally substituted —SO$_2$CH$_3$, an optionally substituted —SO$_2$NH$_2$, an optionally substituted —SO$_2$OH, —C(O)H, an optionally substituted —C(O)CH$_3$, an optionally substituted —C(O)N(CH$_3$)$_2$, an optionally substituted —C(O)NH$_2$, an optionally substituted —SCH$_3$, an optionally substituted C3 to C10 cycloalkyl or carbocycle, an optionally substituted heterocycle, or R$_{3a}$ and the carbon to which it is attached together with Y$_1$, Y$_2$ or Y$_3$ can form a heteroaryl containing 5 to 6 ring atoms or R$_{3a}$ is absent.

R$_{3b}$ is selected from:

H, an optionally substituted aryl, an optionally substituted heteroaryl, an optionally substituted C1-C5 alkyl, an optionally substituted C2-C5 alkenyl, an optionally substituted C2-C5 alkynyl, an optionally substituted C1-C5 alkoxy, —CN, an optionally substituted —SO$_2$CH$_3$, an optionally substituted —SO$_2$NH$_2$, an optionally substituted —SO$_2$OH, an optionally substituted —C(O)CH$_3$, an optionally substituted —C(O)N(CH$_3$)$_2$, an optionally substituted —C(O)NH$_2$, an optionally substituted C3 to C$_{10}$ cycloalkyl or carbocycle, an optionally substituted heterocycle;

R$_{3c}$ is selected from:

H, halogen, an optionally substituted aryl, an optionally substituted heteroaryl, an optionally substituted C1-C5 alkyl, an optionally substituted C2-C5 alkenyl, an optionally substituted C2-C5 alkynyl, an optionally substituted C1-C5 alkoxy, —NO$_2$, —CN, —C(O)OH, an optionally substituted —SO$_2$CH$_3$, an optionally substituted —SO$_2$NH$_2$, and optionally substituted —SO$_2$OH, —C(O)H, an optionally substituted —C(O)CH$_3$, an optionally substituted —C(O)N(CH$_3$)$_2$, an optionally substituted —C(O)NH$_2$, an optionally substituted —SCH$_3$, an optionally substituted C3 to C10 cycloalkyl or carbocycle, an optionally substituted heterocycle, or R$_{3c}$ and the carbon to which it is attached together with a ring atom bonded to the carbon to which R$_{3c}$ is attached can form a heteroaryl containing 5 to 6 ring atoms.

In various embodiments: wherein R$_2$ is selected from H, methyl, Cl and CF$_3$ F; R$_2$ is selected from H, methyl and Cl; R$_2$ is halogen; R$_2$ is Cl; R$_2$ is F; R$_2$ is methyl; R$_2$ is methyl or halogen substituted methyl; m is one; R$_{1a}$ and R$_{1b}$ taken together with the carbon to which they are attached form an optionally substituted C3-C6 cycloalkyl or carbocycle;

wherein $R_{1a}$ and $R_{1b}$ are both H; $R_{1a}$ and $R_{1b}$ are either both methyl or taken together with the carbon to which they are attached form an optionally substituted C3-C6 cycloalkyl or carbocycle or an optionally substituted heterocycle; the $R_{1a}$ attached to a carbon directly bonded to the ring bearing $R_{12}$, taken with $R_{12}$ and the carbon to which $R_{1a}$ is attached form an optionally substituted C3-C6 cycloalkyl or carbocycle or an optionally substituted heterocycle or the $R_{1a}$ attached to a carbon directly bonded to the ring bearing $R_8$, taken with $R_8$ and the carbon to which $R_{1a}$ is attached form an optionally substituted C3-C6 cycloalkyl or carbocycle or an optionally substituted heterocycle; m is 1 and $R_{1a}$ and $R_{1b}$ taken together with the carbon to which they are attached form an optionally substituted C3-C6 cycloalkyl or carbocycle or an optionally substituted heterocycle; $R_{1a}$ and $R_{1b}$ attached to the same carbon, taken together with that carbon, form an optionally substituted C3-C6 cycloalkyl or carbocycle; $R_9$ and $R_{11}$ are both H; $R_8$, $R_9$, $R_{10}$, $R_{11}$ and $R_{12}$ are other than H; $R_8$, $R_9$, $R_{10}$, $R_{11}$ and $R_{12}$ are other than H; no more than two of $R_8$, $R_9$, $R_{10}$, $R_{11}$ and $R_{12}$ are other than H; only one of $R_8$, $R_9$, $R_{10}$, $R_{11}$ and $R_{12}$ is other than H; $R_5$ is methoxy; $R_{10}$ is halogen; $R_4$ is selected from: F, H, an optionally substituted C1-C5 alkyl, an optionally substituted C1-C5 alkoxy; each of $R_4$, $R_5$, $R_6$, and $R_7$ is independently selected from H, a halogen, hydroxy, an optionally substituted C1-C5 alkyl, an optionally substituted C1-C5 alkoxy; $R_5$ is selected from: Cl, F, Br, methoxy, $CH_3$, $CF_3$ and OH.

In some cases: $R_3$ is $R_{3x}$; $R_3$ is $R_{3y}$; $R_3$ is $R_{3z}$.

In some cases: wherein $R_{3x}$ is

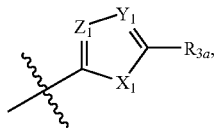

wherein $X_1$, $Y_1$, and $Z_1$ are: (a) O, N and N, respectively; (b) O, N and $C(R_{3c})$, respectively; (c) O, $C(R_{3c})$ and $C(R_{3c})$, respectively; (d) O, $C(R_{3c})$ and N respectively; (e) S, N and N, respectively; (f) S, N and $C(R_{3c})$, respectively; (g) S, $C(R_{3c})$ and $C(R_{3c})$, respectively; (h) S, $C(R_{3c})$ and N respectively; (i) $N(R_{3b})$, N and N, respectively; (j) $N(R_{3b})$, N and $C(R_{3c})$, respectively; (k) $N(R_{3b})$, $C(R_{3c})$ and $C(R_{3c})$, respectively; or (l) $N(R_{3b})$, $C(R_{3c})$ and N respectively; $R_3$ is $R_{3x}$ and $X_1$, $Y_1$, and $Z_1$ are (k) O, N and N, respectively.

In some cases: $R_{3y}$ is

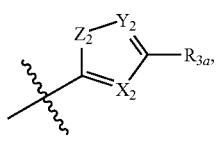

wherein $X_2$, $Y_2$, and $Z_2$ are: (a) N, N and O, respectively; (b) $C(R_{3c})$, N and O, respectively; (c) N, $C(R_{3c})$ and O, respectively; (d) $C(R_{3c})$, $C(R_{3c})$ and O, respectively; (e) N, N and S, respectively; (f) $C(R_{3c})$, N and S, respectively; (g) N, $C(R_{3c})$ and S, respectively; (h) $C(R_{3c})$, $C(R_{3c})$ and S, respectively; (i) N, N and $N(R_{3b})$, respectively; (j) $C(R_{3c})$, N and $N(R_{3b})$, respectively; (k) N, $C(R_{3c})$ and $N(R_{3b})$, respectively; or (l) $C(R_{3c})$, $C(R_{3c})$ and $N(R_{3b})$, respectively; $R_3$ is $R_{3y}$ and $X_2$, $Y_2$, and $Z_2$ are (c) N, N and O, respectively.

In some cases: $R_{3z}$ is

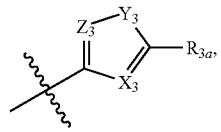

wherein $X_3$, $Y_3$ and $Z_3$ are: (a) N, O and N, respectively; (b) $C(R_{3c})$, O and N, respectively; (c) N, O and $C(R_{3c})$, respectively; (d) $C(R_{3c})$, O and C, respectively; (e) N, S and N, respectively; (f) $C(R_{3c})$, S and N, respectively; (g) N, S and C, respectively; (h) $C(R_{3c})$, S and $C(R_{3c})$, respectively; (i) N, $N(R_{3b})$ and N, respectively; (j) $C(R_{3c})$, $N(R_{3b})$ and N, respectively; (k) N, $N(R_{3b})$ and $C(R_{3c})$, respectively; or (l) $C(R_{3c})$, $N(R_{3b})$ and $C(R_{3c})$, respectively.

In some cases: $R_{3x}$ is

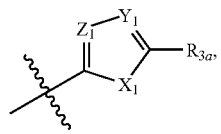

wherein $X_1$, $Y_1$, and $Z_1$ are: (i) O, N and $C(R_{3c})$, respectively; (j) O, $C(R_{3c})$ and N, respectively; or (k) O, N and N respectively;

$R_{3y}$ is

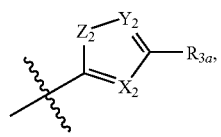

wherein X, Y, and Z are: (c) N, N and O, respectively;

$R_{3z}$ is

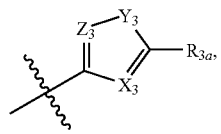

wherein X, Y, and Z are: (a) $C(R_{3c})$, O and N, respectively, (b) $C(R_{3c})$, S and N, respectively; (c) N, O and N, respectively; (d) N, S and N, respectively; or (e) N, $N(R3_b)$ and N, respectively; and $R_{3a}$ is an optionally substituted aryl containing a single ring or an optionally substituted heteroaryl containing a single ring.

In some cases: $R_4$ is H; $R_6$ is H; $R_7$ is H; $R_8$ is H; $R_4$, $R_6$, and $R_7$ are H.

In some cases: $R_{3a}$ is selected from:

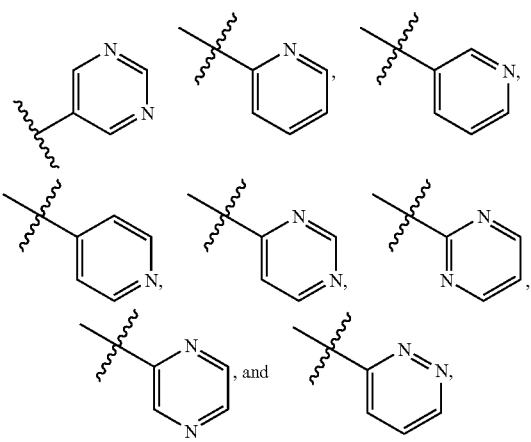
, and and is optionally substituted;
$R_{3a}$ is

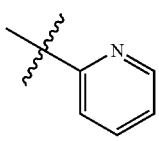

and is optionally substituted;
$R_{3a}$ is

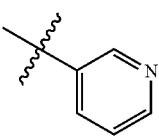

and is optionally substituted;
$R_{3b}$ is

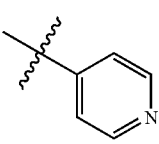

and is optionally substituted; and
$R_{3a}$ is

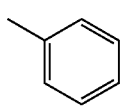

and is optionally substituted;

In some cases: $R_{3a}$ is an optionally substituted pyrimidine; $R_{3a}$ is monosubstituted or unsubstituted; $R_{3a}$ is unsubstituted; $R_{3a}$ is monosubstituted; $R_{3a}$ is selected from:

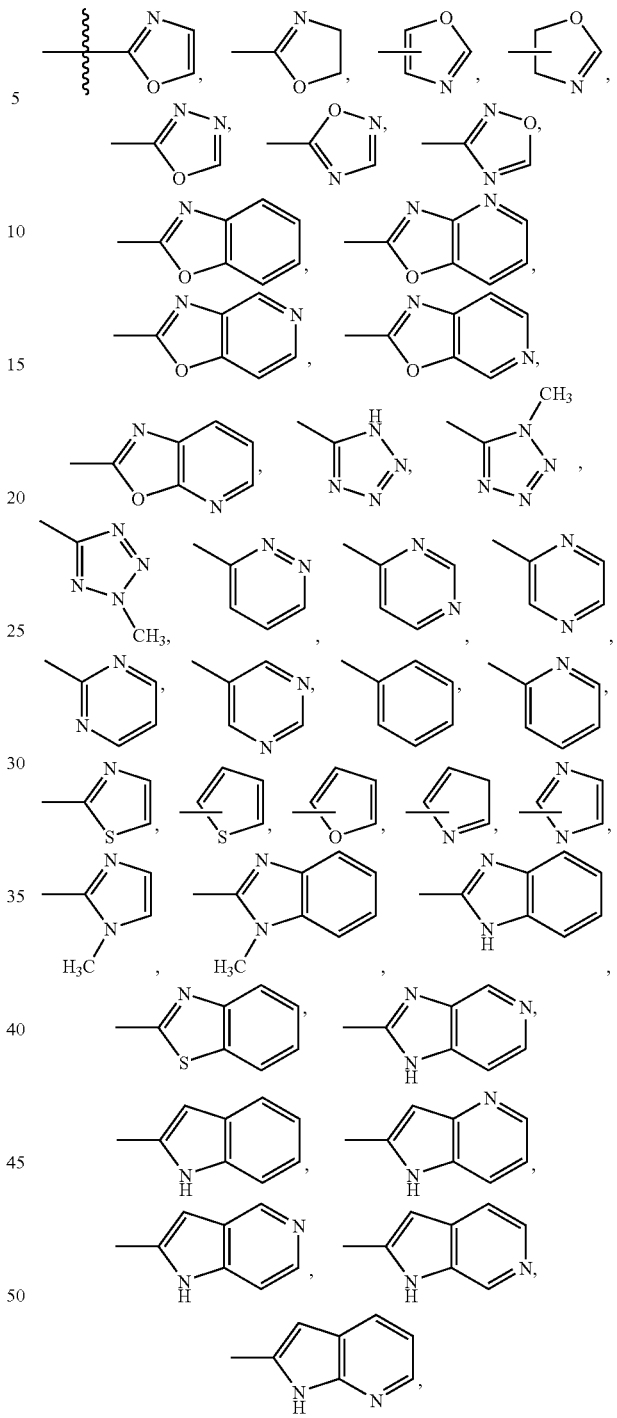

and can be optionally substituted at a substitutable position.

In some cases: $R_{3b}$ is selected from H and C1-C3 alkyl; $R_{3c}$ is selected from H, halogen and C1-C3 alkyl; R3c taken with the carbon to which it is attached and a ring atom adjacent to the ring atom to which it is attached form a heteroaryl; $R_{1a}$ attached to a carbon directly bonded to the ring bearing $R_8$, taken with $R_8$ and the carbon to which $R_{1a}$ is attached, form an optionally substituted C3-C6 cycloalkyl or carbocycle or an optionally substituted heterocycle; or an $R_{1a}$ attached to a carbon directly bonded to the ring bearing $R_{12}$, taken with $R_{12}$ and the carbon to which $R_{1a}$ is attached form an optionally substituted C3-C6 cycloalkyl or carbocycle or an optionally substituted heterocycle and $R_{1b}$ is selected from H or methyl; $R_4$, is an optionally substituted heterocycle or heteroaromatic containing 5 or 6 ring atoms; $R_5$, is an optionally substituted heterocycle or heteroaromatic containing 5 or 6 ring atoms; $R_6$, is an optionally substituted heterocycle or heteroaromatic containing 5 or 6 ring atoms; $R_7$, is an optionally substituted heterocycle or heteroaromatic containing 5 or 6 ring atoms; $R_{2a}$ and $R_{2b}$ attached to the same nitrogen, taken together with that nitrogen form an optionally substituted heterocycle or heteroaromatic containing 5 or 6 ring atoms; $R_8$ is heterocycle or heteroaromatic containing 5 or 6 ring atoms; $R_9$ is heterocycle or heteroaromatic containing 5 or 6 ring atoms; $R_{10}$ is heterocycle or heteroaromatic containing 5 or 6 ring atoms; $R_{11}$ is heterocycle or heteroaromatic containing 5 or 6 ring atoms; and $R_{12}$ is heterocycle or heteroaromatic containing 5 or 6 ring atoms.

Other useful compounds, e.g., DAO inhibitors have Formula II:

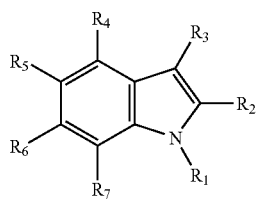

Formula II wherein $R_2$, $R_3$, $R_4$, and $R_7$ are independently selected from: H, $CO_2H$, halogen, C1-C6 alkyl, C2-C6 alkenyl, C2-C6 alkynyl, aryl, heteroaryl, heterocycle, carbocycle-C(O)$R_8$, —$(CH_2)_nC(O)NO$, —$(CH_2)_nN(H)$-aryl, —C(O)N(H)-aryl, —OR$_8$, —C(O)N(OH)(C1-C6 alkyl), —C(O)N(H)(NH$_2$), —NR$_8$, —N(H)OR$_8$, —$(CH_2)_nC(O)OR_8$, —S$(CH_2)_nCO_2H$, —N$(CH_2)_nCO_2H$, —ON(H)$(CH_2)_nCO_2H$, —SO$_3$H, —PO$_3$H$_2$—$(CH_2)_n$aryl, —$(CH_2)_nNH_2$, —$(CH_2)_nN(OH)$(C$_1$-C$_6$ aryl), —NO$_2$, —SR$_8$, —SOR$_8$, —SO$_2$R$_8$, —$(CH_2)_n$CN, —$(CH_2)_n$O-carbocycle, —$(CH_2)_n$S-carbocycle, —$(CH_2)_n$S-cycloalkyl, —$(CH_2)_nS(O)_2$-carbocycle, —$(CH_2)_n$ S(O)$_2$-carbocycle, —$(CH_2)_nN(H)$carbocycle, $(CH_2)_n$ NCOCH$_3$, —$(CH_2)_n$n-carbocycle, —O$(CH_2)_nCO_2H$, CN$_5$H, $(CH_2)_n$CN$_5$H, —B(OH)$_2$, —$(CH_2)_n$N(OH),
$R_5$ is selected from H, halogen, C1-C6 alkyl, C2-C6 alkenyl, C2-C6 alkynyl, aryl, heteroaryl, heterocycle, carbocycle-C(O)R$_8$, CO$_2$H, —NR$_8$, —NOR$_8$, —NO$_2$, —SR$_8$, —SOR$_8$, —SO$_2$R$_8$;
$R_6$ is selected from: H, C1-C6 alkyl, C2-C6 alkenyl, C2-C6 alkynyl, aryl, heteroaryl, heterocycle, carbocycle, OH, —OR$_8$, —NR$_8$, —NOR$_8$, —NO$_2$, —SR$_8$, —SOR$_8$, —SO$_2$R$_8$;
$R_1$ is selected from: H, C1-C6 alkyl, C2-C6 alkenyl, C2-C6 alkynyl, aryl, heteroaryl, heterocycle, carbocycle, $(CH_2)_n$ carbocycle, $(CH_2)_n$phenyl.
wherein $R_8$ is selected from H, C1-C6 alkyl, C2-C6 alkenyl, C2-C6 alkynyl, aryl, heteroaryl, heterocycle, carbocycle;
n=0, 1, 3, 4 or 5; and
any C1-C6 alkyl, C2-C6 alkenyl, C2-C6 alkynyl, aryl, heteroaryl, heterocycle, carbocycle can be optionally substituted and pharmaceutically acceptable salts thereof.

In certain cases: $R_2$, $R_3$, and $R_4$, and $R_7$ are independently selected from: H, CO$_2$H, halogen, C1-C6 alkyl, C2-C6 alkenyl, C2-C6 alkynyl, aryl, heteroaryl, heterocycle, carbocycle-C(O)R$_8$, —$(CH_2)_nC(O)NO$, —$(CH_2)_nN(H)$-aryl, —C(O)N(H)-aryl, —OR$_8$, —C(O)N(OH)(C1-C6 alkyl), —C(O)N(H)(NH$_2$), —NR$_8$, —N(H)OR$_8$, —$(CH_2)_nC(O)OR_8$, —S$(CH_2)_nCO_2H$, —N$(CH_2)_nCO_2H$, —ON(H)$(CH_2)_n$ CO$_2$H, —SO$_3$H, —PO$_3$H$_2$—$(CH_2)_n$aryl, —$(CH_2)_nNH_2$, —$(CH_2)_nN(OH)$(C$_1$-C$_6$ aryl), —NO$_2$, —SR$_8$, —SOR$_8$, —SO$_2$R$_8$, —$(CH_2)_n$CN, —$(CH_2)_n$O-carbocycle, —$(CH_2)_n$ S-carbocycle, —$(CH_2)_n$S-cycloalkyl, —$(CH_2)_n$S(O)2-carbocycle, —$(CH_2)_nS(O)_2$-carbocycle, —$(CH_2)_nN(H)$carbocycle, and $(CH_2)_n$NCOCH$_3$.

In certain cases: $R_2$, $R_3$, $R_4$, and $R_7$ are independently selected from H, CO$_2$H, halogen, C1-C6 alkyl, C2-C6 alkenyl, C2-C6 alkynyl, aryl, heteroaryl, heterocycle, carbocycle-C(O)R$_8$, —$(CH_2)_nC(O)NO$, —$(CH_2)_nN(H)$-aryl, —C(O)N(H)-aryl, —OR$_8$, —C(O)N(OH)(C1-C6 alkyl), —C(O)N(H)(NH$_2$), —NR$_8$, —N(H)OR$_8$, —$(CH_2)_nC(O)OR_8$.

In certain cases: $R_2$, $R_3$, $R_4$, and $R_7$ are independently selected from: H, CO$_2$H, halogen, C1-C6 alkyl, C2-C6 alkenyl, C2-C6 alkynyl, aryl, heteroaryl, heterocycle, carbocycle-C(O)R$_8$, —$(CH_2)_nC(O)NO$, —$(CH_2)_nN(H)$-aryl, —C(O)N(H)-aryl, —OR$_8$.

In certain cases: $R_5$ is selected from H, halogen, C1-C6 alkyl, C2-C6 alkenyl, C2-C6 alkynyl, aryl, heteroaryl, heterocycle, carbocycle-C(O)R$_8$, —NR$_8$, —NOR$_8$, —NO$_2$, —SR$_8$, —SOR$_8$, —SO$_2$R$_8$.

In certain cases: $R_5$ is selected from H, halogen, C1-C6 alkyl, C2-C6 alkenyl, C2-C6 alkynyl, aryl, heteroaryl, heterocycle, carbocycle-C(O)R$_8$.

In certain cases: $R_6$ is selected from: H, C1-C6 alkyl, C2-C6 alkenyl, C2-C6 alkynyl, aryl, heteroaryl, heterocycle, carbocycle, OH, —OR$_8$, —NR$_8$, —NOR$_8$, —NO$_2$, —SR$_8$, —SOR$_8$, —SO$_2$R$_8$.

In certain cases: $R_6$ is H.

In certain cases: $R_1$ is selected from: H, C1-C6 alkyl, C2-C6 alkenyl, C2-C6 alkynyl, aryl, heteroaryl, heterocycle, carbocycle, $(CH_2)_n$carbocycle.

In certain cases: $R_1$ is H.

In certain cases: any heteroaryl is selected from:

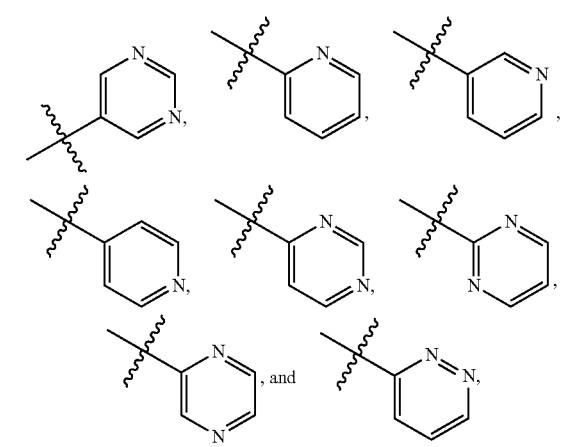

and can be optionally substituted.

In certain cases: the any aryl or carbocycle is a phenyl; any heteroaryl contains 5 or 6 ring atoms; any heterocycle contains 5 or 6 ring atoms; any C1-C6 alkyl is methyl or ethyl; and $R_1$ is $(CH_2)$phenyl.

Useful compounds, e.g., useful DAO inhibitors include: compound having Formula III:

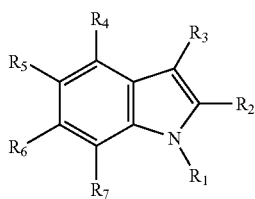

Formula III wherein R$_2$, R$_3$, R$_4$, R$_5$, and R$_8$ are independently selected from: H, —OR$_8$, CO$_2$H, halogen, C1-C6 alkyl, C2-C6 alkenyl, C2-C6 alkynyl, aryl, heteroaryl, heterocycle, carbocycle-C(O)R$_8$, —(CH$_2$)$_n$C(O)NO, —(CH$_2$)$_n$N(H)aryl, —C(O)N(H)aryl, —C(O)N(OH)(C1-C6 alkyl), —C(O)N(H)(NH$_2$), —NR$_8$, —N(H)OR$_8$, —(CH$_2$)$_n$C(O)OR$_8$—S(CH$_2$)$_n$CO$_2$H, —N(CH$_2$)$_n$CO$_2$H, —ON(H)(CH$_2$)$_n$CO$_2$H, —SO$_3$H, —PO$_3$H$_2$—(CH$_2$)$_n$aryl, —(CH$_2$)$_n$NH$_2$, —(CH$_2$)$_n$(OH)(C$_1$-C$_6$ aryl), —NO$_2$, —SR$_8$, —SOR$_8$, —SO$_2$R$_8$, —(CH$_2$)$_n$CN, —(CH$_2$)$_n$Ocarbocycle, —(CH$_2$)$_n$Scarbocycle, —(CH$_2$)$_n$Scycloalkyl, —(CH$_2$)$_n$S(O)$_2$carbocycle, —(CH$_2$)$_n$S(O)$_2$carbocycle, —(CH$_2$)$_n$N(H)carbocycle, (CH$_2$)$_n$NCOCH$_3$-(CH$_2$)$_n$carbocycle, —(O(CH$_2$)$_n$CO$_2$H, CN$_5$H, (CH$_2$)$_n$CN$_5$H, B(OH)$_2$, (CH$_2$)$_n$N(OH).

R$_6$ is selected from H, halogen, C1-C6 alkyl, C2-C6 alkenyl, C2-C6 alkynyl, aryl, heteroaryl, heterocycle, carbocycle-C(O)R8, CO$_2$H, —NR$_8$, —NOR$_8$, —NO$_2$, —SR$_8$, —SOR$_8$, —SO$_2$R$_8$;

R$_7$ is H, C1-C6 alkyl, C2-C6 alkenyl, C2-C6 alkynyl, aryl, heteroaryl, heterocycle, carbocycle, OH, —OR$_8$, —NR$_8$, —NOR$_8$, —NO$_2$, —SR$_8$, —SOR$_8$, —SO$_2$R$_8$;

R$_1$ is H;

n=0, 1, 2, 3, 4 or 5; and wherein R$_8$ is H, C1-C6 alkyl, C2-C6 alkenyl, C2-C6 alkynyl, aryl, heteroaryl, heterocycle, carbocycle; and and wherein any C1-C6 alkyl, C2-C6 alkenyl, C2-C6 alkynyl, aryl, heteroaryl, heterocycle, carbocycle can be optionally substituted and pharmaceutically acceptable salts thereof.

In certain cases: R$_2$, R$_3$, R$_4$, R$_5$, R$_8$ are independently selected from: H, and —OR$_8$, CO$_2$H, halogen, C1-C6 alkyl, C2-C6 alkenyl, C2-C6 alkynyl.

In certain cases: R$_2$, R$_3$, R$_4$, R$_5$, and R$_8$ are independently selected from: H, and —OR$_8$.

In certain cases: R$_6$ is selected from H, halogen, C1-C6 alkyl, C2-C6 alkenyl, C2-C6 alkynyl; R$_6$ is H; R$_7$ is H, C1-C6 alkyl, C2-C6 alkenyl, C2-C6 alkynyl, aryl, heteroaryl, heterocycle, carbocycle, OH, —OR$_8$, —NR$_8$, —NOR$_8$, —NO$_2$, —SR$_8$, —SOR$_8$, —SO$_2$R$_8$; R$_7$ is H, C1-C6 alkyl, C2-C6 alkenyl, C2-C6 alkynyl; R$_7$ is H.

In certain cases: any heteroaryl is selected from:

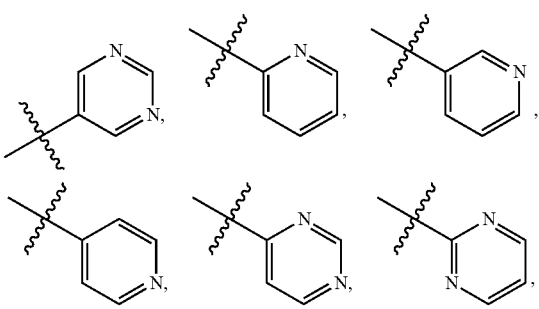

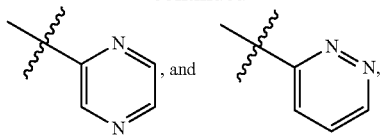

, and and can be optionally substituted.

In certain cases: any aryl is a phenyl; any heteroaryl contains 5 or 6 ring atoms; any heterocycle contains 5 or 6 ring atoms; and any C1-C6 alkyl is methyl or ethyl.

The term "halo" or "halogen" refers to any radical of fluorine, chlorine, bromine or iodine.

The term "alkyl" refers to a hydrocarbon chain that may be a straight chain or branched chain, containing the indicated number of carbon atoms. For example, C1-C12 alkyl indicates that the group may have from 1 to 12 (inclusive carbon atoms in it (i.e., 1, 2, 3, 4, 5, 6, 7, 8, 9, 10, 11, 12). The term "haloalkyl" refers to an alkyl in which one or more hydrogen atoms are replaced by halo, and includes alkyl moieties in which all hydrogens have been replaced by halo (e.g., perfluoroalkyl). The terms "arylalkyl" or "aralkyl" refer to an alkyl moiety in which an alkyl hydrogen atom is replaced by an aryl group. Examples of "arylalkyl" or "aralkyl" include, but are not limited to, benzyl and 9-fluorenyl groups.

The terms "alkylamino" and "dialkylamino" refer to —NH(alkyl) and —N(alkyl)2 radicals respectively. The term "aralkylamino" refers to a —NH(aralkyl) radical. The term "alkoxy" refers to an —O-alkyl radical. Thus, for example, alkoxy or alkoxyl can refer to groups of 1, 2, 3, 4, 5, 6, 7 or 8 carbon atoms of a straight, branched, cyclic configuration and combinations thereof attached to the parent structure through an oxygen atom. Examples include, but are not limited to, methoxy, ethoxy, propoxy, isopropoxy, cyclopropyloxy, cyclohexyloxy and the like. Lower-alkoxy refers to groups containing one to four carbons. The term "mercapto" refers to an SH radical.

The term "thioalkoxy" refers to an —S-alkyl radical.

The term "aryl" refers to an aromatic monocyclic, bicyclic, or tricyclic hydrocarbon ring system, wherein any ring atom capable of substitution can be substituted by a substituent. Examples of aryl moieties include, but are not limited to, phenyl, naphthyl, and anthracenyl. In a multiple ring aromatic ring system, only one ring need be aromatic. In some cases all of the rings are aromatic.

The term "cycloalkyl" as employed herein includes saturated monocyclic, bicyclic, tricyclic, or polycyclic hydrocarbon groups having 3 to 12 carbons, wherein any ring atom capable of substitution can be substituted by a substituent. Examples of cycloalkyl moieties include, but are not limited to, cyclopentyl, norbornyl, cyclopropyl, cyclohexyl, and adamantyl.

The term "carbocycle" as employed herein includes saturated, partially unsaturated or unsaturated monocyclic, bicyclic, tricyclic, or polycyclic hydrocarbon groups having 3 to 12 carbons, wherein any ring atom capable of substitution can be substituted by a substituent. Carbocycles can be aromatic, e.g., a phenyl group is an example of a carbocycle. A subset of carbocycles is non-aromatic carbocycles.

The term "acyl" refers to an alkylcarbonyl, cycloalkylcarbonyl, arylcarbonyl, heterocyclylcarbonyl, or heteroarylcarbonyl substituents, any of which may be further substituted by substituents.

The term "oxo" refers to an oxygen atoms, which forms a carbonyl when attached to carbon, an N-oxide when attached to nitrogen, and a sulfoxide or sulfone when attached to sulfur.

The term "heteroaryl" refers to a mono- and bicyclic aromatic ring system (only one ring needs to be aromatic) having from 5 to 14, preferably 5 to 10 ring atoms such as 5, 6, 7, 8, 9 or 10 ring atoms (mono- or bicyclic), in which one or more of the ring atoms are other than carbon, such as nitrogen, sulfur, oxygen as part of the ring system. Examples of heteroaryl ring systems include, but are not limited to: pyrrole, imidazole, thiophene, furan, thiazole, isothiazole, thiadiazole, oxazole, isoxazole, oxadiazole, pyridine, pyrazine, pyrimidine, pyridazine, pyrazole, triazole, tetrazole, indole, isoindole, indoline (i.e., 2,3-dihydroindole), isoindoline (i.e., 1,3-dihydroisoindole), benzothiophene, benzofuran, 2,3-dihydrobenzofuran, isobenzofuran, benzodioxole, benzothiadiazole, benzotriazole, benzoxazole, 2,1,3-benzoxadiazole, benzopyrazole, 2,1,3-benzothiazole, 2,1,3-benzoselenadiazole, benzimidazole, indazole and benzodioxane. Additional examples are described below. Important subsets include mono-cyclic heteroaryls and bicyclic heteroaryls.

The term "heterocyclic" refers to unsaturated, partially saturated and fully saturated monocyclic and bicyclic rings having from 4 to 14, preferably 4 to 10 ring atoms having one or more heteroatoms (e.g., oxygen, sulfur, or nitrogen) as part of the ring system and the remainder being carbon, such as, for example, the heteroaryl groups mentioned above as well as the corresponding partially saturated or fully saturated heterocyclic rings. Examples of saturated heterocyclic rings, but are not limited to, azetidine, pyrrolidine, piperidine, piperazine, morpholine, and thiomorpholine.

Additional examples are described below.

Heterocycles having a 5-membered ring include, but are not limited to: thiophene, furan, and pyrrole, thiazole, oxazole, and imidazole, isothiazole, isoxazole, and pyrazole, 1,2,3-triazole, 1,2,4-triazole, tetrazole, 1,2,3-oxadiazole, 1,2,4-oxadiazole, 1,2,5-oxadiazole, 1,3,4-oxadiazole, 1,2,3,4-oxatriazole, 1,2,3-thiadiazole, 1,2,4-thiadiazole, 1,2,5-thiadiazole, 1,3,4-thiadiazole, and 1,2,3,4-thiadiazole.

Saturated 5 or 6-membered ring heterocycles include, but are not limited to: piperidine and substituted piperidine; pyyrolidine and substituted pyrrolidine; azetidine and substituted azetidine; piperazine and substituted piperazine; morpholine and substituted morpholine; thiomorpholine and substituted thiomorpholine and their sulfoxide and sulfone derivatives, thioethers, substituted thioethers, their sulfoxides and sulfones; ethers and substituted ethers; 1,4-thioether-ethers and 1,4-dioxane derivatives; 1,4-bis-thioethers, their sulfoxides and sulfones. Also included are tetrahydrofuran, dihydrofuran, tetrahydrothiophene, dihydrothiophene, piperidine, dihyropyrrole, 1,3-dithiolane, 1,2-dithiolane, isoxazolidine, isothiazolidine, pyrazolidine, tetrahydro-2H-pyran, tetrahydro-2H-thiopyran, 3,6-dihydro-2H-thiopyran, 3,4-dihydro-2H-thiopyran, piperidine, 1,2,3,6-tetrahydropyridine, 1,2,3,4-tetrahydropyridine, morpholine, thiomorpholine, piperazine, thiomorpholine 1-oxide, thiomorpholine 1,1-dioxide, and the like.

The 6-membered ring heteroaryls include, but are not limited to: pyridine; pyrimidine; pyrazine; pyridazine; 1,2,3-triazine; 1,2,4-triazine; 1,3,5-triazine; 1,2,3,4-tetrazine; 1,2,3,5-tetrazine; 1,2,4,5-tetrazine; and pentazine.

Carbocycles include, but are not limited to: cyclohexyl and substituted cyclohexyl; cyclopentyl and substituted cyclopentyl; cyclobutyl and substituted cyclobutyl; cyclopropyl and substituted cyclopropyl; cyclohexenyl and substituted cyclohexenyl; cyclopentenyl and substituted cyclopentenyl; and cyclobutenyl and substituted cyclobutenyl.

The 6,5-fused heteroaromatic ring systems having 1, 2, 3 or 4 heteroatoms independently selected from N, O, and S, include, but are not limited to: 1,3-benzoxazole -2- yl; 1,3-benzoxazole-4-yl; 1,3-benzoxazole-5-yl, 1,3-benzoxazole-6-yl; 1,3-benzothiazole-2-yl; 1,2-benzothiaole-4-yl; 1,3-benzothiazole-5-yl; 1,3-benzothiazole-6-yl; 1,3-benzothiazole-7-yl; [1,3]thiazolo[4,5-b]Pyridine-2-yl; [1,3]thiazolo[4,5-b]pyridine-5-yl; [1,3]thiazolo[4,5-b]pyridine-6-yl; [1,3]thiazolo[4,5-b]pyridine-7-yl; [1,3]thiazolo[4,5-c]pyridine-2-yl; [1,3]thiazolo[4,5-c]pyridine-4-yl; [1,3]thiazolo[4,5-c]pyridine-4-yl; [1,3]thiazolo[4,5-c]pyridine-5-yl; [1,3]thiazolo[5,4-c]pyridine-2-yl; [1,3]thiazolo[5,4-c]pyridine-7-yl; [1,3]thiazolo[5,4-c]Pyridine-5-yl; [1,3]thiazolo[5,4-c]pyridine-4-yl; [1,3]thiazolo[5,4-b]pyridine-2-yl; [1,3]thiazolo[5,4-b]pyridine-7-yl; [1,3]thiazolo[5,4-b]pyridine-6-yl; [1,3]thiazolo[5,4-b]Pyridine-5-yl; [1,3]thiazolo[4,5-b]pyrazine-2-yl; [1,3]thiazolo[4,5-b]pyrazine-5-yl; [1,3]thiazolo[4,5-b]pyrazine-6-yl; [1,3]thiazolo[5,4-a]pyrimidine-2-yl; [1,3]thiazolo[5,4-a]pyrimidine-7-yl; [1,3]thiazolo[5,4-a]pyrimidine-5-yl; [1,3]thiazolo[4,5-d]pyrimidine-2-yl; [1,3]thiazolo[4,5-d]pyrimidine-5-yl; [1,3]thiazolo[4,5-d]pyrimidine-7-yl; [1,3]thiazolo[4,5-c]pyridazine-2-yl; [1,3]thiazolo[4,5-c]pyridazine-5-yl; [1,3]thiazolo[4,5-c]pyridazine-4-yl; [1,3]thiazolo[4,5-d]pyridazine-2-yl; [1,3]thiazolo[4,5-d]pyridazine-4-yl; [1,3]thiazolo[4,5-d]pyridazine-7-yl; [1,3]thiazolo[5,4-c]pyridazine-6-yl; [1,3]thiazolo[5,4-c]pyridazine-4-yl, [1,3]thiazolo[5,4-c]pyridazine-3-yl; [1,3]oxazolo[5,4-c]pyridazine-6-yl; [1,3]oxazolo[5,4-c]pyridazine-4-yl; [1,3]oxazolo[5,4-c]pyridazine-3-yl; [1,3]oxazolo[4,5-d]pyridazine-2-yl; [1,3]oxazolo[4,5-d]pyridazine-4-yl; [1,3]oxazolo[4,5-d]pyridazine-7-yl; [1,3]oxazolo[4,5-c]pyridazine-6-yl; [1,3]oxazolo[4,5-c]pyridazine-3-yl; [1,3]oxazolo[4,5-c]pyridazine-4-yl; [1,3]oxazolo[4,5-d]pyrimidine-2-yl; [1,3]oxazolo[4,5-d]pyrimidine-5-yl; [1,3]oxazolo[4,5-d]pyrimidine-7-yl; [1,3]oxazolo[5,4-d]pyrimidine-2-yl; [1,3]oxazolo[5,4-d]pyrimidine-7-yl; [1,3]oxazolo[5,4-d]pyrimidine-5-yl; [1,3]oxazolo[4,5-b]pyrazine-2-yl; [1,3]oxazolo[4,5-b]pyrazine-5-yl; [1,3]oxazolo[4,5-b]pyrazine-6-yl; [1,3]oxazolo[4,5-b]Pyridine-2-yl; [1,3]oxazolo[4,5-b]pyridine-5-yl; [1,3]oxazolo[4,5-b]pyridine-6-yl; [1,3]oxazolo[4,5-b]pyridine-7-yl; [1,3]oxazolo[4,5-c]pyridine-2-yl; [1,3]oxazolo[4,5-c]Pyridine-4-yl; [1,3]oxazolo[4,5-c]pyridine-6-yl; [1,3]oxazolo[4,5-c]pyridine-7-yl; [1,3]oxazolo[5,4-c]pyridine-2-yl, [1,3]oxazolo[5,4-c]pyridine-7-yl, [1,3]oxazolo[5,4-c]Pyridine-6-yl, [1,3]oxazolo[5,4-c]pyridine-4-yl; [1,3]oxazolo[5,4-b]pyridine-2-yl, [1,3]oxazolo[5,4-b]pyridine-7-yl, [1,3]oxazolo[5,4-b]pyridine-6-yl, [1,3]oxazolo[5,4-b]Pyridine-5-yl; furo[2,3-b]pyridine-2-yl, furo[2,3-b]pyridine-3-yl, furo[2,3-b]Pyridine-4-yl, furo[2,3-b]pyridine-5-yl, furo[2,3-b]pyridine-6-yl; furo[2,3-c]Pyridine-2-yl, furo[2,3-c]pyridine-3-yl, furo[2,3-c]pyridine-4-yl, furo[2,3-c]pyridine-5-yl, furo[2,3-c]pyridine-7-yl; furo[3,2-c]pyridine-2-yl, furo[3,2-c]pyridine-3-yl, furo[3,2-c]pyridine-4-yl, furo[3,2-c]pyridine-6-yl, furo[3,2-c]pyridine-7-yl; furo[3,2-b]pyridine-2-yl, furo[3,2-b]pyridine-3-yl, furo[3,2-b]pyridine-5-yl, furo[3,2-b]pyridine-6-yl, furo[3,2-b]pyridine-7-yl; thieno[3,2-d]pyrimidine-6-yl, thieno[3,2-d]pyrimidine-7-yl, thieno[3,2-d]pyrimidine-2-yl, thieno[3,2-d]pyrimidine-4-yl; thieno[2,3-d]pyrimidine-6-yl, thieno[2,3-d]pyrimidine-5-yl, thieno[2,3-d]pyrimidine-4-yl, thieno[2,3-d]pyrimidine-2-yl; thieno[2,3-c]pyridazine-6-yl, thieno[2,3-c]pyridazine-5-yl, thieno[2,3-c]pyridazine-4-yl, thieno[2,3-c]pyridazine-3-yl; thieno[2,3-d]pyridazine-2-yl, thieno[2,3-d]pyridazine-3-yl, thieno[2,3-d]pyridazine-4-yl, thieno[2,3-d]pyridazine-7-yl; thieno[3,2-c]pyridazine-6-yl, thieno[3,2-c]pyridazine-7-yl, thieno[3,2-c]pyridazine-3-yl, thieno[3,2-c]pyridazine-4-yl; thieno[2,3-b]pyrazine-6-yl, thieno[2,3-b]pyrazine-7-yl, thieno[2,3-b]pyrazine-2-yl, thieno[2,3-b]pyrazine-3-yl; thieno[3,2-b]pyridine-2-yl, thieno[3,2-b]

pyridine-3-yl, thieno[3,2-b]pyridine-5-yl, thieno[3,2-b]pyridine-6-yl, thieno[3,2-b]pyridine-7-yl; thieno[3,2-c]pyridine-2-yl, thieno[3,2-c]pyridine-3-yl, thieno[3,2-c]pyridine-4-yl, thieno[3,2-c]pyridine-6-yl, thieno[3,2-c]pyridine-7-yl; thieno[2,3-c]pyridine-2-yl, thieno[2,3-c]pyridine-3-yl, thieno[2,3-c]pyridine-4-yl, thieno[2,3-c]pyridine-5-yl, thieno[2,3-c]pyridine-7-yl; thieno[2,3-b]pyridine-2-yl, thieno[2,3-b]pyridine-3-yl, thieno[2,3-b]pyridine-4-yl, thieno[2,3-b]pyridine-5-yl, thieno[2,3-b]pyridine-6-yl; 1-benzothiophene-2-yl, 1-benzothiophene-3-yl, 1-benzothiophene-4-yl, 1-benzothiophene-5-yl, 1-benzothiophene-6-yl, 1-benzothiophene-7-yl; 1H-benzimidazole-2-yl, 1H-benzimidazole-1-yl, 1H-benzimidazole-4-yl, 1H-benzimidazole-5-yl; 3H-imidazo[4,5-b]pyridine-2-yl, 3H-imidazo[4,5-b]pyridine-1-yl, 3H-imidazo[4,5-b]pyridine-7-yl, 3H-imidazo[4,5-b]pyridine-6-yl, 3H-imidazo[4,5-b]pyridine-5-yl; 3H-imidazo[4,5-c]pyridine-2-yl, 3H-imidazo[4,5-c]pyridine-1-yl, 3H-imidazo[4,5-c]pyridine-7-yl, 3H-imidazo[4,5-c]pyridine-6-yl, 3H-imidazo[4,5-c]pyridine-4-yl; 7H-imadazo[4,5-c]pyridazine-6-yl, 7H-imadazo[4,5-c]pyridazine-7-yl, 7H-imadazo[4,5-c]pyridazine-4-yl, 7H-imadazo[4,5-c]pyridazine-3-yl; 1H-imadazo[4,5-d]pyridazine-2-yl, 1H-imadazo[4,5-d]pyridazine-1-yl, 1H-imadazo[4,5-d]pyridazine-4-yl; 7H-purine-8-yl, 7H-purine-7-yl, 7H-purine-2-yl, 7H-purine-6-yl; 1H-imadazo[4,5-b]pyrazine-2-yl, 1H-imadazo[4,5-b]pyrazine-1-yl, 1H-imadazo[4,5-b]pyrazine-5-yl; 1H-indole-2-yl, 1H-indole-1-yl, 1H-indole-3-yl, 1H-indole-4-yl, 1H-indole-5-yl, 1H-indole-6-yl, 1H-indole-7-yl; 1H-pyrrolo[3,2-b]pyridine-2-yl, 1H-pyrrolo[3,2-b]pyridine-1-yl, 1H-pyrrolo[3,2-b]pyridine-3-yl, 1H-pyrrolo[3,2-b]pyridine-5-yl, 1H-pyrrolo[3,2-b]pyridine-6-yl, 1H-pyrrolo[3,2-b]pyridine-7-yl; 1H-pyrrolo[3,2-c]pyridine-2-yl, 1H-pyrrolo[3,2-c]pyridine-1-yl, 1H-pyrrolo[3,2-c]pyridine-3-yl 1H-pyrrolo[3,2-c]pyridine-4-yl, 1H-pyrrolo[3,2-c]pyridine-6-yl, 1H-pyrrolo[3,2-c]pyridine-7-yl; 1H-pyrrolo[2,3-c]pyridine-2-yl, 1H-pyrrolo[2,3-c]pyridine-1-yl, 1H-pyrrolo[2,3-c]pyridine-3-yl, 1H-pyrrolo-[2,3-c]pyridine-4-yl, 1H-pyrrolo[2,3-c]pyridine-5-yl, 1H-pyrrolo[2,3-c]pyridine-7-yl; 1H-pyrrolo[2,3-b]pyridine-2-yl, 1H-pyrrolo[2,3-b]pyridine-1-yl, 1H-pyrrolo[2,3-b]pyridine-3-yl, 1H-pyrrolo[2,3-b]pyridine-4-yl, 1H-pyrrolo[2,3-b]pyridine-5-yl, 1H-pyrrolo[2,3-b]pyridine-6-yl; 1H-pyrrolo[2,3-d]pyridazine-2-yl, 1H-pyrrolo[2,3-d]pyridazine-1-yl, 1H-pyrrolo[2,3-d]pyridazine-3-yl, 1H-pyrrolo[2,3-d]pyridazine-4-yl, 1H-pyrrolo[2,3-d]pyridazine-7-yl; 5H-pyrrolo[3,2-c]pyridazine-6-yl, 5H-pyrrolo[3,2-c]pyridazine-5-yl, 5H-pyrrolo[3,2-c]pyridazine-7-yl, 5H-pyrrolo[3,2-c]pyridazine-3-yl, 5H-pyrrolo[3,2-c]pyridazine-4-yl; 7H-pyrrolo[2,3-c]pyridazine-6-yl, 7H-pyrrolo[2,3-c]pyridazine-7-yl, 7H-pyrrolo[2,3-c]pyridazine-5-yl, 7H-pyrrolo[2,3-c]pyridazine-4-yl, 7H-pyrrolo[2,3-c]pyridazine-3-yl; 5H-pyrrolo[2,3-b]pyrazine-6-yl, 5H-pyrrolo[2,3-b]pyrazine-5-yl, 5H-pyrrolo[2,3-b]pyrazine-7-yl, 5H-pyrrolo[2,3-b]pyrazine-2-yl, 5H-pyrrolo[2,3-b]pyrazine-3-yl; 5H-pyrrolo[3,2-d]pyrimidine-6-yl, 5H-pyrrolo[3,2-d]pyrimidine-5-yl, 5H-pyrrolo[3,2-d]pyrimidine-7-yl, 5H-pyrrolo[3,2-d]pyrimidine-2-yl, 5H-pyrrolo[3,2-d]pyrimidine-4-yl; 7H-pyrrolo[2,3-d]pyrimidine-6-yl, 7H-pyrrolo[2,3-d]pyrimidine-7-yl, 7H-pyrrolo[2,3-d]pyrimidine-5-yl, 7H-pyrrolo[2,3-d]pyrimidine-4-yl, and 7H-pyrrolo[2,3-d]pyrimidine-2-yl.

Among 6,6-fused heteroaromatic ring systems having 1, 2, 3 or 5 heteroatoms independently selected from N, O and S, include, but are not limited to: 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 3-cinnolyl, 4-cinnolyl, 5-cinnolyl, 6-cinnolyl, 7-cinnolyl, 8-cinnolyl, 2-quinazolyl, 4-quinazolyl, 5-quinazolyl, 6-quinazolyl, 7-quinazolyl, 8-quinazolyl, 2-quinoxalyl, 3-quinoxalyl, 5-quinoxalyl, 6-quinoxalyl, 7-quinoxalyl, 8-quinoxalyl, 1,5-naphthyrid-2-yl, 1,5-naphthyrid-3-, 1,5-naphthyrid-4-yl, 1,6-naphthyrid-2-yl, 1,6-naphthyrid-3-yl, 1,6-naphthyrid-4-yl, 1,6-naphthyrid-5-yl, 1,6-naphthyrid-7-yl, 1,6-naphthyrid-8-yl, 1,7-naphthyrid-2-yl, 1,7-naphthyrid-3-yl, 1,7-naphthyrid-4-yl, 1,7-naphthyrid-5-yl, 1,7-naphthyrid-6-yl, 1,7-naphthyrid-8-yl, 1,8-naphthyrid-2-yl, 1,8-naphthyrid-3-yl, and 1,8-naphthyrid-4-yl.

The term "substituents" refers to a group "substituted" on an alkyl, cycloalkyl, alkenyl, alkynyl, heterocyclyl, heterocycloalkenyl, cycloalkenyl, aryl, or heteroaryl group or other group at any atom of the group. The group can be singly or multiply substituted and where multiply substituted, the substituents are independent. Suitable substituents include, without limitation: F, Cl, Br, I, alkyl, alkenyl, alkynyl, alkoxy, acyloxy, halo, hydroxy, cyano, nitro, amino, SO3H, sulfate, phosphate, perfluoroalkyl, perfluoroalkoxy, methylenedioxy, ethylenedioxy, carboxyl, oxo, thioxo, imino (alkyl, aryl, aralkyl), S(O)n alkyl (where n is 0-2), S(O)n aryl (where n is 0-2), S(O)n heteroaryl (where n is 0-2), S(O)n heterocyclyl (where n is 0-2), amine (mono-, di-, alkyl, cycloalkyl, aralkyl, heteroaralkyl, and combinations thereof), ester (alkyl, aralkyl, heteroaralkyl), amide (mono-, di-, alkyl, aralkyl, heteroaralkyl, and combinations thereof), sulfonamide (mono-, di-, alkyl, aralkyl, heteroaralkyl, and combinations thereof), unsubstituted aryl, unsubstituted heteroaryl, unsubstituted heterocyclyl, and unsubstituted cycloalkyl. In one aspect, the substituents on a group are independently any one single, or any subset of the aforementioned substituents. In some cases the substituents are selected from: F, Cl, Br and I. In other cases the substituents are selected from: halogen, C1-C3 alkyl, C1-C3 alkoxy, hydroxy, cyano, nitro and amino. In some cases the substituents are selected from aryl groups. In some cases the substituents are selected from heteroaryl groups.

Salts, particularly physiologically acceptable salts, and solvates of the compounds having are disclosed. Solvates are forms of the compounds in which the compound forms a complex with solvent molecules by coordination in the solid or liquid states. Hydrates are a special form of solvate in which the compound is coordinated with water. The pharmacologically acceptable addition salts as mentioned above are meant to comprise the therapeutically active non-toxic acid and base addition salt forms that the compounds are able to form. Compounds that have basic properties can be converted to their pharmaceutically acceptable acid addition salts by treating the base form with an appropriate acid. Exemplary acids include inorganic acids, such as hydrogen chloride, hydrogen bromide, hydrogen iodide, sulphuric acid, phosphoric acid; and organic acids such as acetic acid, propanoic acid, hydroxyacetic acid, lactic acid, pyruvic acid, glycolic acid, maleic acid, malonic acid, oxalic acid, benzenesulphonic acid, toluenesulphonic acid, methanesulphonic acid, trifluoroacetic acid, fumaric acid, succinic acid, malic acid, tartaric acid, citric acid, salicylic acid, p aminosalicylic acid, pamoic acid, benzoic acid, ascorbic acid and the like. Exemplary base addition salt forms are the sodium, potassium, calcium salts, and salts with pharmaceutically acceptable amines such as, for example, ammonia, alkylamines, benzathine, and amino acids, such as, e.g. arginine and lysine. The term addition salt as used herein also comprises solvates which the compounds and salts thereof are able to form, such as, for example, hydrates, alcoholates and the like.

Certain compounds may exist in stereoisomeric forms such as enantiomers, diastereomers and mixtures thereof. Mixtures can be separated into stereoisomerically pure constituents.

Certain compounds may be tautomeric and various tautomeric mixtures can be useful.

Also described is a pharmaceutical composition comprising a compound described herein and a method for preparing a pharmaceutical composition comprising admixing a compound described herein and a pharmaceutically acceptable carrier.

Also described are methods for treating a patient for anxiety, depression, bipolar disorder, obesity, pain or a sleep disorder, comprising administering a compound described herein in an effective amount.

Disclosed herein are: a pharmaceutical composition comprising one or more of the compounds, e.g., a compound that inhibits FAAH, described herein and a pharmaceutically acceptable carrier; a method for treating pain (e.g. neuropathic pain) and/or inflammation comprising administering a compound described herein or a pharmaceutical composition comprising a compound described herein; a method for treating anxiety comprising administering a compound described herein or a pharmaceutical composition comprising a compound described herein; a method for treating depression comprising administering a compound described herein or a pharmaceutical composition comprising a compound described herein; a method for treating a sleep disorder comprising administering a compound described herein or a pharmaceutical composition comprising a compound described herein; a method for treating hypertension comprising administering a compound described herein or a pharmaceutical composition comprising a compound described herein; a method for treating a gastrointestinal disorder (e.g. diarrhea and inflammatory bowel disorder) comprising administering a compound described herein or a pharmaceutical composition comprising a compound described herein; and a method for treating obesity comprising administering a compound described herein or a pharmaceutical composition comprising a compound described herein.

Useful compounds include a prodrug of a compound described herein having a hydroxyl moiety wherein the prodrug of a hydroxy moiety is selected from: (a) an ester having a $C_1$ to $C_6$ branched or straight chain alkyl group, (b) phosphate ester having $C_1$ to $C_6$ branched or straight chain alkyl groups, (c) a carbamate having $C_1$ to $C_6$ branched or straight chain alkyl groups, and (d) a carbonate group having a $C_1$ to $C_6$ branched or straight chain alkyl group.

Certain compounds described herein can have activity towards enzymes other than FAAH. For example, certain inhibitors of FAAH can inhibit COX-1, COX-2, DAO, DP-1, TXA2, CB1/CB2, and/or CRTH2. In some cases a compound described herein is not an inhibitor of FAAH, but does inhibit one or more of COX-1, COX-2, DAO, DP-1, TXA2, CB1/CB2, and CRTH2. In some cases the compound activates CRTH2.

In certain embodiments, the compounds that inhibit FAAH are selective for inhibition of FAAH relative to COX-1, COX-2, DAO, DP-1, TXA2, CB1/CB2, and/or CRTH2. Thus, in some cases the $IC_{50}$ of a compound towards COX-1 is at least 5, 10, 15, 20, 50, 100, 500 or 1000 times the $IC_{50}$ of a compound towards FAAH. In some cases the $IC_{50}$ of a compound towards COX-2 is at least 5, 10, 15, 20, 50, 100, 500 or 1000 times the $IC_{50}$ of a compound towards FAAH. In some cases the $IC_{50}$ of a compound towards DP-1 is at least 5, 10, 15, 20, 50, 100, 500 or 1000 times the $IC_{50}$ of a compound towards FAAH. In some cases the $IC_{50}$ of a compound towards DAO is at least 5, 10, 15, 20, 50, 100, 500 or 1000 times the $IC_{50}$ of a compound towards FAAH. Thus, in some cases the $IC_{50}$ of a compound towards TXA2 is at least 5, 10, 15, 20, 50, 100, 500 or 1000 times the $IC_{50}$ of a compound towards FAAH. In some cases the $IC_{50}$ of a compound towards CB1/CB2 is at least 5, 10, 15, 20, 50, 100, 500 or 1000 times the $IC_{50}$ of a compound towards FAAH. In some cases the $IC_{50}$ of a compound towards CRTH2 is at least 5, 10, 15, 20, 50, 100, 500 or 1000 times the $IC_{50}$ of a compound towards FAAH.

Certain of the compounds that inhibit FAAH are selective and do not significantly inhibit one or more of tubulin, PDE4 and PLA2. The selective compounds have an $IC_{50}$ of a compound towards one or more of tubulin, PDE4 and PLA2 that is at least 500, 1000 or 10,000 times the $IC_{50}$ or a compound towards FAAH.

In some embodiments, the composition is administered to a patient that is not being treated with a non-selective NSAID, e.g., a patient that is not being treated with indomethacin.

In certain embodiments the compounds are administered in combination with a second compound useful for reducing inflammation or pain.

The subject can be a mammal, preferably a human. Identifying a subject in need of such treatment can be in the judgment of a subject or a health care professional and can be subjective (e.g., opinion) or objective (e.g., measurable by a test or diagnostic method).

The term "treating" or "treated" refers to administering a compound described herein to a subject with the purpose to cure, heal, alleviate, relieve, alter, remedy, ameliorate, improve, or affect a disease, the symptoms of the disease or the predisposition toward the disease.

"An effective amount" refers to an amount of a compound that confers a therapeutic effect on the treated subject. The therapeutic effect may be objective (i.e., measurable by some test or marker) or subjective (i.e., subject gives an indication of or feels an effect). An effective amount of the compound described above may range from about 0.05 mg/Kg to about 500 mg/Kg, alternatively from about 1 to about 50 mg/Kg. Effective doses will also vary depending on route of administration, as well as the possibility of co-usage with other agents.

The term "mammal" includes, for example, mice, hamsters, rats, cows, sheep, pigs, goats, and horses, monkeys, dogs (e.g., *Canis familiaris*), cats, rabbits, guinea pigs, and primates, including humans.

The term "prodrug" refers to compounds which are drug precursors which, following administration and absorption, release the drug in vivo through a metabolic process. Exemplary prodrugs include acyl amides of the amino compounds described herein such as amides of alkanoic ($C_1$ to $C_6$) acids, amides of aryl acids (e.g., benzoic acid) and alkane ($C_1$ to $C_6$)dioic acids.

The details of one or more embodiments of the invention are set forth herein. Other features, objects, and advantages of the invention will be apparent from the description and drawings, and from the claims. The patents, patent applications, and publications referenced herein are hereby incorporated by reference in their entirety.

DESCRIPTION OF DRAWINGS

FIG. 1 is a table that provides COX-1 $IC_{50}$ (purified enzyme assay) and COX-2 $IC_{50}$ (purified enzyme assay) for a number of compounds.

FIG. 2 is a table that provides COX-1 $IC_{50}$ (human whole blood assay) and COX-2 $IC_{50}$ (human whole blood assay) for a number of compounds.

FIG. 3 is a table that provides FAAH activity data for a number of compounds.

FIG. 4 is a table that provides FAAH activity data for a number of compounds.

FIG. 5 is a table that provides activity data for certain compounds tested in the AAMCA assay.

FIG. 6 is a table that provides FAAH activity data for a number of compounds.

FIG. 7 is a table that provides CRTH2 activity data for a number of compounds.

FIG. 8 is a table that provides CRTH2 activity data for a number of compounds.

FIG. 9 is a table that provides CRTH2 activity data for a number of compounds.

FIG. 10 is a table that provides DP-1 activity data for a number of compounds.

FIG. 11 is a table that provides $TXA_2$ activity data for a number of compounds.

FIG. 12 is a table that provides DAO activity data for a number of compounds.

FIG. 13 is a table that provides DAO activity data for a number of compounds.

FIG. 14 is a table that provides pharmacokinetic data for a number of compounds.

DETAILED DESCRIPTION

Certain compounds described herein can have activity towards enzymes/proteins other than FAAH. For example, certain inhibitors of FAAH can inhibit COX-1, COX-2, DAO, DP-1, TXA2, CB1/CB2, and/or CRTH2. In some cases a compound described herein is not an inhibitor of FAAH, but does inhibit one or more of COX-1, COX-2, DAO, DP-1, TXA2, CB1/CB2, and/or CRTH2.

Certain compounds are expected to have an increased half-life in the human body compared to certain structurally related compounds. Certain compounds are expected to have reduced renal and/or gastric toxicity compared to certain structurally related compounds.

EXAMPLES

Certain useful compounds are described below.

{1-[(5-chlorothien-2-yl)carbonyl]-5-hydroxy-2-methyl-1H-indol-3-yl}acetic acid mp 195° C.
$^1$H NMR (CDCl$_3$/300 MHz) 7.43 (d, 1H, J=4.2 Hz), 7.13-7.10 (m, 2H), 6.87 (d, 1H, J=2.1 Hz), 6.61 (dd, 1H, J=8.7, 2.1 Hz), 3.66 (s, 2H), 2.38 (s, 3H).

{1-[(5-chlorothien-2-yl)carbonyl]-6-fluoro-5-methoxy-2-methyl-1H-indol-3-yl}acetic acid mp 169° C.
$^1$H NMR (CDCl$_3$/300 MHz) 7.35 (d, 1H, J=4.0 Hz), 7.09 (d, 1H, J=11.7 Hz), 7.00 (d, 1H, J=7.2 Hz), 6.98 (d, 1H, J=4.0 Hz), 3.93 (s, 3H), 3.70 (s, 2H), 2.42 (s, 3H).

{1-[(5-chlorothien-2-yl)carbonyl]-6-fluoro-5-hydroxy-2-methyl-1H-indol-3-yl}acetic acid mp 174° C.
$^1$H NMR (CDCl$_3$/300 MHz) 7.34 (d, 1H, J=3.9 Hz), 7.13 (d, 1H, J=11.1 Hz), 7.07 (d, 1H, J=8.4 Hz), 6.98 (d, 1H, J=3.9 Hz), 3.66 (s, 2H), 2.39 (s, 3H).

[6-fluoro-5-methoxy-2-methyl-1-(thien-2-ylcarbonyl)-1H-indol-3-yl]acetic acid mp 137° C.
$^1$H NMR (CDCl$_3$/300 MHz) 7.77 (dd, 1H, J=5.0, 1.2 Hz), 7.54 (dd, 1H, J=3.9, 1.2 Hz), 7.15 (dd, 1H, J=5.0, 3.9 Hz), 7.01 (d, 1H, J=12.0 Hz), 7.00 (d, 1H, J=8.1 Hz), 3.92 (s, 3H), 3.69 (s, 2H), 2.41 (s, 3H).

{6-fluoro-5-methoxy-2-methyl-1-[(5-methylthien-2-yl)carbonyl]-1H-indol-3-yl}acetic acid mp 152° C.
$^1$H NMR (CDCl$_3$/300 MHz) 7.35 (d, 1H, J=3.9 Hz), 7.06 (d, 1H, J=12.3), 6.99 (d, 1H, J=8.1 Hz), 6.81 (d, 1H, J=3.9 Hz), 3.92 (s, 3H), 3.68 (s, 2H), 2.60 (s, 3H), 2.42 (s, 3H).

{6-fluoro-5-hydroxy-2-methyl-1-[(5-methylthien-2-yl)carbonyl]-1H-indol-3-yl}acetic acid mp 197° C.
$^1$H NMR (CD$_3$OD/300 MHz) 7.40 (d, 1H, J=4.0 Hz), 6.99 (d, 1H, J=8.7 Hz), 6.98 (d, 1H, J=11.7 Hz), 6.93 (d, 1H, J=4.0 Hz), 3.64 (s, 2H), 2.62 (s, 3H), 2.34 (s, 3H).

[6-fluoro-5-hydroxy-2-methyl-1-(thien-2-ylcarbonyl)-1H-indol-3-yl]acetic acid mp 219° C.
$^1$H NMR (CD$_3$OD/300 MHz) 7.97 (dd, 1H, J=5.1, 1.2 Hz), 7.59 (dd, 1H, J=3.9, 1.2 Hz), 7.22 (dd, 1H, J=5.1, 3.9 Hz), 7.00 (d, 1H, J=8.7 Hz), 6.94 (d, 1H, J=12.0 Hz), 3.65 (s, 2H), 2.32 (s, 3H).

[1-(cyclohexylcarbonyl)-5-methoxy-2-methyl-1H-indol-3-yl]acetic acid mp 129° C.
$^1$H NMR (CDCl$_3$/300 MHz) 7.62 (d, 1H, J=9.0 Hz), 6.93 (d, 1H, J=2.7), 6.86 (dd, 1H, J=9.0, 2.7 Hz), 3.85 (s, 3H), 3.67 (s, 2H), 3.18 (m, 1H), 2.04-1.32 (m, 10H).

[1(cyclohexylcarbonyl)-5-hydroxy-2-methyl-1H-indol-3-yl]acetic acid $^1$H NMR (CDCl$_3$/300 MHz) 7.50 (d, 1H, J=9.0 Hz), 6.95 (d, 1H, J=2.1), 6.73 (dd, 1H, J=9.0, 2.1 Hz), 3.53 (s, 2H), 3.12 (m, 1H), 2.49 (s, 3H), 2.00-1.05 (m, 10H).

{1-[(6-chloropyridin-3-yl)carbonyl]-5-methoxy-2-methyl-1H-indol-3-yl}acetic acid mp 153° C.
$^1$H NMR (CDCl$_3$/300 MHz) 8.71 (d, 1H, J=2.7 Hz), 8.27 (dd, 1H, J=8.1, 2.7 Hz), 7.98 (dd, 1H, J=8.1, 2.7 Hz), 7.48 (d, 1H, J=8.7 Hz), 6.97 (d, 1H, J=2.4 Hz), 6.76 (dd, 1H, J=8.7, 2.4 Hz), 3.48 (s, 3H), 3.71 (s, 2H), 2.41 (s, 3H).

[1-(cyclohexylcarbonyl)-6-fluoro-5-methoxy-2-methyl-1H-indol-3-yl]acetic acid mp 104° C.
$^1$H NMR (CDCl$_3$/300 MHz) 7.72 (d, 1H, J=12.9 Hz), 7.13 (d, 1H, J=8.1), 3.91 (s, 3H), 3.69 (s, 2H), 3.23 (m, 1H) 2.56 (s, 3H), 2.05-1.27 (m, 10H).

[5-methoxy-2-methyl-1-(piperidin-1-ylcarbonyl)-1H-indol-3-yl]acetic acid yellow oil
$^1$H NMR (CDCl$_3$/300 MHz) 7.16 (d, 1H, J=9.0 Hz), 6.96 (d, 1H, J=2.7), 6.81 (dd, 1H, J=9.0, 2.7 Hz), 3.83 (s, 3H), 3.66 (s, 2H), 3.58-3.30 (m, 4H), 2.40 (s, 3H), 1.70-1.55 (m, 6H).

[5-hydroxy-2-methyl-1-(piperidin-1-ylcarbonyl)-1H-indol-3-yl]acetic acid mp 235° C.
$^1$H NMR (CDCl$_3$/300 MHz) 6.99 (d, 1H, J=8.7 Hz), 6.79 (s, 1H), 6.64 (d, 1H, J=8.7 Hz), 3.47 (s, 2H), 3.47-3.30 (m, 4H), 2.33 (s, 3H), 1.72-1.43 (m, 6H).

[1-(4-chlorobenzyl)-5-methoxy-2-methyl-1H-indol-3-yl](oxo)acetic acid $^1$H NMR (CDCl$_3$/300 MHz) 7.92 (d, 1H, J=2.7 Hz), 7.28 (d, 2H, J=8.7 Hz), 7.12 (d, 1H, J=8.7 Hz), 6.94 (d, 2H, J=8.7 Hz), 6.90 (dd, 1H, J=2.7, 8.7 Hz), 5.35 (s, 2H), 3.90 (s, 3H), 2.74 (s, 3H).

[1-(4-chlorobenzyl)-5-methoxy-2-methyl-1H-indol-3-yl](5-pyridin-2-yl-2-thienyl)methanone $^1$H NMR (CDCl$_3$/300 MHz) 8.64 (m, 1H), 7.75 (m, 2H), 7.65 (m, 2H), 7.39-7.23 (m, 4H), 7.11 (d, 1H, J=9.0 Hz), 6.94 (d, 2H, J=8.4 Hz), 6.83 (dd, 1H, J=2.7, 9.0 Hz), 5.32 (s, 2H), 3.37 (s, 3H), 2.54 (s, 3H).

Additional Useful Compounds
Among the useful compounds are:
[6-chloro-1-(3,4-dichlorobenzyl)-5-methoxy-2-methyl-1H-indol-3-yl]acetic acid
[6-chloro-1-(3,4-difluorobenzyl)-5-methoxy-2-methyl-1H-indol-3-yl]acetic acid
[6-chloro-1-(3,5-dichlorobenzyl)-2,5-dimethyl-1H-indol-3-yl]acetic acid
[1-(3-bromobenzyl)-6-chloro-5-methoxy-2-methyl-1H-indol-3-yl]acetic acid
5-fluoro-2-methyl-1-[3-(trifluoromethoxy)benzyl]-1H-indole-3-carbaldehyde
(2E)-3-{5-fluoro-2-methyl-1-[3-(trifluoromethoxy)benzyl]-1H-indol-3-yl}acrylic acid
{5-methoxy-2-methyl-1-[3-(trifluoromethoxy)benzyl]-1H-indol-3-yl}acetic acid
{4,6-dichloro-2-methyl-1-[3-(trifluoromethoxy)benzyl]-1H-indol-3-yl}acetic acid
{2-methyl-1-[3-(trifluoromethoxy)benzyl]-1H-indol-3-yl}acetic acid
{2-chloro-3-[3-(trifluoromethoxy)benzyl]-1H-indol-1-yl}acetic acid
(2Z)-{2-oxo-1-[3-(trifluoromethoxy)benzyl]-1,2-dihydro-3H-indol-3-ylidene}acetic acid
[6-chloro-1-(3,5-dimethylbenzyl)-5-methoxy-2-methyl-1H-indol-3-yl]acetic acid
{-[3,5-bis(trifluoromethyl)benzyl]-6-chloro-5-methoxy-2-methyl-1H-indol-3-yl}acetic acid
{5-methoxy-1-[3-(trifluoromethoxy)benzyl]-1H-indol-3-yl}acetic acid
{2-oxo-1-[3-(trifluoromethoxy)benzyl]-2,3-dihydro-1H-indol-3-yl}acetic acid
{6-chloro-1-[3-(difluoromethoxy)benzyl]-5-methoxy-2-methyl-1H-indol-3-yl}acetic acid
{5,6-dichloro-2-methyl-1-[3-(trifluoromethoxy)benzyl]-1H-indol-3-yl}acetic acid
{2-chloro-1-[3-(trifluoromethoxy)benzyl]-1H-indol-3-yl}acetic acid
{5-chloro-2-methyl-1-[3-(trifluoromethoxy)benzyl]-1H-indol-3-yl}acetic acid
{5-chloro-2-methyl-1-[3-(trifluoromethyl)benzyl]-1H-indol-3-yl}acetic acid
methyl (1-benzoyl-6-fluoro-5-hydroxy-2-methyl-1H-indol-3-yl)acetate
methyl [1-(4-chlorobenzoyl)-4-fluoro-5-methoxy-2-methyl-1H-indol-3-yl]acetate
methyl [1-(4-chlorobenzoyl)-4-fluoro-5-hydroxy-2-methyl-1H-indol-3-yl]acetate
methyl [1-(3,4-dichlorobenzoyl)-5-methoxy-2-methyl-1H-indol-3-yl]acetate
methyl [1-(4-fluorobenzoyl)-5-hydroxy-2-methyl-1H-indol-3-yl]acetate
methyl {5-methoxy-2-methyl-1-[4-(trifluoromethyl)benzoyl]-1H-indol-3-yl}acetate
methyl [1-(4-bromobenzyl)-5-hydroxy-2-methyl-1H-indol-3-yl]acetate
methyl [1-(4-bromobenzyl)-4,6-difluoro-5-methoxy-2-methyl-1H-indol-3-yl]acetate
methyl [1-(cyclohexylcarbonyl)-6-fluoro-5-methoxy-2-methyl-1H-indol-3-yl]acetate
methyl {1-[(5-chloro-2-thienyl)carbonyl]-6-fluoro-5-methoxy-2-methyl-1H-indol-3-yl}acetate
methyl [6-fluoro-1-(4-fluorobenzoyl)-5-methoxy-2-methyl-1H-indol-3-yl]acetate
methyl {6-fluoro-5-hydroxy-2-methyl-1-[(5-methyl-2-thienyl)carbonyl]-1H-indol-3-yl}acetate
methyl {6-chloro-1-[(5-chloro-2-thienyl)methyl]-5-methoxy-2-methyl-1H-indol-3-yl}acetate
methyl {6-chloro-1-[(5-chloro-2-thienyl)carbonyl]-5-hydroxy-2-methyl-1H-indol-3-yl}acetate
{5-fluoro-2-methyl-1-[3-(trifluoromethoxy)benzyl]-1H-indol-3-yl}acetic acid
(2E)-3-{5-methoxy-2-methyl-1-[3-(trifluoromethoxy)benzyl]-1H-indol-3-yl}acrylic acid
[6-chloro-5-methoxy-2-methyl-1-(3-nitrobenzyl)-1H-indol-3-yl]acetic acid
(5-fluoro-2-methyl-1-{[4-(methylsulfonyl)phenyl]sulfonyl}-1H-indol-3-yl)acetic acid
(6-chloro-5-methoxy-2-methyl-1-{[3-(trifluoromethoxy)phenyl]sulfonyl}-1H-indol-3-yl)acetic acid
[6-chloro-1-(3,5-difluorobenzyl)-5-methoxy-2-methyl-1H-indol-3-yl]acetic acid
methyl {6-fluoro-2,5-dimethyl-1-[3-(trifluoromethoxy)benzyl]-1H-indol-3-yl}acetate
6-chloro-2,3-dimethyl-1-[3-(trifluoromethoxy)benzyl]-1H-indole acetate
methyl {5-hydroxy-2-methyl-1-[4-(trifluoromethoxy)benzoyl]-1H-indol-3-yl}acetate
methyl [5-hydroxy-2-methyl-1-(4-methylbenzoyl)-1H-indol-3-yl]acetate
methyl {5-hydroxy-2-methyl-1-[4-(trifluoromethyl)benzoyl]-1H-indol-3-yl}acetate
methyl [1-(3,4-difluorobenzoyl)-5-methoxy-2-methyl-1H-indol-3-yl]acetate methyl [6-fluoro-5-methoxy-2-methyl-1-(2-thienylcarbonyl)-1H-indol-3-yl]acetate
methyl [6-chloro-1-(4-fluorobenzoyl)-5-methoxy-2-methyl-1H-indol-3-yl]acetate
methyl {6-chloro-1-[(5-chloro-2-thienyl)carbonyl]-5-methoxy-2-methyl-1H-indol-3-yl}acetate
methyl [6-chloro-1-(4-chlorobenzyl)-2,5-dimethyl-1H-indol-3-yl]acetate
methyl [6-chloro-1-(3-chlorobenzyl)-5-fluoro-2-methyl-1H-indol-3-yl]acetate
methyl [6-chloro-1-(3-chlorobenzyl)-2,5-dimethyl-1H-indol-3-yl]acetate
methyl {6-chloro-2,5-dimethyl-1-[3-(trifluoromethoxy)benzyl]-1H-indol-3-yl}acetate
methyl 1-(1,3-benzothiazol-2-ylmethyl)-5-fluoro-2-methyl-1H-indole-3-carboxylate
methyl {5-fluoro-2-methyl-1-[3-(trifluoromethoxy)benzyl]-1H-indol-3-yl}(oxo)acetate
{6-chloro-5-hydroxy-2-methyl-1-[3-(trifluoromethoxy)benzyl]-1H-indol-3-yl}acetic acid
(5-methoxy-2-methyl-1H-indol-3-yl)(5-pyridin-2-yl-1,3,4-oxadiazol-2-yl)methanone
1-[1-(2,4-dichlorobenzyl)-2,5-dimethyl-1H-indol-3-yl]-2-morpholin-4-yl-2-oxoethanone Derivatives of Indole Acids Additional compounds of Formula 1 include derivatives of the compounds in the section below entitled "Indole Acids" in which: (1) the group (e.g., the —CH$_2$C(O)OH group) at the 3 position of the indole group is replaced by —C(O)R$_3$ wherein R$_3$ is the R$_3$ of Formula 1. In some cases R$_3$ is selected from: R$_{3x}$, R$_{3y}$ and R$_{3z}$ wherein:

R$_{3x}$ is

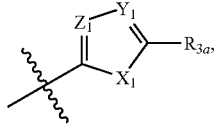

wherein X$_1$, Y$_1$, and Z$_1$ are (a) O, N and N, respectively; (b) O, N and C(R$_{3c}$), respectively; (c) O, C(R$_{3c}$) and C(R$_{3c}$), respectively; (d) O, C(R$_{3c}$) and N respectively; (e) S, N and N, respectively; (f) S, N and C(R$_{3c}$), respectively; (g) S, C(R$_{3c}$) and C(R$_{3c}$), respectively; (h) S, C(R$_{3c}$) and N respectively; (i) N(R$_{3b}$), N and N, respectively; (j) N(R$_{3b}$), N and C(R$_{3c}$), respectively; (k) N(R$_{3b}$), C(R$_{3c}$) and C(R$_{3c}$), respectively; or (l) N(R$_{3b}$), C(R$_{3c}$) and N respectively;

R$_{3y}$ is

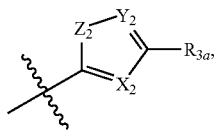

wherein X$_2$, Y$_2$, and Z$_2$ are: (a) N, N and O, respectively; (b) C(R$_{3c}$), N and O, respectively; (c) N, C(R$_{3c}$) and O, respectively; (d) C(R$_{3c}$), C(R$_{3c}$) and O, respectively; (e) N, N and S, respectively; (f) C(R$_{3c}$), N and S, respectively; (g) N, C(R$_{3c}$) and S, respectively; (h) C(R$_{3c}$), C(R$_{3c}$) and S, respectively; (i) N, N and N(R$_{3b}$), respectively; (j) C(R$_{3c}$), N and N(R$_{3b}$), respectively; (k) N, C(R$_{3c}$) and N(R$_{3b}$), respectively; or (l) C(R$_{3c}$), C(R$_{3c}$) and N(R$_{3b}$), respectively;

R$_{3z}$ is

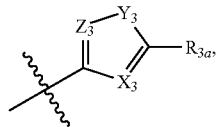

wherein X$_3$, Y$_3$, and Z$_3$ are: (a) N, O and N, respectively; (b) C(R$_{3c}$), O and N, respectively; (c) N, O and C(R$_{3c}$), respectively; (d) C(R$_{3c}$), O and C, respectively; (e) N, S and N, respectively; (f) C(R$_{3c}$), S and N, respectively; (g) N, S and C, respectively; (h) C(R$_{3c}$), S and C(R$_{3c}$), respectively; (i) N, N(R$_{3b}$) and N, respectively; (j) C(R$_{3c}$), N(R$_{3b}$) and N, respectively; (k) N, N(R$_{3b}$) and C(R$_{3c}$), respectively; or (l) C(R$_{3c}$), N(R$_{3b}$) and C(R$_{3c}$), respectively;

R$_{3a}$ is selected from:
H, halogen, an optionally substituted aryl, an optionally substituted heteroaryl, an optionally substituted C1-C5 alkyl, an optionally substituted C2-C5 alkenyl, an optionally substituted C2-C5 alkynyl, an optionally substituted C1-C5 alkoxy, —NO$_2$, —CN, —C(O)OH, an optionally substituted —SO$_2$CH$_3$, an optionally substituted —SO$_2$NH$_2$, an optionally substituted —SO$_2$OH, —C(O)H, an optionally substituted —C(O)CH$_3$, an optionally substituted —C(O)N(CH$_3$)$_2$, an optionally substituted —C(O)NH$_2$, an optionally substituted —SCH$_3$, an optionally substituted C3 to C10 cycloalkyl or carbocycle, an optionally substituted heterocycle, or R$_{3a}$ and the carbon to which it is attached together with Y$_1$, Y$_2$ or Y$_3$ can form a heteroaryl containing 5 to 6 ring atoms or R$_{3a}$ is absent.

R$_{3b}$ is selected from:
H, an optionally substituted aryl, an optionally substituted heteroaryl, an optionally substituted C1-C5 alkyl, an optionally substituted C2-C5 alkenyl, an optionally substituted C2-C5 alkynyl, an optionally substituted C1-C5 alkoxy, —CN, an optionally substituted —SO$_2$CH$_3$, an optionally substituted —SO$_2$NH$_2$, an optionally substituted —SO$_2$OH, an optionally substituted —C(O)CH$_3$, an optionally substituted —C(O)N(CH$_3$)$_2$, an optionally substituted —C(O)NH$_2$, an optionally substituted C3 to C10 cycloalkyl or carbocycle, an optionally substituted heterocycle;

R$_{3c}$ is selected from:
H, halogen, an optionally substituted aryl, an optionally substituted heteroaryl, an optionally substituted C1-C5 alkyl, an optionally substituted C2-C5 alkenyl, an optionally substituted C2-C5 alkynyl, an optionally substituted C1-C5 alkoxy, —NO$_2$, —CN, —C(O)OH, an optionally substituted —SO$_2$CH$_3$, an optionally substituted —SO$_2$NH$_2$, an optionally substituted —SO$_2$OH, —C(O)H, an optionally substituted —C(O)CH$_3$, an optionally substituted —C(O)N(CH$_3$)$_2$, an optionally substituted —C(O)NH$_2$, an optionally substituted —SCH$_3$, an optionally substituted C3 to C10 cycloalkyl or carbocycle, an optionally substituted heterocycle, or R$_{3c}$ and the carbon to which it is attached together with a ring atom bonded to the carbon to which R$_{3c}$ is attached can form a heteroaryl containing 5 to 6 ring atoms.

Indole Acids
[6-fluoro-5-hydroxy-2-methyl-1-(thien-2-ylcarbonyl)-1H-indol-3-yl]acetic acid;
{6-fluoro-1-[(5-fluorothien-2-yl)carbonyl]-5-hydroxy-2-methyl-1H-indol-3-yl}acetic acid;
{1-[(5-chlorothien-2-yl)carbonyl]-6-fluoro-5-hydroxy-2-methyl-1H-indol-3-yl}acetic acid;
{1-[(5-bromothien-2-yl)carbonyl]-6-fluoro-5-hydroxy-2-methyl-1H-indol-3-yl}acetic acid;

{6-fluoro-5-hydroxy-1-[(5-hydroxythien-2-yl)carbonyl]-2-methyl-1H-indol-3-yl}acetic acid;
{6-fluoro-5-hydroxy-1-[(5-methoxythien-2-yl)carbonyl]-2-methyl-1H-indol-3-yl}acectic acid;
{1-[(5-ethoxythien-2-yl)carbonyl]-6-fluoro-5-hydroxy-2-methyl-1H-indol-3-yl}acetic acid;
(1-{[5-(difluoromethoxy)thien-2-yl]carbonyl}-6-fluoro-5-hydroxy-2-methyl-1H-indol-3-yl)acetic acid;
(6-fluoro-5-hydroxy-2-methyl-1-{[5-(trifluoromethoxy)thien-2-yl]carbonyl}-1H-indol-3-yl)acetic acid;
(6-fluoro-5-hydroxy-2-methyl-1-{[5-(pentafluoroethoxy)thien-2-yl]carbonyl}-1H-indol-3-yl)acetic acid;
(6-fluoro-5-hydroxy-2-methyl-1-{[5-(1,1,2,2-tetrafluoroethoxy)thien-2-yl]carbonyl}-1H-indol-3-yl)aetic acid;
{6-fluoro-5-hydroxy-2-methyl-1-[(5-methylthien-2-yl)carbonyl]-1H-indol-3-yl}acetic acid;
(1-{[5-(difluoromethyl)thien-2-yl]carbonyl}-6-fluoro-5-hydroxy-2-methyl-1H-indol-3-yl)acetic acid;
(6-fluoro-5-hydroxy-2-methyl-1-{[5-(trifluoromethyl)thien-2-yl]carbonyl}-1H-indol-3-yl)acetic acid;
(6-fluoro-5-hydroxy-2-methyl-1-{[5-(methylthio)thien-2-yl]carbonyl}-1H-indol-3-yl)acetic acid;
[1-({5-[(difluoromethyl)thio]thien-2-yl}carbonyl)-6-fluoro-5-hydroxy-2-methyl-1H-indol-3-yl]acetic acid;
[6-fluoro-5-hydroxy-2-methyl-1-({5-[(trifluoromethyl)thio]thien-2-yl}carbonyl)-1H-indol-3-yl]acetic acid;
[6-fluoro-5-hydroxy-2-methyl-1-({5-[(pentafluoroethyl)thio]thien-2-yl}carbonyl)-1H-indol-3-yl]acetic acid;
[6-fluoro-5-hydroxy-2-methyl-1-({5-[(1,1,2,2-tetrafluoroethyl)thio]thien-2-yl}carbonyl)-1H-indol-3-yl]acetic acid; and
{1-[(5-cyanothien-2-yl)carbonyl]-6-fluoro-5-hydroxy-2-methyl-1H-indol-3-yl}acetic acid
[6-fluoro-5-hydroxy-2-methyl-1-(thien-3-ylcarbonyl)-1H-indol-3-yl]acetic acid
{6-fluoro-1-[(5-fluorothien-3-yl)carbonyl]-5-hydroxy-2-methyl-1H-indol-3-yl}acetic acid;
{1-[(5-chlorothien-3-yl)carbonyl]-6-fluoro-5-hydroxy-2-methyl-1H-indol-3-yl}acetic acid;
{1-[(5-bromothien-3-yl)carbonyl]-6-fluoro-5-hydroxy-2-methyl-1H-indol-3-yl}acetic acid;
{6-fluoro-5-hydroxy-1-[(5-hydroxythien-3-yl)carbonyl]-2-methyl-1H-indol-3-yl}acetic acid;
{6-fluoro-5-hydroxy-1-[(5-methoxythien-3-yl)carbonyl]-2-methyl-1H-indol-3-yl}acetic acid;
{1-[(5-ethoxythien-3-yl)carbonyl]-6-fluoro-5-hydroxy-2-methyl-1H-indol-3-yl}acetic acid;
(1-{[5-(difluoromethoxy)thien-3-yl]carbonyl}-6-fluoro-5-hydroxy-2-methyl-1H-indol-3-yl)acetic acid;
(6-fluoro-5-hydroxy-2-methyl-1-{[5-(trifluoromethoxy)thien-3-yl]carbonyl}-1H-indol-3-yl)acetic acid;
(6-fluoro-5-hydroxy-2-methyl-1-{[5-(pentafluoroethoxy)thien-3-yl]carbonyl}-1H-indol-3-yl)acetic acid;
(6-fluoro-5-hydroxy-2-methyl-1-{[5-(1,1,2,2-tetrafluoroethoxy)thien-3-yl]carbonyl}-1H-indol-3-yl)acetic acid;
{6-fluoro-5-hydroxy-2-methyl-1-[(5-methylthien-3-yl)carbonyl]-1H-indol-3-yl}acetic acid;
(1-{[5-(difluoromethyl)thien-3-yl]carbonyl}-6-fluoro-5-hydroxy-2-methyl-1H-indol-3-yl)acetic acid;
(6-fluoro-5-hydroxy-2-methyl-1-{[5-(trifluoromethyl)thien-3-yl]carbonyl}-1H-indol-3-yl)acetic acid;
(6-fluoro-5-hydroxy-2-methyl-1-{[5-(methylthio)thien-3-yl]carbonyl}-1H-indol-3-yl)acetic acid;
[1-({5-[(difluoromethyl)thio]thien-3-yl}carbonyl)-6-fluoro-5-hydroxy-2-methyl-1H-indol-3-yl]acetic acid;
[6-fluoro-5-hydroxy-2-methyl-1-({5-[(trifluoromethyl)thio]thien-3-yl}carbonyl)-1H-indol-3-yl]acetic acid;
[6-fluoro-5-hydroxy-2-methyl-1-({5-[(pentafluoroethyl)thio]thien-3-yl}carbonyl)-1H-indol-3-yl]acetic acid;
[6-fluoro-5-hydroxy-2-methyl-1-({5-[(1,1,2,2-tetrafluoroethyl)thio]thien-3-yl}carbonyl)-1H-indol-3-yl]acetic acid; and
{1-[(5-cyanothien-3-yl)carbonyl]-6-fluoro-5-hydroxy-2-methyl-1H-indol-3-yl}acetic acid.
[6-chloro-5-hydroxy-2-methyl-1-(thien-3-ylcarbonyl)-1H-indol-3-yl]acetic acid
{6-chloro-1-[(5-fluorothien-3-yl)carbonyl]-5-hydroxy-2-methyl-1H-indol-3-yl}acetic acid;
{1-[(5-chlorothien-3-yl)carbonyl]-6-chloro-5-hydroxy-2-methyl-1H-indol-3-yl}acetic acid;
{1-[(5-bromothien-3-yl)carbonyl]-6-chloro-5-hydroxy-2-methyl-1H-indol-3-yl}acetic acid;
{6-chloro-5-hydroxy-1-[(5-hydroxythien-3-yl)carbonyl]-2-methyl-1H-indol-3-yl}acetic acid;
{6-chloro-5-hydroxy-1-[(5-methoxythien-3-yl)carbonyl]-2-methyl-1H-indol-3-yl}acetic acid;
{1-[(5-ethoxythien-3-yl)carbonyl]-6-chloro-5-hydroxy-2-methyl-1H-indol-3-yl}acetic acid;
(1-{[5-(difluoromethoxy)thien-3-yl]carbonyl}-6-chloro-5-hydroxy-2-methyl-1H-indol-3-yl)acetic acid;
(6-chloro-5-hydroxy-2-methyl-1-{[5-(trifluoromethoxy)thien-3-yl]carbonyl}-1H-indol-3-yl)acetic acid;
(6-chloro-5-hydroxy-2-methyl-1-{[5-(pentafluoroethoxy)thien-3-yl]carbonyl}-1H-indol-3-yl)acetic acid;
(6-chloro-5-hydroxy-2-methyl-1-{[5-(1,1,2,2-tetrafluoroethoxy)thien-3-yl]carbonyl}-1H-indol-3-yl)acetic acid;
{6-chloro-5-hydroxy-2-methyl-1-[(5-methylthien-3-yl)carbonyl]-1H-indol-3-yl}acetic acid;
(1-{[5-(difluoromethyl)thien-3-yl]carbonyl}-6-chloro-5-hydroxy-2-methyl-1H-indol-3-yl)acetic acid;
(6-chloro-5-hydroxy-2-methyl-1-{[5-(trifluoromethyl)thien-3-yl]carbonyl}-1H-indol-3-yl)acetic acid;
(6-chloro-5-hydroxy-2-methyl-1-{[5-(methylthio)thien-3-yl]carbonyl}-1H-indol-3-yl)acetic acid;
[1-({5-[(difluoromethyl)thio]thien-3-yl}carbonyl)-6-chloro-5-hydroxy-2-methyl-1H-indol-3-yl]acetic acid;
[6-chloro-5-hydroxy-2-methyl-1-({5-[(trifluoromethyl)thio]thien-3-yl}carbonyl)-1H-indol-3-yl]acetic acid;
[6-chloro-5-hydroxy-2-methyl-1-({5-[(pentafluoroethyl)thio]thien-3-yl}carbonyl)-1H-indol-3-yl]acetic acid;
[6-chloro-5-hydroxy-2-methyl-1-({5-[(1,1,2,2-tetrafluoroethyl)thio]thien-3-yl}carbonyl)-1H-indol-3-yl]acetic acid; and
{1-[(5-cyanothien-3-yl)carbonyl]-6-chloro-5-hydroxy-2-methyl-1H-indol-3-yl}acetic acid.
[6-chloro-5-hydroxy-2-methyl-1-(thien-2-ylcarbonyl)-1H-indol-3-yl]acetic acid
{6-chloro-1-[(5-fluorothien-2-yl)carbonyl]-5-hydroxy-2-methyl-1H-indol-3-yl}acetic acid;
{1-[(5-chlorothien-2-yl)carbonyl]-6-chloro-5-hydroxy-2-methyl-1H-indol-3-yl}acetic acid;
{1-[(5-bromothien-2-yl)carbonyl]-6-chloro-5-hydroxy-2-methyl-1H-indol-3-yl}acetic acid;
{6-chloro-5-hydroxy-1-[(5-hydroxythien-2-yl)carbonyl]-2-methyl-1H-indol-3-yl}acetic acid;
{6-chloro-5-hydroxy-1-[(5-methoxythien-2-yl)carbonyl]-2-methyl-1H-indol-3-yl}acetic acid;
{1-[(5-ethoxythien-2-yl)carbonyl]-6-chloro-5-hydroxy-2-methyl-1H-indol-3-yl}acetic acid;
(1-{[5-(difluoromethoxy)thien-2-yl]carbonyl}-6-chloro-5-hydroxy-2-methyl-1H-indol-3-yl)acetic acid;
(6-chloro-5-hydroxy-2-methyl-1-{[5-(trifluoromethoxy)thien-2-yl]carbonyl}-1H-indol-3-yl)acetic acid;

(6-chloro-5-hydroxy-2-methyl-1-{[5-(pentafluoroethoxy)thien-2-yl]carbonyl}-1H-indol-3-yl)acetic acid;

(6-chloro-5-hydroxy-2-methyl-1-{[5-(1,1,2,2-tetrafluoroethoxy)thien-2-yl]carbonyl}-1H-indol-3-yl)acetic acid;

{6-chloro-5-hydroxy-2-methyl-1-[(5-methylthien-2-yl)carbonyl]-1H-indol-3-yl}acetic acid;

(1-{[5-(difluoromethyl)thien-2-yl]carbonyl}-6-chloro-5-hydroxy-2-methyl-1H-indol-3-yl)acetic acid;

(6-chloro-5-hydroxy-2-methyl-1-{[5-(trifluoromethyl)thien-2-yl]carbonyl}-1H-indol-3-yl)acetic acid;

(6-chloro-5-hydroxy-2-methyl-1-{[5-(methylthio)thien-2-yl]carbonyl}-1H-indol-3-yl)acetic acid;

[1-({5-[(difluoromethyl)thio]thien-2-yl}carbonyl)-6-chloro-5-hydroxy-2-methyl-1H-indol-3-yl]acetic acid;

[6-chloro-5-hydroxy-2-methyl-1-({5-[(trifluoromethyl)thio]thien-2-yl}carbonyl)-1H-indol-3-yl]acetic acid;

[6-chloro-5-hydroxy-2-methyl-1-({5-[(pentafluoroethyl)thio]thien-2-yl}carbonyl)-1H-indol-3-yl]acetic acid;

[6-chloro-5-hydroxy-2-methyl-1-({5-[(1,1,2,2-tetrafluoroethyl)thio]thien-2-yl}carbonyl)-1H-indol-3-yl]acetic acid; and {1-[(5-cyanothien-2-yl)carbonyl]-6-chloro-5-hydroxy-2-methyl-1H-indol-3-yl}acetic acid.

[6-fluoro-5-methoxy-2-methyl-1-(thien-3-ylcarbonyl)-1H-indol-3-yl]acetic acid

[6-fluoro-5-methoxy-2-methyl-1-(thien-2-ylcarbonyl)-1H-indol-3-yl]acetic acid;

{6-fluoro-1-[(5-fluorothien-2-yl)carbonyl]-5-methoxy-2-methyl-1H-indol-3-yl}acetic acid;

{1-[(5-chlorothien-2-yl)carbonyl]-6-fluoro-5-methoxy-2-methyl-1H-indol-3-yl}acetic acid;

{1-[(5-bromothien-2-yl)carbonyl]-6-fluoro-5-methoxy-2-methyl-1H-indol-3-yl}acetic acid;

{6-fluoro-5-methoxy-1-[(5-hydroxythien-2-yl)carbonyl]-2-methyl-1H-indol-3-yl}acetic acid;

{6-fluoro-5-methoxy-1-[(5-methoxythien-2-yl)carbonyl]-2-methyl-1H-indol-3-yl}acetic aid;

{1-[(5-ethoxythien-2-yl)carbonyl]-6-fluoro-5-methoxy-2-methyl-1H-indol-3-yl}acetic acid;

(1-{[5-(difluoromethoxy)thien-2-yl]carbonyl}-6-fluoro-5-methoxy-2-methyl-1H-indol-3-yl)acetic acid;

(6-fluoro-5-methoxy-2-methyl-1-{[5-(trifluoromethoxy)thien-2-yl]carbonyl}-1H-indol-3-yl)acetic acid;

(6-fluoro-5-methoxy-2-methyl-1-{[5-(pentafluoroethoxy)thien-2-yl]carbonyl}-1H-indol-3-yl)acetic acid;

(6-fluoro-5-methoxy-2-methyl-1-{[5-(1,1,2,2-tetrafluoroethoxy)thien-2-yl]carbonyl}-1H-indol-3-yl)acetic acid;

{6-fluoro-5-methoxy-2-methyl-1-[(5-methylthien-2-yl)carbonyl]-1H-indol-3-yl}acetic acid;

(1-{[5-(difluoromethyl)thien-2-yl]carbonyl}-6-fluoro-5-methoxy-2-methyl-1H-indol-3-yl)acetic acid;

(6-fluoro-5-methoxy-2-methyl-1-{[5-(trifluoromethyl)thien-2-yl]carbonyl}-1H-indol-3-yl)acetic acid;

(6-fluoro-5-methoxy-2-methyl-1-{[5-(trifluoromethyl)thien-2-yl]carbonyl}-1H-indol-3-yl)acetic acid;

[1-({5-[(difluoromethyl)thio]thien-2-yl}carbonyl)-6-fluoro-5-methoxy-2-methyl-1H-indol-3-yl]acetic acid;

[6-fluoro-5-methoxy-2-methyl-1-({5-[(trifluoromethyl)thio]thien-2-yl}carbonyl)-1H-indol-3-yl]acetic acid;

[6-fluoro-5-methoxy-2-methyl-1-({5-[(pentafluoroethyl)thio]thien-2-yl}carbonyl)-1H-indol-3-yl]acetic acid;

[6-fluoro-5-methoxy-2-methyl-1-({5-[(1,1,2,2-tetrafluoroethyl)thio]thien-2-yl}carbonyl)-1H-indol-3-yl]acetic acid; and {1-[(5-cyanothien-2-yl)carbonyl]-6-fluoro-5-methoxy-2-methyl-1H-indol-3-yl}acetic acid.

[6-chloro-5-methoxy-2-methyl-1-(thien-2-ylcarbonyl)-1H-indol-3-yl]acetic acid: {6-chloro-1-[(5-fluorothien-2-yl)carbonyl]-5-methoxy-2-methyl-1H-indol-3-yl}acetic acid;

{1-[(5-chlorothien-2-yl)carbonyl]-6-chloro-5-methoxy-2-methyl-1H-indol-3-yl}acetic acid;

{1-[(5-bromothien-2-yl)carbonyl]-6-chloro-5-methoxy-2-methyl-1H-indol-3-yl}acetic acid;

{6-chloro-5-methoxy-1-[(5-hydroxythien-2-yl)carbonyl]-2-methyl-1H-indol-3-yl}acetic acid;

{6-chloro-5-methoxy-1-[(5-methoxythien-2-yl)carbonyl]-2-methyl-1H-indol-3-yl}acetic acid;

{1-[(5-ethoxythien-2-yl)carbonyl]-6-chloro-5-methoxy-2-methyl-1H-indol-3-yl}acetic acid;

(1-{[5-(difluoromethoxy)thien-2-yl]carbonyl}-6-chloro-5-methoxy-2-methyl-1H-indol-3-yl)acetic acid;

(6-chloro-5-methoxy-2-methyl-1-{[5-(trifluoromethoxy)thien-2-yl]carbonyl}-1H-indol-3-yl)acetic acid;

(6-chloro-5-methoxy-2-methyl-1-{[5-(pentafluoroethoxy)thien-2-yl]carbonyl}-1H-indol-3-yl)acetic acid;

(6-chloro-5-methoxy-2-methyl-1-{[5-(1,1,2,2-tetrafluoroethoxy)thien-2-yl]carbonyl}-1H-indol-3-yl)acetic acid;

{6-chloro-5-methoxy-2-methyl-1-[(5-methylthien-2-yl)carbonyl]-1H-indol-3-yl}acetic acid;

(1-{[5-(difluoromethyl)thien-2-yl]carbonyl}-6-chloro-5-methoxy-2-methyl-1H-indol-3-yl)acetic acid;

(6-chloro-5-methoxy-2-methyl-1-{[5-(trifluoromethyl)thien-2-yl]carbonyl}-1H-indol-3-yl)acetic acid;

(6-chloro-5-methoxy-2-methyl-1-{[5-(methylthio)thien-2-yl]carbonyl}-1H-indol-3-yl)acetic acid;

[1-({5-[(difluoromethyl)thio]thien-2-yl}carbonyl)-6-chloro-5-methoxy-2-methyl-1H-indol-3-yl]acetic acid;

[6-chloro-5-methoxy-2-methyl-1-({5-[(trifluoromethyl)thio]thien-2-yl}carbonyl)-1H-indol-3-yl]acetic acid;

[6-chloro-5-methoxy-2-methyl-1-({5-[(pentafluoroethyl)thio]thien-2-yl}carbonyl)-1H-indol-3-yl]acetic acid;

[6-chloro-5-methoxy-2-methyl-1-({5-[(1,1,2,2-tetrafluoroethyl)thio]thien-2-yl}carbonyl)-1H-indol-3-yl]acetic acid; and {1-[(5-cyanothien-2-yl)carbonyl]-6-chloro-5-methoxy-2-methyl-1H-indol-3-yl}acetic acid.

[6-fluoro-5-methoxy-2-methyl-1-(thien-3-ylcarbonyl)-1H-indol-3-yl]acetic acid

{6-fluoro-1-[(5-fluorothien-3-yl)carbonyl]-5-methoxy-2-methyl-1H-indol-3-yl}acetic acid;

{1-[(5-chlorothien-3-yl)carbonyl]-6-fluoro-5-methoxy-2-methyl-1H-indol-3-yl}acetic acid;

{1-[(5-bromothien-3-yl)carbonyl]-6-fluoro-5-methoxy-2-methyl-1H-indol-3-yl}acetic acid;

{6-fluoro-5-methoxy-1-[(5-hydroxythien-3-yl)carbonyl]-2-methyl-1H-indol-3-yl}acetic acid;

{6-fluoro-5-methoxy-1-[(5-methoxythien-3-yl)carbonyl]-2-methyl-1H-indol-3-yl}acetic acid;

{1-[(5-ethoxythien-3-yl)carbonyl]-6-fluoro-5-methoxy-2-methyl-1H-indol-3-yl}acetic acid;

(1-{[5-(difluoromethoxy)thien-3-yl]carbonyl}-6-fluoro-5-methoxy-2-methyl-1H-indol-3-yl)acetic acid;

(6-fluoro-5-methoxy-2-methyl-1-{[5-(trifluoromethoxy)thien-3-yl]carbonyl}-1H-indol-3-yl)acetic acid;

(6-fluoro-5-methoxy-2-methyl-1-{[5-(pentafluoroethoxy)thien-3-yl]carbonyl}-1H-indol-3-yl)acetic acid;

(6-fluoro-5-methoxy-2-methyl-1-{[5-(1,1,2,2-tetrafluoroethoxy)thien-3-yl]carbonyl}-1H-indol-3-yl)acetic acid;

{6-fluoro-5-methoxy-2-methyl-1-[(5-methylthien-3-yl)carbonyl]-1H-indol-3-yl}acetic acid;

(1-{[5-(difluoromethyl)thien-3-yl]carbonyl}-6-fluoro-5-methoxy-2-methyl-1H-indol-3-yl)acetic acid;

(6-fluoro-5-methoxy-2-methyl-1-{[5-(trifluoromethyl)thien-3-yl]carbonyl}-1H-indol-3-yl)acetic acid;
(6-fluoro-5-methoxy-2-methyl-1-{[5-(methylthio)thien-3-yl]carbonyl}-1H-indol-3-yl)acetic acid;
[1-({5-[(difluoromethyl)thio]thien-3-yl}carbonyl)-6-fluoro-5-methoxy-2-methyl-1H-indol-3-yl]acetic acid;
[6-fluoro-5-methoxy-2-methyl-1-({5-[(trifluoromethyl)thio]thien-3-yl}carbonyl)-1H-indol-3-yl]acetic acid;
[6-fluoro-5-methoxy-2-methyl-1-({5-[(pentafluoroethyl)thio]thien-3-yl}carbonyl)-1H-indol-3-yl]acetic acid;
[6-fluoro-5-methoxy-2-methyl-1-({5-[(1,1,2,2-tetrafluoroethyl)thio]thien-3-yl}carbonyl)-1H-indol-3-yl]acetic acid; and
{1-[(5-cyanothien-3-yl)carbonyl]-6-fluoro-5-methoxy-2-methyl-1H-indol-3-yl}acetic acid.
[6-chloro-5-methoxy-2-methyl-1-(thien-3-ylcarbonyl)-1H-indol-3-yl]acetic acid
{6-chloro-1-[(5-fluorothien-3-yl)carbonyl]-5-methoxy-2-methyl-1H-indol-3-yl}acetic acid;
{1-[(5-chlorothien-3-yl)carbonyl]-6-chloro-5-methoxy-2-methyl-1H-indol-3-yl}acetic acid;
{1-[(5-bromothien-3-yl)carbonyl]-6-chloro-5-methoxy-2-methyl-1H-indol-3-yl}acetic acid;
{6-chloro-5-methoxy-1-[(5-hydroxythien-3-yl)carbonyl]-2-methyl-1H-indol-3-yl}acetic acid;
{6-chloro-5-methoxy-1-[(5-methoxythien-3-yl)carbonyl]-2-methyl-1H-indol-3-yl}acetic acid;
{1-[(5-ethoxythien-3-yl)carbonyl]-6-chloro-5-methoxy-2-methyl-1H-indol-3-yl}acetic acid;
(1-{[5-(difluoromethoxy)thien-3-yl]carbonyl}-6-chloro-5-methoxy-2-methyl-1H-indol-3-yl)acetic acid;
(6-chloro-5-methoxy-2-methyl-1-{[5-(trifluoromethoxy)thien-3-yl]carbonyl}-1H-indol-3-yl)acetic acid;
(6-chloro-5-methoxy-2-methyl-1-{[5-(pentafluoroethoxy)thien-3-yl]carbonyl}-1H-indol-3-yl)acetic acid;
(6-chloro-5-methoxy-2-methyl-1-{[5-(1,1,2,2-tetrafluoroethoxy)thien-3-yl]carbonyl}-1H-indol-3-yl)acetic acid;
{6-chloro-5-methoxy-2-methyl-1-[(5-methylthien-3-yl)carbonyl]-1H-indol-3-yl}acetic acid;
(1-{[5-(difluoromethyl)thien-3-yl]carbonyl}-6-chloro-5-methoxy-2-methyl-1H-indol-3-yl)acetic acid;
(6-chloro-5-methoxy-2-methyl-1-{[5-(trifluoromethyl)thien-3-yl]carbonyl}-1H-indol-3-yl)acetic acid;
(6-chloro-5-methoxy-2-methyl-1-{[5-(methylthio)thien-3-yl]carbonyl}-1H-indol-3-yl)acetic acid;
[1-({5-[(difluoromethyl)thio]thien-3-yl}carbonyl)-6-chloro-5-methoxy-2-methyl-1H-indol-3-yl]acetic acid;
[6-chloro-5-methoxy-2-methyl-1-({5-[(trifluoromethyl)thio]thien-3-yl}carbonyl)-1H-indol-3-yl]acetic acid;
[6-chloro-5-methoxy-2-methyl-1-({5-[(pentafluoroethyl)thio]thien-3-yl}carbonyl)-1H-indol-3-yl]acetic acid;
[6-chloro-5-methoxy-2-methyl-1-({5-[1,1,2,2-tetrafluoroethyl)thio]thien-3-yl}carbonyl)-1H-indol-3-yl]acetic acid; and
{1-[(5-cyanothien-3-yl)carbonyl]-6-chloro-5-methoxy-2-methyl-1H-indol-3-yl}acetic acid.
[4-fluoro-5-hydroxy-2-methyl-1-(thien-2-ylcarbonyl)-1H-indol-3-yl]acetic acid
{4-fluoro-1-[(5-fluorothien-2-yl)carbonyl]-5-hydroxy-2-methyl-1H-indol-3-yl}acetic acid;
{1-[(5-chlorothien-2-yl)carbonyl]-4-fluoro-5-hydroxy-2-methyl-1H-indol-3-yl}acetic acid;
{1-[(5-bromothien-2-yl)carbonyl]-4-fluoro-5-hydroxy-2-methyl-1H-indol-3-yl}acetic acid;
{4-fluoro-5-hydroxy-1-[(5-hydroxythien-2-yl)carbonyl]-2-methyl-1H-indol-3-yl}acetic acid;
{4-fluoro-5-hydroxy-1-[(5-methoxythien-2-yl)carbonyl]-2-methyl-1H-indol-3-yl}acetic acid;
{1-[(5-ethoxythien-2-yl)carbonyl]-4-fluoro-5-hydroxy-2-methyl-1H-indol-3-yl}acetic acid;
(1-{[5-(difluoromethoxy)thien-2-yl]carbonyl}-4-fluoro-5-hydroxy-2-methyl-1H-indol-3-yl)acetic acid;
(4-fluoro-5-hydroxy-2-methyl-1-{[5-(trifluoromethoxy)thien-2-yl]carbonyl}-1H-indol-3-yl)acetic acid;
(4-fluoro-5-hydroxy-2-methyl-1-{[5-(pentafluoroethoxy)thien-2-yl]carbonyl}-1H-indol-3-yl)acetic acid;
(4-fluoro-5-hydroxy-2-methyl-1-{[5-(1,1,2,2-tetrafluoroethoxy)thien-2-yl]carbonyl}-1H-indol-3-yl)acetic acid;
{4-fluoro-5-hydroxy-2-methyl-1-[(5-methylthien-2-yl)carbonyl]-1H-indol-3-yl}acetic acid;
(1-{[5-(difluoromethyl)thien-2-yl]carbonyl}-4-fluoro-5-hydroxy-2-methyl-1H-indol-3-yl)acetic acid;
(4-fluoro-5-hydroxy-2-methyl-1-{[5-(trifluoromethyl)thien-2-yl]carbonyl}-1H-indol-3-yl)acetic acid;
(4-fluoro-5-hydroxy-2-methyl-1-{[5-(methylthio)thien-2-yl]carbonyl}-1H-indol-3-yl)acetic acid;
[1-({5-[(difluoromethyl)thio]thien-2-yl}carbonyl)-4-fluoro-5-hydroxy-2-methyl-1H-indol-3-yl]acetic acid;
[4-fluoro-5-hydroxy-2-methyl-1-({5-[(trifluoromethyl)thio]thien-2-yl}carbonyl)-1H-indol-3-yl]acetic acid;
[4-fluoro-5-hydroxy-2-methyl-1-({5-[(pentafluoroethyl)thio]thien-2-yl}carbonyl)-1H-indol-3-yl]acetic acid;
[4-fluoro-5-hydroxy-2-methyl-1-({5-[(1,1,2,2-tetrafluoroethyl)thio]thien-2-yl}carbonyl)-1H-indol-3-yl]acetic acid; and
{1-[(5-cyanothien-2-yl)carbonyl]-4-fluoro-5-hydroxy-2-methyl-1H-indol-3-yl}acetic acid
[4-fluoro-5-hydroxy-2-methyl-1-(thien-3-ylcarbonyl)-1H-indol-3-yl]acetic acid
{4-fluoro-1-[(5-fluorothien-3-yl)carbonyl]-5-hydroxy-2-methyl-1H-indol-3-yl}acetic acid;
{1-[(5-chlorothien-3-yl)carbonyl]-4-fluoro-5-hydroxy-2-methyl-1H-indol-3-yl}acetic acid;
{1-[(5-bromothien-3-yl)carbonyl]-4-fluoro-5-hydroxy-2-methyl-1H-indol-3-yl}acetic acid;
{4-fluoro-5-hydroxy-1-[(5-hydroxythien-3-yl)carbonyl]-2-methyl-1H-indol-3-yl}acetic acid;
{4-fluoro-5-hydroxy-1-[(5-methoxythien-3-yl)carbonyl]-2-methyl-1H-indol-3-yl}acetic acid;
{1-[(5-ethoxythien-3-yl)carbonyl]-4-fluoro-5-hydroxy-2-methyl-1H-indol-3-yl}acetic acid;
(1-{[5-(difluoromethoxy)thien-3-yl]carbonyl}-4-fluoro-5-hydroxy-2-methyl-1H-indol-3-yl)acetic acid;
(4-fluoro-5-hydroxy-2-methyl-1-{[5-(trifluoromethoxy)thien-3-yl]carbonyl}-1H-indol-3-yl)acetic acid;
(4-fluoro-5-hydroxy-2-methyl-1-{[5-(pentafluoroethoxy)thien-3-yl]carbonyl}-1H-indol-3-yl)acetic acid;
(4-fluoro-5-hydroxy-2-methyl-1-{[5-(1,1,2,2-tetrafluoroethoxy)thien-3-yl]carbonyl}-1H-indol-3-yl)acetic acid;
{4-fluoro-5-hydroxy-2-methyl-1-[(5-methylthien-3-yl)carbonyl]-1H-indol-3-yl}acetic acid;
(1-{[5-(difluoromethyl)thien-3-yl]carbonyl}-4-fluoro-5-hydroxy-2-methyl-1H-indol-3-yl)acetic acid;
(4-fluoro-5-hydroxy-2-methyl-1-{[5-(trifluoromethyl)thien-3-yl]carbonyl}-1H-indol-3-yl)acetic acid;
(4-fluoro-5-hydroxy-2-methyl-1-{[5-(methylthio)thien-3-yl]carbonyl}-1H-indol-3-yl)acetic acid;
[1-({5-[(difluoromethyl)thio]thien-3-yl}carbonyl)-4-fluoro-5-hydroxy-2-methyl-1H-indol-3-yl]acetic acid;
[4-fluoro-5-hydroxy-2-methyl-1-({5-[(trifluoromethyl)thio]thien-3-yl}carbonyl)-1H-indol-3-yl]acetic acid;
[4-fluoro-5-hydroxy-2-methyl-1-({5-[(pentafluoroethyl)thio]thien-3-yl}carbonyl-1H-indol-3-yl]acetic acid;

[4-fluoro-5-hydroxy-2-methyl-1-({5-[(1,1,2,2-tetrafluoroethyl)thio]thien-3-yl}carbonyl)-1H-indol-3-yl]acetic acid; and
{1-[(5-cyanothien-3-yl)carbonyl]-4-fluoro-5-hydroxy-2-methyl-1H-indol-3-yl}acetic acid.
[4-chloro-5-hydroxy-2-methyl-1-(thien-3-ylcarbonyl)-1H-indol-3-yl]acetic acid
{4-chloro-1-[(5-fluorothien-3-yl)carbonyl]-5-hydroxy-2-methyl-1H-indol-3-yl}acetic acid;
{1-[(5-chlorothien-3-yl)carbonyl]-4-chloro-5-hydroxy-2-methyl-1H-indol-3-yl}acetic acid;
{1-[(5-bromothien-3-yl)carbonyl]-4-chloro-5-hydroxy-2-methyl-1H-indol-3-yl}acetic acid;
{4-chloro-5-hydroxy-1-[(5-hydroxythien-3-yl)carbonyl]-2-methyl-1H-indol-3-yl}acetic acid;
{4-chloro-5-hydroxy-1-[(5-methoxythien-3-yl)carbonyl]-2-methyl-1H-indol-3-yl}acetic acid;
{1-[(5-ethoxythien-3-yl)carbonyl]-4-chloro-5-hydroxy-2-methyl-1H-indol-3-yl}acetic acid;
(1-{[5-(difluoromethoxy)thien-3-yl]carbonyl}-4-chloro-5-hydroxy-2-methyl-1H-indol-3-yl)acetic acid;
(4-chloro-5-hydroxy-2-methyl-1-{[5-(trifluoromethoxy)thien-3-yl]carbonyl}-1H-indol-3-yl)acetic acid;
(4-chloro-5-hydroxy-2-methyl-1-{[5-(pentafluoroethoxy)thien-3-yl]carbonyl}-1H-indol-3-yl)acetic acid;
(4-chloro-5-hydroxy-2-methyl-1-{[5-(1,1,2,2-tetrafluoroethoxy)thien-3-yl]carbonyl}-1H-indol-3-yl)acetic acid;
{4-chloro-5-hydroxy-2-methyl-1-[(5-methylthien-3-yl)carbonyl]-1H-indol-3-yl}acetic acid;
(1-{[5-(difluoromethyl)thien-3-yl]carbonyl}-4-chloro-5-hydroxy-2-methyl-1H-indol-3-yl)acetic acid;
(4-chloro-5-hydroxy-2-methyl-1-{[5-(trifluoromethyl)thien-3-yl]carbonyl}-1H-indol-3-yl)acetic acid;
(4-chloro-5-hydroxy-2-methyl-1-{[5-(methylthio)thien-3-yl]carbonyl}-1H-indol-3-yl)acetic acid;
[1-({5-[(difluoromethyl)thio]thien-3-yl}carbonyl)-4-chloro-5-hydroxy-2-methyl-1H-indol-3-yl]acetic acid;
[4-chloro-5-hydroxy-2-methyl-1-({5-[(trifluoromethyl)thio]thien-3-yl}carbonyl)-1H-indol-3-yl]acetic acid;
[4-chloro-5-hydroxy-2-methyl-1-({5-[(pentafluoroethyl)thio]thien-3-yl}carbonyl)-1H-indol-3-yl]acetic acid;
[4-chloro-5-hydroxy-2-methyl-1-({5-[(1,1,2,2-tetrafluoroethyl)thio]thien-3-yl}carbonyl)-1H-indol-3-yl]acetic acid; and
{1-[(5-cyanothien-3-yl)carbonyl]-4-chloro-5-hydroxy-2-methyl-1H-indol-3-yl}acetic acid.
[4-chloro-5-hydroxy-2-methyl-1-(thien-2-ylcarbonyl)-1H-indol-3-yl]acetic acid
{4-chloro-1-[(5-fluorothien-2-yl)carbonyl]-5-hydroxy-2-methyl-1H-indol-3-yl}acetic acid;
{1-[(5-chlorothien-2-yl)carbonyl]-4-chloro-5-hydroxy-2-methyl-1H-indol-3-yl}acetic acid;
{1-[(5-bromothien-2-yl)carbonyl]-4-chloro-5-hydroxy-2-methyl-1H-indol-3-yl}acetic acid;
{4-chloro-5-hydroxy-1-[(5-hydroxythien-2-yl)carbonyl]-2-methyl-1H-indol-3-yl}acetic acid;
{4-chloro-5-hydroxy-1-[(5-methoxythien-2-yl)carbonyl]-2-methyl-1H-indol-3-yl}acetic acid;
{1-[(5-ethoxythien-2-yl)carbonyl]-4-chloro-5-hydroxy-2-methyl-1H-indol-3-yl}acetic acid;
(1-{[5-(difluoromethoxy)thien-2-yl]carbonyl}-4-chloro-5-hydroxy-2-methyl-1H-indol-3-yl)acetic acid;
(4-chloro-5-hydroxy-2-methyl-1-{[5-(trifluoromethoxy)thien-2-yl]carbonyl}-1H-indol-3-yl)acetic acid;
(4-chloro-5-hydroxy-2-methyl-1-{[5-(pentafluoroethoxy)thien-2-yl]carbonyl}-1H-indol-3-yl)acetic acid;
(4-chloro-5-hydroxy-2-methyl-1-{[5-(1,1,2,2-tetrafluoroethoxy)thien-2-yl]carbonyl}-1H-indol-3-yl)acetic acid;
{4-chloro-5-hydroxy-2-methyl-1-[(5-methylthien-2-yl)carbonyl]-1H-indol-3-yl}acetic acid;
(1-{[5-(difluoromethyl)thien-2-yl]carbonyl}-4-chloro-5-hydroxy-2-methyl-1H-indol-3-yl)acetic acid;
4-chloro-5-hydroxy-2-methyl-1-{[5-(trifluoromethyl)thien-2-yl]carbonyl}-1H-indol-3-yl)acetic acid;
(4-chloro-5-hydroxy-2-methyl-1-{[5-(methylthio)thien-2-yl]carbonyl}-1H-indol-3-yl)acetic acid;
[1-({5-[(difluoromethyl)thio]thien-2-yl}carbonyl)-4-chloro-5-hydroxy-2-methyl-1H-indol-3-yl]acetic acid;
[4-chloro-5-hydroxy-2-methyl-1-({5-[(trifluoromethyl)thio]thien-2-yl}carbonyl)-1H-indol-3-yl]acetic acid;
[4-chloro-5-hydroxy-2-methyl-1-({5-[(pentafluoroethyl)thio]thien-2-yl}carbonyl)-1H-indol-3-yl]acetic acid;
[4-chloro-5-hydroxy-2-methyl-1-({5-[(1,1,2,2-tetrafluoroethyl)thio]thien-2-yl}carbonyl)-1H-indol-3-yl]acetic acid; and
{1-[(5-cyanothien-2-yl)carbonyl]-4-chloro-5-hydroxy-2-methyl-1H-indol-3-yl}acetic acid.
[4-fluoro-5-methoxy-2-methyl-1-(thien-3-ylcarbonyl)-1H-indol-3-yl]acetic acid
{4-fluoro-1-[(5-fluorothien-2-yl)carbonyl]-5-methoxy-2-methyl-1H-indol-3-yl}acetic acid;
{1-[(5-chlorothien-2-yl)carbonyl]-4-fluoro-5-methoxy-2-methyl-1H-indol-3-yl}acetic acid;
{1-[(5-bromothien-2-yl)carbonyl]-4-fluoro-5-methoxy-2-methyl-1H-indol-3-yl}acetic acid;
{4-fluoro-5-methoxy-1-[(5-hydroxythien-2-yl)carbonyl]-2-methyl-1H-indol-3-yl}acetic acid;
{4-fluoro-5-methoxy-1-[(5-methoxythien-2-yl)carbonyl]-2-methyl-1H-indol-3-yl}acetic acid;
{1-[(5-ethoxythien-2-yl)carbonyl]-4-fluoro-5-methoxy-2-methyl-1H-indol-3-yl}acetic acid;
(1-{[5-(difluoromethoxy)thien-2-yl]carbonyl}-4-fluoro-5-methoxy-2-methyl-1H-indol-3-yl)acetic acid;
(4-fluoro-5-methoxy-2-methyl-1-{[5-(trifluoromethoxy)thien-2-yl]carbonyl}-1H-indol-3-yl)acetic acid;
(4-fluoro-5-methoxy-2-methyl-1-{[5-(pentafluoroethoxy)thien-2-yl]carbonyl}-1H-indol-3-yl)acetic acid;
(4-fluoro-5-methoxy-2-methyl-1-{[5-(1,1,2,2-tetrafluoroethoxy)thien-2-yl]carbonyl}-1H-indol-3-yl)acetic acid;
{4-fluoro-5-methoxy-2-methyl-1-[(5-methylthien-2-yl)carbonyl]-1H-indol-3-yl}acetic acid;
(1-{[5-(difluoromethyl)thien-2-yl]carbonyl}-4-fluoro-5-methoxy-2-methyl-1H-indol-3-yl)acetic acid;
(4-fluoro-5-methoxy-2-methyl-1-{[5-(trifluoromethyl)thien-2-yl]carbonyl}-1H-indol-3-yl)acetic acid;
(4-fluoro-5-methoxy-2-methyl-1-{[5-(methylthio)thien-2-yl]carbonyl}-1H-indol-3-yl)acetic acid;
[1-({5-[(difluoromethyl)thio]thien-2-yl}carbonyl)-4-fluoro-5-methoxy-2-methyl-1H-indol-3-yl]acetic acid;
[4-fluoro-5-methoxy-2-methyl-1-({5-[(trifluoromethyl)thio]thien-2-yl}carbonyl)-1H-indol-3-yl]acetic acid;
[4-fluoro-5-methoxy-2-methyl-1-({5-[(pentafluoroethyl)thio]thien-2-yl}carbonyl)-1H-indol-3-yl]acetic acid;
[4-fluoro-5-methoxy-2-methyl-1-({5-[(1,1,2,2-tetrafluoroethyl)thio]thien-2-yl}carbonyl)-1H-indol-3-yl]acetic acid; and
{1-[(5-cyanothien-2-yl)carbonyl]-4-fluoro-5-methoxy-2-methyl-1H-indol-3-yl}acetic acid.
[4-chloro-5-methoxy-2-methyl-1-(thien-2-ylcarbonyl)-1H-indol-3-yl]acetic acid
{4-chloro-1-[(5-fluorothien-2-yl)carbonyl]-5-methoxy-2-methyl-1H-indol-3-yl}acetic acid;

{1-[(5-chlorothien-2-yl)carbonyl]-4-chloro-5-methoxy-2-methyl-1H-indol-3-yl}acetic acid;
{1-[(5-bromothien-2-yl)carbonyl]-4-chloro-5-methoxy-2-methyl-1H-indol-3-yl}acetic acid;
{4-chloro-5-methoxy-1-[(5-hydroxythien-2-yl)carbonyl]-2-methyl-1H-indol-3-yl}acetic acid;
{4-chloro-5-methoxy-1-[(5-methoxythien-2-yl)carbonyl]-2-methyl-1H-indol-3-yl}acetic acid;
{1-[(5-ethoxythien-2-yl)carbonyl]-4-chloro-5-methoxy-2-methyl-1H-indol-3-yl}acetic acid;
(1-{[5-(difluoromethoxy)thien-2-yl]carbonyl}-4-chloro-5-methoxy-2-methyl-1H-indol-3-yl)acetic acid;
(4-chloro-5-methoxy-2-methyl-1-{[5-(trifluoromethoxy)thien-2-yl]carbonyl}-1H-indol-3-yl)acetic acid;
(4-chloro-5-methoxy-2-methyl-1-{[5-(pentafluoroethoxy)thien-2-yl]carbonyl}-1H-indol-3-yl)acetic acid;
(4-chloro-5-methoxy-2-methyl-1-{[5-(1,1,2,2-tetrafluoroethoxy)thien-2-yl]carbonyl}-1H-indol-3-yl)acetic acid;
{4-chloro-5-methoxy-2-methyl-1-[(5-methylthien-2-yl)carbonyl]-1H-indol-3-yl}acetic acid
(1-{[5-(difluoromethyl)thien-2-yl]carbonyl}-4-chloro-5-methoxy-2-methyl-1H-indol-3-yl)acetic acid;
(4-chloro-5-methoxy-2-methyl-1-{[5-(trifluoromethyl)thien-2-yl]carbonyl}-1H-indol-3-yl)acetic acid;
(4-chloro-5-methoxy-2-methyl-1-{[5-(methylthio)thien-2-yl]carbonyl}-1H-indol-3-yl)acetic acid;
[1-({5-[(difluoromethyl)thio]thien-2-yl}carbonyl)-4-chloro-5-methoxy-2-methyl-1H-indol-3-yl]acetic acid;
[4-chloro-5-methoxy-2-methyl-1-({5-[(trifluoromethyl)thio]thien-2-yl}carbonyl)-1H-indol-3-yl]acetic acid;
[4-chloro-5-methoxy-2-methyl-1-({5-[(pentafluoroethyl)thio]thien-2-yl}carbonyl)-1H-indol-3-yl]acetic acid;
[4-chloro-5-methoxy-2-methyl-1-({5-[(1,1,2,2-tetrafluoroethyl)thio]thien-2-yl}carbonyl)-1H-indol-3-yl]acetic acid; and
{1-[(5-cyanothien-2-yl)carbonyl]-4-chloro-5-methoxy-2-methyl-1H-indol-3-yl}acetic acid.
[4-fluoro-5-methoxy-2-methyl-1-(thien-3-ylcarbonyl)-1H-indol-3-yl]acetic acid
{4-fluoro-1-[(5-fluorothien-3-yl)carbonyl]-5-methoxy-2-methyl-1H-indol-3-yl}acetic acid;
{1-[(5-chlorothien-3-yl)carbonyl]-4-fluoro-5-methoxy-2-methyl-1H-indol-3-yl}acetic acid;
{1-[(5-bromothien-3-yl)carbonyl]-4-fluoro-5-methoxy-2-methyl-1H-indol-3-yl}acetic acid;
{4-fluoro-5-methoxy-1-[(5-hydroxythien-3-yl)carbonyl]-2-methyl-1H-indol-3-yl}acetic acid;
{4-fluoro-5-methoxy-1-[(5-methoxythien-3-yl)carbonyl]-2-methyl-1H-indol-3-yl}acetic acid;
{1-[(5-ethoxythien-3-yl)carbonyl]-4-fluoro-5-methoxy-2-methyl-1H-indol-3-yl}acetic acid;
(1-{[5-(difluoromethoxy)thien-3-yl]carbonyl}-4-fluoro-5-methoxy-2-methyl-1H-indol-3-yl)acetic acid;
(4-fluoro-5-methoxy-2-methyl-1-{[5-(trifluoromethoxy)thien-3-yl]carbonyl}-1H-indol-3-yl)acetic acid;
(4-fluoro-5-methoxy-2-methyl-1-{[5-(pentafluoroethoxy)thien-3-yl]carbonyl}-1H-indol-3-yl)acetic acid;
(4-fluoro-5-methoxy-2-methyl-1-{[5-(1,1,2,2-tetrafluoroethoxy)thien-3-yl]carbonyl}-1H-indol-3-yl)acetic acid;
{4-fluoro-5-methoxy-2-methyl-1-[(5-methylthien-3-yl)carbonyl]-1H-indol-3-yl}acetic acid;
(1-{[5-(difluoromethyl)thien-3-yl]carbonyl}-4-fluoro-5-methoxy-2-methyl-1H-indol-3-yl)acetic acid;
(4-chloro-5-methoxy-2-methyl-1-{[5-(trifluoromethyl)thien-3-yl]carbonyl}-1H-indol-3-yl)acetic acid;
(4-fluoro-5-methoxy-2-methyl-1-{[5-(methylthio)thien-3-yl]carbonyl}-1H-indol-3-yl)acetic acid;
[1-({5-[(difluoromethyl)thio]thien-3-yl}carbonyl)-4-fluoro-5-methoxy-2-methyl-1H-indol-3-yl]acetic acid;
[4-fluoro-5-methoxy-2-methyl-1-({5-[(trifluoromethyl)thio]thien-3-yl}carbonyl)-1H-indol-3-yl]acetic acid;
[4-fluoro-5-methoxy-2-methyl-1-({5-[(pentafluoroethyl)thio]thien-3-yl}carbonyl)-1H-indol-3-yl]acetic acid;
[4-chloro-5-methoxy-2-methyl-1-({5-[(trifluoromethyl)thio]thien-3-yl}carbonyl)-1H-indol-3-yl]acetic acid;
[4-chloro-5-methoxy-2-methyl-1-({5-[(pentafluoroethyl)thio]thien-3-yl}carbonyl)-1H-indol-3-yl]acetic acid;
[4-chloro-5-methoxy-2-methyl-1-({5-[(1,1,2,2-tetrafluoroethyl)thio]thien-3-yl}carbonyl)-1H-indol-3-yl]acetic acid; and
{1-[(5-cyanothien-3-yl)carbonyl]-4-chloro-5-methoxy-2-methyl-1H-indol-3-yl}acetic acid.
[6-chloro-1-(cyclohexylcarbonyl)-5-methoxy-2-methyl-1H-indol-3-yl]acetic acid
[6-chloro-1-(cyclohexylcarbonyl)-5-hydroxy-2-methyl-1H-indol-3-yl]acetic acid
[1-(cyclohexylcarbonyl)-6-fluoro-5-hydroxy-2-methyl-1H-indol-3-yl]acetic acid
[1-(cyclohexylcarbonyl)-4-fluoro-5-hydroxy-2-methyl-1H-indol-3-yl]acetic acid
[4-chloro-1-(cyclohexylcarbonyl)-5-hydroxy-2-methyl-1H-indol-3-yl]acetic acid
[4-chloro-1-(cyclohexylcarbonyl)-5-methoxy-2-methyl-1H-indol-3-yl]acetic acid
[1-(cyclohexylcarbonyl)-4-fluoro-5-methoxy-2-methyl-1H-indol-3-yl]acetic acid

[4-fluoro-5-methoxy-2-methyl-1-(pyridin-2-ylcarbonyl)-1H-indol-3-yl]acetic acid
[4-fluoro-5-hydroxy-2-methyl-1-(pyridin-2-ylcarbonyl)-1H-indol-3-yl]acetic acid
[4-chloro-5-methoxy-2-methyl-1-(pyridin-2-ylcarbonyl)-1H-indol-3-yl]acetic acid
[4-chloro-5-hydroxy-2-methyl-1-(pyridin-2-ylcarbonyl)-1H-indol-3-yl]acetic acid
[6-fluoro-5-methoxy-2-methyl-1-(pyridin-2-ylcarbonyl)-1H-indol-3-yl]acetic acid
[6-fluoro-5-hydroxy-2-methyl-1-(pyridin-2-ylcarbonyl)-1H-indol-3-yl]acetic acid
[6-chloro-5-methoxy-2-methyl-1-(pyridin-2-ylcarbonyl)-1H-indol-3-yl]acetic acid
[6-chloro-5-hydroxy-2-methyl-1-(pyridin-2-ylcarbonyl)-1H-indol-3-yl]acetic acid
[5-methoxy-2-methyl-1-(pyridin-2-ylcarbonyl)-1H-indol-3-yl]acetic acid
[5-hydroxy-2-methyl-1-(pyridin-2-ylcarbonyl)-1H-indol-3-yl]acetic acid
[4-fluoro-5-methoxy-2-methyl-1-(pyridin-3-ylcarbonyl)-1H-indol-3-yl]acetic acid
[4-fluoro-5-hydroxy-2-methyl-1-(pyridin-3-ylcarbonyl)-1H-indol-3-yl]acetic acid
[4-chloro-5-methoxy-2-methyl-1-(pyridin-3-ylcarbonyl)-1H-indol-3-yl]acetic acid
[4-chloro-5-hydroxy-2-methyl-1-(pyridin-3-ylcarbonyl)-1H-indol-3-yl]acetic acid
[6-fluoro-5-methoxy-2-methyl-1-(pyridin-3-ylcarbonyl)-1H-indol-3-yl]acetic acid
[6-fluoro-5-hydroxy-2-methyl-1-(pyridin-3-ylcarbonyl)-1H-indol-3-yl]acetic acid
[6-chloro-5-methoxy-2-methyl-1-(pyridin-3-ylcarbonyl)-1H-indol-3-yl]acetic acid
[6-chloro-5-hydroxy-2-methyl-1-(pyridin-3-ylcarbonyl)-1H-indol-3-yl]acetic acid
[5-methoxy-2-methyl-1-(pyridin-3-ylcarbonyl)-1H-indol-3-yl]acetic acid
[5-hydroxy-2-methyl-1-(pyridin-3-ylcarbonyl)-1H-indol-3-yl]acetic acid
[4-fluoro-5-methoxy-2-methyl-1-(pyridin-4-ylcarbonyl)-1H-indol-3-yl]acetic acid
[4-fluoro-5-hydroxy-2-methyl-1-(pyridin-4-ylcarbonyl)-1H-indol-3-yl]acetic acid
[4-chloro-5-methoxy-2-methyl-1-(pyridin-4-ylcarbonyl)-1H-indol-3-yl]acetic acid
[4-chloro-5-hydroxy-2-methyl-1-(pyridin-4-ylcarbonyl)-1H-indol-3-yl]acetic acid
[6-fluoro-5-methoxy-2-methyl-1-(pyridin-4-ylcarbonyl)-1H-indol-3-yl]acetic acid
[6-fluoro-5-hydroxy-2-methyl-1-(pyridin-4-ylcarbonyl)-1H-indol-3-yl]acetic acid
[6-chloro-5-methoxy-2-methyl-1-(pyridin-4-ylcarbonyl)-1H-indol-3-yl]acetic acid
[6-chloro-5-hydroxy-2-methyl-1-(pyridin-4-ylcarbonyl)-1H-indol-3-yl]acetic acid
[5-methoxy-2-methyl-1-(pyridin-4-ylcarbonyl)-1H-indol-3-yl]acetic acid
[5-hydroxy-2-methyl-1-(pyridin-4-ylcarbonyl)-1H-indol-3-yl]acetic acid
[4-fluoro-5-methoxy-2-methyl-1-(tetrahydro-2H-pyran-4-ylcarbonyl)-1H-indol-3-yl]acetic acid
[4-fluoro-5-hydroxy-2-methyl-1-(tetrahydro-2H-pyran-4-ylcarbonyl)-1H-indol-3-yl]acetic acid
[4-chloro-5-methoxy-2-methyl-1-(tetrahydro-2H-pyran-4-ylcarbonyl)-1H-indol-3-yl]acetic acid
[4-chloro-5-hydroxy-2-methyl-1-(tetrahydro-2H-pyran-4-ylcarbonyl)-1H-indol-3-yl]acetic acid
[6-fluoro-5-methoxy-2-methyl-1-(tetrahydro-2H-pyran-4-ylcarbonyl)-1H-indol-3-yl]acetic acid
[6-fluoro-5-hydroxy-2-methyl-1-(tetrahydro-2H-pyran-4-ylcarbonyl)-1H-indol-3-yl]acetic acid
[6-chloro-5-methoxy-2-methyl-1-(tetrahydro-2H-pyran-4-ylcarbonyl)-1H-indol-3-yl]acetic acid
[6-chloro-5-hydroxy-2-methyl-1-(tetrahydro-2H-pyran-4-ylcarbonyl)-1H-indol-3-yl]acetic acid
[5-methoxy-2-methyl-1-(tetrahydro-2H-pyran-4-ylcarbonyl)-1H-indol-3-yl]acetic acid
[5-hydroxy-2-methyl-1-(tetrahydro-2H-pyran-4-ylcarbonyl)-1H-indol-3-yl]acetic acid
[4-fluoro-5-methoxy-2-methyl-1-(tetrahydro-2H-thiopyran-4-ylcarbonyl)-1H-indol-3-yl]acetic acid
[4-fluoro-5-hydroxy-2-methyl-1-(tetrahydro-2H-thiopyran-4-ylcarbonyl)-1H-indol-3-yl]acetic acid
[4-chloro-5-methoxy-2-methyl-1-(tetrahydro-2H-thiopyran-4-ylcarbonyl)-1H-indol-3-yl]acetic acid
[4-chloro-5-hydroxy-2-methyl-1-(tetrahydro-2H-thiopyran-4-ylcarbonyl)-1H-indol-3-yl]acetic acid
[6-fluoro-5-methoxy-2-methyl-1-(tetrahydro-2H-thiopyran-4-ylcarbonyl)-1H-indol-3-yl]acetic acid
[6-fluoro-5-hydroxy-2-methyl-1-(tetrahydro-2H-thiopyran-4-ylcarbonyl)-1H-indol-3-yl]acetic acid
[6-chloro-5-methoxy-2-methyl-1-(tetrahydro-2H-thiopyran-4-ylcarbonyl)-1H-indol-3-yl]acetic acid
[6-chloro-5-hydroxy-2-methyl-1-(tetrahydro-2H-thiopyran-4-ylcarbonyl)-1H-indol-3-yl]acetic acid
[5-methoxy-2-methyl-1-(tetrahydro-2H-thiopyran-4-ylcarbonyl) -1H-indol-3-yl]acetic acid
[5-hydroxy-2-methyl-1-(tetrahydro-2H-thiopyran-4-ylcarbonyl) -1H-indol-3-yl]acetic acid
[4-fluoro-5-methoxy-2-methyl-1-(piperidin-4-ylcarbonyl)-1H-indol-3-yl]acetic acid
[4-fluoro-5-hydroxy-2-methyl-1-(piperidin-4-ylcarbonyl)-1H-indol-3-yl]acetic acid
[4-chloro-5-methoxy-2-methyl-1-(piperidin-4-ylcarbonyl)-1H-indol-3-yl]acetic acid
[4-chloro-5-hydroxy-2-methyl-1-(piperidin-4-ylcarbonyl)-1H-indol-3-yl]acetic acid
[6-fluoro-5-methoxy-2-methyl-1-(piperidin-4-ylcarbonyl)-1H-indol-3-yl]acetic acid
[6-fluoro-5-hydroxy-2-methyl-1-(piperidin-4-ylcarbonyl)-1H-indol-3-yl]acetic acid
[6-chloro-5-methoxy-2-methyl-1-(piperidin-4-ylcarbonyl)-1H-indol-3-yl]acetic acid
[6-chloro-5-hydroxy-2-methyl-1-(piperidin-4-ylcarbonyl)-1H-indol-3-yl]acetic acid
[5-methoxy-2-methyl-1-(piperidin-4-ylcarbonyl)-1H-indol-3-yl]acetic acid
[5-hydroxy-2-methyl-1-(piperidin-4-ylcarbonyl)-1H-indol-3-yl]acetic acid
[4-fluoro-5-methoxy-2-methyl-1-[(1-methylpiperidin-4-yl)carbonyl]-1H-indol-3-yl]acetic acid
[4-fluoro-5-hydroxy-2-methyl-1-[(1-methylpiperidin-4-yl)carbonyl]-1H-indol-3-yl]acetic acid
[4-chloro-5-methoxy-2-methyl-1-[(1-methylpiperidin-4-yl)carbonyl]-1H-indol-3-yl]acetic acid
[4-chloro-5-hydroxy-2-methyl-1-[(1-methylpiperidin-4-yl)carbonyl]-1H-indol-3-yl]acetic acid
[6-fluoro-5-methoxy-2-methyl-1-[(1-methylpiperidin-4-yl)carbonyl]-1H-indol-3-yl]acetic acid
[6-fluoro-5-hydroxy-2-methyl-1-[(1-methylpiperidin-4-yl)carbonyl]-1H-indol-3-yl]acetic acid

[6-chloro-5-methoxy-2-methyl-1-[(1-methylpiperidin-4-yl)carbonyl]-1H-indol-3-yl]acetic acid
[6-chloro-5-hydroxy-2-methyl-1-[(1-methylpiperidin-4-yl)carbonyl]-1H-indol-3-yl]acetic acid
[5-methoxy-2-methyl-1-[(1-methylpiperidin-4-yl)carbonyl]-1H-indol-3-yl]acetic acid
[5-hydroxy-2-methyl-1-[(1-methylpiperidin-4-yl)carbonyl]-1H-indol-3-yl]acetic acid
[4-fluoro-5-methoxy-2-methyl-1-[(4-methylpiperazin-1-yl)carbonyl]-1H-indol-3-yl]acetic acid
[4-fluoro-5-hydroxy-2-methyl-1-[(4-methylpiperazin-1-yl)carbonyl]-1H-indol-3-yl]acetic acid
[4-chloro-5-methoxy-2-methyl-1-[(4-methylpiperazin-1-yl)carbonyl]-1H-indol-3-yl]acetic acid
[4-chloro-5-hydroxy-2-methyl-1-[(4-methylpiperazin-1-yl)carbonyl]-1H-indol-3-yl]acetic acid
[6-fluoro-5-methoxy-2-methyl-1-[(4-methylpiperazin-1-yl)carbonyl]-1H-indol-3-yl]acetic acid
[6-fluoro-5-hydroxy-2-methyl-1-[(4-methylpiperazin-1-yl)carbonyl]-1H-indol-3-yl]acetic acid
[6-chloro-5-methoxy-2-methyl-1-[(4-methylpiperazin-1-yl)carbonyl]-1H-indol-3-yl]acetic acid
[6-chloro-5-hydroxy-2-methyl-1-[(4-methylpiperazin-1-yl)carbonyl]-1H-indol-3-yl]acetic acid
[5-methoxy-2-methyl-1-[(4-methylpiperazin-1-yl)carbonyl]-1H-indol-3-yl]acetic acid
[5-hydroxy-2-methyl-1-[(4-methylpiperazin-1-yl)carbonyl]-1H-indol-3-yl]acetic acid
[4-fluoro-5-methoxy-2-methyl-1-(piperazin-1-ylcarbonyl)-1H-indol-3-yl]acetic acid
[4-fluoro-5-hydroxy-2-methyl-1-(piperazin-1-ylcarbonyl)-1H-indol-3-yl]acetic acid
[4-chloro-5-methoxy-2-methyl-1-(piperazin-1-ylcarbonyl)-1H-indol-3-yl]acetic acid
[4-chloro-5-hydroxy-2-methyl-1-(piperazin-1-ylcarbonyl)-1H-indol-3-yl]acetic acid
[6-fluoro-5-methoxy-2-methyl-1-(piperazin-1-ylcarbonyl)-1H-indol-3-yl]acetic acid
[6-fluoro-5-hydroxy-2-methyl-1-(piperazin-1-ylcarbonyl)-1H-indol-3-yl]acetic acid
[6-chloro-5-methoxy-2-methyl-1-(piperazin-1-ylcarbonyl)-1H-indol-3-yl]acetic acid
[6-chloro-5-hydroxy-2-methyl-1-(piperazin-1-ylcarbonyl)-1H-indol-3-yl]acetic acid
[5-methoxy-2-methyl-1-(piperazin-1-ylcarbonyl)-1H-indol-3-yl]acetic acid
[5-hydroxy-2-methyl-1-(piperazin-1-ylcarbonyl)-1H-indol-3-yl]acetic acid
[4-fluoro-5-methoxy-2-methyl-1-(piperidin-1-ylcarbonyl)-1H-indol-3-yl]acetic acid
[4-fluoro-5-hydroxy-2-methyl-1-(piperidin-1-ylcarbonyl)-1H-indol-3-yl]acetic acid
[4-chloro-5-methoxy-2-methyl-1-(piperidin-1-ylcarbonyl)-1H-indol-3-yl]acetic acid
[4-chloro-5-hydroxy-2-methyl-1-(piperidin-1-ylcarbonyl)-1H-indol-3-yl]acetic acid
[6-fluoro-5-methoxy-2-methyl-1-(piperidin-1-ylcarbonyl)-1H-indol-3-yl]acetic acid
[6-fluoro-5-hydroxy-2-methyl-1-(piperidin-1-ylcarbonyl)-1H-indol-3-yl]acetic acid
[6-chloro-5-methoxy-2-methyl-1-(piperidin-1-ylcarbonyl)-1H-indol-3-yl]acetic acid
[6-chloro-5-hydroxy-2-methyl-1-(piperidin-1-ylcarbonyl)-1H-indol-3-yl]acetic acid
[5-methoxy-2-methyl-1-(piperidin-1-ylcarbonyl)-1H-indol-3-yl]acetic acid
[5-hydroxy-2-methyl-1-(piperidin-1-ylcarbonyl)-1H-indol-3-yl]acetic acid
[6-chloro-1-(cyclopentylcarbonyl)-5-methoxy-2-methyl-1H-indol-3-yl]acetic acid
[6-chloro-1-(cyclopentylcarbonyl)-5-hydroxy-2-methyl-1H-indol-3-yl]acetic acid
[1-(cyclopentylcarbonyl)-6-fluoro-5-methoxy-2-methyl-1H-indol-3-yl]acetic acid
[1-(cyclopentylcarbonyl)-6-fluoro-5-hydroxy-2-methyl-1H-indol-3-yl]acetic acid
[1-(cyclopentylcarbonyl)-4-fluoro-5-hydroxy-2-methyl-1H-indol-3-yl]acetic acid
[4-chloro-1-(cyclopentylcarbonyl)-5-hydroxy-2-methyl-1H-indol-3-yl]acetic acid
[4-chloro-1-(cyclopentylcarbonyl)-5-methoxy-2-methyl-1H-indol-3-yl]acetic acid
[1-(cyclopentylcarbonyl)-4-fluoro-5-methoxy-2-methyl-1H-indol-3-yl]acetic acid
[1-(cyclopentylcarbonyl)-5-methoxy-2-methyl-1H-indol-3-yl]acetic acid
[1-(cyclopentylcarbonyl)-5-hydroxy-2-methyl-1H-indol-3-yl]acetic acid[6-chloro-1-(cyclobutylcarbonyl)-5-methoxy-2-methyl-1H-indol-3-yl]acetic acid
[6-chloro-1-(cyclobutylcarbonyl)-5-hydroxy-2-methyl-1H-indol-3-yl]acetic acid
[1-(cyclobutylcarbonyl)-6-fluoro-5-methoxy-2-methyl-1H-indol-3-yl]acetic acid
[1-(cyclobutylcarbonyl)-6-fluoro-5-hydroxy-2-methyl-1H-indol-3-yl]acetic acid
[1-(cyclobutylcarbonyl)-4-fluoro-5-hydroxy-2-methyl-1H-indol-3-yl]acetic acid
[4-chloro-1-(cyclobutylcarbonyl)-5-hydroxy-2-methyl-1H-indol-3-yl]acetic acid
[4-chloro-1-(cyclobutylcarbonyl)-5-methoxy-2-methyl-1H-indol-3-yl]acetic acid
[1-(cyclobutylcarbonyl)-4-fluoro-5-methoxy-2-methyl-1H-indol-3-yl]acetic acid
[1-(cyclobutylcarbonyl)-5-methoxy-2-methyl-1H-indol-3-yl]acetic acid
[1-(cyclobutylcarbonyl)-5-hydroxy-2-methyl-1H-indol-3-yl]acetic acid
{1-[(4-chlorophenyl)sulfonyl]-5-methoxy-2-methyl-1H-indol-3-yl}acetic acid
{6-chloro-1-[(4-chlorophenyl)sulfonyl]-5-methoxy-2-methyl-1H-indol-3-yl}acetic acid
{6-chloro-1-[(3-chlorophenyl)sulfonyl]-5-methoxy-2-methyl-1H-indol-3-yl}acetic acid
[6-chloro-5-methoxy-2-methyl-1-({4-[(trifluoromethyl)thio]phenyl}sulfonyl)-1H-indol-3-yl]acetic acid
[6-chloro-5-fluoro-2-methyl-1-({4-[(trifluoromethyl)thio]phenyl}sulfonyl)-1H-indol-3-yl]acetic acid
[1-(3,4-dichlorobenzoyl)-5-methoxy-2-methyl-1H-indol-3-yl]acetic acid
[1-(3,4-dichlorobenzoyl)-5-hydroxy-2-methyl-1H-indol-3-yl]acetic acid
[6-chloro-1-(3,4-dichlorobenzoyl)-5-methoxy-2-methyl-1H-indol-3-yl]acetic acid
[6-chloro-1-(3,4-difluorobenzoyl)-5-methoxy-2-methyl-1H-indol-3-yl]acetic acid
[6-chloro-1-(3-chlorobenzoyl)-5-methoxy-2-methyl-1H-indol-3-yl]acetic acid
[1-(4-chlorobenzoyl)-6-fluoro-5-hydroxy-2-methyl-1H-indol-3-yl]acetic acid
[1-(4-chlorobenzoyl)-6-fluoro-5-methoxy-2-methyl-1H-indol-3-yl]acetic acid
[6-chloro-1-(4-chlorobenzoyl)-5-methoxy-2-methyl-1H-indol-3-yl]acetic acid

[1-(4-chlorobenzyl)-6-fluoro-5-methoxy-2-methyl-1H-indol-3-yl]acetic acid
[6-chloro-1-(4-chlorobenzyl)-5-methoxy-2-methyl-1H-indol-3-yl]acetic acid
[6-chloro-1-(4-chlorobenzoyl)-5-fluoro-2-methyl-1H-indol-3-yl]acetic acid
[6-chloro-1-(4-chlorobenzyl)-5-fluoro-2-methyl-1H-indol-3-yl]acetic acid
[6-chloro-1-(4-chlorobenzyl)-5-methoxy-2-methyl-1H-indol-3-yl]acetic acid
[6-chloro-1-(3,4-dichlorobenzyl)-5-methoxy-2-methyl-1H-indol-3-yl]acetic acid
[6-chloro-1-(3,4-difluorobenzyl)-5-methoxy-2-methyl-1H-indol-3-yl]acetic acid
[6-chloro-1-(3-chlorobenzyl)-5-methoxy-2-methyl-1H-indol-3-yl]acetic acid
[1-(4-bromobenzyl)-6-chloro-5-methoxy-2-methyl-1H-indol-3-yl]acetic acid
[6-chloro-1-(4-fluorobenzyl)-5-methoxy-2-methyl-1H-indol-3-yl]acetic acid
[6-chloro-1-(4-trifluoromethoxybenzyl)-5-methoxy-2-methyl-1H-indol-3-yl]acetic acid
[1-(1,3-benzothiazol-2-ylmethyl)-5-methoxy-2-methyl-1H-indol-3-yl]acetic acid
[1-(1,3-benzothiazol-2-ylmethyl)-6-fluoro-5-methoxy-2-methyl-1H-indol-3-yl]acetic acid
[1-(1,3-benzothiazol-2-ylmethyl)-6-chloro-5-methoxy-2-methyl-1H-indol-3-yl]acetic acid
[1-(1,3-benzothiazol-2-ylmethyl)-6-chloro-5-fluoro-2-methyl-1H-indol-3-yl]acetic acid
3-[6-chloro-1-(4-chlorobenzoyl)-5-methoxy-2-methyl-1H-indol-3-yl]propanoic acid;
4-[6-chloro-1-(4-chlorobenzoyl)-5-methoxy-2-methyl-1H-indol-3-yl]butanoic acid; 3-[6-chloro-1-(4-chlorobenzoyl)-5-methoxy-2-methyl-1H-indol-3-yl]-1,1,1-trifluoroacetone; 2-[6-chloro-1-(4-chlorobenzoyl)-5-methoxy-2-methyl-1H-indol-3-yl]-1-[1,3]oxazolo[4,5-b]pyridin-2-ylethanone; 2-[6-chloro-1-(4-chlorobenzoyl)-5-methoxy-2-methyl-1H-indol-3-yl]-1-(1,3-oxazol-2-yl)ethanone; 2-{[6-chloro-1-(4-chlorobenzoyl)-5-methoxy-2-methyl-1H-indol-3-yl]acetyl}-1,3-oxazole-4-carboxylic acid; and 2-{[6-chloro-1-(4-chlorobenzoyl)-5-methoxy-2-methyl-1H-indol-3-yl]acetyl}-1,3-oxazole-5-carboxylic acid.
[6-chloro-5-fluoro-2-methyl-1-(3-trifluoromethylbenzyl)-1H-indol-3-yl]acetic acid;
[6-chloro-5-fluoro-1-(3-trifluoromethoxybenzyl)-2-methyl-1H-indol-3-yl]acetic acid;
[1-(1,3-benzothiazol-2-ylmethyl)-2-methyl-5-(trifluoromethoxy)-1H-indol-3-yl]acetic acid; [1-(3-chlorobenzyl)-2-methyl-5-(trifluoromethoxy)-1H-indol-3-yl]acetic acid;
[1-(3-trifluoromethylbenzyl)-2-methyl-5-(trifluoromethoxy)-1H-indol-3-yl]acetic acid; [1-(3-trifluoromethoxybenzyl)-2-methyl-5-(trifluoromethoxy)-1H-indol-3-yl]acetic acid; [1-(1,3-benzothiazol-2-ylmethyl)-5-chloro-2-methyl-1H-indol-3-yl]acetic acid; [5-chloro-2-methyl-1-(3-trifluoromethylbenzyl)-1H-indol-3-yl]acetic acid; [5-chloro-2-methyl-1-(3-trifluoromethoxybenzyl)-1H-indol-2-yl]acetic acid; [5-chloro-1-(3-chlorobenzyl)-2-methyl-1H-indol-3-yl]acetic acid; [1-(1,3-benzothiazol-2-ylmethyl)-6-chloro-2-methyl-1H-indol-3-yl]acetic acid; [6-chloro-2-methyl-1-(3-trifluoromethylbenzyl)-1H-indol-3-yl]acetic acid; [6-chloro-2-methyl-1-(3-trifluoromethoxybenzyl)-1H-indol-3-yl]acetic acid; [6-chloro-1-(3-chlorobenzyl)-2-methyl-1H-indol-3-yl]acetic acid; 3-[6-chloro-1-(3-chlorobenzyl)-2,5-dimethyl-1H-indol-3-yl]propanoic acid; [1-(3-chlorobenzyl)-6-fluoro-2,5-dimethyl-1H-indol-3-yl]acetic acid; [1-(1,3-benzothiazol-2-ylmethyl)-6-fluoro-2,5-dimethyl-1H-indol-3-yl]acetic acid; [6-fluoro-2,5-dimethyl-1-(3-trifluoromethylbenzyl)-1H-indol-3-yl]acetic acid; [6-fluoro-2,5-dimethyl-1-(3-trifluoromethoxybenzyl)-1H-indol-3-yl]acetic acid; [1-(3-chlorobenzyl)-6-fluoro-2-methyl-5-(trifluoromethyl)-1H-indol-3-yl]acetic acid; [1-(3-trifluoromethylbenzyl)-6-fluoro-2-methyl-5-(trifluoromethyl)-1H-indol-3-yl]acetic acid; [1-(3-trifluoromethoxybenzyl)-6-fluoro-2-methyl-5-(trifluoromethyl)-1H-indol-3-yl]acetic acid; [1-(1,3-benzothiazol-2-ylmethyl)-6-fluoro-2-methyl-5-(trifluoromethyl)-1H-indol-3-yl]acetic acid; [1-(1,3-benzothiazol-2-ylmethyl)-6-chloro-2-methyl-5-(trifluoromethyl)-1H-indol-3-yl]acetic acid; [1-(3-trifluoromethoxybenzyl)-6-chloro-2-methyl-5-(trifluoromethyl)-1H-indol-3-yl]acetic acid; [1-(3-trifluoromethylbenzyl)-6-chloro-2-methyl-5-(fluoromethyl)-1H-indol-3-yl]acetic acid; and [1-(3-chlorobenzyl)-6-chloro-2-methyl-5-(trifluoromethyl)-1H-indol-3-yl]acetic acid
ethyl (6-chloro-5-methoxy-2-methyl-1H-indol-3-yl)acetate
ethyl (4-chloro-5-methoxy-2-methyl-1H-indol-3-yl)acetate
{1-[(4-methylphenyl)sulfonyl]-1H-indol-3-yl}(5-pyridin-2-yl-1,3,4-oxadiazol-2-yl)methanone
2-[1-(4-chlorobenzoyl)-5-methoxy-2-methyl-1H-indol-3-yl]-1-(5-pyridin-2-yl-1,3-oxazol-2-yl)ethanone
ethyl 5-(benzyloxy)-1-butyl-2-methyl-1H-indole-3-carboxylate
ethyl 1-benzyl-5-[3-9benzylamino)-2-hydroxypropoxy]-2-methyl-1H-indole-3-carboxylate
ethyl 4-[(dimethylamino)methyl]-5-hydroxy-2-methyl-1-phenyl-1H-indole-3-carboxylate hydrochloride
ethyl 1-benzyl-4-[(dimethylamino)methyl]-5-hydroxy-2-phenyl-1H-indole-3-carboxylate
2-(2-naphthyl)-1H-indole-3-carboxylic acid
(1-benzyl-6-hydroxy-2-methyl-1H-indol-3-yl)acetic acid
(1-benzyl-4-hydroxy-2-methyl-1H-indol-3-yl)acetic acid
(1-benzyl-6-hydroxy-2-methyl-1H-indol-3-yl)acetic acid
(1-benzyl-7-hydroxy-2-methyl-1H-indol-3-yl)acetic acid
[5-hydroxy-2-methyl-1-(2-phenylethyl)-1H-indol-3-yl]acetic acid
[5-hydroxy-2-(2-phenylethyl)-1H-indol-3-yl]acetic acid
(1-benzyl-2-ethyl-5-hydroxy-1H-indol-3-yl)acetic acid
(1-benzyl-2-ethyl-4-hydroxy-1H-indol-3-yl)acetic acid
(1-benzyl-2-ethyl-6-hydroxy-1H-indol-3-yl)acetic acid
(1-benzyl-2-ethyl-7-hydroxy-1H-indol-3-yl)acetic acid
(1-benzyl-5-hydroxy-2-isopropyl-1H-indol-3-yl)acetic acid
(1-benzyl-4-hydroxy-2-isopropyl-1H-indol-3-yl)acetic acid
(1-benzyl-6-hydroxy-2-isopropyl-1H-indol-3-yl)acetic acid
(1-benzyl-7-hydroxy-2-isopropyl-1H-indol-3-yl)acetic acid
(1-benzyl-5-hydroxy-1H-indol-3-yl)acetic acid
(1-benzyl-4-hydroxy-1H-indol-3-yl)acetic acid
(1-benzyl-6-hydroxy-1H-indol-3-yl)acetic acid
(1-benzyl-7-hydroxy-1H-indol-3-yl)acetic acid
[5-hydroxy-1-(4-hydroxybenzyl)-2-methyl-1H-indol-3-yl]acetic acid
[4-hydroxy-1-(4-hydroxybenzyl)-2-methyl-1H-indol-3-yl]acetic acid
[6-hydroxy-1-(4-hydroxybenzyl)-2-methyl-1H-indol-3-yl]acetic acid
[7-hydroxy-1-(4-hydroxybenzyl)-2-methyl-1H-indol-3-yl]acetic acid
[5-hydroxy-1-(2-hydroxybenzyl)-2-methyl-1H-indol-3-yl]acetic acid
[4-hydroxy-1-(2-hydroxybenzyl)-2-methyl-1H-indol-3-yl]acetic acid

[6-hydroxy-1-(2-hydroxybenzyl)-2-methyl-1H-indol-3-yl] acetic acid
[7-hydroxy-1-(2-hydroxybenzyl)-2-methyl-1H-indol-3-yl] acetic acid
[5-hydroxy-1-(3-hydroxybenzyl)-2-methyl-1H-indol-3-yl] acetic acid
[4-hydroxy-1-(3-hydroxybenzyl)-2-methyl-1H-indol-3-yl] acetic acid
[6-hydroxy-1-(3-hydroxybenzyl)-2-methyl-1H-indol-3-yl] acetic acid
[7-hydroxy-1-(3-hydroxybenzyl)-2-methyl-1H-indol-3-yl] acetic acid
[2-ethyl-5-hydroxy-1-(4-hydroxybenzyl)-1H-indol-3-yl] acetic acid
[2-ethyl-4-hydroxy-1-(4-hydroxybenzyl)-1H-indol-3-yl] acetic acid
[2-ethyl-6-hydroxy-1-(4-hydroxybenzyl)-1H-indol-3-yl] acetic acid
[2-ethyl-7-hydroxy-1-(4-hydroxybenzyl)-1H-indol-3-yl] acetic acid
[2-ethyl-5-hydroxy-1-(2-hydroxybenzyl)-1H-indol-3-yl] acetic acid
[2-ethyl-4-hydroxy-1-(2-hydroxybenzyl)-1H-indol-3-yl] acetic acid
[2-ethyl-6-hydroxy-1-(2-hydroxybenzyl)-1H-indol-3-yl] acetic acid
[2-ethyl-7-hydroxy-1-(2-hydroxybenzyl)-1H-indol-3-yl] acetic acid
[2-ethyl-5-hydroxy-1-(3-hydroxybenzyl)-1H-indol-3-yl] acetic acid
[2-ethyl-4-hydroxy-1-(3-hydroxybenzyl)-1H-indol-3-yl] acetic acid
[2-ethyl-6-hydroxy-1-(3-hydroxybenzyl)-1H-indol-3-yl] acetic acid
[2-ethyl-7-hydroxy-1-(3-hydroxybenzyl)-1H-indol-3-yl] acetic acid
[5-hydroxy-1-(4-hydroxybenzyl)-2-isopropyl-1H-indol-3-yl]acetic acid
[4-hydroxy-1-(4-hydroxybenzyl)-2-isopropyl-1H-indol-3-yl]acetic acid
[6-hydroxy-1-(4-hydroxybenzyl)-2-isopropyl-1H-indol-3-yl]acetic acid
[7-hydroxy-1-(4-hydroxybenzyl)-2-isopropyl-1H-indol-3-yl]acetic acid
[5-hydroxy-1-(2-hydroxybenzyl)-2-isopropyl-1H-indol-3-yl]acetic acid
[4-hydroxy-1-(2-hydroxybenzyl)-2-isopropyl-1H-indol-3-yl]acetic acid
[6-hydroxy-1-(2-hydroxybenzyl)-2-isopropyl-1H-indol-3-yl]acetic acid
[7-hydroxy-1-(2-hydroxybenzyl)-2-isopropyl-1H-indol-3-yl]acetic acid
[5-hydroxy-1-(3-hydroxybenzyl)-2-isopropyl-1H-indol-3-yl]acetic acid
[4-hydroxy-1-(3-hydroxybenzyl)-2-isopropyl-1H-indol-3-yl]acetic acid
[6-hydroxy-1-(3-hydroxybenzyl)-2-isopropyl-1H-indol-3-yl]acetic acid
[7-hydroxy-1-(3-hydroxybenzyl)-2-isopropyl-1H-indol-3-yl]acetic acid
[5-hydroxy-1-(4-hydroxybenzyl)-1H-indol-3-yl]acetic acid
[4-hydroxy-1-(4-hydroxybenzyl)-1H-indol-3-yl]acetic acid
[6-hydroxy-1-(4-hydroxybenzyl)-1H-indol-3-yl]acetic acid
[7-hydroxy-1-(4-hydroxybenzyl)-1H-indol-3-yl]acetic acid
[5-hydroxy-1-(2-hydroxybenzyl)-1H-indol-3-yl]acetic acid
[4-hydroxy-1-(2-hydroxybenzyl)-1H-indol-3-yl]acetic acid
[6-hydroxy-1-(2-hydroxybenzyl)-1H-indol-3-yl]acetic acid
[7-hydroxy-1-(2-hydroxybenzyl)-1H-indol-3-yl]acetic acid
[5-hydroxy-1-(3-hydroxybenzyl)-1H-indol-3-yl]acetic acid
[4-hydroxy-1-(3-hydroxybenzyl)-1H-indol-3-yl]acetic acid
[6-hydroxy-1-(3-hydroxybenzyl)-1H-indol-3-yl]acetic acid
[7-hydroxy-1-(3-hydroxybenzyl)-1H-indol-3-yl]acetic acid
[2-bromo-5-hydroxy-1-(4-hydroxybenzyl)-1H-indol-3-yl] acetic acid
[5-hydroxy-1-(4-hydroxybenzyl)-2-iodo-1H-indol-3-yl]acetic acid
[2-chloro-5-hydroxy-1-(4-hydroxybenzyl)-1H-indol-3-yl] acetic acid
[2-fluoro-5-hydroxy-1-(4-hydroxybenzyl)-1H-indol-3-yl] acetic acid
[2-chloro-4-hydroxy-1-(4-hydroxybenzyl)-1H-indol-3-yl] acetic acid
[2-bromo-4-hydroxy-1-(4-hydroxybenzyl)-1H-indol-3-yl] acetic acid
[2-fluoro-4-hydroxy-1-(4-hydroxybenzyl)-1H-indol-3-yl] acetic acid
[4-hydroxy-1-(4-hydroxybenzyl)-2-iodo-1H-indol-3-yl]acetic acid
[2-bromo-6-hydroxy-1-(4-hydroxybenzyl)-1H-indol-3-yl] acetic acid
[2-chloro-6-hydroxy-1-(4-hydroxybenzyl)-1H-indol-3-yl] acetic acid
[2-fluoro-6-hydroxy-1-(4-hydroxybenzyl)-1H-indol-3-yl] acetic acid
[6-hydroxy-1-(4-hydroxybenzyl)-2-iodo-1H-indol-3-yl]acetic acid
[2-bromo-7-hydroxy-1-(4-hydroxybenzyl)-1H-indol-3-yl] acetic acid
[2-bromo-5-hydroxy-1-(2-hydroxybenzyl)-1H-indol-3-yl] acetic acid
[2-chloro-5-hydroxy-1-(2-hydroxybenzyl)-1H-indol-3-yl] acetic acid
[5-hydroxy-1-(2-hydroxybenzyl)-2-iodo-1H-indol-3-yl]acetic acid
[2-fluoro-5-hydroxy-1-(2-hydroxybenzyl)-1H-indol-3-yl] acetic acid
[2-chloro-7-hydroxy-1-(4-hydroxybenzyl)-1H-indol-3-yl] acetic acid
[7-hydroxy-1-(4-hydroxybenzyl)-2-iodo-1H-indol-3-yl]acetic acid
[2-fluoro-7-hydroxy-1-(4-hydroxybenzyl)-1H-indol-3-yl] acetic acid
[2-bromo-4-hydroxy-1-(2-hydroxybenzyl)-1H-indol-3-yl] acetic acid
[2-chloro-4-hydroxy-1-(2-hydroxybenzyl)-1H-indol-3-yl] acetic acid
[4-hydroxy-1-(2-hydroxybenzyl)-2-iodo-1H-indol-3-yl]acetic acid
[2-fluoro-4-hydroxy-1-(2-hydroxybenzyl)-1H-indol-3-yl] acetic acid
[2-chloro-6-hydroxy-1-(2-hydroxybenzyl)-1H-indol-3-yl] acetic acid
[2-bromo-6-hydroxy-1-(2-hydroxybenzyl)-1H-indol-3-yl] acetic acid
[6-hydroxy-1-(2-hydroxybenzyl)-2-iodo-1H-indol-3-yl]acetic acid
[2-fluoro-6-hydroxy-1-(2-hydroxybenzyl)-1H-indol-3-yl] acetic acid
[2-bromo-7-hydroxy-1-(2-hydroxybenzyl)-1H-indol-3-yl] acetic acid
[7-hydroxy-1-(2-hydroxybenzyl)-2-iodo-1H-indol-3-yl]acetic acid
[2-chloro-7-hydroxy-1-(2-hydroxybenzyl)-1H-indol-3-yl] acetic acid

[2-fluoro-7-hydroxy-1-(2-hydroxybenzyl)-1H-indol-3-yl] acetic acid
3-(carboxymethyl)-1-(4-hydroxybenzyl)-2-methyl-1H-indole-5-carboxylic acid
3-(carboxymethyl)-1-(4-hydroxybenzyl)-2-methyl-1H-indole-4-carboxylic acid
3-(carboxymethyl)-1-(4-hydroxybenzyl)-2-methyl-1H-indole-6-carboxylic acid
3-(carboxymethyl)-1-(4-hydroxybenzyl)-2-methyl-1H-indole-7-carboxylic acid
3-(carboxymethyl)-1-(2-hydroxybenzyl)-2-methyl-1H-indole-5-carboxylic acid
3-(carboxymethyl)-1-(2-hydroxybenzyl)-2-methyl-1H-indole-4-carboxylic acid
3-(carboxymethyl)-1-(2-hydroxybenzyl)-2-methyl-1H-indole-6-carboxylic acid
3-(carboxymethyl)-1-(2-hydroxybenzyl)-2-methyl-1H-indole-7-carboxylic acid
3-(carboxymethyl)-1-(3-hydroxybenzyl)-2-methyl-1H-indole-5-carboxylic acid
3-(carboxymethyl)-1-(3-hydroxybenzyl)-2-methyl-1H-indole-4-carboxylic acid
3-(carboxymethyl)-1-(3-hydroxybenzyl)-2-methyl-1H-indole-6-carboxylic acid
3-(carboxymethyl)-1-(3-hydroxybenzyl)-2-methyl-1H-indole-7-carboxylic acid
3-(carboxymethyl)-2-ethyl-1-(4-hydroxybenzyl)-1H-indole-5-carboxylic acid
3-(carboxymethyl)-2-ethyl-1-(4-hydroxybenzyl)-1H-indole-4-carboxylic acid
3-(carboxymethyl)-2-ethyl-1-(4-hydroxybenzyl)-1H-indole-6-carboxylic acid
3-(carboxymethyl)-2-ethyl-1-(4-hydroxybenzyl)-1H-indole-7-carboxylic acid
3-(carboxymethyl)-2-ethyl-1-(2-hydroxybenzyl)-1H-indole-5-carboxylic acid
3-(carboxymethyl)-2-ethyl-1-(2-hydroxybenzyl)-1H-indole-4-carboxylic acid
3-(carboxymethyl)-2-ethyl-1-(2-hydroxybenzyl)-1H-indole-6-carboxylic acid
3-(carboxymethyl)-2-ethyl-1-(2-hydroxybenzyl)-1H-indole-7-carboxylic acid
3-(carboxymethyl)-2-ethyl-1-(3-hydroxybenzyl)-1H-indole-5-carboxylic acid
3-(carboxymethyl)-2-ethyl-1-(3-hydroxybenzyl)-1H-indole-4-carboxylic acid
3-(carboxymethyl)-2-ethyl-1-(3-hydroxybenzyl)-1H-indole-6-carboxylic acid
3-(carboxymethyl)-2-ethyl-1-(3-hydroxybenzyl)-1H-indole-7-carboxylic acid
3-(carboxymethyl)-1-(4-hydroxybenzyl)-2-isopropyl-1H-indole-5-carboxylic acid
3-(carboxymethyl)-1-(4-hydroxybenzyl)-2-isopropyl-1H-indole-4-carboxylic acid
3-(carboxymethyl)-1-(4-hydroxybenzyl)-2-isopropyl-1H-indole-6-carboxylic acid
3-(carboxymethyl)-1-(4-hydroxybenzyl)-2-isopropyl-1H-indole-7-carboxylic acid
3-(carboxymethyl)-1-(2-hydroxybenzyl)-2-isopropyl-1H-indole-4-carboxylic acid
3-(carboxymethyl)-1-(2-hydroxybenzyl)-2-isopropyl-1H-indole-6-carboxylic acid
3-(carboxymethyl)-1-(2-hydroxybenzyl)-2-isopropyl-1H-indole-7-carboxylic acid
3-(carboxymethyl)-1-(3-hydroxybenzyl)-2-isopropyl-1H-indole-5-carboxylic acid
3-(carboxymethyl)-1-(3-hydroxybenzyl)-2-isopropyl-1H-indole-4-carboxylic acid
3-(carboxymethyl)-1-(3-hydroxybenzyl)-2-isopropyl-1H-indole-6-carboxylic acid
3-(carboxymethyl)-1-(3-hydroxybenzyl)-2-isopropyl-1H-indole-7-carboxylic acid
3-(carboxymethyl)-1-(4-hydroxybenzyl)-1H-indole-5-carboxylic acid
3-(carboxymethyl)-1-(4-hydroxybenzyl)-1H-indole-4-carboxylic acid
3-(carboxymethyl)-1-(4-hydroxybenzyl)-1H-indole-6-carboxylic acid
3-(carboxymethyl)-1-(4-hydroxybenzyl)-1H-indole-7-carboxylic acid
3-(carboxymethyl)-1-(2-hydroxybenzyl)-1H-indole-5-carboxylic acid
3-(carboxymethyl)-1-(2-hydroxybenzyl)-1H-indole-4-carboxylic acid
3-(carboxymethyl)-1-(2-hydroxybenzyl)-1H-indole-6-carboxylic acid
3-(carboxymethyl)-1-(2-hydroxybenzyl)-1H-indole-7-carboxylic acid
3-(carboxymethyl)-1-(3-hydroxybenzyl)-1H-indole-5-carboxylic acid
3-(carboxymethyl)-1-(3-hydroxybenzyl)-1H-indole-4-carboxylic acid
3-(carboxymethyl)-1-(3-hydroxybenzyl)-1H-indole-6-carboxylic acid
3-(carboxymethyl)-1-(3-hydroxybenzyl)-1H-indole-7-carboxylic acid
1-benzyl-5-hydroxy-1H-indole-3-carboxylic acid
1-benzyl-4-hydroxy-1H-indole-3-carboxylic acid
1-benzyl-6-hydroxy-1H-indole-3-carboxylic acid
1-benzyl-7-hydroxy-1H-indole-3-carboxylic acid
1-benzyl-2-ethyl-5-hydroxy-1H-indole-3-carboxylic acid
1-benzyl-2-ethyl-4-hydroxy-1H-indole-3-carboxylic acid
1-benzyl-2-ethyl-6-hydroxy-1H-indole-3-carboxylic acid
1-benzyl-2-ethyl-7-hydroxy-1H-indole-3-carboxylic acid
1-benzyl-5-hydroxy-2-isopropyl-1H-indole-3-carboxylic acid
1-benzyl-4-hydroxy-2-isopropyl-1H-indole-3-carboxylic acid
1-benzyl-6-hydroxy-2-isopropyl-1H-indole-3-carboxylic acid
1-benzyl-7-hydroxy-2-isopropyl-1H-indole-3-carboxylic acid
1-benzyl-5-hydroxy-1H-indole-3-carboxylic acid
1-benzyl-4-hydroxy-1H-indole-3-carboxylic acid
1-benzyl-6-hydroxy-1H-indole-3-carboxylic acid
1-benzyl-7-hydroxy-1H-indole-3-carboxylic acid
2-ethyl-5-hydroxy-1-(4-hydroxybenzyl)-1H-indole-3-carboxylic acid
2-ethyl-4-hydroxy-1-(4-hydroxybenzyl)-1H-indole-3-carboxylic acid
2-ethyl-6-hydroxy-1-(4-hydroxybenzyl)-1H-indole-3-carboxylic acid
2-ethyl-7-hydroxy-1-(4-hydroxybenzyl)-1H-indole-3-carboxylic acid
2-ethyl-5-hydroxy-1-(2-hydroxybenzyl)-1H-indole-3-carboxylic acid
2-ethyl-4-hydroxy-1-(2-hydroxybenzyl)-1H-indole-3-carboxylic acid
2-ethyl-6-hydroxy-1-(2-hydroxybenzyl)-1H-indole-3-carboxylic acid
2-ethyl-7-hydroxy-1-(2-hydroxybenzyl)-1H-indole-3-carboxylic acid 2-ethyl-5-hydroxy-1-(3-hydroxybenzyl)-1H-indole-3-carboxylic acid
2-ethyl-4-hydroxy-1-(3-hydroxybenzyl)-1H-indole-3-carboxylic acid
5-hydroxy-1-(4-hydroxybenzyl)-2-isopropyl-1H-indole-3-carboxylic acid
4-hydroxy-1-(4-hydroxybenzyl)-2-isopropyl-1H-indole-3-carboxylic acid
6-hydroxy-1-(4-hydroxybenzyl)-2-isopropyl-1H-indole-3-carboxylic acid
7-hydroxy-1-(4-hydroxybenzyl)-2-isopropyl-1H-indole-3-carboxylic acid
5-hydroxy-1-(2-hydroxybenzyl)-2-isopropyl-1H-indole-3-carboxylic acid
4-hydroxy-1-(2-hydroxybenzyl)-2-isopropyl-1H-indole-3-carboxylic acid
6-hydroxy-1-(2-hydroxybenzyl)-2-isopropyl-1H-indole-3-carboxylic acid
7-hydroxy-1-(2-hydroxybenzyl)-2-isopropyl-1H-indole-3-carboxylic acid
5-hydroxy-1-(3-hydroxybenzyl)-2-isopropyl-1H-indole-3-carboxylic acid
4-hydroxy-1-(3-hydroxybenzyl)-2-isopropyl-1H-indole-3-carboxylic acid
6-hydroxy-1-(3-hydroxybenzyl)-2-isopropyl-1H-indole-3-carboxylic acid
7-hydroxy-1-(3-hydroxybenzyl)-2-isopropyl-1H-indole-3-carboxylic acid
4-hydroxy-1H-indole-3-carboxylic acid
2-ethyl-7-hydroxy-1-(3-hydroxybenzyl)-1H-indole-3-carboxylic acid
1-benzyl-2-methyl-3-(5H-tetrazol-5-ylmethyl)-1H-indol-4-ol
[2-methyl-1-(3-trifluoromethoxylbenzyl)indolizin-3-yl]acetic acid
[2-chloro-5-methoxy-1-(3-trifluoromethoxylbenzyl)-1H-indol-3-yl]acetic acid
[7-chloro-2-methyl-1-(3-trifluoromethoxylbenzyl)-1H-indol-3-yl]acetic acid
[2,7-dichloro-1-(3-trifluoromethoxylbenzyl)-1H-indol-3-yl]acetic acid
[2,5,6-trichloro-3-(3-trifluoromethoxylbenzyl)-1H-indol-1-yl]acetic acid
[2,5,6-trichloro-1-(3-trifluoromethoxylbenzyl)-1H-indol-1-yl]acetic acid
[2,6-dichloro-3-(3-trifluoromethoxylbenzy)-1H-indol-1-yl]acetic acid
[2,5-dichloro-3-(3-trifluoromethoxylbenzy)-1H-indol-1-yl]acetic acid
[2,6-dichloro-1-(3-trifluoromethoxylbenzy)-1H-indol-3-yl]acetic acid
[2,5-dichloro-1-(3-trifluoromethoxylbenzy)-1H-indol-3-yl]acetic aci
(2E)-3-[2,6-dichloro-1-(3-trifluoromethoxylbenzy)-1H-indol-3-yl]acrylic acid
(2E)-3-[2,5,6-trichloro-1-(3-trifluoromethoxylbenzy)-1H-indol-3-yl]acrylic acid
(2E)-3-[6-chloro-2-methyl-1-(3-trifluoromethoxylbenzy)-1H-indol-3-yl]acrylic acid
Additional Compounds
Additional useful compounds include: 5-Nitroindole; 5-Methoxy-2-methylindole 5-Methoxyindole-3-carboxaldehyde; 5-Methoxyindole; Indole-2-carboxylic acid Indole-3-carbinol; Indole-3-acetic hydrazide; 5-Indolol; 5-Fluoroindole; Ethyl indole-2-carboxylate; Ethyl 5-hydroxy-2-methylindole-3-carboxylate; Indole-5-carbonitrile; 5-Chloroindole; 5-Bromoindole; 5-Benzyloxyindole; 5-Aminoindole; 6-Fluorotryptamine hydrochloride; N-Acetyl-5-hydroxytryptamine; 4-Cyanoindole 7-Nitroindole; 7-Benzyloxyindole; 1-(tert-Butoxycarbonyl)-5-chloroindole; Indole-4-carboxaldehyde; Indole-7-carboxaldehyde; Methyl indole-6-carboxylate; 3-Indoleacetonitrile; Indole-6-carboxylic acid; Indole-5-carboxylic acid; (5-Benzyloxyindol-3-yl)acetonitrile; (6-Methoxyindol-3-ylmethyl) dimethylamine; 5-Iodoindole; tert-Butyl 5-bromoindole-1-carboxylate 5-Hydroxyindole-3-acetic acid; 2-(4-Fluorophenyl)-1H-indole-3-carboxaldehyde 3-(2-Hydroxyethyl)indole; 2-Phenylindole-3-carboxaldehyde; 5-Chloroindole-3-carboxaldehyde; 5-Amino-2-methylindole; 4-Aminoindole 7-Bromo-2-methylindole; 6-Bromoindole; 2-Methyl-5-nitroindole; 5-Bromoindole-3-carboxaldehyde; tert-Butyl 1-indolecarboxylate; Indole-5-carboxaldehyde; 5-Fluoro-2-methylindole; Methyl indole-5-carboxylate; 1-Methylindole-2-carboxaldehyde; 5-Methoxy-4-methylindole; 7-Chloroindole; 7-Bromoindole 6-Fluoroindole; 1-Methylindole-3-carboxylic acid; 4-Fluoroindole 3-(Trifluoroacetyl)indole; 2-(2-Aminophenyl)indole; 3-(2-Bromoethyl)indole 1-Acetyl-3-indolecarboxaldehyde; 1-Methylindole-3-carboxaldehyde; 5-Aminoindole hydrochloride; 5-Methoxytryptamine; Methyl indole-4-carboxylate 4-Nitroindole; 2-Methylindole-3-carboxaldehyde; 4-Methoxyindole; Indole-4-carboxylic acid; 5,6-Dimethoxyindole; 6-Chloroindole; 4-Chloroindole; 4-Benzyloxyindole; 5-Methylindole; 4-Indolol; 6-Methoxyindole; Ethyl 5-chloro-2-indolecarboxylate; 5-(Benzyloxy)indole; 5-Methylindole-3-carboxaldehyde; Indole-3-carboxaldehyde; 7-Methoxyindole; 7-Aminoindole; and 3-Acetylindole, all or some of which may be inhibitors of DAO and some or all of which may have one more additional activities.

DAO inhibitors can include the following compounds:
2-(1H-indol-2-yl)pyridin-3-ol
3-(1H-indol-2-yl)pyridin-2-ol
3-(1H-indol-2-yl)pyridin-4-ol
4-(1H-indol-2-yl)pyridin-3-ol
2-(trifluoromethyl)-1H-indol-5-ol
2-(trifluoromethyl)-1H-indol-4-ol
3-(aminomethyl)-1H-indol-5-ol
5-hydroxy-1H-indole-3-carbonitrile
3-(aminomethyl)-1H-indole-2-carboxylic acid
3-(2-aminoethyl)-1H-indole-2-carboxylic acid
3-cyano-1H-indole-2-carboxylic acid
3-(aminomethyl)-1H-indole-2-carboxylic acid
1-benzyl-5-hydroxy-1H-indole-2-carboxylic acid
1-(3-fluorobenzyl)-5-hydroxy-1H-indole-2-carboxylic acid
1-(3,5-difluorobenzyl)-5-hydroxy-1H-indole-2-carboxylic acid
1-(3-chlorobenzyl)-5-hydroxy-1H-indole-2-carboxylic acid
1-(2-chlorobenzyl)-5-hydroxy-1H-indole-2-carboxylic acid
1-(4-fluorobenzyl)-5-hydroxy-1H-indole-2-carboxylic acid
1-(4-chlorobenzyl)-5-hydroxy-1H-indole-2-carboxylic acid
1-benzyl-5-hydroxy-1H-indole-2-carboxylic acid
1-benzyl-5-hydroxy-1H-indole-2-carboxylic acid
3-(cyanomethyl)-1H-indole-2-carboxylic acid

| 49 | 50 |
|---|---|
| (5-hydroxy-1H-indol-3-yl)acetonitrile | (1-benzyl-6-hydroxy-2-methyl-1H-indol-3-yl)acetic acid |
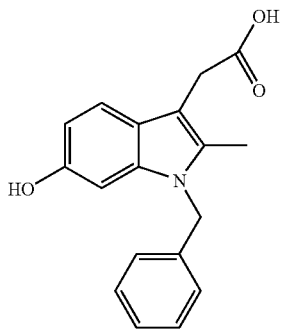
(1-benzyl-6-hydroxy-2-methyl-1H-indol-3-yl)acetic acid
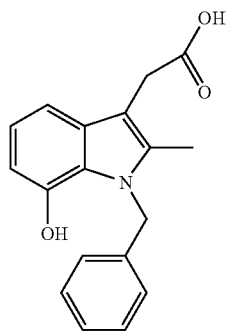
(1-benzyl-7-hydroxy-2-methyl-1H-indol-3-yl)acetic acid
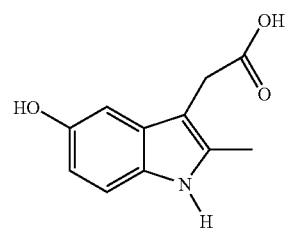
(5-hydroxy-2-methyl-1H-indol-3-yl)acetic acid
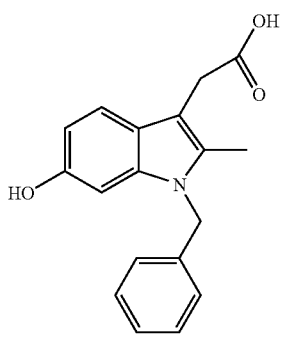
(1-benzyl-4-hydroxy-2-methyl-1H-indol-3-yl)acetic acid
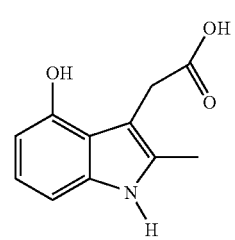
(4-hydroxy-2-methyl-1H-indol-3-yl)acetic acid
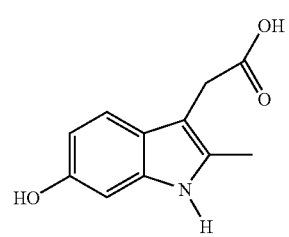

51
(6-hydroxy-2-methyl-1H-indol-3-yl)acetic acid
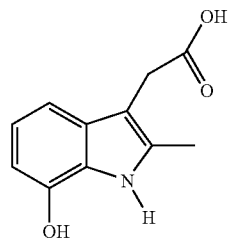
(7-hydroxy-2-methyl-1H-indol-3-yl)acetic acid
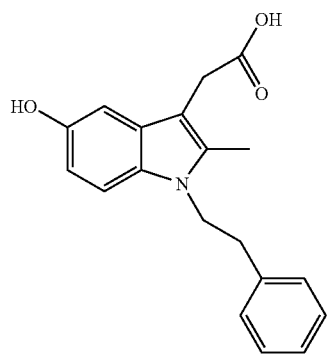
[5-hydroxy-2-methyl-1-(2-phenylethyl)-1H-indol-3-yl]acetic acid
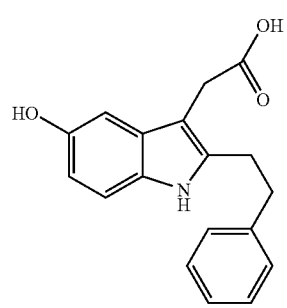
52
[5-hydroxy-2-(2-phenylethyl)-1H-indol-3-yl]acetic acid
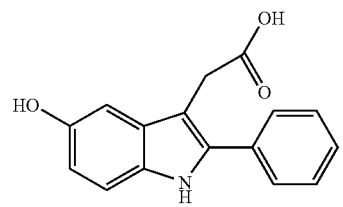
(5-hydroxy-2-phenyl-1H-indol-3-yl)acetic acid
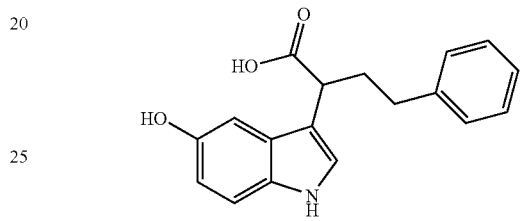
2-(5-hydroxy-1H-indol-3-yl)-4-phenylbutanoic acid
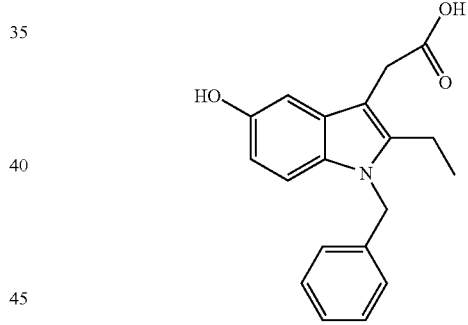
(1-benzyl-2-ethyl-5-hydroxy-1H-indol-3-yl)acetic acid
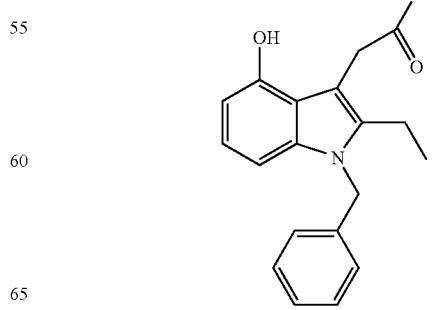

53
(1-benzyl-2-ethyl-4-hydroxy-1H-indol-3-yl)acetic acid
54
(1-benzyl-5-hydroxy-2-isopropyl-1H-indol-3-yl) acetic acid
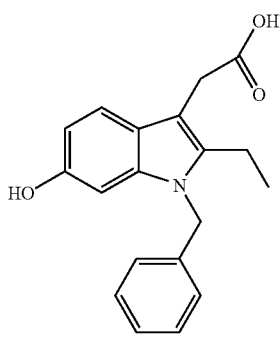
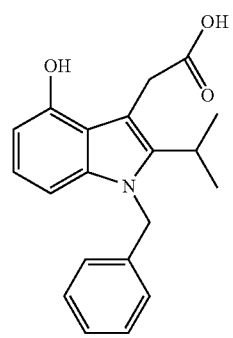
(1-benzyl-2-ethyl-6-hydroxy-1H-indol-3-yl)acetic acid
(1-benzyl-4-hydroxy-2-isopropyl-1H-indol-3-yl) acetic acid
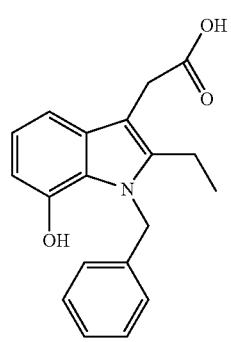
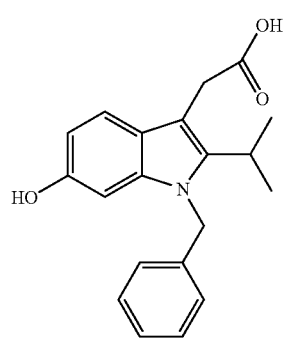
(1-benzyl-2-ethyl-7-hydroxy-1H-indol-3-yl)acetic acid
(1-benzyl-6-hydroxy-2-isopropyl-1H-indol-3-yl) acetic acid
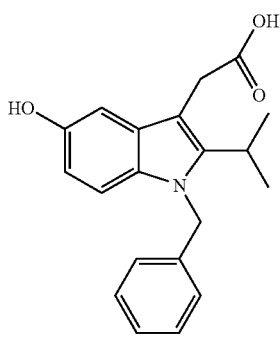
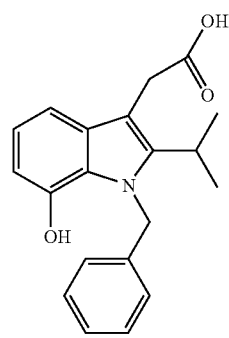

55
(1-benzyl-7-hydroxy-2-isopropyl-1H-indol-3-yl)
acetic acid
56
(1-benzyl-6-hydroxy-1H-indol-3-yl)acetic acid
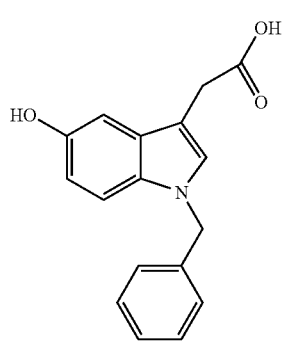
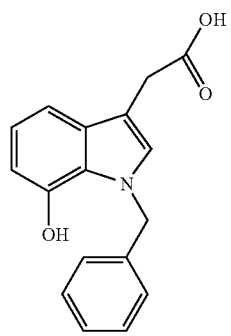
(1-benzyl-7-hydroxy-1H-indol-3-yl)acetic acid
(1-benzyl-5-hydroxy-1H-indol-3-yl)acetic acid
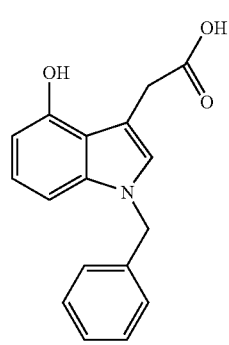
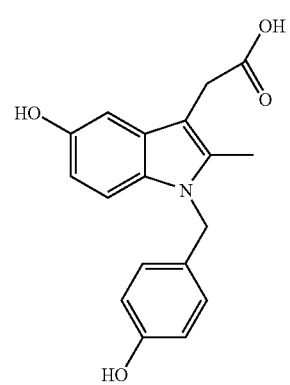
[5-hydroxy-1-(4-hydroxybenzyl)-2-methyl-1H-indol-3-yl]acetic acid
(1-benzyl-4-hydroxy-1H-indol-3-yl)acetic acid
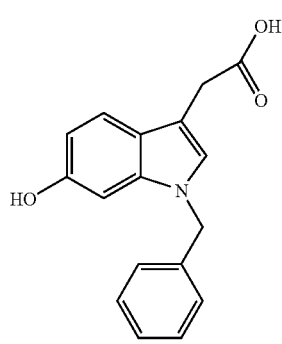
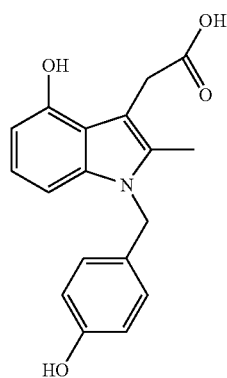

57
[4-hydroxy-1-(4-hydroxybenzyl)-2-methyl-1H-indol-3-yl]acetic acid
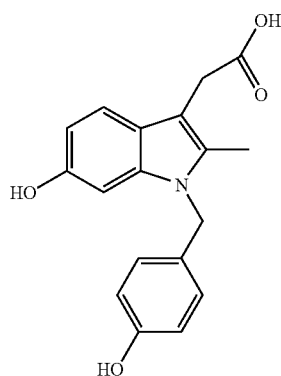
[6-hydroxy-1-(4-hydroxybenzyl)-2-methyl-1H-indol-3-yl]acetic acid
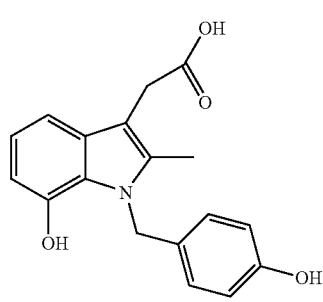
[7-hydroxy-1-(4-hydroxybenzyl)-2-methyl-1H-indol-3-yl]acetic acid
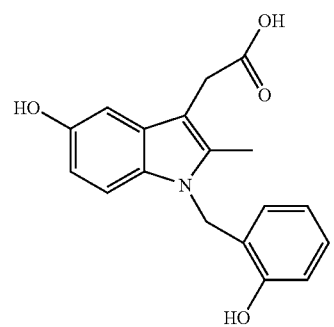
58
[5-hydroxy-1-(2-hydroxybenzyl)-2-methyl-1H-indol-3-yl]acetic acid
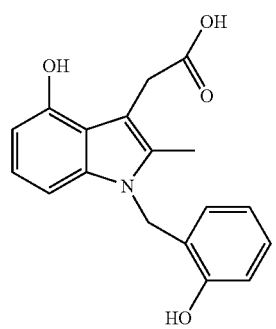
[4-hydroxy-1-(2-hydroxybenzyl)-2-methyl-1H-indol-3-yl]acetic acid
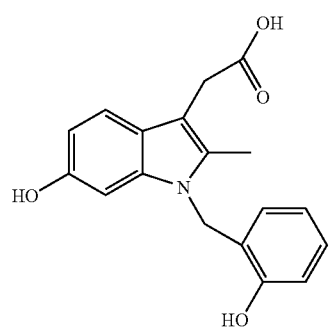
[6-hydroxy-1-(2-hydroxybenzyl)-2-methyl-1H-indol-3-yl]acetic acid
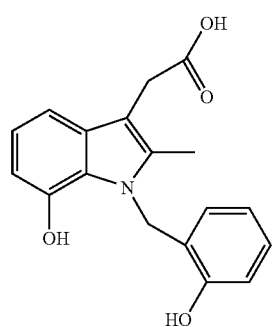

| 59 | 60 |
|---|---|
| [7-hydroxy-1-(2-hydroxybenzyl)-2-methyl-1H-indol-3-yl]acetic acid | [6-hydroxy-1-(3-hydroxybenzyl)-2-methyl-1H-indol-3-yl]acetic acid |
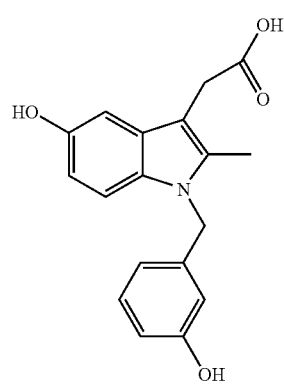
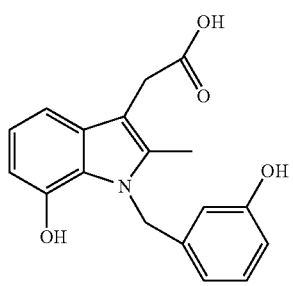
[7-hydroxy-1-(3-hydroxybenzyl)-2-methyl-1H-indol-3-yl]acetic acid
[5-hydroxy-1-(3-hydroxybenzyl)-2-methyl-1H-indol-3-yl]acetic acid
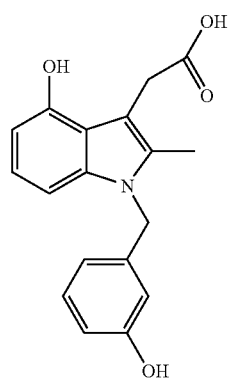
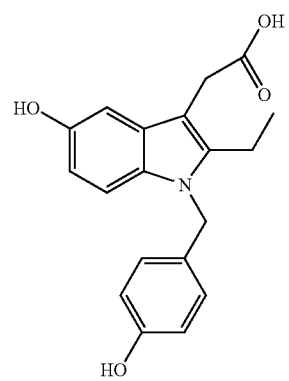
[2-ethyl-5-hydroxy-1-(4-hydroxybenzyl)-1H-indol-3-yl]acetic acid
[4-hydroxy-1-(3-hydroxybenzyl)-2-methyl-1H-indol-3-yl]acetic acid
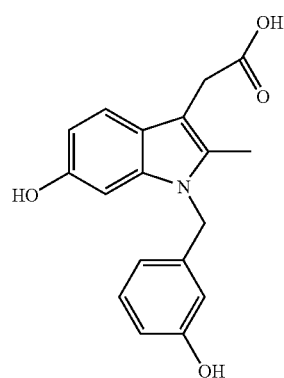
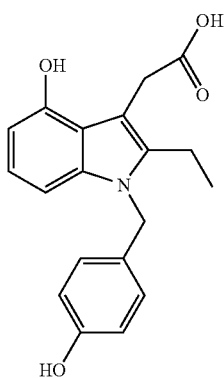

| 61 | 62 |
|---|---|
| [2-ethyl-4-hydroxy-1-(4-hydroxybenzyl)-1H-indol-3-yl]acetic acid | [2-ethyl-5-hydroxy-1-(2-hydroxybenzyl)-1H-indol-3-yl]acetic acid |
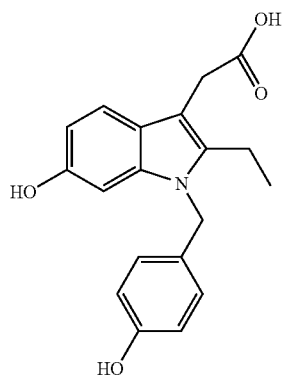
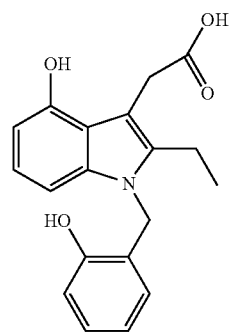
[2-ethyl-6-hydroxy-1-(4-hydroxybenzyl)-1H-indol-3-yl]acetic acid
[2-ethyl-4-hydroxy-1-(2-hydroxybenzyl)-1H-indol-3-yl]acetic acid
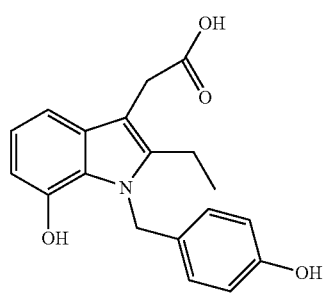
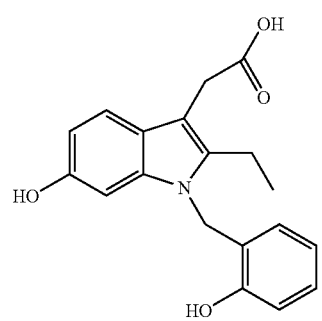
[2-ethyl-7-hydroxy-1-(4-hydroxybenzyl)-1H-indol-3-yl]acetic acid
[2-ethyl-6-hydroxy-1-(2-hydroxybenzyl)-1H-indol-3-yl]acetic acid
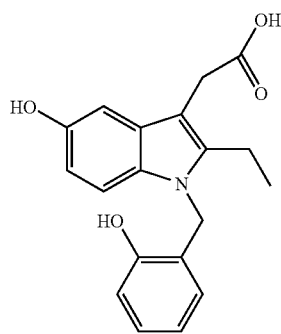
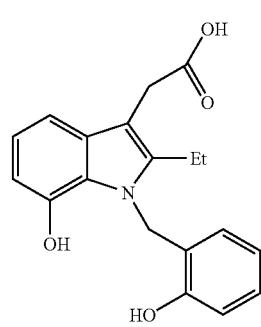

| 63 | 64 |
|---|---|
| [2-ethyl-7-hydroxy-1-(2-hydroxybenzyl)-1H-indol-3-yl]acetic acid | [2-ethyl-6-hydroxy-1-(3-hydroxybenzyl)-1H-indol-3-yl]acetic acid |
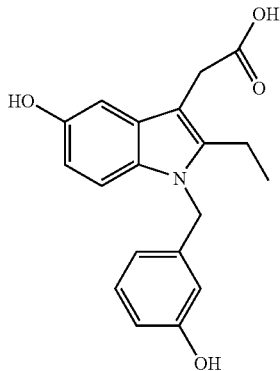 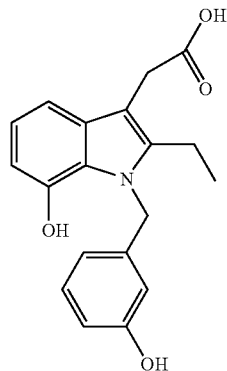
[2-ethyl-5-hydroxy-1-(3-hydroxybenzyl)-1H-indol-3-yl]acetic acid
[2-ethyl-7-hydroxy-1-(3-hydroxybenzyl)-1H-indol-3-yl]acetic acid
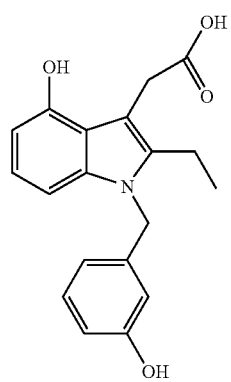 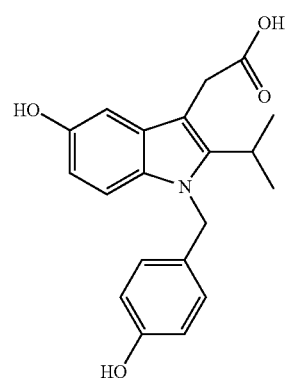
[2-ethyl-4-hydroxy-1-(3-hydroxybenzyl)-1H-indol-3-yl]acetic acid
[5-hydroxy-1-(4-hydroxybenzyl)-2-isopropyl-1H-indol-3-yl]acetic acid
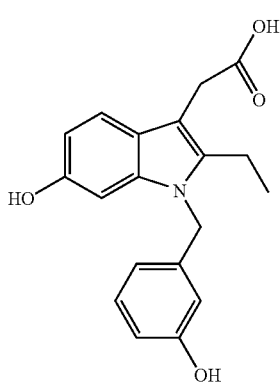 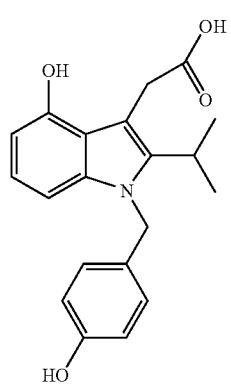

65
[4-hydroxy-1-(4-hydroxybenzyl)-2-isopropyl-1H-indol-3-yl]acetic acid
66
[5-hydroxy-1-(2-hydroxybenzyl)-2-isopropyl-1H-indol-3-yl]acetic acid
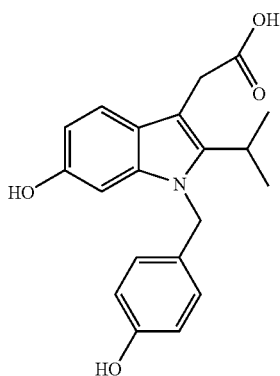
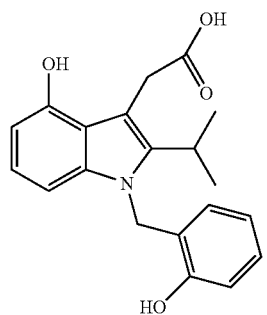
[6-hydroxy-1-(4-hydroxybenzyl)-2-isopropyl-1H-indol-3-yl]acetic acid
[4-hydroxy-1-92-hydroxybenzyl)-2-isopropyl-1H-indol-3-yl]acetic acid
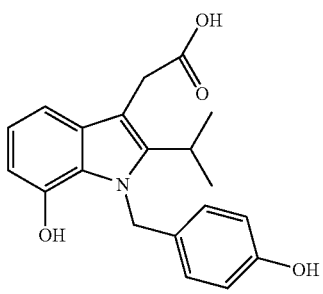
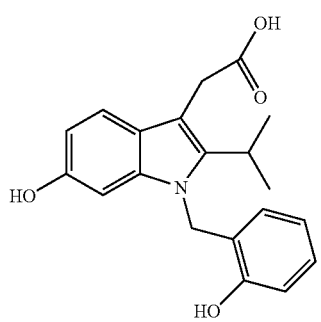
[7-hydroxy-1-(4-hydroxybenzyl)-2-isopropyl-1H-indol-3-yl]acetic acid
[6-hydroxy-1-(2-hydroxybenzyl)-2-isopropyl-1H-indol-3-yl]acetic acid
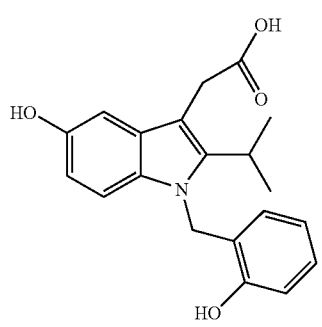
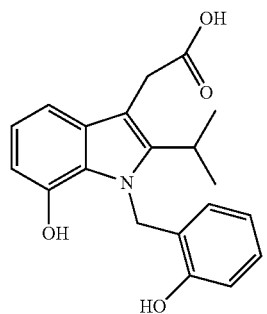

67
[7-hydroxy-1-(2-hydroxybenzyl)-2-isopropyl-1H-indol-3-yl]acetic acid
68
[6-hydroxy-1-(3-hydroxybenzyl)-2-isopropyl-1H-indol-3-yl]acetic acid
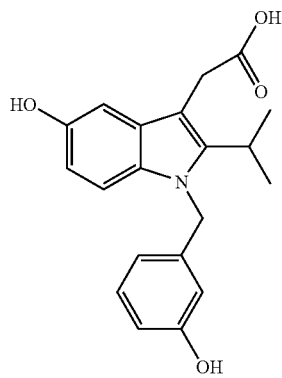
[5-hydroxy-1-(3-hydroxybenzyl)-2-isopropyl-1H-indol-3-yl]acetic acid
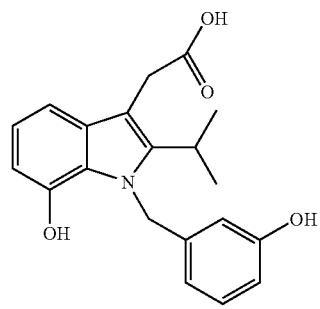
[7-hydroxy-1-(3-hydroxybenzyl)-2-isopropyl-1H-indol-3-yl]acetic acid
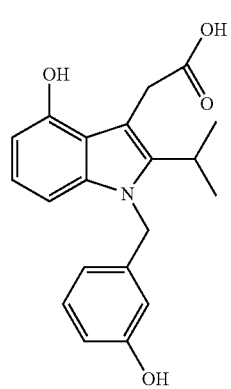
[4-hydroxy-1-(3-hydroxybenzyl)-2-isopropyl-1H-indol-3-yl]acetic acid
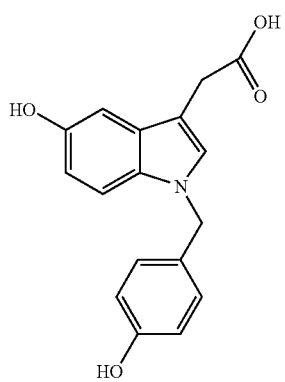
[5-hydroxy-1-(4-hydroxybenzyl)-1H-indol-3-yl]acetic acid
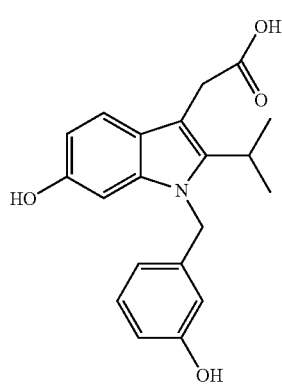
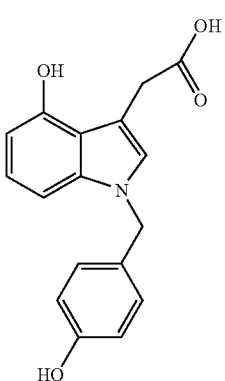

69
[4-hydroxy-1-(4-hydroxybenzyl)-1H-indol-3-yl] acetic acid
70
[5-hydroxy-1-(2-hydroxybenzyl)-1H-indol-3-yl] acetic acid
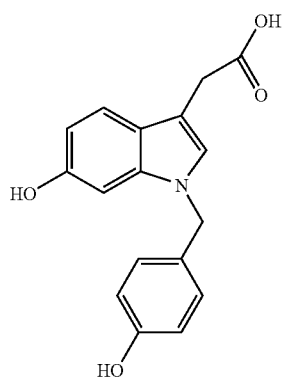
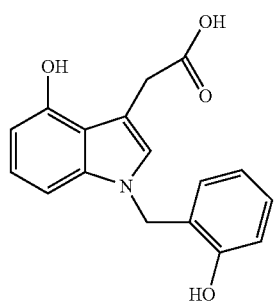
[4-hydroxy-1-(2-hydroxybenzyl)-1H-indol-3-yl] acetic acid
[6-hydroxy-1-(4-hydroxybenzyl)-1H-indol-3-yl] acetic acid
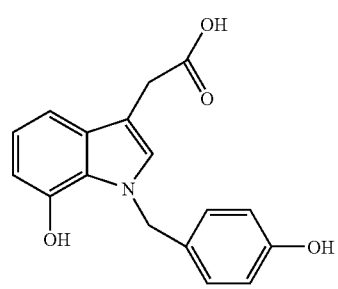
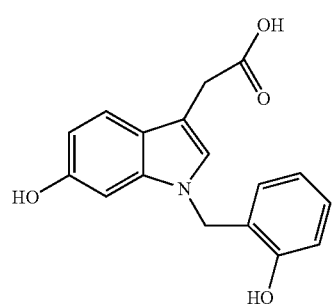
[6-hydroxy-1-(2-hydroxybenzyl)-1H-indol-3-yl] acetic acid
[7-hydroxy-1-(4-hydroxybenzyl)-1H-indol-3-yl] acetic acid
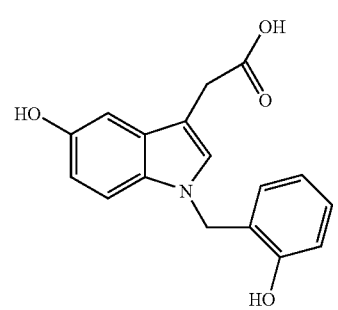
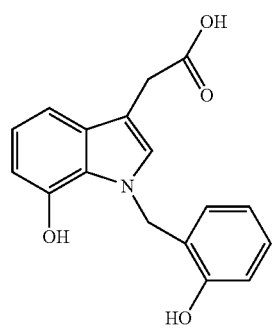

| 71 | 72 |
|---|---|
| [7-hydroxy-1-(2-hydroxybenzyl)-1H-indol-3-yl] acetic acid | [6-hydroxy-1-(3-hydroxybenzyl)-1H-indol-3-yl] acetic acid |
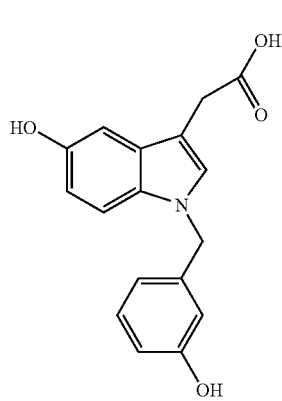
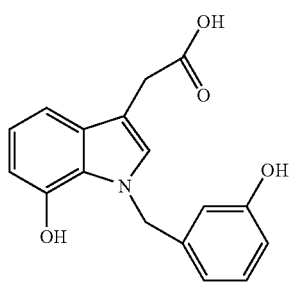
[5-hydroxy-1-(3-hydroxybenzyl)-1H-indol-3-yl] acetic acid
[7-hydroxy-1-(3-hydroxybenzyl)-1H-indol-3-yl] acetic acid
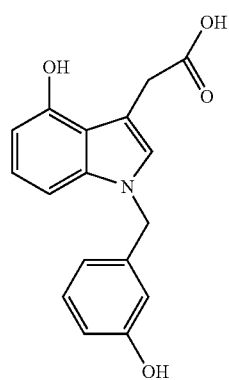
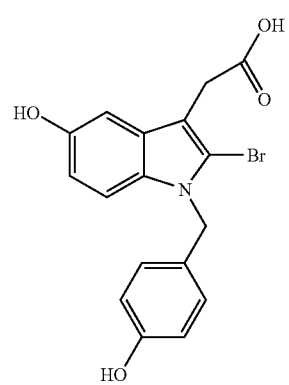
[4-hydroxy-1-(3-hydroxybenzyl)-1H-indol-3-yl] acetic acid
[2-bromo-5-hydroxy-1-(4-hydroxybenzyl)-1H-indol-3-yl]acetic acid
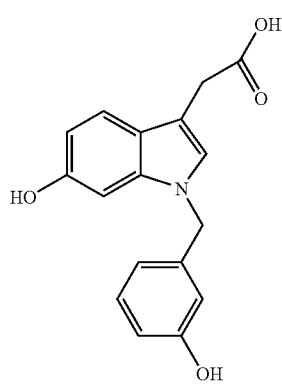
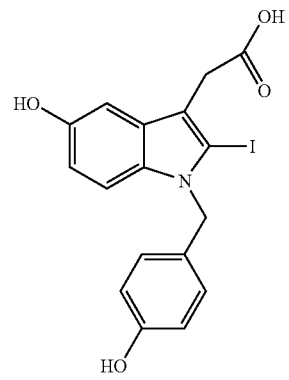

73
[5-hydroxy-1-(4-hydroxybenzyl)-2-iodo-1H-indol-3-yl]acetic acid
74
[2-chloro-4-hydroxy-1-(4-hydroxybenzyl)-1H-indol-3-yl]acetic acid
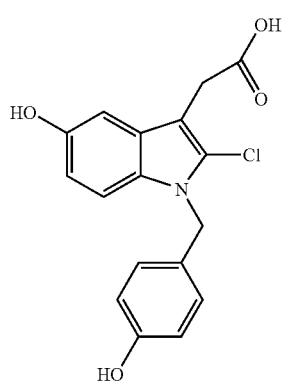
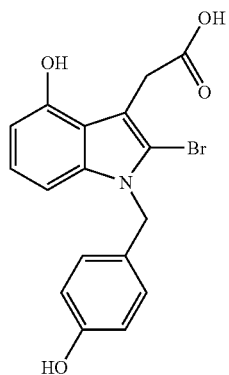
[2-chloro-5-hydroxy-1-(4-hydroxybenzyl)-1H-indol-3-yl]acetic acid
[2-bromo-4-hydroxy-1-(4-hydroxybenzyl)-1H-indol-3-yl]acetic acid
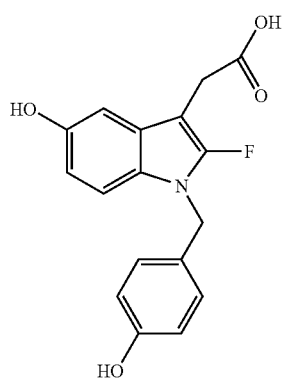
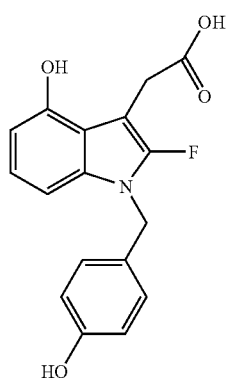
[2-fluoro-5-hydroxy-1-(4-hydroxybenzyl)-1H-indol-3-yl]acetic acid
[2-fluoro-4-hydroxy-1-(4-hydroxybenzyl)-1H-indol-3-yl]acetic acid
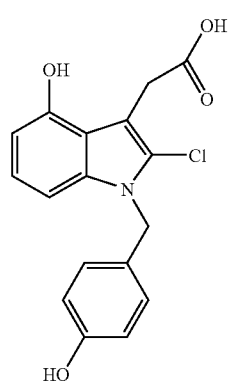
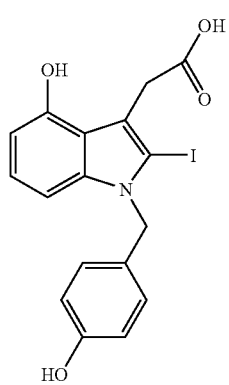

| 75 | 76 |
|---|---|
| [4-hydroxy-1-(4-hydroxybenzyl)-2-iodo-1H-indol-3-yl]acetic acid | [2-fluoro-6-hydroxy-1-(4-hydroxybenzyl)-1H-indol-3-yl]acetic acid |
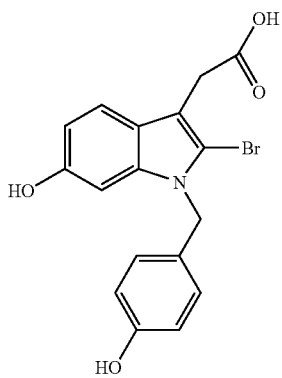
[2-bromo-6-hydroxy-1-(4-hydroxybenzyl)-1H-indol-3-yl]acetic acid
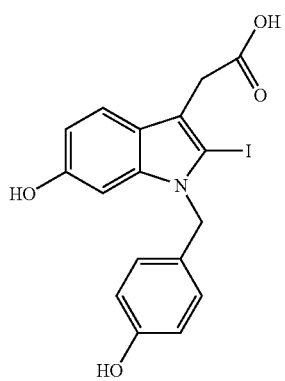
[6-hydroxy-1-(4-hydroxybenzyl)-2-iodo-1H-indol-3-yl]acetic acid
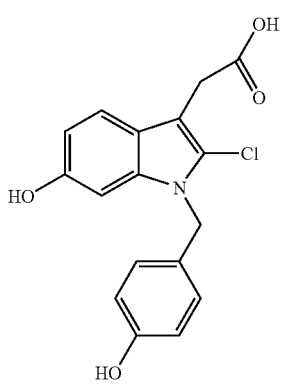
[2-chloro-6-hydroxy-1-(4-hydroxybenzyl)-1H-indol-3-yl]acetic acid
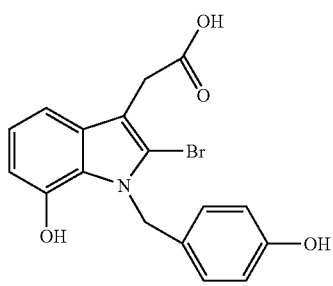
[2-bromo-7-hydroxy-1-(4-hydroxybenzyl)-1H-indol-3-yl]acetic acid
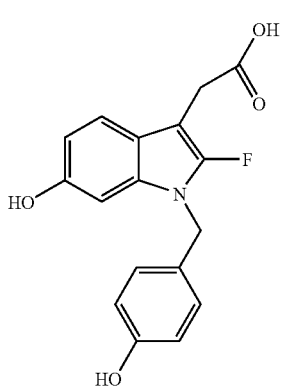
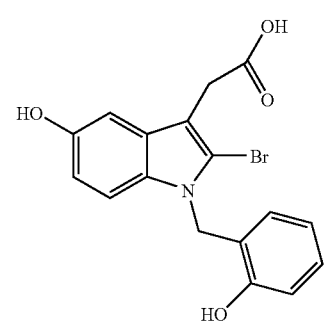

| 77 | 78 |
|---|---|
| [2-bromo-5-hydroxy-1-(2-hydroxybenzyl)-1H-indol-3-yl]acetic acid | [2-fluoro-5-hydroxy-1-(2-hydroxybenzyl)-1H-indol-3-yl]acetic acid |
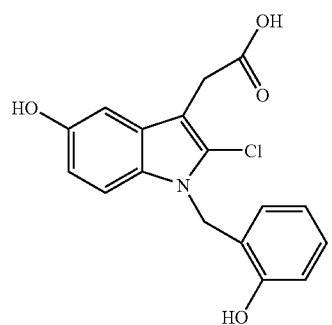
[2-chloro-5-hydroxy-1-(2-hydroxybenzyl)-1H-indol-3-yl]acetic acid
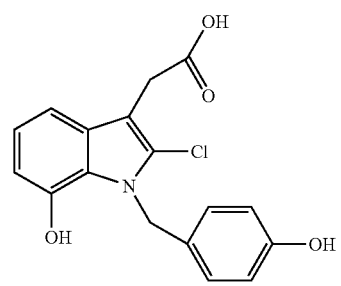
[2-chloro-7-hydroxy-1-(4-hydroxybenzyl)-1H-indol-3-yl]acetic acid
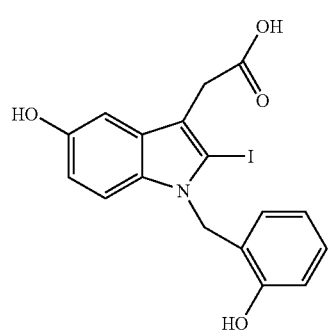
[5-hydroxy-1-(2-hydroxybenzyl)-2-iodo-1H-indol-3-yl]acetic acid
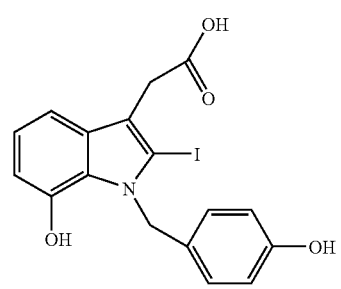
[7-hydroxy-1-(4-hydroxybenzyl)-2-iodo-1H-indol-3-yl]acetic acid
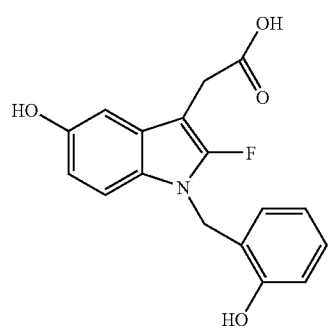
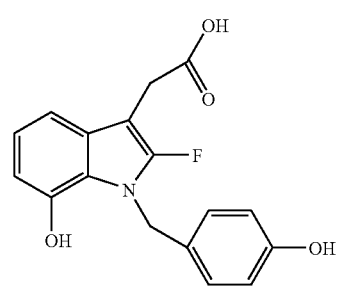

[2-fluoro-7-hydroxy-1-(4-hydroxybenzyl)-1H-indol-3-yl]acetic acid
[4-hydroxy-1-(2-hydroxybenzyl)-2-iodo-1H-indol-3-yl]acetic acid
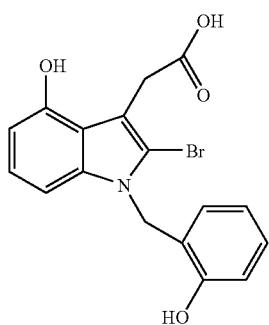
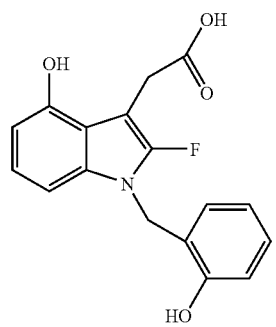
[2-bromo-4-hydroxy-1-(2-hydroxybenzyl)-1H-indol-3-yl]acetic acid
[2-fluoro-4-hydroxy-1-(2-hydroxybenzyl)-1H-indol-3-yl]acetic acid
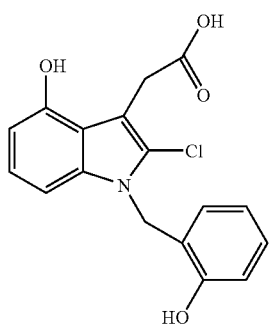
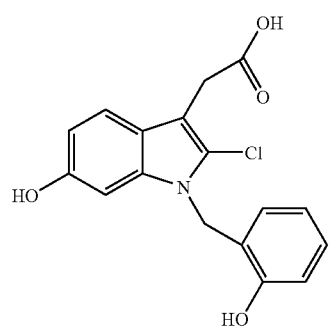
[2-chloro-4-hydroxy-1-(2-hydroxybenzyl)-1H-indol-3-yl]acetic acid
[2-chloro-6-hydroxy-1-(2-hydroxybenzyl)-1H-indol-3-yl]acetic acid
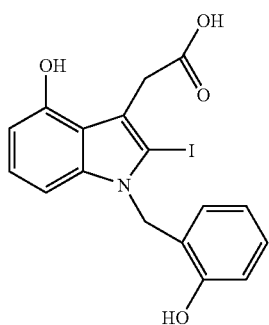
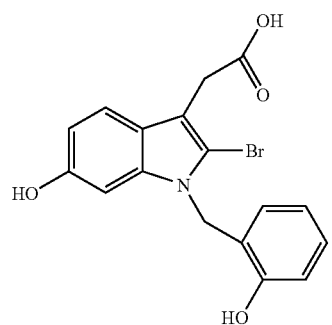

| 81 | 82 |
|---|---|
| [2-bromo-6-hydroxy-1-(2-hydroxybenzyl)-1H-indol-3-yl]acetic acid | [2-bromo-7-hydroxy-1-(2-hydroxybenzyl)-1H-indol-3-yl]acetic acid |
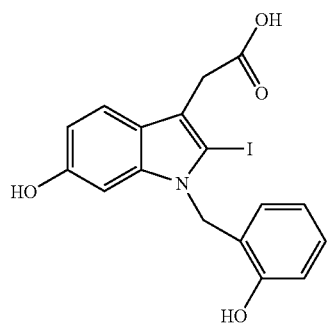
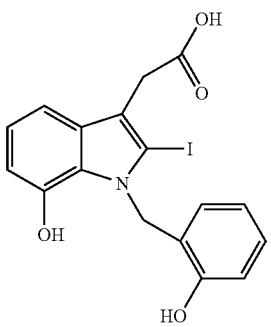
[6-hydroxy-1-(2-hydroxybenzyl)-2-iodo-1H-indol-3-yl]acetic acid
[7-hydroxy-1-(2-hydroxybenzyl)-2-iodo-1H-indol-3-yl]acetic acid
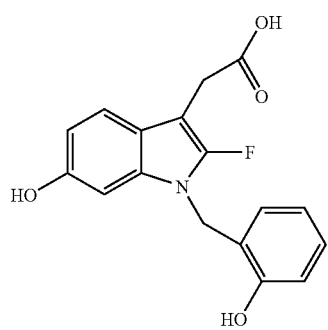
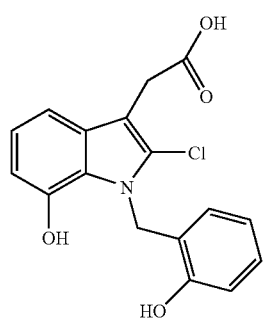
[2-fluoro-6-hydroxy-1-(2-hydroxybenzyl)-1H-indol-3-yl]acetic acid
[2-chloro-7-hydroxy-1-(2-hydroxybenzyl)-1H-indol-3-yl]acetic acid
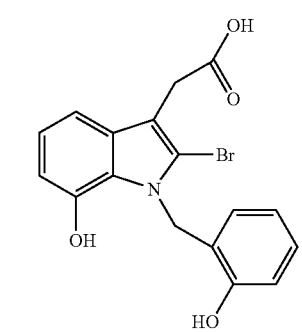
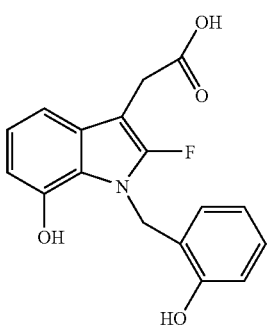

| 83 | 84 |
|---|---|
| [2-fluoro-7-hydroxy-1-(2-hydroxybenzyl)-1H-indol-3-yl]acetic acid | 3-(carboxymethyl)-1-(4-hydroxybenzyl)-2-methyl-1H-indole-6-carboxylic acid |

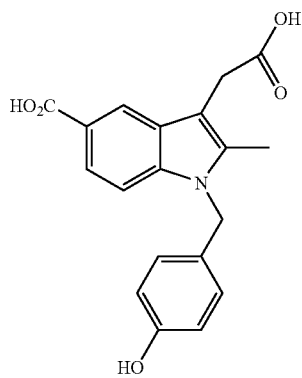

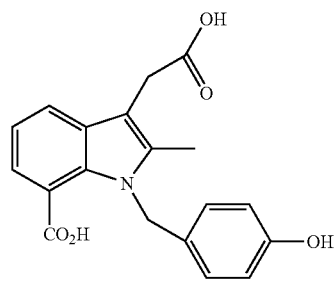

3-(carboxymethyl)-1-(4-hydroxybenzyl)-2-methyl-1H-indole-5-carboxylic acid 3-(carboxymethyl)-1-(4-hydroxybenzyl)-2-methyl-1H-indole-7-carboxylic acid

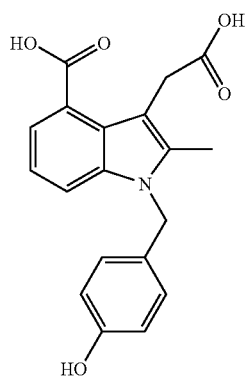

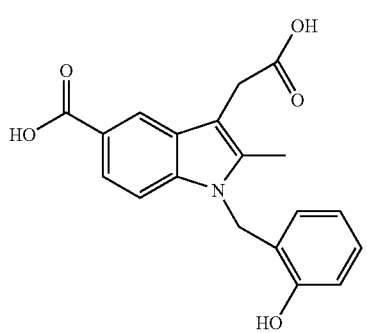

3-(carboxymethyl)-1-(4-hydroxybenzyl)-2-methyl-1H-indole-4-carboxylic acid 3-(carboxymethyl)-1-(2-hydroxybenzyl)-2-methyl-1H-indole-5-carboxylic acid

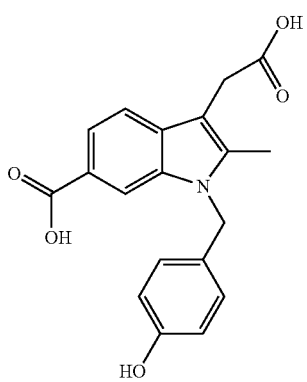

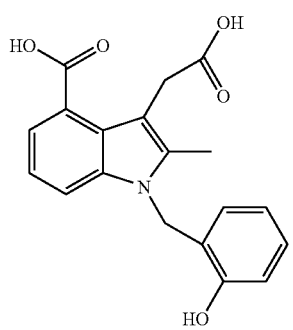

85

86

3-(carboxymethyl)-1-(2-hydroxybenzyl)-2-methyl-
1H-indole-4-carboxylic acid 3-(carboxymethyl)-1-(3-hydroxybenzyl)-2-methyl-
1H-indole-5-carboxylic acid

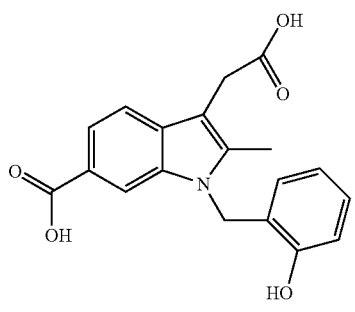

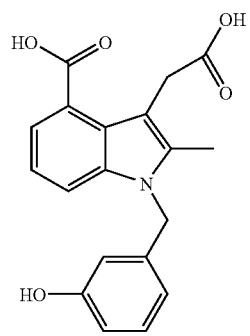

3-(carboxymethyl)-1-(2-hydroxybenzyl)-2-methyl-
1H-indole-6-carboxylic acid 3-(carboxymethyl)-1-(3-hydroxybenzyl)-2-methyl-
1H-indole-4-carboxylic acid

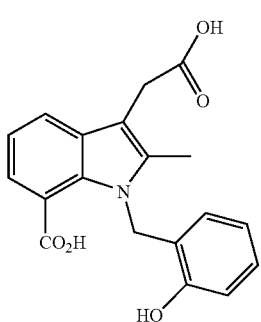

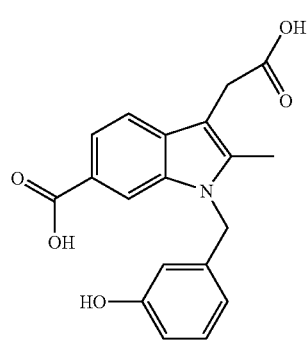

3-(carboxymethyl)-1-(2-hydroxybenzyl)-2-methyl-
1H-indole-7-carboxylic acid 3-(carboxymethyl)-1-(3-hydroxybenzyl)-2-methyl-
1H-indole-6-carboxylic acid

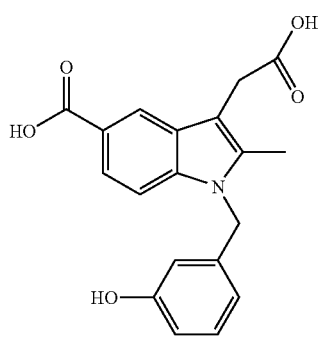

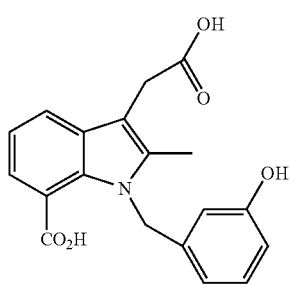

87
3-(carboxymethyl)-1-(3-hydroxybenzyl)-2-methyl-1H-indole-7-carboxylic acid

88
3-(carboxymethyl)-2-ethyl-1-(4-hydroxybenzyl)-1H-indole-6-carboxylic acid

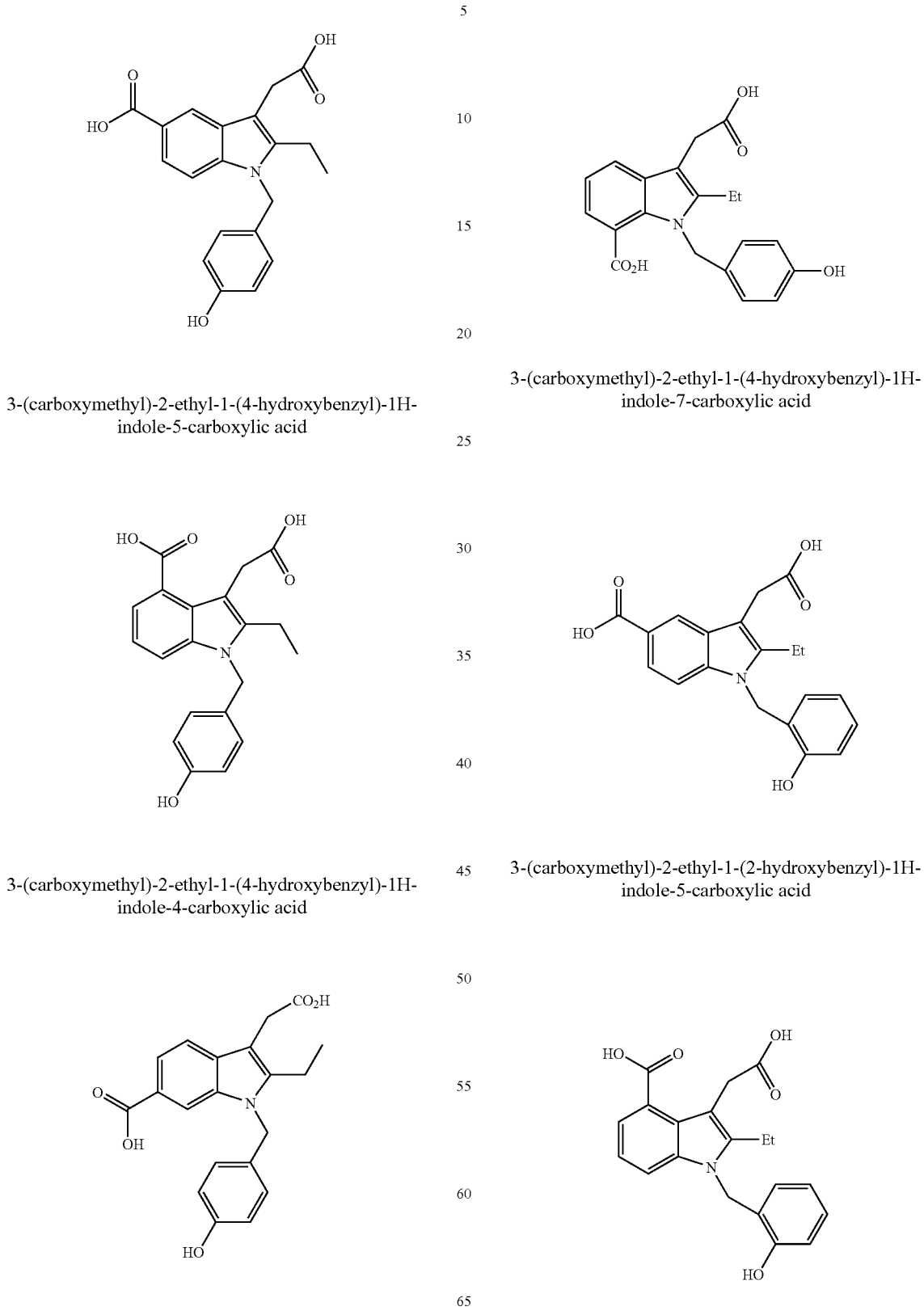

3-(carboxymethyl)-2-ethyl-1-(4-hydroxybenzyl)-1H-indole-5-carboxylic acid 3-(carboxymethyl)-2-ethyl-1-(4-hydroxybenzyl)-1H-indole-7-carboxylic acid 3-(carboxymethyl)-2-ethyl-1-(4-hydroxybenzyl)-1H-indole-4-carboxylic acid 3-(carboxymethyl)-2-ethyl-1-(2-hydroxybenzyl)-1H-indole-5-carboxylic acid

89

3-(carboxymethyl)-2-ethyl-1-(2-hydroxybenzyl)-1H-indole-4-carboxylic acid

90

3-(carboxymethyl)-2-ethyl-1-(3-hydroxybenzyl)-1H-indole-5-carboxylic acid

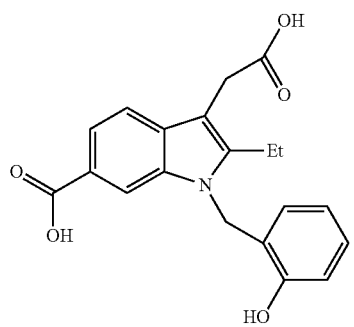

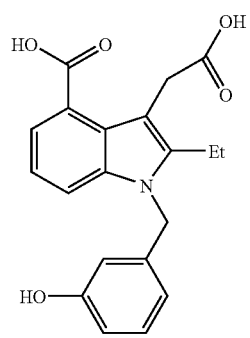

3-(carboxymethyl)-2-ethyl-1-(2-hydroxybenzyl)-1H-indole-6-carboxylic acid 3-(carboxymethyl)-2-ethyl-1-(3-hydroxybenzyl)-1H-indole-4-carboxylic acid

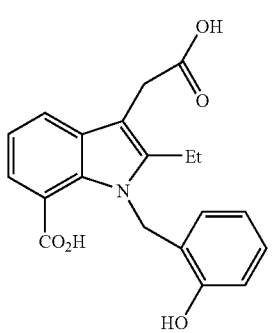

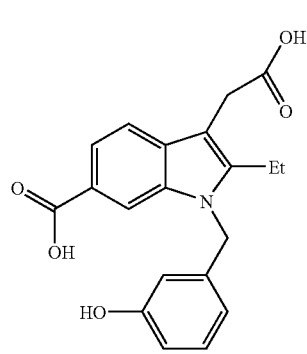

3-(carboxymethyl)-2-ethyl-1-(2-hydroxybenzyl)-1H-indole-7-carboxylic acid 3-(carboxymethyl)-2-ethyl-1-(3-hydroxybenzyl)-1H-indole-6-carboxylic acid

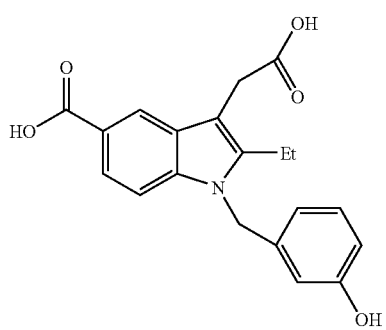

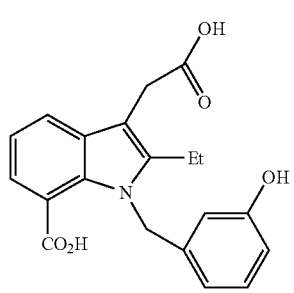

91
3-(carboxymethyl)-2-ethyl-1-(3-hydroxybenzyl)-1H-indole-7-carboxylic acid

92
3-(carboxymethyl)-1-(4-hydroxybenzyl)-2-isopropyl-1H-indole-6-carboxylic acid

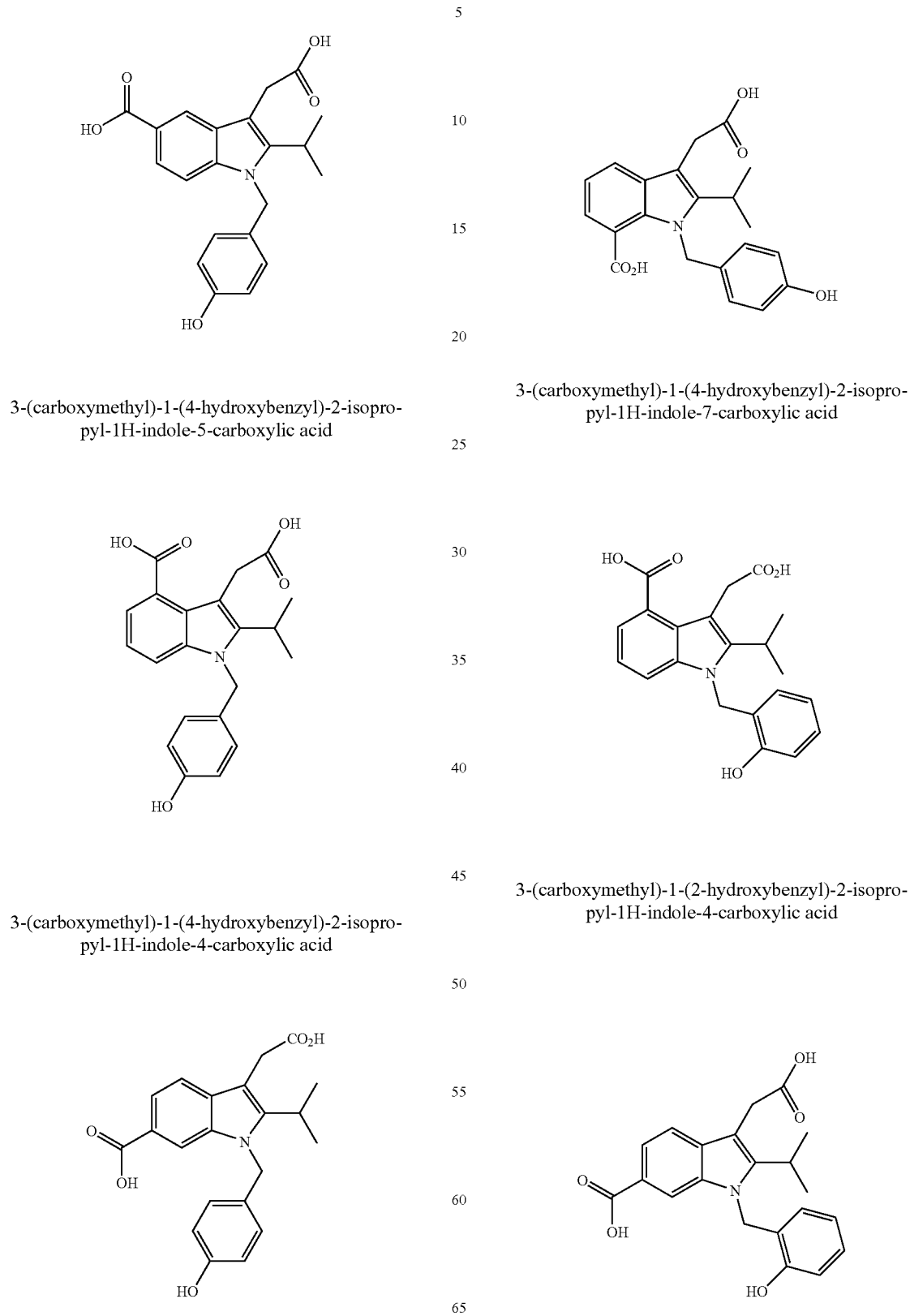

3-(carboxymethyl)-1-(4-hydroxybenzyl)-2-isopropyl-1H-indole-5-carboxylic acid 3-(carboxymethyl)-1-(4-hydroxybenzyl)-2-isopropyl-1H-indole-7-carboxylic acid 3-(carboxymethyl)-1-(4-hydroxybenzyl)-2-isopropyl-1H-indole-4-carboxylic acid 3-(carboxymethyl)-1-(2-hydroxybenzyl)-2-isopropyl-1H-indole-4-carboxylic acid

93

3-(carboxymethyl)-1-(2-hydroxybenzyl)-2-isopropyl-1H-indole-6-carboxylic acid

94

3-(carboxymethyl)-1-(3-hydroxybenzyl)-2-isopropyl-1H-indole-4-carboxylic acid

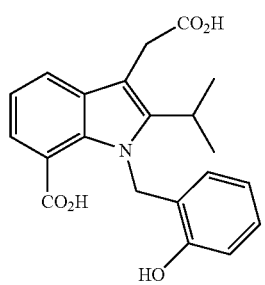

3-(carboxymethyl)-1-(2-hydroxybenzyl)-2-isopropyl-1H-indole-7-carboxylic acid

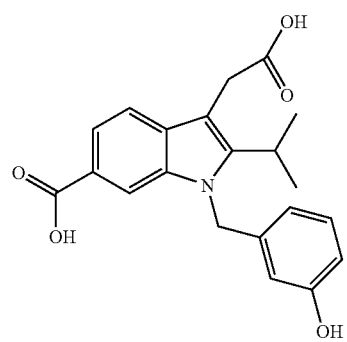

3-(carboxymethyl)-1-(3-hydroxybenzyl)-2-isopropyl-1H-indole-6-carboxylic acid

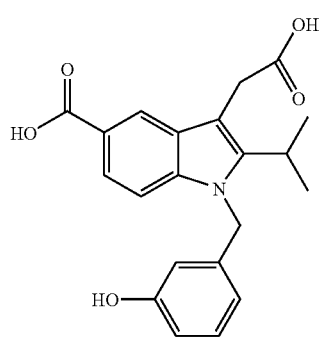

3-(carboxymethyl)-1-(3-hydroxybenzyl)-2-isopropyl-1H-indole-5-carboxylic acid

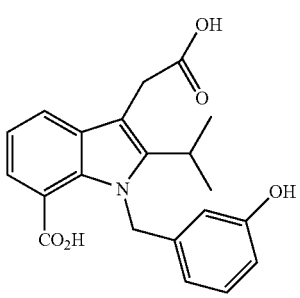

3-(carboxymethyl)-1-(3-hydroxybenzyl)-2-isopropyl-1H-indole-7-carboxylic acid

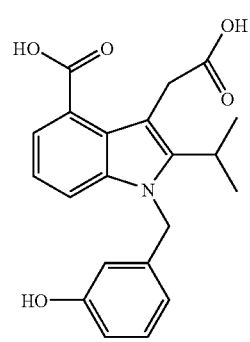

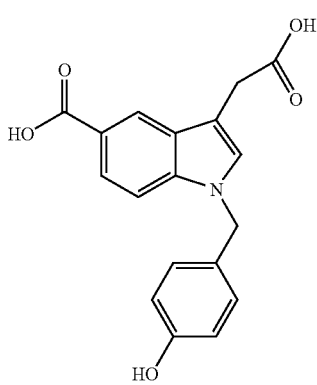

95
3-(carboxymethyl)-1-(4-hydroxybenzyl)-1H-indole-5-carboxylic acid
96
3-(carboxymethyl)-1-(4-hydroxybenzyl)-1H-indole-7-carboxylic acid
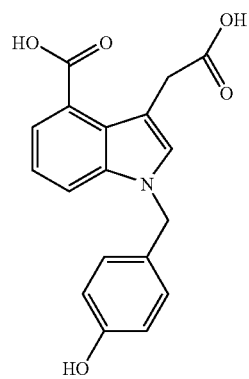
3-(carboxymethyl)-1-(4-hydroxybenzyl)-1H-indole-4-carboxylic acid
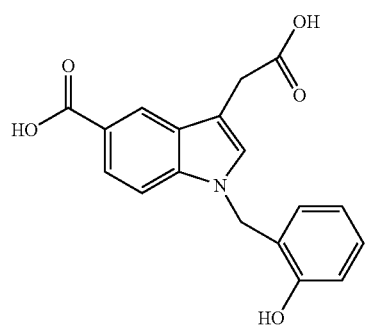
3-(carboxymethyl)-1-(2-hydroxybenzyl)-1H-indole-5-carboxylic acid
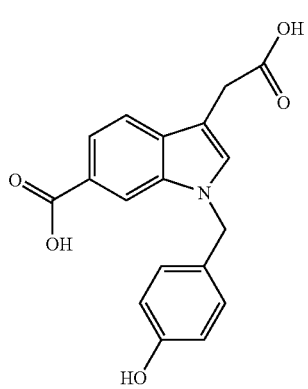
3-(carboxymethyl)-1-(4-hydroxybenzyl)-1H-indole-6-carboxylic acid
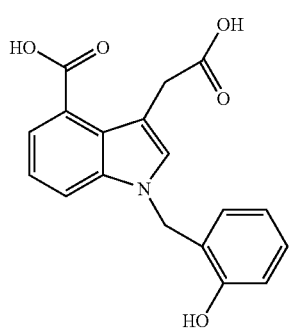
3-(carboxymethyl)-1-(2-hydroxybenzyl)-1H-indole-4-carboxylic acid
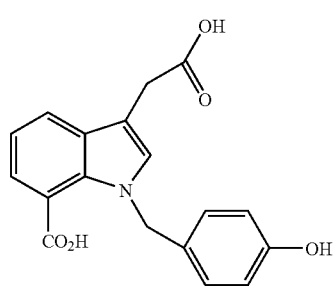
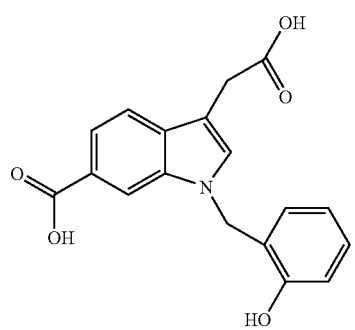

| 97 | 98 |
|---|---|
| 3-(carboxymethyl)-1-(2-hydroxybenzyl)-1H-indole-6-carboxylic acid | 3-(carboxymethyl)-1-(3-hydroxybenzyl)-1H-indole-4-carboxylic acid |
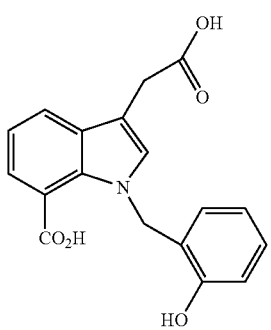
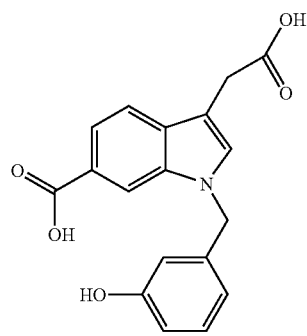
3-(carboxymethyl)-1-(2-hydroxybenzyl)-1H-indole-7-carboxylic acid
3-(carboxymethyl)-1-(3-hydroxybenzyl)-1H-indole-6-carboxylic acid
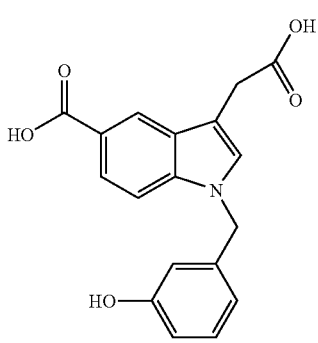
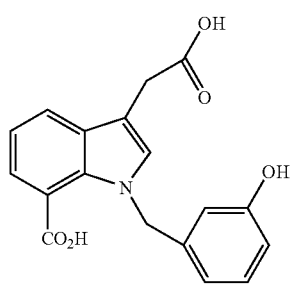
3-(carboxymethyl)-1-(3-hydroxybenzyl)-1H-indole-5-carboxylic acid
3-(carboxymethyl)-1-(3-hydroxybenzyl)-1H-indole-7-carboxylic acid
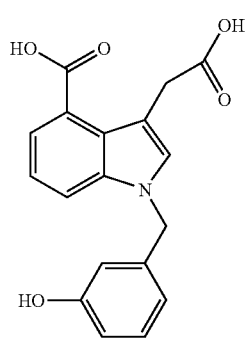
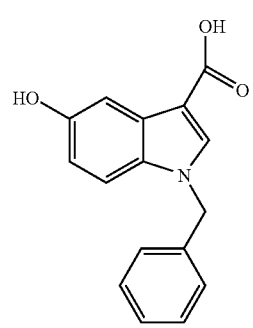

99
1-benzyl-5-hydroxy-1H-indole-3-carboxylic acid
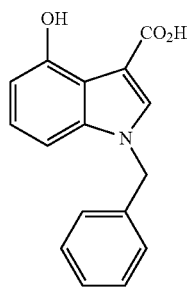
1-benzyl-4-hydroxy-1H-indole-3-carboxylic acid
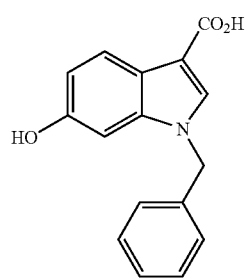
1-benzyl-6-hydroxy-1H-indole-3-carboxylic acid
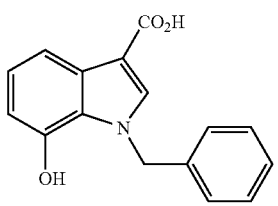
1-benzyl-7-hydroxy-1H-indole-3-carboxylic acid
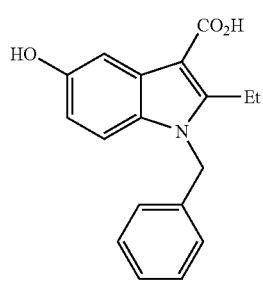
100
1-benzyl-2-ethyl-5-hydroxy-1H-indole-3-carboxylic acid
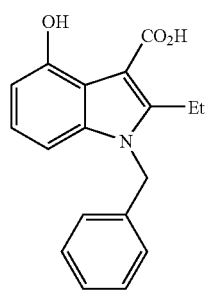
1-benzyl-2-ethyl-4-hydroxy-1H-indole-3-carboxylic acid
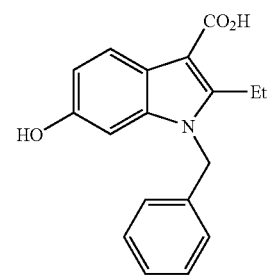
1-benzyl-2-ethyl-6-hydroxy-1H-indole-3-carboxylic acid
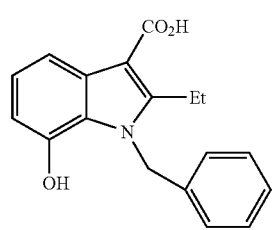

| 101 | 102 |
|---|---|
| 1-benzyl-2-ethyl-7-hydroxy-1H-indole-3-carboxylic acid | 1-benzyl-6-hydroxy-2-isopropyl-1H-indole-3-carboxylic acid |
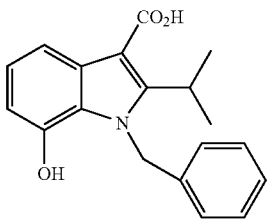
1-benzyl-7-hydroxy-2-isopropyl-1H-indole-3-carboxylic acid
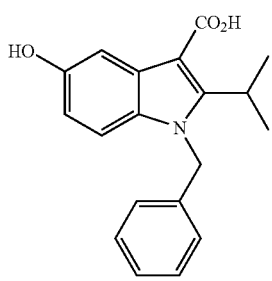
1-benzyl-5-hydroxy-2-isopropyl-1H-indole-3-carboxylic acid
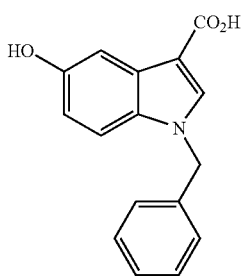
1-benzyl-5-hydroxy-1H-indole-3-carboxylic acid
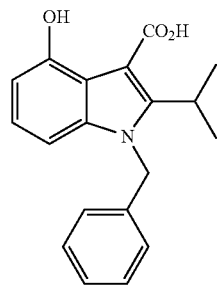
1-benzyl-4-hydroxy-2-isopropyl-1H-indole-3-carboxylic acid
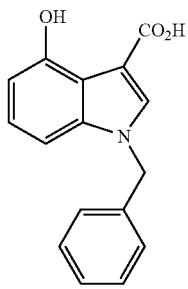
1-benzyl-4-hydroxy-1H-indole-3-carboxylic acid
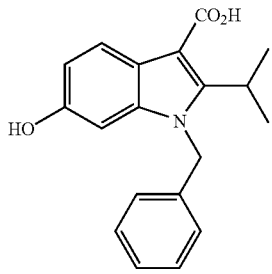
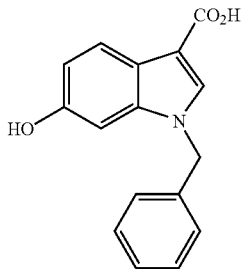

103
1-benzyl-6-hydroxy-1H-indole-3-carboxylic acid
104
2-ethyl-4-hydroxy-1-(4-hydroxybenzyl)-1H-indole-3-carboxylic acid
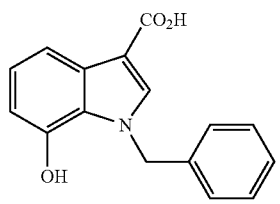
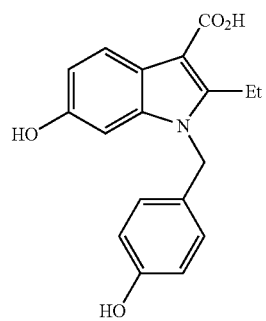
1-benzyl-7-hydroxy-1H-indole-3-carboxylic acid
2-ethyl-6-hydroxy-1-(4-hydroxybenzyl)-1H-indole-3-carboxylic acid
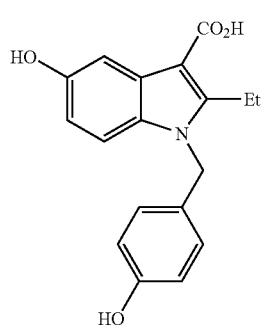
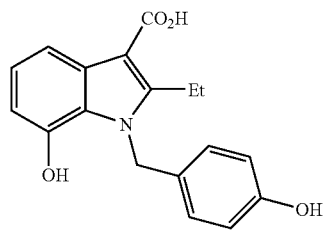
2-ethyl-5-hydroxy-1-(4-hydroxybenzyl)-1H-indole-3-carboxylic acid
2-ethyl-7-hydroxy-1-(4-hydroxybenzyl)-1H-indole-3-carboxylic acid
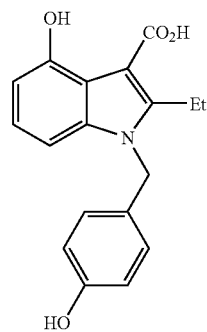
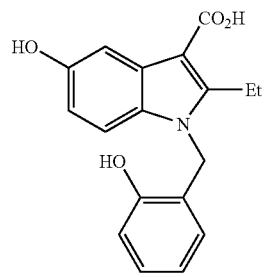

105
2-ethyl-5-hydroxy-1-(2-hydroxybenzyl)-1H-indole-
3-carboxylic acid
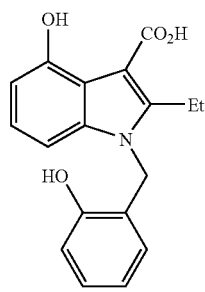
2-ethyl-4-hydroxy-1-(2-hydroxybenzyl)-1H-indole-
3-carboxylic acid
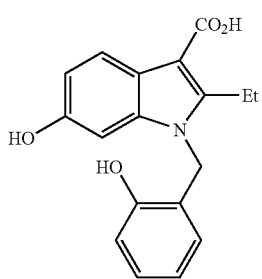
2-ethyl-6-hydroxy-1-(2-hydroxybenzyl)-1H-indole-
3-carboxylic acid
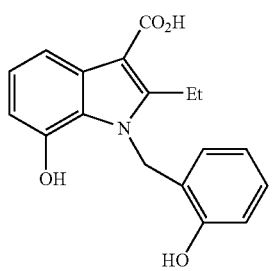
106
2-ethyl-7-hydroxy-1-(2-hydroxybenzyl)-1H-indole-
3-carboxylic acid
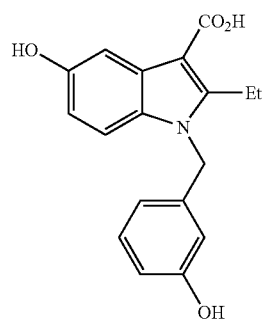
2-ethyl-5-hydroxy-1-(3-hydroxybenzyl)-1H-indole-
3-carboxylic acid
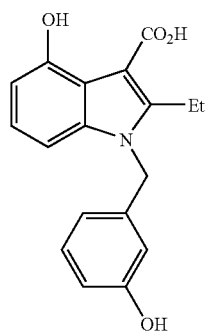
2-ethyl-4-hydroxy-1-(3-hydroxybenzyl)-1H-indole-
3-carboxylic acid
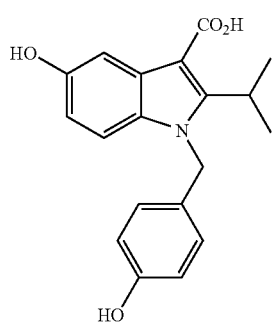

107

5-hydroxy-1-(4-hydroxybenzyl)-2-isopropyl-1H-indole-3-carboxylic acid

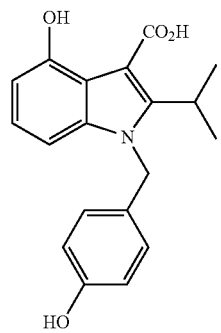

4-hydroxy-1-(4-hydroxybenzyl)-2-isopropyl-1H-indole-3-carboxylic acid

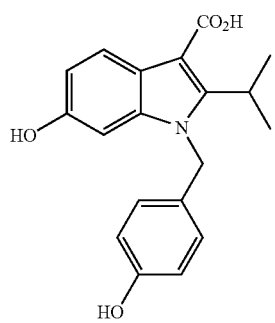

6-hydroxy-1-(4-hydroxybenzyl)-2-isopropyl-1H-indole-3-carboxylic acid

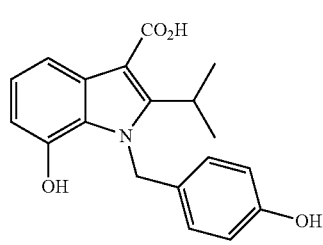

108

7-hydroxy-1-(4-hydroxybenzyl)-2-isopropyl-1H-indole-3-carboxylic acid

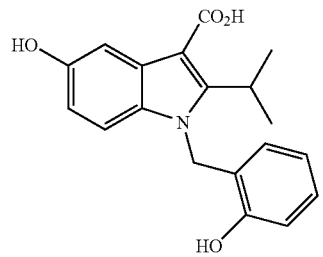

5-hydroxy-1-(2-hydroxybenzyl)-2-isopropyl-1H-indole-3-carboxylic acid

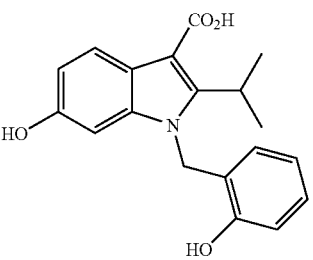

4-hydroxy-1-(2-hydroxybenzyl)-2-isopropyl-1H-indole-3-carboxylic acid 6-hydroxy-1-(2-hydroxybenzyl)-2-isopropyl-1H-indole-3-carboxylic acid

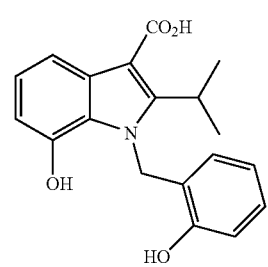

109

7-hydroxy-1-(2-hydroxybenzyl)-2-isopropyl-1H-indole-3-carboxylic acid

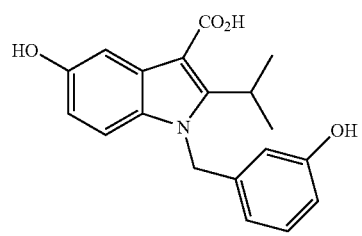

5-hydroxy-1-(3-hydroxybenzyl)-2-isopropyl-1H-indole-3-carboxylic acid

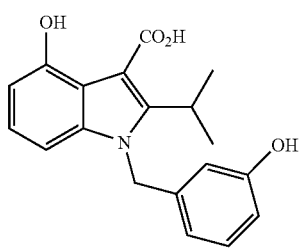

4-hydroxy-1-(3-hydroxybenzyl)-2-isopropyl-1H-indole-3-carboxylic acid

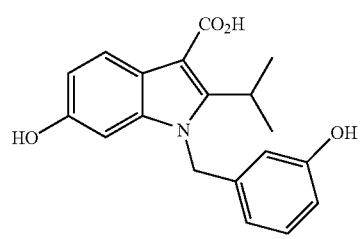

6-hydroxy-1-(3-hydroxybenzyl)-2-isopropyl-1H-indole-3-carboxylic acid

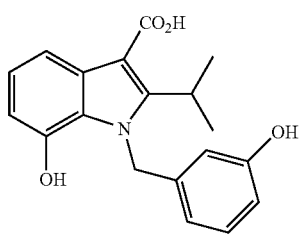

110

7-hydroxy-1-(3-hydroxybenzyl)-2-isopropyl-1H-indole-3-carboxylic acid

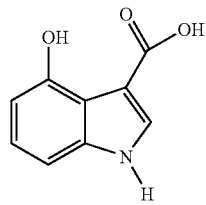

4-hydroxy-1H-indole-3-carboxylic acid

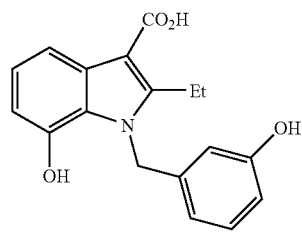

2-ethyl-7-hydroxy-1-(3-hydroxybenzyl)-1H-indole-3-carboxylic acid

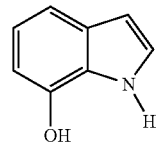

1H-indol-7-ol

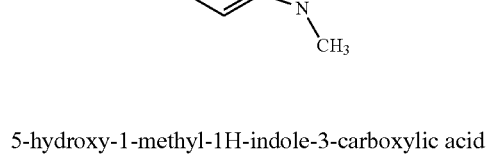

5-hydroxy-1-methyl-1H-indole-3-carboxylic acid

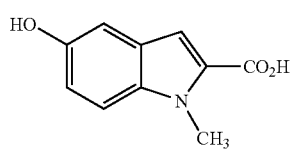

| 111 | 112 |
|---|---|
| 5-hydroxy-1-methyl-1H-indole-2-carboxylic acid | 3,3-difluoroindoline-2-carboxylic acid |
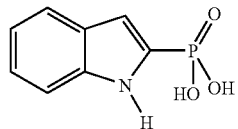
1H-indol-2-ylphosphoric acid
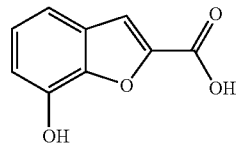
7-hydroxy-1-benzofuran-2-carboxylic acid
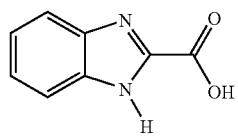
1H-benzimidazole-2-carboxylic acid
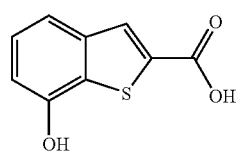
7-hydroxy-1-benzothiophene-2-carboxylic acid
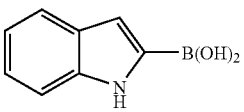
1H-indole-2-boronic acid
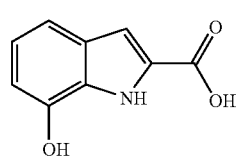
7-hydroxy-1H-indole-2-carboxylic acid
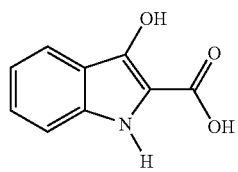
3-hydroxy-1H-indole-2-carboxylic acid
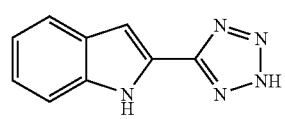
2-(5H-tetrazol-5-yl)-1H-indole
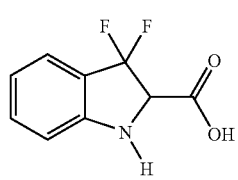
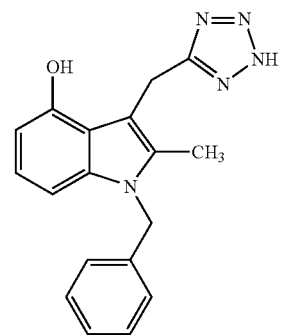

113
1-benzyl-2-methyl-3-(5H-tetrazol-5-ylmethyl)-1H-indol-4-ol
114
4-phenyl-1H-indole-2-carboxylic acid
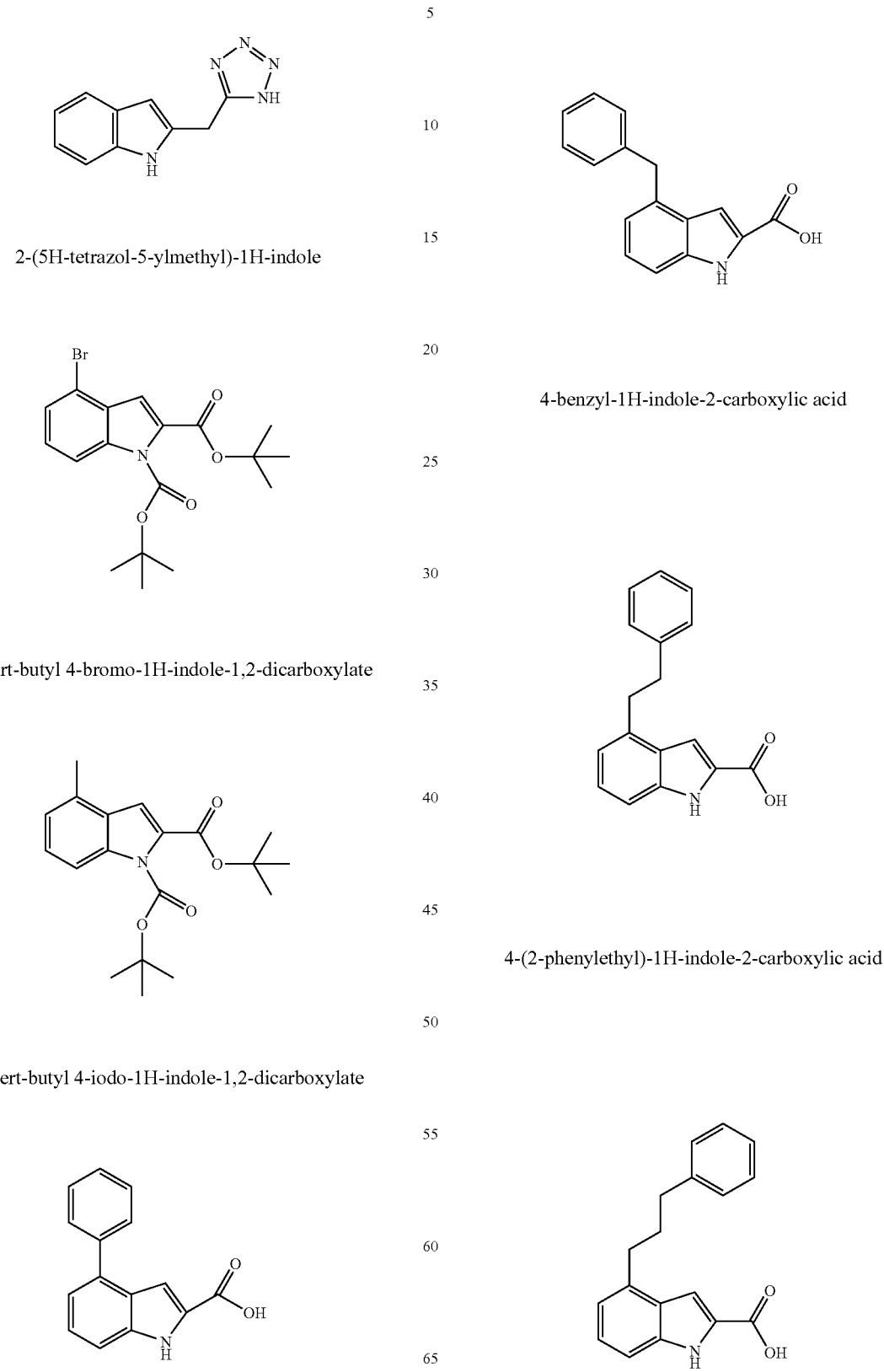
2-(5H-tetrazol-5-ylmethyl)-1H-indole
4-benzyl-1H-indole-2-carboxylic acid
di-tert-butyl 4-bromo-1H-indole-1,2-dicarboxylate
4-(2-phenylethyl)-1H-indole-2-carboxylic acid
di-tert-butyl 4-iodo-1H-indole-1,2-dicarboxylate

115
4-(3-phenylpropyl)-1H-indole-2-carboxylic acid
116
4-[acetyl(phenyl)amino]-1H-indole-2-carboxylic acid
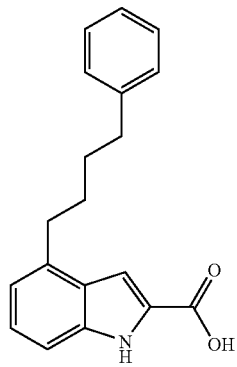
4-(4-phenylbutyl)-1H-indole-2-carboxylic acid
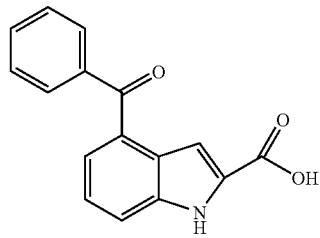
4-benzoyl-1H-indole-2-carboxylic acid
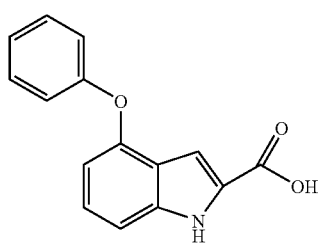
4-phenoxy-1H-indole-2-carboxylic acid
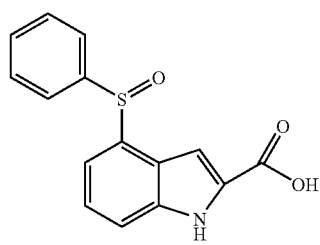
4-(phenylsulfinyl)-1H-indole-2-carboxylic acid
4-(phenylthio)-1H-indole-2-carboxylic acid
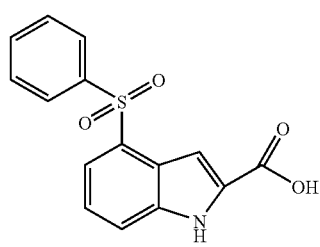
4-(phenylsulfonyl)-1H-indole-2-carboxylic acid
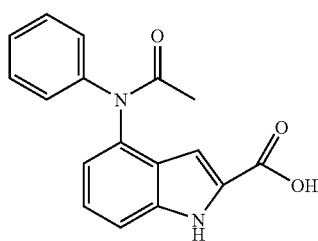
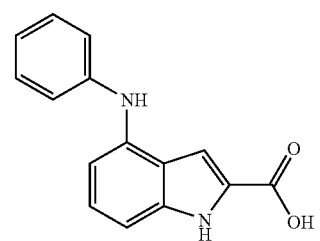

| 117 | 118 |
|---|---|
| 4-anilino-1H-indole-2-carboxylic acid | 4-(4-phenylbutoxy)-1H-indole-2-carboxylic acid |
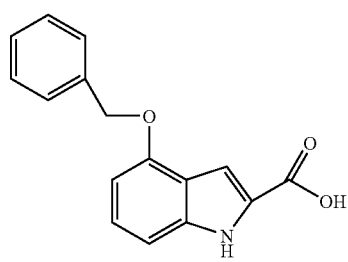 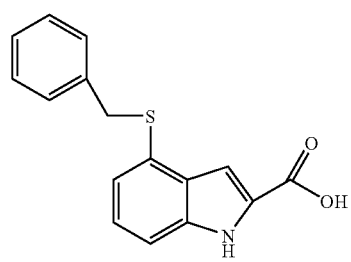
4-(benzyloxy)-1H-indole-2-carboxylic acid    4-(benzylthio)-1H-indole-2-carboxylic acid
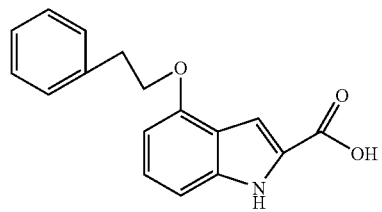 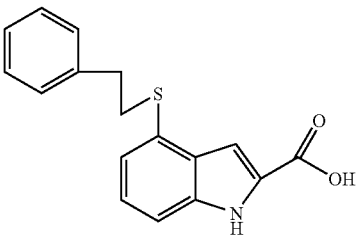
4-(2-phenylethoxy)-1H-indole-2-carboxylic acid    4-[(2-phenylethyl)thio]-1H-indole-2-carboxylic acid
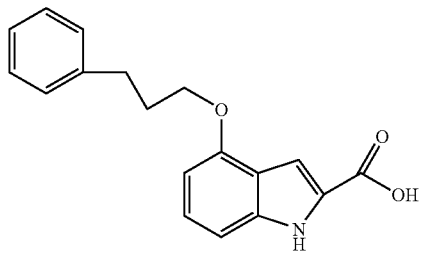 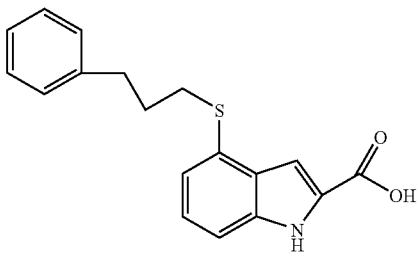
4-(3-phenylpropoxy)-1H-indole-2-carboxylic acid    4-[(3-phenylpropyl)thio]-1H-indole-2-carboxylic acid
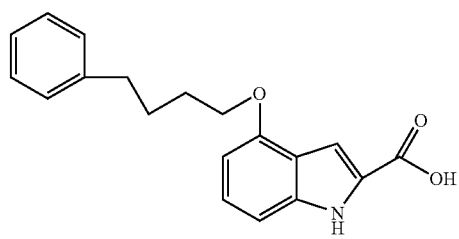 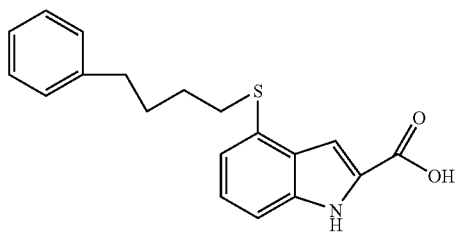

| 119 | 120 |
|---|---|
| 4-[(4-phenylbutyl)thio]-1H-indole-2-carboxylic acid | 4-[(4-phenylbutyl)amino]-1H-indole-2-carboxylic acid |
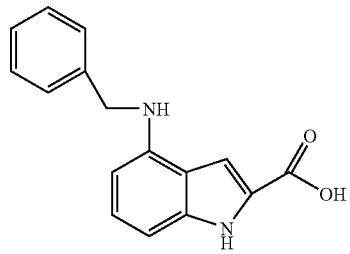
4-(benzylamino)-1H-indole-2-carboxylic acid
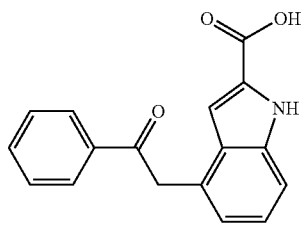
4-(2-oxo-2-phenylethyl)-1H-indole-2-carboxylic acid
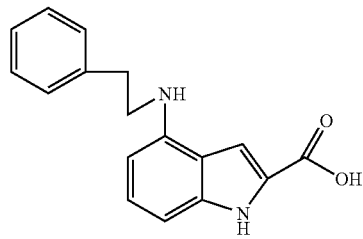
4-[(2-phenylethyl)amino]-1H-indole-2-carboxylic acid
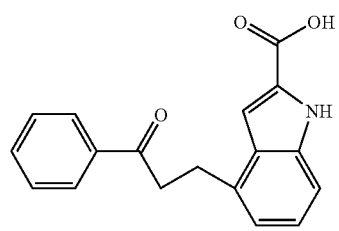
4-(3-oxo-3-phenylpropyl)-1H-indole-2-carboxylic acid
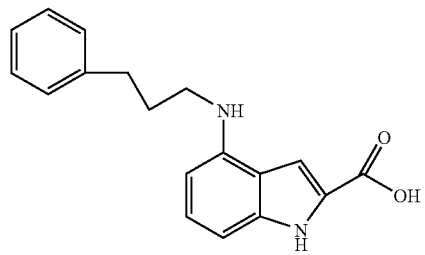
4-[(3-phenylpropyl)amino]-1H-indole-2-carboxylic acid
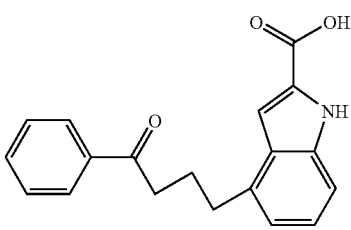
4-(4-oxo-4-phenylbutyl)-1H-indole-2-carboxylic acid
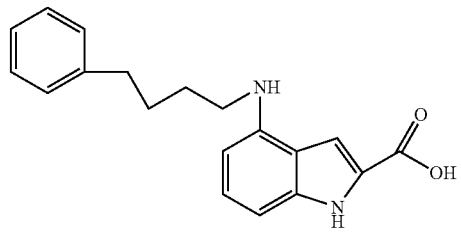
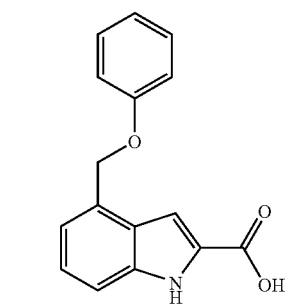

| 121 | 122 |
|---|---|
| 4-(phenoxymethyl)-1H-indole-2-carboxylic acid | 4-{[acetyl(phenyl)amino]methyl}-1H-indole-2-carboxylic acid |
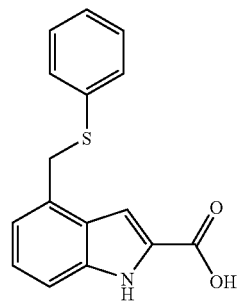
4-[(phenylthio)methyl]-1H-indole-2-carboxylic acid
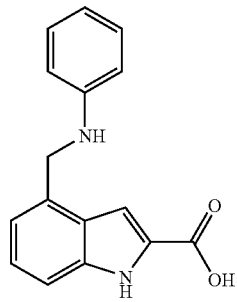
4-(anilinomethyl)-1H-indole-2-carboxylic acid
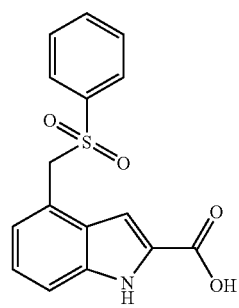
4-[(phenylsulfonyl)methyl]-1H-indole-2-carboxylic acid
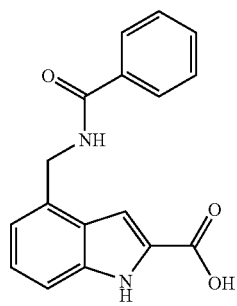
4-[(benzoylamino)methyl]-1H-indole-2-carboxylic acid
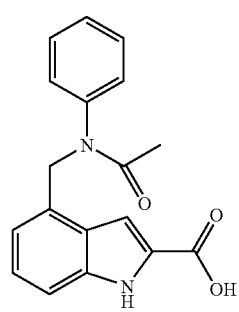
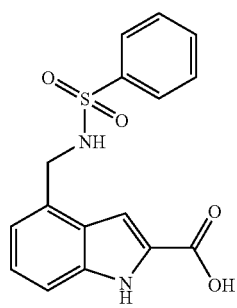

| 123 | 124 |
|---|---|
| 4-{[(phenylsulfonyl)amino]methyl}-1H-indole-2-carboxylic acid | 4-(2-phenoxyethyl)-1H-indole-2-carboxylic acid |
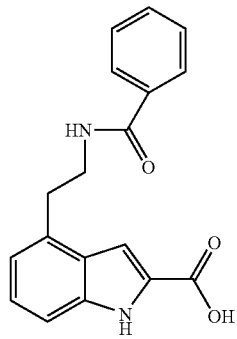
4-[2-(benzoylamino)ethyl]-1H-indole-2-carboxylic acid
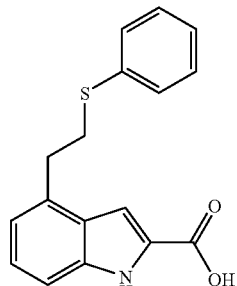
4-[2-(phenylthio)ethyl]-1H-indole-2-carboxylic acid
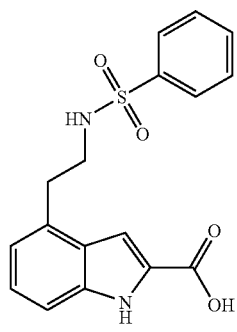
4-{2-[(phenylsulfonyl)amino]ethyl}-1H-indole-2-carboxylic acid
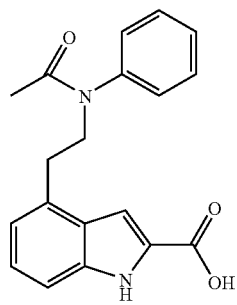
4-{2-[acetyl(phenyl)amino]ethyl}-1H-indole-2-carboxylic acid
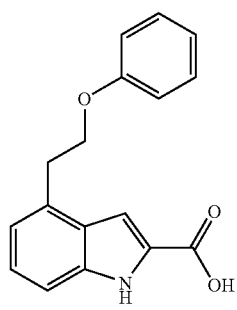
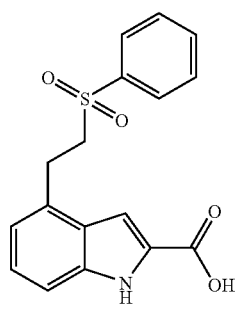

| 125 | 126 |
|---|---|
| 4-[2-9phenylsulfonyl)ethyl]-1H-indole-2-carboxylic acid | 4-(2-phenylethyl)-1,2,3,4-tetrahydroquinolin-8-ol |
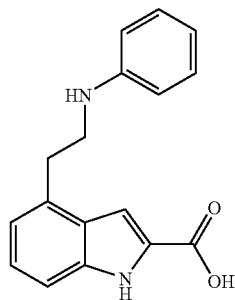
4-(2-anilinoethyl)-1H-indole-2-carboxylic acid
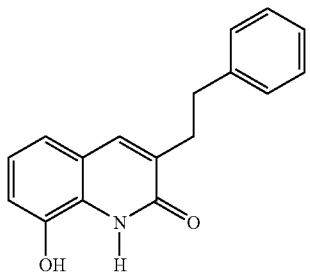
8-hydroxy-3-(2-phenylethyl)quinolin-2(1H)-one
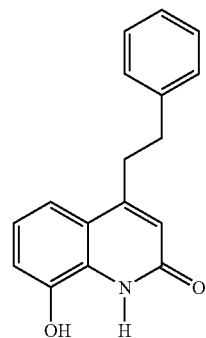
8-hydroxy-4-(2-phenylethyl)quinolin-2(1H)-one
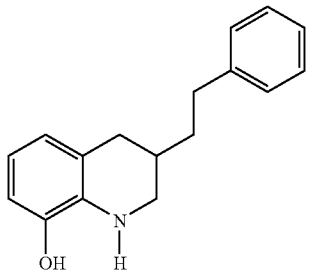
3-(2-phenylethyl)-1,2,3,4-tetrahydroquinolin-8-ol
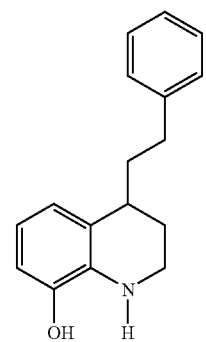
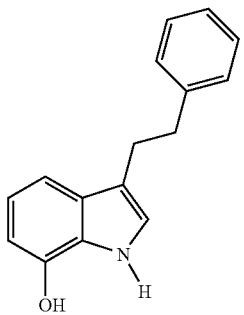

3-(2-phenylethyl)-1H-indol-7-ol

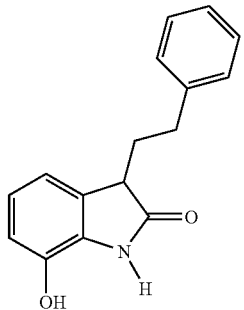

7-hydroxy-3-(2-phenylethyl)-1,3-dihydro-2H-indol-2-one

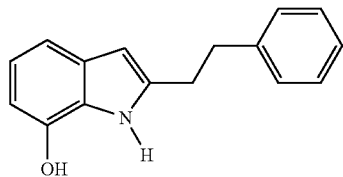

2-(2-phenylethyl)-1H-indol-7-ol

FAAH

Useful compounds (e.g. FAAH inhibitors) include the compounds below.
[1-(2,4-dichlorobenzyl)-5-methoxy-2-methyl-1H-indol-3-yl](3-phenyl-1,2,4-oxadiazol-5-yl)methanone
[1-(2,4-dichlorobenzyl)-5-methoxy-2-methyl-1H-indol-3-yl](3-pyridin-2-yl-1,2,4-oxadiazol-5-yl)methanone
[1-(4-chlorobenzyl)-5-methoxy-2-methyl-1H-indol-3-yl](3-pyridin-2-yl-1,2,4-oxadiazol-5-yl)methanone
[5-methoxy-1-(4-methoxybenzyl)-2-methyl-1H-indol-3-yl](3-pyridin-2-yl-1,2,4-oxadiazol-5-yl)methanone
[1-(4-chlorobenzyl)-5-methoxy-2-methyl-1H-indol-3-yl](5-pyridin-2-yl-1,3,4-oxadiazol-2-yl)methanone
[1-(2,4-dichlorobenzyl)-5-methoxy-2-methyl-1H-indol-3-yl](5-pyridin-2-yl-1,3,4-oxadiazol-2-yl)methanone
[1-(4-chlorobenzyl)-5-methoxy-2-methyl-1H-indol-3-yl][5-(2-furyl)-1,3,4-oxadiazol-2-yl]methanone
[1-(4-chlorobenzyl)-5-methoxy-2-methyl-1H-indol-3-yl]([1,3]oxazolo[4,5-b]pyridin-2-yl)methanone
[1-(4-bromobenzyl)-5-methoxy-2-methyl-1H-indol-3-yl](5-pyridin-2-yl-1,3,4-oxadiazol-2-yl)methanone
[5-methoxy-1-(4-methoxybenzyl)-2-methyl-1H-indol-3-yl](5-pyridin-2-yl-1,3,4-oxadiazol-2-yl)methanone
[1-(4-chlorobenzyl)-5-methoxy-2-methyl-1H-indol-3-yl](5-pyridin-3-yl-1,3,4-oxadiazol-2-yl)methanone
{1-[(5-chloro-2-thienyl)methyl]-5-methoxy-2-methyl-1H-indol-3-yl}(5-pyridin-2-yl-1,3,4-oxadiazol-2-yl)methanone
[1-(4-fluorobenzyl)-5-methoxy-2-methyl-1H-indol-3-yl](5-pyridin-2-yl-1,3,4-oxadiazol-2-yl)methanone
[1-(4-chlorobenzyl)-5-methoxy-2-methyl-1H-indol-3-yl](5-pyridin-4-yl-1,3,4-oxadiazol-2-yl)methanone
{1-[2-(2-chlorophenyl)ethyl]-5-methoxy-2-methyl-1H-indol-3-yl}(5-pyridin-2-yl-1,3,4-oxadiazol-2-yl)methanone
[5-methoxy-2-methyl-1-(4-methylbenzyl)-1H-indol-3-yl](5-pyridin-2-yl-1,3,4-oxadiazol-2-yl)methanone
[1-(4-chlorobenzyl)-5-methoxy-2-methyl-1H-indol-3-yl](5-phenyl-1,3,4-oxadiazol-2-yl)methanone
[1-(3,4-dichlorobenzyl)-5-methoxy-2-methyl-1H-indol-3-yl](5-pyridin-2-yl-1,3,4-oxadiazol-2-yl)methanone
{1-[2-(3-chlorophenyl)ethyl]-5-methoxy-2-methyl-1H-indol-3-yl}(5-pyridin-2-yl-1,3,4-oxadiazol-2-yl)methanone
[1-(4-bromobenzyl)-5-hydroxy-2-methyl-1H-indol-3-yl](5-pyridin-2-yl-1,3,4-oxadiazol-2-yl)methanone
{1-[2-(4-chlorophenyl)ethyl]-5-methoxy-2-methyl-1H-indol-3-yl}(5-pyridin-2-yl-1,3,4-oxadiazol-2-yl)methanone
[1-(3,5-dichlorobenzyl)-5-methoxy-2-methyl-1H-indol-3-yl](5-pyridin-2-yl-1,3,4-oxadiazol-2-yl)methanone
(1-benzyl-5-methoxy-2-methyl-1H-indol-3-yl)(5-pyridin-2-yl-1,3,4-oxadiazol-2-yl)methanone
[1-(2-chlorobenzyl)-5-methoxy-2-methyl-1H-indol-3-yl](5-pyridin-2-yl-1,3,4-oxadiazol-2-yl)methanone
{5-methoxy-2-methyl-1-[4-(trifluoromethyl)benzyl]-1H-indol-3-yl}(5-pyridin-2-yl-1,3,4-oxadiazol-2-yl)methanone
[5-hydroxy-2-methyl-1-(4-methylbenzyl)-1H-indol-3-yl](5-pyridin-2-yl-1,3,4-oxadiazol-2-yl)methanone
[1-(3,4-dichlorobenzyl)-5-hydroxy-2-methyl-1H-indol-3-yl](5-pyridin-2-yl-1,3,4-oxadiazol-2-yl)methanone
[1-(3-chlorobenzyl)-5-methoxy-2-methyl-1H-indol-3-yl](5-pyridin-2-yl-1,3,4-oxadiazol-2-yl)methanone
{5-methoxy-2-methyl-1-[4-(trifluoromethoxy)benzyl]-1H-indol-3-yl}(5-pyridin-2-yl-1,3,4-oxadiazol-2-yl)methanone
[1-(4-chlorobenzyl)-5-methoxy-2-methyl-1H-indol-3-yl](5-pyridin-2-yl-2-thienyl)methanone
[5-chloro-1-(4-chlorobenzyl)-2-methyl-1H-indol-3-yl](5-pyridin-2-yl-1,3,4-oxadiazol-2-yl)methanone
1-[1-(4-chlorobenzyl)-5-methoxy-2-methyl-1H-indol-3-yl]-2,2,2-trifluoroethanone
[5-chloro-1-(4-methoxybenzyl)-2-methyl-1H-indol-3-yl](5-pyridin-2-yl-1,3,4-oxadiazol-2-yl)methanone
[2-chloro-1-(4-chlorobenzyl)-5-methoxy-1H-indol-3-yl](5-pyridin-2-yl-1,3,4-oxadiazol-2-yl)methanone
[2-chloro-1-(4-chlorobenzyl)-5-methoxy-1H-indol-3-yl](3-pyridin-2-yl-1,2,4-oxadiazol-5-yl)methanone
[1-(4-chlorobenzyl)-5-ethoxy-2-methyl-1H-indol-3-yl](5-pyridin-2-yl-1,3,4-oxadiazol-2-yl)methanone
[1-(4-fluorobenzyl)-5-methoxy-2-methyl-1H-indol-3-yl](3-pyridin-2-yl-1,2,4-oxadiazol-5-yl)methanone
[1-(4-chlorobenzyl)-5-ethoxy-2-methyl-1H-indol-3-yl](3-pyridin-2-yl-1,2,4-oxadiazol-5-yl)methanone
[1-(4-chlorobenzyl)-5-methoxy-1H-indol-3-yl](5-pyridin-2-yl-1,3,4-oxadiazol-2-yl)methanone
[1-(4-chlorobenzyl)-5-methoxy-1H-indol-3-yl](3-pyridin-2-yl-1,2,4-oxadiazol-5-yl)methanone
{1-[(2-chloropyridin-4-yl)methyl]-5-methoxy-2-methyl-1H-indol-3-yl}(5-pyridin-2-yl-1,3,4-oxadiazol-2-yl)methanone
[1-(4-chlorobenzyl)-5-methoxy-2-methyl-1H-indol-3-yl](3-pyridin-3-yl-1,2,4-oxadiazol-5-yl)methanone
[1-(4-chlorobenzyl)-7-methoxy-1H-indol-3-yl](5-pyridin-2-yl-1,3,4-oxadiazol-2-yl)methanone
[1-(4-chlorobenzyl)-5-methoxy-2-(trifluoromethyl)-1H-indol-3-yl](3-pyridin-2-yl-1,2,4-oxadiazol-5-yl)methanone
[1-(4-chlorobenzyl)-5-ethoxy-2-(trifluoromethyl)-1H-indol-3-yl](3-pyridin-2-yl-1,2,4-oxadiazol-5-yl)methanone
[1-(4-chlorobenzyl)-5-hydroxy-2-(trifluoromethyl)-1H-indol-3-yl](3-pyridin-2-yl-1,2,4-oxadiazol-5-yl)methanone

[1-(4-chlorobenzyl)-5-methyl-2-(trifluoromethyl)-1H-indol-3-yl](3-pyridin-2-yl-1,2,4-oxadiazol-5-yl)methanone
[5-chloro-1-(4-chlorobenzyl)-2-(trifluoromethyl)-1H-indol-3-yl](3-pyridin-2-yl-1,2,4-oxadiazol-5-yl)methanone
[1-(4-chlorobenzyl)-2-(trifluoromethyl)-1H-indol-3-yl](3-pyridin-2-yl-1,2,4-oxadiazol-5-yl)methanone
[1-(2,4-dichlorobenzyl)-5-methoxy-2-(trifluoromethyl)-1H-indol-3-yl](3-pyridin-2-yl-1,2,4-oxadiazol-5-yl)methanone
[1-(2,4-dichlorobenzyl)-5-ethoxy-2-(trifluoromethyl)-1H-indol-3-yl](3-pyridin-2-yl-1,2,4-oxadiazol-5-yl)methanone
[1-(2,4-dichlorobenzyl)-5-hydroxy-2-(trifluoromethyl)-1H-indol-3-yl](3-pyridin-2-yl-1,2,4-oxadiazol-5-yl)methanone
[1-(2,4-dichlorobenzyl)-5-methyl-2-(trifluoromethyl)-1H-indol-3-yl](3-pyridin-2-yl-1,2,4-oxadiazol-5-yl)methanone
[5-chloro-1-(2,4-dichlorobenzyl)-2-(trifluoromethyl)-1H-indol-3-yl](3-pyridin-2-yl-1,2,4-oxadiazol-5-yl)methanone
[1-(2,4-dichlorobenzyl)-2-(trifluoromethyl)-1H-indol-3-yl](3-pyridin-2-yl-1,2,4-oxadiazol-5-yl)methanone
[1-(4-chlorobenzyl)-5-methoxy-2-(trifluoromethyl)-1H-indol-3-yl](3-pyridin-3-yl-1,2,4-oxadiazol-5-yl)methanone
[1-(4-chlorobenzyl)-5-ethoxy-2-(trifluoromethyl)-1H-indol-3-yl](3-pyridin-3-yl-1,2,4-oxadiazol-5-yl)methanone
[1-(4-chlorobenzyl)-5-hydroxy-2-(trifluoromethyl)-1H-indol-3-yl](3-pyridin-3-yl-1,2,4-oxadiazol-5-yl)methanone
[1-(4-chlorobenzyl)-5-methyl-2-(trifluoromethyl)-1H-indol-3-yl](3-pyridin-3-yl-1,2,4-oxadiazol-5-yl)methanone
[5-chloro-1-(4-chlorobenzyl)-2-(trifluoromethyl)-1H-indol-3-yl](3-pyridin-3-yl-1,2,4-oxadiazol-5-yl)methanone
[1-(4-chlorobenzyl)-2-(trifluoromethyl)-1H-indol-3-yl](3-pyridin-3-yl-1,2,4-oxadiazol-5-yl)methanone
[1-(2,4-dichlorobenzyl)-5-methoxy-2-(trifluoromethyl)-1H-indol-3-yl](3-pyridin-3-yl-1,2,4-oxadiazol-5-yl)methanone
[1-(2,4-dichlorobenzyl)-5-ethoxy-2-(trifluoromethyl)-1H-indol-3-yl](3-pyridin-3-yl-1,2,4-oxadiazol-5-yl)methanone
[1-(2,4-dichlorobenzyl)-5-hydroxy-2-(trifluoromethyl)-1H-indol-3-yl](3-pyridin-3-yl-1,2,4-oxadiazol-5-yl)methanone
[1-(2,4-dichlorobenzyl)-5-methyl-2-(trifluoromethyl)-1H-indol-3-yl](3-pyridin-3-yl-1,2,4-oxadiazol-5-yl)methanone
[5-chloro-1-(2,4-dichlorobenzyl)-2-(trifluoromethyl)-1H-indol-3-yl](3-pyridin-3-yl-1,2,4-oxadiazol-5-yl)methanone
[1-(2,4-dichlorobenzyl)-2-(trifluoromethyl)-1H-indol-3-yl](3-pyridin-3-yl-1,2,4-oxadiazol-5-yl)methanone
[1-(4-chlorobenzyl)-5-methoxy-2-(trifluoromethyl)-1H-indol-3-yl](3-pyridin-4-yl-1,2,4-oxadiazol-5-yl)methanone
[1-(4-chlorobenzyl)-5-ethoxy-2-(trifluoromethyl)-1H-indol-3-yl](3-pyridin-4-yl-1,2,4-oxadiazol-5-yl)methanone
[1-(4-chlorobenzyl)-5-hydroxy-2-(trifluoromethyl)-1H-indol-3-yl](3-pyridin-4-yl-1,2,4-oxadiazol-5-yl)methanone
[1-(4-chlorobenzyl)-5-methyl-2-(trifluoromethyl)-1H-indol-3-yl](3-pyridin-4-yl-1,2,4-oxadiazol-5-yl)methanone
[5-chloro-1-(4-chlorobenzyl)-2-(trifluoromethyl)-1H-indol-3-yl](3-pyridin-4-yl-1,2,4-oxadiazol-5-yl)methanone
[1-(4-chlorobenzyl)-2-(trifluoromethyl)-1H-indol-3-yl](3-pyridin-4-yl-1,2,4-oxadiazol-5-yl)methanone
[1-(2,4-dichlorobenzyl)-5-methoxy-2-(trifluoromethyl)-1H-indol-3-yl](3-pyridin-4-yl-1,2,4-oxadiazol-5-yl)methanone
[1-(2,4-dichlorobenzyl)-5-ethoxy-2-(trifluoromethyl)-1H-indol-3-yl](3-pyridin-4-yl-1,2,4-oxadiazol-5-yl)methanone
[1-(2,4-dichlorobenzyl)-5-hydroxy-2-(trifluoromethyl)-1H-indol-3-yl](3-pyridin-4-yl-1,2,4-oxadiazol-5-yl)methanone
[1-(2,4-dichlorobenzyl)-5-methyl-2-(trifluoromethyl)-1H-indol-3-yl](3-pyridin-4-yl-1,2,4-oxadiazol-5-yl)methanone
[5-chloro-1-(2,4-dichlorobenzyl)-2-(trifluoromethyl)-1H-indol-3-yl](3-pyridin-4-yl-1,2,4-oxadiazol-5-yl)methanone
[1-(2,4-dichlorobenzyl)-2-(trifluoromethyl)-1H-indol-3-yl](3-pyridin-4-yl-1,2,4-oxadiazol-5-yl)methanone
[1-(4-chlorobenzyl)-5-methoxy-2-(trifluoromethyl)-1H-indol-3-yl](3-pyrimidin-4-yl-1,2,4-oxadiazol-5-yl)methanone
[1-(4-chlorobenzyl)-5-ethoxy-2-(trifluoromethyl)-1H-indol-3-yl](3-pyrimidin-4-yl-1,2,4-oxadiazol-5-yl)methanone
[1-(4-chlorobenzyl)-5-hydroxy-2-(trifluoromethyl)-1H-indol-3-yl](3-pyrimidin-4-yl-1,2,4-oxadiazol-5-yl)methanone
[1-(4-chlorobenzyl)-5-methyl-2-(trifluoromethyl)-1H-indol-3-yl](3-pyrimidin-4-yl-1,2,4-oxadiazol-5-yl)methanone
[5-chloro-1-(4-chlorobenzyl)-2-(trifluoromethyl)-1H-indol-3-yl](3-pyrimidin-4-yl-1,2,4-oxadiazol-5-yl)methanone
[1-(4-chlorobenzyl)-2-(trifluoromethyl)-1H-indol-3-yl](3-pyrimidin-4-yl-1,2,4-oxadiazol-5-yl)methanone
[1-(2,4-dichlorobenzyl)-5-methoxy-2-(trifluoromethyl)-1H-indol-3-yl](3-pyrimidin-4-yl-1,2,4-oxadiazol-5-yl)methanone
[1-(2,4-dichlorobenzyl)-5-ethoxy-2-(trifluoromethyl)-1H-indol-3-yl](3-pyrimidin-4-yl-1,2,4-oxadiazol-5-yl)methanone
[1-(2,4-dichlorobenzyl)-5-hydroxy-2-(trifluoromethyl)-1H-indol-3-yl](3-pyrimidin-4-yl-1,2,4-oxadiazol-5-yl)methanone
[1-(2,4-dichlorobenzyl)-5-methyl-2-(trifluoromethyl)-1H-indol-3-yl](3-pyrimidin-4-yl-1,2,4-oxadiazol-5-yl)methanone
[5-chloro-1-(2,4-dichlorobenzyl)-2-(trifluoromethyl)-1H-indol-3-yl](3-pyrimidin-4-yl-1,2,4-oxadiazol-5-yl)methanone
[1-(2,4-dichlorobenzyl)-2-(trifluoromethyl)-1H-indol-3-yl](3-pyrimidin-4-yl-1,2,4-oxadiazol-5-yl)methanone
[1-(4-chlorobenzyl)-5-methoxy-2-(trifluoromethyl)-1H-indol-3-yl](5-phenyl-1,2,4-oxadiazol-3-yl)methanone
[1-(4-chlorobenzyl)-5-ethoxy-2-(trifluoromethyl)-1H-indol-3-yl](5-phenyl-1,2,4-oxadiazol-3-yl)methanone
[1-(4-chlorobenzyl)-5-hydroxy-2-(trifluoromethyl)-1H-indol-3-yl](5-phenyl-1,2,4-oxadiazol-3-yl)methanone
[1-(4-chlorobenzyl)-5-methyl-2-(trifluoromethyl)-1H-indol-3-yl](5-phenyl-1,2,4-oxadiazol-3-yl)methanone
[5-chloro-1-(4-chlorobenzyl)-2-(trifluoromethyl)-1H-indol-3-yl](5-phenyl-1,2,4-oxadiazol-3-yl)methanone
[1-(4-chlorobenzyl)-2-(trifluoromethyl)-1H-indol-3-yl](5-phe [1-(2,4-dichlorobenzyl)-5-methoxy-2-(trifluoromethyl)-1H-indol-3-yl](5-phenyl-1,2,4-oxadiazol-3-yl)methanone
nyl-1,2,4-oxadiazol-3-yl)methanone
[1-(2,4-dichlorobenzyl)-5-ethoxy-2-(trifluoromethyl)-1H-indol-3-yl](5-phenyl-1,2,4-oxadiazol-3-yl)methanone
[1-(2,4-dichlorobenzyl)-5-hydroxy-2-(trifluoromethyl)-1H-indol-3-yl](5-phenyl-1,2,4-oxadiazol-3-yl)methanone
[1-(2,4-dichlorobenzyl)-5-methyl-2-(trifluoromethyl)-1H-indol-3-yl](5-phenyl-1,2,4-oxadiazol-3-yl)methanone

[5-chloro-1-(2,4-dichlorobenzyl)-2-(trifluoromethyl)-1H-indol-3-yl](5-phenyl-1,2,4-oxadiazol-3-yl)methanone
[1-(2,4-dichlorobenzyl)-2-(trifluoromethyl)-1H-indol-3-yl](5-phenyl-1,2,4-oxadiazol-3-yl)methanone
[1-(4-chlorobenzyl)-5-methoxy-2-(trifluoromethyl)-1H-indol-3-yl](5-pyridin-2-yl-1,2,4-oxadiazol-3-yl)methanone
[1-(4-chlorobenzyl)-5-ethoxy-2-(trifluoromethyl)-1H-indol-3-yl](5-pyridin-2-yl-1,2,4-oxadiazol-3-yl)methanone
[1-(4-chlorobenzyl)-5-hydroxy-2-(trifluoromethyl)-1H-indol-3-yl](5-pyridin-2-yl-1,2,4-oxadiazol-3-yl)methanone
[1-(4-chlorobenzyl)-5-methyl-2-(trifluoromethyl)-1H-indol-3-yl](5-pyridin-2-yl-1,2,4-oxadiazol-3-yl)methanone
[5-chloro-1-(4-chlorobenzyl)-2-(trifluoromethyl)-1H-indol-3-yl](5-pyridin-2-yl-1,2,4-oxadiazol-3-yl)methanone
[1-(4-chlorobenzyl)-2-(trifluoromethyl)-1H-indol-3-yl](5-pyridin-2-yl-1,2,4-oxadiazol-3-yl)methanone
[1-(2,4-dichlorobenzyl)-5-methoxy-2-(trifluoromethyl)-1H-indol-3-yl](5-pyridin-2-yl-1,2,4-oxadiazol-3-yl)methanone
[1-(2,4-dichlorobenzyl)-5-ethoxy-2-(trifluoromethyl)-1H-indol-3-yl](5-pyridin-2-yl-1,2,4-oxadiazol-3-yl)methanone
[1-(2,4-dichlorobenzyl)-5-hydroxy-2-(trifluoromethyl)-1H-indol-3-yl](5-pyridin-2-yl-1,2,4-oxadiazol-3-yl)methanone
[1-(2,4-dichlorobenzyl)-5-methyl-2-(trifluoromethyl)-1H-indol-3-yl](5-pyridin-2-yl-1,2,4-oxadiazol-3-yl)methanone
[5-chloro-1-(2,4-dichlorobenzyl)-2-(trifluoromethyl)-1H-indol-3-yl](5-pyridin-2-yl-1,2,4-oxadiazol-3-yl)methanone
[1-(2-4-dichlorobenzyl)-2-(trifluoromethyl)-1H-indol-3-yl](5-pyridin-2-yl-1,2,4-oxadiazol-3-yl)methanone
[1-(4-chlorobenzyl)-5-methoxy-2-(trifluoromethyl)-1H-indol-3-yl](5-pyridin-3-yl-1,2,4-oxadiazol-3-yl)methanone
[1-(4-chlorobenzyl)-5-ethoxy-2-(trifluoromethyl)-1H-indol-3-yl](5-pyridin-3-yl-1,2,4-oxadiazol-3-yl)methanone
[1-(4-chlorobenzyl)-5-hydroxy-2-(trifluoromethyl)-1H-indol-3-yl](5-pyridin-3-yl-1,2,4-oxadiazol-3-yl)methanone
[1-(4-chlorobenzyl)-5-methyl-2-(trifluoromethyl)-1H-indol-3-yl](5-pyridin-3-yl-1,2,4-oxadiazol-3-yl)methanone
[5-chloro-1-(4-chlorobenzyl)-2-(trifluoromethyl)-1H-indol-3-yl](5-pyridin-3-yl-1,2,4-oxadiazol-3-yl)methanone
[1-(4-chlorobenzyl)-2-(trifluoromethyl)-1H-indol-3-yl](5-pyridin-3-yl-1,2,4-oxadiazol-3-yl)methanone
[1-(2,4-dichlorobenzyl)-5-methoxy-2-(trifluoromethyl)-1H-indol-3-yl](5-pyridin-3-yl-1,2,4-oxadiazol-3-yl)methanone
[1-(2,4-dichlorobenzyl)-5-ethoxy-2-(trifluoromethyl)-1H-indol-3-yl](5-pyridin-3-yl-1,2,4-oxadiazol-3-yl)methanone
[1-(2,4-dichlorobenzyl)-5-hydroxy-2-(trifluoromethyl)-1H-indol-3-yl](5-pyridin-3-yl-1,2,4-oxadiazol-3-yl)methanone
[1-(2,4-dichlorobenzyl)-5-methyl-2-(trifluoromethyl)-1H-indol-3-yl](5-pyridin-3-yl-1,2,4-oxadiazol-3-yl)methanone
[5-chloro-1-(2,4-dichlorobenzyl)-2-(trifluoromethyl)-1H-indol-3-yl](5-pyridin-3-yl-1,2,4-oxadiazol-3-yl)methanone
[1-(2,4-dichlorobenzyl)-2-(trifluoromethyl)-1H-indol-3-yl](5-pyridin-3-yl-1,2,4-oxadiazol-3-yl)methanone
[1-(4-chlorobenzyl)-5-methoxy-2-(trifluoromethyl)-1H-indol-3-yl](5-pyridin-4-yl-1,2,4-oxadiazol-3-yl)methanone
[1-(4-chlorobenzyl)-5-ethoxy-2-(trifluoromethyl)-1H-indol-3-yl](5-pyridin-4-yl-1,2,4-oxadiazol-3-yl)methanone
[1-(4-chlorobenzyl)-5-hydroxy-2-(trifluoromethyl)-1H-indol-3-yl](5-pyridin-4-yl-1,2,4-oxadiazol-3-yl)methanone
[1-(4-chlorobenzyl)-5-methyl-2-(trifluoromethyl)-1H-indol-3-yl](5-pyridin-4-yl-1,2,4-oxadiazol-3-yl)methanone
[5-chloro-1-(4-chlorobenzyl)-2-(trifluoromethyl)-1H-indol-3-yl](5-pyridin-4-yl-1,2,4-oxadiazol-3-yl)methanone
[1-(4-chlorobenzyl)-2-(trifluoromethyl)-1H-indol-3-yl](5-pyridin-4-yl-1,2,4-oxadiazol-3-yl)methanone
[1-(2,4-dichlorobenzyl)-5-methoxy-2-(trifluoromethyl)-1H-indol-3-yl](5-pyridin-4-yl-1,2,4-oxadiazol-3-yl)methanone
[1-(2,4-dichlorobenzyl)-5-ethoxy-2-(trifluoromethyl)-1H-indol-3-yl](5-pyridin-4-yl-1,2,4-oxadiazol-3-yl)methanone
[1-(2,4-dichlorobenzyl)-5-hydroxy-2-(trifluoromethyl)-1H-indol-3-yl](5-pyridin-4-yl-1,2,4-oxadiazol-3-yl)methanone
[1-(2,4-dichlorobenzyl)-5-methyl-2-(trifluoromethyl)-1H-indol-3-yl](5-pyridin-4-yl-1,2,4-oxadiazol-3-yl)methanone
[5-chloro-1-(2,4-dichlorobenzyl)-2-(trifluoromethyl)-1H-indol-3-yl](5-pyridin-4-yl-1,2,4-oxadiazol-3-yl)methanone
[1-(2,4-dichlorobenzyl)-2-(trifluoromethyl)-1H-indol-3-yl](5-pyridin-4-yl-1,2,4-oxadiazol-3-yl)methanone
[1-(4-chlorobenzyl)-5-methoxy-2-(trifluoromethyl)-1H-indol-3-yl](5-pyrimidin-4-yl-1,2,4-oxadiazol-3-yl)methanone
[1-(4-chlorobenzyl)-5-ethoxy-2-(trifluoromethyl)-1H-indol-3-yl](5-pyrimidin-4-yl-1,2,4-oxadiazol-3-yl)methanone
[1-(4-chlorobenzyl)-5-hydroxy-2-(trifluoromethyl)-1H-indol-3-yl](5-pyrimidin-4-yl-1,2,4-oxadiazol-3-yl)methanone
[1-(4-chlorobenzyl)-5-methyl-2-(trifluoromethyl)-1H-indol-3-yl](5-pyrimidin-4-yl-1,2,4-oxadiazol-3-yl)methanone
[5-chloro-1-(4-chlorobenzyl)-2-(trifluoromethyl)-1H-indol-3-yl](5-pyrimidin-4-yl-1,2,4-oxadiazol-3-yl)methanone
[1-(4-chlorobenzyl)-2-(trifluoromethyl)-1H-indol-3-yl](5-pyrimidin-4-yl-1,2,4-oxadiazol-3-yl)methanone
[1-(2,4-dichlorobenzyl)-5-methoxy-2-(trifluoromethyl)-1H-indol-3-yl](5-pyrimidin-4-yl-1,2,4-oxadiazol-3-yl)methanone
[1-(2,4-dichlorobenzyl)-5-ethoxy-2-(trifluoromethyl)-1H-indol-3-yl](5-pyrimidin-4-yl-1,2,4-oxadiazol-3-yl)methanone
[1-(2,4-dichlorobenzyl)-5-hydroxy-2-(trifluoromethyl)-1H-indol-3-yl](5-pyrimidin-4-yl-1,2,4-oxadiazol-3-yl)methanone
[1-(2,4-dichlorobenzyl)-5-methyl-2-(trifluoromethyl)-1H-indol-3-yl](5-pyrimidin-4-yl-1,2,4-oxadiazol-3-yl)methanone
[5-chloro-1-(2,4-dichlorobenzyl)-2-(trifluoromethyl)-1H-indol-3-yl](5-pyrimidin-4-yl-1,2,4-oxadiazol-3-yl)methanone
[1-(2,4-dichlorobenzyl)-2-(trifluoromethyl)-1H-indol-3-yl](5-pyrimidin-4-yl-1,2,4-oxadiazol-3-yl)methanone
[1-(4-chlorobenzyl)-5-methoxy-2-(trifluoromethyl)-1H-indol-3-yl](5-phenyl-1,3,4-oxadiazol-2-yl)methanone
[1-(4-chlorobenzyl)-5-ethoxy-2-(trifluoromethyl)-1H-indol-3-yl](5-phenyl-1,3,4-oxadiazol-2-yl)methanone
[1-(4-chlorobenzyl)-5-hydroxy-2-(trifluoromethyl)-1H-indol-3-yl](5-phenyl-1,3,4-oxadiazol-2-yl)methanone
[1-(4-chlorobenzyl)-5-methyl-2-(trifluoromethyl)-1H-indol-3-yl](5-phenyl-1,3,4-oxadiazol-2-yl)methanone
[5-chloro-1-(4-chlorobenzyl)-2-(trifluoromethyl)-1H-indol-3-yl](5-phenyl-1,3,4-oxadiazol-2-yl)methanone

[1-(4-chlorobenzyl)-2-(trifluoromethyl)-1H-indol-3-yl](5-phenyl-1,3,4-oxadiazol-2-yl)methanone
[1-(2,4-dichlorobenzyl)-5-methoxy-2-(trifluoromethyl)-1H-indol-3-yl](5-phenyl-1,3,4-oxadiazol-2-yl)methanone
[1-(2,4-dichlorobenzyl)-5-ethoxy-2-(trifluoromethyl)-1H-indol-3-yl](5-phenyl-1,3,4-oxadiazol-2-yl)methanone
[1-(2,4-dichlorobenzyl)-5-hydroxy-2-(trifluoromethyl)-1H-indol-3-yl](5-phenyl-1,3,4-oxadiazol-2-yl)methanone
[1-(2,4-dichlorobenzyl)-5-methyl-2-(trifluoromethyl)-1H-indol-3-yl](5-phenyl-1,3,4-oxadiazol-2-yl)methanone
[5-chloro-1-(2,4-dichlorobenzyl)-2-(trifluoromethyl)-1H-indol-3-yl](5-phenyl-1,3,4-oxadiazol-2-yl)methanone
[1-(2,4-dichlorobenzyl)-2-(trifluoromethyl)-1H-indol-3-yl](5-phenyl-1,3,4-oxadiazol-2-yl)methanone
[1-(4-chlorobenzyl)-5-methoxy-2-(trifluoromethyl)-1H-indol-3-yl](5-pyridin-2-yl-1,3,4-oxadiazol-2-yl)methanone
[1-(4-chlorobenzyl)-5-ethoxy-2-(trifluoromethyl)-1H-indol-3-yl](5-pyridin-2-yl-1,3,4-oxadiazol-2-yl)methanone
[1-(4-chlorobenzyl)-5-hydroxy-2-(trifluoromethyl)-1H-indol-3-yl](5-pyridin-2-yl-1,3,4-oxadiazol-2-yl)methanone
[1-(4-chlorobenzyl)-5-methyl-2-(trifluoromethyl)-1H-indol-3-yl](5-pyridin-2-yl-1,3,4-oxadiazol-2-yl)methanone
[5-chloro-1-(4-chlorobenzyl)-2-(trifluoromethyl)-1H-indol-3-yl](5-pyridin-2-yl-1,3,4-oxadiazol-2-yl)methanone
[1-(4-chlorobenzyl)-2-(trifluoromethyl)-1H-indol-3-yl](5-pyridin-2-yl-1,3,4-oxadiazol-2-yl)methanone
[1-(2,4-dichlorobenzyl)-5-methoxy-2-(trifluoromethyl)-1H-indol-3-yl](5-pyridin-2-yl-1,3,4-oxadiazol-2-yl)methanone
[1-(2,4-dichlorobenzyl)-5-ethoxy-2-(trifluoromethyl)-1H-indol-3-yl](5-pyridin-2-yl-1,3,4-oxadiazol-2-yl)methanone
[1-(2,4-dichlorobenzyl)-5-hydroxy-2-(trifluoromethyl)-1H-indol-3-yl](5-pyridin-2-yl-1,3,4-oxadiazol-2-yl)methanone
[1-(2,4-dichlorobenzyl)-5-methyl-2-(trifluoromethyl)-1H-indol-3-yl](5-pyridin-2-yl-1,3,4-oxadiazol-2-yl)methanone
[5-chloro-1-(2,4-dichlorobenzyl)-2-(trifluoromethyl)-1H-indol-3-yl](5-pyridin-2-yl-1,3,4-oxadiazol-2-yl)methanone
[1-(2,4-dichlorobenzyl)-2-(trifluoromethyl)-1H-indol-3-yl](5-pyridin-2-yl-1,3,4-oxadiazol-2-yl)methanone
[1-(4-chlorobenzyl)-5-methoxy-2-(trifluoromethyl)-1H-indol-3-yl](5-pyridin-3-yl-1,3,4-oxadiazol-2-yl)methanone
[1-(4-chlorobenzyl)-5-ethoxy-2-(trifluoromethyl)-1H-indol-3-yl](5-pyridin-3-yl-1,3,4-oxadiazol-2-yl)methanone
[1-(4-chlorobenzyl)-5-hydroxy-2-(trifluoromethyl)-1H-indol-3-yl](5-pyridin-3-yl-1,3,4-oxadiazol-2-yl)methanone
[1-(4-chlorobenzyl)-5-methyl-2-(trifluoromethyl)-1H-indol-3-yl](5-pyridin-3-yl-1,3,4-oxadiazol-2-yl)methanone
[5-chloro-1-(4-chlorobenzyl)-2-(trifluoromethyl)-1H-indol-3-yl](5-pyridin-3-yl-1,3,4-oxadiazol-2-yl)methanone
[1-(4-chlorobenzyl)-2-(trifluoromethyl_-1H-indol-3-yl](5-pyridin-3-yl-1,3,4-oxadiazol-2-yl)methanone
[1-(2,4-dichlorobenzyl)-5-methoxy-2-(trifluoromethyl)-1H-indol-3-yl](5-pyridin-3-yl-1,3,4-oxadiazol-2-yl)methanone
[1-(2,4-dichlorobenzyl)-5-ethoxy-2-(trifluoromethyl)-1H-indol-3-yl](5-pyridin-3-yl-1,3,4-oxadiazol-2-yl)methanone
[1-(2,4-dichlorobenzyl)-5-hydroxy-2-(trifluoromethyl)-1H-indol-3-yl](5-pyridin-3-yl-1,3,4-oxadiazol-2-yl)methanone
[1-(2,4-dichlorobenzyl)-5-methyl-2-(trifluoromethyl)-1H-indol-3-yl](5-pyridin-3-yl-1,3,4-oxadiazol-2-yl)methanone
[5-chloro-1-(2,4-dichlorobenzyl)-2-(trifluoromethyl)-1H-indol-3-yl](5-pyridin-3-yl-1,3,4-oxadiazol-2-yl)methanone
[1-(2,4-dichlorobenzyl)-2-(trifluoromethyl)-1H-indol-3-yl](5-pyridin-3-yl-1,3,4-oxadiazol-2-yl)methanone
[1-(4-chlorobenzyl)-5-methoxy-2-(trifluoromethyl)-1H-indol-3-yl](5-pyridin-4-yl-1,3,4-oxadiazol-2-yl)methanone
[1-(4-chlorobenzyl)-5-ethoxy-2-(trifluoromethyl)-1H-indol-3-yl](5-pyridin-4-yl-1,3,4-oxadiazol-2-yl)methanone
[1-(4-chlorobenzyl)-5-hydroxy-2-(trifluoromethyl)-1H-indol-3-yl](5-pyridin-4-yl-1,3,4-oxadiazol-2-yl)methanone
[1-(4-chlorobenzyl)-5-methyl-2-(trifluoromethyl)-1H-indol-3-yl](5-pyridin-4-yl-1,3,4-oxadiazol-2-yl)methanone
[5-chloro-1-(4-chlorobenzyl)-2-(trifluoromethyl)-1H-indol-3-yl](5-pyridin-4-yl-1,3,4-oxadiazol-2-yl)methanone
[1-(4-chlorobenzyl)-2-(trifluoromethyl)-1H-indol-3-yl](5-pyridin-4-yl-1,3,4-oxadiazol-2-yl)methanone
[1-(2,4-dichlorobenzyl)-5-methoxy-2-(trifluoromethyl)-1H-indol-3-yl](5-pyridin-4-yl-1,3,4-oxadiazol-2-yl)methanone
[1-(2,4-dichlorobenzyl)-5-ethoxy-2-(trifluoromethyl)-1H-indol-3-yl](5-pyridin-4-yl-1,3,4-oxadiazol-2-yl)methanone
[1-(2,4-dichlorobenzyl)-5-hydroxy-2-(trifluoromethyl)-1H-indol-3-yl](5-pyridin-4-yl-1,3,4-oxadiazol-2-yl)methanone
[1-(2,4-dichlorobenzyl)-5-methyl-2-(trifluoromethyl)-1H-indol-3-yl](5-pyridin-4-yl-1,3,4-oxadiazol-2-yl)methanone
[5-chloro-1-(2,4-dichlorobenzyl)-2-(trifluoromethyl)-1H-indol-3-yl](5-pyridin-4-yl-1,3,4-oxadiazol-2-yl)methanone
[1-(2,4-dichlorobenzyl)-2-(trifluoromethyl)-1H-indol-3-yl](5-pyridin-4-yl-1,3,4-oxadiazol-2-yl)methanone
[1-(4-chlorobenzyl)-5-methoxy-2-(trifluoromethyl)-1H-indol-3-yl](5-pyrimidin-4-yl-1,3,4-oxadiazol-2-yl)methanone
[1-(4-chlorobenzyl)-5-ethoxy-2-(trifluoromethyl)-1H-indol-3-yl](5-pyrimidin-4-yl-1,3,4-oxadiazol-2-yl)methanone
[1-(4-chlorobenzyl)-5-hydroxy-2-(trifluoromethyl)-1H-indol-3-yl](5-pyrimidin-4-yl-1,3,4-oxadiazol-2-yl)methanone
[1-(4-chlorobenzyl)-5-methyl-2-(trifluoromethyl)-1H-indol-3-yl](5-pyrimidin-4-yl-1,3,4-oxadiazol-2-yl)methanone
[5-chloro-1-(4-chlorobenzyl)-2-(trifluoromethyl)-1H-indol-3-yl](5-pyrimidin-4-yl-1,3,4-oxadiazol-2-yl)methanone
[1-(4-chlorobenzyl)-2-(trifluoromethyl)-1H-indol-3-yl](5-pyrimidin-4-yl-1,3,4-oxadiazol-2-yl)methanone
[1-(2,4-dichlorobenzyl)-5-methoxy-2-(trifluoromethyl)-1H-indol-3-yl](5-pyrimidin-4-yl-1,3,4-oxadiazol-2-yl)methanone
[1-(2,4-dichlorobenzyl)-5-ethoxy-2-(trifluoromethyl)-1H-indol-3-yl](5-pyrimidin-4-yl-1,3,4-oxadiazol-2-yl)methanone
[1-(2,4-dichlorobenzyl)-5-hydroxy-2-(trifluoromethyl)-1H-indol-3-yl](5-pyrimidin-4-yl-1,3,4-oxadiazol-2-yl)methanone
[1-(2,4-dichlorobenzyl)-5-methyl-2-(trifluoromethyl)-1H-indol-3-yl](5-pyrimidin-4-yl-1,3,4-oxadiazol-2-yl)methanone
[5-chloro-1-(2,4-dichlorobenzyl)-2-(trifluoromethyl)-1H-indol-3-yl](5-pyrimidin-4-yl-1,3,4-oxadiazol-2-yl)methanone
[1-(2,4-dichlorobenzyl)-2-(trifluoromethyl)-1H-indol-3-yl](5-pyrimidin-4-yl-1,3,4-oxadiazol-2-yl)methanone

[1-(4-chlorobenzyl)-5-methoxy-2-(trifluoromethyl)-1H-indol-3-yl](2-phenyl-1,3-oxazol-5-yl)methanone
[1-(4-chlorobenzyl)-5-ethoxy-2-(trifluoromethyl)-1H-indol-3-yl](2-phenyl-1,3-oxazol-5-yl)methanone
[1-(4-chlorobenzyl)-5-hydroxy-2-(trifluoromethyl)-1H-indol-3-yl](2-phenyl-1,3-oxazol-5-yl)methanone
[1-(4-chlorobenzyl)-5-methyl-2-(trifluoromethyl)-1H-indol-3-yl](2-phenyl-1,3-oxazol-5-yl)methanone
[5-chloro-1-(4-chlorobenzyl)-2-(trifluoromethyl)-1H-indol-3-yl](2-phenyl-1,3-oxazol-5-yl)methanone
[1-(4-chlorobenzyl)-2-(trifluoromethyl)-1H-indol-3-yl](2-phenyl-1,3-oxazol-5-yl)methanone
[1-(2,4-dichlorobenzyl)-5-methoxy-2-(trifluoromethyl)-1H-indol-3-yl](2-phenyl-1,3-oxazol-5-yl)methanone
[1-(2,4-dichlorobenzyl)-5-ethoxy-2-(trifluoromethyl)-1H-indol-3-yl](2-phenyl-1,3-oxazol-5-yl)methanone
[1-(2,4-dichlorobenzyl)-5-hydroxy-2-(trifluoromethyl)-1H-indol-3-yl](2-phenyl-1,3-oxazol-5-yl)methanone
[1-(2,4-dichlorobenzyl)-5-methyl-2-(trifluoromethyl)-1H-indol-3-yl](2-phenyl-1,3-oxazol-5-yl)methanone
[5-chloro-1-(2,4-dichlorobenzyl)-2-(trifluoromethyl)-1H-indol-3-yl](2-phenyl-1,3-oxazol-5-yl)methanone
[1-(2,4-dichlorobenzyl)-2-(trifluoromethyl)-1H-indol-3-yl](2-phenyl-1,3-oxazol-5-yl)methanone
[1-(4-chlorobenzyl)-5-methoxy-2-(trifluoromethyl)-1H-indol-3-yl](2-pyridin-2-yl-1,3-oxazol-5-yl)methanone
[1-(4-chlorobenzyl)-5-ethoxy-2-(trifluoromethyl)-1H-indol-3-yl](2-pyridin-2-yl-1,3-oxazol-5-yl)methanone
[1-(4-chlorobenzyl)-5-hydroxy-2-(trifluoromethyl)-1H-indol-3-yl](2-pyridin-2-yl-1,3-oxazol-5-yl)methanone
[1-(4-chlorobenzyl)-5-methyl-2-(trifluoromethyl)-1H-indol-3-yl](2-pyridin-2-yl-1,3-oxazol-5-yl)methanone
[5-chloro-1-(4-chlorobenzyl)-2-(trifluoromethyl)-1H-indol-3-yl](2-pyridin-2-yl-1,3-oxazol-5-yl)methanone
[1-(4-chlorobenzyl)-2-(trifluoromethyl)-1H-indol-3-yl](2-pyridin-2-yl-1,3-oxazol-5-yl)methanone
[1-(2,4-dichlorobenzyl)-5-methoxy-2-(trifluoromethyl)-1H-indol-3-yl](2-pyridin-2-yl-1,3-oxazol-5-yl)methanone
[1-(2,4-dichlorobenzyl)-5-ethoxy-2-(trifluoromethyl)-1H-indol-3-yl](2-pyridin-2-yl-1,3-oxazol-5-yl)methanone
[1-(2,4-dichlorobenzyl)-5-hydroxy-2-(trifluoromethyl)-1H-indol-3-yl](2-pyridin-2-yl-1,3-oxazol-5-yl)methanone
[1-(2,4-dichlorobenzyl)-5-methyl-2-(trifluoromethyl)-1H-indol-3-yl](2-pyridin-2-yl-1,3-oxazol-5-yl)methanone
[5-chloro-1-(2,4-dichlorobenzyl)-2-(trifluoromethyl)-1H-indol-3-yl](2-pyridin-2-yl-1,3-oxazol-5-yl)methanone
[1-(2,4-dichlorobenzyl)-2-(trifluoromethyl)-1H-indol-3-yl](2-pyridin-2-yl-1,3-oxazol-5-yl)methanone
[1-(4-chlorobenzyl)-5-methoxy-2-(trifluoromethyl)-1H-indol-3-yl](2-pyridin-3-yl-1,3-oxazol-5-yl)methanone
[1-(4-chlorobenzyl)-5-ethoxy-2-(trifluoromethyl)-1H-indol-3-yl](2-pyridin-3-yl-1,3-oxazol-5-yl)methanone
[1-(4-chlorobenzyl)-5-hydroxy-2-(trifluoromethyl)-1H-indol-3-yl](2-pyridin-3-yl-1,3-oxazol-5-yl)methanone
[1-(4-chlorobenzyl)-5-methyl-2-(trifluoromethyl)-1H-indol-3-yl](2-pyridin-3-yl-1,3-oxazol-5-yl)methanone
[5-chloro-1-(4-chlorobenzyl)-2-(trifluoromethyl)-1H-indol-3-yl](2-pyridin-3-yl-1,3-oxazol-5-yl)methanone
[1-(4-chlorobenzyl)-2-(trifluoromethyl)-1H-indol-3-yl](2-pyridin-3-yl-1,3-oxazol-5-yl)methanone
[1-(2,4-dichlorobenzyl)-5-methoxy-2-(trifluoromethyl)-1H-indol-3-yl](2-pyridin-3-yl-1,3-oxazol-5-yl)methanone
[1-(2,4-dichlorobenzyl)-5-ethoxy-2-(trifluoromethyl)-1H-indol-3-yl](2-pyridin-3-yl-1,3-oxazol-5-yl)methanone
[1-(2,4-dichlorobenzyl)-5-hydroxy-2-(trifluoromethyl)-1H-indol-3-yl](2-pyridin-3-yl-1,3-oxazol-5-yl)methanone
[1-(2,4-dichlorobenzyl)-5-methyl-2-(trifluoromethyl)-1H-indol-3-yl](2-pyridin-3-yl-1,3-oxazol-5-yl)methanone
[5-chloro-1-(2,4-dichlorobenzyl)-2-(trifluoromethyl)-1H-indol-3-yl](2-pyridin-3-yl-1,3-oxazol-5-yl)methanone
[1-(2,4-dichlorobenzyl)-2-(trifluoromethyl)-1H-indol-3-yl](2-pyridin-3-yl-1,3-oxazol-5-yl)methanone
[1-(4-chlorobenzyl)-5-methoxy-2-(trifluoromethyl)-1H-indol-3-yl](2-pyridin-4-yl-1,3-oxazol-5-yl)methanone
[1-(4-chlorobenzyl)-5-ethoxy-2-(trifluoromethyl)-1H-indol-3-yl](2-pyridin-4-yl-1,3-oxazol-5-yl)methanone
1-(4-chlorobenzyl)-5-hydroxy-2-(trifluoromethyl)-1H-indol-3-yl](2-pyridin-4-yl-1,3-oxazol-5-yl)methanone
[1-(4-chlorobenzyl)-5-methyl-2-(trifluoromethyl)-1H-indol-3-yl](2-pyridin-4-yl-1,3-oxazol-5-yl)methanone
[5-chloro-1-(4-chlorobenzyl)-2-(trifluoromethyl)-1H-indol-3-yl](2-pyridin-4-yl-1,3-oxazol-5-yl)methanone
[1-(4-chlorobenzyl)-2-(trifluoromethyl)-1H-indol-3-yl](2-pyridin-4-yl-1,3-oxazol-5-yl)methanone
[1-(2,4-dichlorobenzyl)-5-methoxy-2-(trifluoromethyl)-1H-indol-3-yl](2-pyridin-4-yl-1,3-oxazol-5-yl)methanone
[1-(2,4-dichlorobenzyl)-5-ethoxy-2-(trifluoromethyl)-1H-indol-3-yl](2-pyridin-4-yl-1,3-oxazol-5-yl)methanone
[1-(2,4-dichlorobenzyl)-5-hydroxy-2-(trifluoromethyl)-1H-indol-3-yl](2-pyridin-4-yl-1,3-oxazol-5-yl)methanone
[1-(2,4-dichlorobenzyl)-5-methyl-2-(trifluoromethyl)-1H-indol-5-yl](2-pyridin-4-yl-1,3-oxazol-5-yl)methanone
[5-chloro-1-(2,4-dichlorobenzyl)-2-(trifluoromethyl)-1H-indol-3-yl](2-pyridin-4-yl-1,3-oxazol-5-yl)methanone
[1-(2,4-dichlorobenzyl)-2-(trifluoromethyl)-1H-indol-3-yl](2-pyridin-4-yl-1,3-oxazol-5-yl)methanone
[1-(4-chlorobenzyl)-5-methoxy-2-(trifluoromethyl)-1H-indol-3-yl](2-pyrimidin-4-yl-1,3-oxazol-5-yl)methanone
[1-(4-chlorobenzyl)-5-ethoxy-2-(trifluoromethyl)-1H-indol-3-yl](2-pyrimidin-4-yl-1,3-oxazol-5-yl)methanone
[1-(4-chlorobenzyl)-5-hydroxy-2-(trifluoromethyl)-1H-indol-3-yl](2-pyrimidin-4-yl-1,3-oxazol-5-yl)methanone
[1-(4-chlorobenzyl)-5-methyl-2-(trifluoromethyl)-1H-indol-3-yl](2-pyrimidin-4-yl-1,3-oxazol-5-yl)methanone
[5-chloro-1-(4-chlorobenzyl)-2-(trifluoromethyl)-1H-indol-3-yl](2-pyrimidin-4-yl-1,3-oxazol-5-yl)methanone
[1-(4-chlorobenzyl)-2-(trifluoromethyl)-1H-indol-3-yl](2-pyrimidin-4-yl-1,3-oxazol-5-yl)methanone
[1-(2,4-dichlorobenzyl)-5-methoxy-2-(trifluoromethyl)-1H-indol-3-yl](2-pyrimidin-4-yl-1,3-oxazol-5-yl)methanone
[1-(2,4-dichlorobenzyl)-5-ethoxy-2-(trifluoromethyl)-1H-indol-3-yl](2-pyrimidin-4-yl-1,3-oxazol-5-yl)methanone
[1-(2,4-dichlorobenzyl)-5-hydroxy-2-(trifluoromethyl)-1H-indol-3-yl](2-pyrimidin-4-yl-1,3-oxazol-5-yl)methanone
[1-(2,4-dichlorobenzyl)-5-methyl-2-(trifluoromethyl)-1H-indol-3-yl](2-pyrimidin-4-yl-1,3-oxazol-5-yl)methanone
[5-chloro-1-(2,4-dichlorobenzyl)-2-(trifluoromethyl)-1H-indol-3-yl](2-pyrimidin-4-yl-1,3-oxazol-5-yl)methanone
[1-(2,4-dichlorobenzyl)-2-(trifluoromethyl)-1H-indol-3-yl](2-pyrimidin-4-yl-1,3-oxazol-5-yl)methanone
[1-(4-chlorobenzyl)-5-methoxy-2-(trifluoromethyl)-1H-indol-3-yl](5-phenyl-1,3-oxazol-2-yl)methanone
[1-(4-chlorobenzyl)-5-ethoxy-2-(trifluoromethyl)-1H-indol-3-yl](5-phenyl-1,3-oxazol-2-yl)methanone
[1-(4-chlorobenzyl)-5-hydroxy-2-(trifluoromethyl)-1H-indol-3-yl](5-phenyl-1,3-oxazol-2-yl)methanone
[1-(4-chlorobenzyl)-5-methyl-2-(trifluoromethyl)-1H-indol-3-yl](5-phenyl-1,3-oxazol-2-yl)methanone
[5-chloro-1-(4-chlorobenzyl)-2-(trifluoromethyl)-1H-indol-3-yl](5-phenyl-1,3-oxazol-2-yl)methanone
[1-(4-chlorobenzyl)-2-(trifluoromethyl)-1H-indol-3-yl](5-phenyl-1,3-oxazol-2-yl)methanone

[1-(2,4-dichlorobenzyl)-5-methoxy-2-(trifluoromethyl)-1H-indol-3-yl](5-phenyl-1,3-oxazol-2-yl)methanone
[1-(2,4-dichlorobenzyl)-5-ethoxy-2-(trifluoromethyl)-1H-indol-3-yl](5-phenyl-1,3-oxazol-2-yl)methanone
[1-(2,4-dichlorobenzyl)-5-hydroxy-2-(trifluoromethyl)-1H-indol-3-yl](5-phenyl-1,3-oxazol-2-yl)methanone
[1-(2,4-dichlorobenzyl)-5-methyl-2-(trifluoromethyl)-1H-indol-3-yl](5-phenyl-1,3-oxazol-2-yl)methanone
[5-chloro-1-(2,4-dichlorobenzyl)-2-(trifluoromethyl)-1H-indol-3-yl](5-phenyl-1,3-oxazol-2-yl)methanone
[1-(2,4-dichlorobenzyl)-2-(trifluoromethyl)-1H-indol-3-yl](5-phenyl-1,3-oxazol-2-yl)methanone
[1-(4-chlorobenzyl)-5-methoxy-2-(trifluoromethyl)-1H-indol-3-yl](5-pyridin-2-yl-1,3-oxazol-2-yl)methanone
[1-(4-chlorobenzyl)-5-ethoxy-2-(trifluoromethyl)-1H-indol-3-yl](5-pyridin-2-yl-1,3-oxazol-2-yl)methanone
[1-(4-chlorobenzyl)-5-hydroxy-2-(trifluoromethyl)-1H-indol-3-yl](5-pyridin-2-yl-1,3-oxazol-2-yl)methanone
[1-(4-chlorobenzyl)-5-methyl-2-(trifluoromethyl)-1H-indol-3-yl](5-pyridin-2-yl-1,3-oxazol-2-yl)methanone
[5-chloro-1-(4-chlorobenzyl)-2-(trifluoromethyl)-1H-indol-3-yl](5-pyridin-2-yl-1,3-oxazol-2-yl)methanone
[1-(4-chlorobenzyl)-2-(trifluoromethyl)-1H-indol-3-yl](5-pyridin-2-yl-1,3-oxazol-2-yl)methanone
[1-(2,4-dichlorobenzyl)-5-methoxy-2-(trifluoromethyl)-1H-indol-3-yl](5-pyridin-2-yl-1,3-oxazol-2-yl)methanone
[1-(2,4-dichlorobenzyl)-5-ethoxy-2-(trifluoromethyl)-1H-indol-3-yl](5-pyridin-2-yl-1,3-oxazol-2-yl)methanone
[1-(2,4-dichlorobenzyl)-5-hydroxy-2-(trifluoromethyl)-1H-indol-3-yl](5-pyridin-2-yl-1,3-oxazol-2-yl)methanone
[1-(2,4-dichlorobenzyl)-5-methyl-2-(trifluoromethyl)-1H-indol-3-yl](5-pyridin-2-yl-1,3-oxazol-2-yl)methanone
[5-chloro-1-(2,4-dichlorobenzyl)-2-(trifluoromethyl)-1H-indol-3-yl](5-pyridin-2-yl-1,3-oxazol-2-yl)methanone
[1-(2,4-dichlorobenzyl)-2-(trifluoromethyl)-1H-indol-3-yl](5-pyridin-2-yl-1,3-oxazol-2-yl)methanone
[1-(4-chlorobenzyl)-5-methoxy-2-(trifluoromethyl)-1H-indol-3-yl](5-pyridin-3-yl-1,3-oxazol-2-yl)methanone
[1-(4-chlorobenzyl)-5-ethoxy-2-(trifluoromethyl)-1H-indol-3-yl](5-pyridin-3-yl-1,3-oxazol-2-yl)methanone
[1-(4-chlorobenzyl)-5-hydroxy-2-(trifluoromethyl)-1H-indol-3-yl](5-pyridin-3-yl-1,3-oxazol-2-yl)methanone
[1-(4-chlorobenzyl)-5-methyl-2-(trifluoromethyl)-1H-indol-3-yl](5-pyridin-3-yl-1,3-oxazol-2-yl)methanone
[5-chloro-1-(4-chlorobenzyl)-2-(trifluoromethyl)-1H-indol-3-yl](5-pyridin-3-yl-1,3-oxazol-2-yl)methanone
[1-(4-chlorobenzyl)-2-(trifluoromethyl)-1H-indol-3-yl](5-pyridin-3-yl-1,3-oxazol-2-yl)methanone
[1-(2,4-dichlorobenzyl)-5-methoxy-2-(trifluoromethyl)-1H-indol-3-yl](5-pyridin-3-yl-1,3-oxazol-2-yl)methanone
[1-(2,4-dichlorobenzyl)-5-ethoxy-2-(trifluoromethyl)-1H-indol-3-yl](5-pyridin-3-yl-1,3-oxazol-2-yl)methanone
[1-(2,4-dichlorobenzyl)-5-hydroxy-2-(trifluoromethyl)-1H-indol-3-yl](5-pyridin-3-yl-1,3-oxazol-2-yl)methanone
[1-(2,4-dichlorobenzyl)-5-methyl-2-(trifluoromethyl)-1H-indol-3-yl](5-pyridin-3-yl-1,3-oxazol-2-yl)methanone
[5-chloro-1-(2,4-dichlorobenzyl)-2-(trifluoromethyl)-1H-indol-3-yl](5-pyridin-3-yl-1,3-oxazol-2-yl)methanone
[1-(2,4-dichlorobenzyl)-2-(trifluoromethyl)-1H-indol-3-yl](5-pyridin-3-yl-1,3-oxazol-2-yl)methanone
[1-(4-chlorobenzyl)-5-methoxy-2-(trifluoromethyl)-1H-indol-3-yl](5-pyridin-4-yl-1,3-oxazol-2-yl)methanone
[1-(4-chlorobenzyl)-5-ethoxy-2-(trifluoromethyl)-1H-indol-3-yl](5-pyridin-4-yl-1,3-oxazol-2-yl)methanone
[1-(4-chlorobenzyl)-5-hydroxy-2-(trifluoromethyl)-1H-indol-3-yl](5-pyridin-4-yl-1,3-oxazol-2-yl)methanone
[1-(4-chlorobenzyl)-5-methyl-2-(trifluoromethyl)-1H-indol-3-yl](5-pyridin-4-yl-1,3-oxazol-2-yl)methanone
[5-chloro-1-(4-chlorobenzyl)-2-(trifluoromethyl)-1H-indol-3-yl](5-pyridin-4-yl-1,3-oxazol-2-yl)methanone
[1-(4-chlorobenzyl)-2-(trifluoromethyl)-1H-indol-3-yl](5-pyridin-4-yl-1,3-oxazol-2-yl)methanone
[1-(2,4-dichlorobenzyl)-5-methoxy-2-(trifluoromethyl)-1H-indol-3-yl](5-pyridin-4-yl-1,3-oxazol-2-yl)methanone
[1-(2,4-dichlorobenzyl)-5-ethoxy-2-(trifluoromethyl)-1H-indol-3-yl](5-pyridin-4-yl-1,3-oxazol-2-yl)methanone
[1-(2,4-dichlorobenzyl)-5-hydroxy-2-(trifluoromethyl)-1H-indol-3-yl](5-pyridin-4-yl-1,3-oxazol-2-yl)methanone
[1-(2,4-dichlorobenzyl)-5-methyl-2-(trifluoromethyl)-1H-indol-3-yl](5-pyridin-4-yl-1,3-oxazol-2-yl)methanone
[5-chloro-1-(2,4-dichlorobenzyl)-2-(trifluoromethyl)-1H-indol-3-yl](5-pyridin-4-yl-1,3-oxazol-2-yl)methanone
[1-(2,4-dichlorobenzyl)-2-(trifluoromethyl)-1H-indol-3-yl](5-pyridin-4-yl-1,3-oxazol-2-yl)methanone
[1-(4-chlorobenzyl)-5-methoxy-2-(trifluoromethyl)-1H-indol-3-yl](5-pyrimidin-4-yl-1,3-oxazol-2-yl)methanone
[1-(4-chlorobenzyl)-5-ethoxy-2-(trifluoromethyl)-1H-indol-3-yl](5-pyrimidin-4-yl-1,3-oxazol-2-yl)methanone
[1-(4-chlorobenzyl)-5-hydroxy-2-(trifluoromethyl)-1H-indol-3-yl](5-pyrimidin-4-yl-1,3-oxazol-2-yl)methanone
[1-(4-chlorobenzyl)-5-methyl-2-(trifluoromethyl)-1H-indol-3-yl](5-pyrimidin-4-yl-1,3-oxazol-2-yl)methanone
[5-chloro-1-(4-chlorobenzyl)-2-(trifluoromethyl)-1H-indol-3-yl](5-pyrimidin-4-yl-1,3-oxazol-2-yl)methanone
[1-(4-chlorobenzyl)-2-(trifluoromethyl)-1H-indol-3-yl](5-pyrimidin-4-yl-1,3-oxazol-2-yl)methanone
[1-(2,4-dichlorobenzyl)-5-methoxy-2-(trifluoromethyl)-1H-indol-3-yl](5-pyrimidin-4-yl-1,3-oxazol-2-yl)methanone
[1-(2,4-dichlorobenzyl)-5-ethoxy-2-(trifluoromethyl)-1H-indol-3-yl](5-pyrimidin-4-yl-1,3-oxazol-2-yl)methanone
[1-(2,4-dichlorobenzyl)-5-hydroxy-2-(trifluoromethyl)-1H-indol-3-yl](5-pyrimidin-4-yl-1,3-oxazol-2-yl)methanone
[1-(2,4-dichlorobenzyl)-5-methyl-2-(trifluoromethyl)-1H-indol-3-yl](5-pyrimidin-4-yl-1,3-oxazol-2-yl)methanone
[5-chloro-1-(2,4-dichlorobenzyl)-2-(trifluoromethyl)-1H-indol-3-yl](5-pyrimidin-4-yl-1,3-oxazol-2-yl)methanone
[1-(2,4-dichlorobenzyl)-2-(trifluoromethyl)-1H-indol-3-yl](5-pyrimidin-4-yl-1,3-oxazol-2-yl)methanone
[1-(4-chlorobenzyl)-5-methoxy-2-(chloro)-1H-indol-3-yl](3-pyridin-2-yl-1,2,4-oxadiazol-5-yl)methanone
[1-(4-chlorobenzyl)-5-ethoxy-2-(chloro)-1H-indol-3-yl](3-pyridin-2-yl-1,2,4-oxadiazol-5-yl)methanone
[1-(4-chlorobenzyl)-5-hydroxy-2-(chloro)-1H-indol-3-yl](3-pyridin-2-yl-1,2,4-oxadiazol-5-yl)methanone
[1-(4-chlorobenzyl)-5-methyl-2-(chloro)-1H-indol-3-yl](3-pyridin-2-yl-1,2,4-oxadiazol-5-yl)methanone
[5-chloro-1-(4-chlorobenzyl)-2-(chloro)-1H-indol-3-yl](3-pyridin-2-yl-1,2,4-oxadiazol-5-yl)methanone
[1-(4-chlorobenzyl)-2-(chloro)-1H-indol-3-yl](3-pyridin-2-yl-1,2,4-oxadiazol-5-yl)methanone
[1-(2,4-dichlorobenzyl)-5-methoxy-2-(chloro)-1H-indol-3-yl](3-pyridin-2-yl-1,2,4-oxadiazol-5-yl)methanone
[1-(2,4-dichlorobenzyl)-5-ethoxy-2-(chloro)-1H-indol-3-yl](3-pyridin-2-yl-1,2,4-oxadiazol-5-yl)methanone
[1-(2,4-dichlorobenzyl)-5-hydroxy-2-(chloro)-1H-indol-3-yl](3-pyridin-2-yl-1,2,4-oxadiazol-5-yl)methanone
[1-(2,4-dichlorobenzyl)-5-methyl-2-(chloro)-1H-indol-3-yl](3-pyridin-2-yl-1,2,4-oxadiazol-5-yl)methanone
[5-chloro-1-(2,4-dichlorobenzyl)-2-(chloro)-1H-indol-3-yl](3-pyridin-2-yl-1,2,4-oxadiazol-5-yl)methanone
[1-(2,4-dichlorobenzyl)-2-(chloro)-1H-indol-3-yl](3-pyridin-2-yl-1,2,4-oxadiazol-5-yl)methanone

[1-(4-chlorobenzyl)-5-methoxy-2-(chloro)-1H-indol-3-yl]
(3-pyridin-3-yl-1,2,4-oxadiazol-5-yl)methanone
[1-(4-chlorobenzyl)-5-ethoxy-2-(chloro)-1H-indol-3-yl](3-
pyridin-3-yl-1,2,4-oxadiazol-5-yl)methanone
[1-(4-chlorobenzyl)-5-hydroxy-2-(chloro)-1H-indol-3-yl]
(3-pyridin-3-yl-1,2,4-oxadiazol-5-yl)methanone
[1-(4-chlorobenzyl)-5-methyl-2-(chloro)-1H-indol-3-yl](3-
pyridin-3-yl-1,2,4-oxadiazol-5-yl)methanone
[5-chloro-1-(4-chlorobenzyl)-2-(chloro)-1H-indol-3-yl](3-
pyridin-3-yl-1,2,4-oxadiazol-5-yl)methanone
[1-(4-chlorobenzyl)-2-(chloro)-1H-indol-3-yl](3-pyridin-3-
yl-1,2,4-oxadiazol-5-yl)methanone
[1-(2,4-dichlorobenzyl)-5-methoxy-2-(chloro)-1H-indol-3-
yl](3-pyridin-3-yl-1,2,4-oxadiazol-5-yl)methanone
[1-(2,4-dichlorobenzyl)-5-ethoxy-2-(chloro)-1H-indol-3-yl]
(3-pyridin-3-yl-1,2,4-oxadiazol-5-yl)methanone
[1-(2,4-dichlorobenzyl)-5-hydroxy-2-(chloro)-1H-indol-3-
yl](3-pyridin-3-yl-1,2,4-oxadiazol-5-yl)methanone
[1-(2,4-dichlorobenzyl)-5-methyl-2-(chloro)-1H-indol-3-yl]
(3-pyridin-3-yl-1,2,4-oxadiazol-5-yl)methanone
[5-chloro-1-(2,4-dichlorobenzyl)-2-(chloro)-1H-indol-3-yl]
(3-pyridin-3-yl-1,2,4-oxadiazol-5-yl)methanone
[1-(2,4-dichlorobenzyl)-2-(chloro)-1H-indol-3-yl](3-pyri-
din-3-yl-1,2,4-oxadiazol-5-yl)methanone
[1-(4-chlorobenzyl)-5-methoxy-2-(chloro)-1H-indol-3-yl]
(3-pyridin-4-yl-1,2,4-oxadiazol-5-yl)methanone
[1-(4-chlorobenzyl)-5-ethoxy-2-(chloro)-1H-indol-3-yl](3-
pyridin-4-yl-1,2,4-oxadiazol-5-yl)methanone
[1-(4-chlorobenzyl)-5-hydroxy-2-(chloro)-1H-indol-3-yl]
(3-pyridin-4-yl-1,2,4-oxadiazol-5-yl)methanone
[1-(4-chlorobenzyl)-5-methyl-2-(chloro)-1H-indol-3-yl](3-
pyridin-4-yl-1,2,4-oxadiazol-5-yl)methanone
[5-chloro-1-(4-chlorobenzyl)-2-(chloro)-1H-indol-3-yl](3-
pyridin-4-yl-1,2,4-oxadiazol-5-yl)methanone
[1-(4-chlorobenzyl)-2-(chloro)-1H-indol-3-yl](3-pyridin-4-
yl-1,2,4-oxadiazol-5-yl)methanone
[1-(2,4-dichlorobenzyl)-5-methoxy-2-(chloro)-1H-indol-3-
yl](3-pyridin-4-yl-1,2,4-oxadiazol-5-yl)methanone
[1-(2,4-dichlorobenzyl)-5-ethoxy-2-(chloro)-1H-indol-3-yl]
(3-pyridin-4-yl-1,2,4-oxadiazol-5-yl)methanone
[1-(2,4-dichlorobenzyl)-5-hydroxy-2-(chloro)-1H-indol-3-
yl](3-pyridin-4-yl-1,2,4-oxadiazol-5-yl)methanone
[1-(2,4-dichlorobenzyl)-5-methyl-2-(chloro)-1H-indol-3-yl]
(3-pyridin-4-yl-1,2,4-oxadiazol-5-yl)methanone
[5-chloro-1-(2,4-dichlorobenzyl)-2-(chloro)-1H-indol-3-yl]
(3-pyridin-4-yl-1,2,4-oxadiazol-5-yl)methanone
[1-(2,4-dichlorobenzyl)-2-(chloro)-1H-indol-3-yl](3-pyri-
din-4-yl-1,2,4-oxadiazol-5-yl)methanone
[1-(4-chlorobenzyl)-5-methoxy-2-(chloro)-1H-indol-3-yl]
(3-pyrimidin-4-yl-1,2,4-oxadiazol-5-yl)methanone
[1-(4-chlorobenzyl)-5-ethoxy-2-(chloro)-1H-indol-3-yl](3-
pyrimidin-4-yl-1,2,4-oxadiazol-5-yl)methanone
[1-(4-chlorobenzyl)-5-hydroxy-2-(chloro)-1H-indol-3-yl]
(3-pyrimidin-4-yl-1,2,4-oxadiazol-5-yl)methanone
[1-(4-chlorobenzyl)-5-methyl-2-(chloro)-1H-indol-3-yl](3-
pyrimidin-4-yl-1,2,4-oxadiazol-5-yl)methanone
[5-chloro-1-(4-chlorobenzyl)-2-(chloro)-1H-indol-3-yl](3-
pyrimidin-4-yl-1,2,4-oxadiazol-5-yl)methanone
[1-(4-chlorobenzyl)-2-(chloro)-1H-indol-3-yl](3-pyrimidin-
4-yl-1,2,4-oxadiazol-5-yl)methanone
[1-(2,4-dichlorobenzyl)-5-methoxy-2-(chloro)-1H-indol-3-
yl](3-pyrimidin-4-yl-1,2,4-oxadiazol-5-yl)methanone
[1-(2,4-dichlorobenzyl)-5-ethoxy-2-(chloro)-1H-indol-3-yl]
(3-pyrimidin-4-yl-1,2,4-oxadiazol-5-yl)methanone
[1-(2,4-dichlorobenzyl)-5-hydroxy-2-(chloro)-1H-indol-3-
yl](3-pyrimidin-4-yl-1,2,4-oxadiazol-5-yl)methanone
[1-(2,4-dichlorobenzyl)-5-methyl-2-(chloro)-1H-indol-3-yl]
(3-pyrimidin-4-yl-1,2,4-oxadiazol-5-yl)methanone
[5-chloro-1-(2,4-dichlorobenzyl)-2-(chloro)-1H-indol-3-yl]
(3-pyrimidin-4-yl-1,2,4-oxadiazol-5-yl)methanone
[1-(2,4-dichlorobenzyl)-2-(chloro)-1H-indol-3-yl](3-pyri-
midin-4-yl-1,2,4-oxadiazol-5-yl)methanone
[1-(4-chlorobenzyl)-5-methoxy-2-(chloro)-1H-indol-3-yl]
(5-phenyl-1,2,4-oxadiazol-3-yl)methanone
[1-(4-chlorobenzyl)-5-ethoxy-2-(chloro)-1H-indol-3-yl](5-
phenyl-1,2,4-oxadiazol-3-yl)methanone
[1-(4-chlorobenzyl)-5-hydroxy-2-(chloro)-1H-indol-3-yl]
(5-phenyl-1,2,4-oxadiazol-3-yl)methanone
[1-(4-chlorobenzyl)-5-methyl-2-(chloro)-1H-indol-3-yl](5-
phenyl-1,2,4-oxadiazol-3-yl)methanone
[5-chloro-1-(4-chlorobenzyl)-2-(chloro)-1H-indol-3-yl](5-
phenyl-1,2,4-oxadiazol-3-yl)methanone
[1-(4-chlorobenzyl)-2-(chloro)-1H-indol-3-yl](5-phenyl-1,
2,4-oxadiazol-3-yl)methanone
[1-(2,4-dichlorobenzyl)-5-methoxy-2-(chloro)-1H-indol-3-
yl](5-phenyl-1,2,4-oxadiazol-3-yl)methanone
[1-(2,4-dichlorobenzyl)-5-ethoxy-2-(chloro)-1H-indol-3-yl]
(5-phenyl-1,2,4-oxadiazol-3-yl)methanone
[1-(2,4-dichlorobenzyl)-5-hydroxy-2-(chloro)-1H-indol-3-
yl](5-phenyl-1,2,4-oxadiazol-3-yl)methanone
[1-(2,4-dichlorobenzyl)-5-methyl-2-(chloro)-1H-indol-3-yl]
(5-phenyl-1,2,4-oxadiazol-3-yl)methanone
[5-chloro-1-(2,4-dichlorobenzyl)-2-(chloro)-1H-indol-3-yl]
(5-phenyl-1,2,4-oxadiazol-3-yl)methanone
[1-(2,4-dichlorobenzyl)-2-(chloro)-1H-indol-3-yl](5-phe-
nyl-1,2,4-oxadiazol-3-yl)methanone
[1-(4-chlorobenzyl)-5-methoxy-2-(chloro)-1H-indol-3-yl]
(5-pyridin-2-yl-1,2,4-oxadiazol-3-yl)methanone
[1-(4-chlorobenzyl)-5-ethoxy-2-(chloro)-1H-indol-3-yl](5-
pyridin-2-yl-1,2,4-oxadiazol-3-yl)methanone
[1-(4-chlorobenzyl)-5-hydroxy-2-(chloro)-1H-indol-3-yl]
(5-pyridin-2-yl-1,2,4-oxadiazol-3-yl)methanone
[1-(4-chlorobenzyl)-5-methyl-2-(chloro)-1H-indol-3-yl](5-
pyridin-2-yl-1,2,4-oxadiazol-3-yl)methanone
[5-chloro-1-(4-chlorobenzyl)-2-(chloro)-1H-indol-3-yl](5-
pyridin-2-yl-1,2,4-oxadiazol-3-yl)methanone
[1-(4-chlorobenzyl)-2-(chloro)-1H-indol-3-yl](5-pyridin-2-
yl-1,2,4-oxadiazol-3-yl)methanone
[1-(2,4-dichlorobenzyl)-5-methoxy-2-(chloro)-1H-indol-3-
yl](5-pyridin-2-yl-1,2,4-oxadiazol-3-yl)methanone
[1-(2,4-dichlorobenzyl)-5-ethoxy-2-(chloro)-1H-indol-3-yl]
(5-pyridin-2-yl-1,2,4-oxadiazol-3-yl)methanone
[1-(2,4-dichlorobenzyl)-5-hydroxy-2-(chloro)-1H-indol-3-
yl](5-pyridin-2-yl-1,2,4-oxadiazol-3-yl)methanone [1-(2,
4-dichlorobenzyl)-5-methyl-2-(chloro)-1H-indol-3-yl](5-
pyridin-2-yl-1,2,4-oxadiazol-3-yl)methanone
[5-chloro-1-(2,4-dichlorobenzyl)-2-(chloro)-1H-indol-3-yl]
(5-pyridin-2-yl-1,2,4-oxadiazol-3-yl)methanone
[1-(2,4-dichlorobenzyl)-2-(chloro)-1H-indol-3-yl](5-pyri-
din-2-yl-1,2,4-oxadiazol-3-yl)methanone
[1-(4-chlorobenzyl)-5-methoxy-2-(chloro)-1H-indol-3-yl]
(5-pyridin-2-yl-1,2,4-oxadiazol-3-yl)methanone
[1-(4-chlorobenzyl)-5-ethoxy-2-(chloro)-1H-indol-3-yl](5-
pyridin-3-yl-1,2,4-oxadiazol-3-yl)methanone
[5-chloro-1-(4-chlorobenzyl)-2-(chloro)-1H-indol-3-yl](5-
pyridin-3-yl-1,2,4-oxadiazol-3-yl)methanone
[1-(4-chlorobenzyl)-2-(chloro)-1H-indol-3-yl](5-pyridin-3-
yl-1,2,4-oxadiazol-3-yl)methanone
[1-(2,4-dichlorobenzyl)-5-methoxy-2-(chloro)-1H-indol-3-
yl](5-pyridin-3-yl-1,2,4-oxadiazol-3-yl)methanone
[1-(2,4-dichlorobenzyl)-5-ethoxy-2-(chloro)-1H-indol-3-yl]
(5-pyridin-3-yl-1,2,4-oxadiazol-3-yl)methanone

[1-(2,4-dichlorobenzyl)-5-hydroxy-2-(chloro)-1H-indol-3-yl](5-pyridin-3-yl-1,2,4-oxadiazol-3-yl)methanone
[1-(2,4-dichlorobenzyl)-5-methyl-2-(chloro)-1H-indol-3-yl](5-pyridin-3-yl-1,2,4-oxadiazol-3-yl)methanone
[5-chloro-1-(2,4-dichlorobenzyl)-2-(chloro)-1H-indol-3-yl](5-pyridin-3-yl-1,2,4-oxadiazol-3-yl)methanone
[1-(2,4-dichlorobenzyl)-2-(chloro)-1H-indol-3-yl](5-pyridin-3-yl-1,2,4-oxadiazol-3-yl)methanone
[1-(4-chlorobenzyl)-5-methoxy-2-(chloro)-1H-indol-3-yl](5-pyridin-4-yl-1,2,4-oxadiazol-3-yl)methanone
[1-(4-chlorobenzyl)-5-ethoxy-2-(chloro)-1H-indol-3-yl](5-pyridin-4-yl-1,2,4-oxadiazol-3-yl)methanone
[1-(4-chlorobenzyl)-5-hydroxy-2-(chloro)-1H-indol-3-yl](5-pyridin-4-yl-1,2,4-oxadiazol-3-yl)methanone
[1-(4-chlorobenzyl)-5-methyl-2-(chloro)-1H-indol-3-yl](5-pyridin-4-yl-1,2,4-oxadiazol-3-yl)methanone
[5-chloro-1-(4-chlorobenzyl)-2-(chloro)-1H-indol-3-yl](5-pyridin-4-yl-1,2,4-oxadiazol-3-yl)methanone
[1-(4-chlorobenzyl)-2-(chloro)-1H-indol-3-yl](5-pyridin-4-yl-1,2,4-oxadiazol-3-yl)methanone
[1-(2,4-dichlorobenzyl)-5-methoxy-2-(chloro)-1H-indol-3-yl](5-pyridin-4-yl-1,2,4-oxadiazol-3-yl)methanone
[1-(2,4-dichlorobenzyl)-5-ethoxy-2-(chloro)-1H-indol-3-yl](5-pyridin-4-yl-1,2,4-oxadiazol-3-yl)methanone
[1-(2,4-dichlorobenzyl)-5-hydroxy-2-(chloro)-1H-indol-3-yl](5-pyridin-4-yl-1,2,4-oxadiazol-3-yl)methanone
[1-(2,4-dichlorobenzyl)-5-methyl-2-(chloro)-1H-indol-3-yl](5-pyridin-4-yl-1,2,4-oxadiazol-3-yl)methanone
[5-chloro-1-(2,4-dichlorobenzyl)-2-(chloro)-1H-indol-3-yl](5-pyridin-4-yl-1,2,4-oxadiazol-3-yl)methanone
[1-(2,4-dichlorobenzyl)-2-(chloro)-1H-indol-3-yl](5-pyridin-4-yl-1,2,4-oxadiazol-3-yl)methanone
[1-(4-chlorobenzyl)-5-methoxy-2-(chloro)-1H-indol-3-yl](5-pyrimidin-4-yl-1,2,4-oxadiazol-3-yl)methanone
[1-(4-chlorobenzyl)-5-ethoxy-2-(chloro)-1H-indol-3-yl](5-pyrimidin-4-yl-1,2,4-oxadiazol-3-yl)methanone
[1-(4-chlorobenzyl)-5-hydroxy-2-(chloro)-1H-indol-3-yl](5-pyrimidin-4-yl-1,2,4-oxadiazol-3-yl)methanone
[1-(4-chlorobenzyl)-5-methyl-2-(chloro)-1H-indol-3-yl](5-pyrimidin-4-yl-1,2,4-oxadiazol-3-yl)methanone
[5-chloro-1-(4-chlorobenzyl)-2-(chloro)-1H-indol-3-yl](5-pyrimidin-4-yl-1,2,4-oxadiazol-3-yl)methanone
[1-(4-chlorobenzyl)-2-(chloro)-1H-indol-3-yl](5-pyrimidin-4-yl-1,2,4-oxadiazol-3-yl)methanone
[1-(2,4-dichlorobenzyl)-5-methoxy-2-(chloro)-1H-indol-3-yl](5-pyrimidin-4-yl-1,2,4-oxadiazol-3-yl)methanone
[1-(2,4-dichlorobenzyl)-5-ethoxy-2-(chloro)-1H-indol-3-yl](5-pyrimidin-4-yl-1,2,4-oxadiazol-3-yl)methanone
[1-(2,4-dichlorobenzyl)-5-hydroxy-2-(chloro)-1H-indol-3-yl](5-pyrimidin-4-yl-1,2,4-oxadiazol-3-yl)methanone
[1-(2,4-dichlorobenzyl)-5-methyl-2-(chloro)-1H-indol-3-yl](5-pyrimidin-4-yl-1,2,4-oxadiazol-3-yl)methanone
[5-chloro-1-(2,4-dichlorobenzyl)-2-(chloro)-1H-indol-3-yl](5-pyrimidin-4-yl-1,2,4-oxadiazol-3-yl)methanone
[1-(2,4-dichlorobenzyl)-2-(chloro)-1H-indol-3-yl](5-pyrimidin-4-yl-1,2,4-oxadiazol-3-yl)methanone
[1-(4-chlorobenzyl)-5-methoxy-2-(chloro)-1H-indol-3-yl](5-phenyl-1,3,4-oxadiazol-2-yl)methanone
[1-(4-chlorobenzyl)-5-ethoxy-2-(chloro)-1H-indol-3-yl](5-phenyl-1,3,4-oxadiazol-2-yl)methanone
[1-(4-chlorobenzyl)-5-hydroxy-2-(chloro)-1H-indol-3-yl](5-phenyl-1,3,4-oxadiazol-2-yl)methanone
[1-(4-chlorobenzyl)-5-methyl-2-(chloro)-1H-indol-3-yl](5-phenyl-1,3,4-oxadiazol-2-yl)methanone
[5-chloro-1-(4-chlorobenzyl)-2-(chloro)-1H-indol-3-yl](5-phenyl-1,3,4-oxadiazol-2-yl)methanone
[1-(4-chlorobenzyl)-2-(chloro)-1H-indol-3-yl](5-phenyl-1,3,4-oxadiazol-2-yl)methanone
[1-(2,4-dichlorobenzyl)-5-methoxy-2-(chloro)-1H-indol-3-yl](5-phenyl-1,3,4-oxadiazol-2-yl)methanone
[1-(2,4-dichlorobenzyl)-5-ethoxy-2-(chloro)-1H-indol-3-yl](5-phenyl-1,3,4-oxadiazol-2-yl)methanone
[1-(2,4-dichlorobenzyl)-5-methyl-2-(chloro)-1H-indol-3-yl](5-phenyl-1,3,4-oxadiazol-2-yl)methanone
[5-chloro-1-(2,4-dichlorobenzyl)-2-(chloro)-1H-indol-3-yl](5-phenyl-1,3,4-oxadiazol-2-yl)methanone
[1-(2,4-dichlorobenzyl)-2-(chloro)-1H-indol-3-yl](5-phenyl-1,3,4-oxadiazol-2-yl)methanone
[1-(2,4-dichlorobenzyl)-2-(chloro)-1H-indol-3-yl](5-phenyl-1,3,4-oxadiazol-2-yl)methanone
[1-(4-chlorobenzyl)-5-ethoxy-2-(chloro)-1H-indol-3-yl](5-pyridin-2-yl-1,3,4-oxadiazol-2-yl)methanone
[1-(4-chlorobenzyl)-5-hydroxy-2-(chloro)-1H-indol-3-yl](5-pyridin-2-yl-1,3,4-oxadiazol-2-yl)methanone
[1-(4-chlorobenzyl)-5-methyl-2-(chloro)-1H-indol-3-yl](5-pyridin-2-yl-1,3,4-oxadiazol-2-yl)methanone
[5-chloro-1-(4-chlorobenzyl)-2-(chloro)-1H-indol-3-yl](5-pyridin-2-yl-1,3,4-oxadiazol-2-yl)methanone
[1-(4-chlorobenzyl)-2-(chloro)-1H-indol-3-yl](5-pyridin-2-yl-1,3,4-oxadiazol-2-yl)methanone
[1-(2,4-dichlorobenzyl)-5-methoxy-2-(chloro)-1H-indol-3-yl](5-pyridin-2-yl-1,3,4-oxadiazol-2-yl)methanone
[1-(2,4-dichlorobenzyl)-5-ethoxy-2-(chloro)-1H-indol-3-yl](5-pyridin-2-yl-1,3,4-oxadiazol-2-yl)methanone
[1-(2,4-dichlorobenzyl)-5-hydroxy-2-(chloro)-1H-indol-3-yl](5-pyridin-2-yl-1,3,4-oxadiazol-2-yl)methanone
[1-(2,4-dichlorobenzyl)-5-methyl-2-(chloro)-1H-indol-3-yl](5-pyridin-2-yl-1,3,4-oxadiazol-2-yl)methanone
[5-chloro-1-(2,4-dichlorobenzyl)-2-(chloro)-1H-indol-3-yl](5-pyridin-2-yl-1,3,4-oxadiazol-2-yl)methanone
[1-(4-chlorobenzyl)-5-ethoxy-2-(chloro)-1H-indol-3-yl](5-pyridin-3-yl-1,3,4-oxadiazol-2-yl)methanone
[1-(4-chlorobenzyl)-5-hydroxy-2-(chloro)-1H-indol-3-yl](5-pyridin-3-yl-1,3,4-oxadiazol-2-yl)methanone
[1-(4-chlorobenzyl)-5-methyl-2-(chloro)-1H-indol-3-yl](5-pyridin-3-yl-1,3,4-oxadiazol-2-yl)methanone
[5-chloro-1-(4-chlorobenzyl)-2-(chloro)-1H-indol-3-yl](5-pyridin-3-yl-1,3,4-oxadiazol-2-yl)methanone
[1-(4-chlorobenzyl)-2-(chloro)-1H-indol-3-yl](5-pyridin-3-yl-1,3,4-oxadiazol-2-yl)methanone
[1-(2,4-dichlorobenzyl)-5-methoxy-2-(chloro)-1H-indol-3-yl](5-pyridin-3-yl-1,3,4-oxadiazol-2-yl)methanone
[1-(2,4-dichlorobenzyl)-5-ethoxy-2-(chloro)-1H-indol-3-yl](5-pyridin-3-yl-1,3,4-oxadiazol-2-yl)methanone
[1-(2,4-dichlorobenzyl)-5-methyl-2-(chloro)-1H-indol-3-yl](5-pyridin-3-yl-1,3,4-oxadiazol-2-yl)methanone
[5-chloro-1-(2,4-dichlorobenzyl)-2-(chloro)-1H-indol-3-yl](5-pyridin-3-yl-1,3,4-oxadiazol-2-yl)methanone
[1-(2,4-dichlorobenzyl)-2-(chloro)-1H-indol-3-yl](5-pyridin-3-yl-1,3,4-oxadiazol-2-yl)methanone
[1-(4-chlorobenzyl)-5-methoxy-2-(chloro)-1H-indol-3-yl](5-pyridin-4-yl-1,3,4-oxadiazol-2-yl)methanone
[1-(4-chlorobenzyl)-5-ethoxy-2-(chloro)-1H-indol-3-yl](5-pyridin-4-yl-1,3,4-oxadiazol-2-yl)methanone
[1-(4-chlorobenzyl)-5-hydroxy-2-(chloro)-1H-indol-3-yl](5-pyridin-4-yl-1,3,4-oxadiazol-2-yl)methanone
[1-(4-chlorobenzyl)-5-methyl-2-(chloro)-1H-indol-3-yl](5-pyridin-4-yl-1,3,4-oxadiazol-2-yl)methanone
[5-chloro-1-(4-chlorobenzyl)-2-(chloro)-1H-indol-3-yl](5-pyridin-4-yl-1,3,4-oxadiazol-2-yl)methanone
[1-(4-chlorobenzyl)-2-(chloro)-1H-indol-3-yl](5-pyridin-4-yl-1,3,4-oxadiazol-2-yl)methanone

[1-(2,4-dichlorobenzyl)-5-methoxy-2-(chloro)-1H-indol-3-yl](5-pyridin-4-yl-1,3,4-oxadiazol-2-yl)methanone
[1-(2,4-dichlorobenzyl)-5-ethoxy-2-(chloro)-1H-indol-3-yl](5-pyridin-4-yl-1,3,4-oxadiazol-2-yl)methanone
[1-(2,4-dichlorobenzyl)-5-hydroxy-2-(chloro)-1H-indol-3-yl](5-pyridin-4-yl-1,3,4-oxadiazol-2-yl)methanone
[1-(2,4-dichlorobenzyl)-5-methyl-2-(chloro)-1H-indol-3-yl](5-pyridin-4-yl-1,3,4-oxadiazol-2-yl)methanone
[5-chloro-1-(2,4-dichlorobenzyl)-2-(chloro)-1H-indol-3-yl](5-pyridin-4-yl-1,3,4-oxadiazol-2-yl)methanone
[1-(2,4-dichlorobenzyl)-2-(chloro)-1H-indol-3-yl](5-pyridin-4-yl-1,3,4-oxadiazol-2-yl)methanone
[1-(4-chlorobenzyl)-5-methoxy-2-(chloro)-1H-indol-3-yl](5-pyrimidin-4-yl-1,3,4-oxadiazol-2-yl)methanone
[1-(4-chlorobenzyl)-5-ethoxy-2-(chloro)-1H-indol-3-yl](5-pyrimidin-4-yl-1,3,4-oxadiazol-2-yl)methanone
[1-(4-chlorobenzyl)-5-hydroxy-2-(chloro)-1H-indol-3-yl](5-pyrimidin-4-yl-1,3,4-oxadiazol-2-yl)methanone
[1-(4-chlorobenzyl)-5-methyl-2-(chloro)-1H-indol-3-yl](5-pyrimidin-4-yl-1,3,4-oxadiazol-2-yl)methanone
[5-chloro-1-(4-chlorobenzyl)-2-(chloro)-1H-indol-3-yl](5-pyrimidin-4-yl-1,3,4-oxadiazol-2-yl)methanone
[1-(4-chlorobenzyl)-2-(chloro)-1H-indol-3-yl](5-pyrimidin-4-yl-1,3,4-oxadiazol-2-yl)methanone
[1-(2,4-dichlorobenzyl)-5-methoxy-2-(chloro)-1H-indol-3-yl](5-pyrimidin-4-yl-1,3,4-oxadiazol-2-yl)methanone
[1-(2,4-dichlorobenzyl)-5-ethoxy-2-(chloro)-1H-indol-3-yl](5-pyrimidin-4-yl-1,3,4-oxadiazol-2-yl)methanone
[1-(2,4-dichlorobenzyl)-5-hydroxy-2-(chloro)-1H-indol-3-yl](5-pyrimidin-4-yl-1,3,4-oxadiazol-2-yl)methanone
[1-(2,4-dichlorobenzyl)-5-methyl-2-(chloro)-1H-indol-3-yl](5-pyrimidin-4-yl-1,3,4-oxadiazol-2-yl)methanone
[5-chloro-1-(2,4-dichlorobenzyl)-2-(chloro)-1H-indol-3-yl](5-pyrimidin-4-yl-1,3,4-oxadiazol-2-yl)methanone
[1-(2,4-dichlorobenzyl)-2-(chloro)-1H-indol-3-yl](5-pyrimidin-4-yl-1,3,4-oxadiazol-2-yl)methanone
[1-(4-chlorobenzyl)-5-methoxy-2-(chloro)-1H-indol-3-yl](2-phenyl-1,3-oxazol-5-yl)methanone
[1-(4-chlorobenzyl)-5-ethoxy-2-(chloro)-1H-indol-3-yl](2-phenyl-1,3-oxazol-5-yl)methanone
[1-(4-chlorobenzyl)-5-hydroxy-2-(chloro)-1H-indol-3-yl](2-phenyl-1,3-oxazol-5-yl)methanone
[1-(4-chlorobenzyl)-5-methyl-2-(chloro)-1H-indol-3-yl](2-phenyl-1,3-oxazol-5-yl)methanone
[5-chloro-1-(4-chlorobenzyl)-2-(chloro)-1H-indol-3-yl](2-phenyl-1,3-oxazol-5-yl)methanone
[1-(4-chlorobenzyl)-2-(chloro)-1H-indol-3-yl](2-phenyl-1,3-oxazol-5-yl)methanone
[1-(2,4-dichlorobenzyl)-5-methoxy-2-(chloro)-1H-indol-3-yl](2-phenyl-1,3-oxazol-5-yl)methanone
[1-(2,4-dichlorobenzyl)-5-ethoxy-2-(chloro)-1H-indol-3-yl](2-phenyl-1,3-oxazol-5-yl)methanone
[1-(2,4-dichlorobenzyl)-5-hydroxy-2-(chloro)-1H-indol-3-yl](2-phenyl-1,3-oxazol-5-yl)methanone
[1-(2,4-dichlorobenzyl)-5-methyl-2-(chloro)-1H-indol-3-yl](2-phenyl-1,3-oxazol-5-yl)methanone
[5-chloro-1-(2,4-dichlorobenzyl)-2-(chloro)-1H-indol-3-yl](2-phenyl-1,3-oxazol-5-yl)methanone
[1-(2,4-dichlorobenzyl)-2-(chloro)-1H-indol-3-yl](2-phenyl-1,3-oxazol-5-yl)methanone
[1-(4-chlorobenzyl)-5-methoxy-2-(chloro)-1H-indol-3-yl](2-pyridin-2-yl-1,3-oxazol-5-yl)methanone
[1-(4-chlorobenzyl)-5-ethoxy-2-(chloro)-1H-indol-3-yl](2-pyridin-2-yl-1,3-oxazol-5-yl)methanone
[1-(4-chlorobenzyl)-5-hydroxy-2-(chloro)-1H-indol-3-yl](2-pyridin-2-yl-1,3-oxazol-5-yl)methanone
[1-(4-chlorobenzyl)-5-methyl-2-(chloro)-1H-indol-3-yl](2-pyridin-2-yl-1,3-oxazol-5-yl)methanone
[5-chloro-1-(4-chlorobenzyl)-2-(chloro)-1H-indol-3-yl](2-pyridin-2-yl-1,3-oxazol-5-yl)methanone
[1-(4-chlorobenzyl)-2-(chloro)-1H-indol-3-yl](2-pyridin-2-yl-1,3-oxazol-5-yl)methanone
[1-(2,4-dichlorobenzyl)-5-methoxy-2-(chloro)-1H-indol-3-yl](2-pyridin-2-yl-1,3-oxazol-5-yl)methanone
[1-(2,4-dichlorobenzyl)-5-ethoxy-2-(chloro)-1H-indol-3-yl](2-pyridin-2-yl-1,3-oxazol-5-yl)methanone
[1-(2,4-dichlorobenzyl)-5-hydroxy-2-(chloro)-1H-indol-3-yl](2-pyridin-2-yl-1,3-oxazol-5-yl)methanone
[1-(2,4-dichlorobenzyl)-5-methyl-2-(chloro)-1H-indol-3-yl](2-pyridin-2-yl-1,3-oxazol-5-yl)methanone
[5-chloro-1-(2,4-dichlorobenzyl)-2-(chloro)-1H-indol-3-yl](2-pyridin-2-yl-1,3-oxazol-5-yl)methanone
[1-(2,4-dichlorobenzyl)-2-(chloro)-1H-indol-3-yl](2-pyridin-2-yl-1,3-oxazol-5-yl)methanone
[1-(4-chlorobenzyl)-5-methoxy-2-(chloro)-1H-indol-3-yl](2-pyridin-3-yl-1,3-oxazol-5-yl)methanone
[1-(4-chlorobenzyl)-5-ethoxy-2-(chloro)-1H-indol-3-yl](2-pyridin-3-yl-1,3-oxazol-5-yl)methanone
[1-(4-chlorobenzyl)-5-hydroxy-2-(chloro)-1H-indol-3-yl](2-pyridin-3-yl-1,3-oxazol-5-yl)methanone
[1-(4-chlorobenzyl)-5-methyl-2-(chloro)-1H-indol-3-yl](2-pyridin-3-yl-1,3-oxazol-5-yl)methanone
[5-chloro-1-(4-chlorobenzyl)-2-(chloro)-1H-indol-3-yl](2-pyridin-3-yl-1,3-oxazol-5-yl)methanone
[1-(4-chlorobenzyl)-2-(chloro)-1H-indol-3-yl](2-pyridin-3-yl-1,3-oxazol-5-yl)methanone
[1-(2,4-dichlorobenzyl)-5-methoxy-2-(chloro)-1H-indol-3-yl](2-pyridin-3-yl-1,3-oxazol-5-yl)methanone
[1-(2,4-dichlorobenzyl)-5-ethoxy-2-(chloro)-1H-indol-3-yl](2-pyridin-3-yl-1,3-oxazol-5-yl)methanone
[1-(2,4-dichlorobenzyl)-5-hydroxy-2-(chloro)-1H-indol-3-yl](2-pyridin-3-yl-1,3-oxazol-5-yl)methanone
[1-(2,4-dichlorobenzyl)-5-methyl-2-(chloro)-1H-indol-3-yl](2-pyridin-3-yl-1,3-oxazol-5-yl)methanone
[5-chloro-1-(2,4-dichlorobenzyl)-2-(chloro)-1H-indol-3-yl](2-pyridin-3-yl-1,3-oxazol-5-yl)methanone
[1-(2,4-dichlorobenzyl)-2-(chloro)-1H-indol-3-yl](2-pyridin-3-yl-1,3-oxazol-5-yl)methanone
[1-(4-chlorobenzyl)-5-methoxy-2-(chloro)-1H-indol-3-yl](2-pyridin-4-yl-1,3-oxazol-5-yl)methanone
[1-(4-chlorobenzyl)-5-ethoxy-2-(chloro)-1H-indol-3-yl](2-pyridin-4-yl-1,3-oxazol-5-yl)methanone
[1-(4-chlorobenzyl)-5-hydroxy-2-(chloro)-1H-indol-3-yl](2-pyridin-4-yl-1,3-oxazol-5-yl)methanone
[1-(4-chlorobenzyl)-5-methyl-2-(chloro)-1H-indol-3-yl](2-pyridin-4-yl-1,3-oxazol-5-yl)methanone
[5-chloro-1-(4-chlorobenzyl)-2-(chloro)-1H-indol-3-yl](2-pyridin-4-yl-1,3-oxazol-5-yl)methanone
[1-(4-chlorobenzyl)-2-(chloro)-1H-indol-3-yl](2-pyridin-4-yl-1,3-oxazol-5-yl)methanone
[1-(2,4-dichlorobenzyl)-5-methoxy-2-(chloro)-1H-indol-3-yl](2-pyridin-4-yl-1,3-oxazol-5-yl)methanone
[1-(2,4-dichlorobenzyl)-5-ethoxy-2-(chloro)-1H-indol-3-yl](2-pyridin-4-yl-1,3-oxazol-5-yl)methanone
[1-(2,4-dichlorobenzyl)-5-hydroxy-2-(chloro)-1H-indol-3-yl](2-pyridin-4-yl-1,3-oxazol-5-yl)methanone
[1-(2,4-dichlorobenzyl)-5-methyl-2-(chloro)-1H-indol-3-yl](2-pyridin-4-yl-1,3-oxazol-5-yl)methanone
[5-chloro-1-(2,4-dichlorobenzyl)-2-(chloro)-1H-indol-3-yl](2-pyridin-4-yl-1,3-oxazol-5-yl)methanone
[1-(2,4-dichlorobenzyl)-2-(chloro)-1H-indol-3-yl](2-pyridin-4-yl-1,3-oxazol-5-yl)methanone

[1-(4-chlorobenzyl)-5-methoxy-2-(chloro)-1H-indol-3-yl](2-pyrimidin-4-yl-1,3-oxazol-5-yl)methanone
[1-(4-chlorobenzyl)-5-ethoxy-2-(chloro)-1H-indol-3-yl](2-pyrimidin-4-yl-1,3-oxazol-5-yl)methanone
[1-(4-chlorobenzyl)-5-hydroxy-2-(chloro)-1H-indol-3-yl](2-pyrimidin-4-yl-1,3-oxazol-5-yl)methanone
[1-(4-chlorobenzyl)-5-methyl-2-(chloro)-1H-indol-3-yl](2-pyrimidin-4-yl-1,3-oxazol-5-yl)methanone
[5-chloro-1-(4-chlorobenzyl)-2-(chloro)-1H-indol-3-yl](2-pyrimidin-4-yl-1,3-oxazol-5-yl)methanone
[1-(4-chlorobenzyl)-2-(chloro)-1H-indol-3-yl](2-pyrimidin-4-yl-1,3-oxazol-5-yl)methanone
[1-(2,4-dichlorobenzyl)-5-methoxy-2-(chloro)-1H-indol-3-yl](2-pyrimidin-4-yl-1,3-oxazol-5-yl)methanone
[1-(2,4-dichlorobenzyl)-5-ethoxy-2-(chloro)-1H-indol-3-yl](2-pyrimidin-4-yl-1,3-oxazol-5-yl)methanone
[1-(2,4-dichlorobenzyl)-5-hydroxy-2-(chloro)-1H-indol-3-yl](2-pyrimidin-4-yl-1,3-oxazol-5-yl)methanone
[1-(2,4-dichlorobenzyl)-5-methyl-2-(chloro)-1H-indol-3-yl](2-pyrimidin-4-yl-1,3-oxazol-5-yl)methanone
[5-chloro-1-(2,4-dichlorobenzyl)-2-(chloro)-1H-indol-3-yl](2-pyrimidin-4-yl-1,3-oxazol-5-yl)methanone
[1-(2,4-dichlorobenzyl)-2-(chloro)-1H-indol-3-yl](2-pyrimidin-4-yl-1,3-oxazol-5-yl)methanone
[1-(4-chlorobenzyl)-5-methoxy-2-(chloro)-1H-indol-3-yl](5-phenyl-1,3-oxazol-2-yl)methanone
[1-(4-chlorobenzyl)-5-ethoxy-2-(chloro)-1H-indol-3-yl](5-phenyl-1,3-oxazol-2-yl)methanone
[1-(4-chlorobenzyl)-5-hydroxy-2-(chloro)-1H-indol-3-yl](5-phenyl-1,3-oxazol-2-yl)methanone
[1-(4-chlorobenzyl)-5-methyl-2-(chloro)-1H-indol-3-yl](5-phenyl-1,3-oxazol-2-yl)methanone
[5-chloro-1-(4-chlorobenzyl)-2-(chloro)-1H-indol-3-yl](5-phenyl-1,3-oxazol-2-yl)methanone
[1-(4-chlorobenzyl)-2-(chloro)-1H-indol-3-yl](5-phenyl-1,3-oxazol-2-yl)methanone
[1-(2,4-dichlorobenzyl)-5-methoxy-2-(chloro)-1H-indol-3-yl](5-phenyl-1,3-oxazol-2-yl)methanone
[1-(2,4-dichlorobenzyl)-5-ethoxy-2-(chloro)-1H-indol-3-yl](5-phenyl-1,3-oxazol-2-yl)methanone
[1-(2,4-dichlorobenzyl)-5-hydroxy-2-(chloro)-1H-indol-3-yl](5-phenyl-1,3-oxazol-2-yl)methanone
[1-(2,4-dichlorobenzyl)-5-methyl-2-(chloro)-1H-indol-3-yl](5-phenyl-1,3-oxazol-2-yl)methanone
[5-chloro-1-(2,4-dichlorobenzyl)-2-(chloro)-1H-indol-3-yl](5-phenyl-1,3-oxazol-2-yl)methanone
[1-(4-chlorobenzyl)-5-methoxy-2-(chloro)-1H-indol-3-yl](5-pyridin-2-yl-1,3-oxazol-2-yl)methanone
[1-(4-chlorobenzyl)-5-ethoxy-2-(chloro)-1H-indol-3-yl](5-pyridin-2-yl-1,3-oxazol-2-yl)methanone
[1-(4-chlorobenzyl)-5-hydroxy-2-(chloro)-1H-indol-3-yl](5-pyridin-2-yl-1,3-oxazol-2-yl)methanone
[1-(4-chlorobenzyl)-5-methyl-2-(chloro)-1H-indol-3-yl](5-pyridin-2-yl-1,3-oxazol-2-yl)methanone
[5-chloro-1-(4-chlorobenzyl)-2-(chloro)-1H-indol-3-yl](5-pyridin-2-yl-1,3-oxazol-2-yl)methanone
[1-(4-chlorobenzyl)-2-(chloro)-1H-indol-3-yl](5-pyridin-2-yl-1,3-oxazol-2-yl)methanone
[1-(2,4-dichlorobenzyl)-5-methoxy-2-(chloro)-1H-indol-3-yl](5-pyridin-2-yl-1,3-oxazol-2-yl)methanone
[1-(2,4-dichlorobenzyl)-5-ethoxy-2-(chloro)-1H-indol-3-yl](5-pyridin-2-yl-1,3-oxazol-2-yl)methanone
[1-(2,4-dichlorobenzyl)-5-hydroxy-2-(chloro)-1H-indol-3-yl](5-pyridin-2-yl-1,3-oxazol-2-yl)methanone
[1-(2,4-dichlorobenzyl)-5-methyl-2-(chloro)-1H-indol-3-yl](5-pyridin-2-yl-1,3-oxazol-2-yl)methanone
[5-chloro-1-(2,4-dichlorobenzyl)-2-(chloro)-1H-indol-3-yl](5-pyridin-2-yl-1,3-oxazol-2-yl)methanone
[1-(2,4-dichlorobenzyl)-2-(chloro)-1H-indol-3-yl](5-pyridin-2-yl-1,3-oxazol-2-yl)methanone
[1-(4-chlorobenzyl)-5-methoxy-2-(chloro)-1H-indol-3-yl](5-pyridin-3-yl-1,3-oxazol-2-yl)methanone
[1-(4-chlorobenzyl)-5-ethoxy-2-(chloro)-1H-indol-3-yl](5-pyridin-3-yl-1,3-oxazol-2-yl)methanone
[1-(4-chlorobenzyl)-5-hydroxy-2-(chloro)-1H-indol-3-yl](5-pyridin-3-yl-1,3-oxazol-2-yl)methanone
[1-(4-chlorobenzyl)-5-methyl-2-(chloro)-1H-indol-3-yl](5-pyridin-3-yl-1,3-oxazol-2-yl)methanone
[5-chloro-1-(4-chlorobenzyl)-2-(chloro)-1H-indol-3-yl](5-pyridin-3-yl-1,3-oxazol-2-yl)methanone
[1-(4-chlorobenzyl)-2-(chloro)-1H-indol-3-yl](5-pyridin-3-yl-1,3-oxazol-2-yl)methanone
[1-(2,4-dichlorobenzyl)-5-methoxy-2-(chloro)-1H-indol-3-yl](5-pyridin-3-yl-1,3-oxazol-2-yl)methanone
[1-(2,4-dichlorobenzyl)-5-ethoxy-2-(chloro)-1H-indol-3-yl](5-pyridin-3-yl-1,3-oxazol-2-yl)methanone
[1-(2,4-dichlorobenzyl)-5-hydroxy-2-(chloro)-1H-indol-3-yl](5-pyridin-3-yl-1,3-oxazol-2-yl)methanone
[1-(2,4-dichlorobenzyl)-5-methyl-2-(chloro)-1H-indol-3-yl](5-pyridin-3-yl-1,3-oxazol-2-yl)methanone
[5-chloro-1-(2,4-dichlorobenzyl)-2-(chloro)-1H-indol-3-yl](5-pyridin-3-yl-1,3-oxazol-2-yl)methanone
[1-(2,4-dichlorobenzyl)-2-(chloro)-1H-indol-3-yl](5-pyridin-3-yl-1,3-oxazol-2-yl)methanone
[1-(4-chlorobenzyl)-5-methoxy-2-(chloro)-1H-indol-3-yl](5-pyridin-4-yl-1,3-oxazol-2-yl)methanone
[1-(4-chlorobenzyl)-5-ethoxy-2-(chloro)-1H-indol-3-yl](5-pyridin-4-yl-1,3-oxazol-2-yl)methanone
[1-(4-chlorobenzyl)-5-hydroxy-2-(chloro)-1H-indol-3-yl](5-pyridin-4-yl-1,3-oxazol-2-yl)methanone
[1-(4-chlorobenzyl)-5-methyl-2-(chloro)-1H-indol-3-yl](5-pyridin-4-yl-1,3-oxazol-2-yl)methanone
[5-chloro-1-(4-chlorobenzyl)-2-(chloro)-1H-indol-3-yl](5-pyridin-4-yl-1,3-oxazol-2-yl)methanone
[1-(4-chlorobenzyl)-2-(chloro)-1H-indol-3-yl](5-pyridin-4-yl-1,3-oxazol-2-yl)methanone
[1-(2,4-dichlorobenzyl)-5-methoxy-2-(chloro)-1H-indol-3-yl](5-pyridin-4-yl-1,3-oxazol-2-yl)methanone
[1-(2,4-dichlorobenzyl)-5-ethoxy-2-(chloro)-1H-indol-3-yl](5-pyridin-4-yl-1,3-oxazol-2-yl)methanone
[1-(2,4-dichlorobenzyl)-5-hydroxy-2-(chloro)-1H-indol-3-yl](5-pyridin-4-yl-1,3-oxazol-2-yl)methanone
[1-(2,4-dichlorobenzyl)-5-methyl-2-(chloro)-1H-indol-3-yl](5-pyridin-5-yl-1,3-oxazol-2-yl)methanone
[5-chloro-1-(2,4-dichlorobenzyl)-2-(chloro)-1H-indol-3-yl](5-pyridin-4-yl-1,3-oxazol-2-yl)methanone
[1-(2,4-dichlorobenzyl)-1-(chloro)-1H-indol-3-yl](5-pyridin-4-yl-1,3-oxazol-2-yl)methanone
[1-(4-chlorobenzyl)-5-methoxy-2-(chloro)-1H-indol-3-yl](5-pyrimidin-4-yl-1,3-oxazol-2-yl)methanone
[1-(4-chlorobenzyl)-5-ethoxy-2-(chloro)-1H-indol-3-yl](5-pyrimidin-4-yl-1,3-oxazol-2-yl)methanone
[1-(4-chlorobenzyl)-5-hydroxy-2-(chloro)-1H-indol-3-yl](5-pyrimidin-4-yl-1,3-oxazol-2-yl)methanone
[1-(4-chlorobenzyl)-5-methyl-2-(chloro)-1H-indol-3-yl](5-pyrimidin-4-yl-1,3-oxazol-2-yl)methanone
[5-chloro-1-(4-chlorobenzyl)-2-(chloro)-1H-indol-3-yl](5-pyrimidin-4-yl-1,3-oxazol-2-yl)methanone

[1-(4-chlorobenzyl)-2-(chloro)-1H-indol-3-yl](5-pyrimidin-4-yl-1,3-oxazol-2-yl)methanone

[1-(2,4-dichlorobenzyl)-5-methoxy-2-(chloro)-1H-indol-3-yl](5-pyrimidin-4-yl-1,3-oxazol-2-yl)methanone

[1-(2,4-dichlorobenzyl)-5-ethoxy-2-(chloro)-1H-indol-3-yl](5-pyrimidin-4-yl-1,3-oxazol-2-yl)methanone

[1-(2,4-dichlorobenzyl)-5-hydroxy-2-(chloro)-1H-indol-3-yl](5-pyrimidin-4-yl-1,3-oxazol-2-yl)methanone

[1-(2,4-dichlorobenzyl)-5-methyl-2-(chloro)-1H-indol-3-yl](5-pyrimidin-4-yl-1,3-oxazol-2-yl)methanone

[1-(2,4-dichlorobenzyl)-5-hydroxy-2-(chloro)-1H-indol-3-yl](5-phenyl-1,3,4-oxadiazol-2-yl)methanone

[5-chloro-1-(2,4-dichlorobenzyl)-2-(chloro)-1H-indol-3-yl](5-pyrimidin-4-yl-1,3-oxazol-2-yl)methanone

[1-(2,4-dichlorobenzyl)-2-(chloro)-1H-indol-3-yl](5-pyrimidin-4-yl-1,3-oxazol-2-yl)methanone Also useful are derivatives of the compounds below wherein the carbonyl group attached to the indole N (directly or indirectly) is replaced by —CH$_2$—.

(4-Chloro-phenyl)-[3-(5-pyridin-2-yl-[1,3,4]oxadiazole-2-carbonyl)-indol-1-yl]-methanone (4-Chloro-phenyl)-[5-methoxy-2-methyl-3-(5-pyridin-2-yl-[1,3,4]oxadiazole-2-carbonyl)-indol-1-yl]-methanone

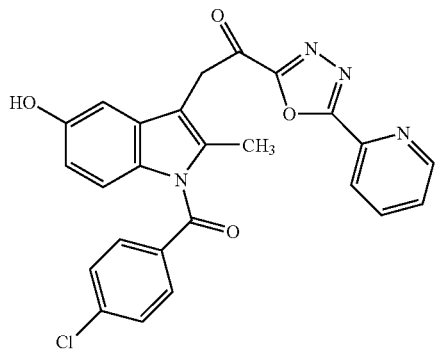

2-[1-(4-Chloro-benzoyl)-5-hydroxy-2-methyl-1H-indol-3-yl]-1-(5-pyridin-2-yl-[1,3,4]oxadiazol-2-yl)-ethanone

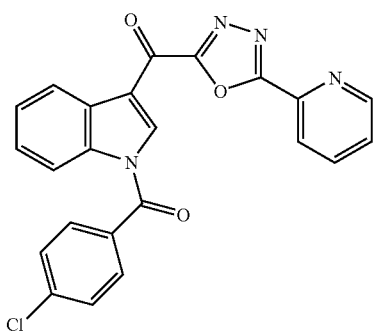

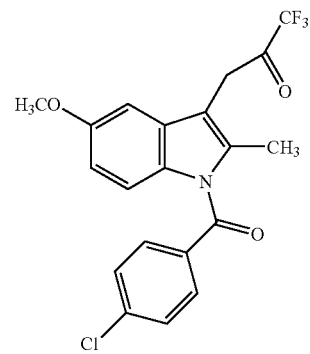

3-[1-(4-Chloro-benzoyl)-5-methoxy-2-methyl-1H-indol-3-yl]-1,1,1-trifluoro-propan-2-one

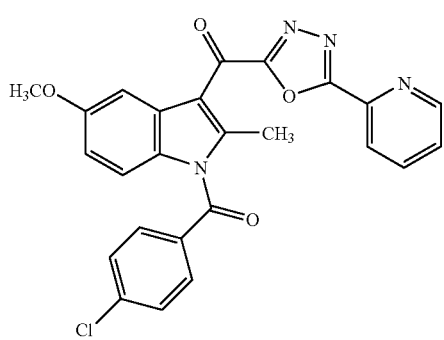

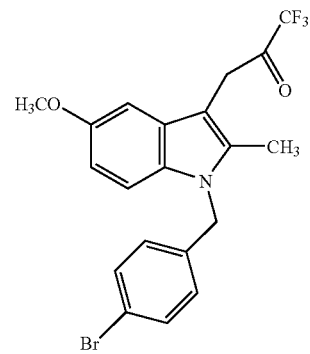

| 149 | 150 |
|---|---|
| 3-[1-(4-Bromo-benzyl)-5-methoxy-2-methyl-1H-indol-3-yl]-1,1,1-trifluoro-propan-2-one | (4-Chloro-phenyl)-[5-methoxy-2-methyl-3-(5-pyridin-2-yl-oxazole-2-carbonyl)-indol-1-yl]-methanone |

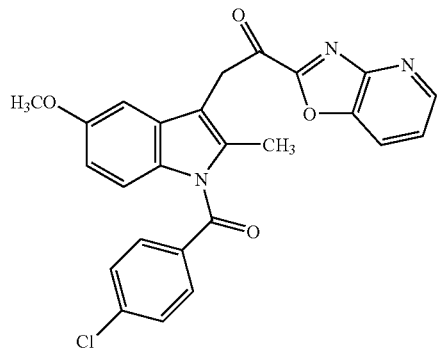

2-[1-(4-Chloro-benzoyl)-5-methoxy-2-methyl-1H-indol-3-yl]-1-oxazolo[4,5-b]pyridin-2-yl-ethanone

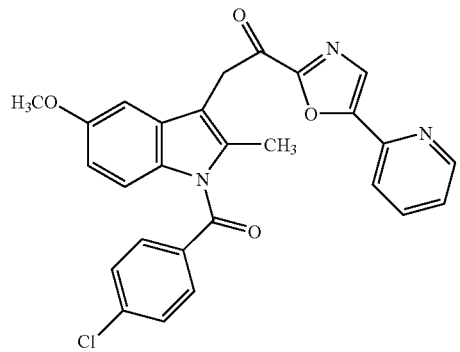

2-[1-(4-Chloro-benzoyl)-5-methoxy-2-methyl-1H-indol-3-yl]-1-(5-pyridin-2-yl-oxazol-2-yl)-ethanone

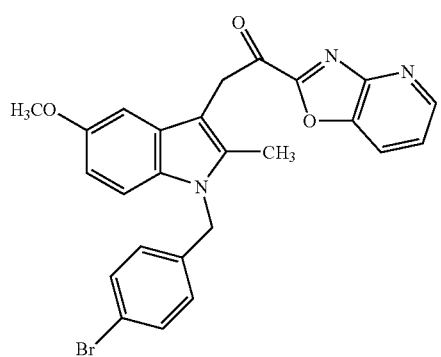

2-[1-(4-Bromo-benzyl)-5-methoxy-2-methyl-1H-indol-3-yl]-1-oxazolo[4,5-b]pyridin-2-yl-ethanone

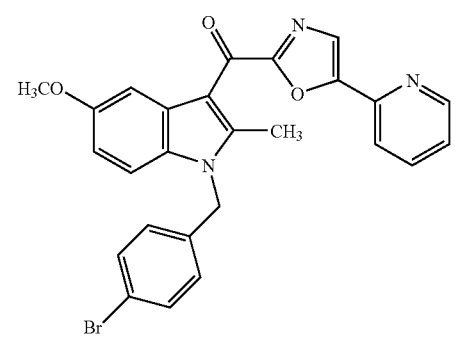

[1-(4-Bromo-benzyl)-5-methoxy-2-methyl-1H-indol-3-yl]-(5-pyridin-2-yl-oxazol-2-yl)-methanone

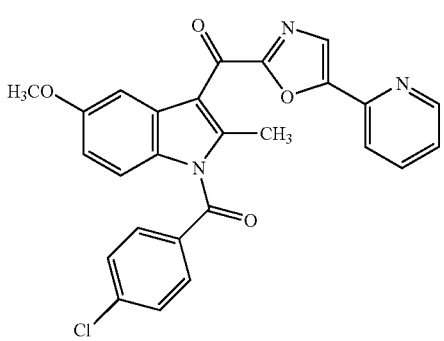

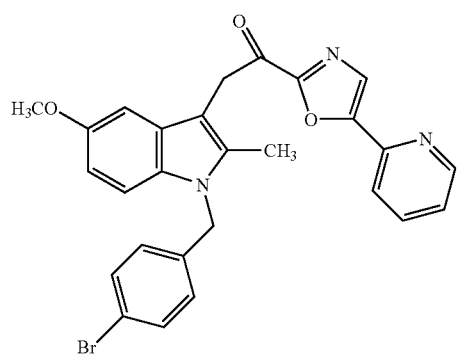

151

2-[1-(4-Bromo-benzyl)-5-methoxy-2-methyl-1H-indol-3-yl]-1-(5-pyridin-2-yl-oxazol-2-yl)-ethanone

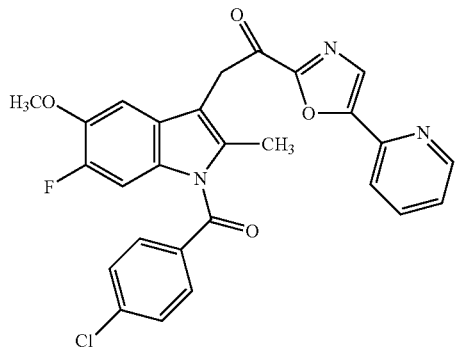

2-[1-(4-Chloro-benzoyl)-6-fluoro-5-methoxy-2-methyl-1H-indol-3-yl]-1-(5-pyridin-2-yl-oxazol-2-yl)-ethanone

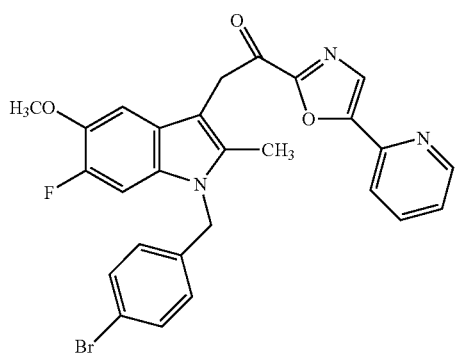

2-[1-(4-Bromo-benzyl)-6-fluoro-5-methoxy-2-methyl-1H-indol-3-yl]-1-(5-pyridin-2-yl-oxazol-2-yl)-ethanone

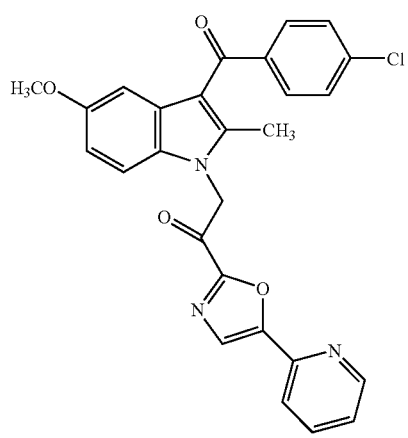

152

2-[3-(4-Chloro-benzoyl)-5-methoxy-2-methyl-indol-1-yl]-1-(5-pyridin-2-yl-oxazol-2-yl)-ethanone

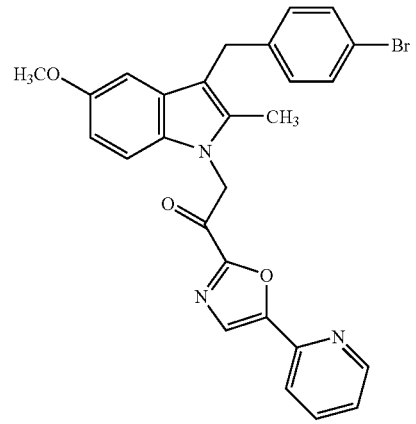

2-[3-(4-Bromo-benzyl)-5-methoxy-2-methyl-indol-1-yl]-1-(5-pyridin-2-yl-oxazol-2-yl)-ethanone

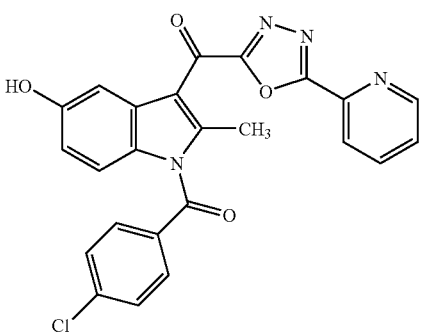

(4-Chloro-phenyl)-[5-hydroxy-2-methyl-3-(5-pyridin-2-yl-[1,3,4]oxadiazole-2-carbonyl)-indol-1-yl]-methanone

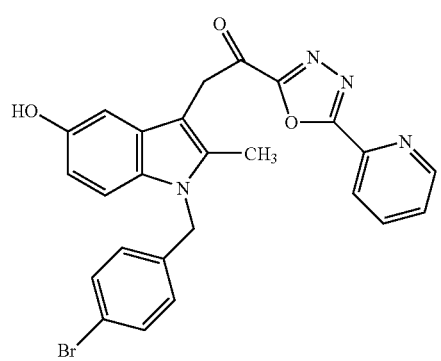

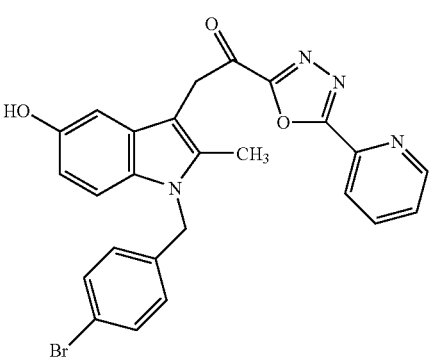

153

2-[1-(4-Bromobenzyl)-5-hydroxy-2-methyl-1H-indol-3-yl]-1-(5-pyridin-2-yl-[1,3,4]oxadiazol-2-yl)-ethanone

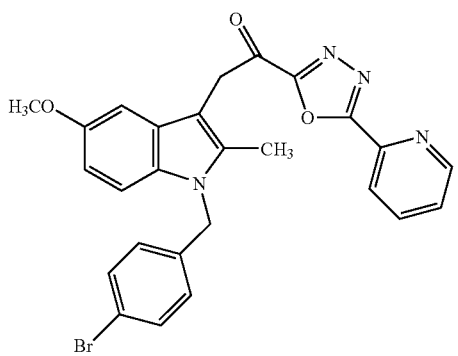

2-[1-(4-Bromobenzyl)-5-methoxy-2-methyl-1H-indol-3-yl]-1-(5-pyridin-2-yl-[1,3,4]oxadiazol-2-yl)-ethanone

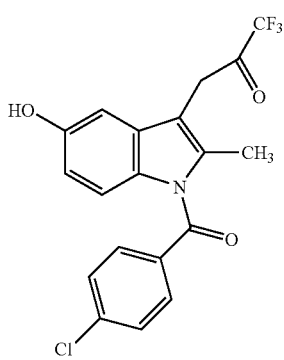

3-[1-(4-Chloro-benzoyl)-5-hydroxy-2-methyl-1H-indol-3-yl]-1,1,1-trifluoro-propan-2-one

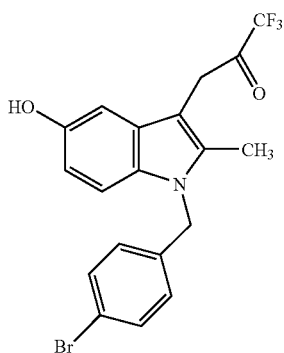

154

3-[1-(4-Bromo-benzyl)-5-hydroxy-2-methyl-1H-indol-3-yl]-1,1,1-trifluoro-propan-2-one

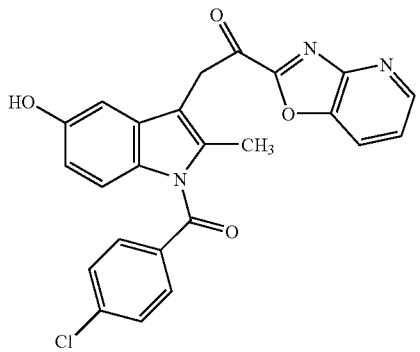

2-[1-(4-Chloro-benzoyl)-5-hydroxy-2-methyl-1H-indol-3-yl]-1-oxazolo[4,5-b]pyridin-2-yl-ethanone

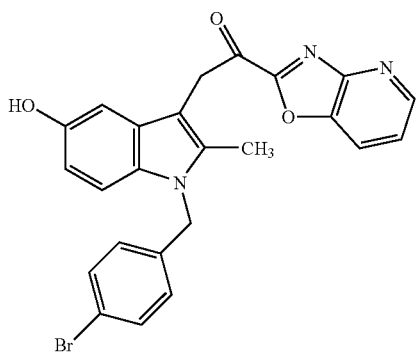

2-[1-(4-Bromo-benzyl)-5-hydroxy-2-methyl-1H-indol-3-yl]-1-oxazolo[4,5-b]pyridin-2-yl-ethanone

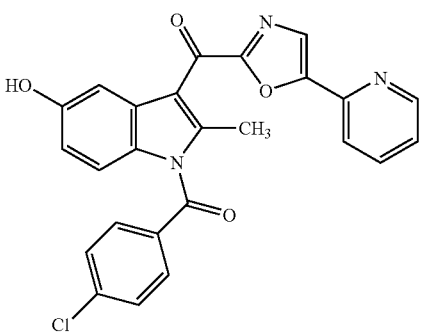

155

(4-Chloro-phenyl)-[5-hydroxy-2-methyl-3-(5-pyridin-2-yl-oxazole-2-carbonyl)-indol-1-yl]methanone

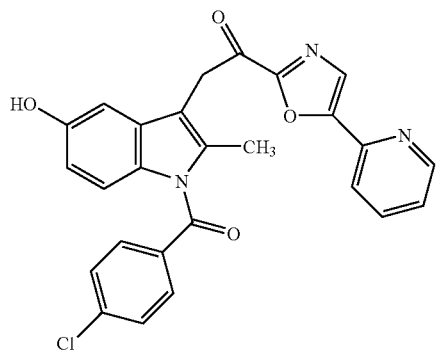

2-[1-(4-Chloro-benzoyl)-5-hydroxy-2-methyl-1H-indol-3-yl]-1-(5-pyridin-2-yl-oxazol-2-yl)-ethanone

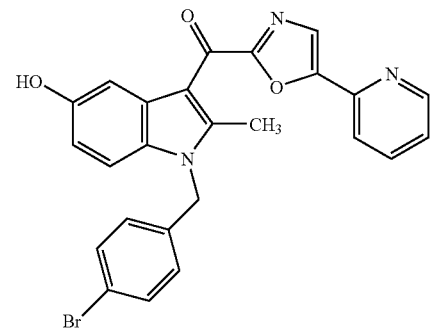

[1-(4-Bromo-benzyl)-5-hydroxy-2-methyl-1H-indol-3-yl]-(5-pyridin-2-yl-oxazol-2-yl)-methanone

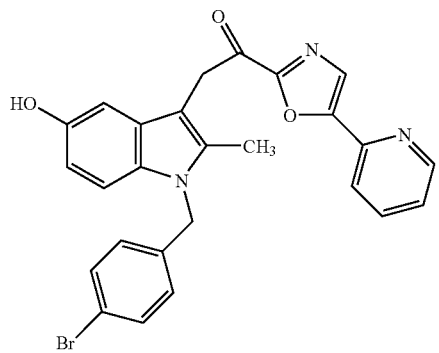

156

2-[1-(4-Bromo-benzyl)-5-hydroxy-2-methyl-1H-indol-3-yl]-1-(5-pyridin-2-yl-oxazol-2-yl)-ethanone

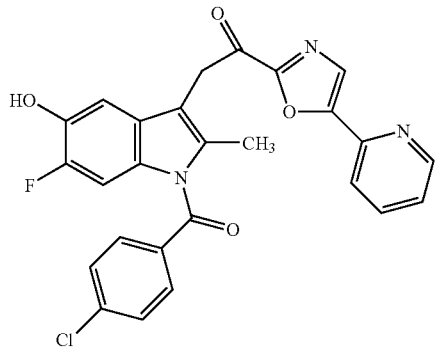

2-[1-(4-Chloro-benzoyl)-6-fluoro-5-hydroxy-2-methyl-1H-indol-3-yl]-1-(5-pyridin-2-yl-oxazol-2-yl)-ethanone

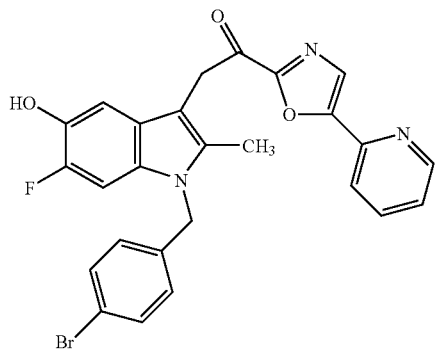

2-[1-(4-Bromo-benzyl)-6-fluoro-5-hydroxy-2-methyl-1H-indol-3-yl]-1-(5-pyridin-2-yl-oxazol-2-yl)-ethanone

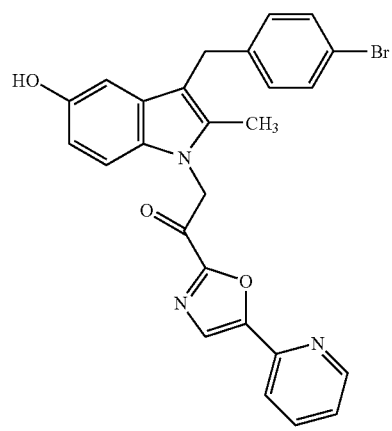

157

2-[3-(4-Bromo-benzyl)-5-hydroxy-2-methyl-indol-1-yl]-1-(5-pyridin-2-yl-oxazol-2-yl)-ethanone

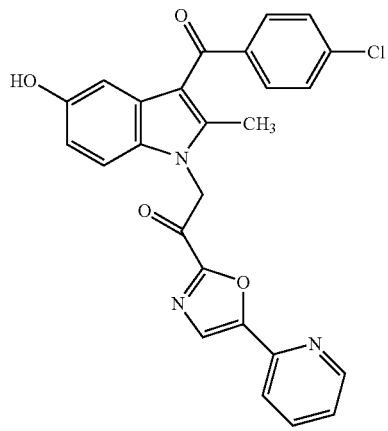

2-[3-(4-Chloro-benzoyl)-5-hydroxy-2-methyl-indol-1-yl]-1-(5-pyridin-2-yl-oxazol-2-yl)-ethanone

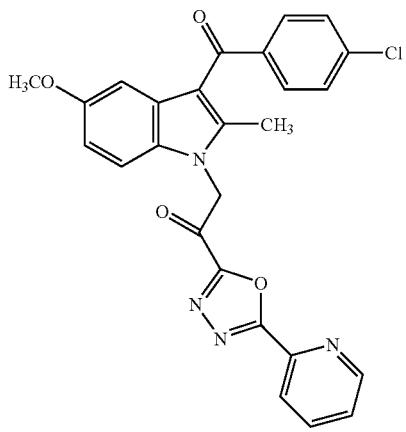

2-[3-(4-Chloro-benzoyl)-5-methoxy-2-methyl-indol-1-yl]-1-(5-pyridin-2-yl-[1,3,4]oxadiazol-2-yl)-ethanone

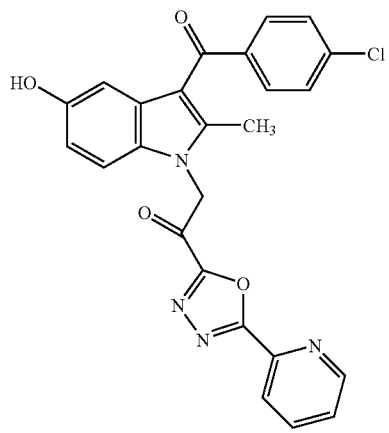

158

2-[3-(4-Chloro-benzoyl)-5-hydroxy-2-methyl-indol-1-yl]-1-(5-pyridin-2-yl[1,3,4]oxadiazo-2-yl)-ethanone 2-[3-(4-Bromo-benzyl)-5-hydroxy-2-methyl-indol-1-yl]-1-(5-pyridin-2-yl-[1,3,4]oxadiazol-2-yl)ethanone

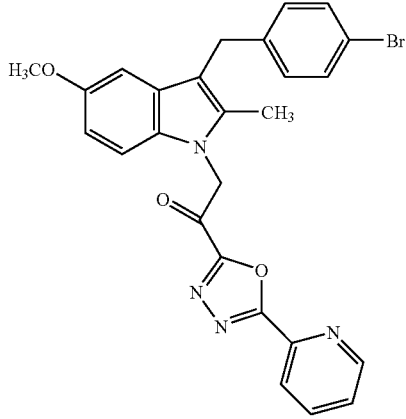

2-[3-(4-Bromo-benzyl)-5-methoxy-2-methyl-indol-1-yl]-1-(5-pyridin-2-yl-[1,3,4]oxadiazol-2-yl)-ethanone

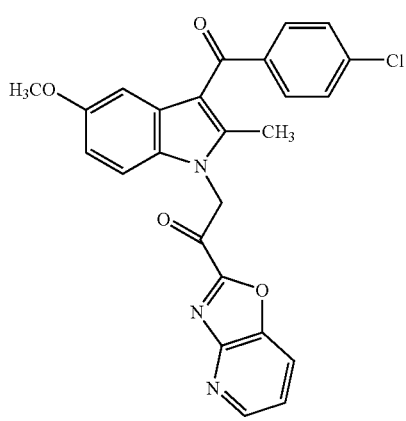

| 159 | 160 |
|---|---|
| 2-[3-(4-Chloro-benzoyl)-5-methoxy-2-methyl-indol-1-yl]-1-oxazolo[4,5-b]pyridin-2-yl-ethanone | 2-[3-(4-Bromobenzyl)-5-hydroxy-2-methyl-indol-1-yl]-1-oxazolo[4,5-b]pyridin-2-yl-ethanone |

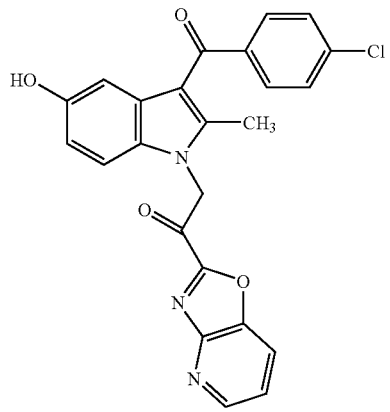

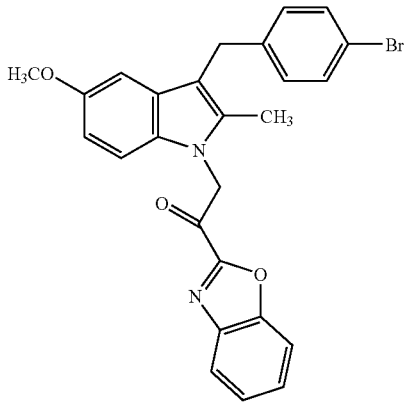

2-[3-(4-Chloro-benzoyl)-5-hydroxy-2-methyl-indol-1-yl]-1-oxazolo[4,5-b]pyridin-2-yl-ethanone 1-Benzooxazol-2-yl-2-[3-(4-bromo-benzyl)-5-methoxy-2-methyl-indol-1-yl]-ethanone

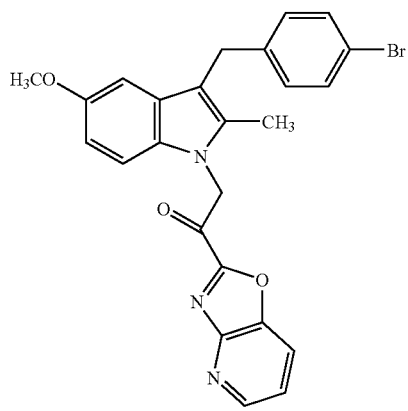

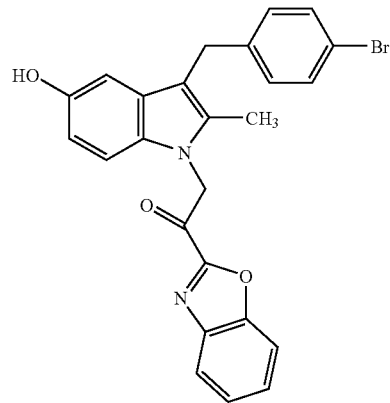

2-[3-(4-Bromobenzyl)-5-methoxy-2-methyl-indol-1-yl]-1-oxazolo[4,5-b]pyridin-2-yl-ethanone 1-Benzooxazol-2-yl-2-[3-(4-bromo-benzyl)-5-hydroxy-2-methyl-indol-1-yl]-ethanone

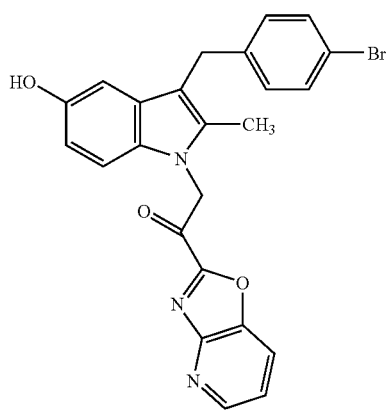

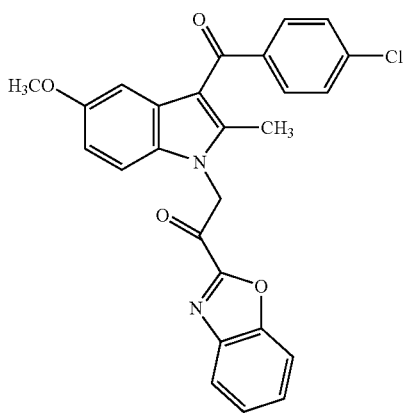

1-Benzooxazol-2-yl-2-[3-(4-chlorobenzoyl)-5-methoxy-2-methyl-indol-1-yl]-ethanone

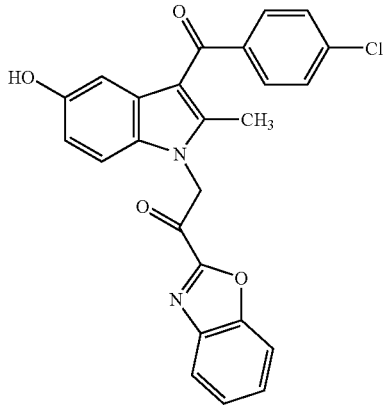

1-Benzooxazol-2-yl-2-[3-(4-chlorobenzoyl)-5-hydroxy-2-methyl-indol-1-yl]-ethanone

[1-(2,4-dichlorobenzyl)-5-methoxy-2-methyl-1H-indol-3-yl](3-pyridin-2-yl-1,2,4-oxadiazol-5-yl)methanone
[1-(4-chlorobenzyl)-5-methoxy-2-methyl-1H-indol-3-yl](3-pyridin-2-yl-1,2,4-oxadiazol-5-yl)methanone
[5-methoxy-1-(4-methoxybenzyl)-2-methyl-1H-indol-3-yl](3-pyridin-2-yl-1,2,4-oxadiazol-5-yl)methanone
[1-(4-chlorobenzyl)-5-methoxy-2-methyl-1H-indol-3-yl](5-pyridin-2-yl-1,3,4-oxadiazol-2-yl)methanone
[1-(2,4-dichlorobenzyl)-5-methoxy-2-methyl-1H-indol-3-yl](5-pyridin-2-yl-1,3,4-oxadiazol-2-yl)methanone
[1-(4-chlorobenzyl)-5-methoxy-2-methyl-1H-indol-3-yl][5-(2-furyl)-1,3,4-oxadiazol-2-yl]methanone [1-(4-chlorobenzyl)-5-methoxy-2-methyl-1H-indol-3-yl]([1,3]oxazolo[4,5-b]pyridin-2-yl)methanone [1-(4-bromobenzyl)-5-methoxy-2-methyl-1H-indol-3-yl](5-pyridin-2-yl-1,3,4-oxadiazol-2-yl)methanone
[5-methoxy-1-(4-methoxybenzyl)-2-methyl-1H-indol-3-yl](5-pyridin-2-yl-1,3,4-oxadiazol-2-yl)methanone
[1-(4-chlorobenzyl)-5-methoxy-2-methyl-1H-indol-3-yl](5-pyridin-3-yl-1,3,4-oxadiazol-2-yl)methanone
{1-[(5-chloro-2-thienyl)methyl]-5-methoxy-2-methyl-1H-indol-3-yl}(5-pyridin-2-yl-1,3,4-oxadiazol-2-yl)methanone
[1-(4-fluorobenzyl)-5-methoxy-2-methyl-1H-indol-3-yl](5-pyridin-2-yl-1,3,4-oxadiazol-2-yl)methanone
[1-(4-chlorobenzyl)-5-methoxy-2-methyl-1H-indol-3-yl](5-pyridin-4-yl-1,3,4-oxadiazol-2-yl)methanone
{1-[2-(2-chlorophenyl)ethyl]-5-methoxy-2-methyl-1H-indol-3-yl}(5-pyridin-2-yl-1,3,4-oxadiazol-2-yl)methanone
[5-methoxy-2-methyl-1-(4-methylbenzyl)-1H-indol-3-yl](5-pyridin-2-yl-1,3,4-oxadiazol-2-yl)methanone
[1-(4-chlorobenzyl)-5-methoxy-2-methyl-1H-indol-3-yl](5-phenyl-1,3,4-oxadiazol-2-yl)methanone
[1-(3,4-dichlorobenzyl)-5-methoxy-2-methyl-1H-indol-3-yl](5-pyridin-2-yl-1,3,4-oxadiazol-2-yl)methanone
{1-[2-(3-chlorophenyl)ethyl]-5-methoxy-2-methyl-1H-indol-3-yl}(5-pyridin-2-yl-1,3,4-oxadiazol-2-yl)methanone
[1-(4-bromobenzyl)-5-hydroxy-2-methyl-1H-indol-3-yl](5-pyridin-2-yl-1,3,4-oxadiazol-2-yl)methanone
{1-[2-(4-chlorophenyl)ethyl]-5-methoxy-2-methyl-1H-indol-3-yl}(5-pyridin-2-yl-1,3,4-oxadiazol-2-yl)methanone
[1-(3,5-dichlorobenzyl)-5-methoxy-2-methyl-1H-indol-3-yl](5-pyridin-2-yl-1,3,4-oxadiazol-2-yl)methanone
(1-benzyl-5-methoxy-2-methyl-1H-indol-3-yl)(5-pyridin-2-yl-1,3,4-oxadiazol-2-yl)methanone
[1-(2-chlorobenzyl)-5-methoxy-2-methyl-1H-indol-3-yl](5-pyridin-2-yl-1,3,4-oxadiazol-2-yl)methanone
{5-methoxy-2-methyl-1-[4-(trifluoromethyl)benzyl]-1H-indol-3-yl}(5-pyridin-2-yl-1,3,4-oxadiazol-2-yl)methanone
[5-hydroxy-2-methyl-1-(4-methylbenzyl)-1H-indol-3-yl](5-pyridin-2-yl-1,3,4-oxadiazol-2-yl)methanone
[1-(3,4-dichlorobenzyl)-5-hydroxy-2-methyl-1H-indol-3-yl](5-pyridin-2-yl-1,3,4-oxadiazol-2-yl)methanone
[1-(3-chlorobenzyl)-5-methoxy-2-methyl-1H-indol-3-yl](5-pyridin-2-yl-1,3,4-oxadiazol-2-yl)methanone
{5-methoxy-2-methyl-1-[4-(trifluoromethoxy)benzyl]-1H-indol-3-yl}(5-pyridin-2-yl-1,3,4-oxadiazol-2-yl)methanone
[1-(4-chlorobenzyl)-5-methoxy-2-methyl-1H-indol-3-yl](5-pyridin-2-yl-2-thienyl)methanone
[5-chloro-1-(4-chlorobenzyl)-2-methyl-1H-indol-3-yl](5-pyridin-2-yl-1,3,4-oxadiazol-2-yl)methanone
1-[1-(4-chlorobenzyl)-5-methoxy-2-methyl-1H-indol-3-yl]-2,2,2-trifluoroethanone
[5-chloro-1-(4-methoxybenzyl)-2-methyl-1H-indol-3-yl](5-pyridin-2-yl-1,3,4-oxadiazol-2-yl)methanone
[2-chloro-1-(4-chlorobenzyl)-5-methoxy-1H-indol-3-yl](5-pyridin-2-yl-1,3,4-oxadiazol-2-yl)methanone
[2-chloro-1-(4-chlorobenzyl)-5-methoxy-1H-indol-3-yl](3-pyridin-2-yl-1,2,4-oxadiazol-5-yl)methanone
[1-(4-chlorobenzyl)-5-ethoxy-2-methyl-1H-indol-3-yl](5-pyridin-2-yl-1,3,4-oxadiazol-2-yl)methanone
[1-(4-fluorobenzyl)-5-methoxy-2-methyl-1H-indol-3-yl](3-pyridin-2-yl-1,2,4-oxadiazol-5-yl)methanone
[1-(4-chlorobenzyl)-5-ethoxy-2-methyl-1H-indol-3-yl](3-pyridin-2-yl-1,2,4-oxadiazol-5-yl)methanone
[1-(4-chlorobenzyl)-5-methoxy-1H-indol-3-yl](5-pyridin-2-yl-1,3,4-oxadiazol-2-yl)methanone
[1-(4-chlorobenzyl)-5-methoxy-1H-indol-3-yl](3-pyridin-2-yl-1,2,4-oxadiazol-5-yl)methanone
{1-[(2-chloropyridin-4-yl-methyl]-5-methoxy-2-methyl-1H-indol-3-yl}(5-pyridin-2-yl-1,3,4-oxadiazol-2-yl)methanone
[1-(4-chlorobenzyl)-5-methoxy-2-methyl-1H-indol-3-yl](3-pyridin-3-yl-1,2,4-oxadiazol-5-yl)methanone
[1-(4-chlorobenzyl)-7-methoxy-1H-indol-3-yl](5-pyridin-2-yl-1,3,4-oxadiazol-2-yl)methanone
[1-(4-chlorobenzyl)-5-methoxy-2-(trifluoromethyl)-1H-indol-3-yl](3-pyridin-2-yl-1,2,4-oxadiazol-5-yl)methanone
[1-(4-chlorobenzyl)-5-ethoxy-2-(trifluoromethyl)-1H-indol-3-yl](3-pyridin-2-yl-1,2,4-oxadiazol-5-yl)methanone
[1-(4-chlorobenzyl)-5-hydroxy-2-(trifluoromethyl)-1H-indol-3-yl](3-pyridin-2-yl-1,2,4-oxadiazol-5-yl)methanone
[1-(4-chlorobenzyl)-5-methyl-2-(trifluoromethyl)-1H-indol-3-yl](3-pyridin-2-yl-1,2,4-oxadiazol-5-yl)methanone
[5-chloro-1-(4-chlorobenzyl)-2-(trifluoromethyl)-1H-indol-3-yl](3-pyridin-2-yl-1,2,4-oxadiazol-5-yl)methanone
[1-(4-chlorobenzyl)-2-(trifluoromethyl)-1H-indol-3-yl](3-pyridin-2-yl-1,2,4-oxadiazol-5-yl)methanone
[1-(2,4-dichlorobenzyl)-5-methoxy-2-(trifluoromethyl)-1H-indol-3-yl](3-pyridin-2-yl-1,2,4-oxadiazol-5-yl)methanone
[1-(2,4-dichlorobenzyl)-5-ethoxy-2-(trifluoromethyl)-1H-indol-3-yl](3-pyridin-2-yl-1,2,4-oxadiazol-5-yl)methanone
[1-(2,4-dichlorobenzyl)-5-hydroxy-2-(trifluoromethyl)-1H-indol-3-yl](3-pyridin-2-yl-1,2,4-oxadiazol-5-yl)methanone

[1-(2,4-dichlorobenzyl)-5-methyl-2-(trifluoromethyl)-1H-indol-3-yl](3-pyridin-2-yl-1,2,4-oxadiazol-5-yl)methanone
[5-chloro-1-(2,4-dichlorobenzyl)-2-(trifluoromethyl)-1H-indol-3-yl](3-pyridin-2-yl-1,2,4-oxadiazol-5-yl)methanone
[1-(2,4-dichlorobenzyl)-2-(trifluoromethyl)-1H-indol-3-yl](3-pyridin-2-yl-1,2,4-oxadiazol-5-yl)methanone
[1-(4-chlorobenzyl)-5-methoxy-2-(trifluoromethyl)-1H-indol-3-yl](3-pyridin-3-yl-1,2,4-oxadiazol-5-yl)methanone
[1-(4-chlorobenzyl)-5-ethoxy-2-(trifluoromethyl)-1H-indol-3-yl](3-pyridin-3-yl-1,2,4-oxadiazol-5-yl)methanone
[1-(4-chlorobenzyl)-5-hydroxy-2-(trifluoromethyl)-1H-indol-3-yl](3-pyridin-3-yl-1,2,4-oxadiazol-5-yl)methanone
[1-(4-chlorobenzyl)-5-methyl-2-(trifluoromethyl)-1H-indol-3-yl](3-pyridin-3-yl-1,2,4-oxadiazol-5-yl)methanone
[5-chloro-1-(4-chlorobenzyl)-2-(trifluoromethyl)-1H-indol-3-yl](3-pyridin-3-yl-1,2,4-oxadiazol-5-yl)methanone
[1-(4-chlorobenzyl)-2-(trifluoromethyl)-1H-indol-3-yl](3-pyridin-3-yl-1,2,4-oxadiazol-5-yl)methanone
[1-(2,4-dichlorobenzyl)-5-methoxy-2-(trifluoromethyl)-1H-indol-3-yl](3-pyridin-3-yl-1,2,4-oxadiazol-5-yl)methanone
[1-(2,4-dichlorobenzyl)-5-ethoxy-2-(trifluoromethyl)-1H-indol-3-yl](3-pyridin-3-yl-1,2,4-oxadiazol-5-yl)methanone
[1-(2,4-dichlorobenzyl)-5-hydroxy-2-(trifluoromethyl)-1H-indol-3-yl](3-pyridin-3-yl-1,2,4-oxadiazol-5-yl)methanone
[1-(2,4-dichlorobenzyl)-5-methyl-2-(trifluoromethyl)-1H-indol-3-yl](3-pyridin-3-yl-1,2,4-oxadiazol-5-yl)methanone
[5-chloro-1-(2,4-dichlorobenzyl)-2-(trifluoromethyl)-1H-indol-3-yl](3-pyridin-3-yl-1,2,4-oxadiazol-5-yl)methanone
[1-(2,4-dichlorobenzyl)-2-(trifluoromethyl)-1H-indol-3-yl](3-pyridin-3-yl-1,2,4-oxadiazol-5-yl)methanone
[1-(4-chlorobenzyl)-5-methoxy-2-(trifluoromethyl)-1H-indol-3-yl](3-pyridin-4-yl-1,2,4-oxadiazol-5-yl)methanone
[1-(4-chlorobenzyl)-5-ethoxy-2-(trifluoromethyl)-1H-indol-3-yl](3-pyridin-4-yl-1,2,4-oxadiazol-5-yl)methanone
[1-(4-chlorobenzyl)-5-hydroxy-2-(trifluoromethyl)-1H-indol-3-yl](3-pyridin-4-yl-1,2,4-oxadiazol-5-yl)methanone
[1-(4-chlorobenzyl)-5-methyl-2-(trifluoromethyl)-1H-indol-3-yl](3-pyridin-4-yl-1,2,4-oxadiazol-5-yl)methanone
[5-chloro-1-(4-chlorobenzyl)-2-(trifluoromethyl)-1H-indol-3-yl](3-pyridin-4-yl-1,2,4-oxadiazol-5-yl)methanone
[1-(4-chlorobenzyl)-2-(trifluoromethyl)-1H-indol-3-yl](3-pyridin-4-yl-1,2,4-oxadiazol-5-yl)methanone
[1-(2,4-dichlorobenzyl)-5-methoxy-2-(trifluoromethyl)-1H-indol-3-yl](3-pyridin-4-yl-1,2,4-oxadiazol-5-yl)methanone
[1-(2,4-dichlorobenzyl)-5-ethoxy-2-(trifluoromethyl)-1H-indol-3-yl](3-pyridin-4-yl-1,2,4-oxadiazol-5-yl)methanone
[1-(2,4-dichlorobenzyl)-5-hydroxy-2-(trifluoromethyl)-1H-indol-3-yl](3-pyridin-4-yl-1,2,4-oxadiazol-5-yl)methanone
[1-(2,4-dichlorobenzyl)-5-methyl-2-(trifluoromethyl)-1H-indol-3-yl](3-pyridin-4-yl-1,2,4-oxadiazol-5-yl)methanone
[5-chloro-1-(2,4-dichlorobenzyl)-2-(trifluoromethyl)-1H-indol-3-yl](3-pyridin-4-yl-1,2,4-oxadiazol-5-yl)methanone
[1-(2,4-dichlorobenzyl)-2-(trifluoromethyl)-1H-indol-3-yl](3-pyridin-4-yl-1,2,4-oxadiazol-5-yl)methanone
[1-(4-chlorobenzyl)-5-methoxy-2-(trifluoromethyl)-1H-indol-3-yl](3-pyrimidin-4-yl-1,2,4-oxadiazol-5-yl)methanone
[1-(4-chlorobenzyl)-5-ethoxy-2-(trifluoromethyl)-1H-indol-3-yl](3-pyrimidin-4-yl-1,2,4-oxadiazol-5-yl)methanone
[1-(4-chlorobenzyl)-5-hydroxy-2-(trifluoromethyl)-1H-indol-3-yl](3-pyrimidin-4-yl-1,2,4-oxadiazol-5-yl)methanone
[1-(4-chlorobenzyl)-5-methyl-2-(trifluoromethyl)-1H-indol-3-yl](3-pyrimidin-4-yl-1,2,4-oxadiazol-5-yl)methanone
[5-chloro-1-(4-chlorobenzyl)-2-(trifluoromethyl)-1H-indol-3-yl](3-pyrimidin-4-yl-1,2,4-oxadiazol-5-yl)methanone
[1-(4-chlorobenzyl)-2-(trifluoromethyl)-1H-indol-3-yl](3-pyrimidin-4-yl-1,2,4-oxadiazol-5-yl)methanone
[1-(2,4-dichlorobenzyl)-5-methoxy-2-(trifluoromethyl)-1H-indol-3-yl](3-pyrimidin-4-yl-1,2,4-oxadiazol-5-yl)methanone
[1-(2,4-dichlorobenzyl)-5-ethoxy-2-(trifluoromethyl)-1H-indol-3-yl](3-pyrimidin-4-yl-1,2,4-oxadiazol-5-yl)methanone
[1-(2,4-dichlorobenzyl)-5-hydroxy-2-(trifluoromethyl)-1H-indol-3-yl](3-pyrimidin-4-yl-1,2,4-oxadiazol-5-yl)methanone
[1-(2,4-dichlorobenzyl)-5-methyl-2-(trifluoromethyl)-1H-indol-3-yl](3-pyrimidin-4-yl-1,2,4-oxadiazol-5-yl)methanone
[5-chloro-1-(2,4-dichlorobenzyl)-2-(trifluoromethyl)-1H-indol-3-yl](3-pyrimidin-4-yl-1,2,4-oxadiazol-5-yl)methanone
[1-(2,4-dichlorobenzyl)-2-(trifluoromethyl)-1H-indol-3-yl](3-pyrimidin-4-yl-1,2,4-oxadiazol-5-yl)methanone
[1-(4-chlorobenzyl)-5-methoxy-2-(trifluoromethyl)-1H-indol-3-yl](5-phenyl-1,2,4-oxadiazol-3-yl)methanone
[1-(4-chlorobenzyl)-5-ethoxy-2-(trifluoromethyl)-1H-indol-3-yl](5-phenyl-1,2,4-oxadiazol-3-yl)methanone
[1-(4-chlorobenzyl)-5-hydroxy-2-(trifluoromethyl)-1H-indol-3-yl](5-phenyl-1,2,4-oxadiazol-3-yl)methanone
[1-(4-chlorobenzyl)-5-methyl-2-(trifluoromethyl)-1H-indol-3-yl](5-phenyl-1,2,4-oxadiazol-3-yl)methanone
[5-chloro-1-(4-chlorobenzyl)-2-(trifluoromethyl)-1H-indol-3-yl](5-phenyl-1,2,4-oxadiazol-3-yl)methanone
[1-(4-chlorobenzyl)-2-(trifluoromethyl)-1H-indol-3-yl](5-phe [1-(2,4-dichlorobenzyl)-5-methoxy-2-(trifluoromethyl)-1H-indol-3-yl](5-phenyl-1,2,4-oxadiazol-3-yl)methanone
nyl-1,2,4-oxadiazol-3-yl)methanone
[1-(2,4-dichlorobenzyl)-5-ethoxy-2-(trifluoromethyl)-1H-indol-3-yl](5-phenyl-1,2,4-oxadiazol-3-yl)methanone
[1-(2,4-dichlorobenzyl)-5-hydroxy-2-(trifluoromethyl)-1H-indol-3-yl](5-phenyl-1,2,4-oxadiazol-3-yl)methanone
[1-(2,4-dichlorobenzyl)-5-methyl-2-(trifluoromethyl)-1H-indol-3-yl](5-phenyl-1,2,4-oxadiazol-3-yl)methanone
[5-chloro-1-(2,4-dichlorobenzyl)-2-(trifluoromethyl)-1H-indol-3-yl](5-phenyl-1,2,4-oxadiazol-3-yl)methanone
[1-(2,4-dichlorobenzyl)-2-(trifluoromethyl)-1H-indol-3-yl](5-phenyl-1,2,4-oxadiazol-3-yl)methanone
[1-(4-chlorobenzyl)-5-methoxy-2-(trifluoromethyl)-1H-indol-3-yl](5-pyridin-2-yl-1,2,4-oxadiazol-3-yl)methanone
[1-(4-chlorobenzyl)-5-ethoxy-2-(trifluoromethyl)-1H-indol-3-yl](5-pyridin-2-yl-1,2,4-oxadiazol-3-yl)methanone
[1-(4-chlorobenzyl)-5-hydroxy-2-(trifluoromethyl)-1H-indol-3-yl](5-pyridin-2-yl-1,2,4-oxadiazol-3-yl)methanone
[1-(4-chlorobenzyl)-5-methyl-2-(trifluoromethyl)-1H-indol-3-yl](5-pyridin-2-yl-1,2,4-oxadiazol-3-yl)methanone
[5-chloro-1-(4-chlorobenzyl)-2-(trifluoromethyl)-1H-indol-3-yl](5-pyridin-2-yl-1,2,4-oxadiazol-3-yl)methanone

[1-(4-chlorobenzyl)-2-(trifluoromethyl)-1H-indol-3-yl](5-pyridin-2-yl-1,2,4-oxadiazol-3-yl)methanone
[1-(2,4-dichlorobenzyl)-5-methoxy-2-(trifluoromethyl)-1H-indol-3-yl](5-pyridin-2-yl-1,2,4-oxadiazol-3-yl)methanone
[1-(2,4-dichlorobenzyl)-5-ethoxy-2-(trifluoromethyl)-1H-indol-3-yl](5-pyridin-2-yl-1,2,4-oxadiazol-3-yl)methanone
[1-(2,4-dichlorobenzyl)-5-hydroxy-2-(trifluoromethyl)-1H-indol-3-yl](5-pyridin-2-yl-1,2,4-oxadiazol-3-yl)methanone
[1-(2,4-dichlorobenzyl)-5-methyl-2-(trifluoromethyl)-1H-indol-3-yl](5-pyridin-2-yl-1,2,4-oxadiazol-3-yl)methanone
[5-chloro-1-(2,4-dichlorobenzyl)-2-(trifluoromethyl)-1H-indol-3-yl](5-pyridin-2-yl-1,2,4-oxadiazol-3-yl)methanone
[1-(2,4-dichlorobenzyl)-2-(trifluoromethyl)-1H-indol-3-yl](5-pyridin-2-yl-1,2,4-oxadiazol-3-yl)methanone
[1-(4-chlorobenzyl)-5-methoxy-2-(trifluoromethyl)-1H-indol-3-yl](5-pyridin-3-yl-1,2,4-oxadiazol-3-yl)methanone
[1-(4-chlorobenzyl)-5-ethoxy-2-(trifluoromethyl)-1H-indol-3-yl](5-pyridin-3-yl-1,2,4-oxadiazol-3-yl)methanone
[1-(4-chlorobenzyl)-5-hydroxy-2-(trifluoromethyl)-1H-indol-3-yl](5-pyridin-3-yl-1,2,4-oxadiazol-3-yl)methanone
[1-(4-chlorobenzyl)-5-methyl-2-(trifluoromethyl)-1H-indol-3-yl](5-pyridin-3-yl-1,2,4-oxadiazol-3-yl)methanone
[5-chloro-1-(4-chlorobenzyl)-2-(trifluoromethyl)-1H-indol-3-yl](5-pyridin-3-yl-1,2,4-oxadiazol-3-yl)methanone
[1-(4-chlorobenzyl)-2-(trifluoromethyl)-1H-indol-3-yl](5-pyridin-3-yl-1,2,4-oxadiazol-3-yl)methanone
[1-(2,4-dichlorobenzyl)-5-methoxy-2-(trifluoromethyl)-1H-indol-3-yl](5-pyridin-3-yl-1,2,4-oxadiazol-3-yl)methanone
[1-(2,4-dichlorobenzyl)-5-ethoxy-2-(trifluoromethyl)-1H-indol-3-yl](5-pyridin-3-yl-1,2,4-oxadiazol-3-yl)methanone
[1-(2,4-dichlorobenzyl)-5-hydroxy-2-(trifluoromethyl)-1H-indol-3-yl](5-pyridin-3-yl-1,2,4-oxadiazol-3-yl)methanone
[1-(2,4-dichlorobenzyl)-5-methyl-2-(trifluoromethyl)-1H-indol-3-yl](5-pyridin-3-yl-1,2,4-oxadiazol-3-yl)methanone
[5-chloro-1-(2,4-dichlorobenzyl)-2-(trifluoromethyl)-1H-indol-3-yl](5-pyridin-3-yl-1,2,4-oxadiazol-3-yl)methanone
[1-(2,4-dichlorobenzyl)-2-(trifluoromethyl)-1H-indol-3-yl](5-pyridin-3-yl-1,2,4-oxadiazol-3-yl)methanone
[1-(4-chlorobenzyl)-5-methoxy-2-(trifluoromethyl)-1H-indol-3-yl](5-pyridin-4-yl-1,2,4-oxadiazol-3-yl)methanone
[1-(4-chlorobenzyl)-5-ethoxy-2-(trifluoromethyl)-1H-indol-3-yl](5-pyridin-4-yl-1,2,4-oxadiazol-3-yl)methanone
[1-(4-chlorobenzyl)-5-hydroxy-2-(trifluoromethyl)-1H-indol-3-yl](5-pyridin-4-yl-1,2,4-oxadiazol-3-yl)methanone
[1-(4-chlorobenzyl)-5-methyl-2-(trifluoromethyl)-1H-indol-3-yl](5-pyridin-4-yl-1,2,4-oxadiazol-3-yl)methanone
[5-chloro-1-(4-chlorobenzyl)-2-(trifluoromethyl)-1H-indol-3-yl](5-pyridin-4-yl-1,2,4-oxadiazol-3-yl)methanone
[1-(4-chlorobenzyl)-2-(trifluoromethyl)-1H-indol-3-yl](5-pyridin-4-yl-1,2,4-oxadiazol-3-yl)methanone
[1-(2,4-dichlorobenzyl)-5-methoxy-2-(trifluoromethyl)-1H-indol-3-yl](5-pyridin-4-yl-1,2,4-oxadiazol-3-yl)methanone
[1-(2,4-dichlorobenzyl)-5-ethoxy-2-(trifluoromethyl)-1H-indol-3-yl](5-pyridin-4-yl-1,2,4-oxadiazol-3-yl)methanone
[1-(2,4-dichlorobenzyl)-5-hydroxy-2-(trifluoromethyl)-1H-indol-3-yl](5-pyridin-4-yl-1,2,4-oxadiazol-3-yl)methanone
[1-(2,4-dichlorobenzyl)-5-methyl-2-(trifluoromethyl)-1H-indol-3-yl](5-pyridin-4-yl-1,2,4-oxadiazol-3-yl)methanone
[5-chloro-1-(2,4-dichlorobenzyl)-2-(trifluoromethyl)-1H-indol-3-yl](5-pyridin-4-yl-1,2,4-oxadiazol-3-yl)methanone
[1-(2,4-dichlorobenzyl)-2-(trifluoromethyl)-1H-indol-3-yl](5-pyridin-4-yl-1,2,4-oxadiazol-3-yl)methanone
[1-(4-chlorobenzyl)-5-methoxy-2-(trifluoromethyl)-1H-indol-3-yl](5-pyrimidin-4-yl-1,2,4-oxadiazol-3-yl)methanone
[1-(4-chlorobenzyl)-5-ethoxy-2-(trifluoromethyl)-1H-indol-3-yl](5-pyrimidin-4-yl-1,2,4-oxadiazol-3-yl)methanone
[1-(4-chlorobenzyl)-5-hydroxy-2-(trifluoromethyl)-1H-indol-3-yl](5-pyrimidin-4-yl-1,2,4-oxadiazol-3-yl)methanone
[1-(4-chlorobenzyl)-5-methyl-2-(trifluoromethyl)-1H-indol-3-yl](5-pyrimidin-4-yl-1,2,4-oxadiazol-3-yl)methanone
[5-chloro-1-(4-chlorobenzyl)-2-(trifluoromethyl)-1H-indol-3-yl](5-pyrimidin-4-yl-1,2,4-oxadiazol-3-yl)methanone
[1-(4-chlorobenzyl)-2-(trifluoromethyl)-1H-indol-3-yl](5-pyrimidin-4-yl-1,2,4-oxadiazol-3-yl)methanone
[1-(2,4-dichlorobenzyl)-5-methoxy-2-(trifluoromethyl)-1H-indol-3-yl](5-pyrimidin-4-yl-1,2,4-oxadiazol-3-yl)methanone
[1-(2,4-dichlorobenzyl)-5-ethoxy-2-(trifluoromethyl)-1H-indol-3-yl](5-pyrimidin-4-yl-1,2,4-oxadiazol-3-yl)methanone
[1-(2,4-dichlorobenzyl)-5-hydroxy-2-(trifluoromethyl)-1H-indol-3-yl](5-pyrimidin-4-yl-1,2,4-oxadiazol-3-yl)methanone
[1-(2,4-dichlorobenzyl)-5-methyl-2-(trifluoromethyl)-1H-indol-3-yl](5-pyrimidin-4-yl-1,2,4-oxadiazol-3-yl)methanone
[5-chloro-1-(2,4-dichlorobenzyl)-2-(trifluoromethyl)-1H-indol-3-yl](5-pyrimidin-4-yl-1,2,4-oxadiazol-3-yl)methanone
[1-(2,4-dichlorobenzyl)-2-(trifluoromethyl)-1H-indol-3-yl](5-pyrimidin-4-yl-1,2,4-oxadiazol-3-yl)methanone
[1-(4-chlorobenzyl)-5-methoxy-2-(trifluoromethyl)-1H-indol-3-yl](5-phenyl-1,3,4-oxadiazol-2-yl)methanone
[1-(4-chlorobenzyl)-5-ethoxy-2-(trifluoromethyl)-1H-indol-3-yl](5-phenyl-1,3,4-oxadiazol-2-yl)methanone
[1-(4-chlorobenzyl)-5-hydroxy-2-(trifluoromethyl)-1H-indol-3-yl](5-phenyl-1,3,4-oxadiazol-2-yl)methanone
[1-(4-chlorobenzyl)-5-methyl-2-(trifluoromethyl)-1H-indol-3-yl](5-phenyl-1,3,4-oxadiazol-2-yl)methanone
[5-chloro-1-(4-chlorobenzyl)-2-(trifluoromethyl)-1H-indol-3-yl](5-phenyl-1,3,4-oxadiazol-2-yl)methanone
[1-(4-chlorobenzyl)-2-(trifluoromethyl)-1H-indol-3-yl](5-phenyl-1,3,4-oxadiazol-2-yl)methanone
[1-(2,4-dichlorobenzyl)-5-methoxy-2-(trifluoromethyl)-1H-indol-3-yl](5-phenyl-1,3,4-oxadiazol-2-yl)methanone
[1-(2,4-dichlorobenzyl)-5-ethoxy-2-(trifluoromethyl)-1H-indol-3-yl](5-phenyl-1,3,4-oxadiazol-2-yl)methanone
[1-(2,4-dichlorobenzyl)-5-hydroxy-2-(trifluoromethyl)-1H-indol-3-yl](5-phenyl-1,3,4-oxadiazol-2-yl)methanone
[1-(2,4-dichlorobenzyl)-5-methyl-2-(trifluoromethyl)-1H-indol-3-yl](5-phenyl-1,3,4-oxadiazol-2-yl)methanone
[5-chloro-1-(2,4-dichlorobenzyl)-2-(trifluoromethyl)-1H-indol-3-yl](5-phenyl-1,3,4-oxadiazol-2-yl)methanone
[1-(2,4-dichlorobenzyl)-2-(trifluoromethyl)-1H-indol-3-yl](5-phenyl-1,3,4-oxadiazol-2-yl)methanone

[1-(4-chlorobenzyl)-5-methoxy-2-(trifluoromethyl)-1H-indol-3-yl](5-pyridin-2-yl-1,3,4-oxadiazol-2-yl)methanone
[1-(4-chlorobenzyl)-5-ethoxy-2-(trifluoromethyl)-1H-indol-3-yl](5-pyridin-2-yl-1,3,4-oxadiazol-2-yl)methanone
[1-(4-chlorobenzyl)-5-hydroxy-2-(trifluoromethyl)-1H-indol-3-yl](5-pyridin-2-yl-1,3,4-oxadiazol-2-yl)methanone
[1-(4-chlorobenzyl)-5-methyl-2-(trifluoromethyl)-1H-indol-3-yl](5-pyridin-2-yl-1,3,4-oxadiazol-2-yl)methanone
[5-chloro-1-(4-chlorobenzyl)-2-(trifluoromethyl)-1H-indol-3-yl](5-pyridin-2-yl-1,3,4-oxadiazol-2-yl)methanone
[1-(4-chlorobenzyl)-2-(trifluoromethyl)-1H-indol-3-yl](5-pyridin-2-yl-1,3,4-oxadiazol-2-yl)methanone
[1-(2,4-dichlorobenzyl)-5-methoxy-2-(trifluoromethyl)-1H-indol-3-yl](5-pyridin-2-yl-1,3,4-oxadiazol-2-yl)methanone
[1-(2,4-dichlorobenzyl)-5-ethoxy-2-(trifluoromethyl)-1H-indol-3-yl](5-pyridin-2-yl-1,3,4-oxadiazol-2-yl)methanone
[1-(2,4-dichlorobenzyl)-5-hydroxy-2-(trifluoromethyl)-1H-indol-3-yl](5-pyridin-2-yl-1,3,4-oxadiazol-2-yl)methanone
[1-(2,4-dichlorobenzyl)-5-methyl-2-(trifluoromethyl)-1H-indol-3-yl](5-pyridin-2-yl-1,3,4-oxadiazol-2-yl)methanone
[5-chloro-1-(2,4-dichlorobenzyl)-2-(trifluoromethyl)-1H-indol-3-yl](5-pyridin-2-yl-1,3,4-oxadiazol-2-yl)methanone
[1-(2,4-dichlorobenzyl)-2-(trifluoromethyl)-1H-indol-3-yl](5-pyridin-2-yl-1,3,4-oxadiazol-2-yl)methanone
[1-(4-chlorobenzyl)-5-methoxy-2-(trifluoromethyl)-1H-indol-3-yl](5-pyridin-3-yl-1,3,4-oxadiazol-2-yl)methanone
[1-(4-chlorobenzyl)-5-ethoxy-2-(trifluoromethyl)-1H-indol-3-yl](5-pyridin-3-yl-1,3,4-oxadiazol-2-yl)methanone
[1-(4-chlorobenzyl)-5-hydroxy-2-(trifluoromethyl)-1H-indol-3-yl](5-pyridin-3-yl-1,3,4-oxadiazol-2-yl)methanone
[1-(4-chlorobenzyl)-5-methyl-2-(trifluoromethyl)-1H-indol-3-yl](5-pyridin-3-yl-1,3,4-oxadiazol-2-yl)methanone
[5-chloro-1-(4-chlorobenzyl)-2-(trifluoromethyl)-1H-indol-3-yl](5-pyridin-3-yl-1,3,4-oxadiazol-2-yl)methanone
[1-(4-chlorobenzyl)-2-(trifluoromethyl)-1H-indol-3-yl](5-pyridin-3-yl-1,3,4-oxadiazol-2-yl)methanone
[1-(2,4-dichlorobenzyl)-5-methoxy-2-(trifluoromethyl)-1H-indol-3-yl](5-pyridin-3-yl-1,3,4-oxadiazol-2-yl)methanone
[1-(2,4-dichlorobenzyl)-5-ethoxy-2-(trifluoromethyl)-1H-indol-3-yl](5-pyridin-3-yl-1,3,4-oxadiazol-2-yl)methanone
[1-(2,4-dichlorobenzyl)-5-hydroxy-2-(trifluoromethyl)-1H-indol-3-yl](5-pyridin-3-yl-1,3,4-oxadiazol-2-yl)methanone
[1-(2,4-dichlorobenzyl)-5-methyl-2-(trifluoromethyl)-1H-indol-3-yl](5-pyridin-3-yl-1,3,4-oxadiazol-2-yl)methanone
[5-chloro-1-(2,4-dichlorobenzyl)-2-(trifluoromethyl)-1H-indol-3-yl](5-pyridin-3-yl-1,3,4-oxadiazol-2-yl)methanone
[1-(2,4-dichlorobenzyl)-2-(trifluoromethyl)-1H-indol-3-yl](5-pyridin-3-yl-1,3,4-oxadiazol-2-yl)methanone
[1-(4-chlorobenzyl)-5-methoxy-2-(trifluoromethyl)-1H-indol-3-yl](5-pyridin-4-yl-1,3,4-oxadiazol-2-yl)methanone
[1-(4-chlorobenzyl)-5-ethoxy-2-(trifluoromethyl)-1H-indol-3-yl](5-pyridin-4-yl-1,3,4-oxadiazol-2-yl)methanone
[1-(4-chlorobenzyl)-5-hydroxy-2-(trifluoromethyl)-1H-indol-3-yl](5-pyridin-4-yl-1,3,4-oxadiazol-2-yl)methanone
[1-(4-chlorobenzyl)-5-methyl-2-(trifluoromethyl)-1H-indol-3-yl](5-pyridin-4-yl-1,3,4-oxadiazol-2-yl)methanone
[5-chloro-1-(4-chlorobenzyl)-2-(trifluoromethyl)-1H-indol-3-yl](5-pyridin-4-yl-1,3,4-oxadiazol-2-yl)methanone
[1-(4-chlorobenzyl)-2-(trifluoromethyl)-1H-indol-3-yl](5-pyridin-4-yl-1,3,4-oxadiazol-2-yl)methanone
[1-(2,4-dichlorobenzyl)-5-methoxy-2-(trifluoromethyl)-1H-indol-3-yl](5-pyridin-4-yl-1,3,4-oxadiazol-2-yl)methanone
[1-(2,4-dichlorobenzyl)-5-ethoxy-2-(trifluoromethyl)-1H-indol-3-yl](5-pyridin-4-yl-1,3,4-oxadiazol-2-yl)methanone
[1-(2,4-dichlorobenzyl)-5-hydroxy-2-(trifluoromethyl)-1H-indol-3-yl](5-pyridin-4-yl-1,3,4-oxadiazol-2-yl)methanone
[1-(2,4-dichlorobenzyl)-5-methyl-2-(trifluoromethyl)-1H-indol-3-yl](5-pyridin-4-yl-1,3,4-oxadiazol-2-yl)methanone
[5-chloro-1-(2,4-dichlorobenzyl)-2-(trifluoromethyl)-1H-indol-3-yl](5-pyridin-4-yl-1,3,4-oxadiazol-2-yl)methanone
[1-(2,4-dichlorobenzyl)-2-(trifluoromethyl)-1H-indol-3-yl](5-pyridin-4-yl-1,2,4-oxadiazol-2-yl)methanone
[1-(4-chlorobenzyl)-5-methoxy-2-(trifluoromethyl)-1H-indol-3-yl](5-pyrimidin-4-yl-1,3,4-oxadiazol-2-yl)methanone
[1-(4-chlorobenzyl)-5-ethoxy-2-(trifluoromethyl)-1H-indol-3-yl](5-pyrimidin-4-yl-1,3,4-oxadiazol-2-yl)methanone
[1-(4-chlorobenzyl)-5-hydroxy-2-(trifluoromethyl)-1H-indol-3-yl](5-pyrimidin-4-yl-1,3,4-oxadiazol-2-yl)methanone
[1-(4-chlorobenzyl)-5-methyl-2-(trifluoromethyl)-1H-indol-3-yl](5-pyrimidin-4-yl-1,3,4-oxadiazol-2-yl)methanone
[5-chloro-1-(4-chlorobenzyl)-2-(trifluoromethyl)-1H-indol-3-yl](5-pyrimidin-4-yl-1,3,4-oxadiazol-2-yl)methanone
[1-(4-chlorobenzyl)-2-(trifluoromethyl)-1H-indol-3-yl](5-pyrimidin-4-yl-1,3,4-oxadiazol-2-yl)methanone
[1-(2,4-dichlorobenzyl)-5-methoxy-2-(trifluoromethyl)-1H-indol-3-yl](5-pyrimidin-4-yl-1,3,4-oxadiazol-2-yl)methanone
[1-(2,4-dichlorobenzyl)-5-ethoxy-2-(trifluoromethyl)-1H-indol-3-yl](5-pyrimidin-4-yl-1,3,4-oxadiazol-2-yl)methanone
[1-(2,4-dichlorobenzyl)-5-hydroxy-2-(trifluoromethyl)-1H-indol-3-yl](5-pyrimidin-4-yl-1,3,4-oxadiazol-2-yl)methanone
[1-(2,4-dichlorobenzyl)-5-methyl-2-(trifluoromethyl)-1H-indol-3-yl](5-pyrimidin-4-yl-1,3,4-oxadiazol-2-yl)methanone
[5-chloro-1-(2,4-dichlorobenzyl)-2-(trifluoromethyl)-1H-indol-3-yl](5-pyrimidin-4-yl-1,3,4-oxadiazol-2-yl)methanone
[1-(2,4-dichlorobenzyl)-2-(trifluoromethyl)-1H-indol-3-yl](5-pyrimidin-4-yl-1,3,4-oxadiazol-2-yl)methanone
[1-(4-chlorobenzyl)-5-methoxy-2-(trifluoromethyl)-1H-indol-3-yl](2-phenyl-1,3-oxazol-5-yl)methanone
[1-(4-chlorobenzyl)-5-ethoxy-2-(trifluoromethyl)-1H-indol-3-yl](2-phenyl-1,3-oxazol-5-yl)methanone
[1-(4-chlorobenzyl)-5-hydroxy-2-(trifluoromethyl)-1H-indol-3-yl](2-phenyl-1,3-oxazol-5-yl)methanone
[1-(4-chlorobenzyl)-5-methyl-2-(trifluoromethyl)-1H-indol-3-yl](2-phenyl-1,3-oxazol-5-yl)methanone
[5-chloro-1-(4-chlorobenzyl)-2-(trifluoromethyl)-1H-indol-3-yl](2-phenyl-1,3-oxazol-5-yl)methanone
[1-(4-chlorobenzyl)-2-(trifluoromethyl)-1H-indol-3-yl](2-phenyl-1,3-oxazol-5-yl)methanone
[1-(2,4-dichlorobenzyl)-5-methoxy-2-(trifluoromethyl)-1H-indol-3-yl](2-phenyl-1,3-oxazol-5-yl)methanone

[1-(2,4-dichlorobenzyl)-5-ethoxy-2-(trifluoromethyl)-1H-indol-3-yl](2-phenyl-1,3-oxazol-5-yl)methanone
[1-(2,4-dichlorobenzyl)-5-hydroxy-2-(trifluoromethyl)-1H-indol-3-yl](2-phenyl-1,3-oxazol-5-yl)methanone
[1-(2,4-dichlorobenzyl)-5-methyl-2-(trifluoromethyl)-1H-indol-3-yl](2-phenyl-1,3-oxazol-5-yl)methanone
[5-chloro-1-(2,4-dichlorobenzyl)-2-(trifluoromethyl)-1H-indol-3-yl](2-phenyl-1,3-oxazol-5-yl)methanone
[1-(2,4-dichlorobenzyl)-2-(trifluoromethyl)-1H-indol-3-yl](2-phenyl-1,3-oxazol-5-yl)methanone
[1-(4-chlorobenzyl)-5-methoxy-2-(trifluoromethyl)-1H-indol-3-yl](2-pyridin-2-yl-1,3-oxazol-5-yl)methanone
[1-(4-chlorobenzyl)-5-ethoxy-2-(trifluoromethyl)-1H-indol-3-yl](2-pyridin-2-yl-1,3-oxazol-5-yl)methanone
[1-(4-chlorobenzyl)-5-hydroxy-2-(trifluoromethyl)-1H-indol-3-yl](2-pyridin-2-yl-1,3-oxazol-5-yl)methanone
[1-(4-chlorobenzyl)-5-methyl-2-(trifluoromethyl)-1H-indol-3-yl](2-pyridin-2-yl-1,3-oxazol-5-yl)methanone
[5-chloro-1-(4-chlorobenzyl)-2-(trifluoromethyl)-1H-indol-3-yl](2-pyridin-2-yl-1,3-oxazol-5-yl)methanone
[1-(4-chlorobenzyl)-2-(trifluoromethyl)-1H-indol-3-yl](2-pyridin-2-yl-1,3-oxazol-5-yl)methanone
[1-(2,4-dichlorobenzyl)-5-methoxy-2-(trifluoromethyl)-1H-indol-3-yl](2-pyridin-2-yl-1,3-oxazol-5-yl)methanone
[1-(2,4-dichlorobenzyl)-5-ethoxy-2-(trifluoromethyl)-1H-indol-3-yl](2-pyridin-2-yl-1,3-oxazol-5-yl)methanone
[1-(2,4-dichlorobenzyl)-5-hydroxy-2-(trifluoromethyl)-1H-indol-3-yl](2-pyridin-2-yl-1,3-oxazol-5-yl)methanone
[1-(2,4-dichlorobenzyl)-5-methyl-2-(trifluoromethyl)-1H-indol-3-yl](2-pyridin-2-yl-1,3-oxazol-5-yl)methanone
[5-chloro-1-(2,4-dichlorobenzyl)-2-(trifluoromethyl)-1H-indol-3-yl](2-pyridin-2-yl-1,3-oxazol-5-yl)methanone
[1-(2,4-dichlorobenzyl)-2-(trifluoromethyl)-1H-indol-3-yl](2-pyridin-2-yl-1,3-oxazol-5-yl)methanone
[1-(4-chlorobenzyl)-5-methoxy-2-(trifluoromethyl)-1H-indol-3-yl](2-pyridin-3-yl-1,3-oxazol-5-yl)methanone
[1-(4-chlorobenzyl)-5-ethoxy-2-(trifluoromethyl)-1H-indol-3-yl](2-pyridin-3-yl-1,3-oxazol-5-yl)methanone
[1-(4-chlorobenzyl)-5-hydroxy-2-(trifluoromethyl)-1H-indol-3-yl](2-pyridin-3-yl-1,3-oxazol-5-yl)methanone
[1-(4-chlorobenzyl)-5-methyl-2-(trifluoromethyl)-1H-indol-3-yl](2-pyridin-3-yl-1,3-oxazol-5-yl)methanone
[5-chloro-1-(4-chlorobenzyl)-2-(trifluoromethyl)-1H-indol-3-yl](2-pyridin-3-yl-1,3-oxazol-5-yl)methanone
[1-(4-chlorobenzyl)-2-(trifluoromethyl)-1H-indol-3-yl](2-pyridin-3-yl-1,3-oxazol-5-yl)methanone
[1-(2,4-dichlorobenzyl)-5-methoxy-2-(trifluoromethyl)-1H-indol-3-yl](2-pyridin-3-yl-1,3-oxazol-5-yl)methanone
[1-(2,4-dichlorobenzyl)-5-ethoxy-2-(trifluoromethyl)-1H-indol-3-yl](2-pyridin-3-yl-1,3-oxazol-5-yl)methanone
[1-(2,4-dichlorobenzyl)-5-hydroxy-2-(trifluoromethyl)-1H-indol-3-yl](2-pyridin-3-yl-1,3-oxazol-5-yl)methanone
[1-(2,4-dichlorobenzyl)-5-methyl-2-(trifluoromethyl)-1H-indol-3-yl](2-pyridin-3-yl-1,3-oxazol-5-yl)methanone
[5-chloro-1-(2,4-dichlorobenzyl)-2-(trifluoromethyl)-1H-indol-3-yl](2-pyridin-3-yl-1,3-oxazol-5-yl)methanone
[1-(2,4-dichlorobenzyl)-2-(trifluoromethyl)-1H-indol-3-yl](2-pyridin-3-yl-1,3-oxazol-5-yl)methanone
[1-(4-chlorobenzyl)-5-methoxy-2-(trifluoromethyl)-1H-indol-3-yl](2-pyridin-4-yl-1,3-oxazol-5-yl)methanone
[1-(4-chlorobenzyl)-5-ethoxy-2-(trifluoromethyl)-1H-indol-3-yl](2-pyridin-4-yl-1,3-oxazol-5-yl)methanone
[1-(4-chlorobenzyl)-5-hydroxy-2-(trifluoromethyl)-1H-indol-3-yl](2-pyridin-4-yl-1,3-oxazol-5-yl)methanone
[1-(4-chlorobenzyl)-5-methyl-2-(trifluoromethyl)-1H-indol-3-yl](2-pyridin-4-yl-1,3-oxazol-5-yl)methanone
[5-chloro-1-(4-chlorobenzyl)-2-(trifluoromethyl)-1H-indol-3-yl](2-pyridin-4-yl-1,3-oxazol-5-yl)methanone
[1-(4-chlorobenzyl)-2-(trifluoromethyl)-1H-indol-3-yl](2-pyridin-4-yl-1,3-oxazol-5-yl)methanone
[1-(2,4-dichlorobenzyl)-5-methoxy-2-(trifluoromethyl)-1H-indol-3-yl](2-pyridin-4-yl-1,3-oxazol-5-yl)methanone
[1-(2,4-dichlorobenzyl)-5-ethoxy-2-(trifluoromethyl)-1H-indol-3-yl](2-pyridin-4-yl-1,3-oxazol-5-yl)methanone
[1-(2,4-dichlorobenzyl)-5-hydroxy-2-(trifluoromethyl)-1H-indol-3-yl](2-pyridin-4-yl-1,3-oxazol-5-yl)methanone
[1-(2,4-dichlorobenzyl)-5-methyl-2-(trifluoromethyl)-1H-indol-3-yl](2-pyridin-4-yl-1,3-oxazol-5-yl)methanone
[5-chloro-1-(2,4-dichlorobenzyl)-2-(trifluoromethyl)-1H-indol-3-yl](2-pyridin-4-yl-1,3-oxazol-5-yl)methanone
[1-(2,4-dichlorobenzyl)-2-(trifluoromethyl)-1H-indol-3-yl](2-pyridin-4-yl-1,3-oxazol-5-yl)methanone
[1-(4-chlorobenzyl)-5-methoxy-2-(trifluoromethyl)-1H-indol-3-yl](2-pyrimidin-4-yl-1,3-oxazol-5-yl)methanone
[1-(4-chlorobenzyl)-5-ethoxy-2-(trifluoromethyl)-1H-indol-3-yl](2-pyrimidin-4-yl-1,3-oxazol-5-yl)methanone
[1-(4-chlorobenzyl)-5-hydroxy-2-(trifluoromethyl)-1H-indol-3-yl](2-pyrimidin-4-yl-1,3-oxazol-5-yl)methanone
[1-(4-chlorobenzyl)-5-methyl-2-(trifluoromethyl)-1H-indol-3-yl](2-pyrimidin-4-yl-1,3-oxazol-5-yl)methanone
[5-chloro-1-(4-chlorobenzyl)-2-(trifluoromethyl)-1H-indol-3-yl](2-pyrimidin-4-yl-1,3-oxazol-5-yl)methanone
[1-(4-chlorobenzyl)-2-(trifluoromethyl)-1H-indol-3-yl](2-pyrimidin-4-yl-1,3-oxazol-5-yl)methanone
[1-(2,4-dichlorobenzyl)-5-methoxy-2-(trifluoromethyl)-1H-indol-3-yl](2-pyrimidin-4-yl-1,3-oxazol-5-yl)methanone
[1-(2,4-dichlorobenzyl)-5-ethoxy-2-(trifluoromethyl)-1H-indol-3-yl](2-pyrimidin-4-yl-1,3-oxazol-5-yl)methanone
[1-(2,4-dichlorobenzyl)-5-hydroxy-2-(trifluoromethyl)-1H-indol-3-yl](2-pyrimidin-4-yl-1,3-oxazol-5-yl)methanone
[1-(2,4-dichlorobenzyl)-5-methyl-2-(trifluoromethyl)-1H-indol-3-yl](2-pyrimidin-4-yl-1,3-oxazol-5-yl)methanone
[5-chloro-1-(2,4-dichlorobenzyl)-2-(trifluoromethyl)-1H-indol-3-yl](2-pyrimidin-4-yl-1,3-oxazol-5-yl)methanone
[1-(2,4-dichlorobenzyl)-2-(trifluoromethyl)-1H-indol-3-yl](2-pyrimidin-4-yl-1,3-oxazol-5-yl)methanone
[1-(4-chlorobenzyl)-5-methoxy-2-(trifluoromethyl)-1H-indol-3-yl](5-phenyl-1,3-oxazol-2-yl)methanone
[1-(4-chlorobenzyl)-5-ethoxy-2-(trifluoromethyl)-1H-indol-3-yl](5-phenyl-1,3-oxazol-2-yl)methanone
[1-(4-chlorobenzyl)-5-hydroxy-2-(trifluoromethyl)-1H-indol-3-yl](5-phenyl-1,3-oxazol-2-yl)methanone
[1-(4-chlorobenzyl)-5-methyl-2-(trifluoromethyl)-1H-indol-3-yl](5-phenyl-1,3-oxazol-2-yl)methanone
[5-chloro-1-(4-chlorobenzyl)-2-(trifluoromethyl)-1H-indol-3-yl](5-phenyl-1,3-oxazol-2-yl)methanone
[1-(4-chlorobenzyl)-2-(trifluoromethyl)-1H-indol-3-yl](5-phenyl-1,3-oxazol-2-yl)methanone
[1-(2,4-dichlorobenzyl)-5-methoxy-2-(trifluoromethyl)-1H-indol-3-yl](5-phenyl-1,3-oxazol-2-yl)methanone
[1-(2,4-dichlorobenzyl)-5-ethoxy-2-(trifluoromethyl)-1H-indol-3-yl](5-phenyl-1,3-oxazol-2-yl)methanone
[1-(2,4-dichlorobenzyl)-5-hydroxy-2-(trifluoromethyl)-1H-indol-3-yl](5-phenyl-1,3-oxazol-2-yl)methanone
[1-(2,4-dichlorobenzyl)-5-methyl-2-(trifluoromethyl)-1H-indol-3-yl](5-phenyl-1,3-oxazol-2-yl)methanone
[5-chloro-1-(2,4-dichlorobenzyl)-2-(trifluoromethyl)-1H-indol-3-yl](5-phenyl-1,3-oxazol-2-yl)methanone
[1-(2,4-dichlorobenzyl)-2-(trifluoromethyl)-1H-indol-3-yl](5-phenyl-1,3-oxazol-2-yl)methanone
[1-(4-chlorobenzyl)-5-methoxy-2-(trifluoromethyl)-1H-indol-3-yl](5-pyridin-2-yl-1,3-oxazol-2-yl)methanone

[1-(4-chlorobenzyl)-5-ethoxy-2-(trifluoromethyl)-1H-indol-3-yl](5-pyridin-2-yl-1,3-oxazol-2-yl)methanone
[1-(4-chlorobenzyl)-5-hydroxy-2-(trifluoromethyl)-1H-indol-3-yl](5-pyridin-2-yl-1,3-oxazol-2-yl)methanone
[1-(4-chlorobenzyl)-5-methyl-2-(trifluoromethyl)-1H-indol-3-yl](5-pyridin-2-yl-1,3-oxazol-2-yl)methanone
[5-chloro-1-(4-chlorobenzyl)-2-(trifluoromethyl)-1H-indol-3-yl](5-pyridin-2-yl-1,3-oxazol-2-yl)methanone
[1-(4-chlorobenzyl)-2-(trifluoromethyl)-1H-indol-3-yl](5-pyridin-2-yl-1,3-oxazol-2-yl)methanone
[1-(2,4-dichlorobenzyl)-5-methoxy-2-(trifluoromethyl)-1H-indol-3-yl](5-pyridin-2-yl-1,3-oxazol-2-yl)methanone
[1-(2,4-dichlorobenzyl)-5-ethoxy-2-(trifluoromethyl)-1H-indol-3-yl](5-pyridin-2-yl-1,3-oxazol-2-yl)methanone
[1-(2,4-dichlorobenzyl)-5-hydroxy-2-(trifluoromethyl)-1H-indol-3-yl](5-pyridin-2-yl-1,3-oxazol-2-yl)methanone
[1-(2,4-dichlorobenzyl)-5-methyl-2-(trifluoromethyl)-1H-indol-3-yl](5-pyridin-2-yl-1,3-oxazol-2-yl)methanone
[5-chloro-1-(2,4-dichlorobenzyl)-2-(trifluoromethyl)-1H-indol-3-yl](5-pyridin-2-yl-1,3-oxazol-2-yl)methanone
[1-(2,4-dichlorobenzyl)-2-(trifluoromethyl)-1H-indol-3-yl](5-pyridin-2-yl-1,3-oxazol-2-yl)methanone
[1-(4-chlorobenzyl)-5-methoxy-2-(trifluoromethyl)-1H-indol-3-yl](5-pyridin-3-yl-1,3-oxazol-2-yl)methanone
[1-(4-chlorobenzyl)-5-ethoxy-2-(trifluoromethyl)-1H-indol-3-yl](5-pyridin-3-yl-1,3-oxazol-2-yl)methanone
[1-(4-chlorobenzyl)-5-hydroxy-2-(trifluoromethyl)-1H-indol-3-yl](5-pyridin-3-yl-1,3-oxazol-2-yl)methanone
[1-(4-chlorobenzyl)-5-methyl-2-(trifluoromethyl)-1H-indol-3-yl](5-pyridin-3-yl-1,3-oxazol-2-yl)methanone
[5-chloro-1-(4-chlorobenzyl)-2-(trifluoromethyl)-1H-indol-3-yl](5-pyridin-3-yl-1,3oxazol-2-yl)methanone
[1-(4-chlorobenzyl)-2-(trifluoromethyl)-1H-indol-3-yl](5-pyridin-3-yl-1,3-oxazol-2-yl)methanone
[1-(2,4-dichlorobenzyl)-5-methoxy-2-(trifluoromethyl)-1H-indol-3-yl](5-pyridin-3-yl-1,3-oxazol-2-yl)methanone
[1-(2,4-dichlorobenzyl)-5-ethoxy-2-(trifluoromethyl)-1H-indol-3-yl](5-pyridin-3-yl-1,3-oxazol-2-yl)methanone
[1-(2,4-dichlorobenzyl)-5-hydroxy-2-(trifluoromethyl)-1H-indol-3-yl](5-pyridin-3-yl-1,3-oxazol-2-yl)methanone
[1-(2,4-dichlorobenzyl)-5-methyl-2-(trifluoromethyl)-1H-indol-3-yl](5-pyridin-3-yl-1,3-oxazol-2-yl)methanone
[5-chloro-1-(2,4-dichlorobenzyl)-2-(trifluoromethyl)-1H-indol-3-yl](5-pyridin-3-yl-1,3-oxazol-2-yl)methanone
[1-(2,4-dichlorobenzyl)-2-(trifluoromethyl)-1H-indol-3-yl](5-pyridin-3-yl-1,3-oxazol-2-yl)methanone
[1-(4-chlorobenzyl)-5-methoxy-2-(trifluoromethyl)-1H-indol-3-yl](5-pyridin-4-yl-1,3-oxazol-2-yl)methanone
[1-(4-chlorobenzyl)-5-ethoxy-2-(trifluoromethyl)-1H-indol-3-yl](5-pyridin-4-yl-1,3-oxazol-2-yl)methanone
[1-(4-chlorobenzyl)-5-hydroxy-2-(trifluoromethyl)-1H-indol-3-yl](5-pyridin-4-yl-1,3-oxazol-2-yl)methanone
[1-(4-chlorobenzyl)-5-methyl-2-(trifluoromethyl)-1H-indol-3-yl](5-pyridin-4-yl-1,3-oxazol-2-yl)methanone
[5-chloro-1-(4-chlorobenzyl)-2-(trifluoromethyl)-1H-indol-3-yl](5-pyridin-4-yl-1,3-oxazol-2-yl)methanone
[1-(4-chlorobenzyl)-2-(trifluoromethyl)-1H-indol-3-yl](5-pyridin-4-yl-1,3-oxazol-2-yl)methanone
[1-(2,4-dichlorobenzyl)-5-methoxy-2-(trifluoromethyl)-1H-indol-3-yl](5-pyridin-4-yl-1,3-oxazol-2-yl)methanone
[1-(2,4-dichlorobenzyl)-5-ethoxy-2-(trifluoromethyl)-1H-indol-3-yl](5-pyridin-4-yl-1,3-oxazol-2-yl)methanone
[1-(2,4-dichlorobenzyl)-5-hydroxy-2-(trifluoromethyl)-1H-indol-3-yl](5-pyridin-4-yl-1,3-oxazol-2-yl)methanone
[1-(2,4-dichlorobenzyl)-5-methyl-2-(trifluoromethyl)-1H-indol-3-yl](5-pyridin-4-yl-1,3-oxazol-2-yl)methanone
[5-chloro-1-(2,4-dichlorobenzyl)-2-(trifluoromethyl)-1H-indol-3-yl](5-pyridin-4-yl-1,3-oxazol-2-yl)methanone
[1-(2,4-dichlorobenzyl)-2-(trifluoromethyl)-1H-indol-3-yl](5-pyridin-4-yl-1,3-oxazol-2-yl)methanone
[1-(4-chlorobenzyl)-5-methoxy-2-(trifluoromethyl)-1H-indol-3-yl](5-pyrimidin-4-yl-1,3-oxazol-2-yl)methanone
[1-(4-chlorobenzyl)-5-ethoxy-2-(trifluoromethyl)-1H-indol-3-yl](5-pyrimidin-4-yl-1,3-oxazol-2-yl)methanone
[1-(4-chlorobenzyl)-5-hydroxy-2-(trifluoromethyl)-1H-indol-3-yl](5-pyrimidin-4-yl-1,3-oxazol-2-yl)methanone
[1-(4-chlorobenzyl)-5-methyl-2-(trifluoromethyl)-1H-indol-3-yl](5-pyrimidin-4-yl-1,3-oxazol-2-yl)methanone
[5-chloro-1-(4-chlorobenzyl)-2-(trifluoromethyl)-1H-indol-3-yl](5-pyrimidin-4-yl-1,3-oxazol-2-yl)methanone
[1-(4-chlorobenzyl)-2-9trifluoromethyl)-1H-indol-3-yl](5-pyrimidin-4-yl-1,3-oxazol-2-yl)methanone
[1-(2,4-dichlorobenzyl)-5-methoxy-2-(trifluoromethyl)-1H-indol-3-yl](5-pyrimidin-4-yl-1,3-oxazol-2-yl)methanone
[1-(2,4-dichlorobenzyl)-5-ethoxy-2-(trifluoromethyl)-1H-indol-3-yl](5-pyrimidin-4-yl-1,3-oxazol-2-yl)methanone
[1-(2,4-dichlorobenzyl)-5-hydroxy-2-(trifluoromethyl)-1H-indol-3-yl](5-pyrimidin-4-yl-1,3-oxazol-2-yl)methanone
[1-(2,4-dichlorobenzyl)-5-methyl-2-(trifluoromethyl)-1H-indol-3-yl](5-pyrimidin-4-yl-1,3-oxazol-2-yl)methanone
[5-chloro-1-(2,4-dichlorobenzyl)-2-(trifluoromethyl)-1H-indol-3-yl](5-pyrimidin-4-yl-1,3-oxazol-2-yl)methanone
[1-(2,4-dichlorobenzyl)-2-(trifluoromethyl)-1H-indol-3-yl](5-pyrimidin-4-yl-1,3-oxazol-2-yl)methanone
[1-(4-chlorobenzyl)-5-methoxy-2-(chloro)-1H-indol-3-yl](3-pyridin-2-yl-1,2,4-oxadiazol-5-yl)methanone
[1-(4-chlorobenzyl)-5-ethoxy-2-(chloro)-1H-indol-3-yl](3-pyridin-2-yl-1,2,4-oxadiazol-5-yl)methanone
[1-(4-chlorobenzyl)-5-hydroxy-2-(chloro)-1H-indol-3-yl](3-pyridin-2-yl-1,2,4-oxadiazol-5-yl)methanone
[1-(4-chlorobenzyl)-5-methyl-2-(chloro)-1H-indol-3-yl](3-pyridin-2-yl-1,2,4-oxadiazol-5-yl)methanone
[5-chloro-1-(4-chlorobenzyl)-2-(chloro)-1H-indol-3-yl](3-pyridin-2-yl-1,2,4-oxadiazol-5-yl)methanone
[1-(4-chlorobenzyl)-2-(chloro)-1H-indol-3-yl](3-pyridin-2-yl-1,2,4-oxadiazol-5-yl)methanone
[1-(2,4-dichlorobenzyl)-5-methoxy-2-(chloro)-1H-indol-3-yl](3-pyridin-2-yl-1,2,4-oxadiazol-5-yl)methanone
[1-(2,4-dichlorobenzyl)-5-ethoxy-2-(chloro)-1H-indol-3-yl](3-pyridin-2-yl-1,2,4-oxadiazol-5-yl)methanone
[1-(2,4-dichlorobenzyl)-5-hydroxy-2-(chloro)-1H-indol-3-yl](3-pyridin-2-yl-1,2,4-oxadiazol-5-yl)methanone
[1-(2,4-dichlorobenzyl)-5-methyl-2-(chloro)-1H-indol-3-yl](3-pyridin-2-yl-1,2,4-oxadiazol-5-yl)methanone
[5-chloro-1-(2,4-dichlorobenzyl)-2-(chloro)-1H-indol-3-yl](3-pyridin-2-yl-1,2,4-oxadiazol-5-yl)methanone
[1-(2,4-dichlorobenzyl)-2-(chloro)-1H-indol-3-yl](3-pyridin-2-yl-1,2,4-oxadiazol-5-yl)methanone
[1-(4-chlorobenzyl)-5-methoxy-2-(chloro)-1H-indol-3-yl](3-pyridin-3-yl-1,2,4-oxadiazol-5-yl)methanone
[1-(4-chlorobenzyl)-5-ethoxy-2-(chloro)-1H-indol-3-yl](3-pyridin-3-yl-1,2,4-oxadiazol-5-yl)methanone
[1-(4-chlorobenzyl)-5-hydroxy-2-(chloro)-1H-indol-3-yl](3-pyridin-3-yl-1,2,4-oxadiazol-5-yl)methanone
[1-(4-chlorobenzyl)-5-methyl-2-(chloro)-1H-indol-3-yl](3-pyridin-3-yl-1,2,4-oxadiazol-5-yl)methanone
[5-chloro-1-(4-chlorobenzyl)-2-(chloro)-1H-indol-3-yl](3-pyridin-3-yl-1,2,4-oxadiazol-5-yl)methanone
[1-(4-chlorobenzyl)-2-(chloro)-1H-indol-3-yl](3-pyridin-3-yl-1,2,4-oxadiazol-5-yl)methanone
[1-(2,4-dichlorobenzyl)-5-methoxy-2-(chloro)-1H-indol-3-yl](3-pyridin-3-yl-1,2,4-oxadiazol-5-yl)methanone

[1-(2,4-dichlorobenzyl)-5-ethoxy-2-(chloro)-1H-indol-3-yl](3-pyridin-3-yl-1,2,4-oxadiazol-5-yl)methanone
[1-(2,4-dichlorobenzyl)-5-hydroxy-2-(chloro)-1H-indol-3-yl](3-pyridin-3-yl-1,2,4-oxadiazol-5-yl)methanone
[1-(2,4-dichlorobenzyl)-5-methyl-2-(chloro)-1H-indol-3-yl](3-pyridin-3-yl-1,2,4-oxadiazol-5-yl)methanone
[5-chloro-1-(2,4-dichlorobenzyl)-2-(chloro)-1H-indol-3-yl](3-pyridin-3-yl-1,2,4-oxadiazol-5-yl)methanone
[1-(2,4-dichlorobenzyl)-2-(chloro)-1H-indol-3-yl](3-pyridin-3-yl-1,2,4-oxadiazol-5-yl)methanone
[1-(4-chlorobenzyl)-5-methoxy-2-(chloro)-1H-indol-3-yl](3-pyridin-4-yl-1,2,4-oxadiazol-5-yl)methanone
[1-(4-chlorobenzyl)-5-ethoxy-2-(chloro)-1H-indol-3-yl](3-pyridin-4-yl-1,2,4-oxadiazol-5-yl)methanone
[1-(4-chlorobenzyl)-5-hydroxy-2-(chloro)-1H-indol-3-yl](3-pyridin-4-yl-1,2,4-oxadiazol-5-yl)methanone
[1-(4-chlorobenzyl)-5-methyl-2-(chloro)-1H-indol-3-yl](3-pyridin-4-yl-1,2,4-oxadiazol-5-yl)methanone
[5-chloro-1-(4-chlorobenzyl)-2-(chloro)-1H-indol-3-yl](3-pyridin-4-yl-1,2,4-oxadiazol-5-yl)methanone
[1-(4-chlorobenzyl)-2-(chloro)-1H-indol-3-yl](3-pyridin-4-yl-1,2,4-oxadiazol-5-yl)methanone
[1-(2,4-dichlorobenzyl)-5-methoxy-2-(chloro)-1H-indol-3-yl](3-pyridin-4-yl-1,2,4-oxadiazol-5-yl)methanone
[1-(2,4-dichlorobenzyl)-5-ethoxy-2-(chloro)-1H-indol-3-yl](3-pyridin-4-yl-1,2,4-oxadiazol-5-yl)methanone
[1-(2,4-dichlorobenzyl)-5-hydroxy-2-(chloro)-1H-indol-3-yl](3-pyridin-4-yl-1,2,4-oxadiazol-5-yl)methanone
[1-(2,4-dichlorobenzyl)-5-methyl-2-(chloro)-1H-indol-3-yl](3-pyridin-4-yl-1,2,4-oxadiazol-5-yl)methanone
[5-chloro-1-(2,4-dichlorobenzyl)-2-(chloro)-1H-indol-3-yl](3-pyridin-4-yl-1,2,4-oxadiazol-5-yl)methanone
[1-(2,4-dichlorobenzyl)-2-(chloro)-1H-indol-3-yl](3-pyridin-4-yl-1,2,4-oxadiazol-5-yl)methanone
[1-(4-chlorobenzyl)-5-methoxy-2-(chloro)-1H-indol-3-yl](3-pyrimidin-4-yl-1,2,4-oxadiazol-5-yl)methanone
[1-(4-chlorobenzyl)-5-ethoxy-2-(chloro)-1H-indol-3-yl](3-pyrimidin-4-yl-1,2,4-oxadiazol-5-yl)methanone
[1-(4-chlorobenzyl)-5-hydroxy-2-(chloro)-1H-indol-3-yl](3-pyrimidin-4-yl-1,2,4-oxadiazol-5-yl)methanone
[1-(4-chlorobenzyl)-5-methyl-2-(chloro)-1H-indol-3-yl](3-pyrimidin-4-yl-1,2,4-oxadiazol-5-yl)methanone
[5-chloro-1-(4-chlorobenzyl)-2-(chloro)-1H-indol-3-yl](3-pyrimidin-4-yl-1,2,4-oxadiazol-5-yl)methanone
[1-(4-chlorobenzyl)-2-(chloro)-1H-indol-3-yl](3-pyrimidin-4-yl-1,2,4-oxadiazol-5-yl)methanone
[1-(2,4-dichlorobenzyl)-5-methoxy-2-(chloro)-1H-indol-3-yl](3-pyrimidin-4-yl-1,2,4-oxadiazol-5-yl)methanone
[1-(2,4-dichlorobenzyl)-5-ethoxy-2-(chloro)-1H-indol-3-yl](3-pyrimidin-4-yl-1,2,4-oxadiazol-5-yl)methanone
[1-(2,4-dichlorobenzyl)-5-hydroxy-2-(chloro)-1H-indol-3-yl](3-pyrimidin-4-yl-1,2,4-oxadiazol-5-yl)methanone
[1-(2,4-dichlorobenzyl)-5-methyl-2-(chloro)-1H-indol-3-yl](3-pyrimidin-4-yl-1,2,4-oxadiazol-5-yl)methanone
[5-chloro-1-(2,4-dichlorobenzyl)-2-(chloro)-1H-indol-3-yl](3-pyrimidin-4-yl-1,2,4-oxadiazol-5-yl)methanone
[1-(2,4-dichlorobenzyl)-2-(chloro)-1H-indol-3-yl](3-pyrimidin-4-yl-1,2,4-oxadiazol-5-yl)methanone
[1-(4-chlorobenzyl)-5-methoxy-2-(chloro)-1H-indol-3-yl](5-phenyl-1,2,4-oxadiazol-3-yl)methanone
[1-(4-chlorobenzyl)-5-ethoxy-2-(chloro)-1H-indol-3-yl](5-phenyl-1,2,4-oxadiazol-3-yl)methanone
[1-(4-chlorobenzyl)-5-hydroxy-2-(chloro)-1H-indol-3-yl](5-phenyl-1,2,4-oxadiazol-3-yl)methanone
[1-(4-chlorobenzyl)-5-methyl-2-(chloro)-1H-indol-3-yl](5-phenyl-1,2,4-oxadiazol-3-yl)methanone
[5-chloro-1-(4-chlorobenzyl)-2-(chloro)-1H-indol-3-yl](5-phenyl-1,2,4-oxadiazol-3-yl)methanone
[1-(4-chlorobenzyl)-2-(chloro)-1H-indol-3-yl](5-phenyl-1,2,4-oxadiazol-3-yl)methanone
[1-(2,4-dichlorobenzyl)-5-methoxy-2-(chloro)-1H-indol-3-yl](5-phenyl-1,2,4-oxadiazol-3-yl)methanone
[1-(2,4-dichlorobenzyl)-5-ethoxy-2-(chloro)-1H-indol-3-yl](5-phenyl-1,2,4-oxadiazol-3-yl)methanone
[1-(2,4-dichlorobenzyl)-5-hydroxy-2-(chloro)-1H-indol-3-yl](5-phenyl-1,2,4-oxadiazol-3-yl)methanone
[1-(2,4-dichlorobenzyl)-5-methyl-2-(chloro)-1H-indol-3-yl](5-phenyl-1,2,4-oxadiazol-3-yl)methanone
[5-chloro-1-(2,4-dichlorobenzyl)-2-(chloro)-1H-indol-3-yl](5-phenyl-1,2,4-oxadiazol-3-yl)methanone
[1-(2,4-dichlorobenzyl)-2-(chloro)-1H-indol-3-yl](5-phenyl-1,2,4-oxadiazol-3-yl)methanone
[1-(4-chlorobenzyl)-5-methoxy-2-(chloro)-1H-indol-3-yl](5-pyridin-2-yl-1,2,4-oxadiazol-3-yl)methanone
[1-(4-chlorobenzyl)-5-ethoxy-2-(chloro)-1H-indol-3-yl](5-pyridin-2-yl-1,2,4-oxadiazol-3-yl)methanone
[1-(4-chlorobenzyl)-5-hydroxy-2-(chloro)-1H-indol-3-yl](5-pyridin-2-yl-1,2,4-oxadiazol-3-yl)methanone
[1-(4-chlorobenzyl)-5-methyl-2-(chloro)-1H-indol-3-yl](5-pyridin-2-yl-1,2,4-oxadiazol-3-yl)methanone
[5-chloro-1-(4-chlorobenzyl)-2-(chloro)-1H-indol-3-yl](5-pyridin-2-yl-1,2,4-oxadiazol-3-yl)methanone
[1-(4-chlorobenzyl)-2-(chloro)-1H-indol-3-yl](5-pyridin-2-yl-1,2,4-oxadiazol-3-yl)methanone
[1-(2,4-dichlorobenzyl)-5-methoxy-2-(chloro)-1H-indol-3-yl](5-pyridin-3-yl-1,2,4-oxadiazol-3-yl)methanone
[1-(2,4-dichlorobenzyl)-5-ethoxy-2-(chloro)-1H-indol-3-yl](5-pyridin-2-yl-1,2,4-oxadiazol-3-yl)methanone
[1-(2,4-dichlorobenzyl)-5-hydroxy-2-(chloro)-1H-indol-3-yl](5-pyridin-2-yl-1,2,4-oxadiazol-3-yl)methanone
[1-(2,4-dichlorobenzyl)-5-methyl-2-(chloro)-1H-indol-3-yl](5-pyridin-2-yl-1,2,4-oxadiazol-3-yl)methanone
[5-chloro-1-(2,4-dichlorobenzyl)-2-(chloro)-1H-indol-3-yl](5-pyridin-2-yl-1,2,4-oxadiazol-3-yl)methanone
[1-(2,4-dichlorobenzyl)-2-(chloro)-1H-indol-3-yl](5-pyridin-2-yl-1,2,4-oxadiazol-3-yl)methanone
[1-(4-chlorobenzyl)-5-methoxy-2-(chloro)-1H-indol-3-yl](5-pyridin-3-yl-1,2,4-oxadiazol-3-yl)methanone
[1-(4-chlorobenzyl)-5-ethoxy-2-(chloro)-1H-indol-3-yl](5-pyridin-3-yl-1,2,4-oxadiazol-3-yl)methanone
[5-chloro-1-(4-chlorobenzyl)-2-(chloro)-1H-indol-3-yl](5-pyridin-3-yl-1,2,4-oxadiazol-3-yl)methanone
[1-(4-chlorobenzyl)-2-(chloro)-1H-indol-3-yl](5-pyridin-3-yl-1,2,4-oxadiazol-3-yl)methanone
[1-(2,4-dichlorobenzyl)-5-methoxy-2-(chloro)-1H-indol-3-yl](5-pyridin-3-yl-1,2,4-oxadiazol-3-yl)methanone
[1-(2,4-dichlorobenzyl)-5-ethoxy-2-(chloro)-1H-indol-3-yl](5-pyridin-3-yl-1,2,4-oxadiazol-3-yl)methanone
[1-(2,4-dichlorobenzyl)-5-hydroxy-2-(chloro)-1H-indol-3-yl](5-pyridin-3-yl-1,2,4-oxadiazol-3-yl)methanone
[1-(2,4-dichlorobenzyl)-5-methyl-2-(chloro)-1H-indol-3-yl](5-pyridin-3-yl-1,2,4-oxadiazol-3-yl)methanone
[5-chloro-1-(2,4-dichlorobenzyl)-2-(chloro)-1H-indol-3-yl](5-pyridin-3-yl-1,2,4-oxadiazol-3-yl)methanone
[1-(2,4-dichlorobenzyl)-2-(chloro)-1H-indol-3-yl](5-pyridin-3-yl-1,2,4-oxadiazol-3-yl)methanone
[1-(4-chlorobenzyl)-5-methoxy-2-(chloro)-1H-indol-3-yl](5-pyridin-4-yl-1,2,4-oxadiazol-3-yl)methanone
[1-(4-chlorobenzyl)-5-ethoxy-2-(chloro)-1H-indol-3-yl](5-pyridin-4-yl-1,2,4-oxadiazol-3-yl)methanone
[1-(4-chlorobenzyl)-5-hydroxy-2-(chloro)-1H-indol-3-yl](5-pyridin-4-yl-1,2,4-oxadiazol-3-yl)methanone

[1-(4-chlorobenzyl)-5-methyl-2-(chloro)-1H-indol-3-yl](5-pyridin-4-yl-1,2,4-oxadiazol-3-yl)methanone
[5-chloro-1-(4-chlorobenzyl)-2-(chloro)-1H-indol-3-yl](5-pyridin-4-yl-1,2,4-oxadiazol-3-yl)methanone
[1-(4-chlorobenzyl)-2-(chloro)-1H-indol-3-yl](5-pyridin-4-yl-1,2,4-oxadiazol-3-yl)methanone
[1-(2,4-dichlorobenzyl)-5-methoxy-2-(chloro)-1H-indol-3-yl](5-pyridin-4-yl-1,2,4-oxadiazol-3-yl)methanone
[1-(2,4-dichlorobenzyl)-5-ethoxy-2-(chloro)-1H-indol-3-yl](5-pyridin-4-yl-1,2,4-oxadiazol-3-yl)methanone
[1-(2,4-dichlorobenzyl)-5-hydroxy-2-(chloro)-1H-indol-3-yl](5-pyridin-4-yl-1,2,4-oxadiazol-3-yl)methanone
[1-(2,4-dichlorobenzyl)-5-methyl-2-(chloro)-1H-indol-3-yl](5-pyridin-4-yl-1,2,4-oxadiazol-3-yl)methanone
[5-chloro-1-(2,4-dichlorobenzyl)-2-(chloro)-1H-indol-3-yl](5-pyridin-4-yl-1,2,4-oxadiazol-3-yl)methanone
[1-(2,4-dichlorobenzyl)-2-(chloro)-1H-indol-3-yl](5-pyridin-4-yl-1,2,4-oxadiazol-3-yl)methanone
[1-(4-chlorobenzyl)-5-methoxy-2-(chloro)-1H-indol-3-yl](5-pyrimidin-4-yl-1,2,4-oxadiazol-3-yl)methanone
[1-(4-chlorobenzyl)-5-ethoxy-2-(chloro)-1H-indol-3-yl](5-pyrimidin-4-yl-1,2,4-oxadiazol-3-yl)methanone
[1-(4-chlorobenzyl)-5-hydroxy-2-(chloro)-1H-indol-3-yl](5-pyrimidin-4-yl-1,2,4-oxadiazol-3-yl)methanone
[1-(4-chlorobenzyl)-5-methyl-2-(chloro)-1H-indol-3-yl](5-pyrimidin-4-yl-1,2,4-oxadiazol-3-yl)methanone
[5-chloro-1-(4-chlorobenzyl)-2-(chloro)-1H-indol-3-yl](5-pyrimidin-4-yl-1,2,4-oxadiazol-3-yl)methanone
[1-(4-chlorobenzyl)-2-(chloro)-1H-indol-3-yl](5-pyrimidin-4-yl-1,2,4-oxadiazol-3-yl)methanone
[1-(2,4-dichlorobenzyl)-5-methoxy-2-(chloro)-1H-indol-3-yl](5-pyrimidin-4-yl-1,2,4-oxadiazol-3-yl)methanone
[1-(2,4-dichlorobenzyl)-5-ethoxy-2-(chloro)-1H-indol-3-yl](5-pyrimidin-4-yl-1,2,4-oxadiazol-3-yl)methanone
[1-(2,4-dichlorobenzyl)-5-hydroxy-2-(chloro)-1H-indol-3-yl](5-pyrimidin-4-yl-1,2,4-oxadiazol-3-yl)methanone
[1-(2,4-dichlorobenzyl)-5-methyl-2-(chloro)-1H-indol-3-yl](5-pyrimidin-4-yl-1,2,4-oxadiazol-3-yl)methanone
[5-chloro-1-(2,4-dichlorobenzyl)-2-(chloro)-1H-indol-3-yl](5-pyrimidin-4-yl-1,2,4-oxadiazol-3-yl)methanone
[1-(2,4-dichlorobenzyl)-2-(chloro)-1H-indol-3-yl](5-pyrimidin-4-yl-1,2,4-oxadiazol-3-yl)methanone
[1-(4-chlorobenzyl)-5-methoxy-2-(chloro)-1H-indol-3-yl](5-phenyl-1,3,4-oxadiazol-2-yl)methanone
[1-(4-chlorobenzyl)-5-ethoxy-2-(chloro)-1H-indol-3-yl](5-phenyl-1,3,4-oxadiazol-2-yl)methanone
[1-(4-chlorobenzyl)-5-hydroxy-2-(chloro)-1H-indol-3-yl](5-phenyl-1,3,4-oxadiazol-2-yl)methanone
[1-(4-chlorobenzyl)-5-methyl-2-(chloro)-1H-indol-3-yl](5-phenyl-1,3,4-oxadiazol-2-yl)methanone
[5-chloro-1-(4-chlorobenzyl)-2-(chloro)-1H-indol-3-yl](5-phenyl-1,3,4-oxadiazol-2-yl)methanone
[1-(4-chlorobenzyl)-2-(chloro)-1H-indol-3-yl](5-phenyl-1,3,4-oxadiazol-2-yl)methanone
[1-(2,4-dichlorobenzyl)-5-methoxy-2-(chloro)-1H-indol-3-yl](5-phenyl-1,3,4-oxadiazol-2-yl)methanone
[1-(2,4-dichlorobenzyl)-5-ethoxy-2-(chloro)-1H-indol-3-yl](5-phenyl-1,3,4-oxadiazol-2-yl)methanone
[1-(2,4-dichlorobenzyl)-5-methyl-2-(chloro)-1H-indol-3-yl](5-phenyl-1,3,4-oxadiazol-2-yl)methanone
[5-chloro-1-(2,4-dichlorobenzyl)-2-(chloro)-1H-indol-3-yl](5-phenyl-1,3,4-oxadiazol-2-yl)methanone
[1-(2,4-dichlorobenzyl)-2-(chloro)-1H-indol-3-yl](5-phenyl-1,3,4-oxadiazol-2-yl)methanone
[1-(2,4-dichlorobenzyl)-2-(chloro)-1H-indol-3-yl](5-phenyl-1,3,4-oxadiazol-2-yl)methanone
[1-(4-chlorobenzyl)-5-ethoxy-2-(chloro)-1H-indol-3-yl](5-pyridin-2-yl-1,3,4-oxadiazol-2-yl)methanone
[1-(4-chlorobenzyl)-5-hydroxy-2-(chloro)-1H-indol-3-yl](5-pyridin-2-yl-1,3,4-oxadiazol-2-yl)methanone
[1-(4-chlorobenzyl)-5-methyl-2-(chloro)-1H-indol-3-yl](5-pyridin-2-yl-1,3,4-oxadiazol-2-yl)methanone
[5-chloro-1-(4-chlorobenzyl)-2-(chloro)-1H-indol-3-yl](5-pyridin-2-yl-1,3,4-oxadiazol-2-yl)methanone
[1-(4-chlorobenzyl)-2-(chloro)-1H-indol-3-yl](5-pyridin-2-yl-1,3,4-oxadiazol-2-yl)methanone
[1-(2,4-dichlorobenzyl)-5-methoxy-2-(chloro)-1H-indol-3-yl](5-pyridin-2-yl-1,3,4-oxadiazol-2-yl)methanone
[1-(2,4-dichlorobenzyl)-5-ethoxy-2-(chloro)-1H-indol-3-yl](5-pyridin-2-yl-1,3,4-oxadiazol-2-yl)methanone
[1-(2,4-dichlorobenzyl)-5-hydroxy-2-(chloro)-1H-indol-3-yl](5-pyridin-2-yl-1,3,4-oxadiazol-2-yl)methanone
[1-(2,4-dichlorobenzyl)-5-methyl-2-(chloro)-1H-indol-3-yl](5-pyridin-2-yl-1,3,4-oxadiazol-2-yl)methanone
[5-chloro-1-(2,4-dichlorobenzyl)-2-(chloro)-1H-indol-3-yl](5-pyridin-2-yl-1,3,4-oxadiazol-2-yl)methanone
[1-(4-chlorobenzyl)-5-ethoxy-2-(chloro)-1H-indol-3-yl](5-pyridin-3-yl-1,3,4-oxadiazol-2-yl)methanone
[1-(4-chlorobenzyl)-5-hydroxy-2-(chloro)-1H-indol-3-yl](5-pyridin-3-yl-1,3,4-oxadiazol-2-yl)methanone
[1-(4-chlorobenzyl)-5-methyl-2-(chloro)-1H-indol-3-yl](5-pyridin-3-yl-1,3,4-oxadiazol-2-yl)methanone
[5-chloro-1-(4-chlorobenzyl)-2-(chloro)-1H-indol-3-yl](5-pyridin-3-yl-1,3,4-oxadiazol-2-yl)methanone
[1-(4-chlorobenzyl)-2-(chloro)-1H-indol-3-yl](5-pyridin-3-yl-1,3,4-oxadiazol-2-yl)methanone
[1-(2,4-dichlorobenzyl)-5-methoxy-2-(chloro)-1H-indol-3-yl](5-pyridin-3-yl-1,3,4-oxadiazol-2-yl)methanone
[1-(2,4-dichlorobenzyl)-5-ethoxy-2-(chloro)-1H-indol-3-yl](5-pyridin-3-yl-1,3,4-oxadiazol-2-yl)methanone
[1-(2,4-dichlorobenzyl)-5-methyl-2-(chloro)-1H-indol-3-yl](5-pyridin-3-yl-1,3,4-oxadiazol-2-yl)methanone
[5-chloro-1-(2,4-dichlorobenzyl)-2-(chloro)-1H-indol-3-yl](5-pyridin-3-yl-1,3,4-oxadiazol-2-yl)methanone
[1-(2,4-dichlorobenzyl)-2-(chloro)-1H-indol-3-yl](5-pyridin-3-yl-1,3,4-oxadiazol-2-yl)methanone
[1-(4-chlorobenzyl)-5-methoxy-2-(chloro)-1H-indol-3-yl](5-pyridin-4-yl-1,3,4-oxadiazol-2-yl)methanone
[1-(4-chlorobenzyl)-5-ethoxy-2-(chloro)-1H-indol-3-yl](5-pyridin-4-yl-1,3,4-oxadiazol-2-yl)methanone
[1-(4-chlorobenzyl)-5-hydroxy-2-(chloro)-1H-indol-3-yl](5-pyridin-4-yl-1,3,4-oxadiazol-2-yl)methanone
[1-(4-chlorobenzyl)-5-methyl-2-(chloro)-1H-indol-3-yl](5-pyridin-4-yl-1,3,4-oxadiazol-2-yl)methanone
[5-chloro-1-(4-chlorobenzyl)-2-(chloro)-1H-indol-3-yl](5-pyridin-4-yl-1,3,4-oxadiazol-2-yl)methanone
[1-(4-chlorobenzyl)-2-(chloro)-1H-indol-3-yl](5-pyridin-4-yl-1,3,4-oxadiazol-2-yl)methanone
[1-(2,4-dichlorobenzyl)-5-methoxy-2-(chloro)-1H-indol-3-yl](5-pyridin-4-yl-1,3,4-oxadiazol-2-yl)methanone
[1-(2,4-dichlorobenzyl)-5-ethoxy-2-(chloro)-1H-indol-3-yl](5-pyridin-4-yl-1,3,4-oxadiazol-2-yl)methanone
[1-(2,4-dichlorobenzyl)-5-hydroxy-2-(chloro)-1H-indol-3-yl](5-pyridin-4-yl-1,3,4-oxadiazol-2-yl)methanone
[1-(2,4-dichlorobenzyl)-5-methyl-2-(chloro)-1H-indol-3-yl](5-pyridin-4-yl-1,3,4-oxadiazol-2-yl)methanone
[5-chloro-1-(2,4-dichlorobenzyl)-2-(chloro)-1H-indol-3-yl](5-pyridin-4-yl-1,3,4-oxadiazol-2-yl)methanone
[1-(2,4-dichlorobenzyl)-2-(chloro)-1H-indol-3-yl](5-pyridin-4-yl-1,3,4-oxadiazol-2-yl)methanone
[1-(4-chlorobenzyl)-5-methoxy-2-(chloro)-1H-indol-3-yl](5-pyrimidin-4-yl-1,3,4-oxadiazol-2-yl)methanone

[1-(4-chlorobenzyl)-5-ethoxy-2-(chloro)-1H-indol-3-yl](5-pyrimidin-4-yl-1,3,4-oxadiazol-2-yl)methanone
[1-(4-chlorobenzyl)-5-hydroxy-2-(chloro)-1H-indol-3-yl](5-pyrimidin-4-yl-1,3,4-oxadiazol-2-yl)methanone
[1-(4-chlorobenzyl)-5-methyl-2-(chloro)-1H-indol-3-yl](5-pyrimidin-4-yl-1,3,4-oxadiazol-2-yl)methanone
[5-chloro-1-(4-chlorobenzyl)-2-(chloro)-1H-indol-3-yl](5-pyrimidin-4-yl-1,3,4-oxadiazol-2-yl)methanone
[1-(4-chlorobenzyl)-2-(chloro)-1H-indol-3-yl](5-pyrimidin-4-yl-1,3,4-oxadiazol-2-yl)methanone
[1-(2,4-dichlorobenzyl)-5-methoxy-2-(chloro)-1H-indol-3-yl](5-pyrimidin-4-yl-1,3,4-oxadiazol-2-yl)methanone
[1-(2,4-dichlorobenzyl)-5-ethoxy-2-(chloro)-1H-indol-3-yl](5-pyrimidin-4-yl-1,3,4-oxadiazol-2-yl)methanone
[1-(2,4-dichlorobenzyl)-5-hydroxy-2-(chloro)-1H-indol-3-yl](5-pyrimidin-4-yl-1,3,4-oxadiazol-2-yl)methanone
[1-(2,4-dichlorobenzyl)-5-methyl-2-(chloro)-1H-indol-3-yl](5-pyrimidin-4-yl-1,3,4-oxadiazol-2-yl)methanone
[5-chloro-1-(2,4-dichlorobenzyl)-2-(chloro)-1H-indol-3-yl](5-pyrimidin-4-yl-1,3,4-oxadiazol-2-yl)methanone
[1-(2,4-dichlorobenzyl)-2-(chloro)-1H-indol-3-yl](5-pyrimidin-4-yl-1,3,4-oxadiazol-2-yl)methanone
[1-(4-chlorobenzyl)-5-methoxy-2-(chloro)-1H-indol-3-yl](2-phenyl-1,3-oxazol-5-yl)methanone
[1-(4-chlorobenzyl)-5-ethoxy-2-(chloro)-1H-indol-3-yl](2-phenyl-1,3-oxazol-5-yl)methanone
[1-(4-chlorobenzyl)-5-hydroxy-2-(chloro)-1H-indol-3-yl](2-phenyl-1,3-oxazol-5-yl)methanone
[1-(4-chlorobenzyl)-5-methyl-2-(chloro)-1H-indol-3-yl](2-phenyl-1,3-oxazol-5-yl)methanone
[5-chloro-1-(4-chlorobenzyl)-2-(chloro)-1H-indol-3-yl](2-phenyl-1,3-oxazol-5-yl)methanone
[1-(4-chlorobenzyl)-2-(chloro)-1H-indol-3-yl](2-phenyl-1,3-oxazol-5-yl)methanone
[1-(2,4-dichlorobenzyl)-5-methoxy-2-(chloro)-1H-indol-3-yl](2-phenyl-1,3-oxazol-5-yl)methanone
[1-(2,4-dichlorobenzyl)-5-ethoxy-2-(chloro)-1H-indol-3-yl](2-phenyl-1,3-oxazol-5-yl)methanone
[1-(2,4-dichlorobenzyl)-5-hydroxy-2-(chloro)-1H-indol-3-yl](2-phenyl-1,3-oxazol-5-yl)methanone
[1-(2,4-dichlorobenzyl)-5-methyl-2-(chloro)-1H-indol-3-yl](2-phenyl-1,3-oxazol-5-yl)methanone
[5-chloro-1-(2,4-dichlorobenzyl)-2-(chloro)-1H-indol-3-yl](2-phenyl-1,3-oxazol-5-yl)methanone
[1-(2,4-dichlorobenzyl)-2-(chloro)-1H-indol-3-yl](2-phenyl-1,3-oxazol-5-yl)methanone
[1-(4-chlorobenzyl)-5-methoxy-2-(chloro)-1H-indol-3-yl](2-pyridin-2-yl-1,3-oxazol-5-yl)methanone
[1-(4-chlorobenzyl)-5-ethoxy-2-(chloro)-1H-indol-3-yl](2-pyridin-2-yl-1,3-oxazol-5-yl)methanone
[1-(4-chlorobenzyl)-5-hydroxy-2-(chloro)-1H-indol-3-yl](2-pyridin-2-yl-1,3-oxazol-5-yl)methanone
[1-(4-chlorobenzyl)-5-methyl-2-(chloro)-1H-indol-3-yl](2-pyridin-2-yl-1,3-oxazol-5-yl)methanone
[5-chloro-1-(4-chlorobenzyl)-2-(chloro)-1H-indol-3-yl](2-pyridin-2-yl-1,3-oxazol-5-yl)methanone
[1-(4-chlorobenzyl)-2-(chloro)-1H-indol-3-yl](2-pyridin-2-yl-1,3-oxazol-5-yl)methanone
[1-(2,4-dichlorobenzyl)-5-methoxy-2-(chloro)-1H-indol-3-yl](2-pyridin-2-yl-1,3-oxazol-5-yl)methanone
[1-(2,4-dichlorobenzyl)-5-ethoxy-2-(chloro)-1H-indol-3-yl](2-pyridin-2-yl-1,3-oxazol-5-yl)methanone
[1-(2,4-dichlorobenzyl)-5-hydroxy-2-(chloro)-1H-indol-3-yl](2-pyridin-2-yl-1,3-oxazol-5-yl)methanone
[1-(2,4-dichlorobenzyl)-5-methyl-2-(chloro)-1H-indol-3-yl](2-pyridin-2-yl-1,3-oxazol-5-yl)methanone
[5-chloro-1-(2,4-dichlorobenzyl)-2-(chloro)-1H-indol-3-yl](2-pyridin-2-yl-1,3-oxazol-5-yl)methanone
[1-(2,4-dichlorobenzyl)-2-(chloro)-1H-indol-3-yl](2-pyridin-2-yl-1,3-oxazol-5-yl)methanone
[1-(4-chlorobenzyl)-5-methoxy-2-(chloro)-1H-indol-3-yl](2-pyridin-3-yl-1,3-oxazol-5-yl)methanone
[1-(4-chlorobenzyl)-5-ethoxy-2-(chloro)-1H-indol-3-yl](2-pyridin-3-yl-1,3-oxazol-5-yl)methanone
[1-(4-chlorobenzyl)-5-hydroxy-2-(chloro)-1H-indol-3-yl](2-pyridin-3-yl-1,3-oxazol-5-yl)methanone
[1-(4-chlorobenzyl)-5-methyl-2-(chloro)-1H-indol-3-yl](2-pyridin-3-yl-1,3-oxazol-5-yl)methanone
[5-chloro-1-(4-chlorobenzyl)-2-(chloro)-1H-indol-3-yl](2-pyridin-3-yl-1,3-oxazol-5-yl)methanone
[1-(4-chlorobenzyl)-2-(chloro)-1H-indol-3-yl](2-pyridin-3-yl-1,3-oxazol-5-yl)methanone
[1-(2,4-dichlorobenzyl)-5-methoxy-2-(chloro)-1H-indol-3-yl](2-pyridin-3-yl-1,3-oxazol-5-yl)methanone
[1-(2,4-dichlorobenzyl)-5-ethoxy-2-(chloro)-1H-indol-3-yl](2-pyridin-3-yl-1,3-oxazol-5-yl)methanone
[1-(2,4-dichlorobenzyl)-5-hydroxy-2-(chloro)-1H-indol-3-yl](2-pyridin-3-yl-1,3-oxazol-5-yl)methanone
[1-(2,4-dichlorobenzyl)-5-methyl-2-(chloro)-1H-indol-3-yl](2-pyridin-3-yl-1,3-oxazol-5-yl)methanone
[5-chloro-1-(2,4-dichlorobenzyl)-2-(chloro)-1H-indol-3-yl](2-pyridin-3-yl-1,3-oxazol-5-yl)methanone
[1-(2,4-dichlorobenzyl)-2-(chloro)-1H-indol-3-yl](2-pyridin-3-yl-1,3-oxazol-5-yl)methanone
[1-(4-chlorobenzyl)-5-methoxy-2-(chloro)-1H-indol-3-yl](2-pyridin-4-yl-1,3-oxazol-5-yl)methanone
[1-(4-chlorobenzyl)-5-ethoxy-2-(chloro)-1H-indol-3-yl](2-pyridin-4-yl-1,3-oxazol-5-yl)methanone
[1-(4-chlorobenzyl)-5-hydroxy-2-(chloro)-1H-indol-3-yl](2-pyridin-4-yl-1,3-oxazol-5-yl)methanone
[1-(4-chlorobenzyl)-5-methyl-2-(chloro)-1H-indol-3-yl](2-pyridin-4-yl-1,3-oxazol-5-yl)methanone
[5-chloro-1-(4-chlorobenzyl)-2-(chloro)-1H-indol-3-yl](2-pyridin-4-yl-1,3-oxazol-5-yl)methanone
[1-(4-chlorobenzyl)-2-(chloro)-1H-indol-3-yl](2-pyridin-4-yl-1,3-oxazol-5-yl)methanone
[1-(2,4-dichlorobenzyl)-5-methoxy-2-(chloro)-1H-indol-3-yl](2-pyridin-4-yl-1,3-oxazol-5-yl)methanone
[1-(2,4-dichlorobenzyl)-5-ethoxy-2-(chloro)-1H-indol-3-yl](2-pyridin-4-yl-1,3-oxazol-5-yl)methanone
[1-(2,4-dichlorobenzyl)-5-hydroxy-2-(chloro)-1H-indol-3-yl])2-pyridin-4-yl-1,3-oxazol-5-yl)methanone
[1-(2,4-dichlorobenzyl)-5-methyl-2-(chloro)-1H-indol-3-yl](2-pyridin-4-yl-1,3-oxazol-5-yl)methanone
[5-chloro-1-(2,4-dichlorobenzyl)-2-(chloro)-1H-indol-3-yl](2-pyridin-4-yl-1,3-oxazol-5-yl)methanone
[1-(2,4-dichlorobenzyl)-2-(chloro)-1H-indol-3-yl](2-pyridin-4-yl-1,3-oxazol-5-yl)methanone
[1-(4-chlorobenzyl)-5-methoxy-2-(chloro)-1H-indol-3-yl](2-pyrimidin-4-yl-1,3-oxazol-5-yl)methanone
[1-(4-chlorobenzyl)-5-ethoxy-2-(chloro)-1H-indol-3-yl](2-pyrimidin-4-yl-1,3-oxazol-5-yl)methanone
[1-(4-chlorobenzyl)-5-hydroxy-2-(chloro)-1H-indol-3-yl](2-pyrimidin-4-yl-1,3-oxazol-5-yl)methanone
[1-(4-chlorobenzyl)-5-methyl-2-(chloro)-1H-indol-3-yl](2-pyrimidin-4-yl-1,3-oxazol-5-yl)methanone
[5-chloro-1-(4-chlorobenzyl)-2-(chloro)-1H-indol-3-yl](2-pyrimidin-4-yl-1,3-oxazol-5-yl)methanone
[1-(4-chlorobenzyl)-2-(chloro)-1H-indol-3-yl](2-pyrimidin-4-yl-1,3-oxazol-5-yl)methanone
[1-(2,4-dichlorobenzyl)-5-methoxy-2-(chloro)-1H-indol-3-yl](2-pyrimidin-4-yl-1,3-oxazol-5-yl)methanone

[1-(2,4-dichlorobenzyl)-5-ethoxy-2-(chloro)-1H-indol-3-yl](2-pyrimidin-4-yl-1,3-oxazol-5-yl)methanone
[1-(2,4-dichlorobenzyl)-5-hydroxy-2-(chloro)-1H-indol-3-yl](2-pyrimidin-4-yl-1,3-oxazol-5-yl)methanone
[1-(2,4-dichlorobenzyl)-5-methyl-2-(chloro)-1H-indol-3-yl](2-pyrimidin-4-yl-1,3-oxazol-5-yl)methanone
[5-chloro-1-(2,4-dichlorobenzyl)-2-(chloro)-1H-indol-3-yl](2-pyrimidin-4-yl-1,3-oxazol-5-yl)methanone
[1-(2,4-dichlorobenzyl)-2-(chloro)-1H-indol-3-yl](2-pyrimidin-4-yl-1,3-oxazol-5-yl)methanone
[1-(4-chlorobenzyl)-5-methoxy-2-(chloro)-1H-indol-3-yl](5-phenyl-1,3-oxazol-2-yl)methanone
[1-(4-chlorobenzyl)-5-ethoxy-2-(chloro)-1H-indol-3-yl](5-phenyl-1,3-oxazol-2-yl)methanone
[1-(4-chlorobenzyl)-5-hydroxy-2-(chloro)-1H-indol-3-yl](5-phenyl-1,3-oxazol-2-yl)methanone
[1-(4-chlorobenzyl)-5-methyl-2-(chloro)-1H-indol-3-yl](5-phenyl-1,3-oxazol-2-yl)methanone
[5-chloro-1-(4-chlorobenzyl)-2-(chloro)-1H-indol-3-yl](5-phenyl-1,3-oxazol-2-yl)methanone
[1-(4-chlorobenzyl)-2-(chloro)-1H-indol-3-yl](5-phenyl-1,3-oxazol-2-yl)methanone
[1-(2,4-dichlorobenzyl)-5-methoxy-2-(chloro)-1H-indol-3-yl](5-phenyl-1,3-oxazol-2-yl)methanone
[1-(2,4-dichlorobenzyl)-5-ethoxy-2-(chloro)-1H-indol-3-yl](5-phenyl-1,3-oxazol-2-yl)methanone
[1-(2,4-dichlorobenzyl)-5-hydroxy-2-(chloro)-1H-indol-3-yl](5-phenyl-1,3-oxazol-2-yl)methanone
[1-(2,4-dichlorobenzyl)-5-methyl-2-(chloro)-1H-indol-3-yl](5-phenyl-1,3-oxazol-2-yl)methanone
[5-chloro-1-(2,4-dichlorobenzyl)-2-(chloro)-1H-indol-3-yl](5-phenyl-1,3-oxazol-2-yl)methanone
[1-(4-chlorobenzyl)-5-methoxy-2-(chloro)-1H-indol-3-yl](5-pyridin-2-yl-1,3-oxazol-2-yl)methanone
[1-(4-chlorobenzyl)-5-ethoxy-2-(chloro)-1H-indol-3-yl](5-pyridin-2-yl-1,3-oxazol-2-yl)methanone
[1-(4-chlorobenzyl)-5-hydroxy-2-(chloro)-1H-indol-3-yl](5-pyridin-2-yl-1,3-oxazol-2-yl)methanone
[1-(4-chlorobenzyl)-5-methyl-2-(chloro)-1H-indol-3-yl](5-pyridin-2-yl-1,3-oxazol-2-yl)methanone
[5-chloro-1-(4-chlorobenzyl)-2-(chloro)-1H-indol-3-yl](5-pyridin-2-yl-1,3-oxazol-2-yl)methanone
[1-(4-chlorobenzyl)-2-(chloro)-1H-indol-3-yl](5-pyridin-2-yl-1,3-oxazol-2-yl)methanone
[1-(2,4-dichlorobenzyl)-5-methoxy-2-(chloro)-1H-indol-3-yl](5-pyridin-2-yl-1,3-oxazol-2-yl)methanone
[1-(2,4-dichlorobenzyl)-5-ethoxy-2-(chloro)-1H-indol-3-yl](5-pyridin-2-yl-1,3-oxazol-2-yl)methanone
[1-(2,4-dichlorobenzyl)-5-hydroxy-2-(chloro)-1H-indol-3-yl](5-pyridin-2-yl-1,3-oxazol-2-yl)methanone
[1-(2,4-dichlorobenzyl)-5-methyl-2-(chloro)-1H-indol-3-yl](5-pyridin-2-yl-1,3-oxazol-2-yl)methanone
[5-chloro-1-(2,4-dichlorobenzyl)-2-(chloro)-1H-indol-3-yl](5-pyridin-2-yl-1,3-oxazol-2-yl)methanone
[1-(2,4-dichlorobenzyl)-2-(chloro)-1H-indol-3-yl](5-pyridin-2-yl-1,3-oxazol-2-yl)methanone
[1-(4-chlorobenzyl)-5-methoxy-2-(chloro)-1H-indol-3-yl](5-pyridin-3-yl-1,3-oxazol-2-yl)methanone
[1-(4-chlorobenzyl)-5-ethoxy-2-(chloro)-1H-indol-3-yl](5-pyridin-3-yl-1,3-oxazol-2-yl)methanone
[1-(4-chlorobenzyl)-5-hydroxy-2-(chloro)-1H-indol-3-yl](5-pyridin-3-yl-1,3-oxazol-2-yl)methanone
[1-(4-chlorobenzyl)-5-methyl-2-(chloro)-1H-indol-3-yl](5-pyridin-3-yl-1,3-oxazol-2-yl)methanone
[5-chloro-1-(4-chlorobenzyl)-2-(chloro)-1H-indol-3-yl](5-pyridin-3-yl-1,3-oxazol-2-yl)methanone
[1-(4-chlorobenzyl)-2-(chloro)-1H-indol-3-yl](5-pyridin-3-yl-1,3-oxazol-2-yl)methanone
[1-(2,4-dichlorobenzyl)-5-methoxy-2-(chloro)-1H-indol-3-yl](5-pyridin-3-yl-1,3-oxazol-2-yl)methanone
[1-(2,4-dichlorobenzyl)-5-ethoxy-2-(chloro)-1H-indol-3-yl](5-pyridin-3-yl-1,3-oxazol-2-yl)methanone
[1-(2,4-dichlorobenzyl)-5-hydroxy-2-(chloro)-1H-indol-3-yl](5-pyridin-3-yl-1,3-oxazol-2-yl)methanone
[1-(2,4-dichlorobenzyl)-5-methyl-2-(chloro)-1H-indol-3-yl](5-pyridin-3-yl-1,3-oxazol-2-yl)methanone
[5-chloro-1-(2,4-dichlorobenzyl)-2-(chloro)-1H-indol-3-yl](5-pyridin-3-yl-1,3-oxazol-2-yl)methanone
[1-(2,4-dichlorobenzyl)-2-(chloro)-1H-indol-3-yl](5-pyridin-3-yl-1,3-oxazol-2-yl)methanone
[1-(4-chlorobenzyl)-5-methoxy-2-(chloro)-1H-indol-3-yl](5-pyridin-4-yl-1,3-oxazol-2-yl)methanone
[1-(4-chlorobenzyl)-5-ethoxy-2-(chloro)-1H-indol-3-yl](5-pyridin-4-yl-1,3-oxazol-2-yl)methanone
[1-(4-chlorobenzyl)-5-hydroxy-2-(chloro)-1H-indol-3-yl](5-pyridin-4-yl-1,3-oxazol-2-yl)methanone
[1-(4-chlorobenzyl)-5-methyl-2-(chloro)-1H-indol-3-yl](5-pyridin-4-yl-1,3-oxazol-2-yl)methanone
[5-chloro-1-(4-chlorobenzyl)-2-(chloro)-1H-indol-3-yl](5-pyridin-4-yl-1,3-oxazol-2-yl)methanone
[1-(4-chlorobenzyl)-2-(chloro)-1H-indol-3-yl](5-pyridin-4-yl-1,3-oxazol-2-yl)methanone
[1-(2,4-dichlorobenzyl)-5-methoxy-2-(chloro)-1H-indol-3-yl](5-pyridin-4-yl-1,3-oxazol-2-yl)methanone
[1-(2,4-dichlorobenzyl)-5-ethoxy-2-(chloro)-1H-indol-3-yl](5-pyridin-4-yl-1,3-oxazol-2-yl)methanone
[1-(2,4-dichlorobenzyl)-5-hydroxy-2-(chloro)-1H-indol-3-yl](5-pyridin-4-yl-1,3-oxazol-2-yl)methanone
[1-(2,4-dichlorobenzyl)-5-methyl-2-(chloro)-1H-indol-3-yl](5-pyridin-4-yl-1,3-oxazol-2-yl)methanone
[5-chloro-1-(2,4-dichlorobenzyl)-2-(chloro)-1H-indol-3-yl](5-pyridin-4-yl-1,3-oxazol-2-yl)methanone
[1-(2,4-dichlorobenzyl)-2-(chloro)-1H-indol-3-yl](5-pyridin-4-yl-1,3-oxazol-2-yl)methanone
[1-(4-chlorobenzyl)-5-methoxy-2-(chloro)-1H-indol-3-yl](5-pyrimidin-4-yl-1,3-oxazol-2-yl)methanone
[1-(4-chlorobenzyl)-5-ethoxy-2-(chloro)-1H-indol-3-yl](5-pyrimidin-4-yl-1,3-oxazol-2-yl)methanone
[1-(4-chlorobenzyl)-5-hydroxy-2-(chloro)-1H-indol-3-yl](5-pyrimidin-4-yl-1,3-oxazol-2-yl)methanone
[1-(4-chlorobenzyl)-5-methyl-2-(chloro)-1H-indol-3-yl](5-pyrimidin-4-yl-1,3-oxazol-2-yl)methanone
[5-chloro-1-(4-chlorobenzyl)-2-(chloro)-1H-indol-3-yl](5-pyrimidin-4-yl-1,3-oxazol-2-yl)methanone
[1-(4-chlorobenzyl)-2-(chloro)-1H-indol-3-yl](5-pyrimidin-4-yl-1,3-oxazol-2-yl)methanone
[1-(2,4-dichlorobenzyl)-5-methoxy-2-(chloro)-1H-indol-3-yl](5-pyrimidin-4-yl-1,3-oxazol-2-yl)methanone
[1-(2,4-dichlorobenzyl)-5-ethoxy-2-(chloro)-1H-indol-3-yl](5-pyrimidin-4-yl-1,3-oxazol-2-yl)methanone
[1-(2,4-dichlorobenzyl)-5-hydroxy-2-(chloro)-1H-indol-3-yl](5-pyrimidin-4-yl-1,3-oxazol-2-yl)methanone
[1-(2,4-dichlorobenzyl)-5-methyl-2-(chloro)-1H-indol-3-yl](5-pyrimidin-4-yl-1,3-oxazol-2-yl)methanone
[1-(2,4-dichlorobenzyl)-5-hydroxy-2-(chloro)-1H-indol-3-yl](5-phenyl-1,3,4-oxadiazol-2-yl)methanone
[5-chloro-1-(2,4-dichlorobenzyl)-2-(chloro)-1H-indol-3-yl](5-pyrimidin-4-yl-1,3-oxazol-2-yl)methanone
[1-(2,4-dichlorobenzyl)-2-(chloro)-1H-indol-3-yl](5-pyrimidin-4-yl-1,3-oxazol-2-yl)methanone Additional useful compounds are those described below under the heading "Other useful compounds (e.g., FAAH inhibitors)" and derivatives thereof within Formula I wherein the group at the 5 position of indole is substituted by H, halogen, —OCH₃, —OCH₂CH₃, —CH₂CH₃ and —OH (wherein any carbon can be optionally, independently singly or multiply substituted with a halogen) and the benzyl group is para substituted, e.g., with Br, methoxy or —OH, or is a 2, 4 substituted, e.g. with Cl.

Other Useful Compounds (e.g. FAAH Inhibitors)

[1-(4-chlorobenzyl)-5-methoxy-2-methyl-1H-indol-3-yl](4-phenyl-1,3-oxazol-2-yl)methanone
[1-(4-chlorobenzyl)-5-methoxy-1H-indol-3-yl](4-phenyl-1,3-oxazol-2-yl)methanone
[1-(4-chlorobenzyl)-5-methoxy-2-methyl-1H-indol-3-yl](4-pyridin-2-yl-1,3-oxazol-2-yl)methanone
[1-(4-chlorobenzyl)-5-methoxy-1H-indol-3-yl](4-pyridin-2-yl-1,3-oxazol-2-yl)methanone
[1-(4-chlorobenzyl)-5-methoxy-2-methyl-1H-indol-3-yl](4-pyridin-3-yl-1,3-oxazol-2-yl)methanone
[1-(4-chlorobenzyl)-5-methoxy-1H-indol-3-yl](4-pyridin-3-yl-1,3-oxazol-2-yl)methanone
[1-(4-chlorobenzyl)-5-methoxy-2-methyl-1H-indol-3-yl](4-pyridin-4-yl-1,3-oxazol-2-yl)methanone
[1-(4-chlorobenzyl)-5-methoxy-1H-indol-3-yl](4-pyridin-4-yl-1,3-oxazol-2-yl)methanone
[1-(4-chlorobenzyl)-5-methoxy-2-methyl-1H-indol-3-yl](5-phenyl-1,3-oxazol-2-yl)methanone
[1-(4-chlorobenzyl)-5-methoxy-1H-indol-3-yl](5-phenyl-1,3-oxazol-2-yl)methanone
[1-(4-chlorobenzyl)-5-methoxy-2-methyl-1H-indol-3-yl](5-pyridin-2-yl-1,3-oxazol-2-yl)methanone
[1-(4-chlorobenzyl)-5-methoxy-1H-indol-3-yl](5-pyridin-2-yl-1,3-oxazol-2-yl)methanone
[1-(4-chlorobenzyl)-5-methoxy-2-methyl-1H-indol-3-yl](5-pyridin-3-yl-1,3-oxazol-2-yl)methanone
[1-(4-chlorobenzyl)-5-methoxy-1H-indol-3-yl](5-pyridin-3-yl-1,3-oxazol-2-yl)methanone
[1-(4-chlorobenzyl)-5-methoxy-2-methyl-1H-indol-3-yl](5-pyridin-4-yl-1,3-oxazol-2-yl)methanone
[1-(4-chlorobenzyl)-5-methoxy-1H-indol-3-yl](5-pyridin-4-yl-1,3-oxazol-2-yl)methanone
[1-(4-chlorobenzyl)-5-methoxy-2-methyl-1H-indol-3-yl](1,3-oxazol-2-yl)methanone
[1-(4-chlorobenzyl)-5-methoxy-1H-indol-3-yl](1,3-oxazol-2-yl)methanone
[1-(4-chlorobenzyl)-5-methoxy-2-methyl-1H-indol-3-yl](1H-imidazol-2-yl)methanone
[1-(4-chlorobenzyl)-5-methoxy-1H-indol-3-yl](1H-imidazol-2-yl)methanone
[1-(4-chlorobenzyl)-5-methoxy-2-methyl-1H-indol-3-yl](1,3-thiazol-2-yl)methanone
[1-(4-chlorobenzyl)-5-methoxy-1H-indol-3-yl](1,3-thiazol-2-yl)methanone
[1-(4-chlorobenzyl)-5-methoxy-2-methyl-1H-indol-3-yl](4-pyridin-2-yl-1,3-thiazol-2-yl)methanone
[1-(4-chlorobenzyl)-5-methoxy-1H-indol-3-yl](4-pyridin-2-yl-1,3-thiazol-2-yl)methanone
[1-(4-chlorobenzyl)-5-methoxy-2-methyl-1H-indol-3-yl](4-pyridin-3-yl-1,3-thiazol-2-yl)methanone
[1-(4-chlorobenzyl)-5-methoxy-1H-indol-3-yl](4-pyridin-3-yl-1,3-thiazol-2-yl)methanone
[1-(4-chlorobenzyl)-5-methoxy-2-methyl-1H-indol-3-yl](4-pyridin-4-yl-1,3-thiazol-2-yl)methanone
[1-(4-chlorobenzyl)-5-methoxy-1H-indol-3-yl](4-pyridin-4-yl-1,3-thiazol-2-yl)methanone
1-(4-chlorobenzyl)-5-methoxy-2-methyl-1H-indol-3-yl](4-phenyl-1,3-thiazol-2-yl)methanone
1-(4-chlorobenzyl)-5-methoxy-1H-indol-3-yl](4-phenyl-1,3-thiazol-2-yl)methanone
[1-(4-chlorobenzyl)-5-methoxy-2-methyl-1H-indol-3-yl](5-phenyl-1,3-thiazol-2-yl)methanone
[1-(4-chlorobenzyl)-5-methoxy-1H-indol-3-yl](5-phenyl-1,3-thiazol-2-yl)methanone
[1-(4-chlorobenzyl)-5-methoxy-2-methyl-1H-indol-3-yl](5-pyridin-2-yl-1,3-thiazol-2-yl)methanone
[1-(4-chlorobenzyl)-5-methoxy-1H-indol-3-yl](5-pyridin-2-yl-1,3-thiazol-2-yl)methanone
[1-(4-chlorobenzyl)-5-methoxy-2-methyl-1H-indol-3-yl](5-pyridin-3-yl-1,3-thiazol-2-yl)methanone
[1-(4-chlorobenzyl)-5-methoxy-1H-indol-3-yl](5-pyridin-3-yl-1,3-thiazol-2-yl)methanone
[1-(4-chlorobenzyl)-5-methoxy-2-methyl-1H-indol-3-yl](5-pyridin-4-yl-1,3-thiazol-2-yl)methanone
[1-(4-chlorobenzyl)-5-methoxy-1H-indol-3-yl](5-pyridin-4-yl-1,3-thiazol-2-yl)methanone
[1-(4-chlorobenzyl)-5-methoxy-2-methyl-1H-indol-3-yl](5-phenyl-2-thienyl)methanone
[1-(4-chlorobenzyl)-5-methoxy-1H-indol-3-yl](5-phenyl-2-thienyl)methanone
[1-(4-chlorobenzyl)-5-methoxy-2-methyl-1H-indol-3-yl](5-pyridin-2-yl-2-thienyl)methanone
[1-(4-chlorobenzyl)-5-methoxy-1H-indol-3-yl](5-pyridin-2-yl-2-thienyl)methanone
[1-(4-chlorobenzyl)-5-methoxy-2-methyl-1H-indol-3-yl](5-pyridin-3-yl-2-thienyl)methanone
[1-(4-chlorobenzyl)-5-methoxy-1H-indol-3-yl](5-pyridin-3-yl-2-thienyl)methanone
[1-(4-chlorobenzyl)-5-methoxy-2-methyl-1H-indol-3-yl](5-pyridin-4-yl-2-thienyl)methanone
[1-(4-chlorobenzyl)-5-methoxy-1H-indol-3-yl](5-pyridin-4-yl-2-thienyl)methanone
[1-(4-chlorobenzyl)-5-methoxy-2-methyl-1H-indol-3-yl](2-thienyl)methanone
[1-(4-chlorobenzyl)-5-methoxy-1H-indol-3-yl](2-thienyl)methanone
[1-(4-chlorobenzyl)-5-methoxy-2-methyl-1H-indol-3-yl](1,3,4-thiadiazol-2-yl)methanone
[1-(4-chlorobenzyl)-5-methoxy-1H-indol-3-yl](1,3,4-thiadiazol-2-yl)methanone
[1-(4-chlorobenzyl)-5-methoxy-2-methyl-1H-indol-3-yl](isothiazol-5-yl)methanone
[1-(4-chlorobenzyl)-5-methoxy-1H-indol-3-yl](isothiazol-5-yl)methanone
[1-(4-chlorobenzyl)-5-methoxy-2-methyl-1H-indol-3-yl](isothiazol-3-yl)methanone
[1-(4-chlorobenzyl)-5-methoxy-1H-indol-3-yl](isothiazol-3-yl)methanone
[1-(4-chlorobenzyl)-5-methoxy-2-methyl-1H-indol-3-yl](isoxazol-3-yl)methanone
[1-(4-chlorobenzyl)-5-methoxy-1H-indol-3-yl](isoxazol-3-yl)methanone
[1-(4-chlorobenzyl)-5-methoxy-2-methyl-1H-indol-3-yl](isoxazol-5-yl)methanone
[1-(4-chlorobenzyl)-5-methoxy-1H-indol-3-yl](isoxazol-5-yl)methanone
[1-(4-chlorobenzyl)-5-methoxy-2-methyl-1H-indol-3-yl](3-phenylisoxazol-5-yl)methanone
[1-(4-chlorobenzyl)-5-methoxy-1H-indol-3-yl](3-phenyl-isoxazol-5-yl)methanone
[1-(4-chlorobenzyl)-5-methoxy-2-methyl-1H-indol-3-yl](3-pyridin-2-ylisoxazol-5-yl)methanone
[1-(4-chlorobenzyl)-5-methoxy-1H-indol-3-yl](3-pyridin-2-ylisoxazol-5-yl)methanone
[1-(4-chlorobenzyl)-5-methoxy-2-methyl-1H-indol-3-yl](3-pyridin-3-ylisoxazol-5-yl)methanone

[1-(4-chlorobenzyl)-5-methoxy-1H-indol-3-yl](3-pyridin-3-ylisoxazol-5-yl)methanone
[1-(4-chlorobenzyl)-5-methoxy-2-methyl-1H-indol-3-yl](3-pyridin-4-ylisoxazol-5-yl)methanone
[1-(4-chlorobenzyl)-5-methoxy-1H-indol-3-yl](3-pyridin-4-ylisoxazol-5-yl)methanone
[1-(4-chlorobenzyl)-5-methoxy-2-methyl-1H-indol-3-yl](3-pyrimidin-4-ylisoxazol-5-yl)methanone
[1-(4-chlorobenzyl)-5-methoxy-1H-indol-3-yl](3-pyrimidin-4-ylisoxazol-5-yl)methanone
[1-(4-chlorobenzyl)-5-methoxy-2-methyl-1H-indol-3-yl](3-pyridazin-3-ylisoxazol-5-yl)methanone
[1-(4-chlorobenzyl)-5-methoxy-1H-indol-3-yl](3-pyridazin-3-ylisoxazol-5-yl)methanone
[1-(4-chlorobenzyl)-5-methoxy-2-methyl-1H-indol-3-yl](3-pyrazin-2-ylisoxazol-5-yl)methanone
[1-(4-chlorobenzyl)-5-methoxy-1H-indol-3-yl](3-pyrazin-2-ylisoxazol-5-yl)methanone
[1-(4-chlorobenzyl)-5-methoxy-2-methyl-1H-indol-3-yl](3-pyrimidin-2-ylisoxazol-5-yl)methanone
[1-(4-chlorobenzyl)-5-methoxy-1H-indol-3-yl](3-pyrimidin-2-ylisoxazol-5-yl)methanone
[1-(4-chlorobenzyl)-5-methoxy-2-methyl-1H-indol-3-yl](3-pyridazin-4-ylisoxazol-5-yl)methanone
[1-(4-chlorobenzyl)-5-methoxy-1H-indol-3-yl](3-pyridazin-4-ylisoxazol-5-yl)methanone
[1-(4-chlorobenzyl)-5-methoxy-2-methyl-1H-indol-3-yl](3-phenyl-1,2,4-oxadiazol-5-yl)methanone
[1-(4-chlorobenzyl)-5-methoxy-1H-indol-3-yl](3-phenyl-1,2,4-oxadiazol-5-yl)methanone
[1-(4-chlorobenzyl)-5-methoxy-2-methyl-1H-indol-3-yl](3-pyridin-3-yl-1,2,4-oxadiazol-5-yl)methanone
[1-(4-chlorobenzyl)-5-methoxy-1H-indol-3-yl](3-pyridin-3-yl-1,2,4-oxadiazol-5-yl)methanone
[1-(4-chlorobenzyl)-5-methoxy-2-methyl-1H-indol-3-yl](3-pyridin-4-yl-1,2,4-oxadiazol-5-yl)methanone
[1-(4-chlorobenzyl)-5-methoxy-1H-indol-3-yl](3-pyridin-4-yl-1,2,4-oxadiazol-5-yl)methanone
[1-(4-chlorobenzyl)-5-methoxy-2-methyl-1H-indol-3-yl](3-pyrimidin-4-yl-1,2,4-oxadiazol-5-yl)methanone
[1-(4-chlorobenzyl)-5-methoxy-1H-indol-3-yl](3-pyrimidin-4-yl-1,2,4-oxadiazol-5-yl)methanone
[1-(4-chlorobenzyl)-5-methoxy-2-methyl-1H-indol-3-yl](3-pyridazin-3-yl-1,2,4-oxadiazol-5-yl)methanone
[1-(4-chlorobenzyl)-5-methoxy-1H-indol-3-yl](3-pyridazin-3-yl-1,2,4-oxadiazol-5-yl)methanone
[1-(4-chlorobenzyl)-5-methoxy-2-methyl-1H-indol-3-yl](3-pyrazin-2-yl-1,2,4-oxadiazol-5-yl)methanone
[1-(4-chlorobenzyl)-5-methoxy-1H-indol-3-yl](3-pyrazin-2-yl-1,2,4-oxadiazol-5-yl)methanone
[1-(4-chlorobenzyl)-5-methoxy-2-methyl-1H-indol-3-yl](3-pyrimidin-2-yl-1,2,4-oxadiazol-5-yl)methanone
[1-(4-chlorobenzyl)-5-methoxy-1H-indol-3-yl](3-pyrimidin-2-yl-1,2,4-oxadiazol-5-yl)methanone
[1-(4-chlorobenzyl)-5-methoxy-2-methyl-1H-indol-3-yl](3-pyridazin-4-yl-1,2,4-oxadiazol-5-yl)methanone
[1-(4-chlorobenzyl)-5-methoxy-1H-indol-3-yl](3-pyridazin-4-yl-1,2,4-oxadiazol-5-yl)methanone
[1-(4-chlorobenzyl)-5-methoxy-2-methyl-1H-indol-3-yl](5-phenyl-1,2,4-oxadiazol-3-yl)methanone
[1-(4-chlorobenzyl)-5-methoxy-1H-indol-3-yl](5-phenyl-1,2,4-oxadiazol-3-yl)methanone
[1-(4-chlorobenzyl)-5-methoxy-2-methyl-1H-indol-3-yl](5-pyridin-2-yl-1,2,4-oxadiazol-3-yl)methanone
[1-(4-chlorobenzyl)-5-methoxy-1H-indol-3-yl](5-pyridin-2-yl-1,2,4-oxadiazol-3-yl)methanone
[1-(4-chlorobenzyl)-5-methoxy-2-methyl-1H-indol-3-yl](5-pyridin-3-yl-1,2,4-oxadiazol-3-yl)methanone
[1-(4-chlorobenzyl)-5-methoxy-1H-indol-3-yl](5-pyridin-3-yl-1,2,4-oxadiazol-3-yl)methanone
[1-(4-chlorobenzyl)-5-methoxy-2-methyl-1H-indol-3-yl](5-pyridin-4-yl-1,2,4-oxadiazol-3-yl)methanone
[1-(4-chlorobenzyl)-5-methoxy-1H-indol-3-yl](5-pyridin-4-yl-1,2,4-oxadiazol-3-yl)methanone
[1-(4-chlorobenzyl)-5-methoxy-2-methyl-1H-indol-3-yl](5-pyrimidin-4-yl-1,2,4-oxadiazol-3-yl)methanone
[1-(4-chlorobenzyl)-5-methoxy-1H-indol-3-yl](5-pyrimidin-4-yl-1,2,4-oxadiazol-3-yl)methanone
[1-(4-chlorobenzyl)-5-methoxy-2-methyl-1H-indol-3-yl](5-pyridazin-3-yl-1,2,4-oxadiazol-3-yl)methanone
[1-(4-chlorobenzyl)-5-methoxy-1H-indol-3-yl](5-pyridazin-3-yl-1,2,4-oxadiazol-3-yl)methanone
[1-(4-chlorobenzyl)-5-methoxy-2-methyl-1H-indol-3-yl](5-pyrazin-2-yl-1,2,4-oxadiazol-3-yl)methanone
[1-(4-chlorobenzyl)-5-methoxy-1H-indol-3-yl](5-pyrazin-2-yl-1,2,4-oxadiazol-3-yl)methanone
[1-(4-chlorobenzyl)-5-methoxy-2-methyl-1H-indol-3-yl](5-pyrimidin-2-yl-1,2,4-oxadiazol-3-yl)methanone
[1-(4-chlorobenzyl)-5-methoxy-1H-indol-3-yl](5-pyrimidin-2-yl-1,2,4-oxadiazol-3-yl)methanone
[1-(4-chlorobenzyl)-5-methoxy-2-methyl-1H-indol-3-yl](5-pyridazin-4-yl-1,2,4-oxadiazol-3-yl)methanone
[1-(4-chlorobenzyl)-5-methoxy-1H-indol-3-yl](5-pyridazin-4-yl-1,2,4-oxadiazol-3-yl)methanone
[1-(4-chlorobenzyl)-5-methoxy-2-methyl-1H-indol-3-yl](5-pyridazin-3-yl-1,3,4-oxadiazol-2-yl)methanone
[1-(4-chlorobenzyl)-5-methoxy-1H-indol-3-yl](5-pyridazin-3-yl-1,3,4-oxadiazol-2-yl)methanone
[1-(4-chlorobenzyl)-5-methoxy-2-methyl-1H-indol-3-yl](5-pyrimidin-4-yl-1,3,4-oxadiazol-2-yl)methanone
[1-(4-chlorobenzyl)-5-methoxy-1H-indol-3-yl](5-pyrimidin-4-yl-1,3,4-oxadiazol-2-yl)methanone
[1-(4-chlorobenzyl)-5-methoxy-2-methyl-1H-indol-3-yl](5-pyrazin-2-yl-1,3,4-oxadiazol-2-yl)methanone
[1-(4-chlorobenzyl)-5-methoxy-1H-indol-3-yl](5-pyrazin-2-yl-1,3,4-oxadiazol-2-yl)methanone
[1-(4-chlorobenzyl)-5-methoxy-2-methyl-1H-indol-3-yl](5-pyrimidin-2-yl-1,3,4-oxadiazol-2-yl)methanone
[1-(4-chlorobenzyl)-5-methoxy-1H-indol-3-yl](5-pyrimidin-2-yl-1,3,4-oxadiazol-2-yl)methanone
[1-(4-chlorobenzyl)-5-methoxy-2-methyl-1H-indol-3-yl](5-pyridazin-4-yl-1,3,4-oxadiazol-2-yl)methanone
[1-(4-chlorobenzyl)-5-methoxy-1H-indol-3-yl](5-pyridazin-4-yl-1,3,4-oxadiazol-2-yl)methanone
[1-(4-chlorobenzyl)-5-methoxy-2-methyl-1H-indol-3-yl](5-phenyl-1,3,4-thiadiazol-2-yl)methanone
[1-(4-chlorobenzyl)-5-methoxy-1H-indol-3-yl](5-phenyl-1,3,4-thiadiazol-2-yl)methanone
[1-(4-chlorobenzyl)-5-methoxy-2-methyl-1H-indol-3-yl](5-pyridin-2-yl-1,3,4-thiadiazol-2-yl)methanone
[1-(4-chlorobenzyl)-5-methoxy-1H-indol-3-yl](5-pyridin-2-yl-1,3,4-thiadiazol-2-yl)methanone
[1-(4-chlorobenzyl)-5-methoxy-2-methyl-1H-indol-3-yl](5-pyridin-3-yl-1,3,4-thiadiazol-2-yl)methanone
[1-(4-chlorobenzyl)-5-methoxy-1H-indol-3-yl](5-pyridin-3-yl-1,3,4-thiadiazol-2-yl)methanone
[1-(4-chlorobenzyl)-5-methoxy-2-methyl-1H-indol-3-yl](5-pyridin-4-yl-1,3,4-thiadiazol-2-yl)methanone
[1-(4-chlorobenzyl)-5-methoxy-1H-indol-3-yl](5-pyridin-4-yl-1,3,4-thiadiazol-2-yl)methanone
[1-(4-chlorobenzyl)-5-methoxy-2-methyl-1H-indol-3-yl](5-pyrimidin-4-yl-1,3,4-thiadiazol-2-yl)methanone

[1-(4-chlorobenzyl)-5-methoxy-1H-indol-3-yl](5-pyrimidin-4-yl-1,3,4-thiadiazol-2-yl)methanone
[1-(4-chlorobenzyl)-5-methoxy-2-methyl-1H-indol-3-yl](5-pyridazin-3-yl-1,3,4-thiadiazol-2-yl)methanone
[1-(4-chlorobenzyl)-5-methoxy-1H-indol-3-yl](5-pyridazin-3-yl-1,3,4-thiadiazol-2-yl)methanone
[1-(4-chlorobenzyl)-5-methoxy-2-methyl-1H-indol-3-yl](5-pyrazin-2-yl-1,3,4-thiadiazol-2-yl)methanone
[1-(4-chlorobenzyl)-5-methoxy-1H-indol-3-yl](5-pyrazin-2-yl-1,3,4-thiadiazol-2-yl)methanone
1-(4-chlorobenzyl)-5-methoxy-2-methyl-1H-indol-3-yl](5-pyrimidin-2-yl-1,3,4-thiadiazol-2-yl)methanone
1-(4-chlorobenzyl)-5-methoxy-1H-indol-3-yl](5-pyrimidin-2-yl-1,3,4-thiadiazol-2-yl)methanone
[1-(4-chlorobenzyl)-5-methoxy-2-methyl-1H-indol-3-yl](5-pyridazin-4-yl-1,3,4-thiadiazol-2-yl)methanone
[1-(4-chlorobenzyl)-5-methoxy-1H-indol-3-yl](5-pyridazin-4-yl-1,3,4-thiadiazol-2-yl)methanone
[1-(4-chlorobenzyl)-5-methoxy-2-methyl-1H-indol-3-yl](3-phenylisothiazol-5-yl)methanone
[1-(4-chlorobenzyl)-5-methoxy-1H-indol-3-yl](3-phenylisothiazol-5-yl)methanone
[1-(4-chlorobenzyl)-5-methoxy-2-methyl-1H-indol-3-yl](3-pyridin-2-ylisothiazol-5-yl)methanone
[1-(4-chlorobenzyl)-5-methoxy-1H-indol-3-yl](3-pyridin-2-ylisothiazol-5-yl)methanone
[1-(4-chlorobenzyl)-5-methoxy-2-methyl-1H-indol-3-yl](3-pyridin-3-ylisothiazol-5-yl)methanone
[1-(4-chlorobenzyl)-5-methoxy-1H-indol-3-yl](3-pyridin-3-ylisothiazol-5-yl)methanone
[1-(4-chlorobenzyl)-5-methoxy-2-methyl-1H-indol-3-yl](3-pyridin-4-ylisothiazol-5-yl)methanone
[1-(4-chlorobenzyl)-5-methoxy-1H-indol-3-yl](3-pyridin-4-ylisothiazol-5-yl)methanone
[1-(4-chlorobenzyl)-5-methoxy-2-methyl-1H-indol-3-yl](3-pyrimidin-4-ylisothiazol-5-yl)methanone
[1-(4-chlorobenzyl)-5-methoxy-1H-indol-3-yl](3-pyrimidin-4-ylisothiazol-5-yl)methanone
[1-(4-chlorobenzyl)-5-methoxy-2-methyl-1H-indol-3-yl](3-pyridazin-3-ylisothiazol-5-yl)methanone
[1-(4-chlorobenzyl)-5-methoxy-1H-indol-3-yl](3-pyridazin-3-ylisothiazol-5-yl)methanone
[1-(4-chlorobenzyl)-5-methoxy-2-methyl-1H-indol-3-yl](3-pyrazin-2-ylisothiazol-5-yl)methanone
[1-(4-chlorobenzyl)-5-methoxy-1H-indol-3-yl](3-pyrazin-2-ylisothiazol-5-yl)methanone
[1-(4-chlorobenzyl)-5-methoxy-2-methyl-1H-indol-3-yl](3-pyrimidin-2-ylisothiazol-5-yl)methanone
[[1-(4-chlorobenzyl)-5-methoxy-1H-indol-yl](3-pyrimidin-2-ylisothiazol-5-yl)methanone
1-(4-chlorobenzyl)-5-methoxy-2-methyl-1H-indol-3-yl](3-pyridazin-4-ylisothiazol-5-yl)methanone
1-(4-chlorobenzyl)-5-methoxy-1H-indol-3-yl](3-pyridazin-4-ylisothiazol-5-yl)methanone
1(4-chlorobenzyl)-5-methoxy-2-methyl-1H-indol-3-yl](5-phenyl-2-furyl)methanone
[1-(4-chlorobenzyl)-5-methoxy-1H-indol-3-yl](5-phenyl-2-furyl)methanone
[1-(4-chlorobenzyl)-5-methoxy-2-methyl-1H-indol-3-yl](5-pyridin-2-yl-2-furyl)methanone
[1-(4-chlorobenzyl)-5-methoxy-1H-indol-3-yl](5-pyridin-2-yl-2-furyl)methanone
[1-(4-chlorobenzyl)-5-methoxy-2-methyl-1H-indol-3-yl](5-pyridin-3-yl-2-furyl)methanone
[1-(4-chlorobenzyl)-5-methoxy-1H-indol-3-yl](5-pyridin-3-yl-2-furyl)methanone
[1-(4-chlorobenzyl)-5-methoxy-2-methyl-1H-indol-3-yl](5-pyridin-4-yl-2-furyl)methanone
[1-(4-chlorobenzyl)-5-methoxy-1H-indol-3-yl](5-pyridin-4-yl-2-furyl)methanone
[1-(4-chlorobenzyl)-5-methoxy-2-methyl-1H-indol-3-yl](5-pyrimidin-4-yl-2-furyl)methanone
[1-(4-chlorobenzyl)-5-methoxy-1H-indol-3-yl](5-pyrimidin-4-yl-2-furyl)methanone
[1-(4-chlorobenzyl)-5-methoxy-2-methyl-1H-indol-3-yl](5-pyridazin-3-yl-2-furyl)methanone
[1-(4-chlorobenzyl)-5-methoxy-1H-indol-3-yl](5-pyridazin-3-yl-2-furyl)methanone
[1-(4-chlorobenzyl)-5-methoxy-2-methyl-1H-indol-3-yl](5-pyrazin-2-yl-2-furyl)methanone
[1-(4-chlorobenzyl)-5-methoxy-1H-indol-3-yl](5-pyrazin-2-yl-2-furyl)methanone
[1-(4-chlorobenzyl)-5-methoxy-2-methyl-1H-indol-3-yl](5-pyrimidin-2-yl-2-furyl)methanone
[1-(4-chlorobenzyl)-5-methoxy-1H-indol-3-yl](5-pyrimidin-2-yl-2-furyl)methanone
[1-(4-chlorobenzyl)-5-methoxy-2-methyl-1H-indol-3-yl](5-pyridazin-4-yl-2-furyl)methanone
[1-(4-chlorobenzyl)-5-methoxy-1H-indol-3-yl](5-pyridazin-4-yl-2-furyl)methanone
[1-(4-chlorobenzyl)-5-methoxy-2-methyl-1H-indol-3-yl](2-phenyl-1,3-oxazol-5-yl)methanone
[1-(4-chlorobenzyl)-5-methoxy-1H-indol-3-yl](2-phenyl-1,3-oxazol-5-yl)methanone
[1-(4-chlorobenzyl)-5-methoxy-2-methyl-1H-indol-3-yl](2-pyridin-2-yl-1,3-oxazol-5-yl)methanone
[1-(4-chlorobenzyl)-5-methoxy-1H-indol-3-yl](2-pyridin-2-yl-1,3-oxazol-5-yl)methanone
[1-(4-chlorobenzyl)-5-methoxy-2-methyl-1H-indol-3-yl](2-pyridin-3-yl-1,3-oxazol-5-yl)methanone
[1-(4-chlorobenzyl)-5-methoxy-1H-indol-3-yl](2-pyridin-3-yl-1,3-oxazol-5-yl)methanone
[1-(4-chlorobenzyl)-5-methoxy-2-methyl-1H-indol-3-yl](2-pyridin-4-yl-1,3-oxazol-5-yl)methanone
[1-(4-chlorobenzyl)-5-methoxy-1H-indol-3-yl](2-pyridin-4-yl-1,3-oxazol-5-yl)methanone
[1-(4-chlorobenzyl)-5-methoxy-2-methyl-1H-indol-3-yl](2-pyrimidin-4-yl-1,3-oxazol-5-yl)methanone
[1-(4-chlorobenzyl)-5-methoxy-1H-indol-3-yl](2-pyrimidin-4-yl-1,3-oxazol-5-yl)methanone
[1-(4-chlorobenzyl)-5-methoxy-2-methyl-1H-indol-3-yl](2-pyridazin-3-yl-1,3-oxazol-5-yl)methanone
[1-(4-chlorobenzyl)-5-methoxy-1H-indol-3-yl](2-pyridazin-3-yl-1,3-oxazol-5-yl)methanone
[1-(4-chlorobenzyl)-5-methoxy-2-methyl-1H-indol-3-yl](2-pyrazin-2-yl-1,3-oxazol-5-yl)methanone
[1-(4-chlorobenzyl)-5-methoxy-1H-indol-3-yl](2-pyrazin-2-yl-1,3-oxazol-5-yl)methanone
[1-(4-chlorobenzyl)-5-methoxy-2-methyl-1H-indol-3-yl](2-pyrimidin-2-yl-1,3-oxazol-5-yl)methanone
[1-(4-chlorobenzyl)-5-methoxy-1H-indol-3-yl](2-pyrimidin-2-yl-1,3-oxazol-5-yl)methanone
[1-(4-chlorobenzyl)-5-methoxy-2-methyl-1H-indol-3-yl](2-pyridazin-4-yl-1,3-oxazol-5-yl)methanone
[1-(4-chlorobenzyl)-5-methoxy-1H-indol-3-yl](2-pyridazin-4-yl-1,3-oxazol-5-yl)methanone
[1-(4-chlorobenzyl)-5-methoxy-2-methyl-1H-indol-3-yl](2-phenyl-1,3-oxazol-4-yl)methanone
[1-(4-chlorobenzyl)-5-methoxy-1H-indol-3-yl](2-phenyl-1,3-oxazol-4-yl)methanone
[1-(4-chlorobenzyl)-5-methoxy-2-methyl-1H-indol-3-yl](2-pyridin-2-yl-1,3-oxazol-4-yl)methanone

[1-(4-chlorobenzyl)-5-methoxy-1H-indol-3-yl](2-pyridin-2-yl-1,3-oxazol-4-yl)methanone
[1-(4-chlorobenzyl)-5-methoxy-2-methyl-1H-indol-3-yl](2-pyridin-3-yl-1,3-oxazol-4-yl)methanone
[1-(4-chlorobenzyl)-5-methoxy-1H-indol-3-yl](2-pyridin-3-yl-1,3-oxazol-4-yl)methanone
[1-(4-chlorobenzyl)-5-methoxy-2-methyl-1H-indol-3-yl](2-pyridin-4-yl-1,3-oxazol-4-yl)methanone
[1-(4-chlorobenzyl)-5-methoxy-1H-indol-3-yl](2-pyridin-4-yl-1,3-oxazol-4-yl)methanone
[1-(4-chlorobenzyl)-5-methoxy-2-methyl-1H-indol-3-yl](2-pyrimidin-4-yl-1,3-oxazol-4-yl)methanone
[1-(4-chlorobenzyl)-5-methoxy-1H-indol-3-yl](2-pyrimidin-4-yl-1,3-oxazol-4-yl)methanone
[1-(4-chlorobenzyl)-5-methoxy-2-methyl-1H-indol-3-yl](2-pyridazin-3-yl-1,3-oxazol-4-yl)methanone
[1-(4-chlorobenzyl)-5-methoxy-1H-indol-3-yl](2-pyridazin-3-yl-1,3-oxazol-4-yl)methanone
[1-(4-chlorobenzyl)-5-methoxy-2-methyl-1H-indol-3-yl](2-pyrazin-2-yl-1,3-oxazol-4-yl)methanone
[1-(4-chlorobenzyl)-5-methoxy-1H-indol-3-yl](2-pyrazin-2-yl-1,3-oxazol-4-yl)methanone
[1-(4-chlorobenzyl)-5-methoxy-2-methyl-1H-indol-3-yl](2-pyrimidin-2-yl-1,3-oxazol-4-yl)methanone
[1-(4-chlorobenzyl)-5-methoxy-1H-indol-3-yl](2-pyrimidin-2-yl-1,3-oxazol-4-yl)methanone
[1-(4-chlorobenzyl)-5-methoxy-2-methyl-1H-indol-3-yl](2-pyridazin-4-yl-1,3-oxazol-4-yl)methanone
[1-(4-chlorobenzyl)-5-methoxy-1H-indol-3-yl](2-pyridazin-4-yl-1,3-oxazol-4-yl)methanone
[1-(4-chlorobenzyl)-5-methoxy-2-methyl-1H-indol-3-yl](2-phenyl-1,3-thiazol-5-yl)methanone
[1-(4-chlorobenzyl)-5-methoxy-1H-indol-3-yl](2-phenyl-1,3-thiazol-5-yl)methanone
[1-(4-chlorobenzyl)-5-methoxy-2-methyl-1H-indol-3-yl](2-pyridin-2-yl-1,3-thiazol-5-yl)methanone
[1-(4-chlorobenzyl)-5-methoxy-1H-indol-3-yl](2-pyridin-2-yl-1,3-thiazol-5-yl)methanone
[1-(4-chlorobenzyl)-5-methoxy-2-methyl-1H-indol-3-yl](2-pyridin-3-yl-1,3-thiazol-5-yl)methanone
[1-(4-chlorobenzyl)-5-methoxy-1H-indol-3-yl](2-pyridin-3-yl-1,3-thiazol-5-yl)methanone
[1-(4-chlorobenzyl)-5-methoxy-2-methyl-1H-indol-3-yl](2-pyridin-4-yl-1,3-thiazol-5-yl)methanone
[1-(4-chlorobenzyl)-5-methoxy-1H-indol-3-yl](2-pyridin-4-yl-1,3-thiazol-5-yl)methanone
[1-(4-chlorobenzyl)-5-methoxy-2-methyl-1H-indol-3-yl](2-pyrimidin-4-yl-1,3-thiazol-5-yl)methanone
[1-(4-chlorobenzyl)-5-methoxy-1H-indol-3-yl](2-pyrimidin-4-yl-1,3-thiazol-5-yl)methanone
[1-(4-chlorobenzyl)-5-methoxy-2-methyl-1H-indol-3-yl](2-pyridazin-3-yl-1,3-thiazol-5-yl)methanone
[1-(4-chlorobenzyl)-5-methoxy-1H-indol-3-yl](2-pyridazin-3-yl-1,3-thiazol-5-yl)methanone
[1-(4-chlorobenzyl)-5-methoxy-2-methyl-1H-indol-3-yl](2-pyrazin-2-yl-1,3-thiazol-5-yl)methanone
[1-(4-chlorobenzyl)-5-methoxy-1H-indol-3-yl](2-pyrazin-2-yl-1,3-thiazol-5-yl)methanone
[1-(4-chlorobenzyl)-5-methoxy-2-methyl-1H-indol-3-yl](2-pyrimidin-2-yl-1,3-thiazol-5-yl)methanone
[1-(4-chlorobenzyl)-5-methoxy-1H-indol-3-yl](2-pyrimidin-2-yl-1,3-thiazol-5-yl)methanone
[1-(4-chlorobenzyl)-5-methoxy-2-methyl-1H-indol-3-yl](2-pyridazin-4-yl-1,3-thiazol-5-yl)methanone
[1-(4-chlorobenzyl)-5-methoxy-1H-indol-3-yl](2-pyridazin-4-yl-1,3-thiazol-5-yl)methanone
[1-(4-chlorobenzyl)-5-methoxy-2-methyl-1H-indol-3-yl](2-phenyl-1,3-thiazol-4-yl)methanone
[1-(4-chlorobenzyl)-5-methoxy-1H-indol-3-yl](2-phenyl-1,3-thiazol-4-yl)methanone
[1-(4-chlorobenzyl)-5-methoxy-2-methyl-1H-indol-3-yl](2-pyridin-2-yl-1,3-thiazol-4-yl)methanone
[1-(4-chlorobenzyl)-5-methoxy-1H-indol-3-yl](2-pyridin-2-yl-1,3-thiazol-4-yl)methanone
[1-(4-chlorobenzyl)-5-methoxy-2-methyl-1H-indol-3-yl](2-pyridin-3-yl-1,3-thiazol-4-yl)methanone
[1-(4-chlorobenzyl)-5-methoxy-1H-indol-3-yl](2-pyridin-3-yl-1,3-thiazol-4-yl)methanone
[1-(4-chlorobenzyl)-5-methoxy-2-methyl-1H-indol-3-yl](2-pyridin-4-yl-1,3-thiazol-4-yl)methanone
[1-(4-chlorobenzyl)-5-methoxy-1H-indol-3-yl](2-pyridin-4-yl-1,3-thiazol-4-yl)methanone
[1-(4-chlorobenzyl)-5-methoxy-2-methyl-1H-indol-3-yl](2-pyrimidin-4-yl-1,3-thiazol-4-yl)methanone
[1-(4-chlorobenzyl)-5-methoxy-1H-indol-3-yl](2-pyrimidin-4-yl-1,3-thiazol-4-yl)methanone
[1-(4-chlorobenzyl)-5-methoxy-2-methyl-1H-indol-3-yl](2-pyridazin-3-yl-1,3-thiazol-4-yl)methanone
[1-(4-chlorobenzyl)-5-methoxy-1H-indol-3-yl](2-pyridazin-3-yl-1,3-thiazol-4-yl)methanone
[1-(4-chlorobenzyl)-5-methoxy-2-methyl-1H-indol-3-yl](2-pyrazin-2-yl-1,3-thiazol-4-yl)methanone
[1-(4-chlorobenzyl)-5-methoxy-1H-indol-3-yl](2-pyrazin-2-yl-1,3-thiazol-4-yl)methanone
[1-(4-chlorobenzyl)-5-methoxy-2-methyl-1H-indol-3-yl](2-pyrimidin-2-yl-1,3-thiazol-4-yl)methanone
[1-(4-chlorobenzyl)-5-methoxy-1H-indol-3-yl](2-pyrimidin-2-yl-1,3-thiazol-4-yl)methanone
[1-(4-chlorobenzyl)-5-methoxy-2-methyl-1H-indol-3-yl](2-pyridazin-4-yl-1,3-thiazol-4-yl)methanone
[1-(4-chlorobenzyl)-5-methoxy-1H-indol-3-yl](2-pyridazin-4-yl-1,3-thiazol-4-yl)methanone
1,3-benzoxazol-2-yl[1-(4-chlorobenzyl)-5-methoxy-2-methyl-1H-indol-3-yl]methanone
1,3-benzoxazol-2-yl[1-(4-chlorobenzyl)-5-methoxy-1H-indol-3-yl]methanone
[1-(4-chlorobenzyl)-5-methoxy-2-methyl-1H-indol-3-yl]([1,3]oxazolo[4,5-b]pyridin-2-yl)methanone
[1-(4-chlorobenzyl)-5-methoxy-1H-indol-3-yl]([1,3]oxazolo[4,5-b]pyridin-2-yl)methanone
[1-(4-chlorobenzyl)-5-methoxy-2-methyl-1H-indol-3-yl]([1,3]oxazolo[4,5-c]pyridin-2-yl)methanone
[1-(4-chlorobenzyl)-5-methoxy-1H-indol-3-yl]([1,3]oxazolo[4,5-c]pyridin-2-yl)methanone
[1-(4-chlorobenzyl)-5-methoxy-2-methyl-1H-indol-3-yl]([1,3]oxazolo[5,4-c]pyridin-2-yl)methanone
[1-(4-chlorobenzyl)-5-methoxy-1H-indol-3-yl]([1,3]oxazolo[5,4-c]pyridin-2-yl)methanone
[1-(4-chlorobenzyl)-5-methoxy-2-methyl-1H-indol-3-yl]([1,3]oxazolo[5,4-b]pyridin-2-yl)methanone
[1-(4-chlorobenzyl)-5-methoxy-1H-indol-3-yl]([1,3]oxazolo[5,4-b]pyridin-2-yl)methanone
[1-(4-chlorobenzyl)-5-methoxy-2-methyl-1H-indol-3-yl](1-phenyl-1H-pyrazol-3-yl)methanone
[1-(4-chlorobenzyl)-5-methoxy-1H-indol-3-yl](1-phenyl-1H-pyrazol-3-yl)methanone
[1-(4-chlorobenzyl)-5-methoxy-2-methyl-1H-indol-3-yl](1-pyridin-2-yl-1H-pyrazol-3-yl)methanone
[1-(4-chlorobenzyl)-5-methoxy-1H-indol-3-yl](1-pyridin-2-yl-1H-pyrazol-3-yl)methanone
[1-(4-chlorobenzyl)-5-methoxy-2-methyl-1H-indol-3-yl](1-pyridin-3-yl-1H-pyrazol-3-yl)methanone

[1-(4-chlorobenzyl)-5-methoxy-1H-indol-3-yl](1-pyridin-3-yl-1H-pyrazol-3-yl)methanone
[1-(4-chlorobenzyl)-5-methoxy-2-methyl-1H-indol-3-yl](1-pyridin-4-yl-1H-pyrazol-3-yl)methanone
[1-(4-chlorobenzyl)-5-methoxy-1H-indol-3-yl](1-pyridin-4-yl-1H-pyrazol-3-yl)methanone
[1-(4-chlorobenzyl)-5-methoxy-2-methyl-1H-indol-3-yl](1-pyrimidin-4-yl-1H-pyrazol-3-yl)methanone
[1-(4-chlorobenzyl)-5-methoxy-1H-indol-3-yl](1-pyrimidin-4-yl-1H-pyrazol-3-yl)methanone
[1-(4-chlorobenzyl)-5-methoxy-2-methyl-1H-indol-3-yl](1-pyridazin-3-yl-1H-pyrazol-3-yl)methanone
[1-(4-chlorobenzyl)-5-methoxy-1H-indol-3-yl](1-pyridazin-3-yl-1H-pyrazol-3-yl)methanone
[1-(4-chlorobenzyl)-5-methoxy-2-methyl-1H-indol-3-yl](1-pyrazin-2-yl-1H-pyrazol-3-yl)methanone
[1-(4-chlorobenzyl)-5-methoxy-1H-indol-3-yl](1-pyrazin-2-yl-1H-pyrazol-3-yl)methanone
[1-(4-chlorobenzyl)-5-methoxy-2-methyl-1H-indol-3-yl](1-pyrimidin-2-yl-1H-pyrazol-3-yl)methanone
[1-(4-chlorobenzyl)-5-methoxy-1H-indol-3-yl](1-pyrimidin-2-yl-1H-pyrazol-3-yl)methanone
[1-(4-chlorobenzyl)-5-methoxy-2-methyl-1H-indol-3-yl](1-pyridazin-4-yl-1H-pyrazol-3-yl)methanone
[1-(4-chlorobenzyl)-5-methoxy-1H-indol-3-yl](1-pyridazin-4-yl-1H-pyrazol-3-yl)methanone
[1-(4-chlorobenzyl)-5-methoxy-2-methyl-1H-indol-3-yl](1-phenyl-1H-pyrazol-4-yl)methanone
[1-(4-chlorobenzyl)-5-methoxy-1H-indol-3-yl](1-phenyl-1H-pyrazol-4-yl)methanone
[1-(4-chlorobenzyl)-5-methoxy-2-methyl-1H-indol-3-yl](1-pyridin-2-yl-1H-pyrazol-4-yl)methanone
[1-(4-chlorobenzyl)-5-methoxy-1H-indol-3-yl](1-pyridin-2-yl-1H-pyrazol-4-yl)methanone
[1-(4-chlorobenzyl)-5-methoxy-2-methyl-1H-indol-3-yl](1-pyridin-3-yl-1H-pyrazol-4-yl)methanone
[1-(4-chlorobenzyl)-5-methoxy-1H-indol-3-yl](1-pyridin-3-yl-1H-pyrazol-4-yl)methanone
[1-(4-chlorobenzyl)-5-methoxy-2-methyl-1H-indol-3-yl](1-pyridin-4-yl-1H-pyrazol-4-yl)methanone
[1-(4-chlorobenzyl)-5-methoxy-1H-indol-3-yl](1-pyridin-4-yl-1H-pyrazol-4-yl)methanone
[1-(4-chlorobenzyl)-5-methoxy-2-methyl-1H-indol-3-yl](1-pyrimidin-4-yl-1H-pyrazol-4-yl)methanone
[1-(4-chlorobenzyl)-5-methoxy-1H-indol-3-yl](1-pyrimidin-4-yl-1H-pyrazol-4-yl)methanone
[1-(4-chlorobenzyl)-5-methoxy-2-methyl-1H-indol-3-yl](1-pyridazin-3-yl-1H-pyrazol-4-yl)methanone
[1-(4-chlorobenzyl)-5-methoxy-1H-indol-3-yl](1-pyridazin-3-yl-1H-pyrazol-4-yl)methanone
[1-(4-chlorobenzyl)-5-methoxy-2-methyl-1H-indol-3-yl](1-pyrazin-2-yl-1H-pyrazol-4-yl)methanone
[1-(4-chlorobenzyl)-5-methoxy-1H-indol-3-yl](1-pyrazin-2-yl-1H-pyrazol-4-yl)methanone
[1-(4-chlorobenzyl)-5-methoxy-2-methyl-1H-indol-3-yl](1-pyrimidin-2-yl-1H-pyrazol-4-yl)methanone
[1-(4-chlorobenzyl)-5-methoxy-1H-indol-3-yl](1-pyrimidin-2-yl-1H-pyrazol-4-yl)methanone
[1-(4-chlorobenzyl)-5-methoxy-2-methyl-1H-indol-3-yl](1-pyridazin-4-yl-1H-pyrazol-4-yl)methanone
[1-(4-chlorobenzyl)-5-methoxy-1H-indol-3-yl](1-pyridazin-4-yl-1H-pyrazol-4-yl)methanone
[1-(4-chlorobenzyl)-5-methoxy-2-methyl-1H-indol-3-yl](1-phenyl-1H-1,2,3-triazol-4-yl)methanone
[1-(4-chlorobenzyl)-5-methoxy-1H-indol-3-yl](1-phenyl-1H-1,2,3-triazol-4-yl)methanone
[1-(4-chlorobenzyl)-5-methoxy-2-methyl-1H-indol-3-yl](1-pyridin-2-yl-1H-1,2,3-triazol-4-yl)methanone
[1-(4-chlorobenzyl)-5-methoxy-1H-indol-3-yl](1-pyridin-2-yl-1H-1,2,3-triazol-4-yl)methanone
[1-(4-chlorobenzyl)-5-methoxy-2-methyl-1H-indol-3-yl](1-pyridin-3-yl-1H-1,2,3-triazol-4-yl)methanone
[1-(4-chlorobenzyl)-5-methoxy-1H-indol-3-yl](1-pyridin-3-yl-1H-1,2,3-triazol-4-yl)methanone
[1-(4-chlorobenzyl)-5-methoxy-2-methyl-1H-indol-3-yl](1-pyridin-4-yl-1H-1,2,3-triazol-4-yl)methanone
[1-(4-chlorobenzyl)-5-methoxy-1H-indol-3-yl](1-pyridin-4-yl-1H-1,2,3-triazol-4-yl)methanone
[1-(4-chlorobenzyl)-5-methoxy-2-methyl-1H-indol-3-yl](1-pyrimidin-4-yl-1H-1,2,3-triazol-4-yl)methanone
[1-(4-chlorobenzyl)-5-methoxyl-1H-indol-3-yl](1-pyrimidin-4-yl-1H-1,2,3-triazol-4-yl)methanone
[1-(4-chlorobenzyl)-5-methoxy-2-methyl-1H-indol-3-yl](1-pyridazin-3-yl-1H-1,2,3-triazol-4-yl)methanone
[1-(4-chlorobenzyl)-5-methoxy-1H-indol-3-yl](1-pyridazin-3-yl-1H-1,2,3-triazol-4-yl)methanone
[1-(4-chlorobenzyl)-5-methoxy-2-methyl-1H-indol-3-yl](1-pyrazin-2-yl-1H-1,2,3-triazol-4-yl)methanone
[1-(4-chlorobenzyl)-5-methoxy-1H-indol-3-yl](1-pyrazin-2-yl-1H-1,2,3-triazol-4-yl)methanone
[1-(4-chlorobenzyl)-5-methoxy-2-methyl-1H-indol-3-yl](1-pyrimidin-2-yl-1H-1,2,3-triazol-4-yl)methanone
[1-(4-chlorobenzyl)-5-methoxy-1H-indol-3-yl](1-pyrimidin-2-yl-1H-1,2,3-triazol-4-yl)methanone
[1-(4-chlorobenzyl)-5-methoxy-2-methyl-1H-indol-3-yl](1-pyridazin-4-yl-1H-1,2,3-triazol-4-yl)methanone
[1-(4-chlorobenzyl)-5-methoxy-1H-indol-3-yl](1-pyridazin-4-yl-1H-1,2,3-triazol-4-yl)methanone Further useful compounds (e.g. FAAH inhibitors) include:

[1-(2,4-dichlorobenzyl)-5-methoxy-2-methyl-1H-indol-3-yl](5-phenyl-1,3,4-oxadiazol-2-yl)methanone

191

[1-(2,4-dichlorobenzyl)-5-methoxy-1H-indol-3-yl]
(5-phenyl-1,3,4-oxadiazol-2-yl)methanone

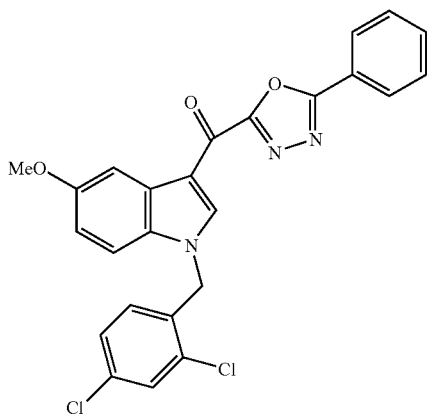

[1-(2,4-dichlorobenzyl)-5-methoxy-2-methyl-1H-
indol-3-yl](5-pyridin-2-yl-1,3,4-oxadiazol-2-yl)
methanone

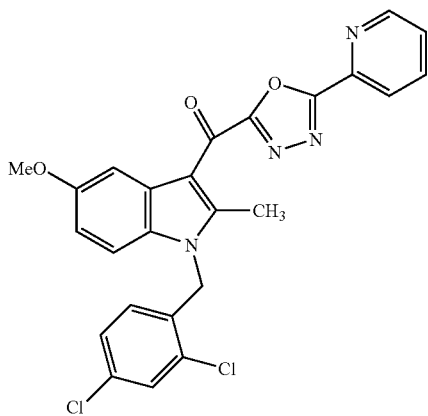

[1-(2,4-dichlorobenzyl)-5-methoxy-1H-indol-3-yl]
(5-pyridin-2-yl-1,3,4-oxadiazol-2-yl)methanone

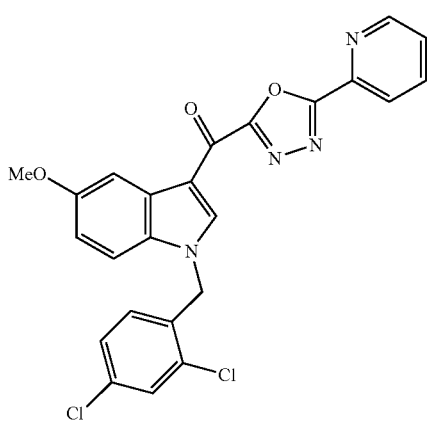

192

[1-(2,4-dichlorobenzyl)-5-methoxy-2-methyl-1H-
indol-3-yl](5-pyridin-3-yl-1,3,4-oxadiazol-2-yl)
methanone

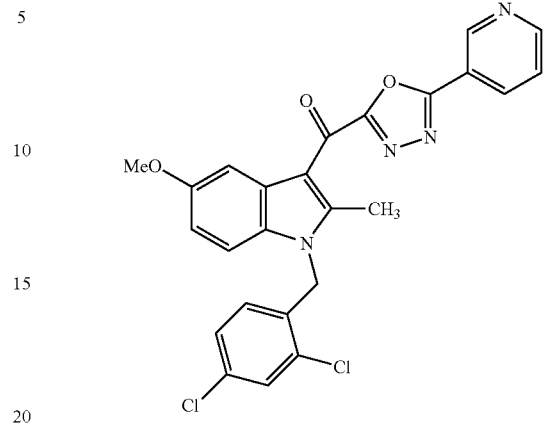

[1-(2,4-dichlorobenzyl)-5-methoxy-1H-indol-3-yl]
(5-pyridin-3-yl-1,3,4-oxadiazol-2-yl)methanone

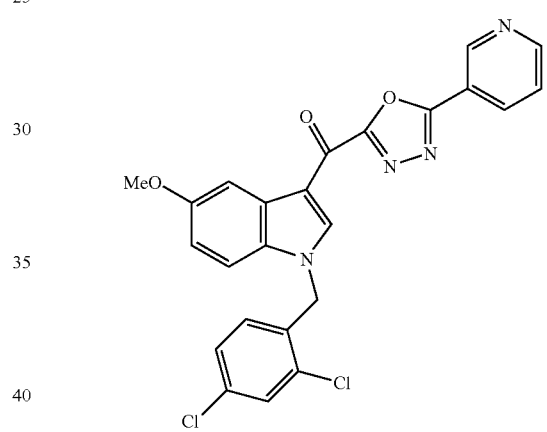

[1-(2,4-dichlorobenzyl)-5-methoxy-2-methyl-1H-
indol-3-yl](5-pyridin-4-yl-1,3,4-oxadiazol-2-yl)
methanone

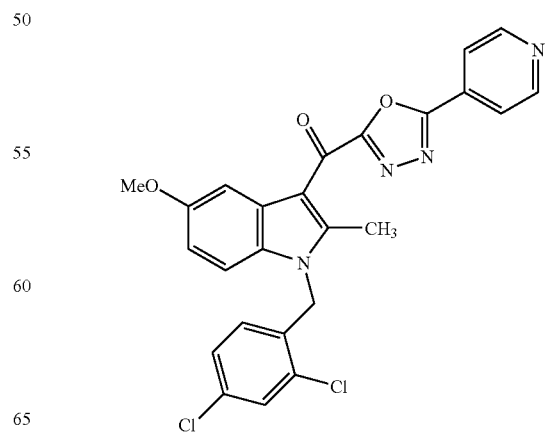

193

[1-(2,4-dichlorobenzyl)-5-methoxy-1H-indol-3-yl]
(5-pyridin-4-yl-1,3,4-oxadiazol-2-yl)methanone

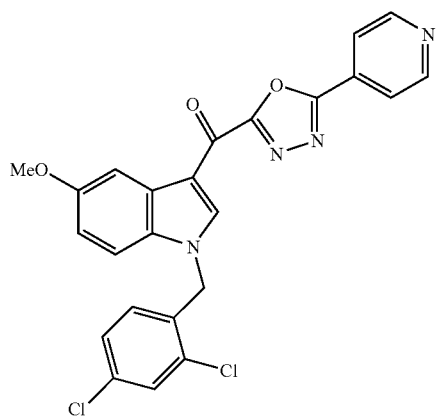

[1-(2,4-dichlorobenzyl)-5-methoxy-2-methyl-1H-
indol-3-yl](5-pyrimidin-4-yl-1,3,4-oxadiazol-2-yl)
methanone

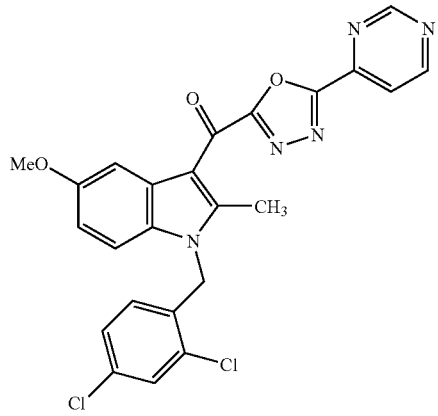

[1-(2,4-dichlorobenzyl)-5-methoxy-1H-indol-3-yl]
(5-pyrimidin-4-yl-1,3,4-oxadiazol-2-yl)methanone

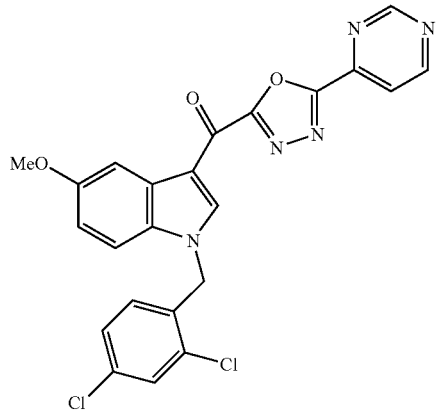

194

[1-(2,4-dichlorobenzyl)-5-methoxy-2-methyl-1H-
indol-3-yl](5-pyrazin-2-yl-1,3,4-oxadiazol-2-yl)
methanone

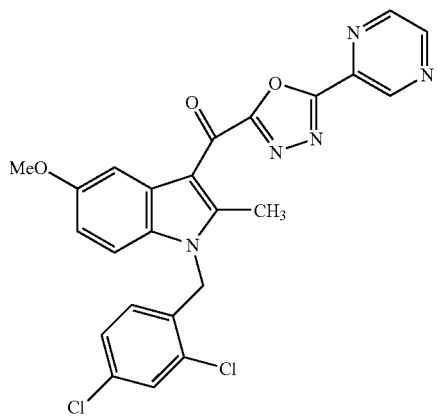

[1-(2,4-dichlorobenzyl)-5-methoxy-1H-indol-3-yl]
(5-pyrazin-2-yl-1,3,4-oxadiazol-2-yl)methanone

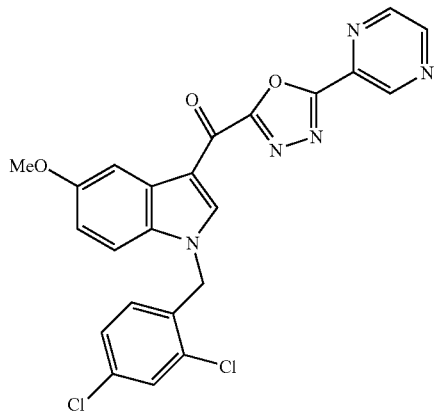

[1-(2,4-dichlorobenzyl)-5-methoxy-2-methyl-1H-
indol-3-yl](5-pyrimidin-2-yl-1,3,4-oxadiazol-2-yl)
methanone

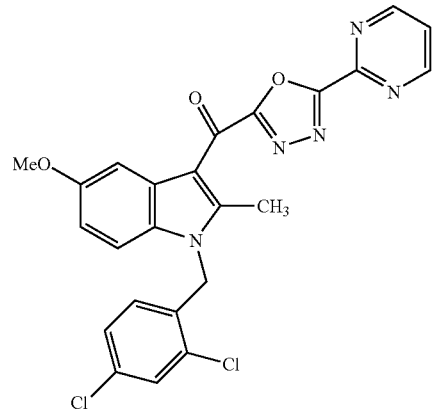

195

[1-(2,4-dichlorobenzyl)-5-methoxy-1H-indol-3-yl]
(5-pyrimidin-2-yl-1,3,4-oxadiazol-2-yl)methanone

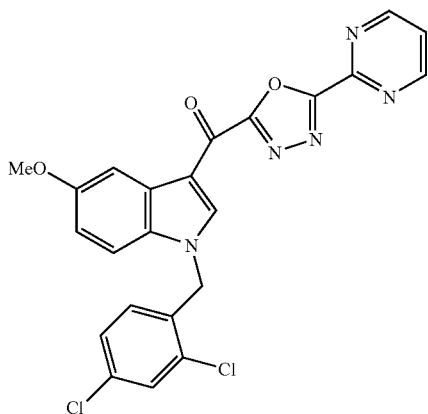

[1-(2,4-dichlorobenzyl)-5-methoxy-2-methyl-1H-
indol-3-yl](5-pyridazin-3-yl-1,3,4-oxadiazol-2-yl)
methanone

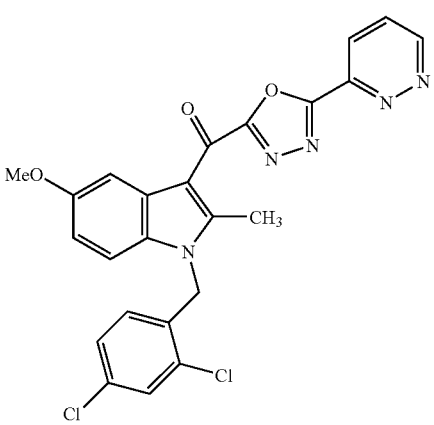

[1-(2,4-dichlorobenzyl)-5-methoxy-1H-indol-3-yl]
(5-pyridazin-3-yl-1,3,4-oxadiazol-2-yl)methanone

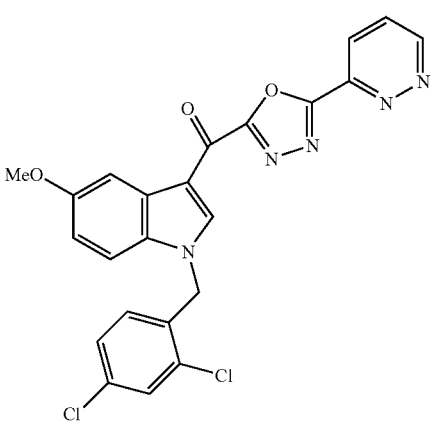

196

[1-(2,4-dichlorobenzyl)-5-methoxy-2-methyl-1H-
indol-3-yl](5-pyridazin-4-yl-1,3,4-oxadiazol-2-yl)
methanone

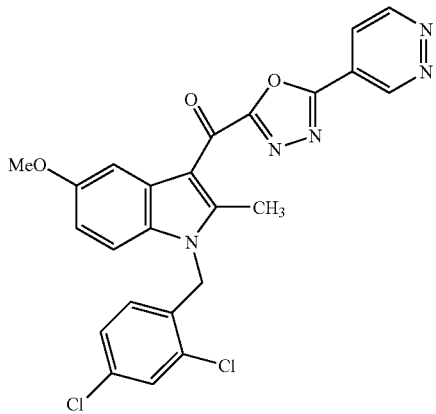

[1-(2,4-dichlorobenzyl)-5-methoxy-1H-indol-3-yl]
(5-pyridazin-4-yl-1,3,4-oxadiazol-2-yl)methanone

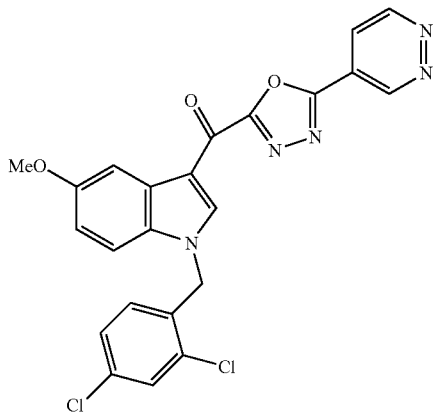

[1-(4-chlorobenzyl)-2,5-dimethyl-1H-indol-3-yl](5-
phenyl-1,3,4-oxadiazol-2-yl)methanone

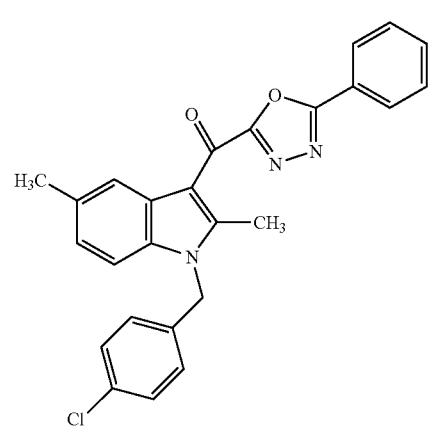

197

[1-(4-chlorobenzyl)-5-methyl-1H-indol-3-yl](5-phenyl-1,3,4-oxadiazol-2-yl)methanone

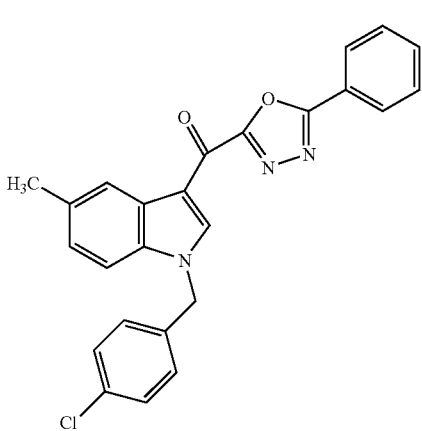

[1-(4-chlorobenzyl)-2,5-dimethyl-1H-indol-3-yl](5-pyridin-2-yl-1,3,4-oxadiazol-2-yl)methanone

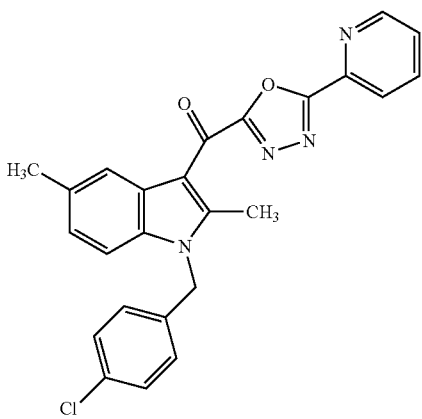

[1-(4-chlorobenzyl)-5-methyl-1H-indol-3-yl](5-pyridin-2-yl-1,3,4-oxadiazol-2-yl)methanone

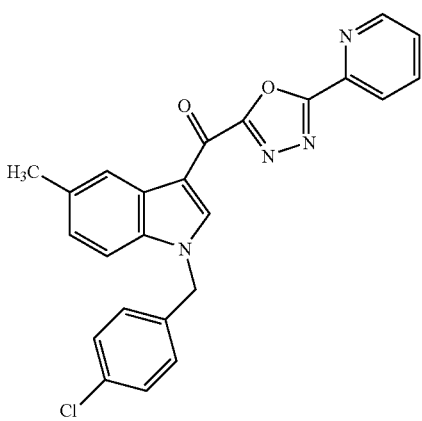

198

[1-(4-chlorobenzyl)-2,5-dimethyl-1H-indol-3-yl](5-pyridin-3-yl-1,3,4-oxadiazol-2-yl)methanone

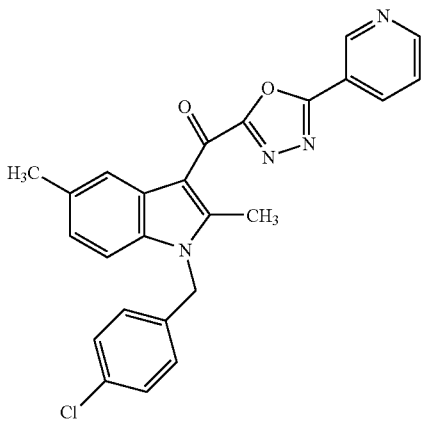

[1-(4-chlorobenzyl)-5-methyl-1H-indol-3-yl](5-pyridin-3-yl-1,3,4-oxadiazol-2-yl)methanone

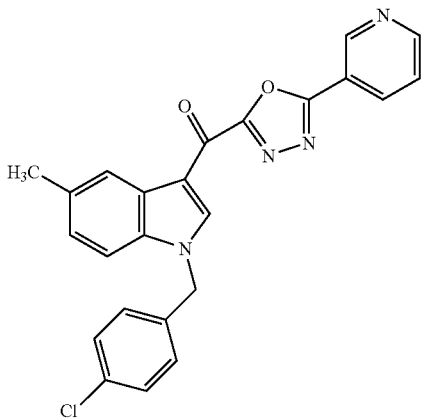

[1-(4-chlorobenzyl)-2,5-dimethyl-1H-indol-3-yl](5-pyridin-4-yl-1,3,4-oxadiazol-2-yl)methanone

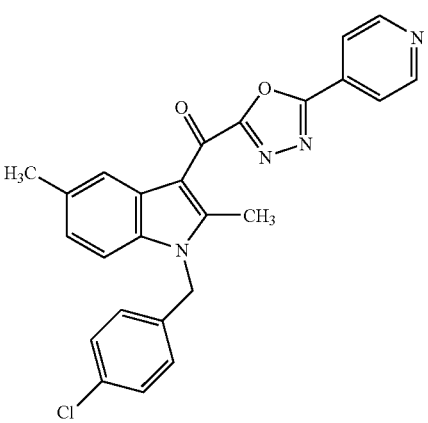

199

[1-(4-chlorobenzyl)-5-methyl-1H-indol-3-yl](5-pyridin-4-yl-1,3,4-oxadiazol-2-yl)methanone

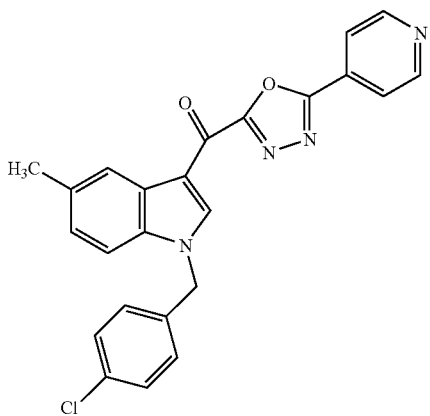

[1-(4-chlorobenzyl)-2,5-dimethyl-1H-indol-3-yl](5-pyrimidin-4-yl-1,3,4-oxadiazol-2-yl)methanone

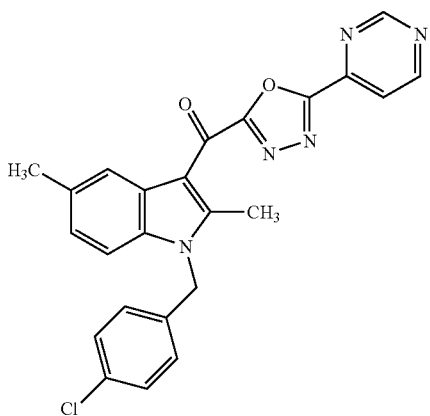

[1-(4-chlorobenzyl)-5-methyl-1H-indol-3-yl](5-pyrimidin-4-yl-1,3,4-oxadiazol-2-yl)methanone

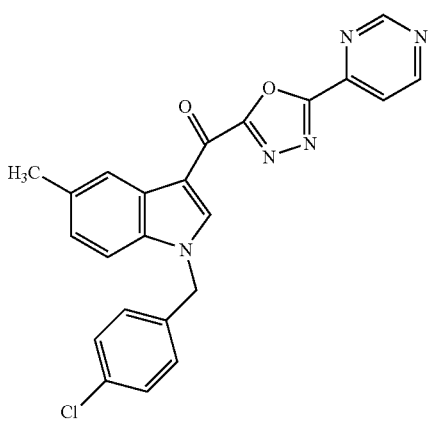

200

[1-(4-chlorobenzyl)-2,5-dimethyl-1H-indol-3-yl](5-pyrazin-2-yl-1,3,4-oxadiazol-2-yl)methanone

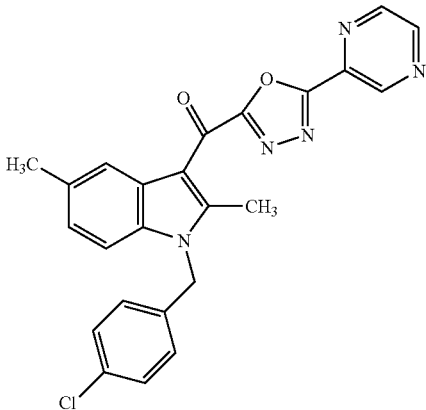

[1-(4-chlorobenzyl)-5-methyl-1H-indol-3-yl](5-pyrazin-2-yl-1,3,4-oxadiazol-2-yl)methanone

[1-(4-chlorobenzyl)-2,5-dimethyl-1H-indol-3-yl](5-pyrimidin-2-yl-1,3,4-oxadiazol-2-yl)methanone

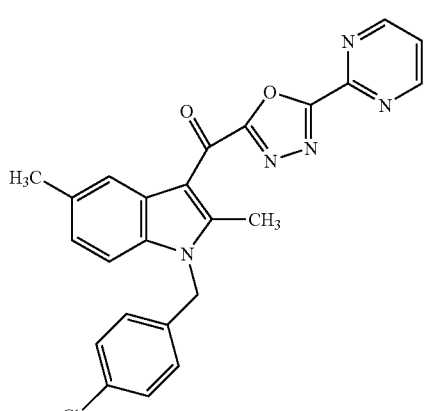

| 201 | 202 |
|---|---|
| [1-(4-chlorobenzyl)-5-methyl-1H-indol-3-yl](5-pyrimidin-2-yl-1,3,4-oxadiazol-2-yl)methanone | [1-(4-chlorobenzyl)-2,5-dimethyl-1H-indol-3-yl](5-pyridazin-4-yl-1,3,4-oxadiazol-2-yl)methanone |

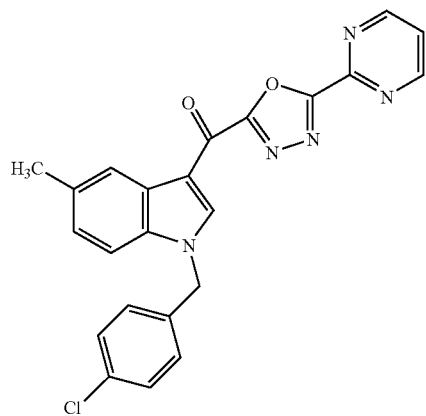

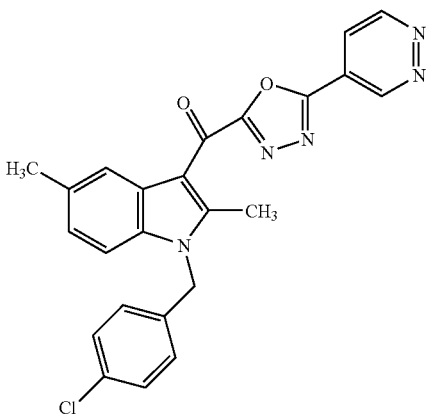

[1-(4-chlorobenzyl)-2,5-dimethyl-1H-indol-3-yl](5-pyridazin-3-yl-1,3,4-oxadiazol-2-yl)methanone

[1-(4-chlorobenzyl)-5-methyl-1H-indol-3-yl](5-pyridazin-4-yl-1,3,4-oxadiazol-2-yl)methanone

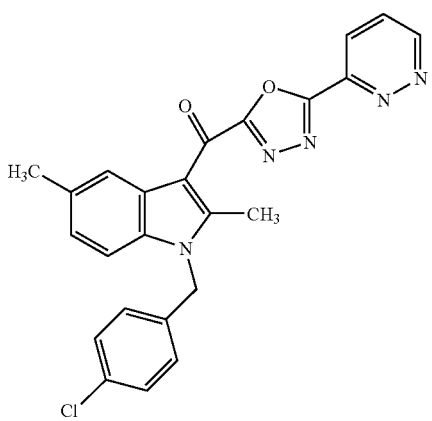

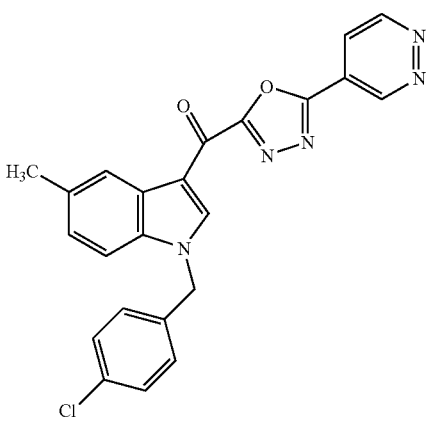

[1-(4-chlorobenzyl)-5-methyl-1H-indol-3-yl](5-pyridazin-3-yl-1,3,4-oxadiazol-2-yl)methanone

[1-(2,4-dichlorobenzyl)-2,5-dimethyl-1H-indol-3-yl](5-phenyl-1,3,4-oxadiazol-2-yl)methanone

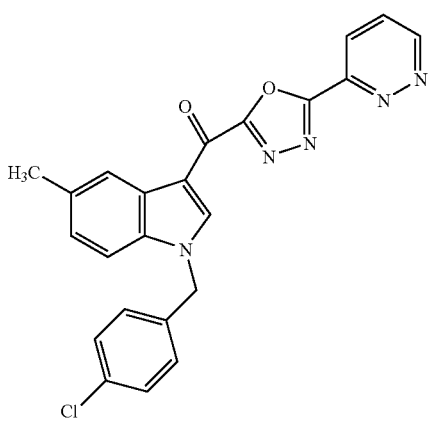

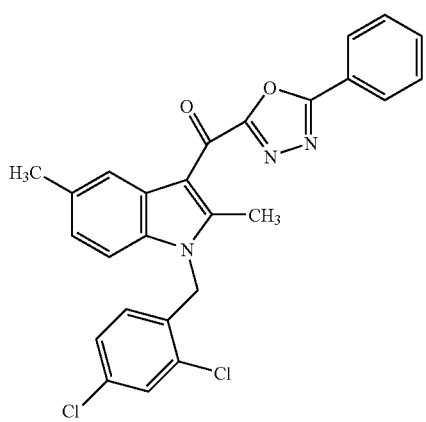

203
[1-(2,4-dichlorobenzyl)-5-methyl-1H-indol-3-yl](5-phenyl-1,3,4-oxadiazol-2-yl)methanone

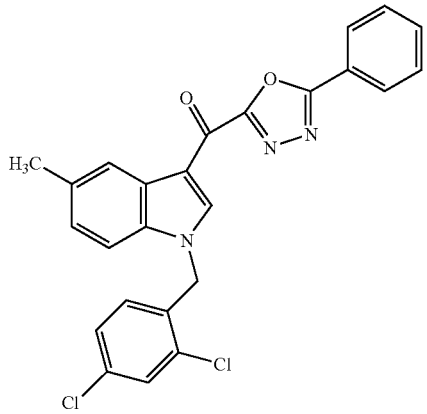

[1-(2,4-dichlorobenzyl)-2,5-dimethyl-1H-indol-3-yl](5-pyridin-2-yl-1,3,4-oxadiazol-2-yl)methanone

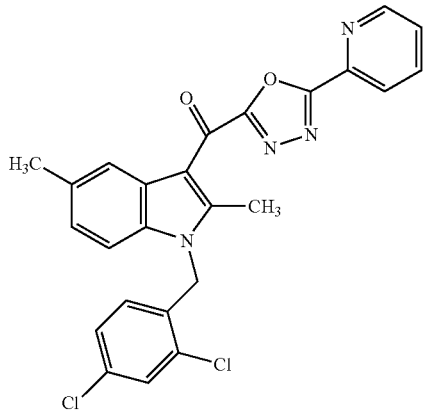

[1-(2,4-dichlorobenzyl)-5-methyl-1H-indol-3-yl](5-pyridin-2-yl-1,3,4-oxadiazol-2-yl)methanone

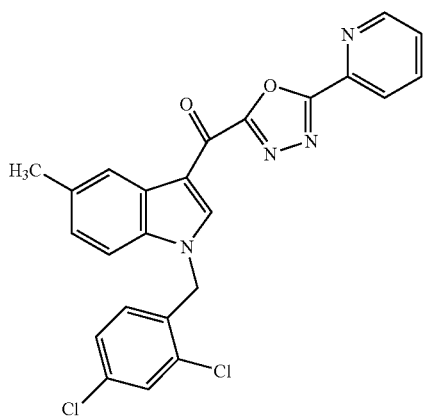

204
[1-(2,4-dichlorobenzyl)-2,5-dimethyl-1H-indol-3-yl](5-pyridin-3-yl-1,3,4-oxadiazol-2-yl)methanone

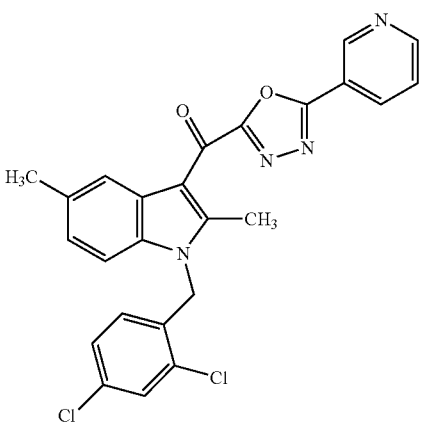

[1-(2,4-dichlorobenzyl)-5-methyl-1H-indol-3-yl](5-pyridin-3-yl-1,3,4-oxadiazol-2-yl)methanone

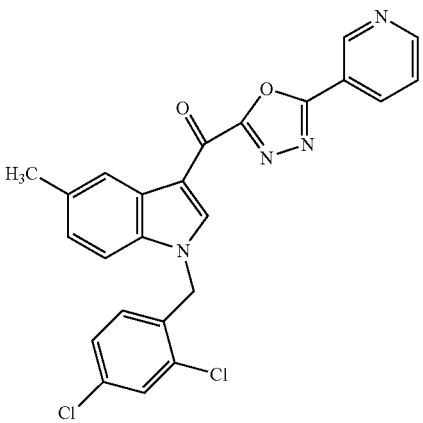

[1-(2,4-dichlorobenzyl)-2,5-dimethyl-1H-indol-3-yl](5-pyridin-4-yl-1,3,4-oxadiazol-2-yl)methanone

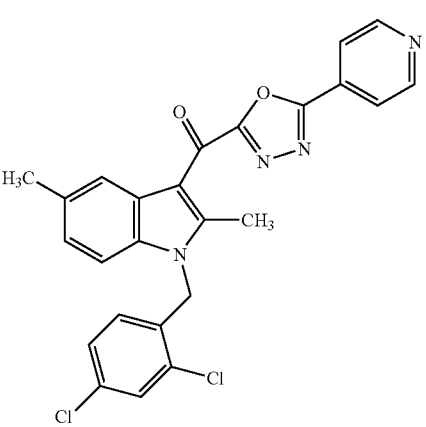

205

[1-(2,4-dichlorobenzyl)-5-methyl-1H-indol-3-yl](5-pyridin-4-yl-1,3,4-oxadiazol-2-yl)methanone

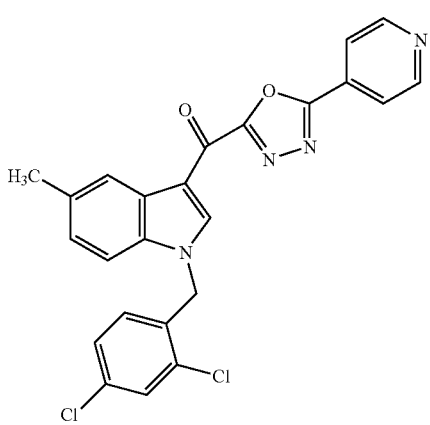

[1-(2,4-dichlorobenzyl)-2,5-dimethyl-1H-indol-3-yl](5-pyrimidin-4-yl-1,3,4-oxadiazol-2-yl)methanone

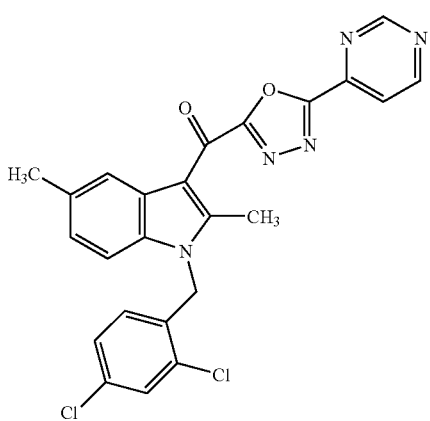

[1-(2,4-dichlorobenzyl)-5-methyl-1H-indol-3-yl](5-pyrimidin-4-yl-1,3,4-oxadiazol-2-yl)methanone

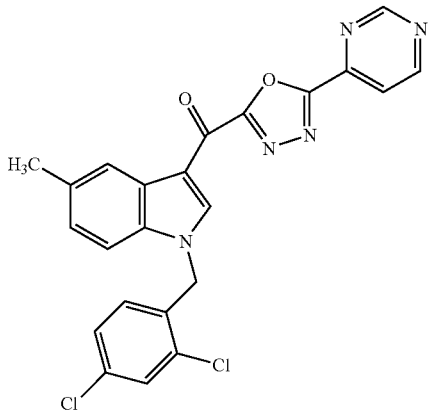

206

[1-(2,4-dichlorobenzyl)-2,5-dimethyl-1H-indol-3-yl](5-pyrazin-2-yl-1,3,4-oxadiazol-2-yl)methanone

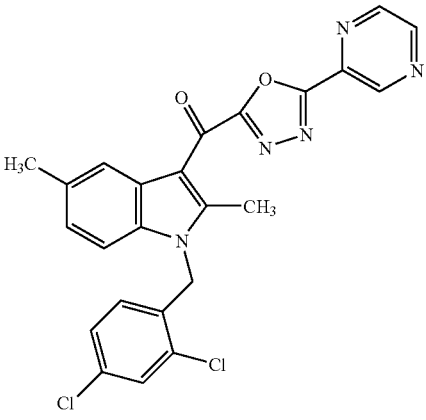

[1-(2,4-dichlorobenzyl)-5-methyl-1H-indol-3-yl](5-pyrazin-2-yl-1,3,4-oxadiazol-2-yl)methanone

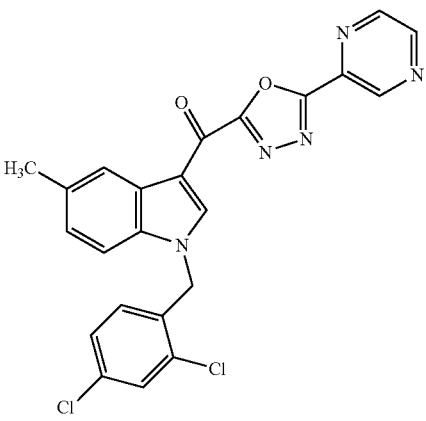

[1-(2,4-dichlorobenzyl)-2,5-dimethyl-1H-indol-3-yl](5-pyrimidin-2-yl-1,3,4-oxadiazol-2-yl)methanone

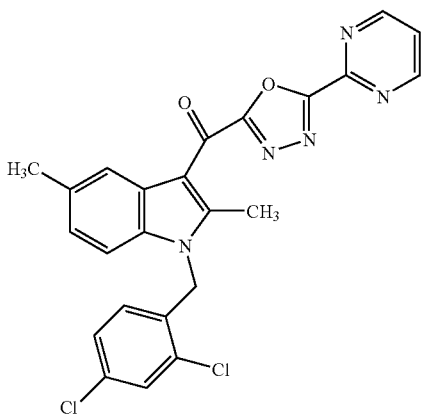

207
[1-(2,4-dichlorobenzyl)-5-methyl-1H-indol-3-yl](5-pyrimidin-2-yl-1,3,4-oxadiazol-2-yl)methanone

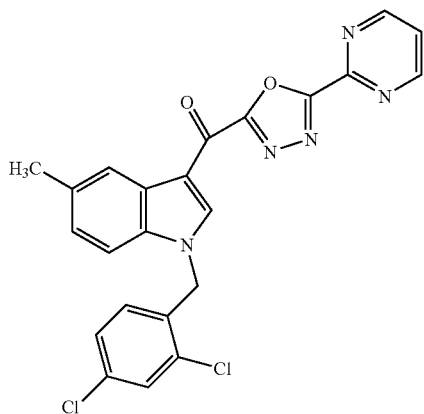

208
[1-(2,4-dichlorobenzyl)-2,5-dimethyl-1H-indol-3-yl](5-pyridazin-4-yl-1,3,4-oxadiazol-2-yl)methanone

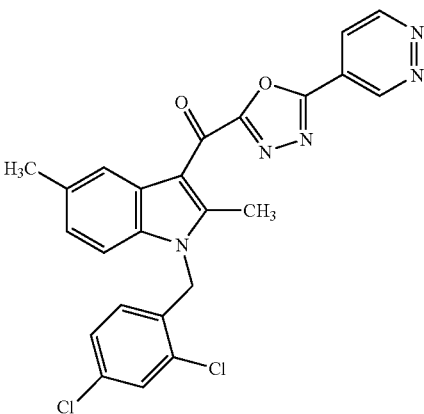

[1-(2,4-dichlorobenzyl)-2,5-dimethyl-1H-indol-3-yl](5-pyridazin-3-yl-1,3,4-oxadiazol-2-yl)methanone

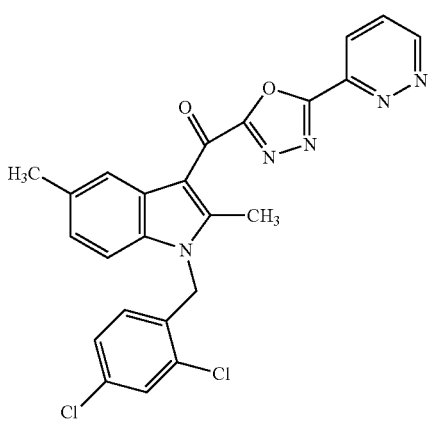

[1-(2,4-dichlorobenzyl)-5-methyl-1H-indol-3-yl](5-pyridazin-4-yl-1,3,4-oxadiazol-2-yl)methanone

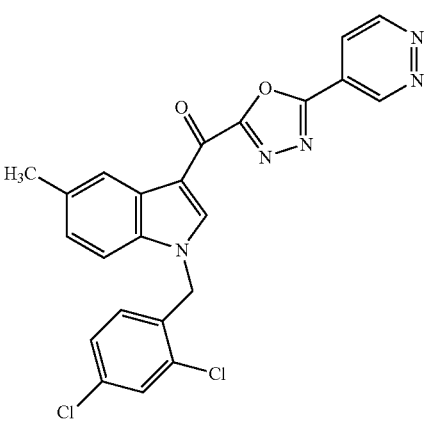

[1-(2,4-dichlorobenzyl)-5-methyl-1H-indol-3-yl](5-pyridazin-3-yl-1,3,4-oxadiazol-2-yl)methanone

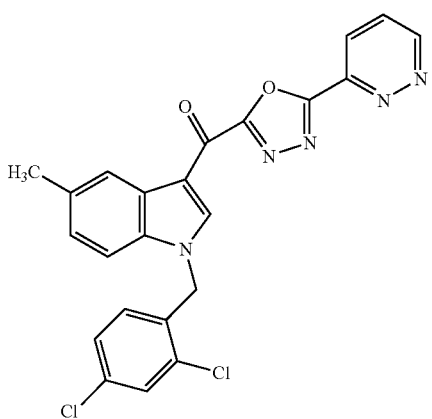

[1-(4-chlorobenzyl)-2-methyl-1H-indol-3-yl](5-phenyl-1,3,4-oxadiazol-2-yl)methanone

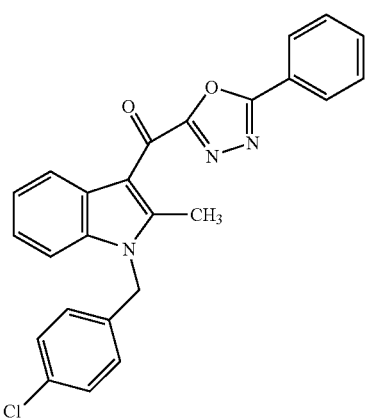

209

[1-(4-chlorobenzyl)-1H-indol-3-yl](5-phenyl-1,3,4-oxadiazol-2-yl)methanone

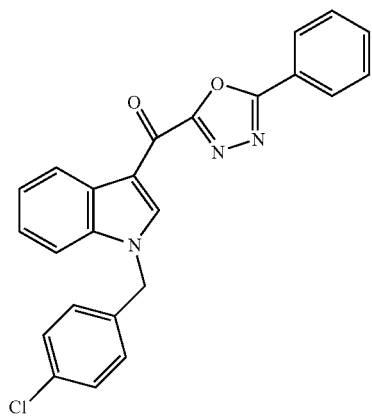

[1-(4-chlorobenzyl)-2-methyl-1H-indol-3-yl](5-pyridin-2-yl-1,3,4-oxadiazol-2-yl)methanone

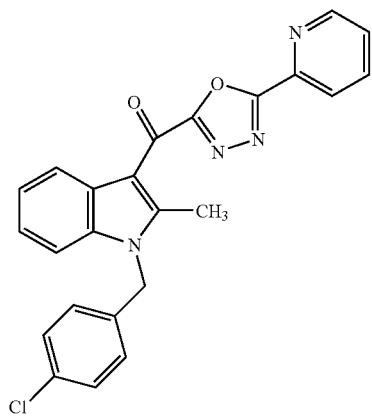

[1-(4-chlorobenzyl)-1H-indol-3-yl](5-pyridin-2-yl-1,3,4-oxadiazol-2-yl)methanone

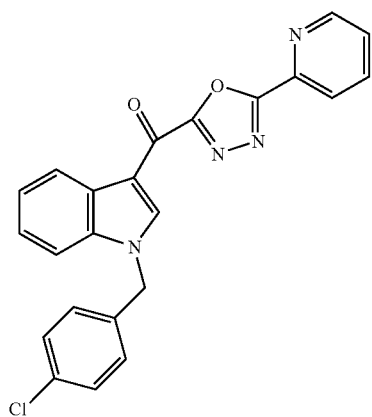

210

[1-(4-chlorobenzyl)-2-methyl-1H-indol-3-yl](5-pyridin-3-yl-1,3,4-oxadiazol-2-yl)methanone

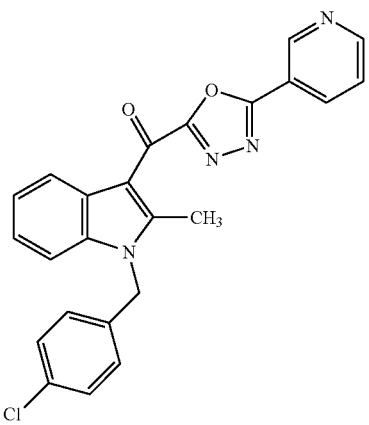

[1-(4-chlorobenzyl)-1H-indol-3-yl](5-pyridin-3-yl-1,3,4-oxadiazol-2-yl)methanone

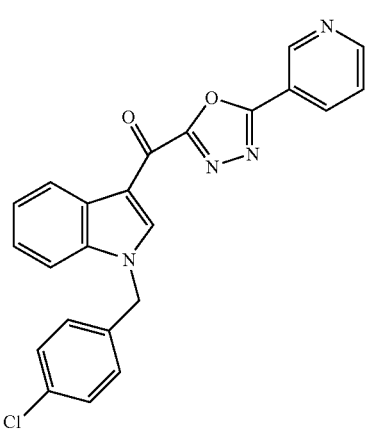

[1-(4-chlorobenzyl)-2-methyl-1H-indol-3-yl](5-pyridin-4-yl-1,3,4-oxadiazol-2-yl)methanone

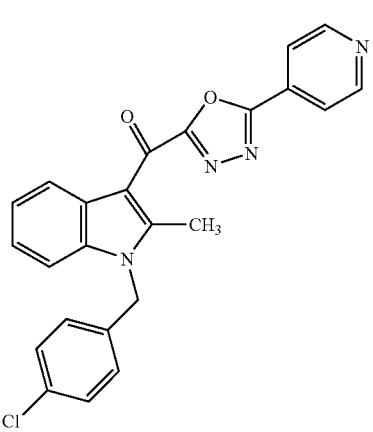

211
[1-(4-chlorobenzyl)-1H-indol-3-yl](5-pyridin-4-yl-1,3,4-oxadiazol-2-yl)methanone

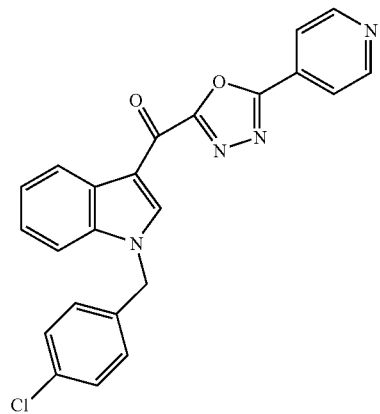

212
[1-(4-chlorobenzyl)-2-methyl-1H-indol-3-yl](5-pyrazin-2-yl-1,3,4-oxadiazol-2-yl)methanone

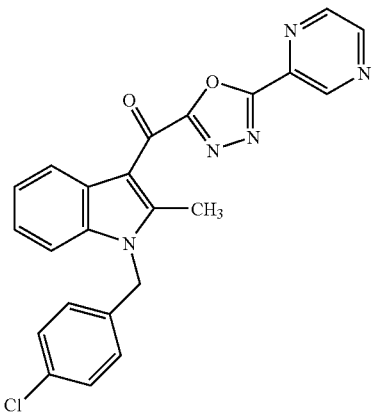

[1-(4-chlorobenzyl)-2-methyl-1H-indol-3-yl](5-pyrimidin-4-yl-1,3,4-oxadiazol-2-yl)methanone

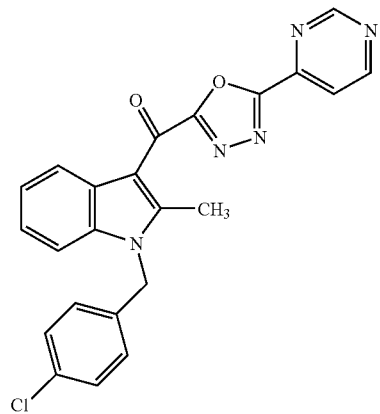

[1-(4-chlorobenzyl)-1H-indol-3-yl](5-pyrazin-2-yl-1,3,4-oxadiazol-2-yl)methanone

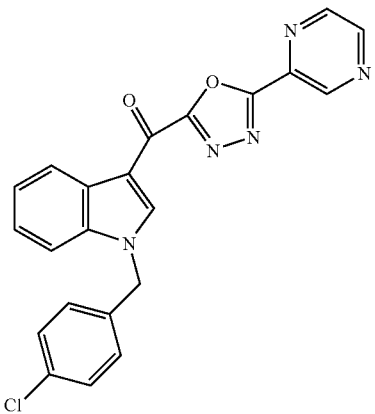

[1-(4-chlorobenzyl)-1H-indol-3-yl](5-pyrimidin-4-yl-1,3,4-oxadiazol-2-yl)methanone

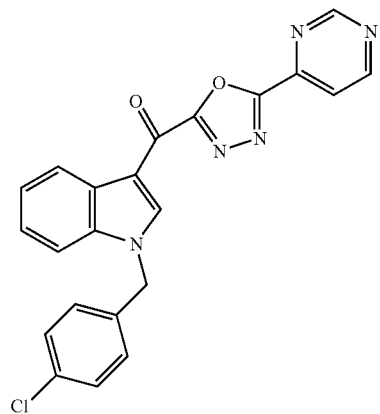

[1-(4-chlorobenzyl)-2-methyl-1H-indol-3-yl](5-pyrimidin-2-yl-1,3,4-oxadiazol-2-yl)methanone

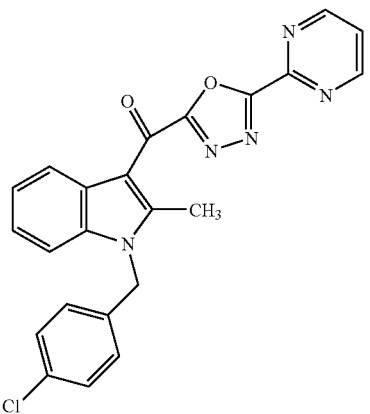

213

[1-(4-chlorobenzyl)-1H-indol-3-yl](5-pyrimidin-2-yl-1,3,4-oxadiazol-2-yl)methanone

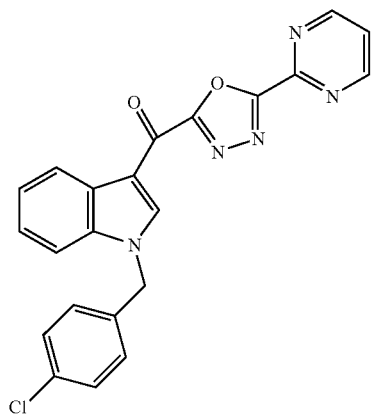

214

[1-(4-chlorobenzyl)-2-methyl-1H-indol-3-yl](5-pyridazin-4-yl-1,3,4-oxadiazol-2-yl)methanone

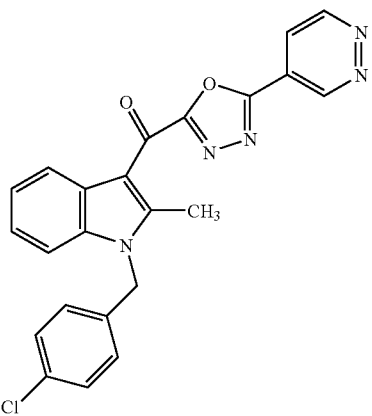

[1-(4-chlorobenzyl)-2-methyl-1H-indol-3-yl](5-pyridazin-3-yl-1,3,4-oxadiazol-2-yl)methanone

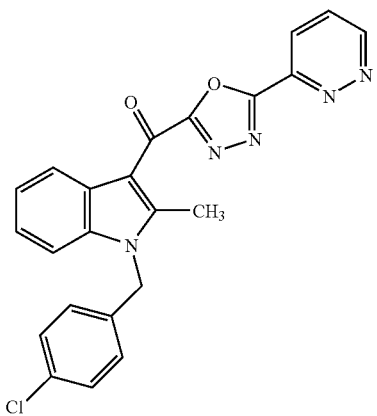

[1-(4-chlorobenzyl)-1H-indol-3-yl](5-pyridazin-4-yl-1,3,4-oxadiazol-2-yl)methanone

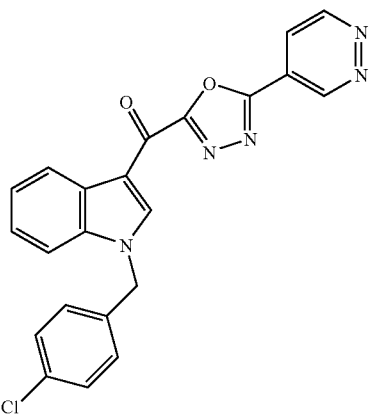

[1-(4-chlorobenzyl)-1H-indol-3-yl](5-pyridazin-3-yl-1,3,4-oxadiazol-2-yl)methanone

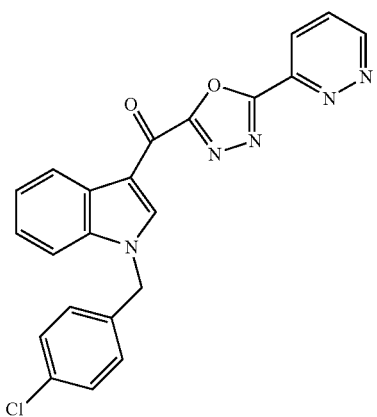

[1-(2,4-dichlorobenzyl)-2-methyl-1H-indol-3-yl](5-phenyl-1,3,4-oxadiazol-2-yl)methanone

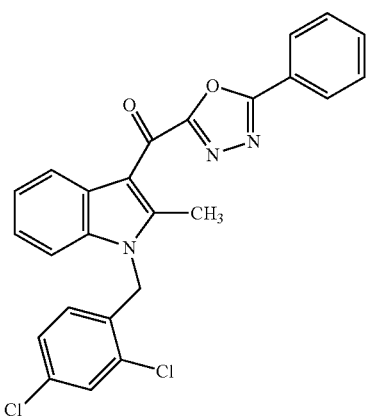

215
[1-(2,4-dichlorobenzyl)-1H-indol-3-yl](5-phenyl-1,3,4-oxadiazol-2-yl)methanone

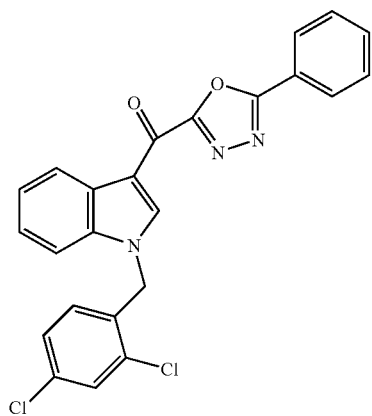

[1-(2,4-dichlorobenzyl)-2-methyl-1H-indol-3-yl](5-pyridin-2-yl-1,3,4-oxadiazol-2-yl)methanone

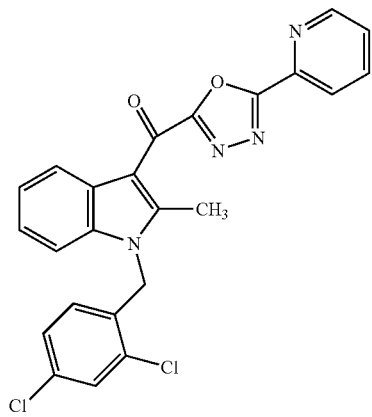

[1-(2,4-dichlorobenzyl)-1H-indol-3-yl](5-pyridin-2-yl-1,3,4-oxadiazol-2-yl)methanone

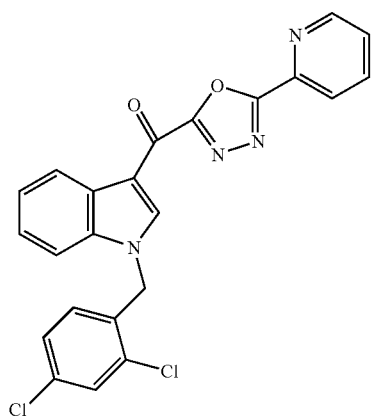

216
[1-(2,4-dichlorobenzyl)-2-methyl-1H-indol-3-yl](5-pyridin-3-yl-1,3,4-oxadiazol-2-yl)methanone

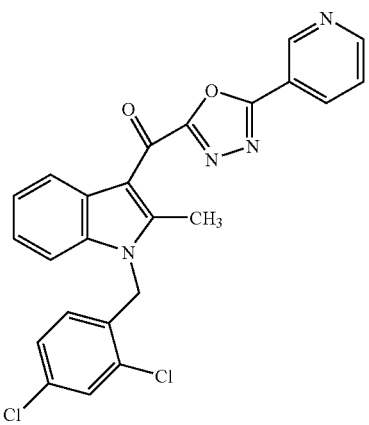

[1-(2,4-dichlorobenzyl)-1H-indol-3-yl](5-pyridin-3-yl-1,3,4-oxadiazol-2-yl)methanone

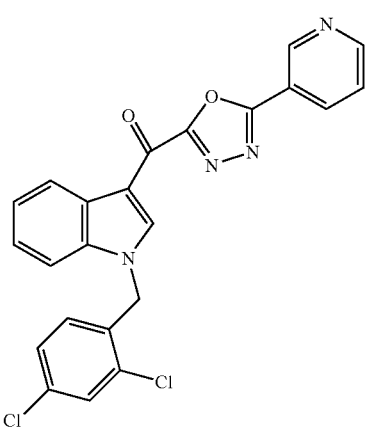

[1-(2,4-dichlorobenzyl)-2-methyl-1H-indol-3-yl](5-pyridin-4-yl-1,3,4-oxadiazol-2-yl)methanone

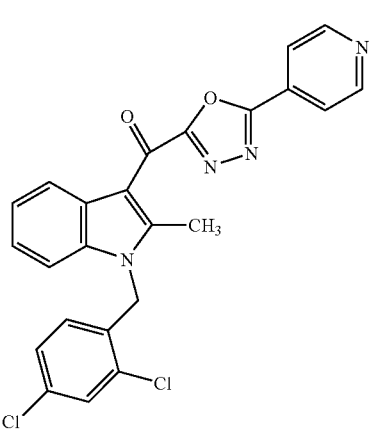

217

[1-(2,4-dichlorobenzyl)-1H-indol-3-yl](5-pyridin-4-yl-1,3,4-oxadiazol-2-yl)methanone

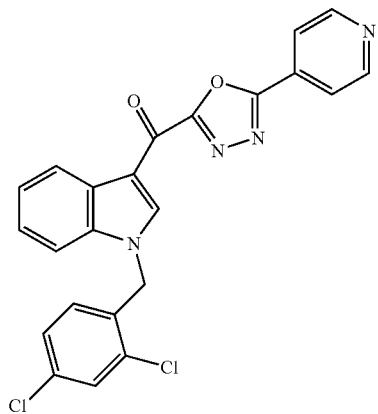

218

[1-(2,4-dichlorobenzyl)-2-methyl-1H-indol-3-yl](5-pyrazin-2-yl-1,3,4-oxadiazol-2-yl)methanone

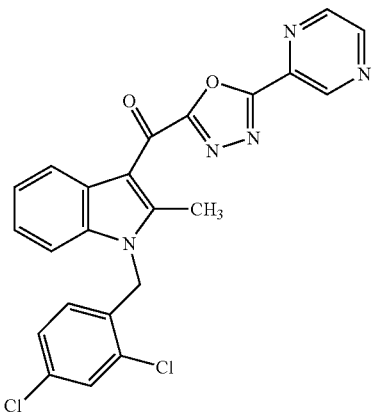

[1-(2,4-dichlorobenzyl)-2-methyl-1H-indol-3-yl](5-pyrimidin-4-yl-1,3,4-oxadiazol-2-yl)methanone

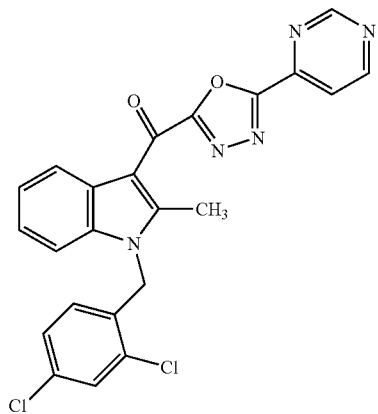

[1-(2,4-dichlorobenzyl)-1H-indol-3-yl](5-pyrazin-2-yl-1,3,4-oxadiazol-2-yl)methanone

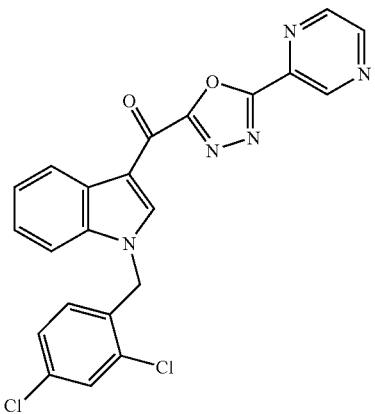

[1-(2,4-dichlorobenzyl)-1H-indol-3-yl](5-pyrimidin-4-yl-1,3,4-oxadiazol-2-yl)methanone

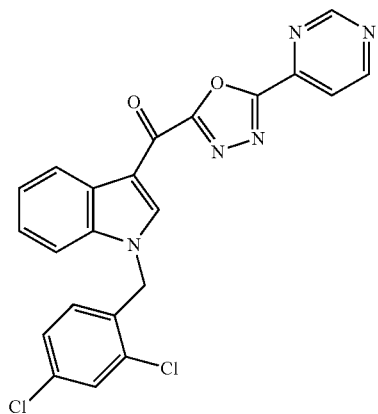

[1-(2,4-dichlorobenzyl)-2-methyl-1H-indol-3-yl](5-pyrimidin-2-yl-1,3,4-oxadiazol-2-yl)methanone

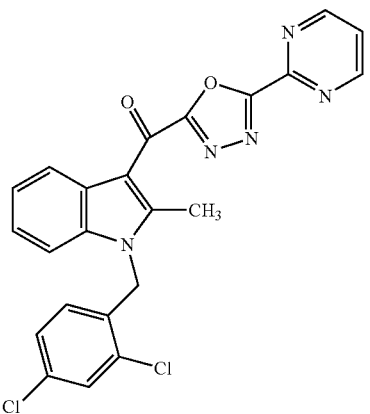

219

[1-(2,4-dichlorobenzyl)-1H-indol-3-yl](5-pyrimidin-2-yl-1,3,4-oxadiazol-2-yl)methanone

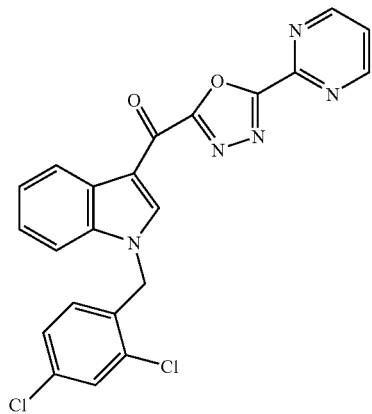

220

[1-(2,4-dichlorobenzyl)-2-methyl-1H-indol-3-yl](5-pyridazin-4-yl-1,3,4-oxadiazol-2-yl)methanone

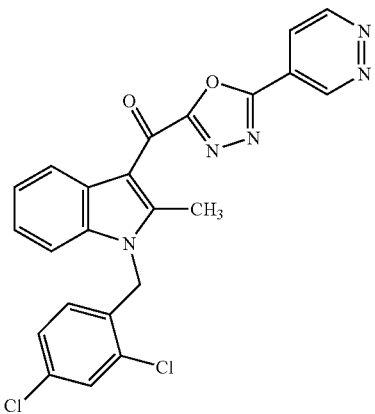

[1-(2,4-dichlorobenzyl)-2-methyl-1H-indol-3-yl](5-pyridazin-3-yl-1,3,4-oxadiazol-2-yl)methanone

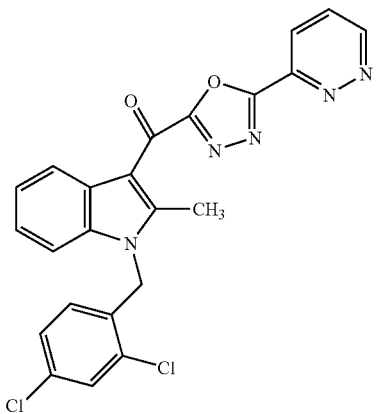

[1-(2,4-dichlorobenzyl)-1H-indol-3-yl](5-pyridazin-4-yl-1,3,4-oxadiazol-2-yl)methanone

[1-(2,4-dichlorobenzyl)-1H-indol-3-yl](5-pyridazin-3-yl-1,3,4-oxadiazol-2-yl)methanone

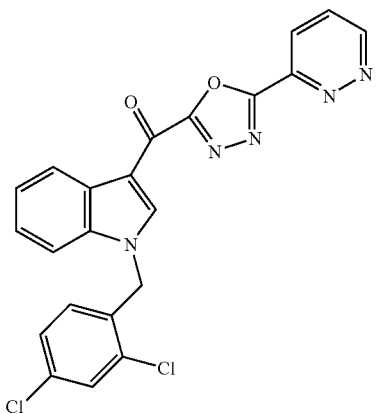

[1-(2,4-dichlorobenzyl)-5-methoxy-2-methyl-1H-indol-3-yl](3-phenyl-1,3,4-oxadiazol-5-yl)methanone

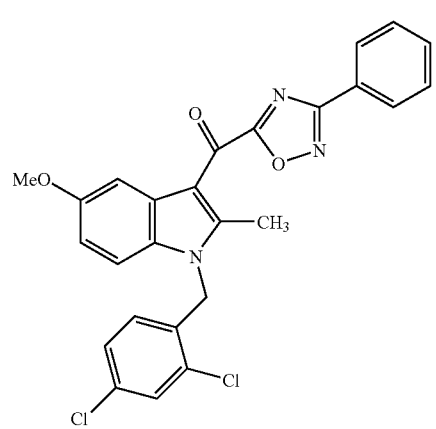

221
[1-(2,4-dichlorobenzyl)-5-methoxy-1H-indol-3-yl] (3-phenyl-1,2,4-oxadiazol-5-yl)methanone

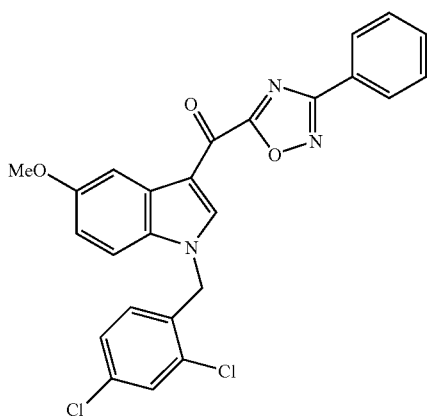

222
[1-(2,4-dichlorobenzyl)-5-methoxy-2-methyl-1H-indol-3-yl](3-pyridin-3-yl-1,2,4-oxadiazol-5-yl) methanone

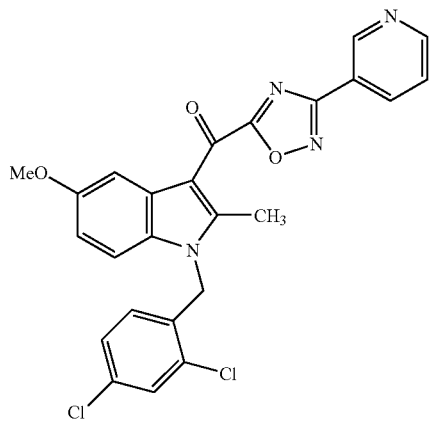

[1-(2,4-dichlorobenzyl)-5-methoxy-2-methyl-1H-indol-3-yl](3-pyridin-2-yl-1,2,4-oxadiazol-5-yl) methanone

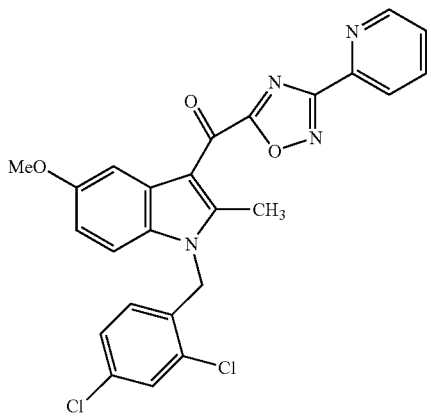

[1-(2,4-dichlorobenzyl)-5-methoxy-1H-indol-3-yl] (3-pyridin-3-yl-1,2,4-oxadiazol-5-yl)methanone

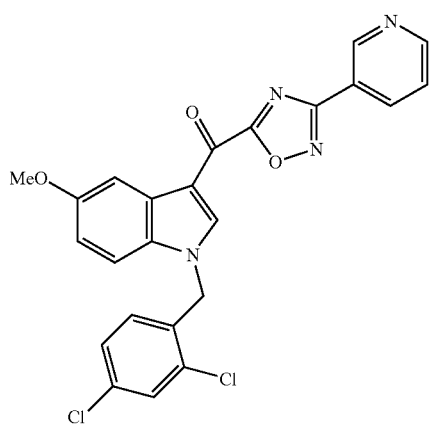

[1-(2,4-dichlorobenzyl)-5-methoxy-1H-indol-3-yl] (3-pyridin-2-yl-1,2,4-oxadiazol-5-yl)methanone

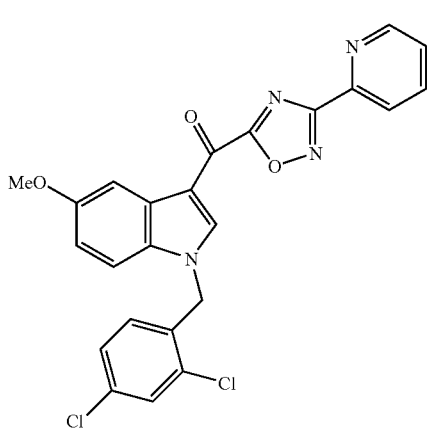

[1-(2,4-dichlorobenzyl)-5-methoxy-2-methyl-1H-indol-3-yl](3-pyridin-4-yl-1,2,4-oxadiazol-5-yl) methanone

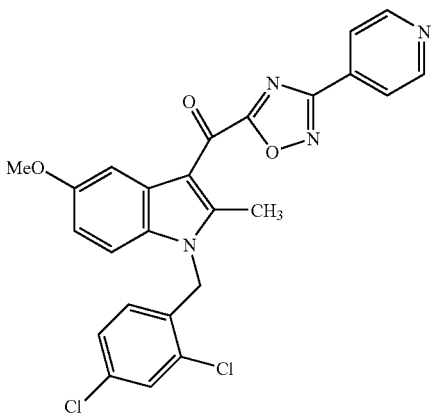

223

[1-(2,4-dichlorobenzyl)-5-methoxy-1H-indol-3-yl]
(3-pyridin-4-yl-1,2,4-oxadiazol-5-yl)methanone

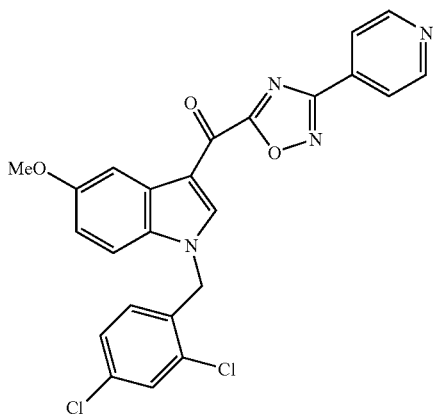

[1-(2,4-dichlorobenzyl)-5-methoxy-2-methyl-1H-
indol-3-yl](3-pyrimidin-4-yl-1,2,4-oxadiazol-5-yl)
methanone

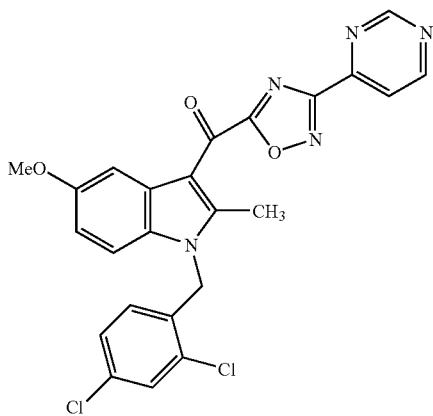

[1-(2,4-dichlorobenzyl)-5-methoxy-1H-indol-3-yl]
(3-pyrimidin-4-yl-1,2,4-oxadiazol-5-yl)methanone

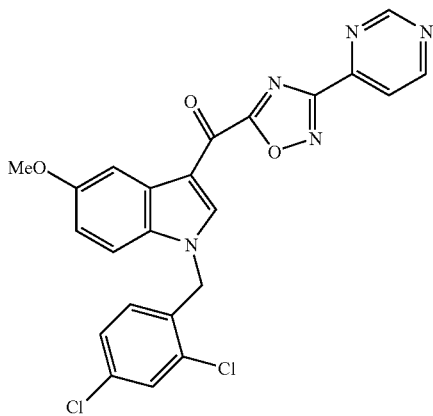

224

[1-(2,4-dichlorobenzyl)-5-methoxy-2-methyl-1H-
indol-3-yl](3-pyrazin-2-yl-1,2,4-oxadiazol-5-yl)
methanone

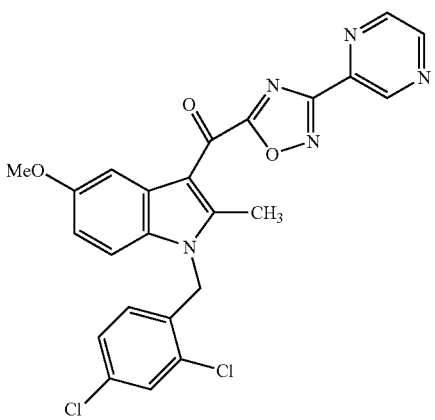

[1-(2,4-dichlorobenzyl)-5-methoxy-1H-indol-3-yl]
(3-pyrazin-2-yl-1,2,4-oxadiazol-5-yl)methanone

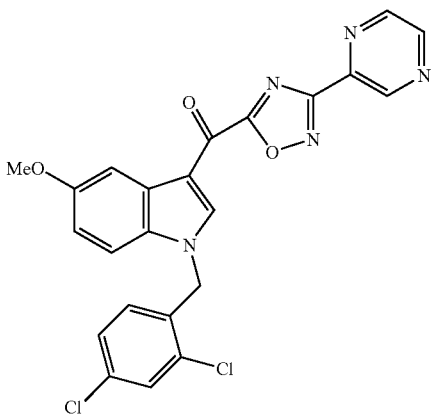

[1-(2,4-dichlorobenzyl)-5-methoxy-2-methyl-1H-
indol-3-yl](3-pyrimidin-2-yl-1,2,4-oxadiazol-5-yl)
methanone

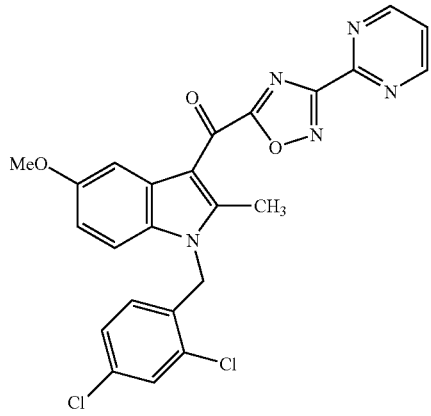

225

[1-(2,4-dichlorobenzyl)-5-methoxy-1H-indol-3-yl]
(3-pyrimidin-2-yl-1,2,4-oxadiazol-5-yl)methanone

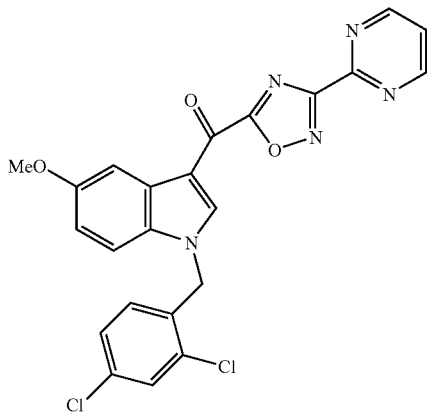

226

[1-(2,4-dichlorobenzyl)-5-methoxy-2-methyl-1H-
indol-3-yl](3-pyridazin-4-yl-1,2,4-oxadiazol-5-yl)
methanone

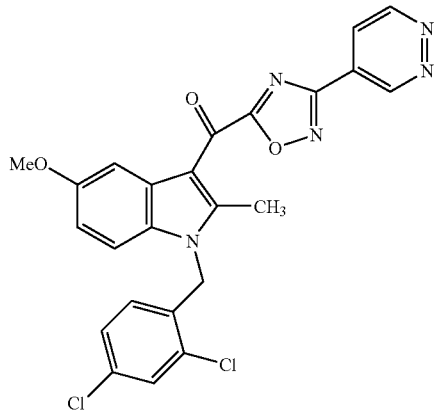

[1-(2,4-dichlorobenzyl)-5-methoxy-2-methyl-1H-
indol-3-yl](3-pyridazin-3-yl-1,2,4-oxadiazol-5-yl)
methanone

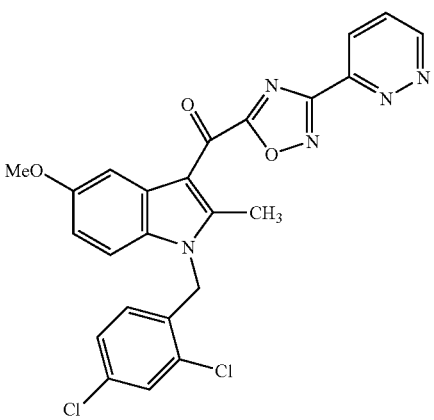

[1-(2,4-dichlorobenzyl)-5-methoxy-1H-indol-3-yl]
(3-pyridazin-4-yl-1,2,4-oxadiazol-5-yl)methanone

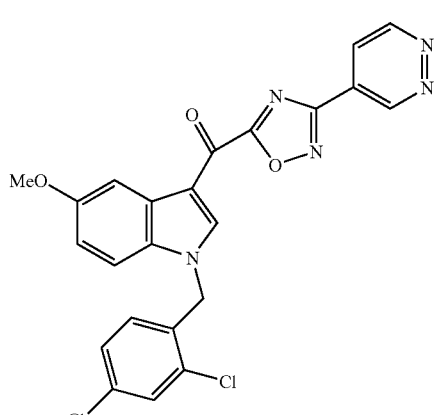

[1-(2,4-dichlorobenzyl)-5-methoxy-1H-indol-3-yl]
(3-pyridazin-3-yl-1,2,4-oxadiazol-5-yl)methanone

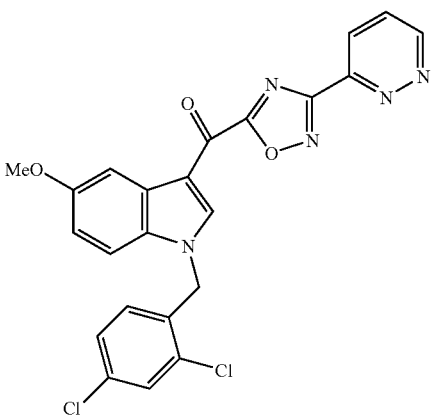

[1-(2,4-dichlorobenzyl)-2,5-dimethyl-1H-indol-3-yl]
(3-phenyl-1,2,4-oxadiazol-5-yl)methanone

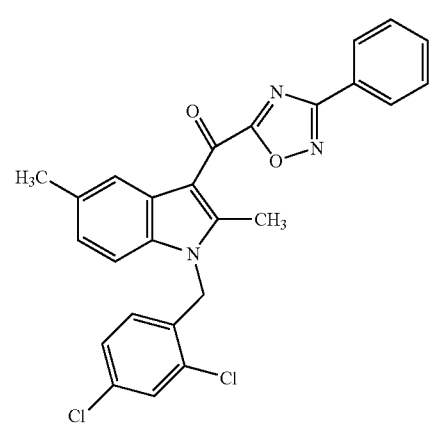

227

[1-(2,4-dichlorobenzyl)-5-methyl-1H-indol-3-yl](3-phenyl-1,2,4-oxadiazol-5-yl)methanone

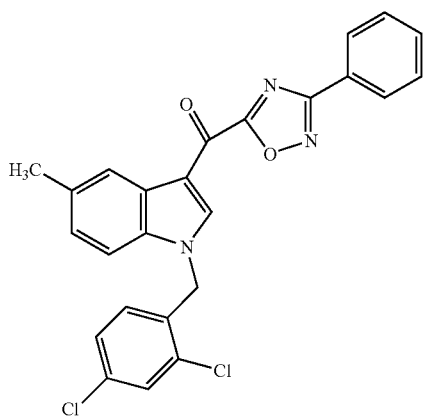

228

[1-(2,4-dichlorobenzyl)-2,5-dimethyl-1H-indol-3-yl](3-pyridin-3-yl-1,2,4-oxadiazol-5-yl)methanone

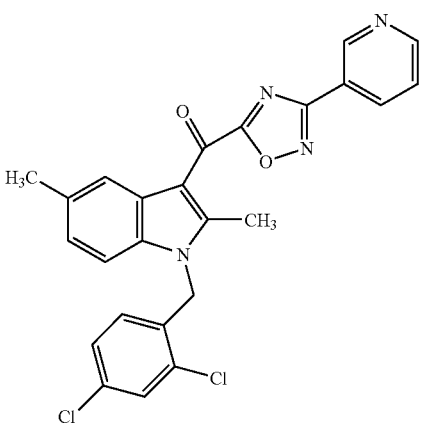

[1-(2,4-dichlorobenzyl)-2,5-dimethyl-1H-indol-3-yl](3-pyridin-2-yl-1,2,4-oxadiazol-5-yl)methanone

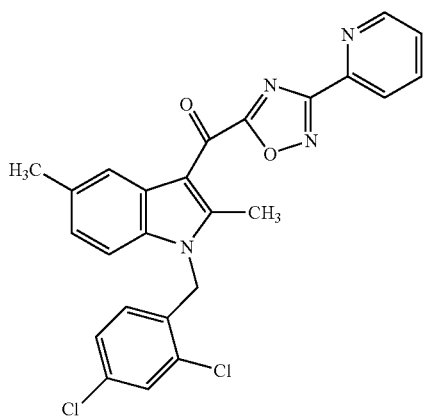

[1-(2,4-dichlorobenzyl)-5-methyl-1H-indol-3-yl](3-pyridin-3-yl-1,2,4-oxadiazol-5-yl)methanone

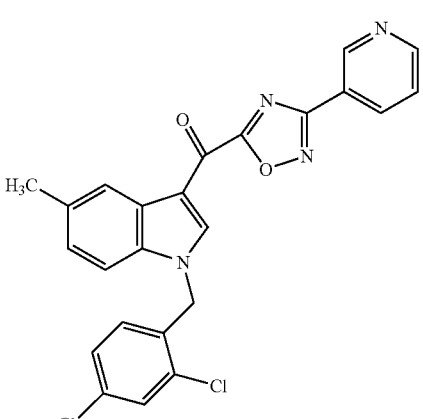

[1-(2,4-dichlorobenzyl)-5-methyl-1H-indol-3-yl](3-pyridin-2-yl-1,2,4-oxadiazol-5-yl)methanone

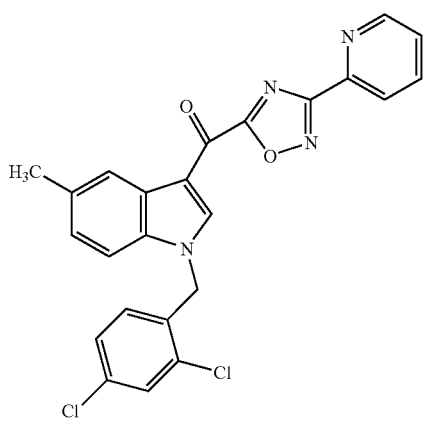

[1-(2,4-dichlorobenzyl)-2,5-dimethyl-1H-indol-3-yl](3-pyridin-4-yl-1,2,4-oxadiazol-5-yl)methanone

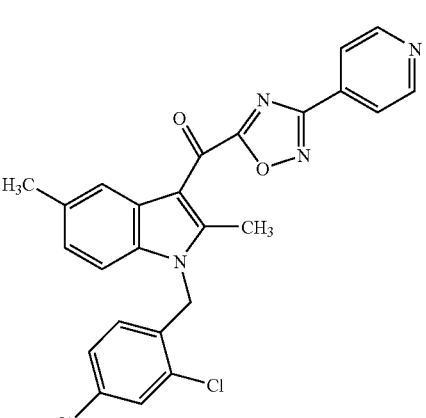

229

[1-(2,4-dichlorobenzyl)-5-methyl-1H-indol-3-yl](3-pyridin-4-yl-1,2,4-oxadiazol-5-yl)methanone

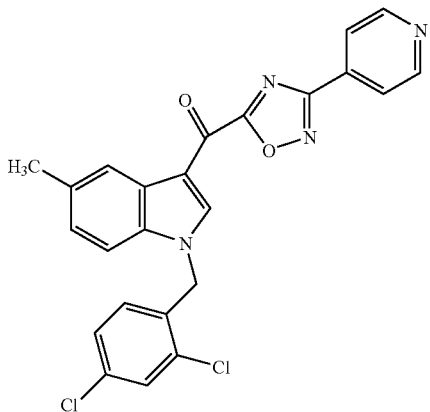

230

[1-(2,4-dichlorobenzyl)-2,5-dimethyl-1H-indol-3-yl](3-pyrazin-2-yl-1,2,4-oxadiazol-5-yl)methanone

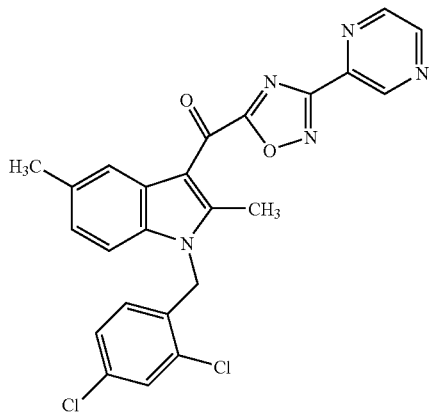

[1-(2,4-dichlorobenzyl)-2,5-dimethyl-1H-indol-3-yl](3-pyrimidin-4-yl-1,2,4-oxadiazol-5-yl)methanone

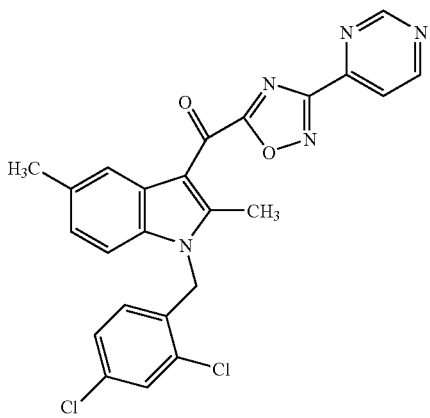

[1-(2,4-dichlorobenzyl)-5-methyl-1H-indol-3-yl](3-pyrazin-2-yl-1,2,4-oxadiazol-5-yl)methanone

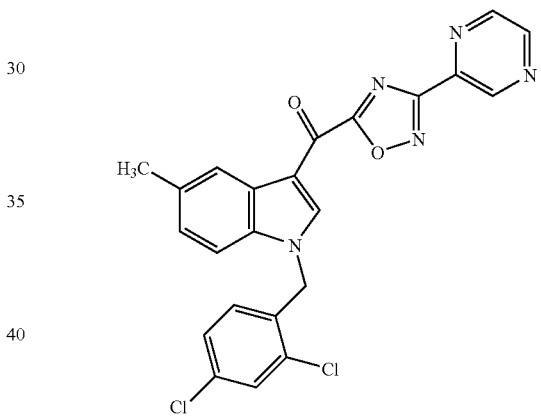

[1-(2,4-dichlorobenzyl)-5-methyl-1H-indol-3-yl](3-pyrimidin-4-yl-1,2,4-oxadiazol-5-yl)methanone

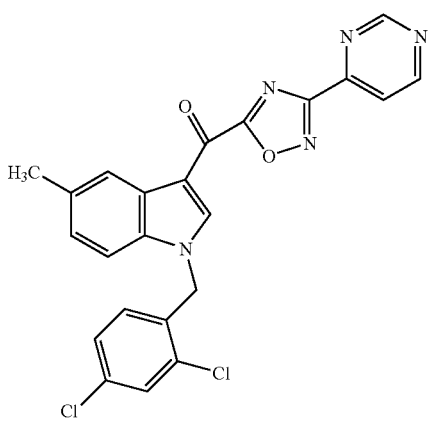

[1-(2,4-dichlorobenzyl)-2,5-dimethyl-1H-indol-3-yl](3-pyrimidin-2-yl-1,2,4-oxadiazol-5-yl)methanone

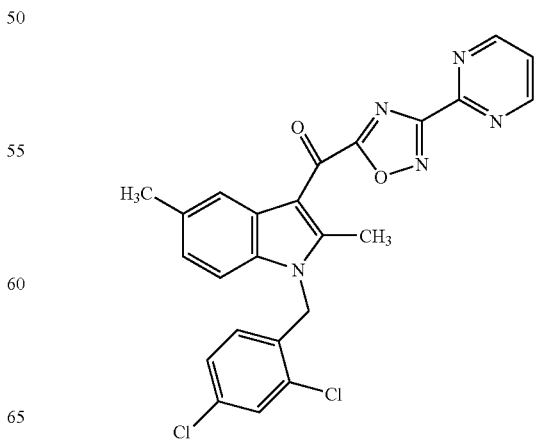

231

[1-(2,4-dichlorobenzyl)-5-methyl-1H-indol-3-yl](3-pyrimidin-2-yl-1,2,4-oxadiazol-5-yl)methanone

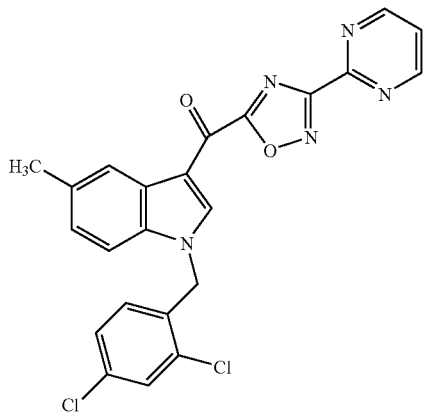

232

[1-(2,4-dichlorobenzyl)-2,5-dimethyl-1H-indol-3-yl](3-pyridazin-4-yl-1,2,4-oxadiazol-5-yl)methanone

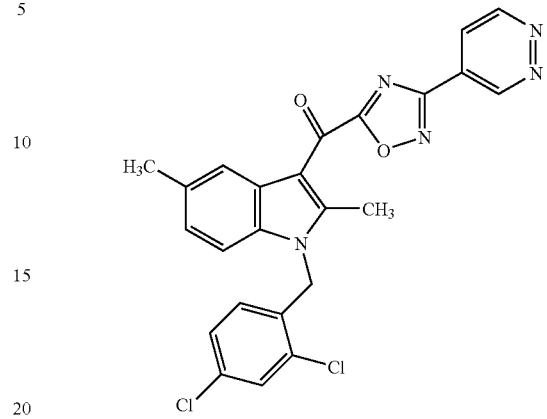

[1-(2,4-dichlorobenzyl)-2,5-dimethyl-1H-indol-3-yl](3-pyridazin-3-yl-1,2,4-oxadiazol-5-yl)methanone

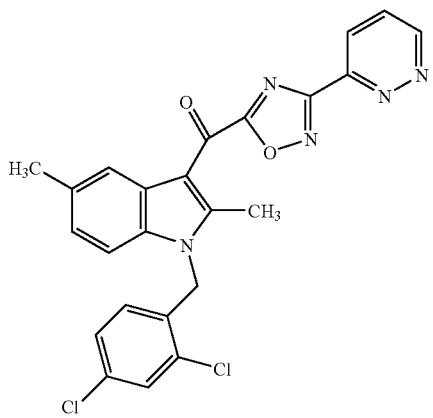

[1-(2,4-dichlorobenzyl)-5-methyl-1H-indol-3-yl](3-pyridazin-4-yl-1,2,4-oxadiazol-5-yl)methanone

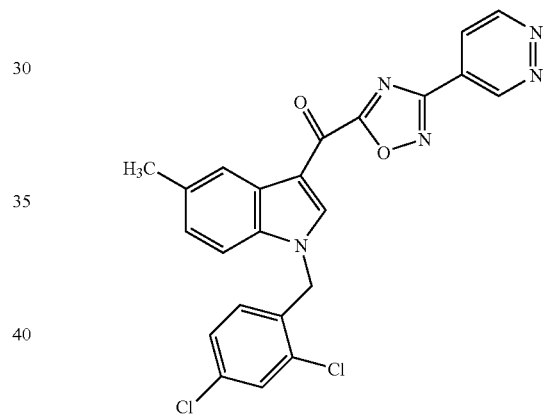

[1-(2,4-dichlorobenzyl)-5-methyl-1H-indol-3-yl](3-pyridazin-3-yl-1,2,4-oxadiazol-5-yl)methanone

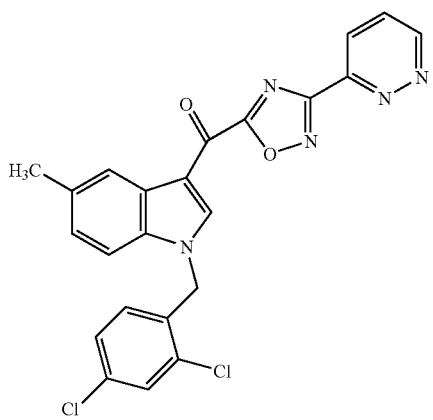

[1-(2,4-dichlorobenzyl)-2-methyl-1H-indol-3-yl](3-phenyl-1,2,4-oxadiazol-5-yl)methanone

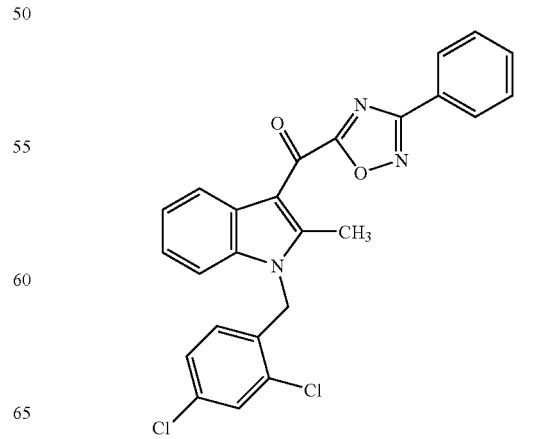

233

[1-(2,4-dichlorobenzyl)-1H-indol-3-yl](3-phenyl-1,2,4-oxadiazol-5-yl)methanone

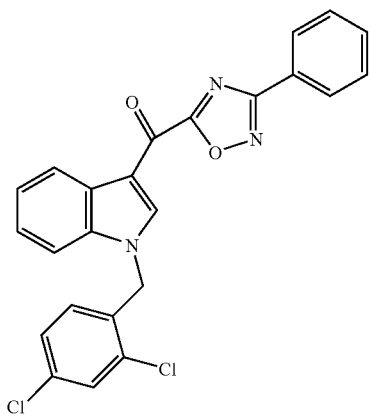

[1-(2,4-dichlorobenzyl)-2-methyl-1H-indol-3-yl](3-pyridin-2-yl-1,2,4-oxadiazol-5-yl)methanone

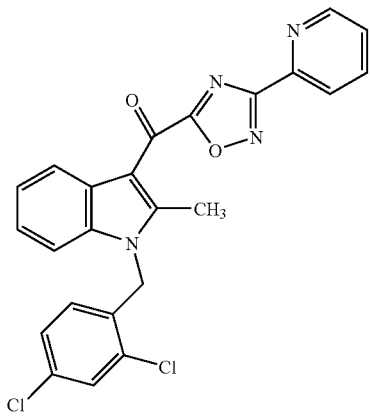

[1-(2,4-dichlorobenzyl)-1H-indol-3-yl](3-pyridin-2-yl-1,2,4-oxadiazol-5-yl)methanone

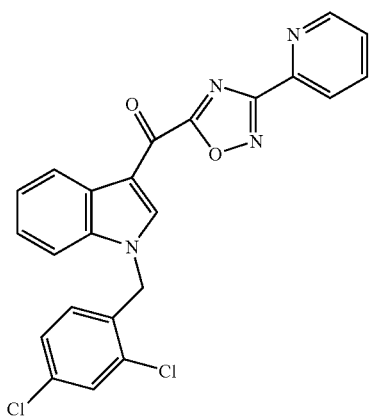

234

[1-(2,4-dichlorobenzyl)-2-methyl-1H-indol-3-yl](3-pyridin-3-yl-1,2,4-oxadiazol-5-yl)methanone

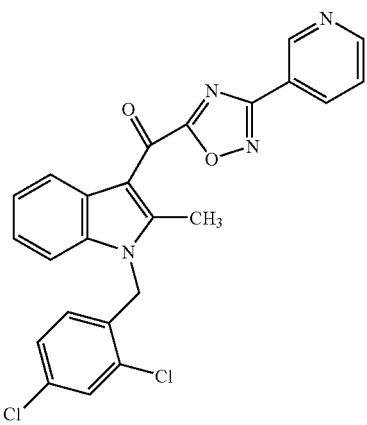

[1-(2,4-dichlorobenzyl)-1H-indol-3-yl](3-pyridin-3-yl-1,2,4-oxadiazol-5-yl)methanone

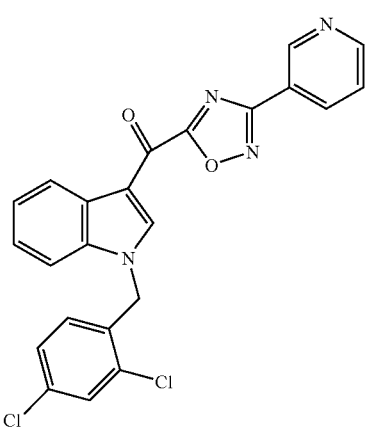

[1-(2,4-dichlorobenzyl)-2-methyl-1H-indol-3-yl](3-pyridin-4-yl-1,2,4-oxadiazol-5-yl)methanone

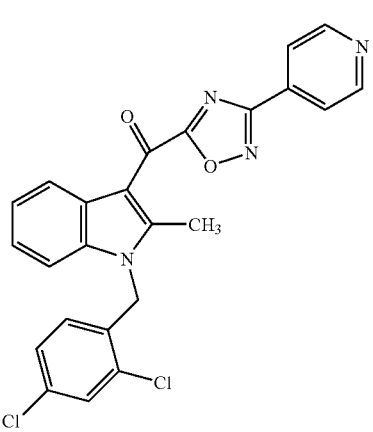

235

[1-(2,4-dichlorobenzyl)-1H-indol-3-yl](3-pyridin-4-yl-1,2,4-oxadiazol-5-yl)methanone

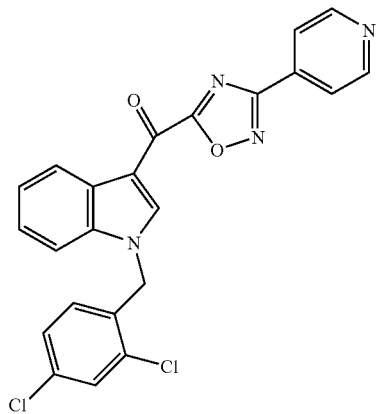

236

[1-(2,4-dichlorobenzyl)-2-methyl-1H-indol-3-yl](3-pyrazin-2-yl-1,2,4-oxadiazol-5-yl)methanone

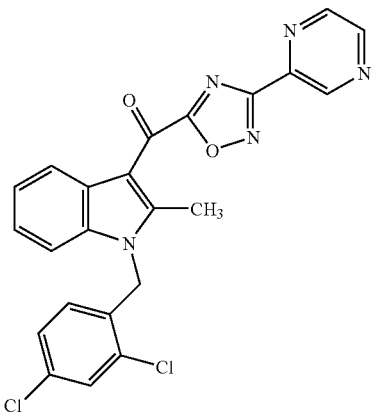

[1-(2,4-dichlorobenzyl)-2-methyl-1H-indol-3-yl](3-pyrimidin-4-yl-1,2,4-oxadiazol-5-yl)methanone

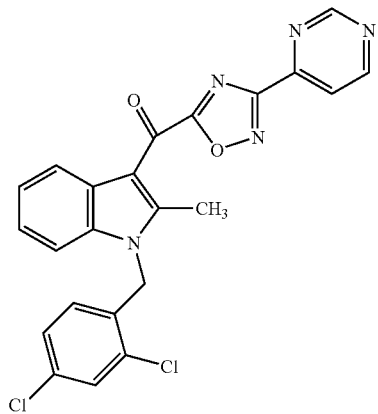

[1-(2,4-dichlorobenzyl)-1H-indol-3-yl](3-pyrazin-2-yl-1,2,4-oxadiazol-5-yl)methanone

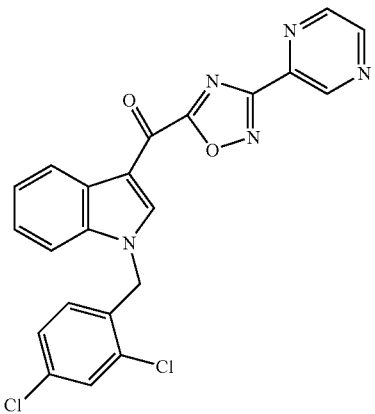

[1-(2,4-dichlorobenzyl)-1H-indol-3-yl](3-pyrimidin-4-yl-1,2,4-oxadiazol-5-yl)methanone

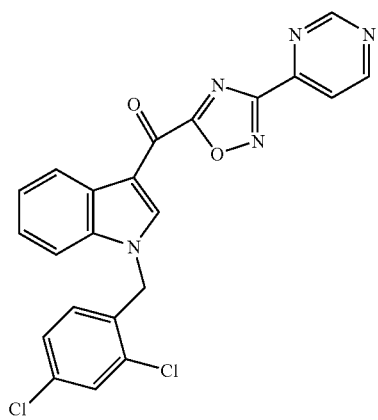

[1-(2,4-dichlorobenzyl)-2-methyl-1H-indol-3-yl](3-pyrimidin-2-yl-1,2,4-oxadiazol-5-yl)methanone

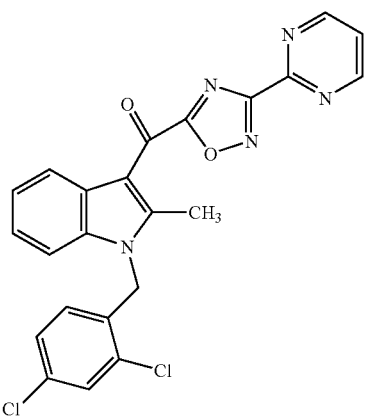

237

[1-(2,4-dichlorobenzyl)-1H-indol-3-yl](3-pyrimidin-2-yl-1,2,4-oxadiazol-5-yl)methanone

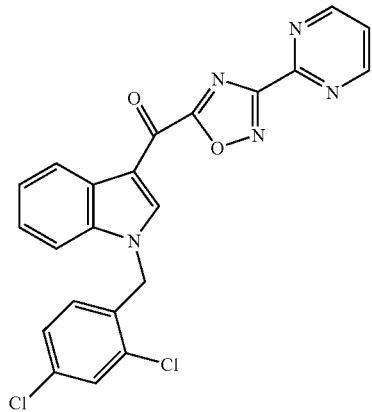

[1-(2,4-dichlorobenzyl)-2-methyl-1H-indol-3-yl](3-pyridazin-3-yl-1,2,4-oxadiazol-5-yl)methanone

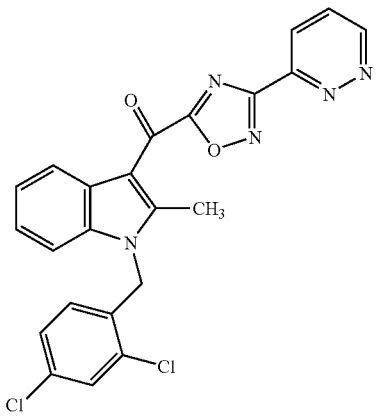

[1-(2,4-dichlorobenzyl)-1H-indol-3-yl](3-pyridazin-3-yl-1,2,4-oxadiazol-5-yl)methanone

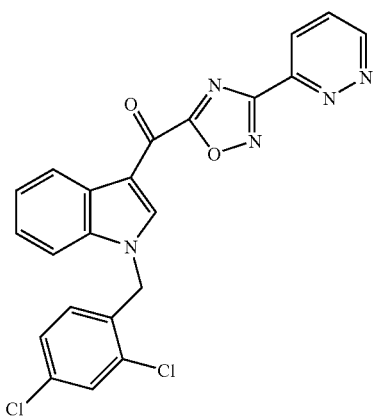

238

[1-(2,4-dichlorobenzyl)-2-methyl-1H-indol-3-yl](3-pyridazin-4-yl-1,2,4-oxadiazol-5-yl)methanone

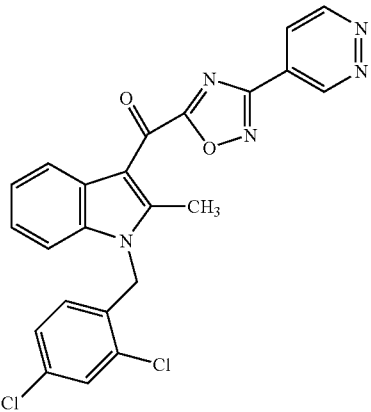

[1-(2,4-dichlorobenzyl)-1H-indol-3-yl](3-pyridazin-4-yl-1,2,4-oxadiazol-5-yl)methanone

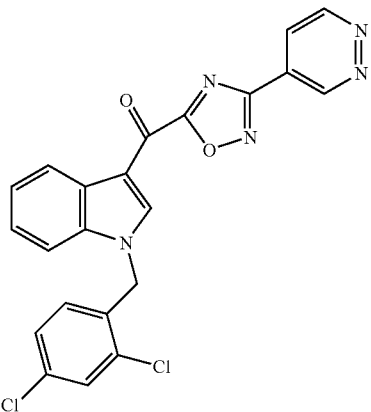

[2-chloro-1-(4-chlorobenzyl)-1H-indol-3-yl](5-phenyl-1,3,4-oxadiazol-2-yl)methanone

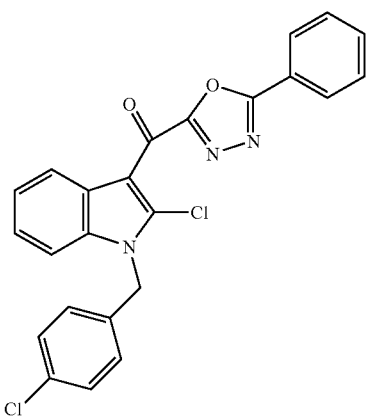

239
[2-chloro-1-(4-chlorobenzyl)-5-methyl-1H-indol-3-yl](5-phenyl-1,3,4-oxadiazol-2-yl)methanone

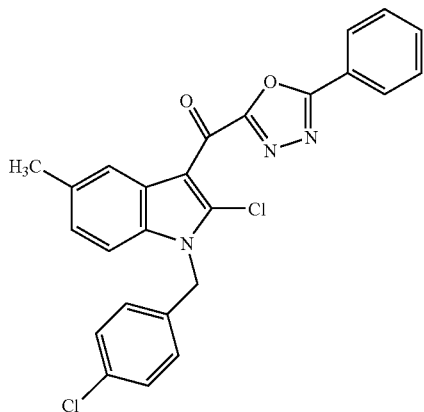

240
[2-chloro-1-(4-chlorobenzyl)-5-methyl-1H-indol-3-yl](5-pyridin-2-yl-1,3,4-oxadiazol-2-yl)methanone

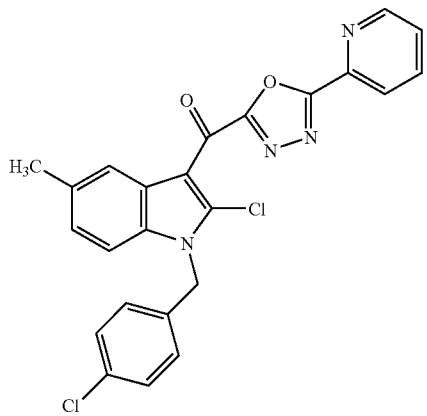

[2-chloro-1-(4-chlorobenzyl)-5-methoxy-1H-indol-3-yl](5-phenyl-1,3,4-oxadiazol-2-yl)methanone

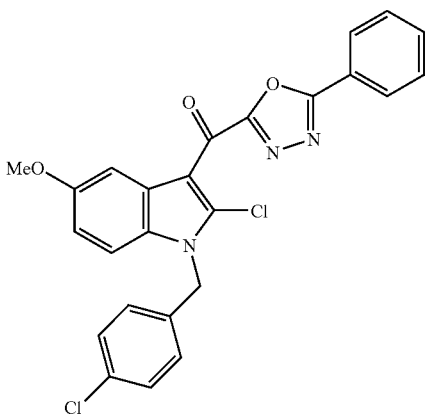

[2-chloro-1-(4-chlorobenzyl)-5-methoxy-1H-indol-3-yl](5-pyridin-2-yl-1,3,4-oxadiazol-2-yl)methanone

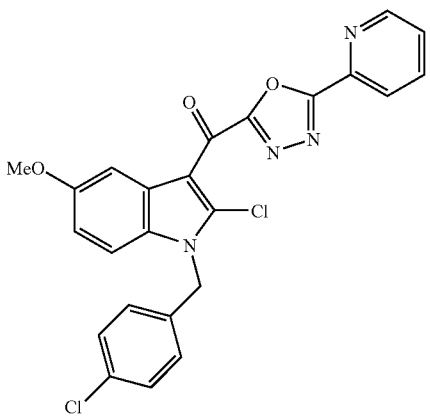

[2-chloro-1-(4-chlorobenzyl)-1H-indol-3-yl](5-pyridin-2-yl-1,3,4-oxadiazol-2-yl)methanone

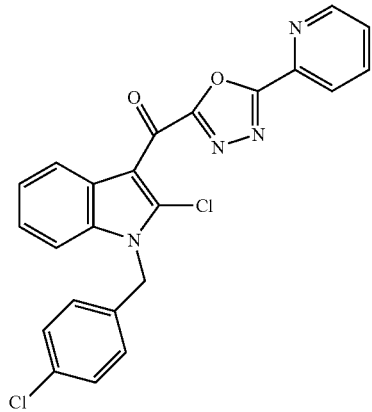

[2-chloro-1-(4-chlorobenzyl)-1H-indol-3-yl](5-pyridin-3-yl-1,3,4-oxadiazol-2-yl)methanone

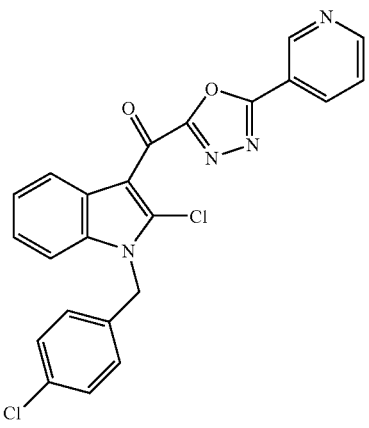

241

[2-chloro-1-(4-chlorobenzyl)-5-methyl-1H-indol-3-yl](5-pyridin-3-yl-1,3,4-oxadiazol-2-yl)methanone

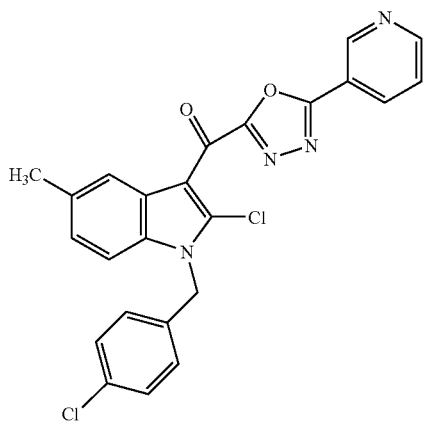

242

[2-chloro-1-(4-chlorobenzyl)-5-methyl-1H-indol-3-yl](5-pyridin-4-yl-1,3,4-oxadiazol-2-yl)methanone

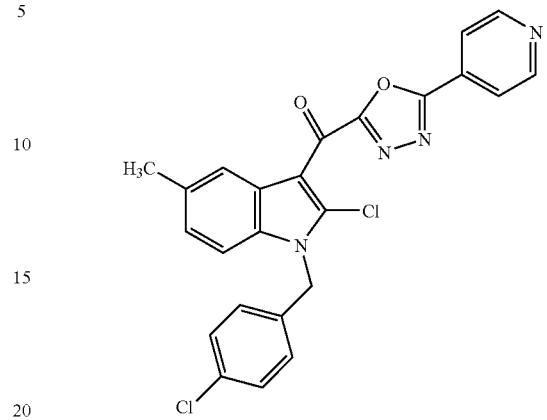

[2-chloro-1-(4-chlorobenzyl)-5-methoxy-1H-indol-3-yl](5-pyridin-3-yl-1,3,4-oxadiazol-2-yl)methanone

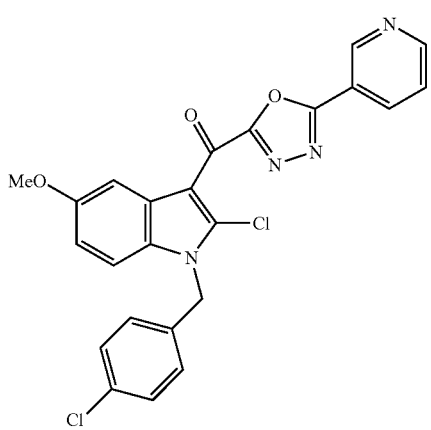

[2-chloro-1-(4-chlorobenzyl)-5-methoxy-1H-indol-3-yl](5-pyridin-4-yl-1,3,4-oxadiazol-2-yl)methanone

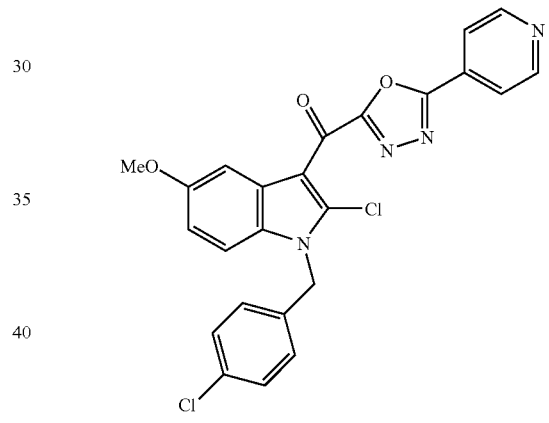

[2-chloro-1-(4-chlorobenzyl)-1H-indol-3-yl](5-pyridin-4-yl-1,3,4-oxadiazol-2-yl)methanone

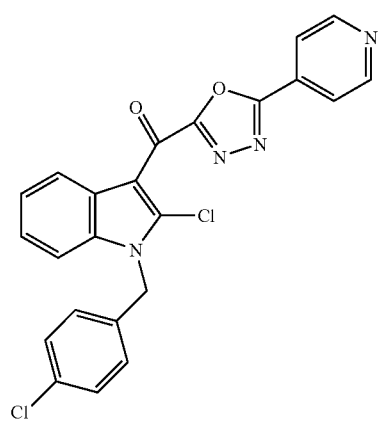

[2-chloro-1-(4-chlorobenzyl)-1H-indol-3-yl](5-pyrimidin-4-yl-1,3,4-oxadiazol-2-yl)methanone

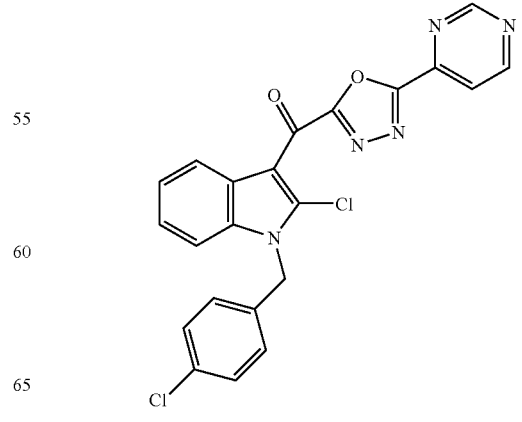

243

[2-chloro-1-(4-chlorobenzyl)-5-methyl-1H-indol-3-yl](5-pyrimidin-4-yl-1,3,4-oxadiazol-2-yl)methanone

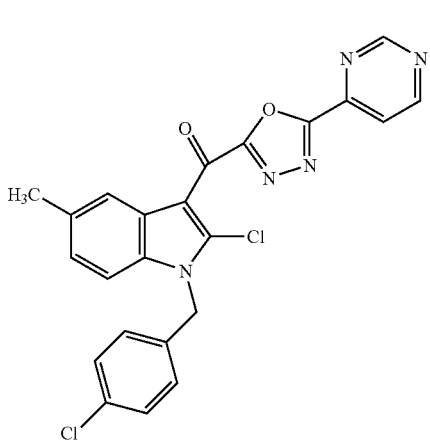

[2-chloro-1-(4-chlorobenzyl)-5-methoxy-1H-indol-3-yl](5-pyrimidin-4-yl-1,3,4-oxadiazol-2-yl)methanone

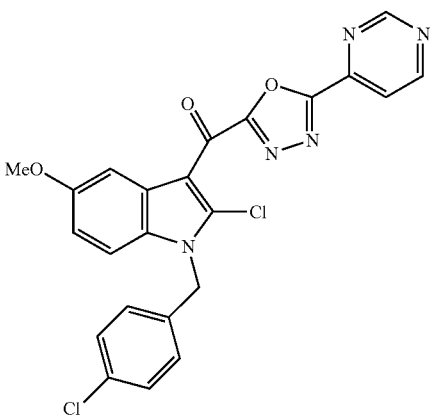

[2-chloro-1-(4-chlorobenzyl)-1H-indol-3-yl](5-pyrazin-2-yl-1,3,4-oxadiazol-2-yl)methanone

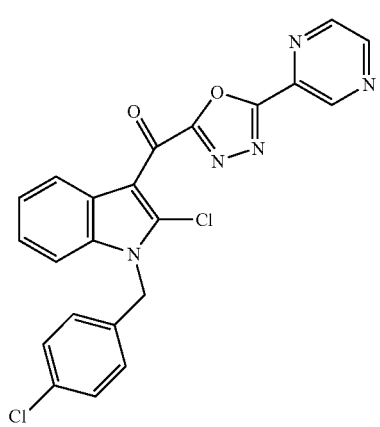

244

[2-chloro-1-(4-chlorobenzyl)-5-methyl-1H-indol-3-yl](5-pyrazin-2-yl-1,3,4-oxadiazol-2-yl)methanone

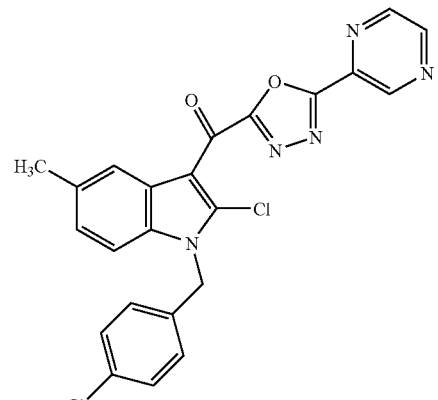

[2-chloro-1-(4-chlorobenzyl)-5-methoxy-1H-indol-3-yl](5-pyrazin-2-yl-1,3,4-oxadiazol-2-yl)methanone

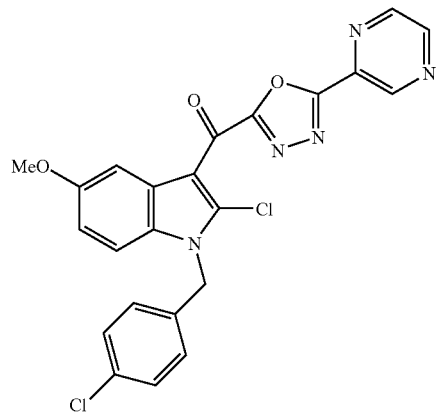

[2-chloro-1-(4-chlorobenzyl)-1H-indol-3-yl](5-pyrimidin-2-yl-1,3,4-oxadiazol-2-yl)methanone

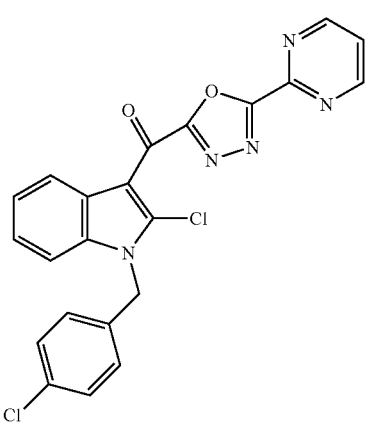

245

[2-chloro-1-(4-chlorobenzyl)-5-methyl-1H-indol-3-yl](5-pyrimidin-2-yl-1,3,4-oxadiazol-2-yl)methanone

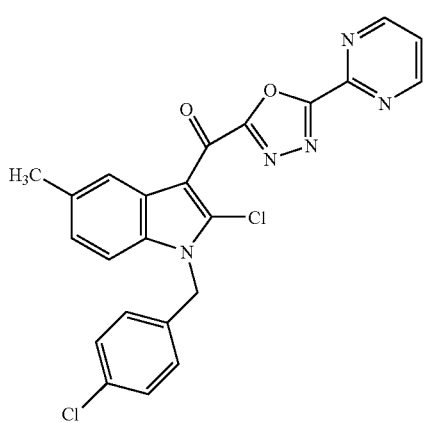

[2-chloro-1-(4-chlorobenzyl)-5-methoxy-1H-indol-3-yl](5-pyrimidin-2-yl-1,3,4-oxadiazol-2-yl)methanone

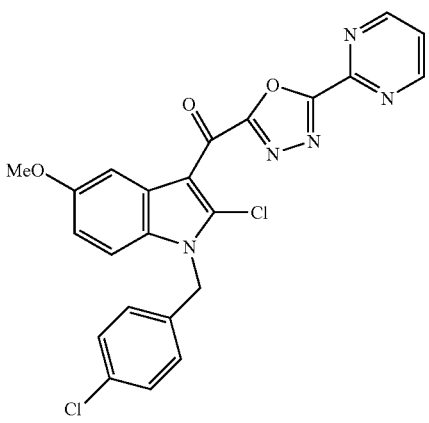

[2-chloro-1-(4-chlorobenzyl)-1H-indol-3-yl](5-pyridazin-3-yl-1,3,4-oxadiazol-2-yl)methanone

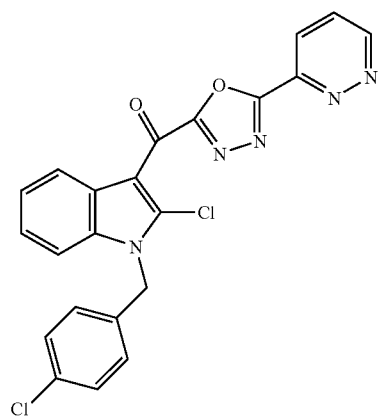

246

[2-chloro-1-(4-chlorobenzyl)-5-methyl-1H-indol-3-yl](5-pyridazin-3-yl-1,3,4-oxadiazol-2-yl)methanone

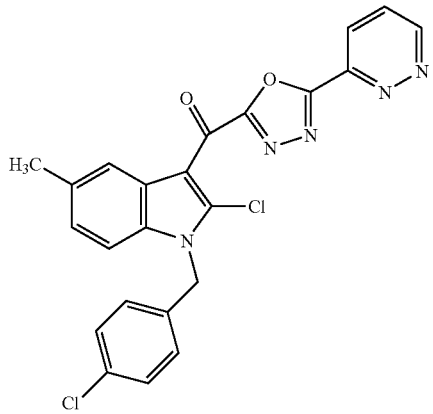

[2-chloro-1-(4-chlorobenzyl)-5-methoxy-1H-indol-3-yl](5-pyridazin-3-yl-1,3,4-oxadiazol-2-yl)methanone

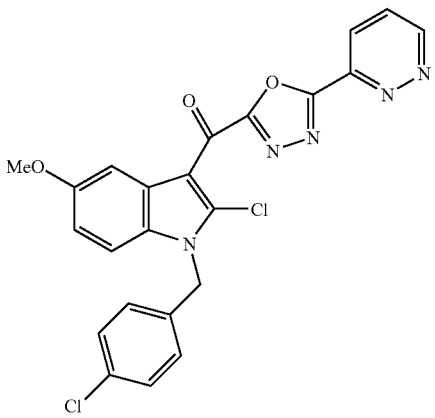

[2-chloro-1-(4-chlorobenzyl)-1H-indol-3-yl](5-pyridazin-4-yl-1,3,4-oxadiazol-2-yl)methanone

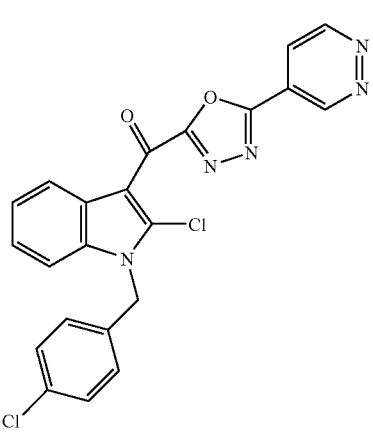

247

[2-chloro-1-(4-chlorobenzyl)-5-methyl-1H-indol-3-yl](5-pyridazin-4-yl-1,3,4-oxadiazol-2-yl)methanone

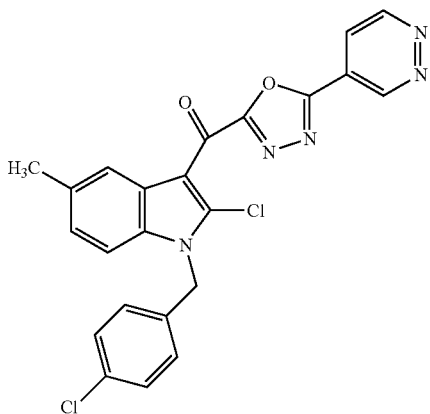

248

[2-chloro-1-(2,4-dichlorobenzyl)-5-methyl-1H-indol-3-yl](5-phenyl-1,3,4-oxadiazol-2-yl)methanone

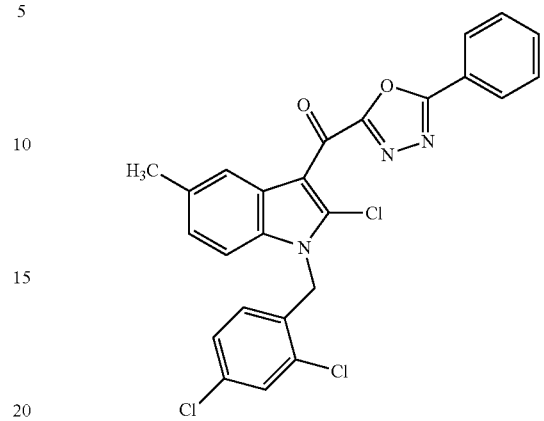

[2-chloro-1-(4-chlorobenzyl)-5-methoxy-1H-indol-3-yl](5-pyridazin-4-yl-1,3,4-oxadiazol-2-yl)methanone

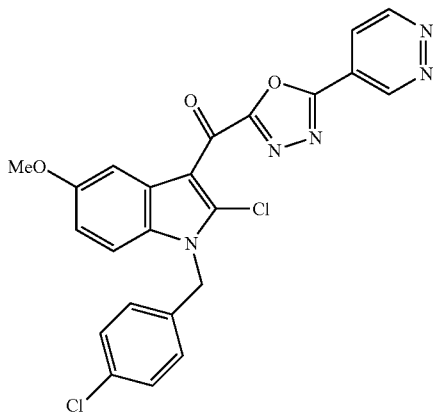

[2-chloro-1-(2,4-dichlorobenzyl)-5-methoxy-1H-indol-3-yl](5-phenyl-1,3,4-oxadiazol-2-yl)methanone

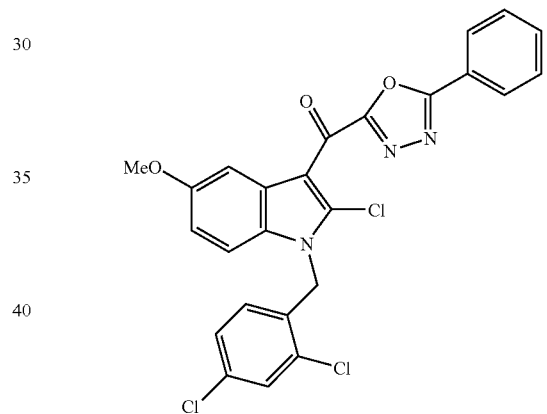

[2-chloro-1-(2,4-dichlorobenzyl)-1H-indol-3-yl](5-phenyl-1,3,4-oxadiazol-2-yl)methanone

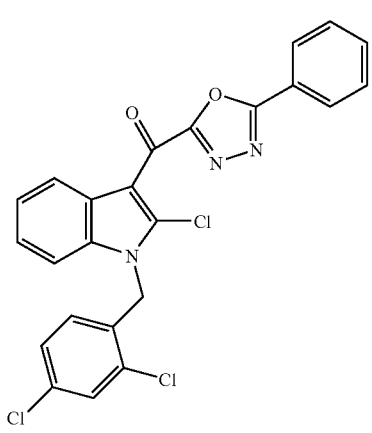

[2-chloro-1-(2,4-dichlorobenzyl)-1H-indol-3-yl](5-pyridin-2-yl-1,3,4-oxadiazol-2-yl)methanone

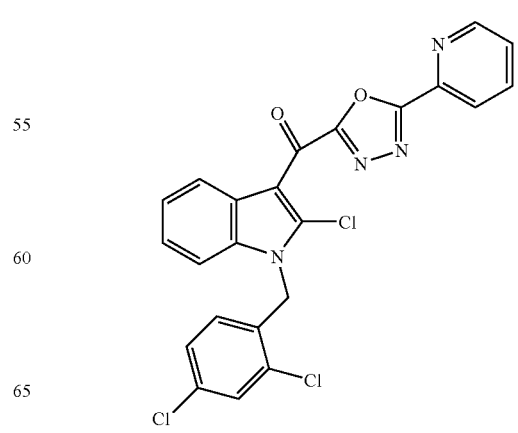

249

[2-chloro-1-(2,4-dichlorobenzyl)-5-methyl-1H-indol-3-yl](5-pyridin-2-yl-1,3,4-oxadiazol-2-yl)methanone

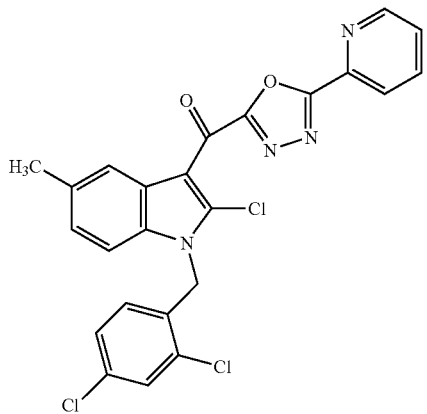

[2-chloro-1-(2,4-dichlorobenzyl)-5-methoxy-1H-indol-3-yl](5-pyridin-2-yl-1,3,4-oxadiazol-2-yl)methanone

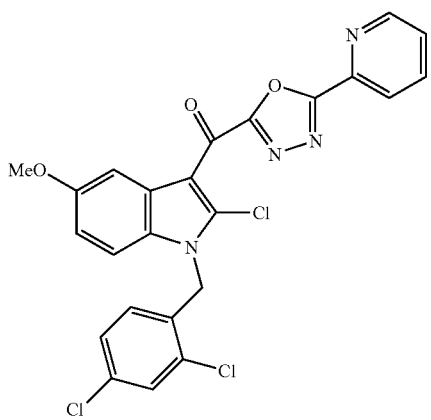

[2-chloro-1-(2,4-dichlorobenzyl)-1H-indol-3-yl](5-pyridin-3-yl-1,3,4-oxadiazol-2-yl)methanone

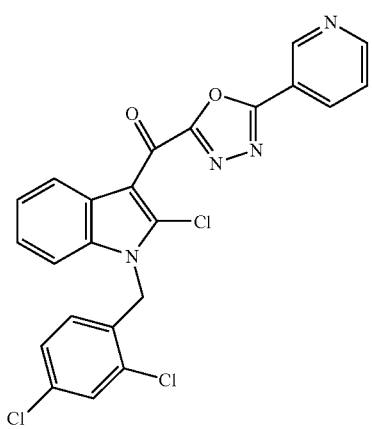

250

[2-chloro-1-(2,4-dichlorobenzyl)-5-methyl-1H-indol-3-yl](5-pyridin-3-yl-1,3,4-oxadiazol-2-yl)methanone

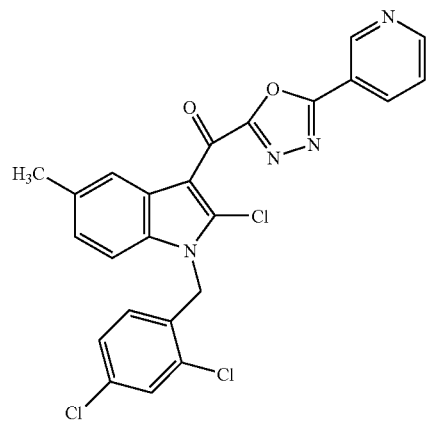

[2-chloro-1-(2,4-dichlorobenzyl)-5-methoxy-1H-indol-3-yl](5-pyridin-3-yl-1,3,4-oxadiazol-2-yl)methanone

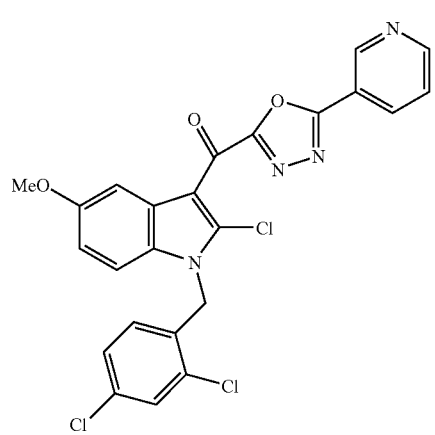

[2-chloro-1-(2,4-dichlorobenzyl)-1H-indol-3-yl](5-pyridin-4-yl-1,3,4-oxadiazol-2-yl)methanone

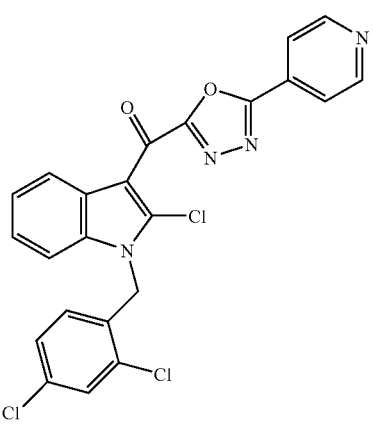

251

[2-chloro-1-(2,4-dichlorobenzyl)-5-methyl-1H-indol-3-yl](5-pyridin-4-yl-1,3,4-oxadiazol-2-yl)methanone

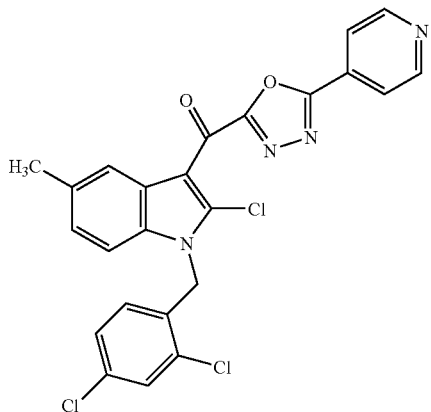

[2-chloro-1-(2,4-dichlorobenzyl)-5-methoxy-1H-indol-3-yl](5-pyridin-4-yl-1,3,4-oxadiazol-2-yl)methanone

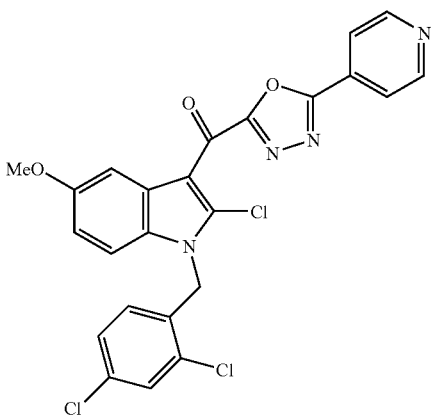

[2-chloro-1-(2,4-dichlorobenzyl)-1H-indol-3-yl](5-pyrimidin-4-yl-1,3,4-oxadiazol-2-yl)methanone

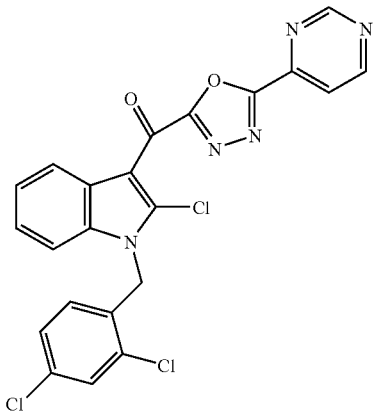

252

[2-chloro-1-(2,4-dichlorobenzyl)-5-methyl-1H-indol-3-yl](5-pyrimidin-4-yl-1,3,4-oxadiazol-2-yl)methanone

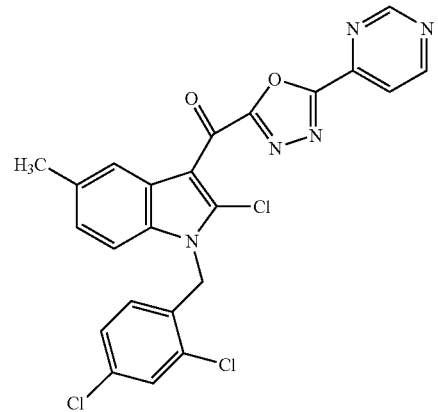

[2-chloro-1-(2,4-dichlorobenzyl)-5-methoxy-1H-indol-3-yl](5-pyrimidin-4-yl-1,3,4-oxadiazol-2-yl)methanone

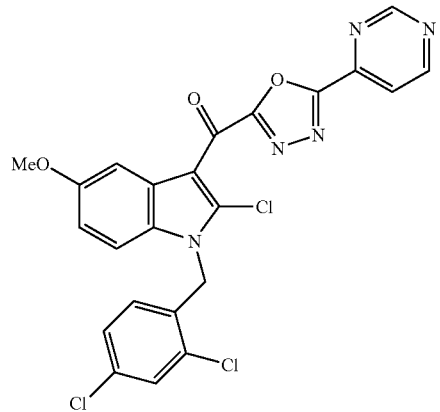

[2-chloro-1-(2,4-dichlorobenzyl)-1H-indol-3-yl](5-pyrazin-2-yl-1,3,4-oxadiazol-2-yl)methanone

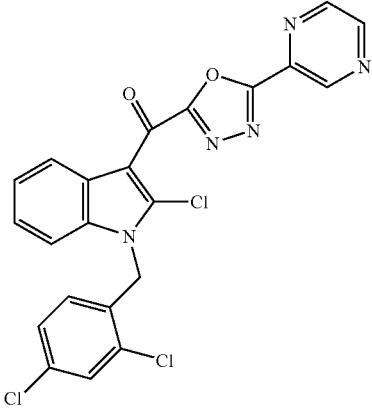

253

[2-chloro-1-(2,4-dichlorobenzyl)-5-methyl-1H-indol-3-yl](5-pyrazin-2-yl-1,3,4-oxadiazol-2-yl)methanone

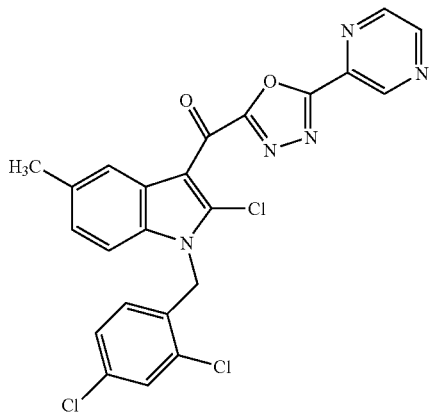

[2-chloro-1-(2,4-dichlorobenzyl)-5-methoxy-1H-indol-3-yl](5-pyrazin-2-yl-1,3,4-oxadiazol-2-yl)methanone

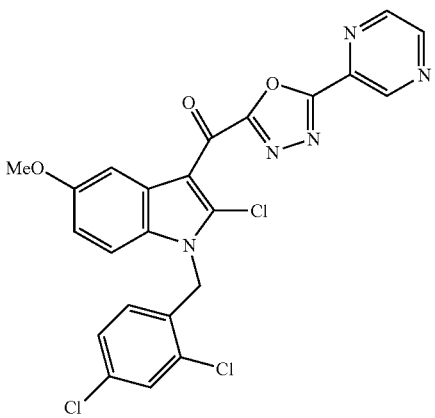

[2-chloro-1-(2,4-dichlorobenzyl)-1H-indol-3-yl](5-pyrimidin-2-yl-1,3,4-oxadiazol-2-yl)methanone

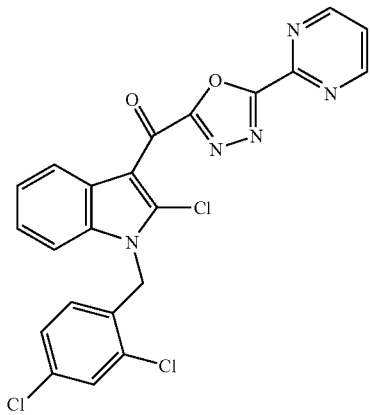

254

[2-chloro-1-(2,4-dichlorobenzyl)-5-methyl-1H-indol-3-yl](5-pyrimidin-2-yl-1,3,4-oxadiazol-2-yl)methanone

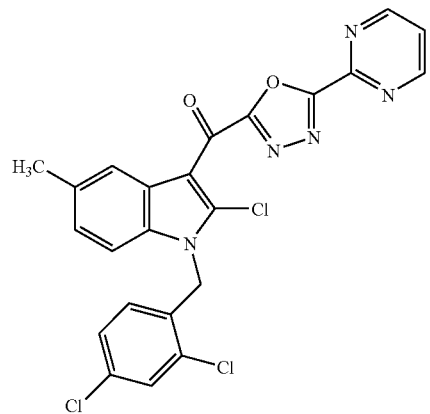

[2-chloro-1-(2,4-dichlorobenzyl)-5-methoxy-1H-indol-3-yl](5-pyrimidin-2-yl-1,3,4-oxadiazol-2-yl)methanone

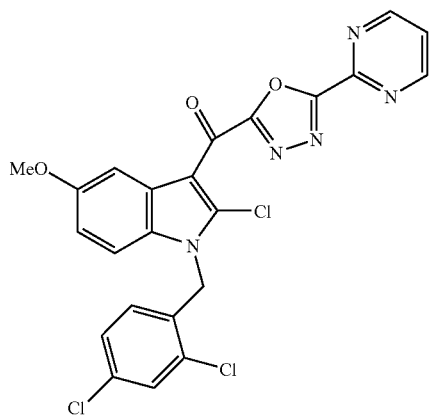

[2-chloro-1-(2,4-dichlorobenzyl)-1H-indol-3-yl](5-pyridazin-3-yl-1,3,4-oxadiazol-2-yl)methanone

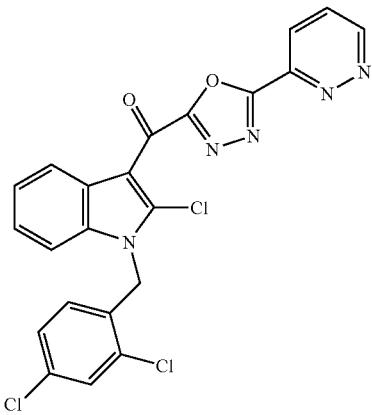

255
[2-chloro-1-(2,4-dichlorobenzyl)-5-methyl-1H-indol-3-yl](5-pyridazin-3-yl-1,3,4-oxadiazol-2-yl)methanone

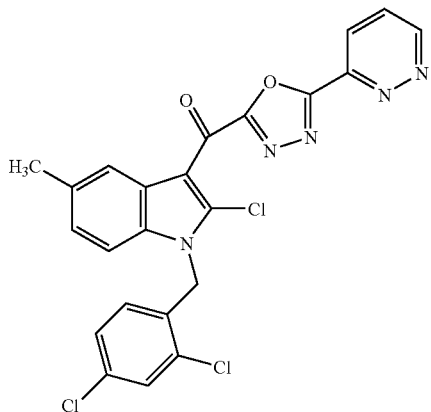

[2-chloro-1-(2,4-dichlorobenzyl)-5-methoxy-1H-indol-3-yl](5-pyridazin-3-yl-1,3,4-oxadiazol-2-yl)methanone

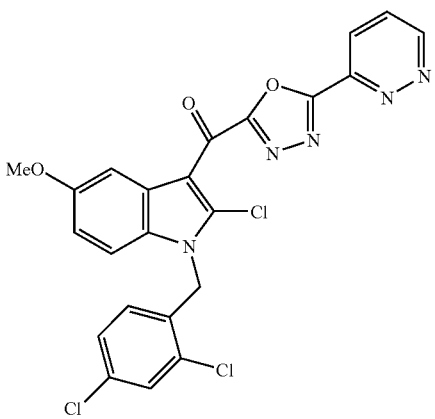

[2-chloro-1-(2,4-dichlorobenzyl)-1H-indol-3-yl](5-pyridazin-4-yl-1,3,4-oxadiazol-2-yl)methanone

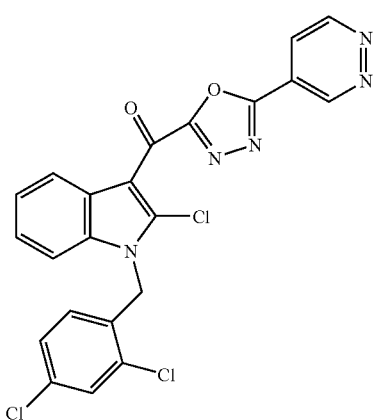

256
[2-chloro-1-(2,4-dichlorobenzyl)-5-methyl-1H-indol-3-yl](5-pyridazin-4-yl-1,3,4-oxadiazol-2-yl)methanone

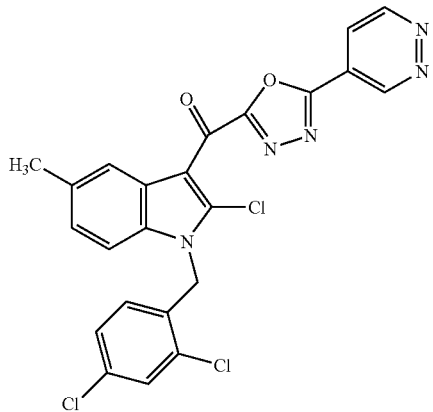

C, 55.39; H, 2.83; Cl, 21.33; N, 14.04; O, 642

[2-chloro-1-(2,4-dichlorobenzyl)-5-methoxy-1H-indol-3-yl](5-pyridazin-4-yl-1,3,4-oxadiazol-2-yl)methanone

[2-chloro-1-(4-chlorobenzyl)-1H-indol-3-yl](3-phenyl-1,2,4-oxadiazol-5-yl)methanone

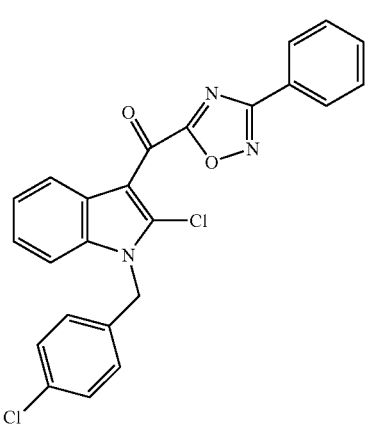

257

[2-chloro-1-(4-chlorobenzyl)-5-methyl-1H-indol-3-yl](3-phenyl-1,2,4-oxadiazol-5-yl)methanone

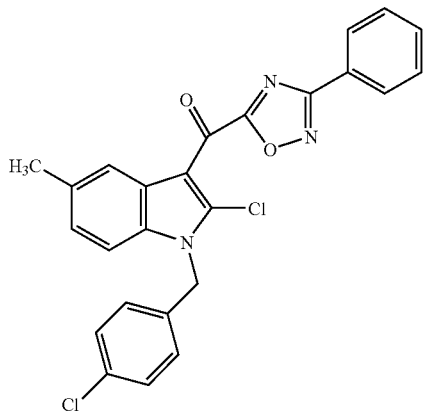

258

[2-chloro-1-(4-chlorobenzyl)-5-methyl-1H-indol-3-yl](3-pyridin-2-yl-1,2,4-oxadiazol-5-yl)methanone

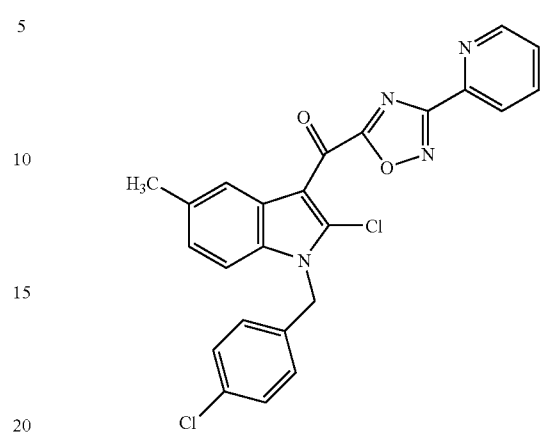

[2-chloro-1-(4-chlorobenzyl)-5-methoxy-1H-indol-3-yl](3-phenyl-1,2,4-oxadiazol-5-yl)methanone

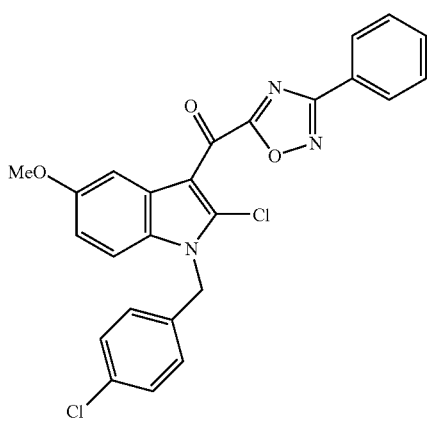

[2-chloro-1-(4-chlorobenzyl)-5-methoxy-1H-indol-3-yl](3-pyridin-2-yl-1,2,4-oxadiazol-5-yl)methanone

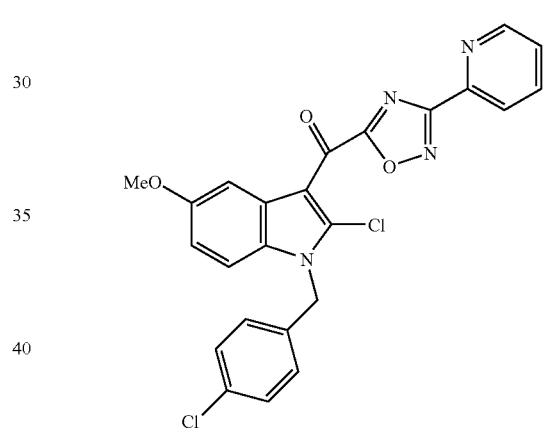

[2-chloro-1-(4-chlorobenzyl)-1H-indol-3-yl](3-pyridin-2-yl-1,2,4-oxadiazol-5-yl)methanone

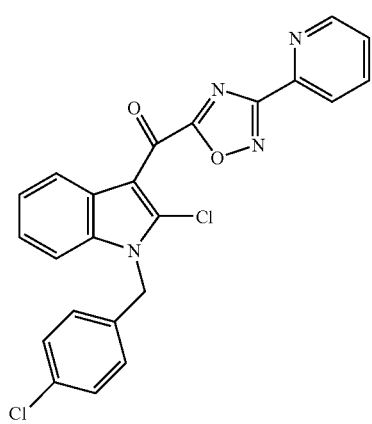

[2-chloro-1-(4-chlorobenzyl)-1H-indol-3-yl](3-pyridin-3-yl-1,2,4-oxadiazol-5-yl)methanone

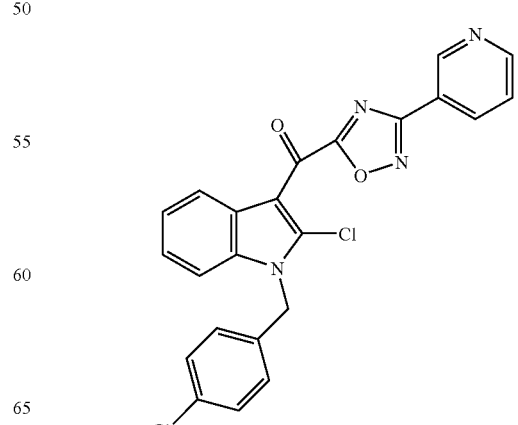

259

[2-chloro-1-(4-chlorobenzyl)-5-methyl-1H-indol-3-yl](3-pyridin-3-yl-1,2,4-oxadiazol-5-yl)methanone

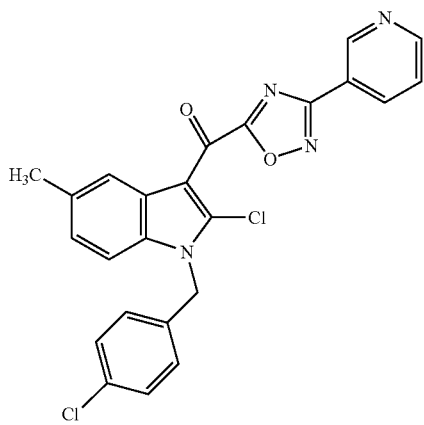

[2-chloro-1-(4-chlorobenzyl)-5-methoxy-1H-indol-3-yl](3-pyridin-3-yl-1,2,4-oxadiazol-5-yl)methanone

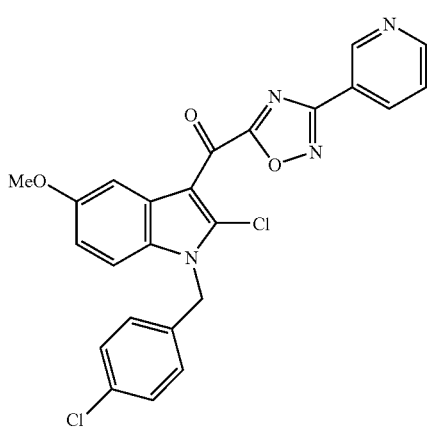

[2-chloro-1-(4-chlorobenzyl)-1H-indol-3-yl](3-pyridin-4-yl-1,2,4-oxadiazol-5-yl)methanone

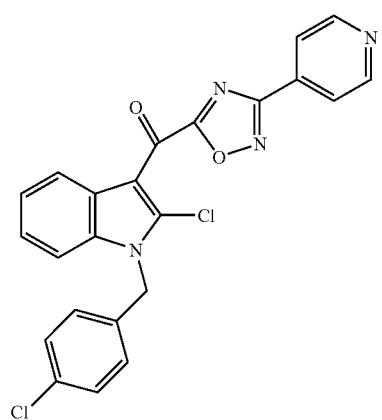

260

[2-chloro-1-(4-chlorobenzyl)-5-methyl-1H-indol-3-yl](3-pyridin-4-yl-1,2,4-oxadiazol-5-yl)methanone

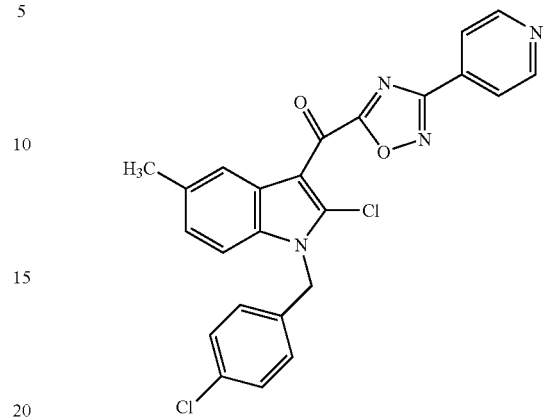

[2-chloro-1-(4-chlorobenzyl)-5-methoxy-1H-indol-3-yl](3-pyridin-4-yl-1,2,4-oxadiazol-5-yl)methanone

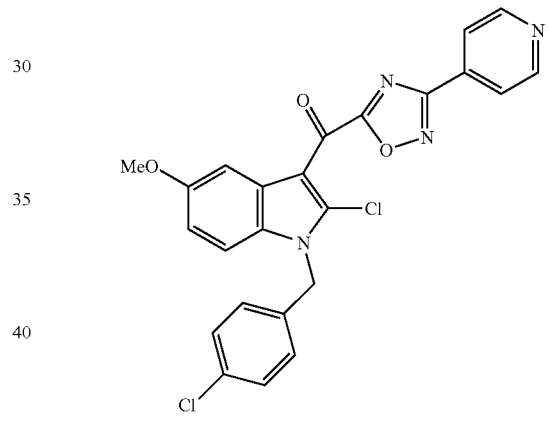

[2-chloro-1-(4-chlorobenzyl)-1H-indol-3-yl](3-pyrimidin-4-yl-1,2,4-oxadiazol-5-yl)methanone

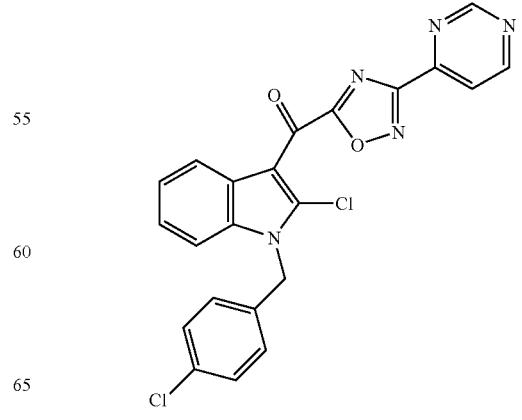

| 261 | 262 |
|---|---|
| [2-chloro-1-(4-chlorobenzyl)-5-methyl-1H-indol-3-yl](3-pyrimidin-4-yl-1,2,4-oxadiazol-5-yl)methanone | [2-chloro-1-(4-chlorobenzyl)-5-methyl-1H-indol-3-yl](3-pyrazin-2-yl-1,2,4-oxadiazol-5-yl)methanone |

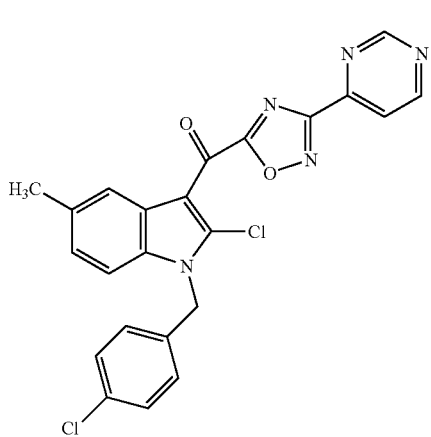
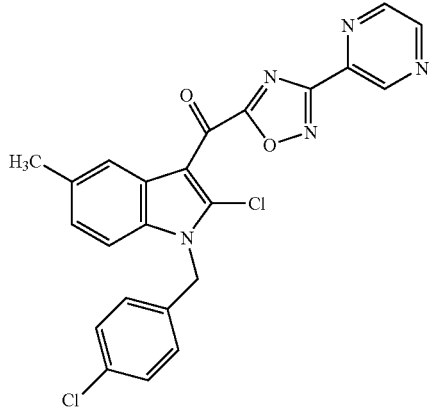

[2-chloro-1-(4-chlorobenzyl)-5-methoxy-1H-indol-3-yl](3-pyrimidin-4-yl-1,2,4-oxadiazol-5-yl)methanone

[2-chloro-1-(4-chlorobenzyl)-5-methoxy-1H-indol-3-yl](3-pyrazin-2-yl-1,2,4-oxadiazol-5-yl)methanone

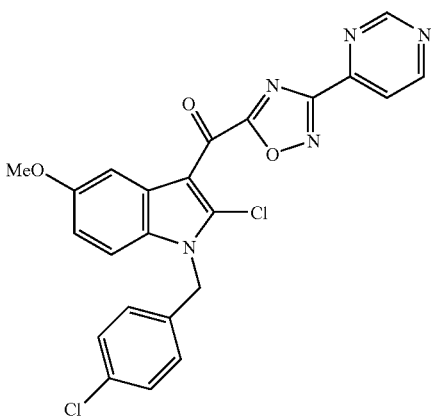
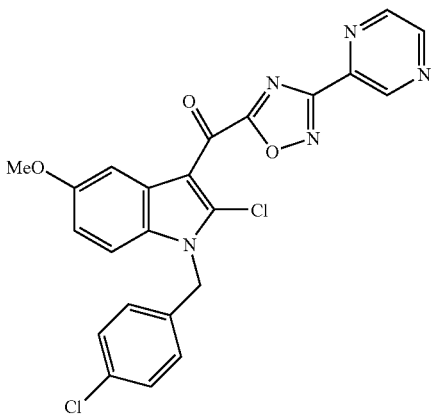

[2-chloro-1-(4-chlorobenzyl)-1H-indol-3-yl](3-pyrazin-2-yl-1,2,4-oxadiazol-5-yl)methanone

[2-chloro-1-(4-chlorobenzyl)-1H-indol-3-yl](3-pyrimidin-2-yl-1,2,4-oxadiazol-5-yl)methanone

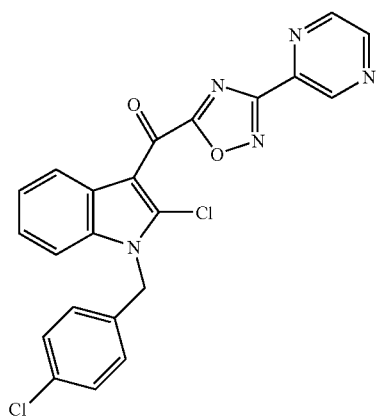
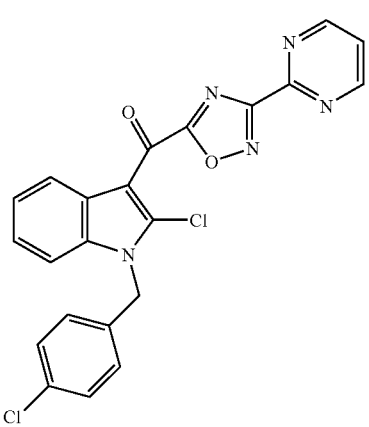

263

[2-chloro-1-(4-chlorobenzyl)-5-methyl-1H-indol-3-yl](3-pyrimidin-2-yl-1,2,4-oxadiazol-5-yl)methanone

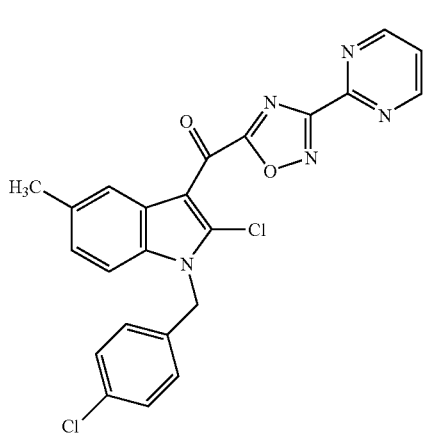

[2-chloro-1-(4-chlorobenzyl)-5-methoxy-1H-indol-3-yl](3-pyrimidin-2-yl-1,2,4-oxadiazol-5-yl)methanone

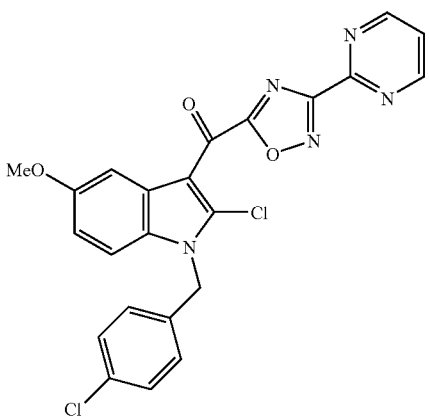

[2-chloro-1-(4-chlorobenzyl)-1H-indol-3-yl](3-pyridazin-3-yl-1,2,4-oxadiazol-5-yl)methanone

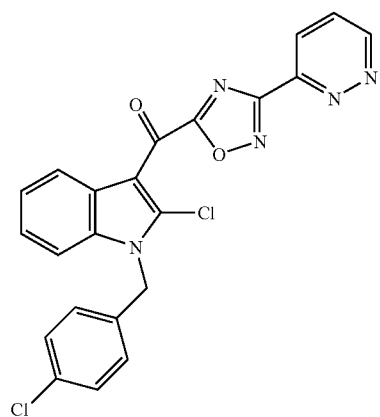

264

[2-chloro-1-(4-chlorobenzyl)-5-methyl-1H-indol-3-yl](3-pyridazin-3-yl-1,2,4-oxadiazol-5-yl)methanone

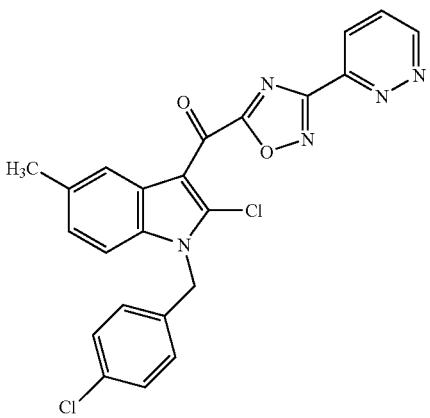

[2-chloro-1-(4-chlorobenzyl)-5-methoxy-1H-indol-3-yl](3-pyridazin-3-yl-1,2,4-oxadiazol-5-yl)methanone

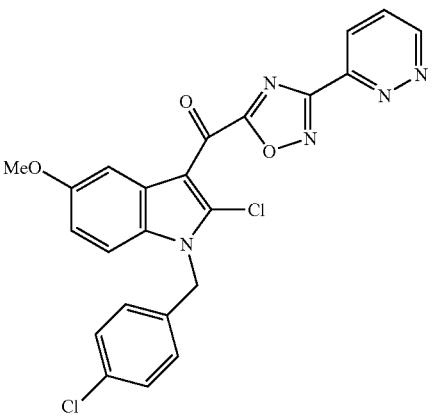

[2-chloro-1-(4-chlorobenzyl)-1H-indol-3-yl](3-pyridazin-4-yl-1,2,4-oxadiazol-5-yl)methanone

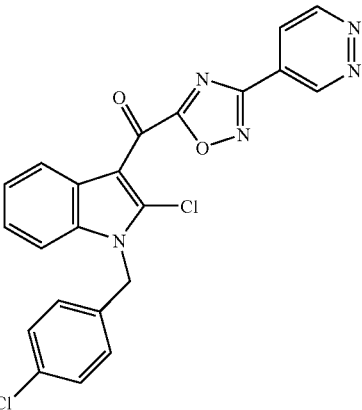

265

[2-chloro-1-(4-chlorobenzyl)-5-methyl-1H-indol-3-yl](3-pyridazin-4-yl-1,2,4-oxadiazol-5-yl)methanone

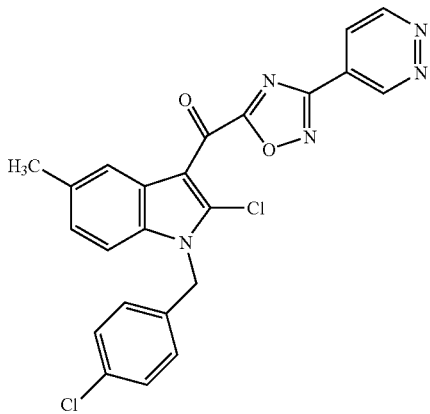

[2-chloro-1-(4-chlorobenzyl)-5-methoxy-1H-indol-3-yl](3-pyridazin-4-yl-1,2,4-oxadiazol-5-yl)methanone

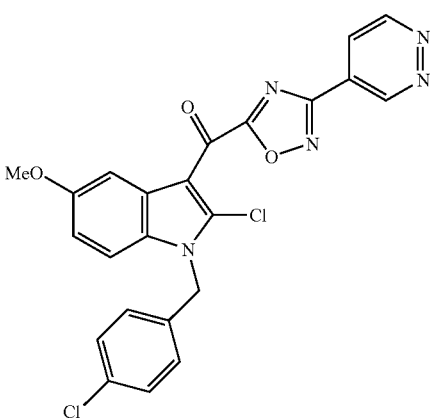

[2-chloro-1-(2,4-dichlorobenzyl)-1H-indol-3-yl](3-phenyl-1,2,4-oxadiazol-5-yl)methanone

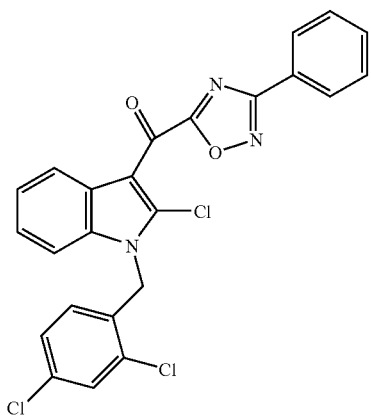

266

[2-chloro-1-(2,4-dichlorobenzyl)-5-methyl-1H-indol-3-yl](3-phenyl-1,2,4-oxadiazol-5-yl)methanone

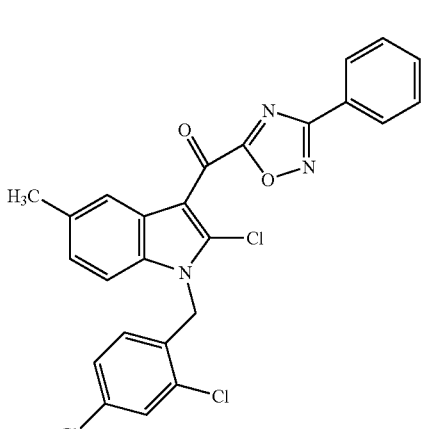

[2-chloro-1-(2,4-dichlorobenzyl)-5-methoxy-1H-indol-3-yl](3-phenyl-1,2,4-oxadiazol-5-yl)methanone

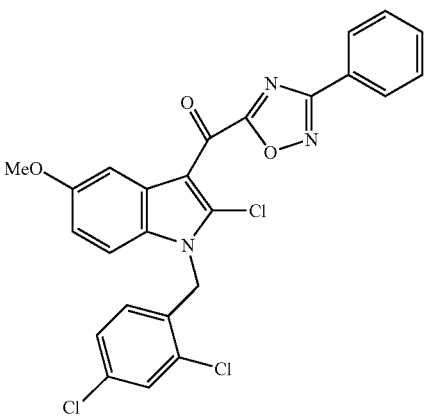

[2-chloro-1-(2,4-dichlorobenzyl)-1H-indol-3-yl](3-pyridin-2-yl-1,2,4-oxadiazol-5-yl)methanone

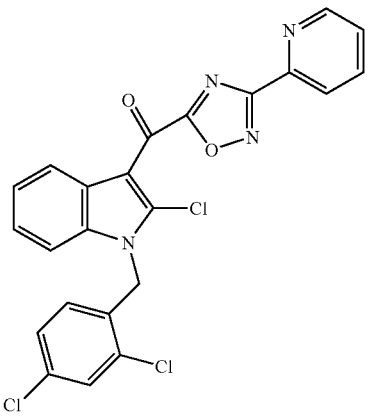

267
[2-chloro-1-(2,4-dichlorobenzyl)-5-methyl-1H-indol-3-yl](3-pyridin-2-yl-1,2,4-oxadiazol-5-yl)methanone

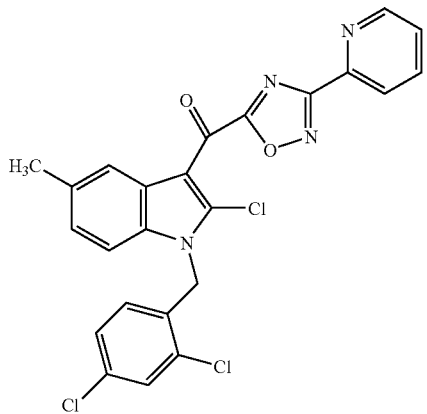

[2-chloro-1-(2,4-dichlorobenzyl)-5-methoxy-1H-indol-3-yl](3-pyridin-2-yl-1,2,4-oxadiazol-5-yl)methanone

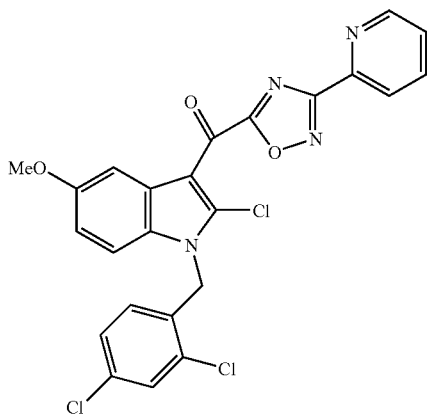

[2-chloro-1-(2,4-dichlorobenzyl)-1H-indol-3-yl](3-pyridin-3-yl-1,2,4-oxadiazol-5-yl)methanone

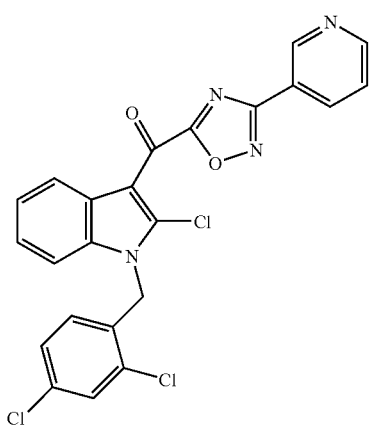

268
[2-chloro-1-(2,4-dichlorobenzyl)-5-methyl-1H-indol-3-yl](3-pyridin-3-yl-1,2,4-oxadiazol-5-yl)methanone

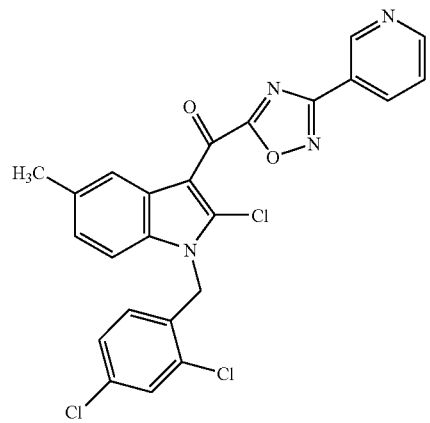

[2-chloro-1-(2,4-dichlorobenzyl)-5-methoxy-1H-indol-3-yl](3-pyridin-3-yl-1,2,4-oxadiazol-5-yl)methanone

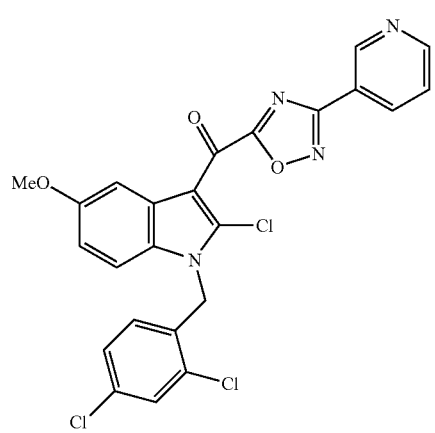

[2-chloro-1-(2,4-dichlorobenzyl)-1H-indol-3-yl](3-pyridin-4-yl-1,2,4-oxadiazol-5-yl)methanone

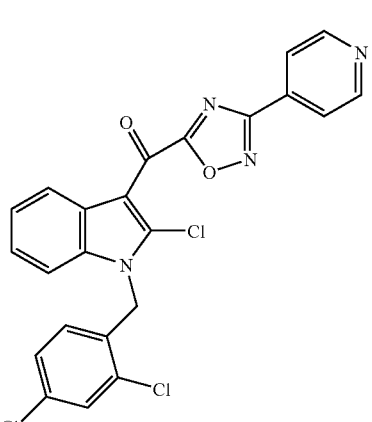

269
[2-chloro-1-(2,4-dichlorobenzyl)-5-methyl-1H-indol-3-yl](3-pyridin-4-yl-1,2,4-oxadiazol-5-yl)methanone

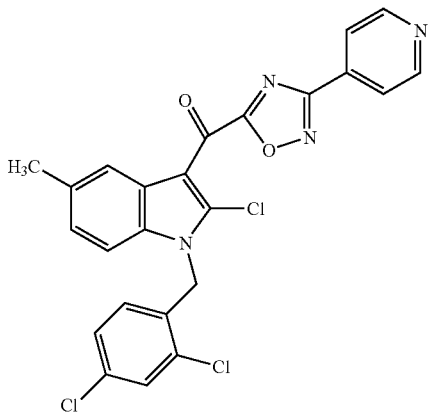

[2-chloro-1-(2,4-dichlorobenzyl)-5-methoxy-1H-indol-3-yl](3-pyridin-4-yl-1,2,4-oxadiazol-5-yl)methanone

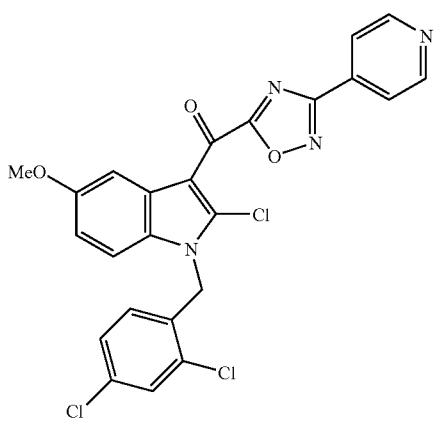

[2-chloro-1-(2,4-dichlorobenzyl)-1H-indol-3-yl](3-pyrimidin-4-yl-1,2,4-oxadiazol-5-yl)methanone

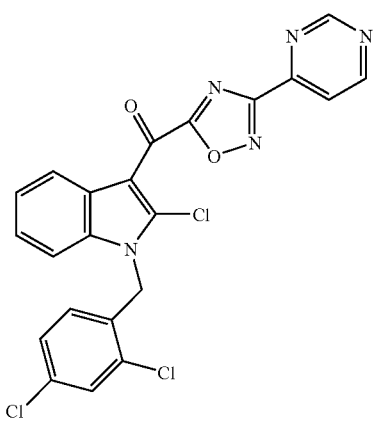

270
[2-chloro-1-(2,4-dichlorobenzyl)-5-methyl-1H-indol-3-yl](3-pyrimidin-4-yl-1,2,4-oxadiazol-5-yl)methanone

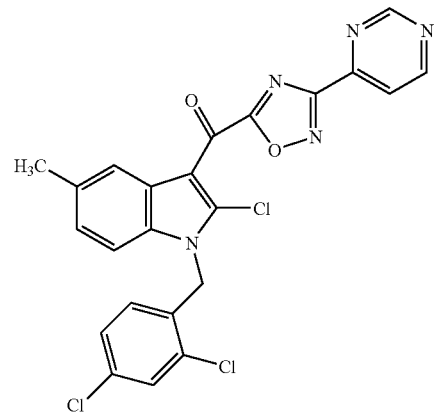

[2-chloro-1-(2,4-dichlorobenzyl)-5-methoxy-1H-indol-3-yl](3-pyrimidin-4-yl-1,2,4-oxadiazol-5-yl)methanone

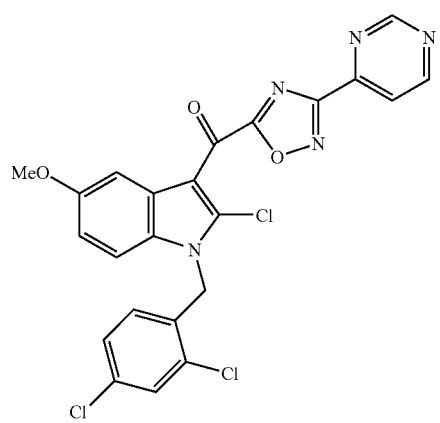

[2-chloro-1-(2,4-dichlorobenzyl)-1H-indol-3-yl](3-pyrazin-2-yl-1,2,4-oxadiazol-5-yl)methanone

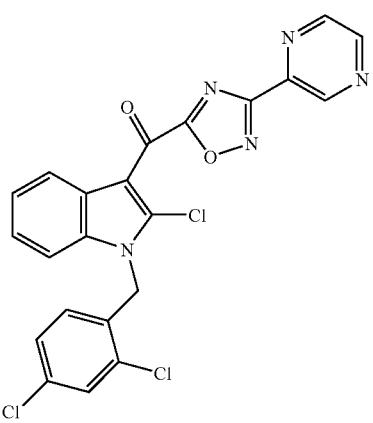

271

[2-chloro-1-(2,4-dichlorobenzyl)-5-methyl-1H-indol-3-yl](3-pyrazin-2-yl-1,2,4-oxadiazol-5-yl)methanone

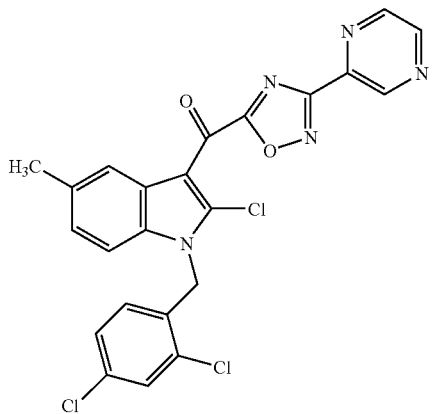

[2-chloro-1-(2,4-dichlorobenzyl)-5-methoxy-1H-indol-3-yl](3-pyrazin-2-yl-1,2,4-oxadiazol-5-yl) methanone

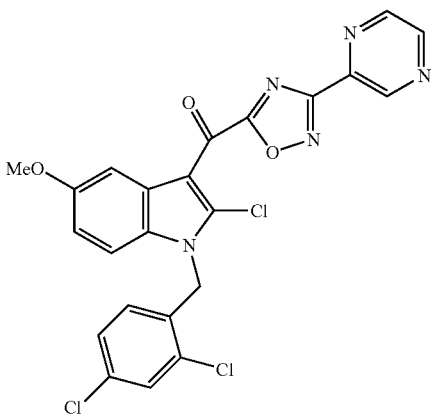

[2-chloro-1-(2,4-dichlorobenzyl)-1H-indol-3-yl](3-pyrimidin-2-yl-1,2,4-oxadiazol-5-yl)methanone

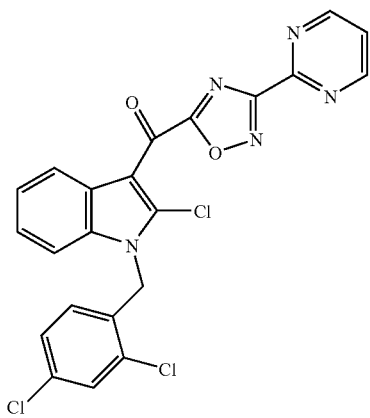

272

[2-chloro-1-(2,4-dichlorobenzyl)-5-methyl-1H-indol-3-yl](3-pyrimidin-2-yl-1,2,4-oxadiazol-5-yl) methanone

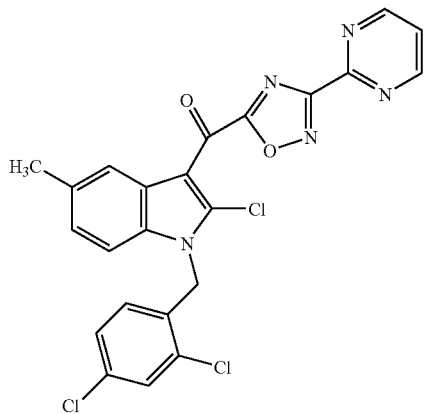

[2-chloro-1-(2,4-dichlorobenzyl)-5-methoxy-1H-indol-3-yl](3-pyrimidin-2-yl-1,2,4-oxadiazol-5-yl) methanone

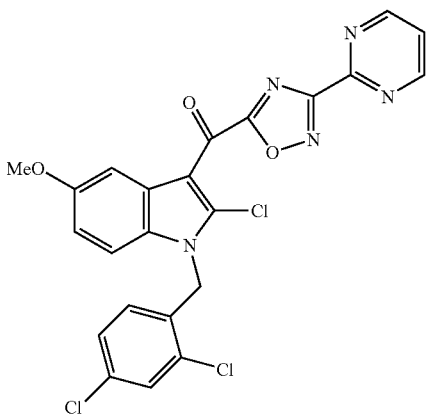

[2-chloro-1-(2,4-dichlorobenzyl)-1H-indol-3-yl](3-pyridazin-3-yl-1,2,4-oxadiazol-5-yl)methanone

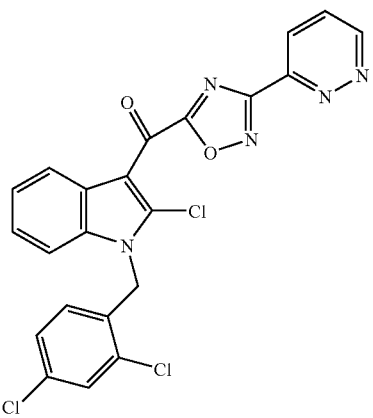

273

[2-chloro-1-(2,4-dichlorobenzyl)-5-methyl-1H-indol-3-yl](3-pyridazin-3-yl-1,2,4-oxadiazol-5-yl)methanone

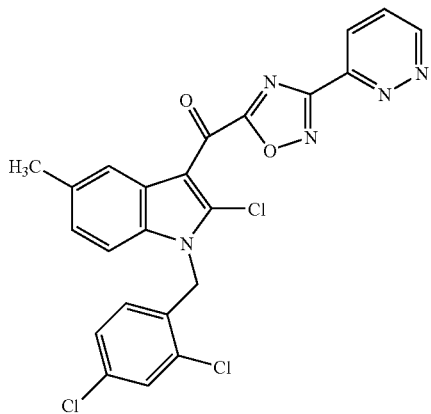

[2-chloro-1-(2,4-dichlorobenzyl)-5-methoxy-1H-indol-3-yl](3-pyridazin-3-yl-1,2,4-oxadiazol-5-yl)methanone

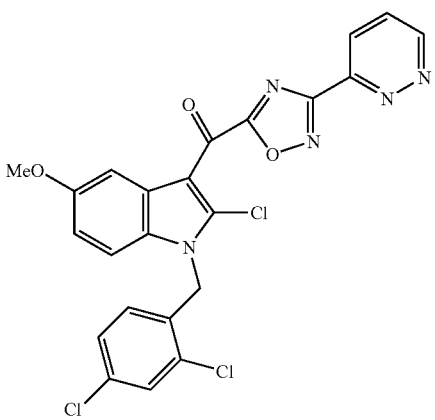

[2-chloro-1-(2,4-dichlorobenzyl)-1H-indol-3-yl](3-pyridazin-4-yl-1,2,4-oxadiazol-5-yl)methanone

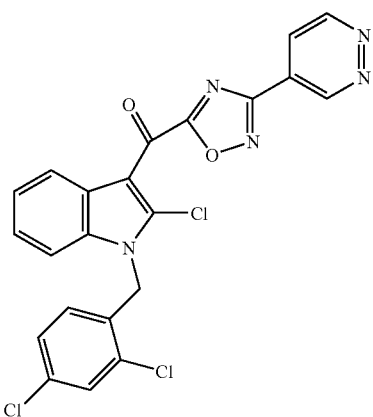

274

[2-chloro-1-(2,4-dichlorobenzyl)-5-methyl-1H-indol-3-yl](3-pyridazin-4-yl-1,2,4-oxadiazol-5-yl)methanone

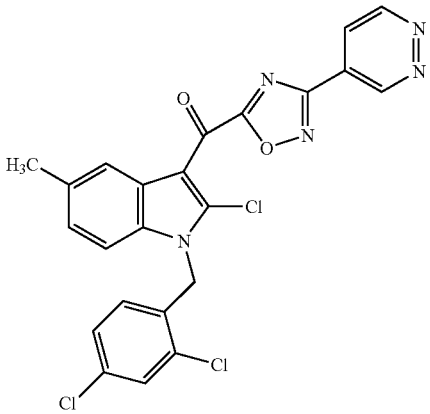

[2-chloro-1-(2,4-dichlorobenzyl)-5-methoxy-1H-indol-3-yl](3-pyridazin-4-yl-1,2,4-oxadiazol-5-yl)methanone

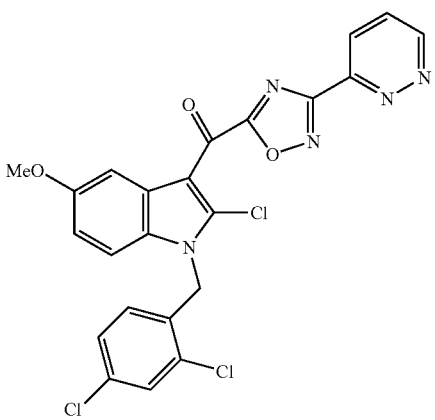

CRTH2 Inhibitors

[2-methyl-1-(3-trifluoromethoxybenzyl)indolizin-3-yl]acetic acid

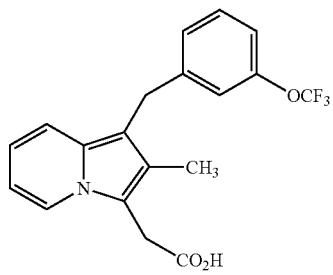

275

[2-chloro-5-methoxy-1-(3-trifluoromethoxylbenzyl)-1H-indol-3-yl]acetic acid

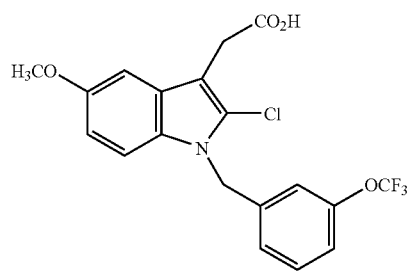

[7-chloro-2-methyl-1-(3-trifluoromethoxylbenzyl)-1H-indol-3-yl]acetic acid

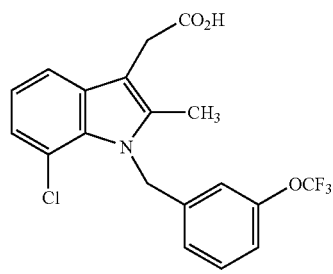

[2,7-dichloro-1-(3-trifluoromethoxylbenzyl)-1H-indol-3-yl]acetic acid

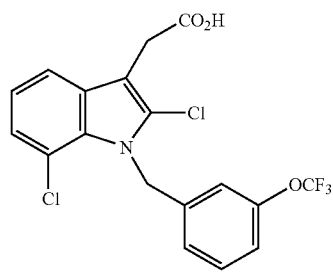

[2,5,6-trichloro-3-(3-trifluoromethoxylbenzyl)-1H-indol-3-yl]acetic acid

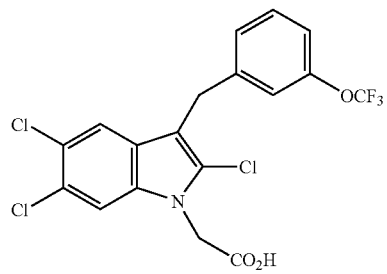

276

[2,5,6-trichloro-1-(3-trifluoromethoxylbenzyl)-1H-indol-3-yl]acetic acid

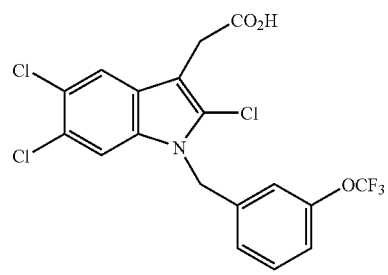

[2,6-dichloro-3-(3-trifluoromethoxylbenzy)-1H-indol-1-yl]acetic acid

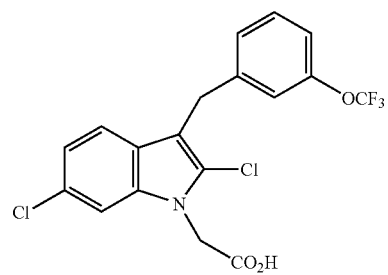

[2,5-dichloro-3-(3-trifluoromethoxylbenzy)-1H-indol-1-yl]acetic acid

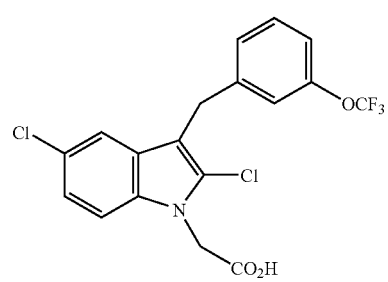

[2,6-dichloro-1-(3-trifluoromethoxylbenzy)-1H-indol-3-yl]acetic acid

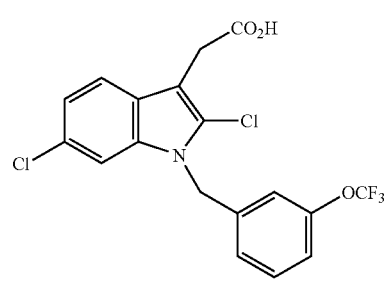

[2,5-dichloro-1-(3-trifluoromethoxylbenzy)-1H-indol-3-yl]acetic acid

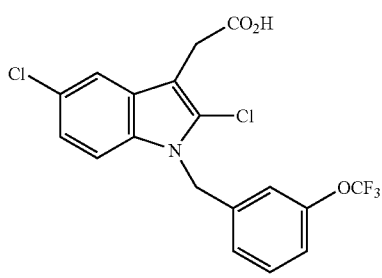

(2E)-3-[2,6-dichloro-1-(3-trifluoromethoxylbenzy)-1H-indol-3-yl]acrylic acid

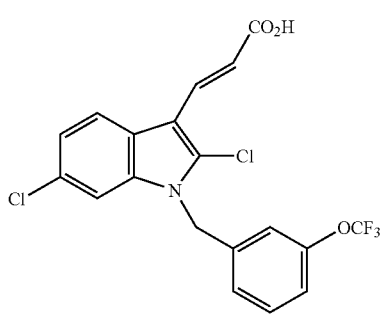

(2E)-3-[2,5,6-trichloro-1-(3-trifluoromethoxylbenzy)-1H-indol-3-yl]acrylic acid

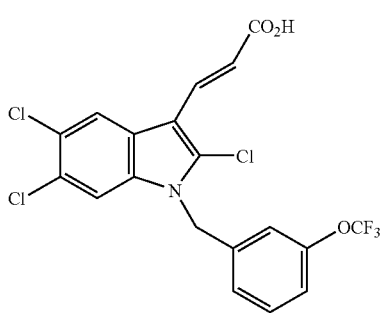

(2E)-3-[6-chloro-2-methyl-1-(3-trifluoromethoxylbenzy)-1H-indol-3-yl]acrylic acid

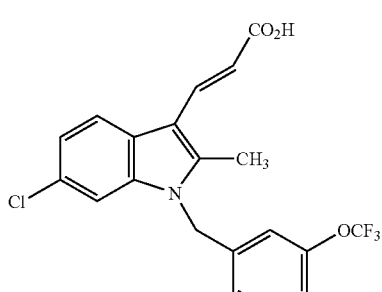

Synthetic Methods

General synthetic methods for the preparation of compounds described herein include:

Section 1.

General synthetic methods for the preparation of compounds described above:

Scheme 1.

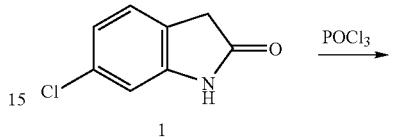

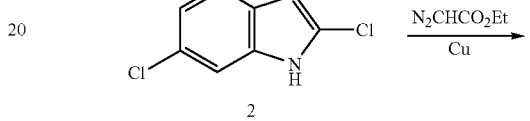

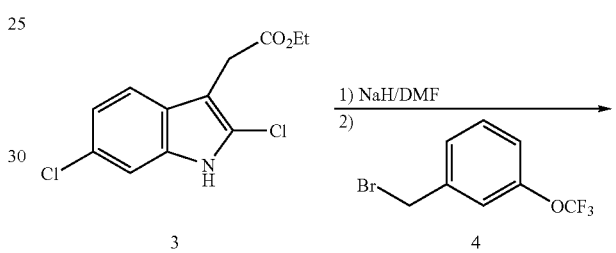

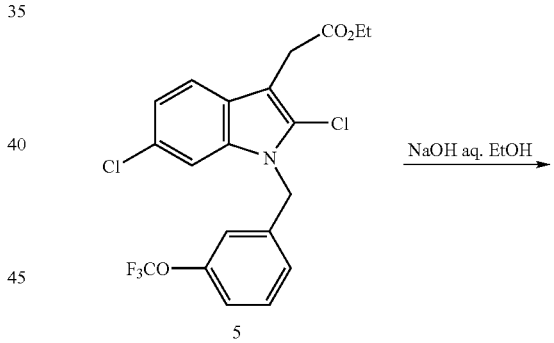

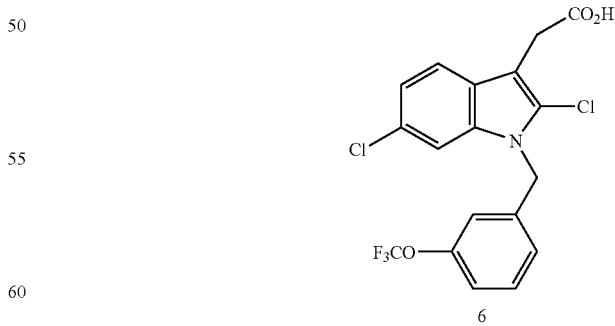

Jackson R. W.; Manske, R. H. *Can. J. Research* 1935, 13, 170-174. Wenkert, E.; Alonso, M. E.; Gottlieb, H. E.; Sanchez, E. L.; Pellicciari, R.; Cogolli, P. *J. Org. Chem.* 1977, 42, 3945-3949.

Scheme 2.

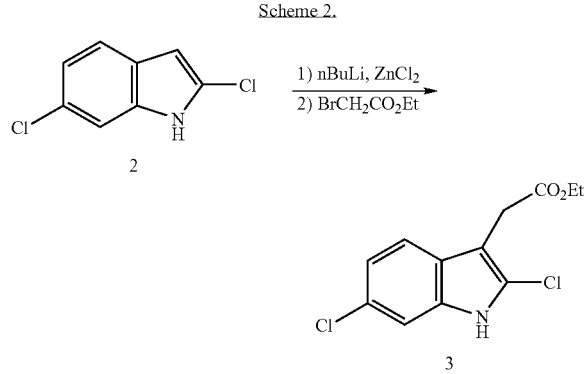

Dillard, R. D.; Bach, N. J.; Draheim, S. E.; Berry, D. R.; Carlson, D. G.; Chirgadze, N. Y.; Clawson, D. K.; Hartley, L. W.; Johnson, L. M.; Jones, N. D.; McKinney, E. R.; Mihelich, E. D.; Olkowski, J. L.; Schevitz, R. W.; Smith, A. C.; Snyder D. W.; Sommers, C. D.; Wery, J. P. *J. Med. Chem.* 1996, 39, 5119-5136.

Scheme 3.

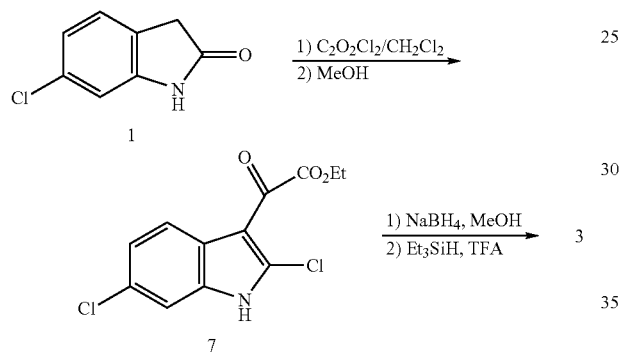

Collot, V.; Schmitt, M.; Marwah, P.; Bourguignon, J. J. *Heterocycles* 1999, 51, 2823-2847.

Scheme 4.

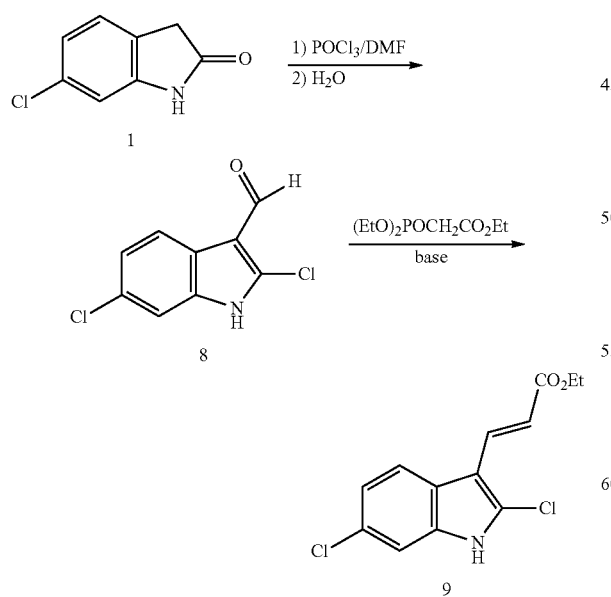

Padras, M. S. C.; Jha, M. *J. Org. Chem.* 2005, 70, 1828-1834

Scheme 5.

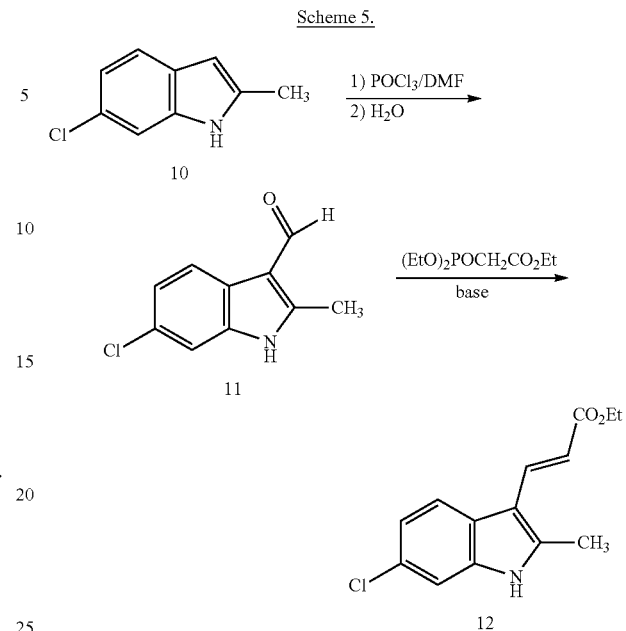

Mahboobi, S.; Eibler, E.; Koller, M.; Kunar, S.; Popp, A. *J. Org. Chem.* 1999, 64, 4697-4704.

Scheme 6.

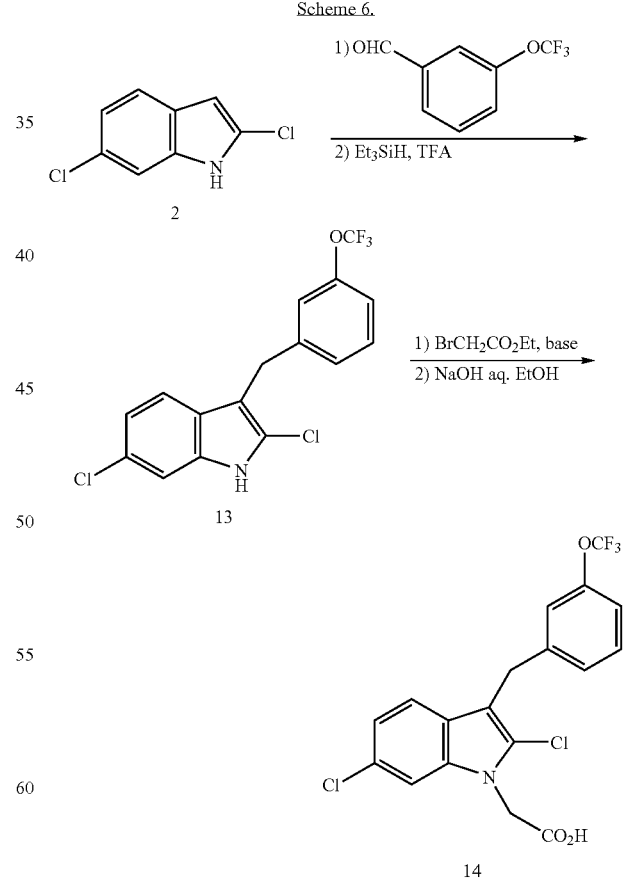

Appleton, J. E.; Dack, K. N.; Green A. D.; Steele, J. *Tetrahedron Lett.* 1993, 34 1529-1532.

Scheme 7.
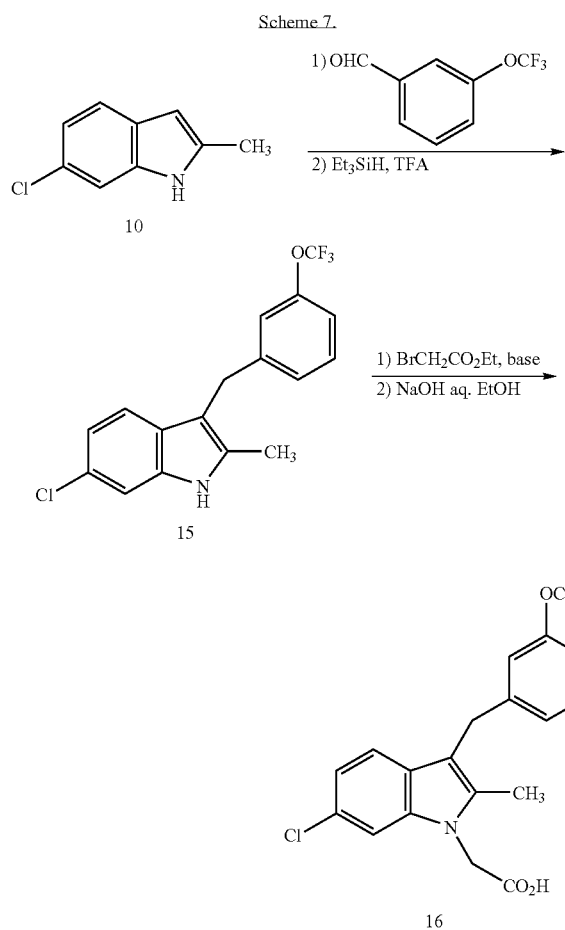
Appleton, J. E.; Dack, K. N.; Green, A. D.; Steele, J. *Tetrahedron Lett.* 1993, 34, 1529-1532.
Scheme 8.
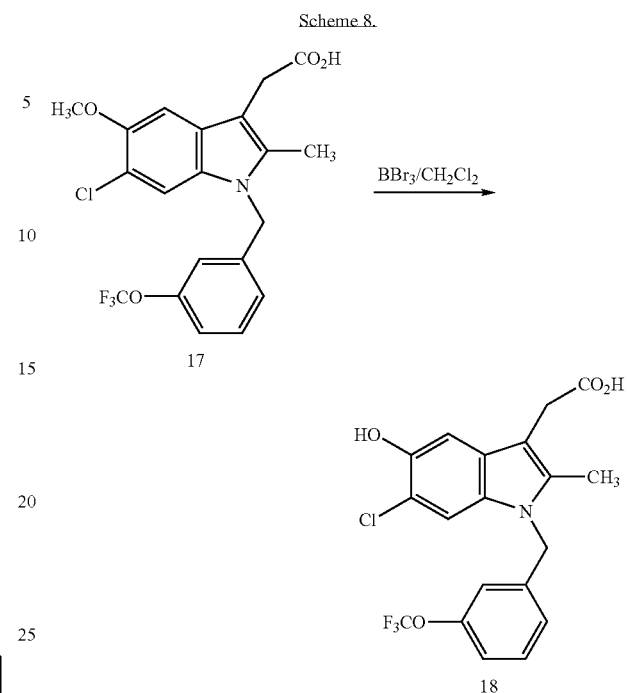
Demuynck, M.; DeClercq, P.; Vanderwalle, M. *J. Org. Chem.* 1979, 44, 4863-4866. Grieco, P. A.; Nishizawa, M.; Oguri, T.; Burke, S. D.; Marinovic, N. *J. Am. Chem. Soc.* 1977, 99, 5773-5780.
Section 2
Preparation of {1-[(5-chlorothien-2-yl)carbonyl]-6-fluoro-5-hydroxy-2-methyl-1H-indol-3-yl}acetic acid
The preparation of this compound can be achieved as follows.
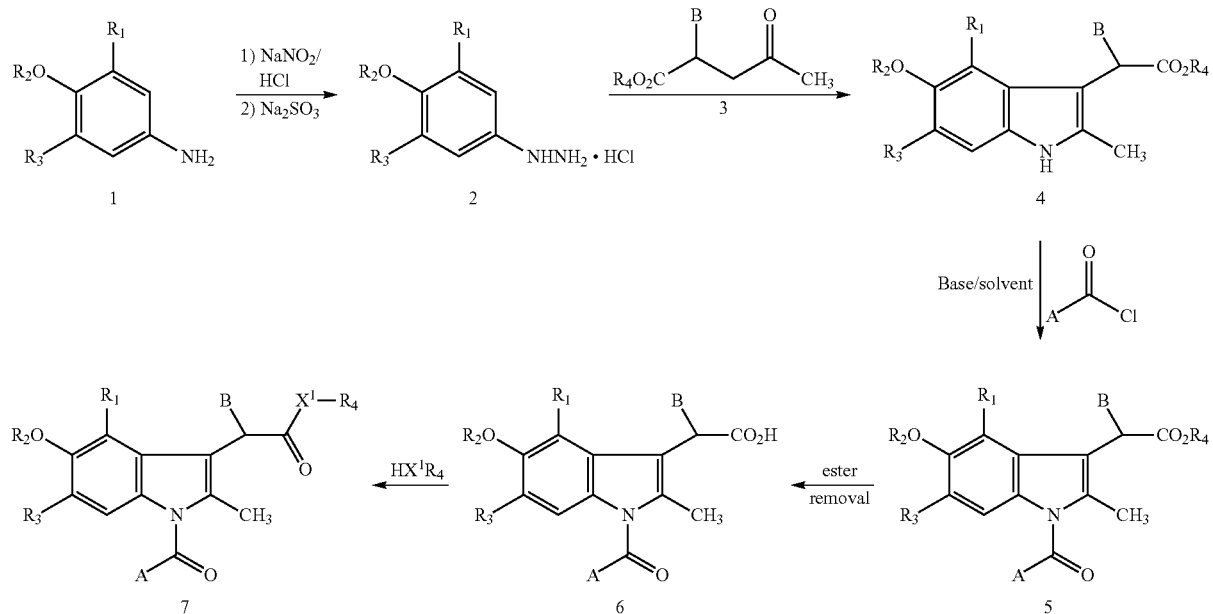

Step 1. Preparation of (3-fluoro-4-methoxyphenyl)hydrazine (2, $R_1$=H, $R_2$=CH$_3$, $R_3$=F)

3-Fluoro-4-methoxyaniline (1, $R_1$=H, $R_2$=CH$_3$, $R_3$=F) (95 g, 0.67 mol) was added to concentrated hydrochloric acid (250 mL), the suspension was stirred at ambient temperature for 18 hours, then it was cooled to 0° C. and a solution of sodium nitrite (53.7 g, 0.78 mol) in water (200 mL) was added dropwise at 0-5° C. When the addition was complete, the resulting solution was stirred at 0° C. for 1 hour then it was added dropwise at 0-5° C. to a stirred solution of tin (II) chloride dihydrate (638.9 g, 2.83 mol) in concentrated hydrochloric acid (500 mL). The mixture was allowed to warm to ambient temperature then it was stored at 4° C. for 18 hours. The resulting precipitate was collected by filtration, washed with water (400 mL), and ether (1000 mL) and dried in vacuo. The solid hydrochloride salt was basified by addition to 10% aqueous sodium hydroxide solution (800 mL), the free base was extracted into ether (2×400 mL), and the combined extracts were dried (MgSO$_4$) and the solvent removed in vacuo to give (3-fluoro-4-methoxyphenyl)hydrazine (2, $R_1$=H, $R_2$=CH$_3$, $R_3$=F) (51.9 g, 50%) as a yellow solid, mp 46-50° C; $^1$HNMR (CDCl$_3$/250 MHz); 1.5 (s, 1H, NH—NH$_2$), 3.85 (s, 3H, OCH$_3$), 5.0 (s, 2H, NH—NH$_2$), 6.44 (m, 1H, phenyl 6-H), 6.60 (dd, 1H, phenyl 5-H), 6.79 (t, 1H, phenyl 2-H).

Step 2A. Preparation of (6-fluoro-5-methoxy-2-methyl-1H-indol-3-yl)acetic acid (4, $R_1$=H, $R_2$=CH$_3$, $R_3$=F, $R_4$=B=H) and (4-fluoro-5-methoxy-2-methyl-1H-indol-3-yl)acetic acid (4, $R_1$=F, $R_2$=CH$_3$, $R_3$=H, $R_4$=B=H)

Levulinic acid (3, B=$R_4$=H) (38 mL, 354 mmol) and 3-fluoro-6-methoxyphenylhydrazine hydrochloride (2, $R_1$=H, $R_2$=CH$_3$, $R_3$=F) (67.5 g, 350 mmol) were combined and 150 mL of glacial acetic acid added and the slurry was stirred at 80° C. for 4 hours. The reaction was cooled to room temperature and added to ice water (500 mL). The resulting aqueous solution was extracted with dichloromethane (3×500 mL) and the organics dried (MgSO$_4$) and concentrated to afford a thick semi-solid. Water (450-500 mL) was added and the slurry was stirred vigorously overnight while manually breaking up large solid pieces with a spatula. The fine tan solid that resulted was isolated by filtration and dried to afford a mixture of indoles 56.3 grams, 67% yield, ~93% pure by HPLC (7/1 ratio of (6-fluoro-5-methoxy-2-methyl-1H-indol-3-yl)acetic acid (4, $R_1$=H, $R_2$=CH$_3$, $R_3$=F, $R_4$=B=H) and (4-fluoro-5-methoxy-2-methyl-1H-indol-3-yl)acetic acid (4, $R_1$=F, $R_2$=CH$_3$, $R_3$=H, $R_4$=B=H) of by NMR). Major isomer $^1$H-NMR (CDCl$_3$/300 MHz) 2.27 (s, 3H), 3.82 (s, 2H), 3.84 (s, 3H), 6.92-6.97 (m, 2H, ArH).

Step 2B. Preparation of 2-trimethylsilylethyl(6-fluoro-5-methoxy-2-methyl-1H-indol-3-yl)acetate (4, $R_1$=B=H, $R_2$=CH$_3$, $R_3$=F, $R_4$=CH$_2$CH$_2$Si(CH$_3$)$_3$)

The indoles from Step 2A (56.3 g, 238 mmol) were combined with 2-trimethylsilylethanol (41 mL, 1.25 eq.) and 4-(dimethylamino)pyridine (DMAP) (4 g) in dichloromethane (600 mL) and cooled to 0° C. 1-[3-(Dimethylamino)propyl)]-3-ethylcarbodiimide hydrochloride (EDCl) (50.2 g, 1.1 eq.) was added in portions and the reaction was stirred for 30 minutes at 0° C. and then allowed to warm to room temperature and stir overnight. The reaction mixture was diluted with dichloromethane (600 mL) and washed with water (2×200 mL), dried and concentrated to give a thick orange syrup which after triturating with hexanes induced solid formation, the solid was recrystallized from hexane-ethyl acetate to afford tan needles of 2-trimethylsilylethyl (6-fluoro-5-methoxy-2-methyl-1H-indol-3-yl)acetate (4, $R_1$=H=B, $R_2$=CH$_3$, $R_3$=F, $R_4$=CH$_2$CH$_2$Si(CH$_3$)$_3$), 52 g, 65% yield, >98% pure; $^1$H-NMR (CDCl$_3$/300 MHz) 0.16 (s, 9H), 0.98 (m, 2H), 2.37 (s, 3H), 3.61 (s, 2H), 3.93 (s, 3H), 4.12 (m, 2H), 7.00-7.05 (m, 2H, ArH). The other regioisomer, 2-trimethylsilylethyl (4-fluoro-5-methoxy-2-methyl-1H-indol-3-yl)acetate (4, $R_1$=F, $R_3$=B=H, $R_2$=CH$_3$, $R_4$=CH$_2$CH$_2$Si(CH$_3$)$_3$), may be isolated by concentration of the filtrate and purification by chromatography on silica gel.

Step 3. Preparation of 2-trimethylsilylethyl-{1-[(5-chlorothien-2-yl)carbonyl]-6-fluoro-5-methoxy-2-methyl-1H-indol-3-yl}acetate (5, $R_1$=H=B, $R_2$=CH$_3$, $R_3$=F, $R_4$=CH$_2$CH$_2$Si(CH$_3$)$_3$, A=5-chlorothiophene)

In a dry flask 2-trimethylsilylethyl (6-fluoro-5-methoxy-2-methyl-1H-indol-3-yl)acetate (4, $R_1$=H=B, $R_2$=CH$_3$, $R_3$=F, $R_4$=CH$_2$CH$_2$Si(CH$_3$)$_3$), (1.0 g, 2.96 mmol) was dissolved in tetrahydrofuran (THF) (10 mL) and hexamethylphosphoramide (HMPA) (1 mL) and cooled to −78° C. Potassium bis(trimethylsilyl)amide 0.5M in toluene (6.52 mL) was added and the reaction was stirred for 30 minutes. 5-Chlorothiophene-2-carbonyl chloride (562 mg, 3.1 mmol) in 3 mL of THF was added and the reaction was stirred for 0.5 hours at −78° C. and 0.5 hours at 0° C., and then treated with saturated ammonium chloride (20 mL) and the reaction extracted with ethyl acetate (3×30 mL), dried over MgSO$_4$ and concentrated to give a thick oil which was purified by chromatography to afford 2-trimethylsilylethyl-{1-[(5-chlorothien-2-yl)carbonyl]-6-fluoro-5-methoxy-2-methyl-1H-indol-3-yl}acetate (5, $R_1$=H=B, $R_2$=CH$_3$, $R_3$=F, $R_4$=CH$_2$CH$_2$Si(CH$_3$)$_3$, A=5-chlorothiophene). (600 mg, 1.24 mmol, 42%, >99% pure) as light yellow oil; $^1$H-NMR (CDCl$_3$/300 MHz) consistent with the assigned structure.

Step 4. Preparation of {1-[(5-chlorothien-2-yl)carbonyl]-6-fluoro-5-methoxy-2-methyl-1H-indol-3-yl}acetic acid (6, $R_1$=H, $R_2$=CH$_3$, $R_3$=F, $R_4$=H, A=5-chlorothiophene)

A solution of the product from Step 3, 2-trimethylsilylethyl-{1-[(5-chlorothien-2-yl)carbonyl]-6-fluoro-5-methoxy-2-methyl-1H-indol-3-yl}acetate 5, $R_1$=H=B, $R_2$=CH$_3$, $R_3$=F, $R_4$=CH$_2$CH$_2$Si(CH$_3$)$_3$, A=5-chlorothiophene) (600 mg, 1.24 mmol) dissolved in 8 mL of THF was treated with a solution of tetrabutylammonium fluoride (1M, 3.1 mL, 3.1 mmol) in THF. The solution was stirred at room temperature until the ester had been cleaved (ca. 1 hour), and then the solution was diluted with saturated aqueous ammonium chloride and extracted with ethyl acetate. The combined extracts were washed with brine, dried over MgSO$_4$ and concentrated to give a solid that was purified by chromatography eluting with hexanes and ethyl acetate to provide 280 mg, 59% of pure {1-[(5-chlorothien-2-yl)carbonyl]-6-fluoro-5-methoxy-2-methyl-1H-indol-3-yl}acetic acid (6, $R_1$=H, $R_2$=CH$_3$, $R_3$=F, $R_4$=H, A=5-chlorothiophene), mp 169° C.

$^1$H NMR (CDCl$_3$/300 MHz) 7.35 (d, 1H, J=4.0 Hz), 7.09 (d, 1H, J=11.7 Hz), 7.00 (d, 1H, J=7.2 Hz), 6.98 (d, 1H, J=4.0 Hz) 3.93 (s, 3H), 3.70 (s, 2H), 2.42 (s, 3H).

Step 5. Preparation of {1-[(5-chlorothien-2-yl)carbonyl]-6-fluoro-5-hydroxy-2-methyl-1H-indol-3-yl}acetic acid (6, $R_1$=H=B, $R_2$=H, $R_3$=F, A=5-chlorothiophene The product from Step 3, 2-trimethylsilylethyl-{1-[(5-chlorothien-2-yl)carbonyl]-6-fluoro-5-methoxy-2-methyl-1H-indol-3-yl}acetate 5, $R_1$=H=B, $R_2$=CH$_3$, $R_3$=F, $R_4$=CH$_2$CH$_2$Si(CH$_3$)$_3$, A=5-chlorothiophene) (400 mg, 0.83 mmol) was dissolved in 10 mL of dry dichloromethane and cooled to −78° C. The solution was then treated with boron tribromide (1M, 4.9 mL, 4.9 mmol) in dichloromethane and the solution allowed to warm to room temperature and stirred at that temperature for an additional 2 hours. The solution was then poured into water and the phases separated and the aqueous phase extracted with dichloromethane. The combined extracts were washed with brine, dried over MgSO$_4$ and concentrated to give a solid that was purified by chromatography eluting with methanol and dichloromethane to provide 150 mg, 40%, of pure {1-[(5-chlorothien-2-yl)carbonyl]-6-fluoro-5-hydroxy-2-methyl-1H-indol-3-yl}acetic acid (6, $R_1$=H=B, $R_2$=H, $R_3$=F, A=5-chlorothiophene) mp 174° C., $^1$H NMR (CDCl$_3$/300 MHz) 7.34 (d, 1H, J=3.9 Hz), 7.13 (d, 1H, J=11.1 Hz), 7.07 (d, 1H, J=8.4 Hz), 6.98 (d, 1H, J=3.9 Hz), 3.66 (s, 2H), 2.39 (s, 3H).

Section 3

General Synthesis Scheme 1

Certain useful compounds may be prepared by the general method outlined in below.

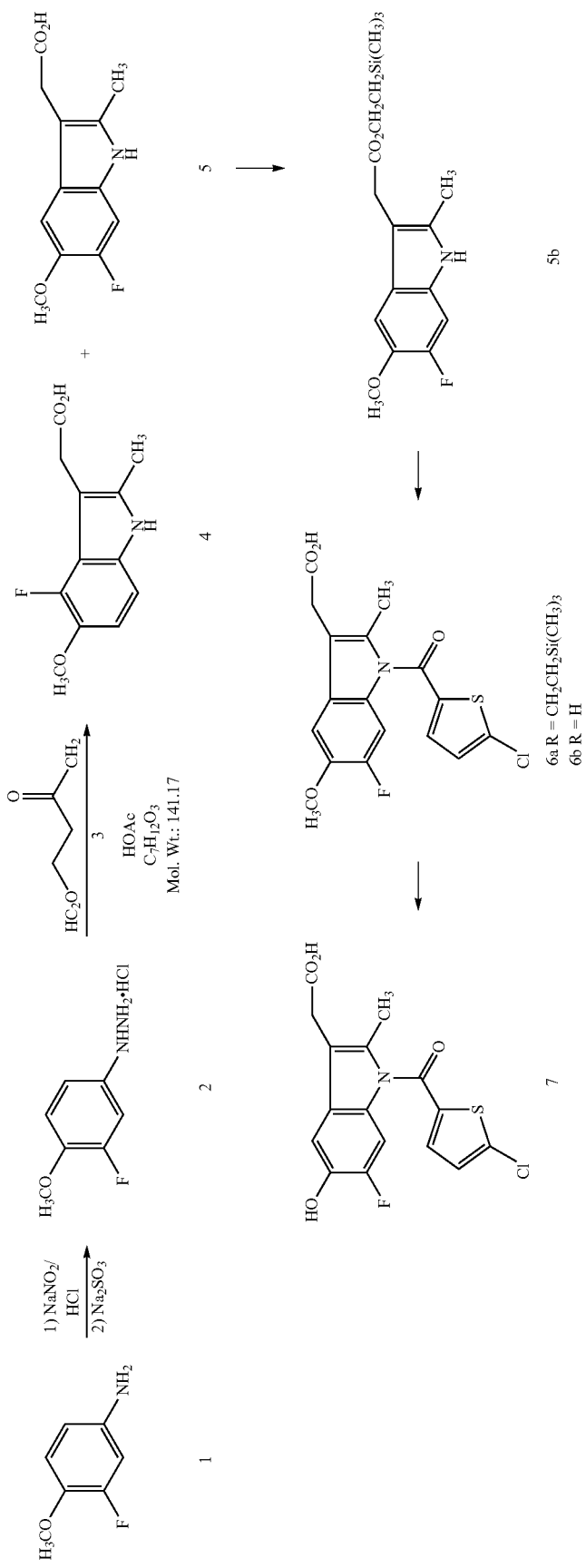

Step 1. Preparation of phenylhydrazines, representative example: (3-fluoro-4-methoxyphenyl)hydrazine (2)

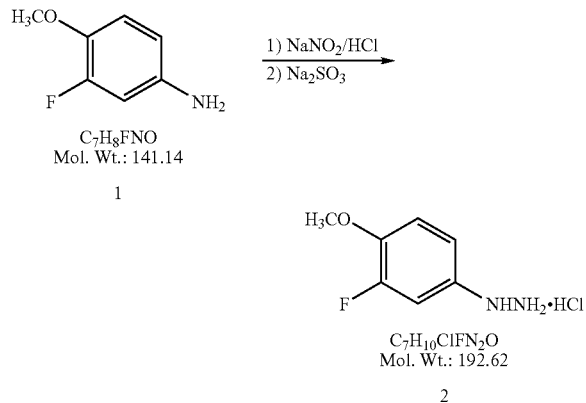

The preparation of phenylhydrazine derivatives (2) begins with treatment of commercially available anilines (1) with nitrous acid, generated from sodium nitrite and concentrated hydrochloric acid, to produce the corresponding diazonium salt. In the same reaction vessel the diazonium salt is treated with sodium sulfite and hydrochloric acid to produce the desired hydrazine hydrochloride (2) in 90% yield. Alternatively, the diazonium salt can be reduced with stannous chloride in hydrochloric acid.

Step 2. Preparation of indoles by the Fisher Indole synthesis, representative example: (6-fluoro-5-methoxy-2-methyl-1H-indol-3-yl)acetic acid (5)

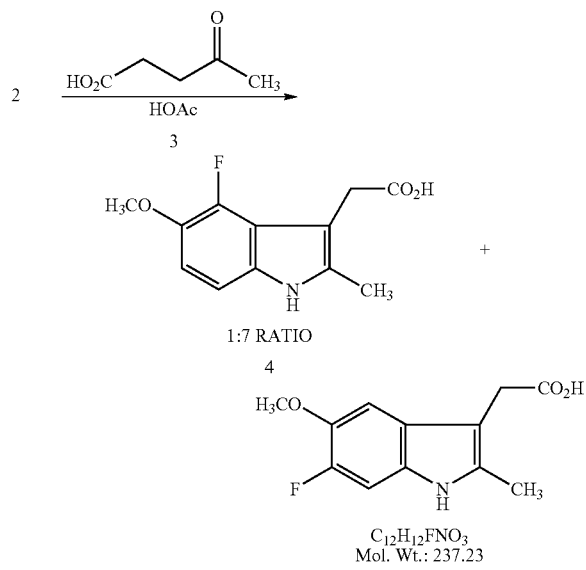

Condensation of hydrazine hydrochloride (2) with levulinic acid (3) in acetic acid results in the formation of two regioisomeric indole derivatives 4 and 5 in a 1:7 ratio. The major regioisomer 5 can be isolated in pure form by crystallization of the reaction mixture. Alternatively, the indole mixture can be esterified with an alcohol such as 2-trimethylsilylethanol to afford the corresponding esters that can then be separated by a number of means, for example by chromatography.

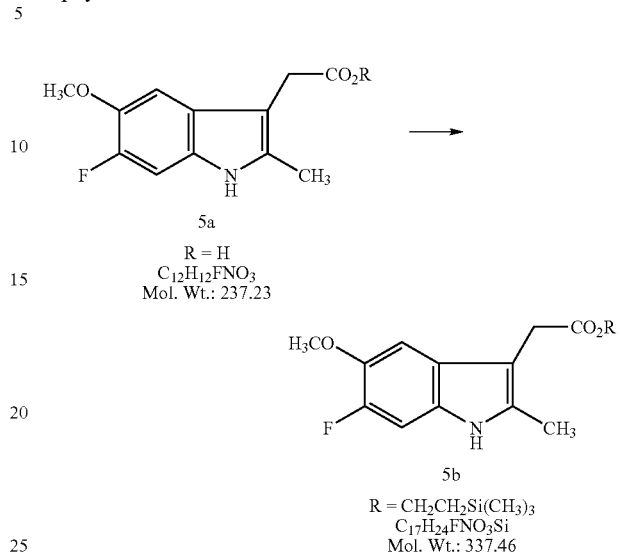

Step 3. Acylation of indole 5b: preparation of 2-trimethylsilylethyl-{1-[(5-chlorothien-2-yl)carbonyl]-6-fluoro-5-methoxy-2-methyl-1H-indol-3-yl}acetate (6b)

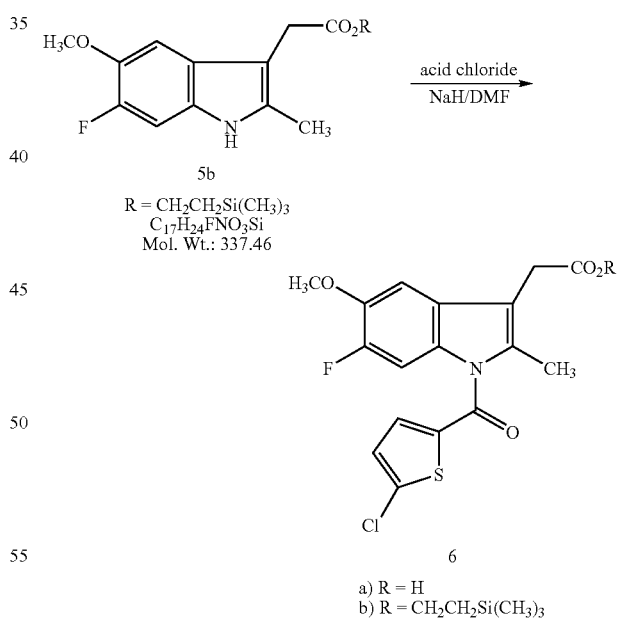

Treatment of the indole ester 5b with sodium hydride in dimethylformamide (DMF) followed by treatment with an acid chloride such as 5-chlorothiophene-2-carbonyl chloride affords the acylated indole derivative 6b in 82% yield. The ester can then be removed by treatment with an acid such as trifluoroacetic acid to produce the corresponding acid, in this instance 6a.

Step 4. Preparation of 5-hydroxy indole derivates: preparation of {1-[(5-chlorothien-2-yl)carbonyl]-6-fluoro-5-methoxy-2-methyl-1H-indol-3-yl}acetic acid General Synthesis Scheme 2

Certain compounds can be prepared according to general synthesis scheme 2 as follows.

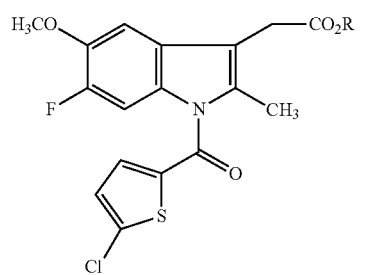

6 a) R = H
b) R = CH₂CH₂Si(CH₃)₃

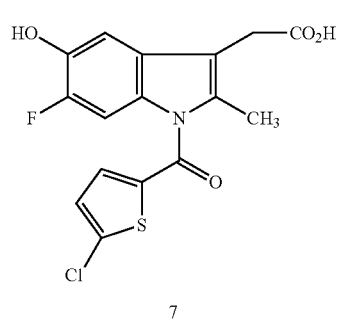

7

Esters such as 6b upon treatment with excess boron tribromide in dichloromethane can be converted to the corresponding acid phenols, such as 7 in good yield. Under these reaction conditions both the ester and the 5-methoxy moieties are dealkylated to the acid and phenol respectively. If desired the carboxylic acids can be converted to their salt derivatives by treatment with a base such as sodium hydroxide.

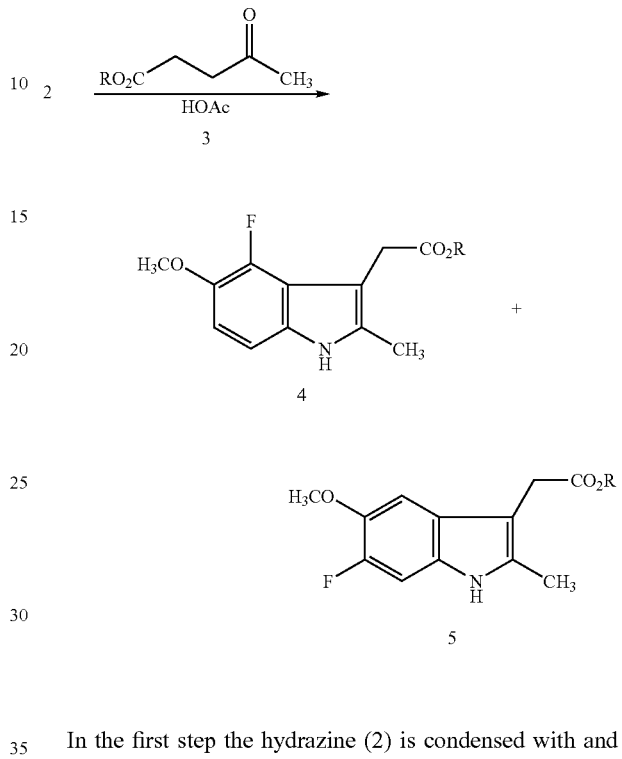

In the first step the hydrazine (2) is condensed with and ester of levulinic acid in acetic acid to afford a mixture of regioisomeric indole esters 4 and 5 (for example if one uses ethyl levulinate (3, R=Et the products (4 and 5) will be the ethyl esters, R=Et). The esters can be separated and then acylated by the procedure outline in Scheme 1 to afford the corresponding acyl derivatives such as 6, R=Et in the present example. Hydrolysis of the ester afffords the corresponding acid, 6a. If desired, the ester and the 5-methoxy groups can be removed in a single operation upon treatment with boron tribromide in dichloromethane to give phenols such as 7.

General Synthesis Scheme 3

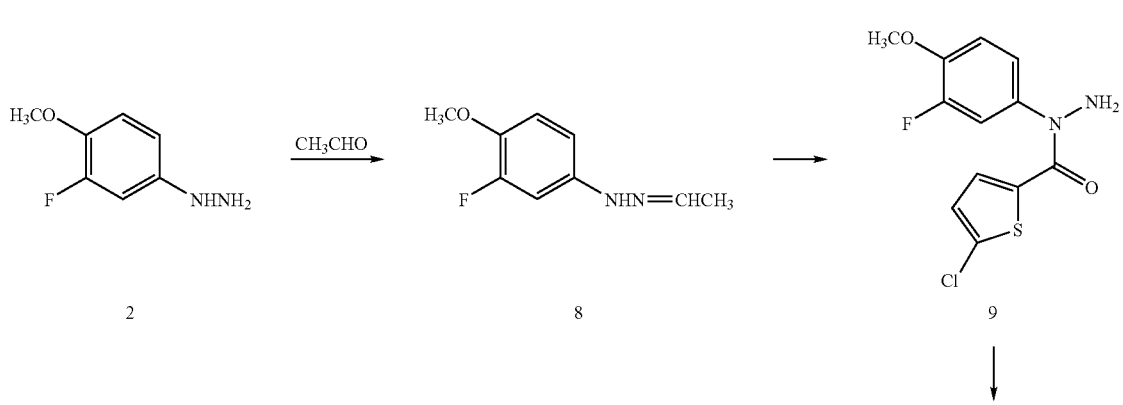

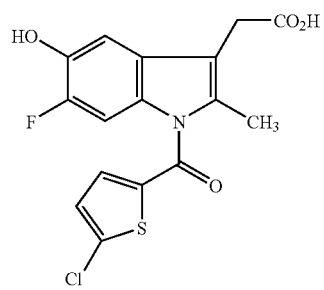

7

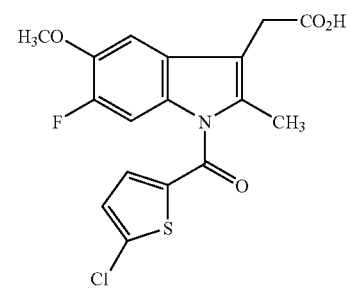

6

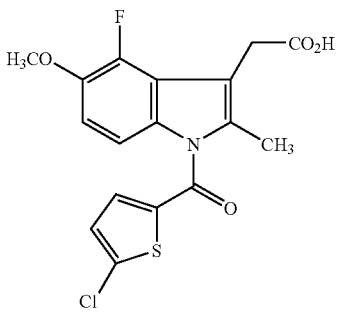

10

The route commences with the condensation of phenylhydrazine derivates such as 2 with acetaldehyde to afford the corresponding hydrazone 8. Acylation of 8 with an acid chloride, in the present example 5-chlorothiophene-2-carbonyl chloride, followed by treatment with gaseous hydrochloric acid in an alcohol such as methanol provides the desired acylated hydrazine 9 after neutralization of the excess acid. Condensation of 9 with levulinic acid provides a mixture of regioisomers that can then be separated to afford acylated indoles, in the present example, 6 and 10. If desired, the 5-methoxy group can then be converted to the corresponding 5-hydroxy substituent by treatment with boron tribromide in dichloromethane for example to prepare 7.

General Synthesis Scheme 4

Certain compounds can be prepared according to general synthesis scheme 4 as follows.

nol in the presence of a dehydrating agent such as dicyclohexylcarbodiimide, with a strong base such as potassium bis(trimethylsilyl)amide in tetrahydrofuran generates the indole anion that can be condensed with a sulfonyl chloride to afford the N-sulfonyl derivatives such as 12. In the present example 4-chlorobenzenesulfonyl chloride was used the sulfonyl chloride. In the second step the N-sulfonyl indole 12 is converted in the corresponding indole acid 13 upon treatment with tetrabutylammonium fluoride in tetrahydrofuran. If desired, the 5-methoxy substituent can be converted to the corresponding 5-hydroxy group upon treatment of 13 with boron tribromide in dichloromethane.

General Synthesis Scheme 5

Certain compounds can be prepared according to general synthesis scheme 5 as follows.

Treatment of the indole ester 11, prepared from the corresponding indole acid by coupling with 2-trimethylsilyletha-

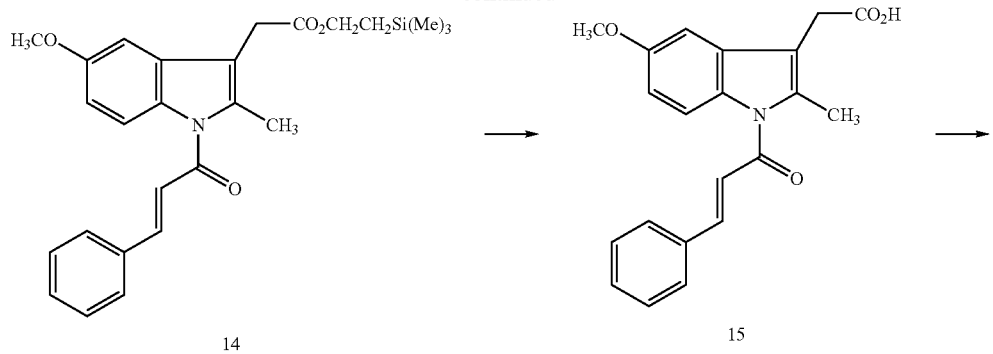

14

15

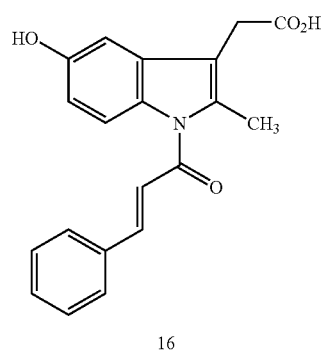

16

Treatment of the indole ester 11, prepared from the corresponding indole acid by coupling with 2-trimethylsilylethanol in the presence of a dehydrating agent such as dicyclohexylcarbodiimide, with a strong base such as potassium bis(trimethylsilyl)amide in tetrahydrofuran generates the indole anion that can be condensed with a cinnamoyl chloride to afford the N-acyl derivative 14. In the second step the N-acyl indole 14 is converted into the corresponding indole acid 15 upon treatment with tetrabutylammonium fluoride in tetrahydrofuran. If desired, the 5-methoxy substituent can be converted to the corresponding 5-hydroxy group, 16, upon treatment of 15 with boron tribromide in dichloromethane.

General Synthesis Scheme 6

Certain compounds can be prepared according to general synthesis scheme 6 as follows

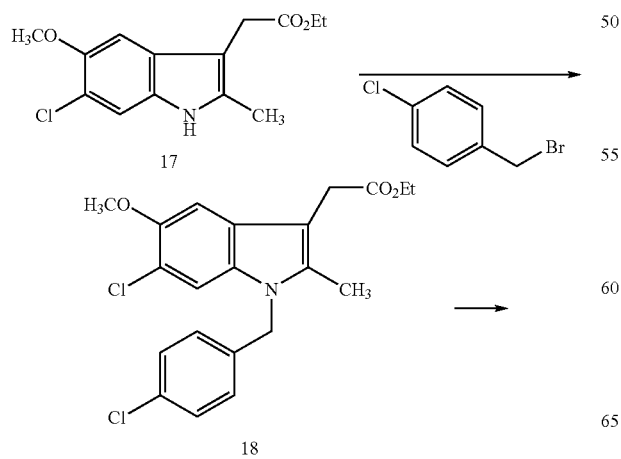

17

18

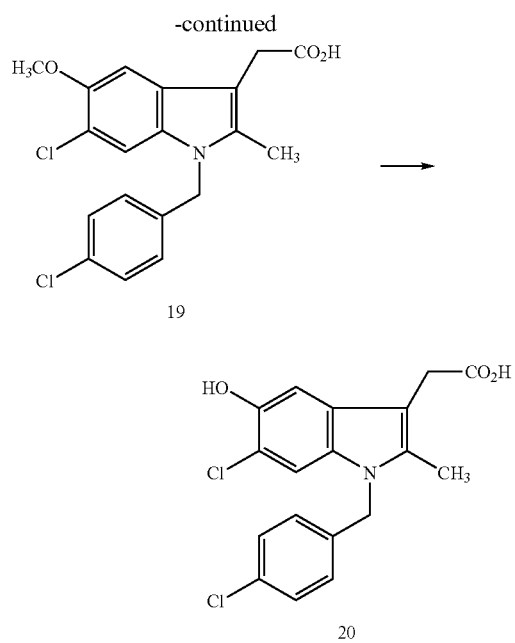

19

20

Treatment of the indole ester 17 with a strong base such as potassium bis(trimethylsilyl)amide in tetrahydrofuran generates the indole anion that can be alkylated with 4-chlorobenzyl bromide to afford the N-benzyl derivative 18. In the second step the N-benzyl indole 18 is converted into the corresponding indole acid 19 upon treatment with sodium hydroxide in aqueous tetrahydrofuran. If desired, the 5-methoxy substituent can be converted to the corresponding 5-hydroxy group, 20, upon treatment of 19 with boron tribromide in dichloromethane.

General Synthesis Scheme 7

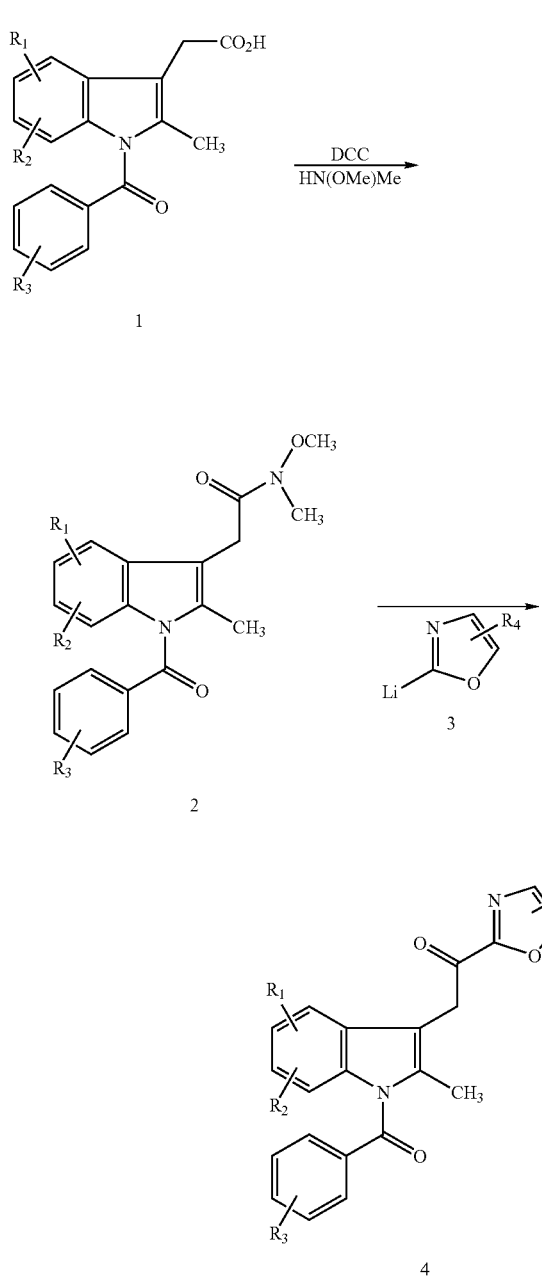

General Synthesis Scheme 8

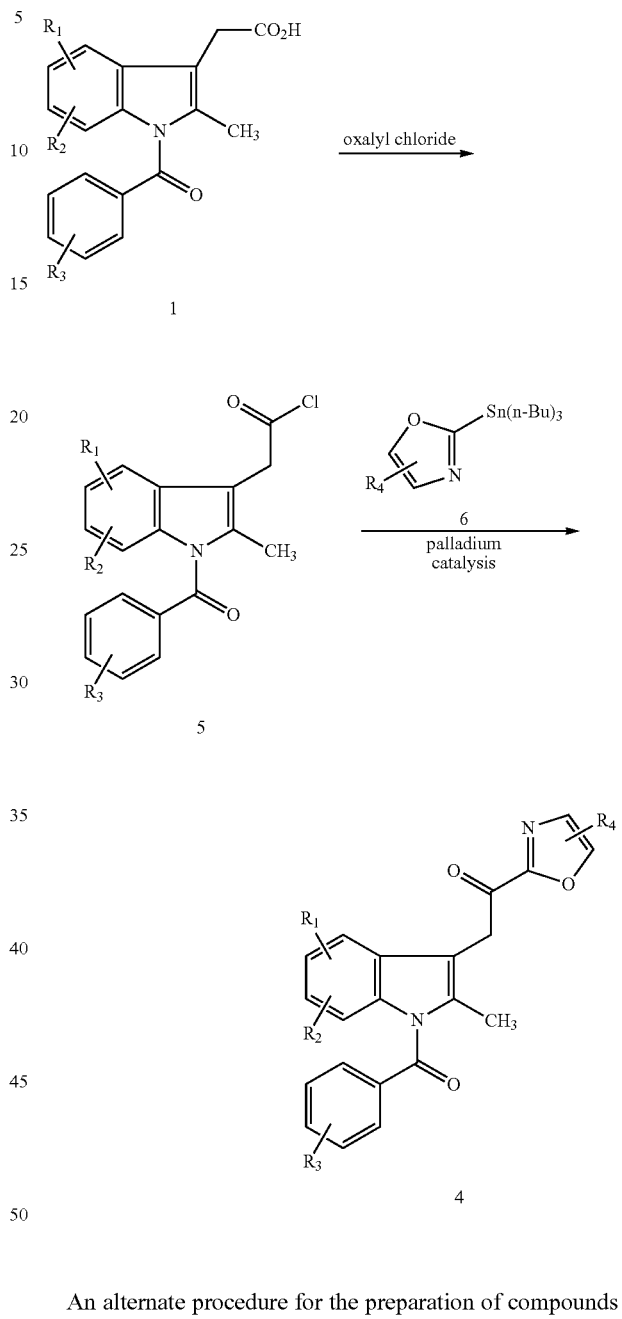

Illustrated in General Synthesis Scheme 7 is the general method for the preparation of FAAH inhibitor compounds of the general formula (4). The synthesis commences with the condensation of an indole carboxylic acid derivative 1 with N,O-dimethylhydroxylamine (generated from N,O-dimethylhydroxylamine hydrochloride with triethylamine) in the presence of a dehydrating agent such as dicyclohexylcarbodiimide (DCC) to provide the so-called Weinreb amide derivative 2. Treatment of amide 2 with the lithium derivative 3, generated by treatment of the corresponding oxazole with n-butyllithium, provides the ketooxazole derivatives of formula 4.

An alternate procedure for the preparation of compounds of the general formula 4 is illustrated in General Synthesis Scheme 8. The indole carboxylic acid derivative 1 is converted to the corresponding acid chloride 5 by treatment with oxalyl chloride or with thionyl chloride ($SOCl_2$). The acid chloride is then treated with an organostannane such as 6 in the presence of palladium catalysts to affect Stille coupling. If necessary this later reaction can be conducted under an atmosphere of carbon monoxide to suppress decarbonylation of the acid chloride during the Stille coupling. In a variation on the above scheme the organolithium derivative 3 can be converted to the corresponding organozine derivative ($ZnCl_2$) and then coupled to acid chloride 5 to produce the compounds of formula 4.

General Synthesis Scheme 9

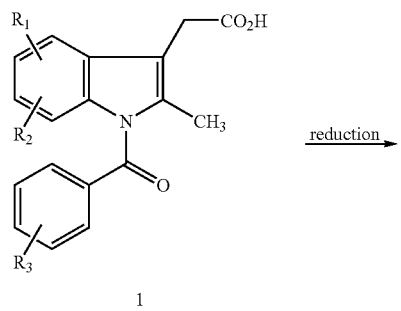

1

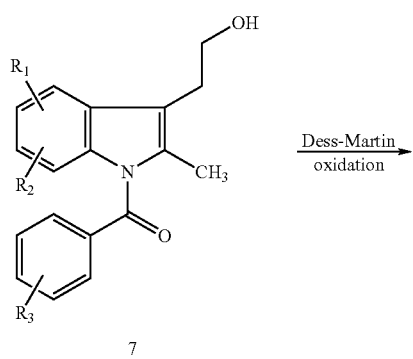

7

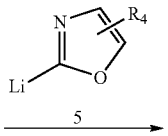

8

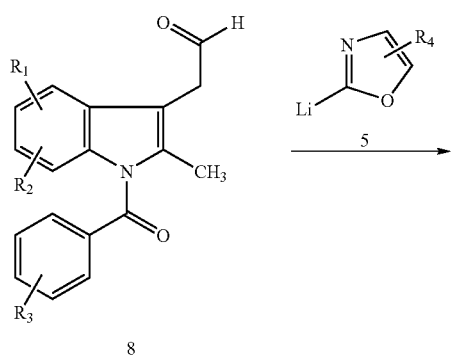

9

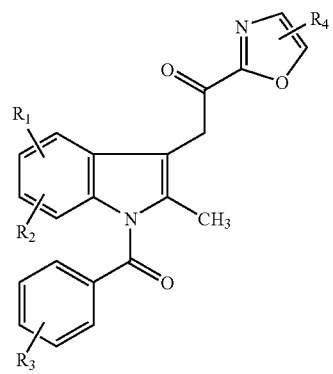

4

In certain instances it may be advantageous to use the route outlined in General Synthesis Scheme 9. This method commences with the reduction of the carboxylic acid moiety of 1 to afford the corresponding alcohol 7 and subsequent conversion to the corresponding aldehyde 8 under suitable oxidation conditions such as with the Dess-Martin periodinane reagent. The aldehyde 8 can then be treated with the organolithium reagent 5 to prepare alcohol 9, which in turn is converted into the desired ketones 4 by oxidation with the Dess-Martin periodinane reagent.

Using the same general methods outlined in General Synthesis Schemes 7, 8 and 9 it is possible to prepare a wide range of ketone derivatives by changing the nature of the organolithium, organozine or organotin derivative. The following generalized examples show how each of the desired ketones can be prepared from the appropriate starting materials.

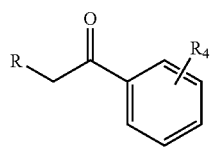

Prepared from the appropriate phenyllithium derivative and the Weinreb amide such as 2.

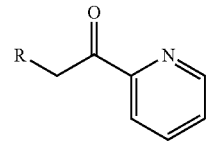

Prepared from 2-bromopyridine by treatment with n-butyllithium and condensation with a Weinreb amide such as 2. Alternatively, 2-bromopyridine can be converted into 2-(tri-n-butylstannanyl)pyridine and then condensed with an acid chloride such as 5 under palladium catalysis.

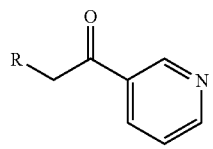

Prepared from 3-bromopyridine by treatment with n-butyllithium and condensation with a Weinreb amide such as 2. Alternatively, 3-bromopyridine can be converted into 3-(tri-n-butylstannanyl)pyridine and then condensed with an acid chloride such as 5 under palladium catalysis.

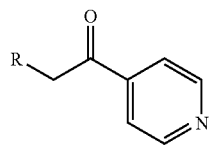

Prepared from 4-bromopyridine by treatment with n-butyllithium and condensation with a Weinreb amide such as 2. Alternatively, 4-bromopyridine can be converted into 4-(tri-n-butylstannanyl)pyridine and then condensed with an acid chloride such as 5 under palladium catalysis.

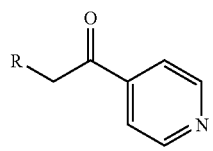

Prepared from pyridazine by treatment with excess lithium tetramethylpiperidide and condensation with a Weinreb amide such as 2. Alternatively, treatment of 3(2H)-pyridazinone with trifluoromethanesulfonic anhydride followed by coupling with hexabutylditin promoted by palladium catalysis affords 3-(tri-n-butylstannanyl)pyridazine which can then be condensed with an acid chloride such as 5 under palladium catalysis.

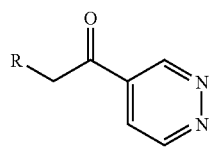

4-(tri-n-Butylstannyl)-pyridazine can be condensed with an acid chloride such as 5 under palladium catalysis to afford these desired ketones.

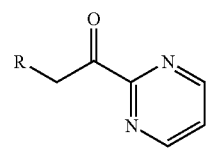

Reaction of tri-n-butylstannyl lithium with 2-chloropyrimidine affords 2-(tributylstannyl)pyrimidine which can be condensed the an acid chloride such as 5 under palladium catalysis to afford these desired ketones.

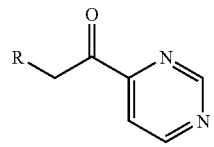

4(3H)-Pyrimidone upon treatment with trifluoromethanesulfonic anhydride in pyridine provides the corresponding triflate that upon reaction with hexabutylditin in the presence of bis-(triphenylphosphine)palladium (II) chloride produces 4-(tributylstannyl)pyrimidine. Treatment of 4-(tributylstannyl)pyrimidine with an acid chloride such as 5 under palladium catalysis affords these desired ketones.

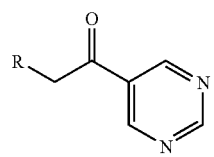

Treatment of 5-bromopyrimidine with hexabutylditin in the presence of a palladium catalyst affords 5-(tributylstannyl)pyrimidine which can be treated with an acid chloride such as 5 to afford these desired ketones.

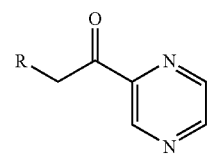

2-(Tributylstannyl)pyrazine prepared by treatment of chloropyrazine with n-butyllithium followed by condensation with tri-n-butyltin chloride is treated with an acid chloride such as 5 to afford the desired ketones. Alternatively, the lithium derivative derived from treatment of chloropyrazine with n-butyllithium can be condensed directly with the Weinreb amides such as 2 to prepare these desired ketones.

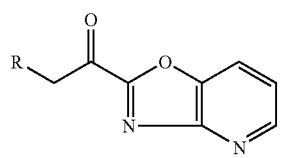

Treatment of aldehydes such as 8 with [1,3]oxazolo[5,4-b]pyridin-2-yllithium followed by oxidation of the incipient alcohol with the Dess-Martin periodinane reagent can be used to prepare these desired ketones

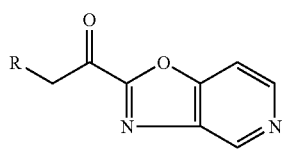

Treatment of aldehydes such as 8 with [1,3]oxazolo[5,4-c]pyridin-2-yllithium followed by oxidation of the incipient alcohol with the Dess-Martin periodinane reagent can be used to prepare these desired ketones.

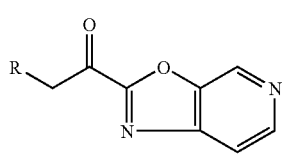

Treatment of aldehydes such as 8 with [1,3]oxazolo[4,5-c]pyridin-2-yllithium followed by oxidation of the incipient alcohol with the Dess-Martin periodinane reagent can be used to prepare these desired ketones.

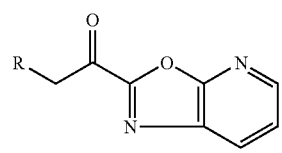

Treatment of aldehydes such as 8 with [1,3]oxazolo[4,5-b]pyridin-2-yllithium followed by oxidation of the incipient alcohol with the Dess-Martin periodinane reagent can be used to prepare these desired ketones.

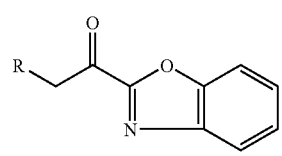

Treatment of aldehydes such as 8 with 1,3-benzoxazol-2-yllithium followed by oxidation of the incipient alcohol with the Dess-Martin periodinane reagent can be used to prepare these desired ketones.

General Synthesis Scheme 10

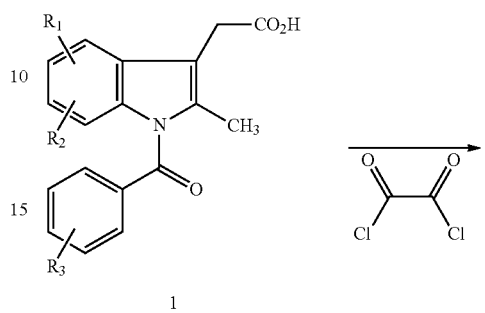

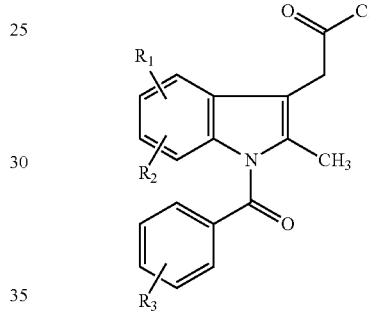

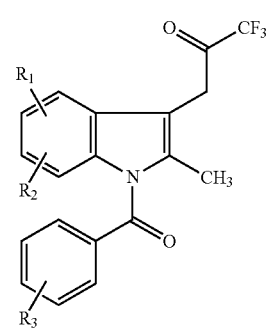

Illustrated in General Synthesis Scheme 10 is the method for the preparation of trifluoromethy ketones such as 10. The carboxylic acids 1 are converted to the corresponding acid chloride 5 with oxalyl chloride and then converted into the trifluoromethyl ketones by treatment with trifluoroacetic anhydride in the presence pyridine according to the method described by Boivin, J.; El Kaim, L.; Zard, S. Z., *Tetrahedron Lett.* 1992, 33, 1285-1288.

General Synthesis Scheme 11

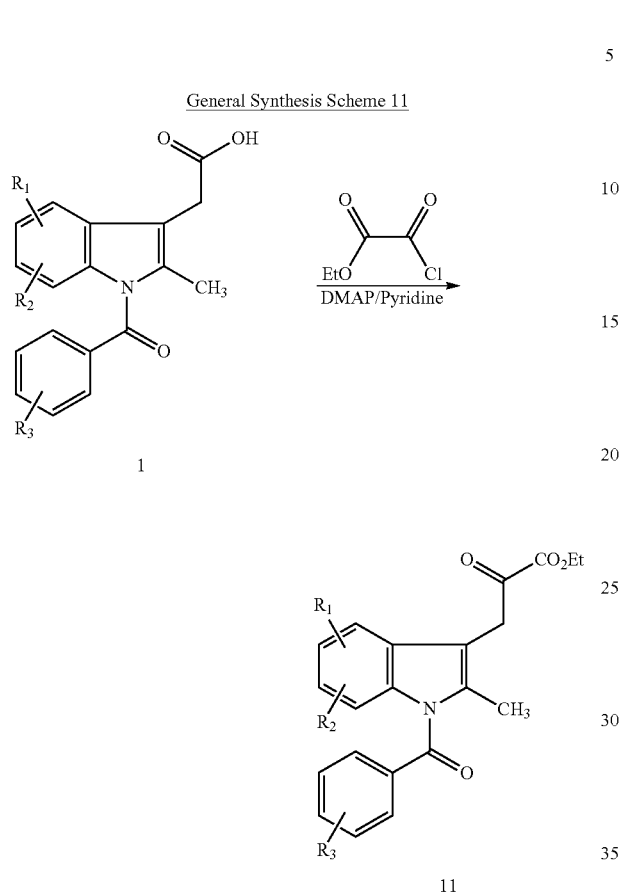

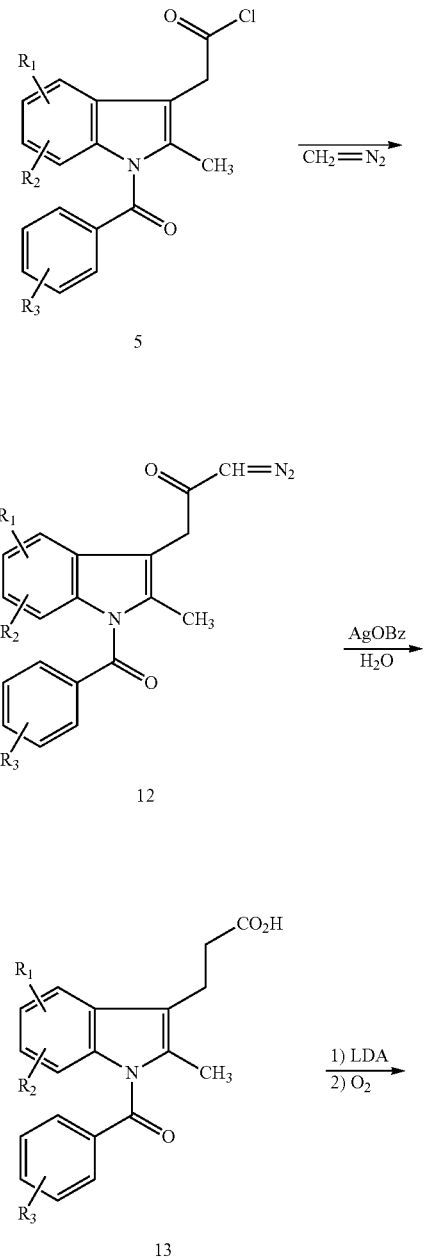

Illustrated in General Synthesis Scheme 11 is the method that was used to prepare alpha-ketoester derivatives of the general formula 11. The procedure involves condensation of the carboxylic acids 1 with ethyl chlorooxoacetate in the presence of pyridine and 4-(dimethylamino)pyridine (DMAP) to produce these desired keto esters 11 according to the method of Li, Z.; Patil, G. S.; Golubski, Z. E.; Hori, H.; Tehrani, K.; Foreman, J. E.; Eveleth, D. D.; Bartus, R. T.; Powers, J. C., *J. Med. Chem.* 1993, 36, 3472-3480.

General Synthesis Scheme 12

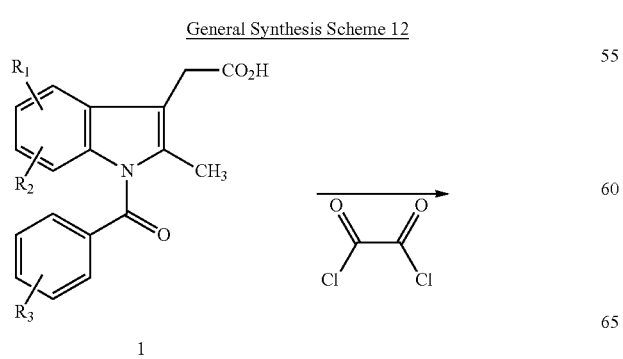

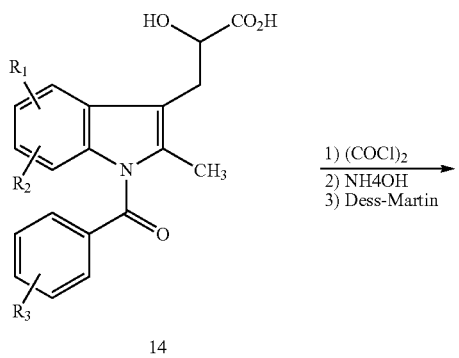

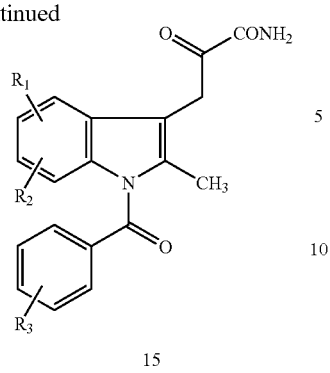

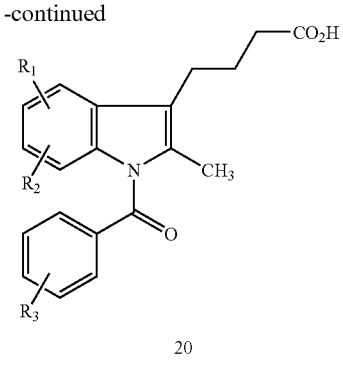

Illustrated in General Synthesis Scheme 12 is the method that was used to prepare inhibitors of the general formula 13-15. The sequence commences with the conversion of carboxylic acids 1 to the corresponding acid chlorides 5 with oxalyl chloride. Treatment of 5 with diazomethane affords the corresponding diazoketones 12 in excellent yield that can then be converted into the chain extended carboxylic acids 13 upon treatment with silver benzoate in aqueous tetrahydrofuran. Oxygenation of the enolate of 13 generated with lithium diisopropylamide provides the alpha-hydroxyacids 14. If desired, the alpha-keto amides 15 can be generated from 14 by a sequence involving conversion to the acid chloride, treatment with aqueous ammonia, and finally oxidation of the alcohol to the corresponding ketones with the Dess-Martin periodinane reagent.

General Synthesis Scheme 13

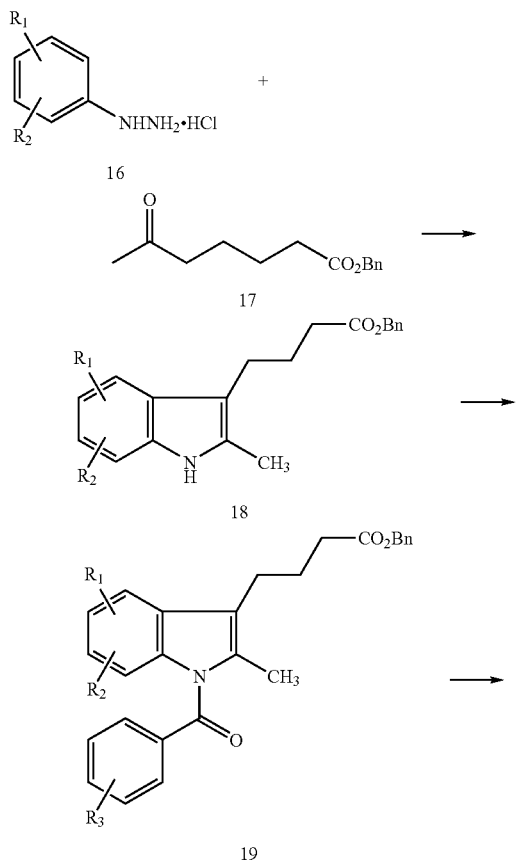

General Synthesis Scheme 13 illustrates the method that can be used for the preparation of compounds of the general formula 20. The process commences with the condensation of an aryl hydrazine derivative 16 with benzyl 6-oxoheptanoate (17) under the standard Fisher indole synthesis conditions to afford indole derivatives 18. Acylation of the indole nitrogen with an acid chloride to provide the new indole derivatives 19 is normally accomplished by generation of the indole anion with a strong base such as sodium hydride. The benzyl ester of 19 is then removed by hydrogenolysis over palladium on carbon to afford the desired indole butyric acid derivatives 20.

Section 4
Synthesis of Heterocylic Fused Ring Systems

Various methods are known for the synthesis of fused heterocyclic ring systems. Several are referenced below. Many others are known and useful.

[1,3]thiazolo[4,5-b]pyridine-2-yl can be prepared according to: WO2004058728.

[1,3]thiazolo[4,5-c]pyridine-2-yl can be prepared according to: International Journal of Sulfur Chemistry, Part B: Quarterly Reports on Sulfur Chemistry (1972), 7(2), 121-153.

[1,3]thiazolo[5,4-c]pyridine-2-yl can be prepared according to Journal of Heterocyclic Chemistry (1990), 27(3), 563-566.

[1,3]thiazolo[5,4-b]pyridine-2-yl can be prepared according to International Journal of Sulfur Chemistry, Part B: Quarterly Reports on Sulfur Chemistry (1972), 7(2), 121-153.

[1,3]thiazolo[4,5-b]pyrazine-2-yl can be prepared according to Science of Synthesis (2002), 11 835-912.

[1,3]thiazolo[4,5-d]pyrimidine-2-yl can be prepared according to Indian Journal of Chemistry (1971), 9(7), 651-654

[1,3]thiazolo[4,5-d]pyridazine-2-yl can be prepared according to Bulletin de la Societe Chimique de France (1971), (4), 1491-1496.

[1,3]oxazolo[4,5-d]pyrimidine-2-yl can be prepared according to Tetrahedron Letters (1990), 31(8), 1155-1156.

[1,3]oxazolo[5,4-d]pyrimidine-2-yl can be prepared according to Australian Journal of Chemistry (1970), 23(6), 1229-1248.

[1,3]oxazolo[4,5-b]pyridine-2-yl can be prepared according to Heterocycles (1995), 41(3), 477-485.

[1,3]oxazolo[4,5-c]pyridine-2-yl can be prepared according to EP 1203766

[1,3]oxazolo[5,4-c]pyridine-2-yl can be prepared according to WO 2004064778

[1,3]oxazolo[5,4-b]pyridine-2-yl can be prepared according to WO 2003048137

Furo[2,3-b]pyridine-2-yl can be prepared according to Synthesis (1981), (6), 464-465.

Furo[2,3-c]pyridine-2-yl can be prepared according to Journal of Heterocyclic Chemistry (1982), 19(5), 1207-1209.

Furo[3,2-c]pyridine-2-yl can be prepared according to Journal of Heterocyclic Chemistry (1971), 8(1), 57-60.

Furo[3,2-b]pyridine-2-yl can be prepared according to Journal of Heterocyclic Chemistry (1986), 23(3), 665-668.

Thieno[3,2-d]pyrimidine-6-yl can be prepared according to Tetrahedron (1971), 27(2), 487-499.

Thieno[2,3-d]pyrimidine-6-yl can be prepared according to Journal of Heterocyclic Chemistry (1975), 12(5), 921-924.

Thieno[2,3-c]pyridazine-6-yl can be prepared according to Phosphorus, Sulfur and Silicon and the Related Elements (2004), 179(2), 321-344.

Thieno[2,3-d]pyridazine-2-yl can be prepared according to Bulletin de la Societe Chimique de France (1967), (7), 2495-2507.

Thieno[3,2-c]pyridazine-6-yl can be prepared according to Journal of the Chemical Society [Section] C: Organic (1971), (7), 1285-1291.

Thieno[2,3-b]pyrazine-6-yl can be prepared according to Journal of Heterocyclic Chemistry (1976), 13(2), 273-275.

Thieno[3,2-b]pyridine-2-yl can be prepared according to Journal of Heterocyclic Chemistry (1984), 21(3), 785-789.

Thieno[3,2-c]pyridine-2-yl can be prepared according to Journal of Heterocyclic Chemistry (1993), 30(1), 289-290.

Thieno[2,3-c]pyridine-2-yl can be prepared according to Synthesis (2004), (12), 1935-1937.

Thieno[2,3-b]pyridine-2-yl can be prepared according to Journal of Organic Chemistry (1987), 52(19), 4280-4287.

3H-imidazo[4,5-b]pyridine-2-yl can be prepared according to Tetrahedron Letters (1993), 34(12), 1897-1900.

3H-imidazo[4,5-c]pyridine-2-yl can be prepared according to Khimiya Geterotsiklicheskikh Soedinenii (1994), (10), 1411-1419.

7H-purine-8-yl can be prepared according to Chemische Berichte (1967), 100(7), 2280-2291.

1H-pyrrolo[3,2-b]pyridine-2-yl can be prepared according to Journal of Heterocyclic Chemistry (1992), 29(2), 359-367.

1H-pyrrolo[3,2-c]pyridine-2-yl can be prepared according to Heterocycles (1992), 34(12), 2379-2384.

1H-pyrrolo[2,3-c]pyridine-2-yl can be prepared according to Synthesis (1996),(7), 877-882.

1H-pyrrolo[2,3-b]pyridine-2-yl can be prepared according to Journal of the Chemical Society [Section] C: Organic (1969), (11), 1505-1514.

1H-pyrrolo[2,3-d]pyridazine-2-yl can be prepared according to Comptes Rendus des Seances de l'Academie des Sciences, Serie C: Sciences Chimiques (1967), 265(22), 1271-1273.

5H-pyrrolo[3,2-c]pyridazine-6-yl can be prepared according to Diss. Abstr. Int. B 1974, 35(3), 1199.

7H-pyrrolo[2,3-c]pyridazine-6-yl can be prepared according to Diss. Abstr. Int. B 1974, 35(3), 1199.

5H-pyrrolo[2,3-b]pyrazine-6-yl can be prepared according to Tetrahedron Letters (2004), 45(43), 8087-8090.

5H-pyrrolo[3,2-d]pyrimidine-6-yl can be prepared according to Synthesis (1974), (12), 837-859.

7H-pyrrolo[2,3-d]pyrimidine-6-yl can be prepared according to WO 2003048120,

Section 5
Preparation of Alpha-Keto Amide Derivatives.

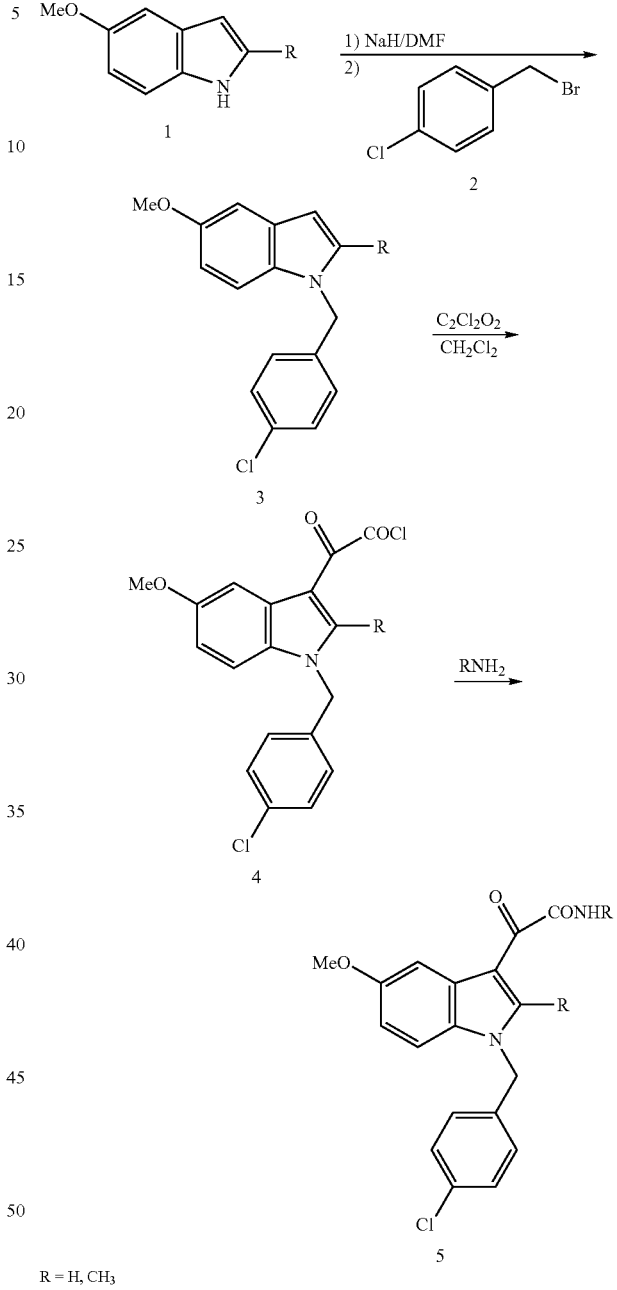

R = H, CH₃

Treatment of indole derivative 1 with sodium hydride in dry dimethylformamide (DMF) and reaction with benzyl bromide 2 provides the alkylated derivative 3. Treatment of 3 with oxalyl chloride in dichloromethane affords acid chloride 4 that can be reacted with amines to provide amide derivatives with the general structure 5. Most of the amines are commercially available or can be prepared by methods described in the literature. These amines include those represented by CA Registry Numbers: 504-29-0 (Alfa Aesar, Ward Hill, Mass. catalog no. A12374); 108-91-8 (Sigma-Aldrich, St. Louis, Mo., catalog no. 240648), 765-30-0 (Sigma-Aldrich, St. Louis, Mo., catalog no. 125504); 2516-34-9 (Alfa Aesar, Ward Hill, Mass., catalog no. A13423); 1003-03-8 (Alfa Aesar, Ward Hill, Mass., catalog no. L01966); 96-50-4 (Alfa Aesar, Ward Hill, Mass., catalog no. A12026); 7720-39-0; 4570-45-0 (GLSynthesis Inc., Worcester, Mass.); 462-08-8 (Sigma-Aldrich, St. Louis, Mo.); 504-24-5; 591-54-8 Sigma-Aldrich, St. Louis, Mo., catalog no. 261823); 5049-61-6 (Alfa Aesar, Ward Hill, Mass., catalog no. A13052); 109-12-6 (Alfa Aesar, Ward Hill, Mass., catalog no. B24594); 5469-70-5 (see Turck, et al. Tetrahedron 1993, 49, 599-606); 20744-39-2 (SNYCHEM OHG, Kassel, Germany, catalog no. ct267); 591-55-9; 14678-05-8 (see Iwai and Nakamura, Chemical & Pharmaceutical Bulletin 1966, 14, 1277-1286); 1750-42-1 (Sigma-Aldrich, St. Louis, Mo., catalog no. 424218); 14678-02-5 (Sigma-Aldrich, St. Louis, Mo., catalog no. 304271); 1072-67-9 (Sigma-Aldrich, St. Louis, Mo., catalog no. 232270); 1820-80-0 (Sigma-Aldrich, St. Louis, Mo., catalog no. 160644); 31230-17-8 (Alfa Aesar, Ward Hill, Mass., catalog no. A11642); 4592-62-5 (see Brown and Sainsbury, Science of Synthesis 2002, 11 507-572); 82357-92-4 (see Goerdeler and Pohland, Angew. Chem. 1960, 72, 77); 128146-85-0; 24340-76-9 (see Samaritoni et al, Journal of Agricultural and Food Chemistry 1997, 45, 1920-1930); 136-95-8 (Sigma-Aldrich, St. Louis, Mo., catalog no. 108812); 4570-41-6; 40926-66-7 (see Kalcheva et al, Zeitschrift fuer Chemie 1981, 21, 219-220); 114498-55-4 (Chemstep, Carbon Blanc, France, catalog no. 17590); 118767-91-2 (Chemstep, Carbon Blanc, France, catalog no. 17511), 4592-62-5, 82357-92-4 (see Goerdeler and Horn, Ber. 1963, 96, 1551-60); 1820-80-0 (Sigma-Aldrich, St. Louis, Mo., catalog no. 160644); 6826-24-0 (see Van Leusen et al, Journal of Organic Chemistry 1981, 46, 2069-72 and Tanimoto et al, Chemical & Pharmaceutical Bulletin 1984, 32, 1032-1039) and 33119-65-2 (see Crank, et al, Australian Journal of Chemistry 1985, 38, 447-458).

They also include those disclosed in Van Leusen et al. Journal of Organic Chemistry 1981, 46, 2069-2072 such as

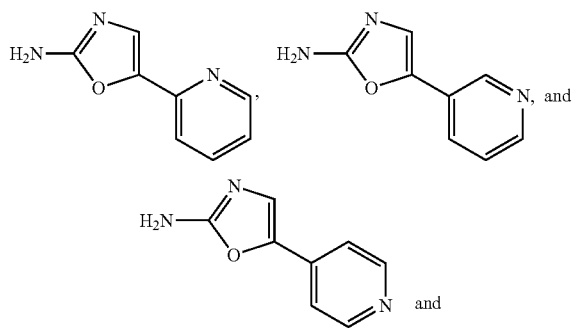

Herdeis and Gebhard Heterocycles 1986, 24, 1019-1024 such as

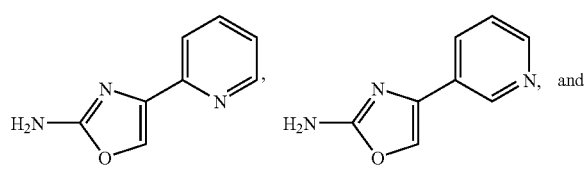

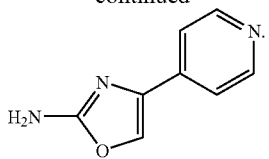

General Method for the Preparation of Selected Ketone Derivatives.

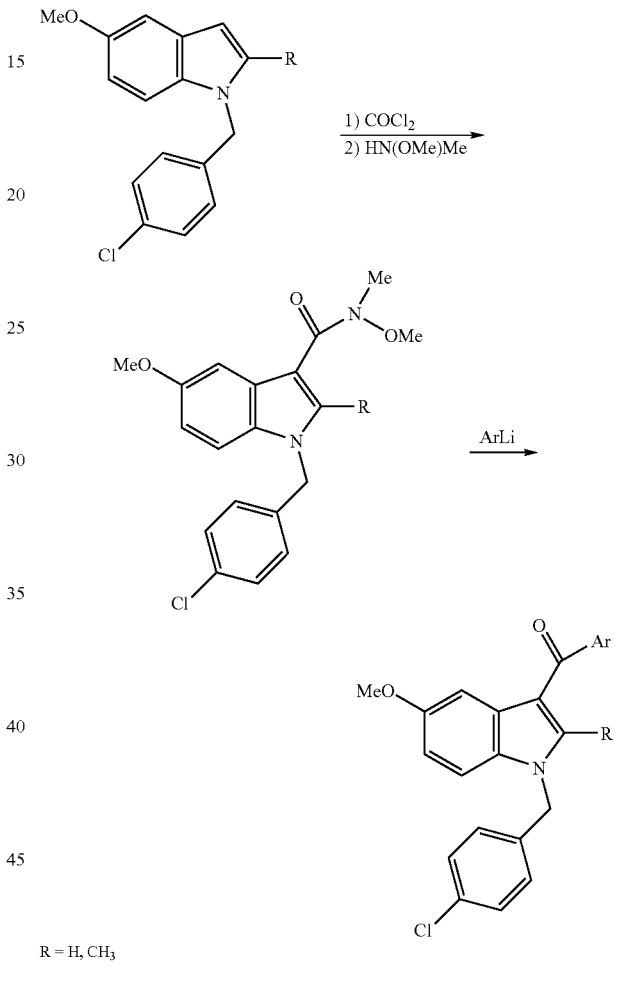

R = H, CH₃

Starting materials for the preparation of ArLi reagents include: CA Registry Numbers 20662-89-9 (see Whitney et al. Journal of Organic Chemistry 1990, 55, 929-935); 133229-54-6 (see Whitney et al. Journal of Organic Chemistry 1991, 56, 3058-3063); 681135-55-7 (Chemstep, Carbon Blanc, France, catalog no. 15867); 681135-57-9 (Chemstep, Carbon Blanc, France, catalog no. 15866); 35299-74-2 (see Boger et al. Journal of Medicinal Chemistry 2005, 48, 1849-1856); 681135-59-1 (Chemstep, Carbon Blanc, France, catalog no. 15865); 1006-68-4 (Ryan Scientific, Inc., Isle of Palms, S.C., catalog no. SEW 004470); 70380-73-3 (Ryan Scientific, Inc., Isle of Palms, S.C., catalog no. SEW 00968); 70380-74-4 (Ryan Scientific, Inc., Isle of Palms, S.C., catalog no. SEW 00967); 70380-75-5 (Ryan Scientific, Inc., Isle of Palms, S.C., catalog no. SEW 00891); 121855-80-9 (see Davies et al. Journal of the Chemical Society, Perkin Trans-actions 1: Organic and Bio-Organic Chemistry 1989, 837-838); as well as compounds

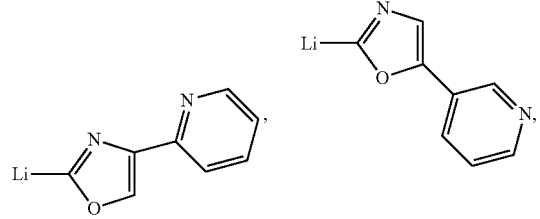

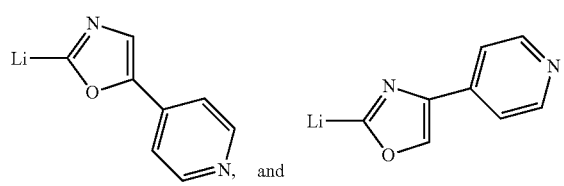

(see Boger et al. Journal of Medicinal Chemistry 2005, 48, 1849-1856);

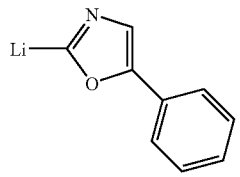

(see Crowe et al. Tetrahedron 1995, 51, 8889-8900);

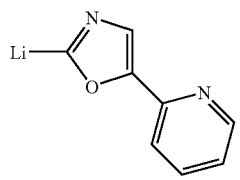

(see Dondoni et al. Journal of Organic Chemistry 1987, 52, 3413-3420), and

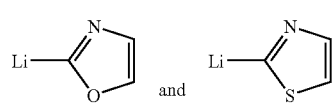

(see Subramanyam et al. Tetrahedron Letters 2002, 43, 6313-6315.

General Method for the Preparation of Selected Ketone Derivatives by Friedel-Crafts Acylation of an Indole.

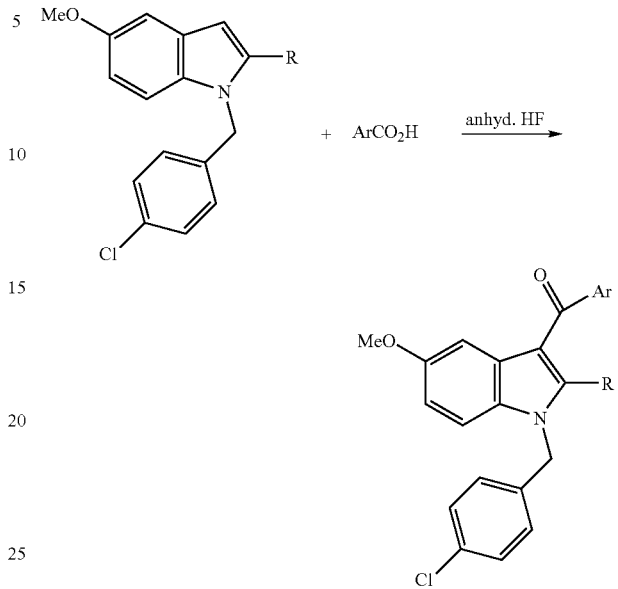

R = H, CH₃

The following compounds (Ar) can be used for the preparation of carboxylic acids for acylation of indole in the 3-position and are either commercially available or can be derived from the literature methods as described: CA Registry Nos. 16042-25-4 (Maybridge plc, Tintagel, Cornwall, United Kingdom, catalog no. CC 08901); 59020-44-9 (J & W Pharm-Lab LLC, Morrisville, Pa., catalog no. 90-0085); 75390-44-2 (ACB Blocks Ltd, Moscow Russia, catalog no. THA-0001); 59020-45-0 (Anichem LLC, Monmouth Junction, N.J., catalog no. S10224); 59020-46-1 (see PCT publication WO2002014311); 59020-47-2 (Anichem LLC, Monmouth Junction, N.J., catalog no. S10225); 862494-59-5 (see PCT publication WO2005074645); 721927-07-7 (see PCT publication WO2004058728); 794500-94-0 and 723733-05-9 (see PCT publication WO2004058728); 19163-24-7 (ASDI Inc, Newark, Del., catalog no. 500022101); 119082-97-2 ((ASDI Inc, Newark, Del., catalog no. 500021267); 35299-74-2 (see Kauffmann et al. Angewandte Chemie, International Edition in English 1971, 10, 741-3); 278803-20-6 and 216867-32-2 (AKos Consulting and Solutions GmbH, Basel Switzerland, catalog nos. BBV-00006978 and BBV-00011817); 527-72-0; 21169-71-1 and 14442-12-7 (Sigma-Aldrich, St. Louis, Mo., catalog nos. 88990, 636258, and 633690); 499770-97-7; 10271-85-9 (AstaTech, Inc., Bristol, Pa., catalog no. 62856); 4576-90-3 (see Holland et al. Journal of the Chemical Society 1965, 7277-7282); 3209-71-0 (ChemPacific USA Sales Marketing and Research Center, Baltimore, Md., catalog no. 37117); 716362-11-7 and 716362-05-9 (Ambinter, Paris France, catalog nos. CIZ-0020 and CIZ-0022), and

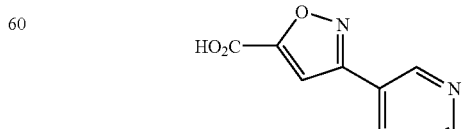

(see PCT publication WO2004054974).

General method for the construction of 3-aryl-5-carboxy isoxazoles by dipolar cycloaddition of nitrile oxides (generated from oximes with N-chlorosuccinimide and triethylamine) with ethyl propiolate

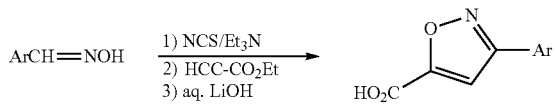

Using this methodology,
CA registry no. 1073-63-0 (Chemstep, Carbon Blanc, France, catalog no. 20123) can be used for the preparation of

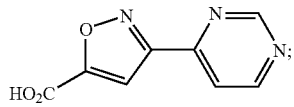

CA registry 1193-98-2 (see Jose et al. Synthetic Communications 2000, 30, 1509-1514) can be used for the preparation of

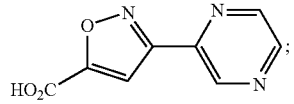

CA registry no. 83959-46-0 (Chemstep, Carbon Blanc, France, catalog no. 18812) can be used for the preparation of

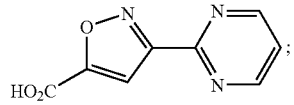

CA registry no. 52348-44-4 (see EP patent publication EP194746A2) can be used for the preparation of

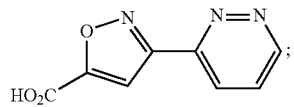

and CA registry no. 50901-50-3 (Chemstep, Carbon Blanc, France, catalog no. 5053) can be used for the preparation of

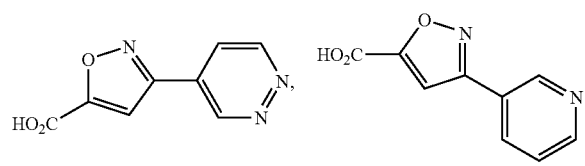

is prepared as described in U.S. Pat. No. 3,957,805.

General method for the preparation of 1,2,4-oxadiazole containing ketone derivatives

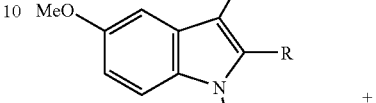

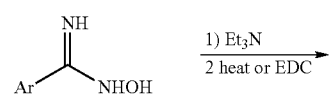

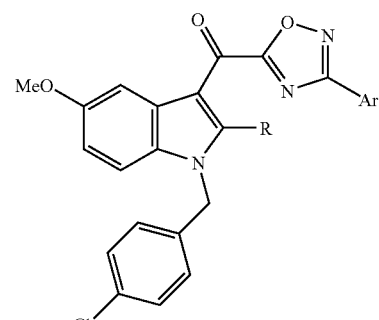

R = H, CH₃

The following is a list of commercially available or literature references for the preparation of carboximides

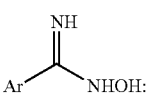

CA Registry Nos. 613-92-3, 1772-01-6, 1594-58-7, and 1594-57-6 (Sigma-Aldrich, St. Louis, Mo., catalog nos. S778176, 542792, 542814, and 542806); 51285-11-1 and 90993-49-0 (Chemstep, Carbon Blanc, France, catalog nos. 19221 and 18704); 90993-48-9 (see Easmon et al. Journal of Medicinal Chemistry 1992, 35, 3288-3296 for the preparation of 3-cyanopyridazine and Robba Ann. Chim. (Paris) 1960, 380, 414 for the preparation of 3-pyridazinecarboxamidoxime); 51285-05-3 (Oakwood Products, Inc, West Columbia, S.C., catalog no. 017309), and 39123-45-0 (see U.S. Pat. No. 3,705,157).

General method for the preparation of 1,3,4-oxadiazole containing ketone derivatives

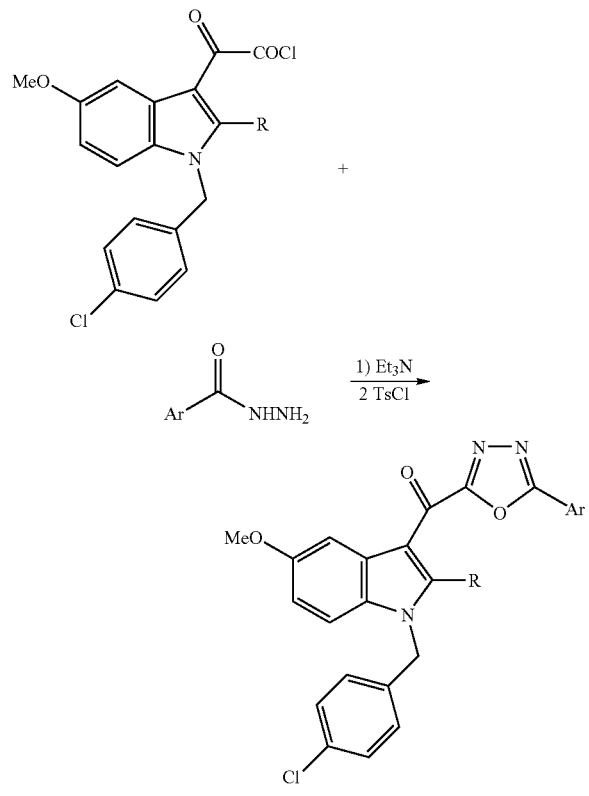

R = H, CH₃

The following is a list of commercially available or literature references for obtaining acylhydrazides.

CA Registry No. 89463-74-1; 87362-28-5; 56932-26-4 (Chemstep, Carbon Blanc, France, catalog no. 29632, 18794, 29637); 39513-54-7; 768-05-8 (J & W PharmLab LLC, Morrisville, Pa., catalog no. 70-0046, 65-0113); 103-28-60-0 (see Ohta et al. Nippon Kagaku Zasshi 1958, 79, 1452-1454); 13363-69-4 (see Beringer et al. Helvetica Chimica Acta 1966, 49, 2466-2469), 52938-97-3 (TCI America, Portland, Oreg., catalog no. P1394); 862089-25-6, 56632-46-3, and 216867-35-5 (AKos Consulting and Solutions GmbH, Base, Switzerland, catalog nos. BBV-00011847, BBV-00011848, and BBV-00011849); and

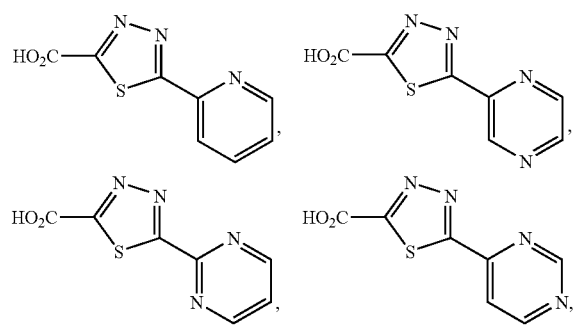

(see WO9854164);

[structures of isothiazole-carboxylic acids with various pyridine/pyrimidine/pyrazine/pyridazine substituents]

(see Beringer et al. Helvetica Chimica Acta 1966, 49, 2466-2469).

General method for the preparation of indole ketones by reaction of 3-lithio-indole with an aldehyde followed by oxidation with the Dess-Martin reagent

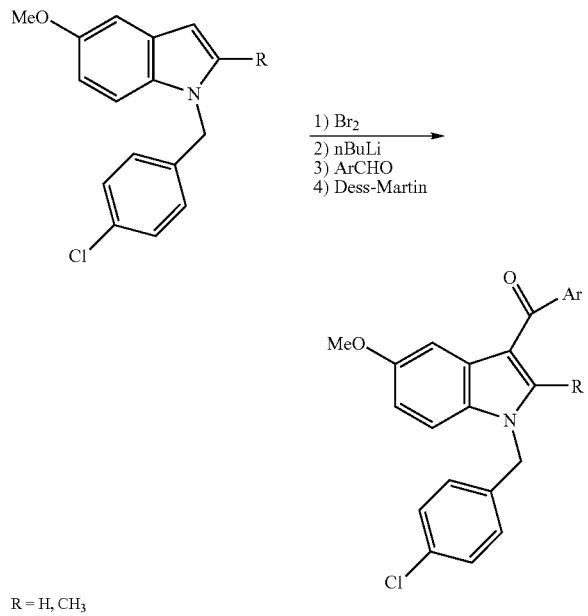

R = H, CH₃

The following is a list of commercially available or literature references for obtaining the requisite aldehydes (ArCHO in above reaction), CA registry numbers: 342601-31-4 (see PCT publication WO2001038332); 1120-95-2 (see Wermuth et al. Journal of Medicinal Chemistry 1987, 30, 239-249); CA registry number 1120-95-2 can be used to synthesize and aldehyde in the following reaction

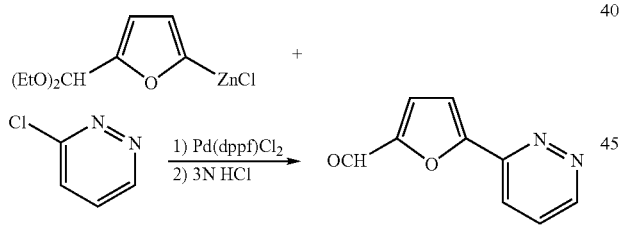

(see Gauthier et al Org. Lett., 2002, 4, 375-378);
CA Registry no. 342603-67-2 which can be derived from the following reaction:

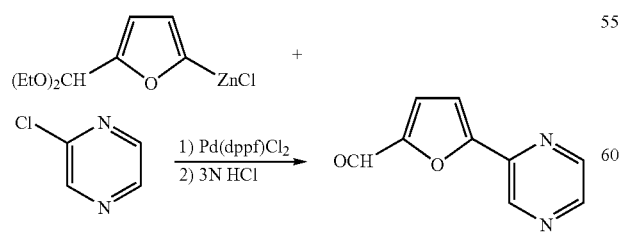

(see Gauthier et al. Org. Lett., 2002, 4, 375-378);
CA Registry no. 545445-71-4 which can be derived from the following reaction:

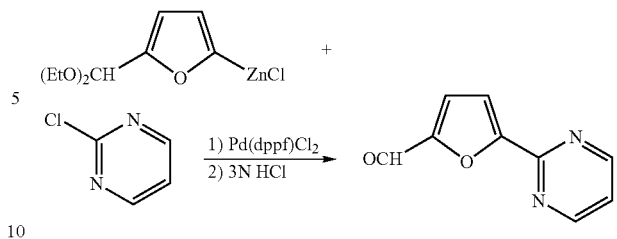

(see Gauthier et al. Org. Lett., 2002, 4, 375-378);
CA Registry no. 342601-17-6 (see WO2001038332); and
CA Registry no. 106833-79-8 (see WO2002016355);

General method for the preparation of ketone derivatives by reaction of an organometallic reagent with the indole Weinreb amide.

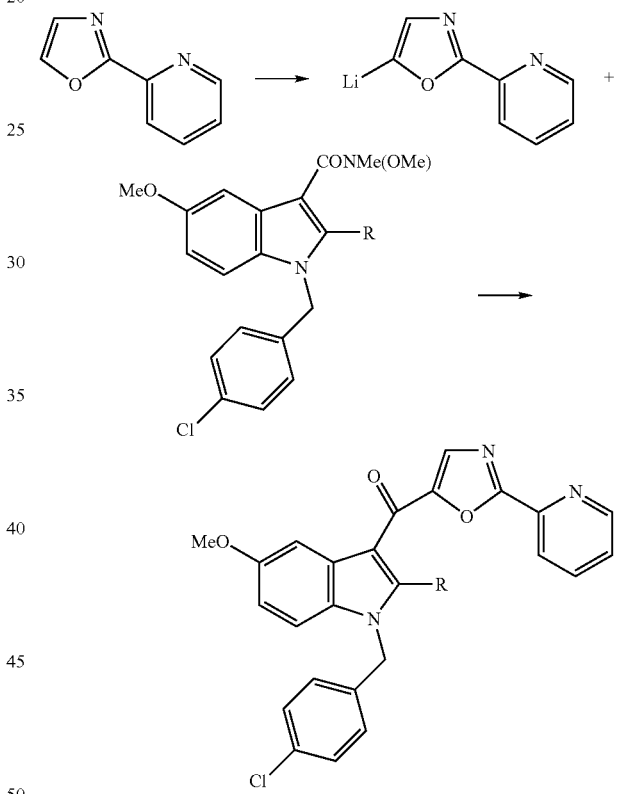

R = H, CH₃

See Boger et al. Journal of Medicinal Chemistry 2005, 48, 1849-1856. Starting material,

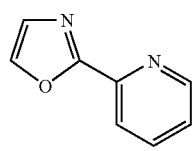

(CA Registry no. 5998-89-0) can be obtained by processes described in Dadkhah and Prijs 1962, 45, 375-381 or using the following reaction:

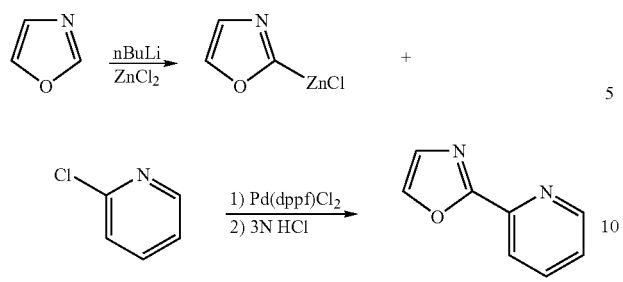
which is described in Gauthier et al. Org. Lett., 2002, 4, 375-378.
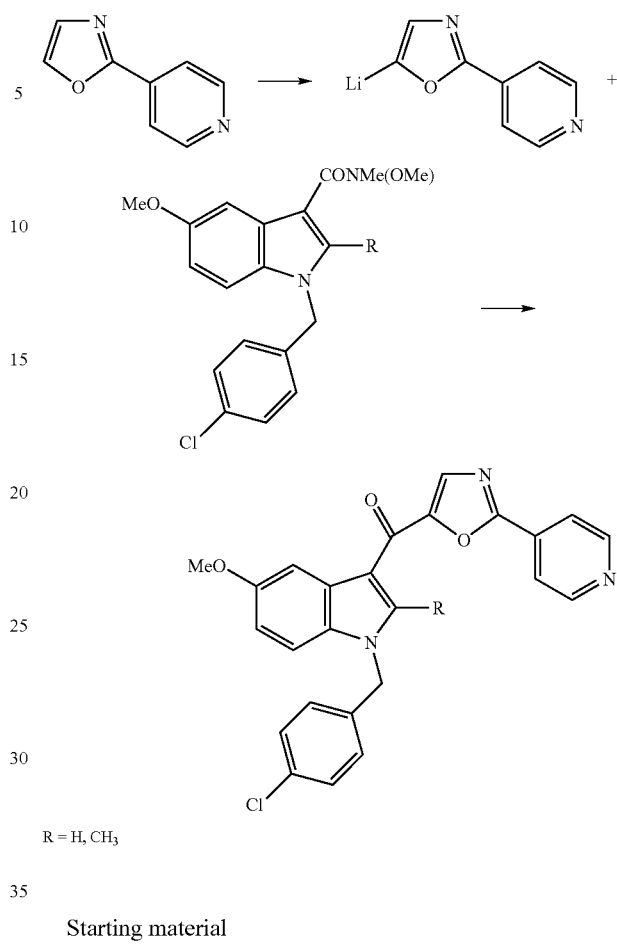
R = H, CH₃
Starting material
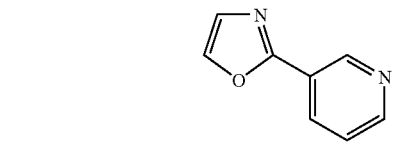
See Boger et al. Journal of Medicinal Chemistry 2005, 48, 1849-1856. For starting material,
(CA Registry no. 5998-85-6) see Dadkhah and Prijs 1962, 45, 375-381.
(CA Registry no. 5998-92-5) is available from the Florida Center for Heterocyclic Compounds (Gainesville, Fla., catalog no. 1265).
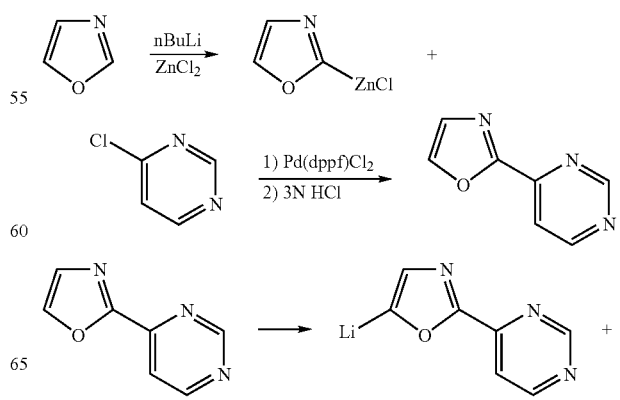

323
-continued
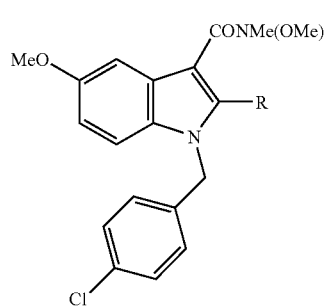
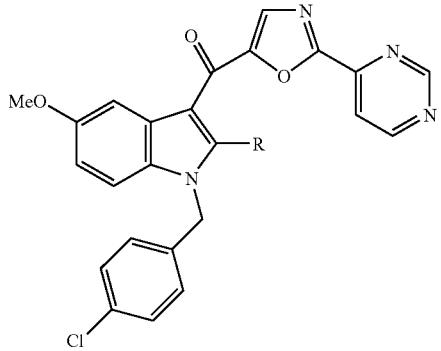
R = H, CH₃
See Gauthier et al org. Lett., 2002, 4, 375-378 and Boger et al. Journal of Medicinal Chemistry 2005, 48, 1849-1856.
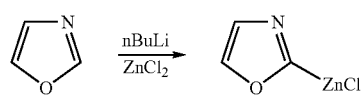
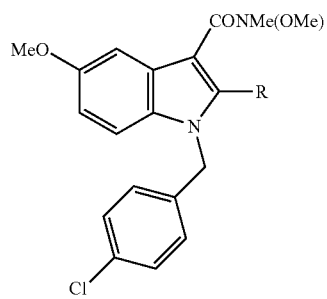
324
-continued
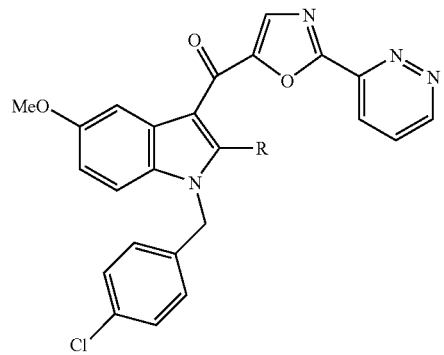
R = H, CH₃
See Gauthier et al Org. Lett., 2002, 4, 375-378 and Boger et al. Journal of Medicinal Chemistry 2005, 48, 1849-1856.
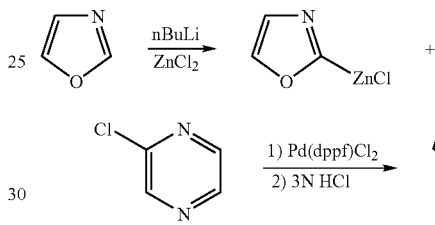
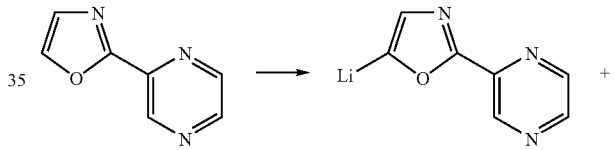
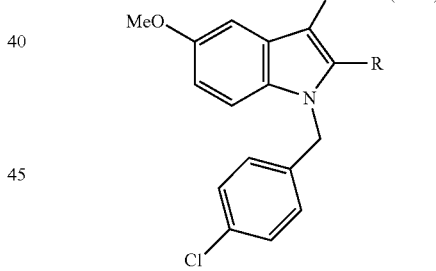
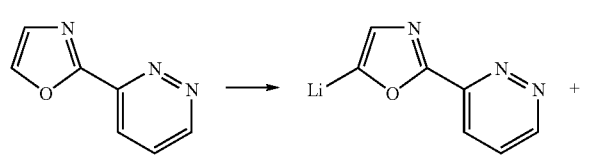
R = H, CH₃
See Gauthier et al Org. Lett., 2002, 4, 375-378 and Boger et al. Journal of Medicinal Chemistry 2005, 48, 1849-1856.

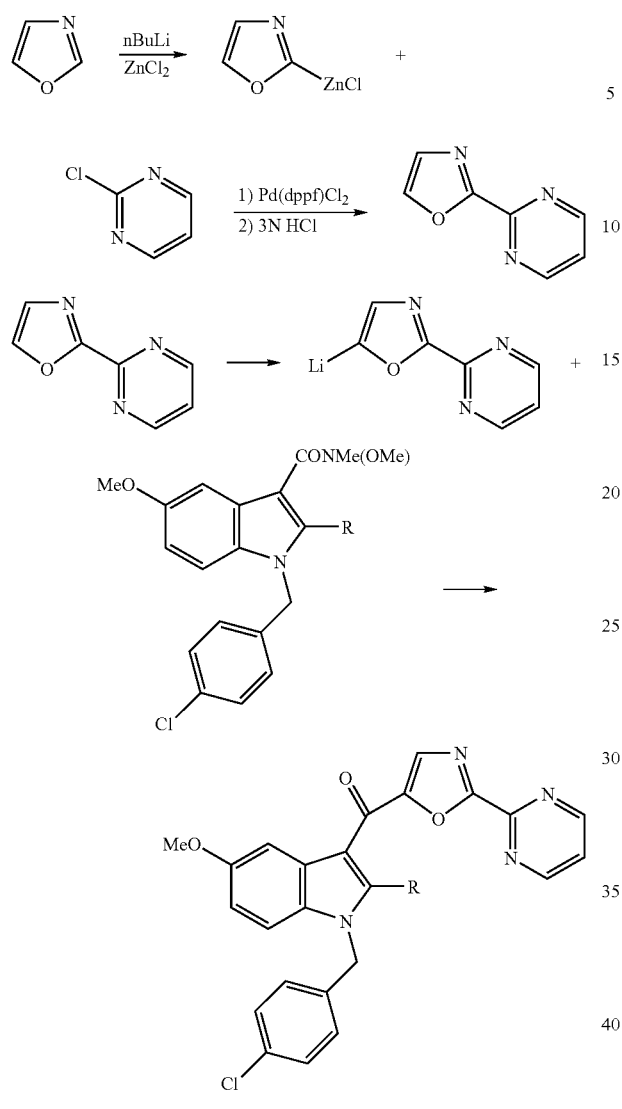
See Gauthier et al Org. Lett., 2002, 4, 375-378 and Boger et al. Journal of Medicinal Chemistry 2005, 48, 1849-1856.
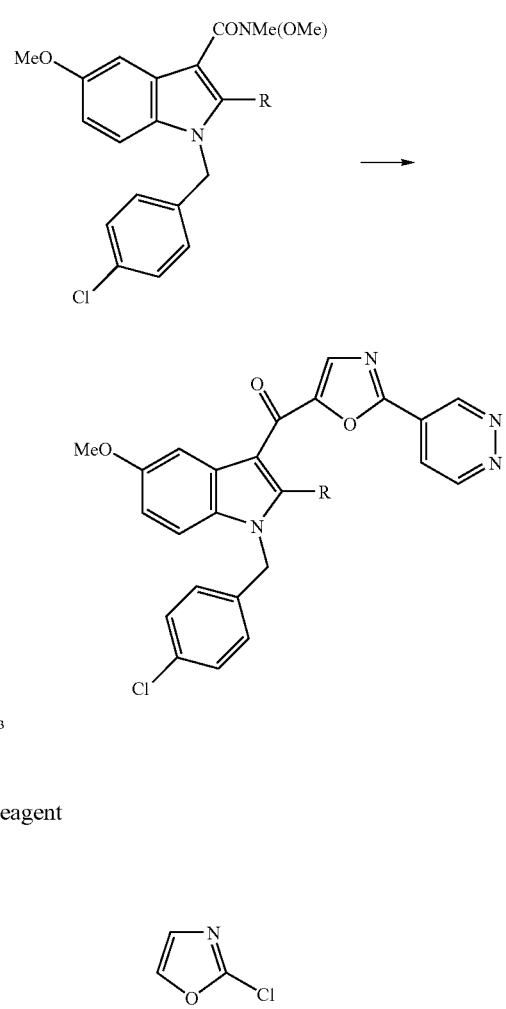
For reagent
(CA registry no. 95458-77-8) see Haviv et al. Journal of Medicinal Chemistry 1988, 31, 1719-1728. For reagent
see Heldmann et al. Tetrahedron Letters 1997, 38, 5791-5794
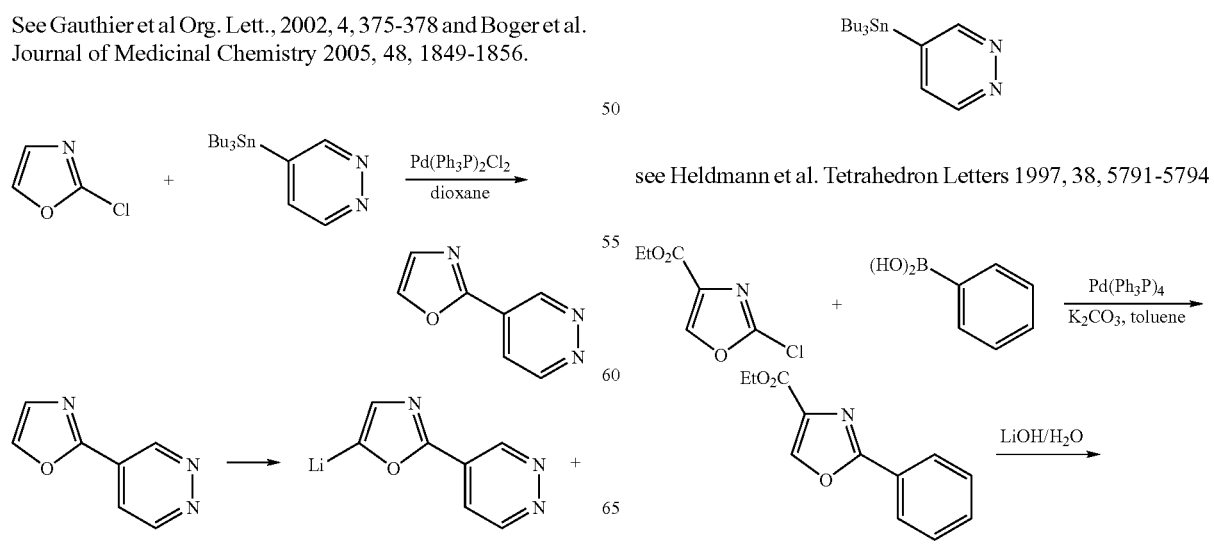

327
-continued
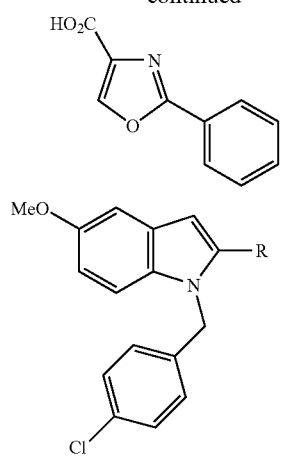
+
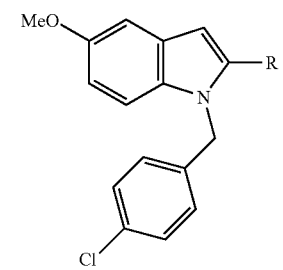
→
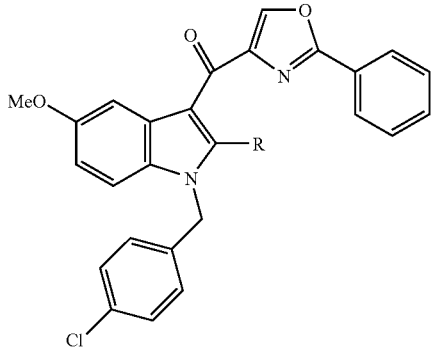
R = H, CH₃
See Hodgetts et al. Org. Lett., 2002, 4, 2905-2907.
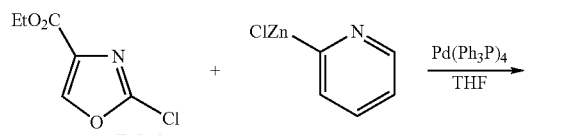
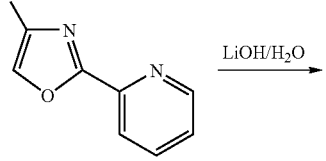
LiOH/H₂O
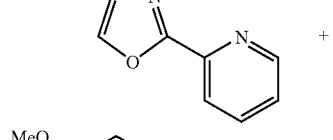
328
-continued
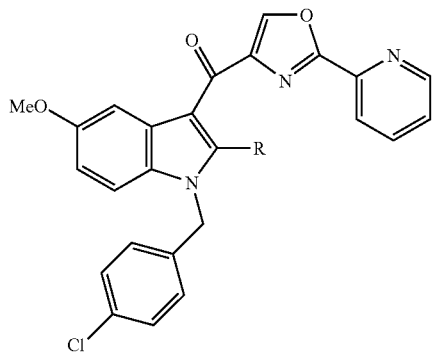
R = H, CH₃
See Hodgetts et al. Org. Lett., 2002, 4, 2905-2907.
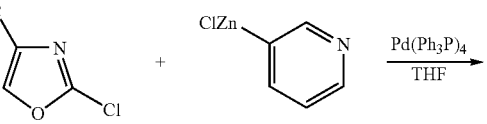
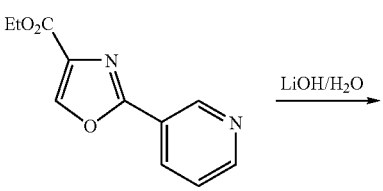
LiOH/H₂O
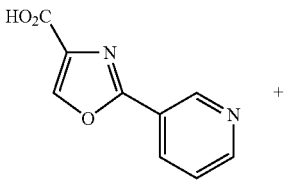
+
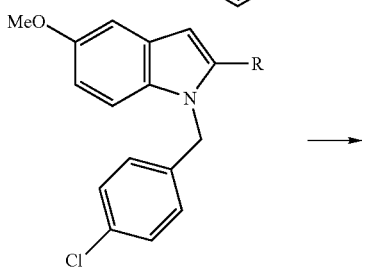
→
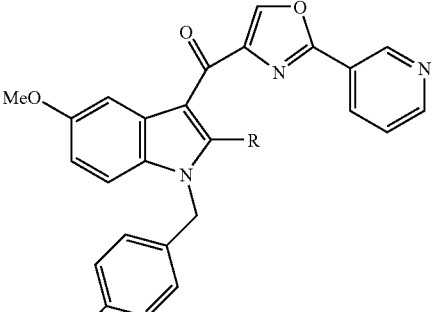
R = H, CH₃

329
See Hodgetts et al. Org. Lett., 2002, 4, 2905-2907.
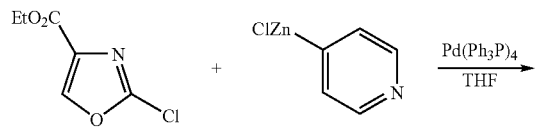
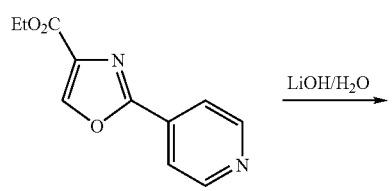
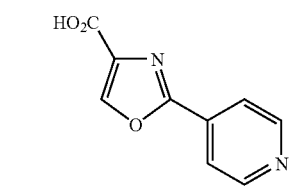
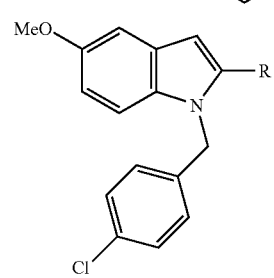
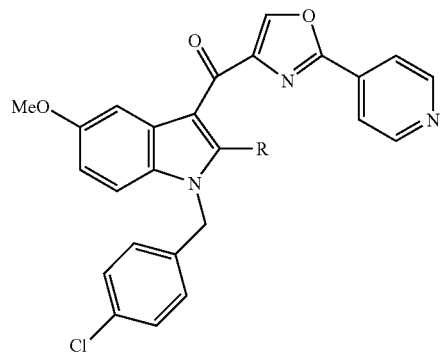
R = H, CH₃
See Hodgetts et al. Org. Lett., 2002, 4, 2905-2907.
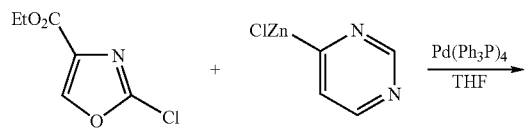
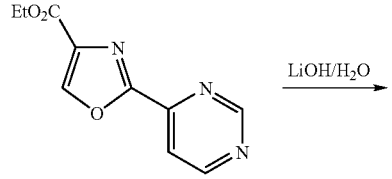
330
-continued
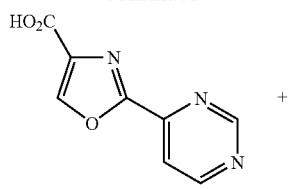
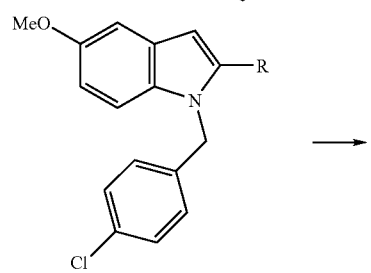
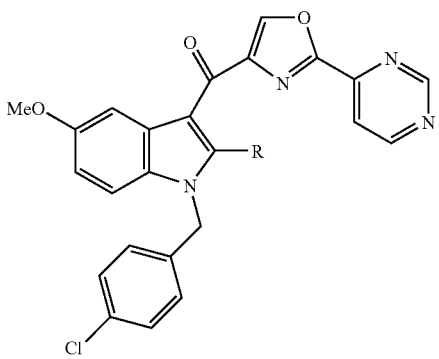
R = H, CH₃
See Hodgetts et al. Org. Lett., 2002, 4, 2905-2907.
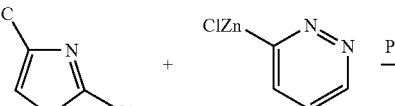
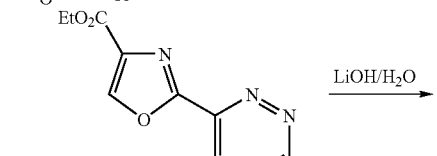
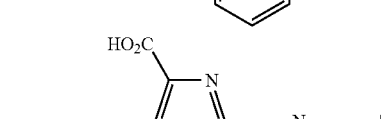
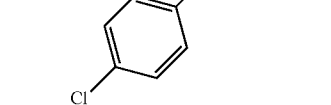

331
-continued
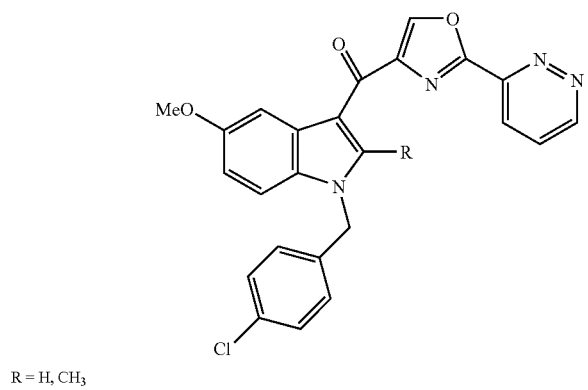
R = H, CH₃
See Hodgetts et al. Org. Lett., 2002, 4, 2905-2907.
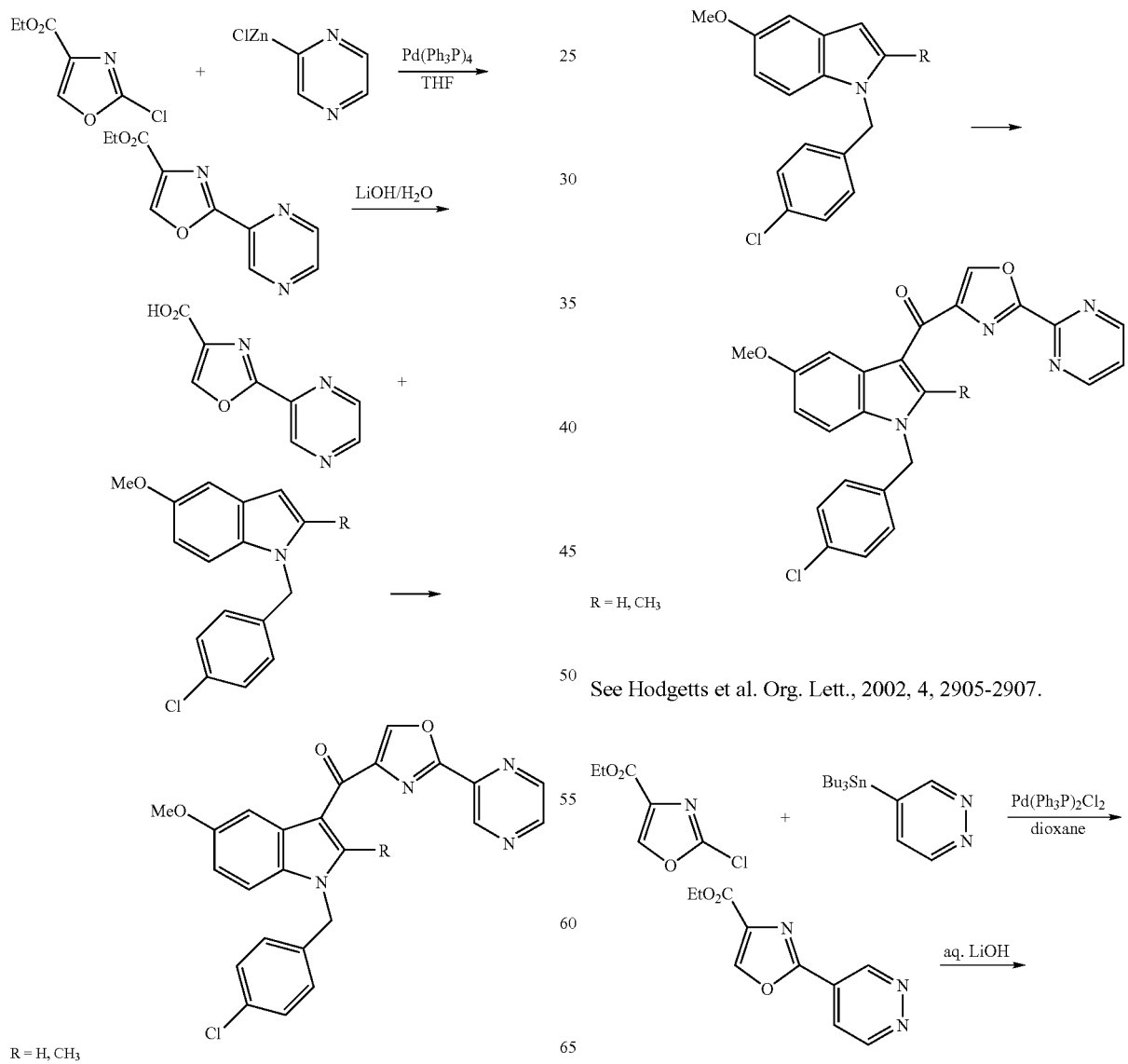
See Hodgetts et al. Org. Lett., 2002, 4, 2905-2907.

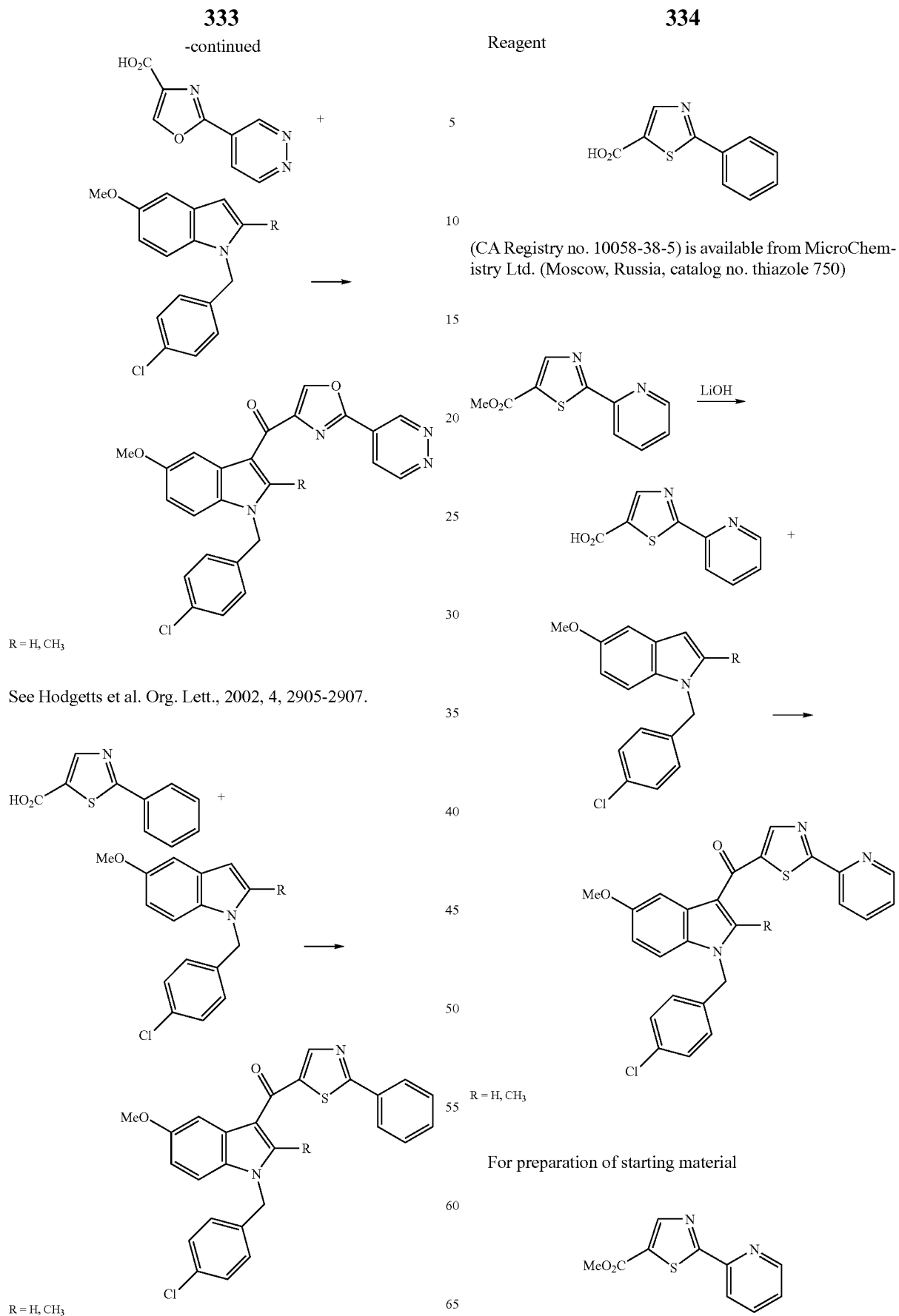
See Hodgetts et al. Org. Lett., 2002, 4, 2905-2907.
R = H, CH₃
(CA Registry no. 10058-38-5) is available from MicroChemistry Ltd. (Moscow, Russia, catalog no. thiazole 750)
R = H, CH₃
For preparation of starting material

335
(CA Registry No. 862500-42-3) see WO2005075469.
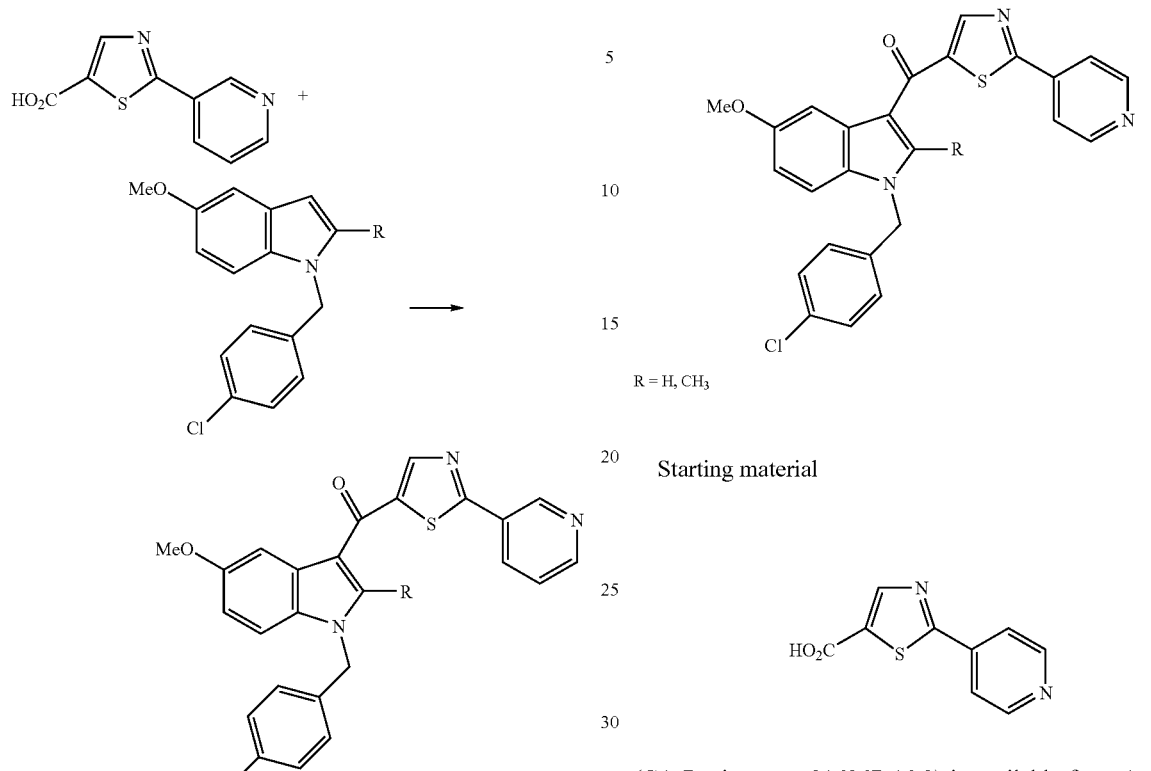
Starting Material
(CA Registry no. 248275-42-5) is available from Anichem LLC (Monmouth Junction, N.J., catalog no. S10219)
336
-continued
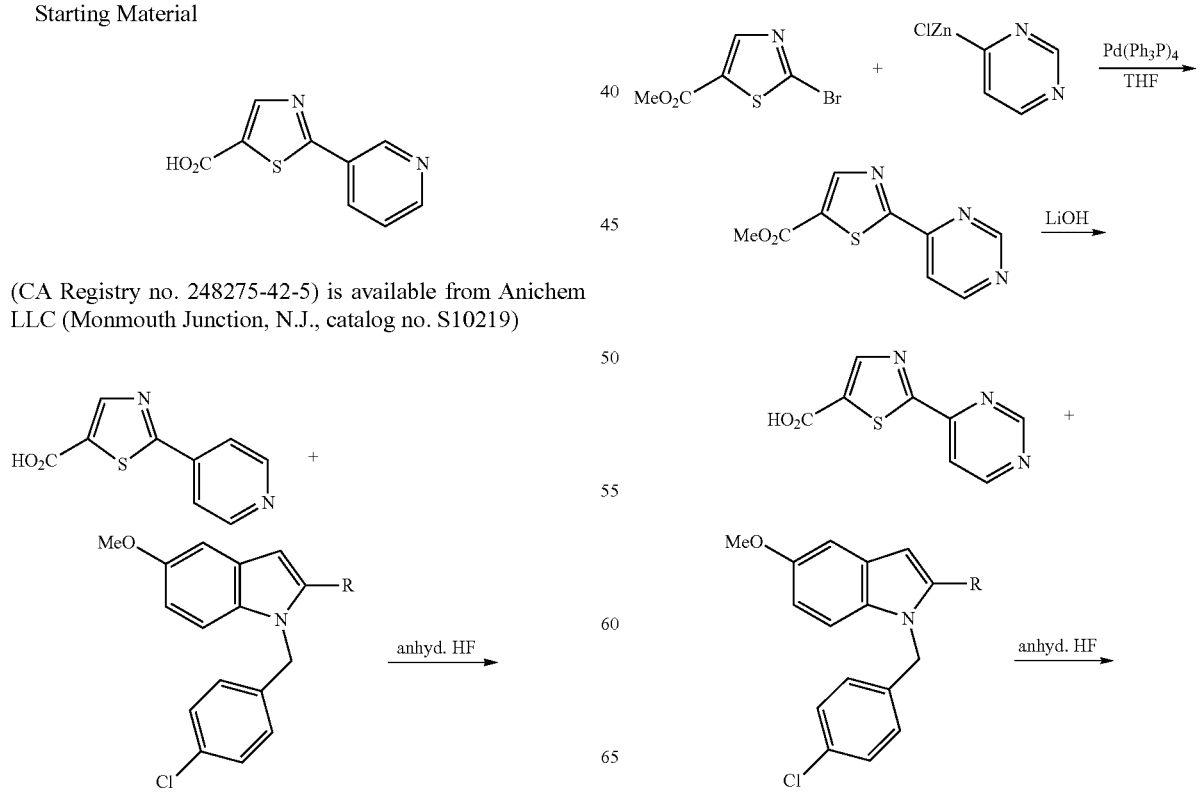
R = H, CH₃
Starting material
(CA Registry no. 216867-46-8) is available from Anichem LLC (Monmouth Junction, N.J., catalog no. S10218)

337
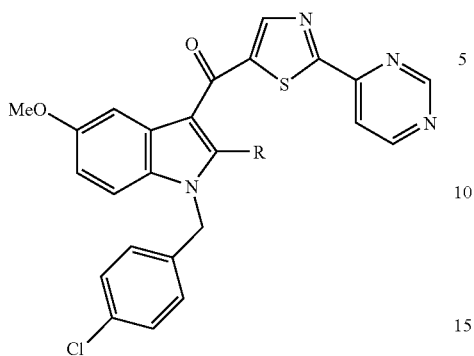
R = H, CH₃
See Hodgetts et al. Org. Lett. 2002, 4, 1363-1365. Starting material
(CA Registry no. 54045-74-8) is available from Combi-Blocks, LLC (San Diego, Calif., HI-1117)
338
See Hodgetts et al. Org. Lett. 2002, 4, 1363-1365.
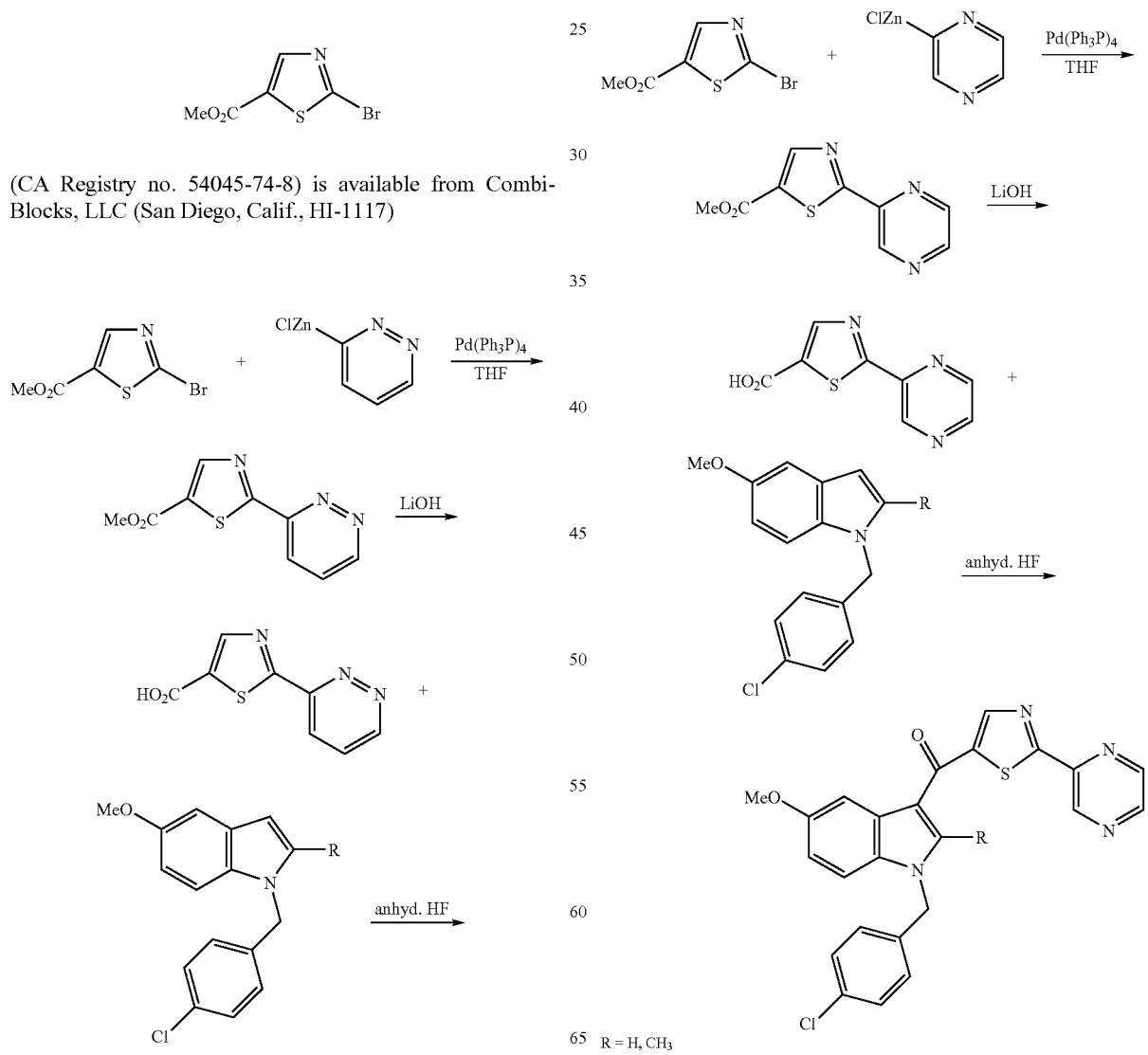
R = H, CH₃

339
See Hodgetts et al. Org. Lett. 2002, 4, 1363-1365.
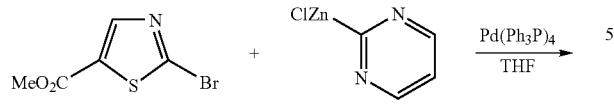
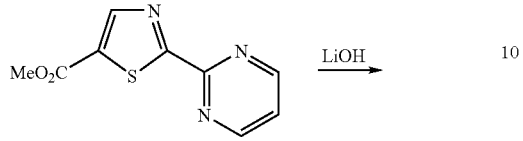
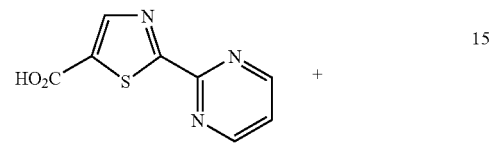
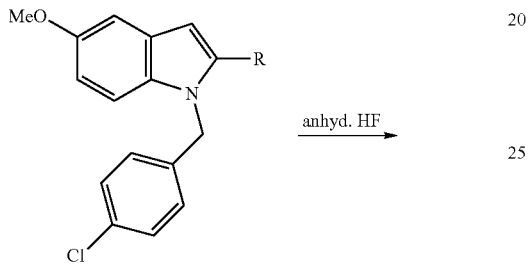
R = H, CH₃
See Hodgetts et al. Org. Lett. 2002, 4, 1363-1365.
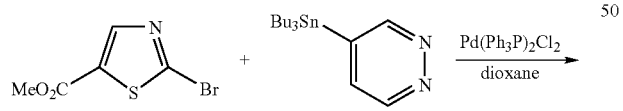
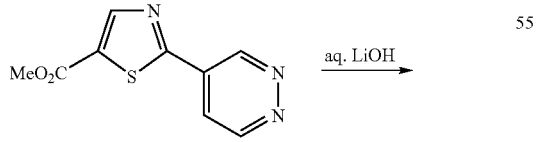
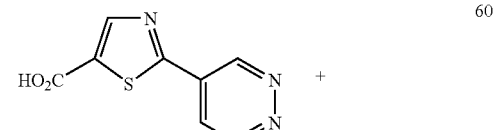
340
-continued
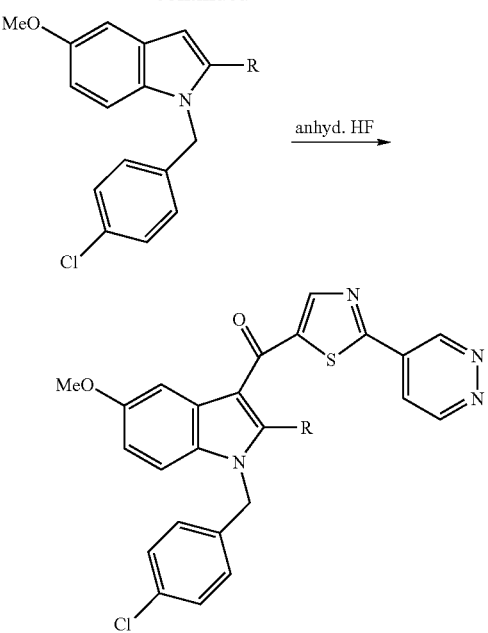
R = H, CH₃
See Hodgetts et al. Org. Lett. 2002, 4, 1363-1365.
See Hodgetts et al. Org. Lett. 2002, 4, 1363-1365. Starting material 341
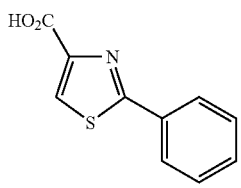
(CA registry no. 7113-10-2) is available from SynChem Inc. (Des Plaines, Ill., catalog no. SC-22021)
342
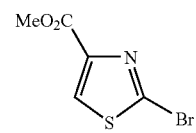
(CA registry no. 170235-26-4) is available from SynChem Inc. (Des Plaines, Ill., catalog no. SC-21789).
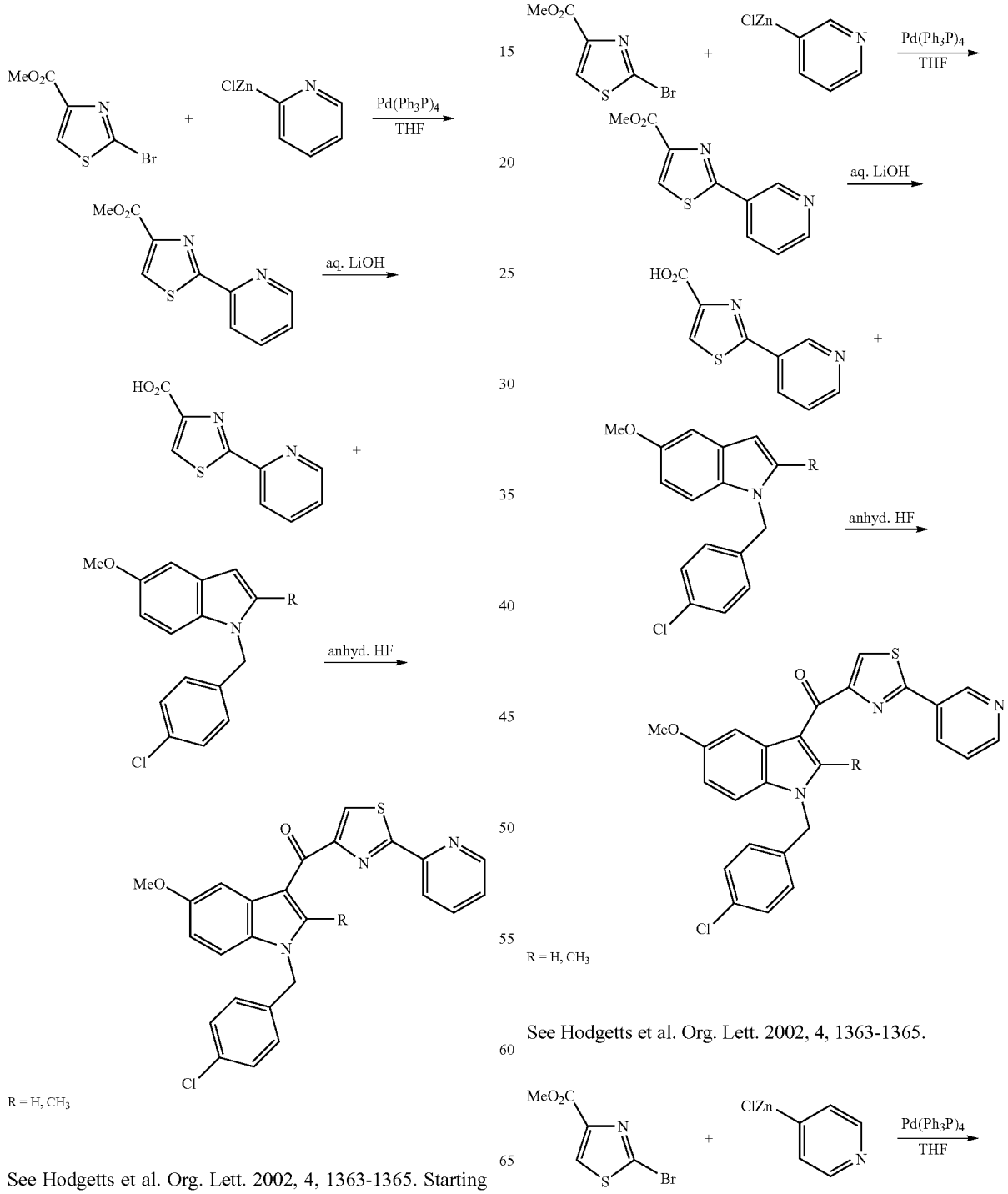
R = H, CH₃
See Hodgetts et al. Org. Lett. 2002, 4, 1363-1365. Starting material

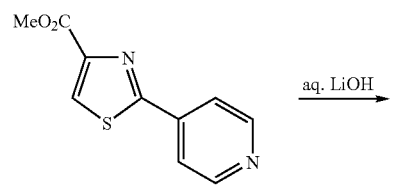
aq. LiOH →
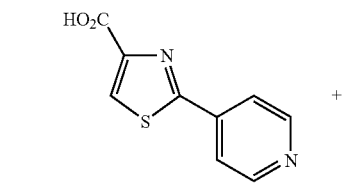
+
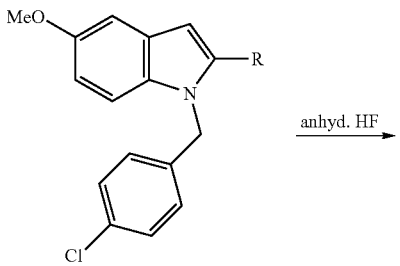
anhyd. HF →
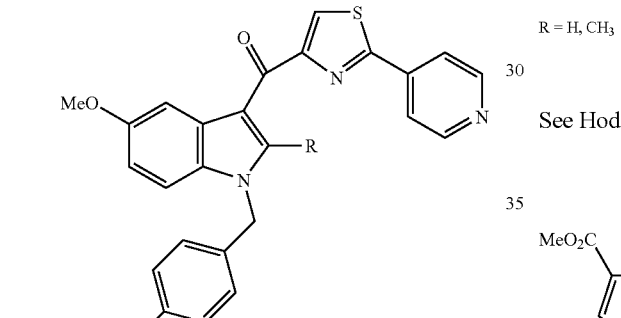
R = H, CH₃
See Hodgetts et al. Org. Lett. 2002, 4, 1363-1365.
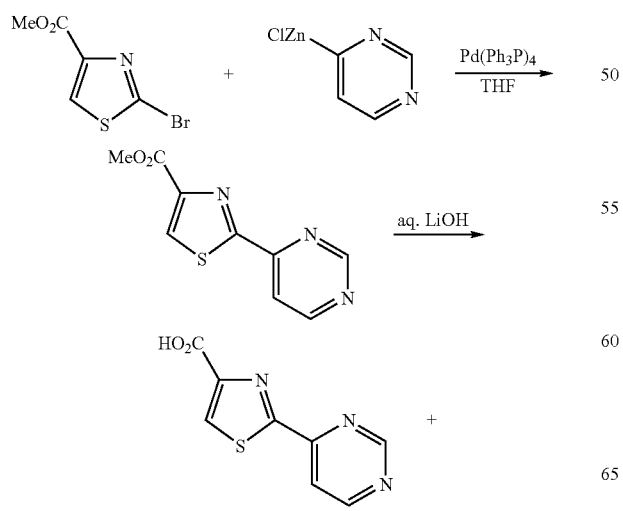
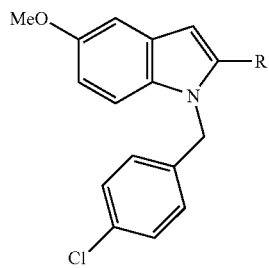
anhyd. HF →
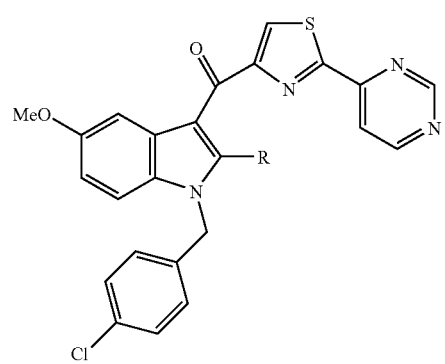
R = H, CH₃
See Hodgetts et al. Org. Lett. 2002, 4, 1363-1365.
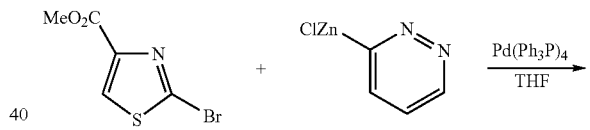
Pd(Ph₃P)₄ / THF →
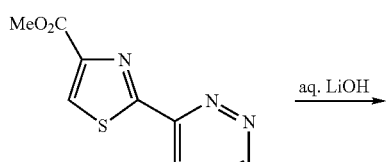
aq. LiOH →
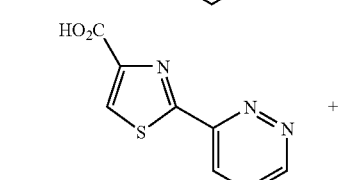
+
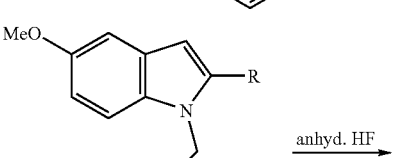
anhyd. HF →
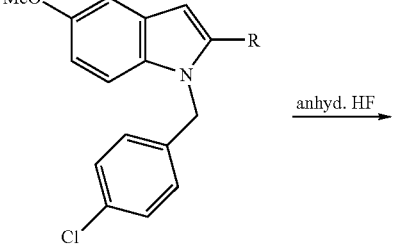

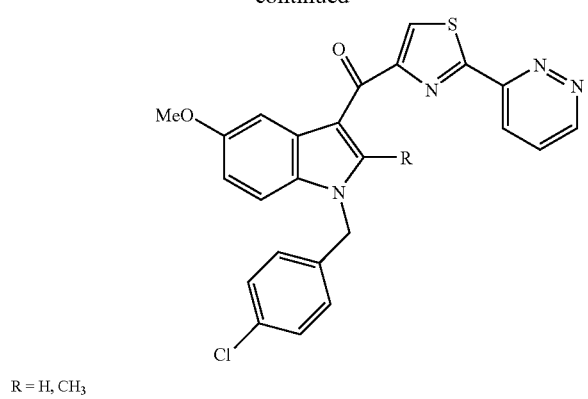
R = H, CH₃
See Hodgetts et al. Org. Lett. 2002, 4, 1363-1365.
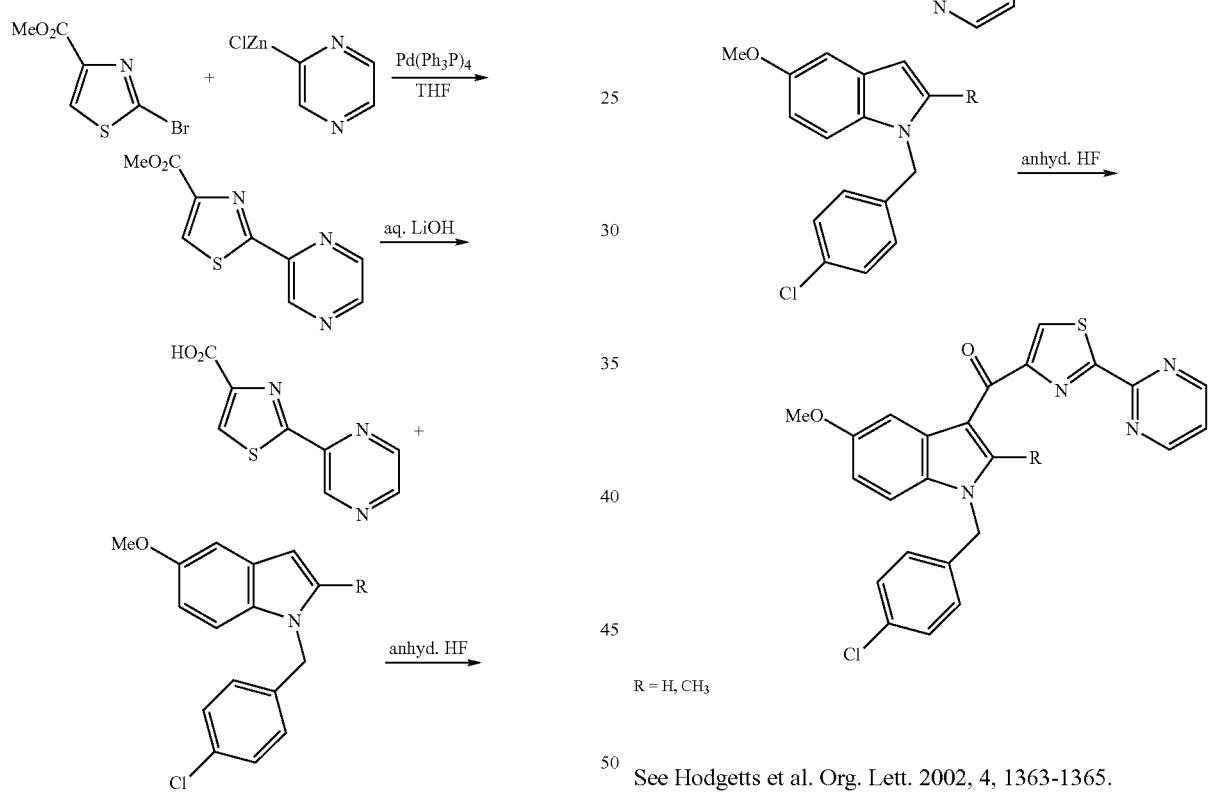
R = H, CH₃
See Hodgetts et al. Org. Lett. 2002, 4, 1363-1365.
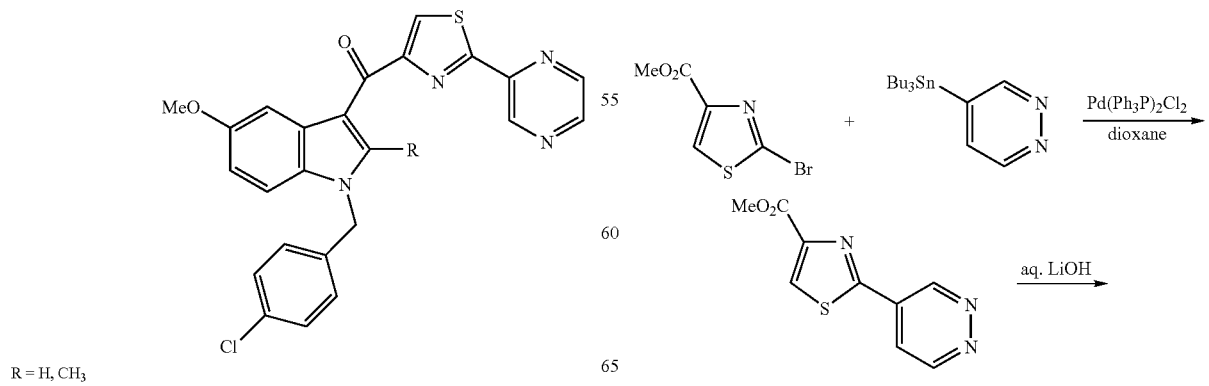

-continued

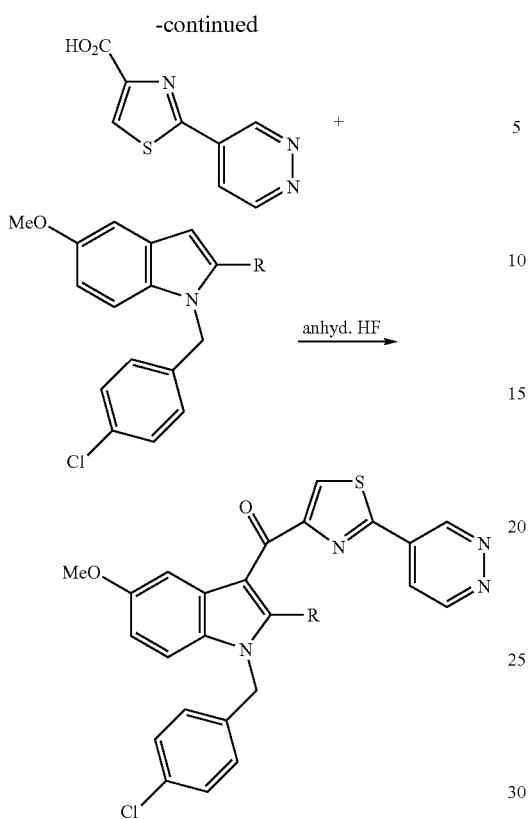

R = H, CH₃

See Hodgettts et al. Org. Lett. 2002, 4, 1363-1365.
Organo-lithium

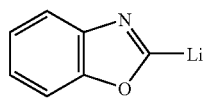

(CA Registry no. 86149-24-8) can be synthesized using the following reaction:

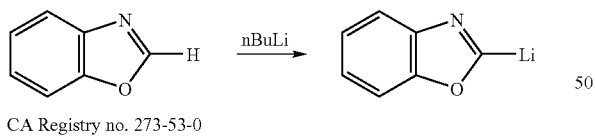

CA Registry no. 273-53-0 as described in Subramanyam and Chang Tetrahedron Letters 2002, 43, 6313-6315. CA Registry 273-53-0 is commercially available (Alfa Aesar, Ward Hill, Mass., catalog no. A17489)
Grignard reagent

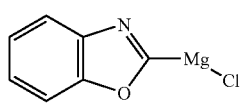

(CA Registry no. 126507-53-7) can be prepared using the methods described in WO2003087068. Although in most cases the organo-lithium derivative is shown, both organo-lithium and Grignard reagents can be prepared and used similarly in the subsequent 5 schema.

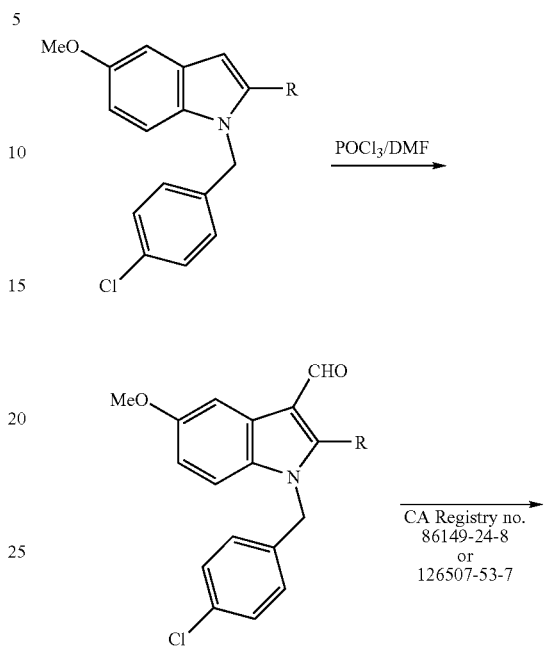

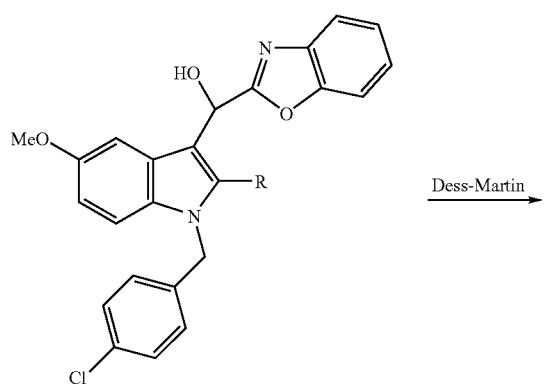

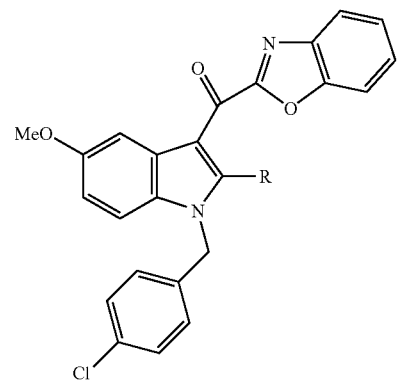

R = H, CH₃

See Boger et al. J. Med. Chem. 2005, 48, 1849-1856.

349
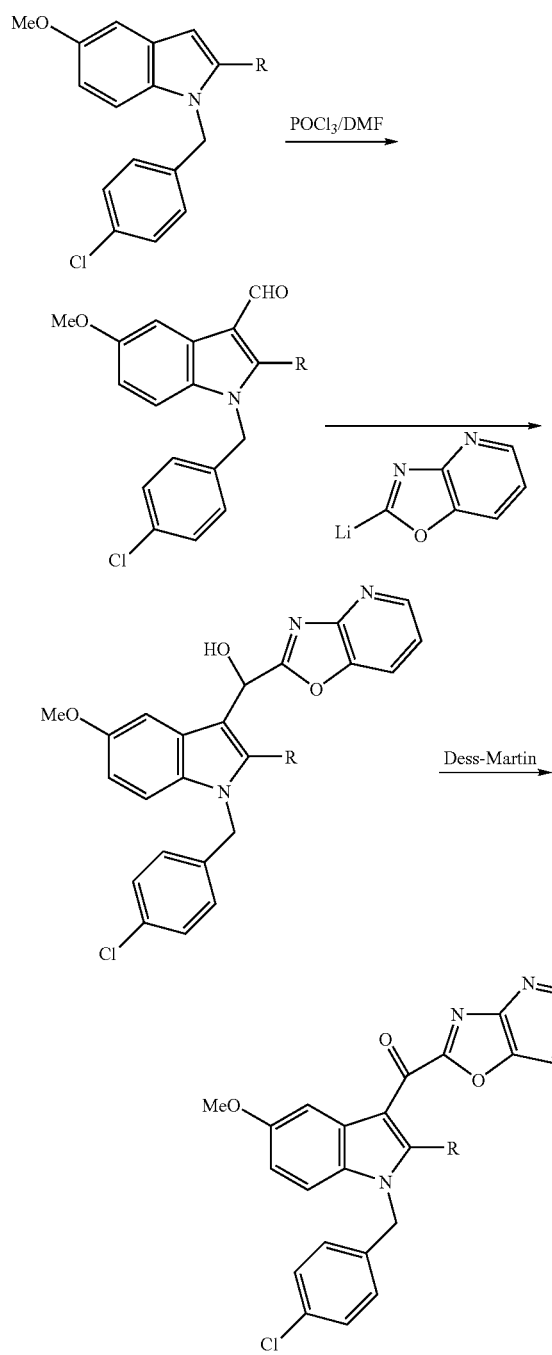
R = H, CH₃
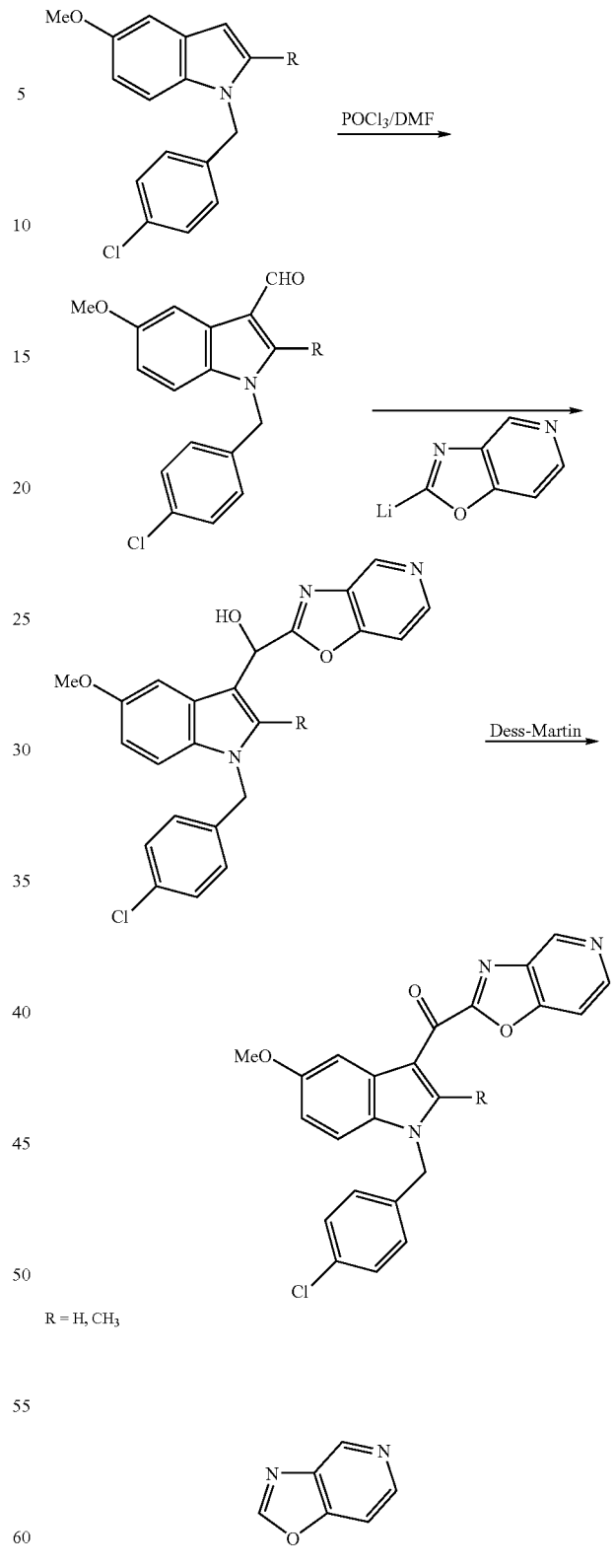
R = H, CH₃
350
is prepared as described in WO2003087068.
See Boger et al. J. Med. Chem. 2005, 48, 1849-1856 for general reaction schema.
(CA Registry no. 273-56-3) can be synthesized using the processes described in Katner and Brown Journal of Heterocyclic Chemistry 1990, 27, 563-536 and an organo-lithium derivative or Grignard derivative prepared as described above.

351
See Boger et al. J. Med. Chem. 2005, 48, 1849-1856 for general reaction schema.
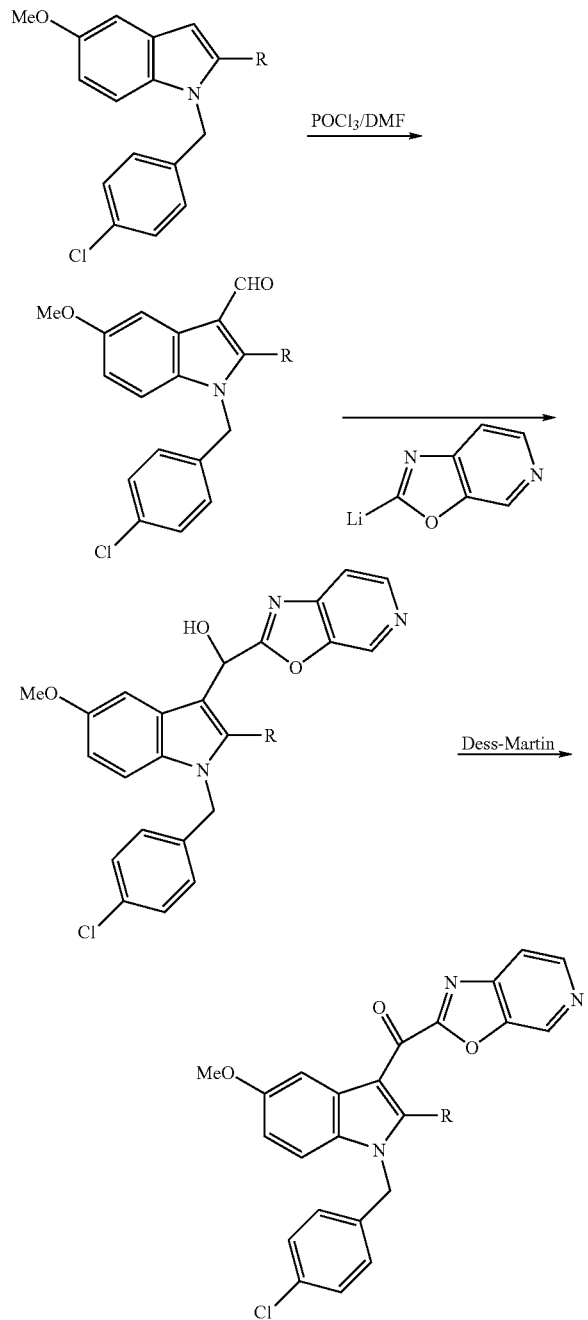
R = H, CH₃
is prepared as described in Heuser et al. Tetrahedron letters 2005, 46, 9001-9004.
352
See Boger et al. J. Med. Chem. 2005, 48, 1849-1856 for general reaction schema.
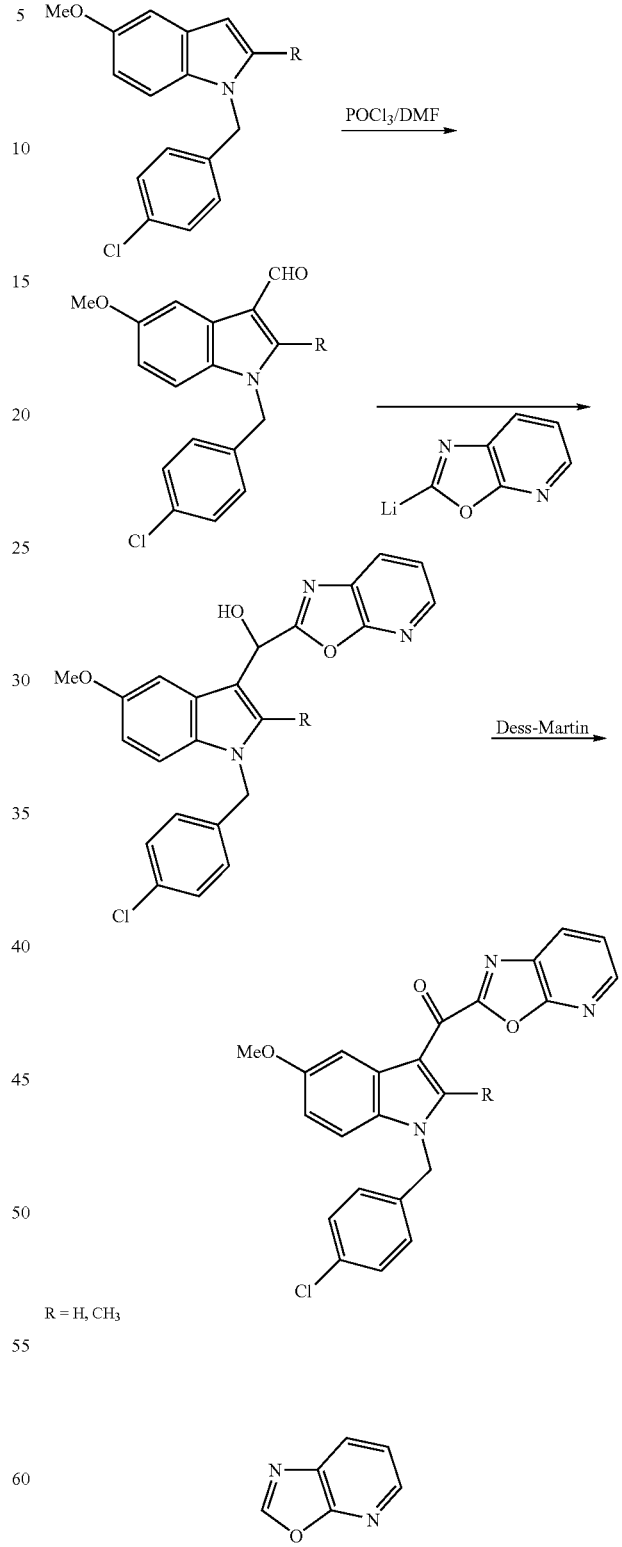
R = H, CH₃
(CA Registry no. 273-62-1) is prepared as described in Takahashi and Koshiro, Chemical & Pharmaceutical Bulletin 1959, 7, 720-725 and the organo-lithium derivative,

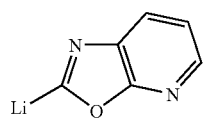
is prepared as described above.
See Boger et al. J. Med. Chem. 2005, 48, 1849-1856 for general reaction schema.
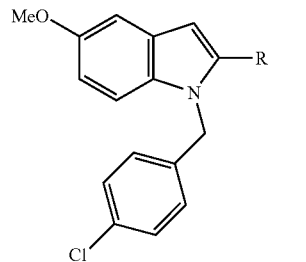
+
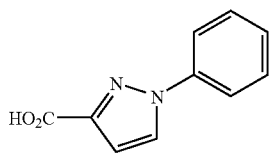
anhyd. HF →
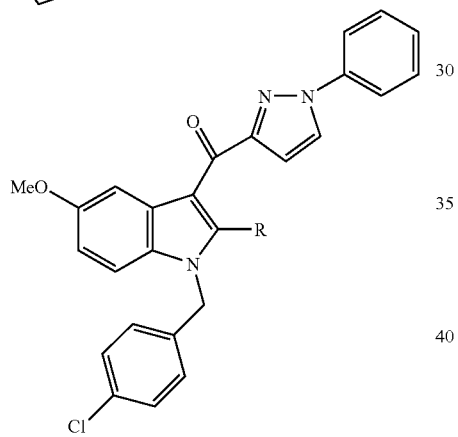
R = H, CH₃
For more information on starting material
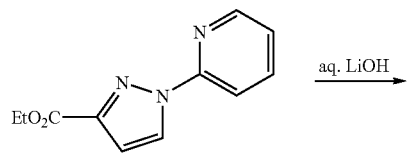
(CA registry no. 4747-46-0) see Tabak et al. Tetrahedron 1966, 22, 2703-2710.
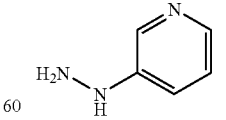
aq. LiOH →
-continued
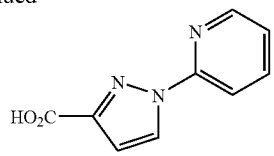
+
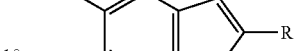
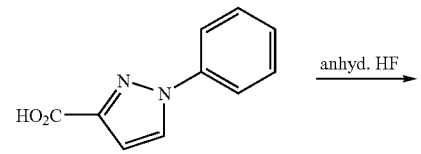
anhyd. HF →
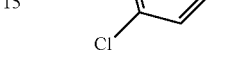
R = H, CH₃
For more information on starting material
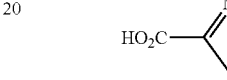
(CA Registry no. 154012-24-5) see Holzer and Seiringer Journal of Heterocyclic Chemistry 1993, 30, 865-872.
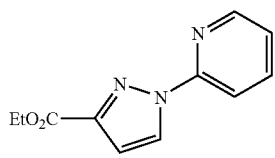

| 355 | 356 |
|---|---|
| -continued | -continued |

R = H, CH₃

Starting material (CA Registry No. 42166-50-7) is available from Beta Pharma, Inc. (New Haven, Conn., catalog no. 23097)

R = H, CH₃

Starting material (CA Registry no. 20815-52-5) is available from Prime Organics, Inc. (Lowell, Mass., catalog no. POI-58-21)

357 358
(CA Registry no. 22930-71-8) is available from Chemstep (Carbon Blanc, France, catalog no. 19541)
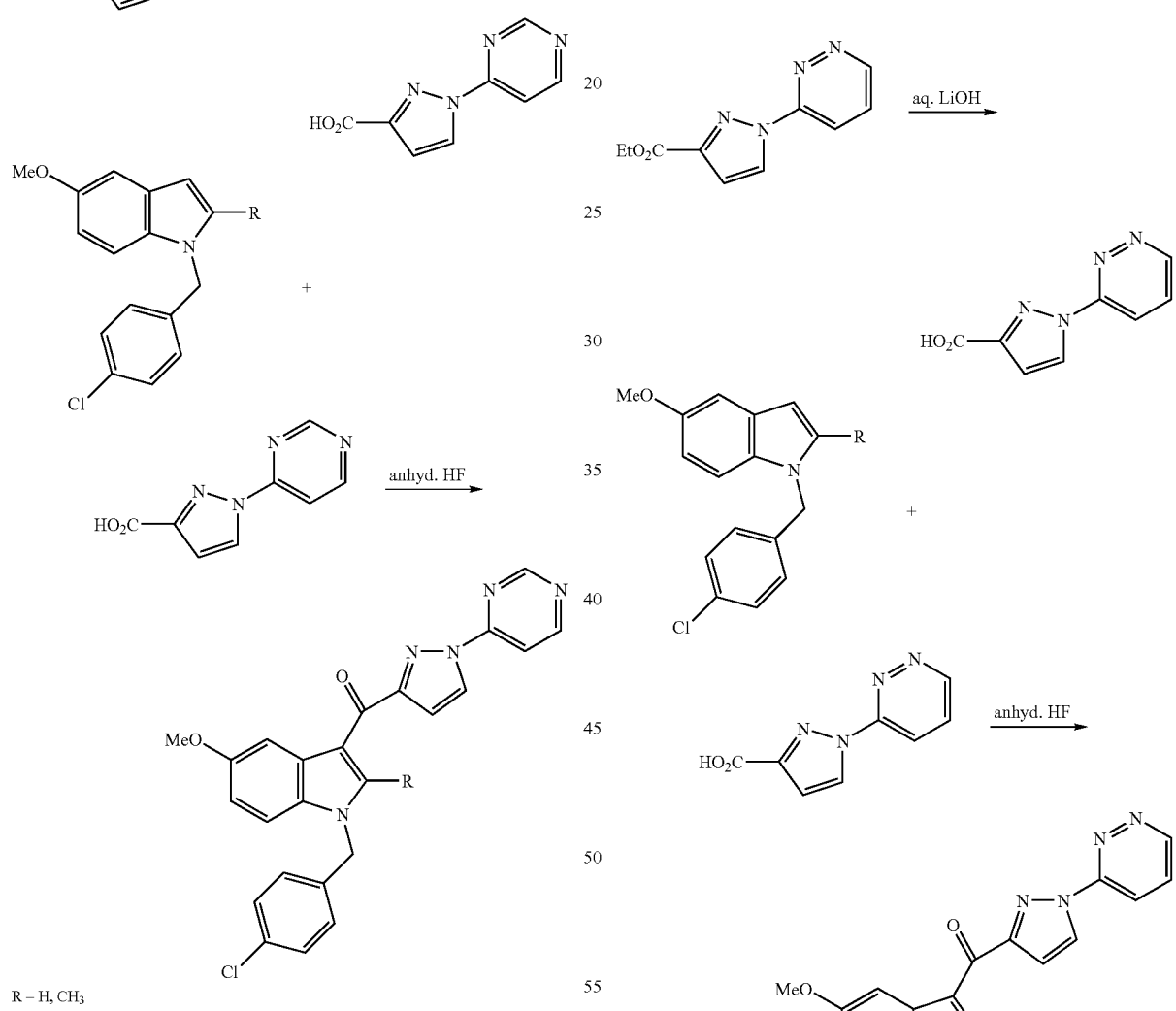
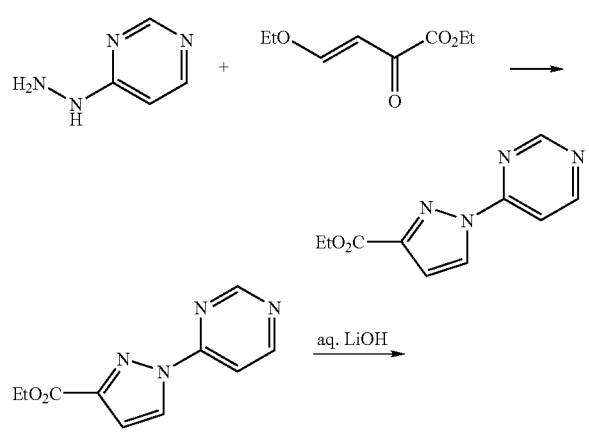
R = H, CH₃
Starting material
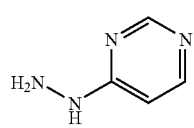
R = H, CH₃

359
For more information on starting material
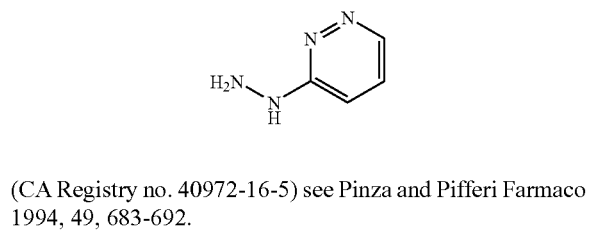
(CA Registry no. 40972-16-5) see Pinza and Pifferi Farmaco 1994, 49, 683-692.
360
For more information on starting material
(CA Registry no. 154012-27-8) see Holzer and Seiringer Journal of Heterocyclic Chemistry 1993, 30, 865-872.
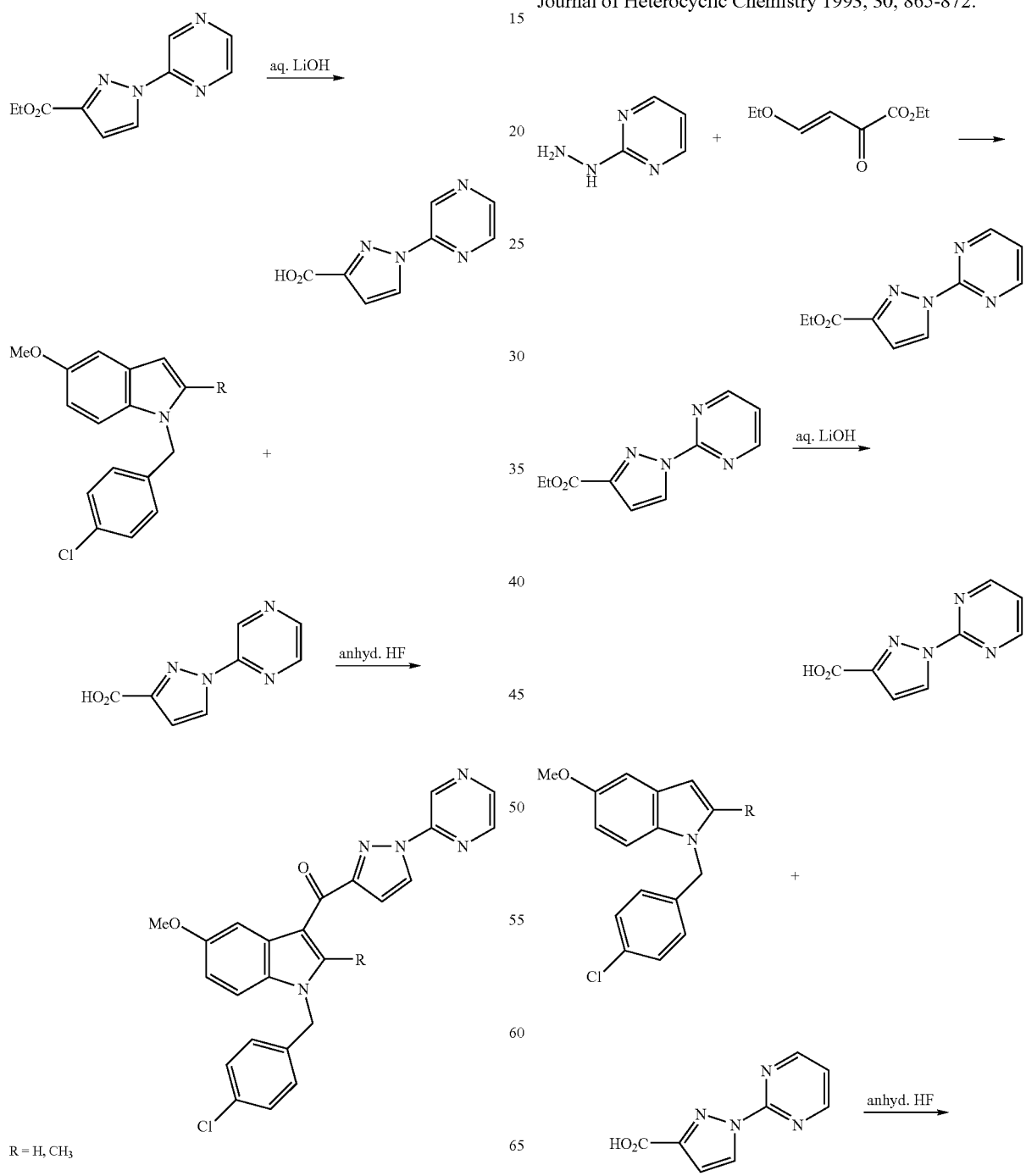
R = H, CH₃

361
-continued
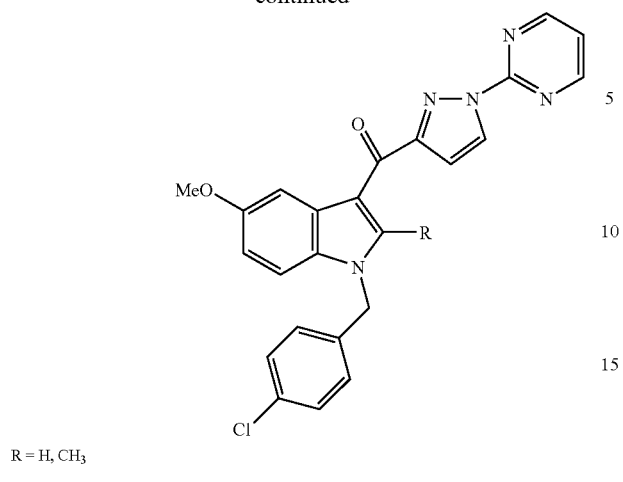
R = H, CH₃
Starting material
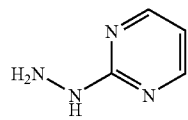
(CA Registry no. 7504-94-1) is available from Scientific Exchange, Inc. (Center Ossipee, N.H., catalog no. M-278979)
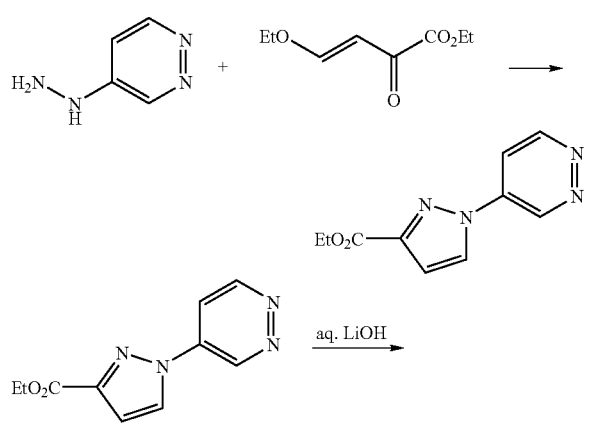
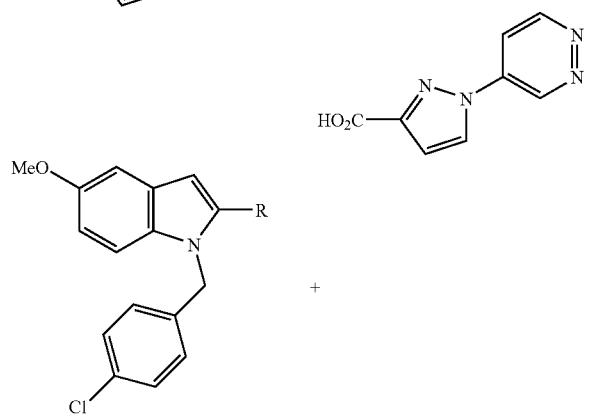
362
-continued
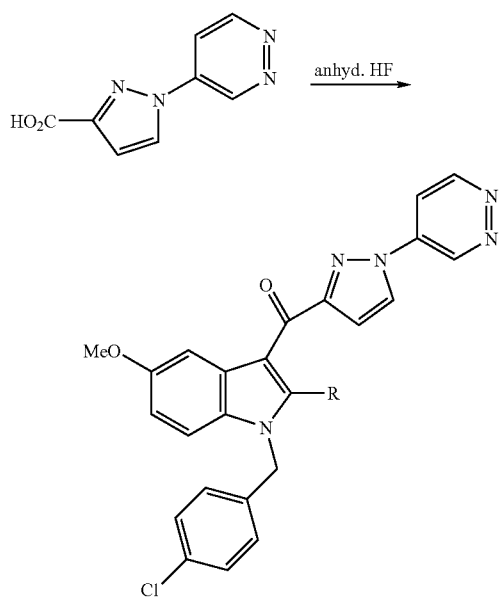
anhyd. HF
R = H, CH₃
For more information on starting material
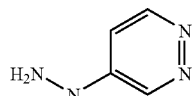
(CA Registry No. 103394-79-2) see Schuler and Wyss, E. Archives Internationales de Pharmacodynamie et de Therapie 1960, 128, 431-468.
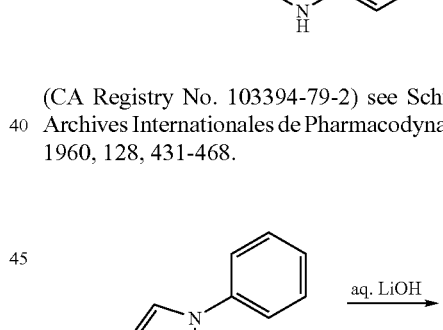
aq. LiOH
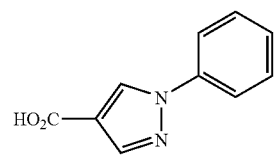
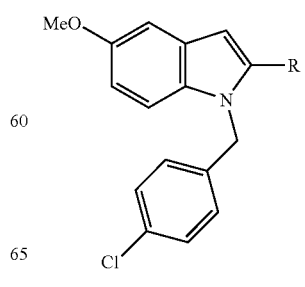
+

363
-continued
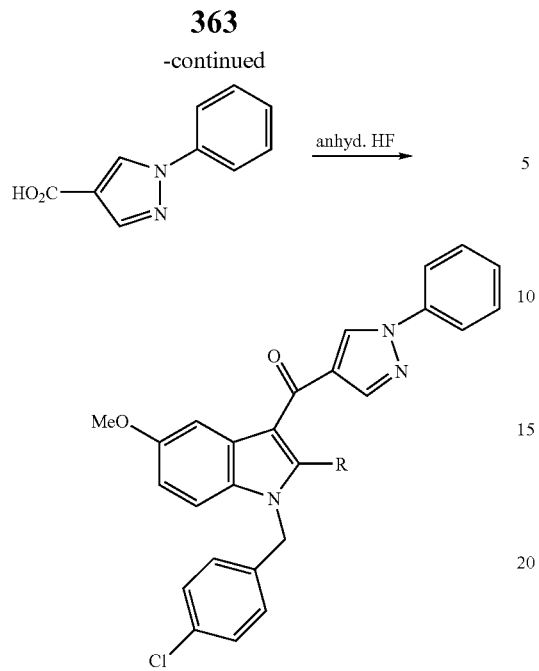
R = H, CH₃
For more information on starting material
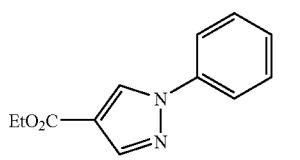
(CA Registry no. 885-94-9) see Holzer and Seiringer Journal of Heterocyclic Chemistry 1993, 30, 865-872.
364
-continued
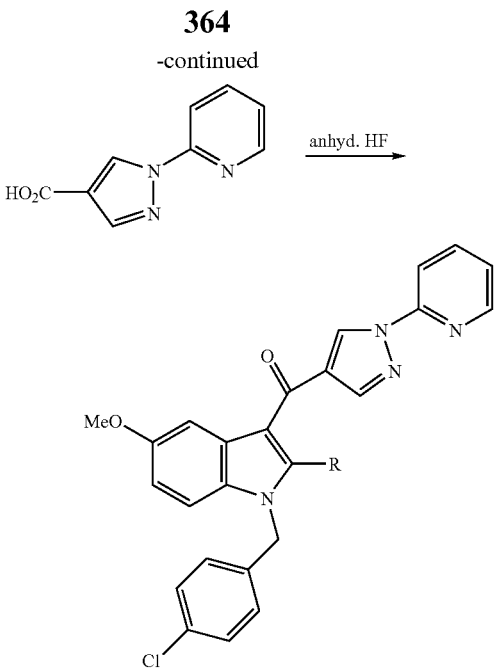
R = H, CH₃
For more information on starting material
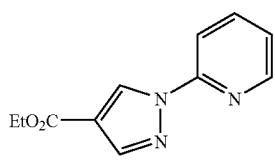
(CA Registry no. 171193-35-4) see: Holzer and Schmid Journal of Heterocyclic Chemistry 1995, 32, 1341-1349.
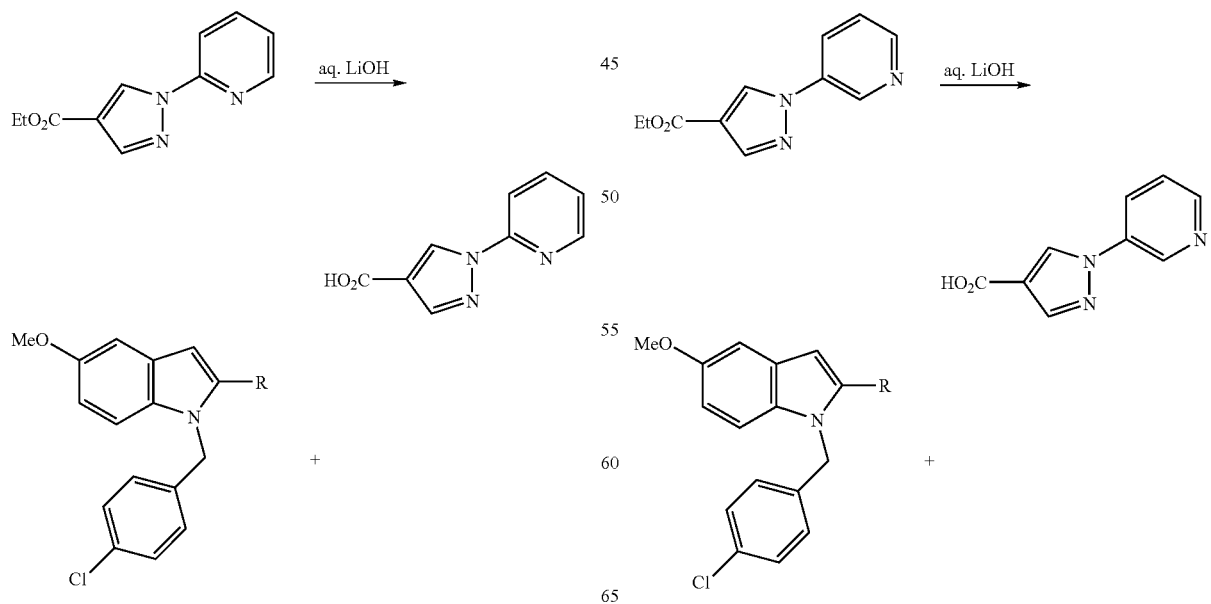

365
-continued
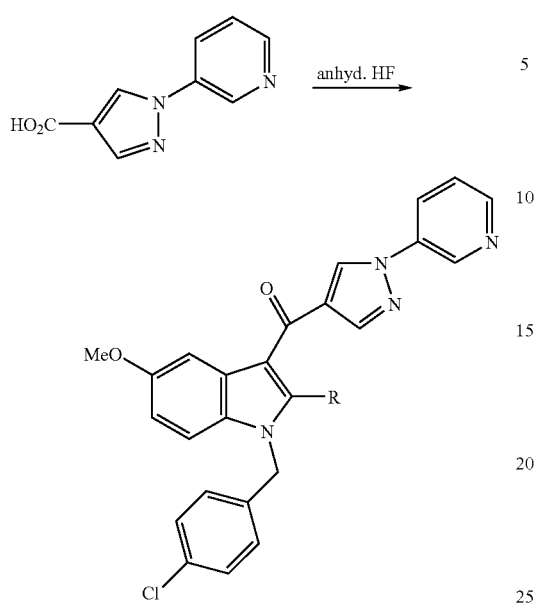
R = H, CH₃
For more information on starting material
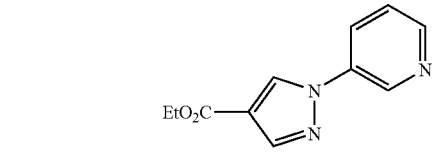
(CA Registry No. 74171-60-2) see Antilla et al. Journal of Organic Chemistry 2004, 69, 5578-5587.
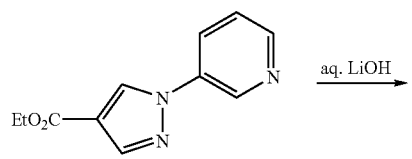
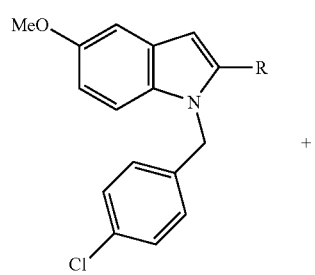
+
366
-continued
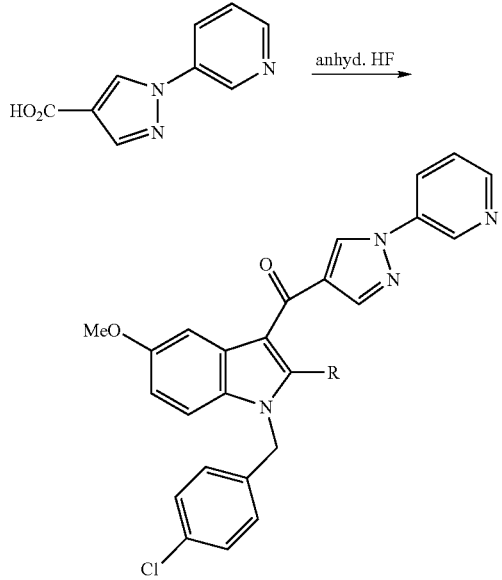
R = H, CH₃
Starting material
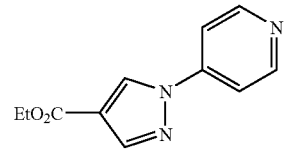
can be synthesized from the following reaction:
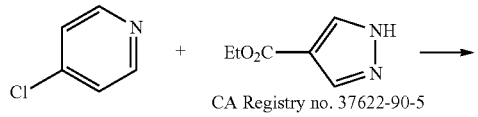
See Antilla et al. Journal of Organic Chemistry 2004, 69, 5578-5587 for more information.
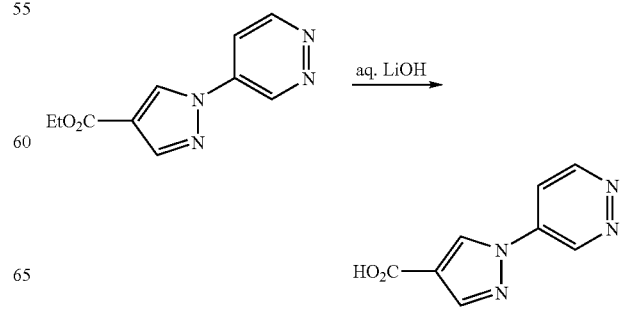

-continued
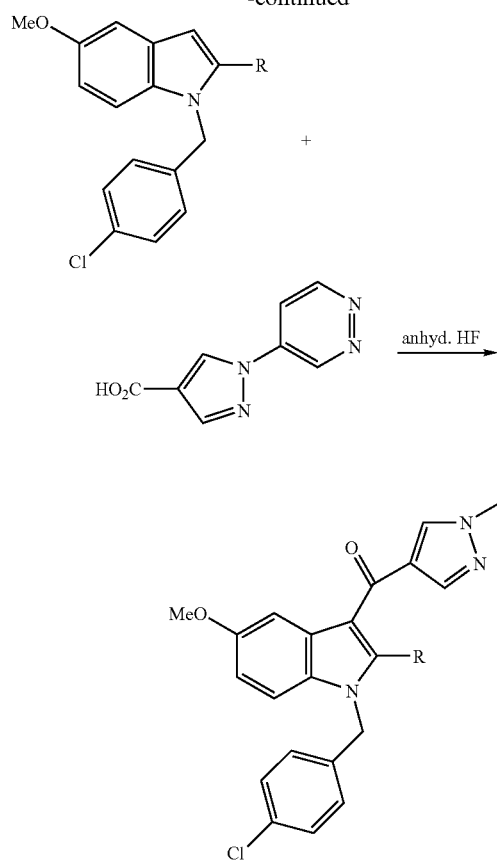
R = H, CH₃
Starting material
can be synthesized from the following reaction:
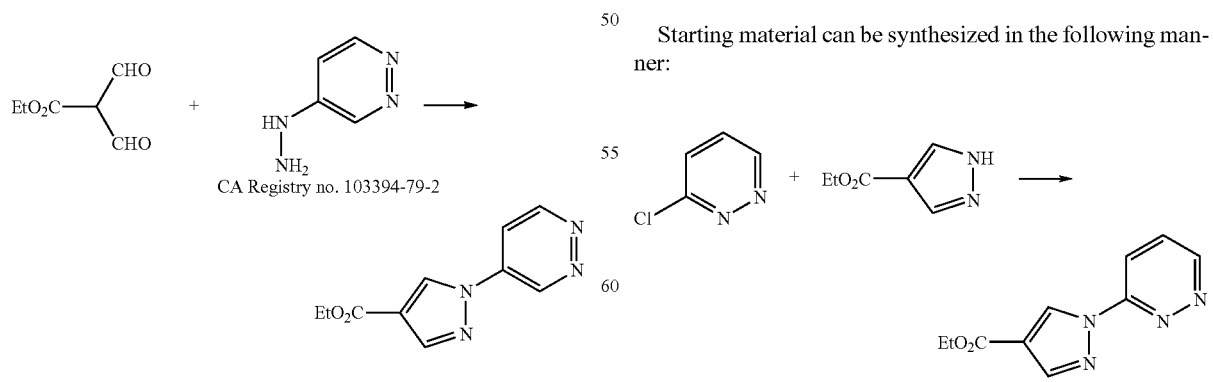
See Schuler et al. Archives Internationales e Pharmacodynamie et de Therapie 1960, 128, 431-468 for more information.
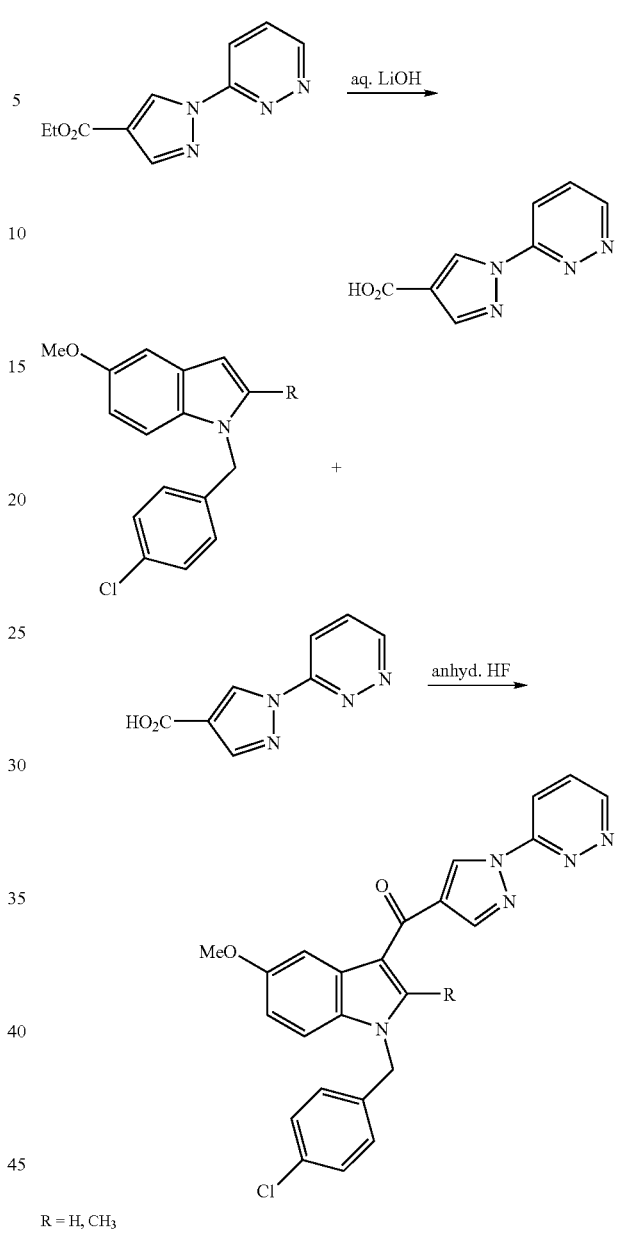
R = H, CH₃
Starting material can be synthesized in the following manner:
See Antilla et al. Journal of Organic Chemistry 2004, 69, 5578-5587 for more information.

369
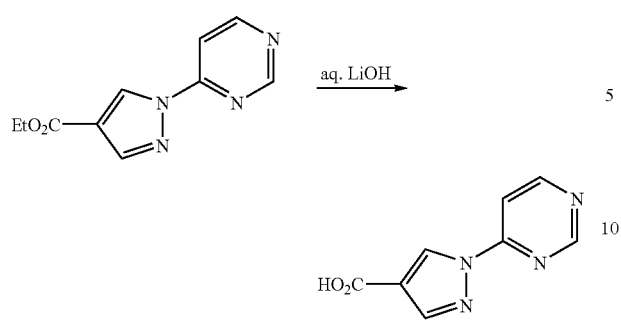
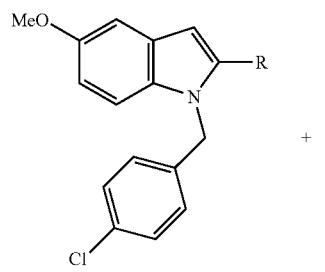
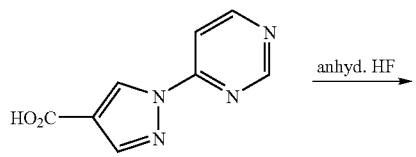
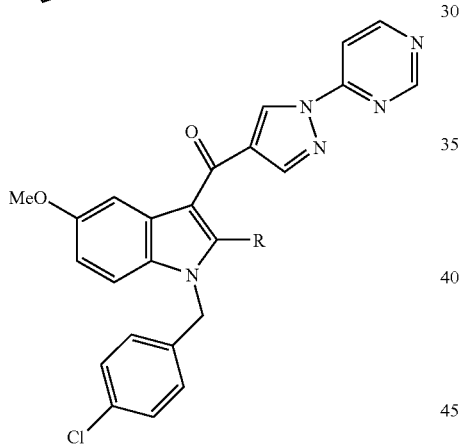
R = H, CH₃
Starting material can be synthesized in the following manner:
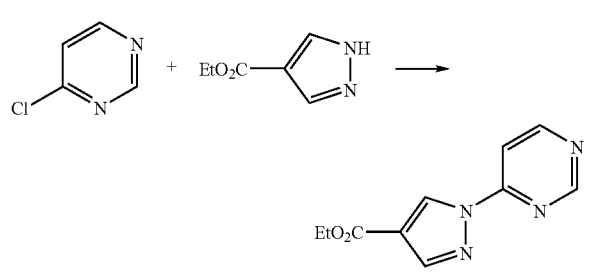
See Antilla et al. Journal of Organic Chemistry 2004, 69, 5578-5587 for more information.
370
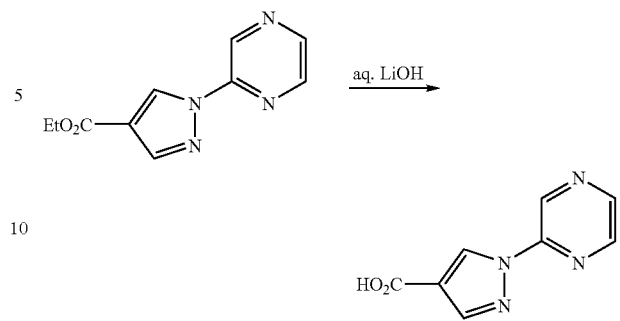
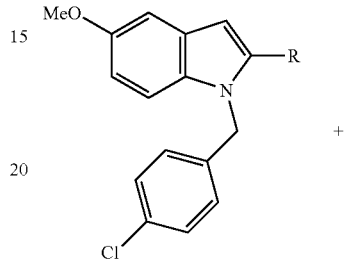
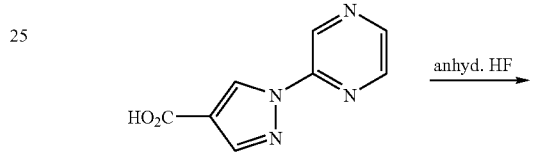
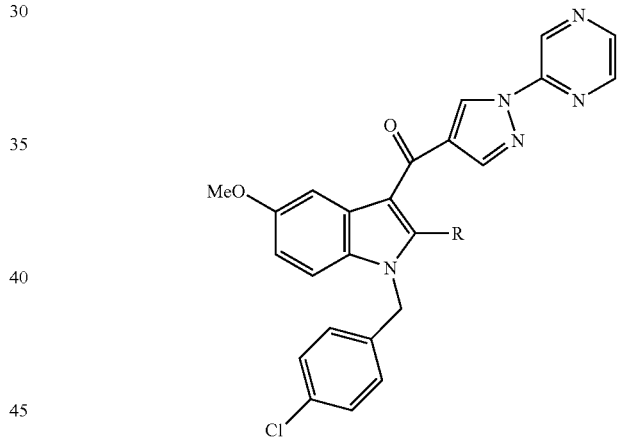
R = H, CH₃
Starting material can be synthesized in the following manner:
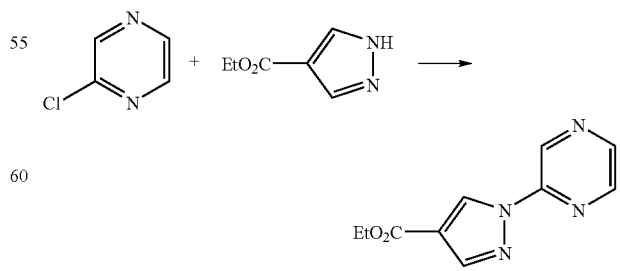
See: Antilla et al. Journal of Organic Chemistry 2004, 69, 5578-5587 for more information.

371
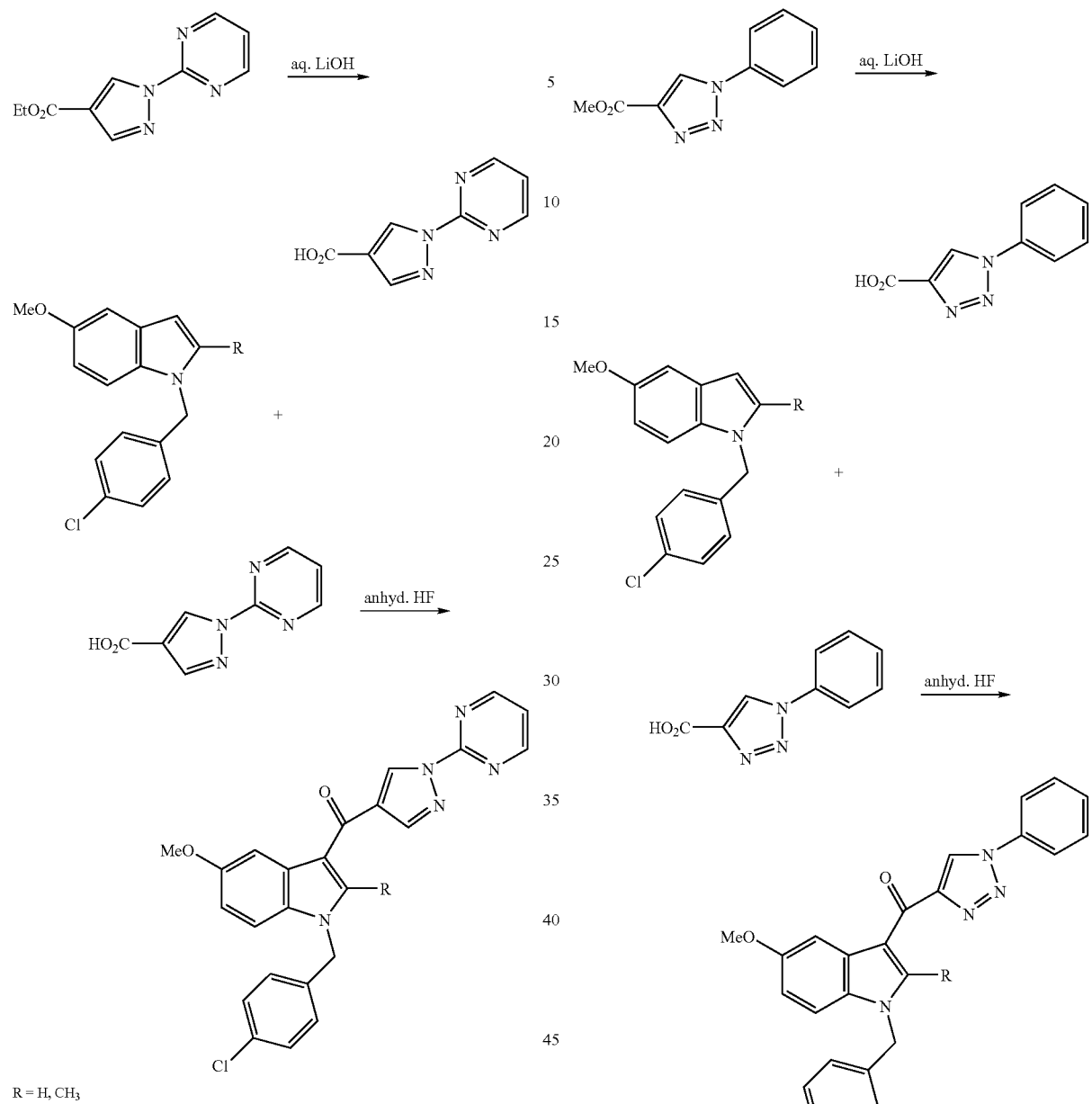
R = H, CH₃
Starting material can be synthesized in the following manner:
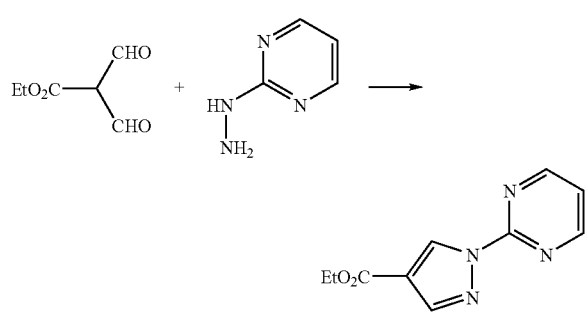
372
R = H, CH₃
for more information on starting material
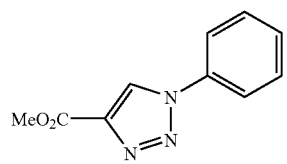
(CA Registry no. 2055-52-9) see Huisgen et al. Chemische Berichte 1965, 98, 4014-4021 and Fulloon et al. Journal of Organic Chemistry 1996, 61, 1363-1368.

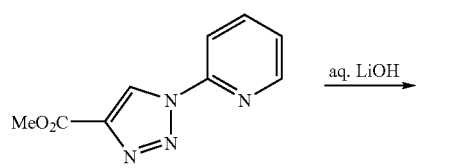
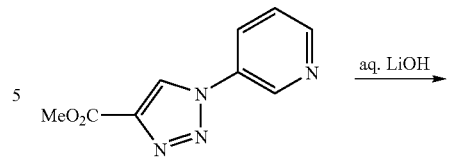
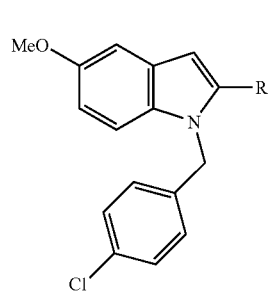
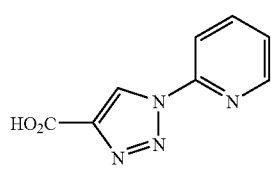
+
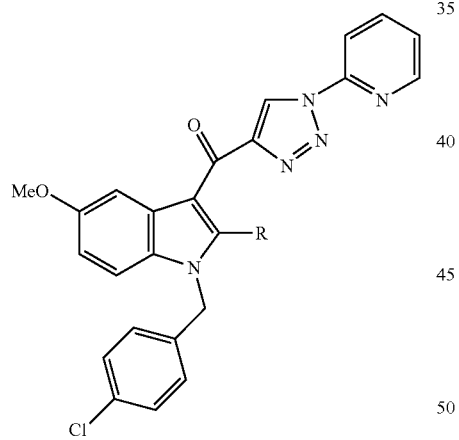
R = H, CH₃
For more information on starting material
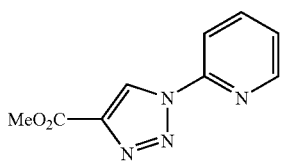
(CA Registry No. 23947-14-0) see Huisgen et al. Tetrahedron Letters 1969, 30, 2589-2594.
R = H, CH₃
Starting material can be synthesized in the following manner:
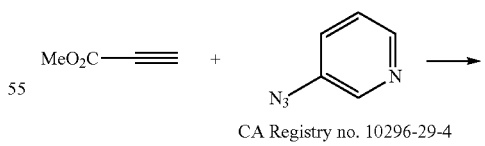
CA Registry no. 10296-29-4
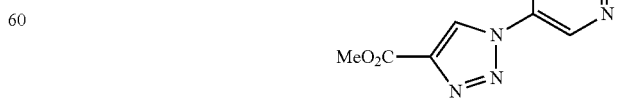
For more information regarding CA Registry no. 10296-29-4 see Dyall et al. Australian Journal of Chemistry 1996, 49, 761-765.

375
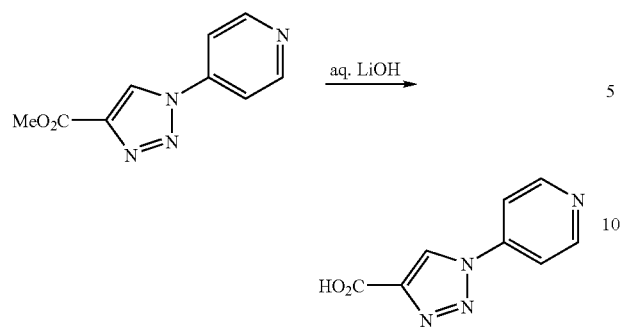
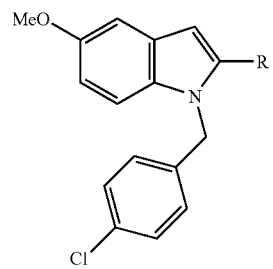
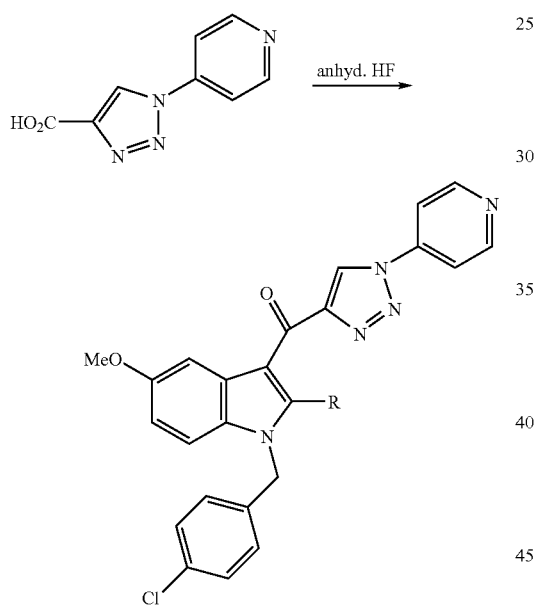
R = H, CH₃
See L'abbe and Beenaerts Tetrahedron 1989, 45, 749-756. The starting material can be obtained using the following reaction:
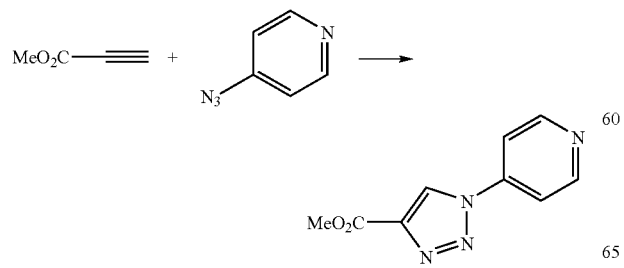
376
See Huisgen, et al. Tetrahedron Letters 1969, 30, 2589-2594.
The following reaction can be used to obtain the starting material:
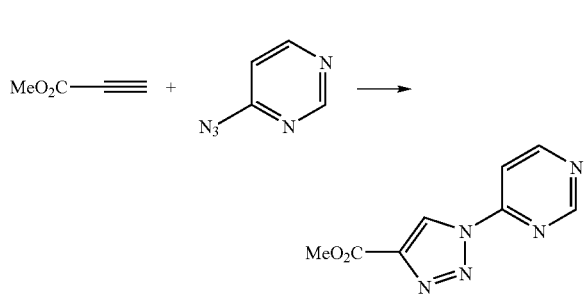

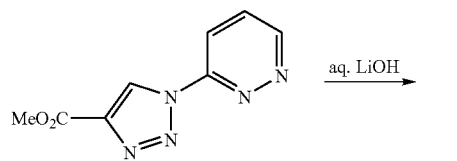
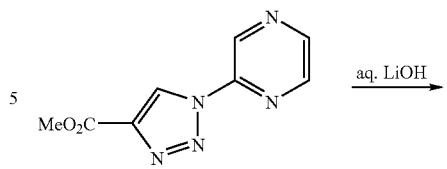
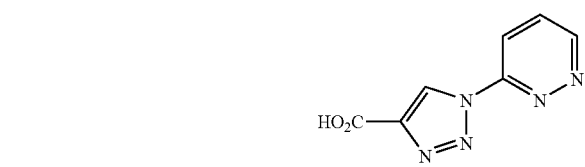
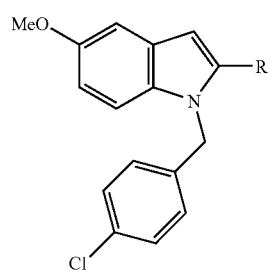
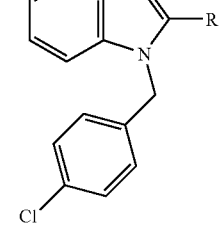
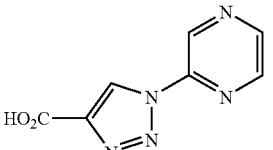
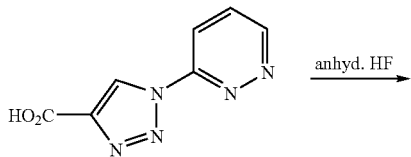
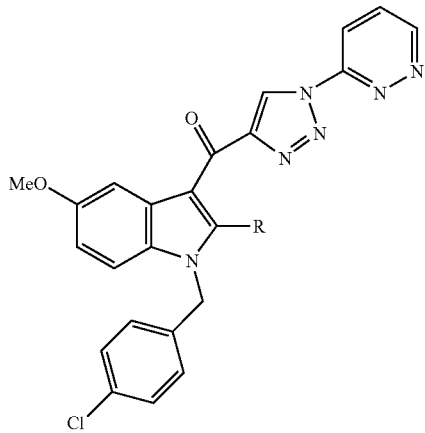
R = H, CH₃
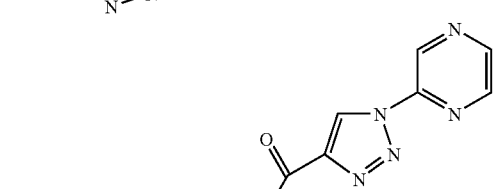
R = H, CH₃
For information regarding the starting material
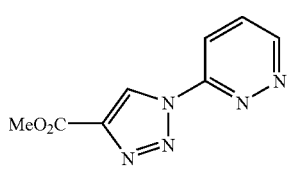
(CA Registry no. 512777-87-6) see Japelj et al. Journal of Heterocyclic Chemistry 2005, 42, 1167-1173.
See Huisgen et al. Tetrahedron Letters 1969, 30, 2589-2594. The starting material can be obtained by the following reaction:
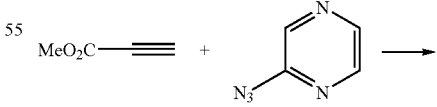
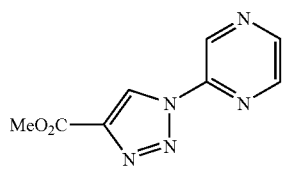
General method for the preparation of 1,2,4-oxadiazole containing ketone derivatives

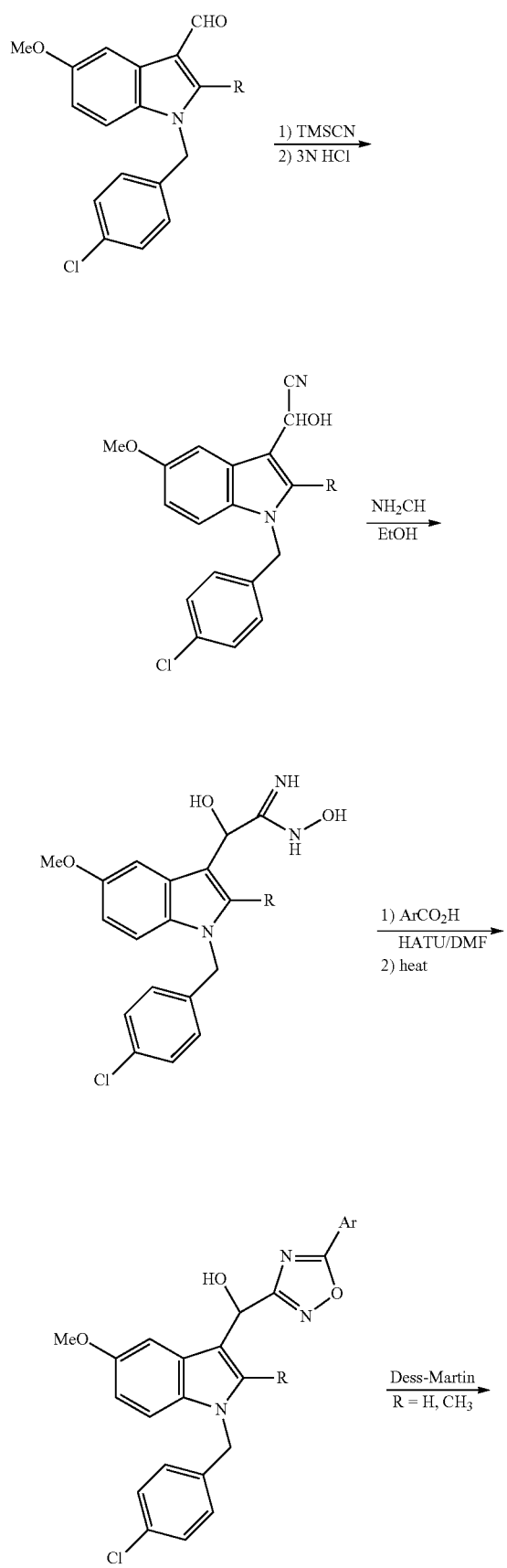

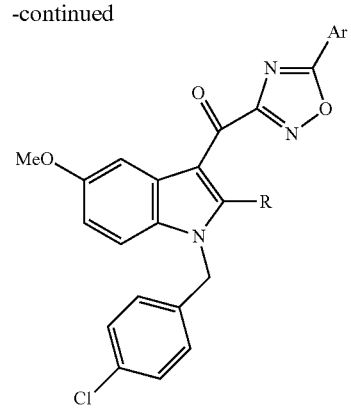

R = H, CH₃

In this schema, HATU is O-(7-Azabenzotriazole-1-yl)-N,N,N'N'-tetramethyluronium hexafluorophosphate (CA Registry no. 148893-10-1), TMSCN is Me₃SiCN (7677-24-9) and Dess-Martin is Periodinane (CA Registry no. 87413-09-0). Also see Lee et al Biorg. Med. Chem. Lett. 2006, 16, 4036-4040.

Other useful syntheses are found in Nazare et al. Angew. Chem. Int. Ed. 2004, 43, 4526-4528 and patent publication WO9303022 (including the syntheses described in examples 1-428.

Labels

It will be recognized that the compounds of this invention can exist in forms in which one isotope of a particular atom may be replaced with a different isotope of that same atom. For example, "hydrogen" may be $^1H$, $^2H$ or $^3H$; "carbon" may be $^{12}C$, $^{13}C$, or $^{14}C$; "nitrogen" may be $^{14}N$ or $^{15}N$; "oxygen" may be $^{16}O$, $^{17}O$ or $^{18}O$; and the like. It will be recognized that the compounds of this invention can exist in radiolabeled form, i.e., the compounds may contain one or more atoms containing an atomic mass or mass number different from the atomic mass or mass number usually found in nature. Radioisotopes of hydrogen, carbon, phosphorous, fluorine, iodine and chlorine include $^3H$, $^{14}C$, $^{35}S$, $^{18}F$, $^{32}P$, $^{33}P$, $^{125}I$, and $^{36}Cl$, respectively. Compounds that contain those radioisotopes and/or other radioisotopes of other atoms are within the scope of this invention. Tritiated, i.e. $^3H$, and carbon-14, i.e., $^{14}C$, radioisotopes are particularly preferred for their ease in preparation and detectability. Radiolabeled compounds described herein and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

The labels can be primary labels (where the label comprises an element which is detected directly) or secondary labels (where the detected label binds to a primary label, e.g., as in common in immunological labeling). An introduction to labels, labeling procedures and detection of labels is found in *Introduction to Immunocytochemistry*, (2d ed.) Polak and Van Noorden., Springer Verlag, N.Y. (1997) and in *Handbook of Fluorescent Probes and Research Chemicals*, Haugland (1996), a combined handbook and catalogue published by Molecular Probes, Inc., Eugene, Oreg. primary and secondary labels can include undetected elements as well as detected elements. Useful primary and secondary labels in the present invention can include spectral labels, which include fluorescent labels such as fluorescent dyes (e.g., fluorescein and derivatives such as fluorescein isothiocyanate (FITC) and Oregon Green™, rhodamine and derivatives (e.g., Texas red, tetramethylrhodamine isothiocyanate (TRITC), etc.), digoxigenin, biotin, phycoerythrin, AMCA, CyDyes™ and the like), radiolabels (including those described above), enzymes (e.g., horseradish peroxidase, alkaline phosphatase etc.) spectral colorimetric labels such as colloidal gold or colored glass or plastic (e.g. polystyrene, polypropylene, latex, etc.) beads. The label may be coupled directly or indirectly to a compound described herein according to methods well known in the art. As indicated above, a wide variety of labels may be used, with the choice of label depending on sensitivity required, ease of conjugation with the compound, stability requirements, available instrumentation, and disposal provisions. In general, a detector which monitors a protein/inhibitory agent interaction is adapted to the particular label which is used.

Typical detectors include spectrophotometers, phototubes and photodiodes, microscopes, scintillation counters, cameras, film and the like, as well as combinations thereof. Examples of suitable detectors are widely available from a variety of commercial sources known to persons of skill.

Nonlimiting examples of labels include those which utilize 1) chemiluminescence (using horseradish peroxidase or alkaline phosphatase with substrates that produce photons as breakdown products) with kits being available, e.g., from Molecular Probes, Amersham, Boehringer-Mannheim, and Life Technologies/Gibco BRL; 2) color production (using both horseradish peroxidase or alkaline phosphatase with substrates that produce a colored precipitate (kits available from Life Technologies/Gibco BRL, and Boehringer-Mannheim); 3) fluorescence (e.g., using Cy-5 (Amersham), fluorescein, and other fluorescent tags); and 4) radioactivity. Other methods for labeling and detection will be readily apparent to one skilled in the art.

In one embodiment, the label is a fluorescent label. Fluorescent labels have the advantage of requiring fewer precautions in handling, and being amenable to high-throughput visualization techniques (optical analysis including digitization of the image for analysis in an integrated system comprising a computer). Preferred labels are typically characterized by one or more of the following: high sensitivity, high stability, low background, low environmental sensitivity and high specificity in labeling. Fluorescent moieties, which are incorporated into the labels of the invention, are generally are known, including Texas red, digoxigenin, biotin, 1- and 2-aminonaphthalene, p,p'-diaminostilbenes, pyrenes, quaternary phenanthridine salts, 9-aminoacridines, p,p'-diaminobenzophenone imines, anthracenes, oxacarbocyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidazolylphenylamine, 2-oxo-3-chromen, indole, xanthen, 7-hydroxycoumarin, phenoxazine, calicylate, strophanthidin, porphyrins, triarylmethanes, flavin and many others. Many fluorescent tags are commercially available from the SIGMA chemical company (St. Louis, Mo.), Molecular Probes, R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka ChemicaBiochemika Analytika (Fluka Chemie AG, Buchs, Switzerland), and Applied Biosystems (Foster City, Calif.), as well as many other commercial sources known to one of skill.

The labels may be covalently bound to the compounds described herein by a tether group. The tether group can be any moiety capable of covalently linking to the compounds and to the labels. Preferred groups are substituted or unsubstituted alkylene, alkenylene or alkynylene of 1 to 10 carbon atoms, more preferably 1 to 4 carbon atoms. Particularly preferred groups are unsubstituted alkynylenes.

Methods for Assessing Activity In Vitro and In Vivo

COX Related Assays

COX-1 and COX-2 Inhibition: Purified Enzyme Assays

The in vitro COX-1 and COX-2 inhibitory activity of the compounds described herein can be measured using a test kit available from Cayman Chemical (Ann Arbor, Mich.) Because COX-1 and COX-2 convert arachidonic acid to prostaglandin $H_2$ ($PGH_2$), one can assess COX inhibitory activity of a test compound by measuring the effect of the compound on $PGH_2$ production in the presence of purified COX-1 enzyme and in the presence of purified COX-2 enzyme. In this assay, the production of $PGH_2$ can be measured by reducing $PGH_2$ to prostaglandin $F_{2\alpha}$ ($PGF_{2\alpha}$) with $SnCl_2$ and then detecting $PGF_{2\alpha}$ by enzyme immunoassay (EIA) using a suitable antibody.

COX-1 and COX-2 Inhibition: Human Whole Blood Assay

A human whole blood assay can also used to measure the inhibitory activity of each compound on COX-1 and COX-2. Briefly, human whole blood is drawn from 3-6 healthy volunteers who have not taken NSAIDS the previous 2 weeks. To measure COX-1 activity in whole blood, 100 µl of whole blood is combined with a 2 µl aliquot of test compound in vehicle or vehicle alone and incubated for 1 hour at 37° C. as described by Berg et al. (1999 *Inflamm. Res.* 48, 369-379). Serum is isolated from the sample by centrifugation at 12,000 g for 5 minutes at 4° C. and then assayed for thromboxane B2 (TXB2) levels using an ELISA assay (e.g., Cayman EIA Kit Catalog Number 519031). To measure COX-2 activity in whole blood, 100 µl of heparinized whole blood is combined with a 1 µl aliquot of 10 mg/mL LPS (lipopolysaccharide) and a 2 µl aliquot of test compound in vehicle or vehicle alone and incubated for 24 hours at 37° C. as described by Berg et al. (supra). Serum is isolated from the sample by centrifugation at 12,000 g for 5 minutes at 4° C. and assayed for prostaglandin $E_2$ ($PGE_2$) using an ELISA assay (e.g., Cayman EIA Kit, catalog Number 514010).

In the Cox-1 and Cox-2 assays 1-(4-chlorobenzoyl)-5-methoxy-2-methyl-1H-indol-3-yl]acetic acid (indomethacin), a non-selective Cox inhibitor was used as a control. The Cox-2 selective inhibitors, 4-[5-(4-methylphenyl)-3-(trifluoromethyl)-1H-pyrazol-1-y]benzenesulfonamide (Celecoxib), 4-(5-methyl-3-phenylisoxazol-4-yl)benzenesulfonamide (valdecoxib), and 4-[4-(methylsulfonyl)phenyl]-3-phenylfuran-2(5H)-one (rofecoxib) were also used as controls.

FAAH Related Assays

FAAH Inhibition: Human Whole Cell Assay and Rat and Human Brain Homogenate Assays The ability of compounds to inhibit FAAH can be measured in human whole cell and human and rodent brain homogenates as described herein.

FAAH Rat Brain Membrane (RBM) Homogenate Preparation

Adult rats (Charles River CD strain, female, 200 g) are anaesthetized with isofluorane and rapidly decapitated, respectively. Each brain is quickly removed and chilled in tubes (3 brains per tube) on ice. About 25 mL of "homogenization buffer" (20 mM HEPES buffer, pH 7.0, with 1 mM $MgCl_2$) is added to 15 to 20 g of brain. The brains are homogenized on ice for 1 minute using an Omni GLH homogenizer (Omni International, Marietta, Ga.). The homogenates are transferred to three centrifuge tubes and centrifuged at 36,500 g for 20 minutes at 4° C. The supernatant is discarded and each pellet is re-suspended in 25 mL "homogenization buffer". The re-suspended material is again centrifuged (36,500 g, for 20 minutes at 4° C.). Pellets are combined by resuspension in 10 mL of "homogenization buffer" and incubated in a 37° C. water bath for 15 minutes. The tubes are then placed on ice for 5 minutes followed by centrifugation at 36,500 g for 20 minutes at 4° C. The supernatant is discarded and the membrane pellets are then re-suspended in 40 mL of "resuspension buffer" (50 mM Tris-HCl buffer, pH 7.4, containing 1 mM EDTA and 3 mM $MgCl_2$). A Bradford Protein assay is performed to determine protein concentration. The protein is aliquotted into screw cap Cryo tubes each containing ~400 µL, flash frozen in liquid nitrogen and stored at −80° C. until used for the assay. A similar protocol can be used to obtain brain membrane homogenates from mice.

FAAH Human Brain Membrane (HBM) Homogenate Preparation

About 10 g of frozen normal human brain cortex tissue is obtained (e.g., from Analytical Biological Services (ABS), Inc. (Wilmington, Del.)). The brain tissue is thawed and transferred to a large ceramic mortar on ice. 50 mL of ice-cold "homogenization buffer" (20 mM HEPES buffer, pH 7.0, with 1 mM $MgCl_2$) is added to the mortar and the tissue is homogenized with a pestle. The homogenate is centrifuged at 36,500 g for 20 minutes at 4° C. The supernatants are discarded and the pellets are re-suspended in "homogenization buffer" and centrifuged as before. The supernatants are again discarded and the pellets are re-suspended in 30 mL homogenization buffer and incubated in a 37° C. water bath for 20 minutes. The homogenate is then centrifuged as before. The supernatant is discarded and the membrane pellets are re-suspended in 30 mL "resuspension buffer" (50 mM Tris-HCl buffer, pH 7.4, containing 1 mM EDTA and 3 mM $MgCl_2$). A Bradford Protein assay is performed to determine protein concentration. The protein is aliquotted into screw cap Cryo tubes each containing ~200 µL, flash frozen in liquid nitrogen and stored at −80° C. until used for the assay.

FAAH Human Carcinoma Cell Membrane (HCM) Homogenate Preparation

Human breast epithelial carcinoma MCF7 cells are obtained from the American Type Culture Collection (ATCC Number HTB-22, Manassa, Va.) and cultured as essentially as described by ATCC. Briefly, cells are grown in Eagle's Minimum Essential Medium (ATCC catalog no. 30-2003) supplemented with 4 mM L-glutamine, 10% final volume of fetal bovine serum (ATCC catalog no. 30-2020), and 0.1 mg/mL human recombinant insulin (Sigma, St. Louis, Mo.). The cells are grown in 5% carbon dioxide in air. When cells reach ~80% confluency, adherent cells are rinsed with Hanks Balanced Salts Solution (ATCC catalog no. 30-2213), scraped into suspension and collected by centrifugation in a clinical centrifuge at room temperature. Cell pellets are then washed by resuspension in Hanks Balanced Salts Solution followed by centrifugation. Cell pellets are then flash frozen in a dry ice and ethanol bath and stored at −80° C. Cell pellets are thawed and 25 mL of homogenization buffer is added. Membrane homogenates of MCF7 cells are then prepared as described above for rat brain homogenates. A Bradford Protein assay is performed to determine the protein concentration. The protein is aliquotted into screw cap Cryo tubes each containing ~200 µL, flash frozen in liquid nitrogen and stored at −80° C. until used for the assay.

Determination of FAAH Activity

FAAH activity is assayed in the respective homogenates (Rat brain, Human brain, or Human breast cell carcinoma MCF7 cell) using a modification of the method of Omeir et al. (1995 Life Sci 56:1999) and Fowler et al. (1997 J. Pharmacol Exp Ther 283:729). For assay of FAAH in rat brain membrane homogenates (RBM), RBM homogenates (7 µg protein in 20 µl final volume of 10 mM Tris pH 6.5) are mixed with 180 µl of a mixture of the following: 2.0 µM unlabelled anandamide, 0.03 µCi radiolabeled anandamide [ethanolamine 1-$^3$H] (40-60 Ci/mmol, product number ART-626, American Radiolabelled Chemicals, St. Louis, Mo.), 1 mg/mL Bovine Serum Albumin (fatty acid-free BSA, electrophoresis grade, Sigma, St. Louis, Mo.), 10 mM Tris-HCl (pH 6.5), and 1 mM EDTA in the presence and absence of test compounds (vehicle is DMSO at a final concentration of 1%) and incubated for 10 minutes at 37° C. Samples are placed on ice to terminate the reactions. $^3$H-ethanolamine product and un-reacted $^3$H-anandamide substrate are separated by either: (1) using chloroform/methanol extraction or (2) bypassing the reaction mixture through a glass fiber filter containing activated charcoal. Samples are extracted with chloroform/methanol by adding 0.4 mL of chloroform/methanol (1:1 v/v), vigorously mixing the samples, and separating the aqueous and organic phases by centrifugation. Radioactivity (corresponding to FAAH-catalyzed breakdown of $^3$H-anandamide) found in aliquots (0.2 mL) of the aqueous phase is determined by liquid scintillation counting with quench correction. $IC_{50}$ values are determined as described by Jonnson et al. (2001 Br J Pharmacol 133:1263). Alternatively, reactions are purified using a modification of the solid-phase extraction method described by Wilson et al (2003 Anal Biochem 318: 270). This method can be modified as follows: after reactions are incubated at 37° C. for 10 minutes and chilled on ice, the reaction mixtures are acidified by adding 10 µl of sodium phosphate solution [0.5M (ph 2.0)]. 90 µl aliquots of the acidified reaction mixtures are applied to activated charcoal (that has been previously washed with methanol as described by Wilson et al. (supra)) containing 80 µl of water on top of a glass fiber filter, centrifuged, and the radioactivity in the eluate is counted as described previously by Wilson et al. (supra) The known FAAH inhibitors 3'-(aminocarbonyl)biphenyl-3-yl cyclohexylcarbamate (URB397), [1-(4-chlorobenzoyl)-5-methoxy-2-methyl-1H-indol-3-yl]acetic acid (indomethacin) and 5-benzoyl-2,3-dihydro-1H-pyrrolizine-1-carboxylic acid (Ketorolac) were used as controls in these assays.

Whole Cell Anandamide Hydrolysis Assay

FAAH activity can be assayed in whole cells using methods disclosed previously (Maccarone et al. 1998 J Biol Chem 273:32332 and Bisogno et al. 1997 J Biol Chem 272:3315). In addition to the cell lines described in Maccarone et al. and Bisogno et al., MCF7 (ATCC designation HTB-22) and T84 (ATCC designation CCL-248) cell lines may be used in these assays.

Determination of Endogenous and Exogenous Anandamide Levels in Rat Plasma and Brain Tissue The effects of test compounds on endogenous and exogenously dosed anandamide (AEA) levels can be measured. Rats dosed with test compound are sacrificed at various time points to determine the levels of anandamide both circulating and within the brain tissue. For experiments measuring exogenous levels of anandamide, the anandamide (Cayman Chemical, Ann Arbor, Mich. or Sigma Chemical, St. Louis, Mo.) is dosed (in the range of 3-30 mg/kg) post dosing of test compound. Animals are sacrificed at 5, 15, 30, or 60 minutes after anandamide administration with anesthesia administration followed by decapitation. Brains are removed immediately and the plasma is recovered from the blood for analysis of anandamide levels.

Flash frozen whole brain (e.g. from rat or mouse) samples are first transferred to clean 50-mL conical tubes and the wet brain weight is recorded. Fifteen mL of 9:1 ethyl acetate: hexane and 40 ng of deuterated anandamide (d8AEA) are added to the brain samples. The samples are then homogenized with an Omni GLH homogenizer until the solution is a uniform slurry, and 5.0 mL of water is added just prior to completion. Upon completion of the homogenization the tubes are held on ice. The chilled tubes are then vortexed and centrifuged at 4° C. at 3500 rpm for 10 minutes. One milliliter of the aqueous layer is sampled for use in a Bradford assay of protein content (Bradford, M. M. *Anal. Biochem.* 1976, 72: 248). The ethyl acetate layer is recovered, placed in a 15-mL glass tube, and evaporated under nitrogen in a TurboVac. Once dry, samples are reconstituted in 1 mL of 1:3 (v/v) $CHCl_3$:methanol and vortexed. Prepared brain samples are transferred to a 96-well plate for analysis by LC/MS/MS.

Stock standards are prepared at 0.0, 0.50, 1.0, 5.0, 10.0, 50.0, 100, 500, and 1000 ng/mL in methanol. Standards for LC/MS/MS are prepared with 0.5 mg Pefabloc, 10 µL of the stock standard to 90 µL of stock rat plasma and vortexing.

Frozen plasma samples containing pefabloc are thawed, and 100 µL of each sample is transferred to a microcentrifuge tube. To each standard and sample tube, 20 ng d8AEA and 100 µL of ice cold acetone (for protein precipitation) is added. Tubes are vortexed, and centrifuged at 13,000 rpm for at least 5 minutes. The supernatants are collected in microcentrifuge tubes and the acetone is evaporated off in a TurboVac for 5-10 minutes. The evaporated supernatant solutions are next extracted with 250 µL of 1:2 (v/v) methanol:$CHCl_3$ and centrifuged at 13,000 rpm for at least 5 minutes. The $CHCl_3$ layer is collected and evaporated under nitrogen (TurboVac) until dry. Standards and samples are then reconstituted in 200 µL of 1:3 (v/v) $CHCl_3$:methanol. Prepared standards and plasma samples are transferred to a 96-well plate for analysis by LC/MS/MS. Similar experiments can be performed using human plasma to which test compounds and exogenous anandamide is dosed or not dosed.

The LC/MS/MS method uses a Waters 2777 sample manager, 1525 binary pump, and Quattro micro mass spectrometer. The separation is performed on a Waters Xterra MS C8, 5 µM, 2.1×20 mm analytical LC column with a Thermo Electron Javelin Basic 8, 2×10 mm guard column at a flow rate of 0.30 mL/minutes and a 25-µL injection volume. A binary linear gradient of mobile phase A (10 mM ammonium acetate in water (pH 9.5)) and mobile phase B (80:20 acetonitrile:methanol) is used from 2.0 to 2.2 minutes from 25% to 90% B, with a total run time of 6.0 minutes per sample injection. AEA and d8-AEA eluate in ~3.5 minutes. The Quattro micro is operated in multiple reaction monitoring (MRM) mode with negative electrospray ionization. The mass transitions of 348 m/z–62 m/z (AEA) and 356 m/z–62 mg/z (d8-AEA) are monitored using optimized collision settings (determined experimentally). Data are analyzed using Micromass QuanLynx software, and standard curves are generated using the ratio of the internal standard (d8-AEA) peak area to AEA peak area in response to AEA concentration. AEA concentration in brain and plasma samples is calculated using the linear regression of the standard curve. AEA concentration in plasma is reported as ng AEA/mL plasma, and AEA concentration in brain is reported as ng AEA/g protein (protein content determined by the Bradford assay).

Arachidonyl 7-amino, 4-methyl coumarin amide (AAMCA) based FAAH activity assay

The ability of certain compounds described herein to inhibit the ability of FAAH to catalyze the hydrolysis of AAMCA (fluorogenic substrate) to generate arachidonic acid and a highly fluorescent 7-amino, 4-methyl coumarin (AMC) was determined using essentially the assay described in Ramarao et al. 2005 Anal Biochem. 343:143-151.

Determination of Exogenous [$^3$H]anandamide Levels in Mouse Blood and Brain Tissue The effects of test compounds on exogenously dosed [$^3$H] anandamide (including metabolites thereof) levels and localization can be measured as described in Glaser et al 2005 J Pharmacol Exp Ther. Nov. 8; 2005.

Measurement of Rectal Temperature in Mice and Rats.

Direct acting cannabinoid type 1 (CB1) receptor agonists, including the endo-cannabinoid amandamide, have been shown to produce a rapid decrease in body temperature (hypothermia) following administration to both mice and rats. Test compounds can be tested in such an assay by assessing their ability to potentiate the hypothermic effects of intravenously (IV) dosed anandamide for example as described in Smith et al. (1994) Pharmacol Exp Ther. 270:219-27. Briefly, mice or rats may be administered vehicle or various doses of test compounds. Then, following a suitable pretreatment time, core body temperature can be measured and recorded using a suitably sized temperature probe inserted in to the anus and rectum. Once baseline temperature is recorded, mice or rats may be administered an IV dose of the endo-cannabinoid anandamide. Subsequently, core body temperature is measured and recorded at various time points until it returns to at or around baseline.

CRTH2 Related Assays

CRTH2 Agonist Assay

CRTH2 agonists increase the expression of CD11b on eosinophils. Neutrophils do not express CRTH2. They do, however, express receptors for other lipid mediators, including 5-oxo-6,8,11,14-eicosatetraenoic acid (5-oxo-ETE), leukotriene B4 (LTB4), and platelet activating factor (PAF). Therefore, any increased expression of CD11b by neutrophils is likely to be caused by an activity other than activation of CRTH2. Accordingly, preferred CRTH2 agonist compounds increase CD11b expression on eosinophils, but not on neutrophils.

The potential CRTH2 agonist activity of certain compounds was tested using a CD11b expression assay using essentially the method described by Monneret et al. (*J Pharmacol Exp Ther* 304:349-55, 2003).

Briefly, polymorphonuclear cells (0.5 ml/$10^6$/ml cells) in PBS containing 0.9 mM $CaCl_2$ and 0.5 mM $MgCl_2$) were incubated with a test compound at room temperature for 10 minutes. The incubations were terminated by the addition of ice-cold FACSFlow (BD Biosciences; Cat# 342003) and centrifugation (400 g for 5 minutes at 4° C.). The cells were then incubated for 30 minutes at 4° C. with a mixture of PE-labeled mouse anti-human VLA-4 (5 µl; BD Biosciences) and FITC-labeled mouse anti-human CD11b (10 µl; Beckman Coulter). The cells were then incubated with Optilyse C (0.25 ml: Beckman Coulter) for 15 minutes, centrifuged, and then fixed in PBS (0.4 ml; calcium and magnesium free) containing 1% formaldehyde. The distribution of fouorescence intensities among 60,000 cells was measured by flow cytometry. Eosinophils were gated out on the basis of their granularity (high side scatter) and labeling with VLA-4 (PE fluorescence), CD11b was then measured in the eosinophil region on the basis of fluorescence due to FITC. All data were corrected for the value obtained for the corresponding isotype control antibody.

To confirm that the CD11b expression is caused by activation of the CRTH2 receptor certain controls were performed. Accordingly, effect of the compounds on CD11b expression in neutrophils was tested. If the compound increases CD11b expression in neutrophils, the mobilization in eosinophils is likely caused by an activity other than activation of the CRTH2 receptor. In all cases tested CD11b expression was only observed in eosinophils.

CRTH2 Antagonist Assay

The potential CRTH2 antagonist activity of certain compounds was tested using an assay that tests the ability of the compounds to block the CD11b expression in eosinophils by 15-R-methyl-PGD$_2$ using essentially the method described above for the agonist assay except that the cells were preincubated with various concentrations of compounds before they were challenged with the agonist 15R-Methyl-PGD$_2$ A CRTH2 antagonist should block CD11b expression by subsequently added 15-Methyl-PGD$_2$. Ramatroban (3-((3R)-3-{[(4-fluorophenyl)sulfonyl]amino}-1,2,3,4-tetrahydro-9H-carbazol-9-yl)propanoic acid) and [1-(1,3-benzothiazol-2-ylmethyl)-5-fluoro-2-methyl-1H-indol-3-yl]acetic acid both known CRTH2 antagonists were used as positive controls in this assay. Compounds with 85% or greater inhibition in this assay are considered to be CRTH2 antagonists. The assay can be also performed in the presence of human plasma which is added to a final concentration of 10% in the initial incubation with PBS buffer.

Alternatively, CRTH2 antagonist activity can be determined by a calcium mobilization assay conducted as follows, adapted from the protocol described by Monneret et al. (*J Pharmacol Exp Ther* 304:349-55, 2003). Briefly, leukocytes ($10^7$ cells/ml) are treated with the acetoxymethyl ester of fluo-3 (2 μM; Molecular Probes, Eugene, Oreg.) in the presence of Pluronic F-127 (0.02%; Molecular Probes) for 60 minutes at 23° C. The mixture is centrifuged at 200×g for 10 minutes and the pellet resuspended in PBS to give a concentration of $5\times10^6$ cells/ml. The leukocytes are treated with PC5-labeled mouse anti-human CD16 (3.3 μl/$10^6$ cells; Beckman-Coulter) for 30 minutes at 0° C. PBS (25 ml) is added, the mixture centrifuged as described above, and the pellet resuspended in PBS to give a concentration of $3\times10^6$ leukocytes/ml. After incubation of 23° C. for 30 minutes, an aliquot (0.95 ml) of the leukocyte suspension is removed and treated with PBS (50 μl) containing $Ca^{++}$ (36 mM) and $Mg^{++}$ (20 mM). After 5 minutes, the cells are analyzed by flow cytometry using a FACS Calibur instrument (Becton-Dickinson, San Jose, Calif.). A total of approximately $10^6$ cells are counted over a period of 3 to 4 minutes for each sample Fluo-3 fluorescence is measured in eosinophils, neutrophils, and monocytes, which are gated out on the basis of CD16 staining and side scatter. Test compounds are added 2 minutes after the start of each run followed 2 minutes later by 15R-Methyl-PGD$_2$. Maximal calcium responses are determined by addition of the calcium ionophore, A23187 (10 μM) one minute after the addition of 15R-Methyl-PGD$_2$.

DP-1 Receptor Assays

DP-1 Receptor Antagonist Assay

Human blood is collected in citrate vacutainer tubes. Platelets are isolated at $1\text{-}5\times10^7$ cells/mL in PBS. Isobutylmethylxanthine (Sigma catalog # 15879) is added to the platelets for a final concentration of 1 mM and 300 μL of platelets are then aliquoted into the appropriate wells of a 96-well assay plate. Samples are then incubated at 37° C. for 8 minutes. Next, 3 μL of test compound are added to the appropriate wells of the assay plate for a final concentration of 10 μM. To create a standard curve, 3 μL of the appropriate concentration of BW-A868C (Cayman chemical catalog # 12060) is added to one row of the assay plate. The standard curve is prepared in dimethylsulfoxide starting at 10 μM and diluting ten-fold to 0.1 nM. Samples are then incubated at 37° C. for 10 minutes. 3 μL of the agonist control, BW-245C (Cayman Chemical catalog # 12050), are added to each sample and the samples are incubated for 10 minutes at 37° C.

After the 10 minutes incubation, 1 mL of ice cold ethanol is added to each sample. Samples are spun for 10 minutes at 600×g and 4° C. 200 μL of supernatant are removed and diluted 1:10 in EIA buffer (provided in Cayman Chemical c-AMP EIA kit-catalog # 581002). A standard curve of cAMP is also prepared in EIA buffer starting at 3000 pmol/mL, diluted two-fold, to 28 pmol/mL. 50 μL of diluted sample are added to the appropriate wells of the ELISA 96-well plate coated with mouse anti-rabbit IgG. 50 μL of the prepared standard curve are also transferred to the ELISA plate. 50 μL of cyclic AMP AChE tracer, reconstituted in 6 mL of EIA buffer, are added to each sample, including the standard curve. 50 μL of cyclic AMP EIA antiserum, reconstituted in 6 mL of EIA buffer, are added to each sample, including the standard curve. Samples are incubated at 4° C. for 16-18 hours. After the overnight incubation, samples are dispensed from the plate. The plate is washed five times with wash buffer provided in the cyclic AMP EIA Kit, 20 mL of ultrapure water are added to the vial of Ellman's reagent provided in the cyclic AMP kit. 200 μL of reconstituted Ellman's reagent are added to each sample well. Samples are incubated for 90 minutes at room temperature while being protected from light. After 90 minutes, the sample plate is read on a fluoremeter set to 412 nm and endpoint mode.

DP-1 Receptor Agonist Assay

Human blood is collected in citrate vacutainer tubes. Platelets are isolated at $1\text{-}5\times10^7$ cells/mL in PBS. Isobutylmethylxanthine (Sigma catalog # 15879) is added to the platelets for a final concentration of 1 mM. 300 μL of platelets are then aliquoted into the appropriate wells of a 96-well assay plate. Samples are then incubated at 37° C. for 8 minutes. 3 μL of test compound or agonist control are added to the appropriate wells of the assay plate for a final concentration of 10 μM. The agonist control used is BW-245C (Cayman Chemical catalog # 12050). Samples are then incubated at 37° C. for 10 minutes. After the 10 minute incubation, 1 mL of ice cold ethanol is added to each sample. Samples are spun for 10 minutes at 600×g and 4° C. 200 μL of supernatant are removed and diluted 1:10 in EIA buffer (provided in Caymen Chemical c-AMP EIA KIT-CATALOG # 581002). A standard curve of cAMP is also prepared in EIA buffer starting at 3000 pmol/mL, diluted two-fold, to 28 pmol/mL. 50 μL of diluted sample are added to the appropriate wells of the ELISA 96-well plate coated with mouse anti-rabbit IgG. 50 μL of the prepared standard curve are also transferred to the ELISA PLATE. 50 μL of cyclic AMP AChE tracer, reconstituted in 6 mL of EIA buffer, are added to each sample, including the standard curve. 50 μL of cyclic AMP EIA antiserum, reconstituted in 6 mL of EIA buffer, are added to each sample, including the standard curve. Samples are incubated at 4° C. for 16-18 hours. After the overnight incubation, samples are dispensed from the plate. The plate is washed five times with wash buffer provided in the cyclic AMP EIA kit. 20 mL of ultrapure water are added to the vial of Ellman's reagent provided in the cyclic AMP kit. 200 μL of reconstituted Ellman's reagent are added to each sample well. Samples are incubated for 90 minutes at room temperature while being protected from light. After 30 minutes, the sample plate is read on a fluoremeter set to 412 nm and endpoint mode.

Thromboxane A2 (TXA$_2$) Related Assays

TXA$_2$ Receptor Binding Assay

Ramatroban, a known CRTH2 antagonist, is also a thromboxane A2 receptor antagonist. Certain compounds described herein were tested for their ability to bind to the TXA$_2$ receptor using an assay similar to that described in Schrör et al. 1995 Biochemical Pharmacol 49:921-927. Purified TXA$_2$ receptors from human platelets (0.6 to 0.8 µg protein/mL) were thawed on ice and preincubated for 1 hour at 4° C. in pH 7.4 or pH 6.0 buffer. The incubation mixture (200 µL final volume) consisted of HEPES (25 mM), EDTA (2 mM), CHAPs buffer (10 mM Tris-HCl, pH 8.0/1 mM MgCl$_2$/1 mM EGTA/0.5% CHAPS/10% glycerol/5 mM 2-mercaptoethanol/1 mM DTT) (5 mM), asolectin (0.5 mg/mL), 60-80 ng purified TXA$_2$ receptor, vehicle or test compounds at various concentrations, 50,000-70,000 cpm [$^{125}$I]BOP (1S-(1α,2β(5Z),3α(1E,3R*),4α)]-7-[3-(3-hydroxy-4-(4'-iodophenoxy)-1-butenyl)7-oxabicyclo-[2.2.1]heptan-2-yl]-5-heptenoic acid; a TXA$_2$ mimetic) and various concentrations of 1-BOP (0.05 to 250 nM) and was incubated for 1 hour at 30° C. Assays were performed in silanized (12×75 mm) glass tubes. The mixture was then filtered rapidly through Whatman GF/C glass-fiber filters, presoaked with 0.3% polyethylenimine. This was followed by three additional washings with ice-cold HEPES (25 mM)/EDTA (2 mM)/CHAP (0.1 mM). The filtration procedure was complete within 10 seconds. Radioactivity was counted using an LKB gammacounter. Nonspecific binding was defined as the amount of radioactivity bound in the presence of 10 µM L 657925 (a TXA$_2$ receptor antagonist; Warner et al. (1997) Prostaglandins, 54:581-99).

Bleeding Time Assay

TXA$_2$ binds to the TXA$_2$ receptor to induce platelet aggregation and hemostasis. Test compounds are evaluated for their ability to modify bleeding time in an in vivo assay. Test compounds or vehicle alone are administered orally. The measurement of coagulation time in rats and mice is performed as a terminal study under general anesthesia. Animals are anesthetized and then positioned horizontally on a platform with their tails taped downwards such that the tail is perpendicular to their body and hangs about 2 cm from the top of a platform. The distal portion of the tail is amputated with a scalpel. The amount of bleeding from the transection is measured in one of four ways: 1) Clotting Time in Water: the tail is immersed into water or saline warmed to 37° C. and the time to clotting is recorded; 2) Clotting Time in Air: Whatman filter paper is applied to the edge of the forming clot every 30 seconds, taking care not to dislodge the clot. blood that continues to flow from the cut during the 30-second interval is allowed to fall on the filter paper at the same point. The amount of time until clotting is recorded; 3) Volume Measurement: blood is collected in a citrated Eppendorf tube for a duration of 5 minutes after the transection. The total volume of whole blood was measured; and 4) Absorbance Reading: the tail is immersed for 10 minutes in 1 mL of 0.9% NaCl warmed at 37° C. Blood loss is determined by measuring the absorbance of saline at 560 nm and the result is compared to a standard curve constructed from known volumes of mouse blood.

D-Amino Acid Oxidase Related Assays

Inhibition of Porcine Kidney DAO

Porcine kidney D-amino acid oxidase (catalog # A-5222 from Sigma) and D-serine (catalog # S-4250 from Sigma) was used to test the DAO inhibitory activity of test compounds. The breakdown of D-serine by DAO produces hydrogen peroxidase, which can be measured using, for example, the Amplex® Red Hydrogen Peroxide Assay Kit (Catalog # A-22188, Molecular Probes, Inc.; Eugene, Oreg.). A working solution was prepared by mixing: distilled water (7.93 mL), sodium phosphate buffer (1 ml, 0.25M, pH 7.4), D-serine solution (1.0 ml, 100 mM in water), horseradish peroxidase (0.02 ml, 100 U/ml in buffer), and Amplex Red solution (0.05 ml, 1 mg dye in 200 ul in DMSO (50 µM in DMSO)). A working enzyme solution is prepared by diluting a D-amino acid oxidase stock solution (65 U/ml) four hundred fold. The working solution (99 µL) was transferred to wells of a Microfluor microtiter plate and a solution of the inhibitor in DMSO (1 µL) is added. The working enzyme solution (20 µL) was added to each well and the rate of reaction (hydrogen peroxide released) was determined by measuring the oxidation of Amplex Red by spectrophotometry, using a plate reader (excitation wavelength 544 nm, emission wavelength, 590 nM) after a reaction time of 15 minutes. Controls were carried out using DMSO in the absence of inhibitor. A known DAO inhibitor, indole-2-carboxylic acid, was used as a control in this assay.

Inhibition of Human DAO

Human D-amino acid oxidase extracts were prepared by harvesting HEK293 cells either transiently or stably transfected with the human DAO clone (huDAO). The stable huDAO cell line was generated by co-transfecting the huDAO gene (Catalog#TC118941, Origene, Rockville, Md.) along with pcDNA3.1 (Invitrogen, Carlsbad, Calif.) at a 100:1 ratio into HEK293 cells under G418 selection. Transient huDAO transfections were implemented using Lipofectamine 2000 (Invitrogen, Carlsbad, Calif.) and following the manufacturers protocol with the following specifics. HEK293 cells were seeded at 2×10$^7$ cells per T150 flask the day before transfection. huDAO DNA (Catalog#TC118941, Origene, Rockville, Md.) was transfected at 37.5 ug per flask and at a 3:1 DNA/Lipofectamine ratio. The DNA/Lipofectamine mixture was incubated on the cells for 48 hrs before cell harvesting. Similar results were obtained with transiently vs stably expressed huDAO. Extracts were harvested as follows. Culture liquid was removed from flasks and replaced with Hank's Buffered Saline Solution (20 mLs). The cells were scraped into the Hank's Buffer and then transferred to a fresh tube. Samples were spun for 10 minutes at 3,000 rpm. The supernatant was decanted and the pellet resuspended in 50 mM Tris-HCL pH 8.7, 1 µM FAD and 1 mM DTT, 20% glycerol (1 mL). Samples were then homogenized on ice for 20 seconds. Homogenates were spun down for 5 minutes at 3,000 rpm. The supernatants were removed and set aside. The pellets were resuspended in 50 mM Tris-HCL pH8.7, 1 µM FAD, 1 mM DTT and 0.1% octyl-β-D-glucoside, 20% glycerol (1 mL) and homogenized on ice for 20 seconds. Homogenates were spun for 5 minutes at 3,000 rpm. The supernatants were collected and combined with previously collected supernatants for a master stock. Extracts were then serially diluted and tested in the D-amino acid oxidase enzyme assay to determine activity based on protein concentration. Stocks were prepared accordingly, typically, for a twenty fold dilution in future assays.

Human D-amino acid oxidase (HEK293 cells stably transfected with huDAO clone) and D-serine (catalog # S-4250 from Sigma) were used to test the DAO inhibitory activity of test compounds. The breakdown of D-serine by DAO produces hydrogen peroxidase, which can be measured using, for example, the Amplex® Red Hydrogen Peroxide Assay Kit (Catalog # A-22188, Molecular Probes, Inc.; Eugene, Oreg.). A working solution was prepared by mixing: distilled water (7.93 mL), sodium phosphate buffer (1 ml, 0.25M, pH 7.4), D-serine solution (1.0 ml, 100 mM in water), horseradish peroxidase (0.02 ml, 100 U/ml in buffer), and Amplex Red solution (0.05 ml, 1 mg dye in 200 ul in DMSO (50 µM in DMSO)). A working enzyme solution was typically prepared by diluting a D-amino acid oxidase stock solution twenty fold. The working solution (99 µl) was transferred to wells of a Microfluor microtiter plate and a solution of the inhibitor in DMSO (1 µL) is added. The working enzyme solution (20 µl) was added to each well and the rate of reaction (hydrogen peroxide released) was determined by measuring the oxidation of Amplex Red by spectrophotometry, using a plate reader (excitation wavelength 544 nm, emission wavelength, 590 nM) after a reaction time of 15 minutes. Controls were carried out using DMSO in the absence of inhibitor. A known DAO inhibitor, indole-2-carboxylic acid, was used as a control in this assay.

DAO Whole Cell Assay 1—Toxicity

Human D-amino acid oxidase (huDAO) and d-serine (catalog # S-4250 from Sigma) are used to test the DAO inhibitory activity of test compounds. A stable hDAO cell line is generated by co-transfecting the huDAO gene (Catalog #TC118941, Origene, Rockville, Md.) along with pcDNA3.1 (Invitrogen, Carlsbad, Calif.) at a 100:1 ratio into HEK293 cells under G418 selection. The intracellular breakdown of D-serine by DAO produces hydrogen peroxide, which induces toxicity to the cell monolayer. This toxicity is measured by, for example, the AlamarBlue™ Reagent (Catalog # BUF012B, AbD Serotec Ltd., Kidlington, Oxford, UK). On day 1 of the assay, the following additions are made, in order, to a black, clear bottom, tissue culture treated 96-well plate (Corning # 3904): 2 ul inhibitor (100× in 100% DMSO, or vehicle), 100 ul 70 mM D-serine in HEK media (DMEM/10% FBS), 100 ul huDAO cells ($2\times10^5$/ml). The cells are incubated for 18-24 hrs at 37° C./5% CO2. On day 2 of the assay, 20 ul of AlamarBlue™ Reagent is added to each well, and the plate is returned to the incubator for another 24 hrs. On day 3 of the assay, the amount of cellular toxicity (induced by hydrogen peroxide produced by intracellular huDAO) is determined by measuring the conversion of AlamarBlue reagent in a fluorescent plate reader (excitation wavelength 545 nm, emission wavelength, 590 nM; @ 37° C.).

DAO Whole Cell Assay 2—Amplex Red

Human D-amino acid oxidase (huDAO) and D-serine (catalog # S-4250 from Sigma) are used to test the DAO inhibitory activity of test compounds. A stable huDAO cell line is created by co-transfecting the huDAO gene (Catalog #TC118941, Origene, Rockville, Md.) along with pcDNA3.1 (Invitrogen, Carlsbad, Calif.) into HEK293 cells under G418 selection. The intracellular breakdown of D-serine by huDAO produces hydrogen peroxide, which is measured by, for example, the Amplex® Red Hydrogen Peroxide Assay Kit (Catalog # A-22188, Molecular Probes, Inc.; Eugene, Oreg.). The following additions are made, in order, to a black, clear bottom, tissue culture treated 96-well plate (Corning # 3904): 2 ul inhibitor (100× in 100% DMSO, or vehicle), 100 ul Detection Solution (30 mM D-serine, 20 uM Amplex Red, 0.05 U/ml HRP in Hanks Balanced Salt Solution/20 mM HEPES 7.4), and 100 ul huDAO cells ($6\times10^5$/ml). The intracellular huDAO activity is proportional to the rate of hydrogen peroxide produced by the cells and is determined by measuring the conversion of Amplex Red in a fluorescent plate reader (excitation wavelength 544 nm, emission wavelength, 590 nM) at 37° C. over a 60 min kinetic read.

Detection of D-amino Acids in Serum and Urine

Serum and urine samples are obtained and immediately frozen in a −80° C. freezer before analysis. Serum and urine levels of D-amino acids (aspartate, glutamate, glycine, D-serine, L-serine) are determined by precolumn derivatization with N-tert, -butyloxy-carbonyl-L-cycteine and o-phthaldialdehyde (Hashimoto et al. J Chromatogr (1992) 52:325-53) coupled with a mobile phase gradient of methanol and 100 mmol/L, pH 7.2 sodium acetate, and reverse phase C-18 column for high-pressure liquid chromatography separation with fluorescent detection at excitation wavelength of 433 nm and emission wavelength of 344 nm. The absolute concentrations of amino acids are determined by computer analysis (Maxima 820, Waters, Mass.) of peak height with internal and external standards. D-amino acid levels (e.g. D-serine) can be determined in the presence and absence of test compound.

Detection of D-amino Acids in Brain and Plasma

Brain and plasma samples are obtained and immediately frozen in a −80° C. freezer before analysis. Amino acids were extracted from plasma using a protein precipitation procedure while brains were homogenized under acidic conditions. Levels of D-amino acids (serine, alanine, leucine and proline) are determined by precolumn derivatization with Marfey's reagent (Fluoro-dinitrophenyl-L-alanine amide) (Berna M. J. and Ackermann B. L. (2006) J Chromatogr B; doi:10.1016/j.chromb.2006.08.029) coupled with a mobile phase gradient of 15 mM ammonium acetate in a combination of water, methanol and acetonitrile on a reverse phase C-18 column for high-pressure liquid chromatography separation with mass spectrometry detection in the negative single ion reaction mode. The absolute concentrations of amino acids are determined by computer peak area ratio with internal standards. D-amino acid levels (e.g. D-serine) can be determined in the presence and absence of test compound.

D-serine Induced Nephrotoxicity

D-serine and D-propargylglycine have been associated with nephrotoxicity and induce one or more of glucosuria, aminoaciduria, proteinuria, and polyuria. Compounds which inhibit DAO activity may also control the production of toxic metabolites of D-amino acid oxidation (e.g. D-serine) such as hydrogen peroxide and ammonia. Hydrogen peroxide and concomitantly produced oxygen radicals may lead to nephrotoxicity. Compounds described herein can be evaluated for their ability to attenuate the nephrotoxicity associated with D-serine or D-propargylglycine administration in rats as described in Williams and Lock 2005 Toxicology: 207:35-48 and Maekawa et al. 2005 Chem Res Toxicol. 18:1678-1682.

Measurements of NMDA Receptor Affinity

To measure the affinity of the compounds reported herein for D-serine's binding site on the NMDA receptor (also known as the "Glycine site" or the "strychnine-insensitive glycine site"), a radioligand-binding assay is performed with membranes prepared from rat cerebral cortex. The radioactive ligand is [$^3$H]MDL105,519 ((E)-3-(2)-phenyl-2-carboxyethenyl)-4,6-di-chloro-1[3H]-indole-2-carboxylicacid), a known glycine site antagonist. The amount of radioactivity displaced by the compounds is assessed by scintillation counting. Non-specific binding is accounted for in the presence of 1 mM Glycine. Affinities are calculated from the values of % inhibition of specific [$^3$H]MDL105,519 binding by the test compounds. Indole-2-carboxylic acid is used as a positive control. The assay is commercially available at MDS Pharma Services (catalog no. 232910).

Assays for Assessing Antinociception Mechanism

Compounds can be tested to determine if they influence pathways involved in nociception. The results of such assays can be used to investigate the mechanism by which a test compound mediates its antinociceptive effect. In addition to the FAAH related assays, the following methods can be used to assess the mechanism by which a test compound mediates its antinociceptive effect.

Elevation of 3α,5α-THP

3α-hydroxy-5α-pregan-20-one (3,α,5α-THP or allopregnanolone) is a pregnane steroid that acts as an agonist of the inhibitory $GABA_A$ receptor subtype and is known to have both anxiolytic and analgesic effects in a variety of animal systems, with supportive evidence for a similar role in humans. Thus, compounds that elevate 3α,5α-THP may have an antinociceptive effect. The level of 3α,5α-THP in the brain of animals treated with a test compound can be measured as described by VanDoren et al. (1982 J Neuroscience 20:200) as follows. Briefly, steroids are extracted from individual cerebral cortical hemispheres dissected in ice-cold saline after euthanasia. Cortices are frozen at −80° C. until use. Samples are digested in 0.3 N NaOH by sonication and extracted three times in 3 mL aliquots of 10% (v/v) ethyl acetate in heptane. The aliquots are combined and diluted with 4 mL of heptane. The extracts are applied to solid phase silica columns (Burdick & Jackson, Muskegon, Mich.), washed with pentane, and steroids of similar polarity to 3α,5α-THP are eluted off of the column by the addition of 25% (v/v) acetone in pentane. The eluant is then dried under $N_2$ and steroids are redissolved in 20% (v/v) isopropanol RIA buffer (0.1 M $NaH_2PO_4$, 0.9 M NaCl, 0.1% w/v BSA, pH 7.0). Extraction efficiency is determined in 50 μl of the redissolved extract by liquid scintillation spectroscopy and the remaining sample is used in the determination of 3α,5α-THP by radioimmunoassay. Reconstituted sample extracts (75 μl) and 3α,5α-THP standards (5-40,000 pg in 6.25% v/v ethanol, 31% v/v isopropyl alcohol in RIA buffer) are assayed in duplicate by the addition of 725 μl of RIA buffer, 100 μl of [$^3$H]3α,5α-THP (20,000 dpm), and 100 μl of anti-3α,5α-THP antibody. Total binding is determined in the absence of unlabeled 3α,5α-THP, and nonspecific binding is determined in the absence of antibody. The antibody-binding reaction is allowed to equilibrate for 120 minutes at room temperature and is terminated by cooling the mixture 4° C. Bound 3α,5α-THP is separated from unbound 3α,5α-THP by incubation with 300 μl of cold dextran coated charcoal (DCC; 0.04% dextran, 0.4% powdered charcoal in double-distilled $H_2O$) for 20 minutes. DCC is removed by centrifugation at 2000×g for 10 minutes. Bound radioactivity in the supernatant is determined by liquid scintillation spectroscopy. Sample values are compared to a concurrently run 3α,5α-THP standard curve and corrected for extraction efficiency.

Cannabinoid Receptor Binding and Functional Activity Assays

Compounds may exert an antinociceptive effect via binding to either or both of the cannabinoid receptors $CB_1$ and $CB_2$ which are G-protein coupled receptors (GPCRs) that bind the endogenous endocannabinoids, anandamide (AEA) and 2-arachidonyl glycerol (2-AG) and modulate a variety of physiological responses such as body temperature, pain, blood pressure, and intestinal motility. SR 141716A (Rimonabant) is a selective CB1 antagonist and is the being developed for the treatment of obesity. $CB_1$ is expressed in the brain (Matsuda et al. 1990 Nature 346:561), and $CB_2$ is expressed by macrophages and in the spleen (Munro et al. 1993 Nature 365:61). Both of these receptors have been implicated in mediating analgesic effects through binding of agonists (see, for example, Clayton et al. 2002 Pain 96:253). Thus, test compounds can be assayed to determine whether they bind to one or both human cannabinoid receptors. Cannabinoid receptor activity can be assessed in a number of ways including binding or functional assays. Examples of such assays are outlined below. An assay for $CB_1$ binding is described by Matsuda et al. (supra). This assay employs recombinant cells expressing $CB_1$. Binding to $CB_2$ can be determined in the same manner using recombinant cells expressing $CB_2$. Briefly, to measure the ability of a test compound to bind to $CB_1$, the binding of a labelled $CB_1$ ligand, e.g., [$^3$H]WIN 55212-2 (2 nM for $CB_1$ and 0.8 nM for $CB_2$) to membranes isolated from HEK-293 cells expressing recombinant $CB_1$ is measured in the presence and absence of a test compound. Non-specific binding is separately determined in the presence of several-fold excess of unlabelled WIN 55212-2 (5 μM for $CB_1$ and 10 μM for $CB_2$). The specific ligand binding to the receptors is defined as the difference between the total binding and the non-specific binding determined in the presence of an excess of unlabelled WIN 55212-2. The $IC_{50}$ values and Hill coefficients ($n_H$) are determined by non-linear regression analysis of the competition curves using Hill equation curve fitting. The inhibition constants ($K_i$) are calculated from the Cheng Prusoff equation ($K_i = IC_{50}/(1+(L/K_D))$, where L=concentration of radioligand in the assay, and $K_D$=affinity of the radioligand for the receptor).

Compounds can be evaluated for their ability to bind to the human CB1 and CB2 receptors in a radioligand binding assay such as that provided by MDS Pharma Services (worldwide, including Taiwan, catalog nos. 217020 and 217100). These assays are similar to those described by Rinaldi-Carmona et al (J Pharmacol Exp Ther (2004) 310:905-14) and Bouaboula et al, (J Biol Chem, (1995) 270:13973-80).

A binding assay is described as follows. Human CB1 (hCB1) and CB2 (hCB2) cDNAs are cloned into a vector optimized for expression of recombinant proteins in Chinese Hamster Ovary (CHO) cells. Plasmids are transfected into CHO cells by a precipitation method. CHO cells are trypsined 48 hours after transfection and selected at a density of 5×10$^5$ cells/dish into culture medium (minimum essential medium-glutamine medium, heat-inactivated dialyzed fetal calf serum (10%), gentamicin (20 mg/l), L-proline (40 mg/l), pyruvate sodium (0.5 mM), and anti-Pichia pastoris lysyl oxidase agent (1%)). After 10 days, surviving clones are recovered and cultivated in the same medium containing Fungizone (0.1%). Cells are used between the third and 22nd passages. Membranes are isolated from transfected CHO cells expressing either hCB1 or hCB2 by washing twice with phosphate-buffered saline (PBS), scraped into 50 mM Tris-HCl, pH 7.7 (buffer A), crushed in a Polytron for 1 minute at 7000 rpm/minutes, then centrifuged for 15 minutes at 1100 g at 4° C. The supernatant is centrifuged for 1 hour at 105,000 g. The pellet is resuspended in buffer A and protein concentration measured. Membranes are stored at −80° C. until use. Alternatively, membranes containing CB1 or CB2 are prepared from the brain or the spleen of rats killed by decapitation. The brain (without the cerebellum) and the spleen are removed and homogenized for 30 seconds at 4° C. in buffer A (50 mM Tris-HCl, pH7.4) in a Polytron for 30 seconds at 7000 rpm/minute then centrifuged for 10 minutes at 1100 g. The supernatant is centrifuged for 30 minutes at 45,000 g. The pellet is resuspended in buffer A and protein concentration measured. Membranes are stored at −80° C. until use. Binding assays are performed by incubating membranes (10-100 μg) at 30° C. with the cannabinoid receptor agonist, [3H]-CP 55,940 (0.2 nM) in 1 ml of buffer A for 1 hour. A rapid filtration technique using Whatman GF/C filters (pretreated with 0.5% (w/v) polyethylenimine, Whatman, Clifton, N.J.), and a 48-well filtration apparatus (Brandel Inc., Gaithersburg, Md.) is used to harvest and rinse labeled membranes (3 times with 5 ml of cold buffer A containing 0.25% bovine serum albumin). The radioactivity bound to the filters is counted with 4 ml of biofluor liquid scintillant. Nonspecific binding is determined in the presence of unlabeled 1 µM CP 55,940. For selectivity studies, binding assays are carried out using standard protocols.

CB1/CB2 Functional Assays.

Functional assays which monitor the G-protein coupled receptor or downstream cellular responses can be used to characterize potential agonist or antagonist activities of compounds of interest at the CB1 and CB2 receptors. Direct activation (or inhibition of activation) can be monitored using a GTPγS assay. Such assays have been described in the scientific literature and are commercially available for both CB1 and CB2 (MDS Pharma Services, worldwide, including Taiwan, catalog nos. 306000 and 306050). These assays are similar to those described by Gonsiorck et al (Mol Pharmacol (2000) 57:1045-50) and Breivogel et al (J Biol Chem (1998) 273:16865-73).

A GTPγS assay can be performed as follows. CHO-K1 cells are transfected with plasmids expressing either CB1 or CB2. Transfection can be achieved using a variety of means including calcium phosphate transfection and lipofectamine 2000 (Invitrogen) according to the manufacturer's instructions. Transfected cells are harvested at 75% confluence with cell dissociation buffer according to the manufacturer's instructions (Life Technologies). Cells are collected by centrifugation and used immediately or stored at 80° C. Cell pellets are resuspended and incubated on ice for 30 minutes in homogenization buffer (10 mM Tris-HCl, 5 mM EDTA, and 3 mM EGTA, pH 7.6) supplemented with 1 mM phenylmethylsulfonyl fluoride (PMSF) as a protease and amidase inhibitor. Cells are then homogenized with 20 strokes at 900 rpm with a Dounce homogenizer with stirrer type RZR1 polytron homogenizer (Caframo, Wiarton, Ontario, Canada). Intact cells and nuclei are removed by low-speed centrifugation (500 g for 5 minutes at 4° C.). Membranes in the supernatant are pelleted by centrifugation at 100,000 g for 30 minutes at 4° C. and then resuspended in gly-gly buffer (20 mM glycylglycine, 1 mM $MgCl_2$, and 250 mM sucrose, pH 7.2) and stored at 80° C. Protein determinations are performed with the Bradford method. $^{35}$S GTPγS binding assays are performed by incubating cell membranes (1-7 µg/point, in triplicate) in the presence or absence of various compounds for 30 minutes at 30° C. in GTP S binding buffer (20 mM HEPES, 100 mM NaCl, 5 mM MgCl2, and 0.2% (w/v) BSA (Factor V, lipid free), pH 7.4) supplemented with 1 to 5 µM GDP. The reaction is carried out in 96-well microplates in a final volume of 100 µl with 0.3 nM [$^{35}$S]GTP S (specific activity=1250 Ci/mmol; NEN, Boston, Mass.). The reaction is terminated by rapid filtration of the membranes through the microfiltration plates coated with 0.5% polyethylenimine (UniFilter GF/C filter plate; Packard, Meriden, Conn.) with a Tomtek 96-well cell harvester (Hamden, Conn.). The filters are washed 10 times at room temperature with 20 mM HEPES and 10 mM sodium pyrophosphate. membrane-bond [$^{35}$S] GTP S radioactivity is measured by liquid scintillation with a TopCount NXT microplate scintillation and luminescence counter (Packard). Nonlinear regression analysis of the data can be performed with Prism 2.0b (GraphPad, San Diego, Calif.).

Activation of the CB1 receptor also affects cell proliferation. CB1 agonists are characterized by inhibition of cellular proliferation of a breast cancer cell line (MCF-7). This has been described by Bisogno et al (Biochem J (2000) 351:817), De Petrocellis et al (Proc Natl Acad Sci USA (1998) 95:8375-80), and Melck et al (Endocrinology (2000) p 118-126). Briefly, cell proliferation assays care carried out with MCF-7 cells in 6-well dishes containing subconfluent cells (at a density of about 50,000 cells/well). Test substances are introduced 3 hours after cell seeding and then daily at each change of medium. Cells are treated with trypsin and counted by a hemocytometer 4 days after the addition of test substances. No significant decrease in cell viability (as assessed by trypan blue) is observed with up to 100 µM of the CB1 agonist, anandamide. Substances are added 3 hours after cell seeding (50,000 cells/well). After 72 hours, cells are treated with trypsin and counted by a hemocytometer. Antagonist activity can be assessed by characterizing the ability of a test compound to inhibit the anti-proliferative effects of a known CB1 agonist such as anandamide.

Measurement of Pharmacokinetic Parameters

To determine the various pharmacokinetic parameters, plasma samples from animals dosed with a test compound are collected and analyzed by LC/MS. Briefly, samples are prepared by protein precipitation with methanol. The supernatents from the precipitation are collected and evaporated to dryness. The dry samples are resuspended in the initial flow conditions for the HPLC. A 10 uL sample volume is injected onto Thermo Electron Hyupersil GOLD 2.1×50 analytical column. The compounds are eluted from the column with a short gradient and detected by an Applied Biosystems Sciex (Toronto, Ontario) API 4000 mass. Concentrations are determined by relative response to an internal standard and calculated based on a standard concentration curve of the test compound. Sciex Analyst Software is used to quantify the samples based on a set of prepared standards and QCs. A concentration versus time plot is generated from the data in WinNonLin (Pharsight, Corp., Mountain View, Calif.) to generate PK curves and PK parameters for each compound, $AUC_n$ (Area Under the Curve, n=length of experiment in hours), oral bioavailability ($F_n$) is calculated using the equation: $F=(AUC_{oral}/AUC_{IV})*(Dose_{IV}/Dose_{oral})$. $C_{max}$ and $T_{max}$ are determined by visual inspection of the oral concentration curve. $C_{max}$ is the maximum concentration of the test compound circulating in the blood through the duration of the experiment reported at time, T ($T_{max}$). the terminal half-life, $t_{1/2}$, is calculated using at least two data points on the IV curve representing the elimination phase. Thus, the $t_{1/2}$ is calculated by inserting the slope (β) of the line generated by plotting the natural log of the test compound concentration versus time (during the elimination phase) into the equation $t_{1/2}=0.693/β$. The volume of distribution (Vd) is calculated using the equation Vd=Cls/β (Cls=systemic clearance, β=slope from $t_{1/2}$ equation). Cls are determined by dividing the absolute dose by the $AUC_{IV}$.

Animal Models

Animal Models for Assessing Anti-Inflammatory Activity

Any of a variety of animal models can be used to test the compounds for their effectiveness in reducing inflammation and treating pain. Useful compounds can exhibit effectiveness in reducing inflammation or pain in one or more animal models.

Carrageenan-Induced Foot Pad Edema Model

The model is described, for example, by Winter et al. (1962 *Proc Soc Exp Biol Med* 111:544) and can be used to assess effects of test compounds on analgesia and/or inflammation. Briefly, rats are fasted with free access to water for 17 to 19 hours before oral treatment with up to three doses of a test compound, indomethacin or celecoxib, or a control vehicle (1% methylcellulose in deionized water). One hour after the last treatment, paw edema is induced by injecting 0.05 mL of a 2% carrageenan solution into the left hindpaw. The left hindpaw volume of each rat is measured using a plethysmometer before oral treatment, at the time of carrageenan injection and at 1.5 hours, 3 hours, and 4.5 hours after the injection of carrageenan. The edema volume of each rat at each time point is expressed as the change from the volume at the time of oral treatment and the anti-inflammatory effect in treated groups is expressed as % inhibition compared to the vehicle only group 1.5 hours, 3 hours and 4.5 hours after the carrageenan injection. The significance of the difference between in edema different groups is assessed by a one-way analysis of variance (ANOVA) followed by the non-paired Dunnett t test. In this model, hyperalgesic response and $PGE_2$ production can also be measured (Zhang et al. 1997 *J Pharmacol and Exp Therap* 283:1069).

Complete Freund's Adjuvant (CFA) Induced Arthritis Model

In this model arthritis is induced in groups of eight Lewis derived male rats weighing 160±10 g by injecting a well-ground suspension of killed *Mycobacterium tuberculosis* (0.3 mg in 0.1 mL of light mineral oil; Complete Freund's Adjuvant, CFA) into the subplantar region of the right hind paw on Day 1. Hind paw volumes are measured by water displacement on Days 0, 1 and 5 (right hind paw, with CFA), and on Days 0, 14 and 18 (left hind paw, without CFA); rats are weighed on Days 0 and 18. Test compounds, dissolved or suspended in 2% Tween 80, are prepared fresh daily and administered orally twice daily for 5 consecutive days (Day 1 through Day 5) beginning one hour before injection of CFA. For CFA-injected vehicle control rats, the increase in paw volume on Day 5 relative to Day 1 (Acute Phase of inflammation) is generally between 0.7 and 0.9 mL; and, that on Day 18 relative to day 14 (Delayed Phase of inflammation) is generally between 0.2 and 0.4 mL. Thus, anti-inflammatory activity in this model may be denoted by values calculated during the Acute Phase as well as the Delayed Phase. Animals are also weighed on Day 0 and Day 18; CFA-injected vehicle control animals generally gain between 40 to 60 g body weight over this time period. A 30 percent or more reduction in paw volume relative to vehicle treated controls is considered of significant anti-inflammatory activity. The mean±SEM for each treatment group is determined and a Dunnett test is applied for comparison between vehicle and treated groups. Differences are considered significant at $P<0.05$. Polyarthritis of fore paw, tail, nose and ear can be scored visually and noted on the first day and final day, wherein positive (+) sign is for swelling response and negative (−) sign is normal. X-ray radiographies of the hindpaws can also be performed for further radiological index determination of arthritic symptoms. Hyperalgesia can also be measured in this model, allowing determination of analgesic effects of test compounds (Bertorelli et al. 1999 *Brit Journ Pharmacol* 128:1252).

Air-Pouch Model

This model is described by Masferrer et al. (1994 *Proc Natl Acad Sci USA* 91:3228). Briefly, male Lewis rats (175-200 g, Harlan Sprague-Dawley) are subcutaneously injected with 20 mL of sterile air into the intrascapular area of the back to create air cavities. An additional 10 mL of air is injected into the cavity every 3 days to keep the space open. Seven days after the initial air injection, 2 mL of a 1% solution of carrageenan dissolved in sterile saline is injected directly into the pouch to produce an inflammatory response. In treated and untreated animals the volume of exudate is measured and the number of leukocytes present in the exudate is determined by Wright-Giemsa staining. In addition, $PGE_2$ and 6-keto-$PGF_{1\alpha}$ are determined in the pouch exudates from treated and untreated animals by specific ELISAs (Cayman Chemicals, Ann Arbor, Mich.).

Animal Models for Assessing Analgesic Activity

Carrageenan-Induced Thermal Hyperalgesia

This model is described by Hargreaves et al. (1998 *Pain* 32:77). Briefly, inflammation is induced by subplantar injection of a 2% carrageenan suspension (0.1 mL) into the right hindpaw. Three hours later, the nociceptive threshold is evaluated using a thermal nociceptive stimulation (plantar test). A light beam (44% of the maximal intensity) is focused beneath the hindpaw and the thermal nociceptive threshold is evaluated by the paw flick reaction latency (cut-off time: 30 seconds). The pain threshold is measured in ipsilateral (inflamed) and contralateral (control) hindpaws, 1 hour after the oral treatment with the test compound or a control. The results can be expressed as the nociceptive threshold in seconds (sec) for each hindpaw and the percentage of variation of the nociceptive threshold (mean±SEM) for each rat from the mean value of the vehicle group. A comparison of the nociceptive threshold between the inflamed paw and the control paw of the vehicle-treated group is performed using a Student's t test, a statistically significant difference is considered for $P<0.05$. Statistical significance between the treated groups and the vehicle group is determined by a Dunnett's test using the residual variance after a one-way analysis of variance ($P<0.05$) using SigmaStat Software.

Phenylbenzoquinone-Induced Writhing Model

This model is described by Siegmund et al. (1957 *Proc Soc Exp Bio Med* 95:729), Briefly, one hour after oral dosing with a test compound, morphine or vehicle, 0.02% phenylbenzoquinone (PBQ) solution (12.5 mL/kg) is injected by intraperitoneal route into the mouse. The number of stretches and writhings are recorded from the 5th to the 10th minutes after PBQ injection, and can also be counted between the $35^{th}$ and $40^{th}$ minutes and between the $60^{th}$ and $65^{th}$ minutes to provide a kinetic assessment. The results are expressed as the number of stretches and writhings (mean±SEM) and the percentage of variation of the nociceptive threshold calculated from the mean value of the vehicle-treated group. The statistical significance of any differences between the treated groups and the control group is determined by a Dunnett's test using the residual variance after a one-way analysis of variance ($P<0.05$) using SigmaStat Software.

Kaolin-Induced Arthritis Model.

This model is described by Hertz et al. (1980 *Arzneim Forsch* 30:1549) and can be used to assess effects on both analgesia and inflammation. Briefly, arthritis is induced by injection of 0.1 mL of kaolin suspension into the knee joint of the right hind leg of a rat. Test compounds are administered subcutaneously after 15 minutes and again after two hours. Reference compounds can be administered orally or subcutaneously. Gait is assessed every hour from 1.5 hours to 5.5 hours after treatment and is scored as follows: normal gait (0), mild disability (1), intermittent raising of paw (2), and elevated paw (3). Results are expressed as the mean gait source (mean±SEM) calculated from individual values at each time point and the percentage of variation of the mean score calculated from the mean value of the vehicle-treated group at 4.5 hours and 5.5 hours after treatment. The statistical significance of differences between the treated groups and the vehicle-treated group is determined by a Dunnett's test using the residual variance after a one-way analysis of variance ($P<0.0.5$) at each time point.

Peripheral Mononeuropathy Model

This model is described by Bennett et al. (1988 *Pain* 33:87) and can be used to assess anti-hyperalgesic effect of an orally administered test compound in a model of peripheral mononeuropathy. The effect of the test substance can be compared to a no treatment control or reference substance, e.g., morphine.

Peripheral mononeuropathy is induced by loose ligation of the sciatic nerve in anaesthetized male Sprague Dawley rats (pentobarbital; 45 mg/kg by intraperitoneal route). Fourteen days later, the nociceptive threshold is evaluated using a mechanical nociceptive stimulation (analgesimeter paw pressure test; Ugo Basile, Italy). The test and reference compounds and the vehicle are orally administered (10 mL/kg carried 1% methylcellulose). Increasing pressure is applied to the hindpaw of the animal until the nociceptive reaction (vocalization or paw withdrawal) is reached. The pain threshold (grams of contact pressure) is measured in ipsilateral (injured) and in contralateral (non injured) hindpaws, 60 minutes after treatment. The results are expressed as: the nociceptive threshold (mean±SEM) in grams of contact pressure for the injured paw and for the non-injured paw (vehicle-treated group) and the percentage of variation the nociceptive threshold calculated from the mean value of the vehicle-treated group. A comparison of the nociceptive threshold between the non injured paw and the injured paw of the vehicle-treated group is performed using a Student's t test. The statistical significance of the difference between the treated groups and the vehicle group is determined for the injured hindpaw by a Dunnett's test using the residual variance after a one-way analysis of variance ($P<0.05$) using SigmaStat Software (SigmaStat® v. 2.0.3 (SPSS Science Software, Erkrath GmbH)).

Diabetic Neuropathy Paw Pressure Test

Complete protocol details can be found in Rakieten et al. (1963 *Cancer Chemother Rep* 29:91). Briefly, diabetes is induced by intraperitoneal injection of streptozotocin in rats. Three weeks later, the nociceptive threshold is measured using the paw pressure test to assess hyperalgesia. Test compound or controls are administered intraperitoneally 30 minutes prior to pain measurement.

Acetic Acid Writhing Test

Briefly, a test compound is administered orally one hour before intraperitoneal injection of acetic acid (0.5%, 10 mL/kg) in rats. Reduction in the number of writhes by 50 percent or more ($\geq 50$) per group of animals observed during the 5 to 11 minutes period after acetic acid administration, relative to a vehicle treated control group, indicates possible analgesic activity. This assay is based on that described in Inoue, K. et al. (1991 Arzneim. Forsch/Drug Res. 41: 235).

Formalin Test

Complete protocol details can be found in Hunskaar et al. (1985 Neurosci. Meth. 14:69). Briefly, 30 minutes after intraperitoneal administration of a test compound or a control, 20 µl of a 5% formalin solution is injected by subplantar route into the right hindpaw of the rat. Hindpaw licking time is recorded during the early phase and the later phase after formalin injection.

Tail Flick Test

Complete protocol details can be found in D'Amour and Smith (1941 *J Pharmacol. Exp Ther.* 72:74). Briefly, 30 minutes after intraperitoneal administration of a test compound or a control, a light beam is focused onto the tail of the rat. The nociceptive reaction latency, characterized by tail withdrawal, is recorded. The cutoff time is set to 15 seconds.

Tail Immersion Test

In this test the tail of the rat is immersed into a 50-60° C. water bath. The nociceptive reaction latency, characterized by tail withdrawal, is measured (Haubrich et al. 1990 *J Pharmacol Exp Ther* 255:511 and Lichtman et al. 2004 *Pain* 109: 319).

Hot Plate Test

Complete protocol details can be found in Eddy et al. (1950 *J Pharmacol. Exp. Ther.* 98:121). Briefly, 30 minutes after intraperitoneal administration of a test compound or a control, the mouse is placed on a metallic hot plate maintained at 52° C. The nociceptive reaction latency, characterized by a licking reflex of the forepaws or by a jumping off the hot plate is recorded. The cut-off time is set to 30 seconds.

Animal Models for Assessing Anxiolytic Activity

Compounds that modulate FAAH activity, and thus fatty acid amide levels, may also have anxiolytic activity. Animal models to assess anxiolytic activity include:

Elevated Plus Maze

The elevated plus maze consists of four maze arms that originate from a central platform, effectively forming a plus sign shape as described in van Gaalen and Steckler (2000 *Behavioural Brain Research* 115:95). The maze can be made of plexiglass and is generally elevated. Two of the maze arms are unwalled (open) and two are walled (closed). The two open arms are well lit and the two enclosed arms are dark (Crawley 2000 *What's Wrong With My Mouse?: Behavioral Phenotyping of Transgenic and Knockout Mice*, Wiley-Liss, New York). The test is premised on the naturalistic conflict between the tendency of an animal to explore a novel environment and the aversive properties of a brightly lit, open area (Pellow et al. 1985 *J. Neuroscience Methods*, 14:149).

Complete protocol details can be found in Fedorova et al. (2001 *J. Pharm. Exp. Ther.* 299: 332). Briefly, following administration of test compound or control, an animal is placed individually on the central platform, facing one of the open arms opposite to the observer. The number of open and closed arm entries, and the time spent in the different compartments of the maze by the animal (central platform, open and closed arms) is scored (as described in Gaalen et al. (supra)). An arm visit is recorded when an animal moves all four paws into the arm as described in Simonin et al. (1998 *EMBO J.* 17: 886). Behavior is scored by an observer and/or via a video camera over a 5-minutes test session. A greater amount of time spent or entries made by the animal in the open versus the closed arms is an indicator of anxiolytic activity.

Elevated Zero Maze

The elevated zero maze is a modification of the elevated plus maze. The elevated zero maze consists of a plexiglass apparatus in the shape of a circle (i.e., a circular runway of 46 cm diameter and 5.5 cm runway width) with two open and two wall-enclosed sectors of equal size. It is elevated up to a meter above the ground. This apparatus is similar to that described in Shepherd et al., (1994 *Psychopharmacology*, 116, 56), but scaled appropriate for mice.

Complete protocol details can be found in Kathuria et al (2003 *Nature Medicine* 9: 76). Briefly, following intraperitoneal administration of test compound or control, and an appropriate pretreatment time, an animal is placed on one open sector in front of an enclosed sector. Time in a new sector is recorded as entry with all four paws. Behavior will be scored by an observer and/or via a video camera over a 5-minutes test session. A greater amount of time spent or entries made by the animal in the open versus the walled sector is an indicator of anxiolytic activity.

Animal Models Related to Allergic Response

Any of a variety of animal models can be used to test the compounds for their effectiveness in reducing allergic and inflammatory activity. Useful compounds can exhibit effectiveness in reducing allergic response and inflammation in one or more animal models.

Systemic Eosinophilia

The model is described, for example, by Shichijo et al. (2000 *J. Pharmacol. Exp. Ther.* 307:519-520). Briefly, seven week old male Brown Norway or Wistar rats are intravenously injected with 250-300 µg/rat of 13,14-dihydro-15- keto-prostaglandin $D_2$ (DK-PGD$_2$), a CRTH2 agonist (dissolved in ethanol and PBS), or the corresponding volume of solvent. Rats are pretreated with or without intravenously injected 3-30 mg/kg Ramatroban [(+)-(3R)-3-(4-fluorobenzenesulfonamido)-1,2,3,4-tetra-hydrocarbazole-9-propionic acid], a CRTH2/thromboxane $A_2$ antagonist (dissolved in NaOH, pH-neutralized by HCl addition, and dosed in a 10% Cremophor solution). Peripheral blood is collected at 0, 1, 2, 3, 4 and 5 hours post-injection for blood smears. Following blood collection, animals are euthanized by complete bleeding and the femoral head and condoles are removed from the left femur. Total white blood cells are counted. Differential cell counts are performed on blood smears stained with May-Gruenwald's and Giemsa's solution based on standard morphologic and histological criteria.

Induction of Contact Hypersensitivity

In this model, induction of contact hypersensitivity (CHS) is created as described by Takeshita et al. (2004, *Int. Immunol.* 16(7):947-59). On days 0 and 1, female Balb/c mice, 7-8 weeks of age are painted onto the shaved abdominal skin with 400 µl of 0.5% fluorescein isothiocyanate (FITC) dissolved in acetone:dibutylpthalate (1:1, DBP). Six days later, mice are challenged by application of 20 µl of 0.5% FITC in DBP onto both sides of the right ear. The solvent control (DBP) is applied to the left ear. Challenge-induced increases in ear thickness are measured by an engineer's micrometer at 0, 24, 48 and 72 hours post-challenge. The CHS response is determined by challenge-induced increases in ear thickness. CHS response=[(right ear thickness post challenge–left ear thickness post challenge)–(right ear thickness pre challenge–left ear thickness pre challenge)].

To determine the presence of leukocyte infiltration, ears and back skins are fixed for 30 hours in zinc fixative at room temperature and embedded in paraffin for histological and immunohistochemical evaluation. For assessment of eosinophil peroxidase activity (EPO), skin sections are homogenized in 1 ml of ice cold buffer (0.05 M Tris-HCl pH 8.0 containing 0.1% Triton X-100). The tissue samples are centrifuged at 10,000 g for 20 minutes at 4° C. and supernatants are collected for measurement of EPO activity. In a 96 well microtiter plate, the substrate solution (100 µl of 10 mM o-phenlyenediamine in 0.05 M Tris-HCl and 4 mM $H_2O_2$) is added to the 20-fold diluted homogenate in buffer (100 µl). The reaction mixture is incubated at room temperature for 1 hour before the reaction is stopped by the addition of 100 µl of 2M sulfuric acid. The microtiter place is measured for absorbance.

Evan's Blue Test

Complete protocol details can be found in Takeshita et al. (2004, *Int. Immunol.* 16(7):947-59). Briefly, female Balb/c mice, 7 weeks of age are injected at two locations intradermally on their shaved backs with increasing concentrations of 0.1-10 µg/site of DK-PGD$_2$. This is followed by an intravenous injection of 0.25 ml of saline containing 1.25 mg of Evan's blue dye. Four hours post-dye injection, mice are euthanized and the back skin is collected. Edema severity is assessed by measuring the density of the extravasated dye. Effects of pharmacological inhibition of the inflammatory reaction to DK-PGD$_2$ will also be assessed by treatment with CRTH2 antagonists, such as Ramatroban.

Ovalabumin-Induced Airway Cell Proliferation and Inflammation

Complete protocol details can be found in Eynott et al. (2003, *J. Pharmacol. Ther.* 304:22-29). Briefly, Brown Norway rats are sensitized on days 1, 2, and 3 with intraperitoneal (i.p.) injections of 1 mg ovalbumin (OVA) and 100 mg Al(OH)$_3$ in 1 mL 0.9% NaCl saline. They are then exposed to either 0.9% NaCl saline or 1% OVA aerosol every 3rd day (days 6, 9, & 12) for 30 minutes. 2 mg/kg dexamethasone is used as a positive control and is dosed i.p. once a day on days 4, 5, 6, 9, & 12. Vehicle (15% β-cyclodextrins in DMSO) and text compounds are dosed orally twice a day on days 5-12. On challenge days, all animals are treated 1 hour prior to OVA allergen exposure and, if required for twice a day treatment, ~4-8 hours after allergen exposure. Samples are collected 24 hours after the last OVA challenge. For sample collection, rats are anaesthetized by administration of 10 mg/kg xylazine and 60 mg/kg ketamine intraperitoneally. Once the rats were fully anesthetized, blood is collected for serum via the retro-orbital route. The rats are subsequently perfused by injecting 30 mL PBS through the right ventricle of the heart after the abdominal aorta is severed. A tracheostomy is then performed and bronchoalveolar lavage fluid (BAL) is collected through five 5 mL rinses using Hank's Balanced Salt Solution, which was kept on ice. Airway inflammatory cell accumulation and proliferation of cells are measured through the BAL fluid collection and subsequent cell counts. Cytospin slides are prepared and eosinophil % are determined by counting ~400 cells per slide. The test compounds are dosed at 5 mg/kg twice daily. Activity is scored based on the ability of the test compound to prevent ovalbumin-induced eosinophil induction (as determined by percentage of eosinophils in BAL fluid).

Ovalbumin-Induced Airway Inflammation in Sensitised Brown Norway Rats

The assay assesses the effect of test compounds on cellular recruitment into the lung after antigen challenge in the sensitised Brown Norway rat. The model is a slightly modified protocol based on that disclosed in Underwood et al. 2002 British Journal of Pharmacology 137: 263-275. Briefly, male Brown Norway rats (200-225 g, from Harlan) are be sensitised on days 0, 14 and 21 with ovalbumin (100 µg/rat, i.p.) administered with Alum™ (20 mg/rat aluminium hydroxide and 20 mg/rat magnesium hydroxide, i.p.). Rats are challenged with inhaled ovalbumin (10 g/l, 30 minutes) or saline aerosol on day 28. Vehicle (5 ml/kg) or test compound (1 or 10 mg/kg, 5 ml/kg) are dosed orally 16 and 1 hour(s) before and 1 and 6 hours after antigen challenge. Budesonide (3 mg/kg) is included as a positive control and dosed at the same time points. End point measurements are as follows: one hour after the challenge the rats have PenH levels monitored for 5 hours to assess late asthmatic reaction.

Cellular burden and inflammatory status are assessed. Twenty-four hours after ovalbumin challenge, rats are euthanised with an overdose of pentobarbitone i.p. A heparinised blood sample is taken via cardiac puncture and the resulting plasma kept frozen. Bronchoalveolar lavage (BAL) is carried out (2×3 ml RPMI media, 30 seconds each). Immediately after BAL, the left lobe is removed, perfused with RPMI to remove the blood pool of cells and 300 mg of lung is chopped and stored in RPMI/FCS (fetal calf serum) containing penicillin/streptomycin. The remaining perfused, chopped lung tissue is flash frozen and stored at −80° C. The remaining lung lobes are insufflated with formalin to a pressure of 20 mmHg, the lungs tied off and stored in formalin until required.

The 300 mg of tissue undergoes collagenase digestion and the cells are recovered (For method see Underwood et al., (1997) *Br. J. Pharm.*, 122, 439-446). Total cell counts recovered from the airway lumen and lung tissue are quantified using a Sysmex cell counter. Differential cell counts (200 cells counted which comprise eosinophils, neutrophils, lymphomononuclear cells expressed as percentage and absolute cell count(s) of cells recovered from the airway lumen and lung tissue are made by light microscopy from cytocentrifuge reparations stained with Wright-Giemsa stain. Remaining BAL samples are spun down and supernatant retained at −20° C.

Sephadex Induced-Pulmonary Eosinophilia in Rodents

Male Swiss Webster mice are used in a model of Sephadex induced-Pulmonary Eosinophilia. In brief, test groups receive vehicle, test compound (10 mg/kg) or positive control, dexamethasone (0.5 mg/kg), by oral gavage, twice per day (p.o., b.i.d.) at a dosing volume of 10 ml/kg, on days −1, 0, 1 and once, 4 hours pre-sacrifice, on day 2. On day 0, test groups are each intravenously administered 3 mg/kg Sephadex beads G-100-120 (Sigma) at a dosing volume of 5 ml/kg or no Sephadex. On day 2, four hours post vehicle/test compound/dexmethasone administration, animals are euthanized by inhalation of $CO_2$ and subsequently undergo histopathologic and lavage evaluation of lungs for severity of eosinophilic infiltrate in peribronchiolar locations. Bronchoalveolar lavage fluid is collected by flushing the lung via the trachea 3 times with 1 ml aliquots of cold saline, and then the lungs are harvested by filling with formalin and allowed fixation a minimum of 1 day. White blood cell counts are prepared from lavage fluids. In addition, lavage fluids are immediately prepared for cytospin and cell differential counts performed. Cytospin slides are stained with a Wrights-Giemsa stain. Whole lung sections are stained with Hematoxylin and eosin stain for morphometry evaluation of severity of inflammatory cell infiltrate in peribronchiolar locations around Sephadex beads. Three sections (initial and 2 steps at 100 µm intervals) are prepared from each animal for analysis of area or diameter of inflammation around 5-8 Sephadex beads/mouse. Morphometric digital imaging analysis is performed to score inflammation. A similar experimental protocol can be performed using Lewis rats with the modification that animals are euthanized on day 1.

Mouse Model of Allergic Airways Disease Using the FlexiVent System

In this model, animals in groups of 10 (8-10 wk old male BALB/c mice) are used to assess allergic airway disease. Mice are quarantined for 14 days. On days 0 (the first day following the end of the 14 day quarantine) and day 7, experimental animals are immunized by intraperitoneal (i.p.) injection with a mixture of ovalbumin (OVA; 10 µg) and aluminum hydroxide (Alum; 2 mg) in sterile water. A second group of animals is immunized with sterile water only and serves as a nonimmunized (negative) control. On days 13, 14, 15, and 16, dexamethasone (positive control), test compound or vehicle only is delivered by oral gavage (all at 10 mg/kg and a dosing volume of 10 ml/kg) twice a day. Animals are exposed to ovalbumin on days 14 and 15. Ovalbumin exposures are generated by aerosolizing 1% heat-aggregated ovalbumin (chicken egg, grade V; Sigma, St. Louis, Mo.), diluted with filtered air, and then delivered to the exposure chambers for 3 hours (H2000, Hazelton Systems). The total mass concentration of ovalbumin is determined by gravimetric analysis of filter samples taken every hour during exposure. The target mass concentration of ovalbumin is 4 mg/m$^3$. Chamber temperatures are maintained at 26±2° C. and lights on a 12 hour on/off cycle. Animals are given food (Teklad™ certified rodent diet (Harlan Teklad, Madison, Wis.)), ad libitum except during the 3 hour exposure period. Water is available ad libitum throughout the duration of the study.

On day 17, animals are anesthetized and tested for pulmonary function (response to methacholine challenge) by force oscillation techniques (FlexiVent). Airway hyperresponsiveness (AHR) to increasing concentrations of aerosolized methacholine (MCh) is measured using a FlexiVent analyzer (SCIREQ, Montreal, Canada). Briefly, each mouse is anesthetized with Avertin 9250 mg/kg; 0.02 ml/g; 1.2% (w/v) solution of 2,2,2 tribromethanol in 0.8% tert-amyl ethanol (2 methyl, 2 butanol)) i.p. and placed on a heating pad. The neck fur is shaved and a small superficial incision made in the skin above the trachea. After the lobes of the salivary gland are separated, a small incision is made in the trachea, and the trachea is cannulated with a blunt-end 20 gauge needle hub. The cannula is secured by suture thread and the skin is pulled back and secured by cyanoacrylate adhesive. Ventilation is performed through the cannula by positive pressure maneuvers on the Flexivent apparatus. Once on the ventilator, pancuronium, (paralytic, 0.5 mg/kg) is administered i.p. Heart rate is monitored via a Grass Instruments Recorder w/Tachograph. Changes in heart rate greater than 50 bpm from baseline require supplementing the anesthesia (Avertin, ip). Additional doses of Avertin are given at a dose of 100 mg/kg and the animal's hear rate is monitored for at least 60 sec to determine if additional doses are needed. After baseline measurements of resistance and compliance, increasing doses of methacholine (Mch; 3, 6, 12, 25, 50 mg/ml nebulizer) are delivered via aerosol and resistance and compliance are measured. Airway resistance is calculated for each concentration of methacholine and the average±SEM is plotted for all treatment groups. Changes in pulmonary resistance (i.e., Mch dose-response curves) are assessed by repeated measures two way analysis of variance (ANOVA) with Bonferroni posttest. All other statistical comparisons re made using ANOVA with the Dunnetts multiple comparison test. A value of $p<0.05$ is considered significant.

Following AHR measurements, blood is collected and saved for further evaluation. The animals are then euthanized by injection with a lethal dose of a pentobarbital-based euthanasia solution. Bronchoalveolar lavage (BAL) cells are obtained from 7 animals per experimental or control group by inserting a catheter into the trachea and lavaging the lung 3 times with 0.8 ml of PBS (without calcium chloride and magnesium chloride). Total BAL cells are determined using a hemacytometer. BAL cells are spun onto slides by cytocentrifugation and stained with a modified Wright-Giemsa stain. Four hundred cells are counted and the percentage of specific cell types determined for each animal. The first lavage fluid sample (after centrifugation) is frozen separately for future cytokine analysis. The whole lung is snap frozen dry for future analyses.

Three animals from each group which are not subjected to BAL are used for histopathologic analysis and have their lungs instilled via the trachea with 10% buffered formalin, removed and fixed in the same solution. Generally, three specimens per treatment, each consisting of multiple axial sections of lung, are examined. All sections are stained with alcian blue-H&E. Lesions are graded on a subjective basis. Lesions are graded as minimal, mild, moderate, and marked (corresponding to severity scores of 1, 2, 3, and 4, respectively) and given a distribution designation of either focal, locally extensive, multifocal, multifocal and coalescing, or diffuse (corresponding to distribution scores of 1, 2, 3, 4 and 5, respectively). The product of the severity and distribution scores is averaged for each treatment group.

Prostaglandin $D_2$-Induced Eosinophilic Airway Inflammation

Complete protocol details can be found in Shiraishi et al (2004, *J. Pharmacol. Ther.* epub as DOI:10:1124/jpet.104.078212). Briefly, Brown Norway rats are intravenously injected with rat interleukin-5 or PBS, one hour prior to intratracheal administration of prostanoid receptor agonists. These agonists can include the following; $PGD_2$, two $CRTH_2$-specific agonists, DK-$PGD_2$, 15R-methyl $PGD_2$ and 11-deoxy-11-methylene-15-keto-PGD$_2$ (MK-PGD$_2$), a DP receptor-specific agonist BW 245C, a thromboxane A$_2$ receptor (TP)-specific agonist, -BOP and Indomethacin. In some experiments, an orally delivered CRTH2/TP antagonist, Ramatroban, an intravenously delivered DP antagonist, BW A868C, or an intravenously delivered TP antagonist are administered two hours prior to administration of agonists. Rats are euthanized at 2, 8 and 24 hours post-agonist administration. Inflammatory cell accumulation in the trachea and lungs is recovered by bronchoalveolar lavage for cell counts and lungs are evaluated by histological examination. In a separate experiment, rats receive intravenous injection of IL-5 (0.2 ng/kg) or PBS one hour prior to intratracheal administration of PGD$_2$ (100 nmoles/animal) or vehicle. A peripheral blood sample is collected hourly post-dose of IL-5 for hematological evaluation.

Murine Allergic Inflammation

Complete protocol details are described in Fujitani et al. (2002 J. Immunol 168:443-449) and Matsuoka et al. (2000 Science 287: 2013-2017). Briefly, transgenic and wildtype mice are immunized with 10 μg ovalbumin (OVA) in 0.2 ml aluminum hydroxide (Alum) on days 0 and 14. On day 21, the mice are exposed to aerosolized OVA (50 mg/ml in sterile saline) for 20 minutes. On days 1 and 3 post-OVA challenge, mice are euthanized, bronchoalveolar lavaged, and the lavage fluid is assessed by differential cell counting.

Allergic Rhinitis in Anesthetized Rodents

In this model described, for example, by Arimura et al. (2001 J. Pharmacol. Ther. 298:411-419) guinea pigs are sensitized to OVA twice by inhalation of an aerosol solution of 1% OVA for 10 minutes. At 7 days after the second sensitization, the animals are anesthetized and artificially ventilated through a tracheal cannula using a respirator. Another glass cannula is inserted into the nasopharynx from the side of the larynx, and a fixed amount of air is continuously insufflated into the nasal cavity via the nasal cannula using another respirator. Insufflation pressure is monitored by a pressure transducer connected to the side arm of the nasal cannula as an indication of intranasal pressure. Nasal antigen challenge is performed by generating an aerosol of 3% OVA between the nasal cannula and the animal respirator for 3 minutes using an ultrasonic nebulizer, and then the intranasal pressure is measured for 30 minutes. Nasal secretion and the nose are collected for further evaluation.

A biphasic allergic rhinitis model in conscious guinea pigs is also fully described in Arimura et al. (2001 J. Pharmacol. Ther. 298:411-419).

Allergic Conjunctivitis Model

Complete protocol details are described in Arimura et al. (2001 J. Pharmacol. Ther. 298:411-419). Briefly, a 2.5% OVA solution is applied topically to both eyes (10 μl/eye) of conscious guinea pigs that have been sensitized as described in the "Allergic Rhinitis Model in Anesthetized Rodents" protocol above. Immediately following OVA application, Evan's blue dye (20 mg/kg i.v.) is injected as a marker of plasma exudation. The amount of Evan's blue extravasated in the conjunctiva and eyelid for 30 minutes is quantified. Independently, histamine 0.001%, PGD$_2$ 0.01%, or a combination of the two are applied to the eyes of nonsensitized guinea pigs, and dye exudation is determined.

Determination of Interleukin-13 Levels in Bronchial Alveolar Lave Fluid

A commercially available ELISA kit (Biosource, Catalog # KRC0132) is used to determine the effects of compounds on the Interleukin-13 (IL-13) levels of bronchial alveolar lavage fluid (BALF) taken from rats that have undergone certain allergen induced (e.g. ovalbumin, sephadex, prostaglandin D$_2$) airway cell proliferation and inflammation.

After collection, BALF samples are concentrated 5-fold with Microcon YM-3 centrifugal devices (Millipore, Catalog #42404) and stored at −80° C. until use. A 500 pg/mL standard stock is prepared by reconstituting the IL-13 standard provided in the kit with the amount of standard diluent specified on the standard vial. A standard curve is then prepared by serially the standard stock down to 7.8 pg/mL. 50 μL of each pint of the standard curve and 50 μL of concentrated BALF sample are added to the ELISA plate. Added to these samples is 150 μL of anti-rat IL-13 biotin conjugate. The plate is then incubated at room temperature for 2 hours. The plate is then washed 4 times with wash buffer and 100 μL of 1-x streptavidin-peroxidase is added to all wells. The samples are then incubated at room temperature for 30 minutes. Again, the plate is washed 4 times with wash buffer, 100 μL of stabilized chromogen are added to each well and the plate is incubated at room temperature for 45 minutes. To stop the reaction, 100 μL of stop solution is added and the plate is read at 450 nm. Levels of other cytokines including IL-1β, IL-4, IL-5 and the chemokine, eotaxin can be similarly assessed in BALF samples to determine the effect of test compounds on Th-2 related function.

Determination of Ovalbumin Specific Immunoglobulin E in Serum

The effects of compounds on serum immunoglobulin E (IgE) levels in rodents that have undergone allergen-induced (e.g. ovalbumin) airway cell proliferation and inflammation can be measured using an assay developed with reference to Salgado et al., Allergol. et Immunopathol., 16, 2 (95-98), 1988.

Serum samples are taken from rats suffering from asthma, induced by the inhalation of ovalbumin, and stored at −80° C. until use. The ELISA plate is coated with 1.25 mg/mL ovalbumin prepared in coating buffer (0.5M Carbonate-Bicarbonate, pH 9.6, Bethyl Labs, Catalog # E107) and incubated overnight at 4° C. After 18 hours, the plate is washed one time with wash buffer (50 mM Tris, 0.14 M NaCl, 0.05% Tween 20, pH 8.0, Bethyl Labs, Catalog # E106). 200 μL of blocking solution (5% skim milk/PBS) is added and the plate is incubated at 4° C. for 1 hour. Serum samples are diluted 1:3000 in sample diluent (Post coat solution containing 50 mM Tris, 1% BSA, pH 8.0 0.05% Tween 20, Bethyl Labs, Catalog # E104). After the one hour incubation with blocking solution, the plate is washed three times with wash solution and 100 μL of diluted sample is added to the appropriate well. Samples are then incubated at room temperature for 3 hours. Once the 3 hour incubation is complete, the plate is washed five times with wash buffer. The sheep anti-rat IgE HRP conjugate detection antibody (Bethyl Labs, Catalog #A110-117P) is diluted 1:100 in a 1% skim milk/PBS solution. 100 μL of this solution is then added to the plate and the plate is incubated for 1 hour at 4° C. The plate is then washed another five times with wash buffer. The TMB peroxidase substrate (Bethyl Labs, Catalog # E102) is prepared by adding equal volumes of TMB peroxidase substrate with peroxidase solution B. 100 μL of substrate is added to plate and incubated at room temperature for 15 minutes. The enzymatic reaction is stopped by adding 100 μL of 2 M sulfuric acid (Sigma Aldrich). The plate is then read at a wavelength of 450 nm.

In the case of compounds (e.g. CRTH2 modulators, CRTH2 inhibitors) useful for treating gastrointestinal disorders in which inflammation plays a role there a number of useful animal models that can be used in the testing of compounds.

TNBS Colitis in Rats:

Complete protocol details for one model can be found in Morris et al. (Gastroenterology 96(3):795-803, 1989). Briefly, to induce chronic colonic inflammation in rats, a rubber catheter is inserted rectally into the colon such that the tip is 8 cm proximal to the anus. Next, 2,4,5-Trinitrobenzenesulfonic acid (TNBS 5-30 mg) dissolved in 50% ethanol is instilled into the lumen of the colon through the rubber catheter. Rats are euthanized at various times (24 hours and 1-8 weeks) following rectal TNBS administration and the colon tissue is examined for damage, inflammation and ulceration. Colon weight and colonic myeloperoxidase (MPO) activity are also assessed.

TNBS Colitis in Mice:

female C57BL/6 mice are used in a model of TNBS-Induced Colitis. Briefly, test groups each receive vehicle or test compound (i.e. test compound (10 mg/kg) or positive control (dexamethasone; 0.5 mg/kg)), by oral gavage, twice per day at a dosing volume of 10 ml/kg, on days −1, 0, 1, 2 and once, 4 hours pre-sacrifice on day 3. On day −1, mice are fasted 16-20 hours prior to TNBS injection. On day 0, mice are infused with 50 µl TNBS solution (Sigma) or vehicle/per mouse via rectal catheter in the colon and rectum held off for approximately 4-7 minutes. Animals are returned to cages and monitored for full recovery. Behavior is monitored daily. Body weights are measured each day and at termination. Mice are euthanized by cervical dislocation and necropsied on day 3 (72 hours post-TNBS injection) for assessment of gross observations, colon clinical observations and collection of all colons into 10% neutral buffered formalin for histopathologic evaluation. Clinical assessments include colon length, colon weight, hemorrhage, stricture formation, ulceration, fecal blood, mucus, diarrhea, erythema, adhesion and edema at necropsy. Colon histopathology quantitates the extent of inflammation (e.g. foamy macrophage, lymphocyte and polymorphonuclear cell infiltrate), gland loss and epithelial loss by clinical scoring of severity and percentage area affected. Scoring is performed in a blinded manner. Colon tissue may also be assessed in an in vitro myeloperoxidase (MPO) assay for MPO enzyme activity. Complete protocol details for an alternative model can be found in Dohi et al. (Gastroenterology 119:724-733, 2000). Briefly mice (C57BL/7; 40 µg/g and Balb/c 36 µg/g) are given a solution of TNBS dissolved in a mixture of phosphate-buffered saline and then mixed with an equal volume of ethanol for a final concentration of 2% TNBS in 50% ethanol. On days 0 and 7, the TNBS enema is administered to mice anesthetized with ketamine and xylazine via a glass microsyringe equpped with a gastric intubation needle. Tissues and cells are assessed 3 days later (day 10).

Oxazolone Colitis in Mice

Complete protocol details for this model can be found in Kojima et al. (J. Pharmacol. Sci. 96:307-313, 2004). Briefly, a metal catheter is inserted 4 cm into the lumen of the colon via the anus in the anesthetized mouse. Oxazolone solution (0.15 mL/mouse) is administered into the colon through the catheter. Colonic tissues from mice on days 0 (before colitis induction), 1, 2, 4 and 7 are collected and examined for evidence of colitis and myeloperoxidase (MPO) activity.

In general any model of colitis can be used, in particular, mouse or rat models in which a chemical, hapten or antigen is used to induce colitis.

Oral Antigen-Induced Gastrointestinal Allergy in Mice

Complete protocol details for one model can be found in Hogan et al. (Nat Immunol. 2(4):353-60, 2001). Briefly, mice are sensitized by intraperitoneal injection with ovalbumin (50 µg) in aluminum hydroxide (alum; 1 mg) in 0.9% sterile saline on day 0. On days 12 and 15, mice are orally administered with encapsulated ovalbumin or placebo enteric-coated beads (20 mg) followed by oral administration of acidified water (300 µl, pH 2.0). In some experiments, mice are intragastrically challenged with soluble ovalbumin (1 mg) in PBS (200 µl) or control PBS on days 12 and 15. Mice are euthanized and parameters are measured 72 hours after the last antigen challenge. The gastrointestinal tract tissue is examined for eosinophilic inflammation. Complete protocol details for another model can be found in Forbes et al. (Gastroenterology 127:105-118, 2004). Briefly, mice are sensitized by an intraperitoneal injection of 50 µg of ovalbumin/1 mg of alum in 200 µL of 0.9% sterile saline on day 0. On days 12, 14, and 16, mice are orally administered 20 mg of either encapsulated ovalbumin enteric coated beads or placebo beads, followed by 200 µL of acidified water 9 pH 2.0). 72 hours after the last antigen challenge, mice are euthanized and disease parameters are measured in various ways. In some experiments, mice are intraperitoneally injected on days 0, 1, and 3 with either rat IgG2b-depleting anti-D4 monoclonal antibody or rat IgG control antibody. Methacholine-induced bronchial hyperresponsiveness is determined on day 4.

Myeloperoxidase Assay

This protocol has been modified from descriptions in Arita et. al. (2005 *Proc Natl Acad Sci USA* 102:7671) and Morris et al. (1989 *Gastroenterology* 96:795). In brief, each colon tissue sample is assessed for levels of myeloperoxidase activity. Tissues are homogenized in potassium phosphate buffer (pH 6.0) containing 0.5% hexadecyltrimethylammonium bromide, followed by three cycles of sonication and freeze-thawing. Particulate matter is removed by centrifugation (13,000 rpm for 20 minutes at 4° C.). 10 µl of supernatant is added to 90 µl of potassium phosphate buffer (pH 6.0) containing 0.2 mg/ml o-dianisidine dihydrochloride (ODD) and 0.0006% hydrogen peroxide. Changes in optical density are measured at 460 nm at 25° C., at 30 second and 60 second intervals up to 30 minutes.

Experimental Oral Allergen-Induced Diarrhea

Complete protocol details can be found in Brandt et al. (J. Clin. Invest. 112(11):1666-1677, 2003). Briefly, mice are sensitized twice, 2 weeks apart, with 50 µg of ovalbumin/1 mg of aluminum potassium sulfate adjuvant by intraperitoneal injection. Two weeks later, mice are held in the supine position 3 times a week and orally administered 250 µL of sterile saline that contains up to 50 mg of ovalbumin. Before each intragastric challenge, mice are deprived of food for 3-4 hours with the aim of limiting antigen degraduation in the stomach. Diarrhea is assessed by visually monitoring mice for up to 1 hour following intragastric challenge.

Other colitis models are described Elson et al. (Gastroenterology 109:1344-1367, 1995) and Kim et al. (Scand. J. Gastroenterol 27:529-537, 1992).

Chitinase Assay

Acidic mammalian chitinase (AMCase) is induced in animal models of asthma and is found to be elevated in human asthmatics (Zhu et al, Science (2004) 304:1678-82). Therefore, AMCase may be a useful biomarker for disease and compounds which treat the causes and/or symptoms of asthma may block AMCase elevation. Direct inhibition of AMCase may also be beneficial as treatment with antibodies to AMCase have been reported to ameliorate inflammation and airway hyperresponsiveness in animal models.

Assays have been described in the scientific literature including Guo et al (J Biol Chem (2000) 275:8032-7) and Zhu et al (Science (2004) 304:1678-82). In models of asthma, mice or rats are sensitized to allergen (e.g., ovalbumin) and subsequently challenged by aerosolized antigen to induce pulmonary infiltration and airway hyperresponsiveness. Chitinase activity in bronchial alveolar lavage fluid (BALF) is assayed with the fluorogenic substrate 4-methylumbelliferyl (4-MU) (Sigma). BALF is incubated with a substrate in citrate/phosphate buffer (0.1 M/0.2 M), pH 5.2, at a concentration of 0.02 mM. After incubation at 37° C. for 15 minutes, the reaction (final volume, 110 μl) is stopped with 1 ml of 0.3 M glycine/NaOH buffer, pH 10.6, and the fluorescent 4-methylumbelliferone released is measured with a fluorimeter (excitation, 350 nm; emission, 450 nm). A 4-methylumbelliferone (Sigma) standard curve is used to quantify the enzyme activity. Protein concentrations are determined using the Pierce micro-BCA protein assay kit. Compounds useful for the treatment of asthma may, when administered to animals at the appropriate times during the course of the experiment, reduce AMCase activity in BALF. Alternatively, compounds that directly inhibit AMCase activity when administered to animals or in an in vitro setting with purified enzyme, may also be useful for the treatment of asthma and/or allergy.

Animal Models of Psychosis

Animals are housed in a temperature-controlled environment with free access to food and water. Animals are allowed to become acclimatized to their new environment and are handled during 1 week before starting the experiment (to permit habituation to the investigator). All experiments are performed in a separate, quiet, light level, temperature-controlled and sound attenuated experimental room. On the test day, food and water are withdrawn during the experiment and immediately replaced after the experiment such that no animal will is without food or water for longer than 8 hours. Behavioral evaluation is observed in one or more of the following models.

Sterotypical Behavior and Hyperactivity Induced by Psychotomimetic Drugs

Each animal is individually placed into plastic test cages and allowed to habituate to the cage for up to 30 minutes prior to testing. Following habituation, animals are administered a psychotomimetic drug (such as MK-801, PCP, etc) and are then immediately replaced into the test box for behavioral observation. The stereotyped behavior and general motor activity are scored by an observer and/or via a video camera/activity monitor for up to 90 minutes post-injection (Hashimoto et al., 2005 Brain Res 1033:210-5). The test cages are thoroughly wiped clean with alcohol followed by a spray water rinse and dried after each session. This removes any olfactory cues that a rodent may leave on the test cage surface. In some cases, no drug treatment, baseline locomotor activity measurements are taken up to 3 days prior to the test day in order to assess the natural motor activity of the animal.

Therefore, a typical study schedule for stereotyped behavior and hyperactivity progresses as follows: Animals are dosed with test compounds 1 hour prior to systemic injection of psychotomimetic drug and returned to their home cages. 30 minutes prior to behavioral testing, animals are placed in test cages to acclimate. Following habituation, animals are subcutaneously injected with a psychotomimetic drug, and placed back into their respective test cages. Behavior is recorded by an observer and/or video tracker for up to 90 minutes post injection. Following behavioral testing, animals are returned to their home cages. Animals are allowed a drug washout period of one week and behavior is re-evaluated in a counterbalanced fashion. At experiment end, animals are euthanized by $CO_2$ inhalation or pentobarbital overdose (>120 mg/kg). When brain tissue collection is necessary in order to analyze levels of neurotransmitters and immediate early genes, decapitation is performed. If blood sampling is necessary, it is done at the study end, after all behavioral observation is complete. To sample blood, animals are under terminal anesthesia by isoflurane or pentobarbital and sampling takes place at the retro-orbital sinus by sterile pipet tip or by cardiac puncture with a sterile needle.

Effects of Psychomimetics and Antipsychotics on Cognition (Prepulse Inhibition Model Startle reactivity is measured by startle chambers. Each chamber consists of a clear nonrestrictive plexiglass 8.2 cm diameter cylinder resting on a 12.5×25.5 cm platform inside a ventilated box. A high-frequency loudspeaker inside the chamber produces both a continuous background noise of 65 decibels (dB) and a range of acoustic dB stimuli. Vibrations of the Plexiglass cylinder caused by the whole-body startle response of the animal are transduced into analog signals by a transduction unit attached to the platform. The signals are saved to a computer. The PPI test session generally consists of a randomized presentation of startle trials (120 dB pulse), prepulse trials (60-90 dB prepulse immediately preceding a 120 dB pulse) and no stimulus trials. This session usually lasts for 15-20 minutes. The acoustic stimuli are not harmful to the animals' hearing.

Therefore, a typical study schedule for PPI may progress as follows: Animals are dosed with test compounds or antipsychotic drugs (i.p. or s.c.). Immediately after this injection, animals are given a systemic injection (i.p. or s.c.) of either vehicle or psychotomimetic drug and 10 minutes later they are placed individually into startle chambers. A 65 dB background noise level is presented for a 10 minute acclimation period and then the PPI test session (consists of a presentation of startle trials (120 dB pulse), prepulse trials (60-90 dB prepulse immediately preceding a 120 dB pulse) and no stimulus trials) begins and lasts for 15 minutes. At the end of the test session, the animals are returned to their home cages. A no treatment, baseline measurement test session may occur up to 5-7 days prior to the drug treated test session. Following behavioral testing, animals are returned to their home cages. Animals are allowed a drug washout period of one week and behavior is re-evaluated in a counterbalanced fashion. Geyer et al. (2001) Psychopharmacology 156(2-3) 117-154 review the use of PPI models in the study of schizophrenia.

Forced Swim Model of Depression

Compounds described herein can be screened for the ability to alleviate the depression induced in a rodent forced swim mode. Examples of such protocols are found in Porsolt et al. 1977 Arch Int Pharmacodyn Ther. 229:327-336 and Porsolt et al. 1979 Eur J Pharmacol. 57:201-210.

In this model the animal is placed in plexiglass cylinder containing water from which there is no obvious means of escape. The animal alternates between vigorous swimming and immobility. The periods of immobility represent a state of despair in the animals. Animals dosed with known anti-depressants show a decrease in duration of immobility. Periods of immobility are measured by an observer with a stop watch.

Tail Suspension Model of Depression

A test for the screening of anti-depressant compounds is the tail suspension test. An example of the protocol can be found in Steru et al. 1985 Psychopharmacology 85: 367-370.

This model, like the forced swim model, places animals in a situation that results in alternating vigorous movement and periods of immobility. In the assay, animals are suspended by their tails away from other objects and the floor. Like the forced swim test, animals treated with known anti-depressants show a decrease periods immobility. These periods of immobility are measured by an observer with a stop watch.

Animal Models for Assessing Memory and Cognitive Ability

In human patients there are a number of tests that can be used to measure cognitive ability. Useful test include Minimental State Examination (MMSE), Alzheimer's Disease Assessment Scale (ADAS), Boston Naming Test (BNT), and Token Test (TK). The test scores are generally analyzed by determining the percent increase or decrease over the test period compared to the baseline score at the beginning of the test period. These tests and others can be used to assess the effectiveness of the agents used for the treatment or prevention of cognitive impairment.

In analyzing candidate memory protective agents it can be useful to measure the effect of a test compound on the cognitive ability in an animal model. There are a wide range of such tests that can be used to assess candidate compounds.

One useful test involves the assessment of working memory/attention in mice. Briefly, the effect of a compound on spatial working memory can be characterized in aged mice (i.e. about 25 months old) and in young mice (i.e. about 3 months old). The working memory of the mice can first be compromised by pharmacological means (i.e. scopolamine-induced impairment). Working memory is the temporary storage of information (Bontempi et al. 2001 *J Pharm and Exp Therap* 299:297), and has been shown to be the primary type of memory disrupted in Alzheimer's disease, stroke and aging (Glasky et al. 1994 *Pharm, Biochem and Behavior* 47:325). Another useful test for assessing working memory measures Spontaneous Alternation behavior in mice. Spontaneous alternation is defined as the innate tendency of rodents to alternate free choices in a T-maze over a series of successive runs (Dember and Fowler 1958 *Psychological Bulletin* 55:412). This is a sequential procedure that relies on working memory because the ability to alternate requires that the animal retain specific information, which varies from trial to trial (Bontempi et al. 2003 *Neuropsychopharmacology* Apr. 2, 2003, 1-12). This test is also sensitive to varying parameters, such as delay intervals and increased number of trials, as well as pharmacological treatments affecting memory processes (Stefani and Gold, 2001 *Journal of Neuroscience* 21:609). In conducting this test, mice are first allowed to briefly explore a T-maze to become familiar with the apparatus. On the following day, a mouse is placed in a start box that is connected to the main stem of the T-maze. The elapsed time between the opening of the start box and the choice of an arm is measured (choice latency). The mouse is confined in the chosen arm for a set amount of time (e.g., 30 seconds) and then returned to the start box for the remaining consecutive trials in a testing session (Bontempi et al, 2003). Working memory performance for each mouse is assessed by the percentage of alternation over the trials in the testing session. Percentage is defined as entry in a different arm of the T-maze over successive trials.

The Delayed Non-Matching to Place (DNMTP) test is another useful animal model for testing the effect of a compound on cognitive ability. In this test, mice are trained and tested in an elevated eight-arm radial maze (Levin E. and Caldwell, D P (2006) Neurobiol Learn and Memory 86(1) 117-122) with a central start box placed in the center of a room with various pictures/objects placed around the room to serve as spatial cues. Each arm has a food pellet cup located at it far end. Food-deprived animals are habituated to the apparatus with all arms open and baited over a couple of successive daily free exploration periods prior to the test day. The exploration period ceases when all arms are visited and all food pellets are consumed (Bontempi et al 2001 (supra), 2003 (supra)). Animals are then trained to the DNMTP rule. A session consists of multiple trials that are separated by a defined interval. A trial consists of a study phase (two forced runs) and a test phase (two choice runs). In the study phase, the animal is given two consecutive forced runs in two different open arms. A forced run is when one arm of the maze opens allowing the animal to travel down to collect the food pellet and return to the central start box. After the second forced run, the test phase ensues. Two doors open simultaneously to begin the first choice run. One door reveals the first arm visited during the study phase and the other is an adjacent unvisited arm. Once the animal makes a choice and then returns to the start box, the next pair of doors open (second choice run). The second choice run consists of the second arm visited in the study phase and an adjacent novel arm. During the choice runs, the animal is reinforced only when it enters the arm that had not been previously visited during the study phase. This is the non-matching to place rule; the rule being not to return to a previously visited arm. Once a mouse is trained to the DNMTP rule, variable delay periods between the study and test phases can be introduced. Mice are allowed to adapt to the delay paradigm over a few consecutive days prior to compound testing. Compound testing is conducted over a several consecutive days followed by a washout period with no paradigm training, followed by a vehicle injection for measurement of baseline performance. Test compound or vehicle injections are acutely administered prior to the start of each testing session. Working memory is evaluated by the comparison of performance on drug days versus baseline days. The effects of putative cognitive enhancing drugs are commonly evaluated in the delayed non-matching to position task (Crawley, What's Wrong With My Mouse? Behavioral Phenotyping of Transgenic and Knockout Mice, Wiley-Liss, New York, 2000). The DNMTP task is similar to schedule-induced operant tasks which include delayed matching and delayed non-matching to position tests in automated chambers, generally used in rats (Bontempi et al., 2001 (supra); Crawley, 2000 (supra)).

In addition to those working memory assays described above, another useful animal model to assess cognitive performance is the novel object recognition (NOR) assay (Ennaceur & Delacoer 1988, Behavioral Brain Res. 31, 47-49). Briefly, this assay assesses the ability of rodents to retain the memory of a "familiar" object by initially exposing them to the "familiar" object and then, after some period of time, exposing the rodent to both the "familiar" and a "novel" object. If the rodents recognize the "familiar object they will spend more time exploring the "novel" object more. If the memory of the "familiar" object is lost, rodents will investigate both objects equally. Test compounds are assessed for their ability to prolong the time period for which rodents can retain the memory of the familiar object (as measured by exploration of the novel).

Working memory tests such as those described above are thought to require identification and use of novel information on each trial (predominately affecting attentional processes) whereas spatial reference memory tasks require the same information to be used across trials.

The Morris Water Maze Task (D'Hooge and De Deyn (2001) Brain Res Rev 36 (1) 60-90) is a spatial navigation task in which an animal uses visual clues to swim to a hidden platform. Animals are motivated to find the fastest, most direct route to the platform in order to escape the water. The test typically consists of pre-training to a visible platform to test the animal's ability to conduct the procedural component of the task. Training for location of a hidden platform follows visible platform acquisition. Finally, a probe trial tests the animal's ability to find the spatial location that previously contained the hidden platform. Successful performance on the probe trial means that the animal spends significantly greater time in the trained quadrant versus non-trained quadrants. A deficit in learning and memory is defined as normal performance in the visible platform task but impaired performance on the hidden platform task.

Other tests, such as avoidance tasks, have been extensively used in the screening of compounds for cognitive enhancement (Crawley, 2000; Sarter et al. 1992 *Psychopharmacology* 107:461). For example, in the passive avoidance task, an animal is placed in a shuttle box containing a light and dark chamber (the dark is the natural preference of the rodent). The animal is trained to associate footshock with the properties of the natural preferred dark chamber. The next day, the animal is placed in the light chamber and latency to enter the dark chamber assesses the memory for the aversive association (Crawley, 2000). Potential drawbacks from these tests are that procedural components (the ability to acquire, store or retrieve memories) cannot be differentiated form declarative memory (remembering a specific item of information) as opposed to the Morris Water Maze task. Latency to enter the dark chamber on the first day is the only inherent control parameter in the avoidance task. It is known that the passive avoidance task can be affected by fear because an animal is negatively affected by the footshock so the test is often used to complement other learning and memory assays (Yamaguchi et al. 2001 *Jpn Journal of Pharmacology* 87:240).

Tests of cognitive ability are generally used in conjunction with tests designed to rule out artifacts that would impair the animal from performing complex tasks. For example, general effects on motor function (hyperactivity or sedation) can be measured by testing locomotor activity, including stereotypy (Crawley, 2000 (supra)). Motor coordination and balance can be assessed by assays such as the rotarod test. This test requires a mouse to continuously walk forward on a rotating cylinder to keep from falling off (Crawley, 2000 (supra)).

Effects of Test Compounds on Neuropathic Pain in a Spinal Nerve Ligation (SNL) Model Compounds are evaluated in a manner similar tot hat described in US20050143443 example 30 (paragraph 224). Adult male Sprague-Dawley rats (Harlan, Indianapolis, Ind.) are given free access to food and water and are maintained on a 12:12 hour light/dark schedule for the entire duration of the study. The animal colony is maintained at 21° C. and 60% humidity. The Spinal Nerve Ligation (SNL) model (Kim and Chung (1992) Pain 50:355-63) is used to induce chronic neuropathic pain. The animals are anesthetized with isoflurane, the left L5 transverse process is removed, and the L5 and L6 spinal nerves are tightly ligated with 6-0 silk suture. The wound is then closed with internal sutures and external staples. Wound clips are removed 10-11 days following surgery. The effect of test compounds on mechanical allodynia testing is determined. Baseline, post-injury and post-treatment values for non-noxious mechanical sensitivity are evaluated using 8 Semmes-Weinstein filaments (Stoelting, Wood Dale, Ill., USA) with varying stiffness (0.4, 0.7, 1.2, 2.0, 3.6, 5.5., 8.5, and 15 g) or von Frey hairs according to the up-down method (Chaplan et al. (1994) J Neurosci Methods 53:55-63). Animals are placed on a perforated metallic platform and allowed to acclimate to their surroundings for a minimum of 30 minutes before testing. The mean and standard error of the mean (SEM) are determined for each animal in each treatment group. Since this stimulus is normally not considered painful, significant injury-induced increases in responsiveness in this test are interpreted as a measure of mechanical allodynia. After a baseline reading, test compound is administered and readings are recorded every 2 hours up until 8 hours post compound administration. The anti-convulsant, gabapentin, is used as a positive control. Statistical analyses are conducted using Prism™ 4.01 (GraphPad, San Diego, Calif.). Mechanical hypersensitivity of the injured paw is determined by comparing contralateral to ipsilateral paw values within the vehicle group. Data are analyzed using the Mann-Whitney test. Stability of vehicle group injured paw values over time is tested using the Friedman two-way analysis of variance by rank. Test compound effect is analyzed at each time point by carrying out a Kruskal-Wallis one-way analysis of variance by rank followed by a Dunn's post hoc test or Mann-Whitney signed rank test.

Effects of Test Compounds Model of Surgical Pain

Compounds are evaluated in a manner similar tot hat described by Whiteside et al. (Br. J. Pharmacol (2004) 141: 85-91). Briefly rats, under general anesthesia, undergo a surgical incision using aseptic technique in the plantar surface of the hind paw in a manner that incises the skin and plantar fascia of the paw starting 0.5 cm from the proximal edge of the heel and extending 1 cm towards the toes. The plantaris muscle is elevated and incised longitudinally. Following hemostatsis with gentle pressure, the skin is opposed with two interrupted sutures. The wound site is treated with povidone-iodine and antibiotic powder, and the rats allowed to recover in their home cage. Twenty four hours following the surgery, thresholds to noxious stimuli may be assessed. The assessments used can include mechanical hyperalgesia using the paw pressure technique (Randall & Selitto, (1957) Arch. Int. Pharmacodynam., 3:409-419), tactile allodynia using von Frey hairs according to the up-down method (Chaplan et al. (1994) J Neurosci Methods 53:55-63), and hind limb weight bearing utilizing an incapacitance meter (Stoelting, CA). Following the measurements of baseline responses 24 hours post surgery compounds can be administered via IP, PO, SC, and or IV routes, and there analgesic and/or anti-allodynic actions assessed at 1, 3, 5, and 24 hours post drug. Threshold response data are analyzed by analysis of variance (ANOVA) followed by suitable post hoc analysis such as Fischer PLSD tests.

Animal Models Assessing Pollakiuria, Urinary Incontinence, and Related Disorders The compounds can be assessed for their effect on cyclophosphamide induced cystitis in rats, guinea pigs, dogs, etc. as described in Ozawa et al., The Journal of Urology, the 162nd volume, the 2211-2216th page, 1999 and Boucher et al., The Journal of Urology, the 164th volume, the 203-208th page, 200. Carlo Alberto Maggi et al. (Journal of the Autonomic Nervous System, the 38th volume, the 201-208th page, 1992) describe a model of overactive bladder function which can be used to assess compound activity.

Electrophysiological Assays

The compounds described herein can be assayed for their effects on human ether-a go-go gene related product (hERG) potassium channel activity. hERG channels are expressed in a human embryonic kidney (HEK293) cell line that lacks endogenous hERG channels. HEK293 cells are stably transfected with hERG cDNA. Stable transfectants are selected by coexpression with the G418-resistance gene incorporated into the expression plasmid. Selection pressure is maintained by including G418 in the culture medium. Cells are cultured in Dulbecco's Modified Eagle Medium/Nutrient Mixture F-12 (D-MEM/F-12) supplemented with 10% fetal bovine serum, 100 U/mL penicillin G sodium, 100 µg/mL streptomycin sulfate and 500 µg/mL G418 or similar. Cells are maintained in tissue culture incubators at 37° C. in a humidified 95% air, 5% $CO_2$ atmosphere, with stocks maintained in cryogenic storage. Cells used for electrophysiology are plated in plastic culture dishes.

Test solution, positive control articles such as E-4031, (500 nm), terfenadine, (60 nm), or cisapride (100 nM) are prepared fresh daily in HEPES-buffered physiological saline (HB-PS)

solution (composition in mM): NaCl, 137; KCl, 4.0; CaCl$_2$, 1.8; MgCl$_2$, 1; HEPES, 10; Glucose, 10; pH adjusted to 7.4 with NaOH or similar. All test and control solutions also contain 0.3% dimethylsulfoxide (DMSO). Thus the vehicle control solution is HB-PS+DMSO≧0.3%.

Cells are transferred to the recording chamber and superfused with vehicle control solution. Micropipette solution for whole cell patch clamp recordings is composed of (mM); potassium aspartate, 130; MgCl$_2$, 5; EGTA, 5; ATP, 4; HEPES, 10; pH adjusted to 7.2 with KOH or similar. The recording is performed at a temperature of 35±2° C. Micropipettes for patch clamp recording are made from glass capillary tubing using a P-97 micropipette puller (Sutter Instruments, Novato, Calif.). A commercial patch clamp amplifier is sued for whole cell recordings. Before digitization, current records are low-pass filtered at one-fifth of the sampling frequency.

Cells stably expressing hERG are held at −70-to −80 mV. Onset and steady state activation of hERG current due to test compound is measured using a pulse pattern with fixed amplitudes (conditioning prepulse: +20 to +40 mV for 1 sec; repolarizing to −50 mV followed by repolarizing to −70 mV repeated at 5-10 s intervals. Each recording may end with a final application of a supramaximal concentration of a positive control article (e.g. E-4031, 500 nM), to assess the contribution of endogenous currents. The remaining unblocked current can then be subtracted off-line digitally from the data to determine the potency of the test substance for hERG activation.

Steady state is defined by the limiting constant rate of change with time (linear time dependence). The steady state before and after test compound application is used to calculate the percentage of current inhibited at each concentration. Percent activation at each concentration in the test group is compared with the vehicle control group using one-way ANOVA followed by Dunnett's multiple comparison test (JMP Version 5.0.1, SAS Institute, Cary, N.C.).

Test compound at different concentrations is applied to cells to determine effect on hERG current amplitude. The average value of at least 3 cells for each group±standard error of the mean (SEM) is determined and compared to the effects of positive control articles.

Selectivity Assays
Measurement of Selectivity

The compounds described herein can be analyzed for target selectivity using the GPCRScreen™ (MDS Pharma Services; worldwide, including Taiwan) which screens the compounds for activity against 92 different human G protein coupled receptors.

Serine Hydrolase Selectivity Assays

Compounds (e.g. FAAH inhibitors) can be tested to determine their ability to modulate (e.g. inhibit) the activity of other serine hydrolases. Thus compounds described herein can be assessed for their ability to modulate the activity (e.g. inhibit) of other serine hydrolases including the heart enzyme triacylglycerol hydrolase (TGH; Alam et al. 2002 Biochemistry 41:6679-6687), arylacetamide deacetylase (ADD; Trickett et al. 2001 J. Biol Chem 276:39522-39532), carboxylesterase 1 (CE-1; Redinbo et el. 2003 Biochem Soc Trans 31:620-4), lipoprotein lipase (LPL; Stein and Stein 2003 Atherosclerosis 170:1-9) and the brain hydrolase KIAA1363 using the procedures described in Lichtman et al. 2004 Journal Pharmacol And Experimental Therapeutics 311:441-448. Furthermore, Leung et al. 2003 Nat Biotechnol 21:687-691 describe a functional proteomic screen in which test compounds are evaluated for their ability to compete the labeling of serine hydrolases by an active site-directed FP-rhodamine probe. Test compounds are tested over a range of concentrations (100 pm-100 µM) against the soluble and membrane fractions of tissue proteomes (e.g. mouse, rat, or human brain, heart, and kidney), and from these data, IC$_{50}$ values are determined for hydrolases that exhibit sensitivity to one or more of inhibitors. Test compound-sensitive hydrolases are then identified using biotinylated FP probes as described in Liu et al. 1999 Proc Natl Acad Sci USA 96:14694-14699 and avidin chromatography-mass spectrometry procedures, as described in Kidd et al. 2001 Biochemistry 40:4005-4015. Briefly, mouse tissues are Dounce-homogenized in tris buffer (50 mM Tris-HCl buffer, pH 8.0) with 320 mM sucrose and separated by high-speed centrifugation at 4° C. Sequential spins of 1100 g for 5 minutes and 22,000 g for 30 minutes yield the membrane fraction, which is washed and resuspended in Tris buffer. Supernatant from the second spin yields the soluble fraction. Proteome samples (1 mg/ml) are preincubated with test compounds over a concentration range of 100 pm to 100 µM for 10 minutes and then treated with fluorophosphonate (FP)-rhodamine (100 nM) (Patricelli et al. 2001 Proteomics 1:1067-1071) at room temperature for 10 minutes. Both test compounds and FP-rhodamine are added from concentrated DMSO stocks to give a final DMSO concentration of 2%. Reactions are quenched by the addition of 1 volume of 2×standard SDS-PAGE loading buffer (reducing), run on SDS-PAGE, and visualized in-gel using a Hitachi FMBio IIe flatbed fluorescence scanner (MiraBio, Alameda, Calif.). Labeled proteins are quantified by measuring integrated band intensities (normalized for volume). The band intensities of proteome samples treated with DMSO alone are considered 100% activity, and band intensities of proteins inhibited by test compounds are expressed as a percentage of remaining activity. Potent inhibitors (IC$_{50}$ values<10 nM) also are tested at 0.5 to 50 nM with proteome samples adjusted to 0.1 mg/ml. IC$_{50}$ values are determined from dose-response curves from three trials at each inhibitor concentration using GraphPad Prism software (GraphPad Software Inc., San Diego, Calif.). Enzyme targets are affinity isolated and identified using biotinylated FP probes (Liu et al., 1999) and avidin chromatograph-mass spectrometry procedures, as described previously (Kidd et al., 2001).

Anandamide Uptake

Levels of anandamide can be modulated by changes in synthesis, degradation (e.g., through FAAH), and sequestration (e.g., uptake). Anandamide uptake has been described in the literature by a number of groups and small molecule inhibitors have been identified that appear to inhibit this process. In some cases, these inhibitors may also have additional pharmacological activities including inhibition of FAAH [Moore et al, Proc Natl Acad Sci (2005) 102:17852-7]. Anandamide uptake assays can be performed commercially at contract laboratories such as MDS Pharma Services (worldwide, including Taiwan, catalog no. 315500). This assay is similar to those described by Maccarrone et al (J Biol Chem (2000) 275:13484-92), Maccarrone et al (J Biol Chem (1998) 273:32332-9), Bisogno et al (J Biol Chem (1997) 272:3315-23), and Moore et al (Proc Natl Acad Sci (2005) 102:17852-7).

An anandamide uptake assay is described here. Briefly, the uptake of [1-14C] anandamide (52 mCi/mmol) can be studied in intact CHP100 or U937, a human neuroblastoma and human leukemic monocyte lymphoma line, respectively. CHP100 or U937 cells are resuspended in their serum-free culture media at a density of 1×106 cells/ml. Cell suspensions (2 ml/test) are incubated for different time intervals at 37° C. with 100 nM [1-14C] anandamide; then they are washed three times in 2 ml of culture medium containing 1% bovine serum albumin and are finally resuspended in 200 μl of phosphate-buffered saline. Membrane lipids are then extracted (Maccarrone, 1996, Eur J. Biochem, 241: 297-302), resuspended in 0.5 ml of methanol, and mixed with 3.5 ml of Sigma-Fluor liquid scintillation mixture for non-aqueous samples (Sigma), and radioactivity is measured in an LKB1214 Rack-beta scintillation counter. To discern non-protein-mediated from protein-mediated transport of anandamide into cell membranes, control experiments are carried out at 4° C. Incubations (15 minutes) are also carried out with different concentrations of [1-14C] anandamide (in the 0-750 nM range) to determine apparent Km and Vmax of the uptake by Lineweaver-Burk analysis (in this case, the uptake at 4° C. is subtracted from that at 37° C.).

Anandamide uptake is expressed as picomoles of anandamide taken up per minute/mg of protein. The effect of different test compounds on anandamide uptake is determined by adding each test compound directly to the incubation medium at the selected concentrations. Cell viability after each treatment is checked with trypan blue. It is noteworthy that no specific binding of [$^3$H]CP55940, a potent cannabinoid, is not observed with plasma membranes of CHP100 cells and U937 cells express hardly detectable levels of CB1 mRNA and very low levels of CB2 mRNA; thus [$^{1-14}$C] anandamide binding to CB receptors is not likely to interfere in the uptake experiments.

PDE4

PDE4 is the major cAMP-metabolizing enzyme found in inflammatory and immune cells. Small molecule PDE4 inhibitors are being actively developed for the treatment of diseases associated with airway inflammation including asthma. PDE4 assays are performed commercially by contract research organizations such as MDS Pharma Services (worldwide, including Taiwan, catalog no. 154000). This assay is similar to that described by Thompson et al (Adv Cyclic Nucleotide Res (1979) 10:69-92], Nicholson et al (Trends Pharmacol Sci (1991) 12:19-27], and Cortijo et al (Br J Pharmacol (1993) 108:562-8].

Tubulin

During mitosis, a cell's DNA is replicated and then divided into two new cells. The process of separating the newly replicated chromosomes into the two forming cells involves spindle fibers constructed with microtubules, which themselves are formed by long chains of smaller protein subunits called tubulins. Spindle microtubules attach to replicated chromosomes and pull one copy to each side of the dividing cell. Without these microtubules, cell division is not possible. Tubulin inhibition assays are performed similar to those described in Bacher et al (Pure and Applied Chemistry (2001), 73:1459-1464) and Li and Sham (Expert Opinion on Therapeutic Patents (2002), 12:1663-1702) including the references described therein.

PLA2

Phospholipase A2 deacylates membrane phospholipids to generate, among other products, arachidonic acid which is a precursor for the synthesis of eicosanoids including prostaglandins and leukotrienes. There are primarily 3 kinds of PLA2s: secretory (sPLA2), cytosolic calcium dependent (cPLA2), and calcium independent (iPLA2) PLA 2. All 3 can degrade the synthetic substrate 2-Deoxy-2-thioarachidonoylphosphatidylcholine (arachidonoyl thio-PC) to release a free thiol that can be detected by DTNB (Dithionitrobenzoic acid). Therefore, selective inhibition of any one of the three kinds of PLA2 can be detected by measuring inhibition of thiol release in analogous reactions utilizing various purified or partially purified PLA2 sources. Additionally, there are a number of PLA2 assays that have been described in the scientific literature or are commercially available. For instance, PLA2 inhibition assays can be performed at contract research organizations such as MDS Pharma Services (worldwide, including Taiwan, e.g., catalog nos. 160000 and 160100) or through the use of kits such as those supplied by Cayman Chemical (e.g., catalog no. 765021). Literature references include Huang et al (Anal Biochem (1994) 222:110-5), Dillard et al (J Med Chem (1996) 39:5119-36), Reynolds et al (Anal Biochem (1994) 25-32) and Snyder et al (J Pharmacol Exp Ther (1999) 288:1117-24).

Therapeutic Methods

The compounds described herein or pharmaceutically acceptable compositions thereof may be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Another aspect of the invention relates altering a biological activity in a biological sample or a patient, which method comprises administering to the patient, or contacting said biological sample with a compound described herein or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Altering a biological activity in a biological sample with a compound described herein or a composition comprising said compound is useful for a variety of purposes that are known to one of skill in the art. Examples of such purposes include, but are not limited to, blood transfusion, organ-transplantation, biological specimen storage, and biological assays.

FAAH Related Therapeutic Methods

Compounds that inhibit FAAH activity are expected to be useful in the treatment and/or prevention of a number of disorders. FAAH inhibitors are expected to reduce one or more symptoms of one or more such disorders.

Compounds describe herein (e.g. FAAH inhibitors) can be used to prevent and/or treat, for example, epilepsy and epileptiform-induced damage, exposure to excitotoxic neurotoxins, excitotoxicity, ischaemic brain damage, cerebral ischaema, traumatic injury (e.g. brain injury), depression, anxiety, sleep disorders, Alzheimer's disease, Parkinson's disease, Huntington's disease, amyotropic lateral sclerosis, multiple sclerosis, tourette's syndrome, schizophrenia, glaucoma, pain, addiction, inflammation, allergic responses, eating disorders, low blood pressure, hypertension, respiratory problems, cancer (tumour growth), chemotherapy complications, asphyxia, attention deficit disorder, and gastrointestinal diseases, including nausea and vomiting, gastric ulcers, secretory diarrhea, paralytic ileus, inflammatory bowel disease, colon cancer and gastro-oesophageal reflux conditions.

Glaucoma and Ocular Disorders

The compounds can be used to prevent and/or treat glaucoma and other disorders characterized by ocular hypertension.

Sleep Disorders

The compounds can be used to prevent and/or treat a sleep disorder that affects the subject's ability to fall asleep and/or remain asleep, and/or results in unrefreshing sleep. The term "sleep disorder" includes insomnia, night terrors, bruxism, somnambulism, sleep apnea, restless leg syndrome, unrefreshing sleep, seasonal affective disorder, circadian rhythm adjustment disorders, and the like.

Insomnia is typically classed into sleep onset insomnia, where a subject takes more than 30 minutes to fall asleep; and sleep maintenance insomnia, where the subject spends more than 30 minutes awake during an expected sleep period, or, for example, waking before the desired wake-up time with an inability to get back to sleep. Sleep disorders include both endogenous disorders, such as sleep apnea, and disorders related to behavioral or external environmental factors. For example, sleep disorders include a subject's difficulty in adjusting to a new circadian rhythm, for example, due to jet lag; night, extended, or irregular work shifts; and the like. A sleep disorder can also arise in a subject that has other disorders, diseases, or injuries, or in a subject being treated with other medications, where the subject as a result has difficulty falling asleep and/or remaining asleep, or experiences unrefreshing sleep. For example, the disclosed method is useful for inducing sleep in a subject having difficulty sleeping as the result of undergoing chemotherapy, or as a result of injuries, or as the result of stress or mood disorders such as depression, anxiety, and the like.

Sleep disorders include conditions recognized by one skilled in the art as sleep disorders, for example, conditions known in the art or conditions which are proposed to be sleep disorders or discovered to be sleep disorders. See, for example, Thorpy, M J International Classification of Sleep Disorders, Revised: Diagnostic and Coding Manual. American Sleep Disorders Association; Rochester, Minn. 1997; and JCD CM, International Classification of Diseases, Ninth Revision, Clinical Modification, National Center for Health Statistics, Hyattsville, Md.

Sleep disorders can be generally classed into dyssomnias, e.g. intrinsic, extrinsic, and circadian rhythm disorders; parasomnias, e.g., arousal, sleep-wake transition, and rapid eye movement (REM) associated disorders, and other parasomnias; disorders associated with mental, neurological, and other medical disorders; and other sleep disorders.

Intrinsic sleep disorders include, for example psychophysiological insomnia, sleep state misperception, idiopathic insomnia, narcolepsy, recurrent hypersomnia, idiopathic hypersomnia, post-traumatic hypersomnia, obstructive sleep apnea syndrome, central sleep apnea syndrome, central alveolar hypoventilation syndrome, periodic limb movement disorder, restless legs syndrome, and the like.

Extrinsic sleep disorders include, for example, inadequate sleep hygiene, environmental sleep disorder, altitude insomnia, adjustment sleep disorder, insufficient sleep syndrome, limit-setting sleep disorder, sleep-onset association disorder, food allergy insomnia, nocturnal eating (drinking) syndrome, hypnotic-dependent sleep disorder, stimulant-dependent sleep disorder, alcohol-dependent sleep disorder, toxin-induced sleep disorder, and the like.

Circadian rhythm sleep disorders include, for example, time-zone change (jet lag) syndrome, shift work sleep disorder, irregular sleep-wake pattern, delayed sleep phase syndrome, advanced sleep phase syndrome non 24 h sleep-wake disorder, and the like.

Arousal sleep disorders include, for example, confusional arousals, sleepwalking, sleep terrors, and the like.

Sleep-wake transition disorders include, for example, rhythmic movement disorder, sleep starts, sleeptalking, nocturnal leg cramps, and the like.

REM-associated sleep disorders include, for example, nightmares, sleep paralysis, impaired sleep-related penile erections, sleep-related painful erections, REM sleep-related sinus arrest, REM sleep behavior disorders, and the like.

Other parasomnias include, for example, sleep bruxism, sleep enuresis, sleep-related abnormal swallowing syndrome, nocturnal paroxysmal dystonia, sudden unexplained nocturnal death syndrome, primary snoring, infant sleep apnea, congenital central hypoventilation syndrome, sudden infant death syndrome, benign neonatal sleep myoclonus, and the like. A "sleep disorder" may also arise in a subject that has other medical disorders, diseases, or injuries, or in a subject being treated with other medications or medical treatments, where the subject as a result has difficulty falling asleep and/or remaining asleep, or experiences unrefreshing sleep, e.g., the subject experiences sleep deprivation. For example, some subjects have difficulty sleeping after undergoing medical treatment for other conditions, e.g., chemotherapy or surgery, or as a result of pain or other effects of physical injuries.

It is well known in the art that certain medical disorders, for example, central nervous system (CNS) disorders, e.g., mental or neurological disorders, e.g., anxiety, can have a sleep disorder component, e.g., sleep deprivation. Thus, treating a sleep disorder also includes treating a sleep disorder component of other disorders, e.g., CNS disorders. Further, treating the sleep disorder component of CNS disorders can also have the beneficial effect of ameliorating other symptoms associated with the disorder. For example, in some subjects experiencing anxiety coupled with sleep deprivation, treating the sleep deprivation component also treats the anxiety component. Thus, the present invention also includes a method of treating such medical disorders.

Sleep disorders associated with mental disorders include psychoses, mood disorders, anxiety disorders, panic disorder, addictions, and the like. Specific mental disorders include, for example, depression, obsessive compulsive disorder, affective neurosis/disorder, depressive neurosis/disorder, anxiety neurosis, dysthymic disorder, behavior disorder, mood disorder, schizophrenia, manic depression, delirium, alcoholism, and the like.

Sleep disorders associated with neurological disorders include, for example, cerebral degenerative disorders, dementia, parkinsonism, fatal familial insomnia, sleep related epilepsy, electrical status epilepticus of sleep, sleep-related headaches, and the like. Sleep disorders associated with other medical disorders include, for example, sleeping sickness, nocturnal cardiac ischemia, chronic obstructive pulmonary disease, sleep-related asthma, sleep-related gastroesophageal reflux, peptic ulcer disease, fibrositis syndrome, and the like.

In some circumstances, sleep disorders are also associated with pain, e.g. neuropathic pain associated with restless leg syndrome; migraine; enhanced or exaggerated sensitivity to pain, such as hyperalgesia, causalgia and allodynia; acute pain; burn pain; atypical facial pain; neuropathic pain; back pain; complex regional pain syndromes I and II; arthritic pain; sports injury pain; pain related to infection, e.g., HIV, post-polio syndrome, and post-herpetic neuralgia; phantom limb pain; labor pain; cancer pain; postchemotherapy pain; post-stroke pain; post-operative pain; neuralgia; conditions associated with visceral pain including irritable bowel syndrome, migraine and angina; and the like.

Other sleep disorders include, for example, short sleeper, long sleeper, subwakefulness syndrome, fragmentary myoclonus, sleep hyperhidrosis, menstrual associated sleep disorder, pregnancy-associated sleep disorder, terrifying hypnagogic hallucinations, sleep-related neurogenic tachypnea, sleep-related laryngospasm, sleep chocking syndrome, and the like.

Insomnia is typically classed into sleep onset insomnia, where a subject takes more than 30 minutes to fall asleep; and sleep maintenance insomnia, where the subject spends more than 30 minutes awake during an expected sleep period, or, for example, waking before the desired wake-up time with difficulty or an inability to get back to sleep. Some of the disclosed compounds are effective in treating sleep onset and sleep maintenance insomnias, insomnia resulting from circadian rhythm adjustment disorders, or insomnia resulting from CNS disorders. In one embodiment, a subject is treated for a circadian rhythm adjustment disorder. In another embodiment a subject is treated for insomnia resulting from a mood disorder. In other embodiments, a subject is treated for sleep apnea, somnambulism, night terrors, restless leg syndrome, sleep onset insomnia, and sleep maintenance insomnia. In other embodiments, a subject is treated for, sleep onset insomnia or sleep maintenance insomnia.

Compounds described herein can be used to for inducing, prolonging and/or enhancing sleep. This can encompass the treatment of a sleep disorder, i.e., a difficulty in achieving satisfactory sleep due to some internal or external factor, e.g. pain, stress or anxiety, misuse of stimulants or depressants, or temporary disturbance of lifestyle and it can encompass elective desires on the part of a user to achieve a particularly beneficial period of sleep. Such a desire may, for instance, arise in anticipation of important events the following day or in the near future for which a person may wish to be fully alert and refreshed.

The compounds can help achieve any of the following goals: getting to sleep, especially stage 1 sleep; staying asleep; sleeping well; waking refreshed; waking alert; faster onset to stage 1 sleep; increasing duration of sleep periods; decreasing the number and duration of awakenings; increasing total duration of sleep; increasing probability of sleeping well; reducing insomnia, especially chronic or mild-moderate insomnia; decreasing disturbances during sleeptime; and improving quality of sleep. Meeting these goals can be determined by any standard or, known subjective or objective measures, for instance the Karolinska scale, Loughborough sleep log or actimetry.

Improved sleep can assist in keeping awake; keeping alert; keeping refreshed; and performing well the next day An effective amount of a compound described herein is the quantity which, when administered to a subject in need of treatment, results in the subject falling asleep more rapidly, results in more refreshing sleep, reduces duration or frequency of waking during a sleep period, or reduces the duration, frequency, or intensity of episodes of night terrors, bruxism, or somnambulism. The amount of the disclosed compound to be administered to a subject will depend on the particular disorder, the mode of administration, co-administered compounds, if any, and the characteristics of the subject, such as general health, other diseases, age, sex, genotype, body weight and tolerance to drugs. The skilled artisan will be able to determine appropriate dosages depending on these and other factors.

The degree of refreshedness and quality of sleep may be determined by the "morning" log of the Loughborough sleep log with the highest degree of refreshedness or quality of sleep being represented as 1 and the lowest being represented as 5. Accordingly, the percentage increase in refreshedness or quality of sleep is measured in this context by the decrease in the mean refreshedness or quality of sleep.

The response of feeling extremely alert, very alert or alert can be determined, for instance, by the Karolinska 9-point scale.

Other measures of sleep parameters include the sleep disturbance index (SDI) and time to sleep onset (TTSO) that can both be measured by actimetry.

The compounds can be used in combination with therapies currently used for the treatment of sleep disorders, e.g., Aldesleukin (Proleukin), Amantadine (Symmetrel), Baclofen (Lioresal), Bepridil (Vascor), Carisoprodol (Soma), Clonazepam (Klonopin), Diazepam (Valium), Diphenhydramine (Sominex, Nytol), Doxylamine (Unisom), Estazolam (ProSom), Flurazepam (Dalmane), Gabapentin, Lorazepam (Ativan), Levodopa-carbidopa (Sinemet), Melatonin, Methylphenidate (Ritalin), Modanfinil (Provigil), Pemoline (Cylert), Pergolide, Pramipexole, Promethazine (Phenergan), Quazepam (Doral), Rimantadine (Flumadine), Sibutramine (Meridia), Sodium oxybate, Synthetic conjugated estrogens (Cenestin), Temazepam (Restoril), Triazolam (Halcion), Zaleplon (Sonata), and Zolpidem (Ambien).

Obesity Related Disorders

The compounds may be used to treat obesity and/or to reduce or control body weight (or fat) or prevent and/or treat obesity or other appetite related disorders related to the excess consumption of food, ethanol and other appetizing substances. The compounds may be used to modulate lipid metabolism, reduce body fat (e.g., via increasing fat utilization) or reduce (or suppress) appetite (e.g., via inducing satiety). Obesity is a condition in which there is an excess of body fat. In many cases, an individual is considered obese if the individual has a body mass index (BMA) greater than or equal to 30 kg/m$^2$ or if the individual has at least one co-morbidity and a BMI greater than or equal to 27 kg/m$^2$. In certain situations, a subject at risk for obesity is an otherwise healthy subject with a BMI of 25 kg/m$^2$ to less than 30 kg/m$^2$ or a subject with at least one co-morbidity with a BMI of 25 kg/m$^2$ to less than 27 kg/m$^2$.

The increased risks associated with obesity is thought to occur at a lower BMI in Asians. In some situations, obesity in an Asian refers to a condition whereby a subject with at least one obesity-induced or obesity-related co-morbidity that requires weight reduction or that would be improved by weight reduction, has a BMI greater than or equal to 25 kg/m$^2$. In Asians, an obese subject sometimes refers to a subject with at least one obesity-induced or obesity-related co-morbidity that requires weight reduction or that would be improved by weight reduction, with a BMI greater than or equal to 25 kg/m$^2$. In some situations, an Asian at risk of obesity is a subject with a BMI of greater than 23 kg/m$^2$ to less that 25 kg/m$^2$.

Obesity-induced or obesity-related co-morbidities include, but are not limited to, diabetes, noninsulin dependent diabetes mellitus type 2, impaired glucose tolerance, impaired fasting glucose, insulin resistance syndrome, dyslipidemia, hypertension, hyperuricacidemia, gout, coronary artery disease, myocardial infarction, angina pectoris, sleep apnea syndrome, Pickwickian syndrome, fatty liver, cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

Treatment (of obesity and obesity-related disorders) refers tot he administration of the compounds described herein to reduce or maintain the body weight of an obese subject. One outcome of treatment may be reducing the body weight of an obese subject relative to that subject's body weight immediately before the administration of the compounds described herein. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention (of obesity and obesity-related disorders) refers to the administration of the compounds described herein to reduce or maintain the body weight of a subject at risk of obesity. One outcome of prevention may be reducing the body weight of a subject at risk of obesity relative to the subject's body weight immediately before the administration of the compounds described herein. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

Obesity are disorders that are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrhythmias, myocardial infarction, congestive heart failure, coronary heart disease, sudden death, stroke, polycystic ovarian disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g., children with acute lymphoblastic leukemia. The compounds described herein may be used to reduce or control body weight (or fat) or to prevent and/or treat obesity or other appetite related disorders related to the excess consumption of food, ethanol and other appetizing substances. The compounds may be used to modulate lipid metabolism, reduce body fat (e.g. via increasing fat utilization) or reduce (or suppress) appetite (e.g. via inducing satiety).

Further examples of obesity-related disorders or metabolic syndrome, also known as syndrome X, insulin resistance syndrome, sexual and reproductive dysfunction, such as infertility, hypogonadism in males and hirsutism in females, gastrointestinal motility disorders, such as obesity-related gastroesophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. The compounds described herein are also useful for reducing the risk of secondary outcomes of obesity, such as reducing the risk of left ventricular hypertrophy.

The compounds can be administered in combination with anti-obesity agents, including, but not limited to 11βHSD-1 (11-beta-hydroxy steroid dehydrogenase type 1) inhibitors, such as BVT 3498, BVT 2733, 3-(1-adamantyl)-4-ethyl-5-(ethylthio)-4H-1,2,4-triazole, 3-(1-adamantyl)-5-(3,4,5-trimethoxyphenyl)-4-methyl-4H-1,2,4-triazole, 3-adamantanyl-4,5,6,7,8,9,10,11,12,3a-decahydro-1,2,4-triazolo[4,3-a][11]annulene, and those compounds disclosed in WO01/90091, WO01/90090, WO01/90092 and WO02/072084; 5HT (serotonin) transporter inhibitors, such as paroxetine, fluoxetine, fenfluramine, fluvoxamine, sertraline, and imipramine, and those disclosed in WO03/00663; 5HT antagonists such as those in WO03/037871, WO03/037887, and the like; 5HT1a modulators such as those disclosed in WO03/031439, and the like;

5HT-2 agonists; 5HT2c (serotonin receptor 2c) agonists, such as BVT993, DPCA37215, IK264, PNU 22394, WAY161503, R-1065, and YM 348 and those disclosed in U.S. Pat. No. 3,914,250 and PCT publication Nos. WO02/36596, WO02/48124, WO02/10169, WO01/66548, WO02/44152, WO02/51844, WO/02/40456, and WO02/40457; 5HT6 receptor modulators, such as those in WO03/030901, WO03/035061, WO03/039547, and the like; ACC2 (acetyl-CoA carboxylase-2) inhibitors; acyl-estrogens, such as oleoyl-estrone, disclosed in del Mar-Grasa, M. et al., Obesity Research, 9:202-9 (2001) and Japanese Patent Application No. JP 2000256190;

alpha-lipoic acid (alpha-LA); anorectic bicyclic compounds such as 1426 (Aventis) and 1954 (Aventis), and the compounds disclosed in WO00/18749, WO01/32638, WO01/62746, WO01/62747, and WO03/015769; AOD9604; appetite suppressants such as those in WO03/40107; ATL-962 (Alizyme PLC); benzocaine; benzphetamine hydrochloride (Didrex); bladderwrack (focus vesiculosus); BRS3 (bombesin receptor subtype 3) agonists; bupropion; caffeine; CB 1 (cannabinoid-1 receptor) antagonist/inverse agonists, such as rimonabant (Acomplia; Sanofi Synthelabo), SR-147778 (Sanofi Synthelabo), BAY 65-2520 (Bayer), and SLV 319 (Solvay), and those disclosed in U.S. Pat. Nos. 4,973,587, 5,013,837, 5,081,122, 5,122,820, 5,292,736, 5,532,237, 5,624,941, 6,028,084, and 6,509,367 and WO96/33159, WO97/29079, WO98/31227, WO98/33765, WO98/37061, WO98/41519, WO98/43635, WO98/43636, WO99/02499, WO00/10967, WO00/10968, WO01/09120, WO01/58869, WO01/64632, WO01/64633, WO01/64634, WO01/70700, WO01/96330, WO02/076949, WO03/006007, WO03/007887, WO03/020217, WO03/026647, WO03/026648, WO03/027069, WO03/027076, WO03/027114, WO03/037332, WO03/040107, WO03/086940, WO03/084943 and U.S. Pat. No. 6,509,367 and EPO Application No. EP-6658546;

CCK agonists; CCK-A (cholecystokinin-A) agonists, such as AR-R 15849, GI 181771, JMV-180, A-71378, A-71623 and SR146131, and those described in U.S. Pat. No. 5,739,106; chitosan; chromium; CNTF (Ciliary neurotrophic factors), such as GI-181771 (Glaxo-SmithKline), SR146131 (Sanofi Synthelabo), butabindide, PD170,292, and PD 149164 (Pfizer); CNTF derivatives, such as axokine (Regeneron), and those disclosed in PCT Application Nos. WO 94/09134, WO 98/22128, and WO 99/43813; conjugated linoleic acid; corticotropin-releasing hormone agonists; dehydroepiandrosterone; DGAT1 (diacylglycerol acyltransferase 1) inhibitors; DGAT2 (diacylglycerol acyltransferase 2) inhibitors; dicarboxylate transporter inhibitors; diethylpropion hydrochloride (Tenuate); dipeptidyl peptidase IV (DP-IV) inhibitors, such as isoleucine thiazolidide, valine pyrrolidide, NVP-DPP728, LAF237, P93/01, TSL 225, TMC-2A/2B/2C, FE 999011, P9310/K364, VIP 0177, SDZ 274-444 and the compounds disclosed in PCT publication Nos. WO02/083128, WO02/062764, WO03/000180, WO03/000181, WO03/000250, WO03/002530, WO03/002531, WO03/002553, WO03/002593, WO03/004498, WO03/004496, WO03/017936, WO03/024942, WO03/024965, WO03/033524, WO03/037327 and EP1258476; ephedra; exendin-4 (an inhibitor of glp-1); FAS (fatty acid synthase) inhibitors, such as Cerlenin and C75; fat resorption inhibitors such as those in WO03/053451, and the like; fatty acid transporter inhibitors, fiber (psyllium, plantago, guar fiber); galanin antagonists; galega (Goat's Rue, French Lilac); garcinia cambogia; germander (teucrium chamaedrys); ghrelin antagonists, such as those disclosed in PTC Application Nos. WO 01/87335, and WO 02/08250; GLP-1 (glucagon-like peptide 1) agonists (e.g. exendin-4); glp-1 (glucagon-like peptide-1); glucocorticoid antagonists; glucose transporter inhibitors; growth hormone secretagogue receptor agonists/antagonists, such as NN703, hexarelin, MK-0677, SM-130686, CP-424,391, L-692,429 and L-163,255, and such as those disclosed in U.S. Pat. No. 6,385,951, U.S. Patent Application Nos. 2002/049196 and 2002/022637, and PCT Application Nos. WO 01/56592 and WO 02/32888; growth hormone secretagogues, such as those disclosed and specifically described in U.S. Pat. No. 5,536,716; H3 (histamine H3) antagonist/inverse agonists, such as thioperamide, 3-(1H-imidazol-4-yl)propyl N-(4-pentenyl)carbamate), clobenpropit, iodophenpropit, imoproxifan, GT2394 (Gliatech), and A331440, and those disclosed in PCT publication No. WO02/15905 and O-[3-(1H-imidazol-4-yl)propanol] carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334:45-52 (2001)), substituted N-phenylcarbamates (Reidemeister, S. et al, Pharmazie, 55:83-6 (2000)), and proxifan derivatives (Sasse, A. et al., J. Med. Chem. 43:3335-43 (2000)) and histamine H3 receptor modulators such as those disclosed in WO03/024928 and WO03/024929; interleukin-6 (IL-6) and modulators thereof, as in WO03/057237, and the like; L-carnitine; leptin derivatives, such as those disclosed in U.S. Pat. Nos. 5,552,524, 5,552,523, 5,552,522, 5,521,283 and PCT International Publication Nos. WO 96/23513, WO 96/23514, WO 96/23515, WO 96/23516, WO 96/23517, WO 96/23518, WO 96/23519, and WO 96/23520; leptin, including recombinant human leptin (PEG-OB, Hoffman La Roche) and recombinant methionyl human leptin (Amgen); lipase inhibitors, such as tetrahydrolipstatin (orlistat/Xenical®), Triton WR1339, RHC80267, lipstatin, teasaponin, and diethylumberlliferyl phosphate, FL-386, WAY-121898, Bay-N-3176, valilactone, esteracin, ebelactone A, ebelactone B, and RHC 80267, and those dissolved in PCT publication No. WO01/77094, and U.S. Pat. Nos. 4,598,089, 4,452,813, 5,512,565, 5,391,571, 5,602,151, 4,405,644, 4,189,438, and 4,242,453; lipid metabolism modulators such as maslinic acid, erythrodiol, ursolic acid uvaol, betulinic acid, betulin, and the like and compounds disclosed in WO03/011267; Mc3r (melanocortin 3 receptor) agonists; Mc4r (melanocortin 4 receptor) agonists, such as CHIR86036 (Chiron), ME-10142, ME-10145, and HS-131 (Melacure), and those disclosed in PCT publication Nos. WO99/64002, WO00/74679, WO01/991752, WO01/25192, WO01/52880, WO01/74844, WO01/70708, WO01/70337, WO01/91752, WO02/059095, WO02/059107, WO02/059108, WO02/059117, WO02/06276, WO02/12166, WO02/11715, WO02/12178, WO02/15909, WO02/38544, WO02/068387, WO02/068388, WO02/067869, WO02/081430, WO03/06604, WO03/007949, WO03/009847, WO03/009850, WO03/013509, and WO03/031410; Me5r (melanocortin 5 receptor) modulators, such as those disclosed in WO97/19952, WO00/15826, WO00/15790, US 20030092041; MCH2R (melanin concentrating hormone 2R) agonist/antagonists; melanin concentrating hormone antagonists; melanin-concentrating hormone 1 receptor (MCHR) antagonists, such as T-226296 (Takeda), SNP-7941 (Synaptic), and those disclosed WO01/21169, WO01/82925, WO01/87834, WO02/051809, WO02/06245, WO02/076929, WO02/076947, WO02/04433, WO02/51809, WO02/083134, WO02/094799, WO03/004027, WO03/13574, WO03/15769, WO03/028641, WO03/035624, WO03/033476, WO03/033480 and Japanese Patent Application Nos. JP 13226269, and JP1437059; melanocortin agonists, such as Melanotan II or those described in WO 99/64002 and WO 00/74679; Metformin (Glucophage®); mGluR5 modulators such as those disclosed in WO03/029210, WO03/047581, WO03/048137, WO03/051315, WO03/051833, WO03/053922, WO03/059904, and the like; monoamine reuptake inhibitors, such as sibutratmine (Meridia®/Reductil®) and salts thereof, and those compounds disclosed in U.S. Pat. Nos. 4,746,680, 4,806,570, and 5,436,272, and U.S. Patent Publication No. 2002/0006964, and WO01/27068, and WO01/62341;

NE (norepinephrine) transport inhibitors, such as GW 320659, despiramine, talsupram, and nomifensine; nomame herba; non-selective serotonin/norepinephrine transport inhibitors, such as sibutramine or fenfluramine; NPY 1 antagonists, such as BIBP3226, J-115814, BIBO 3304, LY-357897, CP-671906, GI-264879A, and those disclosed in U.S. Pat. No. 6,001,836, and PCT Patent Publication Nos. WO 96/14307, WO 01/23387, WO 99/51600, WO 01/85690, WO 01/85098, WO 01/85173, and WO 01/89528; NPY5 (neuropeptide Y Y5) antagonists, such as 152,804, GW-569180A, GW-594884A, GW-587081X, GW-548118X, FR235208, FR226928, FR240662, FR252384, 1229U91, GI-26479A, CGP71683A, LY-377897, LY-366377, PD-160170, SR-120562A, SR-120819A, JCF-104, and H409/22 and those compounds disclosed in U.S. Pat. Nos. 6,140,354, 6,191,160, 6,258,837, 6,313,298, 6,326,375, 6,329,395, 6,335,345, 6,337,332, 6,329,395, and 6,340,683, European Patent Nos. EP-01010691, and EP-01044970 and PCT Publication Nos. WO97/19682, WO97/20820, WO97/20821, WO97/20822, WO97/2083, WO98/27063, WO00/107409, WO00/185714, WO00/185730, WO00/64880, WO00/68197, WO00/69849, WO01/09120, WO01/14376, WO01/85714, WO01/85730, WO01/07409, WO01/02379, WO01/23388, WO01/23389, WO01/44201, WO01/62737, WO01/62738, WO01/09120, WO02/20488, WO02/22592, WO02/48152, WO02/49648, WO02/051806, WO02/094789, WO03/009845, WO03/014083, WO03/022849, WO03/028726 and Normal et al., J.

Med. Chem. 43:4288-4312 (2000); opioid antagonists, such as nalmefene (Revex®), 3-methoxynaltrexone, naloxone, and naltrexone and those disclosed in WO00/21509; orexin antagonists, such as SB-334867-A and those disclosed in PCT publication Nos. WO01/96302, WO01/68609, WO02/44172, WO02/51232, WO02/51838, WO02/089800, WO02/090355, WO03/023561, WO03/032991, and WO03/037847; PDE (phosphodiesterase) inhibitors, such as theophylline, pentoxifylline, zaprinast, sildenafil, amrinone, milrinone, cilostamide, rolipram, and cilomilast; peptide YY and fragments and variants thereof (e.g. $YY_{3-36}$ ($PYY_{3-36}$) (N. Engl. J. Med. 349:941, 2003; ikpeapge daspeelnry yaslrhylnl vtrqry) and PYY agonists such as those disclosed in WO03/026591; phendimetrazine; phentermine, phosphate transporter inhibitors; phosphodiesterase-3B (PDE3B) inhibitors; phytopharm compound 57 (CP 644, 673); pyruvate; SCD-1 (stearoyl-CoA desaturase-1) inhibitors; serotonin reuptake inhibitors, such as dexfenfluramine, fluoxetine, and those in U.S. Pat. No. 6,365,633, and WO01/27060, and WO01/162341; T71 (Tularik; Inc.; Boulder Col.); thyroid hormone β agonists, such as KB-2611 (KaroBioBMS), and those disclosed in WO02/15845 and Japanese Patent Application No. JP 200256190; Topiramate (Topimax®); transcription factor modulators such as those disclosed in WO03/026576; UCP-1 (uncoupling protein-1), 2, or 3 activators, such as phytanic acid, 4-[(E)-2-(5,6,7,8-tetrahydro-5,5,8,8-tetramethyl-2-napthalenyl)-1-propenyl-1]benzoic acid (TTNPB), retinoic acid, and those disclosed in PCT Patent Application No. WO 99/00123; β3 (beta adrenergic receptor 3) agonists, such as AD9677/TAK677 (Dainippon/Takeda), CL-316,243, SB 418790, BRL-37344, L-796568, BMS-196085, BRL-35135A, CGP12177A, BTA-243, GW 427353, Trecadrine, Zeneca D7114, N-5984 (Nisshin Kyorin), LY-377604 (Lilly), and SR 59119A, and those disclosed in U.S. Pat. No. 5,705,515, U.S. Pat. No. 5,451,677 and PCT publication Nos. WO94/18161, WO95/29159, WO97/46556, WO98/04526 and WO98/32753, WO01/74782, WO02/32897, WO03/014113, WO03/016276, WO03/016307, WO03/024948, WO03/024953 and WO03/037881; β-hydroxy steroid dehydrogenase-1 inhibitors (β-HSD-1); β-hydroxy-β-methylbutyrate.

Anxiety Related Disorders

The compounds described herein can also be used to treat anxiety disorder (including generalized anxiety disorder, panic disorder, and social anxiety disorder) and depression. Anxiety disorders are a group of psychological problems whose key features include excessive anxiety, fear, worry, avoidance, and compulsive rituals, and produce or result in inordinate morbidity, over utilization of healthcare services, and functional impairment. They are among the most prevalent psychiatric conditions in the United States and in most other countries. Anxiety disorders listed in the *Diagnostic and Statistical Manual of Mental Disorders* (Fourth Edition, Revised 1994, published by the American Psychiatric Association, Washington, D.C., pages 393-444) include panic disorder with and without agoraphobia, agoraphobia without history of panic disorder, specific phobia, social phobia, obsessive-compulsive disorder (OCD), post-traumatic stress disorder (PTSD), acute stress disorder, generalized anxiety disorder (GAD), anxiety disorder due to a general medical condition, substance-induced anxiety disorder, specific phobia, and anxiety disorder not otherwise specified.

Obsessive compulsive disorder is characterized by recurrent and persistent ideas, thoughts, impulses or images (obsessions) that are ego-dystonic and/or repetitive, purposeful and intentional behaviors (compulsions) that are recognized by the person as excessive or unreasonable. The obsessions or compulsions cause marked distress, are time-consuming, and/or significantly interfere with social or occupational functioning.

Panic disorder is characterized by recurrent unexpected panic attacks and associated concern about having additional attacks, worry about the implications or consequences of the attacks, and/or a significant change in behavior related to the attacks. A panic attack is defined as a discrete period of intense fear or discomfort in which four (or more) of the following symptoms develop abruptly and reach a peak within 10 minutes: (1) palpitations, pounding heart, or accelerated heart rate; (2) sweating; (3) trembling or shaking; (4) sensations of shortness of breath or smothering; (5) feeling of choking; (6) chest pain or discomfort; (7) nausea or abdominal distress; (8) feeling dizzy unsteady, lightheaded, or faint; (9) derealization (feelings of unreality) or depersonalization (being detached from oneself); (10) fear of losing control; (11) fear of dying; (12) paresthesias (numbness or tingling sensations); and (13) chills or hot flushes. Panic disorder may or may not be associated with agoraphobia, or an irrational and often disabling fear of being out in public.

Social anxiety disorder, also known as social phobia, is characterized by a marked and persistent fear of one or more social or performance situations in which the person is exposed to unfamiliar people or to possible scrutiny by others. Exposure to the feared situation almost invariably provokes anxiety, which may approach the intensity of a panic attack. The feared situations are avoided or endured with intense anxiety or distress. The avoidance, anxious anticipation, or distress in the feared situation(s) interferes significantly with the person's normal routine, occupational or academic functioning, or social activities or relationships, or there is marked distress about having the phobias. Lesser degrees of performance anxiety or shyness generally do not require psychopharmacological treatment.

Generalized anxiety disorder is characterized by excessive anxiety and worry (apprehensive expectation) that is persistent for at least 6 months and which the person finds difficult to control. It must be associated with at least 3 of the following 6 symptoms; restlessness or feeling keyed up or on edge, being easily fatigued, difficulty concentrating or mind going blank, irritability, muscle tension, and sleep disturbance. The diagnostic criteria for this disorder are described in further detail in DSM-IV, which is incorporated herein by reference (American Psychiatric Association, 1994).

Post-traumatic stress disorder (PTSD), as defined by DSMIII-R/IV, requires exposure to a traumatic event that involved actual or threatened death or serious injury, or threat to the physical integrity of self or others, and a response which involves intense fear, helplessness, or horror. Symptoms that occur as a result of exposure to the traumatic event include re-experiencing of the event in the form of intrusive thoughts, flashbacks or dreams, and intense psychological distress and physiological reactivity on exposure to cues to the event: avoidance of situations reminiscent of the traumatic event, inability to recall details of the event, and/or numbing of general responsiveness manifested as diminished interest in significant activities, estrangement from others, restricted range of affect, or sense of foreshortened future; and symptoms of autonomic arousal including hypervigilance, exaggerated startle response, sleep disturbance, impaired concentration, and irritability or outbursts of anger. A PTSD diagnosis requires that the symptoms are present for at least a month and that they cause clinically significant distress or impairment in social, occupational, or other important areas of functioning.

It is contemplated that the compounds will be effective in treating obsessions and compulsions in patients who have been diagnosed as having obsessive compulsive disorder based upon administration of appropriate tests, which may include, but are not limited to any of the following: Yale Brown Obsessive Compulsive Scale (YBOCS) (for adults), National Institute of Mental Health Global OCD Scale (NIMH GOCS), and CGI-Severity of Illness scale. It is further contemplated that the compounds will be effective in inducing improvements in certain of the factors measured in these tests, such as a reduction of several points in the YBOCS total score. It is also contemplated that the compounds of this invention will be effective in preventing relapse of obsessive-compulsive disorder.

The invention provides a method of treating obsessions and compulsions in a subject with obsessive-compulsive disorder, which comprises administering to the subject an amount of any of the compounds described herein effective to treat the subject's obsessions and compulsions.

It is contemplated that the compounds will be effective in treating panic disorder in patients who have been diagnosed with panic disorder on the basis of frequency of occurrence of panic attacks, or by means of the CGI-Severity of Illness scale. It is further contemplated that the compounds described herein will be effective in inducing improvements in certain of the factors measured in these evaluations, such as a reduction in frequency or elimination of panic attacks an improvement in the CGI-Severity of Illness scale or a CGI Global Improvement score of 1 (very much improved), 2 (much improved) or 3 (minimally improved). It is also contemplated that the compounds of this invention will be effective in preventing relapse of panic disorder.

It is contemplated that the compounds will be effective in treating social anxiety disorder in patients who have been diagnosed as having social anxiety disorder based upon the administration of any of the following tests: the Liebowitz Social Anxiety Scale (LSAS), the CGI-Severity of Illness scale, the Hamilton Rating Scale for Anxiety (HAM-A), the Hamilton Rating Scale for Depression (HAM-D), the axis V Social and occupational Functioning Assessment Scale of DSM-IV, the axis II (ICD10) World-Health organization Disability Assessment, Schedule 2 (DAS-2), the Sheehan Disability Scales, the Schneier Disability Profile, the World Health Organization Quality of Life-100 (WHOQOL-100)), or other tests as described in Ballenger, J C et al, 1998, J Clin Psychiatry 59 Suppl 17:54-60, which is incorporated herein by reference. It is further contemplated that the compounds described herein will be effective in inducing improvements as measured by these tests, such as the a change from baseline in the Liebowitz Social Anxiety Scale (LSAS), or a CGI-Global Improvement score of 1 (very much improved), 2 (much improved) or 3 (minimally improved). It is also contemplated that the compounds of this invention will be effective in preventing relapse of social anxiety disorder.

It is contemplated that the compounds will be effective in treating generalized anxiety disorder in patients who have been diagnosed as having this disorder based upon the diagnostic criteria described in DSM-IV. It is further contemplated that the compounds described herein will be effective in reducing symptoms of this disorder, such as the following: excessive worry and anxiety, difficulty controlling worry, restlessness or feeling keyed up or on edge, being easily fatigued, difficulty concentrating or mind going blank, irritability, muscle tension, or sleep disturbance. It is also contemplated that the compounds of this invention will be effective in preventing relapse of general anxiety disorder.

It is contemplated that the compounds will be effective in treating PTSD in patients who have been diagnosed has having PTSD based upon the administration of any of the following tests: Clinician-Administered PTSD Scale Part 2 (CAPS) and the patient-rated Impact of Event Scale (IES). It is further contemplated that the compounds described herein will be effective in inducing improvements in the scores of the CAPS, IES, CGI-Severity of Illness or CGI-Global Improvement tests. It is also contemplated that the compounds of this invention will be effective in preventing relapse of PTSD.

The compounds described herein may be used to prevent, control or treat schizophrenia, paranoia or other related disorders of dopamine transmission.

The compounds can be administered in combination with anti-anxiety agents. Classes of anti-anxiety agents include: benzodiazepines (e.g. alprazolam (Xanax®), chlordiazepoxide (Librium®), clonazepam, chlorazepate, diazepam, halazepam, lorazepam, oxazepram, and prazepam, and pharmaceutically acceptable salts thereof); 5-HT1A agonist or antagonist, especially 5HT1A partial agonists (e.g. the 5-HT1A receptor partial agonists buspirone, flesinoxan, gepirone and ipsapirone, and pharmaceutically acceptable salts thereof); corticotropin releasing factor (CRF) antagonists (including those described in WO 94/13643, WO 94/13644, WO 94/13661, WO 94/13676, and WO 94/13677); phenothiazines (including promethazine, chloropromazine, and trifluoperazine); monoamine oxidase inhibitors (MAOIs, e.g. isocarboxazid (Marplan®), phenelzine (Nardil®), tranylcypromine (Parnate®) and selegiline, and pharmaceutically acceptable salts thereof); reversible inhibitors of monoamine oxidase (RIMAs, e.g. moclobemide and pharmaceutically acceptable salts thereof); tricyclic antidepressants (TCAs, e.g. amitriptyline (Elavil®), amoxapine, clomipramine, desipramine (Norpramin®), doxepin, imipramine (Tofranil®), maptroline, nortriptyline (Aventyl® and Pamelor®), perphenazine, protriptyline, and trimipramine (Surmentil®) and pharmaceutically acceptable salts thereof)); atypical antidepressants including bupropion, lithium, nefazodone, trazodone and viloxazine, and pharmaceutically acceptable salts thereof; and selective serotonin reuptake inhibitors (SSRIs, e.g. paroxetine (Paxil®), venlafaxine, fluvoxamine, fluoxetine (Prozac®), citalopram (Celexa®), escitalopram, and sertraline (Zoloft®) and pharmaceutically acceptable salts thereof).

The compounds can also be used in a co-therapy with a second agent that has analgesic activity. Analgesics which can be used in co-therapy include, but are not limited to: NSAIDs (e.g., acemetacin, acetaminophen, acetyl salicylic acid, alclofenac, alminoprofen, apazone, aspirin, benoxaprofen, bezpiperylon, bucloxic acid, carprofen, clidanac, diclofenac, diclofenac, diflunisal, diflusinal, etodolac, fenbufen, fenbufen, fenclofenac, fenclozic acid, fenoprofen, fentiazac, feprazone, flufenamic acid, flufenisal, flufenisal, fluprofen, flurbiprofen, flurbiprofen, furofenac, ibufenac, ibuprofen, indomethacin, indomethacin, indoprofen, isoxepac, isoxicam, ketoprofen, ketoprofen, ketorolac, meclofenamic acid, meclofenamic acid, mefenamic acid, mefenamic acid, miroprofen, mofebutazone, nabumetone oxaprozin, naproxen, naproxen, niflumic acid, oxaprozin, oxpinac, oxyphenbutazone, phenacetin, phenylbutazone, phenylbutazone, piroxicam, piroxicam, pirprofen, pranoprofen, sudoxicam, tenoxican, sulfasalazine, sulindac, sulindac, suprofen, tiaprofenic acid, tiopinac, tioxaprofen, tolfenamic acid, tolmetin, tolmetin, zidometacin, zomepirac, and zomepirac), a non-narcotic analgesic such as tramadol, an opioid or narcotic analgesic (e.g., APF112, beta funaltrexamine, buprenorphine, butorphanol, codeine, cypridime, dezocine, dihydrocodeine, diphenyloxylate, enkephalin pentapeptide, fedotozine, fentanyl, hydrocodone, hydromorphone, levorphanol, loperamide, meperidine, mepivacaine, methadone, methyl nalozone, morphine, nalbuphine, nalmefene, naloxonazine, naloxone, naltrexone, naltrindole, nor-binaltorphimine, oxycodone, oxymorphone, pentazocine, propoxyphene, and trimebutine), NK1 receptor antagonists (e.g., ezlopitant and SR-14033, SSR-241585), CCK receptor antagonists (e.g., loxiglumide), NK3 receptor antagonists (e.g., talnetant, osanetant SR-142801, SSR-241585), norepinephrine-serotonin reuptake inhibitors (NSRI; e.g., milnacipran), vanilloid receptor agonists and antagonists, cannabinoid receptor agonists (e.g., arvanil), sialorphin, compounds or peptides that are inhibitors of neprilysin, frakefamide (H-Tyr-D-Ala-Phe (F)-Phe-NH$_2$; WO 01/019849 A1), Tyr-Arg (kyotorphin), CCK receptor agonists (e.g., caerulein), conotoxin peptides, peptide analogs of thymulin, dexloxiglumide (the R-isomer of Ioxiglumide; WO 88/05774), and analgesic peptides (e.g., endomorphin-1, endomorphin-2, nocistatin, dalargin, lupron, and substance P).

In addition, certain antidepressants can be used in co-therapy either because they have analgesic activity or are otherwise beneficial to use in combination with an analgesic. Examples of such anti-depressants include: selective serotonin reuptake inhibitors (e.g., fluoxetine, paroxetine, sertraline), serotonin-norepinephrine dual uptake inhibitors, venlafaxine and nefazadone. Certain anti-convulsants have analgesic activity and are useful in co-therapy. Such anti-convulsants include: gabapentin, carbamazepine, phenytoin, valproate, clonazepam, topiramate and lamotrigine. Such agents are considered particularly useful for treatment of neuropathic pain, e.g., treatment of trigeminal neuralgia, postherpetic neuralgia, and painful diabetic neuropathy. Additional compounds useful in co-therapy include: alpha-2-adrenergic receptor agonists (e.g., tizanidine and clonidine), mexiletine, corticosteroids, compounds that block the NMDA (N-methyl-Daspartate) receptor (e.g., dextromethorphan, ketamine, and amantadine), glycine antagonists, carisoprodol, cyclobenzaprine, various opiates, nonopioid antitussive (e.g. dextromethorphan, carmiphen, caramiphen and carbetapentane), opioid antitussives (e.g. codeine, hydrocodone, metaxolone. The compounds described herein can also be combined with inhalable gaseous nitric oxide (for treating pulmonary vasoconstriction or airway constriction), a thromboxane A2 receptor antagonist, a stimulant (i.e. caffeine), an H$_2$-antagonist (e.g. ranitidine), an antacid (e.g. aluminum or magnesium hydroxide), an antiflatulent (e.g. simethieone), a decongestant (e.g. phenylephrine, phenylpropanolamine, pseudophedrine, oxymetazoline, ephinephrine, naphazoline, xylometazoline, propylhexedrine, or levodesoxyephedrine), a prostaglandin (e.g. misoprostol, enprostil, rioprostil, ornoprostol or rosaprostol), a diuretic, a sedating or non-sedating histamine HI receptor antagonists/antihistamines (i.e. any compound that is capable of blocking, inhibiting, reducing or otherwise interrupting the interaction between histamine and its receptor) including but not limited to: -4 asternizole, acrivastine, antazoline, asternizole, azatadine, azelastine, astamizole, bromopheniramine, bromopheniramine maleate, carbinoxamine, carebastine, cetirzine, chlorpheniramine, chlorpheniramine maleate, cimetidine, clemastine, cyclizine, cyproheptadine, descarboethoxyloratadine, dexchlorpheniramine, dimethindene, diphenhydramine, diphenylpyraline, doxylamine succinate, doxylamine, ebastine, efletirizine, epinastine, farnotidine, fexofenadine, hydroxyzine, hydroxyzine, ketotifen, levocabastine, levocetirizine, levocetirizine, loratadine, meclizine, mepyramine, mequitazine, methdilazine, mianserin, mizolastine, noberastine, norasternizole, noraztemizole, phenindamine, pheniramine, picumast, promethazine, pynlamine, pyrilamine, ranitidine, temelastine, terfenadine, trimeprazine, tripelenamine, and triprolidine; a 5HTI agonist, such as a triptan (e.g. sumatriptan or naratriptan), an adenosine Al agonist, an EP ligand, a sodium channel blocker (e.g. lamotrigine), a substance P antagonist (e.g. an NK antagonist), a cannabinoid, a 5-lipoxygenase inhibitor, a leukotriene receptor antagonist/leukotriene antagonists/LTD4 antagonists (i.e., any compound that is capable of blocking, inhibiting, reducing or otherwise interrupting the interaction between leukotrienes and the Cys LTI receptor) including but not limited to: zafirlukast, montelukast montelukast sodium (Singulair®), pranlukast, iralukast, pobilukast, SKB-106,203 and compounds described as having LTD4 antagonizing activity described in U.S. Pat. No. 5,565,473, a DMARD (e.g. methotrexate), a neurone stabilising antiepileptic drug, a mono-aminergic uptake inhibitor (e.g. venlafaxine), a matrix metalloproteinase inhibitor, a nitric oxide synthase (NOS) inhibitor, such as an iNOS or an nNOS inhibitor, an inhibitor of the release, or action, of tumor necrosis factor, an antibody therapy, such as a monoclonal antibody therapy, an antiviral agent, such as a nucleoside inhibitor (e.g. lamivudine) or an immune system modulator (e.g. interferon), a local anaesthetic, a known FAAH inhibitor (e.g., PMSF, URB532, URB597, or BMS-1, as well as those described in those described in WO04033652, U.S. Pat. No. 6,462,054, US20030092734, US20020188009, US20030195226, and WO04033422), an antidepressant (e.g., VPI-013), a fatty acid amide (e.g. anandamide, N-palmitoyl ethanolamine, N-oleoyl ethanolamine, 2-arachidonoylglycerol, or oleamide), arvanil, analogs of anadamide and arvanil as described in US 20040122089, and a proton pump inhibitor (e.g., omeprazole, esomeprazole, lansoprazole, pantorazole and rabeprazole).

The compound described herein can also be used in a co-therapy with a second agent that is a cannabinoid receptor antagonist to prevent and/or treat obesity and other appetite related disorders.

Combinations for Co-Morbid Conditions

It will be appreciated by one skilled in the art that a therapy administered in combination with the compounds described herein can be directed to the same or a different disorder target as that being targeted by the compounds described herein.

Administration of the compound described herein may be first, followed by the other therapy; or administration of the other therapy may be first or they may be administered simultaneously either in two separate compositions or combined in a single composition. The other therapy is any known in the art to treat, prevent, or reduce the symptoms of the targeted disorder, e.g., a sleep disorder, or other disorders, e.g., other CNS disorders. In addition, some embodiments of the present invention have compounds administered in combination with other known therapies for the target disorder. Furthermore, the other therapy includes any agent of benefit to the patient when administered in combination with the disclosed compound.

For example, in some embodiments where the other therapy is a drug, it is administered as a separate formulation or in the same formulation as the compound described herein. A compound described herein is administered in combination therapy with any one or more of commercially-available, over-the-counter or prescription medications, including, but not limited to antimicrobial agents, fungistatic agents, germicidal agents, hormones, antipyretic agents, antidiabetic agents, bronchodilators, antidiarrheal agents, antiarrhythmic agents, coronary dilation agents, glycosides, spasmolytics, antihypertensive agents, antidepressants, antianxiety agents, other psychotherapeutic agents, corticosteroids, analgesics, contraceptives, nonsteroidal anti-inflammatory drugs, blood glucose lowering agents, cholesterol lowering agents, anticonvulsant agents, other antiepileptic agents, immunomodulators, anticholinergics, sympatholytics, sympathominietics, vasodilatory agents, anticoagulants, antiarrhythmics, prostaglandins having various pharmacologic activities, diuretics, sleep aids, anthistaininic agents, antineoplastic agents, oncolytic agents, antiandrogens, antimalarial agents, antileprosy agents, and various other types of drugs. See Goodman and Gilman's The Basis of Therapeutics (Eighth Edition, Pergamon Press, Inc., USA, 1990) and The Merck Index (Eleventh Edition, Merck & Co., Inc., USA, 1989).

Combinations Useful in Treatment of Diabetes

Suitable agents of use in combination with a compound described herein include antidiabetic agents such as (1) PPARγ agonists such as glitazones (e.g., ciglitazone; darglitazone; englitazone; isaglitazone (MCC-555); pioglitazone; rosiglitazone; troglitazone; BRL49653; CLX-0921; 5-BTZD, and GW-0207, LG-100641, and LY-300512, and the like and compounds disclosed in PCT publication Nos. WO97/10813, WO97/27857, WO97/28115, WO97/28137, WO97/27847, WO03/000685, WO03/02711 2, WO03/035602, WO03/048130, WO03/055867, and the like; (2) biguanides such as buformin; metformin; and phenformin, and the like; (3) protein tyrosine phosphatase-1B (PTB-1B) inhibitors, such as ISIS 113715, and those disclosed in WO03/032916, WO03/032982, WO03/041729, WO03/055883; (4) sulfonylureas such as acetohexamide; carbutamide; chlorpropamide; diabinese; glibenclamide; glipizide; glyburide (glibenclamide); glimepiride; gliclazide; glipentide; gliquidone; glisolamide; tolazamide; and tolbutamide, and the like; (5) meglitinides such as repaglinide, and nateglinide, and the like; (6) alpha glucoside hydrolase inhibitors such as acarbose; adiposine; camiglibose; emiglitate; miglitol; voglibose; pradimicin-Q; salbostatin; CKD-711; MDL-25,637; MDL-73,945; and MOR 14, and the like; (7) alpha-amylase inhibitors such as tendamistat, trestatin, and A1-3688, and the like; (8) insulin secreatagogues such as linogliride; and A-4166, and the like; (9) fatty acid oxidation inhibitors, such as clomoxir, and etomoxir, and the like; (10) A2 antagonists, such as midaglizole; isaglidole; deriglidole; idazoxan; earoxan; and fluparoxan, and the like; (11) insulin or insulin mimetics, such as biota, LP-100, novarapid, insulin detemir, insulin lispro, insulin glargine, insulin zinc suspension (lente and ultralente); Lys-Pro insulin, GLP-1 (73-7) (insulintropin); and GLP-1 (7-36)-NH2), and the like; (12) non-thiazolidinediones such as JT-501, and farglitazar (GW-2570/GI-262579), and the like; (13) PPARα/γ dual agonists such as BVT-142, CLX-0940, GW-1536, GW-1929, GW-2433, KRP-297, L-796449, LR-90, MK-0767, SB 219994, muraglitazar and reglitazar (JTT-501) and those disclosed in WO99/16758, WO99/19313, WO99/20614, WO99/38850, WO00/23415, WO00/23417, WO00/23445, WO00/50414, WO01/00579, WO01/79150, WO02/062799, WO03/004458, WO03/016265, WO03/018010, WO03/033481, WO03/033450, WO03/033453, WO03/043985, WO 031053976; and (14) other insulin sensitizing drugs; (15) VPAC2 receptor agonists; (16) GLK modulators, such as those disclosed in WO03/015774; (17) retinoid modulators such as those disclosed in WO03/000249; (18) GSK 3β/GSK 3 inhibitors such as 4-[2-(2-bromophenyl)-4-(4-fluorophenyl-1H-imidazol-5-yl]pyridine and those compounds disclosed in WO03/024447, WO03/037869, WO03/037877, WO03/037891, WO03/068773, EP 1295884, EP 1295885, and the like; (19) glycogen phosphorylase (HGLPa) inhibitors, such as those disclosed in WO03/037864; (20) ATP consumption promotors such as those disclosed in WO03/007990; (21) TRB3 inhibitors, (22) vanilloid receptor ligands such as those disclosed in WO03/049702, (23) hypoglycemic agents such as those disclosed in WO03/015781, WO03/040114, (24) glycogen synthase kinase 3 inhibitors such as those disclosed in WO03/035663, (25) and agents such as those disclosed in WO99/51225 and US 20030134890; and WO01/24786, WO03/059870; (26) Insulin-responsive DNA binding protein-1 (IRDBP-1) as disclosed in WO03/057827, and the like; (27) Adenosine A2 antagonists such as those disclosed in WO03/035639, WO03/035640, and the like.

Combinations Useful in Treatment of Hyperlipidemia

Suitable agents of use in combination with a compound described herein include lipid lowering agents such as:

(1) bile acid sequestrants such as, cholestyramine, colesevelem, colestipol, dialkylaminoalkyl derivatives of a cross-linked dextran; Colestid®; LoCholest®; and Questran®, and the like; (2) HMG-CoA reductase inhibitors such as atorvastatin, bervastatin, carvastatin, cerivastatin, crilvastatin, dalvastatin, fluvastatin, glenvastatin, itavastatin, lovastatin, mevastatin, pitavastatin, pravastatin, rivastatin, rosuvastatin, simvastatin, sirrivastatin, and ZD-4522, and the like and compounds disclosed in WO03/033481; (3) HMG-CoA synthase inhibitors; (4) cholesterol absorption inhibitors such as stanol esters, beta-sitosterol, sterol glycosides such as tiqueside; and azetidinones such as ezetimibe, and the like; (5) acyl coenzyme A-cholesterol acyl transferase (ACAT) inhibitors such as avasimibe (Current Opinion in Investigational Drugs. 3(9):291-297 (2003)), eflucimibe, KY505, SMP 297, CL-277,082 (Clin Pharmacol Ther. 48(2):189-94 (1990)) and the like; (6) CETP inhibitors such as JTT 705 identified as in Nature. 406, (6792):203-7 (2000), torcetrapib (CP-529,414 described in US20030186952 and WO2000017164), CP 532,632, BAY63-2149, SC 591, SC 795, and the like including those described in Current Opinion in Investigation Drugs. 4(3):291-297 (2003). (7) squalene synthetase inhibitors; (8) antioxidants such as probucol, AGI-1067 and the like; (9) PPARα agonists such as beclofibrate, benzafibrate, binifibrate, ciprofibrate, clinofibrate, clofibrate, etofibrate, fenofibrate, gemcabene, and gemfibrozil, lifibrol, GW 7647, BM 170744, LY518674; and other fibric acid derivatives, such as Atromid®, Lopid® and Tricor®, and those disclosed in WO03/033456, WO03/033481, WO03/043997, WO03/048116, WO03/053974, WO03/059864, WO03/05875, and the like; (10) FXR receptor modulators such as GW 4064, SR 103912, and the like; (11) LXR receptor modulators such as GW 3965, T9013137, and XTC0179628, and those disclosed in US20030125357, WO03/045382, WO03/053352, WO03/059875, and the like; (12) lipoprotein synthesis inhibitors such as niacin; (13) renin angiotensin system inhibitors; (14) PPARδ partial agonists, such as those disclosed in WO03/024395; (15) bile acid reabsorption inhibitors, such as BARI 1453, SC435, PHA384640, S8921, AZD7706, and the like; (16) PPARδ agonists such as GW 501516, and GW 590735, and the like, such as those disclosed in WO97/28149, WO01/79197, WO02/14291, WO02/46154, WO02/46176, WO02/076957, WO03/016291, WO03/033493; (17) triglyceride synthesis inhibitors; (18) microsomal triglyceride transport (MTTP) inhibitors, such as inplitapide, LAB687, and CP346086, and the like; (19) transcription modulators; (20) squalene epoxidase inhibitors; (21) low density lipoprotein (LDL) receptor inducers; (22) platelet aggregation inhibitors; (23) 5-LO or FLAP inhibitors; and (24) niacin receptor agonists; (25) PPAR modulators such as those disclosed in WO99/07357, WO99/11255, WO99/12534, WO99/15520, WO99/46232, WO00/12491, WO00/23442, WO00/236331, WO00/

236332, WO00/218355, WO00/238553, WO01/25181, WO01/79150, WO02/79162, WO02/100403, WO02/102780, WO02/081428, WO03/016265, WO03/033453, WO03/042194, WO03/043997, WO03/066581, and the like; (26) niacin-bound chromium, as disclosed in WO03/039535; (27) substituted acid derivatives disclosed in WO03/040114; (28) apolipoprotein B inhibitors such as those disclosed in WO02/090347, WO02/28835, WO03/045921, WO03/047575; (29) Factor Xa modulators such as those disclosed in WO03/047517, WO03/047520, WO03/048081

Combinations Useful in Treatment of Hypertension

Suitable agents of use in combination with a compound described herein include antihypertensive agents such as:

(1) diuretics, such as thiazides, including chlorthalidone, chlorthiazide, dichlorophenamide, hydroflumethiazide, indapamide, polythiazide, and hydrochlorothiazide; loop diuretics, such a bumetanide, ethacrynic acid, furosemide, and torsemide; potassium sparing agents, such as amiloride, and triamterene; and aldosterone antagonists, such as spironolactone, epirenone, and the like; (2) beta-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, and verapamil, and the like; (4) angiotensin converting enzyme (ACE) inhibitors, such as benazepril; captopril; ceranapril; cilazapril; delapril; enalapril; enalopril; fosinopril, imidapril; lisinopril; losinopril; moexipril; quinapril; quinaprilat; ramipril; perindopril; perindropril; quanipril; spirapril; tenocapril; trandolapril, and zofenopril, and the like; (5) neutral endopeptidase inhibitors such as omapatrilat, cadoxatril and ecadotril, fosidotril, sampatrilat, AVE7688, ER4030, and the like; (6) endothelin antagonists such as tezosentan, A308165, and YM62899, and the like; (7) vasodilators such as hydralazine, clonidine, minoxidil, and nicotinyl alcohol, and the like; (8) angiotensin II receptor antagonists such as aprosartan, candesartan, eprosartan, irbesartan, losartan, olmesartan, pratosartan, tasosartan, telmisartan, valsartan, and EXP-3137, FI6828K, and RNH6270, and the like; (9) α/β adrenergic blockers such as nipradilol, arotinolol and amosulalol, and the like; (10) alpha 1 blockers, such as terazosin, urapidil, prazosin, bunazosin, trimazosin, doxazosin, naftopidil, indoramin, WHP 164, and XEN010, and the like; (11) alpha 2agonists such as lofexidine, tiamenidine, moxonidine, rilmenidine and guanobenz, and the like; (12) aldosterone inhibitors, and the like; and (13) angiopoietin-2-binding agents such as those disclosed in WO03/030833.

Cox and FAAH Related Therapeutic Methods

The compound can be used, for example, to treat conditions or disorders in which it is considered desirable to reduce or eliminate COX-2 activity and/or FAAH activity. Thus, they can be used in any situation in which a COX-2 inhibitor of FAAH inhibitor is used as well as in other situations. For example, compounds and related prodrugs can be used to treat an inflammatory disorder, including both disorders in which inflammation is considered a significant component of the disorder and those in which inflammation is considered a relatively minor component of the disorder, to treat acute and chronic pain (analgesic) and to treat fever (antipyretic). Among the inflammatory disorders that can be treated are auto-immune disorders.

Disorders that can be treated include: arthritis (including rheumatoid arthritis, spondyloarthopathies, gouty arthritis, degenerative joint diseases (i.e. osteoarthritis), systemic lupus erythematosus, ankylosing spondylitis, acute painful shoulder, psoriatic, and juvenile arthritis), asthma, atherosclerosis, osteoporosis, bronchitis, tendonitis, bursitis, skin inflammation disorders (i.e. psoriasis, eczema, burns, dermatitis), enuresis, eosinophilic disease, gastrointestinal disorders (including inflammatory bowel disease, peptic ulcers, regional enteritis, diverticulitis, gastrointestinal bleeding, Crohn's disease, gastritis, irritable bowel syndrome and ulcerative colitis), and disorders ameliorated by a gastroprokinetic agent (i.e. ileus, for example post-operative ileus and ileus during sepsis; gastroesophageal reflux disease (GORD, or its synonym GERD); eosinophilic esophagitis, gastroparesis such as diabetic gastroparesis; food intolerances and food allergies and other functional bowel disorders, such as non-ulcerative dyspepsia (NUD) and non-cardiac chest pain (NCCP)).

The compounds can also be used in the treatment of symptoms associated with influenza or other viral infections, common cold, sprains and strains, myositis, neuralgia, synovitis, injuries such as sports injuries and those following surgical and dental procedures, coagulation disorders, kidney disease (e.g. impaired renal function), ophthalmic disorders (including glaucoma, retinitis, retinopathies, uveitis and acute injury to the eye tissue), liver diseases (i.e., inflammatory liver disease including chronic viral hepatitis B, chronic viral hepatitis C, alcoholic liver injury, primary biliary cirrhosis, autoimmune hepatitis, nonalcoholic steatohepatitis and liver transplant rejection), and pulmonary inflammatory diseases (e.g., including asthma, allergic rhinitis, respiratory distress syndrome chronic bronchitis, and emphysema). Compositions comprising a compound described herein and related prodrugs thereof can also be used to treat, for example, inflammation associated with: vascular diseases, migraine headaches, tension headaches, periarteritis nodosa, thyroiditis, aplastic anemia, Hodgkin's disease, sclerodoma, rheumatic fever, type I diabetes, myasthenia gravis, sarcoidosis, nephrotic syndrome, Behcet's syndrome, polymyositis, gingivitis, hypersensitivity, conjunctivitis, multiple sclerosis, and ischemia (e.g., myocardial ischemia), and the like. The compounds may be useful for treating neuroinflammation associated with brain disorders (e.g., Parkinson's disease and Alzheimer's disease) and chronic inflammation associated with cranial radiation injury. The compounds may be useful for treating acute inflammatory conditions (such as those resulting from infection) and chronic inflammatory conditions (such as those resulting from asthma, arthritis and inflammatory bowel disease). The compounds may also be useful in treating inflammation associated with trauma and non-inflammatory myalgia. The compounds can also be administered to those prior to surgery or taking anticoagulants. The compounds may reduce the risk of a thrombotic cardiovascular event which is defined as any sudden event of a type known to be caused by platelet aggregation, thrombosis, and subsequent ischemic clinical events, including thrombotic or thromboembolic stroke, myocardial ischemia, myocardial infarction, angina pectoris, transient ischemic attack (TIA; amaurosis fagax), reversible ischemic neurologic deficits, and any similar thrombotic event in any vascular bed (splanchnic, renal, aortic, peripheral, etc.).

The compounds may inhibit uterus contraction caused by hormones and prostanoid-induced smooth muscle contract. The compounds may be useful in treating premature labor, menstrual cramps, menstrual irregularity, and dysmenorrhea.

The compounds described herein may inhibit cellular neoplastic transformations and metastatic tumor growth. The compounds described herein may be associated with reducing the number of adenomatous colorectal polyps. Thus, compounds and prodrugs may also be useful in reducing the risk of certain cancers, e.g., solid tumor cancers such as colon or colorectal cancer. The compounds and prodrugs may also be used in the treatment of prevention of all cancers including cancers of the bladder, cancers associated with overexpression of HER-2/neu cervix, skin, esophagus, head and neck, lung including non small-cell lung cancers, kidney, pancreas, prostate, gall bladder and bile duct and endometrial cancers, gastric cancers, gliomas, hepatocellular carcinomas, colonic adenomas, mammary cancers, ovarian cancers and salivary cancers. In addition, the compounds and prodrugs may be useful in treating large intestine cancer and prostate cancer. The compounds may also be useful in cases where the patient is at risk for cancer including oral premalignant lesions, cervical intraepithelial neoplasia, chronic hepatitis, bile duct hyperplasia, atypical adenomatous hyperplasia of lung, prostatic, intraepithelial neoplasia, bladder dysplasia, actinic keratoses of skin, colorectal adenomas, gastric metaplasia, and Barrett's esophagus.

Compounds described herein are also useful for the treatment of cognitive disorders such as dementia, particularly degenerative dementia (including senile dementia, Alzheimer's disease (and precursors thereof). Pick's disease, Huntington's chorea, Parkinson's disease and Creutzfeldt-Jakob disease), and vascular dementia (including multiinfarct dementia), as well as dementia associated with intracranial space occupying lesions, trauma, infections and related conditions (including HIV infection), metabolism, toxins, anoxia and vitamin deficiency; and mild cognitive impairment associated with ageing, particularly Age Associated Memory Impairment.

Compounds may also prevent neuronal injury by inhibiting the generation of neuronal free radicals (and hence oxidative stress) and therefore are of use in the treatment of stroke; epilepsy; and epileptic seizures (including grand mal, petit mal, myoclonic epilepsy and partial seizures). The compounds may be useful to control or suppress seizures (including those that are chemically induced).

The compounds can be used in treatment of all varieties of pain including pain associated with a cough condition, pain associated with cancer, preoperative pain, arthritic pain and other forms of chronic pain such as post-operative pain, lumbosacral pain, musculo-skeletal pain, headache, migraine, muscle ache, lower back and neck pain, toothache and the like. The compounds are also useful for the treatment of neuropathic pain. Neuropathic pain syndromes can develop following neuronal injury and the resulting pain may persist for months or years, even after the original injury has healed. Neuronal injury may occur in the peripheral nerves, dorsal roots, spinal cord or certain regions in the brain. Neuropathic pain syndromes are traditionally classified according to the disease or event that precipitated them. Neuropathic pain syndromes include: diabetic neuropathy; sciatica; back pain, non-specific lower back pain; multiple sclerosis pain; fibromyalgia; HIV-related neuropathy; neuralgia, such as postherpetic neuralgia and trigeminal neuralgia; pain related to chronic alcoholism, hypothyroidism, uremia, or vitamin deficiencies; pain related to compression of the nerves (e.g., Carpal Tunnel Syndrome), and pain resulting from physical trauma, amputation/phantom limb pain, cancer, toxins or chronic inflammatory conditions. The symptoms of neuropathic pain are incredibly heterogeneous and are often described as spontaneous shooting and lacinating pain, or ongoing, burning pain. In addition, there is pain associated with normally non-painful sensations such as "pins and needle" (parasthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

The compounds may also be of use in the treatment and/or prevention of cyclooxygenase-mediated proliferative disorders such as may occur in diabetic retinopathy and tumor angiogenesis. The compounds may be used to inhibit angiogenesis, such as occurs in wet macular degeneration.

The compounds may also be used for treating sexual behavior problems and/or improving sexual performances.

Certain compounds are useful in the prevention and/or treatment of pain, in particular acute or chronic neurogenic pain, migraine, neuropathic pains including the forms associated with herpes virus and diabetes, acute or chronic pain associated with the inflammatory diseases: arthritis, rheumatoid arthritis, osteoarthritis, spondylitis, gout, vascularitis, Crohn's disease, irritable bowel syndrome and acute/sharp or chronic pains at the periphery. The compounds can also be used to prevent and/or treat emesis, dizziness, vomiting, and nausea, especially after chemotherapy, food behavioral problems/feeding disorders (i.e. eating disorders, in particular anorexias and cachexias of various natures, weight loss associated with cancer and other wasting conditions, or bulimia), neurological pathologies, psychiatric tremors (e.g., dyskinesias, dystonia, spasticity, obsessive compulsive behavior, Tourette's syndrome, all forms of depression and anxiety of any nature and origin, mood disturbances, psychoses), acute or chronic neurodegenerative diseases (e.g., Parkinson's disease, Alzheimer's disease, senile insanity, Huntington's chorea, lesions related to cerebral ischemia and cranial and medullary traumas, epilepsy, sleep disorders (sleep apnea), cardiovascular diseases (in particular hypertension, cardiac arrhythmias, arteriosclerosis, heart attacks, cardiac ischemias, renal ischemia), cancers (benign tumors of the skin, papillomas and cerebral tumors, prostate tumors, cerebral tumors (glioblastomas, medullary epitheliomas, medullary blastomas, neuroblastomas, tumors of origin, astrocytomas, astroblastomas, ependymomas, oligodendrogliomas, plexus tumor, neuroepithelioma, epiphysis tumor, ependyblastomas, malignant meningiomas, sarcomatosis, malignant melanomas, schwan cell cancers), disorders of the immune system (in particular autoimmune diseases including psoriasis, erythematous lupus), diseases of conjunctive or connective tissue, Sjogren's syndrome, spondylarthritis anchylosis, undifferentiated spondylarthritis undifferentiated, Behcet's disease, autoimmune hemolytic anaemias, multiple sclerosis, amyotrophic lateral sclerosis, amyloses, graft rejection, and illnesses affecting the blastocytes, allergic disease (i.e., immediate or delayed hypersensitivity, allergic rhinitis or conjunctivitis, contact dermatitis), viral or bacterial parasitic infectious diseases (i.e. AIDS, meningitis), inflammatory diseases (in particular arthritic diseases: arthritis, rheumatoid arthritis osteoarthritis, spondylitis, gout, vascularitis, Crohn's disease, irritable bowel syndrome, osteoporosis, psoriasis, ocular infections and disorders (i.e. ocular hypertension, glaucoma, wet macular degeneration), lung diseases (i.e. diseases of the respiratory tracts, bronchyospasms, cough, asthma, chronic bronchitis, chronic obstruction of the respiratory tracts, emphysema), gastrointestinal disorders (i.e. irritable bowel syndrome, intestinal inflammatory disorders, ulcers, diarrheas, acid reflux), urinary incontinence, vesical inflammation, movement disorders, psychomotor disorders, hypertension, and AIDS-related complex. The compounds can be used as a sleep aid, to treat insomnia or to induce sleep. The compounds may be used to reduce or control body weight (or fat) or prevent and/or treat obesity or other appetite related disorders related to the excess consumption of food, ethanol and other appetizing substances. The compounds may be used to modulate lipid metabolism, reduce body fat (e.g., via increasing fat utilization) or reduce (suppress) appetite (e.g., via inducing satiety). The compounds may be used to prevent, control or treat schizophrenia, paranoia or other related disorders, or other disorders of dopamine transmission.

The compounds can also be used to treat anxiety (including generalized anxiety disorder, panic disorder, and social anxiety Disorder) and depression.

The compounds (for example, FAAH inhibitors) can also be used in the treatment of pollakiuria, for example in the treatment of urinary incontinence, uresiesthesia urgency, or overactive bladder. Pollakiuria refers to the condition characterized by the voiding or passing of small quantities of urine more frequently than normal. Interstitial cystitis, chronic prostatitis, neuropathy (for example, resulting from neurogenic bladder or cerebral infarction), lower urinary tract prostatic hypertrophy, and aging, are among the conditions associated with pollakiuria.

CRTH2 Related Therapeutic Methods

The compounds described herein that are CRTH2 antagonists can be used, for example, to prevent and/or treat conditions or disorders in which it is considered desirable to reduce or eliminate CRTH2 activity. The compounds described herein that are CRTH2 agonists can be used, for example, to prevent and/or treat conditions in which it is considered desirable to: (1) downregulate CRTH2 activity via desensitization; (2) downregulate non-CRTH2 chemokine receptor activity via cross-desensitization or (3) shift the balance of Th1 and Th2 cells towards Th2 via agonism at CRTH2. CRTH2 agonists are expected to be especially useful in the prevention and/or treatment of disease and disorders characterized by an imbalance of Th1/Th2 that is shifted towards Th1 cells, e.g., rheumatoid arthritis, Type I diabetes, psoriasis gastritis, irritable bowel syndrome, multiple sclerosis, painless thyroiditis, lupus, and Crohn's Disease.

Compounds that are CRTH2 antagonists or agonists may be used to aid in preventing and/or treating a disease or disorder mediated, regulated or influenced by, for example, Th2 cells, eosinophils, basophils, platelets, Langerhans cells, dendritic cells or mast cells. They also may be used to aid in the prevention or treatment of a disease or disorder mediated, regulated or influenced by $PGD_2$ and metabolites thereof, such as 13,14-dihydro-15-keto-$PGD_2$ and 15-deoxy-Al 2,1'-$PGD_2$.

CRTH2 antagonists are expected to be useful in the prevention and/or treatment of disease and disorders characterized by undesirable activation of Th2 cells, eosinophils, and basophils e.g., asthma, atopic dermatitis, allergic rhinitis, allergies (e.g. food allergies, dust allergies, pollen allergies, mold allergies), and Grave's Disease.

Compounds that are CRTH2 antagonists or agonists (and similarly, compounds that are DP-1 agonists or antagonists) may be used to aid in preventing and/or treating the following types of diseases, conditions and disorders:

respiratory tract/obstructive airways diseases and disorders including: rhinorrhea, tracheal constriction, airway contraction, acute-, allergic, atrophic rhinitis or chronic rhinitis (such as rhinitis caseosa, hypertrophic rhinitis, rhinitis purulenta, rhinitis sicca), rhinitis medicamentosa, membranous rhinitis (including croupous, fibrinous and pseudomembranous rhinitis), scrofulous rhinitis, perennial allergic rhinitis, seasonal rhinitis (including rhinitis nervosa (hay fever) and vasomotor rhinitis), asthma (such as bronchial, allergic, intrinsic, extrinsic, exercise-induced, cold air-induced, occupational, bacterial infection-induced, and dust asthma particularly chronic or inveterate asthma (e.g. late asthma and airways hyper-responsiveness)), bronchitis (including chronic, acute, arachidic, catarrhal, croupus, phthinoid and eosinophilic bronchitis), pneumoconiosis, chronic inflammatory disease of the lung which result in interstitial fibrosis, such as interstitial lung disease (ILD) (e.g., idiopathic pulmonary fibrosis, or ILD associated with rheumatoid arthritis, or other autoimmune conditions), acute lung injury (ALI), adult respiratory distress syndrome (ARDS), chronic obstructive pulmonary, airways or lung disease (CORD, COAD, COLD or COPD, such as irreversible COPD), chronic sinusitis, conjunctivitis (e.g. allergic conjunctivitis), cystic fibrosis, extrinsic allergic alveolitis (like farmer's lung and related diseases), fibroid lung, hypersensitivity lung diseases, hypersensitivity pneumonitis, idiopathic interstitial pneumonia, nasal congestion, nasal polyposis, otitis media, and cough (chronic cough associated with inflammation or iatrogenic induced), pleurisy, pulmonary congestion, emphysema, bronichiectasis, sarcoidosis, lung fibrosis, including cryptogenic fibrosing alveolitis, fibrosis complicating anti-neoplastic therapy and chronic infection, including tuberculosis and aspergillosis and other fungal infections, vasculitic and thrombotic disorders of the lung vasculature, and pulmonary hypertension, acute viral infection including the common cold, and infection due to respiratory syncytial virus, influenza, coronavirus (including SARS) and adenovirus;

systemic anaphylaxis or hypersensitivity responses, drug allergies (e.g., to penicillin, cephalosporins), insect sting allergies, and food related allergies which may have effects remote from the gut (such as migraine, rhinitis and eczema);

bone and join related diseases and disorders including: osteoporosis, arthritis (including rheumatic, infectious, autoimmune), seronegative spondyloarthropathies (such as ankylosing spondylitis, rheumatoid spondylitis, psoriatic arthritis, enthesopathy, Bechet's disease, Marie-Strumpell arthritis, arthritis of inflammatory bowel disease, and Reiter's disease), systemic sclerosis, osteoarthritis/osteoarthrosis, both primary and secondary to e.g. congenital hip dysplasia, cervical and lumbar spondylitis, and low back and neck pain, Still's disease, reactive arthritis and undifferentiated spondarthropathy, septic arthritis and other infection-related arthropathies and bone disorders such as tuberculosis, including Pott's disease and Poncet's syndrome, acute and chronic crystal-induced synovitis including urate gout, calcium pyrophosphate deposition disease, and calcium apatite related tendon, bursar and synovial inflammation, primary and secondary Sjogren's syndrome, systemic sclerosis and limited scleroderma, mixed connective tissue disease, and undifferentiated connective tissue disease, inflammatory myopathies including, polymalgia rheumatica, juvenile arthritis including idiopathic inflammatory arthritides of whatever joint distribution and associated syndromes, other joint disease (such as intervertebral disc degeneration or temporomandibular joint degeneration), rheumatic fever and its systemic complications, vasculitides including giant cell arteritis, Takayasu's arteritis, polyarteritis nodosa, microscopic polyarteritis, and vasculitides to associated with viral infection, hypersensitivity reactions, cryoglobulins, paraproteins, low back pain, Familial Mediterranean fever, Muckle-Wells syndrome, and Familial Hibenian Fever, Kikuchi disease, drug-induced arthalgias, tendonititides, polychondritis, and myopathies;

skin and eye related diseases and disorders including, glaucoma, ocular hypertension, cataract, retinal detachment, psoriasis, xerodoma, eczematous diseases (like atopic dermatitis, contact dermatitis, and seborrheic dermatitis), phytodermatitis, photodermatitis, cutaneous eosinophilias, chronic skin ulcers, cutaneous lupus erythematosus, contact hypersensitivity/allergic contact dermatitis (including sensitivity to poison ivy, sumac, or oak), and eosinophilic folliculitis (Ofuji's disease), pruritus, drug eruptions, urticaria (acute or chronic, allergic or non-allergic), acne, erythema, dermatitis herpetiformis, scleroderma, vitiligo, lichen planus, lichen sclerosus et atrophica, pyodenna gangrenosum, skin sarcoid, pemphigus, pemphigoid, epidennolysis bullosa, angioedema, vasculitides, toxic erythemas, cutaneous eosinophilias, alopecia areata, male-pattern baldness, Sweet's syndrome, Stevens-Johnson syndrome, Weber-Christian syndrome, erythema multiforne, cellulitis, botl, infective and non infective, panniculitis, cutaneous Lymphomas, non-melanoma skin cancer and other dysplastic lesions, blepharitis, iritis, anterior and posterior uveitis, choroiditis, autoimmune, degenerative or inflammatory disorders affecting the retina, ophtllalmitis including sympathetic ophthalmitis, sarcoidosis, xerosis (for example as described in US2005192357A1) infections including viral, fungal, and bacterial;

gastrointestinal tract and abdominal related diseases and disorders including: Celiac/coeliac disease (e.g. celiac sprue), cholecystitis, enteritis (including eosinophilic gastroenteritis), eosinophilic esophagitis, eosinophilic gastrointestinal inflammation, allergen induced diarrhea, enteropathy associated with seronegative arthropathies, gastritis, inflammatory bowel disease (Crohn's disease and ulcerative colitis), colitis, irritable bowel syndrome, glossitis, gingivitis, periodontitis, oesophagitis, including reflex, proctitis, fibrosis and cirrhosis of the liver, pancreatitis, both acute and chronic, hepatitis (alcoholic, steatohepatitis and chronic viral), and gastrointestinal related allergic disorders;

hematological disorders including: anemias, myeloproliferative disorders, hemorrhagic disorders, leukopenia, eosinophilic disorders, leukemias, lymphomas, plasma cell dyscrasias, disorders of the spleen;

metabolic disorders including, but not limited to: obesity, amyloidosis, disturbances of the amino and acid metabolism like branched chain disease, hyperaminoacidemia, hyperaminoaciduria, disturbances of the metabolism of urea, hyperammonemia, mucopolysaccharidoses e.g. Maroteaux-Lamy syndrome, storage disease like glycogen storage diseases and lipid storage diseases, glycogenosis I diseases like Cori's disease, malabsorption diseases like intestinal carbohydrate malabsorption, oligosaccharidase deficiency like maltase-, lactase-, sucrase-insufficiency, disorders of the metabolism of fructose, disorders of the metabolism of galactose, galactosaemia, disturbances of carbohydrate utilization like diabetes, hypoglycemia, disturbances of pyruvate metabolism, hypolipidemia, hypolipoproteinemia, hyperlipidemia, hyperlipoproteinemia, carnitine or carnitine acyltransferase deficiency, disturbances of the porphyrin metabolism, porphyrins, disturbances of the purine metabolism, lysosomal diseases, metabolic diseases of nerves and nervous systems like gangliosidoses, sphingolipidoses, sulfatidoses, leucodystrophies, Lesch-Nyhan syndrome; osteoporosis, osteomalacia like osteoporosis, osteopenia, osteogenesis imperfects, osteopetrosis, osteonecrosis, Paget's disease of bone, hypophosphatemia; cerebellar dysfunction, disturbances of brain metabolism like dementia, Alzheimer's disease, Huntington's chores, Parkinson's disease, Pick's disease, toxic encepha-lopathy, demyelinating neuropathies like inflammatory neuropathy, Guillain-Barre syndrome; primary and secondary metabolic disorders associated with hormonal defects like any disorder stemming from either an hyperfunction or hypofunction of some hormone-secreting endocrine gland and any combination thereof. Sipple's syndrome, pituitary gland dysfunction and its effects on other endocrine glands, such as the thyroid, adrenals, ovaries, and testes, acromegaly, hyper- and hypothyroidism, euthyroid goiter, euthyroid sick syndrome, thyroiditis, and thyroid cancer, over or underproduction of the adrenal steroid hormones, adrenogenital syndrome, Cushing's syndrome, Addison's disease of the adrenal cortex, Addison's pernicious anemia, primary and secondary aldosteronism, diabetes insipidus, diabetes mellitus, carcinoid syndrome, disturbances caused by the dysfunction of the parathyroid glands, pancreatic islet cell dysfunction, diabetes, disturbances of the endocrine system of the female like estrogen deficiency, resistant ovary syndrome; muscle weakness, myotonia. Duchenne's and other muscular dystrophies, dystrophia myotonica of Steinert, mitochondrial myopathies like I disturbances of the catabolic metabolism in the muscle, carbohydrate and lipid storage myopathies, glycogenoses, myoglobinuria, malignant hyperthermia, polymyalgia rheumatics, dermatomyositis, primary myocardial disease, cardiomyopathy; disorders of the ectoderm, neurofibromatosis, scleroderma and polyar teritis, Louis-Bar syndrome, von Hippel-Lindau disease, Sturge-Weber syndrome, tuberous sclerosis, amyloidosis, porphyria; sexual dysfunction of the male and female; confused states and seizures due to inappropriate secretion of antidiuretic hormone from the pituitary gland, Liddle's syndrome, Bartter's syndrome, Fanconi's I syndrome, and renal electrolyte wasting;

transplant rejection related conditions including: acute and chronic allograft rejection following solid organ transplant, for example, transplantation of kidney, heart, liver, lung, and cornea, chronic graft versus host disease, skin graft rejection, and bone marrow transplant rejection;

genitourinary related conditions including nephritis (interstitial, acute interstitial (allergic), and glomerulonephritis), nephrotic syndrome, cystitis including acute and chronic (interstitial) cystitis and Hunner's ulcer, acute and chronic urethritis, prostatitis, epididymitis, oophoritis, salpingitis, vulvo vaginitis, Peyronie's disease, and erectile dysfunction;

CNS related diseases and disorders including, but not limited to: neurodegenerative diseases, Alzheimer's disease and other cementing disorders including CJD and nvCJD, amyloidosis, and other demyelinating syndromes, cerebral atherosclerosis and vasculitis, temporal arteritis, myasthenia gravis, acute and chronic so pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HIV-associated neuropathies, neurosarcoidosis, to brain injuries, cerebrovascular diseases and their consequences, Parkinson's disease, corticobasal degeneration, motor neuron disease, dementia, including ALS (Amyotrophic lateral sclerosis), multiple sclerosis, traumatic brain injury, stroke, post-stroke, post-traumatic brain injury, and small-vessel cerebrovascular disease, dementias, vascular dementia, dementia with Lewy bodies, frontotemporal dementia and Parkinsonism linked 1 to chromosome 17, frontotemporal dementias, including Pick's disease, progressive nuclear palsy, corticobasal degeneration, Huntington's disease, thalamic degeneration, HIV dementia, schizophrenia with dementia, and Korsakoff's psychosis, within the meaning of the definition are also considered to be CNS disorders central and peripheral nervous system complications of malignant, infectious or autoimmune processes;

inflammatory or immunological diseases or disorders including: general inflammation (of the nasal, pulmonary, and gastrointestinal passages), mastocytosis/mast cell disorders (cutaneous, systemic, mast cell activation syndrome, and pediatric mast cell diseases), mastitis (mammary gland), vaginitis, vasculitis (e.g., necrotizing, cutaneous, and hypersensitivity vasculitis), Wegener granulamatosis, myyositis (including polyinyositis, dermatomyositis), basophil related diseases including basophilic leukemia and basophilic leukocytosis, and eosinophil related diseases such as Churg-Strauss syndrome, eosinophilic granuloma, lupus erythematosus (such as, systemic lupus erythematosus, subacute cutaneous lupus erythematosus, and discoid lupus erythematosus), Hashimoto's thyroiditis, Grave's disease, type I diabetes, complications arising from diabetes mellitus, other immune disorders, eosinophilia fasciitis, hyper IgE syndrome, Addison's disease, antiphospholipid syndrome, acquired immune deficiency syndrome (AIDS), leprosy, Sezary syndrome, paraneoplastic syndromes, and other autoimmune disorders, many of which are named within;

cardiovascular diseases and disorders including: congestive heart failure, myocardial infarction, ischemic diseases of the heart, all kinds of atrial and ventricular arrhythmias, hypertension, cerebral trauma, occlusive vascular disease, stroke, cerebrovascular disorder, atherosclerosis, restenosis, affecting the coronary and peripheral is circulation, pericarditis, myocarditis, inflammatory and auto-immune cardiomyopathies including myocardial sarcoid, endocarditis, valvulitis, and aortitis including infective (e.g. syphilitic), hypertensive vascular diseases, peripheral vascular diseases, and atherosclerosis, vasculitides, disorders of the proximal and peripheral veins including phlebitis and thrombosis, including deep vein thrombosis and complications of varicose veins;

oncological diseases and disorders including: common cancers (prostate, breast, lung, ovarian, pancreatic, bowel and colon, abdomen, stomach (and any other digestive system cancers), liver, pancreas, peritoneum, endocrine glands (adrenal, parathyroid, pituitary, testicles, ovary, thymus, thyroid), eye, head, neck, nervous system (central and peripheral), lymphatic system, pelvic, skin, bone, soft tissue, spleen, thoracic, urogenital, and brain tumors), malignancies affecting the bone marrow (including the leukaemias) and lymphoproliferative systems, such as Hodgkin's and non-Hodgkin's lymphoma, metastatic disease and tumour recurrences, and paraneoplastic syndromes, as well as hypergammaglobulinemia, lymphoproliferative diseases, disorders, and/or conditions, paraproteinemias, purpura (including idiopathic thrombocytopenic purpura), Waldenstron's Macroglobulinemia, Gaucher's Disease, histiocytosis, and any other hyperproliferative disease; and other diseases and disorders including: pain, migraine, sleep disorders, fever, sepsis, idiopathic thrombocytopenia pupura, post-operative adhesions, flushing, ischemic/reperfusion injury in the heart, brain, peripheral limbs, infection, viral infection, thrombosis, shock, septic shock, thermal regulation including fever, Raynaud's disease, gangrene, diseases requiring anti-coagulation therapy, congestive heart failure, mucus secretion disorders, pulmonary hypotension, prostanoid-induced smooth muscle contract associated with dysmenorrhea and premature labor.

Compounds that are CRTH2 antagonists or agonists (and similarly, compounds that are DP-1 agonists or antagonists) may also be used to reduce hair (e.g. mammalian) growth as described in US20050112075A1.

Compounds that are CRTH2 agonists may be used as eating promoters and compounds that are CRTH2 antagonists may be used as eating inhibitors as described in WO2004030674.

Compounds that are modulators of CRTH2 are useful for the treatment of pain. Pain can also considered to be a CNS disorder. Pain can be associated with CNS disorders, such as multiple sclerosis, spinal cord injury, sciatica, failed back surgery syndrome, traumatic brain injury, epilepsy, Parkinson's disease, post-stroke, and vascular lesions in the brain and spinal cord (e.g., infarct, hemorrhage, vascular malformation). Non-central neuropathic pain includes that associated with post mastectomy pain, phantom feeling, reflex sympathetic dystrophy (RSD), trigeminal neuralgiaradioculopathy, post-surgical pain, HIV/AIDS related pain, cancer pain, metabolic neuropathies (e.g., diabetic neuropathy, vasculitic neuropathy secondary to connective tissue disease), paraneoplastic polyneuropathy associated, for example, with carcinoma of lung, or leukemia, or lymphoma, or carcinoma of prostate, colon or stomach, trigeminal neuralgia, cranial neuralgias, and post-herpetic neuralgia. Pain associated with peripheral nerve damage, central pain (i.e. due to cerebral ischemia) and various chronic pain i.e., lumbago, back pain (low back pain), inflammatory and/or rheumatic pain. Headache pain (for example, migraine with aura, migraine without aura, and other migraine disorders), episodic and chronic tension-type headache, tension-type like headache, cluster headache, and chronic paroxysmal hemicrania are also CNS disorders. Visceral pain such as pancreatitis, intestinal cystitis, dysmenorrhea, irritable Bowel syndrome, Crohn's disease, biliary colic, ureteral colic, myocardial infarction and pain syndromes of the pelvic cavity, e.g., vulvodynia, orchialgia, urethral syndrome and protatodynia are also CNS disorders.

Compounds that are modulators of CRTH2 are useful for the treatment of neuropathic pain, for example as described in WO05102338. Neuropathic pain syndromes can develop following neuronal injury and the resulting pain may persist for months or years, even after the original injury has healed. Neuronal injury may occur in the peripheral nerves, dorsal roots, spinal cord or certain regions in the brain. Neuropathic pain syndromes are traditionally classified according to the disease or event that precipitated them. Neuropathic pain syndromes include: diabetic neuropathy; sciatica; back pain, non-specific lower back pain; multiple sclerosis pain; fibromyalgia; HIV-related neuropathy; neuralgia, such as postherpetic neuralgia and trigeminal neuralgia; pain related to chronic alcoholism, hypothyroidism, uremia, or vitamin deficiencies; pain related to compression of the nerves (ie. Carpal Tunnel Syndrome), and pain resulting from physical trauma, amputation/phantom limb pain), cancer, toxins or chronic inflammatory conditions. The symptoms of neuropathic pain are incredibly heterogeneous and are often described as spontaneous shooting and lancinating pain, or ongoing, burning pain. In addition, there is pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

TXA2 Related Therapeutic Methods

Compounds which are modulators of thromboxane A2 (TXA2) receptor can be used for the prevention or treatment of indications related to an altered TXA2 receptor function including, but not limited to the following: cerebral circulatory disorders, cerebral infarction, cerebral haemorrhages, cerebral vascular thrombosis, thromboembolisms, cerebral stroke, shock, ischemic heart diseases, myocardial infarction, acute hart failure, vasospastic disorders, angina pectoris, hypertension, atherosclerosis, arteriosclerosis, arteriosclerosis obliterans, thromboangiitis, obliterans, hyperlipidemia, cholesterol ester storage disease and atheroma in vein grafts, reperfusion salvage disorders, for example after ischaemic injury, diabetic nephropathy, diabetic neuropathy and hypertriglyceridemia caused by diabetes, proliferative processes in occlusive vascular diseases (including prevention of arterial restenosis after angioplasty, post-surgical thickening of vascular walls), ischemic peripheral blood vessel diseases, post-operative thrombosis and to accelerate the dilation of transplanted blood vessels after an operation; platelet functional disorders; asthma, bronchial asthma, bronchospasms, pulmonary hypertension; prevention and treatment of hepatic and intestinal damage; renal disease (e.g., hydronephrosis, transplant rejection, and renal nephritis); an immune system activation of coagulation, pain, asthma, angiogenesis associated with a developing tumor, a method of preventing or delaying the onset of an inflammatory disorder mediated by TXA2, allergic diseases; preeclampsia and preterm labor; degenerative processes in penile tissue, e.g. insufficiency of erectile tissue caused by e.g. alcoholism or nicotine abuse; nerve cell denaturation caused by amyloid β protein and nerve cell death caused by axonotmesis, central nervous system diseases, nerve degeneration diseases, nerve cell denaturation, amyloid β protein-induced nerve cell denaturation nerve cell death, axonotmesis-induced nerve cell death and, in particular, dementia of Alzheimer type (as mentioned in the following documents U.S. Pat. No. 6,407,096, US20040152695A1, WO0030683A1, WO9502408A1, WO9205782A1, EP0744950B1, EP0484581B1, EP0240107B1, EP0668279B1, EP0522887A1).

DAO Related Therapeutic Methods

Compounds described herein, e.g., that inhibit DAO can be used to treat memory or cognitive disorders or to enhance memory or cognitive function, e.g., in patients that are not suffering from a disorder associated with memory loss or impairment of cognitive function.

The patient can be suffering from one or more disorders chosen from short term memory, loss of long term memory, Alzheimer's Disease, and mild cognitive impairment. The patient can be suffering from or at risk of developing impairment of cognitive function associated with treatment with a therapeutic agent or one or more disorders chosen from: vascular dementia, Huntington's Disease, hydrocephalus, depression, bipolar disorder, amnesia, AIDS-related dementia, Pick's Disease, Creutzfeldt-Jakob Syndrome, and Parkinson's Disease. The compounds can be administered with a second agent, e.g., tacrine, donepezil hydrochloride, galantamine, rivastigmine, a cholinesterase inhibitor, and NMDA receptor antagonist, a M1 muscarinic receptor antagonist, vitamin E/tocopherol, a statin, CX516, aripipazole, CPI-1189, leteprinim potassium phenserine tartrate, pravastatin, conjugated estrogen, risperidone, SB737552, SR 57667, or SR 57746.

The compounds can be used to treat benign forgetfulness, a mild tendency to be unable to retrieve or recall information that was once registered, learned, and stored in memory. Benign forgetfulness typically affects individuals over 40 and can be recognized by standard assessment instruments such as the Wechsler Memory Scale (Russell, 1975, *J. Consult Clin. Psychol.* 43:800-809).

The compounds can be used for treating AD. Methods for diagnosing AD are known in the art. For example, the National Institute of Neurological and Communicative Disorders and Stroke-Alzheimer's Disease-and the Alzheimer's Disease and Related Disorders Association (NINCDS-AADRDA) criteria can be used to diagnose AD (McKhann et al. 1984 Neurology 34:939-944). The patient's cognitive function can be assessed by the Alzheimer's Disease Assessment Scale-cognitive subscale (ADAS-cog; Rosen et al., 1984, Am. J. Psychiatry 141:1356-1364).

The compounds can be used to treat neuropsychiatric disorders such as schizophrenia, autism, attention deficit disorder (ADD), and attention deficit-hyperactivity disorder (ADHD). They may be useful for treating mood disorders; anxiety related disorders; eating disorders; substance-abuse related disorders; personality disorders; and other mental disorders.

The compounds can be used to treat cognitive and memory impairment associated with head injury or trauma, sometimes referred to as amnesic disorder due to a general medical condition.

The compounds can also be used to treat conditions and disorders that include, but are not limited to, childhood learning disorders, and neurodegenerative diseases and disorders, such as MLS (cerebellar ataxia), ataxia, amyotrophic lateral sclerosis, Down syndrome, multi-infarct dementia, status epilecticus, contusive injuries (e.g. spinal cord injury and head injury), viral infection induced neurodegeneration, (e.g. AIDS, encephalopathies), epilepsy, benign forgetfulness, and closed head injury. The compounds may also be useful for the treatment of neurotoxic injury that follows cerebral stroke, thromboembolic stroke, hemorrhagic stroke, cerebral ischemia, cerebral vasospasm, hypoglycemia amnesia, hypoxia, anoxia, perinatal asphyxia and cardiac arrest.

The compounds can be used for the treatment of neuropathic pain. Neuropathic pain syndromes can develop following neuronal injury and the resulting pain may persist for months or years, even after the original injury has healed. Neuronal injury may occur in the peripheral nerves, dorsal roots, spinal cord or certain regions in the brain. Neuropathic pain syndromes are traditionally classified according to the disease or event that precipitated them. Neuropathic pain syndromes include: diabetic neuropathy; sciatica; back pain, non-specific lower back pain; multiple sclerosis pain; fibromyalgia; HIV-related neuropathy; neuralgia, such as post-herpetic neuralgia and trigeminal neuralgia; pain related to chronic alcoholism, hypothyroidism, uremia, or vitamin deficiencies; pain related to compression of the nerves (ie. Carpal Tunnel Syndrome), and pain resulting from physical trauma, amputation/phantom limb pain), cancer, toxins or chronic inflammatory conditions. The symptoms of neuropathic pain are incredibly heterogeneous and are often described as spontaneous shooting and lancinating pain, or ongoing, burning pain. In addition, there is pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

The compounds are administered in combination with a second compound useful for slowing or reducing cognitive impairment or memory loss or increasing cognitive function or memory.

The compound can be a component of a pharmaceutical composition comprising an agent for the treatment of memory loss (e.g., tacrine (Cognex®), donepezil hydrochloride (Aricept®), galantamine (Reminyl®), rivastigmine (Exelon®), a cholinesterase inhibitor, an NMDA receptor antagonist (e.g., memantine), a M1 muscarinic receptor antagonist, vitamin E/tocopherol, a statin (e.g., lovastatin), CX516 (Ampalex®; Cortex Pharmaceuticals, Irvine, Calif.), aripipazole (Bristol-Meyers Squibb, Lawrenceville, N.J.), CP1-1189 (Centaur Pharmaceuticals, Sunnyvale, Calif.), leteprinim potassium (Neotrofin®; Neo Therapeutics, Inrine, Calif.), phenserine tartrate (Axonyx, New York, N.Y.), pravastatin (Pravachol®, Bristol-Meyers Squibb, Lawrenceville, N.J.), conjugated estrogen (Premain®; Wyeth, Philadelphia Pa.), risperidone (Risperdal®, Johnson & Johnson Pharmaceuticals Research and Development, Raritan, N.J.), SB271046 (GlaxoSmithKline, Philadelphia, Pa.), SB737552 (GlaxoSmithKline, Philadelphia, Pa.), SR 57667 (Sanofi-Synthelabo, New York, N.Y.), and SR 57746 (Sanofi-Synthelabo, New York, N.Y.)).

The compounds described herein can be administered with D-serine or an analog thereof (e.g., a salt of D-serine, an ester of D-serine, alkylated D-serine, or a precursor of D-serine). They can administered with an anti-psychotic, an anti-depressant or a psychostimulant.

Treatments for depression can be used in combination with the compounds described herein. Suitable anti-depressants include: tricyclic antidepressants (TCAs); monoamine oxidase inhibitors (MAOIs); serotonin selective reuptake inhibitors (SSRIs); dual serotonin and norepinephrine reuptake inhibitors; serotonin-2 antagonism/reuptake inhibitors; alpha$_2$/serotonin-2/seratonin-3 antagonists; and selective norepinephrine and dopamine reuptake inhibitors.

Anti-psychotic drugs can be used in combination with the compounds described herein. Such treatments include: neuroleptics (e.g., chlorpromazine (Thorazine®); atypical neuroleptics (clozapine (Clozaril®)); risperidone (Risperdal®); and olanzapine (Zyprexa®).

Certain of the useful compounds inhibit the activity of D-aspartate oxidase (DDO), an enzyme that oxidizes D-Asp, D-Glu, D-Asn, D-Gln, D-Asp-dimethyl-ester and N-methyl-D-Asp.

The compounds can be administered in combination with a DAO or DDO inhibitor or antagonists such as those described in U.S. Application 20030166554, hereby incorporated by reference. Suitable DDO inhibitors can include: aminoethylcysteine-ketimine (AECK, thialysine ketimine, 2H-1,4-thiazine-5,6-dihydro-3-carboxylic acid, S-aminoethyl-L-cysteine ketimine, 2H-1,4-Thiazine-3-carboxylic acid, 5,6-dihydro-); aminoethylcysteine (thialysine); cysteamine; pantetheine; cystathionine; and S-adenosylmethionine.

Administration of Compounds

The compounds can be used alone or in combination with other compounds used to treat inflammatory disorders. Combination therapies are useful in a variety of situations, including where an effective dose of one or more of the agents used in the combination therapy is associated with undesirable toxicity or side effects when not used in combination. This is because a combination therapy can be used to reduce the required dosage or duration of administration of the individual agents.

Thus, the compounds can be used in a co-therapy with a second agent, e.g., an anti-inflammatory agent. Anti-inflammatory agents which can be used in co-therapy include: NSAIDs, compounds which are leukotriene biosynthesis inhibitors, 5-lipoxygenase (LO) inhibitors or 5-lipoxygenase activating protein (FLAP) antagonist (e.g., masoprocol, tenidap, zileuton, pranlukast, tepoxalin, rilopirox, and flezelastine hydrochloride, enazadrem phosphate, bunaprolast, ABT-761, fenleuton, tepoxalin, Abbott-79175, Abbott-85761, a N-(5-substituted)-thiophene-2-alkylsulfonamide, 2,6-di-tert-butylphenolhydrazones, a methoxytetrahydropyrans such as Zeneca ZD-2138, the compound SB-210661, a pyridinyl-substituted 2-cyanonaphthalene compound such as L-739,010, a 2-cyanoquinoline compound such as L-746,530, or an indole or quinoline compound such as MK-591, MK-886, and BAY s x 1005), p38 inhibitors (e.g., SB2035830 and Vertex compound VX745), LTB$_4$ antagonists and LTA$_4$ hydrolase inhibitors, CRTH2 modulators (e.g., ramatroban), steroids or corticosteroids (e.g., beclomethasone, beclomethasone dipropionate, betamethasone, budesonide, bunedoside, butixocort, dexamethasone, flunisolide, fluocortin, fluticasone, fluticasone propionate, hydrocortisone, methylprednisolone, mometasone, predonisolone, predonisone, tipredane, tixocortal, triamicinolone, and triamcinolone acetonide), and other compounds including: Bayer compound BAY1005 (CA registry 128253-31-6), Ciba Geigy compound CGS-25019C, Leo Denmark compound ETH-615, Lilly compound LY-293111, Ono compound ONO-4057, Terumo compound TMK-688, Lilly compounds LY-213024, 264086 and 292728, ONO compound ONO-LB457, Searle compound SC-53228, calcitrol, Lilly compounds LY-210073, LY-223982, LY-233469, and LY-255283, ONO compound ONO-LB-448, Searle compounds SC-41930, SC-50605 and SC-51146, and SmithKline SKF-104493. Such anti-inflammatory drugs may also include steroids, in particular, glucocorticosteroids, such as budesonide, beclamethasone, dipropionate, flucticasone propionate, ciclesonide or mometasone furoate; or steroids described in WO 02/88167, WO 02/12266, WO 02/100879, WO 02/00679 (especially those of examples 3, 11, 14, 17, 19, 26, 34, 37, 39, 51, 60, 67, 72, 1 73, 90, 99 and 101), WO 03/035668, WO 03/048181, WO 03/062259, WO 03/064445 and 1 WO 03/072592; non-steroidal glucocorticoid receptor agonists, such as those described in WO 00/00531, WO 02/10143, WO 03/082280, WO 03/082787, WO 03/104195 and WO 04/0052229; LTB4 antagonists, such as those described in U.S. Pat. No. 5,451,700; LTD4 antagonists, such as montelukast and zafirlukast; PDE4 inhibitors, such as ciiomilast (Ariflo GlaxoSmithKline), Roflumilast (Byk Gulden), V-11294A (Napp), BAY19-8004 (Bayer), SCH-351591 (Schering-Plough), Arofylline (Almirall Prodesfarma), PD189659 (Parke-Davis), AWD-12-281 (Asta Medica), CDC-801 (Celgene), SelCID(TM) CC-10004 (Ceigene), KW 4490 (Kyowa Hakko Kogyo), WO 03/104204, WO 03/104205, WO 04/000814, WO 04/000839 and WO 04005258 (Merck), as well as those described in WO 98/18796 and I WO 03/39544; A2a agonists, such as those described in EP 1052264, EP 1241176, EP 409595A2, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462 and WO 03/086408; A2b antagonists, such as those described in WO 02/42298; and beta (O-2 adrenoceptor agonists, such as albuterol (salbutamol), metaproterenol, terbutaline, salmeterol, fenoterol, procaterol, formoterol, bitolterol mesylate, pirbuterol, and chiral enantiomer and pharmaceutically acceptable salts thereof; and compounds (in free or salt or solvate form) of formula (I) of WO 00/75114.

The compounds can be used in combination with selective COX-2 inhibitors, e.g., meloxicam, Celecoxib, Valdecoxib, Parecoxib, Rofecoxib, Etoricoxib, and Lumaricoxib.

The compounds can be used in a co-therapy with an agent used to treat an anxiety disorders, including: benzodiazepines (e.g., Xanax®, Librium®), SSRIs (e.g., Prozac®, Zoloft®), monoamine oxidase inhibitors (MAOIs) and tricyclic antidepressants (TCAs, e.g., amitryptilline).

The compounds can be used in combination with anti-infectives such as fusidic acid and anti-fungals such as clotrimazole (both for the treatment of atopic dermatitis).

The compounds can be used in a co-therapy with an agent used to treat rheumatoid arthritis including etanercept (Enbrel®) and infliximab (Remicade®).

The compounds can also be used in a co-therapy with a second agent that has analgesic activity. Analgesics which can be used in co-therapy include, but are not limited to: NSAIDs (e.g., acemetacin, acetaminophen, acetyl salicylic acid, alclofenac, alminoprofen, apazone, aspirin, azapropazone, benoxaprofen, bezpiperylon, bucloxic acid, carprofen, clidanac, diclofenac, diclofenac, diflunisal, diflusinal, etodolac, fenbufen, fenbufen, fenclofenac, fenclozic acid, fenoprofen, fentiazac, feprazone, flufenamic acid, flufenisal, flufenisal, fluprofen, flurbiprofen, flurbiprofen, furofenac, ibufenac, ibuprofen, indomethacin, indomethacin, indoprofen, isoxepac, isoxicam, ketoprofen, ketoprofen, ketorolac, meclofenamic acid, meclofenamic acid, mefenamic acid, mefenamic acid, miroprofen, mofebutazone, nabumetone oxaprozin, naproxen, naproxen, niflumic acid, oxaprozin, oxpinac, oxyphenbutazone, phenacetin, phenylbutazone, phenylbutazone, piroxicam, pirprofen, pranoprofen, sudoxicam, tenoxican, sulfasalazine, sulindac, sulindac, suprofen, tiaprofenic acid, tiopinac, tioxaprofen, tolfenamic acid, tolmetin, tolmetin, zidometacin, zomepirac, and zomepirac), a non-narcotic analgesic such as tramadol, and opioid or narcotic analgesic (e.g., APF112, beta funaltrexamine, buprenorphine, butorphanol, codeine, cypridime, dezocine, dihydrocodeine, diphenyloxylate, enkephalin pentapeptide, fedotozine, fentanyl, hydrocodone, hydromorphone, lignocaine, levorphanol, loperamide, meperidine, mepivacaine, methadone, methyl nalozone, morphine, nalbuphine, nalmefene, naloxonazine, naloxone, naltrexone, naltrindole, nor-binaltorphimine, oxycodone, oxymorphone, pentazocine, propoxyphene, and trimebutine), NK1 receptor antagonists (e.g., ezlopitant and SR-14033, SSR-241585), CCK receptor antagonists (e.g., loxiglumide), NK3 receptor antagonists (e.g., NKP-608C, talnetant (SB-233412), D-418, osanetant SR-142801, SSR-241585), norepinephrine-serotonin reuptake inhibitors (NSRI; e.g., milnacipran), vanilloid receptor agonists and antagonists, cannabinoid receptor agonists (e.g., arvanil), sialorphin, compounds or peptides that are inhibitors of neprilysin, frakefamide (H-Tyr-D-Ala-Phe (F)-Phe-NH$_2$; WO 01/019849 A1), Tyr-Arg (kyotorphin), CCK receptor agonists (e.g., caerulein), conotoxin peptides, peptide analogs of thymulin, dexloxiglumide (the R-isomer of loxiglumide; WO 88/05774), and analgesic peptides (e.g., endomorphin-1, endomorphin-2, nocistatin, dalargin, lupron, and substance P).

Other agents which can be used in combination with compounds described herein for treating, for example, neuropathic pain include, but are not limited to: (i) an opioid analgesic, e. g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine; (ii) a nonsteroidal antiinflammatory drug (NSAID), e. g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin or zomepirac, or a pharmaceutically acceptable salt thereof; (iii) a barbiturate sedative, e. g. amobarbital, aropbarbital, butabarbital, butabital, mephobarbital, metharbital, methohexital, pentobarbital, phenobartital, secobarbital, talbutal, theamylal or thiopental or a pharmaceutically acceptable salt thereof; (iv) a benzodiazepine having a sedative action, e.g. chlordiazepoxide, clorazepate, diazepam, flurazepam, lorazepam, oxazepam, temazepam or triazolam or a pharmaceutically acceptable slat thereof, (v) and H1 antagonists having a sedative action e. g. diphenhydramine, pyrilamine, promethazine, chlorpheniramine or chlorcyclizine or a pharmaceutically acceptable salt thereof; (vi) a sedative such as glutethimide, meprobamate, methaqualone or dichloralphenazone or a pharmaceutically acceptable salt thereof; (vii) a skeletal muscle relaxant, e.g. baclofen, carisoprodol, chlorzoxazone, cyclobenzaprine, methocarbamol or orphrenadine or a pharmaceutically acceptable salt thereof, (viii) an NMDA receptor antagonists, e. g. dextromethorphan ((+)-3-hydroxy-N-methylmorphinan) or its metabolite dextrorphan ((+)-3-hydroxy-N-methylmorphinan), ketamine, memantine, pyrroloquinoline quinone or cis-4-(phosphonomethyl)-2-piperidinecarboxylic or a pharmaceutically acceptable salt thereof; (ix) an alpha-adrenergic, e. g. doxazosin, tamsulosin, clonidine or 4-amino-6,7-dimethoxy-2-(5-methanesulfonamido-1,2,3,4-tetrahydroisoquinol-2-yl)-5-(2-pyridyl) quinazoline; (x) a tricyclic antidepressant, e. g. desipramine, imipramine, amytriptiline or nortriptline; (xi) an anticonvulsant, e. g. carbamazepine, sodium valproate, or valproate; (xii) a tachykinin (NK) antagonist, particularly an NK-3, NK-2 or NK-1 antagonist, e.g. (aR,9R)-7-[3,5-bis(trifluoromethyl)benzyl-8,9,10,11-tetrahydro-9-methyl-5-(4-methylphenyl)-7H-[1,4]diazocino[2,1-g][1,7]naphthridine-6-13-dione (TAK-637), 5-[[(2R,3S)-2-[(1 R)-1-[3,5-bis(trifluoromethyl)phenyl]ethoxy-3-(4-fluorophenyl)-4-morpholinyl]methyl]-1,2-dihydro-3H-1,2,4-triazol-3-one (MK-869), lanepitant, dapitant or 3-[[2-methoxy-5-(trifluoromethoxy)phenyl]methylamino]-2-phenylpiperidine (2S, 3S); (xiii) a muscarinic antagonist, e. g oxybutin, tolterodine, propiverine, tropsium chloride or darifenacin; (xiv) a COX-2 inhibitor, e. g. celecoxib, rofecoxib or valdecoxib; (xv) a non-selective COX inhibitor (preferably with GI protection), e. g. nitroflurbiprofen (HCT-1026); (xvi) a coal-tar analgesic, in particular paracetamol; (xvii) a neuroleptic such as droperidol; (xviii) a vanilloid receptor agonist (e.g. resiniferatoxin) or antagonist (e. g. capsazepine); (xix) a beta-adrenergic such as propranolol; (xx) a local anasthetic, such as mexiletine; (xxi) a corticosteroid, such as dexamethasone (xxii) a serotonin receptor agonist or antagonist; (xxiii) a cholinergic (nicotinic) analgesic; (xxiv) Tramadol (trade mark); (xxv) a PDEV inhibitor, such as sildenafil, vardenafil or taladafil; (xxvi) an alpha-2-delta ligand such as gabapentin or pregabalin; and (xxvii) a canabinoid.

In addition, certain antidepressants can be used in cotherapy either because they have analgesic activity or are otherwise beneficial to use in combination with an analgesic. Examples of such anti-depressants, include: selective serotonin reuptake inhibitors (e.g., fluoxetine, paroxetine, setraline), serotonin-norepinephrine dual uptake inhibitors, venlafaxine and nefazodone. Certain anti-convulsants have analgesic activity and are useful in co-therapy. Such anti-convulsants include: gabapentin, carbamazepine, phenytoin, valproate, clonazepam, topiramate and lamotrigine. Such agents are considered particularly useful for treatment of neuropathic pain, e.g., treatment of trigeminal neuralgia, postherpetic neuralgia, and painful diabetic neuropathy. Additional compounds useful in co-therapy include: alpha-2-adrenergic receptor agonists (e.g., tizanidine and clonidine), mexiletine, corticosteroids, compounds that block the NMDA (N-methyl-Daspartate) receptor (e.g., dextromethorphan, ketamine, and amantadine), glycine antagonists, carisoprodol, cyclobenzaprine, various opiates, nonopioid antitussive (e.g. dextromethorphan, carmiphen, caramiphen and carbetapentane), opioid antitussives (e.g. codeine, hydrocodone, metaxolone. The compounds can also be combined with inhalable gaseous nitric oxide (for treating pulmonary vasoconstriction or airway constriction), a thromboxane A2 receptor antagonist, a stimulant (i.e. caffeine), and $H_2$-antagonist (e.g. ranitidine), an antacid (e.g. aluminum or magnesium hydroxide), an antiflatulent (e.g. simethicone), a decongestant (e.g. phenylephrine, phenylpropanolamine, pseudophedrine, oxymetazoline, oxymetazoline hydrochloride, ephinephrine, naphazoline, naphazoline hydrochloride, xylometazoline, xylometazoline hydrochloride, tetrahydrozoline hydrochloride, tramazoline hydrochloride or ethylnorepinephrine hydrochloride, propylhexedrine, or levodesoxyphedrine), a prostaglandin (e.g. misoprostol, enprostil, rioprostil, ornoprostol or rosaprostol), a diuretic, a sedating or non-sedating histamine HI receptor antagonists/antihistamines (i.e. any compound that is capable of blocking, inhibiting, reducing or otherwise interrupting the interaction between histamine and its receptor) including but not limited to: 4 astemizole, acetaminophen, acrivastine, antazoline, asternizole, azatadine, azelastine, astamizole, bromopheniramine, bromopheniramine maleate, carbinoxamine, carebastine, cetirizine, chlorpheniramine, chloropheniramine maleate, cimetidine, clemastine, cyclizine, cyproheptadine, descarboethoxyloratadine, desloratidine, loratidine dexchlorpheniramine, dimethindene, diphenhydramine, diphenylpyraline, doxylamine succinate, doxylamine, ebastine, efletirizine, epinastine, farnotidine, fexofenadine, hydroxyzine, hydroxyzine, ketotifen, levocabastine, levocetirizine, levocetirizine, loratadine, meclizine, mepyramine, mequitazine, methdilazine, mianserin, mizolastine, noberastine, norasternizole, noraztemizole, phenindamine, pheniramine, picumast, promethazine, pynlamine, pyrilamine, ranitidine, temelastine, terfenadine, trimeprazine, tripelenamine, and triprolidine; an antagonist of histamine type 4 receptors; a 5HTI agonist, such as a triptan (e.g. sumatriptan or naratriptan), an adenosine Al agonist, an EP ligand, a sodium channel blocker (e.g. lamotrigine), a substance P antagonist (e.g. an NK antagonist), a cannabinoid, a 5-lipoxygenase inhibitor, a leukotriene receptor antagonist/leukotriene antagonists/LTD4 or LTC4 or LTB4 or LTE4 antagonists (i.e., any compound that is capable of blocking, inhibiting, reducing or otherwise interrupting the interaction between leukotrienes and the Cys LTI receptor) including but not limited to: zafirlukast, verlukast (MK-679), montelukast, montelukast sodium (Singulair®), pranlukast, iralukast (CGP 45715A), pobilukast, BAY x 7195, SKB-106,203, phenothiazin-3-Is such as L-651,392, amidino compounds such as CGS-25019c, benzoxalamines such as ontazolast; benzenecarboximidamides such as BIIL 284/260, ablukast, RG-12525, Ro-245913, and compounds described as having LTD4 antagonizing activity described in U.S. Pat No. 5,565,473, a DMARD (e.g. methotrexate), a neurone stabilising antiepileptic drug, a mono-aminergic uptake inhibitor (e.g. venlafaxine), a matrix metalloproteinase inhibitor (the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-9 and MMP-12, including agents such as doxycycline), a nitric oxide synthase (NOS) inhibitor, such as an iNOS or an nNOS inhibitor, an inhibitor of the release, or action, of tumor necrosis factor, an antibody therapy, such as a monoclonal antibody therapy, an antiviral agent, such as a nucleoside inhibitor (e.g. lamivudine) or an immune system modulator (e.g. interferon), a local anaesthetic, a known FAAH inhibitor (e.g., PMSF, URB532, URB597, or BMS-1, as well as those described in those described in WO04033652, U.S. Pat. No. 6,462,054, US20030092734, US20020188009, US20030195226, and WO04033422), an antidepressant (e.g., VPI-013), a fatty acid amide (e.g. anandamide, N-palmitoyl ethanolamine, N-oleoyl ethanolamide, 2-arachidonoylglycerol, or oleamide), arvanil, analogs of anadamide and arvanil as described in US 20040122089, and a proton pump inhibitor (e.g., omeprazole, esomeprazole, lansoprazole, pantorazole and rabeprazole).

The compound can also be used in a co-therapy with a second agent that is a cannabanoid receptor antagonist to prevent and/or treat obesity and other appetite related disorders.

Agents may also be coadministered with one or more of the following:

an immunostimulatory nucleic acids which contain an immunostimulatory motif or backbone that induces Th1 immune response and/or suppresses a Th2 immune response such as CpG motifs, poly-G motifs and T-rich motifs. Examples of immunostimulatory nucleic acids are disclosed in US20030087848;

inactivating antibodies (e.g., monoclonal or polyclonal) to interleukins (e.g., IL-4 and IL-5 (for example see Leckie et al. 2000 *Lancet* 356:2144)); soluble chemokine receptors (e.g. recombinant soluble IL-4 receptor (Steinke and Borish 2001 *Respiratory Research* 2:66));

chemokine receptor modulators including but not limited to antagonists of chemokine receptor superfamilies (e.g. CCR1 (e.g., CP-481,715 (Gladue et al. *J Biol Chem* 278: 40472)), CCR2, CCR2A, CCR2B, CCR3 (e.g., UCB35625 (Sabore et al. *J Biol Chem* 2000 275:25985), CCR4, CCR5, CCR6, CCR7, CCR8, CCR9, CCR10 and CCR11 (for the C-C family); CXCR1, CXCR2, CXCR3, CXCR4 and CXCR5 (for the C-X-C family) and CX3CR1 for the C-X3-C family, as well as the XC family.) These modulators include those compounds described in US20060052413, US20060025432, WO0039125A1, WO02070523A1, WO03035627A1, WO03084954A1, WO04011443A1, WO04014875A1, WO04018425A1, WO04018435A1, WO04026835A1, WO04026880A1, WO04039376A1, WO04039377A1, WO04039787A1, WO04056773A1, WO04056808A1, WO05021513A1, WO04056809A1, EP1541563A1, WO05040167A1. WO05058881A1, WO05073192A1, WO05070903A2, WO05101989A2, WO06024823, WO06001751, WO06001752 and EP1571146A1; $PGD_2$ receptor antagonists including, but not limited to, compounds described as having $PGD_2$ antagonizing activity in United States Published Applications US20020022218, US20010051624, and US20030055077, PCT Published Applications WO9700853, WO9825919, WO03066046, WO03066047, WO03101961, WO03101981, WO04007451, WO0178697, WO04032848, WO03097042, WO03097598, WO03022814, WO03022813, and WO04058164, European Patent Applications EP945450 and EP944614,and those listed in: Torisu et al. 2004 *Bioorg Med Chem Lett* 14:4557, Torisu et al. 2004 *Bioorg Med Chem Lett* 2004 14:4891, and Torisu et al. 2004 *Bioorg & Med Chem* 2004 12:4685;

adhesion molecule inhibitors including VLA-4 antagonists;

purinergic receptor antagonists such as P2X7 receptor antagonists disclosed in WO06025783;

immunosuppressants such as cyclosporine (cyclosporine A, Sandimmune® Neoral®), tacrolimus (FK-506, Prograf®), pimecrolimus, rapamycin (sirolimus, Rapamune®) and other FK-506 type immunosuppressants, and mycophenolate, e.g., mycophenolate mofetil (CellCept®);

β-agonists including but not limited to: albuterol (Porventil®, Salbutamol®, Ventolin®), bambuterol, bitoterol, clenbuterol, fenoterol, formoterol, isoetharine (Bronkosol®, Bronkometer®), metaproterenol (Alupent®, Metaprel®), pitbuterol (Maxair®), reproterol, rimiterol, salmeterol, terbutaline (Brethaire®, Brethine®, Bricanyl®), adrenalin, isoproterenol (Isuprel®), epinephrine bitartrate (Primatene®), ephedrine, orciprenlaine, fenoterol and isoetharine;

β2 agonist-corticosteroid combinations including but not limited to: salmeterol-fluticasone (Advair®), formoterol-budesonid (Symbicort®);

a bronchodilator including but not limited to methylxanathanines such as theophylline and aminophylline;

a mast cell stabilizer including but not limited to cromolyn, cromolyn sodium, sodium cromoglycate, nedocromil, and proxicromil an anticholinergic including but not limited to: atropine, benztropine, biperiden, flutropium, hyoscyamine, hyoscine, ilutropium, ipratropium, ipratropium bromide, methscopolamine, oxybutinin, rispenzepine, scopolamine, oxitropium bromide, tiotropium bromide, glycopyrrolate, pirenzopine, telenzepine, tiotropium salts and CHF 4226 (Chiesi), and also those described in WO 01/04118, WO 02/51841, WO 02/53564, WO 03/00840, 1 19. WO 03/87094, WO 04/05285, WO 02/00652, WO 03/53966, EP 424021, U.S. Pat. Nos. 5,171,744, 3,714,357 and WO 03/33495;

an anti-tussive including but not limited to: dextromethorphan, codeine, and hydromorphone;

a decongestant including but not limited to: pseudoephedrine and phenylpropanolamine;

an expectorant including but not limited to: guafenesin, guaicolsulfate, terpin, ammonium chloride, glycerol guaicolate, and iodinated glycerol;

a PDE inhibitor including but not limited to filaminast, denbufyllene piclamilast, roflumilast, zardaverine, cilomilast, and rolipram;

a recombinant humanized monoclonal antibody including but not limited to Omalizumab (Xolair®) and talizumab (tnx-901);

a lung surfactant including but not limited to dsc-104;

a cardiovascular agent such as a calcium channel blocker, a beta-adrenoceptor blocker, an angiotensin-converting enzyme s (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor;

antithrombotic agents; such as thrombolytic agents (e.g., streptokinase, alteplase, anistreplase and reteplase), heparin, hirudin and warfarin derivatives β- blockers (e.g., atenolol), β-adrenergic agonists (e.g., isoproterenol), ACE inhibitors and vasodilators (e.g., sodium nitroprusside, nicardipine hydrochloride, nitroglycerin and enaloprilat);

anti-diabetic agents such as insulin and insulin mimetics, sulfonylureas (e.g., glyburide, meglinatide), biguanides, e.g., metformin (Glucophage®), α-glucosidase inhibitors (acarbose), PPAR-gamma agonists and/or thiazolidinone compounds, e.g., rosiglitazone (Avandia®), troglitazone (Rezulin®), ciglitazone, pioglitazone (Actos®) and englitazone;

anti-osteoporosis agent including a hormonal agent such as raloxifene, or a biphosphonate such as alendronate;

preparations of interferon (such as interferon β-I α, interferon β-I β, and alpha, beta, and gamma interferons); gold compounds such as auranohm, aurantium, auranofin and aurothioglucose;

cytokinemodulators including but not limited to inhibitors of tumor necrosis factor (TNF) (e.g. etanercept (Enbrel®), antibody therapies such as adalimumab, CDP-870, orthoclone (OKT3), daclizumab (Zenapax®), basiliximab (Simulec®), infliximab (Remicade®), D2E6 TNF antibody), interleukins (including IL1, IL2, IL3, IL4, IL5, IL6, IL7, IL8, IL9, IL10, IL11, IL12, IL13, IL14, IL15, IL16, IL17 and compounds as described in WO05042502A1 and WO05061465A1), interleukin antagonists or inhibitors such as anakinra (kineret) and pentoxyfylline.

lubricants or emollients such as petrolatum and lanolin, keratolytic agents, vitamin $D_3$ derivatives (e.g., thalidomide or a derivative thereof, dithranol, calcipotriene and calcipotriol (Dovonex®)), PUVA, anthralin (Drithrocreme®), etretinate (Tegison®) and isotretinoin;

nicotinic acid or another nicotinic acid receptor agonist (for example, one can coadminister a CRTH2 or DP-1 antagonist to reduce, prevent or eliminate flushing associated with administration with nicotinic acid or a nicotinic receptor agonist). In certain embodiments a compound described herein which is selective for antagonizing DP-1 activity is coadministered with nicotinic acid or a nicotinic acid receptor agonist to prevent and/or treat atherosclerosis in the absence of substantial flushing. In other embodiments a compound described herein which is selective for antagonizing CRTH2 activity is coadministered with nicotinic acid or a nicotinic acid receptor agonist to prevent and/or treat atherosclerosis in the absence of substantial flushing;

antibacterial agents such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, ozalcitabine or zidovodine; or a non-nucleoside reverse transcriptase inhibitor such as nevirapine or efavirenz;

a CNS agent such as an antidepressant (such as sertraline), an anti-Parkinsonian drug (such as deprenyl, L-dopa, ropinirole, pramipexole, a MAOB inhibitor such as selegine and rasagiline, a comP inhibitor such as tasmar, an A-2 inhibitor, a dopamine reuptake inhibitor, an NMDA antagonist, a nicotine agonist, a dopamine agonist or an inhibitor of neuronal nitric oxide synthase), or an anti-Alzheimer's drug such as donepezil, rivastigmine, propentofylline or metrifonate;

an agent for the treatment of cancer, for example, (i) an antiproliferative/antineoplastic drug, such as an alkylating agent (e.g., cisplatin, carboplatin, cyclophosphamide, nitrogen mustard, melphalan, chlorambucil, busulphan or a nitrosourea); and antimetabolite (e.g., an antifolate like fluoropyrimidine, 5-fluorouracil, tegafur, raltitrexed, methotrexate, cytosine arabinoside, hydroxyurea, gemcitabine or paclitaxel); an antitumour antibiotic (e.g., an anthracycline such as adriamycin, bleomycin, doxorubicin, daunomycin, epirubicin, idarubicin, mitomycin-C, dactinomycin or mithramycin); an antimitotic agent (e.g., a vinca alkaloid such as vincristine, vinblastine, vindesine or vinorelbine, or a taxoid such as taxol or taxotere); or a topoisomerase inhibitor (e.g., an epipodophyllotoxin such as etoposide, teniposide, amsacrine, topotecan or a camptothecin); (ii) a cytostatic agent such as an antioestrogen (e.g., tamoxifen, toremifene, raloxifene, droloxifene or iodoxyfene), an estrogen receptor down regulator (e.g., fulvestrant), an antiandrogen (e.g., bicalutamide, flutamide, nilutamide or cyproterone acetate), a LHRH antagonist or LHRH agonist (e.g., goserelin, leuprorelin or buserelin), a progestrogen (e.g., megestrol acetate), an aromatase inhibitor (e.g., anastrozole, letrozole, vorazole or exemestane) or an inhibitor of 5-alpha-reductase such as finasteride; (iii) an agent which inhibits cancer cell invasion (e.g., a metalloproteinase inhibitor like marimastat or an inhibitor of urokinase plasminogen activator receptor function); (iv) an inhibitor of growth factor function (e.g. monoclonal antibodies like Herceptin (trastuzumab) or Erbitux (cetuximab), a farnesyl transferase inhibitor, a tyrosine kinase inhibitor or a serine/threonine kinase inhibitor, an inhibitor of the epidermal growth factor family (e.g., an EGFR family tyrosine kinase inhibitor such as N-(3-chloro-4-fluorophenyl)-7-methoxy-6-(3-morpholinopropoxy)quinazolin-4-amine (geftinib, AZD1839), N-(3-ethynylphenyl)-6,7-bis(2-methoxyethoxy)quinazolin-4-amine (erlotinib, OSI-774) or 6-acrylamido-N-(3-chloro-4-fluorophenyl)-7-(3-morpholinopropoxy)quinazolin-4-amine (CI 1033)), an inhibitor of the platelet-derived growth factor family, or an inhibitor of the hepatocyte growth factor family; (v) an antiangiogenic agent such as one which inhibits the effects of vascular endothelial growth factor (e.g., the anti-vascular endothelial cell growth factor antibody bevacizumab, a compound disclosed in WO 97/22596, WO 97/30035, WO 97/32856 or WO 98/13354), or a compound that works by another mechanism (e.g., linomide, an inhibitor of integrin ocvp3 function or an angiostatin); (vi) a vascular damaging agent such as combretastatin A4, or a compound disclosed in WO 99/02166 WO 00/40529, WO 00/41669, WO 01/92224, WO 02/04434 or WO 02/08213; (vii) an agent used in antisense therapy, e.g., one directed to one of the targets listed above, such as ISIS 2503, an anti-ras antisense; (viii) an agent used in a gene therapy approach, e.g., approaches to replace aberrant genes such as aberrant p53 or aberrant BRCA1 or BRCA2, GDEPT (gene-directed enzyme pro-drug therapy) approaches such as those using cytosine deaminase, thymidine kinase or a Io bacterial nitroreductase enzyme and approaches to increase patient tolerance to chemotherapy or radiotherapy such as multi-drug resistance gene therapy; or (ix) an agent used in an immuno-therapeutic approach, e.g., ex-vivo and in-vivo approaches to increase the immunogenicity of patient turnout cells, such as transfection with cytokines such as interleukin 2, interleukin 4 or granulocyte-macrophage colony stimulating factor, approaches to decrease T-cell energy, approaches using transfected immune cells such as cytokine-transfected dendritic cells, approaches using cytokine-transfected tumour cell lines and approaches using anti-idiotypic antibodies;

multiple sclerosis therapeutic agents such as interferon β-I β (Betaseron®), interferon β-I α (Avonex®), azathioprine (Imurek®, Imuran®), glatiramer acetate (Capoxone®), a glucocorticoid (e.g., prednisolone) and cyclophosphamide; and other compounds such as 5-aminosalicylic acid and prodrugs thereof, DNA-alkylating agents (e.g., cyclophosphamide, ifosfamide), antimetabolites (e.g., azathioprine, 6-mercaptopurine, methotrexate, a folate antagonist, and 5-fluorouracil, a pyrimidine antagonist), microtubule disruptors (e.g., vincristine, vinblastine, paclitaxel, colchicine, nocodazole and vinorelbine), DNA intercalators (e.g., doxorubicin, daunomycin and cisplatin), DNA synthesis inhibitors such as hydroxyurea, DNA cross-linking agents, e.g., mitomycin C, hormone therapy (e.g., tamoxifen, and flutamide), leflunomide, hydroxychloroquine, d-penicillamine, diacerein, intra-articular therapies such as hyaluronic acid derivatives, nutritional supplements such as glucosamine, combinations of aminosalicylates and sulfapyndine such as mesalazine, balsalazide, and olsalazine, immunomodulatory agents such as the thiopurines, a tryptase inhibitor, a platelet activating factor (PAP) antagonist, an interleukin converting enzyme (ICE) inhibitor, an inosine-5'-monophosphate dehydrogenase (IMPDH inhibitor), cathepsin, a kinase inhibitor such as an inhibitor of tyrosine kinase (such as Btk, Itk, Jak3 or MAP, for example Geftinib or Imatinib mesylate), a serine/threonine kinase inhibitor (such as an inhibitor of a MAP kinase such as p38, INK, protein kinase A, B or C, or IKK), or a kianse involved in cell cycle regulation (such as a cylin dependent kinase), a glucose-6 phosphate dehydrogenase inhibitor, a xanthine oxidase inhibitor (e.g. allopurinol), an uricosuric agent (e.g. probenecid, sulenpyrazone or benzbromarone), a growth hormone secretagogue, a transforming growth factor, a platelet-derived growth factor, a fibroblast growth factor (e.g. basic fibroblast growth factor, a granulocyte macrophage colony stimulating factor (GM-CSF), capsaicin cream, an elastase inhibitor (such as UT-77 or ZD-0892), a TNF-alpha converting enzyme inhibitor (TACE), an agent modulating the function of Toll-like receptors (TLR), an inhibitor of transcription factor activation such as NFkB, API, or STATS, and cytostatic agents (e.g., imatinib (STI571, Gleevec®) and rituximab (Rituxan®)).

Compounds described herein (e.g. DAO inhibitors) may be administered in combination with one or more d-amino acids (for example, one or more of D-Asp, D-Ser, D-Ala, D-Leu and D-Pro) when administered to treat, for example, a CNS related disorder.

Combination Therapy

Combination therapy can be achieved by administering two or more agents, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or with 2, 3, 4, 5, 6, 7, 8, 9, or 10 weeks of each other. In some cases even longer intervals are possible. While in many cases it is desirable that the two or more agents used in a combination therapy be present in within the patient's body at the same time, this need not be so.

Combination therapy can also include two or more administrations of one or more of the agents used in the combination. For example, if agent X and agent Y are used in a combination, one could administer them sequentially in any combination one or more times, e.g., in the order X-Y-X, X-X-Y, Y-X-Y, Y-Y-X, X-X-Y-Y, etc.

Administration

The agents, alone or in combination, can be combined with any pharmaceutically acceptable carrier or medium. Thus, they can be combined with materials that do not produce an adverse, allergic or otherwise unwanted reaction when administered to a patient. The carriers or mediums used can include solvents, dispersants, coatings, absorption promoting agents, controlled release agents, and one or more inert excipients (which include starches, polyols, granulating agents, microcrystalline cellulose diluents, lubricants, binders, disintegrating agents, and the like), etc. If desired, tablet dosages of the disclosed compositions may be coated by standard aqueous or nonaqueous techniques.

The agent can be in the form of a pharmaceutically acceptable salt. Such salts are prepared from pharmaceutically acceptable non-toxic bases including inorganic bases and organic bases. Examples of salts derived from inorganic bases include aluminum, ammonium, calcium, copper ferric, ferrous, lithium, magnesium, manganic salts, manganous, potassium, sodium, zinc, and the like. In some embodiments, the salt can be an ammonium, calcium, magnesium, potassium, or sodium salt. Examples of salts derived from inorganic bases include aluminum, ammonium, calcium, copper, ferric, ferrous, lithium, magnesium, manganic salts, manganous, potassium, sodium, zinc, and the like. In some embodiments, the salt can be an ammonium, calcium, magnesium, potassium, or sodium salt. Examples of salts derived from pharmaceutically acceptable organic non-toxic bases include salts of primary, secondary, and tertiary amines, benethamine, N,N'-dibenzylethylenediamine, diethylamine, 2-diethylaminoethanol, 2-dimethylaminoethanol, diethanolamine, ethanolamine, ethylenediamine, N-ethylmorpholine, N-ethylpiperidine, epolamine, glucamine, glucosamine, histidine, hydrabamine, isopropylamine, lysine, methylglucamine, meglumine, morpholine, piperazine, piperidine, polyamine resins, procaine, purines, theobromine, triethylamine, trimethylamine, tripropylamine, and trolamine, tromethamine. Examples of other salts include tris, arecoline, arginine, barium, betaine, bismuth, chloroprocaine, choline, clemizole, deanol, imidazole, and morpholineethanol. In one embodiment are tris salts.

The agents can be administered orally, e.g., as a tablet or cachet containing a predetermined amount of the active ingredient, pellet, gel, paste, syrup, bolus, electuary, slurry, capsule; powder; granules; as a solution or a suspension in an aqueous liquid or a non-aqueous liquid; as an oil-in-water liquid emulsion or a water-in-oil liquid emulsion, via a liposomal formulation (see, e.g., EP 736299) or in some other form. Orally administered compositions can include binders, lubricants, inert diluents, lubricating, surface active or dispersing agents, flavoring agents, and humectants. Orally administered formulations such as tablets may optionally be coated or scored and may be formulated so as to provide sustained, delayed or controlled release of the active ingredient therein. The agents can also be administered by captisol delivery technology, rectal suppository or parenterally.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent.

The tablets may optionally be coated or scored and may be formulated so as to provide sustained, delayed or controlled release of the active ingredient therein. The pharmaceutical compositions may include a "pharmaceutically acceptable inert carrier", and this expression is intended to include one or more inert excipients, which include starches, polyols, granulating agents, microcrystalline cellulose, diluents, lubricants, binders, disintegrating agents, and the like. If desired, tablet dosages of the disclosed compositions may be coated by standard aqueous or nonaqueous techniques, "Pharmaceutically acceptable carrier" also encompasses controlled release means.

Compositions of the present invention may also optionally include other therapeutic ingredients, anti-caking agents, preservatives, sweetening agents, colorants, flavors, desiccants, plasticizers, dyes, and the like. Any such optional ingredient must be compatible with the compound to insure the stability of the formulation.

The composition may contain other additives as needed, including for example lactose, glucose, fructose, galactose, trehalose, sucrose, maltrose, raffinose, maltitol, melezitose, stachyose, lactitol, palatinite, starch, xylitol, mannitol, myoinositol, and the like, and hydrates thereof, and amino acids, for example alanine, glycine and betaine, and peptides and proteins, for example albumen.

Examples of excipients for use as the pharmaceutically acceptable carriers and the pharmaceutically acceptable inert carriers and the aforementioned additional ingredients include, but are not limited to binders, fillers, disintegrants, lubricants, anti-microbial agents, and coating agents such as:

BINDERS: alginic acid, cellulose and its derivatives (e.g. ethyl cellulose, cellulose acetate, carboxymethyl cellulose, carboxymethyl cellulose calcium, sodium carboxymethyl cellulose), citric acid monohydrate, corn starch, gelatin, guar gum, hydroxymethyl cellulose, hydroxypropyl cellulose, hydroxypropyl methyl cellulose, methyl cellulose, microcrystalline cellulose (e.g. AVICEL™ such as AVICEL-PH-101™, -103™, and 105™ sold by FMC Corporation, Marcus Hook, Pa. USA), natural and synthetic gums such as acacia, other alginates, other starches, polyethylene oxide, polyvinyl alcohol, polyvinyl pyrrolidone, potato starch, powdered tragacanth, pre-gelatinized starch (e.g. STARCH 1500® and STARCH 1500 LM®, sold by Colorcon), sodium alginate, or mixtures thereof;

FILLERS: aluminum magnesium hydroxide, aluminum oxide, calcium carbonate (e.g. granules or powder), calcium dihydroxide, calcium sulfate (e.g. granules or powder), dextrates, dextrose, dibasic calcium phosphate, dibasic calcium phosphate anhydrous, fructose (granules or powder), honey, hydrous lactose, iron oxides (e.g. yellow, black, red, e.g. ferric oxide), kaolin, lactose, lactose and aspartame, lactose and cellulose, lactose and microcrystalline cellulose, lactose anhydrate, lactose monohydrate, magnesium aluminate, magnesium carbonate, magnesium hydroxide, maltodextrin, maltose, mannitol, microcrystalline cellulose, microcrystalline cellulose & guar gum, molasses, powdered cellulose, pre-gelatinized starch, silicic acid, silicic anhydride, silicified microcrystalline cellulose, sodium chloride, sorbitol, soybean lecithin, starch, sucrose, talc, triacetin, tribasic calcium phosphate, xanthar gum, or mixtures thereof;

DISINTEGRANTS; agar-agar, alginic acid, calcium carbonate, clays, croscarmellose sodium, crospovidone, gums (like gellan), lactose monohydrate, low-substituted hydroxypropyl cellulose, microcrystalline cellulose, other algins, other celluloses, other starches, polacrilin potassium, potato or tapioca starch, povidone, pre-gelatinized starch, simethicone emulsion, sodium starch glycolate, or mixtures thereof SURFACTANTS: Tween 80 or polyoxyethylene-polyoxypropylene copolymer, polyoxyethylene sorbitan, or mixtures thereof;

LUBRICANTS: a coagulated aerosol of synthetic silica (Degussa Co. Plano Tex. USA), a pyrogenic silicon dioxide (CAB-O-SIL, Cabot Co., Boston, Mass. USA), agar, calcium stearate, ethyl laurate, ethyl oleate, glycerin, hydrogenated vegetable oil (e.g., peanut oil, cottonseed oil, sunflower oil, sesame oil, olive oil, corn oil and soybean oil), light mineral oil, magnesium stearate, mannitol, mineral oil, other glycols, palmitic acid, polyethylene glycol, sodium lauryl sulfate, sodium stearyl fumarate, sorbitol, stearic acid, syloid silica gel (AEROSIL 200, W.R. Grace Co., Baltimore, Md. USA), talc, vegetable based fatty acids lubricant, zinc stearate, or mixtures thereof;

ANTI-CAKING AGENTS: calcium silicate, magnesium silicate, silicon dioxide, colloidal silicon dioxide, talc, or mixtures thereof.

ANTIMICROBIAL AGENTS: benzalkonium chloride, benzethonium chloride, benzoic acid, benzyl alcohol, butyl paraben, cetylpyridinium chloride, cresol, chlorobutanol, dehydroacetic acid, ethylparaben, methylparaben, phenol, phenylethyl alcohol, phenylmercuric acetate, phenylmercuric nitrate, potassium sorbate, propylparaben, sodium benzoate, sodium dehydroacetate, sodium propionate, polysorbate, sorbic acid, thimersol, thymo, or mixtures thereof;

COATING AGENTS: candellilla wax, carnuba wax, cellulose acetate phthalate, ethylcellulose, gelatin, gellan gum, hydroxypropyl cellulose, hydroxypropyl methyl cellulose phthalate, hydroxypropyl methylcellulose (hypromellose), maltodextrin, methacrylates, methylcellulose, microcrystalline cellulose and carrageenan, microcrystalline wax, pharmaceutical glaze, polyethylene glycol (e.g. polyethylene glycol 8000, polyethylene glycol 3000), polyvinyl acetate phthalate, shellac, sodium carboxymethyl cellulose, sucrose, titanium dioxide, or mixtures thereof; COLORANTS: FD&C blue no. 1, D&C yellow ™10 aluminum lake, FD&C yellow #6/sunset yellow FCF aluminum lake, FD&C carmine aluminum lake and FD&C blue #1, or mixtures thereof; and ANTIOXIDANTS: butylated hydroxyanisole, sodium ascorbate, sodium metabisulfate, malic acid, citric acid, ascorbic acid, butylated hydroxytoluene, vitamin C, propyl gallate, or mixtures thereof.

The formulation can also include other excipients and categories thereof including but not limited to L-histidine, Pluronic®, Poloxamers (such as Lutrol® and Poloxamer 188), ascorbic acid, glutathione, permeability enhancers (e.g. lipids, sodium cholate, acylcamitine, salicylates, mixed bile salts, fatty acid micelles, chelators, fatty acid, surfactants, medium chain glycerides), protease inhibitors (e.g. soybean trypsin inhibitor, organic acids), pH lowering agents and absorption enhancers effective to promote bioavailability (including but not limited to those described in U.S. Pat. Nos. 6,086,918 and 5,912,014), creams and lotions (like maltodextrin and carrageenans); materials for chewable tablets (like dextrose, fructose, lactose monohydrate, lactose and aspartame, lactose and cellulose, maltodextrin, maltose, mannitol, microcrystalline cellulose and guar gum, sorbitol cyrstalline); parenterals (like mannitol and providone); plasticizers (like dibutyl sebacate, plasticizers for coatings, polyvinylacetate phthalate); powder lubricants (like glyceryl behenate); soft gelatin capsules (like sorbitol special solution); spheres for coating (like sugar spheres); spheronization agents (like glyceryl behenate and microcrystalline cellulose); suspending/gelling agents (like carrageenan, gellan gum, mannitol, microcrystalline cellulose, povidone, sodium starch glycolate, xanthan gum); sweeteners (like aspartame, aspartame and lactose, dextrose, fructose, honey, maltodextrin, maltose, mannitol, molasses, sorbitol crystalline, sorbitol special solution, sucrose); wet granulation agents (like calcium carbonate, lactose anhydrous, lactose monohydrate, maltodextrin, mannitol, microcrystalline cellulose, povidone, starch); caramel, carboxymethylcellulose sodium, cherry cream flavor and cherry flavor, citric acid anhydrous, citric acid, confectioner's sugar, D&C Red No. 33, D&C Yellow #10 Aluminum Lake, disodium edetate, ethyl alcohol 15%, FD&C yellow No. 6 aluminum lake, FD&C Blue #1 Aluminum Lake, FD&C Blue No. 1, FD&C blue no. 2 aluminum lake, FD&C Green No. 3, FD&C Red No. 40, FD&C Yellow No. 6 Aluminum Lake, FD&C Yellow No. 6, FD&C Yellow No. 10, glycerol palmitostearate, glyceryl monostearate, indigo carmine, lecithin, manitol, methyl and propyl parabens, mono ammonium glycyrrhizinate, natural and artificial orange flavor, pharmaceutical glaze, poloxamer 188, Polydextrose, polysorbate 20, polysorbate 80, polyvidone, pregelatinized corn starch, pregelatinized starch, red iron oxide, saccharin sodium, sodium carboxymethyl ether, sodium chloride, sodium citrate, sodium phosphate, strawberry flavor, synthetic black iron oxide, synthetic red iron oxide, titanium dioxide, and white wax.

Solid oral dosage forms may optionally be treated with coating systems (e.g. Opadry® fx film coating system, for example Opadry® blue (OY-LS-20921), Opadry® white (YS-2-7063), Opadry® white (YS-1-7040), and black ink (S-1-8106).

The dose range for adult humans is generally from 0.005 mg to 10 g/day orally. Tablets or other forms of presentation provided in discrete units may conveniently contain an amount of compound described herein which is effective at such dosage or as a multiple of the same, for instance, units containing 5 mg to 500 mg, usually around 10 mg to 200 mg. The precise amount of compound administered to a patient will be the responsibility of the attendant physician. However, the dose employed will depend on a number of factors, including the age and sex of the patient, the precise disorder being treated, and its severity.

A dosage unit (e.g. an oral dosage unit) can include from, for example, 1 to 30 µg, 1 to 40 µg, 1 to 50 µg, 1 to 100 µg, 1 to 200 µg, 1 to 300 µg, 1 to 400 µg, 1 to 500 µg, 1 to 600 µg, 1 to 700 µg, 1 to 800 µg, 1 to 900 µg, 1 to 1000 µg, 10 to 30 µg, 10 to 40 µg, 10 to 50 µg, 10 to 100 µg, 10 to 200 µg, 10 to 300 µg, 10 to 400 µg, 10 to 500 µg, 10 to 600 µg, 10 to 700 µg, 10 to 800 µg, 10 to 900 µg, 10 to 1000 µg, 100 to 200 µg, 100 to 300 µg, 100 to 400 µg, 100 to 500 µg, 100 to 600 µg, 100 to 700 µg, 100 to 800 µg, 100 to 900 µg, 100 to 1000 µg, 100 to 1250 µg, 100 to 1500 µg, 100 to 1750 µg, 100 to 2000 µg, 100 to 2250 µg, 100 to 2500 µg, 100 to 2750 µg, 100 to 3000 µg, 200 to 300 µg, 200 to 400 µg, 200 to 500 µg, 200 to 600 µg, 200 to 700 µg, 200 to 800 µg, 200 to 900 µg, 200 to 1000 µg, 200 to 1250 µg, 200 to 1500 µg, 200 to 1750 µg, 200 to 2000 µg, 200 to 2250 µg, 200 to 2500 µg, 200 to 2750 µg, 200 to 3000 µg, 300 to 400 µg, 300 to 500 µg, 300 to 600 µg, 300 to 700 µg, 300 to 800 µg, 300 to 900 µg, 300 to 1000 µg, 300 to 1250 µg, 300 to 1500 µg, 300 to 1750 µg, 300 to 2000 µg, 300 to 2250 µg, 300 to 2500 µg, 300 to 2750 µg, 300 to 3000 µg, 400 to 500 µg, 400 to 600 µg, 400 to 700 µg, 400 to 800 µg, 400 to 900 µg, 400 to 1000 µg, 400 to 1250 µg, 400 to 1500 µg, 400 to 1750 µg, 400 to 2000 µg, 400 to 2250 µg, 400 to 2500 µg, 400 to 2750 µg, 400 to 3000 µg, 500 to 600 µg, 500 to 700 µg, 500 to 800 µg, 500 to 900 µg, 500 to 1000 µg, 500 to 1250 µg, 500 to 1500 µg, 500 to 1750 µg, 500 to 2000 µg, 500 to 2250 µg, 500 to 2500 µg, 500 to 2750 µg, 500 to 3000 µg, 600 to 700 µg, 600 to 800 µg, 600 to 900 µg, 600 to 1000 µg, 600 to 1250 µg, 600 to 1500 µg, 600 to 1750 µg, 600 to 2000 µg, 600 to 2250 µg, 600 to 2500 µg, 600 to 2750 µg, 600 to 3000 µg, 700 to 800 µg, 700 to 900 µg, 700 to 1000 µg, 700 to 1250 µg, 700 to 1500 µg, 700 to 1750 µg, 700 to 2000 µg, 700 to 2250 µg, 700 to 2500 µg, 700 to 2750 µg, 700 to 3000 µg, 800 to 900 µg, 800 to 1000 µg, 800 to 1250 µg, 800 to 1500 µg, 800 to 1750 µg, 800 to 2000 µg, 800 to 2250 µg, 800 to 2500 µg, 800 to 2750 µg, 800 to 3000 µg, 900 to 1000 µg, 900 to 1250 µg, 900 to 1500 µg, 900 to 1750 µg, 900 to 2000 µg, 900 to 2250 µg, 900 to 2500 µg, 900 to 2750 µg, 900 to 3000 µg, 1000 to 1250 µg, 1000 to 1500 µg, 1000 to 1750 µg, 1000 to 2000 µg, 1000 to 2250 µg, 1000 to 2500 µg, 1000 to 2750 µg, 1000 to 3000 µg, 2 to 500 µg, 50 to 500 µg, 3 to 100 µg, 5 to 20 µg, 5 to 100 µg, 50 µg, 100 µg, 150 µg, 200 µg, 250 µg, 300 µg, 350 µg, 400 µg, 450 µg, 500 µg, 550 µg, 600 µg, 650 µg, 700 µg, 750 µg, 800 µg, 850 µg, 900 µg, 900 µg, 1000 µg, 1050 µg, 1100 µg, 1150 µg, 1200 µg, 1250 µg, 1300 µg, 1350 µg, 1400 µg, 1450 µg, 1500 µg, 1550 µg, 1600 µg, 1650 µg, 1700 µg, 1750 µg, 1800 µg, 1850 µg, 1900 µg, 1950 µg, 2000 µg, 2050 µg, 2100 µg, 2150 µg, 2200 µg, 2250 µg, 2300 µg, 2350 µg, 2400 µg, 2450 µg, 2500 µg, 2550 µg, 2600 µg, 2650 µg, 2700 µg, 2750 µg, 2800 µg, 2850 µg, 2900 µg, 2950 µg, 3000 µg, 3250 µg, 3500 µg, 3750 µg, 4000 µg, 4250 µg, 4500 µg, 4750 µg, 5000 µg, 1 to 30 mg, 1 to 40 mg, 1 to 100 mg, 1 to 300 mg, 1 to 500 mg, 2 to 500 mg, 3 to 100 mg, 5 to 20 mg, 5 to 100 mg (e.g. 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, 500 mg) of a compound described herein. In certain embodiments the dosage unit and daily dose are equivalent. In various embodiments, the dosage unit is administered with food at anytime of the day, without food at anytime of the day, with food after an overnight fast (e.g. with breakfast), at bedtime after a low fat snack. In various embodiments, the dosage unit is administered once a day, twice a day, three times a day, four times a day.

Combining two or more active ingredients in single dosage form results in the possibility of chemical interactions between the active drug substances. For example, acidic and basic active ingredients can react with each other and acidic active ingredients can facilitate the degradation of acid labile substances. Thus, in certain dosage forms, acidic and basic substances can be physically separated as two distinct or isolated layers in a compressed tablet, or in the core and shell of a press-coated tablet. Additional agents that are compatible with acidic as well as basic substances, have the flexibility of being placed in either layer. In certain multiple layer compositions at least one active ingredient can be enteric-coated. In certain embodiments thereof at least one active ingredient can be presented in a controlled release form. In certain embodiments where a combination of three or more active substances are used, they can be presented as physically isolated segments of a compressed multilayer tablet, which can be optionally film coated.

The therapeutic combinations described herein can be formulated as a tablet or capsule comprising a plurality of beads, granules, or pellets. All active ingredients including the vitamins of the combination are formulated into granules or beads or pellets that are further coated with a protective coat, an enteric coat, or a film coat to avoid the possible chemical interactions. Granulation and coating of granules or beads is done using techniques well known to a person skilled in the art. At least one active ingredient can present in a controlled release form. Finally these coated granules or beads are filled into hard gelatin capsules or compressed to form tablets.

The therapeutic combinations described herein can be formulated as a capsule comprising microtablets or minitablets of all active ingredients. Microtablets of the individual agents can be prepared using well known pharmaceutical procedures of tablet making like direct compression, dry granulation or wet granulation. Individual microtablets can be filled into hard gelatin capsules. A final dosage form may comprise one or more microtablets of each individual component. The microtablets may be film coated or enteric coated.

The therapeutic combinations described herein can be formulated as a capsule comprising one or more microtablets and powder, or one or more microtablets and granules or beads. In order to avoid interactions between drugs, some active ingredients of a said combination can be formulated as microtablets and the others filled into capsules as a powder, granules, or beads. The microtablets may be film coated or enteric coated. At least one active ingredient can be presented in controlled release form.

The therapeutic combinations described herein can be formulated wherein the active ingredients are distributed in the inner and outer phase of tablets. In an attempt to divide chemically incompatible components of proposed combination, few interacting components are converted in granules or beads using well known pharmaceutical procedures in prior art. The prepared granules or beads (inner phase) are then mixed with outer phase comprising the remaining active ingredients and at least one pharmaceutically acceptable excipient. The mixture thus comprising inner and outer phase is compressed into tablets or molded into tablets. The granules or beads can be controlled release or immediate release beads or granules, and can further be coated using an enteric polymer in an aqueous or non-aqueous system, using methods and materials that are known in the art.

The therapeutic combinations described herein can be formulated as single dosage unit comprising suitable buffering agent. All powdered ingredients of said combination are mixed and a suitable quantity of one or more buffering agents is added to the blend to minimize possible interactions.

The agents described herein, alone or in combination, can be combined with any pharmaceutically acceptable carrier or medium. Thus, they can be combined with materials that do not produce an adverse, allergic or otherwise unwanted reaction when administered to a patient. The carriers or mediums used can include solvents, dispersants, coatings, absorption promoting agents, controlled release agents, and one or more inert excipients (which include starches, polyols, granulating agents, microcrystalline cellulose, diluents, lubricants, binders, disintegrating agents, and the like), etc. If desired, tablet dosages of the disclosed compositions may be coated by standard aqueous or nonaqueous techniques.

The agents can be a free acid or base, or a pharmacologically acceptable salt thereof. Solids can be dissolved or dispersed immediately prior to administration or earlier. In some circumstances the preparations include a preservative to prevent the growth of microorganisms. The pharmaceutical forms suitable for injection can include sterile aqueous or organic solutions or dispersions which include, e.g., water, an alcohol, an organic solvent, an oil or other solvent or dispersant (e.g., glycerol, propylene glycol, polyethylene glycol, and vegetable oils). The formulations may contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Pharmaceutical agents can be sterilized by filter sterilization or by other suitable means.

Suitable pharmaceutical compositions in accordance with the invention will generally include an amount of the active compound(s) with an acceptable pharmaceutical diluent or excipient, such as a sterile aqueous solution, to give a range of final concentrations, depending on the intended use. The techniques of preparation are generally well known in the art, as exemplified by Remington's Pharmaceutical Sciences, 18th Ed., Mack Publishing Company, 1995.

Formulation

The agents either in their free form or as a salt can be combined with a polymer such as polylactic-glycoloic acid (PLGA), poly-(I)-lactic-glycolic-tartaric acid (P(I)LGT) (WO 01/12233), polyglycolic acid (U.S. Pat. No. 3,773,919), polylactic acid (U.S. Pat. No. 4,767,628), poly($\epsilon$-caprolactone) and poly(alkylene oxide) (U.S. 20030068384) to create a sustained release formulation. Such formulations can be used to implants that release a compound or another agent over a period of a few days, a few weeks or several months depending on the polymer, the particle size of the polymer, and the size of the implant (see, e.g., U.S. Pat. No. 6,620,422). Other sustained release formulations are described in EP 0 467 389 A2, WO 93/241150, U.S. Pat. No. 5,612,052, WO 97/40085, WO 03/075887, WO 01/01964A2, U.S. Pat. No. 5,922,356, WO 94/155587, WO 02/07424A2, WO 98/25642, U.S. Pat. Nos. 5,968,895, 6,180,608, U.S. 20030171296, U.S. 20020176841, U.S. Pat. Nos. 5,672,659, 5,893,985, 5,134,122, 5,192,741, 5,192,741, 4,668,506, 4,713,244, 5,445,832 4,931,279, 5,980,945, WO 02/058672, WO 9726015, WO 97/04744, and US20020019446. In such sustained release formulations microparticles of compound are combined with microparticles of polymer. U.S. Pat. No. 6,011,011 and WO 94/06452 describe a sustained release formulation providing either polyethylene glycols (where PEG 300 and PEG 400 are most preferred) or triacetin. WO 03/053401 describes a formulation which may both enhance bioavailability and provide controlled release of the agent within the GI tract. Additional controlled release formulations are described in WO 02/38129, EP 326 151, U.S. Pat. No. 5,236,704, WO 02/30398, WO 98/13029; U.S. 20030064105, U.S. 20030138488A1, U.S. 20030216307A1, U.S. Pat. No. 6,667,060, WO 01/49249, WO 01/49311, WO 01/49249, WO 01/49311, and U.S. Pat. No. 5,877,224.

Controlled Release Formulations

In general, one can provide for controlled release of the agents described herein through the use of a wide variety of polymeric carriers and controlled release systems including erodible and non-erodible matrices, osmotic control devices, various reservoir devices, enteric coatings and multiparticulate control devices.

Matrix devices are a common device for controlling the release of various agents. In such devices, the agents described herein are generally present as a dispersion within the polymer matrix, and are typically formed by the compression of a polymer/drug mixture or by dissolution or melting. The dosage release properties of these devices may be dependent upon the solubility of the agent in the polymer matrix or, in the case of porous matrices, the solubility in the sink solution within the pore network, and the tortuosity of the network. In one instance, when utilizing an erodible polymeric matrix, the matrix imbibes water and forms an aqueous-swollen gel that entraps the agent. The matrix then gradually erodes, swells, disintegrates or dissolves in the GI tract, thereby controlling release of one or more of the agents described herein. In non-erodible devices, the agent is released by diffusion through an inert matrix.

Agents described herein can be incorporated into an erodible or non-erodible polymeric matrix controlled release device. By an erodible matrix is meant aqueous-erodible or water-swellable or aqueous-soluble in the sense of being either erodible or swellable or dissolvable in pure water or requiring the presence of an acid or base to ionize the polymeric matrix sufficiently to cause erosion or dissolution. When contacted with the aqueous environment of use, the erodible polymeric matrix imbibes water and forms an aqueous-swollen gel or matrix that entraps the agent described herein. The aqueous-swollen matrix gradually erodes, swells, disintegrates or dissolves in the environment of use, thereby controlling the release of a compound described herein to the environment of use.

The erodible polymeric matrix into which an agent described herein can be incorporated may generally be described as a set of excipients that are mixed with the agent following its formation that, when contacted with the aqueous environment of use imbibes water and forms a water-swollen gel or matrix that entraps the drug form. Drug release may occur by a variety of mechanisms, for example, the matrix may disintegrate or dissolve from around particles or granules of the agent or the agent may dissolve in the imbibed aqueous solution and diffuse from the tablet, beads or granules of the device. One ingredient of this water-swollen matrix is the water-swellable, erodible, or soluble polymer, which may generally be described as an osmopolymer, hydrogel or water-swellable polymer. Such polymers may be linear, branched, or crosslinked. The polymers may be homopolymers or copolymers. In certain embodiments, they may be synthetic polymers derived from vinyl, acrylate, methacrylate, urethane, ester and oxide monomers. In other embodiments, they can be derivatives of naturally occurring polymers such as polysaccharides (e.g. chitin, chitosan, dextran and pullulan, gum agar, gum arabic, gum karaya, locust bean gum, gum tragacanth, carrageenans, gum ghatti, guar gum, xanthan gum and scleroglucan), starches (e.g. dextrin and maltodextrin), hydrophilic colloids (e.g. pectin), phosphatides (e.g. lecithin), alginates (e.g. ammonium alginate, sodium, potassium or calcium alginate, propylene glycol alginate), gelatin, collagen, and cellulosics. Cellulosics are cellulose polymer that has been modified by reaction of at least a portion of the hydroxyl groups on the saccharide repeat units with a compound to form an ester-linked or an ether-linked substituent. For example, the cellulosic ethyl cellulose has an ether linked ethyl substituent attached to the saccharide repeat unit, while the cellulosic cellulose acetate has an ester linked acetate substituent. In certain embodiments, the cellulosics for the erodible matrix comprises aqueous-soluble and aqueous-erodible cellulosics can include, for example, ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC) HPMCP, HPMCAS, hydroxypropyl methyl cellulose acetate trimellitate (HPMCAT), and ethylhydroxy ethylcellulose (EHEC). In certain embodiments, the cellulosics comprises various grades of low viscosity (MW less than or equal to 50,000 daltons, for example, the Dow Methocel™ series E5, E15LV, E50LV and K100LY) and high viscosity (MW greater than 50,000 daltons, for example, E4MCR, E10MCR, K4M, K15M and K100M and the Methocel™ K series) HPMC. Other commercially available types of HPMC include the Shin Etsu Metolose 90SH series.

The choice of matrix material can have a large effect on the maximum drug concentration attained by the device as well as the maintenance of a high drug concentration. The matrix material can be a concentration-enhancing polymer, for example, as described in WO05/011634.

Other materials useful as the erodible matrix material include, but are not limited to, pullulan, polyvinyl pyrrolidone, polyvinyl alcohol, polyvinyl acetate, glycerol fatty acid esters, polyacrylamide, polyacrylic acid, copolymers of ethacrylic acid or methacrylic acid (EUDRAGITO, Rohm America, Inc., Piscataway, N.J.) and other acrylic acid derivatives such as homopolymers and copolymers of butyl-methacrylate, methylmethacrylate, ethylmethacrylate, ethylacrylate (2-dimethylaminoethyl) methacrylate, and (trimethylaminoethyl) methacrylate chloride.

The erodible matrix polymer may contain a wide variety of the same types of additives and excipients known in the pharmaceutical arts, including osmopolymers, osmagens, solubility-enhancing or -retarding agents and excipients that promote stability or processing of the device.

Alternatively, the agents of the present invention may be administered by or incorporated into a non-erodible matrix device. In such devices, an agent described herein is distributed in an inert matrix. The agent is released by diffusion through the inert matrix. Examples of materials suitable for the inert matrix include soluble plastics (e.g methyl acrylate-methyl methacrylate copolymers, polyvinyl chloride, polyethylene), hydrophilic polymers (e.g. ethyl cellulose, cellulose acetate crosslinked polyvinylpyrrolidone (also known as crospovidone)), and fatty compounds (e.g. carnauba wax, microcrystalline wax, and triglycerides). Such devices are described further in Remington: The Science and Practice of Pharmacy, 20th edition (2000).

Matrix controlled release devices may be prepared by blending an agent described herein and other excipients together, and then forming the blend into a tablet, caplet, pill, or other device formed by compressive forces. Such compressed devices may be formed using any of a wide variety of presses used in the fabrication of pharmaceutical devices. Examples include single-punch presses, rotary tablet presses, and multilayer rotary tablet presses, all well known in the art. See for example, Remington: The Science and Practice of Pharmacy, 20th Edition, 2000. The compressed device may be of any shape, including round, oval, oblong, cylindrical, or triangular. The upper and lower surfaces of the compressed device may be flat, round, concave, or convex.

In certain embodiments, when formed by compression, the device has a strength of at least 5 Kilopounds (Kp)/cm$^2$ (for example, at least 7 Kp/cm$^2$). Strength is the fracture force, also known as the tablet hardness required to fracture a tablet formed from the materials, divided by the maximum cross-sectional area of the tablet normal to that force. The fracture force may be measured using a Schleuniger Tablet Hardness Tester, Model 6D. The compression force required to achieve this strength will depend on the size of the tablet, but generally will be greater than about 5 kP/cm$^2$. Friability is a well-know measure of a device's resistance to surface abrasion that measures weight loss in percentage after subjecting the device to a standardized agitation procedure. Friability values of from 0.8 to 1.0% are regarded as constituting the upper limit of acceptability. Devices having a strength of greater than 5 kP/cm$^2$ generally are very robust, having a friability of less than 0.5%. Other methods for forming matrix controlled-release devices are well known in the pharmaceutical arts. See for example, Remington: The Science and Practice of Pharmacy, 20th Edition, 2000.

As noted above, the agents described herein may also be incorporated into an osmotic control device. Such devices generally include a core containing one or more agents as described herein and a water permeable, non-dissolving and non-eroding coating surrounding the core which controls the influx of water into the core from an aqueous environment of use so as to cause drug release by extrusion of some or all of the core to the environment of use. In certain embodiments, the coating is polymeric, aqueous-permeable, and has at least one delivery port. The core of the osmotic device optionally includes an osmotic agent which acts to imbibe water from the surrounding environment via such a semi-permeable membrane. The osmotic agent contained in the core of this device may be an aqueous-swellable hydrophilic polymer or it may be an osmogen, also known as an osmagent. Pressure is generated within the device which forces the agent(s) out of the device via an orifice (of a size designed to minimize solute diffusion while preventing the build-up of a hydrostatic pressure head). Nonlimiting examples of osmotic control devices are disclosed in U.S. patent application Ser. No. 09/495,061.

Osmotic agents create a driving force for transport of water from the environment of use into the core of the device. Osmotic agents include but are not limited to water-swellable hydrophilic polymers, and osmogens (or osmagens). Thus, the core may include water-swellable hydrophilic polymers, both ionic and nonionic, often referred to as osmopolymers and hydrogels. The amount of water-swellable hydrophilic polymers present in the core may range from about 5 to about 80 wt % (including for example, 10 to 50 wt %). Nonlimiting examples of core materials include hydrophilic vinyl and acrylic polymers, polysaccharides such as calcium alginate, polyethylene oxide (PEO), polyethylene glycol (PEG), polypropylene glycol (PPG), poly (2-hydroxyethyl methacrylate), poly (acrylic) acid, poly (methacrylic acid, polyvinylpyrrolidone (PVP) and crosslinked PVP, polyvinyl alcohol (PVA), PVA/PVP copolymers and PVA/PVP copolymers with hydrophobic monomers such as methyl methacrylate, vinyl acetate, and the like hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl cellulose (CEC), sodium alginate, polycarbophil, gelatin, xanthan gum, and sodium starch glycolat. Other materials include hydrogels comprising interpenetrating networks of polymers that may be formed by addition or by condensation polymerization, the components of which may comprise hydrophilic and hydrophobic monomers such as those just mentioned. Water-swellable hydrophilic polymers include but are not limited to PEO, PEG, PVP, sodium croscarmellose, HPMC, sodium starch glycolate, polyacrylic acid and crosslinked versions or mixtures thereof.

The core may also include an osmogen (or osmagent). The amount of osmogen present in the core may range from about 2 to about 70 wt % (including, for example, from 10 to 50 wt %). Typical classes of suitable osmogens are water-soluble organic acids, salts and sugars that are capable of imbibing water to thereby effect on osmotic pressure gradient across the barrier of the surrounding coating. Typical useful osmogens include but are not limited to magnesium sulfate, magnesium chloride, calcium chloride, sodium chloride, lithium chloride, potassium sulfate, sodium carbonate, sodium sulfite, lithium sulfate, potassium chloride, sodium sulfate, mannitol, xylitol, urea, sorbitol, inositol, raffinose, sucrose, glucose, fructose, lactose, citric acid, succinic acid, tartaric acid, and mixtures thereof. In certain embodiments, the osmogen is glucose, lactose, sucrose, mannitol, xylitol, sodium chloride, including combinations thereof.

The core may include a wide variety of additives and excipients that enhance the performance of the dosage form or that promote stability, tableting or processing. Such additives and excipients include tableting aids, surfactant, water-soluble polymers, pH modifiers, fillers, binders, pigments, disintegrants, antioxidants, lubricants and flavorants. Nonlimiting examples of additives and excipients include but are not limited to those described elsewhere herein as well as microcrystalline cellulose, metallic salts of acids (e.g. aluminum stearate, calcium stearate, magnesium stearate, sodium stearate, zinc stearate), pH control agents (e.g. buffers, organic acids, organic acid salts, organic and inorganic bases), fatty acids, hydrocarbons and fatty alcohols (e.g. stearic acid, palmitic acid, liquid paraffin, stearyl alcohol, and palmitol), fatty acid esters (e.g. glyceryl (mono- and di-) stearates, triglycerides, glyceryl (palmiticstearic) ester, sorbitan esters (e.g. sorbitan monostearate, saccharose monostearate, saccharose monopalmitate, sodium stearyl fumarate), polyoxyethylene sorbitan esters), surfactants (e.g. alkyl sulfates (e.g. sodium lauryl sulfate, magnesium lauryl sulfate), polymers (e.g. polyethylene glycols, polyoxyethylene glycols, polyoxyethylene, polyoxypropylene ethers, including copolymers thereof), polytetrafluoroethylene), and inorganic materials (e.g. talc, calcium phosphate), cyclodextrins, sugars (e.g. lactose, xylitol), sodium starch glycolate). Nonlimiting examples of disintegrants are sodium starch glycolate (e.g., Explotab™ CLV, (microcrystalline cellulose (e. g. , Avicel™), microcrystalline silicified cellulose (e.g., ProSolv™), croscarmellose sodium (e. g., Ac-Di-Sol™). When the agent described herein is a solid amorphous dispersion formed by a solvent process, such additives may be added directly to the spray-drying solution when forming an agent described herein/concentration-enhancing polymer dispersion such that the additive is dissolved or suspended in the solution as a slurry, Alternatively, such additives may be added following the spray-drying process to aid in forming the final controlled release device.

A nonlimiting example of an osmotic device consists of one or more drug layers containing an agent described herein, such as a solid amorphous drug/polymer dispersion, and a sweller layer that comprises a water-swellable polymer, with a coating surrounding the drug layer and sweller layer. Each layer may contain other excipients such as tableting aids, osmagents, surfactants, water-soluble polymers and water-swellable polymers.

Such osmotic delivery devices may be fabricated in various geometrics including bilayer (wherein the core comprises a drug layer and a sweller layer adjacent to each other), trilayer (wherein the core comprises a sweller layer sandwiched between two drug layers) and concentric (wherein the core comprises a central sweller agent surrounded by the drug layer). The coating of such a tablet comprises a membrane permeable to water but substantially impermeable to drug and excipients contained within. The coating contains one or more exit passageways or ports in communication with the drug-containing layer(s) for delivering the drug agent. The drug-containing layer(s) of the core contains the drug agent (including optional osmagents and hydrophilic water-soluble polymers), while the sweller layer consists of an expandable hydrogel, with or without additional osmotic agents.

When placed in an aqueous medium, the tablet imbibes water through the membrane, causing the agent to form a dispensable aqueous agent, and causing the hydrogel layer to expand and push against the drug-containing agent, forcing the agent out of the exit passageway. The agent can swell, aiding in forcing the drug out of the passageway. Drug can be delivered from this type of delivery system either dissolved or dispersed in the agent that is expelled from the exit passageway.

The rate of drug delivery is controlled by such factors as the permeability and thickness of the coating, the osmotic pressure of the drug-containing layer, the degree of hydrophilicity of the hydrogel layer, and the surface area of the device. Those skilled in the art will appreciate that increasing the thickness of the coating will reduce the release rate, while any of the following will increase the release rate: increasing the permeability of the coating; increasing the hydrophilicity of the hydrogel layer; increasing the osmotic pressure of the drug-containing layer; or increasing the device's surface area.

Other materials useful in forming the drug-containing agent, in addition to the agent described herein itself, include HPMC, PEO and PVP and other pharmaceutically acceptable carriers. In addition, osmagents such as sugars or salts, including but not limited to sucrose, lactose, xylitol, mannitol, or sodium chloride, may be added. Materials which are useful for forming the hydrogel layer include sodium CMC, PEO (e.g. polymers having an average molecular weight from about 5,000,000 to about 7,500,000 daltons), poly (acrylic acid), sodium (polyacrylate), sodium croscarmellose, sodium starch glycolat, PVP, crosslinked PVP, and other high molecular weight hydrophilic materials.

In the case of a bilayer geometry, the delivery port(s) or exit passageway(s) may be located on the side of the tablet containing the drug agent or may be on both sides of the tablet or even on the edge of the tablet so as to connect both the drug layer and the sweller layer with the exterior of the device. The exit passageway(s) may be produced by mechanical means or by laser drilling, or by creating a difficult-to-coat region on the tablet by use of special tooling during tablet compression or by other means.

The osmotic device can also be made with a homogeneous core surrounded by a semipermeable membrane coating, as in U.S. Pat. No. 3,845,770. The agent described herein can be incorporated into a tablet core and a semipermeable membrane coating can be applied via conventional tablet-coating techniques such as using a pan coater. A drug delivery passageway can then be formed in this coating by drilling a hole in the coating, either by use of a laser or mechanical means. Alternatively, the passageway may be formed by rupturing a portion of the coating or by creating a region on the tablet that is difficult to coat, as described above. In one embodiment, an osmotic device comprises: (a) a single-layer compressed core comprising: (i) an agent described herein, (ii) a hydroxyethylcellulose, and (iii) an osmagent, wherein the hydroxyethylcellulose is present in the core from about 2.0% to about 35% by weight and the osmagent is present from about 15% to about 70% by weight; (b) a water-permeable layer surrounding the core; and (c) at least one passageway within the water-permeable layer (b) for delivering the drug to a fluid environment surrounding the tablet. In certain embodiments, the device is shaped such that the surface area to volume ratio (of a water-swollen tablet) is greater than 0.6 $mm^{-1}$ (including, for example, greater than 1.0 $mm^{-1}$). The passageway connecting the core with the fluid environment can be situated along the tablet band area. In certain embodiments, the shape is an oblong shape where the ratio of the tablet tooling axes, i.e., the major and minor axes which define the shape of the tablet, are between 1.3 and 3 (including, for example, between 1.5 and 2.5). In one embodiment, the combination of the agent described herein and the osmagent have an average ductility from about 100 to about 200 Mpa, an average tensile strength from about 0.8 to about 2.0 Mpa, and an average brittle fracture index less than about 0.2. The single-layer core may optionally include a disintegrant, a bioavailability enhancing additive, and/or a pharmaceutically acceptable excipient, carrier or diluent.

In certain embodiments, entrainment of particles of agents described herein in the extruding fluid during operation of such osmotic device is desirable. For the particles to be well entrained, the agent drug form is dispersed in the fluid before the particles have an opportunity to settle in the tablet core. One means of accomplishing this is by adding a disintegrant that serves to break up the compressed core into its particulate components. Nonlimiting examples of standard disintegrants include materials such as sodium starch glycoate (e. g., Explotab™ CLV), microcrystalline cellulose (e. g., Avicel™), microcrystalline silicified cellulose (e.g., Pro-Solv™) and croscarmellose sodium (e.g., Ac-D-Sol™), and other disintegrants known to those skilled in the art. Depending upon the particular formulation, some disintegrants work better than others. Several disintegrants tend to form gels as they swell with water, thus hindering drug delivery from the device. Non-gelling, non-swelling disintegrants provide a more rapid dispersion of the drug particles within the core as water enters the core. In certain embodiments, non-gelling, non-swelling disintegrants are resins, for example, ion-exchange resins. In one embodiment, the resin is Amberlite™ IRP 88 (available from Rohm and Haas, Philadelphia, Pa.). Then used, the disintegrant is present in amounts ranging from about 1-25% of the core agent.

Water-soluble polymers are added to keep particles of the agent suspended inside the device before they can be delivered through the passageway(s) (e.g., an orifice). High viscosity polymers are useful in preventing settling. However, the polymer in combination with the agent is extruded through the passageway(s) under relatively low pressures. At a given extrusion pressure, the extrusion rate typically slows with increased viscosity. Certain polymers in combination with particles of the agent described herein form high viscosity solutions with eater but are still capable of being extruded from the tablets with a relatively low force. In contrast, polymers having a low weight-average, molecular weight (<about 300,000) do not form sufficiently viscous solutions inside the tablet core to allow complete delivery due to particle settling. Settling of the particles is a problem when such devices are prepared with no polymer added, which leads to poor drug delivery unless the tablet is constantly agitated to keep the particles from settling inside the core. Settling is also problematic when the particles are large and/or of high density such that the rate of settling increases.

In certain embodiments, the water-soluble polymers for such osmotic devices do not interact with the drug. In certain embodiments the water-soluble polymer is a non-ionic polymer. A nonlimiting example of a non-ionic polymer forming solutions having a high viscosity yet still extrudable at low pressures is Natrosol™ 250H (high molecular weight hydroxyethylcellulose, available from Hercules Incorporated, Aqualon Division, Wilmington, Del.; MW equal to about 1 million daltons and a degree of polymerization equal to about 3,700). Natrosol 250H™ provides effective drug delivery at concentrations as low as about 3% by weight of the core when combined with an osmagent. Natrosol 250H™ NF is a high-viscosity grade nonionic cellulose ether that is soluble in hot or cold water. The viscosity of a 1% solution of Natrosol 250H using a Brookfield LVT (30 rpm) at 25° C. is between about 1,500 and about 2,500 cps.

In certain embodiments, hydroxyethylcellulose polymers for use in these monolayer osmotic tablets have a weight-average, molecular weight from about 300,000 to about 1.5 million. The hydroxyethylcellulose polymer is typically present in the core in an amount from about 2.0% to about 35% by weight.

Another example of an osmotic device is an osmotic capsule. The capsule shell or portion of the capsule shell can be semipermeable. The capsule can be filled either by a powder or liquid consisting of an agent described herein, excipients that imbibe water to provide osmotic potential, and/or a water-swellable polymer, or optionally solubilizing excipients. The capsule core can also be made such that it has a bilayer or multilayer agent analogous to the bilayer, trilayer or concentric geometries described above.

Another class of osmotic device useful in this invention comprises coated swellable tablets, for example, as described in EP378404. Coated swellable tablets comprise a tablet core comprising an agent described herein and a swelling material, preferably a hydrophilic polymer, coated with a membrane, which contains holes, or pores through which, in the aqueous use environment, the hydrophilic polymer can extrude and carry out the agent. Alternatively, the membrane may contain polymeric or low molecular weight water-soluble porosigens. Porosigens dissolve in the aqueous use environment, providing pores through which the hydrophilic polymer and agent may extrude. Examples of porosigens are water-soluble polymers such as HPMC, PEG, and low molecular weight compounds such as glycerol, sucrose, glucose, and sodium chloride. In addition, pores may be formed in the coating by drilling holes in the coating using a laser or other mechanical means. In this class of osmotic devices, the membrane material may comprise any film-forming polymer, including polymers which are water permeable or impermeable, providing that the membrane deposited on the tablet core is porous or contains water-soluble porosigens or possesses a macroscopic hole for water ingress and drug release. Embodiments of this class of sustained release devices may also be multilayered, as described, for example, in EP378404.

When an agent described herein is a liquid or oil, such as a lipid vehicle formulation, for example as described in WO05/011634, the osmotic controlled-release device may comprise a soft-gel or gelatin capsule formed with a composite wall and comprising the liquid formulation where the wall comprises a barrier layer formed over the external surface of the capsule, an expandable layer formed over the barrier layer, and a semipermeable layer formed over the expandable layer. A delivery port connects the liquid formulation with the aqueous use environment. Such devices are described, for example, in U.S. Pat. Nos. 6,419,952, 6,342,249, 5,324,280, 4,672,850, 4,627,850, 4,203,440, and 3,995,631.

The osmotic controlled release devices of the present invention can also comprise a coating. In certain embodiments, the osmotic controlled release device coating exhibits one or more of the following features: is water-permeable, has at least one port for the delivery of drug, and is non-dissolving and non-eroding during release of the drug formulation, such that drug is substantially entirely delivered through the delivery port(s) or pores as opposed to delivery primarily via permeation through the coating material itself. Delivery ports include any passageway, opening or pore whether made mechanically, by laser drilling, by pore formation either during the coating process or in situ during use or by rupture during use. In certain embodiments, the coating is present in an amount ranging from about 5 to 30 wt % (including, for example, 10 to 20 wt %) relative to the core weight.

One form of coating is a semipermeable polymeric membrane that has the port(s) formed therein either prior to or during use. Thickness of such a polymeric membrane may vary between about 20 and 800 µm (including, for example, between about 100 to 500 µm). The diameter of the delivery port(s) may generally range in size from 0.1 to 3000 µm or greater (including, for example, from about 50 to 3000 µm in diameter). Such port(s) may be formed post-coating by mechanical or laser drilling or may be formed in situ by rupture of the coatings; such rupture may be controlled by intentionally incorporating a relatively small weak portion into the coating. Delivery ports may also be formed in situ by erosion of a plug of water-soluble material or by rupture of a thinner portion of the coating over an indentation in the core. In addition, delivery ports may be formed during coating, as in the case of asymmetric membrane coatings of the type disclosed in U.S. Pat. Nos. 5,612,059 and 5,698,220. The delivery port may be formed in situ by rupture of the coating, for example, when a collection of beads that may be of essentially identical or of a variable agent are used. Drug is primarily released from such beads following rupture of the coating and, following rupture, such release may be gradual or relatively sudden. When the collection of beads has a variable agent, the agent may be chosen such that the beads rupture at various times following administration, resulting in the overall release of drug being sustained for a desired duration.

Coatings may be dense, microporous or asymmetric, having a dense region supported by a thick porous region such as those disclosed in U.S. Pat. Nos. 5,612,059 and 5,698,220.

When the coating is dense the coating can be composed of a water-permeable material. When the coating is porous, it may be composed of either a water-permeable or a water-impermeable material. When the coating is composed of a porous water-impermeable material, water permeates through the pores of the coating as either a liquid or a vapor. Nonlimiting examples of osmotic devices that utilize dense coatings include U.S. Pat. Nos. 3,995,631 and 3,845,770. Such dense coatings are permeable to the external fluid such as water and may be composed of any of the materials mentioned in these patents as well as other water-permeable polymers known in the art.

The membranes may also be porous as disclosed, for example, in U.S. Pat. Nos. 5,654,005 and 5,458,887 or even be formed from water-resistant polymers. U.S. Pat. No. 5,120,548 describes another suitable process for forming coatings from a mixture of a water-insoluble polymer and a leachable water-soluble additive. The porous membranes may also be formed by the addition of pore-formers as disclosed in U.S. Pat. No. 4,612,008. In addition, vapor-permeable coatings may even be formed from extremely hydrophobic materials such as polyethylene or polyvinylidene difluorid that, when dense, are essentially water-impermeable, as long as such coatings are porous. Materials useful in forming the coating include but are not limited to various grades of acrylic, vinyls, ethers, polyamides, polyesters and cellulosic derivatives that are water-permeable and water-insoluble at physiologically relevant pHs, or are susceptible to being rendered water-insoluble by chemical alteration such as by crosslinking. Nonlimiting examples of suitable polymers (or crosslinked versions) useful in forming the coating include plasticized, unplasticized and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxiated ethylene-vinylacetate, EC, PEG, PPG, PEG/PPG copolymers, PVP, HEC, HPC, CMC, CMEC, HPMC, HPMCP, HPMCAS, HPMCAT, poly (acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes and synthetic waxes. In various embodiments, the coating agent comprises a cellulosic polymer, in particular cellulose ethers, cellulose esters and cellulose ester-ethers, i.e., cellulosic derivatives having a mixture of ester and ether substituents, the coating materials are made or derived from poly (acrylic) acids and esters, poly (methacrylic) acids and esters, and copolymers thereof, the coating agent comprises cellulose acetate, the coating comprises a cellulosic polymer and PEG, the coating comprises cellulose acetate and PEG.

Coating is conducted in conventional fashion, typically by dissolving or suspending the coating material in a solvent and then coating by dipping, spray coating or by pan-coating. In certain embodiments, the coating solution contains 5 to 15 wt % polymer. Typical solvents useful with the cellulosic polymers mentioned above include but are not limited to acetone, methyl acetate, ethyl acetate, isopropyl acetate, n-butyl acetate, methyl isobutyl ketone, methyl propyl ketone, ethylene glycol monoethyl ether, ethylene glycol monoethyl acetate, methylene dichloride, ethylene dichloride, propylene dichloride, nitroethane, nitropropane, tetrachloroethane, 1,4-dioxane, tetrahydrofuran, diglyme, water, and mixtures thereof. Pore-formers and non-solvents (such as water, glycerol and ethanol) or plasticizers (such as diethyl phthalate) may also be added in any amount as long as the polymer remains soluble at the spray temperature. Pore-formers and their use in fabricating coatings are described, for example, in U.S. Pat. No. 5,612,059. Coatings may also be hydrophobic microporous layers wherein the pores are substantially filled with a gas and are not wetted by the aqueous medium but are permeable to water vapor, as disclosed, for example, in U.S. Pat. No. 5,798,119. Such hydrophobic but water-vapor permeable coatings are typically composed of hydrophobic polymers such as polyalkenes, polyacrylic acid derivatives, polyethers, polysulfones, polyethersulfones, polystyrenes, polyvinyl halides, polyvinyl esters and ethers, natural waxes and synthetic waxes. Hydrophobic microporous coating materials include but are not limited to polystyrene, polysulfones, polyethersulfones, polyethylene, polypropylene, polyvinyl chloride, polyvinylidene fluoride and polytetrafluoroethylene. Such hydrophobic coatings can be made by known phase inversion methods using any of vapor-quench, liquid quench, thermal processes, leaching soluble material from the coating or by sintering coating particles. In thermal processes, a solution of polymer in a latent solvent is brought to liquid-liquid phase separation in a cooling step. When evaporation of the solvent is not prevented, the resulting membrane will typically be porous. Such coating processes may be conducted by the processes disclosed, for example, in U.S. Pat. Nos. 4,247,498, 4,490,431 and 4,744,906. Osmotic controlled-release devices may be prepared using procedures known in the pharmaceutical arts. See for example, Remington: The Science and practice of Pharmacy, 20th Edition, 2000.

As further noted above, the agents described herein may be provided in the form of microparticulates, generally ranging in size from about 10 μm to about 2 mm (including, for example, from about 100 μm to 1 mm in diameter). Such multiparticulates may be packaged, for example, in a capsule such as a gelatin capsule or a capsule formed from an aqueous-soluble polymer such as HPMCAS, HPMC or starch; dosed as a suspension or slurry in a liquid; or they may be formed into a tablet, caplet, or pill by compression or other processes known in the art. Such multiparticulates may be made by any known process, such as wet- and dry-granulation processes, extrusion/spheronization, roller-compaction, melt-congealing, or by spray-coating seed cores. For example, in wet- and dry-granulation processes, the agent described herein and optional excipients may be granulated to form multiparticulates of the desired size. Other excipients, such as a binder (e. g., microcrystalline cellulose), may be blended with the agent to aid in processing and forming the multiparticulates. In the case of wet granulation, a binder such as microcrystalline cellulose may be included in the granulation fluid to aid in forming a suitable multiparticulate.

See, for example, Remington: The Science and Practice of Pharmacy, 20" Edition, 2000. In any case, the resulting particles may themselves constitute the therapeutic composition or they may be coated by various film-forming materials such as enteric polymers or water-swellable or water-soluble polymers, or they may be combined with other excipients or vehicles to aid in dosing to patients.

In certain embodiments, it may be desirable to provide for the immediate release of one or more of the agents described herein, and the controlled release of one or more other agents. For example, in one embodiment, a compound described herein can be provided in an immediate release formulation together with a cotherapy agent described herein in a controlled release format. For example, in one embodiment, a compound described herein can be provided in a controlled release format together with a cotherapy agent described herein in an immediate release format.

The agents can be incorporated into microemulsions, which generally are thermodynamically stable, isotropically clear dispersions of two immiscible liquids, such as oil and water, stabilized by an interfacial film of surfactant molecules (Encyclopedia of Pharmaceutical Technology (New York: Marcel Dekker, 1992), volume 9). For the preparation of microemulsions, surfactant (emulsifier) co-surfactant (co-emulsifier), an oil phase and a water phase are necessary. Suitable surfactants include any surfactants that are useful in the preparation of emulsions, e.g., emulsifiers that are typically used in the preparation of creams. The co-surfactant (or "co-emulsifier") is generally selected from the group of polyglycerol derivatives, glycerol derivatives and fatty alcohols. Preferred emulsifier/co-emulsifier combinations are generally although not necessarily selected from the group consisting of: glyceryl monostearate and polyoxyethylene stearate; polyethylene glycol and ethylene glycol palmitostearate; and caprilic and capric triglycerides and oleoyl macrogolglycerides. The water phase includes not only water but also, typically, buffers, glucose, propylene glycol, polyethylene glycols, preferably lower molecular weight polyethylene glycols (e.g., PEG 300 and PEG 400), and/or glycerol, and the like, while the oil phase will generally comprise, for example, fatty acid esters, modified vegetable oils, silicone oils, mixtures of mono- di- and triglycerides, mono- and di-esters of PEG (e.g., oleoyl macrogol glycerides), etc.

The compounds described herein can be incorporated into pharmaceutically-acceptable nanoparticle, nanosphere, and nanocapsule formulations (Delie and Blanco-Preito 2005 Molecule 10:65-80). Nanocapsules can generally entrap compounds in a stable and reproducible way (Henry-Michelland et al., 1987; Quintanar-Guerrero et al., 1998; Douglas et al., 1987). To avoid side effects due to intracellular polymeric overloading, ultrafine particles (sized around 0.1 μm) can be designed using polymers able to be degraded in vivo (e.g. biodegradable polyalkyl-cyanoacrylate nanoparticles). Such particles are described in the prior art (Couvreur et al, 1980; 1988; zur Muhlen et al., 1998; Zambaux et al. 1998; Pinto-Alphandry et al., 1995 and U.S. Pat. No. 5,145,684).

The compounds described herein can be formulated with pH sensitive materials which may include those described in WO04041195 (including the seal and enteric coating described therein) and pH-sensitive coatings that achieve delivery in the colon including those described in U.S. Pat. No. 4,910,021 and WO9001329. U.S. Pat. No. 4,910,021 describes using a pH-sensitive material to coat a capsule. WO9001329 describes using pH-sensitive coatings on beads containing acid, where the acid in the bead core prolongs dissolution of the pH-sensitive coating. U.S. Pat. No. 5,175,003 discloses a dual mechanism polymer mixture composed of pH-sensitive enteric materials and film-forming plasticizers capable of conferring permeability to the enteric material, for use in drug-delivery systems; a matrix pellet composed of a dual mechanism polymer mixture permeated with a drug and sometimes covering a pharmaceutically neutral nucleus; a membrane-coated pellet comprising a matrix pellet coated with a dual mechanism polymer mixture envelope of the same or different composition; and a pharmaceutical dosage form containing matrix pellets. The matrix pellet releases acid-soluble drugs by diffusion in acid pH and by disintegration at pH levels of nominally about 5.0 or higher. The compounds described herein may be formulated in the pH triggered targeted control release systems described in WO04052339. The compounds described herein may be formulated according to the methodology described in any of WO03105812 (extruded hydratable polymers); WO0243767 (enzyme cleavable membrane translocators); WO03007913 and WO03086297 (mucoadhesive systems); WO02072075 (bilayer laminated formulation comprising pH lowering agent and absorption enhancer); WO04064769 (amidated peptides); WO05063156 (solid lipid suspension with pseudotropic and/or thixotropic properties upon melting); WO03035029 and WO03035041 (erodible, gastric retentive dosage forms); U.S. Pat. Nos. 5,007,790 and 5,972,389 (sustained release dosage forms); WO04112711 (oral extended release compositions); WO05027878, WO02072033, and WO02072034 (delayed release compositions with natural or synthetic gum); WO05030182 (controlled release formulations with an ascending rate of release); WO05048998 (microencapsulation system); U.S. Pat. No. 5,952,314 (biopolymer); U.S. Pat. No. 5,108,758 (glass amylose matrix delivery); U.S. Pat. No. 5,840,860 (modified starch based delivery). JP 1032462 (delivery system comprising chitosan and gastric resistant material such as wheat gliadin or zein); U.S. Pat. Nos. 5,866,619 and 6,368,629 (saccharide containing polymer); U.S. Pat. No. 6,531,152 (describes a drug delivery system containing a water soluble core (Ca pectinate or other water-insoluble polymers) and outer coat which bursts (eg hydrophobic polymer—Eudragrit)); U.S. Pat. Nos. 6,234,464; 6,403,130 (coating with polymer containing casein and high methoxy pectin; WO0174175 (Maillard reaction product); WO05063206 (solubility increasing formulation); WO04019872 (transferring fusion proteins). The compounds described herein may be formulated using gastrointestinal retention system technology (GIRES; Merrion Pharmaceuticals). GIRES comprises a controlled-release dosage form inside an inflatable pouch, which is placed in a drug capsule for oral administration. Upon dissolution of the capsule, a gas-generating system inflates the pouch in the stomach where it is retained for 16-24 hours, all the time releasing compounds described herein.

The compounds described herein can be formulated in an osmotic device including the ones disclosed in U.S. Pat. Nos. 4,503,030, 5,609,590 and 5,358,502. U.S. Pat. No. 4,503,030 discloses an osmotic device for dispensing a drug to certain pH regions of the gastrointestinal tract. More particularly, the invention relates to an osmotic device comprising a wall formed of a semi-permeable pH sensitive composition that surround a compartment containing a drug, with a passageway through the wall connecting the exterior of the device with the compartment. The device delivers the drug at a controlled rate in the region of the gastrointestinal tract having a pH of less than 3.5, and the device self-destructs and releases all its drug in the region of the gastrointestinal tract having a pH greater than 3.5, thereby providing total availability for drug absorption. U.S. Pat. Nos. 5,609,590 and 5,358,502 disclose an osmotic bursting device for dispensing a beneficial agent to an aqueous environment. The device comprises a beneficial agent and osmagent surrounded at least in part by a semi-permeable membrane. The beneficial agent may also function as the osmagent. The semi-permeable membrane is permeable to water and substantially impermeable to the beneficial agent and osmagent. A trigger means is attached to the semi-permeable membrane (e. g., joins two capsule halves). The trigger means is activated by a pH of from 3 to 9 and triggers the eventual, but sudden, delivery of the beneficial agent. These devices enable the pH-triggered release of the beneficial agent core as a bolus by osmotic bursting.

The compounds described herein may be formulated based on the invention described in U.S. Pat. No. 5,316,774 which discloses a composition for the controlled release of an active substance comprising a polymeric particle matrix, where each particle defines a network of internal pores. The active substance is entrapped within the pore network together with a blocking agent having physical and chemical characteristics selected to modify the release rate of the active substance from the internal pore network. In one embodiment, drugs may be selectively delivered to the intestines using an enteric material as the blocking agent. The enteric material remains intact in the stomach but degrades under the pH conditions of the intestines. In another embodiment, the sustained release formulation employs a blocking agent, which remains stable under the expected conditions of the environment to which the active substance is to be released. The use of pH-sensitive materials alone to achieve site-specific delivery is difficult because of leaking of the beneficial agent prior to the release site or desired delivery time and it is difficult to achieve long time lags before release of the active ingredient after exposure to high pH (because of rapid dissolution or degradation of the pH-sensitive materials).

The agents may also be formulated in a hybrid system which combines pH-sensitive materials and osmotic delivery systems. These hybrid devices provide delayed initiation of sustained-release of the beneficial agent. In one device a pH-sensitive matrix or coating dissolves releasing osmotic devices that provide sustained release of the beneficial agent see U.S. Pat. Nos. 4,578,075, 4,681,583, and 4,851,231. A second device consists of a semipermeable coating made of a polymer blend of an insoluble and a pH-sensitive material. As the pH increases, the permeability of the coating increases, increasing the rate of release of beneficial agent see U.S. Pat. Nos. 4,096,238, 4,503,030, 4,522,625, and 4,587,117.

The compounds described herein may be formulated in terpolymers according to U.S. Pat. No. 5,484,610 which discloses terpolymers which are sensitive to pH and temperature which are useful carriers for conducting bioactive agents through the gastric juices of the stomach in a protected form. The terpolymers swell at the higher physiologic pH of the intestinal tract causing release of the bioactive agents into the intestine. The terpolymers are linear and are made up of 35 to 99 wt % of a temperature sensitive component, which imparts to the terpolymer LCST (lower critical solution temperature) properties below body temperatures, 1 to 30 wt % of a pH sensitive component having a pKa in the range of from 2 to 8 which functions through ionization or deionization of carboxylic acid groups to prevent the bioactive agent from being lost at low pH but allows bioactive agent release at physiological pH of about 7.4 and a hydrophobic component which stabilizes the LCST below body temperatures and compensates for bioactive agent effects on the terpolymers. The terpolymers provide for safe bioactive agent loading, a simple procedure for dosage form fabrication and the terpolymer functions as a protective carrier in the acidic environment of the stomach and also protects the bioactive agents from digestive enzymes until the bioactive agent is released in the intestinal tract.

The compounds described herein may be formulated in pH sensitive polymers according to those described in U.S. Pat. No. 6,103,865. U.S. Pat. No. 6,103,865 disclosed pH-sensitive polymers containing sulfonamide groups, which can be changed in physical properties, such as swellability and solubility, depending on pH and which can be applied for a drug-delivery system, bio-material, sensor, and the like, and a preparation method therefore. The pH-sensitive polymers are prepared by introduction of sulfonamide groups, various in pKa, to hydrophilic groups of polymers either through coupling to the hydrophilic groups of polymers, such as acrylamide, N,N-dimethylacrylamide, acrylic acid, N-isopropylacrylamide and the like or copolymerization with other polymerizable monomers. These pH-sensitive polymers may have a structure of linear polymer, grafted copolymer, hydrogel or interpenetrating network polymer.

The compounds described herein may be formulated according U.S. Pat. No. 5,656,292 which discloses a composition for pH dependent or pH regulated controlled release of active ingredients especially drugs. The composition consists of a compactable mixture of the active ingredient and starch molecules substituted with acetate and dicarboxylate residues. The preferred dicarboxylate acid is succinate. The average substitution degree of the acetate residue is at least 1 and 0.2-1.2 for the dicarboxylate residue. The starch molecules can have the acetate and dicarboxylate residues attached to the same starch molecule backbone or attached to separate starch molecule backbones. The present invention also discloses methods for preparing said starch acetate dicarboxylates by transesterification or mixing of starch acetates and starch dicarboxylates respectively.

The compounds described herein may be formulated according to the methods described in U.S. Pat. Nos. 5,554,147, 5,788,687, and 6,306,422 which disclose a method for the controlled release of a biologically active agent wherein the agent is released from a hydrophobic, pH-sensitive polymer matrix. The polymer matrix swells when the environment reaches pH 8.5, releasing the active agent. A polymer of hydrophobic and weakly acidic comonomers is disclosed for use in the controlled release system. Also disclosed is a specific embodiment in which the controlled release system may be used. The pH-sensitive polymer is coated onto a latex catheter used in ureteral catheterization. A ureteral catheter coated with a pH-sensitive polymer having an antibiotic or urease inhibitor trapped within its matrix will release the agent when exposed to high pH urine.

The compounds described herein may be formulated in/with bioadhesive polymers according to U.S. Pat. No. 6,365,187. Bioadhesive polymers in the form of, or as a coating on, microcapsules containing drugs or bioactive substances which may serve for therapeutic, or diagnostic purposes in diseases of the gastrointestinal tract, are described in U.S. Pat. No. 6,365,187. The polymeric microspheres all have a bioadhesive force of at least 11 mN/cm$^2$ (110 N/m2) Techniques for the fabrication of bioadhesive microspheres, as well as a method for measuring bioadhesive forces between microspheres and selected segments of the gastrointestinal tract in vitro are also described. This quantitative method provides a means to establish a correlation between the chemical nature, the surface morphology and the dimensions of drug-loaded microspheres on one hand and bioadhesive forces on the other, allowing the screening of the most promising materials from a relatively large group of natural and synthetic polymers which, from theoretical consideration, should be used for making bioadhesive microspheres. Solutions of medicament in buffered saline and similar vehicles are commonly employed to generate an aerosol in a nebulizer. Simple nebulizers operate on Bernoulli's principle and employ a stream of air or oxygen to generate the spray particles. More complex nebulizers employ ultrasound to create the spray particles. Both types are well known in the art and are described in standard textbooks of pharmacy such as Sprowls' American Pharmacy and Remington's The Science and Practice of Pharmacy. Other devices for generating aerosols employ compressed gases, usually hydrofluorocarbons and chlorofluorocarbons, which are mixed with the medicament and any necessary excipients in a pressurized container, these devices are likewise described in standard textbooks such as Sprowls and Remington.

The agents can be administered, e.g., by intravenous injection, intramuscular injection, subcutaneous injection, intraperitoneal injection, topical, sublingual, intraarticular (in the joints), intradermal, buccal, ophthalmic (including intraocular), intranasaly (including using a cannula), or by other routes. The agents can be administered orally, e.g., as a tablet or cachet containing a predetermined amount of the active ingredient, gel, pellet, paste, syrup, bolus, electuary, slurry, capsule, powder, granules, as a solution or a suspension in an aqueous liquid or a non-aqueous liquid, as an oil-in-water liquid emulsion or a water-in-oil liquid emulsion, via a micellar formulation (see, e.g. WO 97/11682) via a liposomal formulation (see, e.g., EP 736299, WO 99/59550 and WO 97/13500), via formulations described in WO 03/094886 or in some other form. Orally administered compositions can include binders, lubricants, inert diluents, lubricating, surface active or dispersing agents, flavoring agents, and humectants. Orally administered formulations such as tablets may optionally be coated or scored and may be formulated so as to provide sustained, delayed or controlled release of the active ingredient therein. The agents can also be administered transdermally (i.e. via reservoir-type or matrix-type patches, microneedles, thermal poration, hypodermic needles, iontophoresis, electroporation, ultrasound or other forms of sonophoresis, jet injection, or a combination of any of the preceding methods (Prausnitz et al. 2004, Nature Reviews Drug Discovery 3:115)). The agents can be administered using high-velocity transdermal particle injection techniques using the hydrogel particle formulation described in U.S. 20020061336. Additional particle formulations are described in WO 00/45792, WO 00/53160, and WO 02/19989. An example of a transdermal formulation containing plaster and the absorption promoter dimethylisosorbide can be found in WO 89/04179. WO 96/11705 provides formulations suitable for transdermal administration. The agents can be administered in the form a suppository or by other vaginal or rectal means. The agents can be administered in a transmembrane formulation as described in WO 90/07923. The agents can be administered non-invasively via the dehydrated particles described in U.S. Pat. No. 6,485,706. The agent can be administered in an enteric-coated drug formulation as described in WO 02/49621. The agents can be administered intranasaly using the formulation described in U.S. Pat. No. 5,179,079. Formulations suitable for parenteral injection are described in WO 00/62759. The agents can be administered using the casein formulation described in U.S. 20030206939 and WO 00/06108. The agents can be administered using the particulate formulations described in U.S. 20020034536.

The agents, alone or in combination with other suitable components, can be administered by pulmonary route utilizing several techniques including but not limited to intratracheal instillation (delivery of solution into the lungs by syringe), intratracheal delivery of liposomes, insufflation (administration of powder formulation by syringe or any other similar device into the lungs) and aerosol inhalation. Aerosols (e.g., jet or ultrasonic nebulizers, metered-dose inhalers (MDIs), and dry-powder inhalers (DPIs)) can also be used in intranasal applications. Aerosol formulations are stable dispersions or suspensions of solid material and liquid droplets in a gaseous medium and can be placed into pressurized acceptable propellants, such as hydrofluroalkanes (HFAs, i.e. HFA-134a and HFA-227, or a mixture thereof), dichlorodifluoromethane (or other chlorofluocarbon propellants such as a mixture of Propellants 11, 12, and/or 114), propane, nitrogen, and the like. Pulmonary formulations may include permeation enhancers such as fatty acids, and saccharides, chelating agents, enzyme inhibitors (e.g., protease inhibitors), adjuvants (e.g., glycocholate, surfactin, span 85, and nafamostat), preservatives (e.g., benzalkonium chloride or chlorobutanol), and ethanol (normally up to 5% but possibly up to 20%, by weight). Ethanol is commonly included in aerosol compositions as it can improve the function of the metering valve and in some cases also improve the stability of the dispersion. Pulmonary formulations may also include surfactants which include but are not limited to bile salts and those described in U.S. Pat. No. 6,524,557 and references therein. The surfactants described in U.S. Pat. No. 6,524,557, e.g., a C8-C16 fatty acid salt, a bile salt, a phospholipid, or alkyl saccharide are advantageous in that some of them also reportedly enhance absorption of the compound in the formulation. Also suitable in the invention are dry powder formulations comprising a therapeutically effective amount of active compound blended with an appropriate carrier and adapted for use in connection with a dry-powder inhaler. Absorption enhancers which can be added to dry powder formulations of the present invention include those described in U.S. Pat. No. 6,632,456. WO 02/080884 describes new methods for the surface modification of powders. Aerosol formulations may include U.S. Pat. Nos. 5,230,884, 5,292,499, WO 017/8694, WO 01/78696, U.S. 2003019437, U.S. 20030165436, and WO 96/40089 (which includes vegetable oil). Sustained release formulations suitable for inhalation are described in U.S. 20010036481A1, 20030232019A1, and U.S. 20040018243A1 as well as in WO 01/13891, WO 02/067902, WO 03/072080, and WO 03/079885. Pulmonary formulations containing microparticles are described in WO 03/015750, U.S. 20030008013, and WO 00/00176. Pulmonary formulations containing stable glassy state powder are described in U.S. 20020141945 and U.S. 6,309,671. Other aerosol formulations are described in EP 1338272A1 WO 90/09781, U.S. Pat. Nos. 5,348,730, 6,436,367, WO 91/04011, and U.S. Pat. Nos. 6,294,153 and 6,290,987 describes a liposomal based formulation that can be administered via aerosol or other means. Powder formulations for inhalation are described in U.S. 20030053960 and WO 01/60341. The agents can be administered intranasally as described in U.S. 20010038824.

Solutions of medicament in buffered saline and similar vehicles are commonly employed to generate an aerosol in a nebulizer. Simple nebulizers operate on Bernoulli's principle and employ a stream of air or oxygen to generate the spray particles. More complex nebulizers employ ultrasound to create the spray particles. Both types are well known in the art and are described in standard textbooks of pharmacy such as Sprowls' American Pharmacy and Remington's The Science and Practice of Pharmacy. Other devices for generating aerosols employ compressed gases, usually hydrofluorocarbons and chlorofluorocarbons, which are mixed with the medicament and any necessary excipients in a pressurized container, these devices are likewise described in standard textbooks such as Sprowls and Remington.

The agent can be fused to immunoglobulins or albumin, or incorporated into a liposome to improve half-like. The agent can also be conjugated to polyethylene glycol (PEG) chains. Methods for pegylation and additional formulations containing PEG-conjugates (i.e. PEG-based hydrogels, PEG modified liposomes) can be found in Harris and Chess, Nature Reviews Drug Discovery 2: 214-221 and the references therein. The agent can be administered via a nanocochleate or cochleate delivery vehicle (BioDelivery Sciences International). The agents can be delivered transmucosally (i.e. across a mucosal surface such as the vagina, eye or nose) using formulations such as that described in U.S. Pat. No. 5,204,108. The agents can be formulated in microcapsules as described in WO 88/01165. The agent can be administered intra-orally using the formulations described in U.S. 20020055496, WO 00/47203, and U.S. Pat. No. 6,495,120. The agent can be delivered using nanoemulsion formulations described in WO 01/91728A2.

The agents can be a free acid or base, or a pharmacologically acceptable salt thereof. Solids can be dissolved or dispersed immediately prior to administration or earlier. In some circumstances the preparations include a preservative to prevent the growth of microorganisms. The pharmaceutical forms suitable for injection can include sterile aqueous or organic solutions or dispersions which include, e.g., water, an alcohol, an organic solvent, an oil or other solvent or dispersant (e.g., glycerol, propylene glycol, polyethylene glycol, and vegetable oils). The formulations may contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Pharmaceutical agents can be sterilized by filter sterilization or by other suitable means Suitable pharmaceutical compositions in accordance with the invention will generally include an amount of the active compound(s) with an acceptable pharmaceutical diluent or excipient, such as a sterile aqueous solution, to give a range of final concentrations, depending on the intended use. The techniques of preparation are generally well know in the art, as exemplified by Remington's Pharmaceutical Sciences, 18th Ed., Mack Publishing Company, 1995.

Methods to increase chemical and/or physical stability of the agents the described herein are found in WO 00/04880, and WO 97/04796 and the references cited therein.

Methods to increase bioavailability of the agents described herein are found in U.S. 20030198619, WO 01/49268, WO 00/32172, and WO 02/064166. Glycyrrhizinate can also be used as an absorption enhancer (see, e.g., EP397447). WO 03/004062 discusses Ulex europaeus I (UEA1) and UEAI mimetics which may be used to target the agents to the GI tract.

Kits

The compounds and pharmaceutical formulations described herein may be contained in a kit. The kit may include single or multiple doses of two or more agents, each packaged for formulated individually, or single or multiple doses of two or more agents packaged or formulated in combination. Thus, one or more agents can be present in first container, and the kit can optionally include one or more agents in a second container. The container or containers are placed within a package, and the package can optionally include administration or dosage instructions. A kit can include additional components such as syringes or other means for administering the agents as well as diluents or other means for formulation. Thus, the kits can comprise: a) a pharmaceutical composition comprising a compound described herein and a pharmaceutically acceptable carrier, vehicle or diluent; and b) a container or packaging. The kits may optionally comprise instructions describing a method of using the pharmaceutical compositions in one or more of the methods described herein (e.g. preventing or treating one or more of the diseases and disorders described herein). The kit may optionally comprise a second pharmaceutical composition comprising one or more additional agents described herein for cotherapy use, a pharmaceutically acceptable carrier, vehicle or diluent. The pharmaceutical composition comprising the compound described herein and the second pharmaceutical composition contained in the kit may be optionally combined in the same pharmaceutical composition.

A kit includes a container or packaging for containing the pharmaceutical compositions and may also include divided containers such as a divided bottle or a divided foil packet. The container can be, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. It is feasible that more than one container can be used together in a single package to market a single dosage form. For example, tablets may be contained in a bottle which is in turn contained within a box.

An example of a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It maybe desirable to provide a written memory aid containing information and/or instructions for the physician, pharmacist or subject regarding when the medication is to be taken. A "daily dose" can be a single tablet or capsule or several tablets or capsules to be taken on a given day. When the kit contains separate compositions, a daily dose of one or more compositions of the kit can consist of one tablet or capsule while a daily dose of another one or more compositions of the kit can consist of several tablets or capsules. A kit can take the form of a dispenser designed to dispense the daily doses one at a time in the order of their intended use. The dispenser can be equipped with a memory-aid, so as to further facilitate compliance with the regimen. An example of such a memory-aid is a mechanical counter which indicates the number of daily doses that have been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

A number of embodiments have been described. Nevertheless, it will be understood that various modifications may be made without departing from the spirit and scope of the invention.

The invention claimed is:
1. A compound having Formula I:

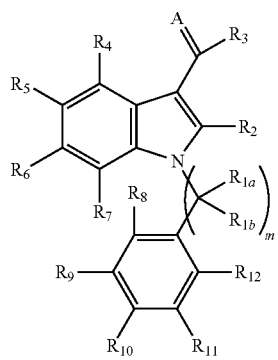

(Formula I)

wherein:
A is O;
each $R_{1a}$ and $R_{1b}$ is independently: H, menthyl, or an $R_{1a}$ and $R_{1b}$ attached to the same carbon, taken together with that carbon, form an optionally substituted C3-C6 cycloalkyl or carbocycle;
m=1;
$R_2$ is H, hydroxyl, —$NO_2$, an optionally substituted C1-C5 alkoxy, —CN, an optionally substituted C1-C5 alkyl, an optionally substituted C2-C5 alkenyl, an optionally substituted C2-C5 alkynyl or halogen;
$R_3$ is

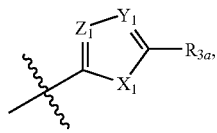

wherein $X_1$, $Y_1$, and $Z_1$ are: (a) O, N and N, respectively; (b) O, N and $C(R_{3c})$, respectively; or (c) O, $C(R_{3c})$ and N respectively; wherein
$R_{3a}$ is selected from:
H, an optionally substituted aryl, an optionally substituted heteroaryl, and an optionally substituted heterocycle, and
$R_{3c}$ is selected from:
H, halogen, and C1-C3 alkyl;
each of $R_4$, $R_5$, $R_6$ and $R_7$ are independently: H, a halogen, an optionally substituted C1-C5 alkyl, hydroxyl, or an optionally substituted C1-C5 alkoxy;
and
each of $R_8$, $R_9$, $R_{10}$, $R_{11}$ and $R_{12}$ is independently H, —CN, hydroxyl, a halogen, an optionally substituted C1-C5 alkcyl, an optionally substituted C2-C5 alkenyl, an optionally substituted C2-C5 alkynyl, hydroxyl, $NO_2$, an optionally substituted C1-C5 alkoxy, -$N(R_{2a})(R_{2B})$, —C(O)OH, an optionally substituted —$SO_2CH_3$, an optionally substituted —$SO_2NH_2$, an optionally substituted —$SO_2OH$, —C(O)H, an optionally substituted —$C(O)CH_3$, an optionally substituted —$C(O)N(CH_3)_2$, an optionally substituted —$C(O)NH_2$, or an optionally substituted —$SCH_3$.

2. The compound of claim 1 wherein $R_2$ is selected from the group consisting of H, methyl, Cl, $CF_3$ and F.

3. The compound of claim 2, wherein $R_2$ is selected from the group consisting of H, methyl and Cl.

4. The compound of claim 1, wherein $R_2$ is halogen.

5. The compound of claim 4, wherein $R_2$ is Cl.

6. The compound of claim 4, wherein $R_2$ is F.

7. The compound of claim 1, wherein $R_2$ is methyl or halogen substituted methyl.

8. The compound of claim 7 wherein $R_2$ is methyl.

9. The compound of claim 1, wherein $R_9$ and $R_{11}$ are both H.

10. The compound of claim 1, wherein no more than four of $R_8$, $R_9$, $R_{10}$, $R_{11}$ and $R_{12}$ are other than H.

11. The compound of claim 10 wherein no more than three of $R_8$, $R_9$, $R_{10}$, $R_{11}$ and $R_{12}$ are other than H.

12. The compound of claim 11 wherein no more than two of $R_8$, $R_9$, $R_{10}$, $R_{11}$ and $R_{12}$ are other than H.

13. The compound of claim 12 wherein only one of $R_8$, $R_9$, $R_{10}$, $R_{11}$ and $R_{12}$ is other than H.

14. The compound of claim 1, wherein $R_{10}$ is halogen.

15. The compound of claim 1, wherein $R_4$ is selected from the group consisting of: F, H, an optionally substituted C1-C5 alkyl, and an optionally substituted C1-C5 alkoxy.

16. The compound of claim 1, wherein $R_5$ is selected from the group consisting of: Cl, F, Br, methoxy, $CH_3$, $CF_3$, and OH.

17. The compound of claim 16, wherein $R_5$ is methoxy.

18. The compound of claim 1, wherein $R_4$ is H.

19. The compound of claim 1, wherein $R_6$ is H.

20. The compound of claim 1, wherein $R_7$ is H.

21. The compound of claim 1, wherein $R_8$ is H.

22. The compound of claim 1, wherein $R_4$, $R_6$, and $R_7$ are H.

23. The compound of claim 1, wherein $R_3$ is

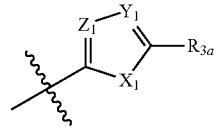

and $X_1$, $Y_1$, and $Z_1$ are (a) 0, N and N, respectively.

24. The compound of claim 23, wherein $R_{3a}$ is an optionally substituted monocyclic aryl or an optionally substituted monocyclic heteroaryl.

25. The compound of claim 23, wherein $R_{3a}$ is selected from:

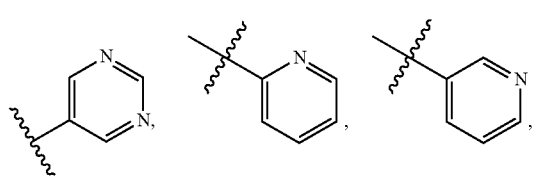

-continued

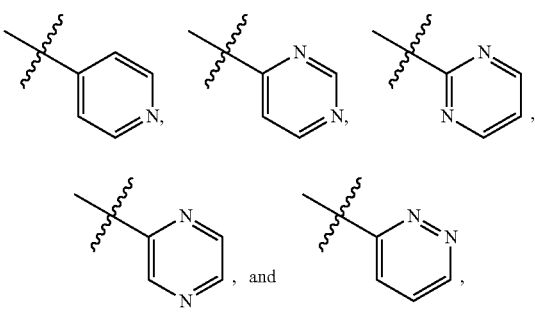

and is optionally substituted.

26. The compound of claim 25, wherein $R_{3a}$ is an optionally substituted pyrimidine.

27. The compound of claim 25, wherein $R_{3a}$ is

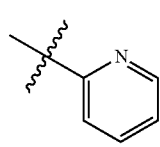

and is optionally substituted.

28. The compound of claim 25, wherein $R_{3a}$ is

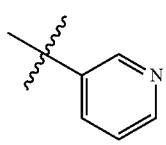

and is optionally substituted.

29. The compound of claim 25, wherein $R_{3a}$ is

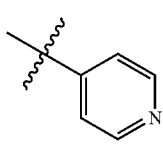

and is optionally substituted.

30. The compound of claim 23, wherein $R_{3a}$ is

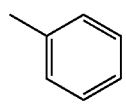

and is optionally substituted.

31. The compound of claim 25, wherein $R_{3a}$ is monosubstituted or unsubstituted.

32. The compound of claim 31, wherein $R_{3a}$ is unsubstituted.

33. The compound of claim 31, wherein $R_{3a}$ is monosubstituted.

34. The compound of claim 23, wherein $R_{3a}$ is selected from:

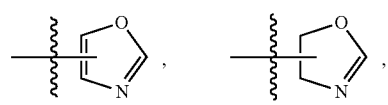

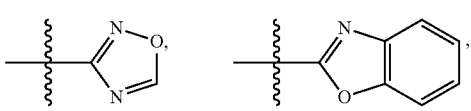

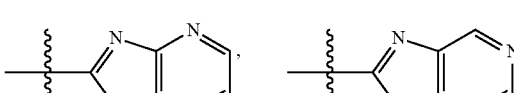

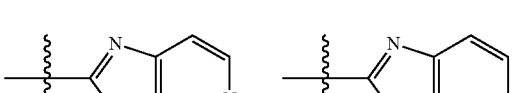

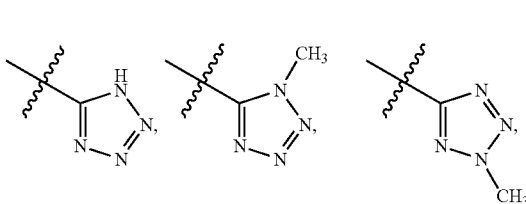

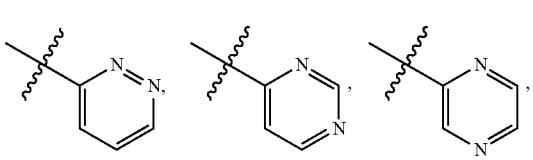

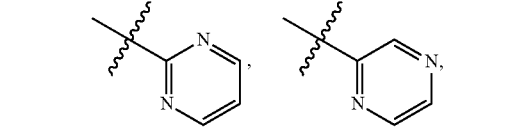

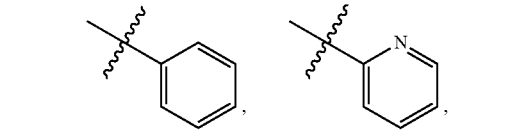

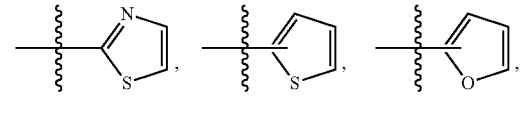

-continued
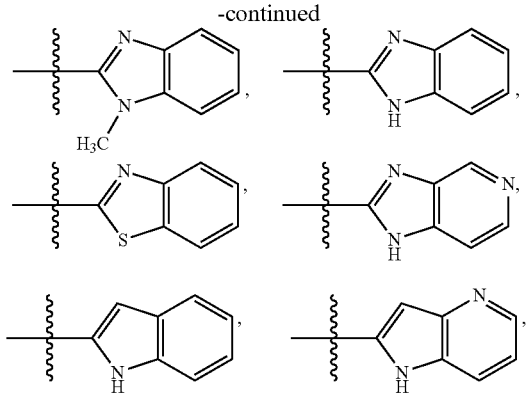
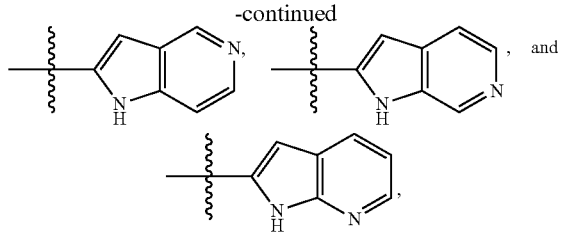
and can be optionally substituted at a substitutable position.
* * * * *

UNITED STATES PATENT AND TRADEMARK OFFICE
CERTIFICATE OF CORRECTION

PATENT NO. : 7,960,544 B2  
APPLICATION NO. : 12/097616  
DATED : June 14, 2011  
INVENTOR(S) : Wilmin Bartolini et al.

Page 1 of 1

It is certified that error appears in the above-identified patent and that said Letters Patent is hereby corrected as shown below:

On the cover page in the list of inventors (75) delete "Lundigran" and replace with -- Lundrigan --

Column 481, line 30, delete "menthyl" and replace with -- methyl --

Column 481, line 63, delete "alkcyl" and replace with -- alkyl --

Column 482, line 53, delete "0" and replace with -- O --

Column 484, line 50, delete " 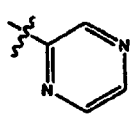 " and replace with -- 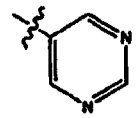 --

Column 484, line 65, insert missing structure -- 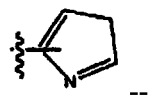 --

Column 484, line 65, delete " 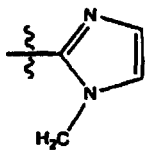 " and replace with -- 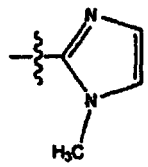 --

Signed and Sealed this  
Thirteenth Day of September, 2011

David J. Kappos  
*Director of the United States Patent and Trademark Office*